United States Patent
Weiss et al.

(10) Patent No.: US 9,458,152 B2
(45) Date of Patent: *Oct. 4, 2016

(54) BICYCLIC SULFONAMIDE COMPOUNDS AS SODIUM CHANNEL INHIBITORS

(71) Applicant: AMGEN INC., Thousand Oaks, CA (US)

(72) Inventors: Matthew Weiss, Boston, MA (US); Alessandro Boezio, Somerville, MA (US); Christiane Boezio, Somerville, MA (US); John R. Butler, Somerville, MA (US); Margaret Yuhua Chu-Moyer, Brookline, MA (US); Erin F. Dimauro, Cambridge, MA (US); Thomas Dineen, Somerville, MA (US); Russell Graceffa, Hampton, NH (US); Angel Guzman-Perez, Belmont, MA (US); Hongbing Huang, Brighton, MA (US); Charles Kreiman, Hopkinton, MA (US); Daniel La, Brookline, MA (US); Isaac E. Marx, Arlington, MA (US); Benjamin Charles Milgram, Cambridge, MA (US); Hanh Nho Nguyen, Jupiter, FL (US); Emily Anne Peterson, Cambridge, MA (US); Karina R. Vaida, Burlington, MA (US); Brian Sparling, Watertown, MA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/920,833

(22) Filed: Oct. 22, 2015

(65) Prior Publication Data

US 2016/0046626 A1    Feb. 18, 2016

Related U.S. Application Data

(63) Continuation of application No. 14/302,337, filed on Jun. 11, 2014, now Pat. No. 9,212,182.

(60) Provisional application No. 61/983,958, filed on Apr. 24, 2014, provisional application No. 61/834,273, filed on Jun. 12, 2013.

(51) Int. Cl.
*A61K 31/00* (2006.01)
*C07D 417/14* (2006.01)
*C07D 471/04* (2006.01)
*C07D 413/12* (2006.01)
*C07D 401/12* (2006.01)
*C07D 413/14* (2006.01)
*C07D 417/12* (2006.01)
*C07C 53/18* (2006.01)
*C07D 215/227* (2006.01)
*C07D 403/12* (2006.01)
*C07D 215/36* (2006.01)
*C07D 241/44* (2006.01)
*C07D 401/14* (2006.01)

(52) U.S. Cl.
CPC ............ *C07D 417/14* (2013.01); *C07C 53/18* (2013.01); *C07D 215/227* (2013.01); *C07D 215/36* (2013.01); *C07D 241/44* (2013.01); *C07D 401/12* (2013.01); *C07D 401/14* (2013.01); *C07D 403/12* (2013.01); *C07D 413/12* (2013.01); *C07D 413/14* (2013.01); *C07D 417/12* (2013.01); *C07D 471/04* (2013.01)

(58) Field of Classification Search
None
See application file for complete search history.

(56) References Cited

U.S. PATENT DOCUMENTS

2014/0371201 A1*  12/2014  Weiss ............... C07D 471/04
                                                    514/210.21

FOREIGN PATENT DOCUMENTS

| WO | 9640641 A1 | 12/1996 |
|---|---|---|
| WO | 9832732 A1 | 7/1998 |
| WO | 03090672 A2 | 11/2003 |
| WO | 2004065379 A1 | 8/2004 |
| WO | 2004083204 A1 | 9/2004 |
| WO | 2006117762 A2 | 11/2006 |
| WO | 2006122014 A2 | 11/2006 |
| WO | 2006124744 A1 | 11/2006 |
| WO | 2007089034 A1 | 8/2007 |

(Continued)

OTHER PUBLICATIONS

Berge, et al., Pharmaceutical Salts, J Pharm Sci., 66: 1-19, 1977.

(Continued)

*Primary Examiner* — Heidi Reese
(74) *Attorney, Agent, or Firm* — Elsa D. Lemoine

(57) ABSTRACT

The present invention provides compounds of Formula I,

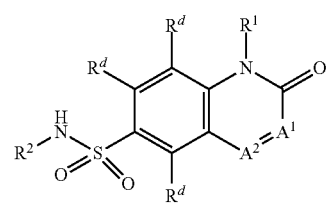

and pharmaceutically acceptable salts thereof, that are inhibitors of voltage-gated sodium channels, in particular Nav1.7. The compounds are useful for the treatment of diseases associated with the activity of sodium channels such as pain disorders and itch. Also provided are pharmaceutical compositions containing compounds of the present invention.

18 Claims, No Drawings

(56) References Cited

FOREIGN PATENT DOCUMENTS

| WO | 2013025883 A1 | 2/2013 |
|---|---|---|
| WO | 2013086229 A1 | 6/2013 |
| WO | 2013122897 A1 | 8/2013 |

OTHER PUBLICATIONS

Cox, et. al., An SCN9A channelopathy causes congenital inability to experience pain, Nature 444:894-898, 2006.
Deuis et. al., An animal model of oxaliplatin-induced cold allodynia reveals a crucial role for Nav1.6 in peripheral pain pathways, *Pain*. 2013;154(9):1749-1757. doi:10.1016/j.pain.2013.05.032.
Dib-Hajj et al., Proc. Natl. Acad. Sci. USA, 95(15):8963-8968, 1988.
Do and Bean, Neuron, 39:109-120, 2003.
Drenth, et al., SCN9A mutations define primary erythermalgia as a neuropathic disorder of voltage gated sodium channels, J Invest Dermatol 124:1333-1338, 2005.
Ettinger and Argoff, Neurotherapeutics, 4:75-83 2007.
Fertleman et al, SCN9A mutations in paroxysmal extreme pain disorder: allelic variants underlie distinct channel defects and phenotypes, Neuron 52:767-774, 2006.
Gillet et. al, "Voltage-gated Sodium Channel Activity Promotes Cysteine Cathepsin-dependent Invasiveness and Colony Growth of Human Cancer Cells" *J. Biol. Chem*. 2009, 284:8680-8691.
Goldberg, et al. Loss-of-function mutations in the Nav1.7 gene underlie congenital indifference to pain in multiple human populations, Clin Genet, 71:311-319, 2007.
Goldin, Resurgence of sodium channel research, Ann Rev Physiol, 63:871-894, 2001.
Gonzalez, Termin, Wilson, Methods and Principles in Medicinal Chemistry, 29:168-192, 2006.
Haws, et al., J. Neuroscience, 23(26):8881-8892, 2003.
Halford, Changing the Channel, C&E News, Mar. 2014.
Hamannn., et. al., Exp. Neurol. 184(2):830-838, 2003.
Haufe et. al., J Mol. Cell Cardiol. 42(3):469-477, 2007.
Higuchi and Stella, Pro-drugs as Novel Delivery Systems, vol. 14 of the A.C.S. Symposium Series, and in Bioreversible Carriers in Drug Design, ed. Edward B. Roche, American Pharmaceutical Association and Pergamon Press, 1975.
Hille, Ion Channels of Excitable Membranes, Sinauer Associates, Inc.: Sunderland MA, 3$^{rd}$ Ed. 2001.
Johannessen, CNS Drugs, 22(1) 24-47, 2008.
Kim, et al. Nat. Cell. Biol. 9(7):755-764, 2007.
Liu, et al., Am. J. Pharmacogenomics, 3(3):173-179, 2003.
McKinney., et. al., Genes Brain Behav. 7(6):629-638, 2008.
Morinville et al., J Comp Neurol., 504:680-689, 2007.
Raymond, et al., J. Biol.Chem, 279 (44) :46234-41, 2004.
Tamaoka, Internal Medicine 9:769-770, 2003.
Waxman, Nature Neuroscience 7 :932-941, 2006.
Wood et al, Voltage-gated sodium channel blockers; target validation and therapeutic potential, Curr. Top Med. Chem. 5:529-537, 2005.
Woodruff-Pak, et. al., Behav. Neurosci. 120(2):229-240, 2006.
Yang, et al. Mutations in SCN9A, encoding a sodium channel alpha subunit, in patients with primary erythermalgia, J. Med. Genet. 41:171-174, 2004.
Yu, et al., Nat. Neuroscience, 9:9 1142-1149, 2006.

* cited by examiner

BICYCLIC SULFONAMIDE COMPOUNDS AS SODIUM CHANNEL INHIBITORS

RELATED APPLICATIONS

This application is a continuation of U.S. Non Provisional patent application Ser. No. 14/302,337, filed on Jun. 11, 2014, which claims the benefit of U.S. Provisional Patent Application Nos. 61/834,273, filed on Jun. 12, 2013 and 61/983,958, filed on Apr. 24, 2014, which specifications are hereby incorporated herein by reference in their entireties.

FIELD OF THE INVENTION

The present invention provides compounds that are inhibitors of voltage-gated sodium channels (Nav), in particular Nav 1.7, and are useful for the treatment of diseases treatable by inhibition of sodium channels such as pain disorders. Also provided are pharmaceutical compositions containing compounds of the present invention.

BACKGROUND OF THE INVENTION

A 2011 report of the institute of medicine estimates that 100 million adults in the US, roughly 30 of the population, suffer from chronic pain (*C & E News*, Bethany Halford, "Changing the Channel", published 3-24-14). Chronic pain by definition involves abnormal electrical spiking of neurons in the pain pathways: peripheral sensory neurons, spinal cord neurons, neurons in the pain matrix of the brain (e.g., somatosensory cortex, insular cortex, anterior cingular cortex), and/or neurons in brainstem. Although firing of these neurons is modulated and governed by many different receptors, enzymes, and growth factors, in most neurons the fast upstroke of the electrical spike is produced by entry of sodium ions through voltage-gated sodium channels (Hille B, Ion Channels of Excitable Membranes. Sinauer Associates, Inc.: Sunderland Mass., $3^{rd}$ Ed. 2001). There are nine different isoforms of voltage-gated sodium channel (Nav 1.1-Nav 1.9), and they have distinct expression patterns in tissues including neurons and cardiac and skeletal muscle (Goldin, A. L, "Resurgence of sodium channel research," *Ann Rev Physiol* 63:871-894, 2001; Wood, J. N. and, Boorman, J. "Voltage-gated sodium channel blockers; target validation and therapeutic potential" *Curr. Top Med. Chem.* 5:529-537, 2005).

Nav1.1 and Nav1.2 are highly expressed in the brain (Raymond, C. K., et al., J. Biol. Chem. (2004) 279 (44): 46234-41) and are vital to normal brain function. Some loss of function due to Nav 1.1 mutations in humans, have resulted in epilepsy, presumably as these channels are expressed in inhibitory neurons (Yu, F. H., et al., Nat. Neuroscience (2006), 9 (9) 1142-1149). Nav1.1 is also expressed in the peripheral nervous system and inhibition of Nav1.1 in the periphery may provide relief of pain. Hence, while inhibiting Nav1.1 may provide use for treating pain, it may also be undesirable possibly leading to anxiety and over excitability. Nav1.3 is expressed primarily in the fetal central nervous system, and expression was found to be upregulated after nerve injury in rats (Hains, B. D., et al., J. Neuroscience (2030) 23(26):8881-8892). Nav1.4 is expressed primarily in skeletal muscle. Mutations of the gene and its' product have significant impact on muscle function, including paralysis (Tamaoka A., Internal Medicine (2003), (9):769-770). Nav1.5 is expressed mainly in cardiac myocytes, including atria, ventricles, the sino-atrial node, atrio-ventircular node and cardiac Purkinje fibers. The rapid upstroke of the cardiac action potential and the rapid impulse conduction through cardiac tissue is due to the opening of the Nav1.5 channel. Mutations of the Nav1.5 channel have resulted in arrhythmic syndromes, including QTc prolongation, Brugada syndrome (BS), sudden unexpected nocturnal death syndrome (SUNDS) and sudden infant death syndrome (SIDS) (Liu, H., et al., Am. J. Pharmacogenomics (2003), 3(3):173-179). Nav1.6 is widely distributed voltage-gated sodium channel expressed throughout the central and peripheral nervous system. Nav1.8 is expressed primarily in sensory ganglia of the peripheral nervous system, such as the dorsal root ganglia. There are no identified Nav1.8 mutations that produce varied pain responses in humans. Nav1.8 differs from most neuronal Nav isotypes in that it is insensitive to inhibition by tetrodotoxin. Nav1.9, similar to nav1.8, is also a tetrodotoxin insensitive sodium channel expressed primarily in dorsal root ganglia neurons (Dib-Hajj, S. D., et al., Proc. Natl. Acad. Sci. USA (1998), 95(15):8963-8968).

Recent evidence from several independent genetic studies has shown that the tetrodotoxin-sensitive voltage-gated sodium ion channel Nav 1.7 (SCN9A) is required to sense pain. Rare genetic forms of severe chronic pain, Primary Erythromelalgia and Paroxysmal Extreme Pain Disorder, result from mutations that increase the activity of Nav 1.7 (Fertleman C. R., Baker M. D., Parker K. A., Moffatt S., et al., "SCN9A mutations in paroxysmal extreme pain disorder: allelic variants underlie distinct channel defects and phenotypes," *Neuron* 52:767-774, 2006; Yang Y., Wang Y., Li S, et al., "Mutations in SCN9A, encoding a sodium channel alpha subunit, in patients with primary erythermalgia," J. Med. Genet. 41:171-174, 2004; Drenth J. P. H., te Morsche R. H. M., Guillet G., Taieb A., et al., "SCN9A mutations define primary erythermalgia as a neuropathic disorder of voltage gated sodium channels," *J Invest Dermatol* 124:1333-1338). Conversely, two separate clinical studies have determined that the root cause of the genetic disorder Congenital Indifference to Pain (CIP) is a loss of function of Nav 1.7 via mutations that truncate the protein and destroy function (Cox J. J., Reimann F, Nicholas A. K., et al. "An SCN9A channelopathy causes congenital inability to experience pain," *Nature* 444:894-898, 2006; Goldberg Y. P., MacFarlane J., MacDonald M. L., Thompson J., et al. "Loss-of-function mutations in the Nav 1.7 gene underlie congenital indifference to pain in multiple human populations," *Clin Genet* 71:311-319, 2007). The disorder is inherited in Mendelian recessive manner with 100% penetrance. The phenotype associated with CIP is extreme: affected individuals are reported to have experienced painless burns, childbirth, appendicitis, and bone fractures, as well as to have insensitivity to clinical measures of pain such as pinprick or tendon pressure. Yet sensory, motor, autonomic, and other measured functions are normal, with the only reported abnormality being anosmia (inability to smell). These studies indicate that among the many possible targets in the pain pathway, Nav 1.7 governs one or more control points critical for pain perception.

Nonselective sodium channel inhibitors such as lidocaine, mexiletine, and carbamazepine show clinical efficacy in chronic pain, including neuropathic pain, but they are limited in dose and in use, likely due to effects on sodium channels outside the pain pathway. Lidocaine is a local anesthetic doctors use for minor surgery. So is the dentists office staple novocaine. But these compounds don't distinguish between the various sodium channel subtypes, making them unsuitable for use as systemic pain killers. "If you give a drug that blocks Nav1.7 but also blocks Nav1.5, the patient will die of heart failure," says Glenn F. King, a professor at Australia's University of Queensland who studies venoms that block ion channels. "It will be a completely painless death, but the patient will die none the less." Thus, selectivity for Nav1.7 is desired, particularly over Nav1.5. Researchers have tailored their efforts to find a molecule that inhibitors or block the activity of only Nav1.7. To compound this problem, the identity, every location, every function and/or the tertiary structures of each subtype of voltage gated sodium channel proteins are not known or completely understood.

Consequently, a number of researchers are attempting to identify small molecule inhibitors of Nav1.7. For example, Chafeev et al disclose spiro-oxindole compound for the treatment and/or prevention of sodium channel-mediated diseases, such as pain, in U.S. Pat. No. 8,101,647. Thus, there is a need to identify Nav1.7 inhibitors selective over at least Nav1.5 to treat pain. The present invention provides compounds that are inhibitors of Nav 1.7.

SUMMARY OF THE INVENTION

In embodiment 1, the present invention provides of Formula I, or a pharmaceutically acceptable salt thereof,

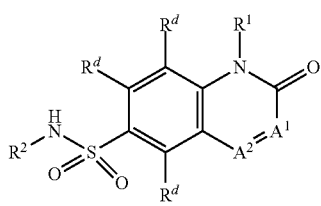

I wherein:
each of $A^1$ and $A^2$ is, independently, $CR^a$ or N, provided no more than one of $A^1$ and $A^2$ is N;
wherein each $R^a$ is independently H, halo, $-NR^cR^c$, $-OH$, hydroxyC$_{1-6}$alkyl, $-C_{1-6}$alkyl, $-OC_{1-6}$alkyl, $-C_{1-6}$haloalkyl, $-OC_{1-6}$haloalkyl or $-CN$;
$R^1$ is a 6 membered aryl or heteroaryl, wherein the aryl or heteroaryl is substituted with from 1 to 4 substituents independently selected from A, halo, OH, $-NR^bR^b$, $-C_{1-6}$ alkyl, $-OC_{1-6}$alkyl, $-OC_{1-6}$alkylCF$_3$, $-OC_{1-6}$alkylCN, $-(CR^eR^e)_m$CN, $-C_{1-6}$alkylOC$_{1-6}$alkyl, $-CF_3$, $-CHF_2$, $-CH_2F$, $-OCF_3$, $-OCHF_2$, $-OCH_2F$, $-(CR^eR^e)_m$A, $-N(R^e)(CR^eR^e)_m$A, $-O(CR^eR^e)_m$A, $-O(CR^eR^e)_m$OA or $-C(=O)A$, provided at least one substituent on $R^1$ is $-(CR^eR^e)_m$A, $-N(R^e)(CR^eR^e)_m$A, $-O(CR^eR^e)_m$A, $-O(CR^eR^e)_m$OA or $-C(=O)A$;
A is a 4 to 9 membered aryl, heteroaryl or heterocycloalkyl group, where the heteroaryl or heterocycloalkyl group can have from 1 to 3 heteroatoms independently selected from O, N or S, or a 3 to 6 membered cycloalkyl group, and the aryl, heteroaryl, heterocycloalkyl or cycloalkyl group can be unsubstituted or substituted with from 1 to 4 substituents independently selected from halo, $-NR^bR^b$, $-C_{1-6}$alkyl, $-OC_{1-6}$alkyl, $-(CR^eR^e)_m$OH, hydroxyC$_{1-6}$alkyl, $-CF_3$, $-CHF_2$, $-CH_2F$, $-OCF_3$, $-OCHF_2$, $-OCH_2F$, $-CN$, $-C(=O)NR^bR^b$, $-O(CR^eR^e)_m$B or $-(CR^eR^e)_m$B;
B is a 3 to 5 membered cycloalkyl group that can be unsubstituted or substituted with from 1 to 4 substituents independently selected from Cl, F, Br, $-NHCH_3$, $-N(CH_3)_2$, $-C_{1-4}$alkyl, $-OC_{1-4}$alkyl, $-CF_3$, $-CHF_2$, $-CH_2F$, $-OCF_3$, $-OCHF_2$, $-OCH_2F$ or $-CN$;
$R^2$ is a 5 to 6 membered aryl or heteroaryl, where the heteroaryl can have from 1 to 3 heteroatoms independently selected from O, N or S, and the aryl and heteroaryl group can be unsubstituted or substituted with from 1 to 4 substituents independently selected from halo, $-NR^bR^b$, $-C_{1-6}$ alkyl, $-OC_{1-6}$alkyl, $-(CR^cR^c)_n NR^bR^b$, $-CF_3$, $-CHF_2$, $-CH_2F$, $-OCF_3$, $-OCHF_2$, $-OCH_2F$, $-CN$ or $-C(=O)NR^bR^b$;
each $R^b$ is independently H or $-C_{1-6}$alkyl;
each $R^c$ is independently H or $-C_{1-6}$alkyl; and
each $R^d$ is independently H, halo, $-CN$, $-NR^cR^c$, $-OH$, $-C_{1-6}$alkyl, $-C_{1-6}$haloalkyl, $-OC_{1-6}$haloalkyl or $-OC_{1-6}$alkyl;
each $R^e$ is independently H, halo, $-CN$, $-NR^cR^c$, $-OH$, $-C_{1-6}$alkyl or $-OC_{1-6}$alkyl;
each n is independently 0, 1, 2, 3 or 4; and
each m is independently 0, 1, 2, 3 or 4.

In embodiment 1a, the present invention provides compounds of Formula I-a, and pharmaceutically acceptable salts thereof,

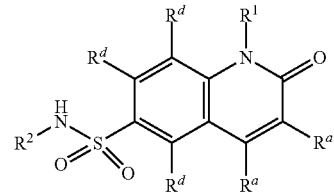

I-a wherein:
each $R^a$ is independently H, halo, $-NR^cR^c$, $-OH$, hydroxyC$_{1-6}$alkyl, $-C_{1-6}$alkyl, $-OC_{1-6}$alkyl, $-C_{1-6}$haloalkyl, $-OC_{1-6}$haloalkyl or $-CN$;
$R^1$ is a 6 membered aryl or heteroaryl, wherein the aryl or heteroaryl is substituted with from 1 to 4 substituents independently selected from A, halo, OH, $-NR^bR^b$, $-C_{1-6}$ alkyl, $-OC_{1-6}$alkyl, $-OC_{1-6}$alkylCF$_3$, $-OC_{1-6}$alkylCN, $-(CR^eR^e)_m$CN, $-C_{1-6}$alkylOC$_{1-6}$alkyl, $-CF_3$, $-CHF_2$, $-CH_2F$, $-OCF_3$, $-OCHF_2$, $-OCH_2F$, $-(CR^eR^e)_m$A, $-N(R^e)(CR^eR^e)_m$A, $-O(CR^eR^e)_m$A, $-O(CR^eR^e)_m$OA or $-C(=O)A$, provided at least one substituent on $R^1$ is $-(CR^eR^e)_m$A, $-N(R^e)(CR^eR^e)_m$A, $-O(CR^eR^e)_m$A, $-O(CR^eR^e)_m$OA or $-C(=O)A$;
A is a 4 to 9 membered aryl, heteroaryl or heterocycloalkyl group, where the heteroaryl or heterocycloalkyl group can have from 1 to 3 heteroatoms independently selected from O, N or S, or a 3 to 6 membered cycloalkyl group, and the aryl, heteroaryl, heterocycloalkyl or cycloalkyl group can be unsubstituted or substituted with from 1 to 4 substituents independently selected from halo, $-NR^bR^b$, $-C_{1-6}$alkyl, $-OC_{1-6}$alkyl, $-(CR^eR^e)_m$OH, hydroxyC$_{1-6}$alkyl, $-CF_3$, $-CHF_2$, $-CH_2F$, $-OCF_3$, $-OCHF_2$, $-OCH_2F$, $-CN$, $-C(=O)NR^bR^b$, $-O(CR^eR^e)_m$B or $-(CR^eR^e)_m$B;
B is a 3 to 5 membered cycloalkyl group that can be unsubstituted or substituted with from 1 to 4 substituents independently selected from Cl, F, Br, $-NHCH_3$, $-N(CH_3)_2$, $-C_{1-4}$alkyl, $-OC_{1-4}$alkyl, $-CF_3$, $-CHF_2$, $-CH_2F$, $-OCF_3$, $-OCHF_2$, $-OCH_2F$ or $-CN$;
$R^2$ is a 5 to 6 membered aryl or heteroaryl, where the heteroaryl can have from 1 to 3 heteroatoms independently selected from O, N or S, and the aryl and heteroaryl group can be unsubstituted or substituted with from 1 to 4 substituents independently selected from halo, —NR$^b$R$^b$, —C$_{1-6}$ alkyl, —OC$_{1-6}$alkyl, —(CR$^c$R$^c$)$_n$NR$^b$R$^b$, —CF$_3$, —CHF$_2$, —CH$_2$F, —OCF$_3$, —OCHF$_2$, —OCH$_2$F, —CN or —C(=O)NR$^b$R$^b$;

each R$^b$ is independently H or —C$_{1-6}$alkyl;
each R$^c$ is independently H or —C$_{1-6}$alkyl; and
each R$^d$ is independently H, halo, —CN, —NR$^c$R$^c$, —OH, —C$_{1-6}$alkyl, —C$_{1-6}$haloalkyl, —OC$_{1-6}$haloalkyl or —OC$_{1-6}$alkyl;
each R$^e$ is independently H, halo, —CN, —NR$^c$R$^c$, —OH, —C$_{1-6}$alkyl or —OC$_{1-6}$alkyl;
each n is independently 0, 1, 2, 3 or 4;
each m is independently 0, 1, 2, 3 or 4;

In embodiment 2, the present invention provides compounds in accordance with any one of embodiments 1 and 1a, or pharmaceutically acceptable salts thereof, wherein each R$^d$ is independently H, F or Cl.

In embodiment 2a, the present invention provides compounds in accordance with any one of embodiments 1 and 1a, or pharmaceutically acceptable salts thereof, wherein each R$^d$ is independently H or F.

In embodiment 2b, the present invention provides compounds in accordance with any one of embodiments 1 and 1a, or pharmaceutically acceptable salts thereof, wherein each R$^d$ is independently H.

In embodiment 3, the present invention provides compounds in accordance with any one of embodiment 1, or pharmaceutically acceptable salts thereof, wherein each of A$^1$ and A$^2$ is, independently, CR$^a$.

In embodiment 3a, the present invention provides compounds in accordance with any one of embodiments 1 and 3, or pharmaceutically acceptable salts thereof, wherein each of A$^1$ and A$^2$ is, independently, CR$^a$ wherein each R$^a$ independently, is H or F.

In embodiment 3b, the present invention provides compounds in accordance with any one of embodiments 1 and 3-3a, or pharmaceutically acceptable salts thereof, wherein each of A$^1$ and A$^2$ is, independently, CH.

In embodiment 4, the present invention provides compounds in accordance with any one of embodiments 1, 1a, 2, 2a-2b, or pharmaceutically acceptable salts thereof, wherein
R$^1$ is a ring selected from phenyl, pyridinyl or pyrimidinyl, wherein the ring is substituted with from 1 to 4 substituents independently selected from halo, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, CN, —C(=O)NR$^b$R$^b$, —C(=O)OR$^b$, —OA or A, provided at least one substituent on R$^1$ is A or —OA; and
A is a 5 to 6 membered aryl or heteroaryl group, or a 4 to 6 membered N-linked heterocycloalkyl group, or a 3 to 6 membered cycloalkyl group, where the heteroaryl can have from 1 to 3 heteroatoms independently selected from O, N or S, the N-linked heterocycloalkyl can have 1 additional heteroatom independently selected from O, N or S, and the aryl, heteroaryl, heterocyclic and cycloalkyl group can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN, or —C(=O)NR$^b$R$^b$.

In embodiment 5, the present invention provides compounds in accordance with any one of embodiments 1, 1a 2, 2a-2b, 3, 3a-3b and 4, or pharmaceutically acceptable salts thereof, wherein R$^1$ is a phenyl ring or pyridyl ring, wherein the ring is substituted with from 1 to 4 substituents independently selected from halo, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, CN, —C(=O)NR$^b$R$^b$ —C(=O)OR$^b$, —OA or A, provided at least one substituent on R$^1$ is A or —OA.

In embodiment 6, the present invention provides compounds in accordance with any one of embodiments 11, 1a 2, 2a-2b, 3, 3a-3b and 4-5, or pharmaceutically acceptable salts thereof, wherein A is a ring selected from phenyl, cyclopropyl, cyclopentyl, cyclohexyl, piperidinyl, piperazinyl, pyrrolidinyl, azetidinyl, pyridyl, pyrimidinyl, pyrazinyl or pyridazinyl, wherein the ring can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN, or —C(=O)NR$^b$R$^b$.

In embodiment 7, the present invention provides compounds in accordance with any one of embodiments 1, 1a 2, 2a-2b, 3, 3a-3b and 4-6, or pharmaceutically acceptable salts thereof, wherein
R$^1$ is a phenyl ring or pyridyl ring, wherein the ring is substituted with from 1 to 4 substituents independently selected from halo, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, CN, —C(=O)NR$^b$R$^b$ —C(=O)OR$^b$, —OA or A, provided at least one substituent on R$^1$ is A or —OA; and
A is a ring selected from phenyl, piperidinyl, piperazinyl, pyrrolidinyl, azetidinyl, cyclopentyl, pyridyl, pyrimidinyl, pyrazolyl or pyridazolyl, wherein the ring can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN, or —C(=O)NR$^b$R$^b$.

In embodiment 8, the present invention provides compounds in accordance with any one of embodiments 1, 1a, 2, 2a-2b, 3, 3a-3b and 4 to 7, or pharmaceutically acceptable salts thereof, wherein R$^1$ is a phenyl ring substituted with from 1 to 4 substituents independently selected from halo, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, CN, —C(=O)NR$^b$R$^b$, —C(=O)OR$^b$, —OA or A, provided at least one substituent on R$^1$ is A or —OA; and
A is a ring selected from phenyl, piperidinyl, pyrrolidinyl, azetidinyl, cyclopentyl, pyridyl or pyrimidinyl, wherein the ring can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN or —C(=O)NR$^b$R$^b$.

In embodiment 9, the present invention provides compounds in accordance with any one of embodiments 1, 1a, 2, 2a-2b, 3, 3a-3b and 4 to 7, or pharmaceutically acceptable salts thereof, wherein
R$^1$ is a pyridyl ring that is substituted with from 1 to 4 substituents independently selected from halo, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, CN, —C(=O)NR$^b$R$^b$, —C(=O)OR$^b$, —OA or A, provided at least one substituent on R$^1$ is A or —OA; and
A is a ring selected from phenyl or pyridyl, wherein the ring can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN, or —C(=O)NR$^b$R$^b$.

In embodiment 10, the present invention provides compounds in accordance with any one of embodiments 1, 1a, 2, 2a-2b, 3, 3a-3b and 4 to 7, or pharmaceutically acceptable salts thereof, wherein
R$^1$ is a phenyl ring or pyridyl ring, wherein the ring is substituted with from 1 to 4 substituents independently selected from F, Cl, —C$_{1-6}$alkyl, —OC$_{1-6}$alkyl, —CF$_3$, —CHF$_2$, —CH$_2$F, —OCF$_3$, —OCHF$_2$, —OCH$_2$F, CN, —OA or A, provided at least one substituent on R$^1$ is A or —OA; and A is a ring selected from phenyl, piperidinyl, pyrrolidinyl, azetidinyl, cyclopentyl, pyridyl, pyrimidinyl, wherein the ring can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN or —C(=O)NR$^b$R$^b$.

In embodiment 11, the present invention provides compounds in accordance with any one of embodiments 1, 1a, 2, 2a-2b, 3, 3a-3b and 4 to 10, or pharmaceutically acceptable salts thereof, wherein one substituent on R$^1$ is —O(CR$^e$R$^e$)$_m$A.

In embodiment 12, the present invention provides compounds in accordance with any one of embodiments 1, 1a, 2, 2a-2b, 3, 3a-3b and 4 to 11, or pharmaceutically acceptable salts thereof, wherein R$^2$ is a 5 to 6 membered aryl or heteroaryl, where the heteroaryl can have from 1 to 3 heteroatoms independently selected from O, N or S, and the aryl or heteroaryl can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —(CR$^c$R$^c$)$_n$NR$^b$R$^b$, —CF$_3$, —CHF$_2$, —CH$_2$F, —OCF$_3$, —OCHF$_2$, —OCH$_2$F, —CN or —C(=O)NR$^b$R$^b$.

In embodiment 13, the present invention provides compounds in accordance with any one of embodiments 1, 1a, 2, 2a-2b, 3, 3a-3b and 4 to 12, or pharmaceutically acceptable salts thereof, wherein R$^2$ is thiadiazolyl, substituted thiadiazolyl, thiazolyl, substituted thiazolyl, oxazolyl, substituted oxazolyl, oxadiazolyl, substituted oxadiazolyl, pyrimidinyl, substituted pyrimidinyl, isoxazolyl, substituted isoxazolyl, pyrazolyl, substituted pyrazolyl, pyridyl, substituted pyridyl, pyridazinyl, substituted pyridazinyl, pyrazinyl or substituted pyrazinyl.

In embodiment 15, the present invention provides compounds in accordance with any one of embodiments 1, 1a, 2, 2a-2b, 3, 3a-3b and 4 to 14, or pharmaceutically acceptable salts thereof, wherein R$^2$ is a ring selected from pyrimidinyl, oxadiazolyl, isoxazolyl, thiazolyl, thiadiazolyl, isothiazolyl or pyridazinyl, where the ring can be unsubstituted or substituted with from 1 to 4 substituents independently selected from F, Cl, —NH(CH$_3$), —CH$_3$, —CH$_2$CH$_3$, propyl, isopropyl, —OCH$_3$, —OCH$_2$CH$_3$, propoxyl, —CF$_3$, —CHF$_2$, —CH$_2$F, —OCF$_3$, —OCHF$_2$, —OCH$_2$F or —CN.

In embodiment 16, the present invention provides compounds in accordance with any one of embodiments 1, 1a, 2, 2a-2b, 3, 3a-3b and 4 to 15, or pharmaceutically acceptable salts thereof, wherein R$^2$ is a ring selected from 3-oxazolyl, 3-oxadiazolyl, 3-isoxazolyl, 2-thiazolyl, 4-thiazolyl, 2-thiadiazolyl, 3-isothiazolyl, 2-pyrimidinyl, 4-pyrimidinyl or 3-pyridazinyl, where the ring can be unsubstituted or substituted with from 1 to 4 substituents independently selected from F, Cl, —NH(CH$_3$), —CH$_3$, —CH$_2$CH$_3$, propyl, isopropyl, —OCH$_3$, —OCH$_2$CH$_3$, propoxyl, —CF$_3$, —CHF$_2$, —CH$_2$F, —OCF$_3$, —OCHF$_2$, —OCH$_2$F or —CN.

In embodiment 17, the present invention provides compounds in accordance with any one of embodiments 1, 1a, 2, 2a-2b, 3, 3a-3b and 4 to 16, or pharmaceutically acceptable salts thereof, wherein R$^2$ is substituted or unsubstituted 2-pyrimidinyl or 4-pyrimidinyl.

In embodiment 18, the present invention provides compounds in accordance with any one of embodiments 1, 1a, 2, 2a-2b, 3, 3a-3b and 4 to 16, or pharmaceutically acceptable salts thereof, wherein R$^2$ is substituted or unsubstituted isoxazolyl.

In embodiment 19, the present invention provides compounds in accordance with any one of embodiments 1, 1a, 2, 2a-2b, 3, 3a-3b, 4 to 16 and 18, or pharmaceutically acceptable salts thereof, wherein R$^2$ is substituted or unsubstituted 3-isoxazolyl.

In embodiment 20, the present invention provides compounds in accordance with any one of embodiments 1, 1a, 2, 2a-2b, 3, 3a-3b and 4 to 16, or pharmaceutically acceptable salts thereof, wherein R$^2$ is substituted or unsubstituted thiadiazolyl.

In embodiment 21, the present invention provides compounds in accordance with any one of embodiments 1, 1a, 2, 2a-2b, 3, 3a-3b and 4 to 16, or pharmaceutically acceptable salts thereof, wherein R$^2$ is substituted or unsubstituted isothiazolyl.

In embodiment 22, the present invention provides compounds in accordance with any one of embodiments 1, 1a, 2, 2a-2b, 3, 3a-3b and 4 to 16, or pharmaceutically acceptable salts thereof, wherein R$^2$ is substituted or unsubstituted oxazolyl.

In embodiment 23, the present invention provides compounds in accordance with any one of embodiments 1, 1a-1q, 2, 2a-2b and 3 to 13, or pharmaceutically acceptable salts thereof, wherein R$^2$ is substituted or unsubstituted oxadiazolyl.

In embodiment 24, the present invention provides compounds in accordance with any one of embodiments 1, 1a, 2, 2a-2b, 3, 3a-3b and 4 to 16, or pharmaceutically acceptable salts thereof, wherein R$^2$ is substituted or unsubstituted pyridazinyl.

In embodiment 25, the present invention provides compounds in accordance with any one of embodiments 1, 1a, 2, 2a-2b, 3, 3a-3b and 4 to 16, or pharmaceutically acceptable salts thereof, wherein R$^2$ is substituted or unsubstituted 3-pyridazinyl.

In embodiment 26, the present invention provides compounds in accordance with any one of embodiments 1, 1a, 2, 2a-2b, 3, 3a-3b and 4 to 16, or pharmaceutically acceptable salts thereof, wherein R$^2$ is substituted or unsubstituted pyrazinyl.

In embodiment 27, the present invention provides compounds in accordance with any one of embodiments 1, 1a, 2, 2a-2b, 3, 3a-3b and 4 to 16, or pharmaceutically acceptable salts thereof, wherein R$^2$ is substituted or unsubstituted 2-pyrazinyl.

In embodiment 28, the present invention provides compounds in accordance with any one of embodiments 1, 1a, 2, 2a-2b, 3, 3a-3b and 4 to 16, or pharmaceutically acceptable salts thereof, wherein R$^2$ is substituted or unsubstituted pyridyl.

In embodiment 29, the present invention provides compounds in accordance with any one of embodiments 1, 1a, 2, 2a-2b, 3, 3a-3b and 4 to 28, or pharmaceutically acceptable salts thereof, wherein each R$^d$ is independently H.

In embodiment 30, the present invention provides compounds in accordance with any one of embodiments 1 or 1a, or pharmaceutically acceptable salts, wherein each of A$^1$ and A$^2$ is, independently, CR$^a$, wherein each R$^a$ is independently H, halo, —C$_{1-6}$alkyl, —OC$_{1-6}$alkyl, —C$_{1-6}$haloalkyl, —OC$_{1-6}$haloalkyl or —CN;

R$^1$ is a ring selected from phenyl or pyridyl, wherein the ring is substituted with from 1 to 4 substituents independently selected from F, Cl, —C$_{1-6}$alkyl, —OC$_{1-6}$alkyl, —CF$_3$, —CHF$_2$, —CH$_2$F, —OCF$_3$, —OCHF$_2$, —OCH$_2$F, CN, —OA or A, provided at least one substituent on R$^1$ is A or —OA;

A is a ring selected from phenyl, piperidinyl, pyrrolidinyl, azetidinyl, cyclopentyl, pyridyl or pyrimidinyl, wherein the ring can be unsubstituted or substituted with from 1 to 4 substituents independently selected from halo, —$C_{1-6}$alkyl, —$OC_{1-6}$alkyl, hydroxy$C_{1-6}$alkyl —$CF_3$, —$CHF_2$, —$CH_2F$, —$OCF_3$, —$OCHF_2$, —$OCH_2F$, —CN or —C(=O)$NR^bR^b$;

$R^2$ is a ring selected from thiazolyl, isothiazolyl, thiadiazolyl, oxazolyl, isoxazolyl, oxadiazolyl, pyrazolyl, pyrimidinyl, pyridyl, pyridazinyl or pyrazinyl, where the ring can be unsubstituted or substituted with from 1 to 4 substituents independently selected from halo, —$NR^bR^b$, —$C_{1-6}$alkyl, —$OC_{1-6}$alkyl, hydroxy$C_{1-6}$alkyl, —$(CR^cR^c)_nNR^bR^b$, —$CF_3$, —$CHF_2$, —$CH_2F$, —$OCF_3$, —$OCHF_2$, —$OCH_2F$ or —CN;

each $R^b$ is independently H or —$C_{1-6}$alkyl; and each $R^d$ is independently H.

In embodiment 31, the present invention provides compounds in accordance with any one of embodiments 1, 1a, or pharmaceutically acceptable salts, wherein each $R^a$ is independently H, F, Cl, —$CH_3$, —$OCH_3$, —$CF_3$, —$CHF_2$, —$CH_2F$, —$OCF_3$, —$OCHF_2$, —$OCH_2F$ or —CN;

$R^1$ is a 2, 4, 5-trisubstituted phenyl ring, wherein the 2- and 5-substituents are independently selected from F, Cl, —$CH_3$, —$OCH_3$, —$CF_3$, —$CHF_2$, —$CH_2F$, —$OCF_3$, —$OCHF_2$, —$OCH_2F$ or CN, and the 4-substituent is A;

A is a phenyl ring, which is substituted with from 1 to 2 substituents independently selected from F, Cl, —$CH_3$, —$CH_2CH_3$, —$OCH_3$, —$CF_3$, —$CHF_2$, —$CH_2F$, —$OCF_3$, —$OCHF_2$, —$OCH_2F$ or CN;

$R^2$ is a ring selected from 3-isoxazolyl, 2-pyrimidinyl, 4-pyrimidinyl or 3-pyridazinyl, where the ring can be unsubstituted or substituted with from 1 to 4 substituents independently selected from F, Cl, —$CH_3$, —$CH_2F$, —$CHF_2$ or —$CF_3$; and each $R^d$ is independently H.

In embodiment 32, the present invention provides compounds in accordance with any one of embodiments 1, 1a or 30-31, or pharmaceutically acceptable salts, wherein each $R^a$ is independently H or F;

$R^1$ is a 2, 4, 5-trisubstituted phenyl ring, wherein the 2- and 5-substituents are independently selected from F, Cl, —$CH_3$, —$OCH_3$, —$CF_3$, —$OCF_3$, and the 4-substituent is A, wherein A is a phenyl ring substituted with 1 to 2 substituents independently selected from F, Cl, —$CH_3$, —$CH_2CH_3$, —$OCH_3$, —$CF_3$, —$CHF_2$, —$CH_2F$, —$OCF_3$, —$OCHF_2$, —$OCH_2F$ or CN;

$R^2$ is a ring selected from 3-isoxazolyl, 2-pyrimidinyl, 4-pyrimidinyl or 3-pyridazinyl, where the ring can be unsubstituted or substituted with from 1 to 2 F substituents or $CH_3$; and each $R^d$ is independently H.

In embodiment 33, the present invention provides compounds in accordance with any one of embodiments 1, 1a or 30-32, or pharmaceutically acceptable salts, wherein each $R^a$ is independently H or F;

$R^1$ is a 2, 4, 5-trisubstituted phenyl ring, wherein the 2- and 5-substituents are independently selected from F, Cl, —$OCH_3$, —$OCF_3$, and the 4-substituent is a phenyl ring substituted with 1 to 2 substituents independently selected from F, Cl, —$CH_3$, —$CH_2CH_3$, —$OCH_3$, —$CF_3$, —$CHF_2$, —$CH_2F$, —$OCF_3$, —$OCHF_2$, —$OCH_2F$ or CN;

$R^2$ is a ring selected from 3-isoxazolyl, 2-pyrimidinyl, 4-pyrimidinyl or 3-pyridazinyl, where the ring is unsubstituted; and each $R^d$ is independently H.

In embodiment 34, the present invention provides compounds in accordance with any one of embodiments 1, 1a or 30-33, or pharmaceutically acceptable salts, wherein each $R^a$ is independently H;

$R^1$ is a 2, 4, 5-trisubstituted phenyl ring, wherein the 2-substituent is —$OCH_3$, the 5-substituent is F, and the 4-substituent is a phenyl ring substituted with 1 to 2 substituents independently selected from F, Cl, —$CH_3$, —$OCH_3$, —$CF_3$, —$CHF_2$, —$CH_2F$, —$OCF_3$, —$OCHF_2$, —$OCH_2F$ or CN;

$R^2$ is a ring selected from 3-isoxazolyl, 2-pyrimidinyl, 4-pyrimidinyl or 3-pyridazinyl, where the ring is unsubstituted; and each $R^d$ is independently H.

In embodiment 35, the present invention provides compounds in accordance with any one of embodiments 1, 1a or 30-34, or pharmaceutically acceptable salts, wherein each $R^a$ is independently H;

$R^1$ is a 2, 4, 5-trisubstituted phenyl ring, wherein the 2-substituent is —$OCH_3$, the 5-substituent is F, and the 4-substituent is a phenyl ring substituted with 1 to 2 substituents independently selected from F, Cl, —$CH_3$, —$OCH_3$, —$CF_3$, —$CHF_2$, —$CH_2F$, —$OCF_3$, —$OCHF_2$, —$OCH_2F$ or CN;

$R^2$ is an unsubstituted 3-isoxazole; and each $R^d$ is independently H.

In embodiment 36, the present invention provides compounds in accordance with any one of embodiments 1, 1a or 30-34, or pharmaceutically acceptable salts, wherein each $R^a$ is independently H;

$R^1$ is a 2, 4, 5-trisubstituted phenyl ring, wherein the 2-substituent is —$OCH_3$, the 5-substituent is F, and the 4-substituent is a phenyl ring substituted with 1 to 2 substituents independently selected from F, Cl, —$CH_3$, —$OCH_3$, —$CF_3$, —$CHF_2$, —$CH_2F$, —$OCF_3$, —$OCHF_2$, —$OCH_2F$ or CN;

$R^2$ is an unsubstituted 2-pyrimidine; and each $R^d$ is independently H.

In embodiment 37, the present invention provides compounds in accordance with any one of embodiments 1, 1a or 30-34, or pharmaceutically acceptable salts, wherein each $R^a$ is independently H;

$R^1$ is a 2, 4, 5-trisubstituted phenyl ring, wherein the 2-substituent is —$OCH_3$, the 5-substituent is F, and the 4-substituent is a phenyl ring substituted with 1 to 2 substituents independently selected from F, Cl, —$CH_3$, —$OCH_3$, —$CF_3$, —$CHF_2$, —$CH_2F$, —$OCF_3$, —$OCHF_2$, —$OCH_2F$ or CN;

$R^2$ is an unsubstituted 3-pyridazine; and each $R^d$ is independently H.

In embodiment 38, the present invention provides compounds of Formula I-b, and pharmaceutically acceptable salts thereof,

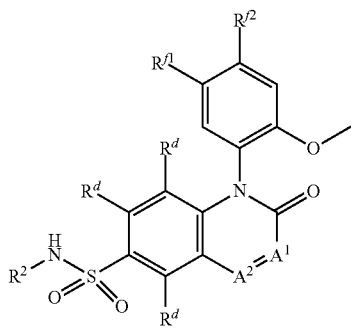

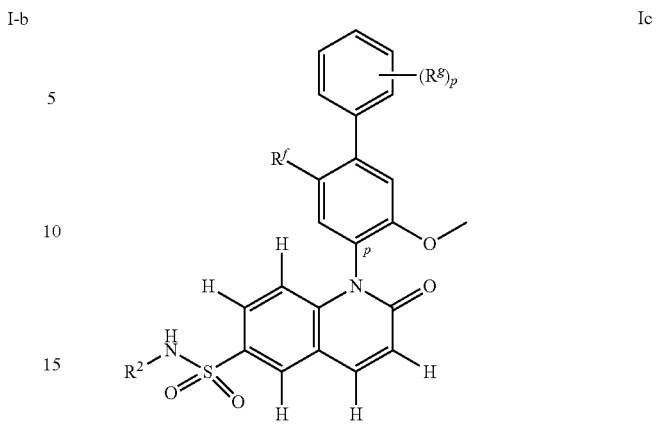

wherein:
each of $A^1$ and $A^2$ is, independently, $CR^a$ or N, provided no more than one of $A^1$ and $A^2$ is N, wherein each $R^a$ is independently H, F, Cl, —$CH_3$, —$OCH_3$, —$CF_3$, —$CHF_2$, —$CH_2F$, —$OCF_3$, —$OCHF_2$, —$OCH_2F$ or —CN;

one of $R^{f1}$ and $R^{f2}$ is A and the other of $R^{f1}$ and $R^{f2}$ is a group selected from H, F, Cl and $CH_3$;

A is a ring selected from phenyl, cyclopropyl, cyclopentyl, cyclohexyl, piperidinyl, piperazinyl, pyrrolidinyl, azetidinyl, pyridyl, pyrimidinyl, pyrazinyl or pyridazinyl, wherein the ring can be unsubstituted or substituted with from 1 to 4 substituents independently selected from halo, —$C_{1-6}$alkyl, —$OC_{1-6}$alkyl, hydroxy$C_{1-6}$alkyl —$CF_3$, —$CHF_2$, —$CH_2F$, —$OCF_3$, —$OCHF_2$, —$OCH_2F$, —CN, or —C(=O)$NR^bR^b$;

$R^2$ is a ring selected from 3-oxazolyl, 3-oxadiazolyl, 3-isoxazolyl, 2-thiazolyl, 4-thiazolyl, 2-thiadiazolyl, 3-isothiazolyl, 2-pyrimidinyl, 4-pyrimidinyl or 3-pyridazinyl, where the ring can be unsubstituted or substituted with from 1 to 4 substituents independently selected from F, Cl, —NH($CH_3$), —$CH_3$, —$CH_2CH_3$, propyl, isopropyl, —$OCH_3$, —$OCH_2CH_3$, propoxyl, —$CF_3$, —$CHF_2$, —$CH_2F$, —$OCF_3$, —$OCHF_2$, —$OCH_2F$ or —CN; and each $R^d$ is independently H, F or $CH_3$.

In embodiment 39, the present invention provides compounds of embodiment 38, or pharmaceutically acceptable salts thereof wherein $R^{f1}$ is a group selected from H, F and Cl.

In embodiment 40, the present invention provides compounds of embodiment 38, or pharmaceutically acceptable salts thereof wherein $R^{f2}$ is a group selected from H, F and Cl.

In embodiment 41, the present invention provides compounds of embodiments 38-40, or pharmaceutically acceptable salts thereof wherein A is a phenyl or pyridyl ring, which ring is substituted with from 1 to 2 substituents independently selected from F, Cl, —$CH_3$, —$CH_2CH_3$, —$OCH_3$, —$CF_3$, —$CHF_2$, —$CH_2F$, —$OCF_3$, —$OCHF_2$, —$OCH_2F$ or CN;

$R^2$ is a ring selected from 3-isoxazolyl, 2-pyrimidinyl, 4-pyrimidinyl or 3-pyridazinyl, where the ring can be unsubstituted or substituted with from 1 to 4 substituents independently selected from F, Cl, —$CH_3$, —$CH_2F$, —$CHF_2$ or —$CF_3$; and each $R^d$ is independently H.

In embodiment 42, the present invention provides compounds of Formula 1c, or pharmaceutically acceptable salts thereof wherein
$R^f$ is a group selected from H, F, Cl and $CH_3$;
$R^g$ is a group selected from F, Cl, —$CH_3$, —$OCH_3$, —$CF_3$, —$CHF_2$, —$CH_2F$, —$OCF_3$, —$OCHF_2$, —$OCH_2F$ or CN;
$R^2$ is a ring selected from 3-isoxazolyl, 2-pyrimidinyl, 4-pyrimidinyl or 3-pyridazinyl, where the ring is unsubstituted; and
p is 0, 1 or 2.

Note that embodiment 42 claims the p orientation round the bond between the $R^1$ group and the quinolone core. The invention also includes the m orientation around this same bond, as shown below in formula Id:

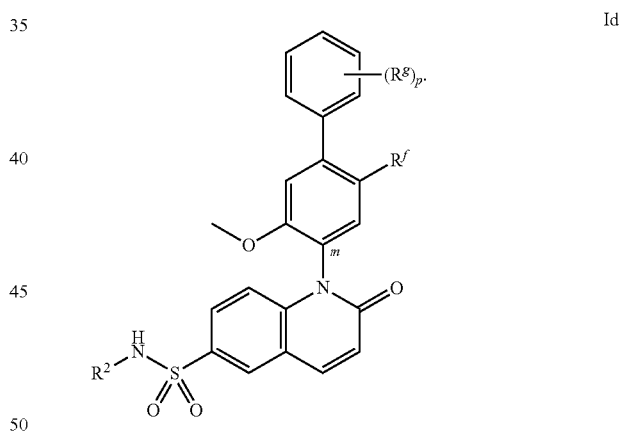

In embodiment 43, the present invention provides compounds of embodiment 42, or pharmaceutically acceptable salts thereof wherein $R^f$ is a group selected from H, F and Cl.

In embodiment 44, the present invention provides compounds of embodiments 42-43, or pharmaceutically acceptable salts thereof wherein $R^f$ is a group selected from H and F.

In embodiment 45, the present invention provides compounds of embodiments 42-43, or pharmaceutically acceptable salts thereof wherein $R^f$ is F.

In embodiment 46, the present invention provides compounds of embodiments 38-45, or pharmaceutically acceptable salts thereof, wherein $R^2$ is an unsubstituted 3-isoxazole ring.

In embodiment 47, the present invention provides compounds of embodiments 38-45, or pharmaceutically acceptable salts thereof, wherein R² is an unsubstituted 2-pyrimidine or an unsubstituted 4-pyrimidinyl ring.

In embodiment 48, the present invention provides compounds of embodiments 38-45, or pharmaceutically acceptable salts thereof, wherein R² is an unsubstituted 3-pyridazine ring.

In embodiment 49, the present invention provides a compound, or a pharmaceutically acceptable salt thereof, selected from:

1-(3-methoxy-3'-(trifluoromethyl)-4-biphenylyl)-2-oxo-N-4-pyrimidinyl-1,2-dihydro-6-quinolinesulfonamide;
2-oxo-N-3-pyridazinyl-1-(2,3',4'-trifluoro-5-methoxy-4-biphenylyl)-1,2-dihydro-6-quinolinesulfonamide;
1-(4'-chloro-2-fluoro-5-methoxy-3'-methyl-4-biphenylyl)-7-fluoro-N-3-isoxazolyl-2-oxo-1,2-dihydro-6-quinolinesulfonamide;
1-(4'-chloro-2-fluoro-5-methoxy-3'-methyl-4-biphenylyl)-N-3-isoxazolyl-2-oxo-1,2-dihydro-6-quinoxalinesulfonamide;
1-(3'-fluoro-3-methoxy-5'-(trifluoromethyl)-4-biphenylyl)-N-3-isoxazolyl-2-oxo-1,2-dihydro-6-quinolinesulfonamide;
1-(4'-chloro-2-fluoro-5-methoxy-3'-methyl-4-biphenylyl)-2-oxo-N-3-pyridazinyl-1,2-dihydro-6-quinolinesulfonamide;
1-(4'-chloro-2-fluoro-5-methoxy-3'-methyl-4-biphenylyl)-2-oxo-N-2-pyrimidinyl-1,2-dihydro-6-quinolinesulfonamide;
1-(4'-chloro-2-fluoro-3',5-dimethoxy-4-biphenylyl)-2-oxo-N-3-pyridazinyl-1,2-dihydro-6-quinolinesulfonamide;
1-(3'-chloro-3,5'-dimethoxy-4-biphenylyl)-N-3-isoxazolyl-2-oxo-1,2-dihydro-6-quinolinesulfonamide;
1-(4'-chloro-3-methoxy-3'-methyl-4-biphenylyl)-2-oxo-N-2-pyrimidinyl-1,2-dihydro-6-quinolinesulfonamide;
1-(3',5'-difluoro-3-methoxy-4-biphenylyl)-N-3-isoxazolyl-2-oxo-1,2-dihydro-6-quinolinesulfonamide;
1-(4'-chloro-2-fluoro-3',5-dimethoxy-4-biphenylyl)-2-oxo-N-2-pyrimidinyl-1,2-dihydro-6-quinolinesulfonamide;
1-(4'-chloro-2-fluoro-5-methoxy-3'-methyl-4-biphenylyl)-2-oxo-N-4-pyrimidinyl-1,2-dihydro-6-quinolinesulfonamide;
1-(4'-chloro-2-fluoro-5-methoxy-3'-methyl-4-biphenylyl)-2-oxo-N-2-pyrazinyl-1,2-dihydro-6-quinolinesulfonamide;
1-(2-fluoro-5-methoxy-4'-(trifluoromethyl)-4-biphenylyl)-N-3-isoxazolyl-2-oxo-1,2-dihydro-6-quinolinesulfonamide;
1-(3,3'-dimethoxy-4'-methyl-4-biphenylyl)-N-3-isoxazolyl-2-oxo-1,2-dihydro-6-quinolinesulfonamide;
1-(3'-(difluoromethoxy)-2-fluoro-5-methoxy-4-biphenylyl)-N-3-isoxazolyl-2-oxo-1,2-dihydro-6-quinolinesulfonamide;
1-(2-fluoro-3',5,5'-trimethoxy-4-biphenylyl)-N-3-isoxazolyl-2-oxo-1,2-dihydro-6-quinolinesulfonamide;
1-(2-fluoro-5-methoxy-3'-(trifluoromethyl)-4-biphenylyl)-N-(6-methyl-4-pyrimidinyl)-2-oxo-1,2-dihydro-6-quinolinesulfonamide;
N-3-isoxazolyl-2-oxo-1-(2,3',4'-trifluoro-5-methoxy-4-biphenylyl)-1,2-dihydro-6-quinolinesulfonamide;
1-(4'-chloro-2-fluoro-5-methoxy-4-biphenylyl)-N-3-isoxazolyl-2-oxo-1,2-dihydro-6-quinolinesulfonamide;
1-(4'-chloro-3-methoxy-3'-methyl-4-biphenylyl)-N-1,3-oxazol-2-yl-2-oxo-1,2-dihydro-6-quinolinesulfonamide;
1-(4-(5-chloro-2-methoxy-3-pyridinyl)-5-fluoro-2-methoxyphenyl)-N-3-isoxazolyl-2-oxo-1,2-dihydro-6-quinolinesulfonamide;
1-(2,4'-difluoro-5-methoxy-4-biphenylyl)-N-3-isoxazolyl-2-oxo-1,2-dihydro-6-quinolinesulfonamide; and
1-(3'-(difluoromethoxy)-2,5'-difluoro-5-methoxy-4-biphenylyl)-N-3-isoxazolyl-2-oxo-1,2-dihydro-6-quinolinesulfonamide.

In embodiment 49-a, the present invention provides each individual compound, or a pharmaceutically acceptable salt thereof, selected from the compounds recited in embodiment 49.

In embodiment 50, the present invention provides a compound, or a pharmaceutically acceptable salt thereof, selected from:

N-3-isoxazolyl-1-(4-methoxy-3'-(trifluoromethyl)-3-biphenylyl)-2-oxo-1,2-dihydro-6-quinolinesulfonamide;
1-(3'-fluoro-4-methoxy-3-biphenylyl)-N-3-isoxazolyl-2-oxo-1,2-dihydro-6-quinolinesulfonamide;
(P)-1-(3'-fluoro-4-methoxy-3-biphenylyl)-N-3-isoxazolyl-2-oxo-1,2-dihydro-6-quinolinesulfonamide;
(P)—N-3-isoxazolyl-1-(4-methoxy-3'-(trifluoromethyl)-3-biphenylyl)-2-oxo-1,2-dihydro-6-quinolinesulfonamide;
(P)-1-(3'-chloro-5-methoxy-2-methyl-4-biphenylyl)-N-3-isoxazolyl-2-oxo-1,2-dihydro-6-quinolinesulfonamide
(P)-1-(3'-chloro-5'-fluoro-5-methoxy-2-methyl-4-biphenylyl)-N-3-isoxazolyl-2-oxo-1,2-dihydro-6-quinolinesulfonamide;
(P)—N-3-isoxazolyl-1-(5-methoxy-2-methyl-3'-(trifluoromethyl)-4-biphenylyl)-2-oxo-1,2-dihydro-6-quinolinesulfonamide;
(P)-1-(2-chloro-5-methoxy-3'-(trifluoromethyl)-4-biphenylyl)-N-3-isoxazolyl-2-oxo-1,2-dihydro-6-quinolinesulfonamide;
(P)-1-(2-fluoro-5-methoxy-3'-(trifluoromethyl)-4-biphenylyl)-N-3-isoxazolyl-2-oxo-1,2-dihydro-6-quinolinesulfonamide;
1-(2,3'-difluoro-5,5'-dimethoxy-4-biphenylyl)-N-3-isoxazolyl-6-isoquinolinesulfonamide;
(P)-1-(4'-chloro-5-methoxy-2,3'-dimethyl-4-biphenylyl)-N-3-isoxazolyl-2-oxo-1,2-dihydro-6-quinolinesulfonamide;
(P)-1-(3',5'-difluoro-5-methoxy-2-methyl-4-biphenylyl)-N-3-isoxazolyl-2-oxo-1,2-dihydro-6-quinolinesulfonamide;
(P)—N-3-isoxazolyl-1-(3-methoxy-3'-(trifluoromethyl)-4-biphenylyl)-2-oxo-1,2-dihydro-6-quinolinesulfonamide;
(P)-1-(3'-chloro-5'-fluoro-3-methoxy-4-biphenylyl)-N-3-isoxazolyl-2-oxo-1,2-dihydro-6-quinolinesulfonamide;
(P)-1-(3'-chloro-5-methoxy-2-methyl-4-biphenylyl)-2-oxo-N-2-pyrimidinyl-1,2-dihydro-6-quinolinesulfonamide;
(P)-1-(3'-chloro-2-cyano-5'-fluoro-5-methoxy-4-biphenylyl)-N-3-isoxazolyl-2-oxo-1,2-dihydro-6-quinolinesulfonamide;
(P)-1-(3'-chloro-2,5'-difluoro-5-methoxy-4-biphenylyl)-2-oxo-N-4-pyrimidinyl-1,2-dihydro-6-quinolinesulfonamide;
(P)-1-(3'-chloro-2,5'-difluoro-5-methoxy-4-biphenylyl)-2-oxo-N-2-pyrimidinyl-1,2-dihydro-6-quinolinesulfonamide;
(P)-1-(3'-chloro-2,5'-difluoro-5-methoxy-4-biphenylyl)-2-oxo-N-3-pyridazinyl-1,2-dihydro-6-quinolinesulfonamide;
(P)-1-(3'-chloro-2,5'-difluoro-5-methoxy-4-biphenylyl)-N-1,2,4-oxadiazol-3-yl-2-oxo-1,2-dihydro-6-quinolinesulfonamide;
(P)-1-(3'-chloro-2,5'-difluoro-5-methoxy-4-biphenylyl)-2-oxo-N-2-pyrazinyl-1,2-dihydro-6-quinolinesulfonamide;
(P)-1-(3'-chloro-2,5'-difluoro-5-methoxy-4-biphenylyl)-N-(5-fluoro-2-pyrimidinyl)-2-oxo-1,2-dihydro-6-quinolinesulfonamide;

(P)-1-(3'-chloro-2-fluoro-5-methoxy-4-biphenylyl)-N-3-isoxazolyl-2-oxo-1,2-dihydro-6-quinolinesulfonamide;
(P)-1-(2-chloro-3'-fluoro-5-methoxy-4-biphenylyl)-2-oxo-N-1,3,4-thiadiazol-2-yl-1,2-dihydro-6-quinolinesulfonamide;
(P)-1-(2-chloro-3'-fluoro-5-methoxy-4-biphenylyl)-N-3-isoxazolyl-2-oxo-1,2-dihydro-6-quinolinesulfonamide;
(P)-1-(2-chloro-3',5'-difluoro-5-methoxy-4-biphenylyl)-N-3-isoxazolyl-2-oxo-1,2-dihydro-6-quinolinesulfonamide;
(P)-1-(2,3'-dichloro-5-methoxy-4-biphenylyl)-N-3-isoxazolyl-2-oxo-1,2-dihydro-6-quinolinesulfonamide;
(P)-1-(2,3'-dichloro-5'-fluoro-5-methoxy-4-biphenylyl)-N-3-isoxazolyl-2-oxo-1,2-dihydro-6-quinolinesulfonamide;
(P)-1-(2,4'-dichloro-5-methoxy-3'-methyl-4-biphenylyl)-N-3-isoxazolyl-2-oxo-1,2-dihydro-6-quinolinesulfonamide;
(P)-1-(2-chloro-3'-fluoro-5-methoxy-4-biphenylyl)-7-fluoro-N-3-isoxazolyl-2-oxo-1,2-dihydro-6-quinolinesulfonamide;
(P)-1-(3'-chloro-2,5'-difluoro-5-methoxy-4-biphenylyl)-N-3-isoxazolyl-2-oxo-1,2-dihydro-6-quinolinesulfonamide;
4-(2-chloro-3'-fluoro-5-methoxy-4-biphenylyl)-N-3-isoxazolyl-3-oxo-2,3-dihydro-7-isoquinolinesulfonamide;
1-(2-fluoro-5-methoxy-3'-(trifluoromethyl)-4-biphenylyl)-N-3-isoxazolyl-2-methyl-3-oxo-2,3-dihydro-6-isoquinolinesulfonamide;
1-(4'-chloro-2-fluoro-5-methoxy-3'-methyl-4-biphenylyl)-N-3-isoxazolyl-3-oxo-2,3-dihydro-6-isoquinolinesulfonamide;
4-(4'-chloro-2-fluoro-5-methoxy-3'-methyl-4-biphenylyl)-N-3-isoxazolyl-3-oxo-2,3-dihydro-7-isoquinolinesulfonamide;
4-(3'-chloro-2,5'-difluoro-5-methoxy-4-biphenylyl)-N-3-isoxazolyl-3-oxo-2,3-dihydro-7-isoquinolinesulfonamide;
(P)—N-3-isoxazolyl-1-(3-methoxy-3'-methyl-4-biphenylyl)-2-oxo-1,2-dihydro-6-quinolinesulfonamide;
(P)-1-(3'-chloro-3-methoxy-5'-methyl-4-biphenylyl)-N-3-isoxazolyl-2-oxo-1,2-dihydro-6-quinolinesulfonamide;
(P)-1-(3'-chloro-2,4'-difluoro-5-methoxy-4-biphenylyl)-N-3-isoxazolyl-2-oxo-1,2-dihydro-6-quinolinesulfonamide;
(P)-1-(2,4'-dichloro-5-methoxy-3'-methyl-4-biphenylyl)-2-oxo-N-4-pyrimidinyl-1,2-dihydro-6-quinolinesulfonamide;
(P)-1-(3-methoxy-3'-(trifluoromethyl)-4-biphenylyl)-2-oxo-N-3-pyridazinyl-1,2-dihydro-6-quinolinesulfonamide;
(P)-1-(3'-chloro-5'-fluoro-3-methoxy-4-biphenylyl)-2-oxo-N-3-pyridazinyl-1,2-dihydro-6-quinolinesulfonamide;
(P)-1-(3'-chloro-2-fluoro-5,5'-dimethoxy-4-biphenylyl)-N-3-isoxazolyl-2-oxo-1,2-dihydro-6-quinolinesulfonamide;
(P)-1-(4'-chloro-2,3'-difluoro-5-methoxy-4-biphenylyl)-N-3-isoxazolyl-2-oxo-1,2-dihydro-6-quinolinesulfonamide;
(P)-1-(4'-chloro-3'-cyano-2-fluoro-5-methoxy-4-biphenylyl)-N-3-isoxazolyl-2-oxo-1,2-dihydro-6-quinolinesulfonamide;
(P)-1-(2,3'-difluoro-5-methoxy-4'-methyl-4-biphenylyl)-N-3-isoxazolyl-2-oxo-1,2-dihydro-6-quinolinesulfonamide;
(P)-1-(2,4'-difluoro-5-methoxy-3'-methyl-4-biphenylyl)-N-3-isoxazolyl-2-oxo-1,2-dihydro-6-quinolinesulfonamide;
(P)-1-(2-fluoro-5-methoxy-3'-methyl-4-biphenylyl)-N-3-isoxazolyl-2-oxo-1,2-dihydro-6-quinolinesulfonamide; and
(P)-1-(3'-chloro-2-fluoro-5-methoxy-4'-methyl-4-biphenylyl)-N-3-isoxazolyl-2-oxo-1,2-dihydro-6-quinolinesulfonamide.

In embodiment 51, the present invention provides a compound, or a pharmaceutically acceptable salt thereof, selected from:

(P)-1-(3'-chloro-5-methoxy-2-methyl-4-biphenylyl)-N-3-isoxazolyl-2-oxo-1,2-dihydro-6-quinolinesulfonamide;
(P)-1-(3'-chloro-5'-fluoro-5-methoxy-2-methyl-4-biphenylyl)-N-3-isoxazolyl-2-oxo-1,2-dihydro-6-quinolinesulfonamide;
(P)—N-3-isoxazolyl-1-(5-methoxy-2-methyl-3'-(trifluoromethyl)-4-biphenylyl)-2-oxo-1,2-dihydro-6-quinolinesulfonamide;
(P)-1-(2-chloro-5-methoxy-3'-(trifluoromethyl)-4-biphenylyl)-N-3-isoxazolyl-2-oxo-1,2-dihydro-6-quinolinesulfonamideinolinesulfonamide;
(P)-1-(2-fluoro-5-methoxy-3'-(trifluoromethyl)-4-biphenylyl)-N-3-isoxazolyl-2-oxo-1,2-dihydro-6-quinolinesulfonamide;
(P)-1-(3'-chloro-2,5'-difluoro-5-methoxy-4-biphenylyl)-2-oxo-N-4-pyrimidinyl-1,2-dihydro-6-quinolinesulfonamide;
(P)-1-(3'-chloro-2,5'-difluoro-5-methoxy-4-biphenylyl)-2-oxo-N-3-pyridazinyl-1,2-dihydro-6-quinolinesulfonamide;
(P)-1-(3'-chloro-2,5'-difluoro-5-methoxy-4-biphenylyl)-N-1,2,4-oxadiazol-3-yl-2-oxo-1,2-dihydro-6-quinolinesulfonamide;
(P)-1-(4'-chloro-3-methoxy-3'-methyl-4-biphenylyl)-N-3-isoxazolyl-2-oxo-1,2-dihydro-6-quinolinesulfonamide;
(P)-1-(2-chloro-3',5'-difluoro-5-methoxy-4-biphenylyl)-N-3-isoxazolyl-2-oxo-1,2-dihydro-6-quinolinesulfonamide;
(P)-1-(2,3'-dichloro-5'-fluoro-5-methoxy-4-biphenylyl)-N-3-isoxazolyl-2-oxo-1,2-dihydro-6-quinolinesulfonamide;
(P)-1-(2,4'-dichloro-5-methoxy-3'-methyl-4-biphenylyl)-N-3-isoxazolyl-2-oxo-1,2-dihydro-6-quinolinesulfonamide;
(P)-1-(4'-chloro-2-fluoro-5-methoxy-3'-methyl-4-biphenylyl)-N-3-isoxazolyl-2-oxo-1,2-dihydro-6-quinolinesulfonamide;
(P)-1-(3'-chloro-2,5'-difluoro-5-methoxy-4-biphenylyl)-N-3-isoxazolyl-2-oxo-1,2-dihydro-6-quinolinesulfonamide;
4-(3'-chloro-2,5'-difluoro-5-methoxy-4-biphenylyl)-N-3-isoxazolyl-3-oxo-2,3-dihydro-7-isoquinolinesulfonamide;
(P)—N-3-isoxazolyl-1-(3-methoxy-3'-methyl-4-biphenylyl)-2-oxo-1,2-dihydro-6-quinolinesulfonamide;
(P)-1-(3'-chloro-3-methoxy-5'-methyl-4-biphenylyl)-N-3-isoxazolyl-2-oxo-1,2-dihydro-6-quinolinesulfonamide;
(P)-1-(2,4'-dichloro-5-methoxy-3'-methyl-4-biphenylyl)-2-oxo-N-4-pyrimidinyl-1,2-dihydro-6-quinolinesulfonamide;
(P)-1-(3'-chloro-2-fluoro-5,5'-dimethoxy-4-biphenylyl)-N-3-isoxazolyl-2-oxo-1,2-dihydro-6-quinolinesulfonamide;
(P)-1-(4'-chloro-2,3'-difluoro-5-methoxy-4-biphenylyl)-N-3-isoxazolyl-2-oxo-1,2-dihydro-6-quinolinesulfonamide;
(P)-1-(4'-chloro-3'-cyano-2-fluoro-5-methoxy-4-biphenylyl)-N-3-isoxazolyl-2-oxo-1,2-dihydro-6-quinolinesulfonamide;
(P)-1-(2,3'-difluoro-5-methoxy-4'-methyl-4-biphenylyl)-N-3-isoxazolyl-2-oxo-1,2-dihydro-6-quinolinesulfonamide;
(P)-1-(2,4'-difluoro-5-methoxy-3'-methyl-4-biphenylyl)-N-3-isoxazolyl-2-oxo-1,2-dihydro-6-quinolinesulfonamide;
(P)-1-(2-fluoro-5-methoxy-3'-methyl-4-biphenylyl)-N-3-isoxazolyl-2-oxo-1,2-dihydro-6-quinolinesulfonamide; and
(P)-1-(3'-chloro-2-fluoro-5-methoxy-4'-methyl-4-biphenylyl)-N-3-isoxazolyl-2-oxo-1,2-dihydro-6-quinolinesulfonamide.

In embodiment 52, the present invention provides a compound, or a pharmaceutically acceptable salt thereof, selected from each compound exemplified herein, either individually or collectively, in example 42, disclosed herein in Table 1 and examples 312-588 disclosed in Table 2.

In embodiment 53, the present invention provides a compound, or a pharmaceutically acceptable salt thereof, individually selected from compound example 42, disclosed herein in Table 1 and examples 312-588 disclosed in Table 2.

In embodiment 54, the present invention provides a compound, or a pharmaceutically acceptable salt thereof, individually selected from compound examples 312-588 disclosed in Table 2.

In embodiment 55, the present invention provides a compound, or a pharmaceutically acceptable salt thereof, individually selected from compound examples 589-1139 disclosed in Table 3.

In embodiment 56, the present invention provides a compound, or a pharmaceutically acceptable salt thereof, individually selected from compound examples 1140-1242 disclosed in Table 4.

In various other embodiments, the present invention provides one or more compounds, or pharmaceutically acceptable salts thereof, individually or collectively selected from the following examples in Table 3: 835, 841, 843, 846, 849, 852, 856-858, 607-608, 610, 613, 861-863, 867, 870, 614, 616, 871, 874-75, 878, 880, 884, 887, 611, 891, 893, 904, 906, 913, 698, 658, 671, 915, 917, 919, 921-930, 933-935, 589, 937, 939-947, 672, 953, 957, 962-963, 967, 969, 970, 977, 978-982, 653, 1001, 695-697, 1013-1018, 1027-1032, 628, 1040, 1048, 1053-1067, 630, 682-685, 662, 691, 1070, 1072-1075, 1079-1080, 1095, 673, 779, 781, 783, 686, 790-793, 632, 687, 633, 636, 795-798, 688, 804, 806, 810, 820, 823, 674-675, 660, 1107-1109, 641, 645, 1137, 699-700, 703-714, 717, 723, 597, 726-728, 676, 740, 742, 747, 750, 752, 677, 678, 760 and 770.

In embodiment 57, the present invention provides multiple compounds, or their pharmaceutically acceptable salts thereof, individually or collectively selected from the following examples in Table 4: 1148, 1172, 1179, 1142, 1194-1196, 1151, 1198, 1200, 1215, 1218 & 1219, 1156-1157, 1160-1162, 1149-1150 & 1164.

In embodiment 58, the present invention provides one or more compounds, or pharmaceutically acceptable salts thereof, selected from examples 312, 417, 359, 533, 421, 423, 430, 540-544, 325-326, 432, 455, 457, 459, 461, 471, 467, 545, 465, 469, 477, 549, 550, 584-585, 365, 367, 369, 480, 501, 504, 506, 508, 510, 512, 519, 522, 528, 414, 379 and 380.

In embodiment 59, the present invention provides methods of treating pain, the methods comprising administering to a patient in need thereof a therapeutically effective amount of a compound in accordance with any one of embodiments 1, 1a, 2, 2a-2b, 3, 3a-3b and 4 to 58, or a pharmaceutically acceptable salt thereof.

In embodiment 60, the present invention provides methods of embodiment 56 wherein the treatment is for chronic pain, acute pain, neuropathic pain, pain associated with rheumatoid arthritis, pain associated with osteoarthritis or pain associated with cancer.

In embodiment 61, the present invention provides pharmaceutical compositions comprising a compound in accordance with any one of embodiments 1, 1a, 2, 2a-2b, 3, 3a-3b and 4 to 58, or a pharmaceutically acceptable salt thereof, and a pharmaceutically acceptable excipient.

In embodiment 62, the present invention provides each individual compound, independently, or a pharmaceutically acceptable salt thereof, as recited in embodiments 50 and 51.

In embodiment 63, the present invention provides one or more compounds, or pharmaceutically acceptable salts thereof, selected from examples 312, 417, 533, 359, 540, 542, 326, 432, 475, 457, 471, 469, 477, 549, 550, 584-585, 365, 367, 369, 480, 501, 504, 506, 508, 510, 512, 522 and 528.

DETAILED DESCRIPTION OF THE INVENTION

The present invention provides compounds of Formula I, as defined above, or pharmaceutically acceptable salts thereof. The present invention also provides pharmaceutical compositions comprising a compound of Formula I, or pharmaceutically acceptable salts thereof, and methods of treating diseases and/or conditions, such as pain, using compounds of Formula I, or pharmaceutically acceptable salts thereof.

The term "alkyl" means a straight or branched chain hydrocarbon. Representative examples of alkyl groups include methyl, ethyl, propyl, isopropyl, butyl, isobutyl, tert-butyl, sec-butyl, pentyl and hexyl. Typical alkyl groups are alkyl groups having from 1 to 8 carbon atoms, which groups are commonly represented as $C_{1-8}$alkyl.

The term "hydroxy$C_{1-6}$alkyl" means a straight or branched alkyl chain having one to six carbons and substituted with one or more hydroxyl groups. Representative examples of hydroxy$C_{1-6}$alkyl groups include hydroxymethyl (—CH$_2$OH), 2-hydroxyethyl, 3-hydroxypropyl, 2,3-dihydroxypropyl (—CH$_2$CH(OH)CH$_2$OH), 3-hydroxyisopropyl, 4-hydroxybutyl and the like. Typical alkyl groups are alkyl groups having from 1 to 8 carbon atoms, which groups are commonly represented as $C_{1-8}$alkyl.

The term "alkoxy" means an alkyl group bonded to an oxygen atom. Representative examples of alkoxy groups include methoxy, ethoxy, tert-butoxy, propoxy and isobutoxy. Common alkoxy groups are $C_{1-8}$alkoxy.

The term "halogen" or "halo" means chlorine, fluorine, bromine or iodine.

The term "alkenyl" means a branched or straight chain hydrocarbon having one or more carbon-carbon double bonds. Representative examples alkenyl groups include ethenyl, propenyl, allyl, butenyl and 4-methylbutenyl. Common alkenyl groups are $C_{2-8}$alkenyl.

The term "alkynyl" means a branched or straight chain hydrocarbon having one or more carbon-carbon triple bonds. Representative examples of alkynyl groups include ethynyl, propynyl (propargyl) and butynyl. Common alkynyl groups are $C_{2-8}$ alkynyl.

The term "cycloalkyl" means a cyclic, nonaromatic hydrocarbon. Examples of cycloalkyl groups include cyclopropyl, cyclobutyl, cyclopentyl, cyclohexyl and cycloheptyl. A cycloalkyl group can contain one or more double bond. Examples of cycloalkyl groups that contain double bonds include cyclopentenyl, cyclohexenyl, cyclohexadienyl and cyclobutadienyl. Common cycloalkyl groups are $C_{3-8}$ cycloalkyl groups.

The term "perfluoroalkyl" means an alkyl group in which all of the hydrogen atoms have been replaced with fluorine atoms. Common perfluoroalkyl groups are $C_{1-8}$perfluoroalkyl. An example of a common perfluoroalkyl group is —CF$_3$.

The term "acyl" means a group derived from an organic acid by removal of the hydroxy group (—OH). For example, the acyl group CH$_3$C(=O)— is formed by the removal of the hydroxy group from CH$_3$C(=O)OH.

The term "aryl" means a cyclic, aromatic hydrocarbon. Examples of aryl groups include phenyl and naphthyl. Common aryl groups are six to thirteen membered rings.

The term "heteroatom" as used herein means an oxygen, nitrogen or sulfur atom.

The term "heteroaryl" means a cyclic, aromatic hydrocarbon in which one or more carbon atoms of an aryl group have been replaced with a heteroatom. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, indolyl, triazolyl, pyridazinyl, indazolyl, purinyl, quinolizinyl, isoquinolyl, quinolyl, naphthyridinyl, quinoxalinyl, isothiazolyl and benzo[b]thienyl. Common heteroaryl groups are five to thirteen membered rings that contain from 1 to 4 heteroatoms. Heteroaryl groups that are five and six membered rings that contain 1 to 3 heteroatoms are particularly common.

The term "heterocycloalkyl" means a cycloalkyl group in which one or more of the carbon atoms has been replaced with a heteroatom. If the heterocycloalkyl group contains more than one heteroatom, the heteroatoms may be the same or different. Examples of heterocycloalkyl groups include tetrahydrofuryl, morpholinyl, piperazinyl, piperidinyl and pyrrolidinyl. It is also possible for the heterocycloalkyl group to have one or more double bonds, but is not aromatic. Examples of heterocycloalkyl groups containing double bonds include dihydrofuran. Common heterocycloalkyl groups are three to ten membered rings containing from 1 to 4 heteroatoms. Heterocycloalkyl groups that are five and six membered rings that contain 1 to 2 heteroatoms are particularly common.

It is also noted that the cyclic ring groups, i.e., aryl, heteroaryl, cycloalkyl, and heterocycloalkyl, can comprise more than one ring. For example, the naphthyl group is a fused bicyclic ring system. It is also intended that the present invention include ring groups that have bridging atoms, or ring groups that have a spiro orientation.

Representative examples of five to six membered aromatic rings, optionally having one or two heteroatoms, are phenyl, furyl, thienyl, pyrrolyl, oxazolyl, thiazolyl, imidazolyl, pyrazolyl, isoxazolyl, isothiazolyl, pyridinyl, pyridazinyl, pyrimidinyl, and pyrazinyl.

Representative examples of partially saturated, fully saturated or fully unsaturated five to eight membered rings, optionally having one to three heteroatoms, are cyclopentyl, cyclohexyl, cycloheptyl, cyclooctyl and phenyl. Further exemplary five membered rings are furyl, thienyl, pyrrolyl, 2-pyrrolinyl, 3-pyrrolinyl, pyrrolidinyl, 1,3-dioxolanyl, oxazolyl, thiazolyl, imidazolyl, 2H-imidazolyl, 2-imidazolinyl, imidazolidinyl, pyrazolyl, 2-pyrazolinyl, pyrazolidinyl, isoxazolyl, isothiazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4oxadiazolyl, 1,2,3-triazolyl, 1,2,4-triazolyl, 1,3,4-thiadiazolyl, 3H-1,2,3-dioxazolyl, 1,2,4-dioxazolyl, 1,3,2-dioxazolyl, 1,3,4-dioxazolyl, 5H-1,2,5-oxathiazolyl, and 1,3-oxathiolyl.

Further exemplary six membered rings are 2H-pyranyl, 4H-pyranyl, pyridinyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-oxathiazinyl, 1,2,6-(3 oxathiazinyl, and 1,4,2-oxadiazinyl.

Further exemplary seven membered rings are azepinyl, oxepinyl, thiepinyl and 1,2,4-triazepinyl.

Further exemplary eight membered rings are cyclooctyl, cyclooctenyl and cyclooctadienyl.

Exemplary bicyclic rings consisting of two fused partially saturated, fully saturated or fully unsaturated five and/or six membered rings, optionally having one to four heteroatoms, are indolizinyl, indolyl, isoindolyl, indolinyl, cyclopenta(b)pyridinyl, pyrano(3,4-b)pyrrolyl, benzofuryl, isobenzofuryl, benzo(b)thienyl, benzo(c)thienyl, 1H-indazolyl, indoxazinyl, benzoxazolyl, anthranilyl, benzimidazolyl, benzthiazolyl, purinyl, quinolinyl, isoquinolinyl, cinnolinyl, phthalazinyl, quinazolinyl, quinoxalinyl, 1,8-naphthyridinyl, pteridinyl, indenyl, isoindenyl, naphthyl, tetralinyl, decalinyl, 2H-1-benzopyranyl, pyrido(3,4-b)pyridinyl, pyrido(3,2-b)pyridinyl, pyrido(4,3-b)-pyridinyl, 2H-1,3-benzoxazinyl, 2H-1,4-benzoxazinyl, 1H-2,3-benzoxazinyl, 4H-3,1-benzoxazinyl, 2H-1,2-benzoxazinyl and 4H-1,4-benzoxazinyl.

A cyclic ring group may be bonded to another group in more than one way. If no particular bonding arrangement is specified, then all possible arrangements are intended. For example, the term "pyridyl" includes 2-, 3-, or 4-pyridyl, and the term "thienyl" includes 2-, or 3-thienyl.

The term "substituted" means that a hydrogen atom on a molecule or group is replaced with a group or atom. Typical substitutents include: halogen, $C_{1-8}$alkyl, hydroxyl, $C_{1-8}$alkoxy, —$NR^xR^x$, nitro, cyano, halo or perhalo$C_{1-8}$ alkyl, $C_{2-8}$alkenyl, $C_{2-8}$alkynyl, —$SR^x$, —$S(=O)_2R^x$, —$C(=O)OR^x$, —$C(=O)R^x$, wherein each $R^x$ is independently hydrogen or $C_1$-$C_8$ alkyl. It is noted that when the substituent is —$NR^xR^x$, the $R^x$ groups may be joined together with the nitrogen atom to form a ring.

The term "oxo", when used as a substituent, means the =O group, which is typically attached to a carbon atom.

A group or atom that replaces a hydrogen atom is also called a substituent. Any particular molecule or group can have one or more substituent depending on the number of hydrogen atoms that can be replaced.

The symbol "—" represents a covalent bond and can also be used in a radical group to indicate the point of attachment to another group. In chemical structures, the symbol is commonly used to represent a methyl group in a molecule.

The term "therapeutically effective amount" means an amount of a compound that ameliorates, attenuates or eliminates one or more symptoms of a particular disease or condition, or prevents or delays the onset of one of more symptoms of a particular disease or condition.

The term "patient" means animals, such as dogs, cats, cows, horses, sheep and humans. Particular patients are mammals. The term patient includes males and females.

The term "pharmaceutically acceptable" means that the referenced substance, such as a compound of the present invention or a formulation containing a compound of the present invention, or a particular excipient, are suitable for administration to a patient.

The terms "treating", "treat" or "treatment" and the like include preventative (e.g., prophylactic) and palliative treatment.

The term "patient in need thereof" means a patient who has or is at risk of having a disease and/or condition that can be treated by inhibition of Nav 1.7, such as chronic pain.

The term "excipient" means any pharmaceutically acceptable additive, carrier, diluent, adjuvant, or other ingredient, other than the active pharmaceutical ingredient (API), which is typically included for formulation and/or administration to a patient.

The compounds of the present invention are administered to a patient in a therapeutically effective amount. The compounds can be administered alone or as part of a pharmaceutically acceptable composition or formulation. In addition, the compounds or compositions can be administered all at once, as for example, by a bolus injection, multiple times, such as by a series of tablets, or delivered substantially uniformly over a period of time, as for example, using transdermal delivery. It is also noted that the dose of the compound can be varied over time.

In addition, the compounds of the present invention can be administered alone, in combination with other compounds of the present invention, or with other pharmaceutically active compounds. The other pharmaceutically active compounds can be intended to treat the same disease or condition as the compounds of the present invention or a different disease or condition. If the patient is to receive or is receiving multiple pharmaceutically active compounds, the compounds can be administered simultaneously, or sequentially. For example, in the case of tablets, the active compounds may be found in one tablet or in separate tablets, which can be administered at once or sequentially in any order. In addition, it should be recognized that the compositions may be different forms. For example, one or more compound may be delivered by a tablet, while another is administered by injection or orally as a syrup. All combinations, delivery methods and administration sequences are contemplated.

The compounds of the present invention may be used in the manufacture of a medicament for the treatment of a disease and/or condition mediated by Nav 1.7, such as pain, chronic cough or itch.

Pain is typically divided into primary types: chronic and acute pain based on the duration of the pain. Typically, chronic pain lasts for longer than 3 months. Examples of chronic pain include pain associated with rheumatoid arthritis, osteoarthritis, lumbosacral radiculopathy or cancer. Chronic pain also includes idiopathic pain, which is pain that has no identified cause. An example of idiopathic pain is fibromyalgia.

Another type of pain is nociceptive pain. Nociceptive pain is caused by stimulation of peripheral nerve fibers that respond to highly noxious events such as thermal, mechanical or chemical stimuli.

Still another type of pain is neuropathic pain. Neuropathic pain is pain that is caused by damage or disease affecting a part of the nervous system. Phantom limb pain is a type of neuropathic pain. In phantom limb pain, the body detects pain from a part of a body that no longer exists. For example, a person who has had a leg amputated may feel leg pain even though the leg no longer exists.

In one embodiment of the methods of treatment provided by the present invention using the compounds of Formula I, or pharmaceutically acceptable salts thereof, the disease is chronic pain. In another aspect, the chronic pain is associated with, but are not limited to, post-herpetic neuralgia (shingles), rheumatoid arthritis, osteoarthritis, diabetic neuropathy, complex regional pain syndrome (CRPS), cancer or chemotherapy-induced pain, chronic back pain, phantom limb pain, trigeminal neuralgia, HIV-induced neuropathy, cluster headache disorders, and migraine, primary erythromelalgia, and paroxysmal extreme pain disorder. Other indications for Nav 1.7 inhibitors include, but are not limited to, depression (Morinville et al., *J Comp Neurol.*, 504:680-689 (2007)), bipolar and other CNS disorders (Ettinger and Argoff, *Neurotherapeutics*, 4:75-83 (2007)), epilepsy: ibid., and Gonzalez, Termin, Wilson, *Methods and Principles in Medicinal Chemistry*, 29:168-192 (2006)), multiple sclerosis (Waxman, *Nature Neurosci.* 7:932-941 (2006)), Parkinson's (Do and Bean, *Neuron* 39:109-120 (2003); Puopolo et al., *J. Neurosci.* 27:645-656 (2007)), restless legs syndrome, ataxia, tremor, muscle weakness, dystonia, tetanus (Hamann M., et. al., *Exp. Neurol.* 184(2):830-838, 2003), anxiety, depression: McKinney B. C, et. al., *Genes Brain Behav.* 7(6):629-638, 2008), learning and memory, cognition (Woodruff-Pak D. S., et. al., *Behav. Neurosci.* 120(2):229-240, 2006), cardiac arrhythmia and fibrillation, contractility, congestive heart failure, sick sinus syndrome (Haufe V., et. al., *J Mol. Cell Cardiol.* 42(3):469-477, 2007), schizophrenia, neuroprotection after stroke, drug and alcohol abuse (Johannessen L. C., *CNS Drugs* 22(1)27-47, 2008), Alzheimer's (Kim D. Y., et. al., *Nat. Cell. Biol.* 9(7):755-764, 2007), and cancer (Gillet L., et. al., *J Biol Chem* 2009, January 28 (epub)).

Another aspect of the invention relates to a method of treating acute and/or chronic inflammatory and neuropathic pain, dental pain, general headache, migraine, cluster headache, mixed-vascular and non-vascular syndromes, tension headache, general inflammation, arthritis, rheumatic diseases, rheumatoid arthritis, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to the present invention. A preferred type of pain to be treated is chronic neuropathic pain. Another preferred type of pain to be treated is chronic inflammatory pain.

In another aspect of the invention, the compounds of the present invention can be used in combination with other compounds that are used to treat pain. Examples of such other compounds include, but are not limited to aspirin, celecoxib, hydrocodone, oxycodone, codeine, fentanyl, ibuprofen, ketoprofen, naproxen, acetaminophen, gabapentin and pregabalin. Examples of classes of medicines that contain compounds that can be used in combination with the compounds of the present invention include non-steroidal anti-inflammatory compounds (NSAIDS), steroidal compounds, cycloxogenase inhibitors and opiod analgesics.

The compounds of the present invention may also be used to treat diabetes, obesity and/or to facilitate weight loss.

The compounds of the present invention may be used in combination with other pharmaceutically active compounds. It is noted that the term "pharmaceutically active compounds" can include biologics, such as proteins, antibodies and peptibodies.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: a compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed by said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of the present invention can consist of one tablet or capsule, while a daily dose of the second compound can consist of several tablets or capsules and vice versa. The memory aid should reflect this and aid in correct administration of the active agents.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The compounds of the present invention and other pharmaceutically active compounds, if desired, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. All methods that are used by those skilled in the art to administer a pharmaceutically active agent are contemplated.

Compositions suitable for parenteral injection may comprise physiologically acceptable sterile aqueous or nonaqueous solutions, dispersions, suspensions, or emulsions, and sterile powders for reconstitution into sterile injectable solutions or dispersions. Examples of suitable aqueous and nonaqueous carriers, diluents, solvents, or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Microorganism contamination can be prevented by adding various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents delaying absorption, for example, aluminum monostearate and gelatin.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid, certain complex silicates, and sodium carbonate; (a) solution retarders, as for example, paraffin; (f) absorption accelerators, as for example, quaternary ammonium compounds; wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, and tablets, the dosage forms may also comprise buffering agents.

Solid compositions of a similar type may also be used as fillers in soft and hard filled gelatin capsules using such excipients as lactose or milk sugar, as well as high molecular weight polyethylene glycols, and the like.

Solid dosage forms such as tablets, dragees, capsules, pills, and granules can be prepared with coatings and shells, such as enteric coatings and others well known in the art. They may also contain opacifying agents, and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the composition can also include adjuvants, such as wetting agents, emulsifying and suspending agents, sweetening, flavoring, and perfuming agents. Suspensions, in addition to the active compound, may contain suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal administration are preferable suppositories, which can be prepared by mixing the compounds of the present invention with suitable non-irritating excipients or carriers such as cocoa butter, polyethylene glycol or a suppository wax, which are solid at ordinary room temperature, but liquid at body temperature, and therefore, melt in the rectum or vaginal cavity and release the active component.

Dosage forms for topical administration of a compound of the present invention include ointments, powders, sprays and inhalants. The active compound or fit compounds are admixed under sterile condition with a physiologically acceptable carrier, and any preservatives, buffers, or propellants that may be required. Opthalmic formulations, eye ointments, powders, and solutions are also contemplated as being within the scope of this invention.

The compounds of the present invention can be administered to a patient at dosage levels in the range of about 0.1 to about 3,000 mg per day. For a normal adult human having a body weight of about 70 kg, a dosage in the range of about 0.01 to about 100 mg per kilogram body weight is typically sufficient. The specific dosage and dosage range that can be used depends on a number of factors, including the requirements of the patient, the severity of the condition or disease being treated, and the pharmacological activity of the compound being administered. The determination of dosage ranges and optimal dosages for a particular patient is within the ordinary skill in the art.

The compounds of the present invention can be administered as pharmaceutically acceptable salts, cocrystyals, esters, amides or prodrugs. The term "salts" refers to inorganic and organic salts of compounds of the present invention. The salts can be prepared in situ during the final isolation and purification of a compound, or by separately reacting a purified compound in its free base or acid form with a suitable organic or inorganic base or acid and isolating the salt thus formed. Representative salts include the hydrobromide, hydrochloride, sulfate, bisulfate, nitrate, acetate, oxalate, palmitiate, stearate, laurate, borate, benzoate, lactate, phosphate, tosylate, citrate, maleate, fumarate, succinate, tartrate, naphthylate, mesylate, glucoheptonate, lactobionate, and laurylsulphonate salts, and the like. The salts may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, for example, S. M. Berge, et al., "Pharmaceutical Salts," J Pharm Sci, 66: 1-19 (1977).

Examples of pharmaceutically acceptable esters of the compounds of the present invention include $C_1$-$C_8$ alkyl esters. Acceptable esters also include $C_5$-$C_7$ cycloalkyl esters, as well as arylalkyl esters such as benzyl. $C_1$-$C_4$ alkyl esters are commonly used. Esters of compounds of the present invention may be prepared according to methods that are well known in the art.

Examples of pharmaceutically acceptable amides of the compounds of the present invention include amides derived from ammonia, primary $C_1$-$C_8$ alkyl amines, and secondary $C_1$-$C_8$ dialkyl amines. In the case of secondary amines, the amine may also be in the form of a 5 or 6 membered heterocycloalkyl group containing at least one nitrogen atom. Amides derived from ammonia, $C_1$-$C_3$ primary alkyl amines and $C_1$-$C_2$ dialkyl secondary amines are commonly used. Amides of the compounds of the present invention may be prepared according to methods well known to those skilled in the art.

The term "prodrug" means compounds that are transformed in vivo to yield a compound of the present invention. The transformation may occur by various mechanisms, such as through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

To illustrate, if the compound of the invention contains a carboxylic acid functional group, a prodrug can comprise an ester formed by the replacement of the hydrogen atom of the acid group with a group such as ($C_1$-$C_8$ alkyl, ($C_2$—$C_{12}$) alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)aminomethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino- or morpholino($C_{2-3}$)alkyl.

Similarly, if a compound of the present invention comprises an alcohol functional group, a prodrug can be formed by the replacement of the hydrogen atom of the alcohol group with a group such as ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$) alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from the naturally occurring L-amino acids, —P(O)(OH)$_2$, —P(O)(O($C_1$-$C_6$)alkyl)$_2$ or glycosyl (the radical resulting from the removal of a hydroxyl group of the hemiacetal form of a carbohydrate).

In addition, if a compound of the present invention comprises a sulfonamide moiety, a prodrug can be formed by replacement of the sulfonamide N(H) with a group such as —CH$_2$P(O)(O($C_1$-$C_6$)alkyl)$_2$ or —CH$_2$OC(O)($C_1$-$C_6$) alkyl.

The compounds of the present invention also include tautomeric forms of prodrugs.

The compounds of the present invention may contain asymmetric or chiral centers, and therefore, exist in different stereoisomeric forms. It is contemplated that all stereoisomeric forms of the compounds as well as mixtures thereof, including racemic mixtures, form part of the present invention. In addition, the present invention contemplates all geometric and positional isomers. For example, if the compound contains a double bond, both the cis and trans forms (designated as S and E, respectively), as well as mixtures, are contemplated.

Mixture of stereoisomers, such as diastereomeric mixtures, can be separated into their individual stereochemical components on the basis of their physical chemical differences by known methods such as chromatography and/or fractional crystallization. Enantiomers can can also be separated by converting the enantiomeric mixture into a diastereomeric mixture by reaction with an appropriate optically active compound (e.g., an alcohol), separating the diastereomers and converting (e.g., hydrolyzing) the individual diastereomers to the corresponding pure enantiomers. Also, some compounds may be atropisomers (e.g., substituted biaryls that are steoisomeric due to hindered rotation around a bond).

The compounds of the present invention may exist in unsolvated as well as solvated forms with pharmaceutically acceptable solvents such as water (hydrate), ethanol, and the like. The present invention contemplates and encompasses both the solvated and unsolvated forms.

It is also possible that compounds of the present invention may exist in different tautomeric forms. All tautomers of compounds of the present invention are contemplated. For example, all of the tautomeric forms of the tetrazole moiety are included in this invention. Also, for example, all keto-enol or imine-enamine forms of the compounds are included in this invention. Other examples of tautomerism are as follows:

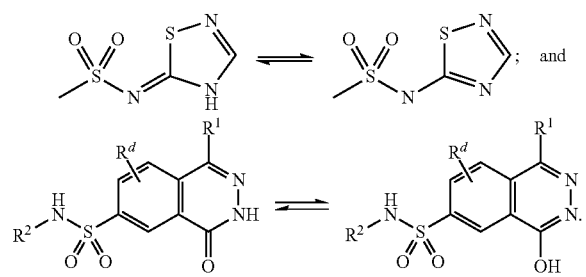

Those skilled in the art will recognize that the compound names and structures contained herein may be based on a particular tautomer of a compound. While the name or structure for only a particular tautomer may be used, it is intended that all tautomers are encompassed by the present invention, unless stated otherwise.

It is also intended that the present invention encompass compounds that are synthesized in vitro using laboratory techniques, such as those well known to synthetic chemists; or synthesized using in vivo techniques, such as through metabolism, fermentation, digestion, and the like. It is also contemplated that the compounds of the present invention may be synthesized using a combination of in vitro and in vivo techniques.

The present invention also includes isotopically-labelled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{16}O$, $^{17}O$, $^{31}P$, $^{32}P$, $^{35}S$, $^{18}F$, and $^{36}Cl$. In another aspect, the compounds of the present invention contain one or more deuterium atoms (2H) in place of one or more hydrogen atoms.

Compounds of the present invention that contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detection. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of this invention can generally be prepared by substituting a readily available isotopically labelled reagent for a non-isotopically labelled reagent.

The compounds of the present invention may exist in various solid states including crystalline states and as an amorphous state. The different crystalline states, also called polymorphs, and the amorphous states of the present compounds are contemplated as part of this invention.

In synthesizing compounds of the present invention, it may be desirable to use certain leaving groups. The term "leaving groups" ("LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxysuccinimide, N-hydroxybenzotriazole, and the like. Examples of nucleophiles include, but are not limited to, amines, thiols, alcohols, Grignard reagents, anionic species (e.g., alkoxides, amides, carbanions) and the like.

All patents and other publications recited herein are hereby incorporated by reference in their entirety.

The examples presented below illustrate specific embodiments of the present invention. These examples are meant to be representative and are not intended to limit the scope of the claims in any manner.

It is noted that when a percent (%) is used with regard to a liquid, it is a percent by volume with respect to the solution. When used with a solid, it is the percent with regard to the solid composition. Materials obtained from commercial suppliers were typically used without further purification. Reactions involving air or moisture sensitive reagents were typically performed under a nitrogen or argon atmosphere. Purity was measured using high performance liquid chromatography (HPLC) system with UV detection at 254 nm and 215 nm (System A: Agilent Zorbax Eclipse XDB-C8 4.6×150 mm, 5 µm, 5 to 100% CH$_3$CN in H$_2$O with 0.1% TFA for 15 min at 1.5 mL/min; System B: Zorbax SB-C8, 4.6×75 mm, 10 to 90% CH$_3$CN in H$_2$O with 0.1% formic acid for 12 min at 1.0 mL/min) (Agilent Technologies, Santa Clara, Calif.). Silica gel chromatography was generally performed with prepacked silica gel cartridges (Biotage, Uppsala, Sweden or Teledyne-Isco, Lincoln, Nebr.). $^1$H NMR spectra were recorded on a Bruker AV-400 (400 MHz) spectrometer (Bruker Corporation, Madison, Wis.) or a Varian (Agilent Technologies, Santa Clara, Calif.) 400 MHz spectrometer at ambient temperature. All observed protons are reported as parts per million (ppm) downfield from tetramethylsilane (TMS) or other internal reference in the appropriate solvent indicated. Data are reported as follows: chemical shift, multiplicity (s=singlet, d=doublet, t=triplet, q=quartet, br=broad, m=multiplet), coupling constants, and number of protons. Low-resolution mass spectral (MS) data were determined on an Agilent 1100 Series (Agilent Technologies, Santa Clara, Calif.) LC/MS with UV detection at 254 nm and 215 nm and a low resonance electrospray mode (ESI).

The following abbreviations may be used herein:
AmPhos 4-(di-tert-butylphosphino)-N,N-dimethylaniline
AcCl acetyl chloride
CAN acetonitrile
AcOH acetic acid
aq or aq. aqueous
BOC or Boc tert-butyloxycarbonyl
DAST diethylaminosulfur trifluoride
DCM dichloromethane
DMAP 4-dimethylaminopyridine
DMB dimethoxybenzyl
DME dimethoxyethane
DMF N,N-dimethylformamide
DMSO dimethyl sulfoxide
Dppf, DPPF or dppf 1,1'-bis(diphenylphosphino)ferrocene
ESI or ES electrospray ionization
Et ethyl
Et$_2$O diethyl ether
TEA or Et$_3$N triethylamine
EtOAc ethyl acetate
eq or eq. equivalent
G grams
h or hr hour
HPLC high pressure liquid chromatography
iPr isopropyl
iPr$_2$Net N-ethyl diisopropylamine (Hunig's base)
KOAc potassium acetate
KHMDS potassium hexamethyldisilazide
LC MS, LCMS, LC-MS or LC/MS liquid chromatography mass spectroscopy
LHMDS or LiHMDS lithium hexamethyldisilazide
m/z mass divided by charge
Me methyl
MeOH methanol
MeCN or CAN acetonitrile
Mg milligrams
Min minutes
mL milliliters
MPLC medium pressure liquid chromatography
MS mass spectra
NaHMDS sodium hexamethyldisilazide
NBS N-bromosuccinimide
NCS N-chlorosuccinimide
n-BuLi n-butyllithium
NMR nuclear magnetic resonance
Pd$_2$(dba)$_3$ tris(dibenzylideneacetone)dipalladium(0)
Ph phenyl
PMB p-methoxybenzyl
Pr or PR or PG protecting group
RBF or round bottomed flask round bottom flask
RT or rt room temperature
SCX strong cation exchange
SEM 2-(trimethylsilyl)ethoxymethyl
SFC supercritical fluid chromatography
TBAF tetra-n-butylammonium fluoride
t-BuOH tert-butanol
TIPS-Cl triisopropylsilyl chloride
TFA trifluoroacetic acid
THF tetrahydrofuran
UV ultraviolet Xantphos 4,5-bis(diphenylphosphino)-9,9-dimethylxanthene
X-Phos 2-dicyclohexylphosphino-2',4',6'-triisopropyl-1,1'-biphenyl

EXAMPLES

Intermediates

Intermediate CC: (P)-perfluorophenyl 1-(3-methoxy-3'-(trifluoromethyl)-[1,1'-biphenyl]-4-yl)-2-oxo-1,2-dihydroquinoline-6-sulfonate

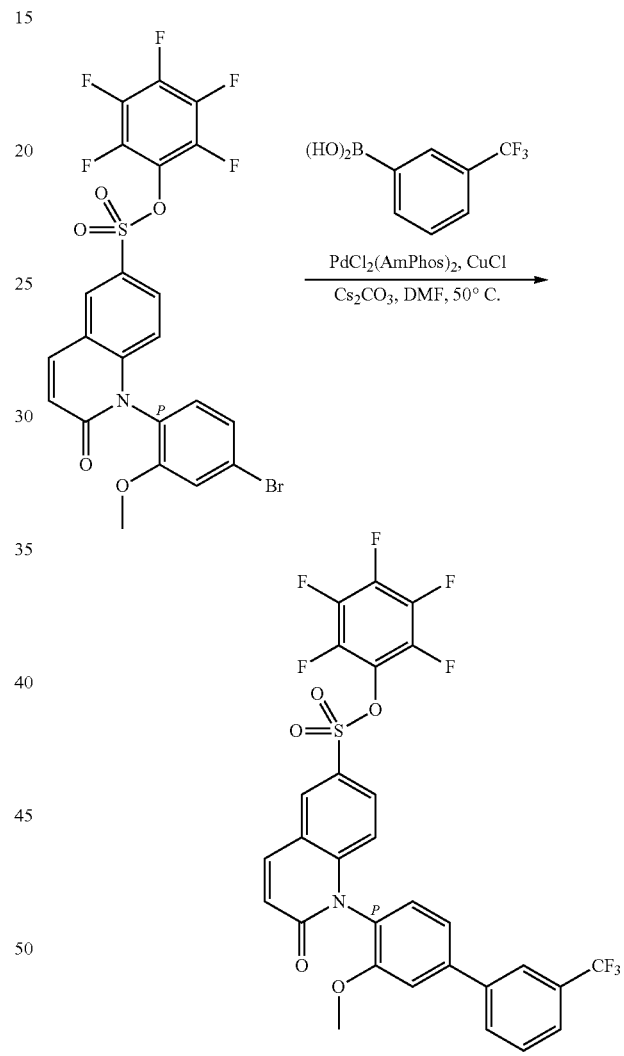

A RBF was charged with (P)-perfluorophenyl 1-(4-bromo-2-methoxyphenyl)-2-oxo-1,2-dihydroquinoline-6-sulfonate (3.081 g, 5.35 mmol), (3-(trifluoromethyl)phenyl)boronic acid (3.05 g, 16.04 mmol), copper(I) chloride (1.588 g, 16.04 mmol), cesium carbonate (6.97 g, 21.39 mmol), and bis(di-tert-butyl(4-dimethylaminophenyl)phosphine)-dichloropalladium(II) (0.036 g, 0.05 mmol). The flask was flushed with Ar (g) and DMF (26.7 ml) was added. The flask was then lowered into a 50° C. heating bath for 1 h. The mixture was cooled and filtered through celite with the aid of EtOAc. The filtrate was partitioned between EtOAc and a saturated aq. solution of EDTA which led to an emulsion.

The layers were separated, and the aq. layer was extracted with EtOAc (2×). The combined organic extracts were washed with brine. A solid was left with the aq. layer. The organic extracts were dried over sodium sulfate, filtered, and concentrated. The residue was purified by chromatography on silica gel (80-g Redi-Sep Gold column, 25-g silica gel loading column, 0-50% EtOAc/Heptane) to give (P)-perfluorophenyl 1-(3-methoxy-3'-(trifluoromethyl)-[1,1'-biphenyl]-4-yl)-2-oxo-1,2-dihydroquinoline-6-sulfonate (2.645 g, 4.12 mmol, 77% yield) as a light-yellow solid. m/z (ESI) 642.0 (M+H)$^+$.

Intermediate CD: (P)-perfluorophenyl 2-oxo-1-(2,3',4'-trifluoro-5-methoxy-[1,1'-biphenyl]-4-yl)-1,2-dihydroquinoline-6-sulfonate lowered into a 50° C. heating bath for 1.5 h. The mixture was cooled and filtered through celite with the aid of EtOAc. The filtrate was partitioned between EtOAc and water which led to an emulsion. The layers were separated, and the aq. layer was extracted with EtOAc (2×). The organic extracts were dried over sodium sulfate, filtered, and concentrated. The residue was purified by chromatography on silica gel (50-g SNAP Ultra column, 25-g silica gel loading column, 0-50% EtOAc/Heptane) to give (P)-perfluorophenyl 2-oxo-1-(2,3',4'-trifluoro-5-methoxy-[1,1'-biphenyl]-4-yl)-1,2-dihydroquinoline-6-sulfonate (431 mg, 40% yield) as a light-yellow solid. m/z (ESI) 628.1 (M+H)$^+$.

Intermediate CE: (P)-perfluorophenyl 1-(3'-chloro-3,5'-dimethoxy-[1,1'-biphenyl]-4-yl)-2-oxo-1,2-dihydroquinoline-6-sulfonate

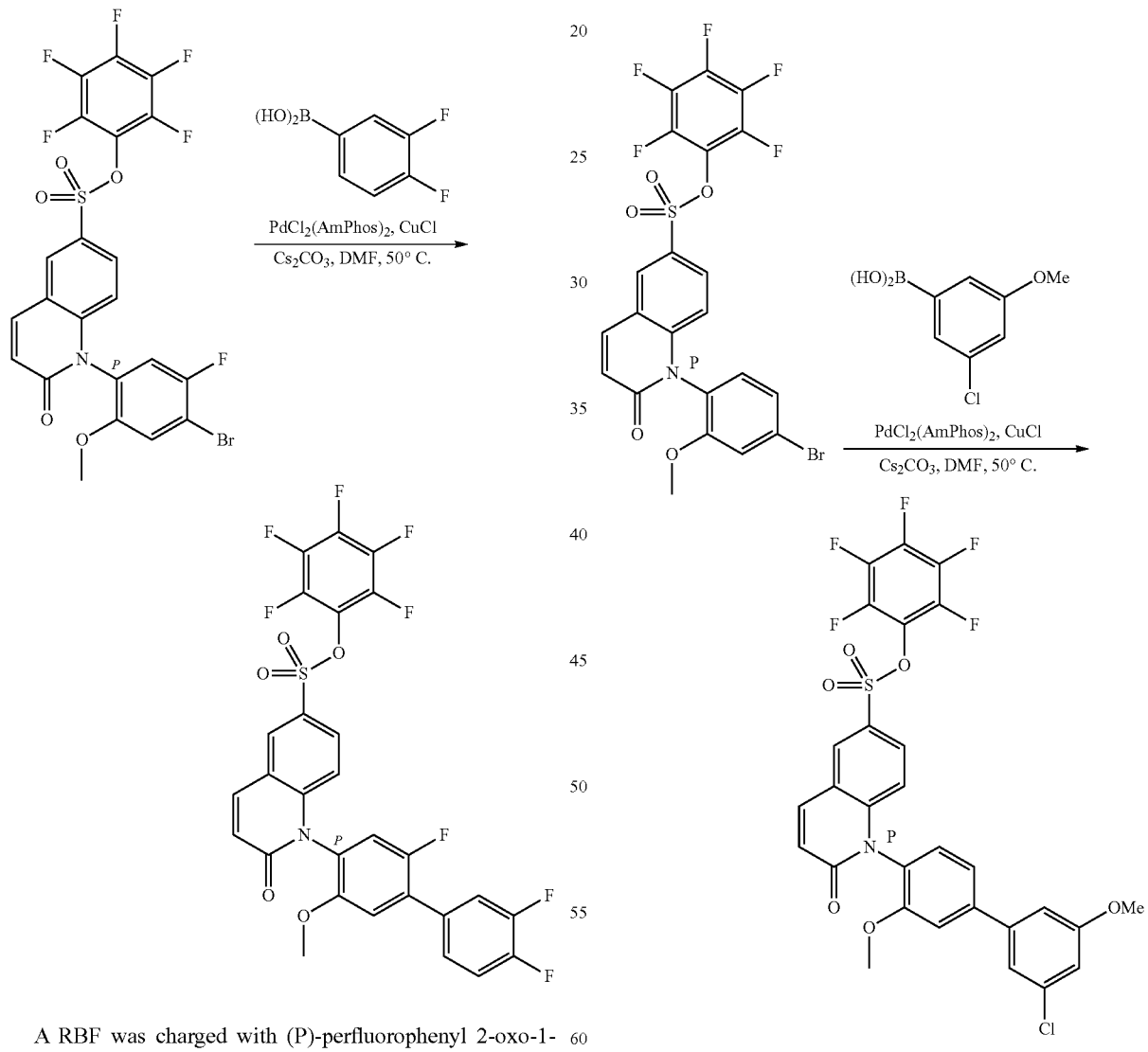

A RBF was charged with (P)-perfluorophenyl 2-oxo-1-(2,3',4'-trifluoro-5-methoxy-[1,1'-biphenyl]-4-yl)-1,2-dihydroquinoline-6-sulfonate, (3,4-difluorophenyl)boronic acid (0.813 g, 5.15 mmol), copper(I) chloride (0.510 g, 5.15 mmol), cesium carbonate (2.238 g, 6.87 mmol), and bis(di-tert-butyl(4-dimethylaminophenyl)phosphine)-dichloropalladium(II) (0.036 g, 0.05 mmol). The flask was flushed with Ar (g) and DMF (8.59 ml) was added. The flask was then A RBF was charged with (P)-perfluorophenyl 1-(4-bromo-2-methoxyphenyl)-2-oxo-1,2-dihydroquinoline-6-sulfonate (1.475, 2.56 mmol), 1,1-bis[(di-t-butyl-p-methyl-aminophenyl]palladium(II) chloride (181 mg, 0.256 mmol), and cesium carbonate (3336 mg, 10.24 mmol). The flask was flushed with Ar (g), then DMF (12.4 mL) was added. The flask was lowered into a 50° C. heating bath. After 3 min, a solid mixture of (3-chloro-5-methoxyphenyl)boronic acid (1431 mg, 7.68 mmol) and copper(I) chloride (760 mg, 7.68 mmol) was added directly. After 50 min, the mixture was cooled, diluted with EtOAc, and filtered through celite. The filtrate was concentrated. The residue was purified by chromatography on silica gel (50-g SNAP Ultra column, 25-g silica gel column, 0-40% EtOAc/Heptane). Fractions containing pure product were combined and concentrated to give (P)-perfluorophenyl 1-(3'-chloro-3,5'-dimethoxy-[1,1'-biphenyl]-4-yl)-2-oxo-1,2-dihydroquinoline-6-sulfonate (980 mg, 1.536 mmol, 60.0% yield) as a pink foam. m/z (ESI) 638.0 (M+H)$^+$.

Intermediate CF: (P)-perfluorophenyl 1-(2,4'-difluoro-5-methoxy-3'-methyl-[1,1'-biphenyl]-4-yl)-2-oxo-1,2-dihydroquinoline-6-sulfonate

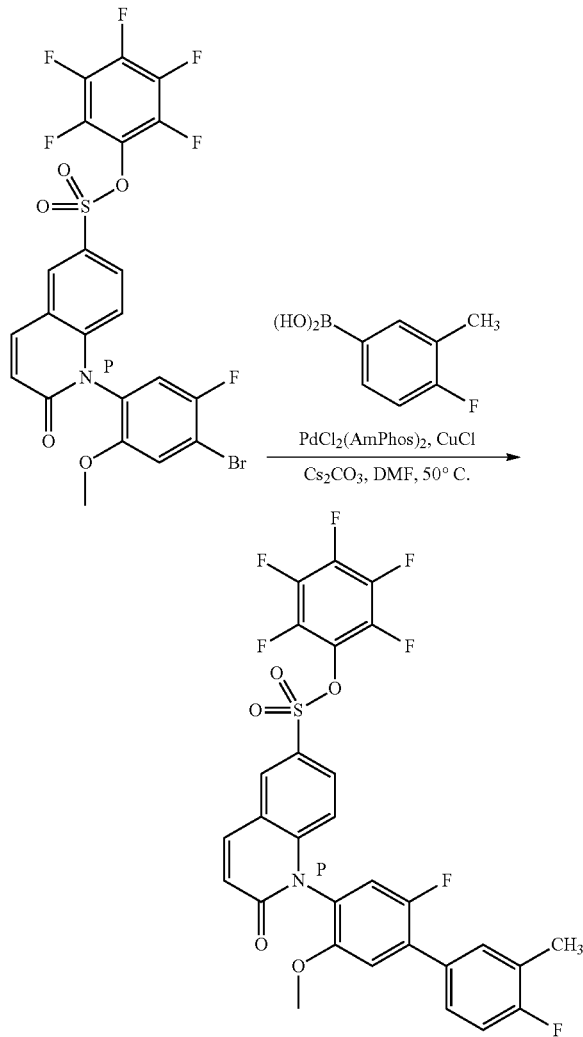

A RBF was charged with (P)-perfluorophenyl 1-(2,4'-difluoro-5-methoxy-3'-methyl-[1,1'-biphenyl]-4-yl)-2-oxo-1,2-dihydroquinoline-6-sulfonate (1.107 g, 1.775 mmol, 90% yield), (4-fluoro-3-methylphenyl)boronic acid (0.907 g, 5.89 mmol), copper(I) chloride (0.583 g, 5.89 mmol), cesium carbonate (2.56 g, 7.85 mmol), and bis(di-tert-butyl (4-dimethylaminophenyl)phosphine)-dichloropalladium(II) (0.036 g, 0.05 mmol). The flask was flushed with Ar (g) and DMF (9.82 ml) was added. The flask was then lowered into a 50° C. heating bath for 1 h. The mixture was cooled and filtered through celite with the aid of EtOAc. The filtrate was partitioned between EtOAc and water which led to an emulsion. The layers were separated, and the aq. layer was extracted with EtOAc (2×). The organic extracts were dried over sodium sulfate, filtered, and concentrated. The residue was purified by chromatography on silica gel (50-g SNAP Ultra column, 25-g silica gel loading column, 0-50% EtOAc/Heptane) to give (P)-perfluorophenyl 1-(2,4'-difluoro-5-methoxy-3'-methyl-[1,1'-biphenyl]-4-yl)-2-oxo-1,2-dihydroquinoline-6-sulfonate (1.107 g, 1.775 mmol, 90% yield) as an off-white solid. m/z (ESI) 624.0 (M+H)$^+$.

Intermediate CG: 2-(5-methoxy-2-methylphenyl)-4,4,5,5-tetramethyl-1,3,2-dioxaborolane

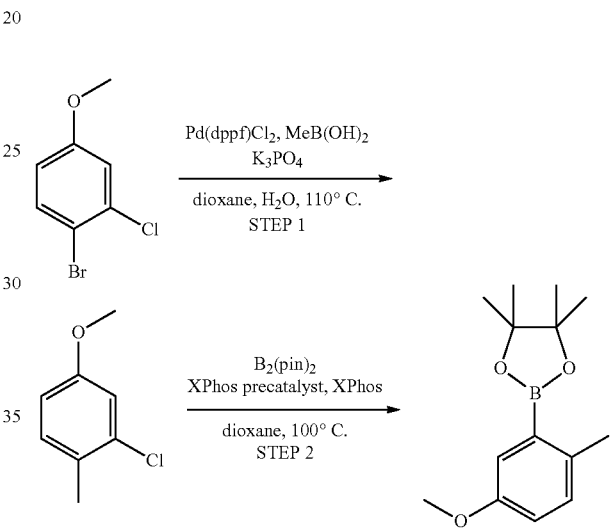

Step 1: 2-chloro-4-methoxy-1-methylbenzene

A solution of PdCl$_2$(dppf)-DCM adduct (0.922 g, 1.129 mmol), methylboronic acid (2.70 g, 45.2 mmol), 4-bromo-3-chloroanisole (6.39 ml, 45.2 mmol), and potassium phosphate (28.8 g, 135 mmol) in 150 mL dioxane and 50 mL water was heated to 110° C. for 2 hours. The reaction mixture was then diluted with heptane, the organics dried over MgSO$_4$ and concentrated to afford 2-chloro-4-methoxy-1-methylbenzene. m/z (ESI) 141.0 (M-CH$_3$)$^+$.

Step 2: 2-(5-methoxy-2-methylphenyl)-4,4,5,5-tetramethyl-1,3,2-dioxaborolane

The residue from the previous step was dissolved in 100 mL dioxane, was treated with bis(pinacolato)diboron (11.47 g, 45.2 mmol), potassium phosphate (28.8 g, 135 mmol), XPhos (0.215 g, 0.452 mmol) and (Xphos) palladium(II) phenethylamine chloride (0.334 g, 0.452 mmol) and was heated to 100° C. After stirring overnight, the reaction mixture was concentrated. Silica gel column chromatography (0-20% EtOAc/heptane) gave 2-(5-methoxy-2-methylphenyl)-4,4,5,5-tetramethyl-1,3,2-dioxaborolane (7.80 g, 31.4 mmol, 69.6% yield over two steps). m/z (ESI) 249.3 (M+H)$^+$.

Intermediate CH: Perfluorophenyl 1-(4'-chloro-2-fluoro-5-methoxy-[1,1'-biphenyl]-4-yl)-2-oxo-1,2-dihydroquinoline-6-sulfonate

Intermediate CI: 1-(5-fluoro-2-methoxy-4-(4-methyl-2-oxopyridin-1(2H)-yl)phenyl)-N-(isoxazol-3-yl)-N-(4-methoxybenzyl)-2-oxo-1,2-dihydroquinoline-6-sulfonamide

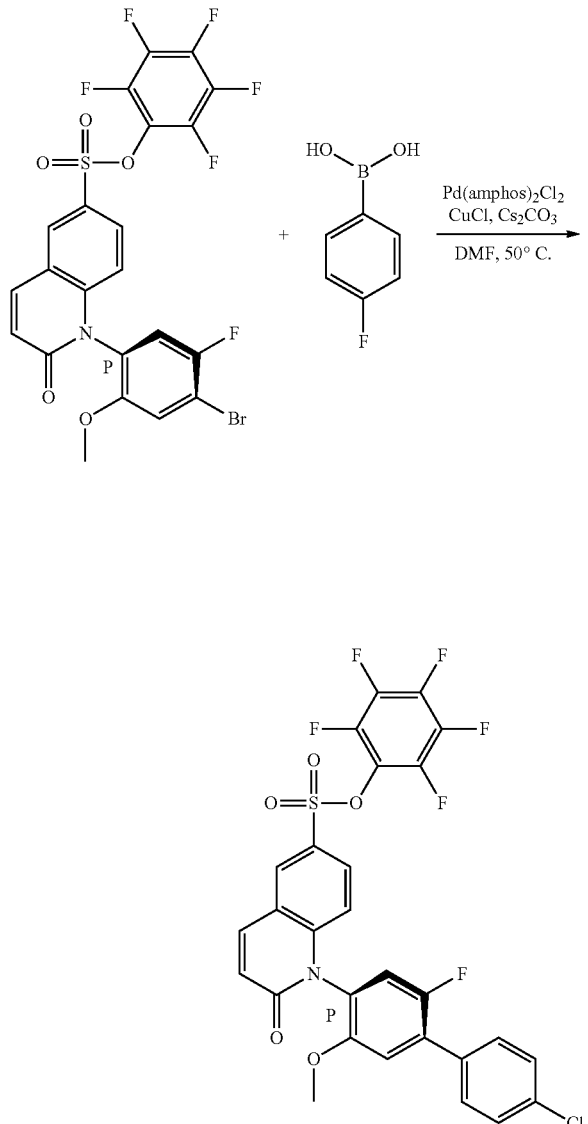

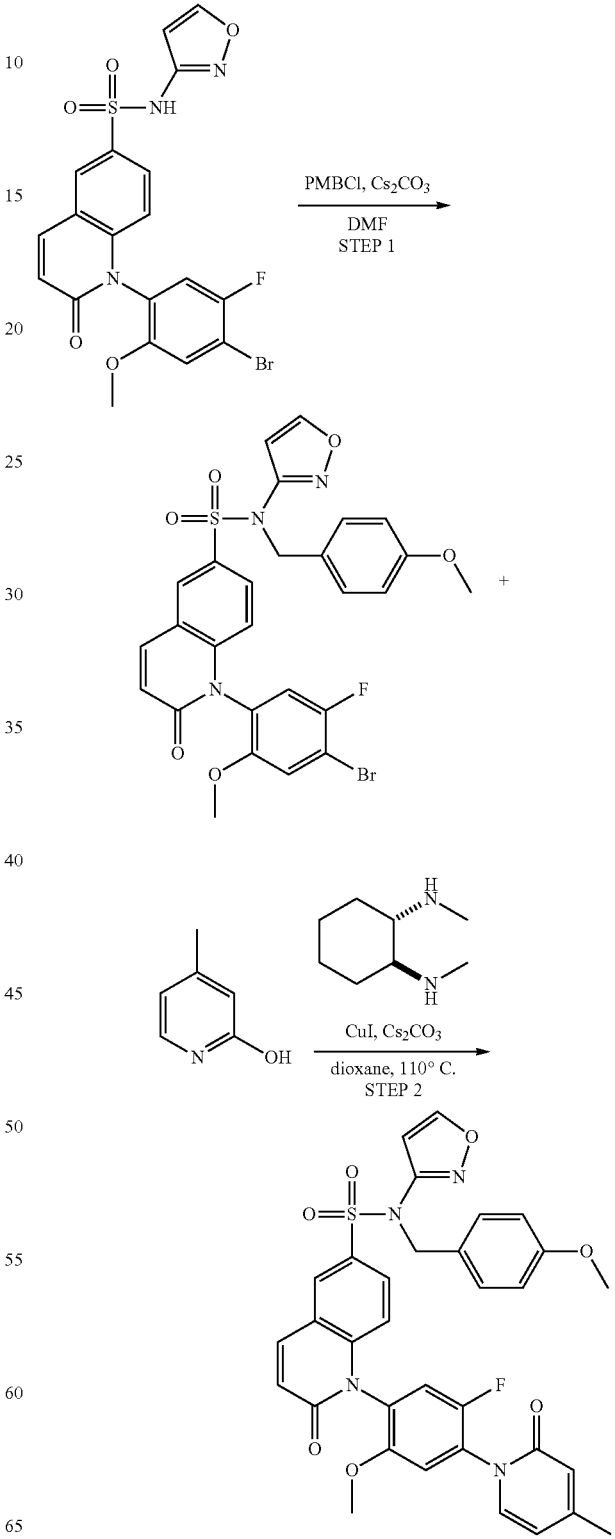

A 40-mL vial containing (P)-perfluorophenyl 1-(4-bromo-5-fluoro-2-methoxyphenyl)-2-oxo-1,2-dihydroquinoline-6-sulfonate (1.025 g, 1.725 mmol), 4-chlorophenylboronic acid (0.809 g, 5.17 mmol), cesium carbonate (2.25 g, 6.90 mmol), 1,1-bis[(di-t-butyl-p-methylaminophenyl]palladium (II) chloride (0.244 g, 0.345 mmol), and copper(I) chloride (0.512 g, 5.17 mmol) was flushed with $N_2$ and then charged with DMF (9 mL). The vial was stirred at 50° C. for 30 min. The brown slurry was cooled to rt, quenched with $H_2O$, and extracted thrice with EtOAc. The organic extracts were combined, washed twice with $H_2O$, once with brine, dried over $Na_2SO_4$, filtered, and concentrated in vacuo to a red oil. Column chromatography (50 g Snap Ultra column, 0% to 50% EtOAc/hept) afforded (P)-perfluorophenyl 1-(4'-chloro-2-fluoro-5-methoxy-[1,1'-biphenyl]-4-yl)-2-oxo-1,2-dihydroquinoline-6-sulfonate (1.186 g, >99% yield) as a tan amorphous solid. m/z (ESI) 626.0 (M+H)$^+$.

Step 1: 1-(4-bromo-5-fluoro-2-methoxyphenyl)-N-(isoxazol-3-yl)-N-(4-methoxybenzyl)-2-oxo-1,2-dihydroquinoline-6-sulfonamide A 40-mL vial containing 1-(4-bromo-5-fluoro-2-methoxyphenyl)-N-(isoxazol-3-yl)-2-oxo-1,2-dihydroquinoline-6-sulfonamide (750 mg, 1.517 mmol) and cesium carbonate (1483 mg, 4.55 mmol) was flushed with $N_2$ and subsequently charged with DMF (2.5 mL) and 4-methoxybenzyl chloride (309 μl, 2.276 mmol). The brown slurry was stirred at rt for 5 d. The reaction was then diluted with $H_2O$ and extracted thrice with EtOAc. The organic extracts were combined, washed with brine, dried over $Na_2SO_4$, filtered, and concentrated in vacuo to an oily orange residue. Column chromatography (25 g Snap Ultra column, 0% to 100% EtOAc/hept with 10% DCM) afforded 1-(4-bromo-5-fluoro-2-methoxyphenyl)-N-(isoxazol-3-yl)-N-(4-methoxybenzyl)-2-oxo-1,2-dihydroquinoline-6-sulfonamide (697.8 mg, 1.136 mmol, 74.8% yield) as a yellow amorphous solid. $^1$H NMR (400 MHz, DMSO-$d_6$) δ ppm 3.71 (d, J=1.76 Hz, 6H) 4.92 (s, 2H) 6.74 (s, 1H) 6.77-6.92 (m, 4H) 7.22-7.29 (m, 2H) 7.59-7.72 (m, 2H) 7.76 (d, J=9.02 Hz, 1H) 8.14-8.20 (m, 1H) 8.38 (d, J=3.45 Hz, 1H) 8.38 (s, 1H) 8.82 (d, J=3.25 Hz, 1H) 8.81 (s, 1H). m/z (ESI) 614.0 (M+H)$^+$.

Step 2: 1-(5-fluoro-2-methoxy-4-(4-methyl-2-oxopyridin-1(2H)-yl)phenyl)-N-(isoxazol-3-yl)-N-(4-methoxybenzyl)-2-oxo-1,2-dihydroquinoline-6-sulfonamide A blue-green dioxane (2.2 mL) slurry of 1-(4-bromo-5-fluoro-2-methoxyphenyl)-N-(isoxazol-3-yl)-N-(4-methoxybenzyl)-2-oxo-1,2-dihydroquinoline-6-sulfonamide (0.683 g, 1.11 mmol), 2-hydroxy-4-methylpyridine (1.21 g, 11.1 mmol), cesium carbonate (0.543 g, 1.67 mmol), copper(I) iodide (0.212 g, 1.11 mmol), and trans-N,N-dimethyl-1,2-cyclohexanediamine (0.18 mL, 1.17 mmol) was sparged with $N_2$ for 45 min in a 40-mL vial. The sealed flask was then heated to 110° C. After stirring for 2 h, the reaction was then quenched with $H_2O$ and extracted thrice with EtOAc. The organic extracts were combined, washed with brine, dried over $Na_2SO_4$, filtered, and concentrated in vacuo. Column chromatography (25 g Snap Ultra column, 0% to 80% [3:1 EtOAc/EtOH]/hept gradient with 10% DCM followed by additional column chromatography (55 g Interchim C18 PuriFlash column, 0-100% MeCN/H2O with 0.1% NH4OH) afforded 1-(5-fluoro-2-methoxy-4-(4-methyl-2-oxopyridin-1(2H)-yl)phenyl)-N-(isoxazol-3-yl)-N-(4-methoxybenzyl)-2-oxo-1,2-dihydroquinoline-6-sulfonamide (25 mg, 0.039 mmol, 3.5% yield). m/z (ESI) 643.2 (M+H)$^+$.

Intermediate CJ: 2-(3-(difluoromethoxy)-5-fluorophenyl)-4,4,5,5-tetramethyl-1,3,2-dioxaborolane

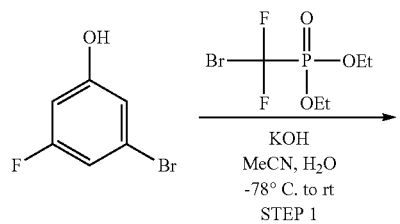

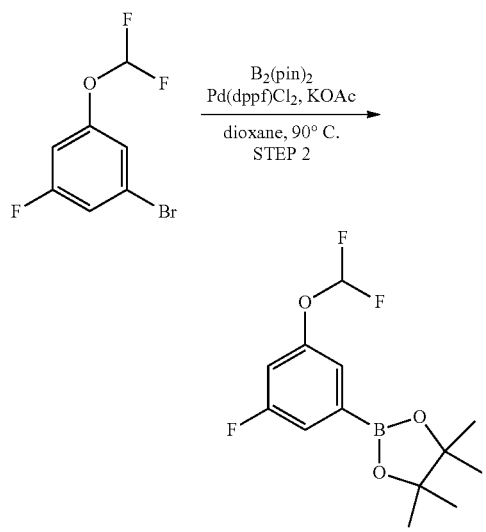

Step 1: 1-Bromo-3-(Difluoromethoxy)-5-Fluorobenzene

A MeCN (6.5 mL)/$H_2O$ (6.5 mL) mixture of potassium hydroxide (1469 mg, 26.2 mmol) and 3-bromo-5-fluorophenol (250 mg, 1.309 mmol) was cooled to −78° C. in an open 50-mL teardrop flask, and bromodifluoromethyl diethylphosphonate (465 μl, 2.62 mmol) was added. The cooling bath was removed, and the white slurry was allowed to warm to rt. After 20 min, the reaction was diluted with EtOAc and the layers were separated. The organic layer was dried over $Na_2SO_4$, filtered, and concentrated in vacuo to a colorless oil. Column chromatography (12 g Redisep Gold column, 0-80% EtOAc/hept) afforded 1-bromo-3-(difluoromethoxy)-5-fluorobenzene (189 mg, 0.784 mmol, 59.9% yield) as a colorless oil. $^1$H NMR (400 MHz, DMSO-$d_6$) δ ppm 7.15-7.59 (m, 4H). $^{19}$F NMR (376 MHz, DMSO-$d_6$) δ ppm −108.47 (s, 2F) −83.75 (s, 1F).

Step 2: 2-(3-(difluoromethoxy)-5-fluorophenyl)-4,4,5,5-tetramethyl-1,3,2-dioxaborolane A 40-mL vial containing 1-bromo-3-(difluoromethoxy)-5-fluorobenzene (388.6 mg, 1.612 mmol), 1,1'-bis(diphenylphosphino)ferrocene palladium(II)dichloride dichloromethane adduct (65.8 mg, 0.081 mmol), bis(pinacolato)diboron (450 mg, 1.774 mmol), and potassium acetate (475 mg, 4.84 mmol) was flushed with $N_2$ and subsequently charged with dioxane (4 mL). The slurry was stirred at 90° C. for 3.5 h. After cooling to rt, the reaction was quenched with $H_2O$ and extracted thrice with EtOAc. The organic extracts were combined, washed with brine, dried over $Na_2SO_4$, filtered, and concentrated in vacuo to a black oil. Column chromatography (25 g Snap Ultra, 0% to 100% EtOAc/hept) afforded 2-(3-(difluoromethoxy)-5-fluorophenyl)-4,4,5,5-tetramethyl-1,3,2-dioxaborolane (228.9 mg, 0.795 mmol, 49.3% yield) as a colorless oil. $^1$H NMR (400 MHz, DMSO-$d_6$) δ ppm 1.31 (s, 12H) 7.13-7.56 (m, 4H). $^{19}$F NMR (376 MHz, DMSO-$d_6$) δ ppm −110.61 (s, 1F) −82.87 (s, 2F).

Intermediate CK: (P)-perfluorophenyl 1-(4-bromo-2-methoxyphenyl)-2-oxo-1,2-dihydroquinoline-6-sulfonate

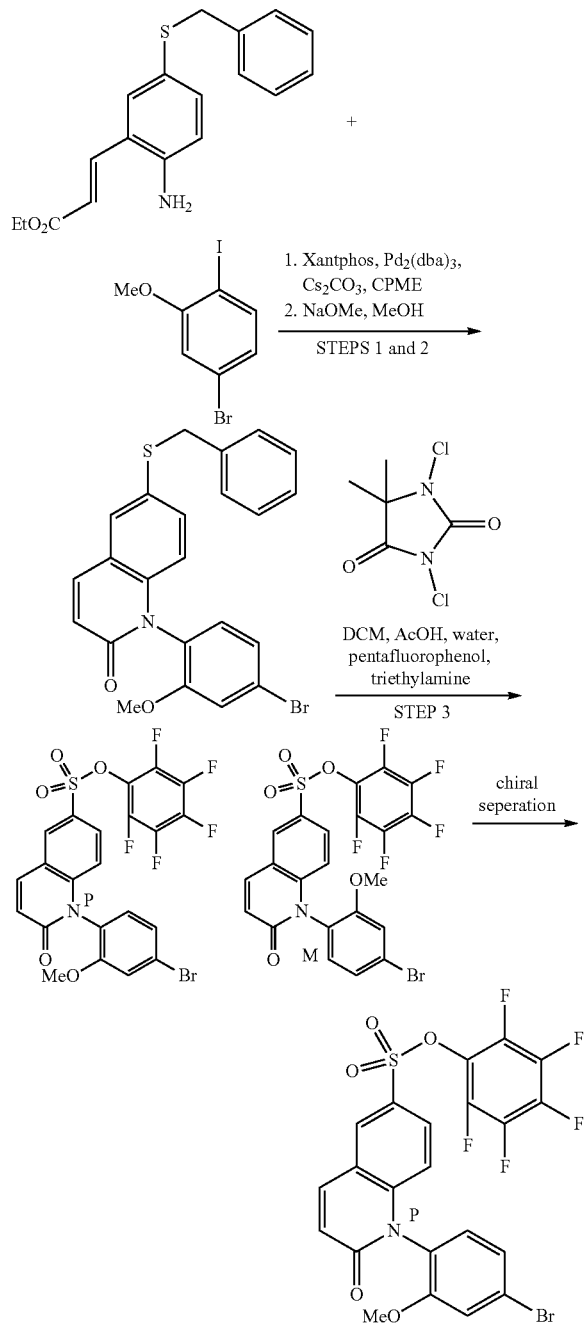

Step 1: (E)-ethyl 3-(5-(benzylthio)-2-((4-bromo-2-methoxyphenyl)amino)phenyl)acrylate A RBF charged with xantphos (9.97 g, 17.23 mmol), pd2(dba)3 (5.26 g, 5.74 mmol), 4-bromo-1-iodo-2-methoxybenzene (74.9 g, 239 mmol), (E)-ethyl 3-(2-amino-5-(benzylthio)phenyl)acrylate (60.000 g, 191 mmol), cesium carbonate (100 g, 306 mmol), and 400 ml cylopentylmethylether was heated to 90° C. overnight. The reaction mixture was then poured into water and extracted with DCM. The organics were dried over MgSO4 and concentrated. The crude residue was triturated with IPA leaving a yellow solid that was collected and dried yielding (E)-ethyl 3-(5-(benzylthio)-2-((4-bromo-2-methoxyphenyl)amino)phenyl)acrylate (86.95 g, 174 mmol, 91% yield). m/z (ESI) 500.1 (M+H)$^+$.

Step 2: 6-(benzylthio)-1-(4-bromo-2-methoxyphenyl)quinolin-2(1H)-one

A suspension of (E)-ethyl 3-(5-(benzylthio)-2-((4-bromo-2-methoxyphenyl)amino)phenyl)acrylate (86.95 g, 174 mmol) in 350 mL MeOH was heated to 70° C., was treated with sodium methoxide 25% wt in MeOH (19.06 ml, 69.8 mmol) and was allowed to stir overnight. The reaction mixture was then concentrated. The crude solid was triturated with IPA yielding 47.13 g clean product. The IPA washings were concentrated. Purification of the crude residue by silica gel column chromatography (0-100% EtOAc/heptane) gave an additional 10.76 g of slightly impure product. 6-(benzylthio)-1-(4-bromo-2-methoxyphenyl)quinolin-2(1H)-one (57.89 g, 128 mmol, 73.4% yield). (ESI) 451.8 (M+H)$^+$.

Step 3: (P)-perfluorophenyl 1-(4-bromo-2-methoxyphenyl)-2-oxo-1,2-dihydroquinoline-6-sulfonate and (M)-perfluorophenyl 1-(4-bromo-2-methoxyphenyl)-2-oxo-1,2-dihydroquinoline-6-sulfonate A solution of 6-(benzylthio)-1-(4-bromo-2-methoxyphenyl)quinolin-2(1H)-one (57.89 g, 128 mmol) in 400 mL DCM was treated with 15 mL HOAc and 10 mL water and was cooled to 0° C. 1,3-dichloro-5,5-dimethylimidazolidine-2,4-dione (25.2 g, 128 mmol) was added portionwise. After stirring for 30 minutes, an additional 0.5 equivalents of 1,3-dichloro-5,5-dimethylimidazolidine-2,4-dione was added portionwise. After stirring for an additional 30 minutes, the reaction mixture was then treated with pentafluorophenol (16.06 mL, 154 mmol) and was maintained at 0° C. triethylamine (71.3 mL, 512 mmol) was added dropwise via addition funnel over 30 minutes. The reaction mixture was diluted with DCM, washed with water, and the organics were dried over MgSO4 and concentrated. The crude residue was triturated with IPA then dried and collected yielding perfluorophenyl 1-(4-bromo-2-methoxyphenyl)-2-oxo-1,2-dihydroquinoline-6-sulfonate (58.7 g, 102 mmol, 80% yield) as a mixture of atrope isomers. m/z (ESI) 576.0 (M+H)$^+$. The atropisomers were separated using supercritical fluid chromatography (SFC). The column used was (S,S) Whelk-O, 2×15 cm. The mobile phase was run under isocratic conditions; CO2 with 50% isopropanol to afford product as an off-white solid. First atropisomer (peak 1): (P)-perfluorophenyl 1-(4-bromo-2-methoxyphenyl)-2-oxo-1,2-dihydroquinoline-6-sulfonate (26.6 g, 46.2 mmol, 36.1% yield) $^1$H NMR (ACETONITRILE-d3): 8.33 (d, J=2.2 Hz, 1H), 8.01 (d, J=9.4 Hz, 1H), 7.85 (dd, J=9.1, 2.2 Hz, 1H), 7.47 (d, J=2.1 Hz, 1H), 7.39 (dd, J=8.3, 2.0 Hz, 1H), 7.23 (d, J=8.3 Hz, 1H), 6.86 (d, J=9.0 Hz, 1H), 6.81 (d, J=9.7 Hz, 1H), 3.73 (s, 3H). m/z (ESI) 576.0 (M+H)$^+$. Second atropisomer (peak 2): (M)-perfluorophenyl 1-(4-bromo-2-methoxyphenyl)-2-oxo-1,2-dihydroquinoline-6-sulfonate (26.6 g, 46.2 mmol, 36.1% yield). $^1$H NMR (ACETONITRILE-d3): 8.33 (d, J=2.2 Hz, 1H), 8.00 (d, J=9.6 Hz, 1H), 7.85 (dd, J=9.0, 2.3 Hz, 1H), 7.46 (d, J=2.0 Hz, 1H), 7.38 (dd, J=8.3, 2.1 Hz, 1H), 7.22 (d, J=8.3 Hz, 1H), 6.86 (d, J=9.0 Hz, 1H), 6.81 (d, J=9.6 Hz, 1H), 3.72 (s, 3H). m/z (ESI) 576.0 (M+H)$^+$.

Intermediate CL: (P)-perfluorophenyl 1-(4'-chloro-3-methoxy-[1,1'-biphenyl]-4-yl)-2-oxo-1,2-dihydroquinoline-6-sulfonate

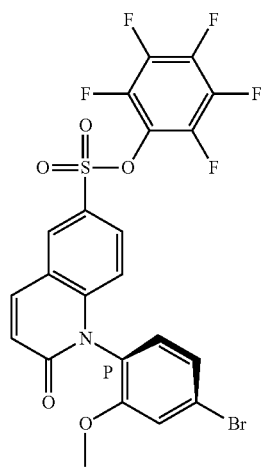

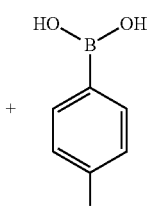

A 40-mL vial containing (P)-perfluorophenyl 1-(4-bromo-2-methoxyphenyl)-2-oxo-1,2-dihydroquinoline-6-sulfonate (1.037 g, 1.799 mmol), 4-chlorophenylboronic acid (0.844 g, 5.40 mmol), cesium carbonate (0.576 ml, 7.20 mmol), 1,1-bis[(di-t-butyl-p-methylaminophenyl]palladium(II) chloride (0.255 g, 0.360 mmol), and copper(I) chloride (0.534 g, 5.40 mmol) was flushed with N2 and then charged with DMF (9 mL). The vial was stirred at 50° C. for 15 min. The brown slurry was cooled to rt, quenched with H$_2$O, and extracted thrice with EtOAc. The organic extracts were combined, washed with brine, dried over Na$_2$SO$_4$, filtered, and concentrated in vacuo to a red oil. Column chromatography (50 g Snap Ultra column, 15% to 75% EtOAc/hept) afforded (P)-perfluorophenyl 1-(4'-chloro-3-methoxy-[1,1'-biphenyl]-4-yl)-2-oxo-1,2-dihydroquinoline-6-sulfonate (1.080 g, 1.777 mmol, 99% yield) as a gray-purple amorphous solid. $^1$H NMR (400 MHz, DMSO-d$_6$) δ ppm 3.80 (s, 3H) 6.90 (t, J=8.30 Hz, 2H) 7.46-7.50 (m, 2H) 7.55-7.63 (m, 3H) 7.86-7.89 (m, 2H) 7.99 (dd, J=9.07, 2.33 Hz, 1H) 8.27 (d, J=9.54 Hz, 1H) 8.60 (d, J=2.28 Hz, 1H). m/z (ESI) 608.0 (M+H)$^+$.

Intermediate CM: Perfluorophenyl 1-(6-(3-fluorophenyl)-4-methoxypyridin-3-yl)-2-oxo-1,2-dihydroquinoline-6-sulfonate

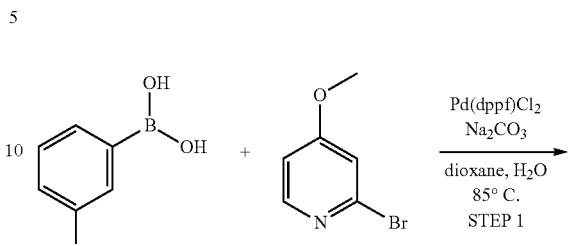

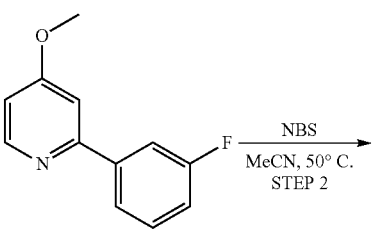

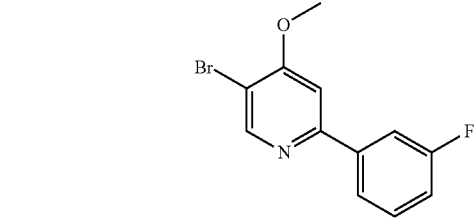

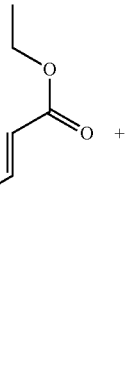

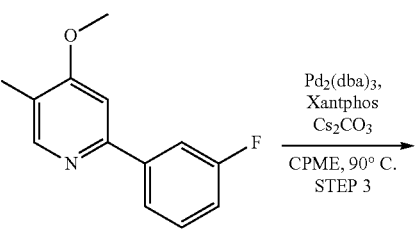

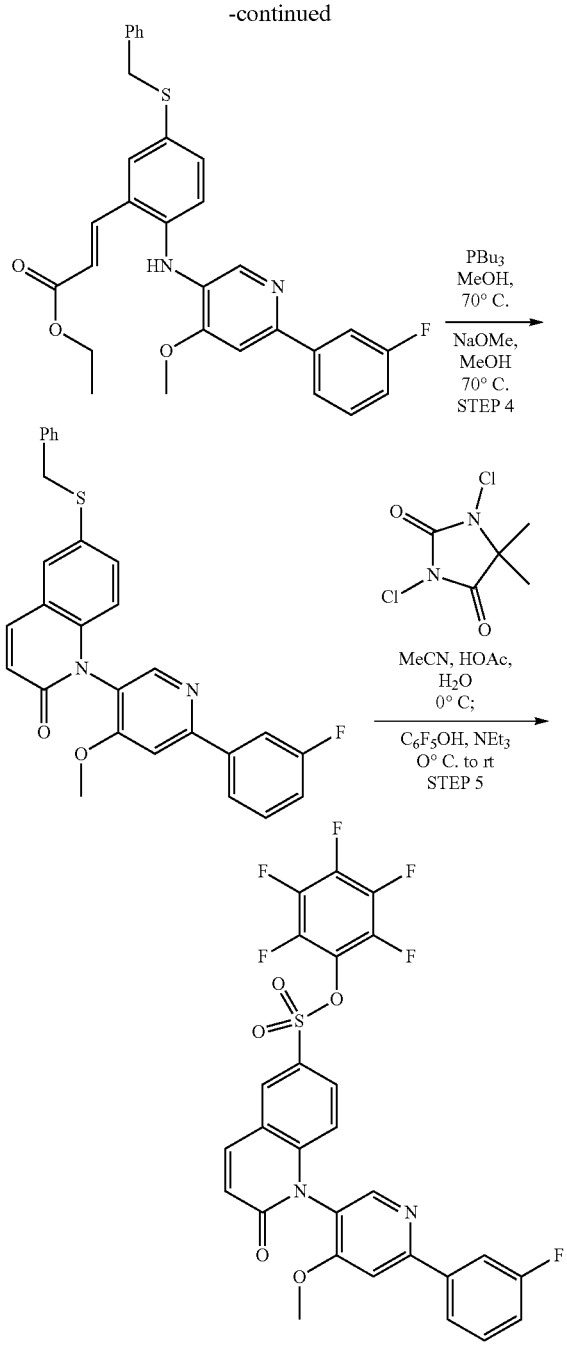

Step 1: 2-(3-fluorophenyl)-4-methoxypyridine

A 100-mL recovery flask containing 2-bromo-4-methoxypyridine (1.446 g, 7.69 mmol, purchased from Combi-Blocks, Inc.), 3-fluorophenylboronic acid (2.152 g, 15.38 mmol, purchased from Oakwood Products, Inc.), and 1,1'-bis(diphenylphosphino)ferrocene palladium(II)dichloride dichloromethane adduct (0.314 g, 0.385 mmol) was flushed with $N_2$ and subsequently charged with dioxane (29 mL) and 1.9 M $Na_2CO_3$ in $H_2O$ (10 mL). The black-red mixture was stirred at 85° C. overnight. The next morning, after cooling to rt, the dark red mixture was diluted with $H_2O$ and extracted thrice with EtOAc. The organic extracts were combined, washed with brine, dried over $Na_2SO_4$, filtered, and concentrated in vacuo to a black oil. Column chromatography (50 g Snap Ultra column, 10-100% EtOAc/hept) afforded 2-(3-fluorophenyl)-4-methoxypyridine (2.25 g, >99% yield) as a viscous yellow oil. m/z (ESI) 204.2 $(M+H)^+$.

Step 2: 5-bromo-2-(3-fluorophenyl)-4-methoxypyridine

A MeCN (22 mL) solution of 2-(3-fluorophenyl)-4-methoxypyridine (2.21 g, 10.88 mmol) and N-bromosuccinimide (2.129 g, 11.96 mmol) in a 40-mL vial was wrapped in aluminum foil and stirred at 55° C. overnight. 22 h later, the reaction was cooled to rt, quenched with 1:1 sat. aq. $NaHCO_3$:sat. aq. $Na_2S_2O_3$ and extracted thrice with EtOAc. The organic extracts were combined, washed with brine, dried over $Na_2SO_4$, filtered, and concentrated in vacuo to a brown oil. Column chromatography (50 g Snap Ultra column, 15% to 100% EtOAc/hept) afforded 5-bromo-2-(3-fluorophenyl)-4-methoxypyridine (0.420 g, 1.489 mmol, 13.69% yield) as a white amorphous solid. m/z (ESI) 282.0 $(M+H)^+$.

Step 3: (E)-ethyl 3-(5-(benzylthio)-2-((6-(3-fluorophenyl)-4-methoxypyridin-3-yl)amino)phenyl)acrylate A 40-mL vial containing 5-bromo-2-(3-fluorophenyl)-4-methoxypyridine (0.420 g, 1.489 mmol), (E)-ethyl 3-(2-amino-5-(benzylthio)phenyl)acrylate (0.560 g, 1.787 mmol), Xantphos (0.172 g, 0.298 mmol), cesium carbonate (0.679 g, 2.084 mmol), and $Pd_2(dba)_3$ (0.136 g, 0.149 mmol) was flushed with $N_2$ and charged with CPME (3 mL). After stirring overnight at 90° C., additional $Pd_2(dba)_3$ (0.136 g, 0.149 mmol) and Xantphos (0.172 g, 0.298 mmol) was added. After stirring an additional 4 h, the reaction was cooled to rt, quenched with $H_2O$ and extracted thrice with EtOAc. The organic extracts were combined, washed with brine, dried over $Na_2SO_4$, filtered, and concentrated in vacuo to a brown-black oil. Column chromatography (50 g Snap Ultra column, 0% to 80% EtOAc/hept) afforded (E)-ethyl 3-(5-(benzylthio)-2-((6-(3-fluorophenyl)-4-methoxypyridin-3-yl)amino)phenyl)acrylate (0.615 g, 1.195 mmol, 80% yield) as a yellow oil. m/z (ESI) 515.2 $(M+H)^+$.

Step 4: 6-(benzylthio)-1-(6-(3-fluorophenyl)-4-methoxypyridin-3-yl)quinolin-2(1H)-one A MeOH solution of (E)-ethyl 3-(5-(benzylthio)-2-((6-(3-fluorophenyl)-4-methoxypyridin-3-yl)amino)phenyl)acrylate (0.615 g, 1.195 mmol) and tributylphosphine (0.060 ml, 0.239 mmol) in a 40-mL vial was stirred overnight at 70° C. Sodium methoxide, 25 wt % solution in methanol (0.106 ml, 0.478 mmol) was then added. After stirring for 2 h, the reaction was concentrated under a stream of $N_2$ and purified via column chromatography (50 g Snap Ultra column, 0% to 100% EtOAc/hept) to afford 6-(benzylthio)-1-(6-(3-fluorophenyl)-4-methoxypyridin-3-yl)quinolin-2(1H)-one (186.7 mg, 0.398 mmol, 33.3% yield) as a yellow amorphous solid. $^1$H NMR (400 MHz, DMSO-$d_6$) δ ppm 3.92 (s, 3H) 4.26 (s, 2H) 6.60 (d, J=8.81 Hz, 1H) 6.72 (d, J=9.53 Hz, 1H) 7.20-7.39 (m, 6H) 7.42 (dd, J=8.81, 2.18 Hz, 1H) 7.61 (dd, J=8.03, 1.92 Hz, 1H) 7.83 (d, J=2.18 Hz, 1H) 7.90 (s, 1H) 8.00 (d, J=9.43 Hz, 1H) 8.04-8.09 (m, 1H) 8.09-8.13 (m, 1H) 8.45 (s, 1H). m/z (ESI) 469.2 $(M+H)^+$.

Step 5: Perfluorophenyl 1-(6-(3-fluorophenyl)-4-methoxypyridin-3-yl)-2-oxo-1,2-dihydroquinoline-6-sulfonate A yellow MeCN (5 mL)/HOAc (0.18 mL)/H$_2$O (0.12 mL) slurry of 6-(benzylthio)-1-(6-(3-fluorophenyl)-4-methoxypyridin-3-yl)quinolin-2(1H)-one (177.8 mg, 0.379 mmol) was cooled to 0° C. open to air and subsequently treated with 1,3-dichloro-5,5-methylhydantoin (64.8 µl, 0.493 mmol). After stirring for 20 min at 0° C., an additional 50 mg of 1,3-dichloro-5,5-methylhydantoin was added. After stirring another 20 min, perfluorophenol (43.7 µl, 0.417 mmol) and triethylamine (211 µl, 1.518 mmol) were then added, and the cooling bath was removed. After stirring for 20 min, the reaction was quenched with H$_2$O and extracted thrice with EtOAc. The organic extracts were combined, washed with brine, dried over Na$_2$SO$_4$, filtered, and concentrated in vacuo to a yellow oil. Column chromatography (25 g Snap Ultra column, 0% to 100% EtOAc/hept) afforded perfluorophenyl 1-(6-(3-fluorophenyl)-4-methoxypyridin-3-yl)-2-oxo-1,2-dihydroquinoline-6-sulfonate (140.1 mg, 0.236 mmol, 62.3% yield) as an amorphous white solid. m/z (ESI) 593.0 (M+H)$^+$.

Intermediate CN: (P)-perfluorophenyl 1-(2,4'-difluoro-5-methoxy-[1,1'-biphenyl]-4-yl)-2-oxo-1,2-dihydroquinoline-6-sulfonate A 40-mL vial containing (P)-perfluorophenyl 1-(4-bromo-5-fluoro-2-methoxyphenyl)-2-oxo-1,2-dihydroquinoline-6-sulfonate (1.050 g, 1.767 mmol), 4-fluorophenylboronic acid (0.742 g, 5.30 mmol), cesium carbonate (0.565 ml, 7.07 mmol), 1,1-bis[(di-t-butyl-p-methylaminophenyl]palladium (II) chloride (0.250 g, 0.353 mmol), and copper(I) chloride (0.149 ml, 5.30 mmol) was flushed with N$_2$ and then charged with DMF (9 mL). The vial was stirred at 50° C. for 1 h. The brown slurry was then cooled to rt, quenched with H2O, and extracted thrice with EtOAc. The organic extracts were combined, washed with brine, dried over Na2SO4, filtered, and concentrated in vacuo to a brown oil. Column chromatography (50 g Snap Ultra column, 15% to 75% EtOAc/hept) afforded (P)-perfluorophenyl 1-(2,4'-difluoro-5-methoxy-[1,1'-biphenyl]-4-yl)-2-oxo-1,2-dihydroquinoline-6-sulfonate (560 mg, 0.919 mmol, 52.0% yield) as a brown amorphous solid. m/z (ESI) 610.0 (M+H)$^+$.

Intermediate CO: (P)-perfluorophenyl 1-(4-(5-chloro-2-methoxypyridin-3-yl)-5-fluoro-2-methoxyphenyl)-2-oxo-1,2-dihydroquinoline-6-sulfonate

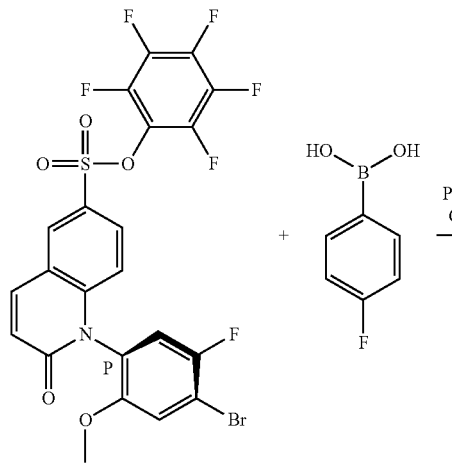

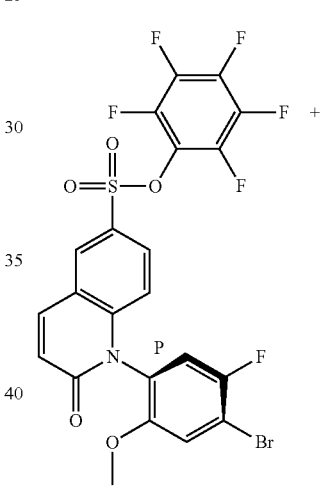

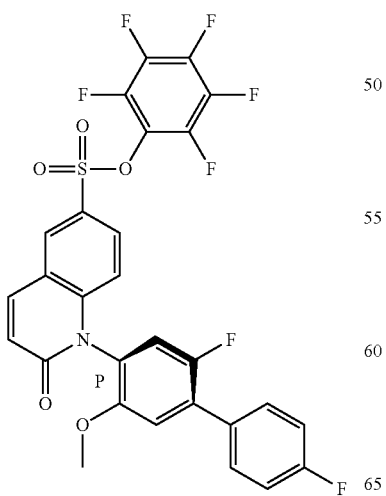

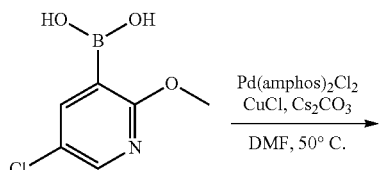

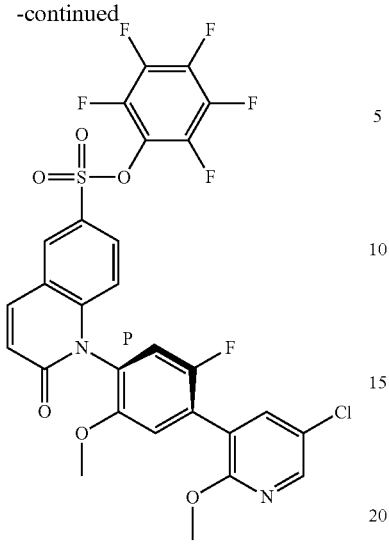

A 40-mL vial containing (P)-perfluorophenyl 1-(4-bromo-5-fluoro-2-methoxyphenyl)-2-oxo-1,2-dihydroquinoline-6-sulfonate (1.438 g, 2.419 mmol), (5-chloro-2-methoxypyridin-3-yl)boronic acid (0.971 ml, 7.26 mmol, purchased from Combi-Blocks, Inc.), cesium carbonate (0.774 ml, 9.68 mmol), 1,1-bis[(di-t-butyl-p-methylaminophenyl]palladium (II) chloride (0.343 g, 0.484 mmol), and copper(I) chloride (0.204 ml, 7.26 mmol) was flushed with $N_2$ and then charged with DMF (12 mL). The vial was stirred at 50° C. for 3 h. The brown slurry was cooled to rt, quenched with H2O, diluted with ~1:1 EtOAc/hept, and filtered through a plug of celite. The layers of the filtrate were separated, and the aqueous layer was extracted twice more with ~1:1 EtOAc/hept. The organic extracts were combined, washed twice with $H_2O$ and once with brine, dried over $Na_2SO_4$, filtered, and concentrated under a stream of $N_2$ to a brown oil. Column chromatography (50 g Snap Ultra column, 15% to 85% EtOAc/hept) afforded (P)-perfluorophenyl 1-(4-(5-chloro-2-methoxypyridin-3-yl)-5-fluoro-2-methoxyphenyl)-2-oxo-1,2-dihydroquinoline-6-sulfonate (783 mg, 1.192 mmol, 49.3% yield) as an off-white amorphous solid. m/z (ESI) 657.0 (M+H)$^+$.

Intermediate CP: Perfluorophenyl 1-(4-bromo-5-fluoro-2-hydroxyphenyl)-2-oxo-1,2-dihydroquinoline-6-sulfonate

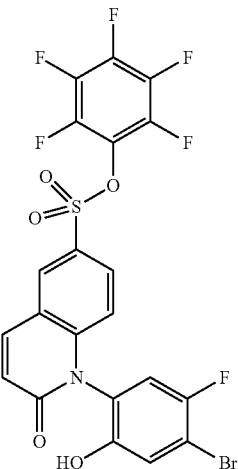

To a solution of perfluorophenyl 1-(4-bromo-5-fluoro-2-methoxyphenyl)-2-oxo-1,2-dihydroquinoline-6-sulfonate (5.0 g, 8.41 mmol) in DCM (56.1 ml) was added boron tribromide (0.811 ml, 8.41 mmol) at room temperature. The resulting mixture was stirred for 48 hr. The crude mixture was transferred to a sep. funnel containing saturated aqueous bicarb and the aqueous layer was washed 3× with DCM. The organic layers were combined, dried with MgSO4, filtered and concentrated to a white solid. The product was concentrated to a solid, redissolved in toluene (100 mls) and heated to 100° C. for 1 hour to racemize the product. The solution was then cooled to room temperature and concentrated to a solid (4.4 g, 89% crude yield). m/z (ESI) 582.0 (M+1)$^+$.

Intermediate CQ: 1-(4-bromo-5-fluoro-2-hydroxyphenyl)-N-(isoxazol-3-yl)-N-(4-methoxybenzyl)-2-oxo-1,2-dihydroquinoline-6-sulfonamide

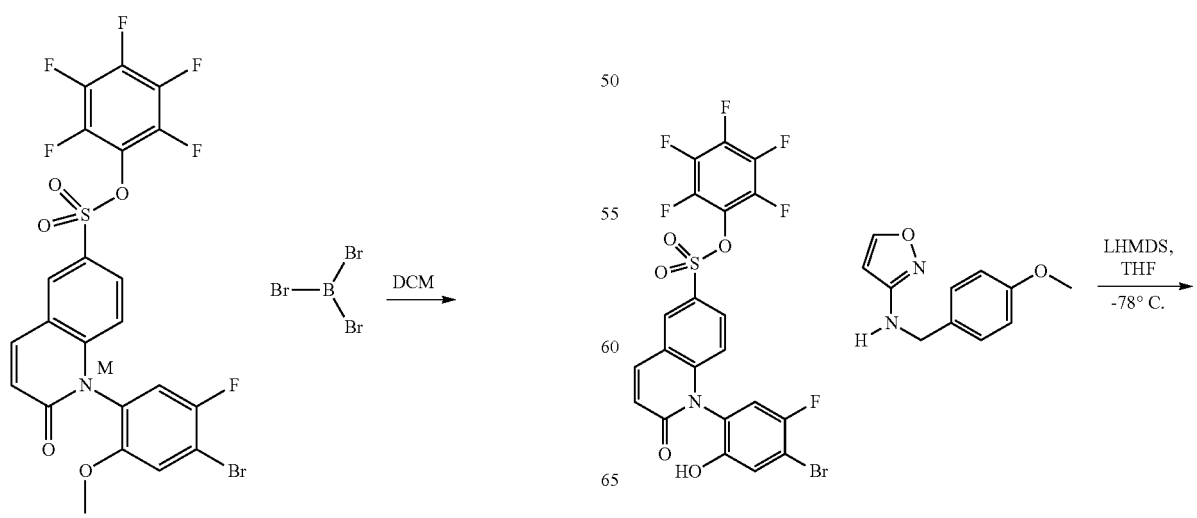

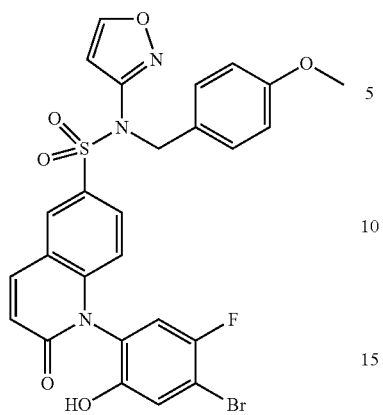

A solution of N-(4-methoxybenzyl)isoxazol-3-amine (3.37 g, 16.49 mmol) in THF (30.0 ml) was cooled to −78° C. LHMDS (15.74 ml, 15.74 mmol) was then added dropwise and the acetone/dry ice bath was removed for 5 minutes. The solution was then returned to −78° C. and a solution of perfluorophenyl 1-(4-bromo-5-fluoro-2-hydroxyphenyl)-2-oxo-1,2-dihydroquinoline-6-sulfonate (4.35 g, 7.50 mmol) in THF (30.0 ml) was added dropwise. The resulting solution was stirred for 4 hours warming to room temperature. Saturated ammonium chloride was added to the reaction mixture. The resulting mixture was transferred to a sep. funnel containing water and the aqueous layer was washed 3× with EtOAc. The organic layers were combined, dried with MgSO4, filtered and concentrated to an oil. The crude product was purified by ISCO MPLC (100% heptanes to 60% 3:1 EtOAc:EtOH). The product eluted at 50% 3:1 EtOAc:EtOH. m/z (ESI) 602.1 (M+1)+.

Intermediate CR: 1-(4-bromo-2-(cyanomethoxy)-5-fluorophenyl)-N-(isoxazol-3-yl)-N-(4-methoxybenzyl)-2-oxo-1,2-dihydroquinoline-6-sulfonamide

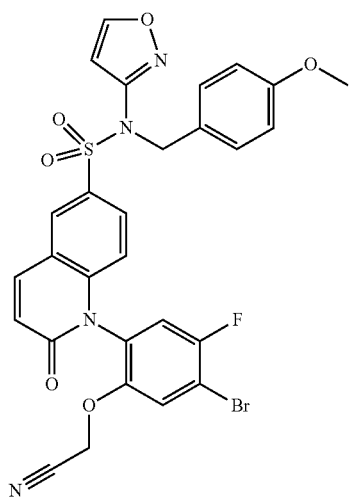

To a solution of 1-(4-bromo-5-fluoro-2-hydroxyphenyl)-N-(isoxazol-3-yl)-N-(4-methoxybenzyl)-2-oxo-1,2-dihydroquinoline-6-sulfonamide (0.80 g, 1.332 mmol) in DMF (2.66 ml) at room temperature was added potassium carbonate (0.184 g, 1.332 mmol) followed by bromoacetonitrile (0.102 ml, 1.466 mmol). The reaction mixture was stirred overnight. The resulting mixture was transferred to a sep. funnel containing water and the aqueous layer was washed 3× with DCM. The organic layers were combined, dried with MgSO4, filtered and concentrated to an oil. The crude material was used without further purification. m/z (ESI) 642.9 (M+1)+.

Intermediate CS: 1-(4-bromo-2-(cyanomethoxy)-5-fluorophenyl)-N-(isoxazol-3-yl)-2-oxo-1,2-dihydroquinoline-6-sulfonamide

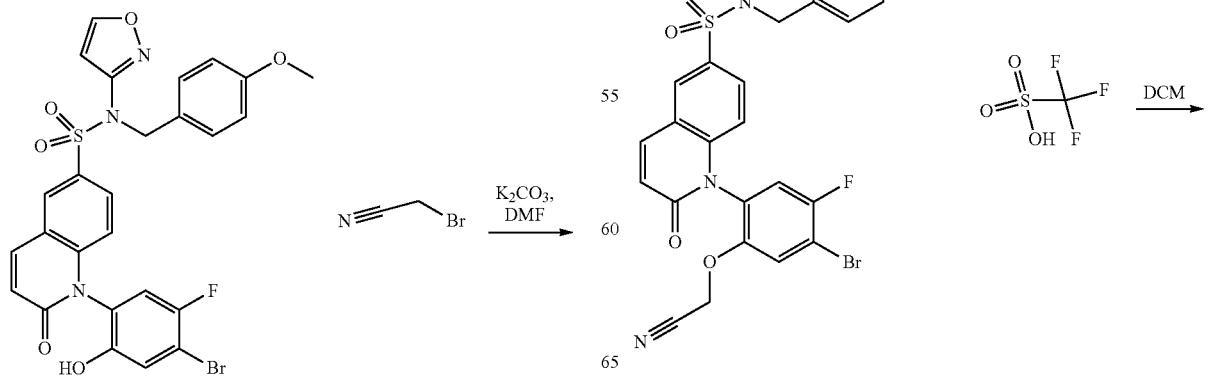

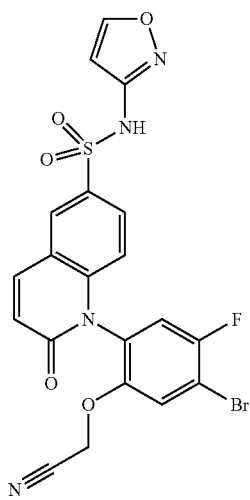

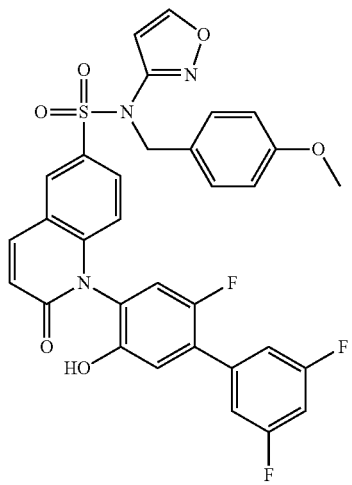

To a solution of 1-(4-bromo-2-(cyanomethoxy)-5-fluorophenyl)-N-(isoxazol-3-yl)-N-(4-methoxybenzyl)-2-oxo-1,2-dihydroquinoline-6-sulfonamide (0.80 g, 1.251 mmol) in DCM (12.51 ml) at room temperature was added trifluoromethanesulfonic acid (0.333 ml, 3.75 mmol). The resulting solution was stirred for 20 minutes and LCMS indicated that the reaction was complete. The reaction mixture was concentrated and loaded directly onto an silica column and purified by ISCO MPLC (100% heptanes to 75% 3:1 EtOAc:EtOH). The product eluted at 75% 3:1 EtOAc:EtOH. m/z (ESI) 522.9 (M+1)$^+$.

Intermediate CT: N-(isoxazol-3-yl)-N-(4-methoxybenzyl)-2-oxo-1-(2,3',5'-trifluoro-5-hydroxy-[1,1'-biphenyl]-4-yl)-1,2-dihydroquinoline-6-sulfonamide To a solution of 1-(4-bromo-5-fluoro-2-hydroxyphenyl)-N-(isoxazol-3-yl)-N-(4-methoxybenzyl)-2-oxo-1,2-dihydroquinoline-6-sulfonamide (0.037 g, 0.062 mmol) and (3,5-difluorophenyl)boronic acid (0.015 g, 0.092 mmol) in DMF (0.246 ml) and water (0.062 ml) was added potassium carbonate (0.026 g, 0.185 mmol) followed by PdCl$_2$dppf, DCM adduct (2.255 mg, 3.08 μmol). The resulting mixture was heated to 50° C. and stirred for 2.5 hours. The solution was then cooled to room temperature and transferred to a sep. funnel containing water. The aqueous layer was washed 2× with DCM. The aqueous layer was subsequently neutralized and washed 3× with DCM. The organic layers were combined, dried with MgSO$_4$, filtered and concentrated to an oil. The crude product was used without further purification assuming quantitative yield. m/z (ESI) 634.2 (M+H)$^+$.

Intermediate CU: Tert-butyl 3-(5-bromo-4-fluoro-2-(6-(N-(isoxazol-3-yl)-N-(4-methoxybenzyl)sulfamoyl)-2-oxoquinolin-1(2H)-yl)phenoxy)pyrrolidine-1-carboxylate

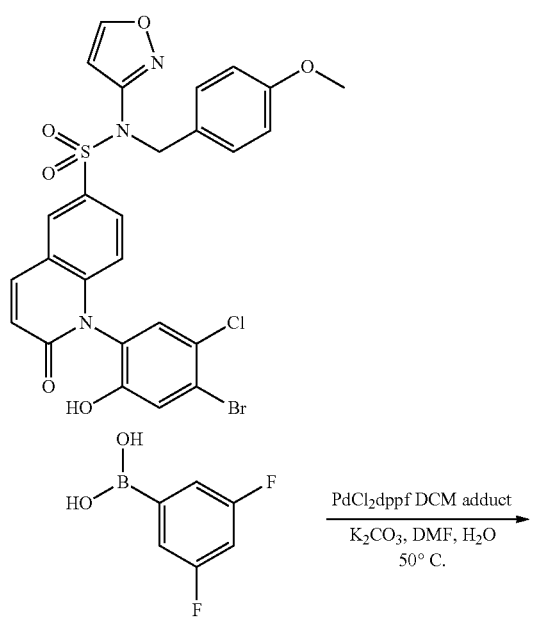

PdCl$_2$dppf DCM adduct
K$_2$CO$_3$, DMF, H$_2$O
50° C.

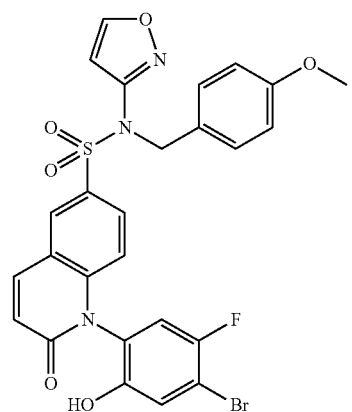

53

-continued

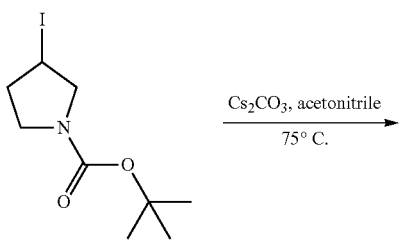

Cs₂CO₃, acetonitrile
75° C.

54

Intermediate CV: 1-(5-(1-cyanoethoxy)-2,3',5'-trifluoro-[1,1'-biphenyl]-4-yl)-N-(isoxazol-3-yl)-2-oxo-1,2-dihydroquinoline-6-sulfonamide

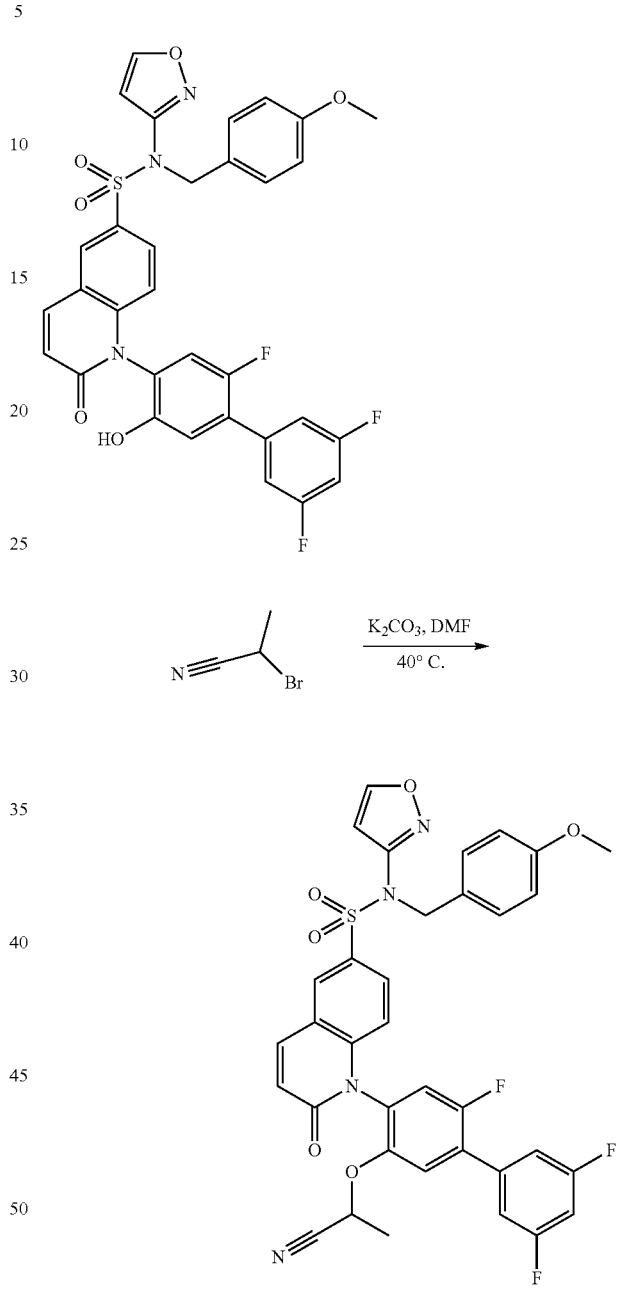

Tert-butyl 3-iodopyrrolidine-1-carboxylate (0.029 g, 0.097 mmol) was added to a solution of 1-(4-bromo-5-fluoro-2-hydroxyphenyl)-N-(isoxazol-3-yl)-N-(4-methoxybenzyl)-2-oxo-1,2-dihydroquinoline-6-sulfonamide (0.058 g, 0.097 mmol) and cesium carbonate (0.063 g, 0.193 mmol) in acetonitrile (0.242 ml) and stirred for 48 hr. The reaction vessel was cooled to room temperature. The reaction mixture was then transferred to a sep. funnel and the aqueous layer was washed 3× with EtOAc. The organic layers were combined, dried with MgSO₄, filtered and concentrated to an oil. The crude mixture was taken onward to the next step assuming quantitative yield. m/z (ESI) 670.9 (M+H)⁺.

To a solution of N-(isoxazol-3-yl)-N-(4-methoxybenzyl)-2-oxo-1-(2,3',5'-trifluoro-5-hydroxy-[1,1'-biphenyl]-4-yl)-1,2-dihydroquinoline-6-sulfonamide (0.066 g, 0.104 mmol) in DMF (0.208 ml) at room temperature was added potassium carbonate (0.016 g, 0.115 mmol) followed by 2-bromopropanenitrile (0.014 ml, 0.156 mmol). The reaction mixture was stirred 16 hr. The resulting mixture was transferred to a sep. funnel containing water and the aqueous layer was washed 3× with DCM. The organic layers were combined, dried with MgSO₄, filtered and concentrated to an oil. The crude material was taken onward to the next step without further purification, assuming quantitative yield. m/z (ESI) 687.1 (M+H)⁺.

55

Intermediate CW: (P)-perfluorophenyl 1-(2-fluoro-3',5,5'-trimethoxy-[1,1'-biphenyl]-4-yl)-2-oxo-1,2-dihydroquinoline-6-sulfonate

56

Intermediate CX: (P)-perfluorophenyl 1-(3'-(difluoromethoxy)-2-fluoro-5-methoxy-[-[1,1'-biphenyl]-4-yl)-2-oxo-1,2-dihydroquinoline-6-sulfonate

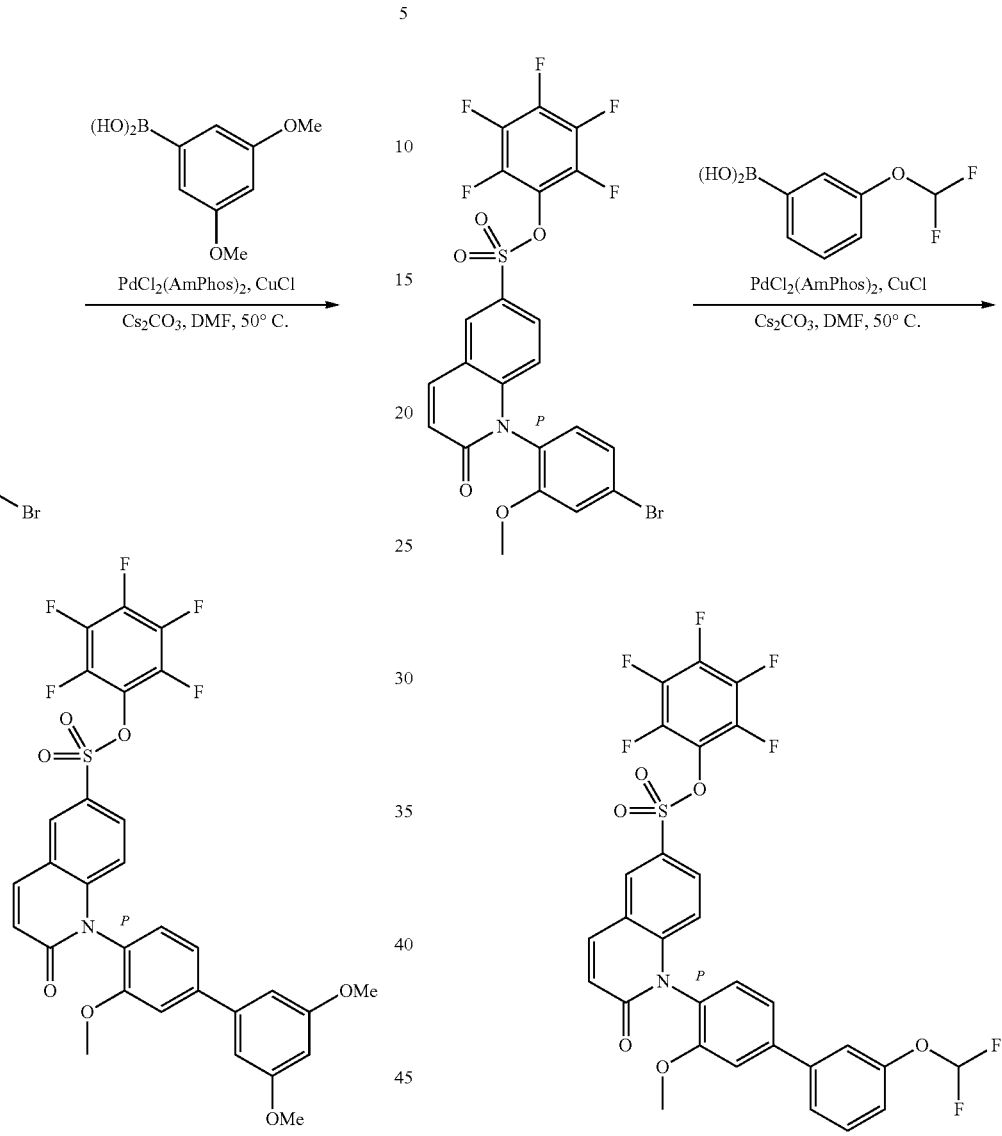

A 20-mL vial containing perfluorophenyl 1-(4-bromo-5-fluoro-2-methoxyphenyl)-2-oxo-1,2-dihydroquinoline-6-sulfonate (0.3 g, 0.505 mmol), 3,5-dimethoxyphenylboronic acid (0.14 g, 0.76 mmols), cesium carbonate (0.162 ml, 2.019 mmol), 1,1-bis[(di-t-butyl-p-methylaminophenyl]palladium(ii) chloride (0.071 g, 0.101 mmol), and copper(i) chloride (0.150 g, 1.514 mmol) was flushed with $N_2$ and then charged with N, N-dimethylformamide (2.52 ml). The vial was stirred at 50° C. for 2 hours. The brown slurry was cooled to rt, quenched with $H_2O$, and extracted thrice with EtOAc. The organic extracts were combined, washed with brine, dried over $Na_2SO_4$, filtered, and concentrated in vacuo to a red oil. Biotage column chromatography (50 g Snap Ultra, 15% to 75% EtOAc/hept) afforded (P)-perfluorophenyl 1-(2-fluoro-3',5,5'-trimethoxy-[1,1'-biphenyl]-4-yl)-2-oxo-1,2-dihydroquinoline-6-sulfonate (0.2688 g, 0.413 mmol, 82% yield) as an orange amorphous solid. m/z (ESI) 651.9 $(M+H)^+$.

A 20-mL vial containing perfluorophenyl 1-(4-bromo-5-fluoro-2-methoxyphenyl)-2-oxo-1,2-dihydroquinoline-6-sulfonate (0.3 g, 0.505 mmol), 3-(difluoromethoxy)phenylboronic acid (0.17 g, 0.91 mmol), cesium carbonate (0.162 ml, 2.019 mmol), 1,1-bis[(di-t-butyl-p-methylaminophenyl] palladium(ii) chloride (0.071 g, 0.101 mmol), and copper(i) chloride (0.150 g, 1.514 mmol) was flushed with $N_2$ and then charged with N, N-dimethylformamide (2.52 ml). The vial was stirred at 50° C. for 1.75 hours. The brown slurry was cooled to rt, quenched with $H_2O$, and diluted with EtOAc, 1 N HCl and saturated $NH_4Cl$. The aqueous layer was extracted 2× with EtOAc. The organic extracts were combined, washed with brine, dried over $Na_2SO_4$, filtered, and concentrated in vacuo to a red oil. Biotage column chromatography (25 g Snap Ultra, 20% to 100% EtOAc/hept) followed by a second column (25 g puriFlash, 0% to 80% EtOAc/hept) afforded (P)-perfluorophenyl 1-(3'-(difluoromethoxy)-2-fluoro-5-methoxy-[1,1'-biphenyl]-4-yl)-2- oxo-1,2-dihydroquinoline-6-sulfonate (0.202 g, 0.307 mmol, 60.9% yield) as a orange foam. m/z (ESI) 657.9 (M+H)+.

Intermediate CY: (P)-perfluorophenyl 1-(3,3'-dimethoxy-4'-methy-[1,1'-biphenyl]-4-yl)-2-oxo-1,2-dihydroquinoline-6-sulfonate

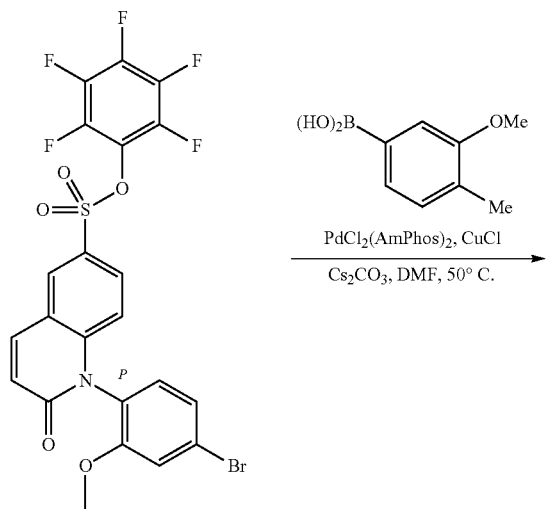

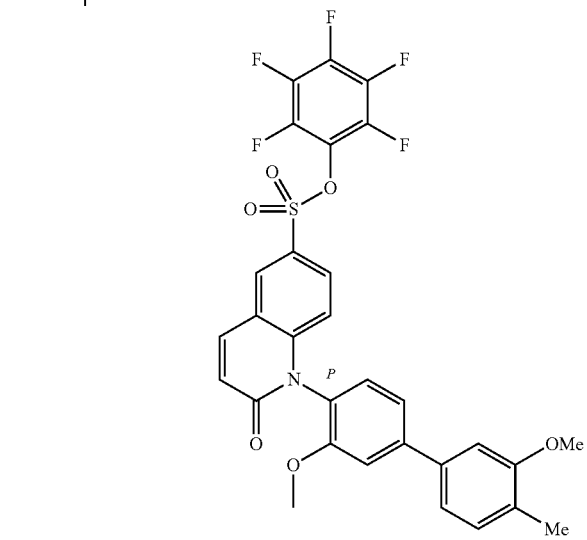

A 20-mL vial containing perfluorophenyl 1-(4-bromo-2-methoxyphenyl)-2-oxo-1,2-dihydroquinoline-6-sulfonate (0.45 g, 0.781 mmol), 3-methoxy-4-methylphenylboronic acid (0.259 g, 1.562 mmol), cesium carbonate (0.250 ml, 3.12 mmol), 1,1-bis[(di-t-butyl-p-methylaminophenyl]palladium(ii) chloride (0.111 g, 0.156 mmol), and copper(i) chloride (0.232 g, 2.343 mmol) was flushed with $N_2$ and then charged with N, N-dimethylformamide (3.90 ml). The vial was stirred at 50° C. for 1.75 hours. The brown slurry was cooled to rt, quenched with $H_2O$, and diluted with EtOAc and saturated $NH_4Cl$. The aqueous layer was extracted 2× with EtOAc. The organic extracts were combined, washed with brine, dried over $MgSO_4$, filtered over a 1"pad of $SiO_2$, and concentrated in vacuo to a red oil. Biotage column chromatography (25 g Snap Ultra, 0% to 100% EtOAc/hept) followed by a second column (25 g puriFlash, 0% to 80% EtOAc/hept) afforded (p)-perfluorophenyl 1-(3,3'-dimethoxy-4'-methyl-[1,1'-biphenyl]-4-yl)-2-oxo-1,2-dihydroquinoline-6-sulfonate (0.481 g, 0.779 mmol, 100% yield) as a orange foam m/z (ESI) 618.0 (M+H)+.

Intermediate CZ: 2-(3-(difluoromethyl)-5-fluorophenyl)-4,4,5,5-tetramethyl-1,3,2-dioxaborolane

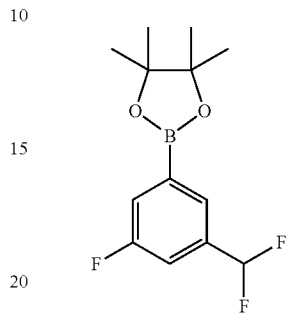

A solution of $PdCl_2$(dppf)-DCM adduct (0.399 g, 0.489 mmol), bis(pinacolato)diboron (2.73 g, 10.76 mmol), 1-bromo-3-(difluoromethyl)-5-fluorobenzene (Oakwood Chemicals, 2.200 g, 9.78 mmol) and potassium acetate (3.84 g, 39.1 mmol) in 35 mL DMF was heated to 100° C. overnight. The reaction mixture was then diluted with DCM and was washed with water. The organics were dried over $MgSO_4$ and concentrated. Purification of the crude residue by silica gel column chromatography (0-70% EtOAc/heptane) gave 2-(3-(difluoromethyl)-5-fluorophenyl)-4,4,5,5-tetramethyl-1,3,2-dioxaborolane (1.64 g, 6.03 mmol, 61.6% yield) as a yellow oil. $^1$H NMR (Acetone): 7.72-7.78 (m, 1H), 7.44-7.58 (m, 2H), 6.99 (s, 1H), 1.32-1.43 (m, 12H). (ESI) 273.2 (M+H)+.

Intermediates DA and DB: Perfluorophenyl 3-chloro-1-(2,3'-difluoro-5-methoxy-[1,1'-biphenyl]-4-yl)-2-methyl-4-oxo-1,4-dihydroquinoline-6-sulfonate and Perfluorophenyl 1-(2,3'-difluoro-5-methoxy-[1,1'-biphenyl]-4-yl)-2-methyl-4-oxo-1,4-dihydroquinoline-6-sulfonate

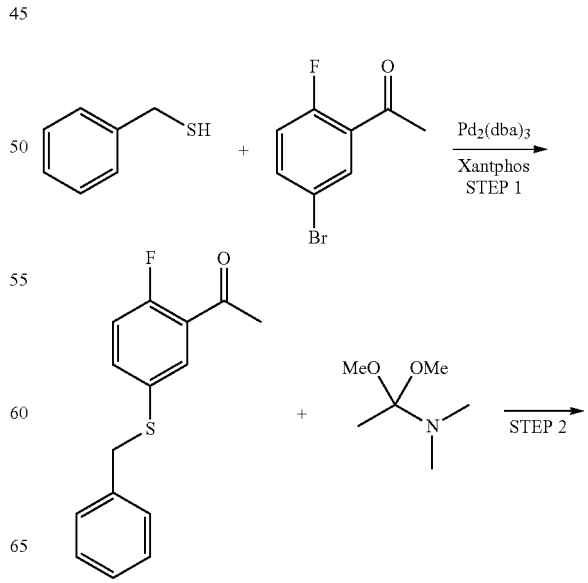

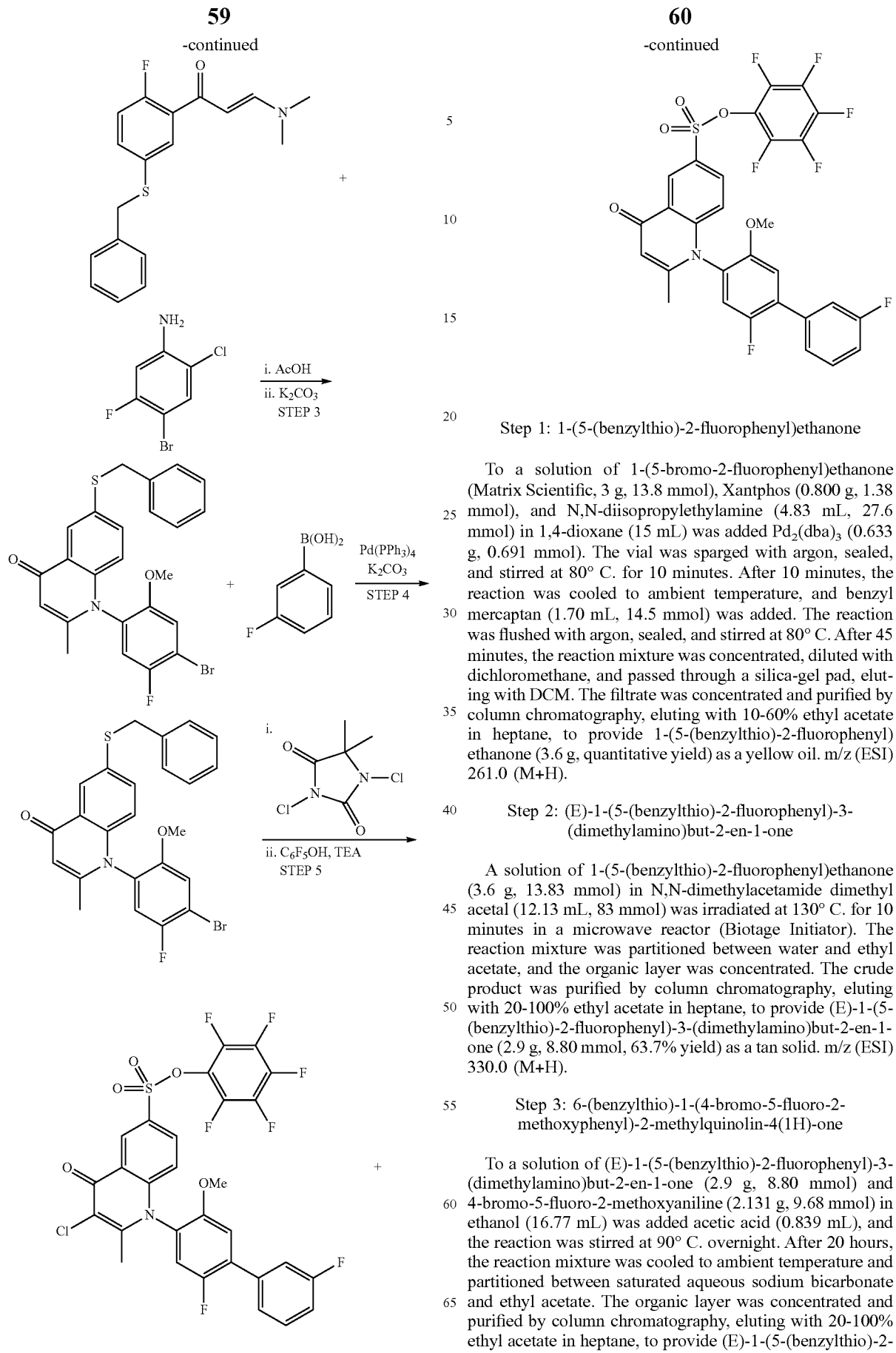

Step 1: 1-(5-(benzylthio)-2-fluorophenyl)ethanone

To a solution of 1-(5-bromo-2-fluorophenyl)ethanone (Matrix Scientific, 3 g, 13.8 mmol), Xantphos (0.800 g, 1.38 mmol), and N,N-diisopropylethylamine (4.83 mL, 27.6 mmol) in 1,4-dioxane (15 mL) was added $Pd_2(dba)_3$ (0.633 g, 0.691 mmol). The vial was sparged with argon, sealed, and stirred at 80° C. for 10 minutes. After 10 minutes, the reaction was cooled to ambient temperature, and benzyl mercaptan (1.70 mL, 14.5 mmol) was added. The reaction was flushed with argon, sealed, and stirred at 80° C. After 45 minutes, the reaction mixture was concentrated, diluted with dichloromethane, and passed through a silica-gel pad, eluting with DCM. The filtrate was concentrated and purified by column chromatography, eluting with 10-60% ethyl acetate in heptane, to provide 1-(5-(benzylthio)-2-fluorophenyl)ethanone (3.6 g, quantitative yield) as a yellow oil. m/z (ESI) 261.0 (M+H).

Step 2: (E)-1-(5-(benzylthio)-2-fluorophenyl)-3-(dimethylamino)but-2-en-1-one

A solution of 1-(5-(benzylthio)-2-fluorophenyl)ethanone (3.6 g, 13.83 mmol) in N,N-dimethylacetamide dimethyl acetal (12.13 mL, 83 mmol) was irradiated at 130° C. for 10 minutes in a microwave reactor (Biotage Initiator). The reaction mixture was partitioned between water and ethyl acetate, and the organic layer was concentrated. The crude product was purified by column chromatography, eluting with 20-100% ethyl acetate in heptane, to provide (E)-1-(5-(benzylthio)-2-fluorophenyl)-3-(dimethylamino)but-2-en-1-one (2.9 g, 8.80 mmol, 63.7% yield) as a tan solid. m/z (ESI) 330.0 (M+H).

Step 3: 6-(benzylthio)-1-(4-bromo-5-fluoro-2-methoxyphenyl)-2-methylquinolin-4(1H)-one To a solution of (E)-1-(5-(benzylthio)-2-fluorophenyl)-3-(dimethylamino)but-2-en-1-one (2.9 g, 8.80 mmol) and 4-bromo-5-fluoro-2-methoxyaniline (2.131 g, 9.68 mmol) in ethanol (16.77 mL) was added acetic acid (0.839 mL), and the reaction was stirred at 90° C. overnight. After 20 hours, the reaction mixture was cooled to ambient temperature and partitioned between saturated aqueous sodium bicarbonate and ethyl acetate. The organic layer was concentrated and purified by column chromatography, eluting with 20-100% ethyl acetate in heptane, to provide (E)-1-(5-(benzylthio)-2- fluorophenyl)-3-((4-bromo-5-fluoro-2-methoxyphenyl) amino)but-2-en-1-one (3.7 g, 7.34 mmol, 83% yield) as a yellow oil. LC/MS (ESI+): 503.9, 505.9 (M+H; two bromine isotopes).

To a solution of (E)-1-(5-(benzylthio)-2-fluorophenyl)-3-((4-bromo-5-fluoro-2-methoxyphenyl)amino)but-2-en-1-one (3.7 g, 7.34 mmol) in dimethyl sulfoxide (20 mL) was added potassium carbonate (2.028 g, 14.67 mmol), and the reaction was stirred at 80° C. After 2 hours, the reaction mixture was cooled to ambient temperature and partitioned between water and ethyl acetate. The organic layer was concentrated and purified by column chromatography, eluting with 20-60% (3:1 ethanol/ethyl acetate) in heptane, to provide 6-(benzylthio)-1-(4-bromo-5-fluoro-2-methoxyphenyl)-2-methylquinolin-4(1H)-one (2.2 g, 4.54 mmol, 61.9% yield) as an off-white solid. LC/MS (ESI+): m/z (ESI) 484.0, 486.0 (M+H; two bromine isotopes).

Step 4: 6-(benzylthio)-1-(2,3'-difluoro-5-methoxy-[1,1'-biphenyl]-4-yl)-2-methylquinolin-4(1H)-one To a suspension of 6-(benzylthio)-1-(4-bromo-5-fluoro-2-methoxyphenyl)-2-methylquinolin-4(1H)-one (1.0 g, 2.06 mmol) and 3-fluorophenylboronic acid (0.462 g, 3.30 mmol) in 1,4-dioxane (7.74 mL) and water (2.58 mL) was added potassium carbonate (0.856 g, 6.19 mmol) and tetrakis (triphenylphosphine)palladium (0.239 g, 0.206 mmol). The reaction was sparged with argon and then stirred at 80° C. After 1 hour, the reaction mixture was partitioned between water and ethyl acetate, and the organic layer was concentrated. The crude product was purified by column chromatography, eluting with 10-50% (3:1 ethyl acetate/ethanol) in heptane to provide 6-(benzylthio)-1-(2,3'-difluoro-5-methoxy-[1,1'-biphenyl]-4-yl)-2-methylquinolin-4(1H)-one (1.0 g, 2.0 mmol, 97% yield) as a yellow oil. m/z (ESI) 500.0 (M+H)+.

Step 5: Perfluorophenyl 3-chloro-1-(2,3'-difluoro-5-methoxy-[1,1'-biphenyl]-4-yl)-2-methyl-4-oxo-1,4-dihydroquinoline-6-sulfonate and Perfluorophenyl 1-(2,3'-difluoro-5-methoxy-[1,1'-biphenyl]-4-yl)-2-methyl-4-oxo-1,4-dihydroquinoline-6-sulfonate To a suspension of 6-(benzylthio)-1-(2,3'-difluoro-5-methoxy-[1,1'-biphenyl]-4-yl)-2-methylquinolin-4(1H)-one (500 mg, 1.00 mmol) in acetonitrile (3.14 mL) was added acetic acid (119 μL) and water (78 μL). The solution was cooled to 0° C., and 1,3-dichloro-5,5-dimethylhydantoin (316 mg, 1.60 mmol) was added. The reaction was stirred at 0° C.

After 30 minutes, pentafluorophenol (115 μL, 1.10 mmol) and triethylamine (558 μL, 4.00 mmol) were added to the reaction, and the reaction was allowed to warm to ambient temperature. After another 20 minutes, the reaction mixture was partitioned between water and ethyl acetate; the organic layer was concentrated. The crude product was purified by column chromatography, eluting with 20-80% ethyl acetate in heptane, to provide perfluorophenyl 3-chloro-1-(2,3'-difluoro-5-methoxy-[1,1'-biphenyl]-4-yl)-2-methyl-4-oxo-1,4-dihydroquinoline-6-sulfonate (350 mg, 0.532 mmol, 53.2% yield) and perfluorophenyl 1-(2,3'-difluoro-5-methoxy-[1, 1'-biphenyl]-4-yl)-2-methyl-4-oxo-1,4-dihydroquinoline-6-sulfonate reaction (100 mg, 0.160 mmol, 16.0% yield) as off-white powders. m/z (ESI) 657.8 (M+H)+ and 623.8 (M+H)+.

Intermediate DC: (P)-perfluorophenyl 1-(2-fluoro-5-methoxy-4'-(trifluoromethyl)-[1,1'-biphenyl]-4-yl)-2-oxo-1,2-dihydroquinoline-6-sulfonate

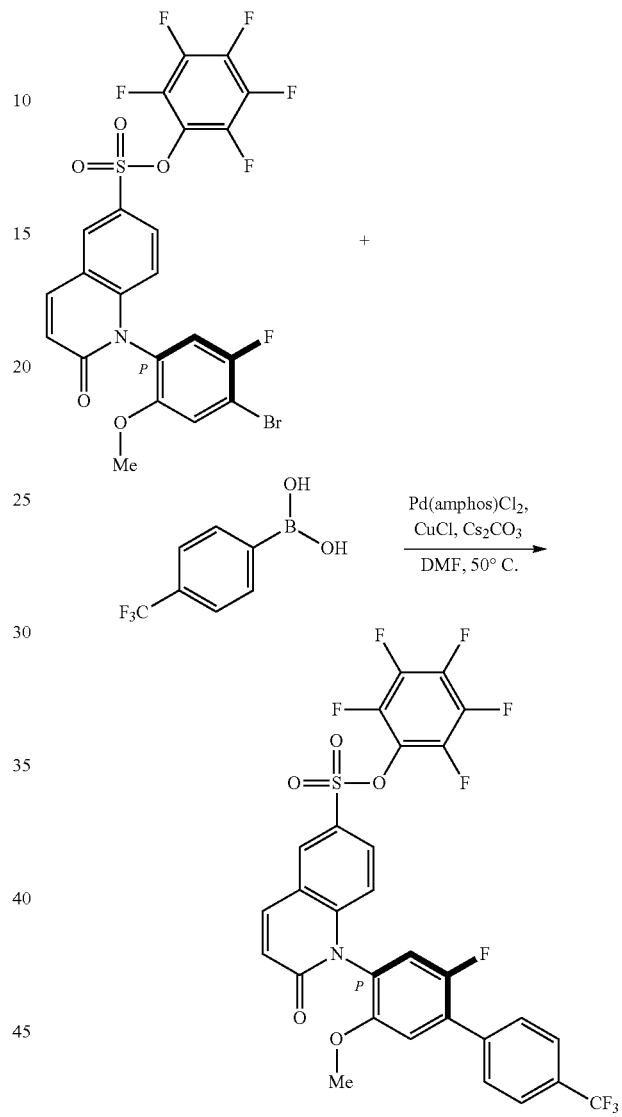

A 100-mL RBF was charged with perfluorophenyl 1-(4-bromo-5-fluoro-2-methoxyphenyl)-2-oxo-1,2-dihydroquinoline-6-sulfonate (3 g, 5.05 mmol), (4-(trifluoromethyl) phenyl)boronic acid (2.88 g, 15.14 mmol), copper (I) chloride (0.425 ml, 15.14 mmol), cesium carbonate (1.616 ml, 20.19 mmol), and 1,1-bis[(di-t-butyl-p-methylaminophenyl]palladium(II) chloride (0.715 g, 1.010 mmol) then evacuated and back-filled with nitrogen (×3). DMF (25.2 ml) was introduced and the reaction mixture was warmed to 50° C. After 3 h, the reaction mixture was allowed to cool to ambient temperature and poured into a separatory funnel containing water (50 mL) and diluted with EtOAc (50 mL). The layers were separated and the aqueous layer was extracted with EtOAc (3×50 mL). The combined organic layers were dried over anhydrous sodium sulfate, filtered, and concentrated under reduced pressure to furnish a tan oil, which was purified by flash column chromatography (100-g Biotage column, eluent: gradient, 0 to 100% EtOAc in heptane with 10% $CH_2Cl_2$ as an additive) to afford (P)-perfluorophenyl 1-(2-fluoro-5-methoxy-4'-(trifluoromethyl)-[1,1'-biphenyl]-4-yl)-2-oxo-1,2-dihydroquinoline-6-sulfonate (2.55 g, 3.87 mmol, 77% yield) as a white flocculent solid. $^1$H NMR (400 MHz, DMSO-$d_6$) δ=8.62 (d, J=2.3 Hz, 1H), 8.28 (d, J=9.5 Hz, 1H), 8.00 (dd, J=2.3, 9.1 Hz, 1H), 7.98-7.90 (m, 4H), 7.65 (d, J=10.4 Hz, 1H), 7.51 (d, J=6.8 Hz, 1H), 6.98 (d, J=9.0 Hz, 1H), 6.92 (d, J=9.6 Hz, 1H), 3.77 (s, 3H). m/z (ESI) 660.0 (M+H)$^+$.

Intermediate DD: (P)-perfluorophenyl 1-(2-fluoro-5-methoxy-3'-(trifluoromethyl)-[1,1'-biphenyl]-4-yl)-2-oxo-1,2-dihydroquinoline-6-sulfonate

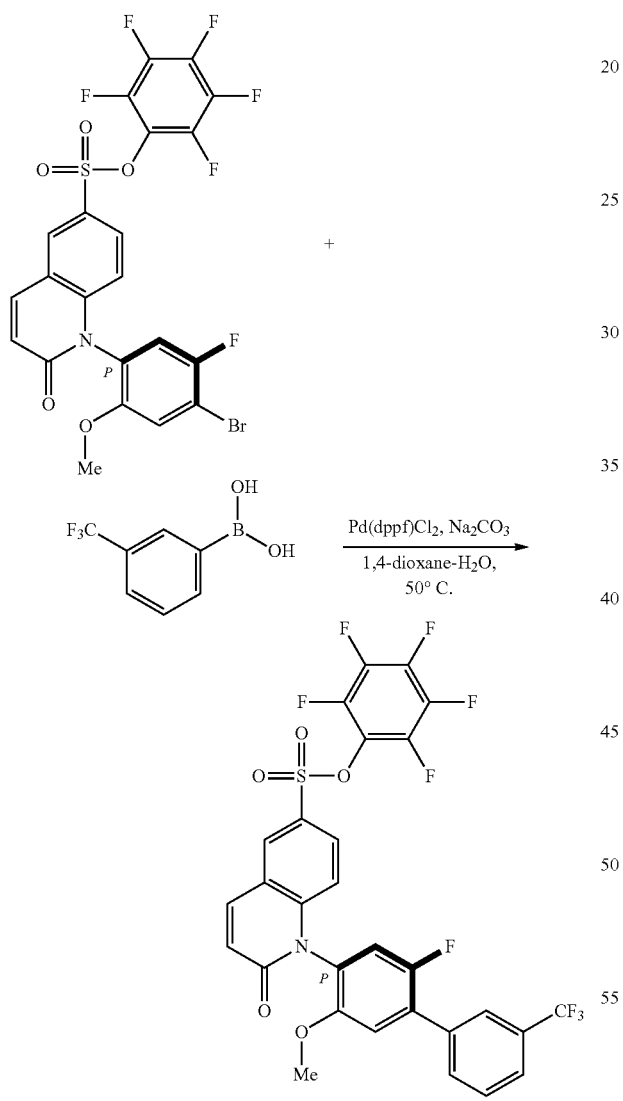

A 100-mL RBF was charged with perfluorophenyl 1-(4-bromo-5-fluoro-2-methoxyphenyl)-2-oxo-1,2-dihydroquinoline-6-sulfonate (3 g, 5.05 mmol), (3-(trifluoromethyl)phenyl)boronic acid (2.88 g, 15.14 mmol), copper (I) chloride (0.425 ml, 15.14 mmol), cesium carbonate (1.616 ml, 20.19 mmol), and 1,1'-bis(diphenylphosphino)ferrocene palladium(II)dichloride dichloromethane adduct (0.825 g, 1.010 mmol) then evacuated and back-filled with nitrogen (×3). 1,4-Dioxane (37.9 ml) and an aqueous solution of sodium carbonate (12.6 mL, 1.9 M) were introduced via syringe and the reaction mixture was warmed to 50° C. After 3 h, the reaction mixture was allowed to cool to ambient temperature and poured into a separatory funnel containing water (50 mL) and diluted with EtOAc (50 mL). The layers were separated and the aqueous layer was extracted with EtOAc (3×50 mL). The combined organic layers were dried over anhydrous sodium sulfate, filtered, and concentrated under reduced pressure to furnish a tan oil, which was purified by flash column chromatography (100-g Biotage column, eluent: gradient, 0 to 100% EtOAc in heptane with 10% $CH_2Cl_2$ as an additive) to afford (P)-perfluorophenyl 1-(2-fluoro-5-methoxy-4'-(trifluoromethyl)-[1,1'-biphenyl]-4-yl)-2-oxo-1,2-dihydroquinoline-6-sulfonate (2.55 g, 3.87 mmol, 77% yield) as a purple flocculent solid. $^1$H NMR (400 MHz, DMSO-$d_6$) δ=8.60 (d, J=2.3 Hz, 1H), 8.25 (d, J=9.4 Hz, 1H), 7.94 (dd, J=2.3, 9.1 Hz, 1H), 7.71 (d, J=6.3 Hz, 1H), 7.68 (d, J=8.6 Hz, 1H), 6.94 (d, J=9.0 Hz, 1H), 6.89 (d, J=9.6 Hz, 1H), 3.71 (s, 3H). m/z (ESI) 660.0 (M+H)$^+$.

Intermediate DE: (P)-perfluorophenyl 1-(2-fluoro-5-methoxy-3'-methyl-[1,1'-biphenyl]-4-yl)-2-oxo-1,2-dihydroquinoline-6-sulfonate

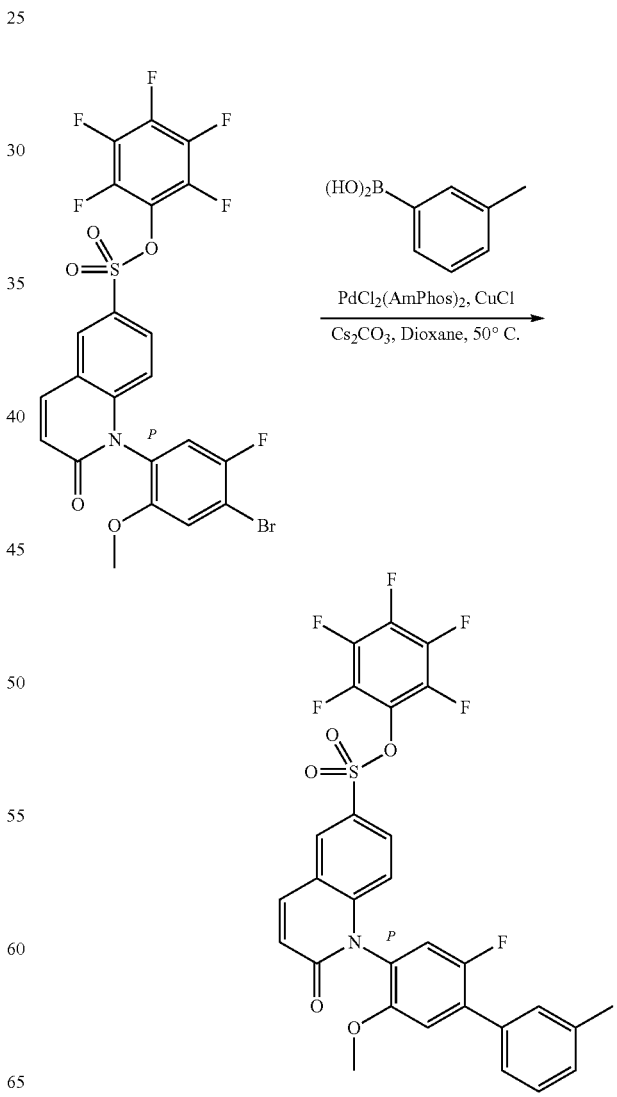

A RBF was charged with (P)-perfluorophenyl 1-(4-bromo-5-fluoro-2-methoxyphenyl)-2-oxo-1,2-dihydroquinoline-6-sulfonate (1.567 g, 2.64 mmol), cesium carbonate (3.44 g, 10.55 mmol), m-tolylboronic acid (1.075 g, 7.91 mmol), copper(i) chloride (0.783 g, 7.91 mmol) and bis(di-tert-butyl(4-dimethylaminophenyl)phosphine)-dichloropalladium(II) (0.317 g, 0.448 mmol). The flask was flushed with Ar (g) and Dioxane (13.18 ml) was added. The flask was then lowered into a 50° C. heating bath for 1.5 h. The mixture was cooled and filtered through celite with the aid of EtOAc. The filtrate was partitioned between EtOAc and water which led to an emulsion. The layers were separated, and the aq. layer was extracted with EtOAc (2×). The organic extracts were dried over sodium sulfate, filtered, and concentrated. The residue was purified by chromatography on silica gel (100-g SNAP Ultra column, 25-g silica gel loading column, 10-60% EtOAc/Heptane) to give (P)-perfluorophenyl 1-(2-fluoro-5-methoxy-3'-methyl-[1,1'-biphenyl]-4-yl)-2-oxo-1,2-dihydroquinoline-6-sulfonate (1.1 g, 1.82 mmol, 68.9% yield) as a light-yellow solid. m/z (ESI) 605.9 (M+H)$^+$.

Intermediate DF: (P)-perfluorophenyl 1-(3-methoxy-3'-methyl-[1,1'-biphenyl]-4-yl)-2-oxo-1,2-dihydroquinoline-6-sulfonate A RBF was charged with (P)-perfluorophenyl 1-(4-bromo-2-methoxyphenyl)-2-oxo-1,2-dihydroquinoline-6-sulfonate (0.601 g, 1.041 mmol), m-tolylboronic acid (0.425 g, 3.12 mmol), copper (i) chloride (0.088 ml, 3.12 mmol), cesium carbonate (0.333 ml, 4.16 mmol), and 1,1-bis[(di-t-butyl-p-methylaminophenyl]palladium(ii) chloride (0.147 g, 0.208 mmol). The flask was flushed with Ar (g) and DMF (5.21 ml) was added. The flask was then lowered into a 50° C. heating bath for 1.5 h. The mixture was cooled and filtered through celite with the aid of EtOAc. The filtrate was partitioned between EtOAc and water which led to an emulsion. The layers were separated, and the aq. layer was extracted with EtOAc (2×). The organic extracts were dried over sodium sulfate, filtered, and concentrated. The residue was purified by chromatography on silica gel (100-g SNAP Ultra column, 25-g silica gel loading column, 5-40% EtOAc/Heptane) to give (P)-perfluorophenyl 1-(3-methoxy-3'-methyl-[1,1'-biphenyl]-4-yl)-2-oxo-1,2-dihydroquinoline-6-sulfonate (0.33 g, 0.562 mmol, 53.9% yield) as an off-white solid. m/z (ESI) 587.9 (M+H)$^+$.

Intermediate DG: (P)-perfluorophenyl 1-(2,3'-difluoro-5-methoxy-4'-methyl-[1,1'-biphenyl]-4-yl)-2-oxo-1,2-dihydroquinoline-6-sulfonate

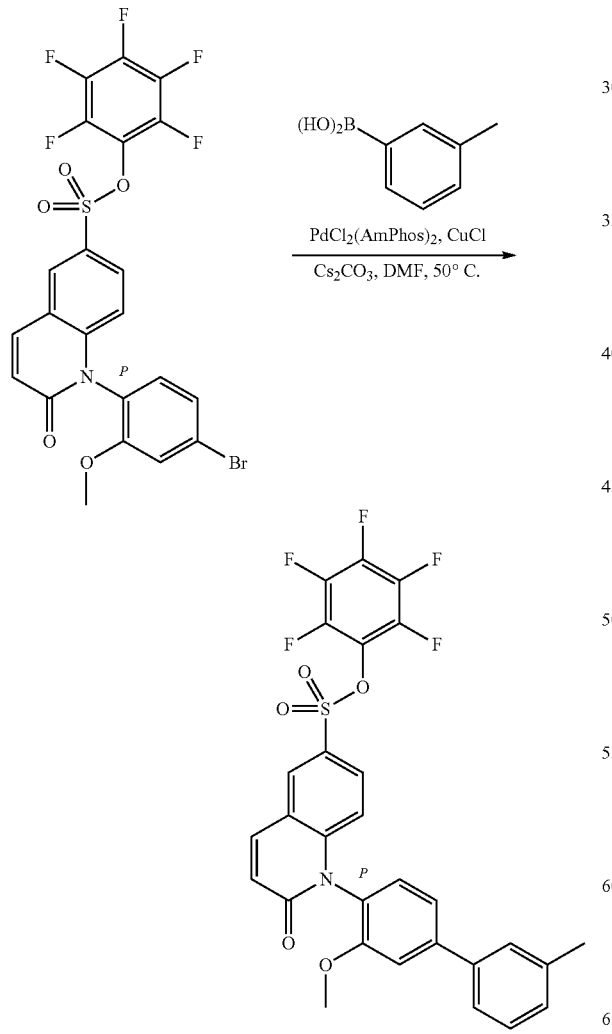

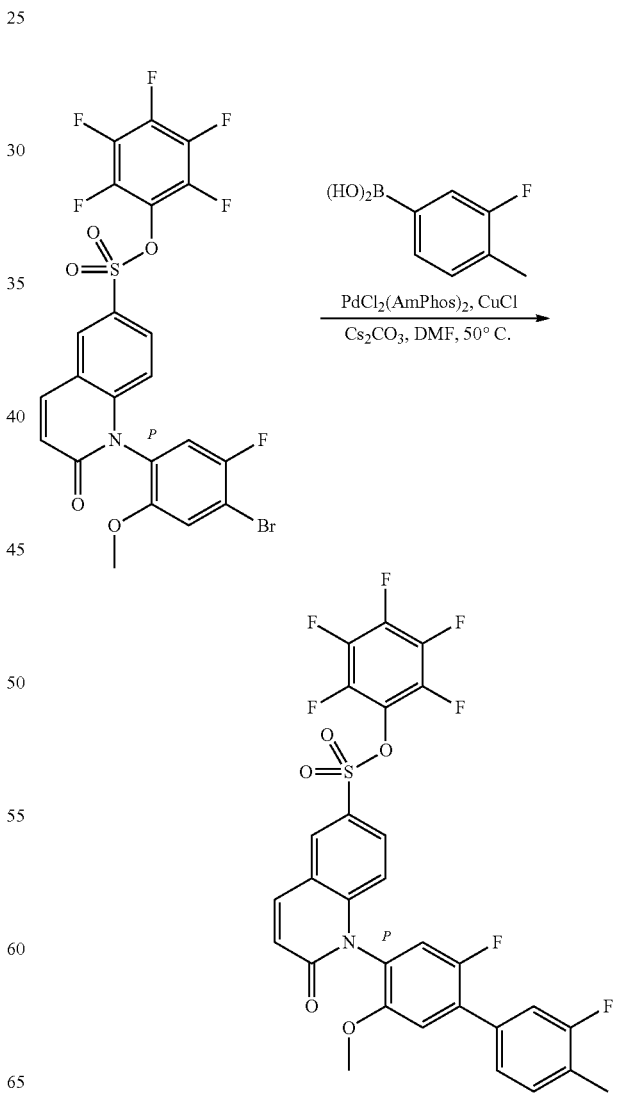

A RBF was charged with (P)-perfluorophenyl 1-(4-bromo-5-fluoro-2-methoxyphenyl)-2-oxo-1,2-dihydroquinoline-6-sulfonate (1.65 g, 2.78 mmol), (3-fluoro-4-methylphenyl)boronic acid (1.282 g, 8.33 mmol), copper (i) chloride (0.234 ml, 8.33 mmol), cesium carbonate (0.889 ml, 11.11 mmol), and 1,1-bis[(di-t-butyl-p-methylaminophenyl]palladium(ii) chloride (0.393 g, 0.555 mmol) The flask was flushed with Ar (g) and DMF (13.88 ml) was added. The flask was then lowered into a 50° C. heating bath for 1.5 h. The mixture was cooled and filtered through celite with the aid of EtOAc. The filtrate was partitioned between EtOAc and water which led to an emulsion. The layers were separated, and the aq. layer was extracted with EtOAc (2×). The organic extracts were dried over sodium sulfate, filtered, and concentrated. The residue was purified by chromatography on silica gel (100-g SNAP Ultra column, 25-g silica gel loading column, 10-60% EtOAc/Heptane) to give (P)-perfluorophenyl 1-(2,3'-difluoro-5-methoxy-4'-methyl-[1,1'-biphenyl]-4-yl)-2-oxo-1,2-dihydroquinoline-6-sulfonate (1.22 g, 1.957 mmol, 70.5% yield) as an off-white solid. m/z (ESI) 624.0 (M+H)$^+$.

Intermediate DH: (P)-1-(4-bromo-2-methoxy-5-methylphenyl)-2-oxo-N-(pyrimidin-2-yl)-1,2-dihydroquinoline-6-sulfonamide

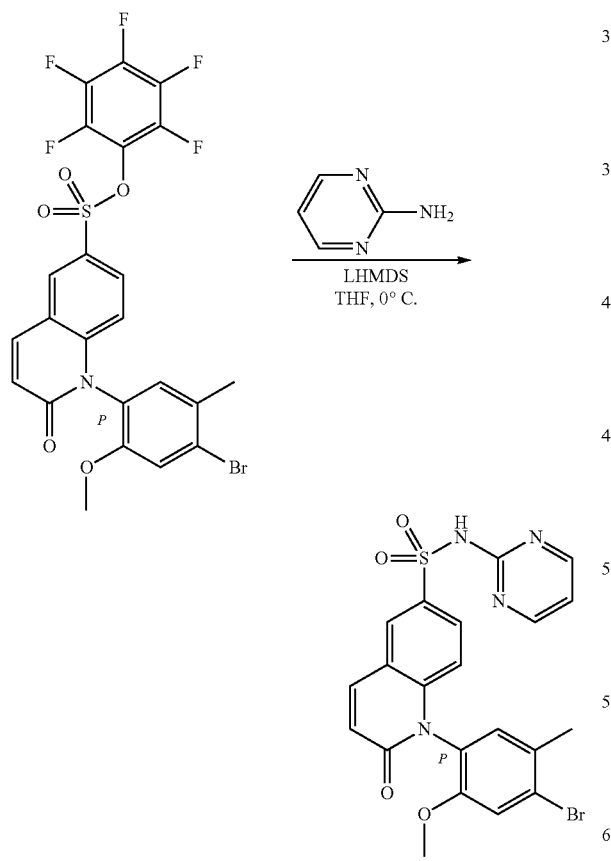

A RBF was charged with perfluorophenyl 1-(4-bromo-2-methoxy-5-methylphenyl)-2-oxo-1,2-dihydroquinoline-6-sulfonate (5.00 g, 8.47 mmol), and THF (85 ml). To this, was added pyrimidin-2-amine (1.208 g, 12.71 mmol) and the reaction was cooled to 0° C. Lithium bis(trimethylsilyl) amide, 1.0 M solution in tetrahydrofuran (18.63 ml, 18.63 mmol) was added dropwise and allowed to stir at 0° C. After 1 hour, the mixture was diluted with 1N aq. HCl (10 mL) and EtOAc. The layers were separated, and the aq. layer was extracted with EtOAc (2×). The combined organic extracts were dried over sodium sulfate, filtered, and concentrated. The residue was purified by chromatography on silica gel (40-g Redi-Sep Gold column, 10-50% of a 3:1 EtOAc/EtOH solution in heptane) to give 1-(4-bromo-2-methoxy-5-methylphenyl)-2-oxo-N-(pyrimidin-2-yl)-1,2-dihydroquinoline-6-sulfonamide (3.54 g, 7.06 mmol, 83% yield) as an off white solid. m/z (ESI) 502.8 (M+H)$^+$.

Intermediate DI: (P)-perfluorophenyl 1-(4'-chloro-2-fluoro-3',5-dimethyl-[1,1'-biphenyl]-4-yl)-2-oxo-1,2-dihydroquinoline-6-sulfonate

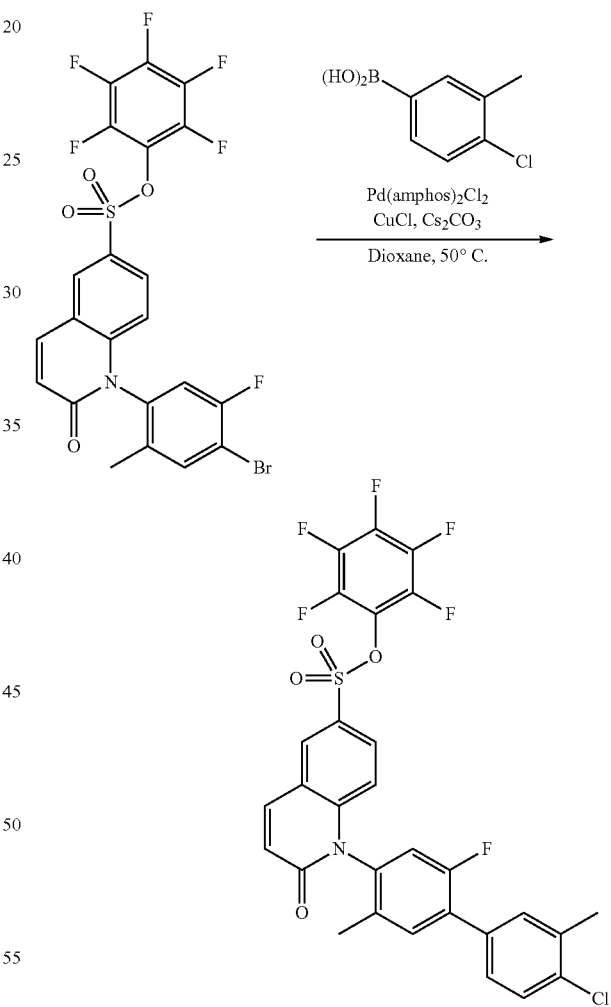

A RBF was charged with perfluorophenyl 1-(4-bromo-5-fluoro-2-methylphenyl)-2-oxo-1,2-dihydroquinoline-6-sulfonate (1.20 g, 2.075 mmol), (4-chloro-3-methylphenyl)boronic acid (1.061 g, 6.23 mmol), copper(i) chloride (0.616 g, 6.23 mmol), cesium carbonate (2.70 g, 8.30 mmol), and bis(di-tert-butyl(4-dimethylaminophenyl)phosphine)-dichloropalladium(ii) (0.036 g, 0.05 mmol). The flask was flushed with Ar (g), then Dioxane (10.38 ml) was added. The reaction was heated to 50° C. and stirred for one hour. The reaction was diluted with ethyl acetate and washed three times with water containing excess n-(2-hydroxyethyl)ethylenediaminetriacetic acid, trisodium salt hydrate. The organic layer was washed with water, washed with brine, dried with sodium sulfate, filtered, and concentrated. The material was purified via column chromatography (RediSep Gold 120 g, gradient elution 0-30% EtOAc:Heptane) to afford perfluorophenyl 1-(4'-chloro-2-fluoro-3',5-dimethyl-[1,1'-biphenyl]-4-yl)-2-oxo-1,2-dihydroquinoline-6-sulfonate (1.01 g, 1.619 mmol, 78% yield) as an off-white solid. m/z (ESI) 624.0 (M+H)$^+$.

Intermediate DJ: (P)-1-(4-bromo-5-fluoro-2-methoxyphenyl)-7-fluoro-N-(isoxazol-3-yl)-2-oxo-1,2-dihydroquinoline-6-sulfonamide

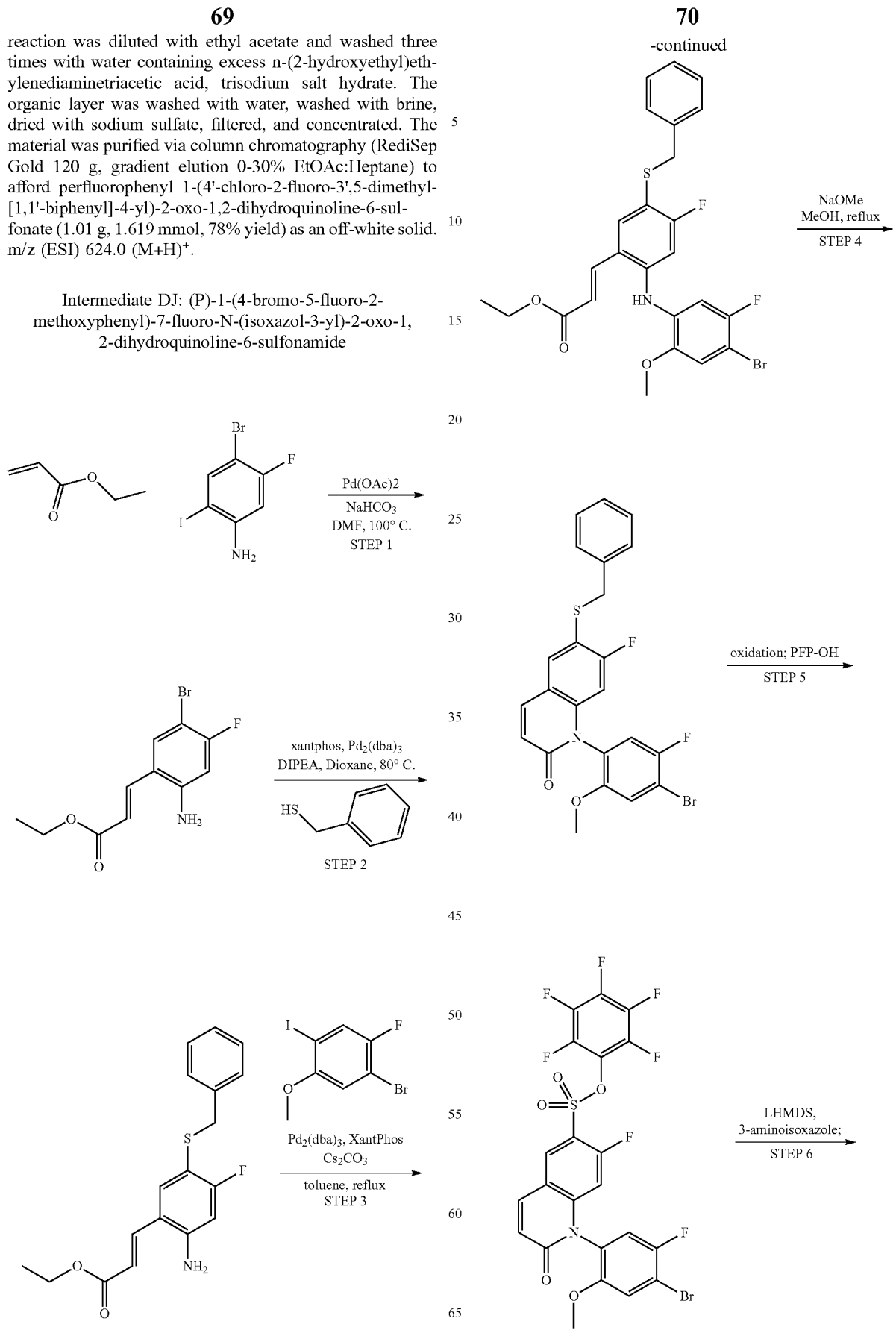

71
-continued

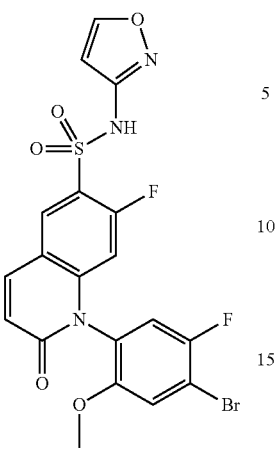

This intermediate was prepared analogous to Method 96, with the exception that 1-bromo-2-fluoro-4-iodo-5-methoxybenzene was used as the coupling partner in Step 3 instead of 1-bromo-2-chloro-4-iodo-5-methoxybenzene. m/z (ESI) 513.2 (M+H)$^+$.

Intermediate DK: (P)-1-(4-bromo-2-methoxyphenyl)-7-fluoro-2-oxo-N-(pyrimidin-2-yl)-1,2-dihydroquinoline-6-sulfonamide

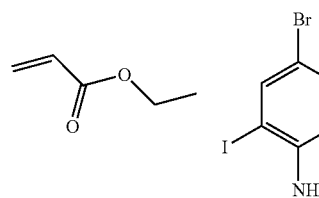 Pd(OAc)2, NaHCO$_3$, DMF, 100° C. STEP 1

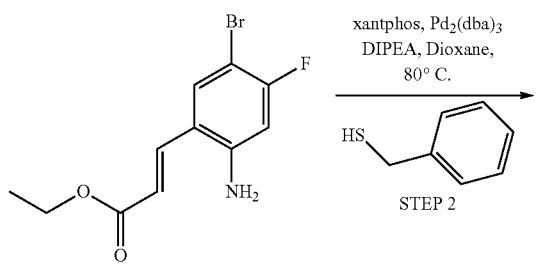 xantphos, Pd$_2$(dba)$_3$, DIPEA, Dioxane, 80° C. STEP 2

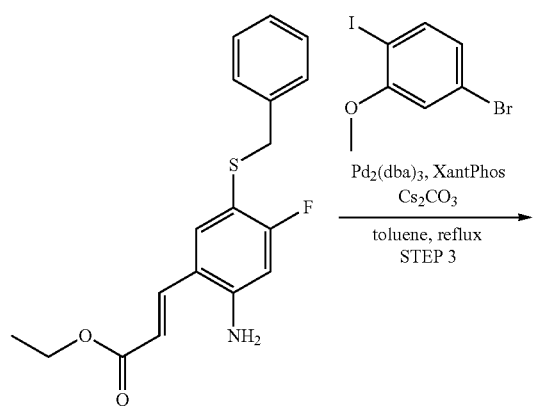 Pd$_2$(dba)$_3$, XantPhos, Cs$_2$CO$_3$, toluene, reflux STEP 3

72
-continued

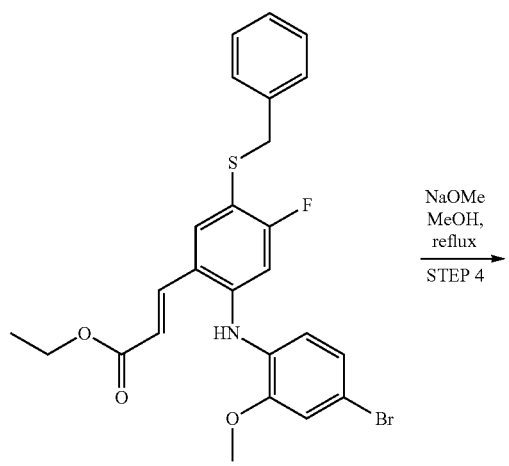 NaOMe, MeOH, reflux STEP 4

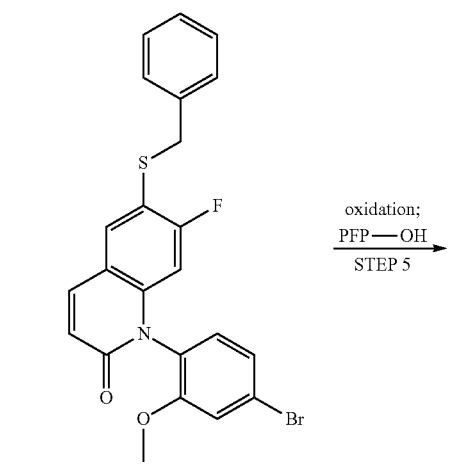 oxidation; PFP—OH STEP 5

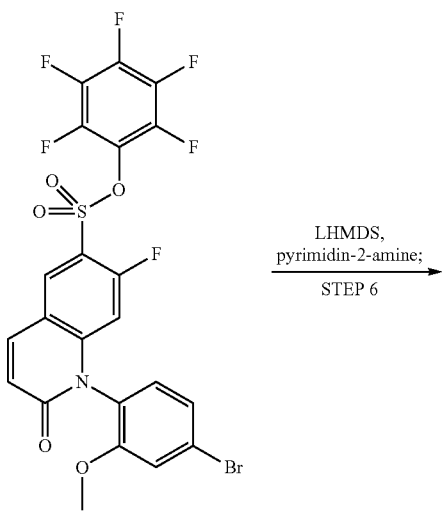 LHMDS, pyrimidin-2-amine; STEP 6

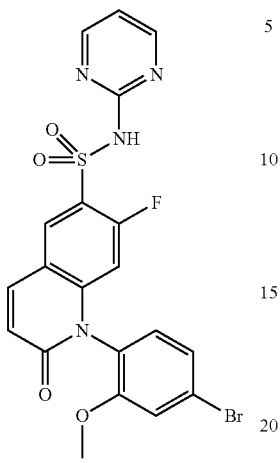

This intermediate was prepared analogous to method 96, with the exception that 1-bromo-4-iodo-5-methoxybenzene was used as the coupling partner in Step 3 instead of 1-bromo-2-chloro-4-iodo-5-methoxybenzene, and pyrimidin-2-amine was used instead of 3-aminoisoxazole in Step 6. m/z (ESI) 595.2 (M+H)+.

Intermediate DL: (P)-perfluorophenyl 1-(3'-fluoro-3,5'-dimethoxy-[1,1'-biphenyl]-4-yl)-2-oxo-1,2-dihydroquinoline-6-sulfonate

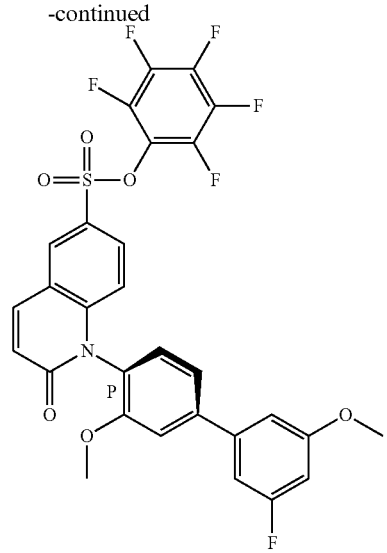

A 40-mL vial containing perfluorophenyl 1-(4-bromo-2-methoxyphenyl)-2-oxo-1,2-dihydroquinoline-6-sulfonate (2.00 g, 3.47 mmol), (3-fluoro-5-methoxyphenyl)boronic acid (1.180 g, 6.94 mmol), and Pd catalyst (0.567 g, 0.694 mmol) was flushed with N₂ and subsequently charged with dioxane (26.0 ml) and 1.9 M Na₂CO₃ (8.68 ml). After stirring vigorously overnight (18 h) at 50° C., the reaction was cooled to rt, quenched with 1 N HCl, diluted with EtOAc, and filtered through a plug of celite. The layers of the filtrate were separated, and the aqueous fraction was extracted twice with EtOAc. The organic extracts were combined, washed with brine, dried over Na₂SO₄, filtered, and concentrated in vacuo to an orange oil. Biotage column chromatography (12 g Redisep Gold, 0-80% [3:1 EtOAc/EtOH]/hept gradient with 10% DCM) afforded the productorded 7-fluoro-1-(2-fluoro-5-methoxy-3'-(trifluoromethyl)-[1,1'-biphenyl]-4-yl)-N-(isoxazol-3-yl)-2-oxo-1,2-dihydroquinoline-6-sulfonamide (85.2 mg, 0.148 mmol, 37.8% yield) as an amorphous white solid. m/z (ESI) 622.2 (M+H)+.

Intermediate DM: (P)-perfluorophenyl 1-(2,4'-difluoro-3',5-dimethoxy-[1,1'-biphenyl]-4-yl)-2-oxo-1,2-dihydroquinoline-6-sulfonate

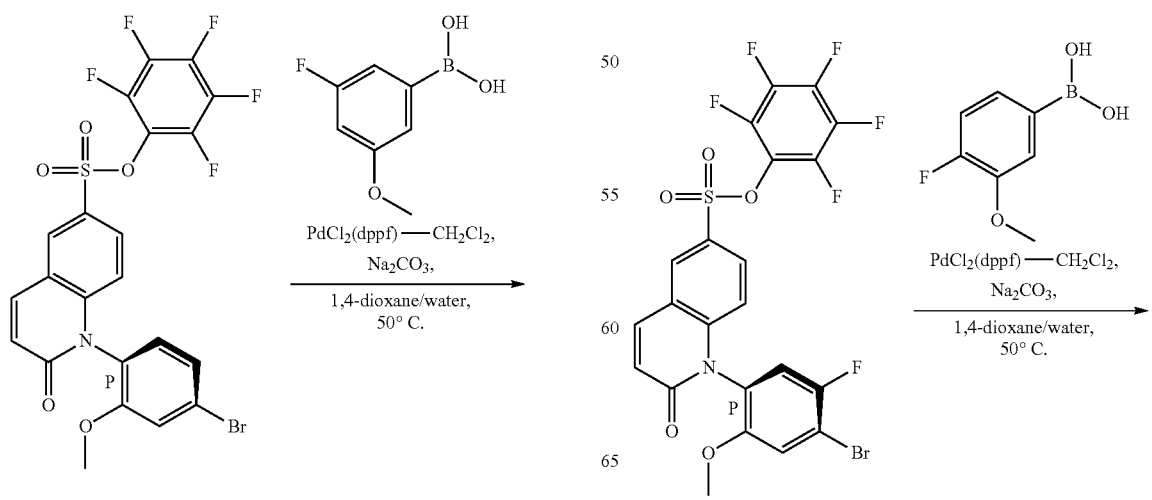

75

-continued

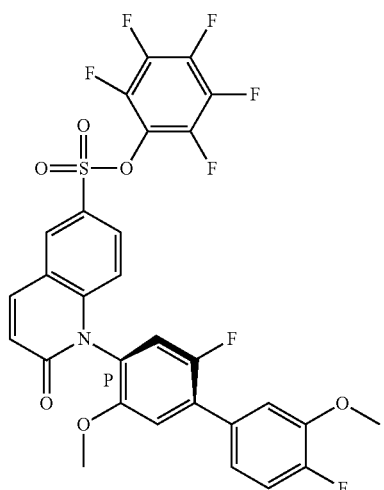

A 40-mL vial containing perfluorophenyl 1-(4-bromo-5-fluoro-2-methoxyphenyl)-2-oxo-1,2-dihydroquinoline-6-sulfonate (1.50 g, 2.52 mmol), (4-fluoro-3-methoxyphenyl) boronic acid (0.858 g, 5.05 mmol), and Pd catalyst (0.412 g, 0.505 mmol) was flushed with $N_2$ and subsequently charged with dioxane (18.93 ml) and 1.9M $Na_2CO_3$ (6.31 ml). After stirring vigorously overnight (18 h) at 50° C., the reaction was cooled to rt, quenched with 1 N HCl, diluted with EtOAc, and filtered through a plug of celite. The layers of the filtrate were separated, and the aqueous fraction was extracted twice with EtOAc. The organic extracts were combined, washed with brine, dried over $Na_2SO_4$, filtered, and concentrated in vacuo to an orange oil. Biotage column chromatography (12 g Redisep Gold, 0-80% [3:1 EtOAc/EtOH]/hept gradient with 10% DCM) afforded the productorded 7-fluoro-1-(2-fluoro-5-methoxy-3'-(trifluoromethyl)-[1,1'-biphenyl]-4-yl)-N-(isoxazol-3-yl)-2-oxo-1,2-dihydroquinoline-6-sulfonamide (85.2 mg, 0.148 mmol, 37.8% yield) as an amorphous white solid. m/z (ESI) 640.2 (M+H)⁺.

Intermediate DN: 1-(4'-chloro-2-fluoro-5-methoxy-3'-methyl-[1,1'-biphenyl]-4-yl)-2-oxo-1,2-dihydroquinoxaline-6-sulfonyl chloride

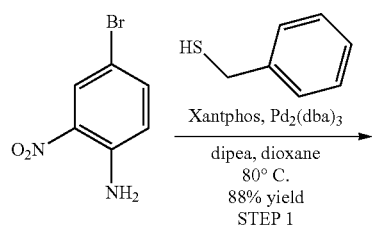

76

-continued

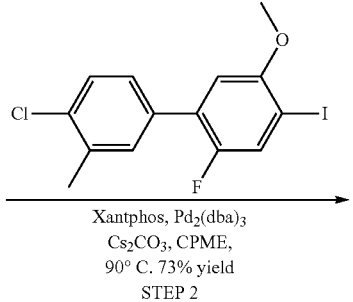

Xantphos, Pd₂(dba)₃
Cs₂CO₃, CPME,
90° C. 73% yield
STEP 2

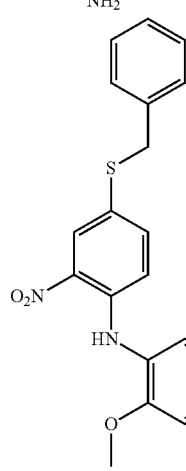

Zn,
Acetic Acid
70° C.
78% yield
STEP 3

K₂CO₃, DMF,
90° C. 65% yield
STEP 4

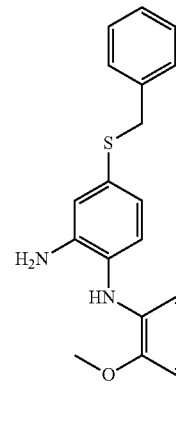

TFA,
DCM

Microwave,
30 min
80° C.
78% yield
STEP 5

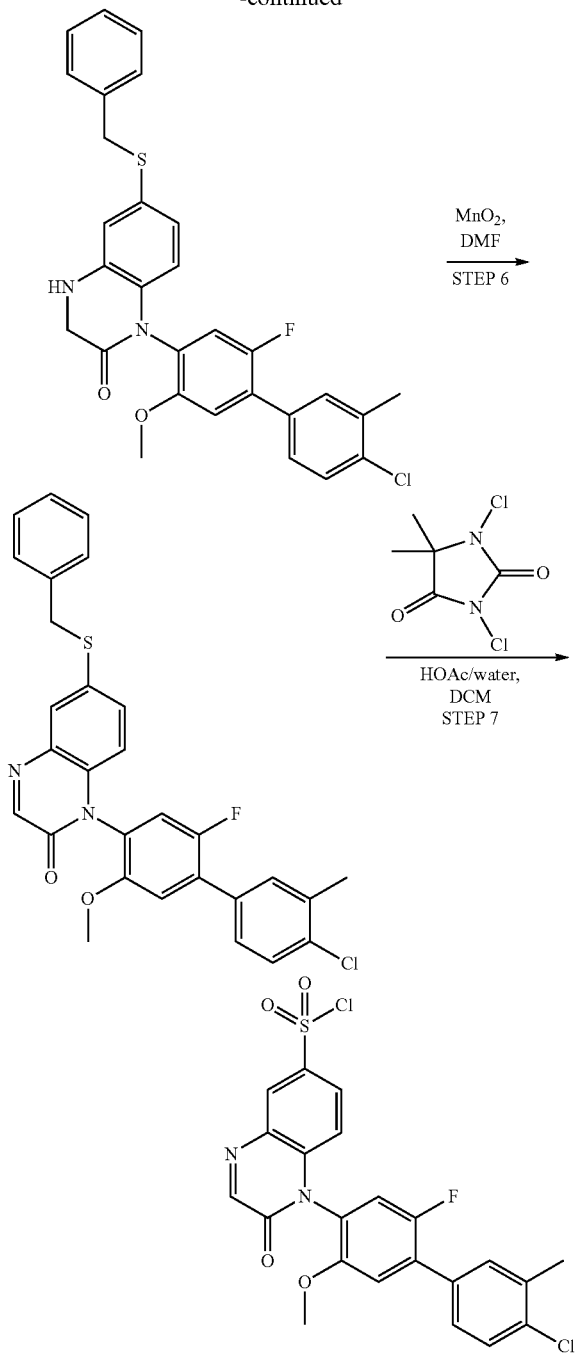

Step 1: 4-(benzylthio)-2-nitroaniline

A screw cap vial was charged with 4-bromo-2-nitroaniline (7.00 g, 32.3 mmol), xantphos (0.933 g, 1.613 mmol), tris(dibenzylideneacetone)dipalladium (0) (0.738 g, 0.806 mmol), 1,4-Dioxane (32.3 ml), and DIPEA (11.22 ml, 64.5 mmol). The vial was purged with Argon, sealed and heated to 80° C. for 10 minutes. The reaction was cooled to room temperature and benzyl mercaptan (4.01 ml, 33.9 mmol) was added and the reaction heated at 80° C. for 3 hours. The reaction was cooled to room temperature, diluted with water and extracted with DCM (3×). The combined organics were washed with water and brine, dried over magnesium sulfate, filtered and concentrated. The resulting material was concentrated, dissolved in minimal DCM and purified via column chromatography (silica gel 40 g, gradient elution 0 to 50% EtOAc:Heptane) to afford 4-(benzylthio)-2-nitroaniline (7.43 g, 28.5 mmol, 88% yield). m/z (ESI) 261.2 (M+H)$^+$.

Step 2: N-(4-(benzylthio)-2-nitrophenyl)-4'-chloro-2-fluoro-5-methoxy-3'-methyl-[1,1'-biphenyl]-4-amine A RBF was charged with 4-(benzylthio)-2-nitroaniline (1.80 g, 6.91 mmol), 4'-chloro-2-fluoro-4-iodo-5-methoxy-3'-methyl-1,1'-biphenyl (2.86 g, 7.61 mmol), xantphos (0.200 g, 0.346 mmol), Pd$_2$(dba)$_3$ (0.158 g, 0.173 mmol), CPME (13.83 ml) and cesium carbonate (3.15 g, 9.68 mmol). A reflux condenser was attached and the flask was lowered into a 110° C. heating for 3 hours. The mixture was cooled to room temperature, diluted with EtOAc, and filtered through celite with the aid of EtOAc. The filtrate was concentrated. The oily residue was purified using Biotage and eluting with 0-50% EtOAc/Heptane to give N-(4-(benzylthio)-2-nitrophenyl)-4'-chloro-2-fluoro-5-methoxy-3'-methyl-[1,1'-biphenyl]-4-amine (2.56 g, 5.03 mmol, 72.7% yield) as a bright-yellow solid. m/z (ESI) 509.1 (M+H)$^+$.

Step 3: 4-(benzylthio)-N1-(4'-chloro-2-fluoro-5-methoxy-3'-methyl-[1,1'-biphenyl]-4-yl)benzene-1,2-diamine To a vial was added N-(4-(benzylthio)-2-nitrophenyl)-4'-chloro-2-fluoro-5-methoxy-3'-methyl-[1,1'-biphenyl]-4-amine (2.56 g, 5.03 mmol), acetic acid (25.9 mL, 453 mmol) and zinc powder (0.463 mL, 50.3 mmol). The cloudy maroon reaction mixture was capped and stirred for 60 min at 70° C. The reaction mixture was filtered through Celite and washed with MeOH. The residual filtrate was concentrated in vacuo, then partitioned between EtOAc (2×300 ml) and saturated aqueous NaHCO$_3$ (350 ml). The combined organic layers were dried over Na$_2$SO$_4$ and concentrated. Reaction was purified using Biotage and eluted with 0-50% EtOAc/Heptane. Collected fractions and removed solvent in vaccuo, affording the title compound, 4-(benzylthio)-N1-(4'-chloro-2-fluoro-5-methoxy-3'-methyl-[1,1'-biphenyl]-4-yl)benzene-1,2-diamine (1.87 g, 3.90 mmol, 78% yield). m/z (ESI) 480.2 (M+H)$^+$.

Step 4: Ethyl 2-((5-(benzylthio)-2-((4'-chloro-2-fluoro-5-methoxy-3'-methyl-[1,1'-biphenyl]-4-yl)amino)phenyl)amino)acetate To a vial was added, 4-(benzylthio)-N1-(4'-chloro-2-fluoro-5-methoxy-3'-methyl-[1,1'-biphenyl]-4-yl)benzene-1,2-diamine (1.87 g, 3.90 mmol), potassium carbonate (0.647 g, 4.68 mmol), and DMF (19.52 ml). To this, ethyl bromoacetate (0.563 ml, 5.08 mmol) was added, the vial capped and began heating to 90° C. After 5 hours, the reaction was complete. Quenched with water and extracted with EtOAc. Dried over MgSO$_4$ and filtered. Removed solvent in vaccuo and purified on Biotage, eluting with 0-50% EtOAc/Heptane. Collected fractions and removed solvent in vaccuo to yield ethyl 2-((5-(benzylthio)-2-((4'-chloro-2-fluoro-5-methoxy-3'-methyl-[1,1'-biphenyl]-4-yl)amino)phenyl)amino)acetate (1.43 g, 2.53 mmol, 65% yield). m/z (ESI) 566.2 (M+H)+.

Step 5: 6-(Benzylthio)-1-(4'-chloro-2-fluoro-5-methoxy-3'-methyl-[1,1'-biphenyl]-4-yl)-3,4-dihydroquinoxalin-2(1H)-one To a microwave vial was added, ethyl 2-((5-(benzylthio)-2-((4'-chloro-2-fluoro-5-methoxy-3'-methyl-[1,1'-biphenyl]-4-yl)amino)phenyl)amino)acetate (2.00 g, 3.54 mmol) followed by DCM (11.80 ml) and TFA (2.73 ml, 35.4 mmol). The vial was placed in the microwave for 30 min at 80° C. Solvent was removed in vaccuo and sodium bicarbate solution was added. The solution was extracted with DCM and organics dried over MgSO4, filtered and removed solvent in vaccuo. Used 6-(benzylthio)-1-(4'-chloro-2-fluoro-5-methoxy-3'-methyl-[1,1'-biphenyl]-4-yl)-3,4-dihydroquinoxalin-2(1H)-one (1.43 g, 2.76 mmol, 78% yield) without further purification. m/z (ESI) 520.2 (M+H)+.

Step 6: 6-(benzylthio)-1-(4'-chloro-2-fluoro-5-methoxy-3'-methyl-[1,1'-biphenyl]-4-yl)-3,4-dihydroquinoxalin-2(1H)-one A mixture of 6-(benzylthio)-1-(4'-chloro-2-fluoro-5-methoxy-3'-methyl-[1,1'-biphenyl]-4-yl)-3,4-dihydroquinoxalin-2(1H)-one (1.43 g, 2.76 mmol), and manganese dioxide (0.095 ml, 5.51 mmol) in DMF (13.78 ml) was stirred at room temperature for 4 hour. The reaction mixture was filtered through Celite, washed with methanol and the solvent was removed. The residue was purified using Biotage, eluting with a 0-50% ethyl acetate in hexane gradient, to afford 6-(benzylthio)-1-(4'-chloro-2-fluoro-5-methoxy-3'-methyl-[1,1'-biphenyl]-4-yl)quinoxalin-2(1H)-one (0.897 g, 1.735 mmol, 63.0% yield). m/z (ESI) 518.2 (M+H)+.

Step 7: 1-(4'-chloro-2-fluoro-5-methoxy-3'-methyl-[1,1'-biphenyl]-4-yl)-2-oxo-1,2-dihydroquinoxaline-6-sulfonyl chloride A RBF was charged with 6-(benzylthio)-1-(4'-chloro-2-fluoro-5-methoxy-3'-methyl-[1,1'-biphenyl]-4-yl)quinoxalin-2(1H)-one (0.400 g, 0.774 mmol), acetonitrile (3.64 ml), acetic acid (0.137 ml), and water (0.091 ml) to give a suspension. The flask was cooled in an ice-water bath for 15 min, then 1,3-dichloro-5,5-dimethylimidazolidine-2,4-dione (0.152 g, 0.774 mmol) was added in 2 portions over 10 min. The mixture was allowed to warm to room temperature, then solvent was removed. Purified using column chromatography, eluting with 0-50% EtOAc/Heptane to give 1-(4'-chloro-2-fluoro-5-methoxy-3'-methyl-[1,1'-biphenyl]-4-yl)-2-oxo-1,2-dihydroquinoxaline-6-sulfonyl chloride (0.325 g, 0.507 mmol, 65.5% yield). m/z (ESI) 493.0 (M+H)+.

Intermediate DO: (P)-perfluorophenyl 1-(4'-chloro-3-methoxy-3'-methyl-[1,1'-biphenyl]-4-yl)-2-oxo-1,2-dihydroquinoline-6-sulfonate

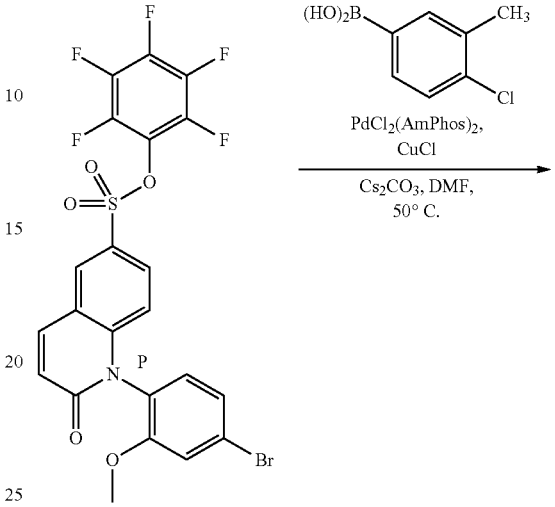

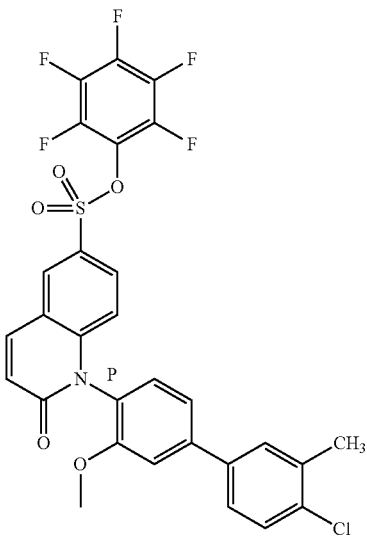

Intermediate (P)-perfluorophenyl 1-(4'-chloro-3-methoxy-3'-methyl-[1,1'-biphenyl]-4-yl)-2-oxo-1,2-dihydroquinoline-6-sulfonate was prepared according to the method described for (P)-perfluorophenyl 1-(3-methoxy-3'-(trifluoromethyl)-[1,1'-biphenyl]-4-yl)-2-oxo-1,2-dihydroquinoline-6-sulfonate, starting from (P)-perfluorophenyl 1-(4-bromo-2-methoxyphenyl)-2-oxo-1,2-dihydroquinoline-6-sulfonate and (4-chloro-3-methylphenyl)boronic acid. LCMS m/z (ESI) 621.9 (M+H)+.

Intermediate DP: 1-(4-bromo-5-fluoro-2-methoxy-phenyl)-2-oxo-N-2-pyrimidinyl-1,2-dihydro-6-quinolinesulfonamide

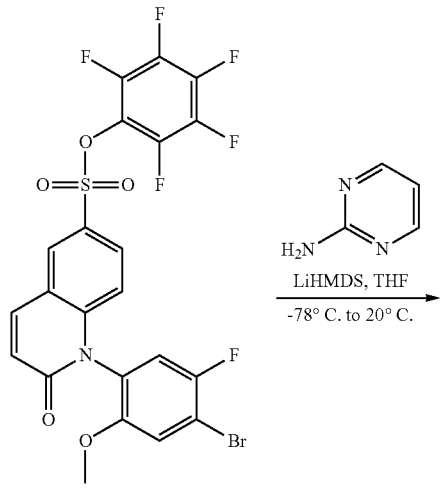

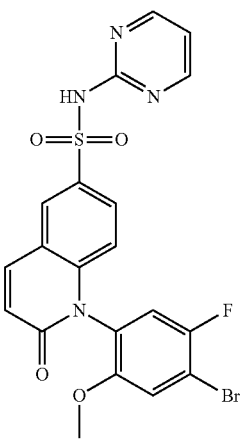

To a solution of perfluorophenyl 1-(4-bromo-5-fluoro-2-methoxyphenyl)-2-oxo-1,2-dihydroquinoline-6-sulfonate (15.0 g, 25.24 mmol) and pyrimidin-2-amine (4.8 g, 50.48 mmol, Alfa Aesar) in THF (300 mL) was added lithium bis(trimethylsilyl)amide (1.0 M solution in THF, 50.5 mL, 50.5 mmol, Aldrich) at −78° C. The reaction mixture was slowly warmed to room temperature and stirred for 1 h. The reaction mixture was quenched with 1.5 N HCl (300 mL) and extracted with ethyl acetate (2×300 mL). The combined organic layers were washed with 1.5N HCl (200 mL). The organic layer was dried over sodium sulfate, filtered and concentrated under reduced pressure to get the crude product which was purified by column chromatography (Silica gel; 60-120 mesh, eluent: 3-5% Methanol in DCM) to obtain 1-(4-bromo-5-fluoro-2-methoxyphenyl)-2-oxo-N-2-pyrimidinyl-1,2-dihydro-6-quinolinesulfonamide (9.6 g, 75.3%) as off white solid. $^1$H NMR (400 MHz, DMSO-$d_6$) δ 11.81 (s, 1H), 8.56-8.42 (m, 3H), 8.26 (d, J=9.6 Hz, 1H), 7.95 (dd, J=8.9, 2.1 Hz, 1H), 7.66 (d, J=6.2 Hz, 1H), 7.61 (d, J=8.6 Hz, 1H), 7.05 (s, 1H), 6.79 (dd, J=16.1, 9.3 Hz, 2H), 3.68 (s, 3H); LCMS (ESI) m/z 505.2 (M+H)$^+$.

Intermediate DQ: (Tetrahydro-2H-pyran-4-yl)zinc(II) iodide

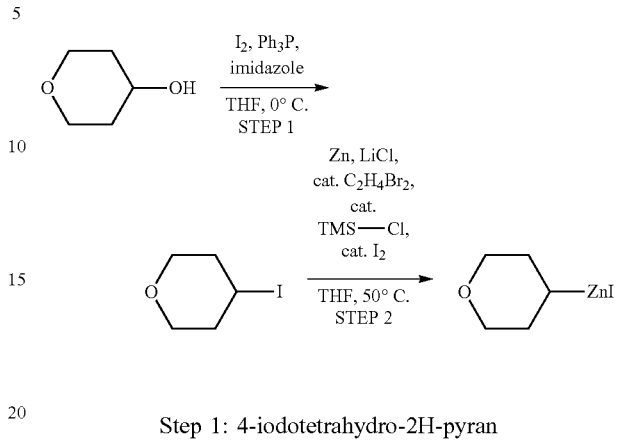

Step 1: 4-iodotetrahydro-2H-pyran

A RBF was charged with tetrahydro-2H-pyran-4-ol (2.0 g, 19.58 mmol), imidazole (1.600 g, 23.50 mmol), triphenylphosphine (5.39 g, 20.56 mmol), and tetrahydrofuran (39.2 ml) and cooled to 0° C. A solution of iodine (5.96 g, 23.50 mmol) in tetrahydrofuran (39.2 ml) was added slowly dropwise. The reaction was warmed to room temperature and stirred overnight. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 80 g, gradient elution 0-50% EtOAc:Heptane) to afford 4-iodotetrahydro-2H-pyran (2.67 g, 12.59 mmol, 64.3% yield) as a clear light yellow oil.

Step 2: (Tetrahydro-2H-pyran-4-yl)zinc(II) iodide

An oven-dried round-bottom flask equipped with a magnetic stir bar and a rubber septum was charged with lithium chloride (0.740 g, 17.45 mmol). The vessel was heated with a heat gun for 10 min under high vacuum and backfilled with nitrogen after cooling to room temperature. Zinc (1.141 g, 17.45 mmol) was added. The vessel was again heated with a heat gun for 10 minutes under high vacuum and backfilled with nitrogen after cooling to room temperature. THF (17.45 ml) and 1,2-dibromoethane (0.038 ml, 0.436 mmol) were added via syringe and the reaction mixture was heated at 60° C. until bubbling occurred. After cooling to room temperature, TMS-Cl (0.033 ml, 0.262 mmol) and a solution of iodine (0.011 g, 0.044 mmol) in THF (0.2 mL) were added via syringe. The reaction mixture was heated at 60° C. for 20 min and then cooled to room temperature. 4-iodotetrahydro-2H-pyran (1.011 ml, 8.73 mmol) was added and the reaction was stirred at 50° C. for 18 h. The reaction mixture was allowed to stand at RT for 1 h and the solution was taken up in a syringe. The syringe was fitted with a 0.45 μM filter and the solution was filtered into an oven-dried screw top vial with teflon septum. The solution was titrated by adding dropwise to a 0° C. solution of iodine (0.0204 g, 0.080 mmol) in lithium chloride, 0.5 m in anhydrous tetrahydrofuran (1.0 ml, 0.500 mmol) until the orange color disappeared. 0.29 mL of solution was used, corresponding to a concentration of 0.28 M.

Intermediate DR: (4-methoxycyclohexyl)zinc(II) iodide (0.28 M in THF)

The title compound was prepared in an analogous manner to (tetrahydro-2H-pyran-4-yl)zinc(II) iodide except that 4-methoxycyclohexanol was used instead of tetrahydro-2H-pyran-4-ol in Step 1 to afford a 0.28M solution of (4-methoxycyclohexyl)zinc(II) iodide in THF.

Intermediate DS: (1R,2S,4S)-7-oxabicyclo[2.2.1]heptan-2-ylmethanol

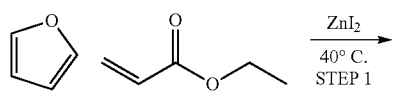

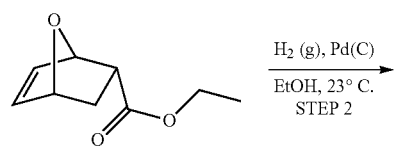

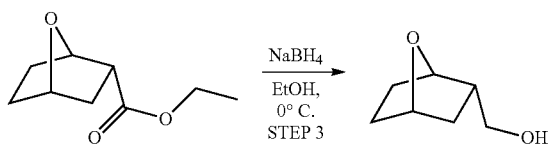

Step 1: (1R,2R,4R)-ethyl 7-oxabicyclo[2.2.1]hept-5-ene-2-carboxylate

A flask was charged with zinc iodide (1.010 ml, 14.98 mmol), then heated with a heat gun under high vacuum for 5 minutes. The flask was charged with furan (5.09 ml, 69.9 mmol) and ethyl acrylate (5.43 ml, 49.9 mmol), then covered in foil and heated at 40° C. for 48 hours. The solution was then diluted with ethyl acetate and washed with 10% aqueous Na2SO3. After drying with Na2SO4 and filtration, the solvents were removed under reduced pressure then purified by silica gel chromatography (RediSep Gold 80 g, gradient elution 0-50% EtOAc:Heptane) to afford (1R,2R,4R)-ethyl 7-oxabicyclo[2.2.1]hept-5-ene-2-carboxylate (3.91 g, 23.25 mmol, 46.5% yield) as a clear colorless oil (2.5:1 mixture of endo and exo isomers). $^1$H NMR (400 MHz, CHLOROFORM-d) δ=6.44 (dd, J=1.7, 5.8 Hz, 1H), 6.41-6.38 (m, 1H), 6.38-6.34 (m, 1H), 6.24 (dd, J=1.6, 5.8 Hz, 1H), 5.19 (dd, J=0.7, 1.6 Hz, 1H), 5.18-5.16 (m, 1H), 5.08 (dd, J=0.7, 4.6 Hz, 1H), 5.02 (ddd, J=0.7, 1.7, 4.7 Hz, 1H), 4.19 (q, J=7.1 Hz, 2H), 4.10 (ttd, J=3.6, 7.1, 10.7 Hz, 1H), 3.11 (ddd, J=3.8, 4.9, 9.1 Hz, 1H), 2.42 (dd, J=3.9, 8.5 Hz, 1H), 2.17 (td, J=4.4, 11.2 Hz, 1H), 2.11 (ddd, J=4.7, 9.3, 11.4 Hz, 1H), 1.60 (dd, J=3.8, 11.5 Hz, 1H), 1.56 (dd, J=8.6, 11.6 Hz, 1H), 1.29 (t, J=7.2 Hz, 3H), 1.25 (t, J=7.2 Hz, 1H)

Step 2: (1R,2R,4S)-ethyl 7-oxabicyclo[2.2.1]heptane-2-carboxylate

A flask was charged with (1R,2R,4R)-ethyl 7-oxabicyclo[2.2.1]hept-5-ene-2-carboxylate (3.91 g, 23.25 mmol) and ethanol (35 mL). The solution was degassed with nitrogen for 5 minutes, then palladium on carbon (5 wt. % wet) (1.0 g, 0.470 mmol) was added portionwise. The flask was evacuated and backfilled three times with nitrogen, then evacuated and backfilled with hydrogen (balloon). The reaction was stirred overnight at room temperature. The reaction was filtered through a plug of Celite and washed several times with ethanol, making sure to keep the catalyst wet with solvent (a layer of sand was added after the first wash). The filtrate was concentrated to afford (1R,2R,4S)-ethyl 7-oxabicyclo[2.2.1]heptane-2-carboxylate (3.63 g, 21.33 mmol, 92% yield). $^1$H NMR (400 MHz, CHLOROFORM-d) δ=4.82 (d, J=5.0 Hz, 1H), 4.72 (t, J=5.0 Hz, 1H), 4.66 (t, J=5.0 Hz, 1H), 4.63-4.59 (m, 1H), 4.22-4.10 (m, 3H), 3.08-2.97 (m, 1H), 2.59 (dd, J=4.9, 9.1 Hz, 1H), 2.14 (dtd, J=2.6, 5.0, 12.3 Hz, 1H), 1.95-1.87 (m, 1H), 1.83-1.63 (m, 4H), 1.62-1.41 (m, 3H), 1.34-1.21 (m, 4H)

Step 3: (1R,2S,4S)-7-oxabicyclo[2.2.1]heptan-2-ylmethanol (1R,2R,4S)-ethyl 7-oxabicyclo[2.2.1]heptane-2-carboxylate (3.63 g, 21.33 mmol) was dissolved in ethanol (107 ml) and cooled to 0° C. Sodium borohydride (4.84 g, 128 mmol) was added portionwise and the reaction was warmed to room temperature and stirred overnight. The reaction was quenched with saturated NH4Cl solution and extracted three times with ethyl acetate. The combined organic layers were washed with brine, dried over sodium sulfate, filtered, and concentrated. The material was purified via column chromatography (RediSep Gold 40 g, gradient elution 0-100% EtOAc:Heptane) to afford (1R,2S,4S)-7-oxabicyclo[2.2.1]heptan-2-ylmethanol (0.973 g, 7.59 mmol, 35.6% yield) as a clear colorless oil. $^1$H NMR (400 MHz, CHLOROFORM-d) δ=4.57 (t, J=5.0 Hz, 1H), 4.49 (d, J=5.1 Hz, 1H), 3.78 (dd, J=6.8, 10.7 Hz, 1H), 3.57 (dd, J=9.3, 10.6 Hz, 1H), 3.51-3.42 (m, 2H), 2.44-2.31 (m, 1H), 2.00-1.92 (m, 1H), 1.85-1.79 (m, 1H), 1.76-1.69 (m, 2H), 1.60 (dd, J=8.6, 12.1 Hz, 1H), 1.49-1.43 (m, 2H), 1.39-1.31 (m, 1H), 1.29-1.24 (m, 1H), 0.94 (dd, J=5.1, 11.9 Hz, 1H)

Intermediate DT: ((1R,2R,4S)-7-oxabicyclo[2.2.1]heptan-2-ylmethyl)zinc(II) iodide

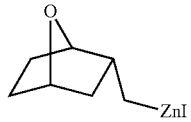

The title compound was prepared in an analogous manner to tetrahydro-2H-pyran-4-yl)zinc(II) iodide except that (1R,2S,4S)-7-oxabicyclo[2.2.1]heptan-2-ylmethanol was used instead of tetrahydro-2H-pyran-4-ol in Step 1 to afford a 0.15M solution of ((1R,2R,4S)-7-oxabicyclo[2.2.1]heptan-2-ylmethyl)zinc(II) iodide in THF.

Intermediate DU: (2,2-dimethyltetrahydro-2H-pyran-4-yl)zinc(II) iodide

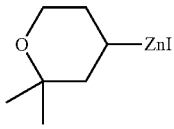

The title compound was prepared in an analogous manner to tetrahydro-2H-pyran-4-yl)zinc(II) iodide except that 2,2-dimethyltetrahydro-2H-pyran-4-ol (Combi Blocks) was used instead of tetrahydro-2H-pyran-4-ol in Step 1 to afford a 0.24M solution of (2,2-dimethyltetrahydro-2H-pyran-4-yl)zinc(II) iodide in THF.

Intermediate DV: (4,4-difluorocyclohexyl)zinc(II) iodide

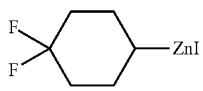

The title compound was prepared in an analogous manner to tetrahydro-2H-pyran-4-yl)zinc(II) iodide except that 4,4-difluorocyclohexanol (Affinity Chemicals) was used instead of tetrahydro-2H-pyran-4-ol in Step 1 to afford a 0.26 M solution of (4,4-difluorocyclohexyl)zinc(II) iodide in THF.

Intermediate DW: Tert-butyl 3-((3',5',6-trifluoro-4-(6-(N-(isoxazol-3-yl)-N-(4-methoxybenzyl)sulfamoyl)-2-oxoquinolin-1(2H)-yl)-[1,1'-biphenyl]-3-yl)oxy)azetidine-1-carboxylate

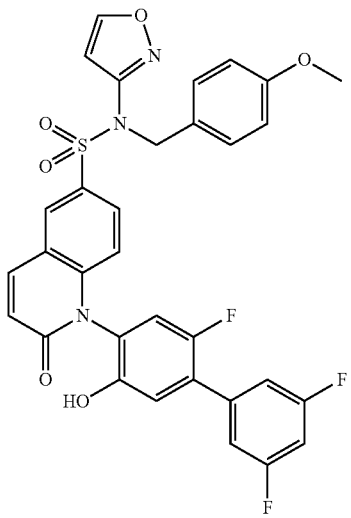

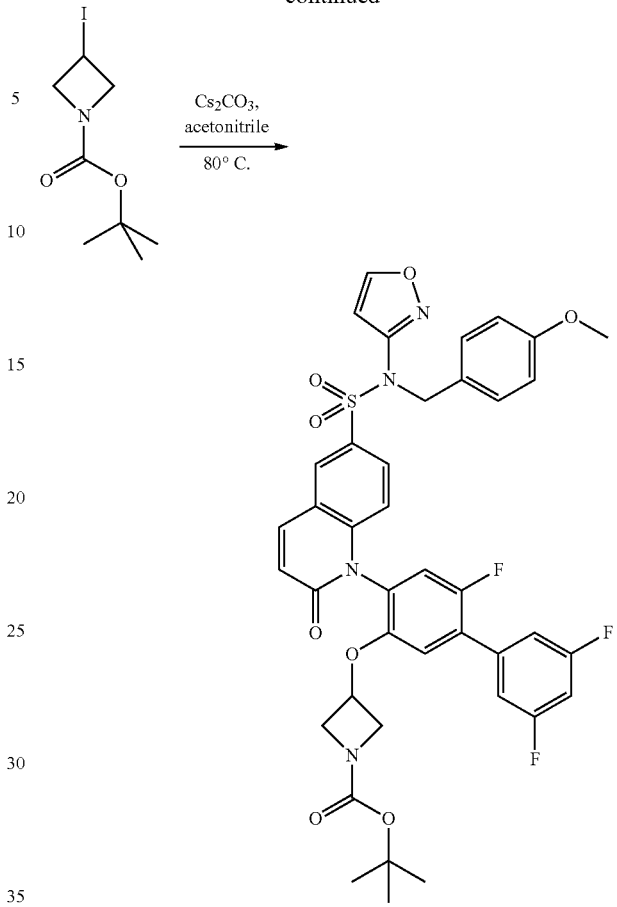

N-boc-3-iodoazetidine (0.076 ml, 0.268 mmol) was added to a solution of N-(isoxazol-3-yl)-N-(4-methoxybenzyl)-2-oxo-1-(2,3',5'-trifluoro-5-hydroxy-[1,1'-biphenyl]-4-yl)-1,2-dihydroquinoline-6-sulfonamide (0.085 g, 0.134 mmol) and cesium carbonate (0.087 g, 0.268 mmol) in acetonitrile (0.335 ml) and stirred over night. LCMS indicated that the reaction was complete (mass—Boc group). The resulting mixture was transferred to a sep. funnel containing water and the aqueous layer was washed 3× with DCM. The organic layers were combined, dried with MgSO4, filtered and concentrated to an oil. The yield was assumed to be quantitative and taken directly on to the next step. m/z (ESI) 691.0 (M+1-Boc)$^+$.

Example 42

(Method 42): 1-(2,3'-difluoro-5-methoxy-[1,1'-biphenyl]-4-yl)-6-(isoxazol-3-ylsulfonyl)quinolin-2(1H)-one

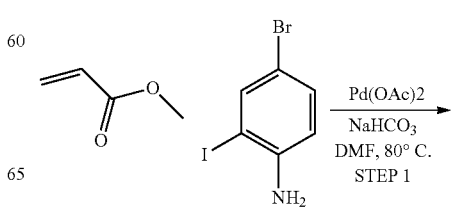

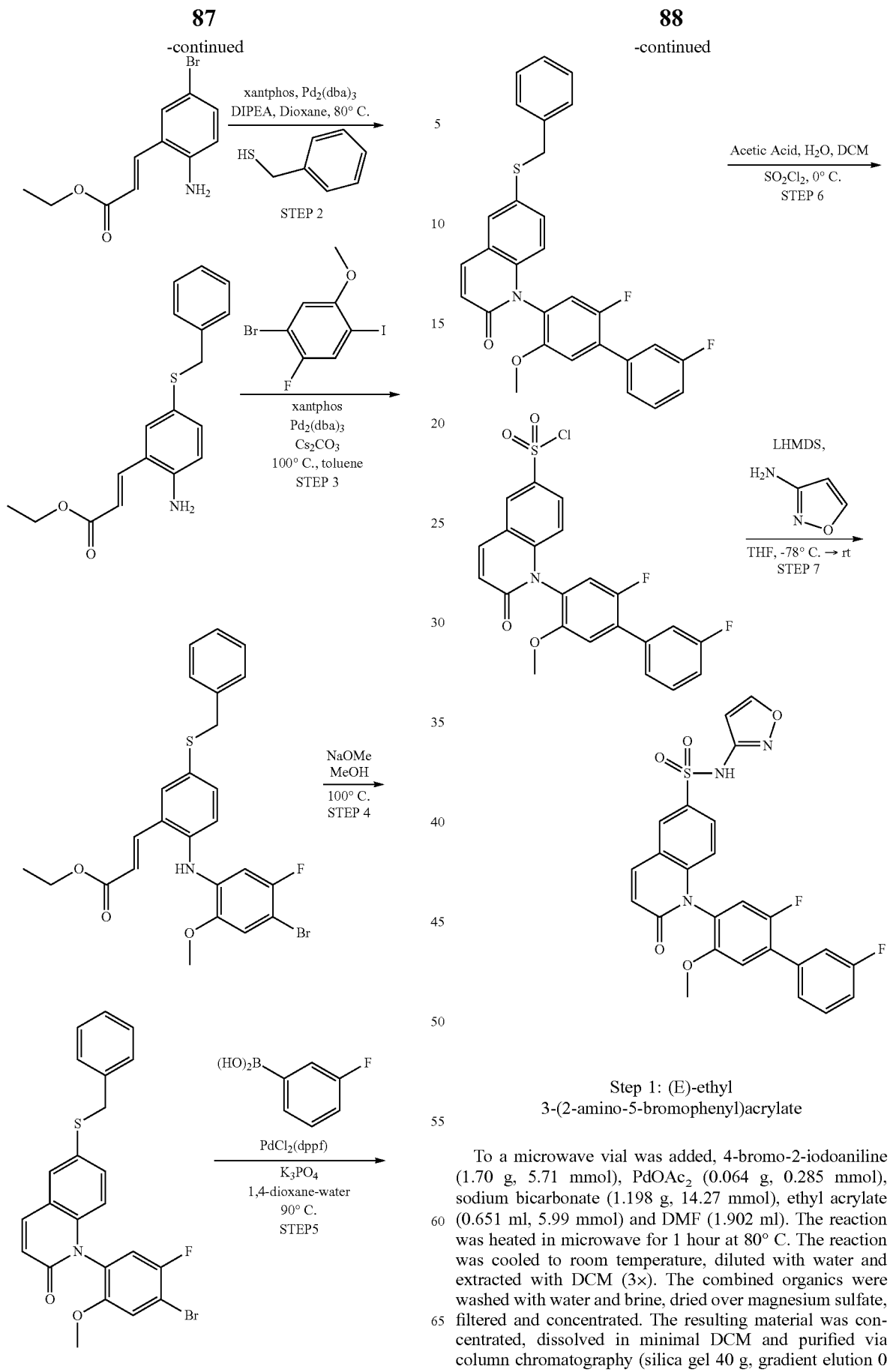

Step 1: (E)-ethyl 3-(2-amino-5-bromophenyl)acrylate

To a microwave vial was added, 4-bromo-2-iodoaniline (1.70 g, 5.71 mmol), PdOAc$_2$ (0.064 g, 0.285 mmol), sodium bicarbonate (1.198 g, 14.27 mmol), ethyl acrylate (0.651 ml, 5.99 mmol) and DMF (1.902 ml). The reaction was heated in microwave for 1 hour at 80° C. The reaction was cooled to room temperature, diluted with water and extracted with DCM (3×). The combined organics were washed with water and brine, dried over magnesium sulfate, filtered and concentrated. The resulting material was concentrated, dissolved in minimal DCM and purified via column chromatography (silica gel 40 g, gradient elution 0 to 50% EtOAc:Heptane) to afford 0.860 g of (E)-ethyl 3-(2-amino-5-bromophenyl)acrylate. m/z (ESI) 270.1 (M+H)+.

Step 2: (E)-ethyl 3-(2-amino-5-(benzylthio)phenyl) acrylate

A screw cap vial was charged with (E)-ethyl 3-(2-amino-5-bromophenyl)acrylate (0.820 g, 2.086 mmol), xantphos (0.092 g, 0.159 mmol), tris(dibenzylideneacetone)dipalladium (0.073 g, 0.080 mmol), 1,4-Dioxane (3.18 ml), and DIPEA (1.108 ml, 6.37 mmol). The vial was purged with Argon, sealed and heated to 80° C. for 10 minutes. The reaction was cooled to RT and benzyl mercaptan (0.395 ml, 3.34 mmol) was added and the reaction was continued heating at 80° C. for an additional 30 minutes. The reaction was cooled to RT, diluted with water and extracted with DCM (3×). The combined organics were washed with water and brine, dried over magnesium sulfate, filtered and concentrated. The resulting material was concentrated, dissolved in minimal DCM and purified via column chromatography (silica gel 40 g, gradient elution 0 to 50% EtOAc: Heptane) to afford 0.80 g of (E)-ethyl 3-(2-amino-5-(benzylthio)phenyl)acrylate. m/z (ESI) 314.1 (M+H)+.

Step 3: (E)-ethyl 3-(5-(benzylthio)-2-((4-bromo-5-fluoro-2-methoxyphenyl)amino)phenyl)acrylate A screw cap vial was charged with (E)-ethyl 3-(2-amino-5-(benzylthio)phenyl)acrylate (0.500 g, 1.595 mmol), xantphos (0.185 g, 0.319 mmol), Pd$_2$(dba)$_3$ (0.146 g, 0.160 mmol), sodium tert-butoxide (0.153 g, 1.595 mmol) and toluene (7.98 ml). The vial was purged with Argon, sealed and heated to 130° C. for 10 minutes. The reaction was cooled to RT and 1-bromo-2-fluoro-4-iodo-5-methoxybenzene (0.581 g, 1.755 mmol) was added and the reaction was continued heating at 100° C. for an additional 30 minutes. The reaction was cooled to RT, diluted with water and extracted with DCM (3×). The combined organics were washed with water and brine, dried over magnesium sulfate, filtered and concentrated. The resulting material was concentrated, dissolved in minimal DCM and purified via column chromatography (silica gel 40 g, gradient elution 0 to 50% EtOAc:Heptane) to afford 0.40 g of (E)-ethyl 3-(5-(benzylthio)-2-((4-bromo-5-fluoro-2-methoxyphenyl) amino)phenyl)acrylate (0.400 g, 0.775 mmol, 48.6% yield). m/z (ESI) 471.0

Step 4: 6-(benzylthio)-1-(4-bromo-5-fluoro-2-methoxyphenyl)-quinolin-2(1H)-one (E)-ethyl 3-(5-(benzylthio)-2-((4-bromo-5-fluoro-2-methoxyphenyl)amino)phenyl)-acrylate (0.400 g, 0.775 mmol was added to a flask followed by MeOH (10.00 mL) and sodium methoxide (1.6 mL, 1.641 mmol). The flask was fitted with reflux condenser and heated to 100° C. for 1 hour. The reaction was cooled to RT and poured into 20 mL HCl (1N). Extracted with EtOAc (3×), dried over magnesium sulfate and filtered. The resulting material was concentrated and used without further purification to yield 0.362 g of 6-(benzylthio)-1-(4-bromo-5-fluoro-2-methoxyphenyl)quinolin-2(1H)-one. m/z (ESI) 516.0 (M+H)+.

Step 5: 6-(benzylthio)-1-(2,3'-difluoro-5-methoxy-[1,1'-biphenyl]-4-yl)quinolin-2(1H)-one A vial was charged with 6-(benzylthio)-1-(4-bromo-5-fluoro-2-methoxyphenyl)quinolin-2(1H)-one (0.200 g, 0.425 mmol), (3-fluorophenyl)boronic acid (0.065 g, 0.468 mmol), potassium phosphate, dibasic (0.296 g, 1.701 mmol), and PdCl$_2$(dppf) (0.031 g, 0.043 mmol)). The vial was flushed with Ar (g), then 1,4-dioxane (1.134 ml) and water (0.567 ml) were added. The vial was sealed and heated in a Biotage Initiator microwave reactor for 1 h at 90° C. LCMS showed clean desired product. The mixture was extracted with EtOAc (3×), then the combined organic extracts were concentrated. The residue was purified by chromatography on silica gel (12-g Redi-Sep Gold column, 0-50%, then 50-100% EtOAc/Heptane) to give 6-(benzylthio)-1-(2,3'-difluoro-5-methoxy-[1,1'-biphenyl]-4-yl)quinolin-2(1H)-one (0.154 g, 0.317 mmol, 74.6% yield). m/z (ESI) 486.0 (M+H)+.

Step 6: 1-(2,3'-difluoro-5-methoxy-[1,1'-biphenyl]-4-yl)-2-oxo-1,2-dihydroquinoline-6-sulfonyl chloride A RBF cooled to 0° C., was charged with 6-(benzylthio)-1-(2,3'-difluoro-5-methoxy-[1,1'-biphenyl]-4-yl)quinolin-2 (1H)-one (0.168 g, 0.346 mmol), DCM (3.30 ml), Acetic Acid (0.082 ml), and Water (0.082 ml). After stirring for 5 minutes at 0° C., sulfuryl chloride (0.028 ml, 0.346 mmol) was added and stirring was continued for an additional 1 hour at 0° C. The reaction was concentrated, dissolved in minimal DCM and purified via column chromatography (silica gel 40 g, gradient elution 0 to 50% EtOAc:Heptane) to afford 1-(2,3'-difluoro-5-methoxy-[1,1'-biphenyl]-4-yl)-2-oxo-1,2-dihydroquinoline-6-sulfonyl chloride (0.135 g, 0.292 mmol, 84% yield). m/z (ESI) 462.0 (M+H)+.

Step 7: 1-(2,3'-difluoro-5-methoxy-[1,1'-biphenyl]-4-yl)-N-(isoxazol-3-yl)-2-oxo-1,2-dihydroquinoline-6-sulfonamide A RBF was charged with isoxazol-3-amine (0.016 g, 0.191 mmol) and THF (1.6 mL), and the vessel was cooled to −78° C. for 15 minutes. Lithium bis(trimethylsilyl)amide (1.0 M in THF) (0.208 ml, 0.208 mmol) was then added dropwise over 1 minute. The reaction was stirred for 10 minutes, and then a solution of 1-(2,3'-difluoro-5-methoxy-[1,1'-biphenyl]-4-yl)-2-oxo-1,2-dihydroquinoline-6-sulfonyl chloride (0.080 g, 0.173 mmol) in THF (1.6 mL) was added dropwise. The bath was removed, and the resulting mixture was stirred for 45 minutes. The reaction was diluted with saturated ammonium chloride (aq.) solution (30 mL), and was washed with ethyl acetate (20 mL×3). The organic layers were combined, dried over magnesium sulfate, filtered and concentrated. The resulting material was purified via MPLC (ISCO, 40 g), eluting with 0 to 100% ethyl acetate in heptanes. The solid was dried under reduced pressure to provide 1-(2,3'-difluoro-5-methoxy-[1,1'-biphenyl]-4-yl)-N-(isoxazol-3-yl)-2-oxo-1,2-dihydroquinoline-6-sulfonamide (0.012 g, 0.024 mmol, 13.60% yield) as a mixture of atropisomers. $^1$H NMR (400 MHz, CHLOROFORM-d) δ ppm 8.27 (d, J=1.76 Hz, 1H) 8.15 (d, J=2.05 Hz, 1H) 7.97 (br. s., 1H) 7.74-7.84 (m, 2H) 7.43-7.53 (m, 1H) 7.37-7.42 (m, 1H) 7.33 (d, J=9.98 Hz, 1H) 7.11-7.18 (m, 2H) 7.09 (d, J=9.49 Hz, 1H) 6.86 (dd, J=14.67, 9.29 Hz, 2H) 6.61 (d, J=1.76 Hz, 1H) 3.72-3.81 (m, 3H). m/z (ESI) 510.0 (M+H)+.

Separation of Atropisomers:

The atropisomers were separated using supercritical fluid chromatography (SFC). The column used was Chiralpak AS-H, 2×15 cm. The mobile phase was run under isocratic conditions; $CO_2$ with 30% methanol to afford as an off-white solid. First atropisomer: $^1$H NMR (400 MHz, DMSO-d$_6$) δ ppm 8.64 (d, J=1.17 Hz, 1H) 8.34 (d, J=2.05 Hz, 1H) 8.23 (d, J=9.59 Hz, 1H) 7.85 (dd, J=8.90, 2.15 Hz, 1H) 7.66-7.75 (m, 2H) 7.56-7.62 (m, 3H) 7.43 (d, J=6.85 Hz, 1H) 7.29-7.38 (m, 1H) 6.83 (dd, J=17.46, 9.24 Hz, 2H) 6.40 (d, J=1.76 Hz, 1H) 3.75 (s, 3H). m/z (ESI) 510.0 (M+H)$^+$. Second atropisomer: $^1$H NMR (400 MHz, DMSO-d$_6$) ppm 8.63 (d, J=1.37 Hz, 1H) 8.34 (d, J=2.15 Hz, 1H) 8.22 (d, J=9.68 Hz, 1H) 7.85 (dd, J=8.95, 2.20 Hz, 1H) 7.66-7.75 (m, 2H) 7.54-7.62 (m, 3H) 7.43 (d, J=6.94 Hz, 1H) 7.33 (d, J=1.56 Hz, 1H) 6.80-6.89 (m, 2H) 6.39 (d, J=1.66 Hz, 1H) 3.75 (s, 3H). m/z (ESI) 510.0 (M+H)$^+$.

Table I provides data for the example, as representative compound of the present invention, as follows: compound name (as named by ACD software, version 12; while the compound names in the written examples presented herein were named using ChemDraw Ultra version 12); molecular weight measured (MW); the method by which the compound was made; the NMR of the representative example; and biological data including in-vitro Nav 1.7 PX data (IC$_{50}$ in uM) and Nav 1.5 PX data (IC$_{50}$ in uM), where available.

TABLE I

| Example No. | Compound name | LCMS | Method Use to Make | NMR | Nav 1.7 PX IC$_{50}$ (μM) | Nav 1.5 PX IC$_{50}$ (μM) |
|---|---|---|---|---|---|---|
| 42 | 1-(2,3'-difluoro-5-metboxy-4-biphenylyl)-N-3-isoxazolyl-2-oxo-1,2-dihydro-6-quinolinesulfonamide | 510.0 | 42 | $^1$H NMR (400 MHz, CHLOROFORM-d) d ppm 8.27 (d, J = 1.76 Hz, 1 H) 8.15 (d, J = 2.05 Hz, 1 H) 7.97 (br. s., 1 H) 7.74-7.84 (m, 2 H) 7.43-7.53 (m, 1 H) 7.37-7.42 (m, 1 H) 7.33 (d, J = 9.98 Hz, 1 H) 7.11-7.18 (m, 2 H) 7.09 (d, J = 9.49 Hz, 1 H) 6.86 (dd, J = 14.67, 9.29 Hz, 2 H) 6.61 (d, J = 1.76 Hz, 1 H) 3.72-3.81 (m, 3 H). m/z (ESI) 510.0 (M + H)$^+$. | 0.027 | |

Examples 312 & 313

Method 65

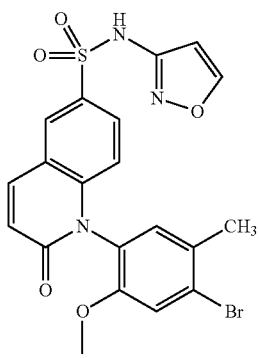

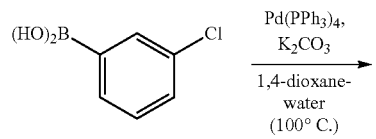

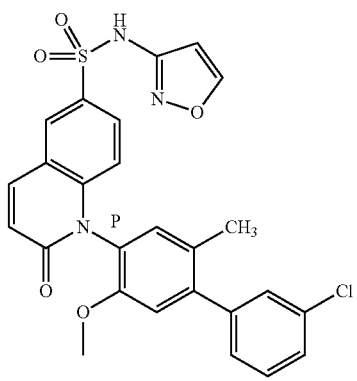

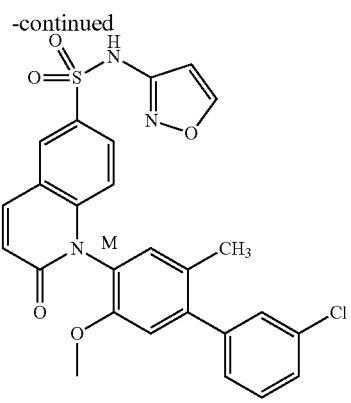

Synthesis of (P)-1-(3'-chloro-5-methoxy-2-methyl-4-biphenylyl)-N-3-isoxazolyl-2-oxo-1,2-dihydro-6-quinolinesulfonamide (ex 312) and (M)-1-(3'-chloro-5-methoxy-2-methyl-4-biphenylyl)-N-3-isoxazolyl-2-oxo-1,2-dihydro-6-quinolinesulfonamide (ex. 313)

A vial was charged with 1-(4-bromo-2-methoxy-5-methylphenyl)-N-(isoxazol-3-yl)-2-oxo-1,2-dihydroquinoline-6-sulfonamide (298 mg, 0.608 mmol), (3-chlorophenyl)boronic acid (143 mg, 0.912 mmol), potassium carbonate (252 mg, 1.823 mmol), and Pd(Ph₃P)₄ (70.2 mg, 0.061 mmol). The vial was flushed with Ar (g), then 1,4-dioxane (2279 µl) and water (760 µl) were added. The vial was sealed and heated to 100° C. for 5 h. The mixture was cooled and extracted with EtOAc (5×), and the combined organic extracts were concentrated. The residue was purified by chromatography on silica gel (25-g SNAP Ultra column, 0-10% MeOH/DCM) to give 407 mg of a yellow foam. This material was purified by chiral SFC on Chiralpak AD-H column (40% MeOH/60% CO₂) to give (P)-1-(3'-chloro-5-methoxy-2-methyl-4-biphenylyl)-N-3-isoxazolyl-2-oxo-1, 2-dihydro-6-quinolinesulfonamide as peak 1 and (M)-1-(3'-chloro-5-methoxy-2-methyl-4-biphenylyl)-N-3-isoxazolyl-2-oxo-1,2-dihydro-6-quinolinesulfonamide as peak 2, both as off-white solids. Data for peak 1: ¹H NMR (400 MHz, DMSO-d₆) δ=11.66 (s, 1H), 8.72 (d, J=1.8 Hz, 1H), 8.37 (d, J=2.2 Hz, 1H), 8.22 (d, J=9.6 Hz, 1H), 7.86 (dd, J=2.2, 9.0 Hz, 1H), 7.60-7.40 (m, 4H), 7.26 (s, 1H), 7.14 (s, 1H), 6.87-6.73 (m, 2H), 6.44 (d, J=1.8 Hz, 1H), 3.68 (s, 3H), 2.20 (s, 3H). m/z (ESI) 522.0 (M+H)⁺. Data for peak 2: ¹H NMR (400 MHz, DMSO-d₆) δ=11.66 (s, 1H), 8.72 (d, J=1.8 Hz, 1H), 8.37 (d, J=2.2 Hz, 1H), 8.22 (d, J=9.6 Hz, 1H), 7.86 (dd, J=2.2, 9.0 Hz, 1H), 7.60-7.40 (m, 4H), 7.26 (s, 1H), 7.14 (s, 1H), 6.87-6.73 (m, 2H), 6.44 (d, J=1.8 Hz, 1H), 3.68 (s, 3H), 2.20 (s, 3H). m/z (ESI) 522.0 (M+H)⁺.

Example 319 & 320

(Method 70): (M)-1-(3'-chloro-3-fluoro-5-methoxy-4-biphenylyl)-N-3-isoxazolyl-2-oxo-1,2-dihydro-6-quinolinesulfonamide (319) and (P)-1-(3'-chloro-3-fluoro-5-methoxy-4-biphenylyl)-N-3-isoxazolyl-2-oxo-1,2-dihydro-6-quinolinesulfonamide (ex. 320)

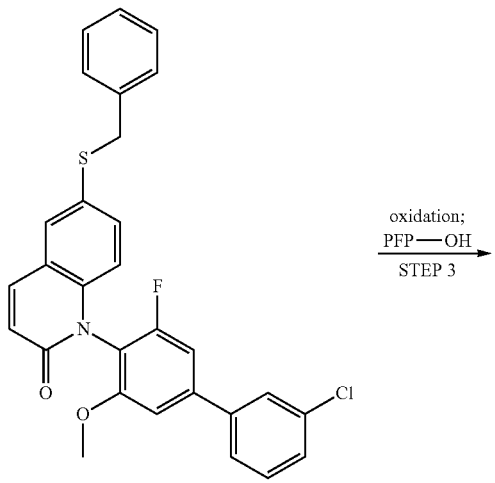
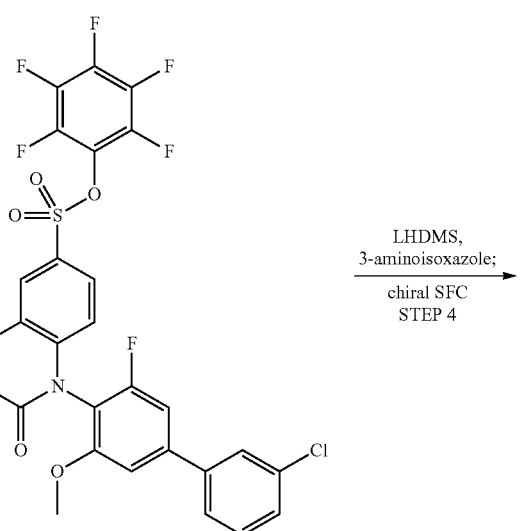
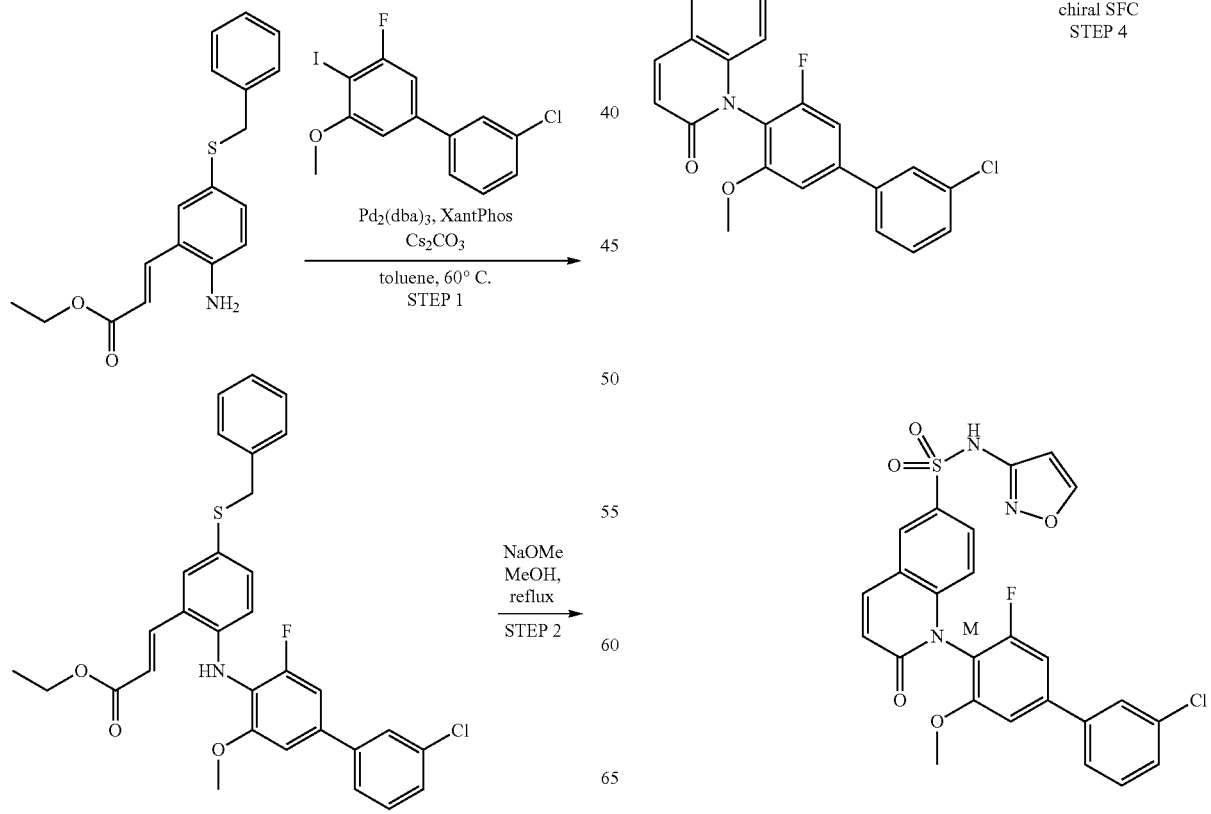
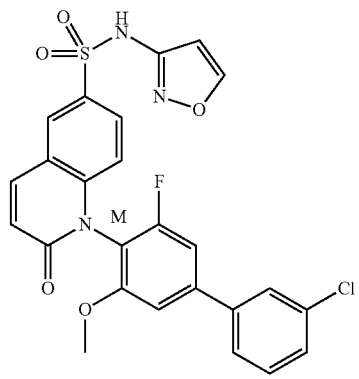

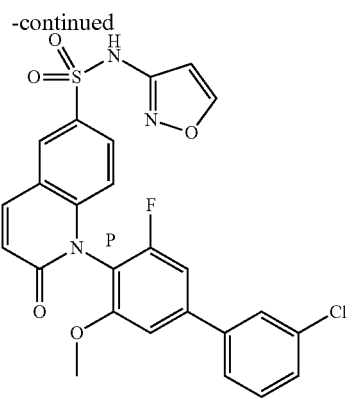

Step 1: (E)-ethyl 3-(5-(benzylthio)-2-((3'-chloro-3-fluoro-5-methoxy-[1,1'-biphenyl]-4-yl)amino)phenyl)acrylate A pressure vessel was charged with (E)-ethyl 3-(2-amino-5-(benzylthio)phenyl)acrylate (497.91 mg, 1.589 mmol, made via Method 42, Steps 1-2), 3'-chloro-3-fluoro-4-iodo-5-methoxy-1,1'-biphenyl (605 mg, 1.668 mmol), Xantphos (46.0 mg, 0.079 mmol), Pd$_2$(dba)$_3$ (36.4 mg, 0.040 mmol), and cesium carbonate (1035 mg, 3.18 mmol) were added. The vessel was flushed with Ar (g), then toluene (3177 μl) was added. The vessel was sealed and lowered into a 110° C. heating bath for 4 h. The heating bath was turned off, and the vessel was allowed to cool to RT with the bath. In the morning, the mixture was filtered through celite. The filter pad was washed with EtOAc (3×). The filtrate was concentrated. The residue was purified by chromatography on silica gel (40-g Redi-Sep Gold column, 0-30% EtOAc/Heptane with 5% DCM) to give (E)-ethyl 3-(5-(benzylthio)-2-((3'-chloro-3-fluoro-5-methoxy-[1,1'-biphenyl]-4-yl)amino)phenyl)acrylate (468.1 mg, 0.854 mmol, 53.8% yield) as a yellow solid. m/z (ESI) 548.2 (M+H)$^+$.

Step 2: 6-(benzylthio)-1-(3'-chloro-3-fluoro-5-methoxy-[1,1'-biphenyl]-4-yl)quinolin-2(1H)-one A RBF was charged with (E)-ethyl 3-(5-(benzylthio)-2-((3'-chloro-3-fluoro-5-methoxy-[1,1'-biphenyl]-4-yl)amino)phenyl)acrylate (468 mg, 0.854 mmol) and MeOH (4270 μl) to give a yellow suspension. Sodium methoxide (25 wt % in MeOH) (36.9 μl, 0.171 mmol) was added. A reflux condenser was attached, and the flask was lowered into a 70° C. heating bath. The mixture was heated overnight. LCMS in the morning showed mainly the desired product. The mixture was diluted with DCM and concentrated. The residue was purified by chromatography on silica gel (25-g Ultra SNAP column, 10-60% EtOAc/Heptane) to give 6-(benzylthio)-1-(3'-chloro-3-fluoro-5-methoxy-[1,1'-biphenyl]-4-yl)quinolin-2(1H)-one (404 mg, 0.805 mmol, 94% yield) as a clear oil. m/z (ESI) 502.1 (M+H)$^+$.

Step 3: Perfluorophenyl 1-(3'-chloro-3-fluoro-5-methoxy-[1,1'-biphenyl]-4-yl)-2-oxo-1,2-dihydroquinoline-6-sulfonate A RBF was charged with 6-(benzylthio)-1-(3'-chloro-3-fluoro-5-methoxy-[1,1'-biphenyl]-4-yl)quinolin-2(1H)-one (403 mg, 0.803 mmol), DCM (6296 μl), Acetic Acid (236 μl), and Water (157 μl) to give clear, light-brown. The flask was cooled in an ice-water bath for 10 min, then 1,3-dichloro-5,5-dimethylimidazolidine-2,4-dione (395 mg, 2.007 mmol) was added in one portion. After 20 min, an additional 130 mg of oxidant was added. Following another 10 min of stirring, 2,3,4,5,6-pentafluorophenol (222 mg, 1.204 mmol) was added, then triethylamine (448 μl, 3.21 mmol) was added dropwise. After 20 min, additional portions of triethylamine (0.15 mL) and PFP—OH (85 mg) were added. The mixture was stirred for 5 min, then loaded directly onto a 25-g silica gel column. The column was dried by applying a vacuum hose to one end for 10 min. Then the column was eluted onto a 25-g SNAP Ultra column with 0-50% EtOAc/Heptane. The main spot was collected with a slightly lower spot. The fractions were concentrated to give 408 mg of perfluorophenyl 1-(3'-chloro-3-fluoro-5-methoxy-[1,1'-biphenyl]-4-yl)-2-oxo-1,2-dihydroquinoline-6-sulfonate as a white solid that was about 70% pure and was used directly in the next step without further purification. m/z (ESI) 626.0 (M+H)$^+$.

Step 4: (M)-1-(3'-chloro-3-fluoro-5-methoxy-4-biphenylyl)-N-3-isoxazolyl-2-oxo-1,2-dihydro-6-quinolinesulfonamide and (P)-1-(3'-chloro-3-fluoro-5-methoxy-4-biphenylyl)-N-3-isoxazolyl-2-oxo-1,2-dihydro-6-quinolinesulfonamide A solution of perfluorophenyl 1-(3'-chloro-3-fluoro-5-methoxy-[1,1'-biphenyl]-4-yl)-2-oxo-1,2-dihydroquinoline-6-sulfonate (408 mg, 0.652 mmol), isoxazol-3-amine (67.4 μl, 0.913 mmol) and THF (6518 μl) was cooled in an ice-bath for 15 min, then lithium bis(trimethylsilyl)amide (1M in THF) (1630 μl, 1.630 mmol) was added dropwise. After 10 min, additional portions of isoxazol-3-amine (67.4 μl, 0.913 mmol) and LHMDS solution (0.8 mL) were added. The mixture was stirred for 20 min, then an additional portion of amine (0.04 mL) was added. After another 20 min, the mixture was diluted with 1N aq. HCl and EtOAc. The layers were separated, and the organic layer was washed with 1N aq. HCl. The aq. layers were combined and extracted with EtOAc (2×). The combined organic extracts were dried over sodium sulfate, filtered, and concentrated. The residue was purified by chromatography on silica gel (40-g Redi-Sep Gold column, 0-3% MeOH/DCM, then again on a 40-g Redi-Sep Gold column, 20-70% EtOAc/Heptane) to give 140 mg of an off-white solid. This material was separated by chiral SFC on a Chiralpak OZ-H column with 40% MeOH/60% CO$_2$ to give (M)-1-(3'-chloro-3-fluoro-5-methoxy-4-biphenylyl)-N-3-isoxazolyl-2-oxo-1,2-dihydro-6-quinolinesulfonamide as a peak 1 and (P)-1-(3'-chloro-3-fluoro-5-methoxy-4-biphenylyl)-N-3-isoxazolyl-2-oxo-1,2-dihydro-6-quinolinesulfonamide as peak 2, both as light-yellow solids. Data for peak 1: $^1$H NMR (400 MHz, DMSO-d$_6$) δ=8.52 (d, J=1.2 Hz, 1H), 8.30 (d, J=2.1 Hz, 1H), 8.24 (d, J=9.7 Hz, 1H), 7.97 (t, J=1.7 Hz, 1H), 7.86-7.82 (m, 2H), 7.59-7.48 (m, 3H), 7.45 (s, 1H), 6.86-6.76 (m, 2H), 6.31 (d, J=1.8 Hz, 1H), 3.84 (s, 3H). m/z (ESI) 526.2 (M+H)$^+$. Data for peak 2: $^1$H NMR (400 MHz, DMSO-d$_6$) δ=8.52 (d, J=1.2 Hz, 1H), 8.30 (d, J=2.1 Hz, 1H), 8.24 (d, J=9.7 Hz, 1H), 7.97 (t, J=1.7 Hz, 1H), 7.86-7.82 (m, 2H), 7.59-7.48 (m, 3H), 7.45 (s, 1H), 6.86-6.76 (m, 2H), 6.31 (d, J=1.8 Hz, 1H), 3.84 (s, 3H). m/z (ESI) 526.2 (M+H)$^+$.

Example 321 & 322

(Method 71): (P)-1-(3'-chloro-5-methoxy-2-methyl-4-biphenylyl)-2-oxo-N-2-pyrimidinyl-1,2-dihydro-6-quinolinesulfonamide (ex. 321) and (M)-1-(3'-chloro-5-methoxy-2-methyl-4-biphenylyl)-2-oxo-N-2-pyrimidinyl-1,2-dihydro-6-quinolinesulfonamide (ex. 322)

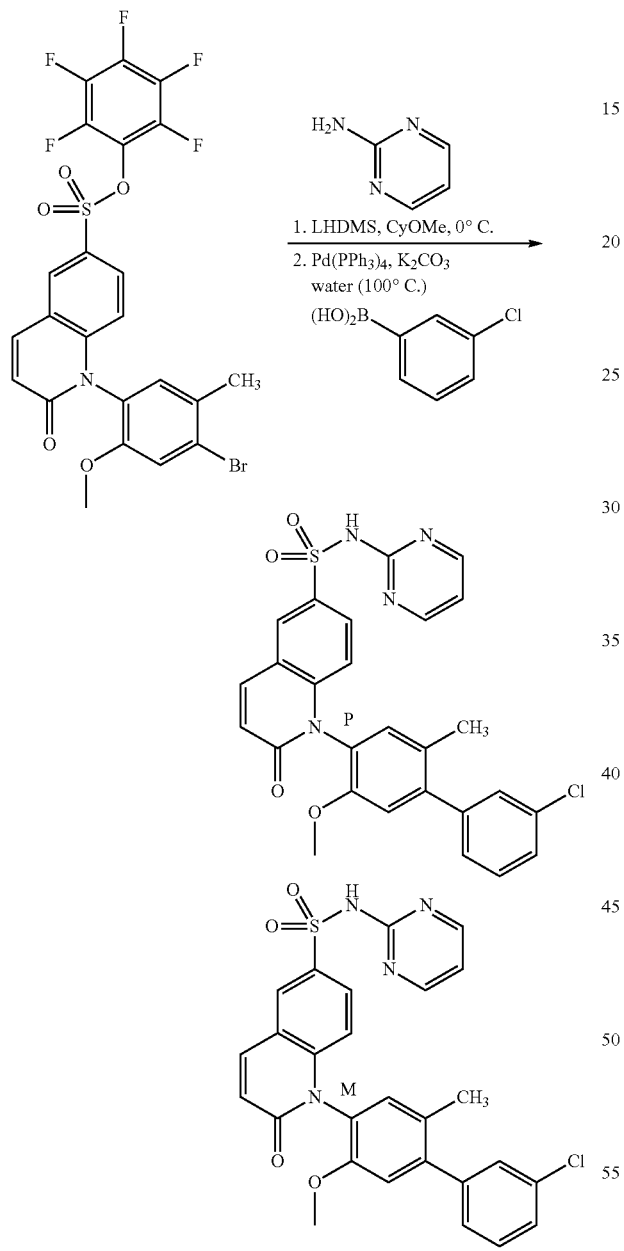

A solution of perfluorophenyl 1-(4-bromo-2-methoxy-5-methylphenyl)-2-oxo-1,2-dihydroquinoline-6-sulfonate (210.66 mg, 0.357 mmol), pyrimidin-2-amine (37.3 mg, 0.393 mmol), and CPME (1338 μl) were cooled in an ice-bath for 15 min, then lithium bis(trimethylsilyl)amide (1M in THF) (785 μl, 0.785 mmol) was added dropwise (12:25 pm). After 50 min, the mixture was diluted with water (446 μl), then warmed to room temperature. (3-Chlorophenyl)boronic acid (84 mg, 0.535 mmol) and tetrakis(triphenylphosphine) palladium(0) (41.2 mg, 0.036 mmol) were added. The vial was flushed with Ar (g), sealed, and placed in a 90° C. heating bath for 2.5 h. The mixture was diluted with EtOAc and 2N aq. HCl. The aq. layer was extracted with EtOAc (2×). The combined organic extracts were dried over sodium sulfate, filtered, and concentrated. The residue was purified by chromatography on silica gel (25-g Ultra SNAP column, 0-5% MeOH/DCM). The resulting yellow oil was repurified by chromatography on silica gel (25-g Ultra SNAP column, 30-80% EtOAc/Heptane) to give 74 mg of an off-white solid. This material was purified by chiral SFC on Regis Whelk-O (S,S) column with 55% MeOH/45% $CO_2$ to give (P)-1-(3'-chloro-5-methoxy-2-methyl-4-biphenylyl)-2-oxo-N-2-pyrimidinyl-1,2-dihydro-6-quinolinesulfonamide as peak 1 and (M)-1-(3'-chloro-5-methoxy-2-methyl-4-biphenylyl)-2-oxo-N-2-pyrimidinyl-1,2-dihydro-6-quinolinesulfonamide as peak 2. Both were obtained as light-yellow solids. Data for peak 1: $^1$H NMR (400 MHz, DMSO-$d_6$) δ=11.92 (br. s., 1H), 8.48-8.39 (m, 3H), 8.24 (d, J=9.6 Hz, 1H), 7.97 (dd, J=2.2, 9.0 Hz, 1H), 7.59-7.40 (m, 4H), 7.24 (s, 1H), 7.14 (s, 1H), 6.97 (t, J=4.4 Hz, 1H), 6.84-6.72 (m, 2H), 3.67 (s, 3H), 2.20 (s, 3H). m/z (ESI) 533.2 (M+H)$^+$. Data for peak 2: $^1$H NMR (400 MHz, DMSO-$d_6$) δ=11.92 (br. s., 1H), 8.48-8.39 (m, 3H), 8.24 (d, J=9.6 Hz, 1H), 7.97 (dd, J=2.2, 9.0 Hz, 1H), 7.59-7.40 (m, 4H), 7.24 (s, 1H), 7.14 (s, 1H), 6.97 (t, J=4.4 Hz, 1H), 6.84-6.72 (m, 2H), 3.67 (s, 3H), 2.20 (s, 3H). m/z (ESI) 533.2 (M+H)$^+$.

Example 323 & 324

Method 72: (P)—N-3-isoxazolyl-1-(3-methoxy-3'-(trifluoromethyl)-4-biphenylyl)-2-oxo-1,2-dihydro-6-quinolinesulfonamide (ex. 323) and (M)-N-3-isoxazolyl-1-(3-methoxy-3'-(trifluoromethyl)-4-biphenylyl)-2-oxo-1,2-dihydro-6-quinolinesulfonamide (ex. 324)

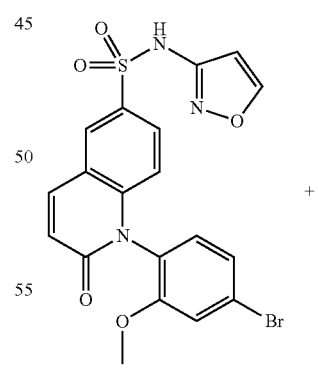

+

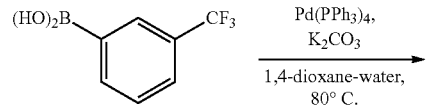

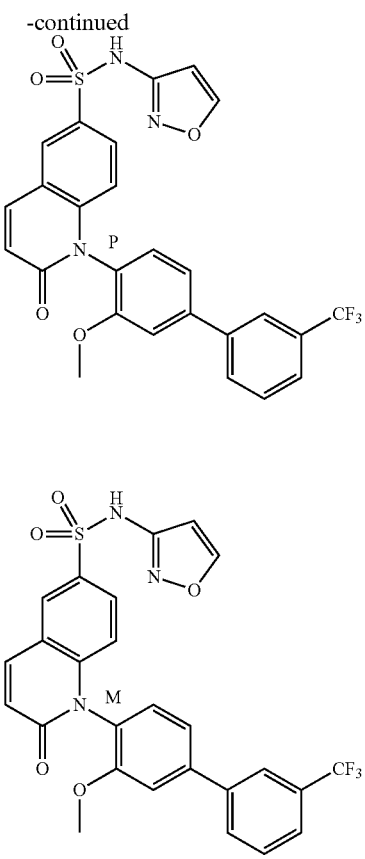

A vial was charged with 1-(4-bromo-2-methoxyphenyl)-N-(isoxazol-3-yl)-2-oxo-1,2-dihydroquinoline-6-sulfonamide (270.9 mg, 0.569 mmol)_(3-(trifluoromethyl)phenyl) boronic acid (140 mg, 0.739 mmol), potassium carbonate (236 mg, 1.706 mmol), and tetrakis(triphenylphosphine)palladium(0) (32.9 mg, 0.028 mmol). The vial was flushed with Ar (g), then 1,4-dioxane (2133 µl) and water (711 µl) were added. The vial was sealed and heated to 80° C. for 6 h. The layers were separated (via pipette), the aq. layer was extracted with EtOAc (5×), and the combined organic extracts were concentrated. The residue was purified by chromatography on silica gel (50-g Redi-Sep column, 25-g loading column, 20-70% EtOAc/Heptane) to give 126 mg of an off-white solid. This material was separated by chiral SFC on a AS-H column with 25% MeOH/75% $CO_2$ to give (P)—N-3-isoxazolyl-1-(3-methoxy-3'-(trifluoromethyl)-4-biphenylyl)-2-oxo-1,2-dihydro-6-quinolinesulfonamide as peak 1 and (M)-N-3-isoxazolyl-1-(3-methoxy-3'-(trifluoromethyl)-4-biphenylyl)-2-oxo-1,2-dihydro-6-quinolinesulfonamide as peak 2. Both materials were obtained as off-white solids. Data for peak 1: $^1$H NMR (400 MHz, DMSO-$d_6$) δ=11.65 (br. s., 1H), 8.71 (d, J=1.8 Hz, 1H), 8.36 (d, J=2.2 Hz, 1H), 8.23 (d, J=9.6 Hz, 1H), 8.17-8.05 (m, 2H), 7.91-7.71 (m, 3H), 7.61 (d, J=1.8 Hz, 1H), 7.56-7.49 (m, 1H), 7.43 (d, J=8.1 Hz, 1H), 6.80 (dd, J=5.5, 9.3 Hz, 2H), 6.43 (d, J=1.9 Hz, 1H), 3.80 (s, 3H). m/z (ESI) 542.2 (M+H)$^+$. Data for peak 2: $^1$H NMR (400 MHz, DMSO-$d_6$) δ=11.65 (br. s., 1H), 8.71 (d, J=1.8 Hz, 1H), 8.36 (d, J=2.2 Hz, 1H), 8.23 (d, J=9.6 Hz, 1H), 8.17-8.05 (m, 2H), 7.91-7.71 (m, 3H), 7.61 (d, J=1.8 Hz, 1H), 7.56-7.49 (m, 1H), 7.43 (d, J=8.1 Hz, 1H), 6.80 (dd, J=5.5, 9.3 Hz, 2H), 6.43 (d, J=1.9 Hz, 1H), 3.80 (s, 3H). m/z (ESI) 542.2 (M+H)$^+$.

Example 325

(Method 73): (P)-1-(3'-chloro-2,5'-difluoro-5-methoxy-4-biphenylyl)-N-1,3-oxazol-2-yl-2-oxo-1,2-dihydro-6-quinolinesulfonamide

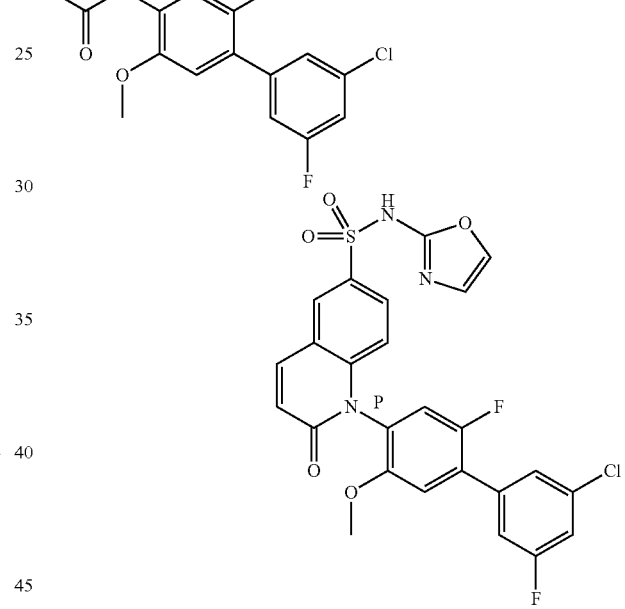

A RBF was charged with perfluorophenyl 1-(3'-chloro-2,5'-difluoro-5-methoxy-[1,1'-biphenyl]-4-yl)-2-oxo-1,2-dihydroquinoline-6-sulfonate (106.08 mg, 0.165 mmol), oxazol-2-amine (16.62 mg, 0.198 mmol), and DMSO (412 µl) to give a clear solution. THF (1236 µl) was added, and the solution was cooled in an ice-water bath for 5 min. Lithium bis(trimethylsilyl)amide (1M in THF) (362 µl, 0.362 mmol) dropwise. After 15 min total, the mixture was diluted with 1N aq. HCl and EtOAc. The layers were separated, and the aq. layer was extracted with EtOAc (1×). The combined organic extracts were dried over sodium sulfate, filtered, and concentrated. The residue was purified by chromatography on silica gel (12-g Redi-Sep Gold column, 10-60% of a 3:1 EtOAc/EtOH solution in heptane with 10% DCM as additive) to give (P)-1-(3'-chloro-2,5'-difluoro-5-methoxy-4-biphenylyl)-n-1,3-oxazol-2-yl-2-oxo-1,2-dihydro-6-quinolinesulfonamide (25 mg, 0.046 mmol, 27.9% yield) as an off-white solid. $^1$H NMR (400 MHz, DMSO-$d_6$) δ=12.17 (br. s., 1H), 8.34 (d, J=2.1 Hz, 1H), 8.20 (d, J=9.6 Hz, 1H), 7.87 (dd, J=2.2, 8.9 Hz, 1H), 7.73-7.52

(m, 5H), 7.48 (d, J=6.9 Hz, 1H), 7.27 (d, J=1.7 Hz, 1H), 6.78 (dd, J=3.8, 9.2 Hz, 2H), 3.76 (s, 3H). m/z (ESI) 544.1 (M+H)$^+$.

Example 326

(Method 74): (P)-1-(3'-chloro-2,5'-difluoro-5-methoxy-4-biphenylyl)-N-1,2,4-oxadiazol-3-yl-2-oxo-1,2-dihydro-6-quinolinesulfonamide

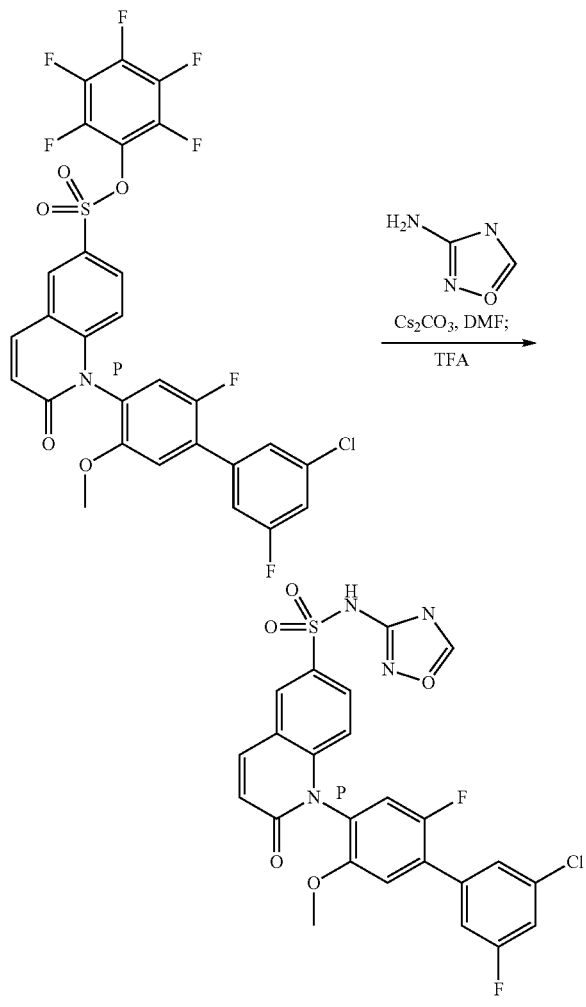

A vial was charged with perfluorophenyl 1-(3'-chloro-2,5'-difluoro-5-methoxy-[1,1'-biphenyl]-4-yl)-2-oxo-1,2-dihydroquinoline-6-sulfonate (111.9 mg, 0.174 mmol), tert-butyl 1,2,4-oxadiazol-3-ylcarbamate (41.8 mg, 0.226 mmol), and cesium carbonate (85 mg, 0.261 mmol). The flask was flushed with Ar (g), then DMF (869 μL) was added. The mixture was stirred for 3 h then additional portions of the amine (60 mg) and cesium carbonate (120 mg) were added in sequence. The resulting mixture was stirred overnight. The mixture was diluted with water and extracted with EtOAc. The organic extract was dried over sodium sulfate, filtered, and concentrated. The residue was taken up in DCM (1 mL) and TFA (1 mL). The mixture was stirred for 3 h then concentrated, and the residue was concentrated from DCM. The residue was purified by chromatography on silica gel (25-g SNAP Ultra column, 10-60% of a 3:1 EtOAc/EtOH in Heptane with 10% DCM as an additive) to give 22 mg of a white solid. The material was purified further by chromatography on silica gel (12-g Redi-Sep Gold column, 0-8% MeOH/DCM) to give (P)-1-(3'-chloro-2,5'-difluoro-5-methoxy-4-biphenylyl)-N-1,2,4-oxadiazol-3-yl-2-oxo-1,2-dihydro-6-quinolinesulfonamide (12.07 mg, 0.022 mmol, 12.75% yield) as an off-white solid. $^1$H NMR (400 MHz, DMSO-d$_6$) δ=12.44 (br. s., 1H), 9.24 (s, 1H), 8.40 (d, J=2.1 Hz, 1H), 8.26 (d, J=9.6 Hz, 1H), 7.91 (dd, J=2.2, 9.0 Hz, 1H), 7.67 (d, J=1.2 Hz, 1H), 7.63-7.53 (m, 3H), 7.48 (d, J=6.9 Hz, 1H), 6.82 (dd, J=9.3, 15.2 Hz, 2H), 3.76 (s, 3H). m/z (ESI) 545.0 (M+H)$^+$.

Example 327

(Method 75): 1-(3-((2R)-2,3-dihydroxypropyl)-3'-fluoro-4-biphenylyl)-N-3-isoxazolyl-2-oxo-1,2-dihydro-6-quinolinesulfonamide, 1-(3-((2S)-2,3-dihydroxypropyl)-3'-fluoro-4-biphenylyl)-N-3-isoxazolyl-2-oxo-1,2-dihydro-6-quinolinesulfonamide

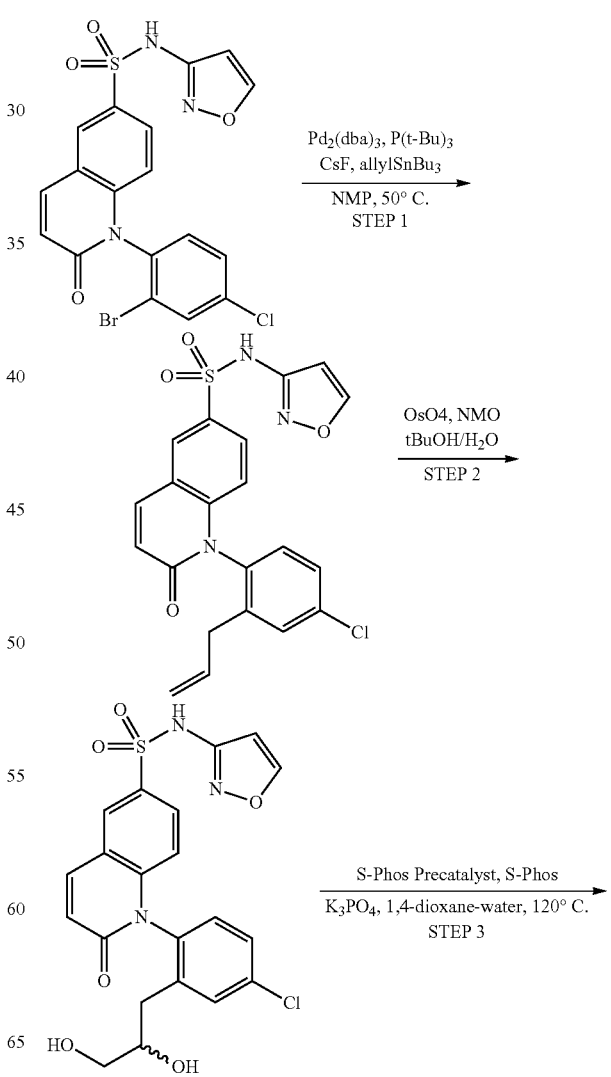

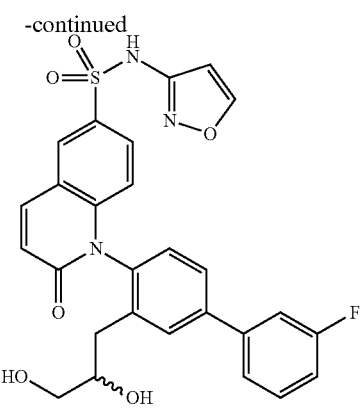

Step 1: 1-(2-allyl-4-chlorophenyl)-N-(isoxazol-3-yl)-2-oxo-1,2-dihydroquinoline-6-sulfonamide A RBF was charged with 1-(2-bromo-4-chlorophenyl)-N-(isoxazol-3-yl)-2-oxo-1,2-dihydroquinoline-6-sulfonamide (891 mg, 1.853 mmol), Pd$_2$(dba)$_3$ (85 mg, 0.093 mmol), bis(tri-t-butylphosphine)palladium(0) (95 mg, 0.185 mmol), and cesium fluoride (845 mg, 5.56 mmol). The flask was flushed with Ar (g), then NMP (7414 µl) and allyltributylstannane (1724 µl, 5.56 mmol) were added in sequence. The flask was placed in a 50° C. heating bath and stirred for 3 hr. The mixture was cooled to room temperature, then partitioned between 1N aq. HCl and EtOAc, then stirred vigorously for 10 min. The layers were the separated. The aq. layer was extracted with EtOAc (2×), and the combined organic extracts were dried over sodium sulfate, filtered, and concentrated. The residue was purified by chromatography on silica gel (50-g SNAP Ultra column, 25-g silica gel column) to give 735 mg of 1-(2-allyl-4-chlorophenyl)-N-(isoxazol-3-yl)-2-oxo-1,2-dihydroquinoline-6-sulfonamide as an off-white solid that also contained some reduced starting material. m/z (ESI) 442.1 (M+H)$^+$.

Step 2: 1-(4-chloro-2-(2,3-dihydroxypropyl)phenyl)-N-(isoxazol-3-yl)-2-oxo-1,2-dihydroquinoline-6-sulfonamide A RBF was charged with 1-(2-allyl-4-chlorophenyl)-N-(isoxazol-3-yl)-2-oxo-1,2-dihydroquinoline-6-sulfonamide (735 mg, 1.331 mmol), THF (4436 µl), water (2218 µl), and 4-methylmorpholine n-oxide (312 mg, 2.66 mmol). Osmium tetroxide, 4% solution in water (813 µl, 0.133 mmol) was added, and the resulting mixture was stirred further for 1 h. The mixture was diluted with saturated aq. sodium thiosulfate solution. The resulting biphasic mixture was stirred vigorously for 20 min, then was extracted with EtOAc (3×). The combined organic extracts were dried over sodium sulfate, filtered, and concentrated. The residue was purified by chromatography on silica gel (50-g SNAP Ultra column, 25-g silica gel loading column, 25-75% of a 3:1 EtOAc/EtOH mixture in heptane with 10% DCM) to give ca. 60 mg of 1-(4-chloro-2-(2,3-dihydroxypropyl)phenyl)-N-(isoxazol-3-yl)-2-oxo-1,2-dihydroquinoline-6-sulfonamide as an off-white solid. m/z (ESI) 476.2 (M+H)$^+$.

Step 3: 1-(3-((2R)-2,3-dihydroxypropyl)-3'-fluoro-4-biphenylyl)-N-3-isoxazolyl-2-oxo-1,2-dihydro-6-quinolinesulfonamide, 1-(3-((2S)-2,3-dihydroxypropyl)-3'-fluoro-4-biphenylyl)-N-3-isoxazolyl-2-oxo-1,2-dihydro-6-quinolinesulfonamide A vial was charged with 1-(4-chloro-2-(2,3-dihydroxypropyl)phenyl)-N-(isoxazol-3-yl)-2-oxo-1,2-dihydroquinoline-6-sulfonamide (60 mg, 0.126 mmol), (3-fluorophenyl) boronic acid (35.3 mg, 0.252 mmol), dicyclohexyl(2',6'-dimethoxy-[1,1'-biphenyl]-2-yl)phosphine (2.59 mg, 6.30 mol), S-Phos Precatalyst (4.78 mg, 6.30 mol), and potassium phosphate (134 mg, 0.630 mmol). The vial was flushed with Ar (g), then charged with 1,4-dioxane (573 µl) and water (57.3 µl). The vial was sealed and heated to 120° C. for 1 h in a Biotage Initiator microwave. The mixture was extracted with EtOAc (3×), then acidified with 1N aq. HCl and extracted with EtOAc (2×). The combined organic extracts were concentrated. The residue was purified by chromatography on silica gel (25-g SNAP Ultra column, 35-85% of a 3:1 EtOAc/EtOH mixture in heptane with 10% DCM) to give 28 mg of a light-yellow solid. The material was purified further by chromatography on silica gel (12-g Redi-Sep Gold column, 0-8% MeOH/DCM) to give (R)-1-(3-(2,3-dihydroxypropyl)-3'-fluoro-[1,1'-biphenyl]-4-yl)-N-(isoxazol-3-yl)-2-oxo-1,2-dihydroquinoline-6-sulfonamide compound with (S)-1-(3-(2,3-dihydroxypropyl)-3'-fluoro-[1,1'-biphenyl]-4-yl)-N-(isoxazol-3-yl)-2-oxo-1,2-dihydroquinoline-6-sulfonamide (1:1) (21.8 mg, 0.020 mmol, 16.14% yield) as a white solid. $^1$H NMR (400 MHz, DMSO-d$_6$) δ=8.73 (dd, J=0.8, 1.7 Hz, 1H), 8.40 (d, J=4.0 Hz, 1H), 8.26 (dd, J=4.4, 9.5 Hz, 1H), 7.92 (dd, J=2.1, 8.5 Hz, 1H), 7.85 (ddd, J=2.3, 5.7, 8.9 Hz, 1H), 7.76 (td, J=2.5, 8.2 Hz, 1H), 7.63 (dd, J=1.5, 8.0 Hz, 4H), 7.34 (dd, J=1.0, 8.2 Hz, 2H), 6.84 (dd, J=4.0, 9.6 Hz, 2H), 6.45 (dd, J=1.8, 2.9 Hz, 1H), 5.76 (s, 1H), 4.53 (dd, J=5.5, 20.0 Hz, 1H), 4.42 (q, J=5.4 Hz, 1H), 3.69-3.56 (m, 1H), 3.47-3.37 (m, 1H), 3.18 (dt, J=4.7, 10.4 Hz, 1H), 3.15-3.03 (m, 2H), 2.24 (ddd, J=8.9, 14.3, 19.9 Hz, 1H). m/z (ESI) 536.1 (M+H)$^+$.

Example 341

(Method 84): 1-(5-chloro-6-(3-fluorophenyl)-2-methoxypyridin-3-yl)-N-(isoxazol-3-yl)-2-oxo-1,2-dihydroquinoline-6-sulfonamide

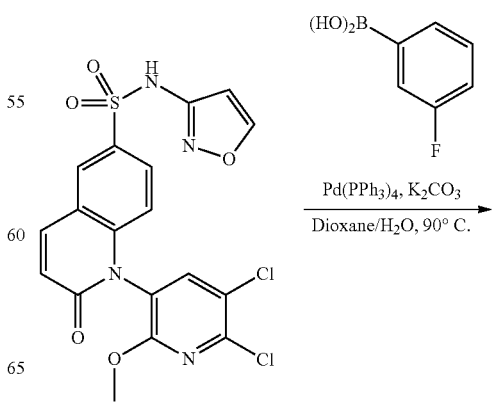

105

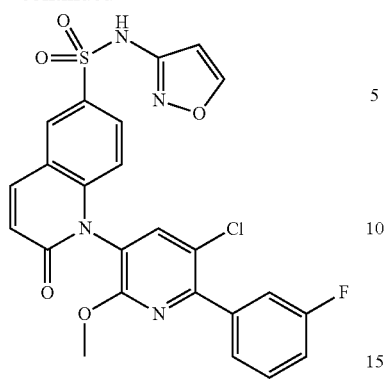

A microwave vial was charged with 1-(5,6-dichloro-2-methoxypyridin-3-yl)-N-(isoxazol-3-yl)-2-oxo-1,2-dihydroquinoline-6-sulfonamide (0.100 g, 0.214 mmol), (3-fluorophenyl)boronic acid (0.045 g, 0.321 mmol), potassium carbonate (0.089 g, 0.642 mmol), and Pd(Ph3P)4 (0.025 g, 0.021 mmol). The vial was flushed with Ar (g), then dioxane (0.803 ml) and water (0.268 ml) were added. The reaction was microwaved at 90° C. for 30 minutes. The organic layer was pipetted off of the aqueous layer and concentrated. The resulting film was dissolved in DMSO and filtered through a syringe filter. The resulting solution was purified via reverse phase HPLC (Xbridge 19×100 mm, 10 um, 40 ml/min, 25-85% 0.1% TFA in Acetonitrile) to afford 1-(5-chloro-6-(3-fluorophenyl)-2-methoxypyridin-3-yl)-N-(isoxazol-3-yl)-2-oxo-1,2-dihydroquinoline-6-sulfonamide (0.047 g, 0.089 mmol, 41.7% yield) as a tan solid. $^1$H NMR (500 MHz, DMSO-$d_6$) δ=11.67 (br. s., 1H), 8.73 (d, J=1.6 Hz, 1H), 8.40 (d, J=1.9 Hz, 1H), 8.30 (s, 1H), 8.27 (d, J=9.7 Hz, 1H), 7.87 (dd, J=2.1, 9.0 Hz, 1H), 7.73 (d, J=7.7 Hz, 1H), 7.67 (d, J=9.7 Hz, 1H), 7.64-7.58 (m, 1H), 7.42-7.33 (m, 1H), 7.04 (d, J=9.0 Hz, 1H), 6.84 (d, J=9.7 Hz, 1H), 6.46 (d, J=1.6 Hz, 1H), 3.83 (s, 3H). m/z (ESI) 527.1 (M+H)$^+$.

106

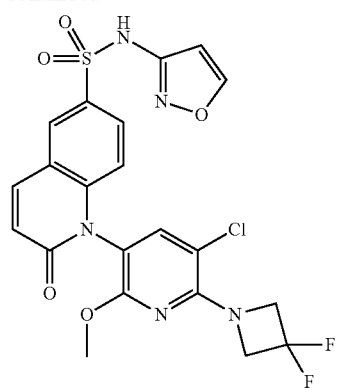

A vial was charged with 1-(5,6-dichloro-2-methoxypyridin-3-yl)-N-(isoxazol-3-yl)-2-oxo-1,2-dihydroquinoline-6-sulfonamide (0.100 g, 0.214 mmol), 3,3-difluoroazetidine hydrochloride (0.055 ml, 0.428 mmol), and potassium carbonate (0.053 g, 0.384 mmol). DMSO (1.070 ml) was added and the reaction was stirred at 130° C. overnight. The reaction was filtered through a syringe filter. The resulting solution was purified via reverse phase HPLC (Xbridge 19×100 mm, 10 um, 40 ml/min, 25-85% 0.1% TFA in Acetonitrile) to afford 1-(5-chloro-6-(3,3-difluoroazetidin-1-yl)-2-methoxypyridin-3-yl)-N-(isoxazol-3-yl)-2-oxo-1,2-dihydroquinoline-6-sulfonamide (0.038 g, 0.073 mmol, 33.9% yield) as a brown oily solid. $^1$H NMR (500 MHz, DMSO-$d_6$) δ=11.65 (br. s., 1H), 8.73 (d, J=1.7 Hz, 1H), 8.35 (d, J=2.0 Hz, 1H), 8.20 (d, J=9.7 Hz, 1H), 7.92-7.80 (m, 2H), 6.97 (d, J=9.0 Hz, 1H), 6.78 (d, J=9.6 Hz, 1H), 6.44 (d, J=1.7 Hz, 1H), 4.68 (t, J=12.6 Hz, 4H), 3.75 (s, 3H). m/z (ESI) 524.0 (M+H)$^+$.

Example 342

(Method 85): 1-(5-chloro-6-(3,3-difluoroazetidin-1-yl)-2-methoxypyridin-3-yl)-N-(isoxazol-3-yl)-2-oxo-1,2-dihydroquinoline-6-sulfonamide Example (Method 86): 1-(5-fluoro-2-methoxy-4-neopentylphenyl)-N-(isoxazol-3-yl)-2-oxo-1,2-dihydroquinoline-6-sulfonamide

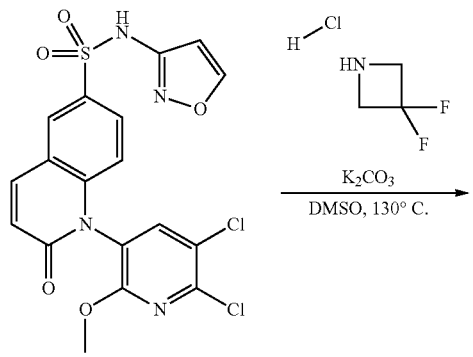

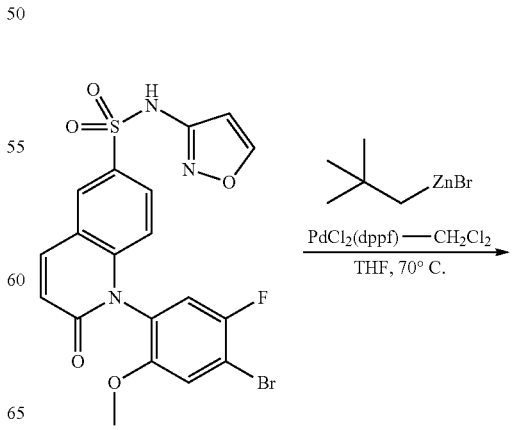

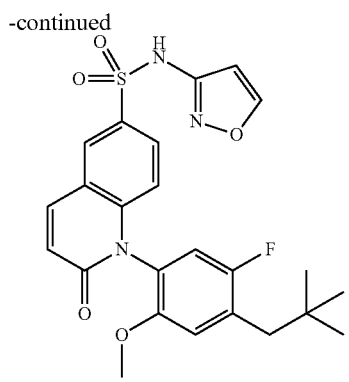

A vial was charged with 1-(4-bromo-5-fluoro-2-methoxyphenyl)-N-(isoxazol-3-yl)-2-oxo-1,2-dihydroquinoline-6-sulfonamide (0.100 g, 0.202 mmol) and PdCl$_2$(dppf)-CH$_2$Cl$_2$ (0.017 g, 0.020 mmol). The vial was flushed with Ar (g), then THF (1.012 ml) and neopentylzinc bromide, 0.5 M in THF (1.5 ml, 0.750 mmol) were added. The reaction was heated to 70° C. and stirred for one hour. The reaction was purified via column chromatography (RediSep Gold 40 g, gradient elution 10-75% [3:1 EtOAc/EtOH]:Heptane) to afford 1-(5-fluoro-2-methoxy-4-neopentylphenyl)-N-(isoxazol-3-yl)-2-oxo-1,2-dihydroquinoline-6-sulfonamide (0.024 g, 0.049 mmol, 24.43% yield) as a tan solid. $^1$H NMR (400 MHz, DMSO-d$_6$) δ=11.66 (s, 1H), 8.72 (d, J=1.8 Hz, 1H), 8.35 (d, J=2.2 Hz, 1H), 8.21 (d, J=9.6 Hz, 1H), 7.85 (dd, J=2.2, 9.0 Hz, 1H), 7.29 (d, J=9.5 Hz, 1H), 7.10 (d, J=6.6 Hz, 1H), 6.77 (t, J=9.8 Hz, 2H), 6.44 (d, J=1.8 Hz, 1H), 3.64 (s, 3H), 2.62 (s, 2H), 0.99 (s, 9H). m/z (ESI) 486.2 (M+H)$^+$.

Example 346 & 347

(Method 90): P-1-(2-(1H-pyrazol-4-yl)-4-(trifluoromethyl)phenyl)-N-(isoxazol-3-yl)-2-oxo-1,2-dihydroquinoline-6-sulfonamide (346) and M-1-(2-(1H-pyrazol-4-yl)-4-(trifluoromethyl)phenyl)-N-(isoxazol-3-yl)-2-oxo-1,2-dihydroquinoline-6-sulfonamide (347)

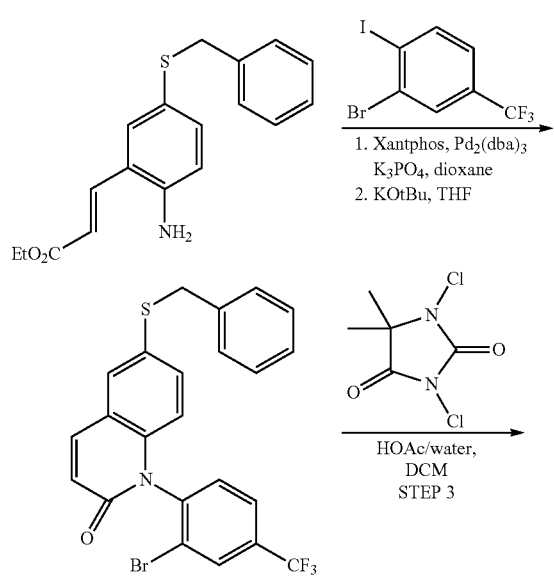

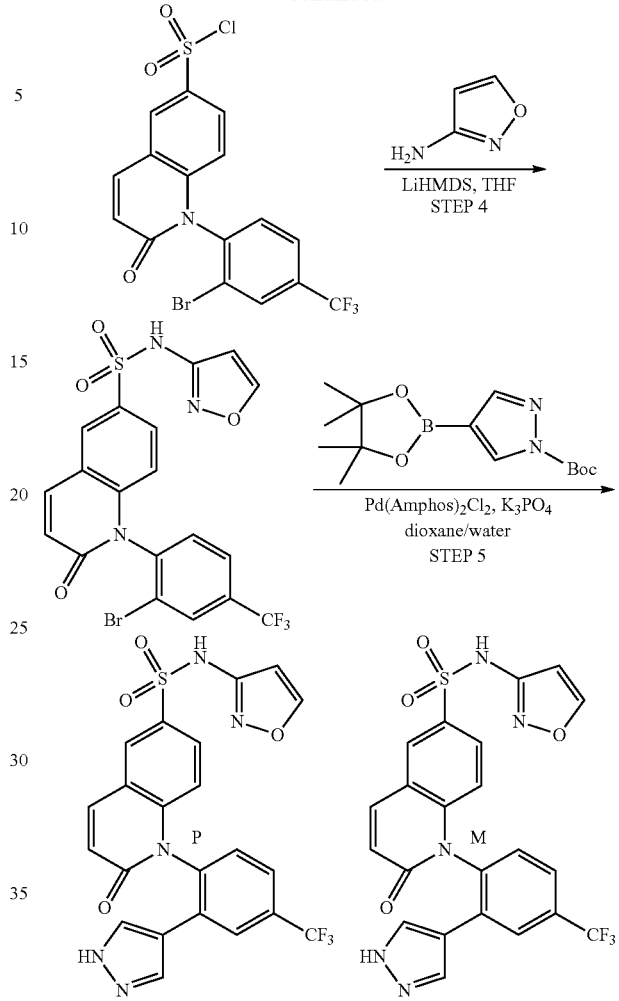

Step 1: 6-(benzylthio)-1-(2-bromo-4-(trifluoromethyl)phenyl)quinolin-2(1H)-one

A solution of xantphos (0.277 g, 0.479 mmol), Pd$_2$(dba)$_3$ (0.146 g, 0.160 mmol), 2-bromo-1-iodo-4-(trifluoromethyl)benzene (Oakwood Chemical, 1.232 g, 3.51 mmol), (E)-ethyl 3-(2-amino-5-(benzylthio)phenyl)acrylate (1.000 g, 3.19 mmol), and potassium phosphate (2.032 g, 9.57 mmol) in 10 mL dioxane was heated to 90° C. for 5 hours. The reaction mixture was diluted with water and extracted with DCM. The organics were dried over MgSO$_4$ and concentrated. The crude residue was used in the next step without purification. m/z (ESI) 536.0 (M+H)$^+$.

Step 2: 6-(benzylthio)-1-(2-bromo-4-(trifluoromethyl)phenyl)quinolin-2(1H)-one

The crude residue from step one was treated with potassium tert-butoxide 1N in THF (6.38 ml, 6.38 mmol) and was heated to 70° C. for one hour. The reaction mixture was then concentrated. Purification of the crude residue by silica gel column chromatography (0-100% EtOAc/heptane) gave 6-(benzylthio)-1-(2-bromo-4-(trifluoromethyl)phenyl)quinolin-2(1H)-one (1.630 g, 3.32 mmol, 104% yield) with minor impurities. m/z (ESI) 490.1 (M+H)$^+$.

Step 3: 1-(2-bromo-4-(trifluoromethyl)phenyl)-2-oxo-1,2-dihydroquinoline-6-sulfonyl chloride A solution of 6-(benzylthio)-1-(2-bromo-4-(trifluoromethyl)phenyl)quinolin-2(1H)-one (1.400 g, 2.86 mmol) in 30 mL DCM was treated with 3 mL AcOH/water (1.5:1) followed by 1,3-dichloro-5,5-dimethylhydantoin (0.750 ml, 5.71 mmol). After stirring for 30 minutes, the reaction mixture was diluted with DCM, dried over MgSO4 and concentrated. Purification of the crude residue by silica gel column chromatography (0-100% EtOAc/heptane) gave 1-(2-bromo-4-(trifluoromethyl)phenyl)-2-oxo-1,2-dihydroquinoline-6-sulfonyl chloride (1.20 g, 2.57 mmol, 90% yield). m/z (ESI) 467.9 (M+H)+.

Step 4: 1-(2-bromo-4-(trifluoromethyl)phenyl)-N-(isoxazol-3-yl)-2-oxo-1,2-dihydroquinoline-6-sulfonamide A solution of 3-aminoisoxazole (0.380 ml, 5.14 mmol) and 1-(2-bromo-4-(trifluoromethyl)phenyl)-2-oxo-1,2-dihydroquinoline-6-sulfonyl chloride (1.200 g, 2.57 mmol) in 10 mL THF was cooled to 0° C. and was treated with LHMDS 1N in THF (2.57 ml, 2.57 mmol). After stirring for 30 minutes, the reaction mixture was concentrated. Purification of the crude residue by reverse phase column chromatography [Puriflash C18, 10-100% (0.1% NH4OH in MeOH)/(0.1% NH4OH in water)] gave 1-(2-bromo-4-(trifluoromethyl)phenyl)-N-(isoxazol-3-yl)-2-oxo-1,2-dihydroquinoline-6-sulfonamide (0.438 g, 0.852 mmol, 33.1% yield) with minor impurities. m/z (ESI) 514.0 (M+H)+.

Step 5: 1-(2-(1H-pyrazol-4-yl)-4-(trifluoromethyl)phenyl)-N-(isoxazol-3-yl)-2-oxo-1,2-dihydroquinoline-6-sulfonamide A microwave vial charged with Pd(Amphos)2Cl2 (0.016 g, 0.023 mmol), tert-butyl 4-(4,4,5,5-tetramethyl-1,3,2-dioxaborolan-2-yl)-1H-pyrazole-1-carboxylate (0.136 g, 0.463 mmol), 1-(2-bromo-4-(trifluoromethyl)phenyl)-N-(isoxazol-3-yl)-2-oxo-1,2-dihydroquinoline-6-sulfonamide (0.119 g, 0.231 mmol), potassium phosphate (0.196 g, 0.926 mmol), 1.5 ml dioxane and 0.5 ml water was heated to 150° C. in a Biotage initiator microwave reactor for 30 minutes. The reaction mixture was then diluted with DCM and washed with water. The organics were dried over MgSO4 and concentrated. Purification of the crude residue by reverse phase column chromatography [Puriflash C18, 10-100% (0.1% NH4OH in MeOH)/(0.1% NH4OH in water)] gave 140 mg of product. The atrope isomers were separated by chiral SFC: whelk-O (s,s) 40% MeOH, yielding (P)-1-(2-(1H-pyrazol-4-yl)-4-(trifluoromethyl)phenyl)-N-(isoxazol-3-yl)-2-oxo-1,2-dihydroquinoline-6-sulfonamide (0.025 g, 0.050 mmol, 21.55% yield) and (M)-1-(2-(1H-pyrazol-4-yl)-4-(trifluoromethyl)phenyl)-N-(isoxazol-3-yl)-2-oxo-1,2-dihydroquinoline-6-sulfonamide (0.022 g, 0.044 mmol, 18.96% yield). Analytical data for both isomers is identical. m/z (ESI) 502.1 (M+H)+. 1H NMR (ACETONITRILE-d3) δ: 8.36 (d, J=1.8 Hz, 1H), 8.26 (d, J=2.2 Hz, 1H), 8.08 (d, J=1.6 Hz, 1H), 8.03 (d, J=9.6 Hz, 1H), 7.78-7.84 (m, 1H), 7.73 (dd, J=9.0, 2.2 Hz, 1H), 7.51 (d, J=8.2 Hz, 1H), 7.35 (s, 2H), 6.77 (d, J=9.7 Hz, 1H), 6.66 (d, J=9.0 Hz, 1H), 6.41 (d, J=1.9 Hz, 1H)

Example 348 & 349

(Method 91): P-1-(2-chloro-3'-fluoro-5-methoxy-[1,1'-biphenyl]-4-yl)-N-(isoxazol-3-yl)-4-methyl-2-oxo-1,2-dihydroquinoline-6-sulfonamide (348) and M-1-(2-chloro-3'-fluoro-5-methoxy-[1,1'-biphenyl]-4-yl)-N-(isoxazol-3-yl)-4-methyl-2-oxo-1,2-dihydroquinoline-6-sulfonamide (349)

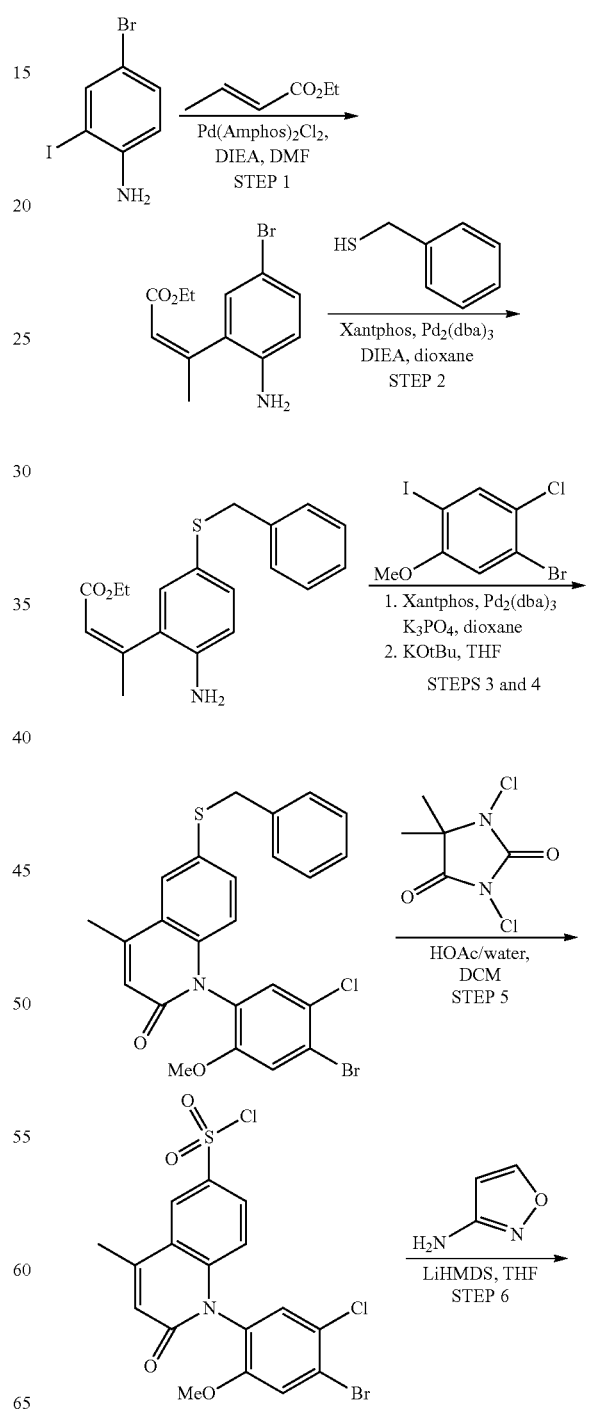

-continued

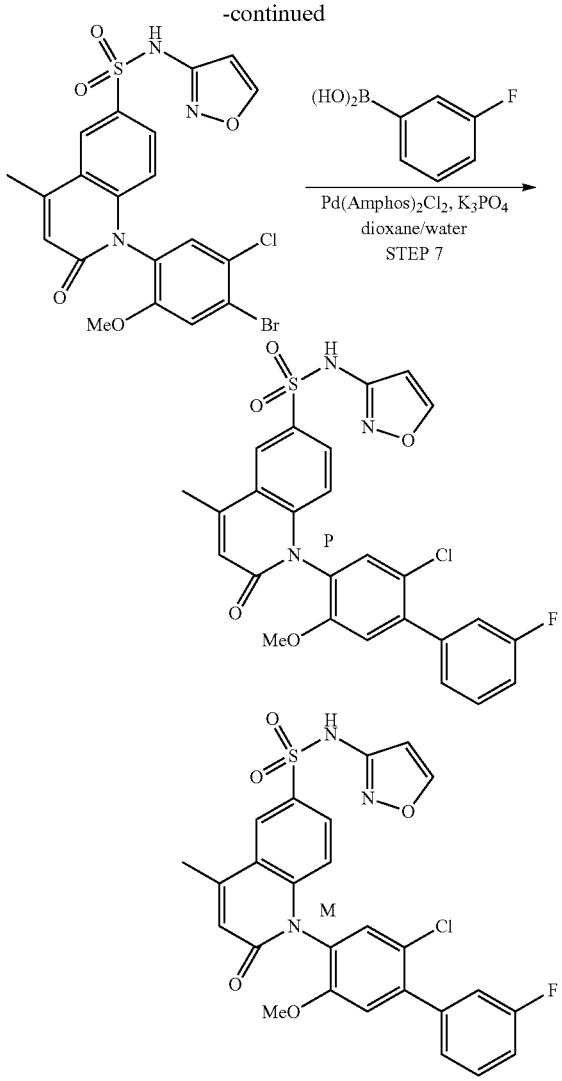

Step 1: (Z)-ethyl 3-(2-amino-5-bromophenyl)but-2-enoate

A solution of Pd(Amphos)$_2$Cl$_2$ (1.188 g, 1.678 mmol), ethyl crotonate (5.01 ml, 40.3 mmol), 4-bromo-2-iodoaniline (Spectrum Bioscience, 10.000 g, 33.6 mmol), and n,n-diisopropylethylamine (7.03 ml, 40.3 mmol) in 6 mL DMF was heated to 90° C. for 6 hours. The reaction mixture was then poured into water and was extracted with DCM. The organics were dried over MgSO$_4$ and concentrated. Purification of the crude residue by silica gel column chromatography (0-100% EtOAc/heptane) gave (Z)-ethyl 3-(2-amino-5-bromophenyl)but-2-enoate (3.817 g, 13.43 mmol, 40.0% yield) with minor impurities. m/z (ESI) 286.1 (M+H)$^+$.

Step 2: (Z)-ethyl 3-(2-amino-5-(benzylthio)phenyl)but-2-enoate

A solution of (Z)-ethyl 3-(2-amino-5-bromophenyl)but-2-enoate (3.3817 g, 11.90 mmol), xantphos (1.033 g, 1.785 mmol), pd2(dba)3 (0.545 g, 0.595 mmol), and n,n-diisopropylethylamine (6.24 ml, 35.7 mmol) in 24 mL dioxane was heated to 80° C. then was treated with benzyl mercaptan (2.252 ml, 19.04 mmol). After stirring for 36 hours, an additional portion of xantphos (1.033 g, 1.785 mmol), pd$_2$(dba)$_3$ (0.545 g, 0.595 mmol), and n,n-diisopropylethylamine (6.24 ml, 35.7 mmol) was added, and the reaction mixture was heated to 90° C. overnight. The reaction mixture was then poured into water and was extracted with DCM. The organics were dried over MgSO$_4$ and concentrated. Purification of the crude residue by silica gel column chromatography (0-100% EtOAc/heptane) gave (Z)-ethyl 3-(2-amino-5-(benzylthio)phenyl)but-2-enoate (2.26 g, 6.90 mmol, 58.0% yield). m/z (ESI) 328.2 (M+H)$^+$.

Step 3: (Z)-ethyl 3-(5-(benzylthio)-2-((4-bromo-5-chloro-2-methoxyphenyl)amino)phenyl)but-2-enoate A solution of xantphos (0.265 g, 0.458 mmol), pd2(dba)3 (0.140 g, 0.153 mmol), 1-bromo-2-chloro-4-iodo-5-methoxybenzene (1.167 g, 3.36 mmol), (Z)-ethyl 3-(2-amino-5-(benzylthio)phenyl)but-2-enoate (1.000 g, 3.05 mmol), and potassium phosphate (1.945 g, 9.16 mmol) in 10 mL dioxane was heated to 100° C. for 2 hours. The reaction mixture was then poured into water and extracted with DCM. The organics were dried over MgSO$_4$ and concentrated. The crude residue was used in the next step without purification. m/z (ESI) 546.0 (M+H)$^+$.

Step 4: 6-(benzylthio)-1-(4-bromo-5-chloro-2-methoxyphenyl)-4-methylquinolin-2(1H)-one The crude residue from step 3 was dissolved in 6 mL THF, was treated with potassium tert-butoxide 1N in THF (3.05 ml, 3.05 mmol) and was heated to reflux for 20 minutes. The reaction mixture was then concentrated. The crude residue was used in the next step without purification. m/z (ESI) 502.0 (M+H)$^+$.

Step 5: 1-(5-chloro-2-methoxy-4-methylphenyl)-4-methyl-2-oxo-1,2-dihydroquinoline-6-sulfonyl chloride The crude residue from step 4 was dissolved in 20 mL DCM, treated with 4 mL (1.5:1 HOAc/water) followed by 1,3-dichloro-5,5-dimethylhydantoin (0.802 ml, 6.11 mmol). After stirring for 30 minutes, the reaction mixture was diluted with DCM, dried over MgSO4 and concentrated. Purification of the crude residue by silica gel column chromatography (0-100% EtOAc/heptane) gave 1-(4-bromo-5-chloro-2-methoxyphenyl)-4-methyl-2-oxo-1,2-dihydroquinoline-6-sulfonyl chloride (1.120 g, 2.347 mmol, 77% yield). m/z (ESI) 477.9 (M+H)$^+$.

Step 6: 1-(4-bromo-5-chloro-2-methoxyphenyl)-N-(isoxazol-3-yl)-4-methyl-2-oxo-1,2-dihydroquinoline-6-sulfonamide A solution of 3-aminoisoxazole (0.867 ml, 11.74 mmol) and 1-(4-bromo-5-chloro-2-methoxyphenyl)-4-methyl-2-oxo-1,2-dihydroquinoline-6-sulfonyl chloride (1.120 g, 2.347 mmol) in 10 mL THF, was cooled to 0° C. LHMDS 1N in THF (11.74 ml, 11.74 mmol) was added, and the cooling bath was removed. After stirring for an additional hour, the reaction mixture was treated with hcl 4N in dioxane (5.87 ml, 23.47 mmol) and was concentrated. Purification of the crude residue by reverse phase column chromatography [Redisep Gold C18, 10-100% (0.1% NH4OH in MeOH)/(0.1% NH4OH in water)] gave 1-(4-bromo-5-chloro-2-methoxyphenyl)-N-(isoxazol-3-yl)-4- methyl-2-oxo-1,2-dihydroquinoline-6-sulfonamide (0.307 g, 0.585 mmol, 24.92% yield). m/z (ESI) 525.9 (M+H)+.

Step 7: 1-(2-chloro-3'-fluoro-5-methoxy-[1,1'-biphenyl]-4-yl)-N-(isoxazol-3-yl)-4-methyl-2-oxo-1,2-dihydroquinoline-6-sulfonamide A microwave vial charged with Pd(Amphos)₂Cl₂ (0.041 g, 0.059 mmol), (3-fluorophenyl)boronic acid (0.164 g, 1.170 mmol), 1-(4-bromo-5-chloro-2-methoxyphenyl)-N-(isoxazol-3-yl)-4-methyl-2-oxo-1,2-dihydroquinoline-6-sulfonamide (0.307 g, 0.585 mmol), potassium phosphate (0.497 g, 2.340 mmol), 3 ml dioxane and 1 ml water was heated to 150° C. in a Biotage initiator microwave reactor for 60 minutes. The organics were separated, treated with hcl 4N in dioxane (0.585 ml, 2.340 mmol) then concentrated. Purification of the crude residue by reverse phase column chromatography [Puriflash C18, 10-100% (0.1% NH4OH in MeOH)/(0.1% NH4OH in water)] gave 35 mg of product. Chiral separation was performed by SFC: Chiralcel OJH 20% MeOH yielding (P)-1-(2-chloro-3'-fluoro-5-methoxy-[1,1'-biphenyl]-4-yl)-N-(isoxazol-3-yl)-4-methyl-2-oxo-1,2-dihydroquinoline-6-sulfonamide (0.008 g, 0.015 mmol, 2.88% yield) and (M)-1-(2-chloro-3'-fluoro-5-methoxy-[1,1'-biphenyl]-4-yl)-N-(isoxazol-3-yl)-4-methyl-2-oxo-1,2-dihydroquinoline-6-sulfonamide (0.008 g, 0.015 mmol, 2.88% yield). Analytical data for both isomers is identical. m/z (ESI) 540.0 (M+H)+. ¹H NMR (ACETONITRILE-d3): 8.36-8.40 (m, 1H), 8.27-8.30 (m, 1H), 7.81-7.87 (m, 1H), 7.50-7.58 (m, 1H), 7.43-7.45 (m, 1H), 7.38-7.43 (m, 1H), 7.33-7.38 (m, 1H), 7.19-7.27 (m, 2H), 6.85-6.90 (m, 1H), 6.66-6.70 (m, 1H), 6.46-6.50 (m, 1H), 3.70 (s, 3H), 2.56 (d, J=1.2 Hz, 3H).

Example 350 & 351

(Method 92): P-1-(3'-chloro-3-methoxy-[1,1'-biphenyl]-4-yl)-N-(isoxazol-3-yl)-2-oxo-1,2-dihydroquinoline-6-sulfonamide (350) and M-1-(3'-chloro-3-methoxy-[1,1'-biphenyl]-4-yl)-N-(isoxazol-3-yl)-2-oxo-1,2-dihydroquinoline-6-sulfonamide (351)

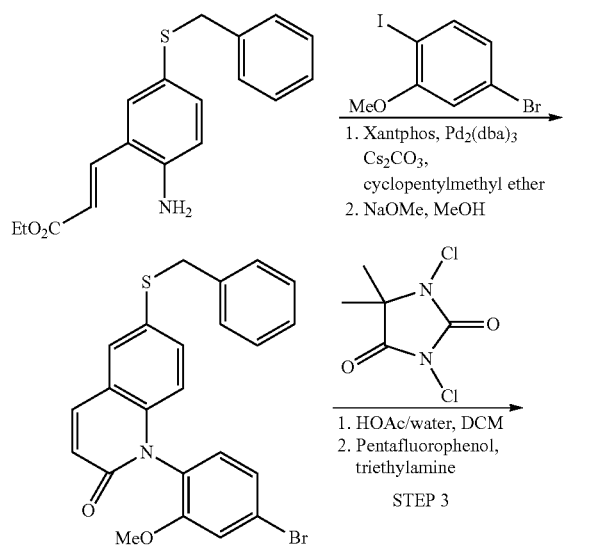

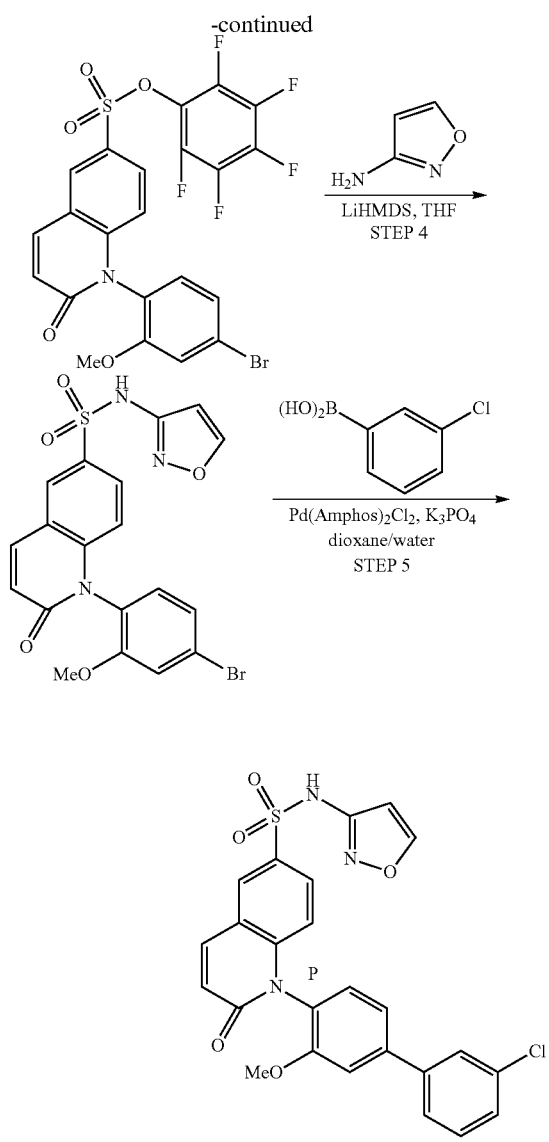

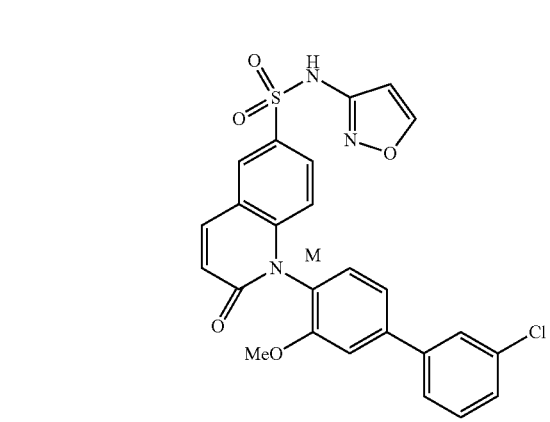

Step 1: (E)-ethyl 3-(5-(benzylthio)-2-((4-bromo-2-methoxyphenyl)amino)phenyl)acrylate A RBF charged with xantphos (9.97 g, 17.23 mmol), pd2(dba)3 (5.26 g, 5.74 mmol), 4-bromo-1-iodo-2-methoxybenzene (74.9 g, 239 mmol), (E)-ethyl 3-(2-amino-5-(benzylthio)phenyl)acrylate (60.000 g, 191 mmol), cesium carbonate (100 g, 306 mmol), and 400 ml cylopentylmethylether was heated to 90° C. overnight. The reaction mixture was then poured into water and extracted with DCM. The organics were dried over MgSO4 and concentrated. The crude residue was triturated with IPA leaving a yellow solid that was collected and dried (E)-ethyl 3-(5-(benzylthio)-2-((4-bromo-2-methoxyphenyl)amino)phenyl) acrylate (86.95 g, 174 mmol, 91% yield). m/z (ESI) 500.1 (M+H)+.

Step 2: 6-(benzylthio)-1-(4-bromo-2-methoxyphenyl)quinolin-2(1H)-one

A suspension of (E)-ethyl 3-(5-(benzylthio)-2-((4-bromo-2-methoxyphenyl)amino)phenyl)acrylate (86.95 g, 174 mmol) in 350 mL MeOH was heated to 70° C., was treated with sodium methoxide 25% wt in MeOH (19.06 ml, 69.8 mmol) and was allowed to stir overnight. The reaction mixture was then concentrated. The crude solid was triturated with IPA yielding 47.13 g clean product. The IPA washings were concentrated. Purification of the crude residue by silica gel column chromatography (0-100% EtOAc/heptane) gave an additional 10.76 g of slightly impure product. 6-(benzylthio)-1-(4-bromo-2-methoxyphenyl)quinolin-2(1H)-one (57.89 g, 128 mmol, 73.4% yield). m/z (ESI) 451.8 (M+H)+.

Step 3: Perfluorophenyl 1-(4-bromo-2-methoxyphenyl)-2-oxo-1,2-dihydroquinoline-6-sulfonate A solution of 6-(benzylthio)-1-(4-bromo-2-methoxyphenyl)quinolin-2(1H)-one (57.89 g, 128 mmol) in 400 mL DCM was treated with 15 mL HOAc 10 mL water and was cooled to 0° C. 1,3-Dichloro-5,5-dimethylimidazolidine-2,4-dione (25.2 g, 128 mmol) was added portionwise. After stirring for 30 minutes, an additional 0.5 eq of hydantoin was added portionwise. After stirring for an additional 30 minutes, the reaction mixture was then treated with pentafluorophenol (16.06 mL, 154 mmol) and was maintained at 0° C. Triethylamine (71.3 mL, 512 mmol) was added dropwise via addition funnel over 30 minutes. The reaction mixture was then diluted with DCM, washed with water, the organics dried over MgSO4 and concentrated. The crude residue was triturated with IPA then dried and collected yielding perfluorophenyl 1-(4-bromo-2-methoxyphenyl)-2-oxo-1,2-dihydroquinoline-6-sulfonate (58.7 g, 102 mmol, 80% yield) with minor impurities. Chiral separation was performed by SFC: Whelk-O (S,S) 50% IPA, yielding (P)-perfluorophenyl 1-(4-bromo-2-methoxyphenyl)-2-oxo-1,2-dihydroquinoline-6-sulfonate (26.6 g, 46.2 mmol, 36.1% yield) (peak one) as well as (M)-perfluorophenyl 1-(4-bromo-2-methoxyphenyl)-2-oxo-1,2-dihydroquinoline-6-sulfonate (29.1 g, 50.5 mmol, 39.5% yield) (peak 2). m/z (ESI) 576.0 (M+H)+.

Step 4: 1-(4-bromo-2-methoxyphenyl)-N-(isoxazol-3-yl)-2-oxo-1,2-dihydroquinoline-6-sulfonamide A solution of 3-aminoisoxazole (0.664 ml, 8.98 mmol) and racemic perfluorophenyl 1-(4-bromo-2-methoxyphenyl)-2-oxo-1,2-dihydroquinoline-6-sulfonate (4.705 g, 8.16 mmol) in 100 mL THF, was cooled to 0° C. LHMDS 1N in THF (17.15 ml, 17.15 mmol) was added dropwise. After stirring for an hour, HCl 1N aqueous (32.7 ml, 32.7 mmol) was added, and the reaction mixture was extracted with DCM. The organics were dried over MgSO4 and concentrated. The crude residue was triturated with ether, and the resulting solid was collected and dried yielding 1-(4-bromo-2-methoxyphenyl)-N-(isoxazol-3-yl)-2-oxo-1,2-dihydroquinoline-6-sulfonamide (3.20 g, 6.72 mmol, 82% yield). A portion of this material was resolved. Chiral separation was performed by SFC: (S,S) Whelk-O, 50% isopropanol yielding (P)-1-(4-bromo-2-methoxyphenyl)-N-(isoxazol-3-yl)-2-oxo-1,2-dihydroquinoline-6-sulfonamide (0.150 g, 0.315 mmol, 3.86% yield) and (M)-1-(4-bromo-2-methoxyphenyl)-N-(isoxazol-3-yl)-2-oxo-1,2-dihydroquinoline-6-sulfonamide (0.154 g, 0.323 mmol, 3.96% yield). Analytical data for both isomers is identical. m/z (ESI) 476.1 (M+H)+. $^1$H NMR (ACETONITRILE-d3) δ: 8.37 (d, J=1.9 Hz, 1H), 8.23 (d, J=2.3 Hz, 1H), 7.97 (d, J=9.6 Hz, 1H), 7.78 (dd, J=8.9, 2.2 Hz, 1H), 7.43 (d, J=2.1 Hz, 1H), 7.34 (dd, J=8.3, 2.1 Hz, 1H), 7.16 (d, J=8.3 Hz, 1H), 6.71-6.79 (m, 2H), 6.45 (d, J=1.8 Hz, 1H), 3.69 (s, 3H).

Step 5: 1-(3'-chloro-3-methoxy-[1,1'-biphenyl]-4-yl)-N-(isoxazol-3-yl)-2-oxo-1,2-dihydroquinoline-6-sulfonamide A solution of Pd(Ph₃P)₄ (0.849 g, 0.735 mmol), (3-chlorophenyl)boronic acid (0.230 g, 1.470 mmol), 1-(4-bromo-2-methoxyphenyl)-N-(isoxazol-3-yl)-2-oxo-1,2-dihydroquinoline-6-sulfonamide (0.350 g, 0.735 mmol), and potassium carbonate (0.406 g, 2.94 mmol) in 2 mL dioxane 1 mL water was heated to 90° C. for one hour. The reaction mixture was then diluted with DCM and washed with HCl 1N aqueous (7.35 ml, 7.35 mmol). The organics were then concentrated. Purification of the crude residue by reverse phase column chromatography [Puriflash C18, 10-100% (0.1% NH4OH in MeOH)/(0.1% NH4OH in water)] gave product. Chiral separation was performed by SFC: Regis Whelk-O (s,s) 50% MeOH yielding (P)-1-(3'-chloro-3-methoxy-[1,1'-biphenyl]-4-yl)-N-(isoxazol-3-yl)-2-oxo-1,2-dihydroquinoline-6-sulfonamide (0.065 g, 0.128 mmol, 17.41% yield) and (M)-1-(3'-chloro-3-methoxy-[1,1'-biphenyl]-4-yl)-N-(isoxazol-3-yl)-2-oxo-1,2-dihydroquinoline-6-sulfonamide (0.060 g, 0.118 mmol, 16.07% yield). Analytical data for both isomers is identical. m/z (ESI) 508.1 (M+H)+. $^1$H NMR (ACETONITRILE-d3) δ: 8.23 (dd, J=13.2, 1.8 Hz, 2H), 7.97 (d, J=9.6 Hz, 1H), 7.76-7.83 (m, 2H), 7.66-7.74 (m, 1H), 7.47-7.54 (m, 1H), 7.38-7.47 (m, 3H), 7.32 (d, J=8.0 Hz, 1H), 6.70-6.77 (m, 2H), 6.35 (d, J=1.6 Hz, 1H), 3.78 (s, 3H)

Example 353 & 354

(Method 94): (P)-1-(2-chloro-3'-fluoro-5-methoxy-[1,1'-biphenyl]-4-yl)-2-oxo-N-(1,3,4-thiadiazol-2-yl)-1,2-dihydroquinoline-6-sulfonamide (353) and (M)-1-(2-chloro-3'-fluoro-5-methoxy-[1,1'-biphenyl]-4-yl)-2-oxo-N-(1,3,4-thiadiazol-2-yl)-1,2-dihydroquinoline-6-sulfonamide (354)

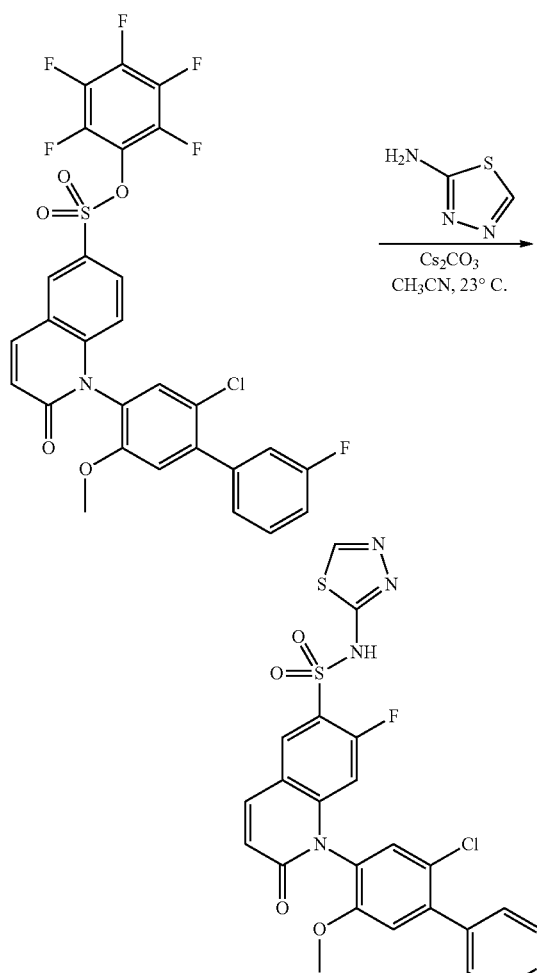

A vial was charged with perfluorophenyl 1-(2-chloro-3'-fluoro-5-methoxy-[1,1'-biphenyl]-4-yl)-2-oxo-1,2-dihydroquinoline-6-sulfonate (0.140 g, 0.224 mmol), 2-amino-1,3,4-thiadiazole (0.027 g, 0.268 mmol), and cesium carbonate (0.219 g, 0.671 mmol). The vial was flushed with Ar (g), then acetonitrile (2.2 mL) was added. The reaction was stirred overnight at RT. The mixture was diluted with EtOAc and NH$_4$Cl (sat.). The layers were separated, and the aqueous layer was extracted with EtOAc (2×). The combined organic extracts were dried over magnesium sulfate, filtered, and concentrated. The residue was purified by chromatography on silica gel (25-g SNAP Ultra column, 0-50% EtOAc/Heptane) to give 125 mgs of 1-(2-chloro-3'-fluoro-5-methoxy-[1,1'-biphenyl]-4-yl)-2-oxo-N-(1,3,4-thiadiazol-2-yl)-1,2-dihydroquinoline-6-sulfonamide as an off-white solid. This material was purified by chiral SFC on Chiralpak AS-H column (40% MeOH/60% CO$_2$) to give (P)-1-(2-chloro-3'-fluoro-5-methoxy-[1,1'-biphenyl]-4-yl)-2-oxo-N-(1,3,4-thiadiazol-2-yl)-1,2-dihydroquinoline-6-sulfonamide as peak 1 and (M)-1-(2-chloro-3'-fluoro-5-methoxy-[1,1'-biphenyl]-4-yl)-2-oxo-N-(1,3,4-thiadiazol-2-yl)-1,2-dihydroquinoline-6-sulfonamide as peak 2, both as off-white solids. Data for peak 1: $^1$H NMR (400 MHz, DMSO-d$_6$) δ=14.36 (br. s., 1H), 8.77 (s, 1H), 8.31 (d, J=2.15 Hz, 1H), 8.24 (d, J=9.59 Hz, 1H), 7.84 (dd, J=2.15, 8.90 Hz, 1H), 7.68 (s, 1H), 7.60 (dt, J=6.36, 8.07 Hz, 1H), 7.41-7.48 (m, 2H), 7.36 (s, 1H), 7.29-7.34 (m, 1H), 6.78-6.85 (m, 2H), 3.74 (s, 3H). m/z (ESI) 544.0 (M+H)$^+$. Data for peak 2: $^1$H NMR (400 MHz, DMSO-d$_6$) δ=14.36 (br. s., 1H), 8.77 (s, 1H), 8.31 (d, J=2.25 Hz, 1H), 8.24 (d, J=9.49 Hz, 1H), 7.84 (dd, J=2.20, 8.95 Hz, 1H), 7.68 (s, 1H), 7.59 (dt, J=6.36, 8.07 Hz, 1H), 7.41-7.48 (m, 2H), 7.36 (s, 1H), 7.30-7.35 (m, 1H), 6.81 (dd, J=6.80, 9.24 Hz, 2H), 3.74 (s, 3H). m/z (ESI) 544.0 (M+H)$^+$.

Example 355 & 356

(Method 95): (P)-1-(2-chloro-3'-fluoro-5-methoxy-[1,1'-biphenyl]-4-yl)-2-oxo-N-(pyrimidin-2-yl)-1,2-dihydroquinoline-6-sulfonamide (355) and (M)-1-(2-chloro-3'-fluoro-5-methoxy-[1,1'-biphenyl]-4-yl)-2-oxo-N-(pyrimidin-2-yl)-1,2-dihydroquinoline-6-sulfonamide (356)

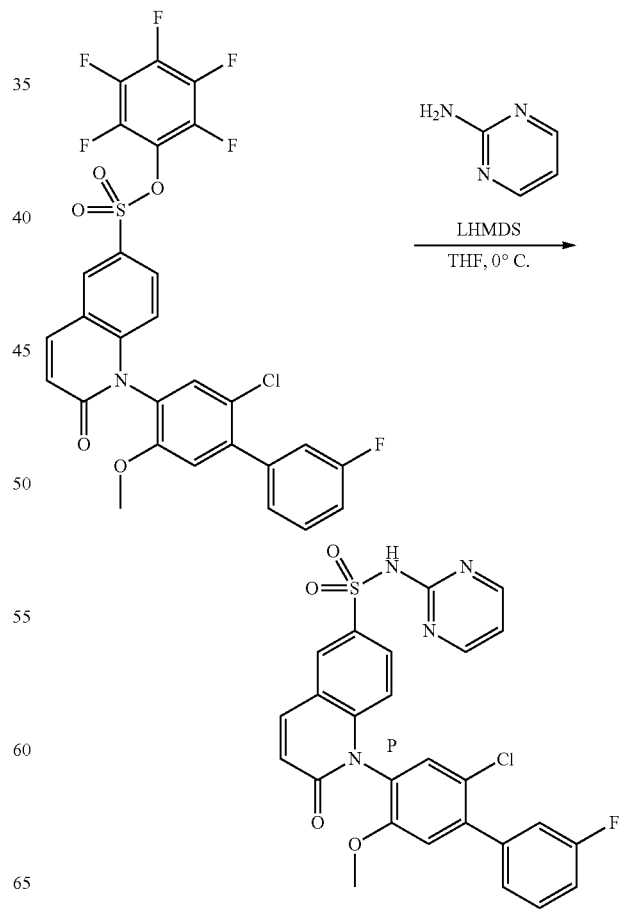

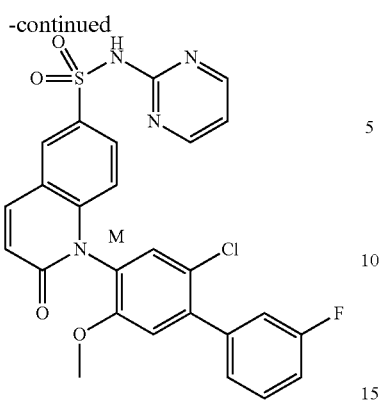

1-(2-Chloro-3'-fluoro-5-methoxy-[1,1'-biphenyl]-4-yl)-2-oxo-N-(pyrimidin-2-yl)-1,2-dihydroquinoline-6-sulfonamide was prepared in an analogous manner to that of method 2, Step 1, except that 2-aminopyrimidine was used in place of isoxazol-3-amine. The racemic product was separated via chiral SFC on a Whelk-O column (40% methanol/60% $CO_2$) to give (P)-1-(2-chloro-3'-fluoro-5-methoxy-[1,1'-biphenyl]-4-yl)-2-oxo-N-(pyrimidin-2-yl)-1,2-dihydroquinoline-6-sulfonamide as peak 1 and (M)-1-(2-chloro-3'-fluoro-5-methoxy-[1,1'-biphenyl]-4-yl)-2-oxo-N-(pyrimidin-2-yl)-1,2-dihydroquinoline-6-sulfonamide as peak 2. Both materials were obtained as white solids. Data for peak 1: $^1$H NMR (400 MHz, DMSO-$d_6$) δ=11.91 (s, 1H), 8.46-8.55 (m, 3H), 8.27 (d, J=9.59 Hz, 1H), 8.01 (dd, J=2.15, 9.00 Hz, 1H), 7.69 (s, 1H), 7.59 (dt, J=6.36, 8.07 Hz, 1H), 7.42-7.48 (m, 2H), 7.29-7.38 (m, 2H), 7.03 (br. s., 1H), 6.77-6.88 (m, 2H), 3.73 (s, 3H). m/z (ESI) 537.0 (M+H)$^+$. Data for peak 2: $^1$H NMR (400 MHz, DMSO-$d_6$) δ 11.94 (br. s., 1H), 8.45-8.53 (m, 3H), 8.27 (d, J=9.59 Hz, 1H), 8.00 (dd, J=2.20, 8.95 Hz, 1H), 7.69 (s, 1H), 7.55-7.63 (m, 1H), 7.41-7.48 (m, 2H), 7.29-7.38 (m, 2H), 7.03 (br. s., 1H), 6.77-6.87 (m, 2H), 3.73 (s, 3H). m/z (ESI) 537.0 (M+H)$^+$.

Example 357 & 358

(Method 96): (M)-1-(2-chloro-3'-fluoro-5-methoxy-[1,1'-biphenyl]-4-yl)-7-fluoro-N-(isoxazol-3-yl)-2-oxo-1,2-dihydroquinoline-6-sulfonamide (357) and (P)-1-(2-chloro-3'-fluoro-5-methoxy-[1,1'-biphenyl]-4-yl)-7-fluoro-N-(isoxazol-3-yl)-2-oxo-1,2-dihydroquinoline-6-sulfonamide (358)

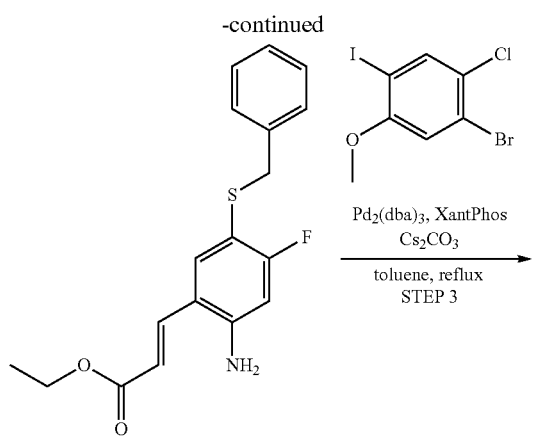

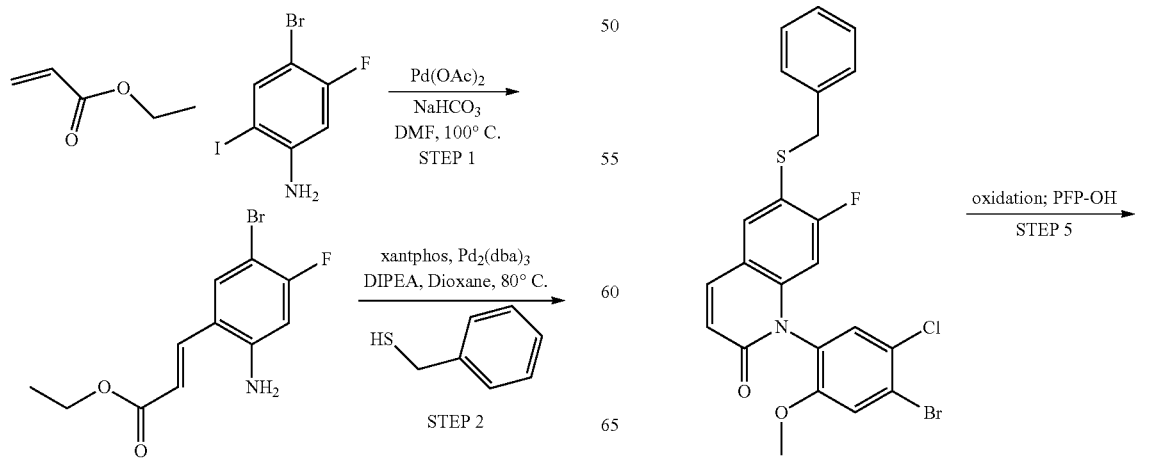

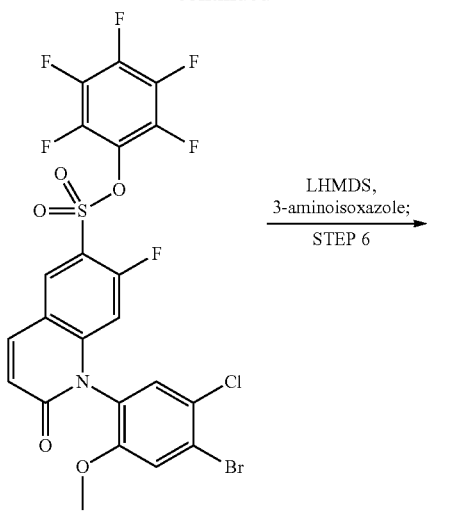

LHMDS,
3-aminoisoxazole;
STEP 6

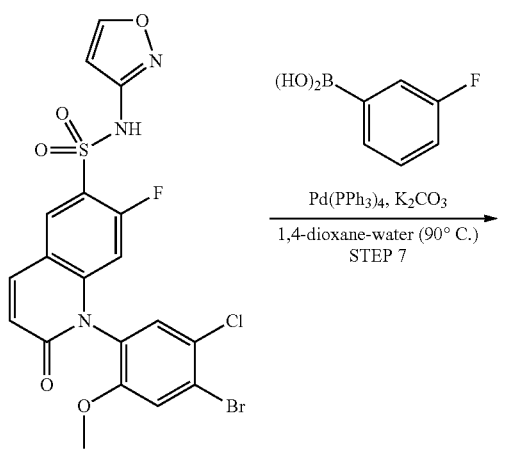

(HO)₂B—⟨⟩—F

Pd(PPh₃)₄, K₂CO₃
1,4-dioxane-water (90° C.)
STEP 7

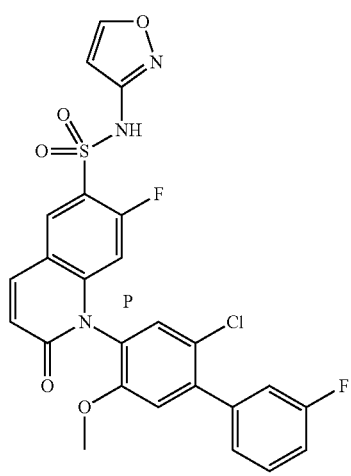

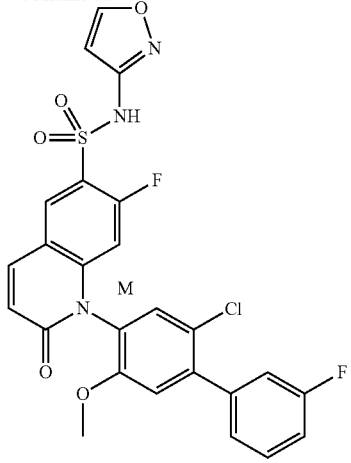

Step 1: (E)-ethyl 3-(2-amino-5-bromo-4-fluorophenyl)acrylate

To a vial was added, 4-bromo-5-fluoro-2-iodoaniline (5.67 g, 17.95 mmol), PdOAc₂ (0.201 g, 0.897 mmol), sodium bicarbonate (3.77 g, 44.9 mmol), ethyl acrylate (2.049 ml, 18.85 mmol) and DMF (12.0 ml). The reaction was heated for 3 hour at 100° C. The reaction was cooled to RT, diluted with water and extracted with DCM (3×). The combined organics were washed with water and brine, dried over magnesium sulfate, filtered and concentrated. The resulting material was triturated with heptane overnight and then filtered to afford (E)-ethyl 3-(2-amino-5-bromo-4-fluorophenyl)acrylate (4.00 g, 13.88 mmol, 77% yield) as a light yellow solid. m/z (ESI) 288.0 (M+H)⁺.

Step 2: (E)-ethyl 3-(2-amino-5-(benzylthio)-4-fluorophenyl)acrylate

A screw cap vial was charged with (E)-ethyl 3-(2-amino-5-bromo-4-fluorophenyl)acrylate (4.00 g, 13.88 mmol), xantphos (0.402 g, 0.694 mmol) 9), tris(dibenzylideneacetone)dipalladium (0.318 g, 0.347 mmol), 1,4-Dioxane (13.9 ml), and DIPEA (4.83 ml, 27.8 mmol). The vial was purged with Argon, sealed and heated to 80° C. for 10 minutes. The reaction was cooled to RT and benzyl mercaptan (1.724 ml, 14.58 mmol) was added and the reaction was continued heating at 80° C. for an additional 90 minutes. The reaction was cooled to RT, diluted with water and extracted with DCM (3×). The combined organics were washed with water and brine, dried over magnesium sulfate, filtered and concentrated. The resulting material was concentrated, dissolved in minimal DCM and purified via column chromatography (silica gel 40 g, gradient elution 0 to 50% EtOAc:Heptane) to afford (E)-ethyl 3-(2-amino-5-(benzylthio)-4-fluorophenyl)acrylate (2.75 g, 8.30 mmol, 59.8% yield). m/z (ESI) 332.1 (M+H)⁺.

Step 3: (E)-ethyl 3-(5-(benzylthio)-2-((4-bromo-5-chloro-2-methoxyphenyl)amino)-4-fluorophenyl)acrylate A RBF was charged with (E)-ethyl 3-(2-amino-5-(benzylthio)-4-fluorophenyl)acrylate (1.60 g, 4.83 mmol), 1-bromo-2-chloro-4-iodo-5-methoxybenzene (2.013 g, 5.79 mmol), xantphos (0.140 g, 0.241 mmol), Pd₂(dba)₃ (0.111 g, 0.121 mmol), cesium carbonate (2.360 g, 7.24 mmol) and toluene (7.98 ml). The flask was kept under Argon, a reflux condenser was attached and the flask was lowered into a 110° C. heating bath and heated for 4 hours. The mixture was cooled to RT, diluted with EtOAc, and filtered through celite with the aid of EtOAc. The filtrate was concentrated. The oily residue was taken up in 2-PrOH (it remained an oil). The mixture was then concentrated to give a yellow solid with some oily solid present. The mixture was taken up in 2-PrOH to give a suspension, and the suspension was stirred overnight, which broke up the darker, oily solid. The mixture was filtered, and the filtered solid was washed with 2-PrOH (3×). The collected solid was dried on the filter under a flow of $N_2$ (g) for 15 min to give ((E)-ethyl 3-(5-(benzylthio)-2-((4-bromo-5-chloro-2-methoxyphenyl) amino)-4-fluorophenyl)acrylate (1.8 g, 3.27 mmol, 67.7% yield) as a bright-yellow solid. m/z (ESI) 548.1

Step 4: 6-(benzylthio)-1-(4-bromo-5-chloro-2-methoxyphenyl)-7-fluoroquinolin-2(1H)-one A RBF was charged with (E)-ethyl 3-(5-(benzylthio)-2-((4-bromo-5-chloro-2-methoxyphenyl)amino)-4-fluorophenyl)acrylate (1.80 g, 3.27 mmol) and MeOH (16.3 ml) to give a yellow suspension. Sodium methoxide (25 wt % in MeOH) (0.291 ml, 1.307 mmol) was added. A reflux condenser was attached, and the flask was lowered into a 70° C. heating bath. After 16 h, the mixture was cooled and concentrated under vacuum. The residue was triturated with 2-PrOH and filtered to give 6-(benzylthio)-1-(4-bromo-5-chloro-2-methoxyphenyl)-7-fluoroquinolin-2(1H)-one (1.23 g, 2.44 mmol, 74.6% yield) as a tan solid. m/z (ESI) 504.0 $(M+H)^+$.

Step 5: Perfluorophenyl 1-(4-bromo-5-chloro-2-methoxyphenyl)-7-fluoro-2-oxo-1,2-dihydroquinoline-6-sulfonate A RBF was charged with 6-(benzylthio)-1-(4-bromo-5-chloro-2-methoxyphenyl)-7-fluoroquinolin-2(1H)-one (0.680 g, 1.347 mmol), MeCN (4.22 ml), acetic acid (0.161 ml), and water (0.106 ml) to give clear, light-brown. The flask was cooled in an ice-water bath for 10 min, then 1,3-dichloro-5,5-methylhydantoin (0.186 ml, 1.414 mmol) was added in one portion. After 10 min, an additional portion of oxidant (84 mg) was added. After 30 min, an additional portion of oxidant (56 mg) was added. The mixture was stirred for another 10 min, then 2,3,4,5,6-pentafluorophenol (0.169 ml, 1.616 mmol) and triethylamine (0.751 ml, 5.39 mmol) (added dropwise) were added in sequence. After 20 min, the mixture was diluted with water. The layers were separated, and the aq. layer was extracted with EtOAc (1×). The combined organic extracts were dried over magnesium sulfate, filtered, and concentrated. The residue was purified by chromatography on silica gel (80-g Redi-Sep Gold column, 25-g silica gel loading column, 0-30% EtOAc/Heptane). Fractions containing the main spot were combined and concentrated to give an perfluorophenyl 1-(4-bromo-5-chloro-2-methoxyphenyl)-7-fluoro-2-oxo-1,2-dihydroquinoline-6-sulfonate (0.460 g, 0.732 mmol, 54.3% yield). m/z (ESI) 627.6 $(M+H)^+$.

Step 6: 1-(4-bromo-5-chloro-2-methoxyphenyl)-7-fluoro-N-(isoxazol-3-yl)-2-oxo-1,2-dihydroquinoline-6-sulfonamide A solution of perfluorophenyl 1-(4-bromo-5-chloro-2-methoxyphenyl)-7-fluoro-2-oxo-1,2-dihydroquinoline-6-sulfonate (0.440 g, 0.700 mmol), 3-aminoisoxazole (0.057 ml, 0.770 mmol) and THF (7.0 ml) was cooled in an ice-bath for 15 min, then lithium bis(trimethylsilyl)amide (1M in THF) (1.47 ml, 1.47 mmol) was added dropwise. After 60 min, the mixture was diluted with 1N aq. HCl and EtOAc. The aq. layer was extracted with EtOAc (2×). The combined organic extracts were dried over magnesium sulfate, filtered, and concentrated. The residue was concentrated and then triturated with in Et2O. The resulting suspension was sonicated, then filtered. The collected solid was washed with Et2O (2×), dried under a stream of $N_2$ (g), then dried under vacuum to give 1-(4-bromo-5-chloro-2-methoxyphenyl)-7-fluoro-N-(isoxazol-3-yl)-2-oxo-1,2-dihydroquinoline-6-sulfonamide (0.370 g, 0.700 mmol, 100% yield) as an off white solid. m/z (ESI) 527.7 $(M+H)^+$.

Step 7: 1-(2-chloro-3'-fluoro-5-methoxy-[1,1'-biphenyl]-4-yl)-7-fluoro-N-(isoxazol-3-yl)-2-oxo-1,2-dihydroquinoline-6-sulfonamide and (P)-1-(2-chloro-3'-fluoro-5-methoxy-[1,1'-biphenyl]-4-yl)-7-fluoro-N-(isoxazol-3-yl)-2-oxo-1,2-dihydroquinoline-6-sulfonamide (3102123) and (M)-1-(2-chloro-3'-fluoro-5-methoxy-[1,1'-biphenyl]-4-yl)-7-fluoro-N-(isoxazol-3-yl)-2-oxo-1,2-dihydroquinoline-6-sulfonamide A vial was charged with 1-(4-bromo-5-chloro-2-methoxyphenyl)-7-fluoro-N-(isoxazol-3-yl)-2-oxo-1,2-dihydroquinoline-6-sulfonamide (0.370 g, 0.700 mmol), (3-fluorophenyl)boronic acid (0.147 g, 1.050 mmol), potassium carbonate (0.290 g, 2.099 mmol), and Pd(Ph$_3$P)$_4$ (0.081 g, 0.88 mmol). The vial was flushed with Ar (g), then 1,4-dioxane (2.62 mL) and water (0.070 mL) were added. The vial was sealed and heated to 90° C. for 30 min. The mixture was cooled and extracted with EtOAc (5×), and the combined organic extracts were concentrated. The residue was purified via column chromatography (silica gel 40 g, gradient elution 0 to 50% EtOAc:Heptane) to afford racemic 1-(2-chloro-3'-fluoro-5-methoxy-[1,1'-biphenyl]-4-yl)-7-fluoro-N-(isoxazol-3-yl)-2-oxo-1,2-dihydroquinoline-6-sulfonamide. $^1$H NMR (400 MHz, DMSO-d$_6$) δ=12.02 (br. s., 1H), 8.74 (d, J=1.66 Hz, 1H), 8.49 (d, J=7.63 Hz, 1H), 8.26 (d, J=9.59 Hz, 1H), 7.69 (s, 1H), 7.59 (dt, J=6.36, 8.02 Hz, 1H), 7.42-7.48 (m, 2H), 7.29-7.36 (m, 2H), 6.79 (d, J=9.68 Hz, 1H), 6.67 (d, J=12.03 Hz, 1H), 6.40 (d, J=1.76 Hz, 1H), 3.75 (s, 3H). m/z (ESI) 544.1 $(M+H)^+$. This material was purified by chiral SFC on Chiralpak AS-H column (25% MeOH/75% CO$_2$) to give (P)-1-(2-chloro-3'-fluoro-5-methoxy-[1,1'-biphenyl]-4-yl)-7-fluoro-N-(isoxazol-3-yl)-2-oxo-1,2-dihydroquinoline-6-sulfonamide as peak 1 and (M)-1-(2-chloro-3'-fluoro-5-methoxy-[1,1'-biphenyl]-4-yl)-7-fluoro-N-(isoxazol-3-yl)-2-oxo-1,2-dihydroquinoline-6-sulfonamide as peak 2, both as off-white solids. Data for peak 1: $^1$H NMR (400 MHz, DMSO-d$_6$) δ=12.02 (br. s., 1H), 8.74 (d, J=1.76 Hz, 1H), 8.49 (d, J=7.77 Hz, 1H), 8.21-8.30 (m, 1H), 7.66-7.71 (m, 1H), 7.54-7.63 (m, 1H), 7.42-7.49 (m, 2H), 7.28-7.37 (m, 2H), 6.79 (d, J=9.64 Hz, 1H), 6.67 (d, J=11.92 Hz, 1H), 6.40 (d, J=1.76 Hz, 1H), 3.75 (s, 3H). m/z (ESI) 544.1 $(M+H)^+$. Data for peak 2: $^1$H NMR (400 MHz, DMSO-d$_6$) δ=12.02 (br. s., 1H), 8.74 (d, J=1.76 Hz, 1H), 8.49 (d, J=7.77 Hz, 1H), 8.26 (d, J=9.64 Hz, 1H), 7.69 (s, 1H), 7.53-7.63 (m, 1H), 7.42-7.49 (m, 2H), 7.29-7.38 (m, 2H), 6.79 (d, J=9.64 Hz, 1H), 6.67 (d, J=11.92 Hz, 1H), 6.40 (d, J=1.87 Hz, 1H), 3.75 (s, 3H). m/z (ESI) 544.1 $(M+H)^+$.

Example

(Method 97): N-(isoxazol-3-yl)-1-(3-methoxynaphthalen-2-yl)-2-oxo-1,2-dihydroquinoline-6-sulfonamide

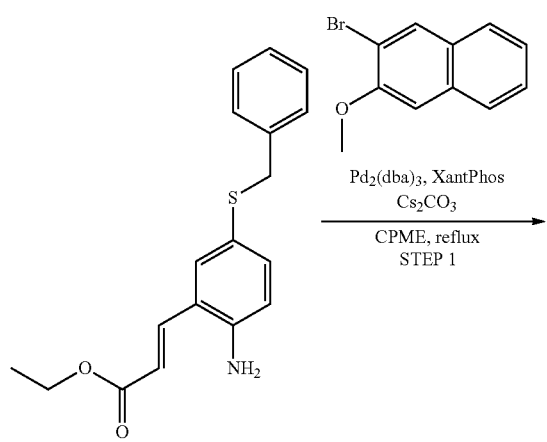

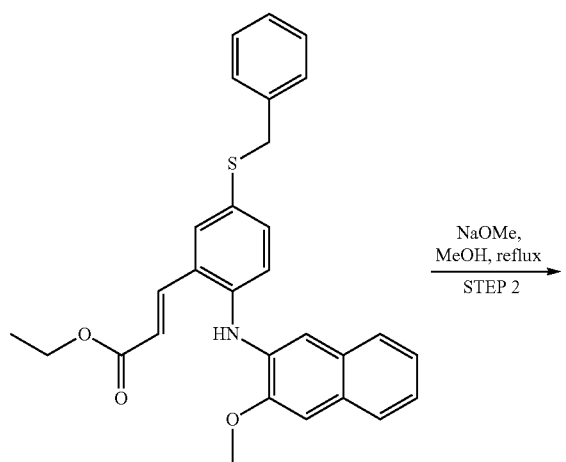

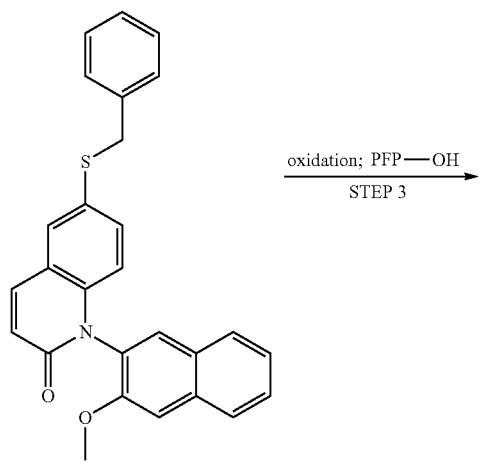

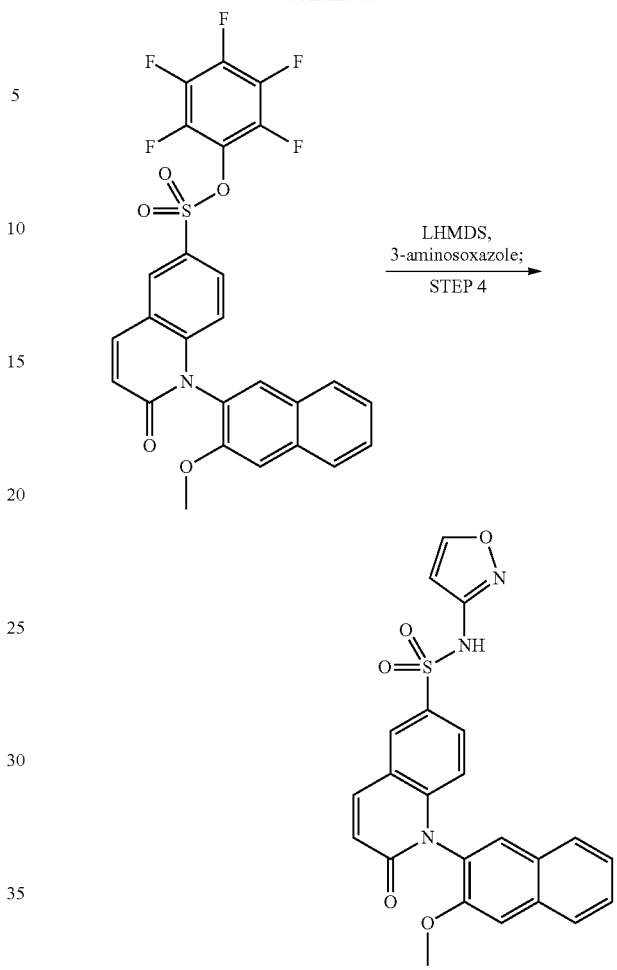

Step 1: (E)-ethyl 3-(5-(benzylthio)-2-((3-methoxynaphthalen-2-yl)amino)phenyl)acrylate A screw cap vial was charged with (E)-ethyl 3-(2-amino-5-(benzylthio)phenyl)acrylate (1.00 g, 3.19 mmol), xantphos (0.092 g, 0.160 mmol), pd$_2$(dba)$_3$ (0.073 g, 0.080 mmol), cesium carbonate (2.079 g, 6.38 mmol) and CPME (6.38 ml). The vial was purged with Argon, sealed and heated to 110° C. for 10 minutes. The reaction was cooled to room temperature and 2-bromo-3-methoxynaphthalene (0.832 g, 3.51 mmol) was added and the reaction was continued heating at 110° C. for an additional 90 min. The mixture was cooled to room temperature, diluted with EtOAc, and filtered through celite with the aid of EtOAc. The filtrate was concentrated. The oily residue was taken up in 2-PrOH (it did not dissolve and remained an oil). The mixture was then concentrated to give a yellow solid with some oily solid present. The mixture was taken up in 2-PrOH to give a suspension, and the suspension was stirred overnight, which broke up the darker, oily solid. The mixture was then filtered, and the filtered solid was washed with 2-PrOH (3×). The collected solid was dried on the filter under a flow of N$_2$ (g) for 15 min to give (E)-ethyl 3-(5-(benzylthio)-2-((3-methoxynaphthalen-2-yl)amino)phenyl)acrylate (1.35 g, 2.87 mmol, 90% yield). m/z (ESI) 470.1

Step 2: 6-(benzylthio)-1-(3-methoxynaphthalen-2-yl)quinolin-2(1H)-one

A RBF was charged with (E)-ethyl 3-(5-(benzylthio)-2-((3-methoxynaphthalen-2-yl)amino)phenyl)acrylate (1.30 g, 2.77 mmol) and MeOH (13.8 ml) to give a yellow suspension. Sodium methoxide (25 wt % in MeOH) (0.0.25 ml, 1.107 mmol) was added. A reflux condenser was attached, and the flask was lowered into a 70° C. heating bath. After 16 h, the mixture was cooled, filtered through a pad of Celite, and concentrated under vacuum. The residue was purified via column chromatography (silica gel 40 g, gradient elution 0 to 50% EtOAc:Heptane) to afford (0.811 g, 1.915 mmol, 69.2% yield) as a tan solid. m/z (ESI) 423.9 (M+H)$^+$.

Step 3: Perfluorophenyl 1-(3-methoxynaphthalen-2-yl)-2-oxo-1,2-dihydroquinoline-6-sulfonate A round-bottom flask was charged with 6-(benzylthio)-1-(3-methoxynaphthalen-2-yl)quinolin-2(1H)-one (0.81 g, 1.913 mmol), MeCN (6.00 ml), acetic acid (0.228 ml), and water (0.150 ml) to give clear, light-brown. The flask was cooled in an ice-water bath for 10 min, then 1,3-dichloro-5,5-dimethylhydantoin (0.264 ml, 2.008 mmol) was added in one portion. After 10 min, an additional portion of oxidant (118 mg) was added. The mixture was stirred for another 50 min, then 2,3,4,5,6-pentafluorophenol (0.240 ml, 2.295 mmol) and triethylamine (1.06 ml, 7.65 mmol) (added dropwise) were added in sequence. After 20 min, the mixture was diluted with water. The layers were separated, and the aq. layer was extracted with EtOAc (1×). The combined organic extracts were dried over magnesium sulfate, filtered, and concentrated. The residue was purified by chromatography on silica gel (80-g Redi-Sep Gold column, 25-g silica gel loading column, 0-50% EtOAc/Heptane). Fractions containing the main spot were combined and concentrated to give perfluorophenyl 1-(3-methoxynaphthalen-2-yl)-2-oxo-1,2-dihydroquinoline-6-sulfonate (0.659 g, 1.204 mmol, 62.9% yield). m/z (ESI) 548.1 (M+H)$^+$.

Step 4: N-(isoxazol-3-yl)-1-(3-methoxynaphthalen-2-yl)-2-oxo-1,2-dihydroquinoline-6-sulfonamide A solution of perfluorophenyl 1-(3-methoxynaphthalen-2-yl)-2-oxo-1,2-dihydroquinoline-6-sulfonate (0.250 g, 0.457 mmol), 3-aminoisoxazole (0.037 ml, 0.502 mmol) and THF (4.57 ml) was cooled in an ice-bath for 15 min, then lithium bis(trimethylsilyl)amide (1M in THF) (0.959 ml, 0.959 mmol) was added dropwise. After 60 min, the mixture was diluted with 1N aq. HCl and EtOAc. The aq. layer was extracted with EtOAc (2×). The combined organic extracts were dried over magnesium sulfate, filtered, and concentrated. The residue was concentrated and then triturated with in Et$_2$O. The resulting suspension was sonicated, then filtered. The collected solid was washed with Et2O (2×), dried under a stream of N$_2$ (g), then dried under vacuum to give N-(isoxazol-3-yl)-1-(3-methoxynaphthalen-2-yl)-2-oxo-1,2-dihydroquinoline-6-sulfonamide (0.175 g, 0.391 mmol, 86% yield) as an off white solid. $^1$H NMR (400 MHz, DMSO-d$_6$) δ 11.49-11.79 (m, 1H), 8.68-8.78 (m, 1H), 8.38-8.42 (m, 1H), 8.24-8.29 (m, 1H), 7.96-8.01 (m, 2H), 7.86-7.91 (m, 1H), 7.78-7.84 (m, 1H), 7.66 (s, 1H), 7.56-7.64 (m, 1H), 7.42-7.50 (m, 1H), 6.75-6.86 (m, 2H), 6.42-6.47 (m, 1H), 3.72-3.81 (m, 3H). m/z (ESI) 447.9 (M+H)$^+$.

Example 359 & 360

(Method 99): (P)-1-(2-fluoro-5-methoxy-3'-(trifluoromethyl)-[1,1'-biphenyl]-4-yl)-N-(isoxazol-3-yl)-2-oxo-1,2-dihydroquinoline-6-sulfonamide (359) and (M)-1-(2-fluoro-5-methoxy-3'-(trifluoromethyl)-[1,1'-biphenyl]-4-yl)-N-(isoxazol-3-yl)-2-oxo-1,2-dihydroquinoline-6-sulfonamide (360)

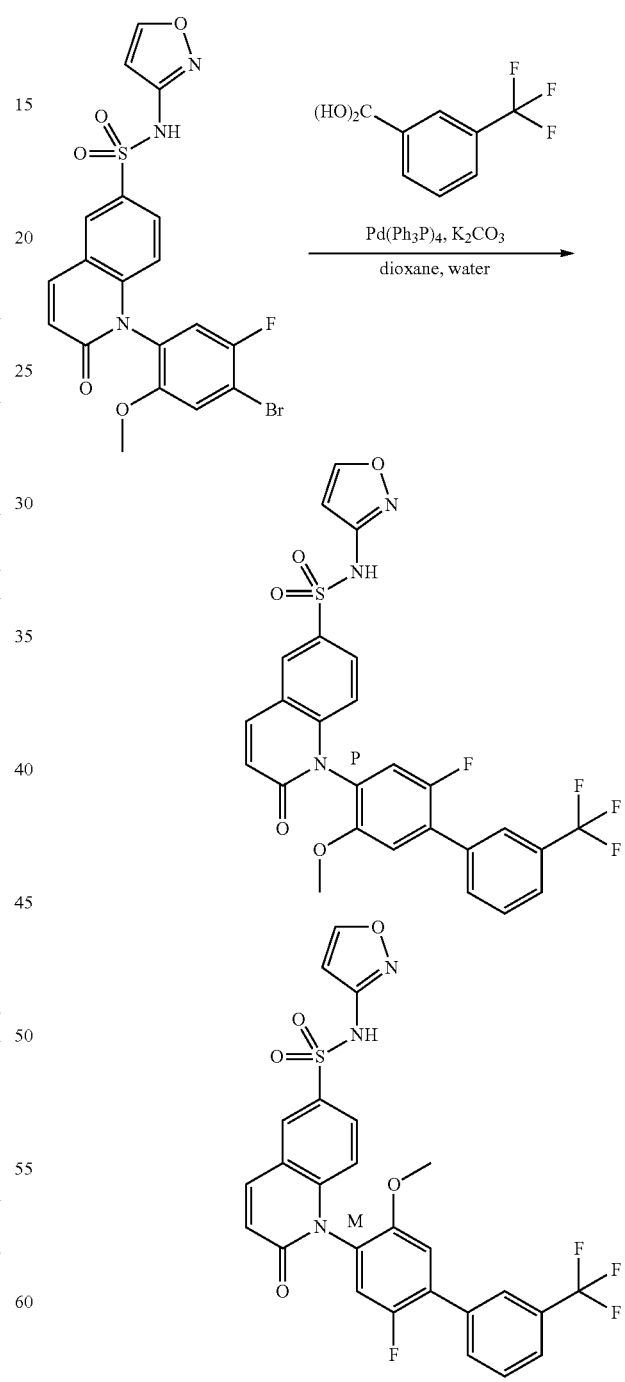

A flask was charged with 1-(4-bromo-5-fluoro-2-methoxyphenyl)-N-(isoxazol-3-yl)-2-oxo-1,2-dihydroquinoline-6-sulfonamide (257 mg, 0.520 mmol), 3-(trifluoromethyl)benzeneboronic acid (148 mg, 0.780 mmol), potassium carbonate (216 mg, 1.560 mmol), and Pd(Ph₃P)₄, (60.1 mg, 0.052 mmol). The vial was sealed with a septum cap and flushed with N₂ (g), then Dioxane (1.950 mL) and Water (0.650 mL) were added via syringe. The mixture heated at 90° C. for 40 min. HCl (4 mL, 1M aq) was added and the mixture was extracted with EtOAc (2×10 mL). The combined organic layers were concentrated and the resulting residue was absorbed onto a plug of silica gel for purification by silica gel chromatography. The product was eluted through a Redi-Sep pre-packed silica gel column (12 g), eluting with a gradient of 0% to 3% MeOH in CH₂Cl₂, to provide racemic 1-(2-fluoro-5-methoxy-3'-(trifluoromethyl)-[1,1'-biphenyl]-4-yl)-N-(isoxazol-3-yl)-2-oxo-1,2-dihydroquinoline-6-sulfonamide. Racemic 1-(2-fluoro-5-methoxy-3'-(trifluoromethyl)-[1,1'-biphenyl]-4-yl)-N-(isoxazol-3-yl)-2-oxo-1,2-dihydroquinoline-6-sulfonamide was subjected to chiral separation by SFC on an AS-H column (20% MeOH/80% CO₂) to give (P)-1-(2-fluoro-5-methoxy-3'-(trifluoromethyl)-[1,1'-biphenyl]-4-yl)-N-(isoxazol-3-yl)-2-oxo-1,2-dihydroquinoline-6-sulfonamide as peak 1 and (M)-1-(2-fluoro-5-methoxy-3'-(trifluoromethyl)-[1,1'-biphenyl]-4-yl)-N-(isoxazol-3-yl)-2-oxo-1,2-dihydroquinoline-6-sulfonamide as peak 2. Both peaks were isolated as off-white solids. Data for peak 1: $^1$H NMR (500 MHz, DMSO-d₆) δ 11.6 (br s, 1H), 8.72 (d, J=1.71 Hz, 1H), 8.38 (d, J=2.03 Hz, 1H), 8.24 (d, J=9.72 Hz, 1H), 8.01 (br. s., 2H), 7.77-7.90 (m, 3H), 7.56 (d, J=10.31 Hz, 1H), 7.48 (d, J=6.89 Hz, 1H), 6.89 (d, J=8.98 Hz, 1H), 6.82 (d, J=9.67 Hz, 1H), 6.45 (d, J=1.71 Hz, 1H), 3.70-3.80 (s, 3H). m/z (ESI) 558.0 (M−H)⁻. Data for peak 2: $^1$H NMR (500 MHz, DMSO-d₆) δ 11.66 (br. s., 1H), 8.72 (d, J=1.71 Hz, 1H), 8.38 (d, J=2.03 Hz, 1H), 8.24 (d, J=9.67 Hz, 1H), 8.01 (br. s., 2H), 7.76-7.90 (m, 3H), 7.56 (d, J=10.31 Hz, 1H), 7.48 (d, J=6.89 Hz, 1H), 6.89 (d, J=8.98 Hz, 1H), 6.82 (d, J=9.67 Hz, 1H), 6.45 (d, J=1.71 Hz, 1H), 3.75 (s, 3H). m/z (ESI) 558.0 (M−H)⁻.

Examples 363 & 364

(Method 102): (P)—N-3-isoxazolyl-2-oxo-1-(2,3',5'-trifluoro-5-methoxy-4-biphenylyl)-1,2-dihydro-6-quinolinesulfonamide (363) and (M)-N-3-isoxazolyl-2-oxo-1-(2,3',5'-trifluoro-5-methoxy-4-biphenylyl)-1,2-dihydro-6-quinolinesulfonamide (364)

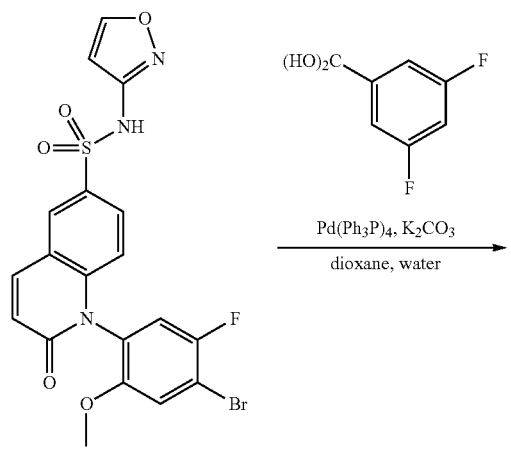

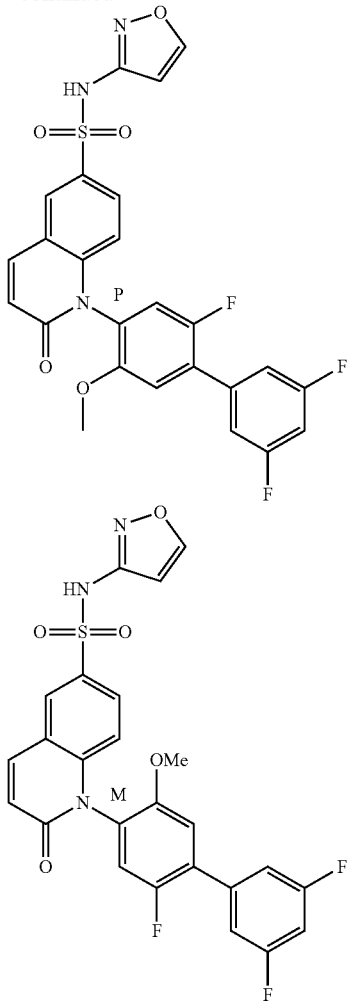

A RBF was charged with 1-(4-bromo-5-fluoro-2-methoxyphenyl)-N-(isoxazol-3-yl)-2-oxo-1,2-dihydroquinoline-6-sulfonamide (272 mg, 0.550 mmol), (3,5-difluorophenyl)boronic acid (130 mg, 0.825 mmol), potassium carbonate (228 mg, 1.651 mmol), and Pd(Ph₃P)₄ (63.6 mg, 0.055 mmol). The vial was sealed with a septum cap and flushed with N₂ (g), then Dioxane (2064 μl) and Water (688 μl) were added via syringe. The mixture was heated at 90° C. for 40 min. The mixture was diluted with HCl (8 mL, 1M aq) then extracted with EtOAc (2×20 mL). The organic layers were combined and concentrated. The residue was absorbed onto a plug of silica gel and purified by chromatography through a Redi-Sep pre-packed silica gel column (12 g), eluting with a gradient of 0%3% MeOH in DCM, to provide N-(isoxazol-3-yl)-2-oxo-1-(2,3',5'-trifluoro-5-methoxy-[1,1'-biphenyl]-4-yl)-1,2-dihydroquinoline-6-sulfonamide. The racemic N-(isoxazol-3-yl)-2-oxo-1-(2,3',5'-trifluoro-5-methoxy-[1,1'-biphenyl]-4-yl)-1,2-dihydroquinoline-6-sulfonamide was subjected to chiral separation by SFC on an AS-H column (25% MeOH/75% CO₂) to give (P)—N-(isoxazol-3-yl)-2-oxo-1-(2,3',5'-trifluoro-5-methoxy-[1,1'-biphenyl]-4-yl)-1,2-dihydroquinoline-6-sulfonamide as peak 1 and (M)-N-(isoxazol-3-yl)-2-oxo-1-(2,3',5'-trifluoro-5-methoxy-[1,1'-biphenyl]-4-yl)-1,2-dihydroquinoline-6-sulfonamide as peak 2. Data for peak 1: $^1$H NMR (500 MHz, DMSO-d₆) δ 11.65 (br. s., 1H), 8.72

(d, J=1.66 Hz, 1H), 8.38 (d, J=1.98 Hz, 1H), 8.16-8.31 (m, 1H), 7.86 (dd, J=2.08, 8.98 Hz, 1H), 7.56 (d, J=10.47 Hz, 1H), 7.47 (t, J=6.79 Hz, 3H), 7.33-7.43 (m, 1H), 6.84-6.91 (m, 1H), 6.77-6.84 (m, 1H), 6.41-6.49 (m, 1H), 3.70-3.83 (s, 3H). m/z (ESI) 528.0 (M+H)+. Data for peak 2: $^1$H NMR (500 MHz, DMSO-d$_6$) δ 11.65 (br. s., 1H), 8.72 (d, J=1.66 Hz, 1H), 8.38 (d, J=1.98 Hz, 1H), 8.16-8.31 (m, 1H), 7.86 (dd, J=2.08, 8.98 Hz, 1H), 7.56 (d, J=10.47 Hz, 1H), 7.47 (t, J=6.79 Hz, 3H), 7.33-7.43 (m, 1H), 6.84-6.91 (m, 1H), 6.77-6.84 (m, 1H), 6.41-6.49 (m, 1H), 3.70-3.83 (s, 3H). m/z (ESI) 528.0 (M+H)+.

Example 365 & 366

(Method 103): (P)-1-(3'-chloro-2,4'-difluoro-5-methoxy-4-biphenylyl)-N-3-isoxazolyl-2-oxo-1,2-dihydro-6-quinolinesulfonamide (365) and (M)-1-(3'-chloro-2,4'-difluoro-5-methoxy-4-biphenylyl)-N-3-isoxazolyl-2-oxo-1,2-dihydro-6-quinolinesulfonamide (366)

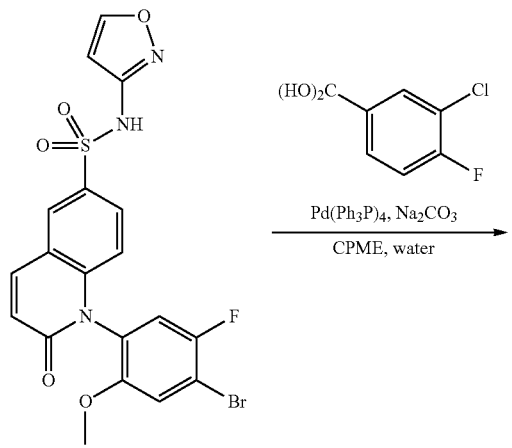

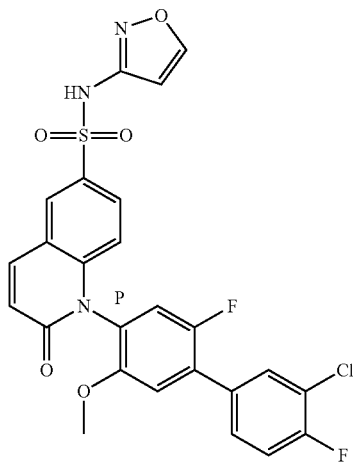

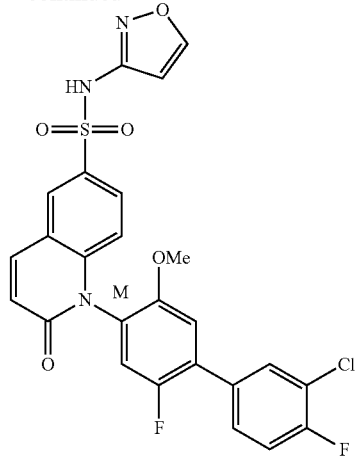

A vial was charged with 1-(4-bromo-5-fluoro-2-methoxyphenyl)-N-(isoxazol-3-yl)-2-oxo-1,2-dihydroquinoline-6-sulfonamide (0.310 g, 0.627 mmol). (3-chloro-4-fluorophenyl)boronic acid (0.175 g, 1.003 mmol), Pd(Ph$_3$P)$_4$ (0.072 g, 0.063 mmol). The vial was sealed with a septum cap and flushed with Ar (g), then CPME (3.14 ml) and sodium carbonate 1.9 M (0.990 ml, 1.881 mmol) were added via syringe. The mixture was heated to 100° C. for 1 h and then partitioned between water (20 mL) and EtOAc (30 mL). The layers were separated and the aqueous layer was acidified with 1N HCl. The aqueous layer was extracted with EtOAc (2×20 mL) and all the organic layers were combined, dried (Na$_2$SO$_4$) and concentrated for purification by MPLC (Biotage Isolera). The crude residue was taken up in minimal CH$_2$Cl$_2$ and absorbed onto a 5 g loading cartridge and passed through a Redi-Sep® Gold pre-packed silica gel column (40 g) using 90:10 Heptane:EtOAc to 100% EtOAc gradient to afford racemic 1-(3'-chloro-2,4'-difluoro-5-methoxy-[1,1'-biphenyl]-4-yl)-N-(isoxazol-3-yl)-2-oxo-1,2-dihydroquinoline-6-sulfonamide (0.325 g, 0.598 mmol, 95% yield) as a light-yellow film. Racemic 1-(3'-chloro-2,4'-difluoro-5-methoxy-[1,1'-biphenyl]-4-yl)-N-(isoxazol-3-yl)-2-oxo-1,2-dihydroquinoline-6-sulfonamide was subjected to chiral separation by SFC using a Regis Whelk-O (s,s) column and 50% MeOH in CO$_2$. Peak 1 was (P)-1-(3'-chloro-2,4'-difluoro-5-methoxy-[1,1'-biphenyl]-4-yl)-N-(isoxazol-3-yl)-2-oxo-1,2-dihydroquinoline-6-sulfonamide and peak 2 was (M)-1-(3'-chloro-2,4'-difluoro-5-methoxy-[1,1'-biphenyl]-4-yl)-N-(isoxazol-3-yl)-2-oxo-1,2-dihydroquinoline-6-sulfonamide. Data for peak 1: $^1$H NMR (500 MHz, DMSO-d6) δ 11.49-11.82 (br s, 1H), 8.71 (d, J=1.55 Hz, 1H), 8.37 (d, J=1.87 Hz, 1H), 8.17-8.28 (m, 1H), 7.94 (d, J=5.88 Hz, 1H), 7.86 (dd, J=1.98, 8.92 Hz, 1H), 7.69-7.77 (m, 1H), 7.60 (t, J=8.98 Hz, 1H), 7.53 (d, J=10.31 Hz, 1H), 7.40-7.47 (m, 1H), 6.86 (d, J=8.98 Hz, 1H), 6.81 (d, J=9.62 Hz, 1H), 6.38-6.52 (m, 1H), 3.75 (s, 3H). m/z (ESI) 544.0 (M+H)+. Data for peak 2: $^1$H NMR (500 MHz, DMSO-d6) δ 11.49-11.82 (br s, 1H), 8.71 (d, J=1.55 Hz, 1H), 8.37 (d, J=1.87 Hz, 1H), 8.17-8.28 (m, 1H), 7.94 (d, J=5.88 Hz, 1H), 7.86 (dd, J=1.98, 8.92 Hz, 1H), 7.69-7.77 (m, 1H), 7.60 (t, J=8.98 Hz, 1H), 7.53 (d, J=10.31 Hz, 1H), 7.40-7.47 (m, 1H), 6.86 (d, J=8.98 Hz, 1H), 6.81 (d, J=9.62 Hz, 1H), 6.38-6.52 (m, 1H), 3.75 (s, 3H). m/z (ESI) 544.0 (M+H)+.

Example 367 & 368

(Method 104): (P)-1-(2,4'-dichloro-5-methoxy-3'-methyl-4-biphenylyl)-2-oxo-N-4-pyrimidinyl-1,2-dihydro-6-quinolinesulfonamide (367) and (M)-1-(2,4'-dichloro-5-methoxy-3'-methyl-4-biphenylyl)-2-oxo-N-4-pyrimidinyl-1,2-dihydro-6-quinolinesulfonamide (368)

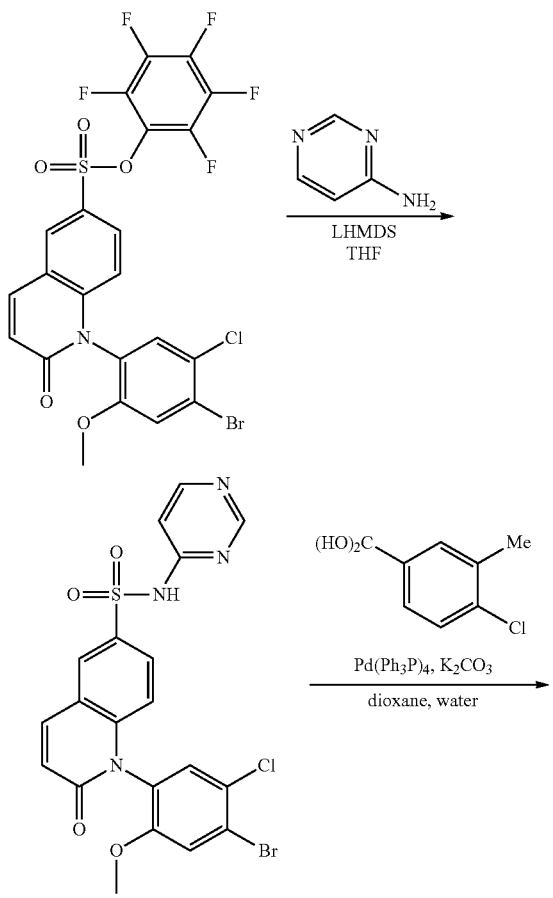

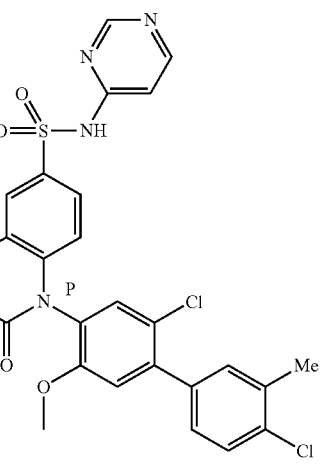

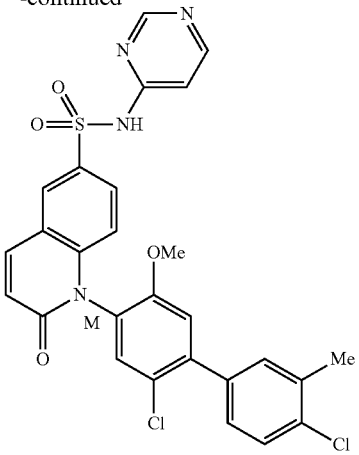

Step 1: 1-(4-bromo-5-chloro-2-methoxyphenyl)-2-oxo-N-(pyrimidin-4-yl)-1,2-dihydroquinoline-6-sulfonamide A flask was charged with perfluorophenyl 1-(4-bromo-5-chloro-2-methoxyphenyl)-2-oxo-1,2-dihydroquinoline-6-sulfonate (0.256 g, 0.419 mmol) and pyrimidin-4-amine (0.048 g, 0.503 mmol). A septum was attached and THF (2.096 ml) was added under $N_2$ flow. The mixture was cooled to 0° C. A THF solution of lithium bis(trimethylsilyl)amide (0.880 ml, 0.880 mmol, 1 M) was added dropwise to give a brown solution with a tan precipitate. The solution was maintained at 0° C. for 20 min, and allowed to warm to rt and maintained for 2 h. The reaction mixture was partitioned between 1 N HCl (10 mL) and EtOAc (20 mL), the layers were separated and the aqueous layer was extracted with 1:1 MeOH: EtOAc (1×20 mL). The combined organic layers which were dried ($Na_2SO_4$) and concentrated to provide 1-(4-bromo-5-chloro-2-methoxyphenyl)-2-oxo-N-(pyrimidin-4-yl)-1,2-dihydroquinoline-6-sulfonamide (0.219 g, 0.419 mmol), which was of sufficient purity for the subsequent step. m/z (ESI) 521.1 (M+H)+.

Step 2: (P)-1-(2,4'-dichloro-5-methoxy-3'-methyl-4-biphenylyl)-2-oxo-N-4-pyrimidinyl-1,2-dihydro-6-quinolinesulfonamide and (M)-1-(2,4'-dichloro-5-methoxy-3'-methyl-4-biphenylyl)-2-oxo-N-4-pyrimidinyl-1,2-dihydro-6-quinolinesulfonamide A vial was charged with 1-(4-bromo-5-chloro-2-methoxyphenyl)-2-oxo-N-(pyrimidin-4-yl)-1,2-dihydroquinoline-6-sulfonamide (0.219 g, 0.419 mmol), (4-chloro-3-methylphenyl)boronic acid (0.147 g, 0.865 mmol), Pd(Ph$_3$P)$_4$ (0.062 g, 0.054 mmol) and potassium carbonate (0.224 g, 1.621 mmol). The vial was flushed with Ar (g), then dioxane (2.027 ml) and water (0.676 ml) were added. The vial was sparged with $N_2$ for 1 min and heated at 90° C. for 2 h. The mixture was partitioned between 1 N HCl (10 mL) and EtOAc (20 mL), the layers were separated and the aqueous layer was extracted with EtOAc. The combined organic layers were dried ($Na_2SO_4$) and concentrated for purification by MPLC (Biotage Isolera). The crude residue was taken up in minimal DCM and absorbed directly onto a dry Biotage SNAP pre-packed silica gel column (50 g) and eluted using a gradient of 100% Heptane—100% of 3:1 EtOAc:EtOH blend to afford 1-(2,4'-dichloro-5-methoxy-3'-methyl-[1,1'-biphenyl]-4-yl)-2-oxo-N-(pyrimidin-4-yl)-1,2-dihydroquinoline-6-sulfonamide as a light-yellow foam. The racemic 1-(2,4'-dichloro-5-methoxy-3'-methyl-[1,1'-biphenyl]-4-yl)-2-oxo-N-(pyrimidin-4-yl)-1,2-dihydroquinoline-6-sulfonamide was subjected to chiral separation by SFC using a Chiralpak AD column with 40% isopropanol in $CO_2$ to provide (P)-1-(2,4'-dichloro-5-methoxy-3'-methyl-[1,1'-biphenyl]-4-yl)-2-oxo-N-(pyrimidin-4-yl)-1,2-dihydroquinoline-6-sulfonamide as peak 1 and (M)-1-(2,4'-dichloro-5-methoxy-3'-methyl-[1,1'-biphenyl]-4-yl)-2-oxo-N-(pyrimidin-4-yl)-1,2-dihydroquinoline-6-sulfonamide as peak 2. Data for peak 1: $^1$H NMR (500 MHz, DMSO-$d_6$) δ 12.46-12.80 (br. s., 1H), 8.61 (br. s., 1H), 8.43 (br. s., 1H), 8.27-8.37 (m, 1H), 8.23 (d, J=9.72 Hz, 1H), 7.94 (d, J=8.82 Hz, 1H), 7.65 (s, 1H), 7.51-7.61 (m, 2H), 7.43 (dd, J=1.63, 8.04 Hz, 1H), 7.31 (s, 1H), 7.02 (br. s., 1H), 6.73-6.88 (m, 2H), 3.72 (s, 3H), 2.43 (s, 3H). m/z (ESI) 567.0 (M+H)$^+$. Data for peak 2: $^1$H NMR (500 MHz, DMSO-$d_6$) δ 8.61 (br. s., 1H), 8.43 (br. s., 1H), 8.30 (br. s., 1H), 8.23 (d, J=9.72 Hz, 1H), 7.94 (d, J=8.65 Hz, 1H), 7.65 (s, 1H), 7.57 (dd, J=3.29, 4.73 Hz, 2H), 7.39-7.48 (m, 1H), 7.31 (s, 1H), 7.02 (br. s., 1H), 6.75-6.87 (m, 2H), 3.66-3.75 (m, 3H), 2.43 (s, 3H) (sulfonamide NH missing due to exchange with water). m/z (ESI) 567.0 (M+H)$^+$.

Example 369 & 370

(Method 105): (P)-1-(3-methoxy-3'-(trifluoromethyl)-4-biphenylyl)-2-oxo-N-3-pyridazinyl-1,2-dihydro-6-quinolinesulfonamide (369) and (M)-1-(3-methoxy-3'-(trifluoromethyl)-4-biphenylyl)-2-oxo-N-3-pyridazinyl-1,2-dihydro-6-quinolinesulfonamide (370)

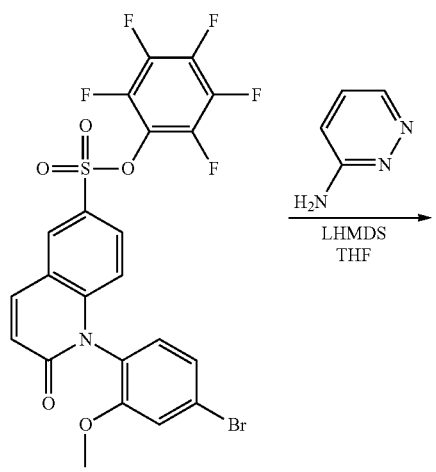

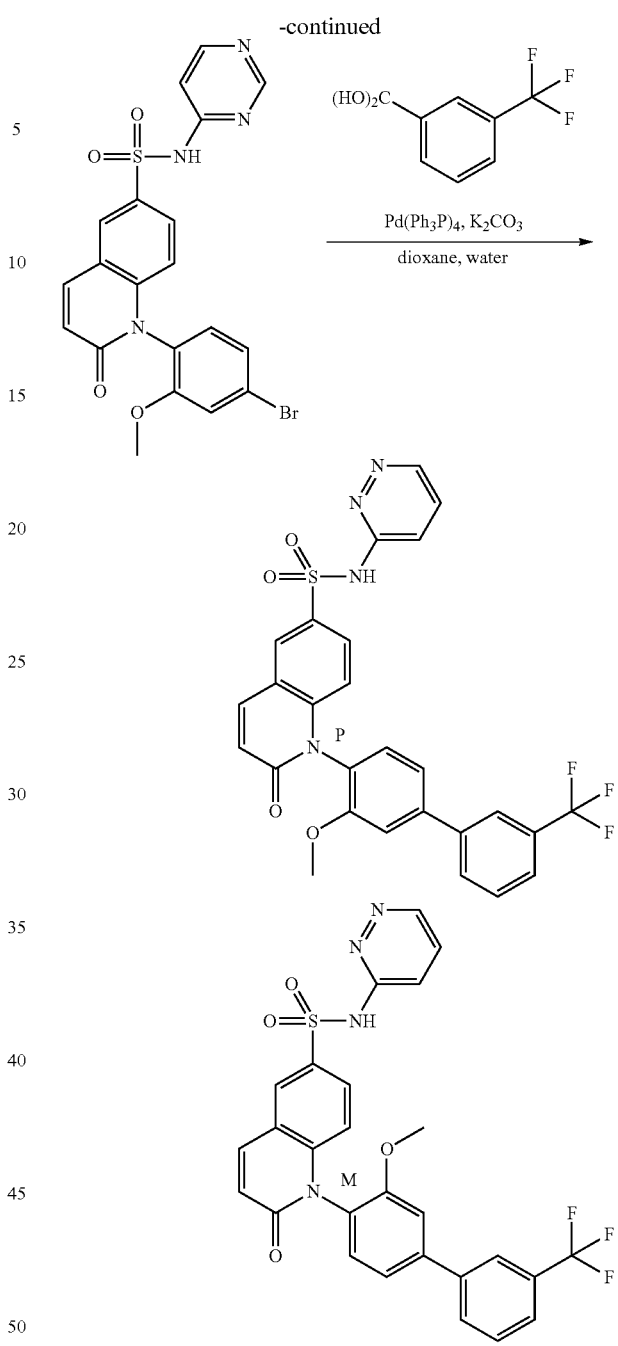

Step 1: Perfluorophenyl 1-(4-bromo-2-methoxyphenyl)-2-oxo-1,2-dihydroquinoline-6-sulfonate Perfluorophenyl 1-(4-bromo-2-methoxyphenyl)-2-oxo-1,2-dihydroquinoline-6-sulfonate was synthesized in a manner similar to that described for perfluorophenyl 1-(4-bromo-5-chloro-2-methoxyphenyl)-2-oxo-1,2-dihydroquinoline-6-sulfonate, except using 5-bromo-2-iodoanisole (Oakwood) instead of 1-bromo-2-chloro-4-iodo-5-methoxybenzene in step 1. m/z (ESI) 575.7 (M+H)$^+$.

Step 2: 1-(4-bromo-2-methoxyphenyl)-2-oxo-N-(pyridazin-3-yl)-1,2-dihydroquinoline-6-sulfonamide A flask was charged with perfluorophenyl 1-(4-bromo-2-methoxyphenyl)-2-oxo-1,2-dihydroquinoline-6-sulfonate (3.33 g, 5.78 mmol) and pyridazin-3-amine (0.659 g, 6.93 mmol). A septum was attached and THF (28.9 ml) was added. The mixture was cooled to 0° C. and a THF solution of lithium bis(trimethylsilyl)amide (12.13 ml, 12.13 mmol, 1 M) was added dropwise to give a brown solution. The solution was maintained at 0° C. for 20 min. The reaction mixture was partitioned between 1 N HCl (200 mL) and EtOAc (200 mL), the layers were separated and the aqueous layer was extracted with DCM (100 mL) and EtOAc (200 mL). The combined organic layers were dried (Na$_2$SO$_4$) and concentrated to provide 1-(4-bromo-2-methoxyphenyl)-2-oxo-N-(pyridazin-3-yl)-1,2-dihydroquinoline-6-sulfonamide (3.39 g, 6.96 mmol, 120% yield) as a light yellow foam. Although contaminated with solvent, the product was of sufficient purity for use in the next step. m/z (ESI) 485.1 (M−H)⁻.

Step 3: (P)-1-(3-methoxy-3'-(trifluoromethyl)-4-biphenylyl)-2-oxo-N-3-pyridazinyl-1,2-dihydro-6-quinolinesulfonamide and (M)-1-(3-methoxy-3'-(trifluoromethyl)-4-biphenylyl)-2-oxo-N-3-pyridazinyl-1,2-dihydro-6-quinolinesulfonamide A vial was charged with 1-(4-bromo-2-methoxyphenyl)-2-oxo-N-(pyridazin-3-yl)-1,2-dihydroquinoline-6-sulfonamide (0.406 g, 0.833 mmol), (3-(trifluoromethyl)phenyl)boronic acid (0.253 g, 1.333 mmol), Pd(Ph$_3$P)$_4$ (0.096 g, 0.083 mmol) and potassium carbonate (0.345 g, 2.499 mmol). A septum cap was attached and the vial was flushed with Ar (g), then dioxane (3.12 ml) and water (1.041 ml) were added sequentially via syringe. The vial was sparged with N$_2$ for 1 min and heated to 90° C. for 2 h, the temperature was increased to 105° C. for 1 h. The mixture was partitioned between 1 N HCl (30 mL) and EtOAc (50 mL), the layers were separated and the aqueous layer was extracted with EtOAc (1×20 mL). The combined organic layers were dried (Na$_2$SO$_4$) and concentrated for purification by MPLC (Biotage Isolera). The crude residue was taken up in minimal DCM and absorbed directly onto a dry Biotage SNAP pre-packed silica gel column (50 g) and eluted using a gradient of 0.1%-10% MeOH in DCM to afford 1-(2,4'-dichloro-5-methoxy-3'-methyl-[1,1'-biphenyl]-4-yl)-2-oxo-N-(pyrimidin-4-yl)-1,2-dihydroquinoline-6-sulfonamide as a brown film. The racemic 1-(2,4'-dichloro-5-methoxy-3'-methyl-[1,1'-biphenyl]-4-yl)-2-oxo-N-(pyrimidin-4-yl)-1,2-dihydroquinoline-6-sulfonamide was subjected to chiral separation by SFC using a Chiralpak AD-H column with 45% isopropanol in CO$_2$ to provide (P)-1-(2,4'-dichloro-5-methoxy-3'-methyl-[1,1'-biphenyl]-4-yl)-2-oxo-N-(pyrimidin-4-yl)-1,2-dihydroquinoline-6-sulfonamide as peak 1 and (M)-1-(2,4'-dichloro-5-methoxy-3'-methyl-[1,1'-biphenyl]-4-yl)-2-oxo-N-(pyrimidin-4-yl)-1,2-dihydroquinoline-6-sulfonamide as peak 2. Data for peak 1: ¹H NMR (500 MHz, DMSO-d$_6$) δ 8.29-8.40 (m, 2H), 8.21 (d, J=9.67 Hz, 1H), 8.11-8.17 (m, 2H), 7.83-7.94 (m, 2H), 7.75-7.83 (m, 2H), 7.68 (dd, J=4.14, 9.54 Hz, 1H), 7.62 (d, J=1.60 Hz, 1H), 7.50-7.57 (m, 1H), 7.42 (d, J=8.01 Hz, 1H), 6.79 (d, J=9.56 Hz, 1H), 6.74 (d, J=8.92 Hz, 1H), 3.80 (s, 3H), sulfonamide NH missing due to exchange with water. m/z (ESI) 552.9 (M+H)⁺. Data for peak 2: ¹H NMR (500 MHz, DMSO-d$_6$) δ 8.29-8.40 (m, 2H), 8.21 (d, J=9.67 Hz, 1H), 8.11-8.17 (m, 2H), 7.83-7.94 (m, 2H), 7.75-7.83 (m, 2H), 7.68 (dd, J=4.14, 9.54 Hz, 1H), 7.62 (d, J=1.60 Hz, 1H), 7.50-7.57 (m, 1H), 7.42 (d, J=8.01 Hz, 1H), 6.79 (d, J=9.56 Hz, 1H), 6.74 (d, J=8.92 Hz, 1H), 3.80 (s, 3H), sulfonamide NH missing due to exchange with water. m/z (ESI) 552.9 (M+H)⁺.

Example 371 & 372

(Method 106): (P)-1-(4'-chloro-3-methoxy-3'-methyl-4-biphenylyl)-2-oxo-N-3-pyridazinyl-1,2-dihydro-6-quinolinesulfonamide (371) and (M)-1-(4'-chloro-3-methoxy-3'-methyl-4-biphenylyl)-2-oxo-N-3-pyridazinyl-1,2-dihydro-6-quinolinesulfonamide (372)

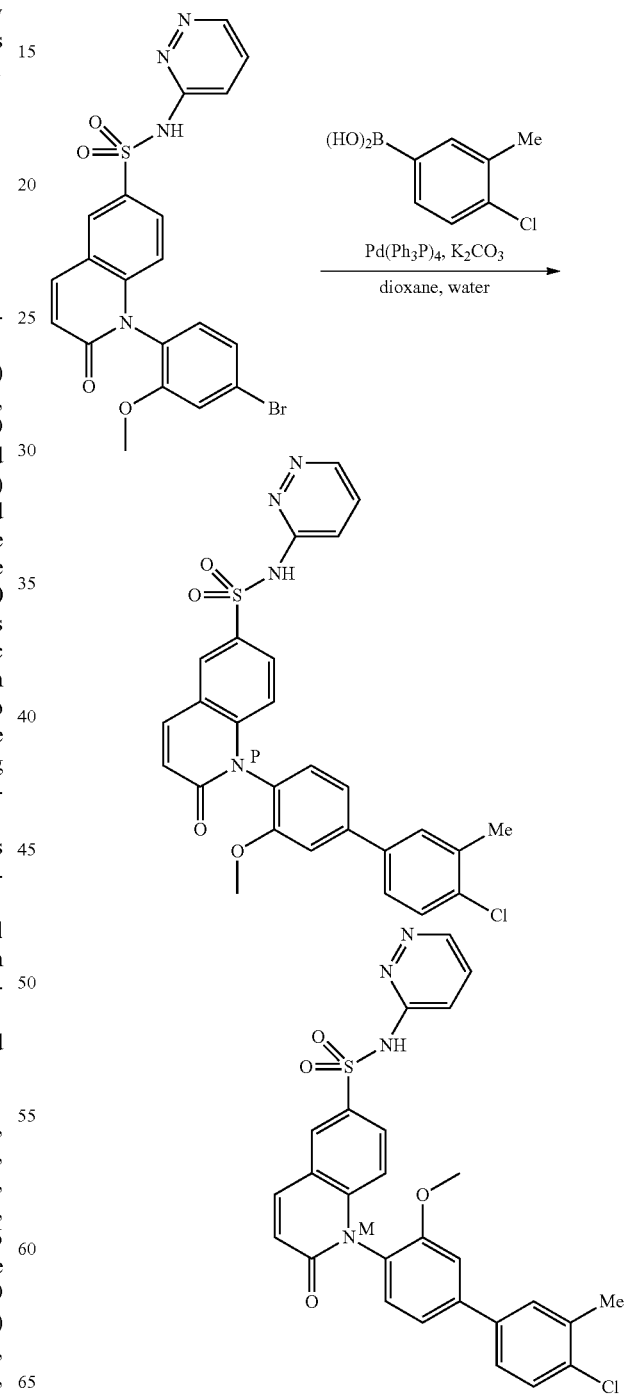

A vial was charged with 1-(4-bromo-2-methoxyphenyl)-2-oxo-N-(pyridazin-3-yl)-1,2-dihydroquinoline-6-sulfonamide (0.406 g, 0.833 mmol), (4-chloro-3-methylphenyl)boronic acid (0.227 g, 1.333 mmol), Pd(Ph₃P)₄ (0.096 g, 0.083 mmol) and potassium carbonate (0.345 g, 2.499 mmol). The vial was sealed with a septum cap and the vial was flushed with N₂ (g), then dioxane (3.12 ml) and water (1.041 ml) were added sequentially via syringe. The vial was sparged with N₂ (g) for 1 min and heated at 90° C. for 2 h. The temperature was then increased to 105° C. and maintained for 1 h. The mixture was partitioned between 1 N HCl (10 mL) and EtOAc (20 mL), the layers were separated and the aqueous layer was extracted with EtOAc (2×10 mL). The combined organic layers were dried (Na₂SO₄) and concentrated for purification by MPLC (Biotage Isolera). The crude residue was taken up in minimal DCM and absorbed directly onto a dry Biotage SNAP pre-packed silica gel column (50 g) and eluted using a gradient of 0.5-10% MeOH in DCM to afford 1-(2,4'-dichloro-5-methoxy-3'-methyl-[1,1'-biphenyl]-4-yl)-2-oxo-N-(pyrimidin-4-yl)-1,2-dihydroquinoline-6-sulfonamide as a light-yellow foam. The racemic 1-(4'-chloro-3-methoxy-3'-methyl-4-biphenylyl)-2-oxo-N-3-pyridazinyl-1,2-dihydro-6-quinolinesulfonamide was subjected to chiral separation by SFC using a Chiralcel OJ column with 40% MeOH in CO₂ to provide (M)-1-(3'-chloro-5'-fluoro-3-methoxy-4-biphenylyl)-2-oxo-N-3-pyridazinyl-1,2-dihydro-6-quinolinesulfonamide as peak 1 and provide (P)-1-(3'-chloro-5'-fluoro-3-methoxy-4-biphenylyl)-2-oxo-N-3-pyridazinyl-1,2-dihydro-6-quinolinesulfonamide as peak 2. Data for peak 1: ¹H NMR (500 MHz, DMSO-d₆) δ 8.33 (d, J=1.95 Hz, 2H), 8.18 (d, J=9.60 Hz, 1H), 7.76-7.89 (m, 3H), 7.58-7.72 (m, 2H), 7.49-7.57 (m, 2H), 7.43 (dd, J=1.72, 8.01 Hz, 1H), 7.36 (d, J=8.04 Hz, 1H), 6.77 (d, J=9.67 Hz, 1H), 6.71 (d, J=8.95 Hz, 1H), 3.77 (s, 3H), 2.37-2.46 (m, 3H), sulfonamide NH proton absent due to exchange with water. m/z (ESI) 532.8 (M−H)⁻. Data for peak 2: ¹H NMR (500 MHz, DMSO-d₆) δ 8.33 (d, J=1.95 Hz, 2H), 8.18 (d, J=9.60 Hz, 1H), 7.76-7.89 (m, 3H), 7.58-7.72 (m, 2H), 7.49-7.57 (m, 2H), 7.43 (dd, J=1.72, 8.01 Hz, 1H), 7.36 (d, J=8.04 Hz, 1H), 6.77 (d, J=9.67 Hz, 1H), 6.71 (d, J=8.95 Hz, 1H), 3.77 (s, 3H), 2.37-2.46 (m, 3H), sulfonamide NH proton absent due to exchange with water. m/z (ESI) 532.8 (M−H)⁻.

Example 312, 381 & 382

(Method 115): N-3-isoxazolyl-1-(4-methoxy-3'-(trifluoromethyl)-3-biphenylyl)-2-oxo-1,2-dihydro-6-quinolinesulfonamide (312), (P)—N-3-isoxazolyl-1-(4-methoxy-3'-(trifluoromethyl)-3-biphenylyl)-2-oxo-1,2-dihydro-6-quinolinesulfonamide (381) and (M)-N-3-isoxazolyl-1-(4-methoxy-3'-(trifluoromethyl)-3-biphenylyl)-2-oxo-1,2-dihydro-6-quinolinesulfonamide (382)

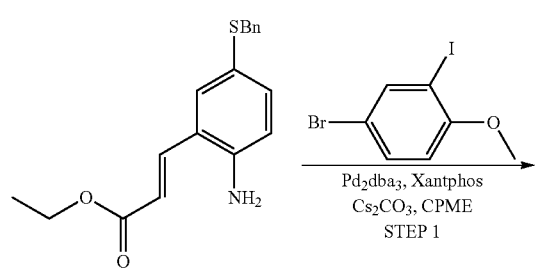

-continued

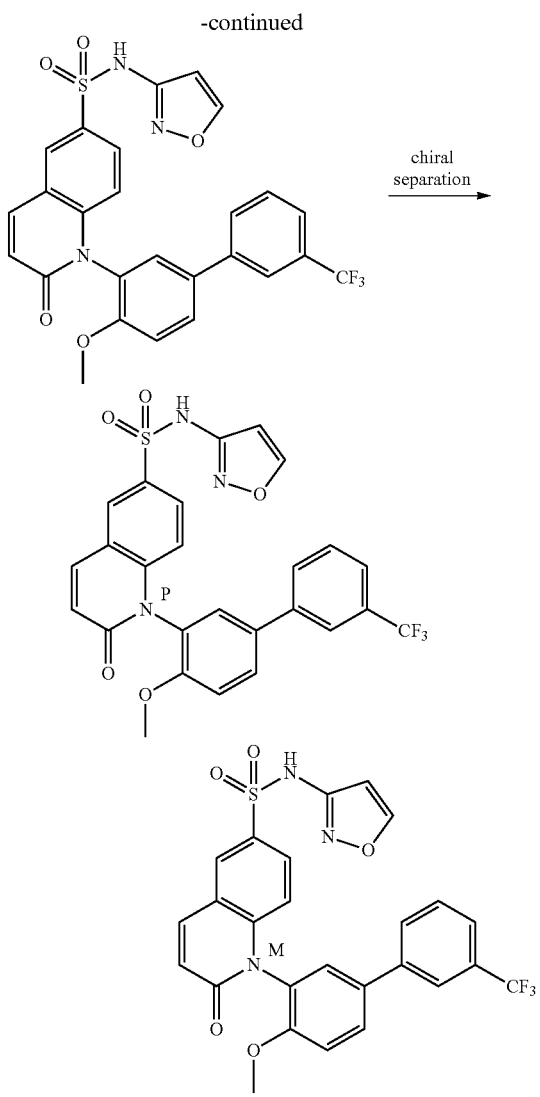

chiral separation →

Step 1: (E)-ethyl 3-(5-(benzylthio)-2-((5-bromo-2-methoxyphenyl)amino)phenyl)acrylate 4-Bromo-2-iodo-1-methoxybenzene (6.07 g, 19.40 mmol), (E)-ethyl 3-(2-amino-5-(benzylthio)phenyl)acrylate (5.066 g, 16.16 mmol), $Pd_2(dba)_3$ (0.370 g, 0.404 mmol), Xantphos (0.468 g, 0.808 mmol) and cesium carbonate (7.37 g, 22.63 mmol) were combined in CPME (32.3 ml) and the reaction was heated to 90° C. overnight. The reaction was cooled to RT, diluted with EtOAc and filtered over a pad of Celite (washing with EtOAc). The filtrate was concentrated in vacuo and the crude oil was then taken up in DCM and purified via MPLC, eluting with 0-20% ethyl acetate in heptanes to yield (E)-ethyl 3-(5-(benzylthio)-2-((5-bromo-2-methoxyphenyl)amino)phenyl)acrylate (6.92 g, 13.88 mmol, 86% yield) as a yellow solid. MS (ESI, pos. ion) m/z: [M+1] 498.0

Step 2: 6-(benzylthio)-1-(5-bromo-2-methoxyphenyl)quinolin-2(1H)-one

A RBF, fitted with a reflux condenser, was charged with (E)-ethyl 3-(5-(benzylthio)-2-((5-bromo-2-methoxyphenyl) amino)phenyl)acrylate (6.92 g, 13.88 mmol) and MeOH (69.4 ml) to give a yellow suspension. Sodium methoxide (0.5N solution in methanol) (11.11 ml, 5.55 mmol) was added and the reaction was heated at 70° C. overnight. The reaction was cooled to RT and the solids were filtered over a frit and washed well with MeOH to yield 6-(benzylthio)-1-(5-bromo-2-methoxyphenyl)quinolin-2(1H)-one (5.48 g, 12.11 mmol, 87% yield) as a tan solid. MS (ESI, pos. ion) m/z: [M+1] 452.0

Step 3: Perfluorophenyl 1-(5-bromo-2-methoxyphenyl)-2-oxo-1,2-dihydroquinoline-6-sulfonate 6-(Benzylthio)-1-(5-bromo-2-methoxyphenyl)quinolin-2 (1H)-one (5.48 g, 12.11 mmol) was diluted with MeCN (38.0 ml), AcOH (1.444 ml) and water (0.950 ml), and the mixture was cooled to 0° C. 1,3-Dichloro-5,5-dimethylimidazolidine-2,4-dione (3.58 g, 18.17 mmol) was added in portions and the reaction was stirred in the ice bath for 5 minutes until complete conversion to the sulfonyl chloride (reaction went from heterogeneous yellow mixture to yellow solution upon addition). With the solution at 0° C., 2,3,4,5,6-pentafluorophenol (2.68 g, 14.54 mmol) was added, followed by TEA (6.75 ml, 48.5 mmol), and the reaction was allowed to warm to RT for 20 min. Water was added and the organics were extracted with DCM (×3), followed by drying via phase separator. The organics were then concentrated in vacuo and purified via MPLC eluting with 0-100% ethyl acetate in heptanes (with 10% DCM additive) to yield perfluorophenyl 1-(5-bromo-2-methoxyphenyl)-2-oxo-1,2-dihydroquinoline-6-sulfonate (5.92 g, 10.27 mmol, 85% yield) as a white solid. MS (ESI, pos. ion) m/z: [M+1] 576.0

Step 4: 1-(5-bromo-2-methoxyphenyl)-N-(isoxazol-3-yl)-2-oxo-1,2-dihydroquinoline-6-sulfonamide To a RBF was added perfluorophenyl 1-(5-bromo-2-methoxyphenyl)-2-oxo-1,2-dihydroquinoline-6-sulfonate (5.92 g, 10.27 mmol) and THF (103 ml). Isoxazol-3-amine (0.950 g, 11.30 mmol) was added, and the reaction was cooled to 0° C. Lithium bis(trimethylsilyl)amide (1.0M in THF) (21.57 ml, 21.57 mmol) was added drop wise (reaction turned from clear solution to bright yellow suspension) and the reaction was allowed to stir in the ice bath for 1 h. The reaction was warmed to RT, and 1N HCl was added. The product was extracted with EtOAc (×3), and the resulting organics were dried with $MgSO_4$ and concentrated in vacuo. The resulting light yellow solid was triturated in diethyl ether and filtered over a fine frit, rinsing with minimal ether, to yield 1-(5-bromo-2-methoxyphenyl)-N-(isoxazol-3-yl)-2-oxo-1,2-dihydroquinoline-6-sulfonamide (4.245 g, 8.91 mmol, 87% yield) as an off-white solid. MS (ESI, pos. ion) m/z: [M+1] 476.1

Step 5: N-3-isoxazolyl-1-(4-methoxy-3'-(trifluoromethyl)-3-biphenylyl)-2-oxo-1,2-dihydro-6-quinolinesulfonamide 1-(5-Bromo-2-methoxyphenyl)-N-(isoxazol-3-yl)-2-oxo-1,2-dihydroquinoline-6-sulfonamide (0.300 g, 0.630 mmol), (3-(trifluoromethyl)phenyl)boronic acid (0.179 g, 0.945 mmol), potassium carbonate (0.261 g, 1.890 mmol), and $Pd(PPh_3)_4$ (0.073 g, 0.063 mmol) were combined in 1,4-dioxane (2.362 ml) and water (0.787 ml). The reaction was heated to 90° C. for 3 h. The reaction was cooled to RT and quenched with $NH_4Cl$ (saturated aqueous solution), and extracted with DCM (×3) and the organics were then dried via phase separator and concentrated in vacuo. The material was purified via MPLC, eluting with 0-100% ethyl acetate in heptanes to yield N-(isoxazol-3-yl)-1-(4-methoxy-3'-(trifluoromethyl)-[1,1'-biphenyl]-3-yl)-2-oxo-1,2-dihydroquinoline-6-sulfonamide (0.149 g, 0.275 mmol, 43.7% yield) as a light yellow solid. MS (ESI, pos. ion) m/z: [M+1] 542.2 $^1$H NMR (400 MHz, DMSO-$d_6$) ppm 3.74 (s, 3H) 6.44 (d, J=1.76 Hz, 1H) 6.82 (dd, J=9.24, 3.77 Hz, 2H) 7.42 (d, J=8.80 Hz, 1H) 7.66-7.70 (m, 2H) 7.84 (dd, J=9.05, 2.20 Hz, 1H) 7.89 (d, J=2.45 Hz, 1H) 7.97-8.07 (m, 3H) 8.23 (d, J=9.49 Hz, 1H) 8.38 (d, J=2.35 Hz, 1H) 8.72 (d, J=1.76 Hz, 1H) 11.65 (s, 1H). N-3-Isoxazolyl-1-(4-methoxy-3'-(trifluoromethyl)-3-biphenylyl)-2-oxo-1,2-dihydro-6-quinolinesulfonamide was separated by chiral SFC on a Chiralpak AD with 35% MeOH to give (P)—N-3-isoxazolyl-1-(4-methoxy-3'-(trifluoromethyl)-3-biphenylyl)-2-oxo-1,2-dihydro-6-quinolinesulfonamide as peak 1 and (M)-N-3-isoxazolyl-1-(4-methoxy-3'-(trifluoromethyl)-3-biphenylyl)-2-oxo-1,2-dihydro-6-quinolinesulfonamide as peak 2, both as white solids. Data for peak 1: $^1$H NMR (400 MHz, DMSO-$d_6$) δ ppm 3.73 (s, 3H) 6.16-6.27 (m, 1H) 6.66-6.72 (m, 1H) 6.72-6.77 (m, 1H) 7.35-7.45 (m, 1H) 7.64-7.69 (m, 2H) 7.73-7.79 (m, 1H) 7.83-7.87 (m, 1H) 7.96-8.06 (m, 3H) 8.13-8.20 (m, 1H) 8.20-8.24 (m, 1H) 8.35-8.43 (m, 1H). MS (ESI, pos. ion) m/z: [M+1] 542.2; Data for peak 2: $^1$H NMR (400 MHz, DMSO-$d_6$) δ ppm 3.73 (s, 3H) 6.08-6.18 (m, 1H) 6.58-6.67 (m, 1H) 6.68-6.75 (m, 1H) 7.36-7.44 (m, 1H) 7.61-7.74 (m, 3H) 7.80-7.86 (m, 1H) 7.96-8.06 (m, 3H) 8.11-8.18 (m, 2H) 8.20-8.25 (m, 1H); MS (ESI, pos. ion) m/z: [M+1] 542.0.

Example 383

(Method 116): N-3-isoxazolyl-1-(2-methoxy-5-(4-pyridinyl)phenyl)-2-oxo-1,2-dihydro-6-quinolinesulfonamide

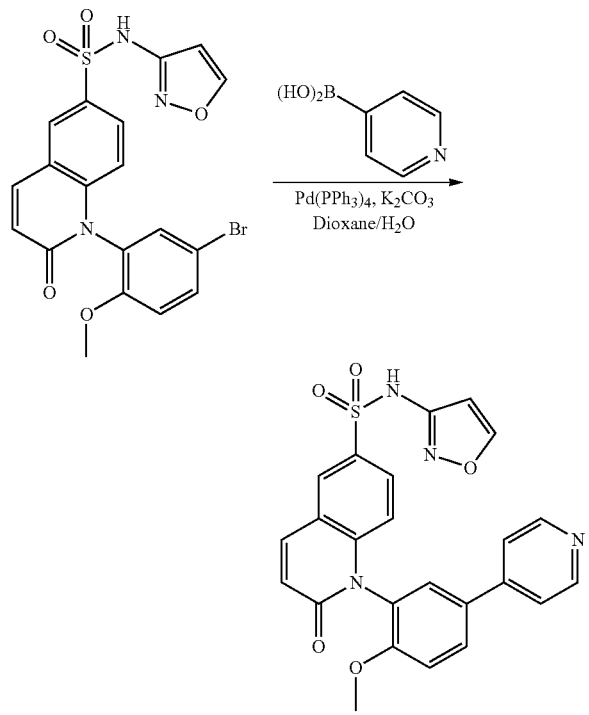

The title compound was prepared via method 115, using pyridin-4-ylboronic acid (Maybridge). After reaction completion, the reaction was filtered through a frit, washing well with DCM. The solvents were evaporated overnight in a Genevac and then purified via RP-HPLC, using an XBridge 19×100 mm column, 0.1% TFA in water/acetonitrile with a flow rate of 40 ml/min over 10 min with a gradient of 10-60%. MS (ESI, pos. ion) m/z: [M+1]475.2. $^1$H NMR (500 MHz, DMSO-$d_6$) δ ppm 3.77 (s, 3H) 6.45 (d, J=1.69 Hz, 1H) 6.83 (d, J=9.60 Hz, 2H) 7.48 (d, J=4.61 Hz, 1H) 7.84 (d, J=8.61 Hz, 1H) 7.94 (br. s., 2H) 8.01 (s, 1H) 8.17 (d, J=8.41 Hz, 1H) 8.24 (d, J=7.29 Hz, 1H) 8.39 (s, J=7.02 Hz, 1H) 8.67 (d, J=5.64 Hz, 2H) 8.72 (d, J=7.98 Hz, 1H) 11.57-11.72 (m, 1H).

Example 384

(Method 117): N-3-isoxazolyl-1-(2-methoxy-5-(2-pyridinyl)phenyl)-2-oxo-1,2-dihydro-6-quinolinesulfonamide

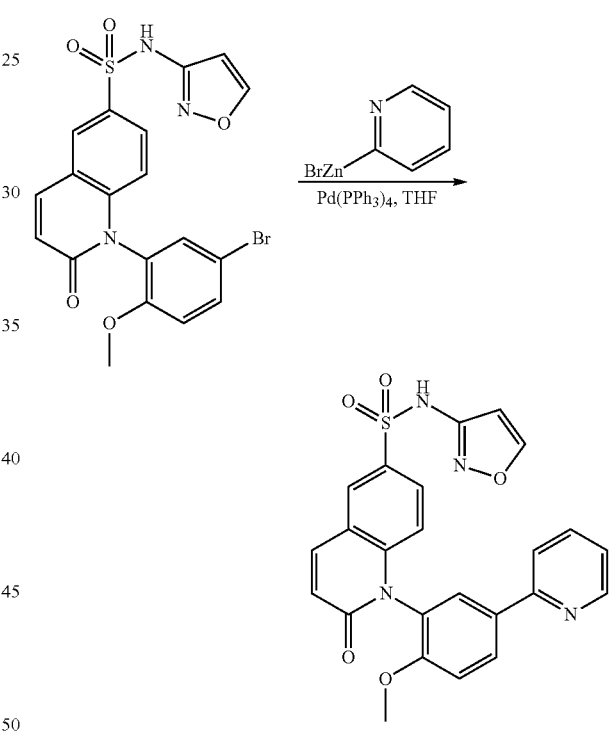

To a vial charged with 1-(5-bromo-2-methoxyphenyl)-N-(isoxazol-3-yl)-2-oxo-1,2-dihydroquinoline-6-sulfonamide (0.100 g, 0.210 mmol) and Pd(Ph$_3$P)$_4$ (0.024 g, 0.021 mmol) in THF (1.050 ml) was added pyridin-2-ylzinc(II) bromide (0.5M in THF) (2.100 ml, 1.050 mmol). The reaction was sealed and heated to 60° C. for 6.5 h. After cooling to RT, ammonium chloride (sat. aq) was added and the product extracted (×3) with DCM. The organics were dried via phase separator and concentrated in vacuo. The crude material was purified via MPLC, eluting with 20-100% ethyl acetate in heptanes to yield desired product, contaminated with triphenylphosphine oxide. The material was triturated in diethyl ether and filtered to yield N-(isoxazol-3-yl)-1-(2-methoxy-5-(pyridin-2-yl)phenyl)-2-oxo-1,2-dihydroquinoline-6-sulfonamide (0.070 g, 0.148 mmol, 70.3% yield) as a light yellow solid. MS (ESI, pos. ion) m/z: [M+1] 475.1. $^1$H NMR (400 MHz, DMSO-d$_6$) δ ppm 3.74 (s, 3H) 6.44 (d, J=1.76 Hz, 1H) 6.79-6.85 (m, 2H) 7.31 (t, J=5.85 Hz, 1H) 7.42 (d, J=8.81 Hz, 1H) 7.52-7.67 (m, 2H) 7.97 (d, J=8.01 Hz, 1H) 8.06 (d, J=2.28 Hz, 1H) 8.23 (d, J=9.64 Hz, 1H) 8.31-8.41 (m, 2H) 8.59-8.64 (m, 1H) 8.72 (d, J=1.87 Hz, 1H) 11.59-11.69 (m, 1H).

Example 385

(Method 118): N-3-isoxazolyl-1-(2-methoxy-5-(1-methyl-1H-pyrazol-5-yl)phenyl)-2-oxo-1,2-dihydro-6-quinolinesulfonamide

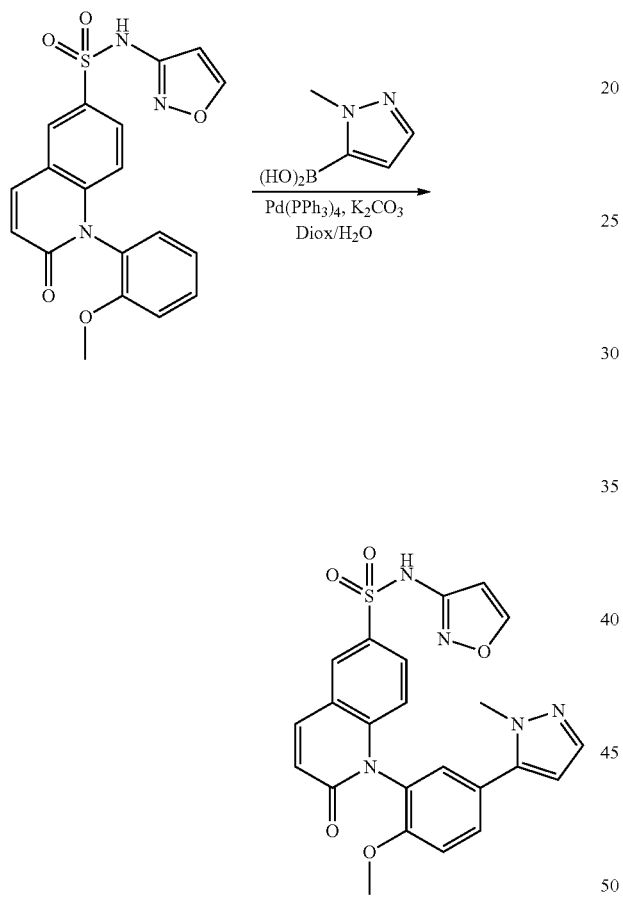

The title compound was prepared via method 116, using 1-methyl-1H-pyrazole-5-boronic acid pinacol ester (Frontier Scientific). The compound was further purified via reverse-phase preparative HPLC using a Phenomenex Luna column, 5 micron, C18(2), 100 Å, 150×30 mm, 0.1% TFA in CH$_3$CN/H$_2$O, gradient 25% to 90% over 12 min to provide N-(isoxazol-3-yl)-1-(2-methoxy-5-(1-methyl-1H-pyrazol-5-yl)phenyl)-2-oxo-1,2-dihydroquinoline-6-sulfonamide as a white solid. MS (ESI, pos. ion) m/z: [M+1] 478.1. $^1$H NMR (400 MHz, DMSO-d$_6$) δ ppm 3.73 (s, 3H) 3.85 (s, 3H) 6.43 (dd, J=17.57, 1.81 Hz, 2H) 6.83 (dd, J=15.08, 9.28 Hz, 2H) 7.40-7.46 (m, 2H) 7.56 (d, J=2.28 Hz, 1H) 7.72 (dd, J=8.60, 2.38 Hz, 1H) 7.85 (dd, J=8.91, 2.28 Hz, 1H) 8.22 (d, J=9.64 Hz, 1H) 8.37 (d, J=2.18 Hz, 1H) 8.73 (d, J=1.76 Hz, 1H) 11.65 (s, 1H).

Example 387

(Method 120): 1-(5-(cyanomethoxy)-2,3'-difluoro-[1,1'-biphenyl]-4-yl)-N-(isoxazol-3-yl)-2-oxo-1,2-dihydroquinoline-6-sulfonamide

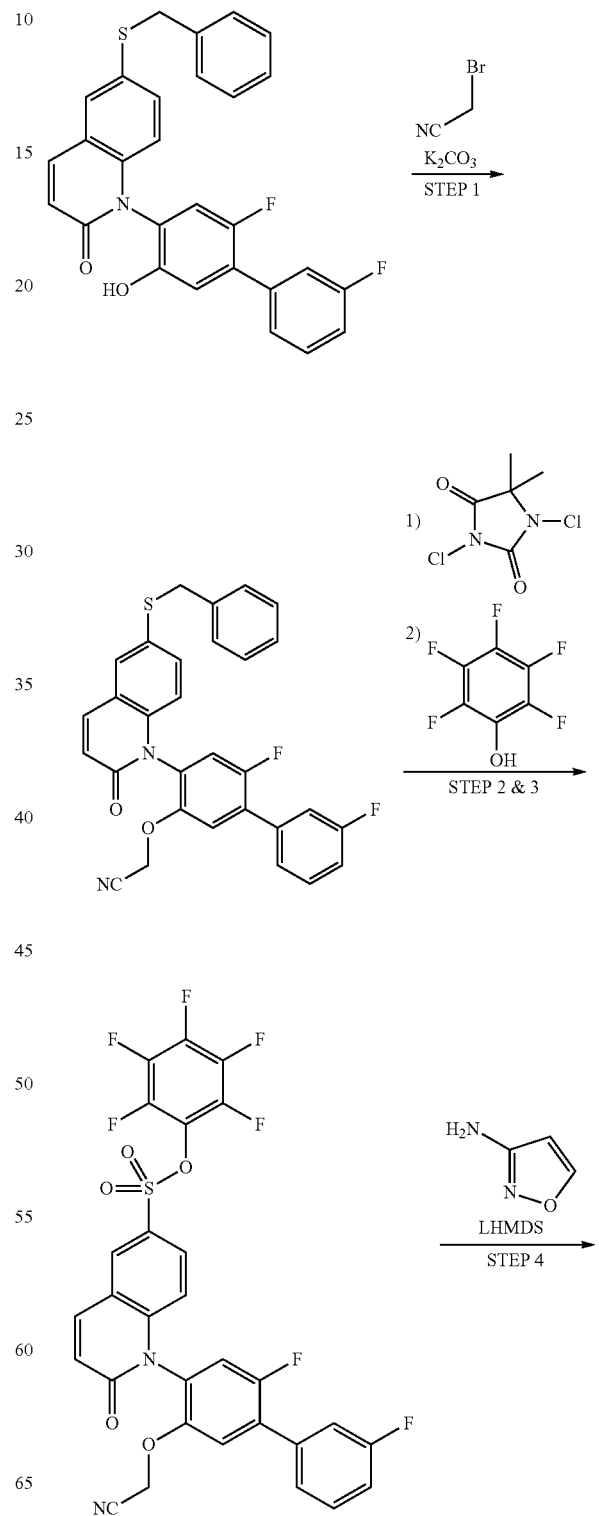

-continued

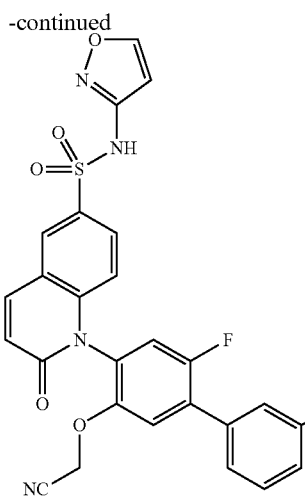

Step 1: 6-(benzylthio)-1-(2,3'-difluoro-5-hydroxy-[1,1'-biphenyl]-4-yl)quinolin-2(1H)-one 6-(Benzylthio)-1-(2,3'-difluoro-5-hydroxy-[1,1'-biphenyl]-4-yl)quinolin-2(1H)-one (528 mg, 1.120 mmol) was dissolved in DMF (2240 μl). Then potassium carbonate (155 mg, 1.120 mmol) was added followed by 2-bromoacetonitrile (86 μl, 1.232 mmol). The whole was stirred at rt for 1 d. Water (1 mL) was added. White precipitate was collected with an aid of water, and dried to afford 2-((4-(6-(benzylthio)-2-oxoquinolin-1(2H)-yl)-3',6-difluoro-[1,1'-biphenyl]-3-yl)oxy)acetonitrile (612 mg, 107% yield). m/z (ESI): [M+H]$^+$=511.0. $^1$H NMR (400 MHz, DMSO-d$_6$) δ ppm 4.25 (s, 2H) 5.14-5.31 (m, 2H) 6.59 (d, J=8.80 Hz, 1H) 6.71 (d, J=9.59 Hz, 1H) 7.19-7.40 (m, 6H) 7.44 (dd, J=8.80, 2.15 Hz, 1H) 7.53-7.68 (m, 5H) 7.81 (d, J=2.15 Hz, 1H) 7.95 (br. s., 1H) 7.99 (d, J=9.49 Hz, 1H).

Step 2 & 3: Perfluorophenyl 1-(5-(cyanomethoxy)-2,3'-difluoro-[1,1'-biphenyl]-4-yl)-2-oxo-1,2-dihydroquinoline-6-sulfonate To a RBF, 2-((4-(6-(benzylthio)-2-oxoquinolin-1(2H)-yl)-3',6-difluoro-[1,1'-biphenyl]-3-yl)oxy)acetonitrile (512 mg, 1.003 mmol), acetonitrile (3145 μl), acetic Acid (119 μl), and water (79 μl) were added. The whole was cooled to 0° C. Then, 1,3-dichloro-5,5-dimethylimidazolidine-2,4-dione (296 mg, 1.504 mmol) was added as a solid in a single portion and stirred for 30 min. At 0° C., 2,3,4,5,6-pentafluorophenol (222 mg, 1.203 mmol) was added, followed by triethylamine (559 μl, 4.01 mmol) dropwise. After 30 min at 0° C., the whole was warmed to rt and stir for 20 min. The reaction was quenched with water (15 mL). The whole was extracted with EtOAc (2×25-mL), then with DCM (2×20 mL). The organic layer was dried over MgSO$_4$, filtered, and concentrated to afford yellow residue. Trituration with ether provide perfluorophenyl 1-(5-(cyanomethoxy)-2,3'-difluoro-[1,1'-biphenyl]-4-yl)-2-oxo-1,2-dihydroquinoline-6-sulfonate (450 mg, 70.7% yield) as white solid. m/z (ESI) [M+H]$^+$=635.1. $^1$H NMR (400 MHz, CHLOROFORM-d) δ ppm 4.75 (d, J=1.97 Hz, 2H) 6.97 (d, J=9.02 Hz, 2H) 6.95 (d, J=9.64 Hz, 1H) 7.16-7.25 (m, 2H) 7.33-7.39 (m, 2H) 7.42 (dd, J=7.77, 1.04 Hz, 1H) 7.52 (td, J=7.96, 5.96 Hz, 1H) 7.92 (d, J=9.64 Hz, 1H) 7.96 (dd, J=9.02, 2.18 Hz, 1H) 8.30 (d, J=2.07 Hz, 1H).

Steps 4: Synthesis of 1-(5-(cyanomethoxy)-2,3'-difluoro-[1,1'-biphenyl]-4-yl)-N-(isoxazol-3-yl)-2-oxo-1,2-dihydroquinoline-6-sulfonamide Under a nitrogen atmosphere, a solution of perfluorophenyl 1-(5-(cyanomethoxy)-2,3'-difluoro-[1,1'-biphenyl]-4-yl)-2-oxo-1,2-dihydroquinoline-6-sulfonate (250 mg, 0.394 mmol), isoxazol-3-amine (40.8 μl, 0.552 mmol) and THF (3940 μl) was cooled in an ice-bath for 15 min, then lithium bis(trimethylsilyl)amide (1M in THF, 985 μl, 0.985 mmol) was added dropwise. The whole was warmed to rt and stirred for 30 min. An additional 1 mL of 1M LHMDS in THF was added and stirred for 30 min. The whole was quenched with 0.2 mL of TFA and concentrated. The product was purified further by RPLC on the acidic Gilson.

Fractions containing the product were combined and concentrated. Precipitate was filtered with an aid of water, dried to afford pink solid. m/z (ESI), [M+H]$^+$=535.2. $^1$H NMR (500 MHz, DMSO-d$_6$) δ ppm 5.11-5.33 (m, 2H) 6.45 (d, J=1.76 Hz, 1H) 6.77-6.96 (m, 2H) 7.28-7.46 (m, 1H) 7.50-7.59 (m, 2H) 7.59-7.72 (m, 3H) 7.87 (dd, J=8.98, 2.08 Hz, 1H) 8.26 (d, J=9.83 Hz, 1H) 8.40 (d, J=2.03 Hz, 1H) 8.73 (d, J=1.76 Hz, 1H) 11.66 (br. s., 1H).

Examples 388 & 389

(Method 121): (P)-1-(5-ethoxy-2,3'-difluoro-[1,1'-biphenyl]-4-yl)-N-(isoxazol-3-yl)-2-oxo-1,2-dihydroquinoline-6-sulfonamide (388) and (M)-1-(5-ethoxy-2,3'-difluoro-[1,1'-biphenyl]-4-yl)-N-(isoxazol-3-yl)-2-oxo-1,2-dihydroquinoline-6-sulfonamide (389)

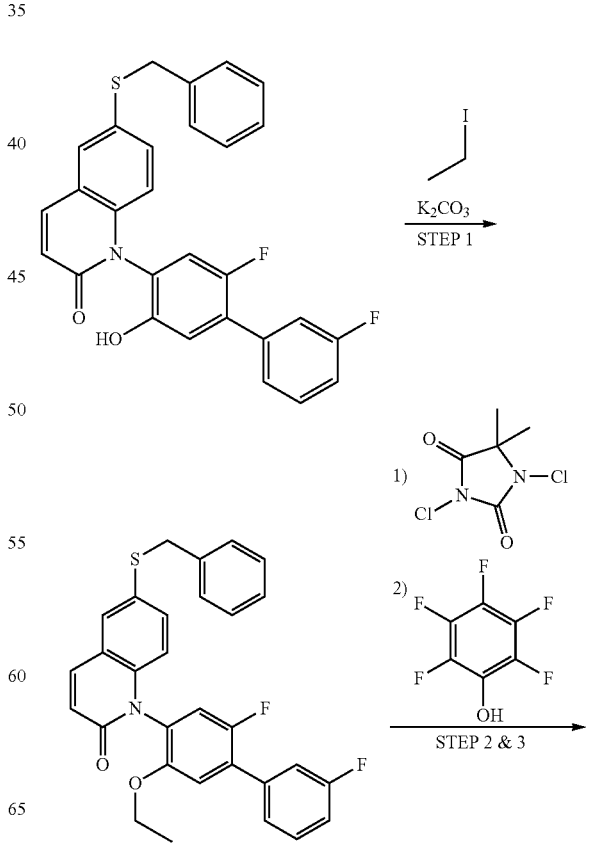

149
-continued

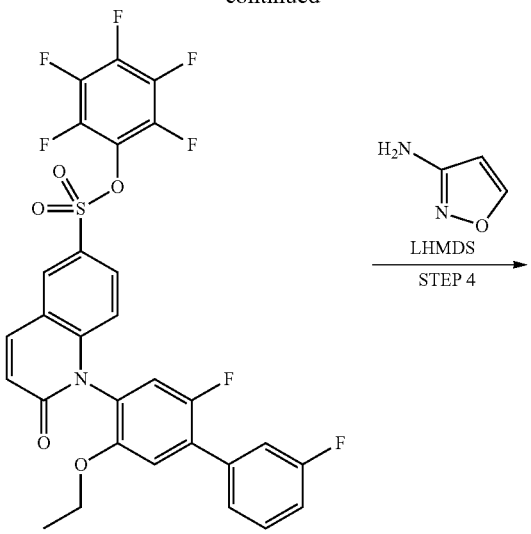

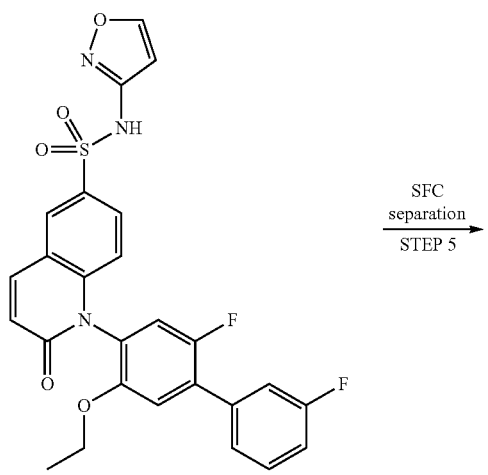

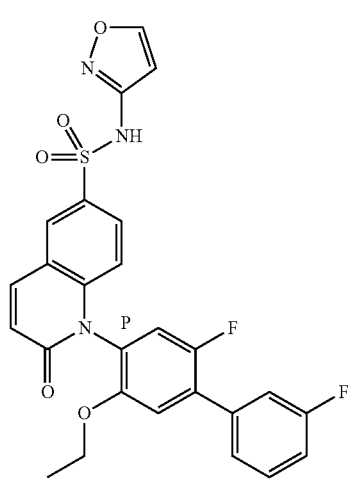

150
-continued

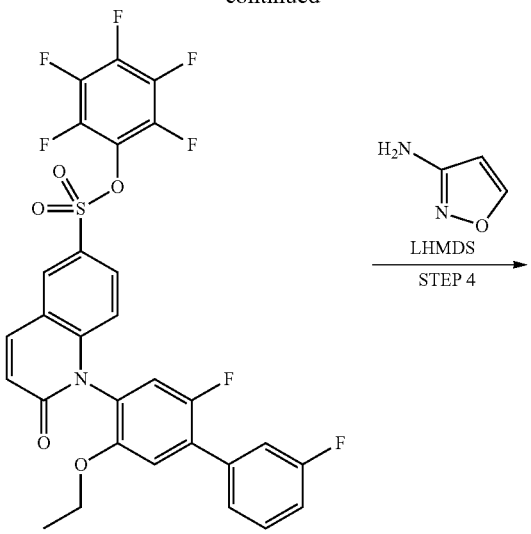

Step 1: 6-(benzylthio)-1-(5-ethoxy-2,3'-difluoro-[1,1'-biphenyl]-4-yl)quinolin-2(1H)-one 6-(Benzylthio)-1-(2,3'-difluoro-5-hydroxy-[1,1'-biphenyl]-4-yl)quinolin-2(1H)-one (510 mg, 1.082 mmol) was dissolved in DMF (2163 μl). Then potassium carbonate (149 mg, 1.082 mmol) was added followed by iodoethane (96 μl, 1.190 mmol). After stirring at rt for 1 d, water was added. A gummy solid was collected with an aid of water, and dried. The crude material was absorbed onto a plug of silica gel and purified by chromatography through a Redi-Sep pre-packed silica gel column (40 g), eluting with a gradient of 0% to 50% EtOAc in heptane, to provide 6-(benzylthio)-1-(5-ethoxy-2,3'-difluoro-[1,1'-biphenyl]-4-yl)quinolin-2 (1H)-one (534 mg, 99% yield) as white solid. m/z (ESI) [M+H]$^+$=500.0. $^1$H NMR (400 MHz, DMSO-d$_6$) δ ppm 1.00 (t, J=6.94 Hz, 3H) 4.01-4.13 (m, 2H) 4.24 (s, 2H) 6.60 (d, J=8.80 Hz, 1H) 6.70 (d, J=9.59 Hz, 1H) 7.18-7.35 (m, 6H) 7.38-7.48 (m, 3H) 7.49-7.63 (m, 3H) 7.79 (d, J=2.15 Hz, 1H) 7.96 (d, J=9.59 Hz, 1H).

Steps 2 & 3: Perfluorophenyl 1-(5-ethoxy-2,3'-difluoro-[1,1'-biphenyl]-4-yl)-2-oxo-1,2-dihydroquinoline-6-sulfonate A RBF was charged with 6-(benzylthio)-1-(5-ethoxy-2,3'-difluoro-[1,1'-biphenyl]-4-yl)quinolin-2(1H)-one (443 mg, 0.887 mmol), acetonitrile (2781 μl), acetic acid (106 μl), and water (69.5 μl). After cooling to 0° C., 1,3-dichloro-5,5-dimethylimidazolidine-2,4-dione (175 mg, 0.887 mmol) was added as a solid in a single portion. The whole was maintained at 0° C. for 10 min. After 30 min additional 1,3-dichloro-5,5-dimethylimidazolidine-2,4-dione (88 mg, 0.5 equiv) was added and stirred for 3 h. At 0° C., 2,3,4,5,6-pentafluorophenol (196 mg, 1.064 mmol) was added followed by triethylamine (494 μl, 3.55 mmol) dropwise. Reaction was maintained at 0° C. for 30 min and then allowed to warm to rt and stir for 20 min. The reaction was quenched with water (10 mL). The whole was extracted with EtOAc (3×25-mL). The organic layer was separated, combined, dried over MgSO$_4$, filtered, and concentrated to afford white residue. The crude material was absorbed onto a plug of silica gel and purified by chromatography through a Redi-Sep pre-packed silica gel column (40 g), eluting with a gradient of 0% to 30% EtOAc in heptane, to provide perfluorophenyl 1-(5-ethoxy-2,3'-difluoro-[1,1'-biphenyl]-

4-yl)-2-oxo-1,2-dihydroquinoline-6-sulfonate (398 mg, 72.0% yield) as white solid. m/z (ESI) [M+H]⁺=624.0. ¹H NMR (400 MHz, CHLOROFORM-d) δ ppm 1.07 (t, J=6.94 Hz, 3H) 3.90-4.01 (m, 2H) 6.83-6.92 (m, 2H) 7.03-7.12 (m, 3H) 7.26 (dt, J=9.88, 1.17 Hz, 1H) 7.33 (dd, J=7.73, 1.17 Hz, 1H) 7.40 (td, J=7.97, 5.87 Hz, 1H) 7.78-7.86 (m, 2H) 8.18 (d, J=2.15 Hz, 1H).

Step 4: 1-(5-ethoxy-2,3'-difluoro-[1,1'-biphenyl]-4-yl)-N-(isoxazol-3-yl)-2-oxo-1,2-dihydroquinoline-6-sulfonamide A solution of perfluorophenyl 1-(5-ethoxy-2,3'-difluoro-[1,1'-biphenyl]-4-yl)-2-oxo-1,2-dihydroquinoline-6-sulfonate (398 mg, 0.638 mmol), isoxazol-3-amine (66.0 μl, 0.894 mmol) and THF (6383 μl) was cooled in an ice-bath for 15 min, then lithium bis (trimethylsilyl)amide (1M in THF) (1596 μl, 1.596 mmol) was added dropwise. After 1.5 h, the mixture was diluted with 1N aq. HCl and EtOAc. The layers were separated, and the organic layer was washed with 1N aq. HCl. The aq. layers were combined and extracted with EtOAc (2×). The combined organic extracts were dried over sodium sulfate, filtered, and concentrated. The crude material was absorbed onto a plug of silica gel and purified by chromatography through a Redi-Sep pre-packed silica gel column (40 g), eluting with a gradient of 0% to 70% EtOAc in heptane, to provide 1-(5-ethoxy-2,3'-difluoro-[1,1'-biphenyl]-4-yl)-N-(isoxazol-3-yl)-2-oxo-1,2-dihydroquinoline-6-sulfonamide (270 mg, 81% yield) as light-yellow solid. m/z [M+H]⁺=524.0. ¹H NMR (400 MHz, DMSO-d₆) δ ppm 0.97 (t, J=6.99 Hz, 2H) 4.01-4.13 (m, 2H) 6.42 (s, 1H) 6.82 (d, J=9.68 Hz, 1H) 6.88 (d, J=9.10 Hz, 1H) 7.27-7.37 (m, 1H) 7.43 (d, J=6.94 Hz, 1H) 7.50-7.67 (m, 4H) 7.86 (dd, J=8.95, 2.20 Hz, 1H) 8.24 (d, J=9.59 Hz, 1H) 8.37 (d, J=2.05 Hz, 1H) 8.69 (s, 1H) 11.66 (br. s., 1H).

Step 5: (P)-1-(5-ethoxy-2,3'-difluoro-[1,1'-biphenyl]-4-yl)-N-(isoxazol-3-yl)-2-oxo-1,2-dihydroquinoline-6-sulfonamide and (M)-1-(5-ethoxy-2,3'-difluoro-[1,1'-biphenyl]-4-yl)-N-(isoxazol-3-yl)-2-oxo-1,2-dihydroquinoline-6-sulfonamide Chiral separation gave two atropisomers with ee>99%. Chiral separation by SFC: Chiralpak OZ-H, 40% methanol. Both materials were off-white solids. Atropisomer 1, (P)-1-(5-ethoxy-2,3'-difluoro-[1,1'-biphenyl]-4-yl)-N-(isoxazol-3-yl)-2-oxo-1,2-dihydroquinoline-6-sulfonamide (64 mg, 19% yield). m/z (ESI) [M+H]⁺=524.1. ¹H NMR (400 MHz, DMSO-d₆) δ ppm 0.97 (t, J=7.00 Hz, 3H) 4.00-4.16 (m, 2H) 6.44 (d, J=1.76 Hz, 1H) 6.83 (d, J=9.64 Hz, 1H) 6.89 (d, J=9.02 Hz, 1H) 7.29-7.35 (m, 1H) 7.44 (d, J=7.15 Hz, 1H) 7.50-7.65 (m, 4H) 7.87 (dd, J=8.97, 2.23 Hz, 1H) 8.24 (d, J=9.54 Hz, 1H) 8.38 (d, J=2.28 Hz, 1H) 8.73 (d, J=1.76 Hz, 1H) 11.67 (br. s., 1H). Atropisomer 2, (M)-1-(5-ethoxy-2,3'-difluoro-[1,1'-biphenyl]-4-yl)-N-(isoxazol-3-yl)-2-oxo-1,2-dihydroquinoline-6-sulfonamide (67 mg, 20% yield). m/z (ESI) [M+H]=524.1. ¹H NMR (400 MHz, DMSO-d₆) δ ppm 0.97 (t, J=6.95 Hz, 3H) 4.08 (qd, J=7.03, 4.20 Hz, 2H) 6.45 (d, J=1.87 Hz, 1H) 6.83 (d, J=9.64 Hz, 1H) 6.90 (d, J=9.02 Hz, 1H) 7.29-7.38 (m, 1H) 7.44 (d, J=7.05 Hz, 1H) 7.52-7.65 (m, 4H) 7.87 (dd, J=9.02, 2.28 Hz, 1H) 8.25 (d, J=9.54 Hz, 1H) 8.39 (d, J=2.18 Hz, 1H) 8.73 (d, J=1.76 Hz, 1H) 11.67 (br. s., 1H).

Examples 390 & 391

(Method 122): (P)-1-(2,3'-difluoro-5-methyl-[1,1'-biphenyl]-4-yl)-N-(isoxazol-3-yl)-2-oxo-1,2-dihydroquinoline-6-sulfonamide and (M)-1-(2,3'-difluoro-5-methyl-[1,1'-biphenyl]-4-yl)-N-(isoxazol-3-yl)-2-oxo-1,2-dihydroquinoline-6-sulfonamide

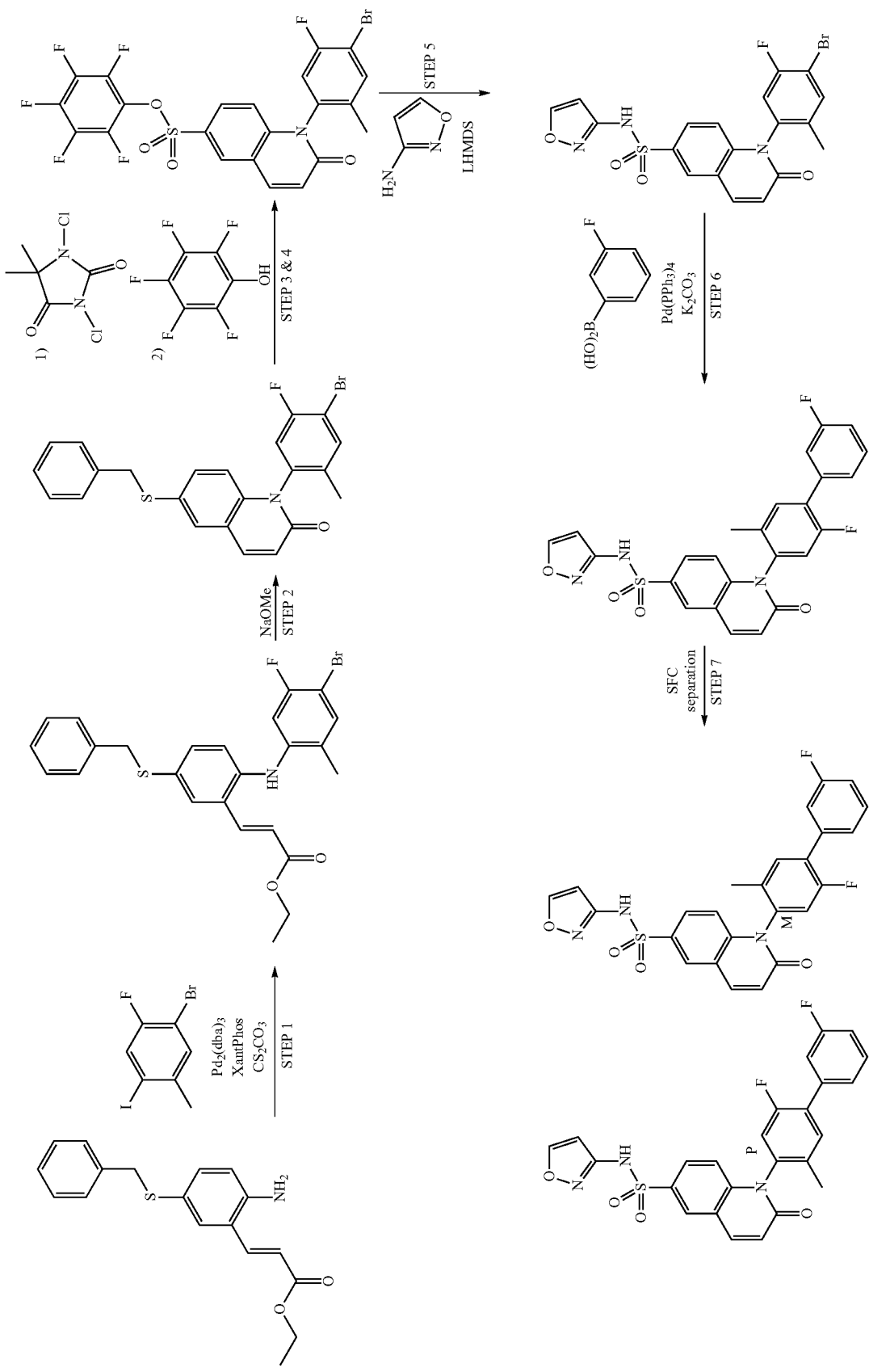

Step 1: (E)-ethyl 3-(5-(benzylthio)-2-((4-bromo-5-fluoro-2-methylphenyl)amino)phenyl)acrylate A pressure tube was charged with (E)-ethyl 3-(2-amino-5-(benzylthio)phenyl)acrylate (2.31 g, 7.37 mmol), 1-bromo-2-fluoro-4-iodo-5-methylbenzene (2.79 g, 8.84 mmol, Oakwood Chemicals), XantPhos (0.213 g, 0.369 mmol), $Pd_2(dba)_3$ (0.169 g, 0.184 mmol), and cesium carbonate (6.00 g, 18.43 mmol). The whole was purged with argon. Then toluene (14.74 ml) was added. The tube was sealed and heated in the heating block at 110° C. for 17 h. The mixture was cooled to room temperature, diluted with EtOAc, and filtered through celite with an aid of EtOAc. The filtrate was concentrated. The crude material was absorbed onto a plug of silica gel and purified by chromatography through a Redi-Sep pre-packed silica gel column (80 g), eluting with a gradient of 0% to 30% EtOAc in heptane, to provide (E)-ethyl 3-(5-(benzylthio)-2-((4-bromo-5-fluoro-2-methylphenyl)amino)phenyl)acrylate (3.19 g, 86% yield) as yellow solid. m/z (ESI) $[M+H]^+$=500.0. $^1H$ NMR (400 MHz, DMSO-$d_6$) δ ppm 1.12 (t, J=7.09 Hz, 3H) 2.04 (s, 3H) 4.04 (q, J=7.11 Hz, 2H) 4.16 (s, 2H) 6.27 (d, J=11.05 Hz, 1H) 6.47 (d, J=15.94 Hz, 1H) 6.78 (d, J=8.41 Hz, 1H) 7.09-7.26 (m, 6H) 7.34 (dd, J=8.02, 0.68 Hz, 1H) 7.53-7.66 (m, 3H).

Step 2: 6-(benzylthio)-1-(4-bromo-5-fluoro-2-methylphenyl)quinolin-2(1H)-one A pressure tube was charged with (E)-ethyl 3-(5-(benzylthio)-2-((4-bromo-5-fluoro-2-methylphenyl)amino)phenyl)acrylate (3.19 g, 6.37 mmol) and MeOH (31.9 ml) to give a yellow suspension. Sodium methoxide (25 wt % in MeOH) (0.697 ml, 2.55 mmol) was added. The tube was sealed and heated to 70° C. for 18 h. The whole was cooled to rt, quenched with saturated aq $NH_4Cl$, and concentrated. The whole was extracted with EtOAc (3×50-mL). The organic layer was separated, combined, dried over $MgSO_4$, filtered, and concentrated to afford orange residue. The crude material was absorbed onto a plug of silica gel and purified by chromatography through a Redi-Sep pre-packed silica gel column (40 g), eluting with a gradient of 0% to 20% EtOAc in heptane, to provide 6-(benzylthio)-1-(4-bromo-5-fluoro-2-methylphenyl)quinolin-2(1H)-one (2.45 g, 85% yield) as yellow solid. m/z (ESI) $[M+H]^+$=454.0. $^1H$ NMR (400 MHz, DMSO-$d_6$) δ ppm 1.10 (s, 3H) 3.36 (s, 2H) 5.74 (d, J=8.80 Hz, 1H) 5.93 (d, J=9.59 Hz, 1H) 6.34-6.50 (m, 6H) 6.62 (dd, J=8.85, 2.10 Hz, 1H) 6.89 (d, J=2.05 Hz, 1H) 6.99 (m, 1H) 7.16 (d, J=9.39 Hz, 1H).

Steps 3 & 4: Perfluorophenyl 1-(4-bromo-5-fluoro-2-methylphenyl)-2-oxo-1,2-dihydroquinoline-6-sulfonate A RBF was charged with 6-(benzylthio)-1-(4-bromo-5-fluoro-2-methylphenyl)quinolin-2(1H)-one (2.45 g, 5.39 mmol), acetonitrile (16.91 ml), acetic acid (0.643 ml), and water (0.423 ml). After cooling to 0° C., 1,3-dichloro-5,5-dimethylimidazolidine-2,4-dione (1.594 g, 8.09 mmol) was added as a solid in a single portion. The reaction was maintained at 0° C. for 40 min. At 0° C., 2,3,4,5,6-pentafluorophenol (1.191 g, 6.47 mmol) was added followed by triethylamine (3.01 ml, 21.57 mmol) dropwise. After maintaining at 0° C. for 30 min, the whole was warmed to rt and stir for 20 min. The reaction was quenched with water (15 mL). The whole was extracted with EtOAc (2×25-mL), then with DCM (2×20 mL). The organic layer was dried over $MgSO_4$, filtered, and concentrated to afford yellow residue. The crude material was absorbed onto a plug of silica gel and purified by chromatography through a Redi-Sep pre-packed silica gel column (40 g), eluting with a gradient of 0% to 30% EtOAc in heptane, to provide perfluorophenyl 1-(4-bromo-5-fluoro-2-methylphenyl)-2-oxo-1,2-dihydroquinoline-6-sulfonate (2.65 g, 85% yield) as off-white solid. m/z (ESI) $[M+H]^+$=578.1. $^1H$ NMR (400 MHz, CHLOROFORM-d) δ ppm 1.99 (s, 3H) 6.80 (d, J=9.02 Hz, 1H) 6.94 (d, J=9.64 Hz, 1H) 7.04 (d, J=7.98 Hz, 1H) 7.71 (dd, J=7.15, 0.52 Hz, 1H) 7.86-7.95 (m, 2H) 8.29 (d, J=2.18 Hz, 1H).

Step 5: 1-(4-bromo-5-fluoro-2-methylphenyl)-N-(isoxazol-3-yl)-2-oxo-1,2-dihydroquinoline-6-sulfonamide Under a nitrogen atmosphere, a solution of perfluorophenyl 1-(4-bromo-5-fluoro-2-methylphenyl)-2-oxo-1,2-dihydroquinoline-6-sulfonate (1.50 g, 2.59 mmol), isoxazol-3-amine (0.268 ml, 3.63 mmol) and THF (25.9 ml) was cooled in an ice-bath for 15 min, then lithium bis(trimethylsilyl) amide (1M in THF) (6.48 ml, 6.48 mmol) was added dropwise. After 10 min, the whole was warmed to rt and stirred for 30 min. 6.48 mL of additional LHMDS was added and the reaction was stirred for 1 h. The mixture was diluted with 1N aq. HCl and EtOAc. The layers were separated, and the organic layer was washed with 1N aq. HCl. The aq. layers were combined and extracted with EtOAc (2×). The combined organic extracts were dried over sodium sulfate, filtered, and concentrated. The crude material was absorbed onto a plug of silica gel and purified by chromatography through a Redi-Sep pre-packed silica gel column (40 g), eluting with a gradient of 0% to 70% EtOAc in heptane, to provide 1-(4-bromo-5-fluoro-2-methylphenyl)-N-(isoxazol-3-yl)-2-oxo-1,2-dihydroquinoline-6-sulfonamide (873 mg, 70.4% yield) as brown solid. m/z (ESI) $[M+H]^+$=477.9. $^1H$ NMR (400 MHz, DMSO-$d_6$) δ ppm 1.17 (t, J=7.15 Hz, 1H) 1.86 (s, 2H) 1.99 (s, 1H) 5.55 (br. s., 1H) 5.88 (d, J=1.76 Hz, 1H) 6.44 (d, J=1.87 Hz, 1H) 6.78 (d, J=9.02 Hz, 1H) 6.83 (d, J=9.64 Hz, 1H) 7.55 (d, J=9.12 Hz, 1H) 7.84 (dd, J=8.91, 2.28 Hz, 1H) 7.92 (dd, J=7.57, 0.52 Hz, 1H) 8.27 (d, J=9.54 Hz, 1H) 8.32 (d, J=1.76 Hz, 1H) 8.40 (d, J=2.28 Hz, 1H) 8.72 (d, J=1.76 Hz, 1H) 11.67 (s, 1H).

Step 6: 1-(2,3'-difluoro-5-methyl-[1,1'-biphenyl]-4-yl)-N-(isoxazol-3-yl)-2-oxo-1,2-dihydroquinoline-6-sulfonamide A vial was charged with 1-(4-bromo-5-fluoro-2-methylphenyl)-N-(isoxazol-3-yl)-2-oxo-1,2-dihydroquinoline-6-sulfonamide (307 mg, 0.642 mmol), (3-fluorophenyl)boronic acid (117 mg, 0.834 mmol), potassium carbonate (266 mg, 1.926 mmol), and $Pd(PPh_3)_4$ (37.1 mg, 0.032 mmol). The vial was flushed with Ar (g), then 1,4-dioxane (2407 μl) and water (802 μl) were added. The vial was sealed and heated to 90° C. for 19 h. The reaction was cooled down to rt. The whole was extracted with EtOAc (3×25-mL). The organic layer was separated, combined, dried over $MgSO_4$, filtered, and concentrated to afford colorless residue. The crude material was absorbed onto a plug of silica gel and purified by chromatography through a Redi-Sep pre-packed silica gel column (40 g), eluting with a gradient of 0% to 70% EtOAc in heptane, to provide 1-(2,3'-difluoro-5-methyl-[1,1'-biphenyl]-4-yl)-N-(isoxazol-3-yl)-2-oxo-1,2-dihydroquinoline-6-sulfonamide (179 mg, 56.5% yield) as off-white solid. m/z (ESI) $[M+H]^+$=493.2. $^1H$ NMR (400 MHz, DMSO-$d_6$) δ ppm 1.91 (s, 3H) 6.44 (d, J=1.87 Hz, 1H)

6.80 (d, J=9.02 Hz, 1H) 6.85 (d, J=9.64 Hz, 1H) 7.26-7.37 (m, 1H) 7.44-7.54 (m, 3H) 7.54-7.64 (m, 1H) 7.75 (d, J=8.40 Hz, 1H) 7.88 (dd, J=8.97, 2.23 Hz, 1H) 8.28 (d, J=9.64 Hz, 1H) 8.41 (d, J=2.18 Hz, 1H) 8.71 (d, J=1.76 Hz, 1H) 11.68 (s, 1H).

Step 7: (P)-1-(2,3'-difluoro-5-methyl-[1,1'-biphenyl]-4-yl)-N-(isoxazol-3-yl)-2-oxo-1,2-dihydroquinoline-6-sulfonamide and (M)-1-(2,3'-difluoro-5-methyl-[1,1'-biphenyl]-4-yl)-N-(isoxazol-3-yl)-2-oxo-1,2-dihydroquinoline-6-sulfonamide Chiral separation yielded two atropisomers both with ee>99%. Chiral separation by SFC: Regis Whelk-O (s,s), 45% methanol. Atropisomer 1, (P)-1-(2,3'-difluoro-5-methyl-[1,1'-biphenyl]-4-yl)-N-(isoxazol-3-yl)-2-oxo-1,2-dihydroquinoline-6-sulfonamide (35 mg, 11% yield). m/z (ESI) [M+H]⁺=494.1. ¹H NMR (400 MHz, CHLOROFORM-d) δ ppm 2.04 (s, 3H) 6.63 (d, J=1.87 Hz, 1H) 6.79 (d, J=9.02 Hz, 1H) 6.93 (d, J=9.64 Hz, 1H) 7.04 (d, J=9.95 Hz, 1H) 7.15 (tdd, J=8.37, 8.37, 2.59, 1.09 Hz, 1H) 7.32-7.37 (m, 1H) 7.38-7.42 (m, 1H) 7.44-7.56 (m, 2H) 7.82 (dd, J=8.91, 2.18 Hz, 1H) 7.87 (d, J=9.54 Hz, 1H) 8.20 (d, J=2.18 Hz, 1H) 8.29 (d, J=1.76 Hz, 1H). Atropisomer 2, (M)-1-(2,3'-difluoro-5-methyl-[1,1'-biphenyl]-4-yl)-N-(isoxazol-3-yl)-2-oxo-1,2-dihydroquinoline-6-sulfonamide (49 mg, 15% yield). m/z (ESI) [M+H]⁺=494.1. ¹H NMR (400 MHz, CHLOROFORM-d) δ ppm 2.04 (s, 3H) 6.63 (d, J=1.76 Hz, 1H) 6.79 (d, J=8.91 Hz, 1H) 6.93 (d, J=9.64 Hz, 1H) 7.04 (d, J=10.05 Hz, 1H) 7.15 (tdd, J=8.36, 8.36, 2.57, 1.04 Hz, 1H) 7.32-7.37 (m, 1H) 7.38-7.43 (m, 1H) 7.45-7.56 (m, 2H) 7.82 (dd, J=8.91, 2.18 Hz, 1H) 7.87 (d, J=9.64 Hz, 1H) 8.20 (d, J=2.18 Hz, 1H) 8.29 (d, J=1.87 Hz, 1H).

Example 404

(Method 133): 1-(5-fluoro-2-methoxy-4-(3-pyridinyl)phenyl)-N-3-isoxazolyl-2-oxo-1,2-dihydro-6-quinolinesulfonamide

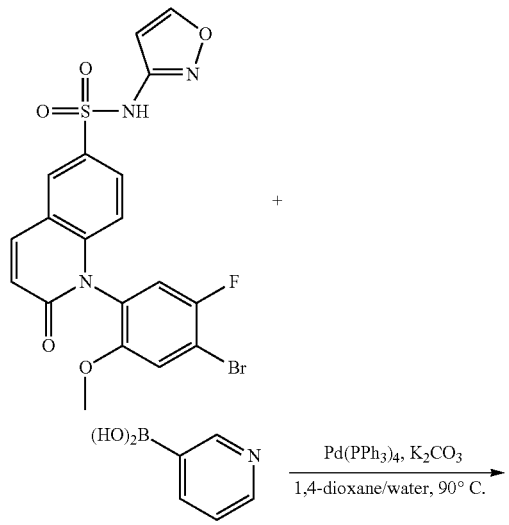

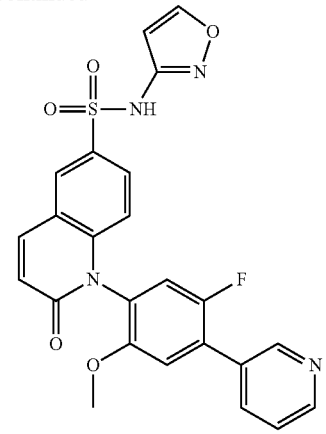

A dioxane (1.5 mL)/water (0.5 mL) slurry of 1-(4-bromo-5-fluoro-2-methoxyphenyl)-N-(isoxazol-3-yl)-2-oxo-1,2-dihydroquinoline-6-sulfonamide (200 mg, 0.405 mmol), potassium carbonate (168 mg, 1.214 mmol), tetrakis(triphenylphosphine)palladium (46.8 mg, 0.040 mmol), and 3-pyridylboronic acid (80 mg, 0.647 mmol) in a 40-ml vial was sparged for 15 min with N₂ and then stirred at 90° C. for 1.5 h. The reaction was then cooled to rt, quenched with 1 N HCl, and extracted thrice with DCM. The organic extracts were combined, washed with dried over Na₂SO₄, filtered, and concentrated in vacuo to an orange oil. Preparatory HPLC (10% to 60% MeCN/H2O with 0.1% TFA) afforded the trifluoroacetate salt of 1-(5-fluoro-2-methoxy-4-(3-pyridinyl)phenyl)-N-3-isoxazolyl-2-oxo-1,2-dihydro-6-quinolinesulfonamide as a white powder. ¹H NMR (400 MHz, DMSO-d₆) δ ppm 3.76 (s, 5H) 6.46 (d, J=1.76 Hz, 1H) 6.83 (d, J=9.64 Hz, 1H) 6.90 (d, J=9.02 Hz, 1H) 7.53 (d, J=6.95 Hz, 1H) 7.60 (d, J=10.26 Hz, 1H) 7.70 (dd, J=7.62, 5.34 Hz, 1H) 7.88 (dd, J=8.97, 2.23 Hz, 1H) 8.23-8.28 (m, 2H) 8.40 (d, J=2.18 Hz, 1H) 8.73-8.75 (m, 2H) 8.98 (s, 1H) 11.67 (br. s., 1H). m/z (ESI) 493.2 (M+H)⁺.

Example 405

(Method 134): 1-(5-fluoro-2-methoxy-4-(1-methyl-1H-pyrazol-4-yl)phenyl)-N-3-isoxazolyl-2-oxo-1,2-dihydro-6-quinolinesulfonamide

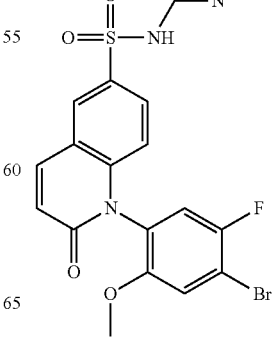

-continued

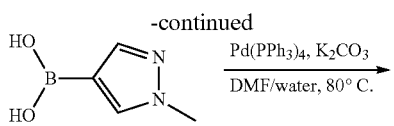

A DMF (1.6 mL)/H₂O (0.4 mL) slurry of 1-(4-bromo-5-fluoro-2-methoxyphenyl)-N-(isoxazol-3-yl)-2-oxo-1,2-dihydroquinoline-6-sulfonamide (200 mg, 0.405 mmol), potassium carbonate (168 mg, 1.214 mmol), tetrakis(triphenylphosphine)palladium (46.8 mg, 0.040 mmol), and 1-methyl-1h-pyrazole-4-boronic acid (82 mg, 0.647 mmol, purchased from Matrix Scientific) in a 40-mL vial was stirred at 80° C. for 1 h. The reaction was then cooled to rt, quenched with 1 N HCl, and extracted thrice with EtOAc. The organic extracts were combined, washed with brine, dried over Na₂SO₄, filtered, and concentrated in vacuo to an orange flocculent solid. Preparatory HPLC (10% to 60% MeCN/H₂O with 0.1% TFA) afforded 1-(5-fluoro-2-methoxy-4-(1-methyl-1H-pyrazol-4-yl)phenyl)-N-(isoxazol-3-yl)-2-oxo-1,2-dihydroquinoline-6-sulfonamide 2,2,2-trifluoroacetate (119 mg, 0.195 mmol, 48.3% yield) as a white amorphous solid. ¹H NMR (400 MHz, DMSO-d₆) δ ppm 3.73 (s, 3H) 3.94 (s, 3H) 6.45 (d, J=1.87 Hz, 1H) 6.80 (d, J=9.64 Hz, 1H) 6.88 (d, J=9.02 Hz, 1H) 7.41 (d, J=10.78 Hz, 1H) 7.54 (d, J=6.95 Hz, 1H) 7.84 (d, J=2.18 Hz, 1H) 8.07 (s, 1H) 8.22 (d, J=9.54 Hz, 1H) 8.29 (d, J=2.07 Hz, 1H) 8.37 (d, J=2.18 Hz, 1H) 8.74 (d, J=1.87 Hz, 1H) 11.66 (s, 1H). m/z (ESI) 496.1 (M+H)⁺.

Example 406

(Method 135): 1-(4-(3,3-difluoro-1-azetidinyl)-5-fluoro-2-methoxyphenyl)-N-3-isoxazolyl-2-oxo-1,2-dihydro-6-quinolinesulfonamide

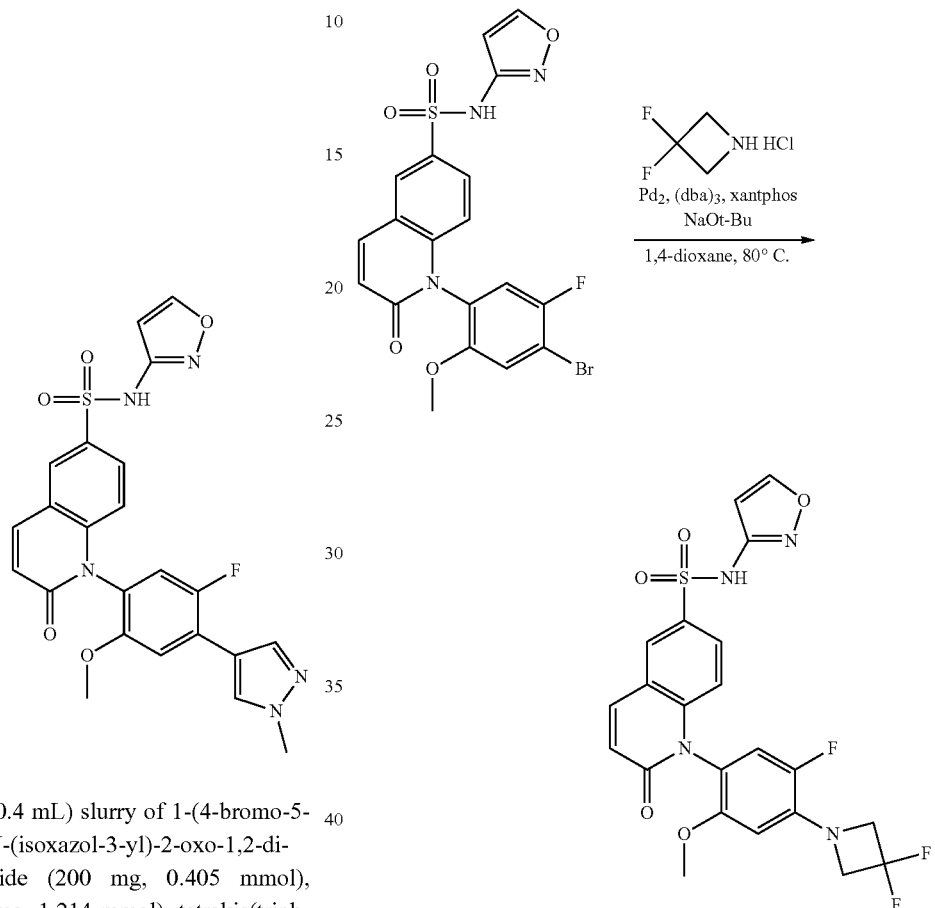

A dioxane (2 mL) slurry of 1-(4-bromo-5-fluoro-2-methoxyphenyl)-N-(isoxazol-3-yl)-2-oxo-1,2-dihydroquinoline-6-sulfonamide (200 mg, 0.405 mmol), sodium tert-butoxide (117 mg, 1.214 mmol), xantphos (70.2 mg, 0.121 mmol), Pd₂(dba)₃ (55.6 mg, 0.061 mmol), and 3,3-difluoroazetidine hydrochloride (79 mg, 0.607 mmol) in a 40 mL vial was stirred at 80° C. for 2 h. The resulting heterogeneous tan mixture was cooled to rt, quenched with 1 N HCl, and extracted thrice with EtOAc. The organic extracts were combined, washed with brine, dried over Na₂SO₄, filtered, and concentrated in vacuo to an orange residue. Preparatory HPLC (10-90% MeCN/H2O with 0.1% TFA) afforded the trifluoroacetate salt of 1-(4-(3,3-difluoro-1-azetidinyl)-5-fluoro-2-methoxyphenyl)-N-3-isoxazolyl-2-oxo-1,2-dihydro-6-quinolinesulfonamide (67.0 mg, 0.108 mmol, 26.7% yield) as an off-white amorphous solid. ¹H NMR (400 MHz, DMSO-d₆) δ ppm 3.65 (s, 3H) 4.45-4.55 (m, 4H) 6.45 (s, 1H) 6.52 (d, J=8.29 Hz, 1H) 6.77 (d, J=9.58 Hz, 1H) 6.83 (d, J=9.03 Hz, 1H) 7.24 (d, J=12.13 Hz, 1H) 7.84 (d, J=9.02 Hz, 1H) 8.18 (d, J=9.54 Hz, 1H) 8.34 (d, J=2.28 Hz, 1H) 8.74 (s, 1H) 11.64 (s, 1H). m/z (ESI) 507.1 (M+H)⁺.

Examples 407, 408 & 409

(Method 136): 1-(4-(5-chloro-3-pyridinyl)-5-fluoro-2-methoxyphenyl)-N-3-isoxazolyl-2-oxo-1,2-dihydro-6-quinolinesulfonamide (407), (P)-1-(4-(5-chloro-3-pyridinyl)-5-fluoro-2-methoxyphenyl)-N-3-isoxazolyl-2-oxo-1,2-dihydro-6-quinolinesulfonamide (408) and (M)-1-(4-(5-chloro-3-pyridinyl)-5-fluoro-2-methoxyphenyl)-N-3-isoxazolyl-2-oxo-1,2-dihydro-6-quinolinesulfonamide (409)

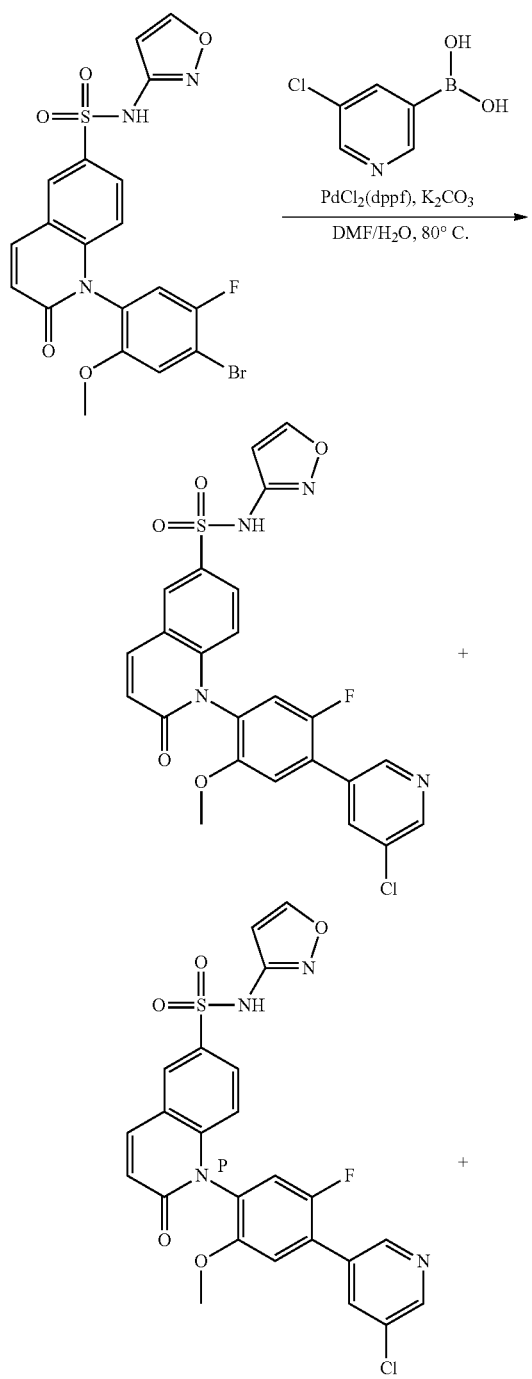

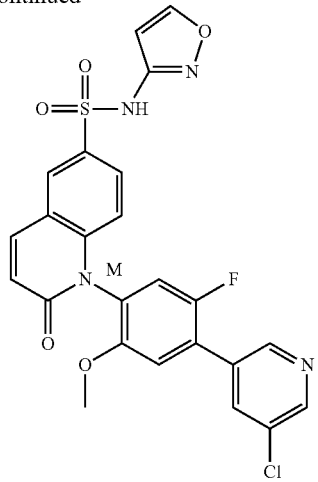

A 40-mL vial containing 1-(4-bromo-5-fluoro-2-methoxyphenyl)-N-(isoxazol-3-yl)-2-oxo-1,2-dihydroquinoline-6-sulfonamide (200 mg, 0.405 mmol), potassium carbonate (280 mg, 2.023 mmol), 1,1'-bis(diphenylphosphino)ferrocene palladium(II)dichloride dichloromethane adduct (33.0 mg, 0.040 mmol), and 3-chloropyridine-5-boronic acid (96 mg, 0.607 mmol, purchased from Frontier Scientific) was flushed with $N_2$. DMF (1.6 mL) and water (0.4 mL) were added and the black slurry was stirred at 80° C. for 30 min. The reaction was then cooled to rt, quenched with 1 N HCl, and extracted thrice with EtOAc. The organic extracts were combined, washed with brine, dried over $Na_2SO_4$, filtered, and concentrated in vacuo to a dark brown oil. Preparatory HPLC (10% to 70% MeCN/$H_2O$ with 0.1% TFA) afforded the trifluoroacetate salt of 1-(4-(5-chloro-3-pyridinyl)-5-fluoro-2-methoxyphenyl)-N-3-isoxazolyl-2-oxo-1,2-dihydro-6-quinolinesulfonamide (62.7 mg, 0.098 mmol, 24.18% yield) as an off-white amorphous solid. $^1$H NMR (400 MHz, DMSO-$d_6$) δ ppm 3.77 (s, 3H) 6.46 (d, J=1.95 Hz, 1H) 6.83 (d, J=9.64 Hz, 1H) 6.88 (d, J=9.02 Hz, 1H) 7.56 (d, J=6.59 Hz, 1H) 7.61 (d, J=10.24 Hz, 1H) 7.87 (d, J=9.04 Hz, 1H) 8.25 (d, J=9.54 Hz, 1H) 8.33 (s, 1H) 8.39 (d, J=2.18 Hz, 1H) 8.73-8.76 (m, 2H) 8.89 (t, J=1.81 Hz, 1H) 11.67 (s, 1H). m/z (ESI) 527.1 (M+H)$^+$. A portion of the racemic product was separated via Chiralpak IA column (55% MeOH/45% $CO_2$) to give (P)-1-(4-(5-chloro-3-pyridinyl)-5-fluoro-2-methoxyphenyl)-N-3-isoxazolyl-2-oxo-1,2-dihydro-6-quinolinesulfonamide and (M)-1-(4-(5-chloro-3-pyridinyl)-5-fluoro-2-methoxyphenyl)-N-3-isoxazolyl-2-oxo-1,2-dihydro-6-quinolinesulfonamide as light yellow crystalline solids. Data for peak 1: $^1$H NMR (400 MHz, DMSO-$d_6$) δ ppm 3.77 (s, 3H) 6.46 (s, 1H) 6.83 (d, J=9.64 Hz, 1H) 6.88 (d, J=9.02 Hz, 1H) 7.55-7.64 (m, 2H) 7.87 (dd, J=8.97, 2.23 Hz, 1H) 8.25 (d, J=9.64 Hz, 1H) 8.32 (s, J=4.46 Hz, 1H) 8.39 (d, J=2.28 Hz, 1H) 8.75 (dd, J=3.52, 2.07 Hz, 2H) 8.89 (s, 1H) 11.67 (s, 1H). m/z (ESI) 527.2 (M+H)$^+$. Data for peak 2: $^1$H NMR (400 MHz, DMSO-$d_6$) δ ppm 3.77 (s, 3H) 6.46 (s, 1H) 6.83 (d, J=9.64 Hz, 1H) 6.88 (d, J=9.02 Hz, 1H) 7.55-7.64 (m, 2H) 7.87 (dd, J=8.97, 2.23 Hz, 1H) 8.25 (d, J=9.64 Hz, 1H) 8.32 (s, J=4.46 Hz, 1H) 8.39 (d, J=2.28 Hz, 1H) 8.75 (dd, J=3.52, 2.07 Hz, 2H) 8.89 (s, 1H) 11.67 (s, 1H). m/z (ESI) 527.2 (M+H)$^+$.

Example 410

(Method 137): (P)-1-(4'-cyano-2-fluoro-5-methoxy-3'-methyl-4-biphenylyl)-N-3-isoxazolyl-2-oxo-1,2-dihydro-6-quinolinesulfonamide

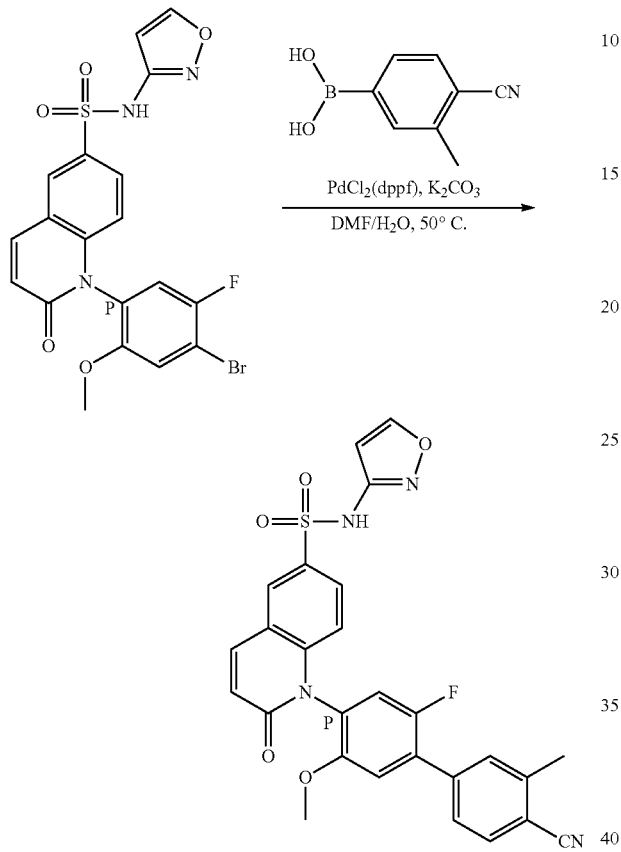

A 20-mL vial was charged with (P)-1-(4-bromo-5-fluoro-2-methoxyphenyl)-N-(isoxazol-3-yl)-2-oxo-1,2-dihydroquinoline-6-sulfonamide (116.8 mg, 0.236 mmol), potassium carbonate (163 mg, 1.181 mmol), 4-cyano-3-methylphenyl)boronic acid (57.1 mg, 0.354 mmol, purchased from Combi-blocks), and 1,1'-bis(diphenylphosphino)ferrocene palladium(II)dichloride dichloromethane adduct (19.30 mg, 0.024 mmol). The vial was flushed with $N_2$, charged with DMF (1.0 mL) and water (0.25 mL), and heated at 50° C. for 50 min. Afterwards, the reaction was cooled to rt, acidified with 1 N HCl, and extracted thrice with EtOAc. The organic extracts were combined, washed with brine, dried over $Na_2SO_4$, filtered, and concentrated in vacuo to a brown oil. Column chromatography (12 g silica gel, 40% to 100% EtOAc/hept gradient) followed by preparatory HPLC (25% to 70% MeCN/$H_2O$ with 0.1% TFA) afforded (P)-1-(4'-cyano-2-fluoro-5-methoxy-3'-methyl-4-biphenylyl)-N-3-isoxazolyl-2-oxo-1,2-dihydro-6-quinolinesulfonamide (4.5 mg, 8.48 µmol, 3.59% yield) as an amorphous white solid. $^1$H NMR (400 MHz, DMSO-$d_6$) δ ppm 2.60 (s, 3H) 3.75 (s, 3H) 6.46 (s, 1H) 6.83 (d, J=9.54 Hz, 1H) 6.89 (d, J=9.12 Hz, 1H) 7.57 (d, J=10.16 Hz, 1H) 7.71 (d, J=7.67 Hz, 1H) 7.82 (br. s., 1H) 7.87 (d, J=7.98 Hz, 1H) 7.95 (d, J=7.57 Hz, 1H) 8.24 (d, J=9.85 Hz, 1H) 8.39 (br. s., 1H) 8.74 (s, 1H) 11.68 (br. s., 1H). m/z (ESI) 531.2 (M+H)$^+$.

Example 411

(Method 138): 1-(5-fluoro-2-methoxy-4-(1-methyl-1H-imidazol-4-yl)phenyl)-N-3-isoxazolyl-2-oxo-1,2-dihydro-6-quinolinesulfonamide

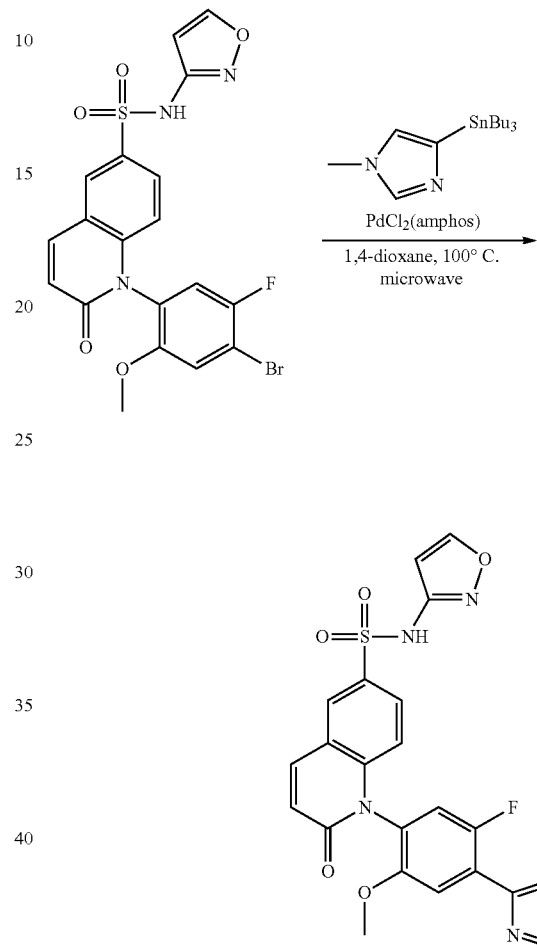

A 5-mL microwave vial was charged with 1-(4-bromo-5-fluoro-2-methoxyphenyl)-N-(isoxazol-3-yl)-2-oxo-1,2-dihydroquinoline-6-sulfonamide (200 mg, 0.405 mmol) and 1,1-bis[(di-tert-butyl-para-methylaminophenyl]palladium (II) chloride (28.7 mg, 0.040 mmol) and flushed with $N_2$. Dioxane (2 mL) and N-methyl-4-(tributylstannyl)imidazole (200 µl, 0.607 mmol) were added, and the vial was microwave irradiated at 100° C. for 1 h. Volatiles were then removed under a stream of $N_2$ overnight, and the viscous golden yellow oil was purified by preparatory HPLC (10% to 90% MeCN/H2O with 0.1% TFA) to afford the trifluoroacetate salt of 1-(5-fluoro-2-methoxy-4-(1-methyl-1H-imidazol-4-yl)phenyl)-N-3-isoxazolyl-2-oxo-1,2-dihydro-6-quinolinesulfonamide (10.3 mg, 0.017 mmol, 4.18% yield) as a white amorphous solid. $^1$H NMR (400 MHz, DMSO-$d_6$) δ ppm 3.74 (s, 3H) 3.89 (s, 3H) 6.46 (s, 1H) 6.82 (d, J=9.64 Hz, 1H) 6.88 (d, J=9.02 Hz, 1H) 7.57 (d, J=10.68 Hz, 1H) 7.81 (d, J=6.63 Hz, 1H) 7.85 (dd, J=9.02, 2.18 Hz, 1H) 7.98 (br. s., 1H) 8.24 (d, J=9.64 Hz, 1H) 8.39 (d, J=2.18 Hz, 1H) 8.69 (br. s., 1H) 8.74 (d, J=1.76 Hz, 1H) 11.67 (br. s., 1H). m/z (ESI) 496.1 (M+H)$^+$.

Example 412

(Method 139): (P)-1-(4'-chloro-2-fluoro-2',5-dimethoxy-4-biphenylyl)-N-3-isoxazolyl-2-oxo-1,2-dihydro-6-quinolinesulfonamide

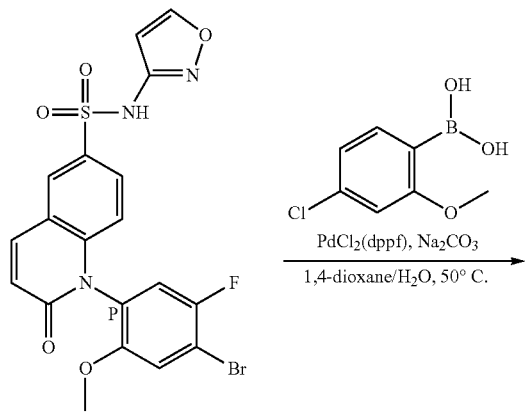

A 5-mL vial containing (P)-1-(4-bromo-5-fluoro-2-methoxyphenyl)-N-(isoxazol-3-yl)-2-oxo-1,2-dihydroquinoline-6-sulfonamide (90.7 mg, 0.183 mmol), (4-chloro-2-methoxyphenyl)boronic acid (68.4 mg, 0.367 mmol, purchased from Combi-blocks), and 1,1'-bis(diphenylphosphino)ferrocene palladium(II)dichloride dichloromethane adduct (14.98 mg, 0.018 mmol) was flushed with $N_2$ and subsequently charged with dioxane (0.70 mL) and $Na_2CO_3$, 1.9 M in $H_2O$ (0.23 mL). The red solution was stirred at 50° C. for 4 h. After cooling the dark red solution to rt, it was quenched with 1 N HCl and extracted thrice with EtOAc. The organic extracts were combined, washed with brine, dried over $Na_2SO_4$, filtered, and concentrated in vacuo to a brown residue. Preparatory HPLC (25% to 70% $MeCN/H_2O$ with 0.1% TFA) afforded (P)-1-(4'-chloro-2-fluoro-2',5-dimethoxy-4-biphenylyl)-N-3-isoxazolyl-2-oxo-1,2-dihydro-6-quinolinesulfonamide (12.6 mg, 0.023 mmol, 12.35% yield) as an off-white amorphous solid. $^1H$ NMR (400 MHz, DMSO-$d_6$) δ ppm 3.68 (s, 3H) 3.86 (s, 3H) 6.46 (d, J=1.98 Hz, 1H) 6.84 (t, J=8.87 Hz, 2H) 7.18 (dd, J=8.14, 2.02 Hz, 1H) 7.23-7.31 (m, 2H) 7.43 (dd, J=8.81, 5.08 Hz, 2H) 7.89 (d, J=9.01 Hz, 1H) 8.24 (d, J=9.54 Hz, 1H) 8.39 (d, J=2.18 Hz, 1H) 8.74 (d, J=1.98 Hz, 1H) 11.68 (s, 1H). m/z (ESI) 556.1 $(M+H)^+$.

Examples 413 & 414

(Method 140): (M)-1-(4'-chloro-2-fluoro-5-methoxy-3'-methyl-[1,1'-biphenyl]-4-yl)-N-(isoxazol-3-yl)-3-methoxy-2-oxo-1,2-dihydroquinoline-6-sulfonamide (413) and (P)-1-(4'-chloro-2-fluoro-5-methoxy-3'-methyl-[1,1'-biphenyl]-4-yl)-N-(isoxazol-3-yl)-3-methoxy-2-oxo-1,2-dihydroquinoline-6-sulfonamide (414)

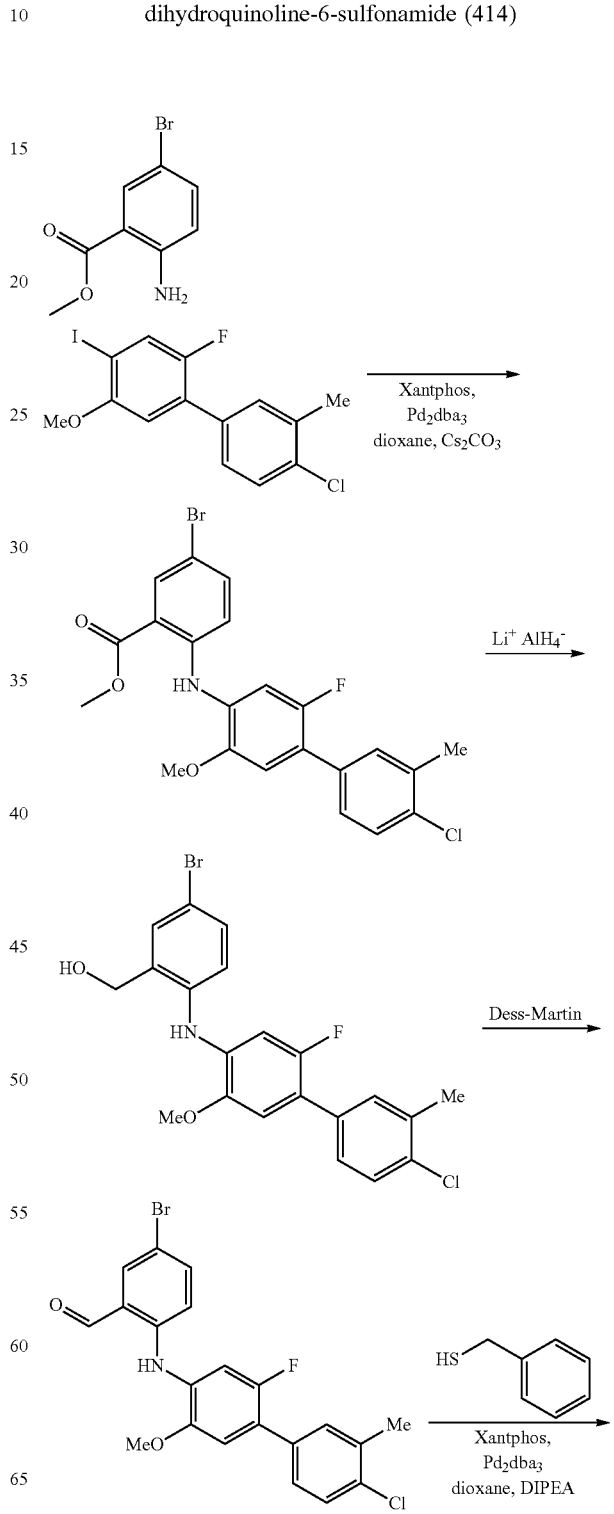

-continued

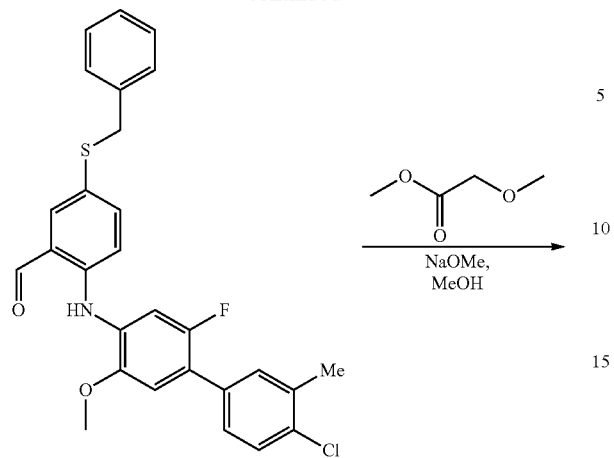

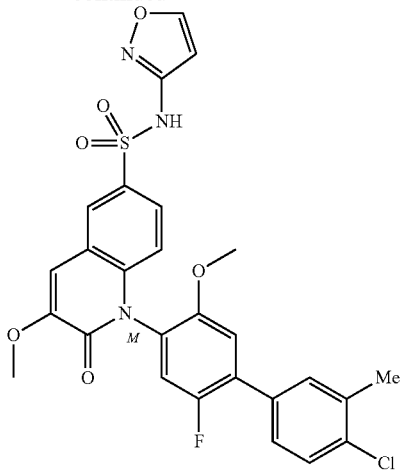

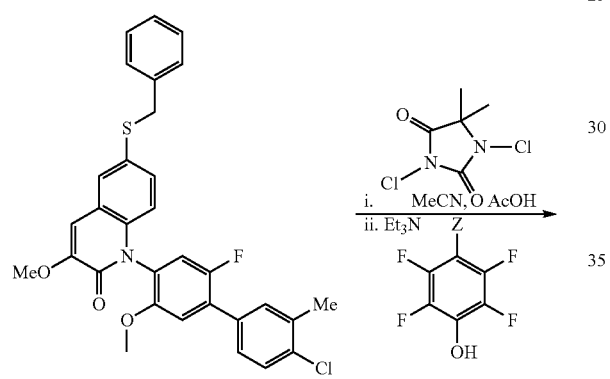

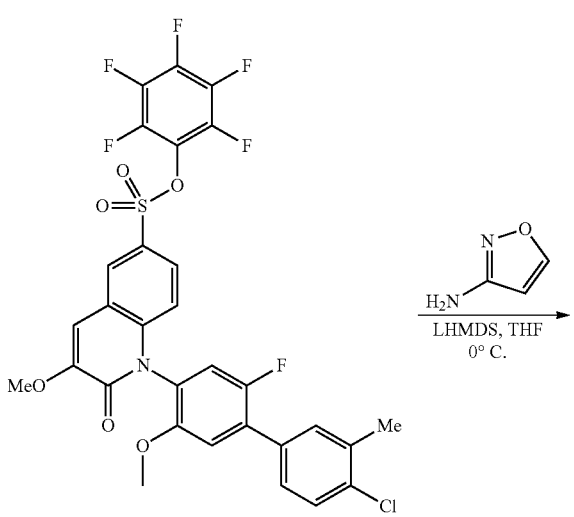

Step 1: Methyl 5-bromo-2-((4'-chloro-2-fluoro-5-methoxy-3'-methyl-[1,1'-biphenyl]-4-yl)amino)benzoate A sealable vial was charged vial with methyl 2-amino-5-bromobenzoate (3.63 g, 15.80 mmol), cesium carbonate (8.75 g, 26.9 mmol), Pd$_2$(dba)$_3$ (0.362 g, 0.395 mmol), xantphos (0.457 g, 0.790 mmol), and 4'-chloro-2-fluoro-4-iodo-5-methoxy-3'-methyl-1,1'-biphenyl (7.14 g, 18.96 mmol). The vial was sealed with septum cap and CPME (31.6 ml) was added. The mixture was heated at 100° C. for 2 h. The mixture was cooled and partitioned between water (30 mL) and EtOAc (50 mL). There was an insoluble solid that was suspended between the layers. The organic layer and the solid were collected together and the mixture was concentrated. The resulting yellow solid was taken up in DCM (100 mL) and filtered through a plug of celite. The mother liquor was concentrated to give a yellow solid that was slurried in IPA (100 mL) and collected by vacuum filtration to provide methyl 5-bromo-2-((4'-chloro-2-fluoro-5-methoxy-3'-methyl-[1,1'-biphenyl]-4-yl)amino)benzoate (7.15 g, 14.94 mmol, 95% yield) as a yellow solid. (ESI) 476.1 (M–H)⁻.

Step 2: (5-bromo-2-((4'-chloro-2-fluoro-5-methoxy-3'-methyl-[1,1'-biphenyl]-4-yl)amino)phenyl)methanol A flask was charged with methyl 5-bromo-2-((4'-chloro-2-fluoro-5-methoxy-3'-methyl-[1,1'-biphenyl]-4-yl)amino)

benzoate (7.15 g, 14.94 mmol). A septum was attached and the flask was flushed with $N_2$. To the flask was added THF (149 ml) and the solution was cooled to 0° C. An ethyl ether solution of lithium aluminum hydride solution (17.92 ml, 17.92 mmol, 1M) was added dropwise via syringe to generate an orange solution. After 10 minutes, water (0.68 mL), and 15% NaOH (0.68 mL) were added. The mixture was stirred 10 minutes and then an additional 2.0 mL water was added to generate a white precipitate. The mixture was filtered through a plug of silica and the mother liquor was concentrated to give a tan foam. This was used in the next reaction without further purification. (ESI) 450.0 (M–H)⁻.

Step 3: 5-bromo-2-((4'-chloro-2-fluoro-5-methoxy-3'-methyl-[1,1'-biphenyl]-4-yl)amino)benzaldehyde A flask was charged with (5-bromo-2-((4'-chloro-2-fluoro-5-methoxy-3'-methyl-[1,1'-biphenyl]-4-yl)amino)phenyl)methanol (6.56 g, 14.55 mmol) and DCM (72.8 ml). The solution was cooled to 0° C. To the solution was added Dess-Martin Periodinane (8.02 g, 18.92 mmol) as a solid in a single portion to give a red solution. The cold bath was removed and the solution was allowed to warm to rt. After 30 min, the solution was partitioned between DCM (100 mL) and sat. aq. sodium thiosulfite (30 mL) and 1 N NaOH (20 mL). The layers were separated and the aqueous layer was extracted with DCM (2×50 mL). The combined organic layers were dried ($Na_2SO_4$) and filtered through a plug of silica. The red mother liquor was concentrated, then taken up in minimal DCM (10 mL). To the solution was added IPA (200 mL) and a brown/yellow solid precipitated, which was collected by vacuum filtration to yield 5-bromo-2-((4'-chloro-2-fluoro-5-methoxy-3'-methyl-[1,1'-biphenyl]-4-yl)amino)benzaldehyde (2.339 g, 5.21 mmol, 35.8% yield) as brown/yellow solid. (ESI) 446.1 (M–H)⁻.

Step 4: 5-(benzylthio)-2-((4'-chloro-2-fluoro-5-methoxy-3'-methyl-[1,1'-biphenyl]-4-yl)amino)benzaldehyde A small microwave vial was charged with $Pd_2(dba)_3$ (0.064 g, 0.070 mmol), xantphos (0.081 g, 0.140 mmol). The vial was sealed with a septum cap and 0.3 mL dioxane was added. The vial was heated at 90° C. in an oil bath for 3 min. The solution was then cooled to rt. A separate vial was charged with 5-bromo-2-((4'-chloro-2-fluoro-5-methoxy-3'-methyl-[1,1'-biphenyl]-4-yl)amino)benzaldehyde (1.26 g, 2.81 mmol) and sealed with a septum cap. The vial was flushed with $N_2$ and 1,4-dioxane (9.36 ml), phenylmethanethiol (0.399 ml, 3.37 mmol) and dipea (1.471 ml, 8.42 mmol) were added. The pre-activated catalyst solution prepared in the microwave vial was transferred to the vial containing the reactants via syringe and the resulting mixture was heated at 90° C. for 3 h. The reaction mixture was partitioned between 1 N HCl/brine (20 mL) and EtOAc (30 mL). The layers were separated and the aqueous layer was extracted with EtOAc (1×20 mL). The combined organic layers were dried ($Na_2SO_4$) and concentrated for purification by MPLC (Biotage Isolera). The crude residue was taken up in minimal DCM and absorbed onto a 25 g loading cartridge and passed through a Redi-Sep® Gold pre-packed silica gel column (80 g) using 100% Heptane to 60:40 Heptane:EtOAc gradient to afford 5-(benzylthio)-2-((4'-chloro-2-fluoro-5-methoxy-3'-methyl-[1,1'-biphenyl]-4-yl)amino)benzaldehyde as a bright yellow foam. (ESI) 490.2 (M–H)⁻.

Step 5: 6-(benzylthio)-1-(4'-chloro-2-fluoro-5-methoxy-3'-methyl-[1,1'-biphenyl]-4-yl)-3-methoxyquinolin-2(1H)-one A flask was charged with 5-(benzylthio)-2-((4'-chloro-2-fluoro-5-methoxy-3'-methyl-[1,1'-biphenyl]-4-yl)amino)benzaldehyde (0.809 g, 1.644 mmol) and a MeOH solution of sodium methoxide (16.44 ml, 8.22 mmol) was added. Then methyl methoxyacetate (0.489 ml, 4.93 mmol) followed by toluene (1.644 ml) were added. A reflux condenser was attached and the mixture was heated at 70° C. for 48 h. The resulting solution was concentrated for purification by MPLC (Biotage Isolera). The crude residue was taken up in minimal DCM and absorbed onto a 25 g loading cartridge and passed through a Redi-Sep® Gold pre-packed silica gel column (40 g) using 95:5 Heptane:EtOAc to 100% EtOAc gradient (with 1% DCM for solubility) to afford 6-(benzylthio)-1-(4'-chloro-2-fluoro-5-methoxy-3'-methyl-[1,1'-biphenyl]-4-yl)-3-methoxyquinolin-2(1H)-one (0.410 g, 0.751 mmol, 45.7% yield) as a off-white amorphous solid. (ESI) 546.0 (M+H)+.

Step 6: Perfluorophenyl 1-(4'-chloro-2-fluoro-5-methoxy-3'-methyl-[1,1'-biphenyl]-4-yl)-3-methoxy-2-oxo-1,2-dihydroquinoline-6-sulfonate A flask was charged with 6-(benzylthio)-1-(4'-chloro-2-fluoro-5-methoxy-3'-methyl-[1,1'-biphenyl]-4-yl)-3-methoxyquinolin-2(1H)-one (0.337 g, 0.617 mmol), followed by acetonitrile (2.90 ml) acetic acid (0.110 ml) and water (0.073 ml). The solution was cooled to 0° C. and (1.3 equiv) 1,3-dichloro-5,5-dimethylimidazolidine-2,4-dione (0.158 g, 0.802 mmol) was added as a solid in a single portion. The solution was maintained at 0° C. for 10 min and then and additional 0.3 equiv 1,3-dichloro-5,5-dimethylimidazolidine-2,4-dione (0.036 g, 0.185 mmol) was added. After 10 min, 2,3,4,5,6-pentafluorophenol (0.136 g, 0.741 mmol) was added as a solution in minimal MeCN. Following this, triethylamine (0.344 ml, 2.469 mmol) was added dropwise and the resulting mixture was maintained at 0° C. for 5 min. The solution was allowed to warm to rt and maintained for 20 min. The reaction mixture was partitioned between 1:1 brine:water (30 mL) and EtOAc (30 mL). The layers were separated and the aqueous layer was extracted with EtOAc (2×20 mL). The combined organic layers were dried ($Na_2SO_4$) and concentrated for purification by MPLC (Biotage Isolera). The crude residue was taken up in minimal DCM and absorbed onto a 25 g loading cartridge and passed through a Redi-Sep® Gold pre-packed silica gel column (40 g) using a gradient of 5-90% EtOAc in Heptane to afford perfluorophenyl 1-(4'-chloro-2-fluoro-5-methoxy-3'-methyl-[1,1'-biphenyl]-4-yl)-3-methoxy-2-oxo-1,2-dihydroquinoline-6-sulfonate (0.270 g, 0.403 mmol, 65.3% yield) as a white foam. m/z (ESI) 669.9 (M+H)+.

Step 7: (M)-1-(4'-chloro-2-fluoro-5-methoxy-3'-methyl-[1,1'-biphenyl]-4-yl)-N-(isoxazol-3-yl)-3-methoxy-2-oxo-1,2-dihydroquinoline-6-sulfonamide and (P)-1-(4'-chloro-2-fluoro-5-methoxy-3'-methyl-[1,1'-biphenyl]-4-yl)-N-(isoxazol-3-yl)-3-methoxy-2-oxo-1,2-dihydroquinoline-6-sulfonamide A flask was charged with perfluorophenyl 1-(4'-chloro-2-fluoro-5-methoxy-3'-methyl-[1,1'-biphenyl]-4-yl)-3-methoxy-2-oxo-1,2-dihydroquinoline-6-sulfonate (0.2262 g, 0.338 mmol) and isoxazol-3-amine (0.034 g, 0.405 mmol). A septum was attached and THF (3.4 ml) was added under N₂ flow. The solution was cooled to 0° C. and LHMDS (0.709 ml, 0.709 mmol) was added to give a bright yellow solution. After 10 min, 5 mL of 1 N HCl was added and the mixture was partitioned between 1 N HCL (10 mL) and EtOAc (20 mL). The layers were separated and the aqueous layer was extracted with EtOAc (1×10 mL). The combined organic layers were dried (Na₂SO₄) and concentrated for purification by MPLC (Biotage Isolera). The crude residue was taken up in minimal DCM and absorbed onto a 5 g loading cartridge and passed through a Interchim 25 g spherical silical gel column using a gradient of 5% EtOH and 15% EtOAc in heptane to 25% EtOH in EtOAc with 10% DCM constant additive to afford 1-(4'-chloro-2-fluoro-5-methoxy-3'-methyl-[1,1'-biphenyl]-4-yl)-N-(isoxazol-3-yl)-3-methoxy-2-oxo-1,2-dihydroquinoline-6-sulfonamide (0.187 g, 0.328 mmol, 97% yield) as a colorless foam. The racemic product was subjected to chiral separation by SFC on a Chiralcel OJ column (45% MeOH/80% CO₂) to give (M)-1-(4'-chloro-2-fluoro-5-methoxy-3'-methyl-[1,1'-biphenyl]-4-yl)-N-(isoxazol-3-yl)-3-methoxy-2-oxo-1,2-dihydroquinoline-6-sulfonamide as peak 1 and (P)-1-(4'-chloro-2-fluoro-5-methoxy-3'-methyl-[1,1'-biphenyl]-4-yl)-N-(isoxazol-3-yl)-3-methoxy-2-oxo-1,2-dihydroquinoline-6-sulfonamide as peak 2. Data for peak 1: ¹H NMR (500 MHz, DMSO-d₆) δ 11.59 (br. s, 1H), 8.66 (d, J=1.62 Hz, 1H), 8.20 (d, J=1.88 Hz, 1H), 7.60-7.70 (m, 2H), 7.40-7.58 (m, 4H), 7.25-7.38 (m, 1H), 6.74 (d, J=8.89 Hz, 1H), 6.38 (d, J=1.56 Hz, 1H), 3.84 (s, 3H), 3.67 (s, 3H), 2.37 (s, 3H). m/z (ESI) 568.2 (M+H)+. Data for peak 2: ¹H NMR (500 MHz, DMSO-d₆) δ 11.56 (br. s, 1H), 8.65 (d, J=1.56 Hz, 1H), 8.19 (d, J=1.95 Hz, 1H), 7.60-7.71 (m, 2H), 7.40-7.57 (m, 4H), 7.32 (d, J=6.88 Hz, 1H), 6.73 (d, J=8.89 Hz, 1H), 6.37 (d, J=1.62 Hz, 1H), 3.83 (s, 3H), 3.66 (s, 3H), 2.37 (s, 3H). m/z (ESI) 568.2 (M+H)+.

Examples 415 & 416

(P)-1-(4-bromo-2-methoxy-5-methylphenyl)-N-3-isoxazolyl-2-oxo-1,2-dihydro-6-quinolinesulfonamide (415) and (M)-1-(4-bromo-2-methoxy-5-methylphenyl)-N-3-isoxazolyl-2-oxo-1,2-dihydro-6-quinolinesulfonamide (416)

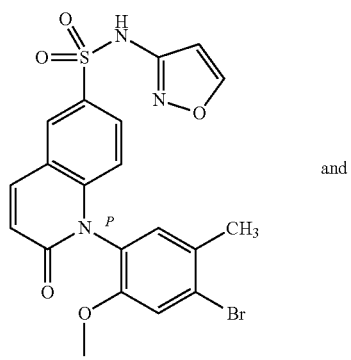

and

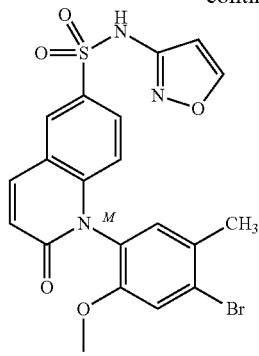

Racemic 1-(4-bromo-2-methoxy-5-methylphenyl)-N-(isoxazol-3-yl)-2-oxo-1,2-dihydroquinoline-6-sulfonamide was subjected to chiral separation by SFC on a Chiralpak AD-H column (45% MeOH/55% CO₂) to give (P)-1-(4-bromo-2-methoxy-5-methylphenyl)-N-3-isoxazolyl-2-oxo-1,2-dihydro-6-quinolinesulfonamide as peak 1 and (M)-1-(4-bromo-2-methoxy-5-methylphenyl)-N-3-isoxazolyl-2-oxo-1,2-dihydro-6-quinolinesulfonamide as peak 2. Both peaks were isolated as off-white solids. Data for peak 1: ¹H NMR (400 MHz, DMSO-d₆) δ=11.66 (br. s., 1H), 8.72 (d, J=1.8 Hz, 1H), 8.35 (d, J=2.2 Hz, 1H), 8.21 (d, J=9.6 Hz, 1H), 7.83 (dd, J=2.2, 8.9 Hz, 1H), 7.52 (s, 1H), 7.34 (d, J=0.4 Hz, 1H), 6.78 (d, J=9.6 Hz, 2H), 6.43 (d, J=1.9 Hz, 1H), 3.67 (s, 3H), 2.31 (s, 3H). m/z (ESI) 489.9 (M+H)⁺. Data for peak 2: ¹H NMR (400 MHz, DMSO-d₆) δ=11.66 (br. s., 1H), 8.72 (d, J=1.8 Hz, 1H), 8.35 (d, J=2.2 Hz, 1H), 8.21 (d, J=9.6 Hz, 1H), 7.83 (dd, J=2.2, 8.9 Hz, 1H), 7.52 (s, 1H), 7.34 (d, J=0.4 Hz, 1H), 6.78 (d, J=9.6 Hz, 2H), 6.43 (d, J=1.9 Hz, 1H), 3.67 (s, 3H), 2.31 (s, 3H). m/z (ESI) 489.9 (M+H)⁺.

Examples 417 & 418

(P)-1-(3'-chloro-5'-fluoro-5-methoxy-2-methyl-4-biphenylyl)-N-3-isoxazolyl-2-oxo-1,2-dihydro-6-quinolinesulfonamide (417) and (M)-1-(3'-chloro-5'-fluoro-5-methoxy-2-methyl-4-biphenylyl)-N-3-isoxazolyl-2-oxo-1,2-dihydro-6-quinolinesulfonamide (418)

These compounds were prepared via method 65 using (3-chloro-5-fluorophenyl)boronic acid as the boronic acid. The racemic product was separated via chiral SFC on a Chiralpak AD-H column (40% MeOH/60% CO₂) to give (P)-1-(3'-chloro-5'-fluoro-5-methoxy-2-methyl-4-biphenylyl)-N-3-isoxazolyl-2-oxo-1,2-dihydro-6-quinolinesulfonamide as peak 1 and (M)-1-(3'-chloro-5'-fluoro-5-methoxy-2-methyl-4-biphenylyl)-N-3-isoxazolyl-2-oxo-1,2-dihydro-6-quinolinesulfonamide as peak 2. Both materials were obtained as white solids. Data for peak 1: ¹H NMR (400 MHz, DMSO-d₆) δ=11.66 (br. s., 1H), 8.73 (d, J=1.9 Hz, 1H), 8.37 (d, J=2.2 Hz, 1H), 8.22 (d, J=9.7 Hz, 1H), 7.86 (dd, J=2.2, 8.9 Hz, 1H), 7.52 (td, J=2.1, 8.8 Hz, 1H), 7.46-7.35 (m, 2H), 7.27 (s, 1H), 7.17 (s, 1H), 6.80 (t, J=8.8 Hz, 2H), 6.45 (d, J=1.8 Hz, 1H), 3.69 (s, 3H), 2.21 (s, 3H). m/z (ESI) 540.0 (M+H)⁺. Data for peak 2: ¹H NMR (400 MHz, DMSO-d₆) δ=11.66 (br. s., 1H), 8.73 (d, J=1.9 Hz, 1H), 8.37 (d, J=2.2 Hz, 1H), 8.22 (d, J=9.7 Hz, 1H), 7.86 (dd, J=2.2, 8.9 Hz, 1H), 7.52 (td, J=2.1, 8.8 Hz, 1H), 7.46-7.35 (m, 2H), 7.27 (s, 1H), 7.17 (s, 1H), 6.80 (t, J=8.8 Hz, 2H), 6.45 (d, J=1.8 Hz, 1H), 3.69 (s, 3H), 2.21 (s, 3H). m/z (ESI) 540.0 (M+H)$^+$.

Examples 419 & 420

(P)—N-3-isoxazolyl-1-(5-methoxy-2-methyl-3'-(trifluoromethyl)-4-biphenylyl)-2-oxo-1,2-dihydro-6-quinolinesulfonamide (419) and (M)-N-3-isoxazolyl-1-(5-methoxy-2-methyl-3'-(trifluoromethyl)-4-biphenylyl)-2-oxo-1,2-dihydro-6-quinolinesulfonamide (420)

These compounds were prepared via method 65 using 3-trifluoromethylphenyl boronic acid as the boronic acid. The racemic product was separated via chiral SFC on a Chiralpak AD-H column (20% MeOH/80% CO$_2$) to give (P)—N-3-isoxazolyl-1-(5-methoxy-2-methyl-3'-(trifluoromethyl)-4-biphenylyl)-2-oxo-1,2-dihydro-6-quinolinesulfonamide as peak 1 and (M)-N-3-isoxazolyl-1-(5-methoxy-2-methyl-3'-(trifluoromethyl)-4-biphenylyl)-2-oxo-1,2-dihydro-6-quinolinesulfonamide as peak 2. Both materials were obtained as white solids. Data for peak 1: $^1$H NMR (400 MHz, DMSO-d$_6$) δ=11.66 (br. s., 1H), 8.73 (d, J=1.8 Hz, 1H), 8.37 (d, J=2.2 Hz, 1H), 8.23 (d, J=9.7 Hz, 1H), 7.90-7.72 (m, 5H), 7.28 (s, 1H), 7.18 (s, 1H), 6.82 (dd, J=4.9, 9.3 Hz, 2H), 6.45 (d, J=1.8 Hz, 1H), 3.69 (s, 3H), 2.19 (s, 3H). m/z (ESI) 556.2 (M+H)$^+$. Data for peak 2: $^1$H NMR (400 MHz, DMSO-d$_6$) δ=11.66 (br. s., 1H), 8.73 (d, J=1.8 Hz, 1H), 8.37 (d, J=2.2 Hz, 1H), 8.23 (d, J=9.7 Hz, 1H), 7.90-7.72 (m, 5H), 7.28 (s, 1H), 7.18 (s, 1H), 6.82 (dd, J=4.9, 9.3 Hz, 2H), 6.45 (d, J=1.8 Hz, 1H), 3.69 (s, 3H), 2.19 (s, 3H). m/z (ESI) 556.2 (M+H)$^+$.

Examples 421 & 422 (P)-1-(4'-chloro-5-methoxy-2,3'-dimethyl-4-biphenylyl)-N-3-isoxazolyl-2-oxo-1,2-dihydro-6-quinolinesulfonamide (421) and (M)-1-(4'-chloro-5-methoxy-2,3'-dimethyl-4-biphenylyl)-N-3-isoxazolyl-2-oxo-1,2-dihydro-6-quinolinesulfonamide (422)

These compounds were prepared via method 65 using (4-chloro-3-methylphenyl)boronic acid as the boronic acid. The racemic product was separated via chiral SFC on a Chiralpak AD-H column with 40% MeOH/60% CO$_2$ to give (P)-1-(4'-chloro-5-methoxy-2,3'-dimethyl-4-biphenylyl)-N-3-isoxazolyl-2-oxo-1,2-dihydro-6-quinolinesulfonamide as peak 1 and (M)-1-(4'-chloro-5-methoxy-2,3'-dimethyl-4-biphenylyl)-N-3-isoxazolyl-2-oxo-1,2-dihydro-6-quinolinesulfonamide as peak 2. Both materials were obtained as light-yellow solids. Data for peak 1: $^1$H NMR (400 MHz, DMSO-d$_6$) δ=11.66 (br. s., 1H), 8.65 (s, 1H), 8.33 (d, J=2.1 Hz, 1H), 8.21 (d, J=9.6 Hz, 1H), 7.85 (dd, J=2.1, 8.9 Hz, 1H), 7.56-7.44 (m, 2H), 7.33 (dd, J=1.7, 8.2 Hz, 1H), 7.23 (s, 1H), 7.10 (s, 1H), 6.83-6.70 (m, 2H), 6.40 (d, J=1.7 Hz, 1H), 3.67 (s, 3H), 2.42 (s, 3H), 2.20 (s, 3H). m/z (ESI) 536.1. Data for peak 2: $^1$H NMR (400 MHz, DMSO-d$_6$) δ=11.66 (br. s., 1H), 8.65 (s, 1H), 8.33 (d, J=2.1 Hz, 1H), 8.21 (d, J=9.6 Hz, 1H), 7.85 (dd, J=2.1, 8.9 Hz, 1H), 7.56-7.44 (m, 2H), 7.33 (dd, J=1.7, 8.2 Hz, 1H), 7.23 (s, 1H), 7.10 (s, 1H), 6.83-6.70 (m, 2H), 6.40 (d, J=1.7 Hz, 1H), 3.67 (s, 3H), 2.42 (s, 3H), 2.20 (s, 3H). m/z (ESI) 536.1.

Examples 423 & 424

(P)-1-(3',5'-difluoro-5-methoxy-2-methyl-4-biphenylyl)-N-3-isoxazolyl-2-oxo-1,2-dihydro-6-quinolinesulfonamide (423) and (M)-1-(3',5'-difluoro-5-methoxy-2-methyl-4-biphenylyl)-N-3-isoxazolyl-2-oxo-1,2-dihydro-6-quinolinesulfonamide (424)

These compounds were prepared via method 65 using (3,5-difluorophenyl)boronic acid as the boronic acid. The racemic product was separated via chiral SFC on a Chiralpak AD-H column with 35% MeOH/65% CO$_2$ to give (P)-1-(3',5'-difluoro-5-methoxy-2-methyl-4-biphenylyl)-N-3-isoxazolyl-2-oxo-1,2-dihydro-6-quinolinesulfonamide as peak 1 and (M)-1-(3',5'-difluoro-5-methoxy-2-methyl-4-biphenylyl)-N-3-isoxazolyl-2-oxo-1,2-dihydro-6-quinolinesulfonamide as peak 2. Both materials were obtained as light-yellow solids. Data for peak 1: $^1$H NMR (400 MHz, DMSO-d$_6$) δ=11.66 (br. s., 1H), 8.71 (d, J=1.8 Hz, 1H), 8.36 (d, J=2.2 Hz, 1H), 8.22 (d, J=9.6 Hz, 1H), 7.86 (dd, J=2.2, 9.0 Hz, 1H), 7.37-7.23 (m, 4H), 7.17 (s, 1H), 6.80 (dd, J=7.6, 9.2 Hz, 2H), 6.44 (d, J=1.8 Hz, 1H), 3.69 (s, 3H), 2.23 (s, 3H). m/z (ESI) 524.1 (M+H)$^+$. Data for peak 2: $^1$H NMR (400 MHz, DMSO-d$_6$) δ=11.66 (br. s., 1H), 8.71 (d, J=1.8 Hz, 1H), 8.36 (d, J=2.2 Hz, 1H), 8.22 (d, J=9.6 Hz, 1H), 7.86 (dd, J=2.2, 9.0 Hz, 1H), 7.37-7.23 (m, 4H), 7.17 (s, 1H), 6.80 (dd, J=7.6, 9.2 Hz, 2H), 6.44 (d, J=1.8 Hz, 1H), 3.69 (s, 3H), 2.23 (s, 3H). m/z (ESI) 524.1 (M+H)$^+$.

Examples 425 & 426

(M)-1-(4-(5-fluoro-2-methoxy-3-pyridinyl)-2-methoxy-5-methylphenyl)-N-3-isoxazolyl-2-oxo-1,2-dihydro-6-quinolinesulfonamide (425) and (P)-1-(4-(5-fluoro-2-methoxy-3-pyridinyl)-2-methoxy-5-methylphenyl)-N-3-isoxazolyl-2-oxo-1,2-dihydro-6-quinolinesulfonamide (426)

These compounds were prepared via method 65 using (5-fluoro-2-methoxypyridin-3-yl)boronic acid as the boronic acid. The racemic product was separated via chiral SFC on a Chiralpak OJ-H column with 25% MeOH/75% CO$_2$ to give (M)-1-(4-(5-fluoro-2-methoxy-3-pyridinyl)-2-methoxy-5-methylphenyl)-N-3-isoxazolyl-2-oxo-1,2-dihydro-6-quinolinesulfonamide as peak 1 and (P)-1-(4-(5-fluoro-2-methoxy-3-pyridinyl)-2-methoxy-5-methylphenyl)-N-3-isoxazolyl-2-oxo-1,2-dihydro-6-quinolinesulfonamide as peak 2. Both materials were obtained as light-yellow solids. Data for peak 1: $^1$H NMR (400 MHz, DMSO-d$_6$) δ=11.66 (br. s., 1H), 8.71 (d, J=1.8 Hz, 1H), 8.37 (d, J=2.2 Hz, 1H), 8.29-8.16 (m, 2H), 7.88 (dd, J=2.2, 9.0 Hz, 1H), 7.75 (dd, J=3.0, 8.4 Hz, 1H), 7.23 (s, 1H), 7.15 (s, 1H), 6.81 (d, J=9.7 Hz, 1H), 6.76 (d, J=9.0 Hz, 1H), 6.44 (d, J=1.8 Hz, 1H), 3.90 (s, 3H), 3.65 (s, 3H), 2.06 (s, 3H). m/z (ESI) 537.2 (M+H)$^+$. Data for peak 2: $^1$H NMR (400 MHz, DMSO-d$_6$) δ=11.66 (br. s., 1H), 8.71 (d, J=1.8 Hz, 1H), 8.37 (d, J=2.2 Hz, 1H), 8.29-8.16 (m, 2H), 7.88 (dd, J=2.2, 9.0 Hz, 1H), 7.75 (dd, J=3.0, 8.4 Hz, 1H), 7.23 (s, 1H), 7.15 (s, 1H), 6.81 (d, J=9.7 Hz, 1H), 6.76 (d, J=9.0 Hz, 1H), 6.44 (d, J=1.8 Hz, 1H), 3.90 (s, 3H), 3.65 (s, 3H), 2.06 (s, 3H). m/z (ESI) 537.2 (M+H)$^+$.

Examples 427 & 428 (P)-1-(3'-fluoro-5-methoxy-2-methyl-4-biphenylyl)-N-3-isoxazolyl-2-oxo-1,2-dihydro-6-quinolinesulfonamide (427) and (M)-1-(3'-fluoro-5-methoxy-2-methyl-4-biphenylyl)-N-3-isoxazolyl-2-oxo-1,2-dihydro-6-quinolinesulfonamide (428)

These compounds were made via a modification of 65. A vial was charged with 1-(4-bromo-2-methoxy-5-methylphenyl)-N-(isoxazol-3-yl)-2-oxo-1,2-dihydroquinoline-6-sulfonamide (302.9 mg, 0.618 mmol). (3-fluorophenyl)boronic acid (130 mg, 0.927 mmol), potassium carbonate (256 mg, 1.853 mmol), and Pd(Ph₃P)₄ (71.4 mg, 0.062 mmol). The vial was flushed with Ar (g), then 1,4-dioxane (2317 µl) and water (772 µl) were added. The vial was sealed and heated to 100° C. for 1 h. The mixture was cooled then extracted with EtOAc (5×), and the combined organic extracts were concentrated. The residue was purified by chromatography on silica gel (25-g SNAP Ultra column, 0-10% MeOH/DCM) to give 362 mg of a yellow foam. The racemic product was separated via chiral SFC on a Chiralpak AD-H column with 35% MeOH/65% $CO_2$ to give (P)-1-(3'-fluoro-5-methoxy-2-methyl-4-biphenylyl)-N-3-isoxazolyl-2-oxo-1,2-dihydro-6-quinolinesulfonamide as peak 1 and (M)-1-(3'-fluoro-5-methoxy-2-methyl-4-biphenylyl)-N-3-isoxazolyl-2-oxo-1,2-dihydro-6-quinolinesulfonamide as peak 2. Both materials were obtained as light-yellow solids. Data for peak 1: $^1$H NMR (400 MHz, DMF) δ=11.66 (br. s., 1H), 8.73 (d, J=1.9 Hz, 1H), 8.37 (d, J=2.2 Hz, 1H), 8.22 (d, J=9.7 Hz, 1H), 7.87 (dd, J=2.2, 9.0 Hz, 1H), 7.55 (dt, J=6.3, 8.0 Hz, 1H), 7.38-7.32 (m, 2H), 7.30-7.24 (m, 2H), 7.14 (s, 1H), 6.84-6.77 (m, 2H), 6.45 (d, J=1.8 Hz, 1H), 3.68 (s, 3H), 2.21 (s, 3H). m/z (ESI) 506.1 (M+H)⁺. Data for peak 2: $^1$H NMR (400 MHz, DMF) δ=11.66 (br. s., 1H), 8.73 (d, J=1.9 Hz, 1H), 8.37 (d, J=2.2 Hz, 1H), 8.22 (d, J=9.7 Hz, 1H), 7.87 (dd, J=2.2, 9.0 Hz, 1H), 7.55 (dt, J=6.3, 8.0 Hz, 1H), 7.38-7.32 (m, 2H), 7.30-7.24 (m, 2H), 7.14 (s, 1H), 6.84-6.77 (m, 2H), 6.45 (d, J=1.8 Hz, 1H), 3.68 (s, 3H), 2.21 (s, 3H). m/z (ESI) 506.1 (M+H)⁺.

Examples 429 & 430

(M)-1-(3'-chloro-5'-fluoro-3-methoxy-4-biphenylyl)-N-3-isoxazolyl-2-oxo-1,2-dihydro-6-quinolinesulfonamide (429) and (P)-1-(3'-chloro-5'-fluoro-3-methoxy-4-biphenylyl)-N-3-isoxazolyl-2-oxo-1,2-dihydro-6-quinolinesulfonamide (430)

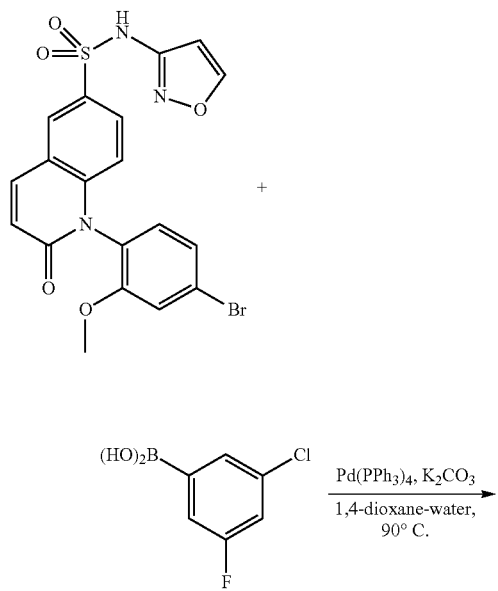

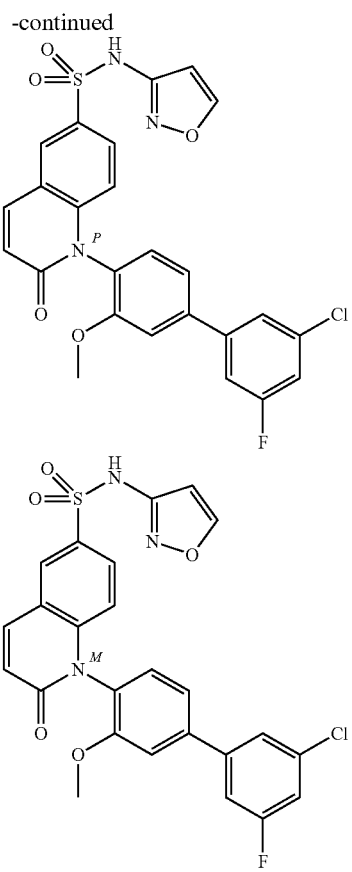

These compounds were prepared via method 72. A vial was charged with 1-(4-bromo-2-methoxyphenyl)-N-(isoxazol-3-yl)-2-oxo-1,2-dihydroquinoline-6-sulfonamide (273 mg, 0.573 mmol). (3-chloro-5-fluorophenyl)boronic acid (130 mg, 0.745 mmol), potassium carbonate (238 mg, 1.720 mmol), and tetrakis(triphenylphosphine)palladium(0) (33.1 mg, 0.029 mmol). The vial was flushed with Ar (g), then 1,4-dioxane (2149 µl) and water (716 µl) were added. The vial was sealed and heated to 90° C. for 4 h. The layers were separated (via pipette), the aq. layer was extracted with EtOAc (5×), and the combined organic extracts were concentrated. The residue was purified by chromatography on silica gel (50-g Redi-Sep column, 25-g loading column, 20-70% EtOAc/Heptane) to give 117 mg of an off-white solid. This material subjected to chiral SFC purification (OJ-H column eluted with 35% MeOH/$CO_2$) to give (M)-1-(3'-chloro-5'-fluoro-3-methoxy-4-biphenylyl)-N-3-isoxazolyl-2-oxo-1,2-dihydro-6-quinolinesulfonamide as peak 1 and (P)-1-(3'-chloro-5'-fluoro-3-methoxy-4-biphenylyl)-N-3-isoxazolyl-2-oxo-1,2-dihydro-6-quinolinesulfonamide as peak 2. Both materials were isolated as off-white solids. Data for peak 1: $^1$H NMR (400 MHz, DMSO-d₆) δ=8.55 (d, J=1.7 Hz, 1H), 8.29 (d, J=2.1 Hz, 1H), 8.19 (d, J=9.7 Hz, 1H), 7.83-7.71 (m, 3H), 7.60 (d, J=1.9 Hz, 1H), 7.55-7.47 (m, 2H), 7.40 (d, J=8.0 Hz, 1H), 6.81-6.67 (m, 2H), 6.34 (d, J=1.8 Hz, 1H), 3.79 (s, 3H). m/z (ESI) 526.1 (M+H)⁺. Data for peak 2: $^1$H NMR (400 MHz, DMSO-d₆) δ=8.55 (d, J=1.7 Hz, 1H), 8.29 (d, J=2.1 Hz, 1H), 8.19 (d, J=9.7 Hz, 1H), 7.83-7.71 (m, 3H), 7.60 (d, J=1.9 Hz, 1H), 7.55-7.47 (m, 2H), 7.40 (d, J=8.0 Hz, 1H), 6.81-6.67 (m, 2H), 6.34 (d, J=1.8 Hz, 1H), 3.79 (s, 3H). m/z (ESI) 526.1 (M+H)⁺.

Examples 431 & 432

(m)-1-(4'-chloro-3-methoxy-3'-methyl-4-biphenylyl)-N-3-isoxazolyl-2-oxo-1,2-dihydro-6-quinolinesulfonamide (431) and (P)-1-(4'-chloro-3-methoxy-3'-methyl-4-biphenylyl)-N-3-isoxazolyl-2-oxo-1,2-dihydro-6-quinolinesulfonamide (432)

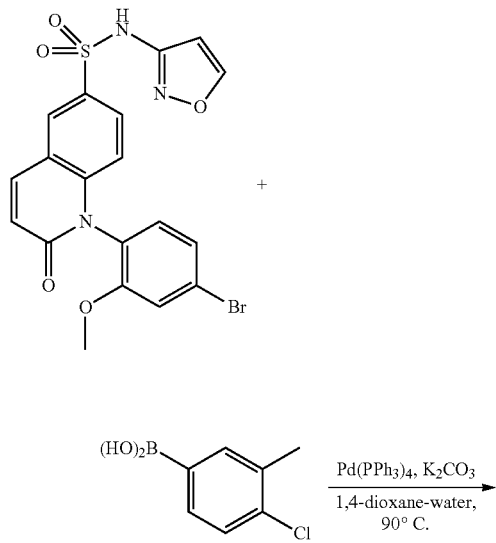

These compounds were prepared via method 72. A vial was charged with 1-(4-bromo-2-methoxyphenyl)-N-(isoxazol-3-yl)-2-oxo-1,2-dihydroquinoline-6-sulfonamide (293 mg, 0.615 mmol), (4-chloro-3-methylphenyl)boronic acid (136 mg, 0.800 mmol), potassium carbonate (255 mg, 1.845 mmol), and tetrakis(triphenylphosphine)palladium(0) (35.5 mg, 0.031 mmol). The vial was flushed with Ar (g), then 1,4-dioxane (2307 µl) and water (769 µl) were added. The vial was sealed and heated to 90° C. overnight. The layers were separated (via pipette), the aq. layer was extracted with EtOAc (5×), and the combined organic extracts were concentrated. The residue was purified by chromatography on silica gel (50-g Redi-Sep column, 25-g loading column, 20-70% EtOAc/Heptane) to give 107 mg of a white solid. This material subjected to chiral SFC purification (Chiralpak IC column eluted with 60% MeOH/$CO_2$) to give (M)-1-(4'-chloro-3-methoxy-3'-methyl-4-biphenylyl)-N-3-isoxazolyl-2-oxo-1,2-dihydro-6-quinolinesulfonamide as peak 1 and (P)-1-(4'-chloro-3-methoxy-3'-methyl-4-biphenylyl)-N-3-isoxazolyl-2-oxo-1,2-dihydro-6-quinolinesulfonamide as peak 2, both of which were isolated as off-white solids. Data for peak 1: $^1$H NMR (400 MHz, DMSO-$d_6$)=8.47 (d, J=1.5 Hz, 1H), 8.25 (d, J=1.9 Hz, 1H), 8.17 (d, J=9.6 Hz, 1H), 7.83 (d, J=1.9 Hz, 1H), 7.79 (dd, J=2.1, 8.9 Hz, 1H), 7.66 (dd, J=2.1, 8.3 Hz, 1H), 7.58-7.50 (m, 2H), 7.46-7.32 (m, 2H), 6.80-6.64 (m, 2H), 6.28 (d, J=1.6 Hz, 1H), 3.77 (s, 3H), 2.44 (s, 3H). m/z (ESI) 522.0 (M+H)$^+$. Data for peak 2: $^1$H NMR (400 MHz, DMSO-$d_6$)=8.47 (d, J=1.5 Hz, 1H), 8.25 (d, J=1.9 Hz, 1H), 8.17 (d, J=9.6 Hz, 1H), 7.83 (d, J=1.9 Hz, 1H), 7.79 (dd, J=2.1, 8.9 Hz, 1H), 7.66 (dd, J=2.1, 8.3 Hz, 1H), 7.58-7.50 (m, 2H), 7.46-7.32 (m, 2H), 6.80-6.64 (m, 2H), 6.28 (d, J=1.6 Hz, 1H), 3.77 (s, 3H), 2.44 (s, 3H). m/z (ESI) 522.0 (M+H)$^+$.

Examples 433 & 434

(P)-1-(3'-chloro-2-cyano-5'-fluoro-5-methoxy-4-biphenylyl)-N-3-isoxazolyl-2-oxo-1,2-dihydro-6-quinolinesulfonamide (433) and (M)-1-(3'-chloro-2-cyano-5'-fluoro-5-methoxy-4-biphenylyl)-N-3-isoxazolyl-2-oxo-1,2-dihydro-6-quinolinesulfonamide (434)

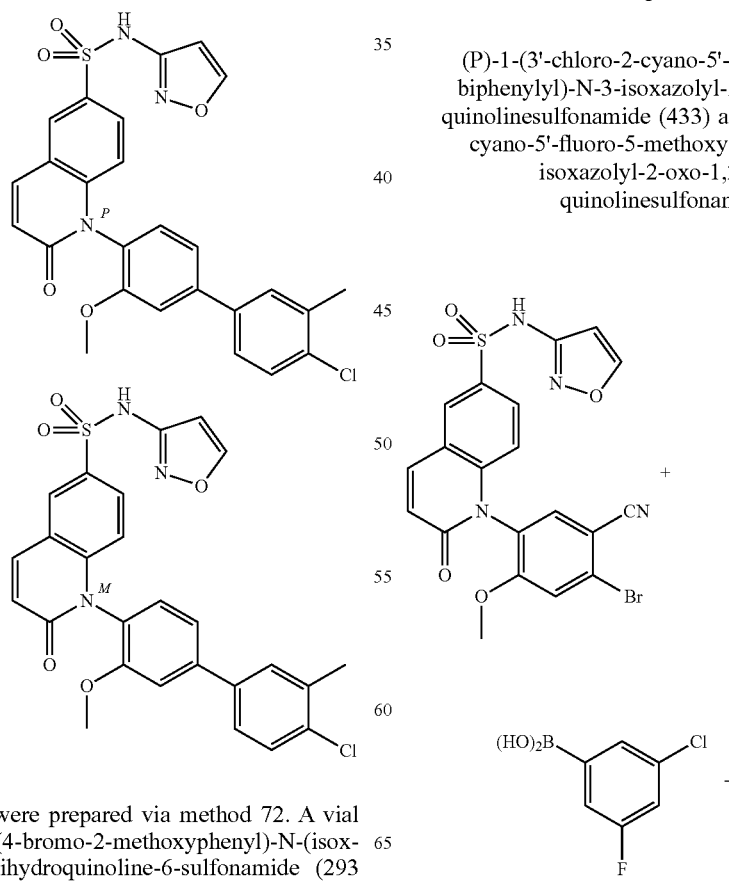

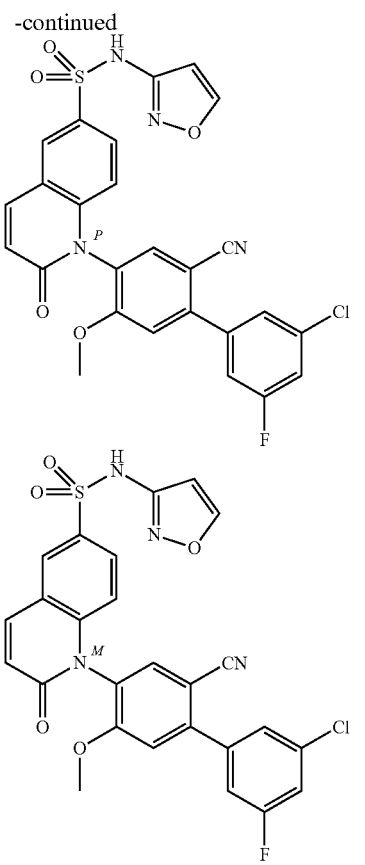

These compounds were prepared via method 72. A vial was charged with 1-(4-bromo-5-cyano-2-methoxyphenyl)-N-(isoxazol-3-yl)-2-oxo-1,2-dihydroquinoline-6-sulfonamide (178 mg, 0.320 mmol). (3-chloro-5-fluorophenyl)boronic acid (72.4 mg, 0.415 mmol), potassium carbonate (132 mg, 0.959 mmol), and tetrakis(triphenylphosphine) palladium(0 18.46 mg, 0.016 mmol). The vial was flushed with Ar (g), then 1,4-dioxane (1198 μl) and water (399 μl) were added. The vial was sealed and heated to 90° C. for 4 h. The layers were separated (via pipette), the aq. layer was acidified with 1N aq. HCl and then extracted with EtOAc (5×), and the combined organic extracts were concentrated. The residue was purified by chromatography on silica gel (40-g Redi-Sep column, 25-75% EtOAc/Heptane) to give 76 mg of an off-white solid. This material subjected to chiral SFC purification (Chiralpak AS-H column eluted with 35% MeOH/CO$_2$) to give (P)-1-(3'-chloro-2-cyano-5'-fluoro-5-methoxy-4-biphenylyl)-N-3-isoxazolyl-2-oxo-1,2-dihydro-6-quinolinesulfonamide as peak 1 and (M)-1-(3'-chloro-2-cyano-5'-fluoro-5-methoxy-4-biphenylyl)-N-3-isoxazolyl-2-oxo-1,2-dihydro-6-quinolinesulfonamide as peak 2, both as off-white solids. Data for peak 1: $^1$H NMR (400 MHz, DMSO-d$_6$)=8.65 (d, J=1.5 Hz, 1H), 8.36 (d, J=2.0 Hz, 1H), 8.24 (d, J=9.7 Hz, 1H), 8.12 (s, 1H), 7.83 (dd, J=2.1, 8.9 Hz, 1H), 7.71 (d, J=1.5 Hz, 1H), 7.67 (dd, J=1.3, 8.3 Hz, 2H), 7.57 (s, 1H), 6.82 (dd, J=4.4, 9.3 Hz, 2H), 6.40 (d, J=1.7 Hz, 1H), 3.85 (s, 3H). m/z (ESI) 551.2 (M+H)$^+$. Data for peak 2: $^1$H NMR (400 MHz, DMSO-d$_6$)=8.65 (d, J=1.5 Hz, 1H), 8.36 (d, J=2.0 Hz, 1H), 8.24 (d, J=9.7 Hz, 1H), 8.12 (s, 1H), 7.83 (dd, J=2.1, 8.9 Hz, 1H), 7.71 (d, J=1.5 Hz, 1H), 7.67 (dd, J=1.3, 8.3 Hz, 2H), 7.57 (s, 1H), 6.82 (dd, J=4.4, 9.3 Hz, 2H), 6.40 (d, J=1.7 Hz, 1H), 3.85 (s, 3H). m/z (ESI) 551.2 (M+H)$^+$.

Example 447

1-(5-chloro-6-(3,5-difluorophenyl)-2-methoxypyridin-3-yl)-N-(isoxazol-3-yl)-2-oxo-1,2-dihydroquinoline-6-sulfonamide

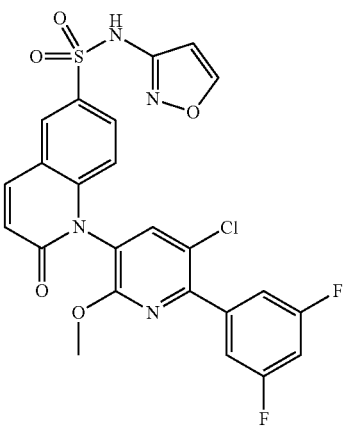 [SMILES: COc1nc(-c2cc(F)cc(F)c2)c(Cl)cc1-n1c(=O)ccc2cc(S(=O)(=O)Nc3ccon3)ccc21]

The title compound was prepared via method 84 except that (3,5-difluorophenyl)boronic acid was used instead of (3-fluorophenyl)boronic acid in to afford 1-(5-chloro-6-(3,5-difluorophenyl)-2-methoxypyridin-3-yl)-N-(isoxazol-3-yl)-2-oxo-1,2-dihydroquinoline-6-sulfonamide (0.035 g, 0.064 mmol, 30.0% yield) as a tan solid. $^1$H NMR (500 MHz, DMSO-d$_6$) δ=11.67 (br. s., 1H), 8.73 (d, J=1.6 Hz, 1H), 8.40 (d, J=1.9 Hz, 1H), 8.33 (s, 1H), 8.27 (d, J=9.7 Hz, 1H), 7.87 (dd, J=2.0, 9.0 Hz, 1H), 7.59 (d, J=6.2 Hz, 2H), 7.45 (t, J=9.3 Hz, 1H), 7.02 (d, J=9.0 Hz, 1H), 6.84 (d, J=9.7 Hz, 1H), 6.46 (d, J=1.6 Hz, 1H), 3.87-3.82 (m, 3H). m/z (ESI) 545.0 (M+H)$^+$.

Example 448

1-(5-chloro-6-(4-chloro-3-methylphenyl)-2-methoxypyridin-3-yl)-N-(isoxazol-3-yl)-2-oxo-1,2-dihydroquinoline-6-sulfonamide

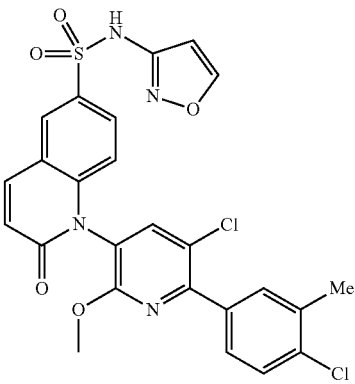 [SMILES: COc1nc(-c2ccc(Cl)c(C)c2)c(Cl)cc1-n1c(=O)ccc2cc(S(=O)(=O)Nc3ccon3)ccc21]

The title compound was prepared via method 84 except that (4-chloro-3-methylphenyl)boronic acid was used instead of (3-fluorophenyl)boronic acid in to afford 1-(5-chloro-6-(4-chloro-3-methylphenyl)-2-methoxypyridin-3-yl)-N-(isoxazol-3-yl)-2-oxo-1,2-dihydroquinoline-6-sulfonamide (0.042 g, 0.075 mmol, 35.2% yield) as a tan solid. ¹H NMR (500 MHz, DMSO-d₆) δ=11.67 (br. s., 1H), 8.73 (s, 1H), 8.40 (s, 1H), 8.30-8.23 (m, 2H), 7.87 (d, J=9.1 Hz, 1H), 7.82 (s, 1H), 7.70 (d, J=8.5 Hz, 1H), 7.60 (d, J=8.2 Hz, 1H), 7.03 (d, J=9.0 Hz, 1H), 6.84 (d, J=9.7 Hz, 1H), 6.45 (s, 1H), 3.82 (s, 3H). m/z (ESI) 559.0 (M+H)⁺.

Example 449

1-(5-chloro-6-(3-chloro-5-fluorophenyl)-2-methoxypyridin-3-yl)-N-(isoxazol-3-yl)-2-oxo-1,2-dihydroquinoline-6-sulfonamide

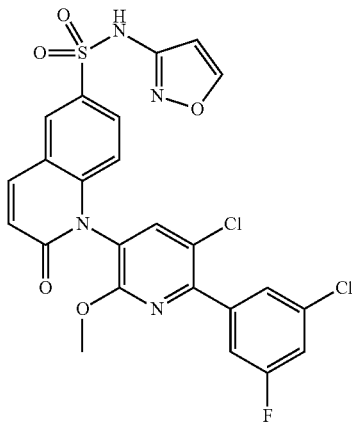 [SMILES: COc1nc(-c2cc(F)cc(Cl)c2)c(Cl)cc1-n1c(=O)ccc2cc(S(=O)(=O)Nc3ccon3)ccc21]

The title compound was prepared via method 84 except that (3-chloro-5-fluorophenyl)boronic acid was used instead of (3-fluorophenyl)boronic acid in to afford 1-(5-chloro-6-(3-chloro-5-fluorophenyl)-2-methoxypyridin-3-yl)-N-(isoxazol-3-yl)-2-oxo-1,2-dihydroquinoline-6-sulfonamide (0.040 g, 0.071 mmol, 33.3% yield) as a tan solid. ¹H NMR (500 MHz, DMSO-d₆) δ=11.65 (br. s., 1H), 8.73 (d, J=1.7 Hz, 1H), 8.35 (d, J=2.0 Hz, 1H), 8.20 (d, J=9.7 Hz, 1H), 7.92-7.80 (m, 2H), 6.97 (d, J=9.0 Hz, 1H), 6.78 (d, J=9.6 Hz, 1H), 6.44 (d, J=1.7 Hz, 1H), 4.68 (t, J=12.6 Hz, 4H), 3.75 (s, 3H). m/z (ESI) 563.0 (M+H)⁺.

Example 450

1-(4-cyclopentyl-5-fluoro-2-methoxyphenyl)-N-(isoxazol-3-yl)-2-oxo-1,2-dihydroquinoline-6-sulfonamide

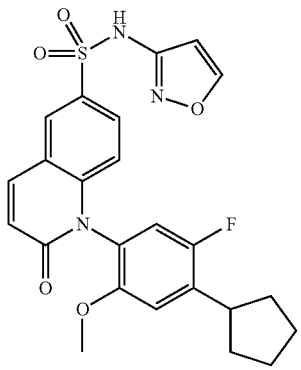 [SMILES: COc1cc(C2CCCC2)c(F)cc1-n1c(=O)ccc2cc(S(=O)(=O)Nc3ccon3)ccc21]

The title compound was prepared via method 86 except that cyclopentylzinc bromide, 0.5 M solution in THF was used instead of neopentylzinc bromide to afford 1-(4-cyclopentyl-5-fluoro-2-methoxyphenyl)-N-(isoxazol-3-yl)-2-oxo-1,2-dihydroquinoline-6-sulfonamide (0.033 g, 0.068 mmol, 33.7% yield) as an off-white solid. ¹H NMR (400 MHz, DMSO-d₆) δ=11.66 (s, 1H), 8.73 (d, J=1.8 Hz, 1H), 8.35 (d, J=2.2 Hz, 1H), 8.20 (d, J=9.6 Hz, 1H), 7.85 (dd, J=2.2, 9.0 Hz, 1H), 7.27 (d, J=10.1 Hz, 1H), 7.19 (d, J=6.6 Hz, 1H), 6.78 (dd, J=3.1, 9.3 Hz, 2H), 6.44 (d, J=1.8 Hz, 1H), 3.66 (s, 3H), 3.30-3.20 (m, 1H), 2.07 (d, J=5.0 Hz, 2H), 1.85 (br. s., 2H), 1.70 (br. s., 4H). m/z (ESI) 484.1 (M+H)⁺.

Examples 455 & 456

(P)-1-(2-chloro-3'-fluoro-5-methoxy-[1,1'-biphenyl]-4-yl)-N-(isoxazol-3-yl)-2-oxo-1,2-dihydroquinoline-6-sulfonamide (455) and (M)-1-(2-chloro-3'-fluoro-5-methoxy-[1,1'-biphenyl]-4-yl)-N-(isoxazol-3-yl)-2-oxo-1,2-dihydroquinoline-6-sulfonamide (456)

These compounds were prepared via method 65 using 3-fluorophenyl boronic acid as the boronic acid. The racemic product was separated via chiral SFC on a Chiralpak AS-H column (30% MeOH/70% CO₂) to give (P)-1-(2-chloro-3'-fluoro-5-methoxy-[1,1'-biphenyl]-4-yl)-N-(isoxazol-3-yl)-2-oxo-1,2-dihydroquinoline-6-sulfonamide as peak 1 and (M)-1-(2-chloro-3'-fluoro-5-methoxy-[1,1'-biphenyl]-4-yl)-N-(isoxazol-3-yl)-2-oxo-1,2-dihydroquinoline-6-sulfonamide as peak 2. Both materials were obtained as white solids. Data for peak 1: ¹H NMR (400 MHz, DMSO-d₆) δ=11.68 (s, 1H), 8.74 (d, J=1.76 Hz, 1H), 8.39 (d, J=2.25 Hz, 1H), 8.24 (d, J=9.49 Hz, 1H), 7.88 (dd, J=8.95, 2.20 Hz, 1H), 7.70 (s, 1H), 7.56-7.63 (m, 1H), 7.42-7.47 (m, 2H), 7.30-7.38 (m, 2H), 6.88 (d, J=9.00 Hz, 1H), 6.83 (d, J=9.68 Hz, 1H) 6.46 (d, J=1.86 Hz, 1H), 3.74 (s, 3H). m/z (ESI) 526.0 (M+H)⁺. Data for peak 2: ¹H NMR (400 MHz, DMSO-d₆) δ=11.68 (s, 1H), 8.73 (d, J=1.76 Hz, 1H), 8.38 (d, J=2.15 Hz, 1H), 8.24 (d, J=9.49 Hz, 1H), 7.88 (dd, J=8.95, 2.20 Hz, 1H), 7.70 (s, 1H), 7.60 (td, J=8.09, 6.41 Hz, 1H), 7.43-7.48 (m, 2H), 7.30-7.37 (m, 2H), 6.88 (d, J=9.00 Hz, 1H), 6.83 (d, J=9.68 Hz, 1H), 6.45 (d, J=1.76 Hz, 1H), 3.74 (s, 3H). m/z (ESI) 526.0 (M+H)⁺.

Examples 457 & 458

(P)-1-(2-chloro-3',5'-difluoro-5-methoxy-[1,1'-biphenyl]-4-yl)-N-(isoxazol-3-yl)-2-oxo-1,2-dihydroquinoline-6-sulfonamide (457) and (M)-1-(2-chloro-3',5'-difluoro-5-methoxy-[1,1'-biphenyl]-4-yl)-N-(isoxazol-3-yl)-2-oxo-1,2-dihydroquinoline-6-sulfonamide (458)

These compounds were prepared via method 65 using (3,5-difluorophenyl)boronic acid as the boronic acid. The racemic product was separated via chiral SFC on a Chiralpak AS-H column (25% MeOH w/0.2% diethylamine/75% CO₂) to give (P)-1-(2-chloro-3',5'-difluoro-5-methoxy-[1,1'-biphenyl]-4-yl)-N-(isoxazol-3-yl)-2-oxo-1,2-dihydroquinoline-6-sulfonamide as peak 1 and (M)-1-(2-chloro-3',5'-difluoro-5-methoxy-[1,1'-biphenyl]-4-yl)-N-(isoxazol-3-yl)-2-oxo-1,2-dihydroquinoline-6-sulfonamide as peak 2. Both materials were obtained as white solids. Data for peak 1: ¹H NMR (400 MHz, DMSO-d₆) δ=11.67 (s, 1H), 8.74 (d, J=1.76 Hz, 1H), 8.39 (d, J=2.15 Hz, 1H), 8.24 (d, J=9.49 Hz, 1H), 7.88 (dd, J=9.00, 2.25 Hz, 1H), 7.72 (s, 1H), 7.34-7.44 (m, 4H), 6.85 (dd, J=15.06, 9.29 Hz, 2H), 6.46 (d, J=1.76

Hz, 1H), 3.72-3.78 (m, 3H). m/z (ESI) 544.1 (M+H)⁺. Data for peak 2: ¹H NMR (400 MHz, DMSO-d₆) δ=11.67 (s, 1H), 8.74 (d, J=1.66 Hz, 1H), 8.39 (d, J=2.15 Hz, 1H), 8.24 (d, J=9.68 Hz, 1H), 7.88 (dd, J=8.95, 2.10 Hz, 1H), 7.72 (s, 1H), 7.35-7.41 (m, 4H), 6.81-6.89 (m, 2H), 6.46 (d, J=1.66 Hz, 1H), 3.74 (s, 3H). m/z (ESI) 544.1 (M+H)⁺.

Examples 459 & 460

(P)-1-(2,3'-dichloro-5-methoxy-[1,1'-biphenyl]-4-yl)-N-(isoxazol-3-yl)-2-oxo-1,2-dihydroquinoline-6-sulfonamide (459) and (M)-1-(2,3'-dichloro-5-methoxy-[1,1'-biphenyl]-4-yl)-N-(isoxazol-3-yl)-2-oxo-1,2-dihydroquinoline-6-sulfonamide (460)

These compounds were prepared via method 65 using (3-chlorophenyl)boronic acid as the boronic acid. The racemic product was separated via chiral SFC on a Chiralpak AS-H column (30% MeOH/70% CO₂) to give (P)-1-(2,3'-dichloro-5-methoxy-[1,1'-biphenyl]-4-yl)-N-(isoxazol-3-yl)-2-oxo-1,2-dihydroquinoline-6-sulfonamides peak 1 and (M)-1-(2,3'-dichloro-5-methoxy-[1,1'-biphenyl]-4-yl)-N-(isoxazol-3-yl)-2-oxo-1,2-dihydroquinoline-6-sulfonamide as peak 2. Both materials were obtained as white solids. Data for peak 1: ¹H NMR (400 MHz, DMSO-d₆) δ=11.68 (br. s., 1H), 8.73 (d, J=1.76 Hz, 1H), 8.38 (d, J=2.15 Hz, 1H), 8.24 (d, J=9.59 Hz, 1H), 7.87 (dd, J=2.20, 8.95 Hz, 1H), 7.70 (s, 1H), 7.64-7.67 (m, 1H), 7.55-7.59 (m, 3H), 7.35-7.39 (m, 1H), 6.88 (d, J=8.90 Hz, 1H), 6.83 (d, J=9.59 Hz, 1H), 6.45 (d, J=1.86 Hz, 1H), 3.74 (s, 3H). m/z (ESI) 542.0 (M+H)⁺. Data for peak 2: ¹H NMR (400 MHz, DMSO-d₆) δ 11.69 (br. s., 1H), 8.72 (d, J=1.76 Hz, 1H), 8.38 (d, J=2.25 Hz, 1H), 8.24 (d, J=9.59 Hz, 1H), 7.87 (dd, J=2.25, 9.00 Hz, 1H), 7.70 (s, 1H), 7.64-7.66 (m, 1H), 7.56-7.59 (m, 3H), 7.37 (s, 1H), 6.88 (d, J=9.00 Hz, 1H), 6.82 (d, J=9.68 Hz, 1H), 6.45 (d, J=1.76 Hz, 1H), 3.74 (s, 3H). m/z (ESI) 542.0 (M+H)⁺.

Examples 461 & 462

(P)-1-(2,3'-dichloro-5'-fluoro-5-methoxy-[1,1'-biphenyl]-4-yl)-N-(isoxazol-3-yl)-2-oxo-1,2-dihydroquinoline-6-sulfonamide (461) and (M)-1-(2,3'-dichloro-5'-fluoro-5-methoxy-[1,1'-biphenyl]-4-yl)-N-(isoxazol-3-yl)-2-oxo-1,2-dihydroquinoline-6-sulfonamide (462)

These compounds were prepared via method 65 using (3-chloro-5-fluorophenyl)boronic acid as the boronic acid. The racemic product was separated via chiral SFC on a Chiralpak AS-H column (25% MeOH/75% CO₂) to give (P)-1-(2,3'-dichloro-5'-fluoro-5-methoxy-[1,1'-biphenyl]-4-yl)-N-(isoxazol-3-yl)-2-oxo-1,2-dihydroquinoline-6-sulfonamide as peak 1 and (M)-1-(2,3'-dichloro-5'-fluoro-5-methoxy-[1,1'-biphenyl]-4-yl)-N-(isoxazol-3-yl)-2-oxo-1,2-dihydroquinoline-6-sulfonamide as peak 2. Both materials were obtained as white solids. Data for peak 1: ¹H NMR (400 MHz, DMSO-d₆) δ=11.68 (br. s., 1H), 8.68 (d, J=1.57 Hz, 1H), 8.36 (d, J=2.15 Hz, 1H), 8.23 (d, J=9.59 Hz, 1H), 7.85 (dd, J=2.15, 8.90 Hz, 1H), 7.72 (s, 1H), 7.59 (td, J=2.15, 8.80 Hz, 1H), 7.54 (t, J=1.52 Hz, 1H), 7.49 (ddd, J=1.47, 2.40, 9.44 Hz, 1H), 7.40 (s, 1H), 6.79-6.86 (m, 2H), 6.42 (d, J=1.76 Hz, 1H), 3.74 (s, 3H). m/z (ESI) 561.0 (M+H)⁺. Data for peak 2: ¹H NMR (400 MHz, DMSO-d₆) δ=11.68 (br. s., 1H), 8.71 (d, J=1.76 Hz, 1H), 8.38 (d, J=2.25 Hz, 1H), 8.24 (d, J=9.59 Hz, 1H), 7.86 (dd, J=2.25, 9.00 Hz, 1H), 7.71 (s, 1H), 7.59 (td, J=2.15, 8.80 Hz, 1H), 7.54 (t, J=1.52 Hz, 1H), 7.49 (ddd, J=1.47, 2.37, 9.46 Hz, 1H), 7.41 (s, 1H), 6.80-6.87 (m, 2H), 6.44 (d, J=1.76 Hz, 1H), 3.72-3.75 (m, 3H). m/z (ESI) 561.0 (M+H)⁺.

Examples 463 & 464

(P)-1-(2-methoxy-4-(trifluoromethyl)phenyl)-2-oxo-N-(thiazol-2-yl)-1,2-dihydroquinoline-6-sulfonamide (463) and (M)-1-(2-methoxy-4-(trifluoromethyl)phenyl)-2-oxo-N-(thiazol-2-yl)-1,2-dihydroquinoline-6-sulfonamide (464)

These compounds were prepared via method 42. The racemic product was separated via chiral SFC on a Whelk-O column (40% methanol w/0.2% diethylamine/60% CO₂) to give (P)-1-(2-methoxy-4-(trifluoromethyl)phenyl)-2-oxo-N-(thiazol-2-yl)-1,2-dihydroquinoline-6-sulfonamide as peak 1 and (M)-1-(2-methoxy-4-(trifluoromethyl)phenyl)-2-oxo-N-(thiazol-2-yl)-1,2-dihydroquinoline-6-sulfonamide as peak 2. Both materials were obtained as white solids. Data for peak 1: ¹H NMR (400 MHz, DMSO-d₆) δ=8.15-8.24 (m, 2H), 7.76 (dd, J=1.76, 8.90 Hz, 1H), 7.50-7.63 (m, 3H), 7.04 (d, J=4.11 Hz, 1H), 6.73 (d, J=9.68 Hz, 1H), 6.56-6.63 (m, 2H), 3.77 (s, 3H). m/z (ESI) 482.2 (M+H)⁺. Data for peak 2: ¹H NMR (400 MHz, DMSO-d₆) δ=8.15-8.23 (m, 2H), 7.76 (dd, J=1.91, 8.85 Hz, 1H), 7.50-7.63 (m, 3H), 7.03 (d, J=4.01 Hz, 1H), 6.72 (d, J=9.59 Hz, 1H), 6.56-6.60 (m, 2H), 3.77 (s, 3H). m/z (ESI) 482.2 (M+H)⁺.

Examples 465 & 466

(P)-1-(2-chloro-3'-fluoro-5-methoxy-[1,1'-biphenyl]-4-yl)-2-oxo-N-(pyrimidin-4-yl)-1,2-dihydroquinoline-6-sulfonamide (465) and (M)-1-(2-chloro-3'-fluoro-5-methoxy-[1,1'-biphenyl]-4-yl)-2-oxo-N-(pyrimidin-4-yl)-1,2-dihydroquinoline-6-sulfonamide (466)

1-(2-Chloro-3'-fluoro-5-methoxy-[1,1'-biphenyl]-4-yl)-2-oxo-N-(pyrimidin-4-yl)-1,2-dihydroquinoline-6-sulfonamide was prepared in an analogous manner to that of method 2, step 1, except that pyrimidin-4-amine was used in place of isoxazol-3-amine. The racemic product was separated via chiral SFC on a Chiralpak OJ-H column (20% methanol/80% CO₂) to give (M)-1-(2-chloro-3'-fluoro-5-methoxy-[1,1'-biphenyl]-4-yl)-2-oxo-N-(pyrimidin-4-yl)-1,2-dihydroquinoline-6-sulfonamide as peak 1 and (P)-1-(2-chloro-3'-fluoro-5-methoxy-[1,1'-biphenyl]-4-yl)-2-oxo-N-(pyrimidin-4-yl)-1,2-dihydroquinoline-6-sulfonamide as peak 2. Both materials were obtained as white solids. Data for peak 1: ¹H NMR (400 MHz, DMSO-d₆) δ=12.50-12.83 (br. s., 1H), 8.58 (br. s., 1H), 8.41 (br. s., 1H), 8.24 (d, J=9.68 Hz, 2H), 7.93 (d, J=7.43 Hz, 1H), 7.68 (s, 1H), 7.59 (dt, J=6.26, 8.02 Hz, 2H), 7.42-7.49 (m, 1H), 7.29-7.38 (m, 2H), 6.96 (br. s., 1H), 6.76-6.85 (m, 2H), 3.73 (s, 3H). m/z (ESI) 537.0 (M+H)⁺. Data for peak 2: ¹H NMR (500 MHz, DMSO-d6) δ=12.55-12.87 (br s, 1H), 8.61 (br. s., 1H), 8.43 (br. s., 1H), 8.30 (br. s., 1H), 8.24 (d, J=9.67 Hz, 1H), 7.94 (d, J=7.53 Hz, 1H), 7.67 (s, 1H), 7.53-7.63 (m, 1H), 7.43 (d, J=8.04 Hz, 2H), 7.28-7.38 (m, 2H), 7.02 (br. s., 1H), 6.81 (dd, J=9.41, 12.72 Hz, 2H), 3.73 (s, 3H). m/z (ESI) 537.0 (M+H)⁺.

Examples 467 & 468

(P)-1-(2-chloro-3'-fluoro-5-methoxy-[1,1'-biphenyl]-4-yl)-2-oxo-N-(pyridazin-3-yl)-1,2-dihydroquinoline-6-sulfonamide (467) and (M)-1-(2-chloro-3'-fluoro-5-methoxy-[1,1'-biphenyl]-4-yl)-2-oxo-N-(pyridazin-3-yl)-1,2-dihydroquinoline-6-sulfonamide (468)

1-(2-Chloro-3'-fluoro-5-methoxy-[1,1'-biphenyl]-4-yl)-2-oxo-N-(pyridazin-3-yl)-1,2-dihydroquinoline-6-sulfonamide was prepared in an analogous manner to that of method 2, step 1, except that pyridazin-3-amine was used in place of isoxazol-3-amine. The racemic product was separated via chiral SFC on a Chiralpak OJ-H column (20% methanol/80% CO$_2$) to give (M)-1-(2-chloro-3'-fluoro-5-methoxy-[1,1'-biphenyl]-4-yl)-2-oxo-N-(pyrimidin-4-yl)-1,2-dihydroquinoline-6-sulfonamide as peak 1 and (P)-1-(2-chloro-3'-fluoro-5-methoxy-[1,1'-biphenyl]-4-yl)-2-oxo-N-(pyrimidin-4-yl)-1,2-dihydroquinoline-6-sulfonamide as peak 2. Both materials were obtained as white solids. Data for peak 1: $^1$H NMR (400 MHz, DMSO-d$_6$) δ=12.50-12.83 (br. s., 1H), 8.58 (br. s., 1H), 8.41 (br. s., 1H), 8.24 (d, J=9.68 Hz, 2H), 7.93 (d, J=7.43 Hz, 1H), 7.68 (s, 1H), 7.59 (dt, J=6.26, 8.02 Hz, 2H), 7.42-7.49 (m, 1H), 7.29-7.38 (m, 2H), 6.96 (br. s., 1H), 6.76-6.85 (m, 2H), 3.73 (s, 3H). m/z (ESI) 537.0 (M+H)$^+$. Data for peak 2: $^1$H NMR (500 MHz, DMSO-d6) δ=12.55-12.87 (br s, 1H), 8.61 (br. s., 1H), 8.43 (br. s., 1H), 8.30 (br. s., 1H), 8.24 (d, J=9.67 Hz, 1H), 7.94 (d, J=7.53 Hz, 1H), 7.67 (s, 1H), 7.53-7.63 (m, 1H), 7.43 (d, J=8.04 Hz, 2H), 7.28-7.38 (m, 2H), 7.02 (br. s., 1H), 6.81 (dd, J=9.41, 12.72 Hz, 2H), 3.73 (s, 3H). m/z (ESI) 537.0 (M+H)$^+$.

Examples 469 & 470

(P)-1-(4'-chloro-2-fluoro-5-methoxy-3'-methyl-[1,1'-biphenyl]-4-yl)-N-(isoxazol-3-yl)-2-oxo-1,2-dihydroquinoline-6-sulfonamide (469) and (M)-1-(4'-chloro-2-fluoro-5-methoxy-3'-methyl-[1,1'-biphenyl]-4-yl)-N-(isoxazol-3-yl)-2-oxo-1,2-dihydroquinoline-6-sulfonamide (470)

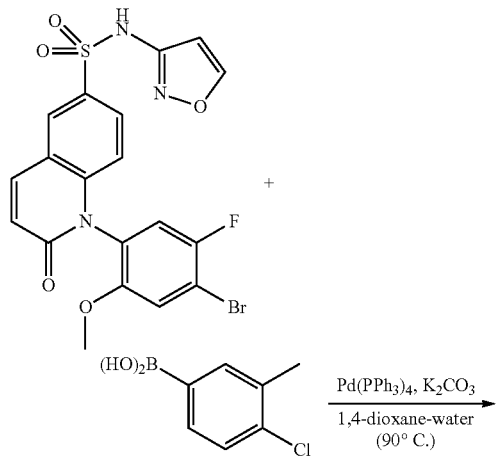

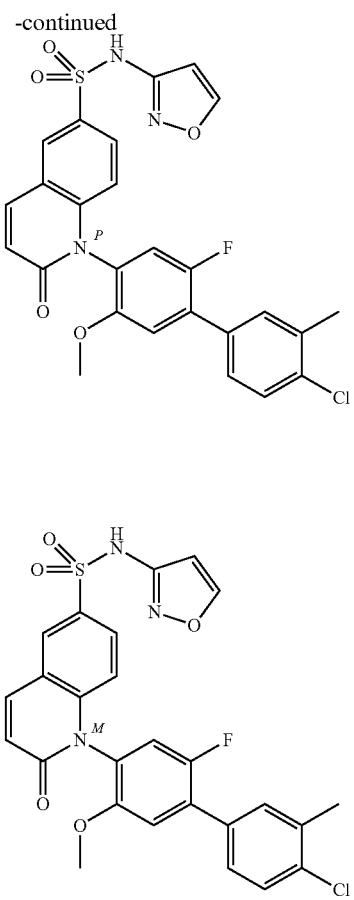

These compounds were made via method 65. A vial was charged with 1-(4-bromo-5-fluoro-2-methoxyphenyl)-N-(isoxazol-3-yl)-2-oxo-1,2-dihydroquinoline-6-sulfonamide (32.00 g, 64.7 mmol). (4-chloro-3-methylphenyl)boronic acid (16.55 g, 97 mmol), potassium carbonate (26.8 g, 194 mmol), and Pd(Ph$_3$P)$_4$ (7.48 g, 6.47 mmol). The vial was flushed with Ar (g), then 1,4-dioxane (243 mL) and water (81 mL) were added. The vial was sealed and heated to 90° C. for 2.5 h. The mixture was cooled and extracted with EtOAc (5×), and the combined organic extracts were concentrated. The residue was triturated with diethylether (600 mL) overnight, and filtered to give 30 g of a light yellow solid. This material was purified by chiral SFC on Chiralpak AS-H column (40% MeOH/60% CO$_2$) to give (P)-1-(4'-chloro-2-fluoro-5-methoxy-3'-methyl-[1,1'-biphenyl]-4-yl)-N-(isoxazol-3-yl)-2-oxo-1,2-dihydroquinoline-6-sulfonamide as peak 1 and (M)-1-(4'-chloro-2-fluoro-5-methoxy-3'-methyl-[1,1'-biphenyl]-4-yl)-N-(isoxazol-3-yl)-2-oxo-1,2-dihydroquinoline-6-sulfonamide as peak 2, both as off-white solids. Data for peak 1: $^1$H NMR (400 MHz, DMSO-d$_6$) δ 11.67 (br. s., 1H), 8.74 (d, J=1.76 Hz, 1H), 8.38 (d, J=2.15 Hz, 1H), 8.24 (d, J=9.68 Hz, 1H), 7.87 (dd, J=2.15, 9.00 Hz, 1H), 7.70 (s, 1H), 7.49-7.62 (m, 3H), 7.39 (d, J=6.94 Hz, 1H), 6.79-6.92 (m, 2H), 6.46 (d, J=1.86 Hz, 1H), 3.74 (s, 3H), 2.45 (s, 3H). m/z (ESI) 540.0 (M+H)$^+$. Data for peak 2: $^1$H NMR (500 MHz, DMSO-d$_6$) δ 11.63 (br. S., 1H), 8.71 (d, J=1.60 Hz, 1H), 8.37 (d, J=1.92 Hz, 1H), 8.23 (d, J=9.67 Hz, 1H), 7.85 (dd, J=2.03, 8.98 Hz, 1H), 7.66 (s, 1H), 7.52-7.62 (m, 3H), 7.47 (d, J=6.89 Hz, 1H), 6.77-6.90 (m, 2H), 6.44 (d, J=1.55 Hz, 1H), 3.75 (s, 3H), 2.50 (br. s., 3H). m/z (ESI) 540.0 (M+H)$^+$.

Examples 471 & 472

(P)-1-(2,4'-dichloro-5-methoxy-3'-methyl-[1,1'-biphenyl]-4-yl)-N-(isoxazol-3-yl)-2-oxo-1,2-dihydroquinoline-6-sulfonamide (471) and (M)-1-(2,4'-dichloro-5-methoxy-3'-methyl-[1,1'-biphenyl]-4-yl)-N-(isoxazol-3-yl)-2-oxo-1,2-dihydroquinoline-6-sulfonamide (472)

The following compounds were made via method 65. A vial was charged with 1-(4-bromo-5-chloro-2-methoxyphenyl)-N-(isoxazol-3-yl)-2-oxo-1,2-dihydroquinoline-6-sulfonamide (0.300 g, 0.587 mmol), (4-chloro-3-methylphenyl) boronic acid (0.150 g, 0.881 mmol), potassium carbonate (0.244 g, 1.762 mmol), and Pd(Ph$_3$P)$_4$ (0.068 g, 0.059 mmol). The vial was flushed with Ar (g), then 1,4-dioxane (2.2 mL) and water (0.73 mL) were added. The vial was sealed and heated to 90° C. for 2 h. The mixture was cooled, quenched with NH$_4$Cl and extracted with EtOAc (5×). The combined organic extracts were concentrated, dried over magnesium sulfate and concentrated. The residue was purified by chromatography on silica gel (40-g Ultra SNAP column, 25-g silica gel loading column, 0-50% EtOAc/Heptane) to give 1-(2,4'-dichloro-5-methoxy-3'-methyl-[1,1'-biphenyl]-4-yl)-N-(isoxazol-3-yl)-2-oxo-1,2-dihydroquinoline-6-sulfonamide. This material was purified by chiral SFC on Chiralpak AS-H column (25% MeOH/75% CO$_2$) to give (P)-1-(2,4'-dichloro-5-methoxy-3'-methyl-[1,1'-biphenyl]-4-yl)-N-(isoxazol-3-yl)-2-oxo-1,2-dihydroquinoline-6-sulfonamide as peak 1 and (M)-1-(2,4'-dichloro-5-methoxy-3'-methyl-[1,1'-biphenyl]-4-yl)-N-(isoxazol-3-yl)-2-oxo-1,2-dihydroquinoline-6-sulfonamide as peak 2, both as off-white solids. Data for peak 1: $^1$H NMR (400 MHz, DMSO-d$_6$) δ=11.68 (br. s., 1H), 8.66 (s, 1H), 8.35 (d, J=1.96 Hz, 1H), 8.23 (d, J=9.68 Hz, 1H), 7.86 (dd, J=2.10, 8.95 Hz, 1H), 7.67 (s, 1H), 7.55-7.61 (m, 2H), 7.44 (dd, J=1.71, 8.27 Hz, 1H), 7.32 (s, 1H), 6.77-6.88 (m, 2H), 6.41 (d, J=1.66 Hz, 1H), 3.73 (s, 3H), 2.44 (s, 3H). m/z (ESI) 557.1 (M+H)$^+$. Data for peak 2: $^1$H NMR (400 MHz, DMSO-d$_6$) δ=11.68 (br. s., 1H), 8.63 (br. s., 1H), 8.33 (d, J=1.86 Hz, 1H), 8.22 (d, J=9.68 Hz, 1H), 7.82-7.88 (m, 1H), 7.67 (s, 1H), 7.57-7.60 (m, 2H), 7.41-7.47 (m, 1H), 7.32 (s, 1H), 6.77-6.85 (m, 2H), 6.39 (s, 1H), 3.72 (s, 3H), 2.44 (s, 3H). m/z (ESI) 557.1 (M+H)$^+$.

Examples 473 & 474

(P)-1-(4-bromo-5-chloro-2-methoxyphenyl)-N-(isoxazol-3-yl)-2-oxo-1,2-dihydroquinoline-6-sulfonamide (473) and (M)-1-(4-bromo-5-chloro-2-methoxyphenyl)-N-(isoxazol-3-yl)-2-oxo-1,2-dihydroquinoline-6-sulfonamide (474)

These compounds were prepared via method 97 using 1-bromo-2-chloro-4-iodo-5-methoxybenzene as the coupling partner in step 1. Racemic 1-(4-bromo-5-chloro-2-methoxyphenyl)-N-(isoxazol-3-yl)-2-oxo-1,2-dihydroquinoline-6-sulfonamide was subjected to chiral separation by SFC on a Chiralpak AS-H column (30% MeOH/70% CO$_2$) to give (P)-1-(4-bromo-5-chloro-2-methoxyphenyl)-N-(isoxazol-3-yl)-2-oxo-1,2-dihydroquinoline-6-sulfonamide as peak 1 and (M)-1-(4-bromo-5-chloro-2-methoxyphenyl)-N-(isoxazol-3-yl)-2-oxo-1,2-dihydroquinoline-6-sulfonamide as peak 2. Both peaks were isolated as off-white solids. Data for peak 1: $^1$H NMR (400 MHz, DMSO-d$_6$) δ=11.66 (br. s., 1H), 8.69 (d, J=1.47 Hz, 1H), 8.35 (d, J=2.15 Hz, 1H), 8.22 (d, J=9.59 Hz, 1H), 7.83 (dd, J=8.95, 2.20 Hz, 1H), 7.77 (s, 1H) 7.70-7.74 (m, 1H), 6.85 (d, J=8.90 Hz, 1H), 6.79 (d, J=9.59 Hz, 1H), 6.42 (d, J=1.76 Hz, 1H), 3.72 (s, 3H). m/z (ESI) 511.0 (M+H)$^+$. Data for peak 2: $^1$H NMR (400 MHz, DMSO-d$_6$) δ=11.67 (br. s., 1H), 8.69 (d, J=1.66 Hz, 1H), 8.35 (d, J=2.15 Hz, 1H), 8.22 (d, J=9.59 Hz, 1H), 7.83 (dd, J=8.95, 2.20 Hz, 1H), 7.76 (s, 1H), 7.73 (s, 1H), 6.85 (d, J=8.90 Hz, 1H), 6.79 (d, J=9.68 Hz, 1H), 6.42 (d, J=1.76 Hz, 1H), 3.72 (s, 3H). m/z (ESI) 511.0 (M+H)$^+$.

Examples 475 & 476

(P)-1-(3'-chloro-2-fluoro-5-methoxy-4-biphenylyl)-N-3-isoxazolyl-2-oxo-1,2-dihydro-6-quinolinesulfonamide (475) and (M)-1-(3'-chloro-2-fluoro-5-methoxy-4-biphenylyl)-N-3-isoxazolyl-2-oxo-1,2-dihydro-6-quinolinesulfonamide (476)

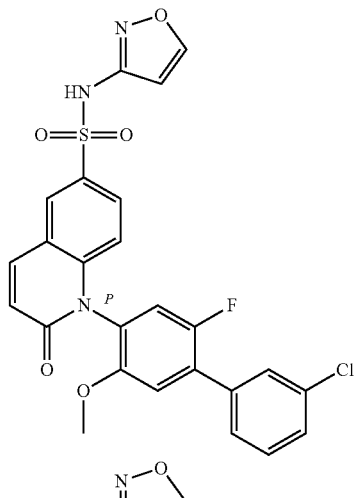

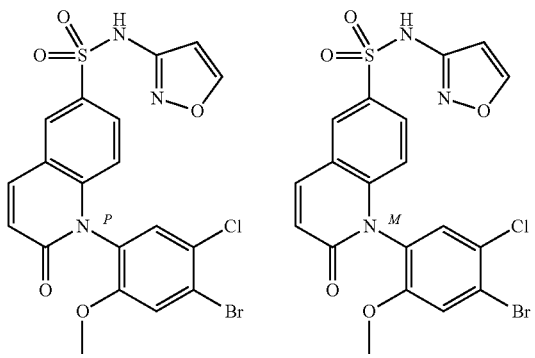

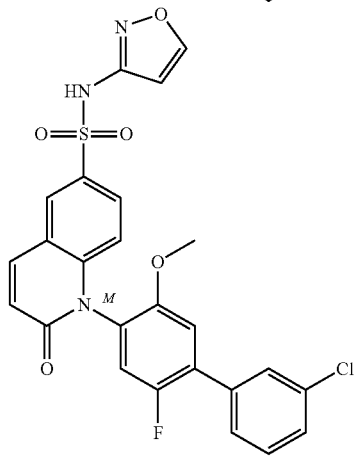

(P)-1-(3'-chloro-2-fluoro-5-methoxy-4-biphenylyl)-N-3-isoxazolyl-2-oxo-1,2-dihydro-6-quinolinesulfonamide and (M)-1-(3'-chloro-2-fluoro-5-methoxy-4-biphenylyl)-N-3-isoxazolyl-2-oxo-1,2-dihydro-6-quinolinesulfonamide were prepared via method 99, except using 3-chlorophenylboronic acid instead of 3-(trifluoromethyl)benzeneboronic acid. The racemic 1-(3'-chloro-2-fluoro-5-methoxy-4-biphenylyl)-N-3-isoxazolyl-2-oxo-1,2-dihydro-6-quinolinesulfonamide was subjected to chiral separation by SFC on an AS-H column (30% MeOH/70% $CO_2$) to give (P)-1-(3'-chloro-2-fluoro-5-methoxy-4-biphenylyl)-N-3-isoxazolyl-2-oxo-1,2-dihydro-6-quinolinesulfonamide as peak 1 and (M)-1-(3'-chloro-2-fluoro-5-methoxy-4-biphenylyl)-N-3-isoxazolyl-2-oxo-1,2-dihydro-6-quinolinesulfonamide as peak 2. Data for peak 1: $^1$H NMR (500 MHz, DMSO-$d_6$) δ 11.60-11.73 (br s, 1H), 8.70 (s, 1H), 8.36 (s, 1H), 8.22 (d, J=9.78 Hz, 1H), 7.83-7.92 (m, 1H), 7.77 (s, 1H), 7.67 (d, J=7.16 Hz, 1H), 7.49-7.63 (m, 3H), 7.43 (d, J=6.79 Hz, 1H), 6.86 (d, J=8.92 Hz, 1H), 6.81 (d, J=9.56 Hz, 1H), 6.43 (s, 1H), 3.74 (s, 3H). m/z (ESI) 524.1 (M–H)⁻. Data for peak 2: $^1$H NMR (500 MHz, DMSO-$d_6$) δ 11.53-11.78 (br s, 1H), 8.67 (s, 1H), 8.35 (d, J=1.87 Hz, 1H), 8.22 (d, J=9.72 Hz, 1H), 7.85 (dd, J=2.00, 9.00 Hz, 1H), 7.77 (s, 1H), 7.67 (d, J=7.00 Hz, 1H), 7.49-7.63 (m, 3H), 7.43 (d, J=6.89 Hz, 1H), 6.85 (d, J=8.92 Hz, 1H), 6.80 (d, J=9.67 Hz, 1H), 6.42 (s, 1H), 3.74 (s, 3H). m/z (ESI) 524.1 (M–H)⁻.

Examples 477 & 478

(P)-1-(3'-chloro-2,5'-difluoro-5-methoxy-4-biphenylyl)-N-3-isoxazolyl-2-oxo-1,2-dihydro-6-quinolinesulfonamide (477) and (M)-1-(3'-chloro-2,5'-difluoro-5-methoxy-4-biphenylyl)-N-3-isoxazolyl-2-oxo-1,2-dihydro-6-quinolinesulfonamide (478)

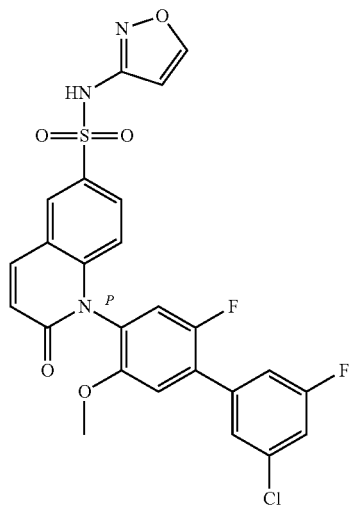

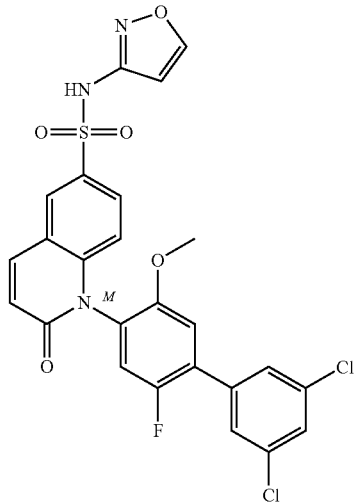

(P)-1-(3'-chloro-2,5'-difluoro-5-methoxy-4-biphenylyl)-N-3-isoxazolyl-2-oxo-1,2-dihydro-6-quinolinesulfonamide and (M)-1-(3'-chloro-2,5'-difluoro-5-methoxy-4-biphenylyl)-N-3-isoxazolyl-2-oxo-1,2-dihydro-6-quinolinesulfonamide were prepared via method 99, except using (3-chloro-5-fluorophenyl)boronic acid instead of 3-(trifluoromethyl)benzeneboronic acid. The racemic 1-(3'-chloro-2,5'-difluoro-5-methoxy-4-biphenylyl)-N-3-isoxazolyl-2-oxo-1,2-dihydro-6-quinolinesulfonamide was subjected to chiral separation by SFC an AS-H column (25% MeOH/75% $CO_2$) to give (P)-1-(3'-chloro-2,5'-difluoro-5-methoxy-4-biphenylyl)-N-3-isoxazolyl-2-oxo-1,2-dihydro-6-quinolinesulfonamide as peak 1 and (M)-1-(3'-chloro-2,5'-difluoro-5-methoxy-4-biphenylyl)-N-3-isoxazolyl-2-oxo-1,2-dihydro-6-quinolinesulfonamide as peak 2. Data for peak 1: $^1$H NMR (500 MHz, DMSO-$d_6$) δ 11.56-11.84 (br s, 1H), 11.56-11.84 (m, 1H), 8.71 (d, J=1.60 Hz, 1H), 8.37 (d, J=1.87 Hz, 1H), 8.23 (d, J=9.67 Hz, 1H), 7.86 (dd, J=2.00, 8.95 Hz, 1H), 7.66 (s, 1H), 7.53-7.63 (m, 3H), 7.47 (d, J=6.84 Hz, 1H), 6.86 (d, J=8.98 Hz, 1H), 6.81 (d, J=9.67 Hz, 1H), 3.75 (s, 3H). m/z (ESI) 542.1 (M–H)⁻. Data for Peak 2: $^1$H NMR (500 MHz, DMSO-$d_6$) δ 11.39-11.86 (br s, 1H), 8.71 (d, J=1.55 Hz, 1H), 8.37 (d, J=1.87 Hz, 1H), 8.23 (d, J=9.72 Hz, 1H), 7.85 (dd, J=2.06, 8.90 Hz, 1H), 7.66 (s, 1H), 7.51-7.63 (m, 3H), 7.47 (d, J=6.89 Hz, 1H), 6.85 (d, J=9.03 Hz, 1H), 6.81 (d, J=9.67 Hz, 1H), 6.44 (d, J=1.55 Hz, 1H), 3.75 (s, 4H). m/z (ESI) 542.1 (M–H)⁻.

Examples 480 & 481

(P)-1-(3'-chloro-5'-fluoro-3-methoxy-4-biphenylyl)-2-oxo-N-3-pyridazinyl-1,2-dihydro-6-quinolinesulfonamide (480) and (M)-1-(3'-chloro-5'-fluoro-3-methoxy-4-biphenylyl)-2-oxo-N-3-pyridazinyl-1,2-dihydro-6-quinolinesulfonamide (481)

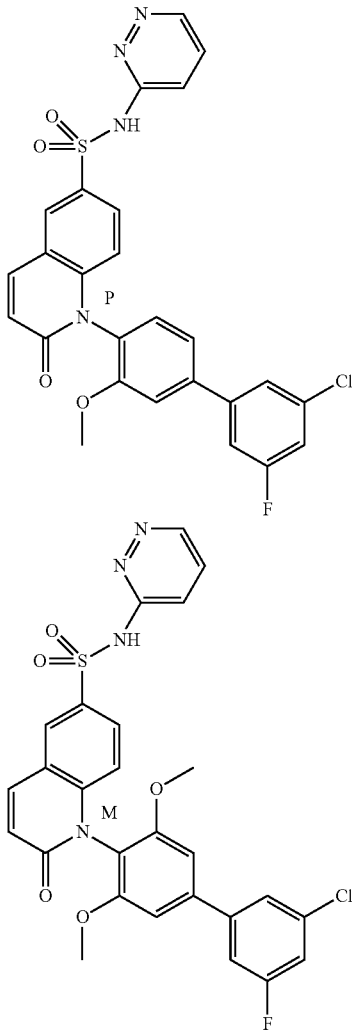

1-(3'-Chloro-5'-fluoro-3-methoxy-4-biphenylyl)-2-oxo-N-3-pyridazinyl-1,2-dihydro-6-quinolinesulfonamide was prepared from 1-(4-bromo-2-methoxyphenyl)-2-oxo-N-(pyridazin-3-yl)-1,2-dihydroquinoline-6-sulfonamide via method 105, using (3-chloro-5-fluorophenyl)boronic acid (Accela) instead of (3-(trifluoromethyl)phenyl)boronic acid in step 3. The racemic 1-(3'-chloro-5'-fluoro-3-methoxy-4-biphenylyl)-2-oxo-N-3-pyridazinyl-1,2-dihydro-6-quinolinesulfonamide was subjected to chiral separation by SFC using a Regis Whelk-O (S,S) column with 60% MeOH in $CO_2$ to provide (P)-1-(3'-chloro-5'-fluoro-3-methoxy-4-biphenylyl)-2-oxo-N-3-pyridazinyl-1,2-dihydro-6-quinolinesulfonamide as peak 1 and (M)-1-(3'-chloro-5'-fluoro-3-methoxy-4-biphenylyl)-2-oxo-N-3-pyridazinyl-1,2-dihydro-6-quinolinesulfonamide as peak 2. Data for peak 1: $^1$H NMR (500 MHz, DMSO-$d_6$) δ 8.34 (br. s., 2H), 8.19 (d, J=9.67 Hz, 1H), 7.70-7.91 (m, 4H), 7.61 (d, J=1.43 Hz, 2H), 7.47-7.56 (m, 2H), 7.40 (d, J=8.04 Hz, 1H), 6.77 (d, J=9.60 Hz, 1H), 6.70 (d, J=8.89 Hz, 1H), 3.80 (s, 3H) sulfonamide NH proton absent due to exchange with water. m/z (ESI) 537.0 (M+H)$^+$. Data for peak 2: $^1$H NMR (500 MHz, DMSO-$d_6$) δ 8.34 (br. s., 2H), 8.19 (d, J=9.67 Hz, 1H), 7.70-7.91 (m, 4H), 7.61 (d, J=1.43 Hz, 2H), 7.47-7.56 (m, 2H), 7.40 (d, J=8.04 Hz, 1H), 6.77 (d, J=9.60 Hz, 1H), 6.70 (d, J=8.89 Hz, 1H), 3.80 (s, 3H), sulfonamide NH proton absent due to exchange with water. m/z (ESI) 537.0 (M+H)$^+$.

Example 482

1-(3'-fluoro-4-methoxy-3-biphenylyl)-N-3-isoxazolyl-2-oxo-1,2-dihydro-6-quinolinesulfonamide

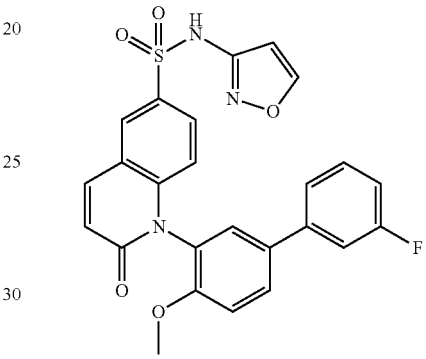

The title compound was via method 115, using (3-fluorophenyl)boronic acid. MS (ESI, pos. ion) m/z: [M+1] 492.2. $^1$H NMR (400 MHz, DMSO-$d_6$) δ ppm 3.73 (s, 3H) 6.44 (d, J=1.76 Hz, 1H) 6.78-6.85 (m, 2H) 7.11-7.18 (m, 1H) 7.40 (d, J=8.80 Hz, 1H) 7.43-7.50 (m, 1H) 7.53-7.59 (m, 2H) 7.78 (d, J=2.45 Hz, 1H) 7.85 (dd, J=9.00, 2.25 Hz, 1H) 7.96 (dd, J=8.71, 2.45 Hz, 1H) 8.23 (d, J=9.49 Hz, 1H) 8.37 (d, J=2.25 Hz, 1H) 8.72 (d, J=1.76 Hz, 1H) 11.65 (s, 1H).

Examples 483 and 484

(P)-1-(3'-fluoro-4-methoxy-3-biphenylyl)-N-3-isoxazolyl-2-oxo-1,2-dihydro-6-quinolinesulfonamide (483) and (M)-1-(3'-fluoro-4-methoxy-3-biphenylyl)-N-3-isoxazolyl-2-oxo-1,2-dihydro-6-quinolinesulfonamide (484)

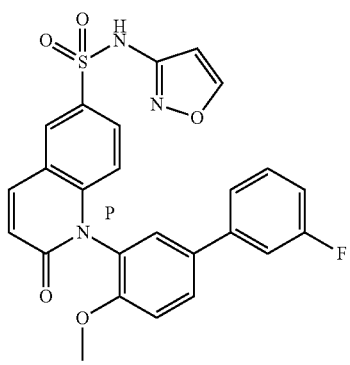 [SMILES: COc1ccc(-c2cccc(F)c2)cc1-n1c(=O)ccc2cc(S(=O)(=O)Nc3ccon3)ccc21]

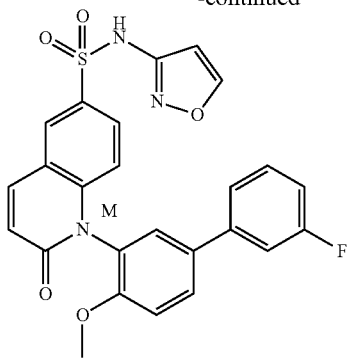

1-(3'-Fluoro-4-methoxy-3-biphenylyl)-n-3-isoxazolyl-2-oxo-1,2-dihydro-6-quinolinesulfonamide was separated by chiral SFC on a Chiralpak AD with 50% MeOH to give (P)-1-(3'-fluoro-4-methoxy-3-biphenylyl)-n-3-isoxazolyl-2-oxo-1,2-dihydro-6-quinolinesulfonamide as peak 1 and (M)-1-(3'-fluoro-4-methoxy-3-biphenylyl)-n-3-isoxazolyl-2-oxo-1,2-dihydro-6-quinolinesulfonamide as peak 2. Data for peak 1: $^1$H NMR (400 MHz, DMSO-$d_6$) δ ppm 3.73 (s, 3H) 6.19-6.31 (m, 1H) 6.67-6.72 (m, 1H) 6.72-6.78 (m, 1H) 7.10-7.19 (m, 1H) 7.36-7.42 (m, 1H) 7.42-7.51 (m, 1H) 7.53-7.59 (m, 2H) 7.73-7.80 (m, 2H) 7.91-7.98 (m, 1H) 8.15-8.21 (m, 1H) 8.22-8.26 (m, 1H) 8.38-8.45 (m, 1H). MS (ESI, pos. ion) m/z: [M+1] 492.0. Data for peak 2: $^1$H NMR (400 MHz, DMSO-$d_6$) δ ppm 3.72 (s, 3H) 6.08-6.15 (m, 1H) 6.58-6.64 (m, 1H) 6.66-6.72 (m, 1H) 7.07-7.17 (m, 1H) 7.34-7.40 (m, 1H) 7.41-7.49 (m, 1H) 7.53-7.60 (m, 2H) 7.68-7.74 (m, 2H) 7.90-7.96 (m, 1H) 8.11-8.16 (m, 2H) 8.18-8.22 (m, 1H). MS (ESI, pos. ion) m/z: [M+1] 492.0.

Example 485

1-(5-(5-fluoro-3-pyridinyl)-2-methoxyphenyl)-N-3-isoxazolyl-2-oxo-1,2-dihydro-6-quinolinesulfonamide

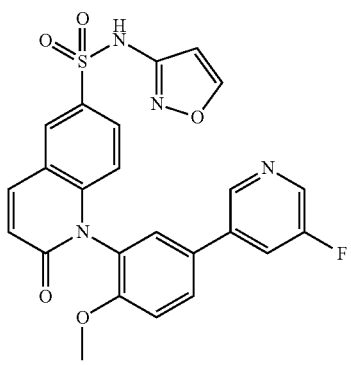 [SMILES: COc1ccc(-c2cncc(F)c2)cc1-n1c(=O)ccc2cc(S(=O)(=O)Nc3ccon3)ccc21]

The title compound was prepared via method 115, using 5-fluoropyridine-3-boronic acid (Combi-Blocks). The compound was purified by reverse-phase preparative HPLC using a Phenomenex Luna column, 10 micron, C8(2), 100 Å, 150×30 mm, 0.1% TFA in CH$_3$CN/H$_2$O, gradient 25% to 90% over 15 min to provide 1-(5-(5-fluoropyridin-3-yl)-2-methoxyphenyl)-N-(isoxazol-3-yl)-2-oxo-1,2-dihydroquinoline-6-sulfonamide (0.020 g, 0.041 mmol, 25.8% yield) as a white solid. MS (ESI, pos. ion) m/z: [M+1] 493.2. $^1$H NMR (400 MHz, DMSO-$d_6$) ppm 3.74 (s, 3H) 6.45 (d, J=1.76 Hz, 1H) 6.83 (dd, J=9.28, 3.37 Hz, 2H) 7.44 (d, J=8.81 Hz, 1H) 7.85 (dd, J=8.97, 2.23 Hz, 1H) 7.90 (d, J=2.38 Hz, 1H) 8.04-8.13 (m, 2H) 8.24 (d, J=9.43 Hz, 1H) 8.38 (d, J=2.28 Hz, 1H) 8.52 (d, J=2.90 Hz, 1H) 8.73 (d, J=1.76 Hz, 1H) 8.85 (t, J=1.76 Hz, 1H) 11.66 (s, 1H).

Example 486

N-3-isoxazolyl-1-(2-methoxy-5-(1-methyl-1H-pyrazol-4-yl)phenyl)-2-oxo-1,2-dihydro-6-quinolinesulfonamide

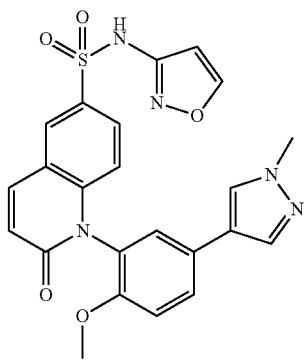 [SMILES: COc1ccc(-c2cnn(C)c2)cc1-n1c(=O)ccc2cc(S(=O)(=O)Nc3ccon3)ccc21]

The title compound was prepared via method 115 using 1-methyl-1h-pyrazole-4-boronic acid (Matrix Scientific) and was isolated in a similar manner to 1-(5-(5-fluoro-3-pyridinyl)-2-methoxyphenyl)-N-3-isoxazolyl-2-oxo-1,2-dihydro-6-quinolinesulfonamide. MS (ESI, pos. ion) m/z: [M+1] 478.1. $^1$H NMR (400 MHz, DMSO-$d_6$) δ ppm 3.67 (s, 3H) 3.82 (s, 3H) 6.42-6.47 (m, 1H) 6.76-6.84 (m, 2H) 7.24-7.32 (m, 1H) 7.51-7.55 (m, 1H) 7.71-7.77 (m, 1H) 7.81-7.87 (m, 2H) 8.07-8.11 (m, 1H) 8.19-8.26 (m, 1H) 8.35-8.40 (m, 1H) 8.63-8.81 (m, 1H) 11.53-11.71 (m, 1H).

Example 487

1-(5-(6-fluoro-3-pyridinyl)-2-methoxyphenyl)-N-3-isoxazolyl-2-oxo-1,2-dihydro-6-quinolinesulfonamide

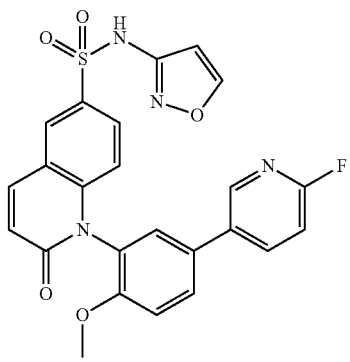 [SMILES: COc1ccc(-c2ccc(F)nc2)cc1-n1c(=O)ccc2cc(S(=O)(=O)Nc3ccon3)ccc21]

The title compound was prepared via method 115 using (6-fluoropyridin-3-yl)boronic acid (Synthonix) and isolated in a similar to 1-(5-(5-fluoro-3-pyridinyl)-2-methoxyphenyl)-N-3-isoxazolyl-2-oxo-1,2-dihydro-6-quinolinesulfonamide. MS (ESI, pos. ion) m/z: [M+1]492.3. ¹H NMR (400 MHz, DMSO-d₆) δ ppm 3.73 (s, 3H) 6.44 (d, J=1.76 Hz, 1H) 6.78-6.86 (m, 2H) 7.21-7.28 (m, 1H) 7.44 (s, 1H) 7.80 (d, J=2.38 Hz, 1H) 7.82-7.87 (m, 1H) 7.93-8.00 (m, 1H) 8.21-8.26 (m, 1H) 8.27-8.34 (m, 1H) 8.35-8.40 (m, 1H) 8.55-8.60 (m, 1H) 8.71-8.74 (m, 1H) 11.61-11.69 (m, 1H).

Example 488

1-(5-(5-fluoro-2-methoxy-3-pyridinyl)-2-methoxyphenyl)-N-3-isoxazolyl-2-oxo-1,2-dihydro-6-quinolinesulfonamide

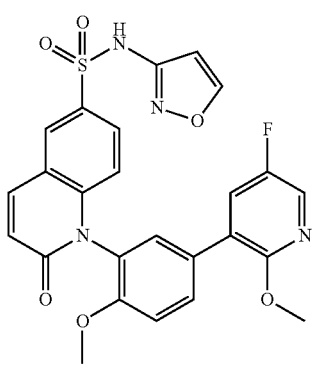 [SMILES: COc1ccc(-c2cc(F)cnc2OC)cc1-n1c(=O)ccc2cc(S(=O)(=O)Nc3ccon3)ccc21]

The title compound was prepared via method 115 using 5-fluoro-2-methoxy-3-pyridineboronic acid (Combi-Blocks) and isolated in a similar manner to N-(isoxazol-3-yl)-1-(4-methoxy-3'-(trifluoromethyl)-[1,1'-biphenyl]-3-yl)-2-oxo-1,2-dihydroquinoline-6-sulfonamide. MS (ESI, pos. ion) m/z: [M+1] 523.1. ¹H NMR (400 MHz, DMSO-d₆) δ ppm 3.71-3.75 (m, 3H) 3.84-3.88 (m, 3H) 6.42-6.46 (m, 1H) 6.78-6.86 (m, 2H) 7.35-7.41 (m, 1H) 7.60-7.63 (m, 1H) 7.79-7.91 (m, 3H) 8.11-8.14 (m, 1H) 8.20-8.25 (m, 1H) 8.35-8.40 (m, 1H) 8.67-8.78 (m, 1H) 11.54-11.73 (m, 1H).

Example 489

N-3-isoxazolyl-1-(2-methoxy-5-(5-pyrimidinyl)phenyl)-2-oxo-1,2-dihydro-6-quinolinesulfonamide

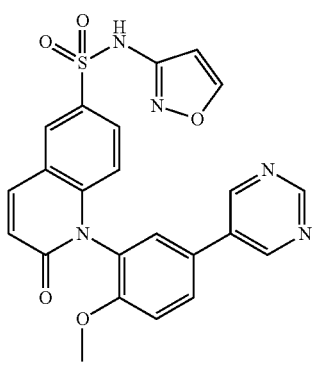 [SMILES: COc1ccc(-c2cncnc2)cc1-n1c(=O)ccc2cc(S(=O)(=O)Nc3ccon3)ccc21]

The title compound was prepared via method 116, using pyrimidin-5-ylboronic acid (Frontier Scientific). MS (ESI, neg. ion) m/z: [M−1]474.0. ¹H NMR (500 MHz, DMSO-d₆) δ ppm 3.75 (s, 3H) 6.44 (d, J=1.69 Hz, 1H) 6.83 (t, J=8.38 Hz, 2H) 7.47 (d, J=8.76 Hz, 1H) 7.84 (d, J=8.64 Hz, 1H) 7.92 (d, J=2.27 Hz, 1H) 8.07 (d, J=8.37 Hz, 1H) 8.24 (d, J=10.18 Hz, 1H) 8.38 (d, J=6.87 Hz, 1H) 8.72 (d, J=1.56 Hz, 1H) 9.11-9.19 (m, 3H) 11.65 (br. s., 1H).

Example 490

N-3-isoxazolyl-1-(2-methoxy-5-(3-pyridinyl)phenyl)-2-oxo-1,2-dihydro-6-quinolinesulfonamide

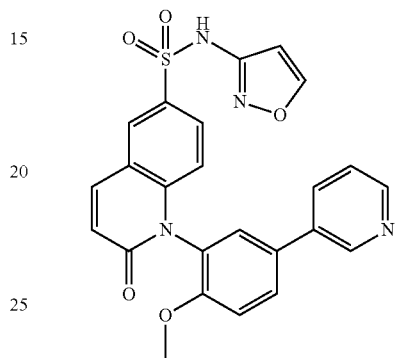

The title compound was prepared via method 116, using pyridin-3-ylboronic acid (Boron Molecular). MS (ESI, pos. ion) m/z: [M+1] 475.0. ¹H NMR (500 MHz, DMSO-d₆) δ ppm 3.75 (s, 3H) 6.45 (d, J=1.75 Hz, 1H) 6.83 (dd, J=9.28, 6.03 Hz, 2H) 7.46 (d, J=8.76 Hz, 1H) 7.58-7.66 (m, 1H) 7.83-7.88 (m, 2H) 8.03 (d, J=7.95 Hz, 1H) 8.22-8.33 (m, 2H) 8.38 (d, J=2.01 Hz, 1H) 8.60 (d, J=4.61 Hz, 1H) 8.72 (d, J=7.54 Hz, 1H) 9.01 (br. s., 1H) 11.65 (br. s., 1H).

Example 491

1-(5-(5-cyano-3-pyridinyl)-2-methoxyphenyl)-N-3-isoxazolyl-2-oxo-1,2-dihydro-6-quinolinesulfonamide

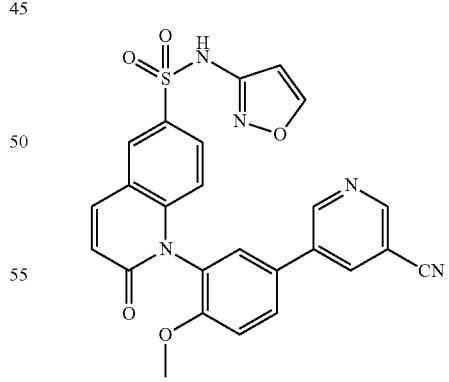

The title compound was prepared via method 118, using (5-cyanopyridin-3-yl)boronic acid (Combi-Blocks). MS (ESI, pos. ion) m/z: [M+1] 500.1. ¹H NMR (400 MHz, DMSO-d₆) δ ppm 3.75 (s, 3H) 6.45 (d, J=1.76 Hz, 1H) 6.83 (dd, J=9.33, 2.28 Hz, 2H) 7.47 (d, J=8.91 Hz, 1H) 7.85 (dd, J=9.02, 2.28 Hz, 1H) 7.95 (d, J=2.38 Hz, 1H) 8.11 (dd, J=8.76, 2.44 Hz, 1H) 8.25 (d, J=9.43 Hz, 1H) 8.39 (d, J=2.28

Hz, 1H) 8.68 (t, J=2.12 Hz, 1H) 8.73 (d, J=1.76 Hz, 1H) 8.95 (d, J=1.87 Hz, 1H) 9.24 (d, J=2.28 Hz, 1H) 11.66 (s, 1H).

Example 492

N-3-isoxazolyl-1-(2-methoxy-5-(5-(trifluoromethyl)-3-pyridinyl)phenyl)-2-oxo-1,2-dihydro-6-quinolinesulfonamide

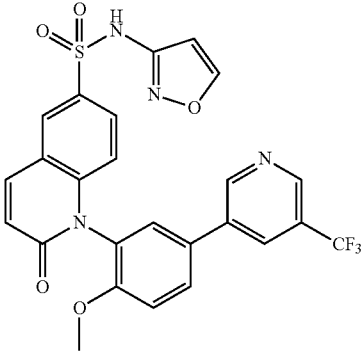 [SMILES: COc1ccc(-c2cncc(C(F)(F)F)c2)cc1-n1c(=O)ccc2cc(S(=O)(=O)Nc3ccon3)ccc21]

The title compound was prepared via method 118, using (5-(trifluoromethyl)pyridin-3-yl)boronic acid (Combi-Blocks). MS (ESI, pos. ion) m/z: [M+1] 543.1. $^1$H NMR (400 MHz, DMSO-d$_6$) δ ppm 3.69 (s, 3H) 6.38 (d, J=1.87 Hz, 1H) 6.77 (dd, J=9.28, 5.23 Hz, 2H) 7.39 (d, J=8.91 Hz, 1H) 7.78 (dd, J=9.02, 2.28 Hz, 1H) 7.94 (d, J=2.38 Hz, 1H) 8.08 (dd, J=8.71, 2.38 Hz, 1H) 8.18 (d, J=9.43 Hz, 1H) 8.32 (d, J=2.18 Hz, 1H) 8.42-8.45 (m, 1H) 8.66 (d, J=1.87 Hz, 1H) 8.84 (s, 1H) 9.20 (d, J=2.07 Hz, 1H) 11.59 (s, 1H).

Example 493

1-(3'-cyano-4-methoxy-3-biphenylyl)-N-3-isoxazolyl-2-oxo-1,2-dihydro-6-quinolinesulfonamide

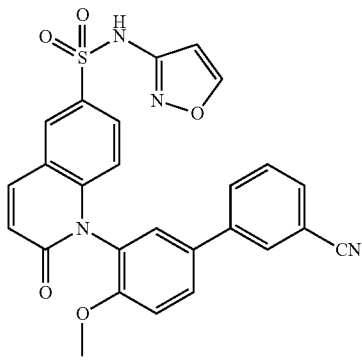 [SMILES: COc1ccc(-c2cccc(C#N)c2)cc1-n1c(=O)ccc2cc(S(=O)(=O)Nc3ccon3)ccc21]

The title compound was prepared via method 118, using (3-cyanophenyl)boronic acid. MS (ESI, pos. ion) m/z: [M+1] 499.1. $^1$H NMR (400 MHz, DMSO-d$_6$) δ ppm 3.75 (s, 3H) 6.45 (d, J=1.76 Hz, 1H) 6.83 (dd, J=9.33, 2.18 Hz, 2H) 7.43 (d, J=8.81 Hz, 1H) 7.64 (t, J=7.49 Hz, 1H) 7.78 (dt, J=7.88, 1.24 Hz, 1H) 7.83-7.89 (m, 2H) 8.03 (dd, J=8.71, 2.49 Hz, 1H) 8.05-8.10 (m, 1H) 8.21-8.27 (m, 2H) 8.39 (d, J=2.28 Hz, 1H) 8.74 (d, J=1.76 Hz, 1H) 11.66 (s, 1H).

Example 494

1-(5-(5-chloro-3-pyridinyl)-2-methoxyphenyl)-N-3-isoxazolyl-2-oxo-1,2-dihydro-6-quinolinesulfonamide

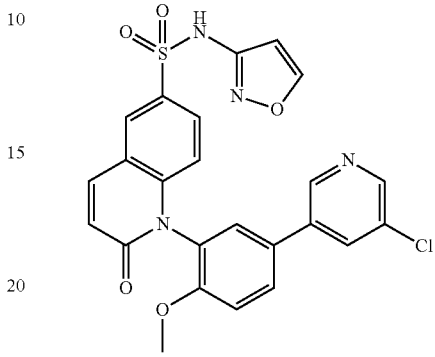

The title compound was prepared via method 118, using (5-chloropyridin-3-yl)boronic acid (Frontier Scientific). MS (ESI, pos. ion) m/z: [M+1] 509.1. $^1$H NMR (400 MHz, DMSO-d$_6$) δ ppm 3.75 (s, 3H) 6.45 (d, J=1.87 Hz, 1H) 6.83 (dd, J=9.28, 3.06 Hz, 2H) 7.44 (d, J=8.81 Hz, 1H) 7.85 (dd, J=8.91, 2.28 Hz, 1H) 7.92 (d, J=2.38 Hz, 1H) 8.08 (dd, J=8.71, 2.38 Hz, 1H) 8.25 (d, J=9.64 Hz, 1H) 8.28-8.31 (m, 1H) 8.39 (d, J=2.18 Hz, 1H) 8.58 (d, J=2.18 Hz, 1H) 8.73 (d, J=6.86 Hz, 1H) 8.93 (d, J=28.42 Hz, 1H) 11.67 (s, J=5.97 Hz, 1H).

Example 495

1-(5-(2-fluoro-3-pyridinyl)-2-methoxyphenyl)-N-3-isoxazolyl-2-oxo-1,2-dihydro-6-quinolinesulfonamide

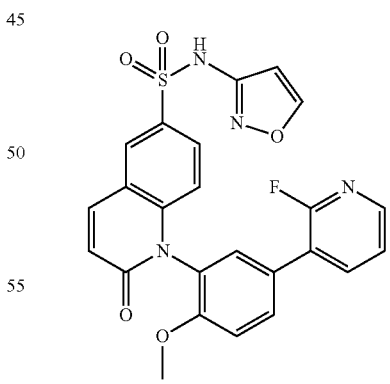

The title compound was prepared via method 118, using (2-fluoropyridin-3-yl)boronic acid. MS (ESI, pos. ion) m/z: [M+1] 493.1. $^1$H NMR (400 MHz, DMSO-d$_6$) δ ppm 3.74 (s, 3H) 6.44-6.47 (m, 1H) 6.83 (ddd, J=9.23, 4.77, 2.49 Hz, 2H) 7.42-7.49 (m, 2H) 7.65 (s, 1H) 7.86 (d, J=8.91 Hz, 2H) 8.11-8.26 (m, 3H) 8.36-8.40 (m, 1H) 8.72-8.75 (m, 1H) 11.66 (s, 1H).

Example 496

1-(5-(2-fluoro-4-pyridinyl)-2-methoxyphenyl)-N-3-isoxazolyl-2-oxo-1,2-dihydro-6-quinolinesulfonamide

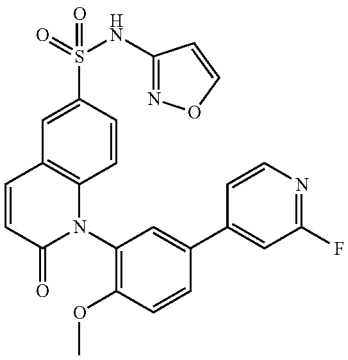 [SMILES: COc1ccc(-c2ccnc(F)c2)cc1-n1c(=O)ccc2cc(S(=O)(=O)Nc3ccon3)ccc21]

The title compound was prepared via method 118, using (2-fluoropyridin-4-yl)boronic acid. MS (ESI, pos. ion) m/z: [M+1] 493.1. ¹H NMR (400 MHz, DMSO-d₆) δ ppm 3.77 (s, 3H) 6.45 (d, J=1.87 Hz, 1H) 6.83 (dd, J=9.33, 2.70 Hz, 2H) 7.46 (d, J=8.81 Hz, 1H) 7.58 (s, 1H) 7.75 (d, J=5.52 Hz, 1H) 7.85 (dd, J=8.97, 2.23 Hz, 1H) 8.01 (d, J=2.38 Hz, 1H) 8.17 (dd, J=8.76, 2.44 Hz, 1H) 8.21-8.30 (m, 2H) 8.39 (d, J=2.18 Hz, 1H) 8.74 (d, J=1.76 Hz, 1H) 11.67 (s, 1H).

Example 497

1-(4-fluoro-5-(6-fluoro-3-pyridinyl)-2-methoxyphenyl)-N-3-isoxazolyl-6-isoquinolinesulfonamide The compound was prepared via method 123 using (6-fluoropyridin-3-yl)boronic acid. ¹H NMR (400 MHz, MeOH) δ 8.76 (s, 1H), 8.71 (d, J=6.06 Hz, 1H), 8.48 (d, J=1.86 Hz, 1H), 8.43 (d, J=0.78 Hz, 1H), 8.29 (dd, J=2.59, 6.02 Hz, 1H), 8.18 (dddd, J=1.42, 2.54, 7.48, 8.71 Hz, 1H), 8.11 (d, J=1.17 Hz, 2H), 7.70 (d, J=8.71 Hz, 1H), 7.29 (d, J=12.62 Hz, 1H), 7.16-7.22 (m, 1H), 6.54 (d, J=1.86 Hz, 1H), 3.82 (s, 3H). m/z (ESI) 495.0 [M+1].

Examples 498 and 499

(P)-1-(3'-cyano-2-fluoro-5-methoxy-4-biphenylyl)-N-3-isoxazolyl-2-oxo-1,2-dihydro-6-quinolinesulfonamide (498) and (M)-1-(3'-cyano-2-fluoro-5-methoxy-4-biphenylyl)-N-3-isoxazolyl-2-oxo-1,2-dihydro-6-quinolinesulfonamide (499)

These compounds were prepared via method 133 using (3-cyanophenyl)boronic acid as the boronic acid. The racemic product was separated via Chiralpak AS-H column (30% MeOH/70% CO2) to give (P)-1-(3'-cyano-2-fluoro-5-methoxy-4-biphenylyl)-N-3-isoxazolyl-2-oxo-1,2-dihydro-6-quinolinesulfonamide and (M)-1-(3'-cyano-2-fluoro-5-methoxy-4-biphenylyl)-N-3-isoxazolyl-2-oxo-1,2-dihydro-6-quinolinesulfonamide as off-white solids. Data for peak 1: ¹H NMR (400 MHz, DMSO-d₆) δ ppm 3.76 (s, 3H) 6.45 (d, J=1.87 Hz, 1H) 6.83 (d, J=9.64 Hz, 1H) 6.88 (d, J=8.91 Hz, 1H) 7.50 (d, J=6.95 Hz, 1H) 7.58 (d, J=10.37 Hz, 1H) 7.73-7.79 (m, 1H) 7.87 (dd, J=8.97, 2.33 Hz, 1H) 7.95-7.98 (m, 1H) 8.06 (d, J=7.05 Hz, 1H) 8.19-8.27 (m, 3H) 8.39 (d, J=2.07 Hz, 1H) 8.73 (d, J=1.76 Hz, 1H) 11.67 (s, 1H). m/z (ESI) 517.1 (M+H)⁺. Data for peak 2: ¹H NMR (400 MHz, DMSO-d₆) δ ppm 3.76 (s, 3H) 6.45 (d, J=0.87 Hz, 1H) 6.83 (d, J=9.64 Hz, 1H) 6.88 (d, J=8.91 Hz, 1H) 7.50 (d, J=6.95 Hz, 1H) 7.58 (d, J=10.37 Hz, 1H) 7.73-7.79 (m, 1H) 7.87 (dd, J=8.97, 2.33 Hz, 1H) 7.95-7.98 (m, 1H) 8.06 (d, J=7.05 Hz, 1H) 8.19-8.27 (m, 3H) 8.39 (d, J=2.07 Hz, 1H) 8.73 (d, J=0.76 Hz, 1H) 11.67 (s, 1H). m/z (ESI) 517.1 (M+H)⁺.

Example 500

1-(5-fluoro-2-methoxy-4-(6-methyl-3-pyridinyl)phenyl)-N-3-isoxazolyl-2-oxo-1,2-dihydro-6-quinolinesulfonamide This compound was prepared via method 133 using 2-methylpyridine-5-boronic acid (purchased from Combi-Blocks) as the boronic acid. ¹H NMR (400 MHz, DMSO-d₆) δ ppm 2.63 (s, 4H) 3.76 (s, 4H) 6.46 (d, J=1.87 Hz, 1H) 6.83 (d, J=9.74 Hz, 1H) 6.89 (d, J=8.91 Hz, 1H) 7.50 (d, J=6.74 Hz, 1H) 7.55-7.66 (m, 2H) 7.87 (dd, J=9.02, 2.18 Hz, 1H) 8.15-8.31 (m, 2H) 8.39 (d, J=2.28 Hz, 1H) 8.75 (d, J=0.76 Hz, 1H) 8.88 (s, 1H) 11.67 (s, 1H). m/z (ESI) 507.2 (M+H)⁺.

Examples 501 and 502

(P)-1-(3'-chloro-2-fluoro-5,5'-dimethoxy-4-biphenylyl)-N-3-isoxazolyl-2-oxo-1,2-dihydro-6-quinolinesulfonamide (501) and (M)-1-(3'-chloro-2-fluoro-5,5'-dimethoxy-4-biphenylyl)-N-3-isoxazolyl-2-oxo-1,2-dihydro-6-quinolinesulfonamide (502)

These compounds were prepared via method 133 using (3-chloro-5-methoxyphenyl)boronic acid (purchased from Aurum Pharmatech) as the boronic acid. The racemic product was separated via Chiralpak AS-H column (40% MeOH/60% CO2) to give (P)-1-(3'-chloro-2-fluoro-5,5'-dimethoxy-4-biphenylyl)-N-3-isoxazolyl-2-oxo-1,2-dihydro-6-quinolinesulfonamide and (M)-1-(3'-chloro-2-fluoro-5,5'-dimethoxy-4-biphenylyl)-N-3-isoxazolyl-2-oxo-1,2-dihydro-6-quinolinesulfonamide as off-white solids. Data for peak 1: ¹H NMR (400 MHz, DMSO-d₆) δ ppm 3.75 (s, 3H) 3.88 (s, 3H) 6.44 (d, J=1.76 Hz, 1H) 6.82 (d, J=9.54 Hz, 1H) 6.86 (d, J=8.81 Hz, 1H) 7.16-7.17 (m, 1H) 7.22 (s, 1H) 7.33 (d, J=1.56 Hz, 1H) 7.42 (d, J=7.05 Hz, 1H) 7.53 (d, J=10.37 Hz, 1H) 7.86 (dd, J=9.02, 2.28 Hz, 1H) 8.24 (d, J=9.54 Hz, 1H) 8.37 (d, J=2.07 Hz, 1H) 8.71 (s, 1H) 11.66 (s, 1H). m/z (ESI) 555.9 (M+H)⁺. Data for peak 2: ¹H NMR (400 MHz, DMSO-d₆) δ ppm 3.75 (s, 3H) 3.88 (s, 3H) 6.44 (d, J=1.76 Hz, 1H) 6.82 (d, J=9.54 Hz, 1H) 6.86 (d, J=8.81 Hz, 1H) 7.16-7.17 (m, 1H) 7.22 (s, 1H) 7.33 (d, J=1.56 Hz, 1H) 7.42 (d, J=7.05 Hz, 1H) 7.53 (d, J=10.37 Hz, 1H) 7.86 (dd, J=9.02, 2.28 Hz, 1H) 8.24 (d, J=9.54 Hz, 1H) 8.37 (d, J=2.07 Hz, 1H) 8.71 (s, 1H) 11.66 (s, 1H). m/z (ESI) 555.9 (M+H)⁺.

Examples 503 and 504

(P)-1-(4'-chloro-2,3'-difluoro-5-methoxy-4-biphenylyl)-N-3-isoxazolyl-2-oxo-1,2-dihydro-6-quinolinesulfonamide (503) and (M)-1-(4'-chloro-2,3'-difluoro-5-methoxy-4-biphenylyl)-N-3-isoxazolyl-2-oxo-1,2-dihydro-6-quinolinesulfonamide (504)

These compounds were prepared via method 133 using (4-chloro-3-fluorophenyl)boronic acid (purchased from Aurum Pharmatech) as the boronic acid. The racemic product was separated via Chiralpak IA column (30% MeOH/ 70% CO2) to give (P)-1-(4'-chloro-2,3'-difluoro-5-methoxy-4-biphenylyl)-N-3-isoxazolyl-2-oxo-1,2-dihydro-6-quinolinesulfonamide and (M)-1-(4'-chloro-2,3'-difluoro-5-methoxy-4-biphenylyl)-N-3-isoxazolyl-2-oxo-1,2-dihydro-6-quinolinesulfonamide as white solids. Data for peak 1: $^1$H NMR (400 MHz, DMSO-$d_6$) δ ppm 3.75 (s, 3H) 6.42 (d, J=1.87 Hz, 1H) 6.81 (d, J=9.74 Hz, 1H) 6.86 (d, J=8.81 Hz, 1H) 7.46 (d, J=6.95 Hz, 1H) 7.53-7.64 (m, 2H) 7.75-7.89 (m, 4H) 8.23 (d, J=9.74 Hz, 1H) 8.36 (d, J=1.97 Hz, 1H) 8.69 (s, 1H) 11.67 (br. s., 1H). m/z (ESI) 544.1 (M+H)$^+$. Data for peak 2: $^1$H NMR (400 MHz, DMSO-$d_6$) δ ppm 3.75 (s, 3H) 6.42 (d, J=1.87 Hz, 1H) 6.81 (d, J=9.74 Hz, 1H) 6.86 (d, J=8.81 Hz, 1H) 7.46 (d, J=6.95 Hz, 1H) 7.53-7.64 (m, 2H) 7.75-7.89 (m, 4H) 8.23 (d, J=9.74 Hz, 1H) 8.36 (d, J=1.97 Hz, 1H) 8.69 (s, 1H) 11.67 (br. s., 1H). m/z (ESI) 544.1 (M+H)$^+$.

Examples 505

1-(5-fluoro-2-methoxy-4-(4-pyridinyl)phenyl)-N-3-isoxazolyl-2-oxo-1,2-dihydro-6-quinolinesulfonamide This compound was prepared via method 133 using pyridine-4-boronic acid as the boronic acid. $^1$H NMR (500 MHz, DMSO-$d_6$) δ ppm 3.76 (s, 3H) 6.45 (s, =7.67 Hz, 1H) 6.82 (d, J=9.08 Hz, 1H) 6.89 (d, J=4.68 Hz, 1H) 7.52 (d, J=6.44 Hz, 1H) 7.62 (d, J=9.41 Hz, 1H) 7.82-7.88 (m, 3H) 8.24 (d, J=8.84 Hz, 1H) 8.39 (s, 1H) 8.73 (s, J=5.97 Hz, 1H) 8.81 (br. s., 2H) 11.65 (br. s., 1H). m/z (ESI) 493.0 (M+H)$^+$.

Examples 506 and 507

(P)-1-(3'-chloro-2-fluoro-5-methoxy-5'-methyl-4-biphenylyl)-N-3-isoxazolyl-2-oxo-1,2-dihydro-6-quinolinesulfonamide (506) and (M)-1-(3'-chloro-2-fluoro-5-methoxy-5'-methyl-4-biphenylyl)-N-3-isoxazolyl-2-oxo-1,2-dihydro-6-quinolinesulfonamide (507)

These compounds were prepared via method 133 using (3-chloro-5-methylphenyl)boronic acid (purchased from Combi-blocks) as the boronic acid. The racemic product was separated via Whelk-01 (R,R) column (50% MeOH/50% $CO_2$) to give (P)-1-(3'-chloro-2-fluoro-5-methoxy-5'-methyl-4-biphenylyl)-N-3-isoxazolyl-2-oxo-1,2-dihydro-6-quinolinesulfonamide and (M)-1-(3'-chloro-2-fluoro-5-methoxy-5'-methyl-4-biphenylyl)-N-3-isoxazolyl-2-oxo-1,2-dihydro-6-quinolinesulfonamide as yellow solids. Data for peak 1: $^1$H NMR (400 MHz, DMSO-$d_6$) δ ppm 2.43 (s, 3H) 3.32 (s, 3H) 6.45 (d, J=1.76 Hz, 1H) 6.82 (d, J=9.64 Hz, 1H) 6.87 (d, J=9.02 Hz, 1H) 7.40 (s, 1H) 7.41 (d, J=7.89 Hz, 1H) 7.49-7.58 (m, 3H) 7.86 (d, J=8.34 Hz, 1H) 8.24 (d, J=9.64 Hz, 1H) 8.38 (d, J=1.97 Hz, 1H) 8.73 (d, J=1.76 Hz, 1H) 11.67 (br. s., 1H). m/z (ESI) 540.0 (M+H)$^+$. Data for peak 2: $^1$H NMR (400 MHz, DMSO-$d_6$) δ ppm 2.43 (s, 3H) 3.32 (s, 3H) 6.45 (d, J=1.76 Hz, 1H) 6.82 (d, J=9.64 Hz, 1H) 6.87 (d, J=9.02 Hz, 1H) 7.40 (s, 1H) 7.41 (d, J=7.89 Hz, 1H) 7.49-7.58 (m, 3H) 7.86 (d, J=8.34 Hz, 1H) 8.24 (d, J=9.64 Hz, 1H) 8.38 (d, J=1.97 Hz, 1H) 8.73 (d, J=1.76 Hz, 1H) 11.67 (br. s., 1H). m/z (ESI) 540.0 (M+H)$^+$.

Examples 508 and 509

(P)-1-(4'-chloro-3'-cyano-2-fluoro-5-methoxy-4-biphenylyl)-N-3-isoxazolyl-2-oxo-1,2-dihydro-6-quinolinesulfonamide (508) and (M)-1-(4'-chloro-3'-cyano-2-fluoro-5-methoxy-4-biphenylyl)-N-3-isoxazolyl-2-oxo-1,2-dihydro-6-quinolinesulfonamide (509)

These compounds were prepared via method 133 using (4-chloro-3-cyanophenyl)boronic acid (purchased from Aurum Pharmatech) as the boronic acid. The racemic product was separated via Whelk-O (R,R) column (40% MeOH/ 60% CO2) to give (P)-1-(4'-chloro-3'-cyano-2-fluoro-5-methoxy-4-biphenylyl)-N-3-isoxazolyl-2-oxo-1,2-dihydro-6-quinolinesulfonamide and (M)-1-(4'-chloro-3'-cyano-2-fluoro-5-methoxy-4-biphenylyl)-N-3-isoxazolyl-2-oxo-1,2-dihydro-6-quinolinesulfonamide as orange solids. Data for peak 1: $^1$H NMR (400 MHz, DMSO-$d_6$) δ ppm 3.76 (s, 3H) 6.44 (s, 1H) 6.82 (d, J=9.64 Hz, 1H) 6.86 (d, J=9.02 Hz, 1H) 7.52 (d, J=7.05 Hz, 1H) 7.59 (d, J=10.47 Hz, 1H) 7.86 (dd, J=8.97, 2.23 Hz, 1H) 7.94 (d, J=8.50 Hz, 1H) 8.08 (dt, J=8.60, 1.97 Hz, 1H) 8.24 (d, J=9.54 Hz, 1H) 8.38 (t, J=2.07 Hz, 2H) 8.71 (d, J=1.76 Hz, 1H) 11.68 (br. s., 1H). m/z (ESI) 550.8 (M+H)$^+$. Data for peak 2: $^1$H NMR (400 MHz, DMSO-$d_6$) δ ppm 3.76 (s, 3H) 6.44 (s, 1H) 6.82 (d, J=9.64 Hz, 1H) 6.86 (d, J=9.02 Hz, 1H) 7.52 (d, J=7.05 Hz, 1H) 7.59 (d, J=10.47 Hz, 1H) 7.86 (dd, J=8.97, 2.23 Hz, 1H) 7.94 (d, J=8.50 Hz, 1H) 8.08 (dt, J=8.60, 1.97 Hz, 1H) 8.24 (d, J=9.54 Hz, 1H) 8.38 (t, J=2.07 Hz, 2H) 8.71 (d, J=1.76 Hz, 1H) 11.68 (br. s., 1H). m/z (ESI) 550.8 (M+H)$^+$.

Examples 510 and 511

(P)-1-(2,3'-difluoro-5-methoxy-4'-methyl-4-biphenylyl)-N-3-isoxazolyl-2-oxo-1,2-dihydro-6-quinolinesulfonamide (510) and (M)-1-(2,3'-difluoro-5-methoxy-4'-methyl-4-biphenylyl)-N-3-isoxazolyl-2-oxo-1,2-dihydro-6-quinolinesulfonamide (511)

These compounds were prepared via method 133 using (3-fluoro-4-methylphenyl)boronic acid (purchased from Aurum Pharmatech) as the boronic acid. The racemic product was separated via Chiralpak AS-H column (30% MeOH/ 70% $CO_2$) to give (P)-1-(2,3'-difluoro-5-methoxy-4'-methyl-4-biphenylyl)-N-3-isoxazolyl-2-oxo-1,2-dihydro-6-quinolinesulfonamide and (M)-1-(2,3'-difluoro-5-methoxy-4'-methyl-4-biphenylyl)-N-3-isoxazolyl-2-oxo-1,2-dihydro-6-quinolinesulfonamide as white crystalline solids. Data for peak 1: $^1$H NMR (400 MHz, DMSO-$d_6$) δ ppm 2.33 (d, J=1.66 Hz, 3H) 3.74 (s, 3H) 6.34 (s, 1H) 6.76-6.83 (m, 2H) 7.40 (d, J=6.95 Hz, 1H) 7.45-7.57 (m, 4H) 7.83 (d, J=8.60 Hz, 1H) 8.20 (d, J=9.43 Hz, 1H) 8.30 (s, J=4.65 Hz, 1H) 8.56 (br. s., 1H) 11.47-11.85 (m, 1H). m/z (ESI) 523.8 (M+H)$^+$. Data for peak 2: $^1$H NMR (400 MHz, DMSO-$d_6$) δ ppm 2.33 (d, J=1.66 Hz, 3H) 3.74 (s, 3H) 6.34 (s, 1H) 6.76-6.83 (m, 2H) 7.40 (d, J=6.95 Hz, 1H) 7.45-7.57 (m, 4H) 7.83 (d, J=8.60 Hz, 1H) 8.20 (d, J=9.43 Hz, 1H) 8.30 (s, J=4.65 Hz, 1H) 8.56 (br. s., 1H) 11.47-11.85 (m, 1H). m/z (ESI) 523.8 (M+H)$^+$.

Examples 512 and 513

(P)-1-(2,4'-difluoro-5-methoxy-3'-methyl-4-biphenylyl)-N-3-isoxazolyl-2-oxo-1,2-dihydro-6-quinolinesulfonamide (512) and (M)-1-(2,4'-difluoro-5-methoxy-3'-methyl-4-biphenylyl)-N-3-isoxazolyl-2-oxo-1,2-dihydro-6-quinolinesulfonamide (513)

These compounds were prepared via method 133 using (4-fluoro-3-methylphenyl)boronic acid as the boronic acid.

The racemic product was separated via Whelk-O (R,R) column (40% MeOH/60% CO₂) to give (P)-1-(2,4'-difluoro-5-methoxy-3'-methyl-4-biphenylyl)-N-3-isoxazolyl-2-oxo-1,2-dihydro-6-quinolinesulfonamide and (M)-1-(2,4'-difluoro-5-methoxy-3'-methyl-4-biphenylyl)-N-3-isoxazolyl-2-oxo-1,2-dihydro-6-quinolinesulfonamide as light-yellow crystalline solids. Data for peak 1: $^1$H NMR (400 MHz, DMSO-$d_6$) δ ppm 2.35 (d, J=1.55 Hz, 3H) 3.72-3.76 (m, 3H) 6.43 (d, J=1.76 Hz, 1H) 6.81 (d, J=9.64 Hz, 1H) 6.86 (d, J=8.91 Hz, 1H) 7.29-7.42 (m, 2H) 7.49 (d, J=10.37 Hz, 1H) 7.53-7.59 (m, 1H) 7.64 (d, J=7.26 Hz, 1H) 7.86 (dd, J=9.02, 2.18 Hz, 1H) 8.23 (d, J=9.64 Hz, 1H) 8.36 (d, J=2.18 Hz, 1H) 8.69 (d, J=1.66 Hz, 1H) 11.43-11.84 (m, 1H). m/z (ESI) 524.1 (M+H)⁺. Data for peak 2: $^1$H NMR (400 MHz, DMSO-$d_6$) δ ppm 2.35 (d, J=1.55 Hz, 3H) 3.72-3.76 (m, 3H) 6.43 (d, J=1.76 Hz, 1H) 6.81 (d, J=9.64 Hz, 1H) 6.86 (d, J=8.91 Hz, 1H) 7.29-7.42 (m, 2H) 7.49 (d, J=10.37 Hz, 1H) 7.53-7.59 (m, 1H) 7.64 (d, J=7.26 Hz, 1H) 7.86 (dd, J=9.02, 2.18 Hz, 1H) 8.23 (d, J=9.64 Hz, 1H) 8.36 (d, J=2.18 Hz, 1H) 8.69 (d, J=1.66 Hz, 1H) 11.43-11.84 (m, 1H). m/z (ESI) 524.1 (M+H)⁺.

Examples 514 and 515

(P)—N-3-isoxazolyl-2-oxo-1-(2,2',3',5'-tetrafluoro-5-methoxy-4-biphenylyl)-1,2-dihydro-6-quinolinesulfonamide (514) and (M)-N-3-isoxazolyl-2-oxo-1-(2,2',3',5'-tetrafluoro-5-methoxy-4-biphenylyl)-1,2-dihydro-6-quinolinesulfonamide (515)

These compounds were prepared via method 133 using (2,3,5-trifluorophenyl)boronic acid (purchased from Aurum Pharmatech) as the boronic acid. The racemic product was separated via Chiralpak AS-H column (30% MeOH/70% CO2) to give (P)—N-3-isoxazolyl-2-oxo-1-(2,2',3',5'-tetrafluoro-5-methoxy-4-biphenylyl)-1,2-dihydro-6-quinolinesulfonamide and (M)-N-3-isoxazolyl-2-oxo-1-(2,2',3',5'-tetrafluoro-5-methoxy-4-biphenylyl)-1,2-dihydro-6-quinolinesulfonamide as white crystalline solids. Data for peak 1: $^1$H NMR (400 MHz, DMSO-$d_6$) δ ppm 3.73 (s, 3H) 6.45 (d, J=5.63 Hz, 1H) 6.84 (t, J=9.12 Hz, 2H) 7.46 (d, J=6.43 Hz, 2H) 7.61 (d, J=9.74 Hz, 1H) 7.74 (d, J=3.21 Hz, 1H) 7.89 (dd, J=8.97, 2.02 Hz, 1H) 8.25 (d, J=9.54 Hz, 1H) 8.39 (d, J=1.97 Hz, 1H) 8.73 (d, J=1.76 Hz, 1H) 11.68 (s, J=5.25, 5.25 Hz, 1H). m/z (ESI) 546.0 (M+H)⁺. Data for peak 2: $^1$H NMR (400 MHz, DMSO-$d_6$) δ ppm 3.73 (s, 3H) 6.45 (d, J=5.63 Hz, 1H) 6.84 (t, J=9.12 Hz, 2H) 7.46 (d, J=6.43 Hz, 2H) 7.61 (d, J=9.74 Hz, 1H) 7.74 (d, J=3.21 Hz, 1H) 7.89 (dd, J=8.97, 2.02 Hz, 1H) 8.25 (d, J=9.54 Hz, 1H) 8.39 (d, J=1.97 Hz, 1H) 8.73 (d, J=1.76 Hz, 1H) 11.68 (s, J=5.25, 5.25 Hz, 1H). m/z (ESI) 546.0 (M+H)⁺.

Examples 516 and 517

(P)—N-3-isoxazolyl-2-oxo-1-(2,2',4',5'-tetrafluoro-5-methoxy-4-biphenylyl)-1,2-dihydro-6-quinolinesulfonamide (516) and (M)-N-3-isoxazolyl-2-oxo-1-(2,2',4',5'-tetrafluoro-5-methoxy-4-biphenylyl)-1,2-dihydro-6-quinolinesulfonamide (517)

These compounds were prepared via method 133 using (2,4,5-trifluorophenyl)boronic acid (purchased from Aurum Pharmatech) as the boronic acid. The racemic product was separated via Chiralcel OJ-H column (30% EtOH/70% CO2) to give (P)—N-3-isoxazolyl-2-oxo-1-(2,2',4',5'-tetrafluoro-5-methoxy-4-biphenylyl)-1,2-dihydro-6-quinolinesulfonamide and (M)-N-3-isoxazolyl-2-oxo-1-(2,2',4',5'-tetrafluoro-5-methoxy-4-biphenylyl)-1,2-dihydro-6-quinolinesulfonamide as off-white crystalline solids. Data for peak 1: $^1$H NMR (400 MHz, DMSO-$d_6$) δ ppm 3.72 (s, 3H) 6.45 (d, J=3.71 Hz, 1H) 6.83 (dd, J=9.33, 5.70 Hz, 2H) 7.41 (d, J=6.43 Hz, 1H) 7.57 (m, J=9.64 Hz, 1H) 7.79 (d, J=6.32 Hz, 1H) 7.88 (dd, J=8.97, 2.23 Hz, 2H) 8.25 (m, J=9.64 Hz, 1H) 8.39 (d, J=2.28 Hz, 1H) 8.72 (d, J=1.76 Hz, 1H) 11.68 (br. s., 1H). m/z (ESI) 546.9 (M+H)⁺. Data for peak 2: $^1$H NMR (400 MHz, DMSO-$d_6$) δ ppm 3.72 (s, 3H) 6.45 (d, J=3.71 Hz, 1H) 6.83 (dd, J=9.33, 5.70 Hz, 2H) 7.41 (d, J=6.43 Hz, 1H) 7.57 (m, J=9.64 Hz, 1H) 7.79 (d, J=6.32 Hz, 1H) 7.88 (dd, J=8.97, 2.23 Hz, 2H) 8.25 (m, J=9.64 Hz, 1H) 8.39 (d, J=2.28 Hz, 1H) 8.72 (d, J=1.76 Hz, 1H) 11.68 (br. s., 1H). m/z (ESI) 546.9 (M+H)⁺.

Examples 518 and 519

(P)-1-(3'-chloro-5'-cyano-2-fluoro-5-methoxy-4-biphenylyl)-N-3-isoxazolyl-2-oxo-1,2-dihydro-6-quinolinesulfonamide (518) and (M)-1-(3'-chloro-5'-cyano-2-fluoro-5-methoxy-4-biphenylyl)-N-3-isoxazolyl-2-oxo-1,2-dihydro-6-quinolinesulfonamide (519)

These compounds were prepared via method 133 using (3-chloro-5-cyanophenyl)boronic acid (purchased from Wonda Science) as the boronic acid. The racemic product was separated via Chiralpak IA column (40% EtOH/60% CO₂) to give (P)-1-(3'-chloro-5'-cyano-2-fluoro-5-methoxy-4-biphenylyl)-N-3-isoxazolyl-2-oxo-1,2-dihydro-6-quinolinesulfonamide and (M)-1-(3'-chloro-5'-cyano-2-fluoro-5-methoxy-4-biphenylyl)-N-3-isoxazolyl-2-oxo-1,2-dihydro-6-quinolinesulfonamide as light yellow crystalline solids. Data for peak 1: $^1$H NMR (400 MHz, DMSO-$d_6$) δ ppm 3.77 (s, 3H) 6.46 (s, 1H) 6.83 (d, J=9.74 Hz, 1H) 6.86 (d, J=9.80 Hz, 1H) 7.55 (d, J=6.95 Hz, 1H) 7.60 (d, J=10.37 Hz, 1H) 7.86 (d, J=9.02 Hz, 1H) 8.14-8.27 (m, 4H) 8.39 (d, J=5.31 Hz, 1H) 8.74 (d, J=4.64 Hz, 1H) 11.67 (s, J=5.48 Hz, 1H). m/z (ESI) 551.1 (M+H)⁺. Data for peak 2: $^1$H NMR (400 MHz, DMSO-$d_6$) δ ppm 3.77 (s, 3H) 6.46 (s, 1H) 6.83 (d, J=9.74 Hz, 1H) 6.86 (d, J=9.80 Hz, 1H) 7.55 (d, J=6.95 Hz, 1H) 7.60 (d, J=10.37 Hz, 1H) 7.86 (d, J=9.02 Hz, 1H) 8.14-8.27 (m, 4H) 8.39 (d, J=5.31 Hz, 1H) 8.74 (d, J=4.64 Hz, 1H) 11.67 (s, J=5.48 Hz, 1H). m/z (ESI) 551.1 (M+H)⁺.

Examples 520 and 521

(P)-1-(3'-chloro-4'-cyano-2-fluoro-5-methoxy-4-biphenylyl)-N-3-isoxazolyl-2-oxo-1,2-dihydro-6-quinolinesulfonamide (520) and (M)-1-(3'-chloro-4'-cyano-2-fluoro-5-methoxy-4-biphenylyl)-N-3-isoxazolyl-2-oxo-1,2-dihydro-6-quinolinesulfonamide (521)

These compounds were prepared via method 133 using 2-chloro-4-(4,4,5,5-tetramethyl-1,3,2-dioxaborolan-2-yl)benzonitrile (purchased from Aurum Pharmatech) as the boronic acid ester. The racemic product was separated via Chiralpak IA column (35% MeOH/65% CO2) to give (P)-1-(3'-chloro-4'-cyano-2-fluoro-5-methoxy-4-biphenylyl)-N-3-isoxazolyl-2-oxo-1,2-dihydro-6-quinolinesulfonamide and (M)-1-(3'-chloro-4'-cyano-2-fluoro-5-methoxy-4-biphenylyl)-N-3-isoxazolyl-2-oxo-1,2-dihydro-6-quinolinesulfonamide as off-white crystalline solids. Data for peak 1: $^1$H NMR (400 MHz, DMSO-$d_6$) δ ppm 3.76 (s, 3H) 6.28 (d, J=1.66 Hz, 1H) 6.76 (dd, J=9.17, 1.92 Hz, 2H) 7.51 (d, J=6.95 Hz, 1H) 7.58 (d, J=10.47 Hz, 1H) 7.79 (dd, J=8.81, 2.07 Hz, 1H) 7.91 (d, J=8.39 Hz, 1H) 8.12-8.22 (m, 3H) 8.26 (d, J=1.97 Hz, 1H) 8.45 (s, 1H). m/z (ESI) 551.2 (M+H)$^+$. Data for peak 2: $^1$H NMR (400 MHz, DMSO-d$_6$) δ ppm 3.76 (s, 3H) 6.28 (d, J=1.66 Hz, 1H) 6.76 (dd, J=9.17, 1.92 Hz, 2H) 7.51 (d, J=6.95 Hz, 1H) 7.58 (d, J=10.47 Hz, 1H) 7.79 (dd, J=8.81, 2.07 Hz, 1H) 7.91 (d, J=8.39 Hz, 1H) 8.12-8.22 (m, 3H) 8.26 (d, J=1.97 Hz, 1H) 8.45 (s, 1H). m/z (ESI) 551.2 (M+H)$^+$.

Examples 522 and 523

(P)-1-(2-fluoro-5-methoxy-3'-methyl-4-biphenylyl)-N-3-isoxazolyl-2-oxo-1,2-dihydro-6-quinolinesulfonamide (522) and (M)-1-(2-fluoro-5-methoxy-3'-methyl-4-biphenylyl)-N-3-isoxazolyl-2-oxo-1,2-dihydro-6-quinolinesulfonamide (523)

These compounds were prepared via method 133 using (3-methylphenyl)boronic acid (purchased from Lancaster Synthesis) as the boronic acid. The racemic product was separated via Chiralpak AS-H column (40% EtOH/60% CO$_2$) to give (P)-1-(2-fluoro-5-methoxy-3'-methyl-4-biphenylyl)-N-3-isoxazolyl-2-oxo-1,2-dihydro-6-quinolinesulfonamide and (M)-1-(2-fluoro-5-methoxy-3'-methyl-4-biphenylyl)-N-3-isoxazolyl-2-oxo-1,2-dihydro-6-quinolinesulfonamide as off-white crystalline solids. Data for peak 1: $^1$H NMR (400 MHz, DMSO-d$_6$) δ ppm 2.42 (s, 3H) 3.72-3.76 (m, 3H) 6.46 (s, 1H) 6.83 (d, J=9.67 Hz, 1H) 6.89 (d, J=9.01 Hz, 1H) 7.28-7.52 (m, 6H) 7.88 (d, J=9.06 Hz, 1H) 8.24 (d, J=9.59 Hz, 1H) 8.39 (s, 1H) 8.74 (s, 1H) 11.67 (s, 1H). m/z (ESI) 506.1 (M+H)$^+$. Data for peak 2: $^1$H NMR (400 MHz, DMSO-d$_6$) δ ppm 2.42 (s, 3H) 3.72-3.76 (m, 3H) 6.46 (s, 1H) 6.83 (d, J=9.67 Hz, 1H) 6.89 (d, J=9.01 Hz, 1H) 7.28-7.52 (m, 6H) 7.88 (d, J=9.06 Hz, 1H) 8.24 (d, J=9.59 Hz, 1H) 8.39 (s, 1H) 8.74 (s, 1H) 11.67 (s, 1H). m/z (ESI) 506.1 (M+H)$^+$.

Examples 524 and 525

(P)-1-(3'-cyano-2-fluoro-5-methoxy-4'-methyl-4-biphenylyl)-N-3-isoxazolyl-2-oxo-1,2-dihydro-6-quinolinesulfonamide (524) and (M)-1-(3'-cyano-2-fluoro-5-methoxy-4'-methyl-4-biphenylyl)-N-3-isoxazolyl-2-oxo-1,2-dihydro-6-quinolinesulfonamide (525)

These compounds were prepared via method 133 using (3-cyano-4-methylphenyl)boronic acid (purchased from Aurum Pharmatech) as the boronic acid. The racemic product was separated via Whelk-O (S,S) column (45% MeOH/55% CO$_2$) to give (P)-1-(3'-cyano-2-fluoro-5-methoxy-4'-methyl-4-biphenylyl)-N-3-isoxazolyl-2-oxo-1,2-dihydro-6-quinolinesulfonamide and (M)-1-(3'-cyano-2-fluoro-5-methoxy-4'-methyl-4-biphenylyl)-N-3-isoxazolyl-2-oxo-1,2-dihydro-6-quinolinesulfonamide as amorphous yellow solids. Data for peak 1: $^1$H NMR (400 MHz, DMSO-d$_6$) δ ppm 2.58 (s, 3H) 3.76 (s, 3H) 6.46 (s, 1H) 6.83 (d, J=9.64 Hz, 1H) 6.88 (d, J=9.02 Hz, 1H) 7.48 (d, J=7.05 Hz, 1H) 7.55 (d, J=10.47 Hz, 1H) 7.65 (d, J=8.09 Hz, 1H) 7.87 (dd, J=8.97, 2.23 Hz, 1H) 7.95 (d, J=8.49 Hz, 1H) 8.14 (s, 1H) 8.24 (d, J=9.74 Hz, 1H) 8.39 (d, J=2.18 Hz, 1H) 8.74 (s, 1H) 11.67 (br. s., 1H). m/z (ESI) 531.0 (M+H)$^+$. Data for peak 2: $^1$H NMR (400 MHz, DMSO-d$_6$) δ ppm 2.58 (s, 3H) 3.76 (s, 3H) 6.46 (s, 1H) 6.83 (d, J=9.64 Hz, 1H) 6.88 (d, J=9.02 Hz, 1H) 7.48 (d, J=7.05 Hz, 1H) 7.55 (d, J=10.47 Hz, 1H) 7.65 (d, J=8.09 Hz, 1H) 7.87 (dd, J=8.97, 2.23 Hz, 1H) 7.95 (d, J=8.49 Hz, 1H) 8.14 (s, 1H) 8.24 (d, J=9.74 Hz, 1H) 8.39 (d, J=2.18 Hz, 1H) 8.74 (s, 1H) 11.67 (br. s., 1H). m/z (ESI) 531.0 (M+H)$^+$.

Examples 526 and 527

(P)-1-(3'-cyano-2-fluoro-5-methoxy-5'-methyl-4-biphenylyl)-N-3-isoxazolyl-2-oxo-1,2-dihydro-6-quinolinesulfonamide (526) and (M)-1-(3'-cyano-2-fluoro-5-methoxy-5'-methyl-4-biphenylyl)-N-3-isoxazolyl-2-oxo-1,2-dihydro-6-quinolinesulfonamide (527)

These compounds were prepared via method 133 using 3-methyl-5-(4,4,5,5-tetramethyl-1,3,2-dioxaborolan-2-yl)benzonitrile (purchased from Bepharm Limited) as the boronic acid ester. The racemic product was separated via Whelk-O (R,R) column (50% MeOH/50% CO$_2$) to give (P)-1-(3'-cyano-2-fluoro-5-methoxy-5'-methyl-4-biphenylyl)-N-3-isoxazolyl-2-oxo-1,2-dihydro-6-quinolinesulfonamide and (M)-1-(3'-cyano-2-fluoro-5-methoxy-5'-methyl-4-biphenylyl)-N-3-isoxazolyl-2-oxo-1,2-dihydro-6-quinolinesulfonamide as off-white crystalline solids. Data for peak 1: $^1$H NMR (400 MHz, DMSO-d$_6$) δ ppm 2.47 (s, 3H) 3.32 (s, 3H) 6.45 (d, J=1.66 Hz, 1H) 6.82 (d, J=9.64 Hz, 1H) 6.86 (d, J=8.91 Hz, 1H) 7.47 (d, J=6.95 Hz, 1H) 7.56 (d, J=10.37 Hz, 1H) 7.79 (s, 1H) 7.82-7.92 (m, 2H) 7.99 (s, 1H) 8.24 (d, J=9.64 Hz, 1H) 8.38 (d, J=2.28 Hz, 1H) 8.72 (d, J=1.76 Hz, 1H) 11.67 (br. s., 1H). m/z (ESI) 531.2 (M+H)$^+$. Data for peak 2: $^1$H NMR (400 MHz, DMSO-d$_6$) δ ppm 2.47 (s, 3H) 3.32 (s, 3H) 6.45 (d, J=1.66 Hz, 1H) 6.82 (d, J=9.64 Hz, 1H) 6.86 (d, J=8.91 Hz, 1H) 7.47 (d, J=6.95 Hz, 1H) 7.56 (d, J=10.37 Hz, 1H) 7.79 (s, 1H) 7.82-7.92 (m, 2H) 7.99 (s, 1H) 8.24 (d, J=9.64 Hz, 1H) 8.38 (d, J=2.28 Hz, 1H) 8.72 (d, J=1.76 Hz, 1H) 11.67 (br. s., 1H). m/z (ESI) 531.2 (M+H)$^+$.

Examples 528 and 529

(P)-1-(3'-chloro-2-fluoro-5-methoxy-4'-methyl-4-biphenylyl)-N-3-isoxazolyl-2-oxo-1,2-dihydro-6-quinolinesulfonamide (528) and (M)-1-(3'-chloro-2-fluoro-5-methoxy-4'-methyl-4-biphenylyl)-N-3-isoxazolyl-2-oxo-1,2-dihydro-6-quinolinesulfonamide (529)

These compounds were prepared via method 133 using (3-chloro-4-methylphenyl)boronic acid as the boronic acid. The racemic product was separated via Chiralpak AS-H column (35% MeOH/65% CO$_2$) to give (P)-1-(3'-chloro-2-fluoro-5-methoxy-4'-methyl-4-biphenylyl)-N-3-isoxazolyl-2-oxo-1,2-dihydro-6-quinolinesulfonamide and (M)-1-(3'-chloro-2-fluoro-5-methoxy-4'-methyl-4-biphenylyl)-N-3-isoxazolyl-2-oxo-1,2-dihydro-6-quinolinesulfonamide as light-yellow crystalline solids. Data for peak 1: $^1$H NMR (400 MHz, DMSO-d$_6$) δ ppm 2.42 (s, 3H) 3.32 (s, 3H) 6.45 (s, 1H) 6.82 (d, J=9.64 Hz, 1H) 6.88 (d, J=9.02 Hz, 1H) 7.41 (d, J=6.84 Hz, 1H) 7.47-7.57 (m, 2H) 7.57-7.64 (m, 1H) 7.76 (s, 1H) 7.86 (dd, J=8.97, 2.23 Hz, 1H) 8.24 (d, J=9.54 Hz, 1H) 8.38 (d, J=2.18 Hz, 1H) 8.72 (d, J=1.87 Hz, 1H) 11.67 (s, 1H). m/z (ESI) 540.2 (M+H)$^+$. Data for peak 2: $^1$H NMR (400 MHz, DMSO-d$_6$) δ ppm 2.42 (s, 3H) 3.32 (s, 3H) 6.45 (s, 1H) 6.82 (d, J=9.64 Hz, 1H) 6.88 (d, J=9.02 Hz, 1H) 7.41 (d, J=6.84 Hz, 1H) 7.47-7.57 (m, 2H) 7.57-7.64 (m, 1H) 7.76 (s, 1H) 7.86 (dd, J=8.97, 2.23 Hz, 1H) 8.24 (d, J=9.54 Hz, 1H) 8.38 (d, J=2.18 Hz, 1H) 8.72 (d, J=1.87 Hz, 1H) 11.67 (s, 1H). m/z (ESI) 540.2 (M+H)⁺.

Example 530

1-(5-fluoro-2-methoxy-4-(3-(trifluoromethyl)-1-azetidinyl)phenyl)-N-3-isoxazolyl-2-oxo-1,2-dihydro-6-quinolinesulfonamide This compound was prepared via method 135 using 3-(trifluoromethyl)azetidine hydrochloride (purchased from Enamine) as the amine. ¹H NMR (500 MHz, DMSO-d₆) δ ppm 3.63 (s, 3H) 3.77 (br. s., 1H) 4.02-4.18 (m, 2H) 4.29 (t, J=8.04 Hz, 2H) 6.42 (dd, J=4.77, 3.21 Hz, 2H) 6.75 (d, J=9.60 Hz, 1H) 6.80 (d, J=8.95 Hz, 1H) 7.16 (d, J=12.20 Hz, 1H) 7.82 (dd, J=8.95, 2.08 Hz, 1H) 8.16 (d, J=9.73 Hz, 1H) 8.31 (d, J=1.88 Hz, 1H) 8.69 (s, 1H) 11.61 (br. s., 1H). m/z (ESI) 539.1 (M+H)⁺.

Example 531

1-(5-fluoro-4-(5-fluoro-2-methoxy-3-pyridinyl)-2-methoxyphenyl)-N-3-isoxazolyl-2-oxo-1,2-dihydro-6-quinolinesulfonamide This compound was prepared via method 136 using 5-fluoro-2-methoxy-3-pyridineboronic acid (purchased from Combi-blocks) as the boronic acid. ¹H NMR (500 MHz, DMSO-d₆) δ ppm 3.69 (s, 3H) 3.92 (s, 3H) 6.45 (s, J=5.95 Hz, 1H) 6.82 (d, J=9.37 Hz, 2H) 7.39 (d, J=6.30 Hz, 1H) 7.49 (d, J=9.08 Hz, 1H) 7.87-7.95 (m, 2H) 8.23 (d, J=10.08 Hz, 1H) 8.30 (d, J=2.92 Hz, 1H) 8.38 (s, 1H) 8.72 (s, J=6.96 Hz, 1H) 11.65 (br. s., 1H). m/z (ESI) 541.1 (M+H)⁺.

Example 532

1-(4-(5-chloro-6-methyl-3-pyridinyl)-5-fluoro-2-methoxyphenyl)-N-3-isoxazolyl-2-oxo-1,2-dihydro-6-quinolinesulfonamide This compound was prepared via method 136 using 3-chloro-2-methyl-5-(4,4,5,5-tetramethyl-1,3,2-dioxaborolan-2-yl)pyridine as the boronic acid. ¹H NMR (400 MHz, DMSO-d₆) δ ppm 2.65 (s, 3H) 3.76 (s, 3H) 6.46 (s, 1H) 6.83 (d, J=9.65 Hz, 1H) 6.88 (d, J=9.08 Hz, 1H) 7.53 (d, J=9.08 Hz, 1H) 7.58 (d, J=9.65 Hz, 1H) 7.87 (d, J=9.16 Hz, 1H) 8.21-8.28 (m, 2H) 8.39 (d, J=6.97 Hz, 1H) 8.73-8.75 (m, 1H) 8.76 (s, 1H) 11.67 (s, 1H). m/z (ESI) 541.1 (M+H)⁺.

Examples 533 and 534

(P)-1-(2-chloro-5-methoxy-3'-(trifluoromethyl)-[1,1'-biphenyl]-4-yl)-N-(isoxazol-3-yl)-2-oxo-1,2-dihydroquinoline-6-sulfonamide (533) and (M)-1-(2-chloro-5-methoxy-3'-(trifluoromethyl)-[1,1'-biphenyl]-4-yl)-N-(isoxazol-3-yl)-2-oxo-1,2-dihydroquinoline-6-sulfonamide (534)

These compounds were prepared via method 65 using (3-(trifluoromethyl)phenyl)boronic acid as the boronic acid. The racemic product was separated via chiral SFC on a Chiralpak AS-H column (20% MeOH/80% CO₂) to give (P)-1-(2,3'-dichloro-5-methoxy-[1,1'-biphenyl]-4-yl)-N-(isoxazol-3-yl)-2-oxo-1,2-dihydroquinoline-6-sulfonamides peak 1 and (M)-1-(2,3'-dichloro-5-methoxy-[1,1'-biphenyl]-4-yl)-N-(isoxazol-3-yl)-2-oxo-1,2-dihydroquinoline-6-sulfonamide as peak 2. Both materials were obtained as white solids. Data for peak 1: ¹H NMR (400 MHz, DMSO-d₆) δ=11.69 (br. S., 1H), 8.74 (d, J=1.76 Hz, 1H), 8.39 (d, J=2.25 Hz, 1H), 8.25 (d, J=9.49 Hz, 1H), 7.84-7.94 (m, 4H), 7.81 (d, J=7.34 Hz, 1H), 7.71-7.74 (m, 1H), 7.41 (s, 1H), 6.90 (d, J=9.00 Hz, 1H), 6.83 (d, J=9.68 Hz, 1H), 6.46 (d, J=1.76 Hz, 1H), 3.74 (s, 3H). m/z (ESI) 576.0 (M+H)⁺. Data for peak 2: ¹H NMR (400 MHz, DMSO-d₆) δ 11.69 (br. s., 1H), 8.73 (d, J=1.76 Hz, 1H), 8.39 (d, J=2.25 Hz, 1H), 8.25 (d, J=9.59 Hz, 1H), 7.86-7.95 (m, 4H), 7.81 (d, J=7.43 Hz, 1H), 7.73 (s, 1H), 7.41 (s, 1H), 6.90 (d, J=9.00 Hz, 1H), 6.83 (d, J=9.68 Hz, 1H), 6.46 (d, J=1.76 Hz, 1H), 3.74 (s, 3H). m/z (ESI) 576.0 (M+H)⁺.

Intermediate AK: Perfluorophenyl 1-(4-bromo-5-fluoro-2-methoxyphenyl)-2-oxo-1,2-dihydro quinoline-6-sulfonate

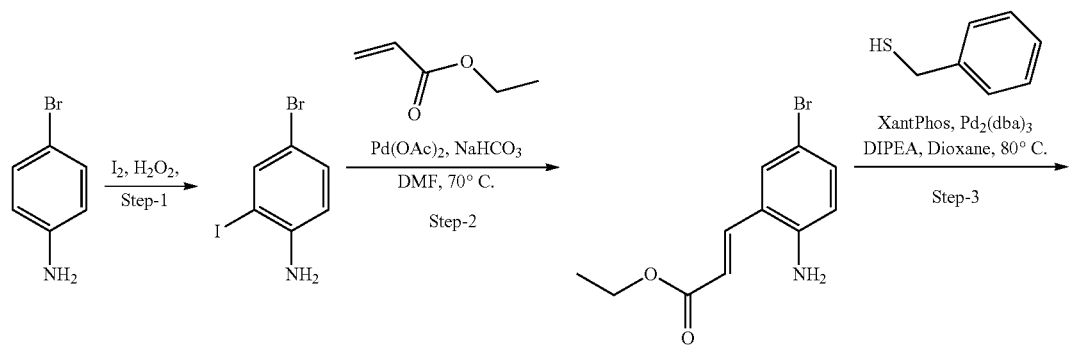

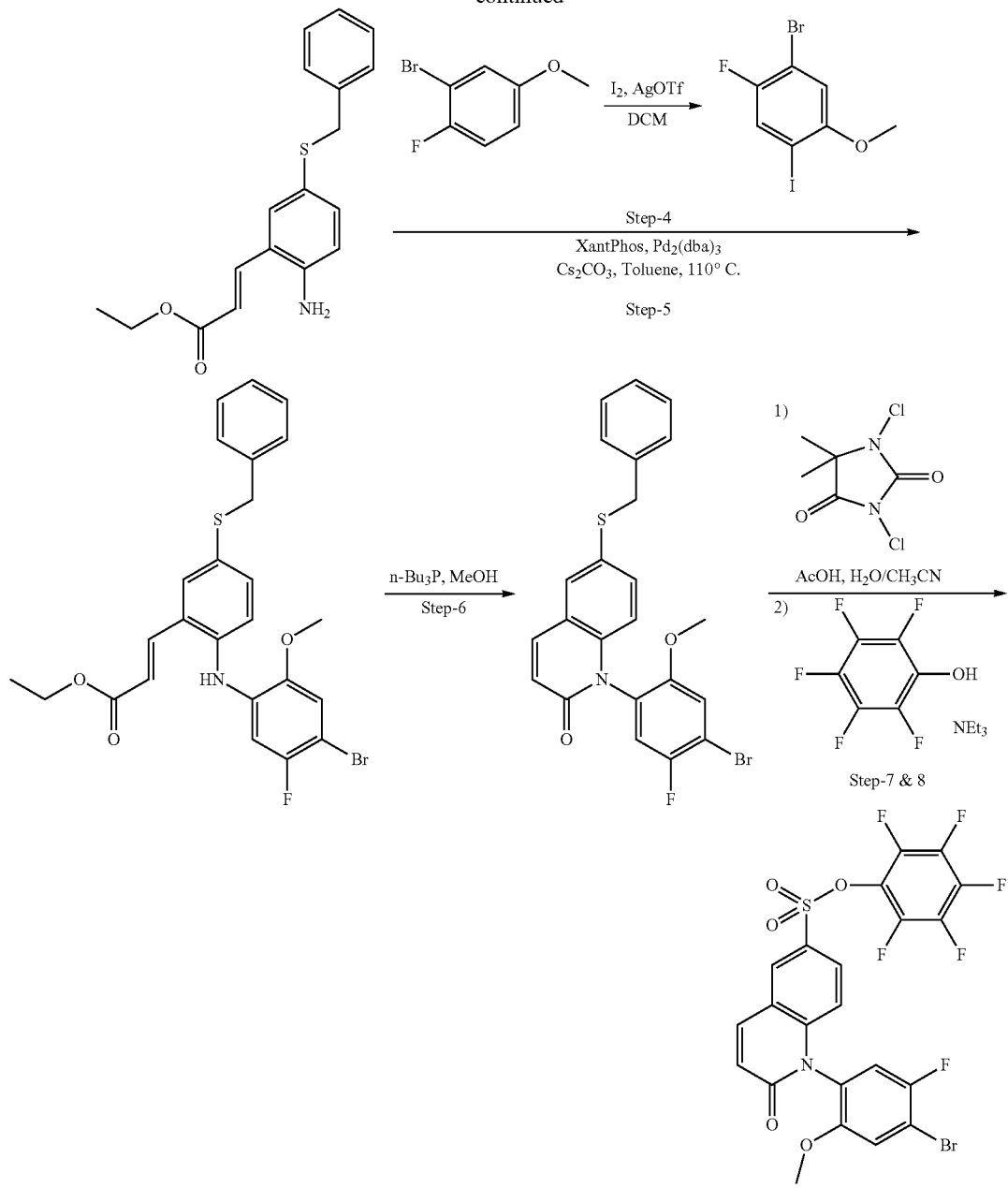

Step-1: 4-bromo-2-iodoaniline

To a solution of 4-bromo-aniline (500 g, 2.90 mol, 2.0 equiv, Saibain Chem) in cyclohexane (2.5 L) was added iodine (368 g, 1.45 mol, 1.0 equiv, Qualigens) and the mixture was heated at 50° C. After 30 min, the reaction mixture became homogenous. 30% aqueous hydrogen peroxide solution (250 mL, Spectrochem) was added to the reaction mixture. The reaction was heated for 4 h at 50° C. The reaction was cooled to room temperature, diluted with ethyl acetate (5.0 L) and washed with aqueous sodium-sulphite (2.5 Kg in 4.0 L) solution. The organic layer was washed with water (3.0 L) and brine (3.0 L) dried over magnesium sulfate, filtered and concentrated under reduced pressure to obtain the crude material which was purified by column chromatography (silica gel; mesh size 60-120, elution 0-20% ethyl acetate and hexanes) to get 4-bromo-2-iodoaniline (650 g, 75.0%), as off white solid. TLC solvent system: 100% hexanes. Product's $R_f$: 0.6. MS (ESI, positive ion) m/z: 297.0 (M+1). $^1$H NMR (400 MHz, CDCl$_3$) δ 7.72 (d, J=2.5 Hz, 1H), 7.23 (dd, J=8.4, 2.1 Hz, 1H), 6.62 (d, J=8.3 Hz, 1H), 4.09 (s, 2H).

Step-2: Ethyl (E)-3-(2-amino-5-bromophenyl)acrylate

To a solution of 4-bromo-2-iodoaniline (750 g, 2.51 mol, 1.0 equiv) in DMF (5.0 L) was added ethyl acrylate (277 g, 2.76 mol, 1.1 equiv, Avra) and sodium bicarbonate (680 g, 6.29 mol, 2.5 equiv). The reaction mixture was degassed with nitrogen for 20 min followed by the addition of palladium acetate (28.8 g, 128.27 mmol, 0.05 equiv, Hindustan Platinum). The reaction mixture was heated at 70° C. for 3 h. The reaction was filtered through celite and the celite bed was washed with ethyl acetate (2×500 mL). The filtrate was concentrated under reduced pressure to obtain the crude residue which was purified by column chromatography (silica gel; mesh size 60-120, elution 0-20% ethyl acetate in hexanes) to obtain (E)-ethyl 3-(2-amino-5-bromophenyl) acrylate (620 g, 77.0%), as yellow solid. TLC solvent system: 20% ethyl acetate in hexanes. Product's $R_f$: 0.4. MS (ESI, positive ion) m/z; 270.2 (M+1). $^1$H NMR (400 MHz, DMSO) δ 7.75 (d, J=16.1 Hz, 1H), 7.57 (d, J=2.0 Hz, 1H), 7.16 (dd, J=9.1, 2.4 Hz, 1H), 6.66 (d, J=8.6 Hz, 1H), 6.43 (d, J=8.6 Hz, 1H), 5.81 (s, 2H), 4.20 (q, J=7.2 Hz, 2H), 1.27 (t, J=7.2 Hz, 3H).

Step-3: Ethyl (E)-3-(2-amino-5-(benzylthio)phenyl) acrylate

To a solution of (E)-ethyl 3-(2-amino-5-bromophenyl) acrylate (620 g, 2.29 mol, 1.0 equiv) in 1,4-dioxane (4.0 L) was added DIPEA (1.26 L, 8.88 mol, 3.9 equiv, GLR) and degassed with nitrogen for 20 mins. XantPhos (92.9 g, 106 mmol, 0.05 equiv, GLR), and tris(dibenzylideneacetone) dipalladium (84 g, 91.0 mmol, 0.04 equiv, Hindustan Platinum) was added to the reaction mixture. The mixture was purged with nitrogen and heated to 80° C. for 30 mins. The reaction was cooled to RT and benzyl mercaptan (455.5 g, 3.67 mol, 1.6 equiv, Alfa Aesar) was added and the reaction was heated at 80° C. for an additional 4 h. The reaction was cooled to room temperature and diluted with ethyl acetate (4.0 L). The mixture was filtered through celite and the celite bed was washed with ethyl acetate (2×1.0 L). The filtrate was concentrated under reduced pressure to obtain the crude material which was purified by chromatography (silica gel; mesh size 60-120, elution 0-40% ethyl acetate and petroleum ether) to obtain (E)-ethyl 3-(2-amino-5-(benzylthio) phenyl)acrylate (520 g, 72.0%), as yellow solid. TLC solvent system: 30% ethyl acetate in hexanes. Product's $R_f$: 0.4. MS (ESI, positive ion) m/z; 314.1 (M+1). $^1$H NMR (400 MHz, DMSO) δ 7.79 (d, J=16.1 Hz, 1H), 7.37 (d, J=2.0 Hz, 1H), 7.25-7.17 (m, 5H) 7.10 (dd, J=8.4, 2.1 Hz, 1H), 6.61 (d, J=8.3 Hz, 1H), 6.32 (d, J=15.2 Hz, 1H), 5.75 (s, 2H), 4.20 (q, J=7.2 Hz, 2H), 4.01 (s, 2H), 1.27 (t, J=7.2 Hz, 3H).

Step-4: 1-bromo-2-fluoro-4-iodo-5-methoxybenzene

To a solution of 2-bromo-1-fluoro-4-methoxybenzene (500.0 g, 2.44 mol, 1.0 equiv) in DCM (5.0 L) was added silver trifluoromethane sulfonate (686.0 g, 2.68 mol, 1.1 equiv, Angene) and the reaction mixture was stirred for 20 mins. Iodine (678.0 g, 2.68 mol, 1.1 equiv) was added to the reaction and the mixture was stirred at room temperature for 16 h. The mixture was diluted with DCM (3.0 L) and filtered through celite. The celite bed was washed with DCM (2×1.0 L) and the filtrate was washed with 20% aqueous sodium thiosulfate (3.0 L) and saturated aqueous sodium bicarbonate solution (3.0 L). The organic layer was dried over sodium sulfate, filtered and concentrated under reduced pressure to obtain the crude material which was purified by chromatography (silica gel; mesh size 60-120, elution 0-5% ethyl acetate and petroleum ether) to get 1-bromo-2-fluoro-4-iodo-5-methoxybenzene (720 g, 87%), as off-white solid. TLC solvent system: 100% hexanes. Product's $R_f$: 0.6. MS (ESI, positive ion) m/z: 331.0 (M+1). $^1$H NMR (400 MHz, CDCl$_3$) δ 7.55 (d, J=7.2 Hz, 1H), 6.95 (d, J=5.6 Hz, 1H), 3.89 (s, 3H).

Step-5: Ethyl (E)-3-(5-(benzylthio)-2-((4-bromo-5-fluoro-2-methoxyphenyl)amino)phenyl) acrylate To a solution of (E)-ethyl 3-(2-amino-5-(benzylthio)phenyl)acrylate (300 g, 958.1 mmol, 1.0 equiv) and 1-bromo-2-fluoro-4-iodo-5-methoxybenzene (348.0 g, 1051.6 mmol, 1.1 equiv) in toluene (2.5 L) was added Cs$_2$CO$_3$ (468 g, 1436.3 mmol, 1.5 equiv, Spectrochem) and the mixture was degassed with nitrogen for 20 mins. Pd$_2$(dba)$_3$ (35 g, 38.2 mmol, 0.04 equiv, Hindustan Platinum) and XantPhos (44.6 g, 76.4 mmol, 0.08 equiv, GLR) were added to the reaction mixture and the mixture was heated at 110° C. for 5 h. The reaction mixture was allowed to cool to room temperature, diluted with dichloromethane (2.0 L) and filtered through celite. The filtrate was concentrated under reduced pressure to obtain the crude material which was purified by stirring with 5% ethyl acetate in hexanes (3.0 L) for 30 min and filtered to obtain (E)-ethyl 3-(5-(benzylthio)-2-((4-bromo-5-fluoro-2-methoxyphenyl)amino)phenyl)acrylate (350 g, 71%) as yellow solid. TLC solvent system: 30% ethyl acetate in hexanes. Product's $R_f$: 0.5. MS (ESI, positive ion) m/z; 516.2 (M+1). $^1$H NMR (400 MHz, DMSO) δ 7.73-7.61 (m, 3H), 7.34-7.15 (m, 6H), 7.02 (d, J=11.4 Hz, 1H), 6.60 (d, J=21.2 Hz, 1H), 6.33 (d, J=14.1 Hz, 1H), 4.26 (s, 2H), 4.16-4.09 (m, 2H), 3.81 (s, 3H), 1.22 (t, J=7.2 Hz, 3H). Note: NH proton not observed.

Step-6: 6-(benzylthio)-1-(4-bromo-5-fluoro-2-methoxyphenyl)quinolin-2(1H)-one

To a solution of (E)-ethyl 3-(5-(benzylthio)-2-((4-bromo-5-fluoro-2-methoxyphenyl)amino)phenyl)acrylate (250.0 g, 484.0 mmol, 1.0 equiv) in methanol (2.5 L) was added tri(n-butyl)phosphine (50% solution in ethyl acetate, 48.9 mL, 96.8 mmol, 0.2 equiv, Spectrochem) and the reaction mixture was heated at 70° C. for 5 h. The reaction mixture was allowed to cool to rt, concentrated under reduced pressure to obtain the crude material which was purified by stirring with 5% ethyl acetate in hexanes (1.0 mL) and filtered to obtain 6-(benzylthio)-1-(4-bromo-5-fluoro-2-methoxyphenyl)quinolin-2(1H)-one (201.0 g, 88%) as off white solid. TLC solvent system: 30% ethyl acetate in hexanes. Product's $R_f$: 0.3. MS (ESI, positive ion) m/z; 470.0 (M+1). $^1$H NMR (400 MHz, DMSO) δ 7.92 (d, J=9.1 Hz, 1H), 7.79 (d, J=1.7 Hz, 1H), 7.65 (d, J=6.1 Hz, 1H), 7.57 (d, J=8.8 Hz, 1H), 7.40-7.22 (m, 6H), 6.68 (d, J=9.6 Hz, 1H), 6.56 (d, J=8.8 Hz, 1H), 4.24 (s, 2H), 3.69 (s, 3H).

Step-7 & 8: Perfluorophenyl 1-(4-bromo-5-fluoro-2-methoxyphenyl)-2-oxo-1,2-dihydro quinoline-6-sulfonate To a solution of 6-(benzylthio)-1-(4-bromo-5-fluoro-2-methoxyphenyl)quinolin-2(1H)-one (250.0 g, 531.5 mmol, 1.0 equiv) in acetonitrile (2.5 L) were added acetic acid (200 mL) and water (130 mL). The resulting mixture was cooled to 0° C. and 1,3-dichloro-5,5-dimethylimidazolidine-2,4-dione (188.5 g, 956.7 mmol, 1.8 equiv, Aldrich) was added portion-wise over 20 min keeping the internal temperature below 5° C. The resulting suspension was stirred at 0-5° C. under nitrogen for 45 min. Then a solution of pentafluorophenol (127.2 g, 690.95 mmol, 1.3 equiv, Apollo) in acetonitrile (200 mL) was added over 5 min followed by NEt$_3$ (307.7 mL, 2.12 mol, 4.0 equiv) over 20 min keeping the internal temperature below 5° C. The mixture was continued to be stirred at 0-5° C. for 30 min. Water (4.0 L) was added and extracted with ethyl acetate (2×2.0 L). The organic layer was washed with brine (1.0 L), dried over sodium sulfate, filtered and concentrated under reduced pressure to obtain the crude which was purified by stirring with isopropyl alcohol:hexanes (1:1, 1.0 L) and filtered to obtain perfluorophenyl 1-(4-bromo-5-fluoro-2-methoxyphenyl)-2-oxo-1,2-dihydroquinoline-6-sulfonate (190 g, 60%) as white solid. TLC solvent system: 30% ethyl acetate in pet ether, Product's $R_f$: 0.4. MS (ESI, positive ion) m/z; 594.2 (M+1). $^1$H-NMR (400 MHz, DMSO) δ 8.60 (d, J=2.0 Hz, 1H), 8.26 (d, J=9.8 Hz, 1H), 7.95 (dd, J=2.2, 9.1 Hz, 1H), 7.70 (t, J=8.6 Hz, 2H), 6.95-6.88 (m, 2H), 3.72 (s, 3H).

Intermediate AL: 1-(4-bromo-2-methoxy-5-methylphenyl)-N-(isoxazol-3-yl)-2-oxo-1,2-dihydroquinoline-6-sulfonamide

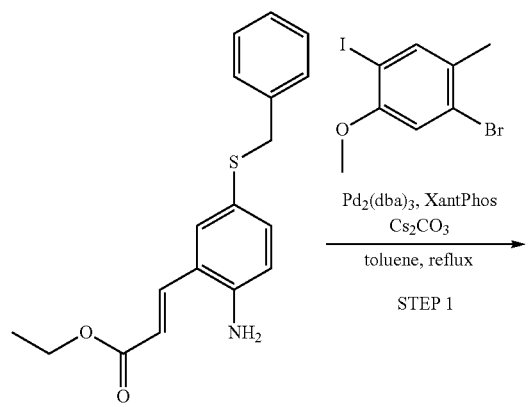

Step 1: (E)-ethyl 3-(5-(benzylthio)-2-((4-bromo-2-methoxy-5-methylphenyl)amino)phenyl)acrylate A RBF was charged with (E)-ethyl 3-(2-amino-5-(benzylthio)phenyl)acrylate (4.729 g, 15.09 mmol, made via Method 42, Steps 1-2), 1-bromo-4-iodo-5-methoxy-2-methylbenzene (5.18 g, 15.84 mmol, Oakwood), Xantphos (0.437 g, 0.754 mmol), Pd$_2$(dba)$_3$ (0.345 g, 0.377 mmol), cesium carbonate (9.83 g, 30.2 mmol), and toluene (30 mL) were added. A reflux condenser was attached, and the mixture was heated to reflux. After 4 h, additional portions of Pd$_2$(dba)$_3$ (172 mg) and Xantphos (213 mg) were added. After 2 h, additional portions of cesium carbonate (ca. 2 g) and 1-bromo-4-iodo-5-methoxy-2-methylbenzene (600 mg) were added. Following an additional 30 min of reflux, mixture was cooled and filtered through celite. The filter pad was washed with EtOAc (3×). The filtrate was concentrated. The residue was concentrated from MeOH, and taken up in MeOH. The resulting suspension was heated to boiling, then sonicated and cooled to RT. The mixture was filtered, and the collected solid was washed with MeOH (3×) and dried under a stream of N$_2$ (g) for 48 hrs to give (E)-ethyl 3-(5-(benzylthio)-2-((4-bromo-2-methoxy-5-methylphenyl)amino)phenyl)acrylate (5.21 g, 10.17 mmol, 67.4% yield) as a bright-yellow solid. $^1$H NMR (400 MHz, DMSO-d$_6$)=7.75 (d, J=15.9 Hz, 1H), 7.66 (d, J=2.1 Hz, 1H), 7.42 (s, 1H), 7.37-7.20 (m, 6H), 7.14 (s, 1H), 6.85 (d, J=8.5 Hz, 1H), 6.62 (s, 1H), 6.51 (d, J=15.9 Hz, 1H), 4.23 (s, 2H), 4.15 (q, J=7.0 Hz, 2H), 3.78 (s, 3H), 2.14 (s, 2H), 1.23 (t, J=7.1 Hz, 3H). m/z (ESI) 512.2 (M+H)$^+$.

Step 2: 6-(benzylthio)-1-(4-bromo-2-methoxy-5-methylphenyl)quinolin-2(1H)-one A RBF was charged with (E)-ethyl 3-(5-(benzylthio)-2-((4-bromo-2-methoxy-5-methylphenyl)amino)phenyl)acrylate (5.12 g, 9.99 mmol) and MeOH (50.0 ml) to give a yellow suspension. Sodium methoxide (25 wt % in MeOH) (0.432 ml, 1.998 mmol) was added. A reflux condenser was attached, and the flask was lowered into a 70° C. heating bath. After 1 h, additional portions of MeOH (25 mL) and sodium methoxide solution (ca. 0.85 mL) were added in sequence. After 7 h, the mixture was cooled and concentrated under vacuum. The residue was purified by chromatography on silica gel (80-g Redi-Sep column, 25-g silica gel loading column, loaded as a solution in MeOH-DCM, then eluted with 25-75% EtOAc/Heptane containing 10% DCM). The fractions containing product were combined and concentrated to give 6-(benzylthio)-1-(4-bromo-2-methoxy-5-methylphenyl)quinolin-2(1H)-one (4.233 g, 9.08 mmol, 91% yield) as a tan solid. m/z (ESI) 466.1 (M+H)$^+$.

Step 3: Perfluorophenyl 1-(4-bromo-2-methoxy-5-methylphenyl)-2-oxo-1,2-dihydroquinoline-6-sulfonate A RBF was charged with 6-(benzylthio)-1-(4-bromo-2-methoxy-5-methylphenyl)quinolin-2(1H)-one (4.23 g, 9.07 mmol), DCM (71.1 ml), acetic acid (2.67 ml), and water (1.778 ml) to give clear, light-brown. The flask was cooled in an ice-water bath for 10 min, then 1,3-dichloro-5,5-dimethylimidazolidine-2,4-dione (3.66 g, 18.59 mmol) was added in one portion. After 40 min, an additional portion of oxidant (850 mg) was added. The mixture was stirred for another 20 min, then 2,3,4,5,6-pentafluorophenol (2.504 g, 13.60 mmol) and triethylamine (5.06 ml, 36.3 mmol) (added dropwise) were added in sequence. After 20 min, the mixture was diluted with water. The layers were separated, and the aq. layer was extracted with DCM (1×). The combined organic extracts were dried over sodium sulfate, filtered, and concentrated. The residue was purified by chromatography on silica gel (80-g Redi-Sep Gold column, 25-g silica gel loading column, 10-60% EtOAc/Heptane with 10% DCM). Fractions containing the main spot were combined and concentrated to give an off-white foam. LCMS and NMR showed that it was contaminated with 30 mol % of the peak with a mass of 425. This was equal to 82 wt % purity. This meant a yield of product: perfluorophenyl 1-(4-bromo-2-methoxy-5-methylphenyl)-2-oxo-1,2-dihydroquinoline-6-sulfonate (3.37 g, 5.71 mmol, 62.9% yield). m/z (ESI) 590.0 (M+H)$^+$.

Step 4: 1-(4-bromo-2-methoxy-5-methylphenyl)-N-(isoxazol-3-yl)-2-oxo-1,2-dihydroquinoline-6-sulfonamide A solution of perfluorophenyl 1-(4-bromo-2-methoxy-5-methylphenyl)-2-oxo-1,2-dihydroquinoline-6-sulfonate (3.508 g, 4.87 mmol), isoxazol-3-amine (0.540 ml, 7.31 mmol) and THF (48.7 ml) was cooled in an ice-bath for 15 min, then lithium bis(trimethylsilyl)amide (1M in THF) (12.18 ml, 12.18 mmol) was added dropwise. After 20 min, additional portions of 3-aminoisoxazole (0.1 mL) and LHMDS solution (2 mL) were added. After 5 min, the mixture was diluted with 1N aq. HCl and EtOAc. The layers were separated, and the organic layer was washed with 1N aq. HCl. The aq. layers were combined and extracted with EtOAc (2×). The combined organic extracts were dried over sodium sulfate, filtered, and concentrated. The residue was concentrated from DCM, and then taken up in DCM. The resulting suspension was sonicated and filtered. The collected solid was washed with DCM (2×), dried under a stream of N$_2$ (g), then dried under vacuum to give 1-(4-bromo-2-methoxy-5-methylphenyl)-N-(isoxazol-3-yl)-2-oxo-1,2-dihydroquinoline-6-sulfonamide (2.169 g, 4.42 mmol, 91% yield) as a white solid. $^1$H NMR (400 MHz, DMSO-d$_6$)=11.66 (br. s., 1H), 8.72 (d, J=1.8 Hz, 1H), 8.35 (d, J=2.2 Hz, 1H), 8.21 (d, J=9.6 Hz, 1H), 7.83 (dd, J=2.2, 8.9 Hz, 1H), 7.52 (s, 1H), 7.34 (d, J=0.4 Hz, 1H), 6.78 (d, J=9.6 Hz, 2H), 6.43 (d, J=1.9 Hz, 1H), 3.67 (s, 3H), 2.31 (s, 3H). m/z (ESI) 489.9 (M+H)$^+$.

Intermediate AN: (3'-chloro-3-fluoro-5-methoxy-[1,1'-biphenyl]-4-yl)boronic acid

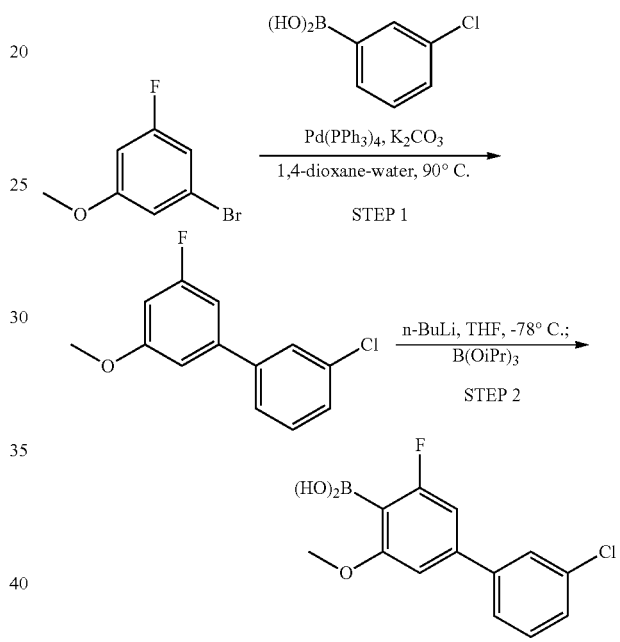

Step 1: 3'-chloro-3-fluoro-5-methoxy-1,1'-biphenyl

A RBF was charged with 1-bromo-3-fluoro-5-methoxybenzene (2.104 g, 10.26 mmol), (3-chlorophenyl)boronic acid (1.765 g, 11.29 mmol), potassium carbonate (4.25 g, 30.8 mmol), and Pd(Ph$_3$P)$_4$ (0.593 g, 0.513 mmol). The flask was flushed with Ar (g), then 1,4-dioxane (25.7 ml) and water (8.55 ml) were added. A reflux condenser was attached, and the flask was lowered into a 90° C. heating bath for 45 min. The mixture was cooled to room temperature, diluted with water, and extracted with EtOAc (2×). The combined organic extracts were dried over sodium sulfate, filtered, and concentrated. The residue was purified by chromatography on silica gel (50-g SNAP Ultra column, 25-g silica gel column, 0-5% EtOAc/Heptane) to give 3'-chloro-3-fluoro-5-methoxy-1,1'-biphenyl (2.47 g, 10.44 mmol, 102% yield) as a clear oil containing about 10 wt % impurities.

Step 2: (3'-chloro-3-fluoro-5-methoxy-[1,1'-biphenyl]-4-yl)boronic acid

A RBF was charged with 3'-chloro-3-fluoro-5-methoxy-1,1'-biphenyl (513 mg, 2.168 mmol) and THF (7225 µl) to give a clear solution. The flask was cooled in a dry ice-acetone bath for 10 min, then n-butyllithium (1.8M in hexanes) (1445 µl, 2.60 mmol) was added dropwise. After 30 min, triisopropyl borate (597 µl, 2.60 mmol) was added dropwise, and the cooling bath was removed. After 10 min, the mixture was diluted with 2N aq. NaOH, and the resulting biphasic mixture was stirred for 40 min. The mixture was diluted with water and ether. The layers were separated, and the organic layer was extracted with water (1×). The combined aq. extracts were acidified with 2N aq. HCl (30 mL). The resulting suspension was stirred for 20 min then filtered. The collected solid was washed with water (3×), then dried under a stream of N$_2$ (g) for 1 h to give (3'-chloro-3-fluoro-5-methoxy-[1,1'-biphenyl]-4-yl)boronic acid (147 mg, 0.524 mmol, 24.18% yield) as an off-white solid. m/z (ESI) 281.0 (M+H)$^+$.

Intermediate AO: 3'-chloro-3-fluoro-4-iodo-5-methoxy-1,1'-biphenyl

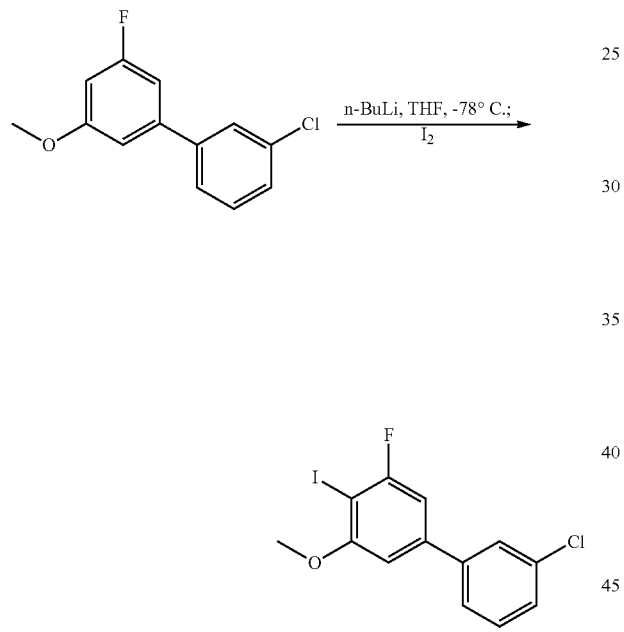

A RBF was charged with 3'-chloro-3-fluoro-5-methoxy-1,1'-biphenyl (577.6 mg, 2.441 mmol) and THF (8135 µl) to give a clear solution. The flask was cooled in a dry ice-acetone bath for 10 min, then n-butyllithium (1.8M in hexanes) (1627 µl, 2.93 mmol) was added dropwise. After 30 min, a solution of iodine (929 mg, 3.66 mmol) in THF (3 mL) was added dropwise. TLC after 5 min showed conversion to a slightly lower spot. The mixture was diluted with saturated aq. sodium thiosulfate solution and warmed to room temperature. The mixture was diluted with water and extracted with EtOAc (2×), and the combined organic extracts were dried over sodium sulfate, filtered, and concentrated. The residue was purified by chromatography on silica gel (25-g Ultra SNAP column, 0-5% EtOAc/Heptane) to give 3'-chloro-3-fluoro-4-iodo-5-methoxy-1,1'-biphenyl (687 mg, 1.895 mmol, 78% yield) as an off-white solid. $^1$H NMR (400 MHz, DMSO-d$_6$)=7.87 (td, J=1.0, 1.8 Hz, 1H), 7.74 (td, J=1.8, 7.0 Hz, 1H), 7.55-7.43 (m, 2H), 7.25 (dd, J=1.8, 9.1 Hz, 1H), 7.14-7.07 (m, 1H), 3.97 (s, 3H).

Intermediate AP: 1-(4-bromo-2-methoxyphenyl)-N-(isoxazol-3-yl)-2-oxo-1,2-dihydroquinoline-6-sulfonamide

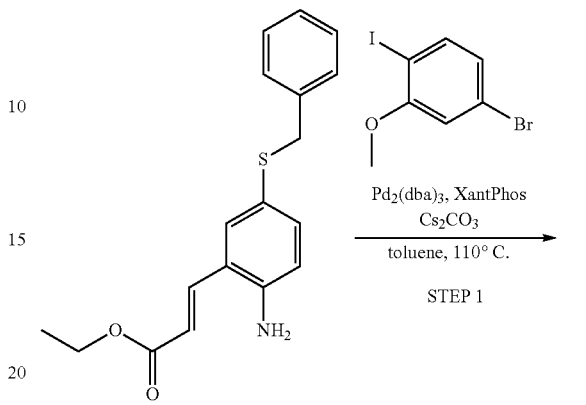

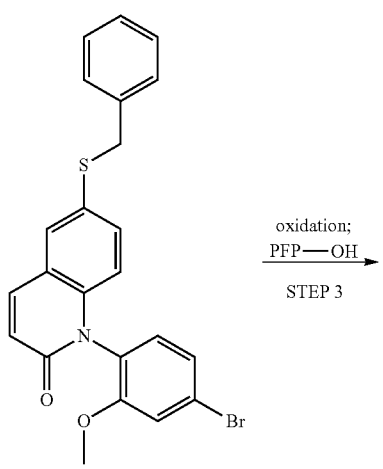

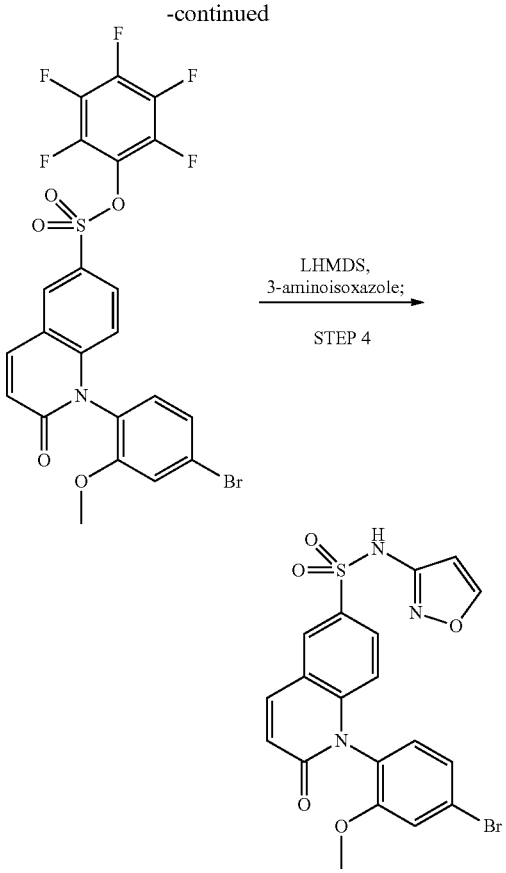

Step 1: (E)-ethyl 3-(5-(benzylthio)-2-((4-bromo-2-methoxyphenyl)amino)phenyl)acrylate A RBF was charged with (E)-ethyl 3-(2-amino-5-(benzylthio)phenyl)acrylate (2.39 g, 7.63 mmol, made via Method 42, Steps 1-2), 4-bromo-1-iodo-2-methoxybenzene (2.86 g, 9.15 mmol), Xantphos (0.221 g, 0.381 mmol), Pd$_2$(dba)$_3$ (0.175 g, 0.191 mmol), and cesium carbonate (4.97 g, 15.25 mmol) were added. A reflux condenser was attached and the flask was lowered into a 110° C. heating bath. After 2 h, an additional portion of cesium carbonate (1.4 g) was added, and the bath temperature was raised to 120° C. The mixture was heated for another 2 h then cooled to room temperature, diluted with EtOAc, and filtered through celite with the aid of EtOAc. The filtrate was concentrated. The oily residue was taken up in 2-PrOH. The mixture was concentrated to give a yellow solid with some oily solid present. The mixture was taken up in 2-PrOH to give a suspension, and the suspension was stirred for 16 hrs. The mixture was filtered, and the filtered solid was washed with 2-PrOH (3×). The collected solid was dried on the filter under a flow of N$_2$ (g) for 15 min to give (E)-ethyl 3-(5-(benzylthio)-2-((4-bromo-2-methoxyphenyl)amino)phenyl) acrylate (3.136 g, 6.29 mmol, 83% yield) as a bright-yellow solid. $^1$H NMR (400 MHz, DMSO-d$_6$)=7.72 (d, J=16.0 Hz, 1H), 7.68 (d, J=2.2 Hz, 1H), 7.47 (s, 1H), 7.37-7.19 (m, 6H), 7.13 (d, J=2.2 Hz, 1H), 6.94 (dd, J=2.2, 8.4 Hz, 1H), 6.86 (d, J=8.5 Hz, 1H), 6.55 (s, 1H), 6.52 (d, J=7.7 Hz, 1H), 4.24 (s, 2H), 4.15 (q, J=7.1 Hz, 2H), 3.82 (s, 3H), 1.23 (t, J=7.1 Hz, 3H). m/z (ESI) 498.0 (M+H)$^+$.

Step 2: 6-(benzylthio)-1-(4-bromo-2-methoxyphenyl)quinolin-2(1H)-one

A RBF was charged with (E)-ethyl 3-(5-(benzylthio)-2-((4-bromo-2-methoxyphenyl)amino)phenyl)acrylate (3.13 g, 6.28 mmol) and MeOH (31.4 ml) to give a yellow suspension. Sodium methoxide (25 wt % in MeOH) (0.271 ml, 1.256 mmol) was added. A reflux condenser was attached, and the flask was lowered into a 75° C. heating bath. The bath quickly spiked to ca. 80-85° C., but returned to 70-75° C. after 30 min. The reaction was stirred for 16 hrs, and the mixture was diluted with DCM and concentrated. The residue was purified by chromatography on silica gel (50-g SNAP Ultra column, 25-g silica gel loading column, 10-60% EtOAc/Heptane) to give 6-(benzylthio)-1-(4-bromo-2-methoxyphenyl)quinolin-2(1H)-one (1.95 g, 4.31 mmol, 68.6% yield) as a yellow solid. $^1$H NMR (400 MHz, DMSO-d$_6$)=7.94 (d, J=9.5 Hz, 1H), 7.78 (d, J=2.2 Hz, 1H), 7.50 (d, J=2.1 Hz, 1H), 7.43-7.16 (m, 8H), 6.66 (d, J=9.6 Hz, 1H), 6.47 (d, J=8.8 Hz, 1H), 4.23 (s, 2H), 3.69 (s, 3H). m/z (ESI) 452.0 (M+H)$^+$.

Step 3: Perfluorophenyl 1-(4-bromo-2-methoxyphenyl)-2-oxo-1,2-dihydroquinoline-6-sulfonate A RBF was charged with 6-(benzylthio)-1-(4-bromo-2-methoxyphenyl)quinolin-2(1H)-one (1.777 g, 3.93 mmol), acetonitrile (18.49 ml), acetic acid (0.693 ml), and water (0.462 ml) to give a solution. The flask was cooled in an ice-water bath for 10 min, then 1,3-dichloro-5,5-dimethylimidazolidine-2,4-dione (0.813 g, 4.12 mmol) was added in one portion. After 20 min, an additional portion of 1,3-dichloro-5,5-dimethylimidazolidine-2,4-dione (0.813 g, 4.12 mmol) was added in one portion. After another 20 min, 2,3,4,5,6-pentafluorophenol (1.085 g, 5.89 mmol) was added, and the mixture was stirred for 5 min. Triethylamine (2.190 ml, 15.71 mmol) was added dropwise over 30 s then the mixture was stirred for 20 min. The reaction mixture was diluted with water and extracted with DCM (3×). The combined organic extracts were dried over sodium sulfate, filtered, and concentrated. The residue was purified by chromatography on silica gel (50-g SNAP Ultra column, 25-g silica gel loading column, 10-60% EtOAc/Heptane). Perfluorophenyl 1-(4-bromo-2-methoxyphenyl)-2-oxo-1,2-dihydroquinoline-6-sulfonate (1.644 g, 2.85 mmol, 72.6% yield) was isolated as a white foam. $^1$H NMR (400 MHz, DMSO-d$_6$)=8.59 (d, J=2.2 Hz, 1H), 8.24 (d, J=9.6 Hz, 1H), 7.95 (dd, J=2.3, 9.1 Hz, 1H), 7.56 (d, J=1.9 Hz, 1H), 7.44-7.26 (m, 2H), 6.86 (dd, J=9.4, 13.7 Hz, 2H), 3.72 (s, 3H). m/z (ESI) 575.9 (M+H)$^+$.

Step 4: 1-(4-bromo-2-methoxyphenyl)-N-(isoxazol-3-yl)-2-oxo-1,2-dihydroquinoline-6-sulfonamide A RBF was charged with perfluorophenyl 1-(4-bromo-2-methoxyphenyl)-2-oxo-1,2-dihydroquinoline-6-sulfonate (1.070 g, 1.857 mmol), isoxazol-3-amine (0.158 ml, 2.135 mmol) and THF (12.38 ml) to give a clear solution. The flask was cooled in an ice-water bath for 10 min, then lithium bis(trimethylsilyl)amide (1M in THF) (3.90 ml, 3.90 mmol) was added dropwise. After 10 min, the mixture was diluted with EtOAc and washed with 1N aq. HCl. The aq. layer was washed with EtOAc. The combined organic extracts were dried over sodium sulfate, filtered, and concentrated. The residue was purified by chromatography (50-g SNAP Ultra column, 25-g silica gel loading column, 0-5% MeOH/DCM) to give 1-(4-bromo-2-methoxyphenyl)-N-(isoxazol-3-yl)-2- oxo-1,2-dihydroquinoline-6-sulfonamide (0.867 g) as a tan foam that was ca. 90% pure. m/z (ESI) 476.1 (M+H)+.

Intermediate AQ:
2-bromo-5-iodo-4-methoxybenzonitrile

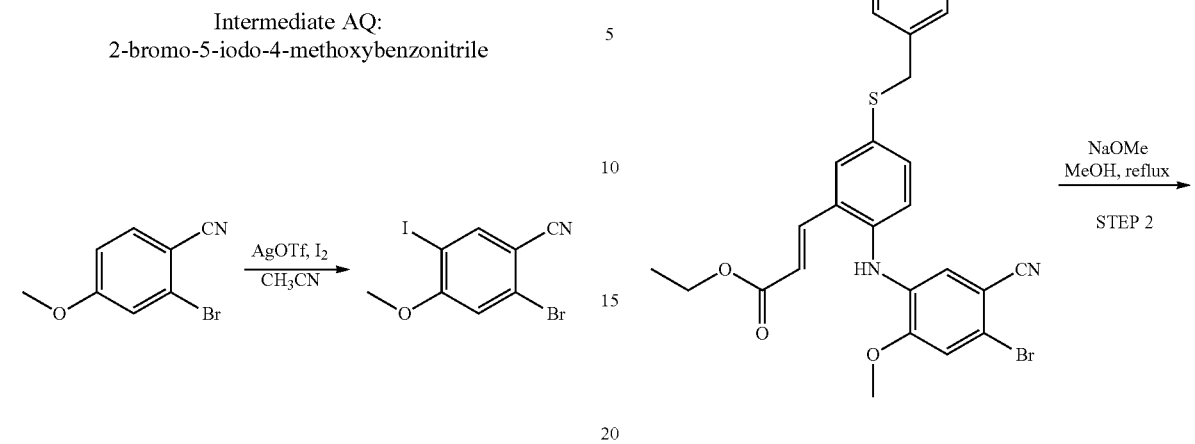

A RBF was charged with 2-bromo-4-methoxybenzonitrile (891 mg, 4.20 mmol, Matrix Scientific) and DCM (1.68E+04 µl) to give a clear solution. silver trifluoromethanesulfonate (1188 mg, 4.62 mmol) and iodine (1173 mg, 4.62 mmol) were added in sequence. The resulting mixture was stirred for 2 d. Additional portions of silver trifluoromethanesulfonate (1188 mg, 4.62 mmol) and iodine (1173 mg, 4.62 mmol) were added, and the mixture was stirred for another 5 h. The reaction mixture was then filtered through celite with the aid of DCM. The filtrate was shaken with saturated aq. sodium thiosulfate until the color disappeared. The biphasic mixture was diluted with water then the layers were separated. The aq. layer was extracted with DCM (2×). The combined organic extracts were dried over sodium sulfate, filtered, and concentrated. The residue was purified by chromatography on silica gel (40-g Redi-Sep Gold column, 25-g silica gel column, 5-30% EtOAc/Heptane) give 2-bromo-5-iodo-4-methoxybenzonitrile (811 mg, 2.400 mmol, 57.1% yield) as an off-white solid. m/z (ESI) 337.8 (M+H)+.

Intermediate AR: 1-(4-bromo-5-cyano-2-methoxyphenyl)-N-(isoxazol-3-yl)-2-oxo-1,2-dihydroquinoline-6-sulfonamide

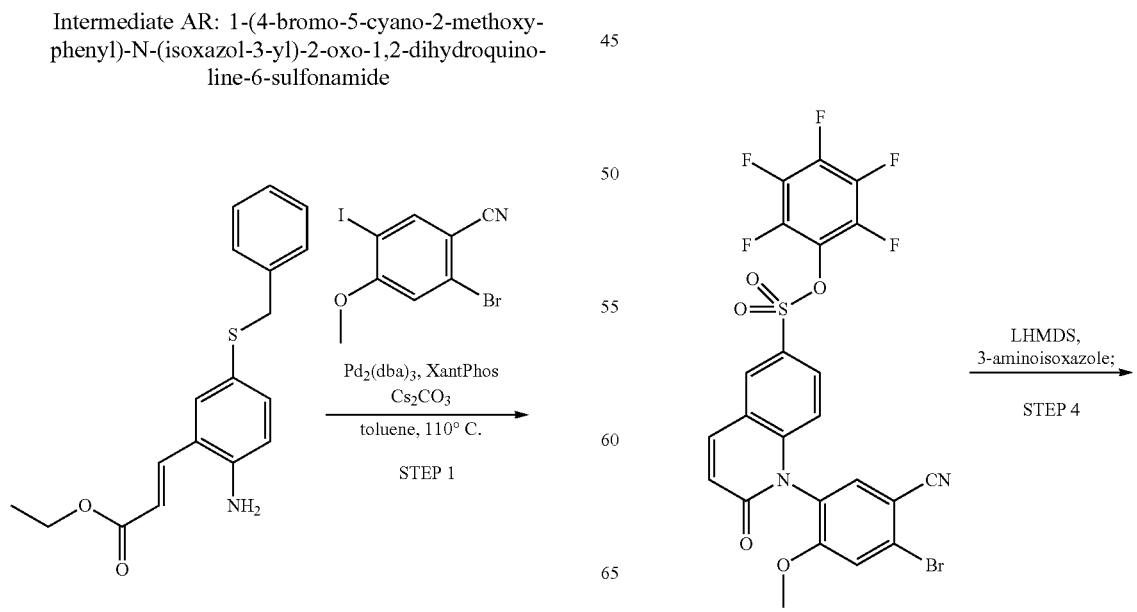

-continued

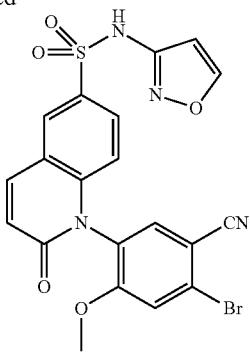

Step 1: (E)-ethyl 3-(5-(benzylthio)-2-((4-bromo-5-cyano-2-methoxyphenyl)amino)phenyl)acrylate A RBF was charged with (E)-ethyl 3-(2-amino-5-(benzylthio)phenyl)acrylate (625 mg, 1.994 mmol, made via Method 42, Steps 1-2), 2-bromo-5-iodo-4-methoxybenzonitrile (809 mg, 2.393 mmol), Xantphos (57.7 mg, 0.100 mmol), Pd$_2$(dba)$_3$ (45.7 mg, 0.050 mmol), and cesium carbonate (1624 mg, 4.99 mmol) were added. A reflux condenser was attached, and the flask was heated to 110° C. overnight. The mixture was cooled, diluted with EtOAc, and filtered through celite with the aid of EtOAc. The filtrate was concentrated. The residue was taken up in 2-PrOH, and the mixture was heated to boiling briefly then sonicated for 30 s. When the mixture had returned to room temperature, it was filtered, and the filtered solid was washed with 2-PrOH (3×). The collected solid was dried on the filter under a flow of N$_2$ (g) for 15 min to give (E)-ethyl 3-(5-(benzylthio)-2-((4-bromo-5-cyano-2-methoxyphenyl)amino)phenyl)acrylate (963 mg, 1.840 mmol, 92% yield) as a bright-yellow solid. m/z (ESI) 545.0 (M+Na)$^+$.

Step 2: 5-(6-(benzylthio)-2-oxoquinolin-1(2H)-yl)-2-bromo-4-methoxybenzonitrile A RBF was charged with (E)-ethyl 3-(5-(benzylthio)-2-((4-bromo-5-cyano-2-methoxyphenyl)amino)phenyl)acrylate (963 mg, 1.840 mmol) and MeOH (9199 µl) to give a thick, yellow suspension. Sodium methoxide (25 wt % in MeOH) (80 µl, 0.368 mmol) was added. A reflux condenser was attached, and the flask was heated to 80° C. overnight. In the morning, the mixture was diluted with DCM and concentrated. The residue was taken up in 2-PrOH, heated briefly to boiling, then sonicated for 20 s. The mixture was cooled then filtered. The collected solid was washed with 2-PrOH, then dried under a stream of N$_2$ (g). The filtration was repeated with the filtrate. The two lots of material were combined to give 5-(6-(benzylthio)-2-oxoquinolin-1(2H)-yl)-2-bromo-4-methoxybenzonitrile (798 mg, 1.672 mmol, 91% yield) as a light-orange solid. m/z (ESI) 477.0 (M+H)$^+$.

Step 3: Perfluorophenyl 1-(4-bromo-5-cyano-2-methoxyphenyl)-2-oxo-1,2-dihydroquinoline-6-sulfonate A RBF was charged with 5-(6-(benzylthio)-2-oxoquinolin-1(2H)-yl)-2-bromo-4-methoxybenzonitrile (798 mg, 1.672 mmol), acetonitrile (7867 µl), acetic acid (295 µl), and water (197 µl) to give a solution. The flask was cooled in an ice-water bath for 10 min, then 1,3-dichloro-5,5-dimethylimidazolidine-2,4-dione (165 mg, 0.836 mmol) was added (0.5 equiv). After 10 min, an additional portion of 1,3-dichloro-5,5-dimethylimidazolidine-2,4-dione (165 mg, 0.836 mmol) was added. After another 10 min, a final portion of 1,3-dichloro-5,5-dimethylimidazolidine-2,4-dione (165 mg, 0.836 mmol) was added to the mixture. 2,3,4,5,6-pentafluorophenol (385 mg, 2.090 mmol) was added. After another minute, triethylamine (932 µl, 6.69 mmol) was added dropwise over 15 s. The mixture was stirred for 10 min then was diluted with water and EtOAc, and the layers were separated. The aq. layer was extracted with DCM (2×). The combined organic extracts were dried over sodium sulfate, filtered, and concentrated. The residue was concentrated from EtOAc, then taken up in EtOAc and filtered. The collected solid was washed with EtOAc (3×), then dried under a stream of N$_2$ (g) for 14 h to give perfluorophenyl 1-(4-bromo-5-cyano-2-methoxyphenyl)-2-oxo-1,2-dihydroquinoline-6-sulfonate (566 mg, 0.941 mmol, 56.3% yield) as an off-white solid. $^1$H NMR (400 MHz, DMSO-d$_6$)=8.61 (d, J=2.3 Hz, 1H), 8.27 (d, J=9.6 Hz, 1H), 8.18 (s, 1H), 7.93 (dd, J=2.3, 9.0 Hz, 1H), 7.88 (s, 1H), 6.98 (d, J=9.0 Hz, 1H), 6.90 (d, J=9.7 Hz, 1H), 3.83 (s, 3H). m/z (ESI) 601.0 (M+H)$^+$.

Step 4: 1-(4-bromo-5-cyano-2-methoxyphenyl)-N-(isoxazol-3-yl)-2-oxo-1,2-dihydroquinoline-6-sulfonamide A RBF was charged with perfluorophenyl 1-(4-bromo-5-cyano-2-methoxyphenyl)-2-oxo-1,2-dihydroquinoline-6-sulfonate (330.64 mg, 0.550 mmol), isoxazol-3-amine (46.7 µl, 0.632 mmol) and THF (3666 µl) to give a clear solution. The flask was cooled in an ice-water bath for 10 min, then lithium bis(trimethylsilyl)amide (1M in THF) (1155 µl, 1.155 mmol) was added dropwise. After 15 min, the mixture was diluted with EtOAc and washed with 1N aq. HCl. The aq. layer was extracted with EtOAc (2×). The combined organic extracts were dried over sodium sulfate, filtered, and concentrated. The residue was purified by chromatography (45-g Redi-Sep column, 25-g silica gel loading column, 0-5% MeOH/DCM) to give 1-(4-bromo-5-cyano-2-methoxyphenyl)-N-(isoxazol-3-yl)-2-oxo-1,2-dihydroquinoline-6-sulfonamide (185 mg, 0.369 mmol, 67.1% yield) as a light-yellow solid. $^1$H NMR (400 MHz, DMSO-d$_6$)=11.67 (br. s., 1H), 8.73 (d, J=1.8 Hz, 1H), 8.38 (d, J=2.2 Hz, 1H), 8.27-8.21 (m, 1H), 8.12-8.06 (m, 1H), 7.90-7.78 (m, 2H), 6.90 (d, J=9.0 Hz, 1H), 6.85-6.76 (m, 1H), 6.45 (d, J=1.8 Hz, 1H), 3.81 (s, 3H). m/z (ESI) 501.0 (M+H)$^+$.

Intermediate AS: Perfluorophenyl 1-(3'-chloro-2,5'-difluoro-5-methoxy-[1,1'-biphenyl]-4-yl)-2-oxo-1,2-dihydroquinoline-6-sulfonate

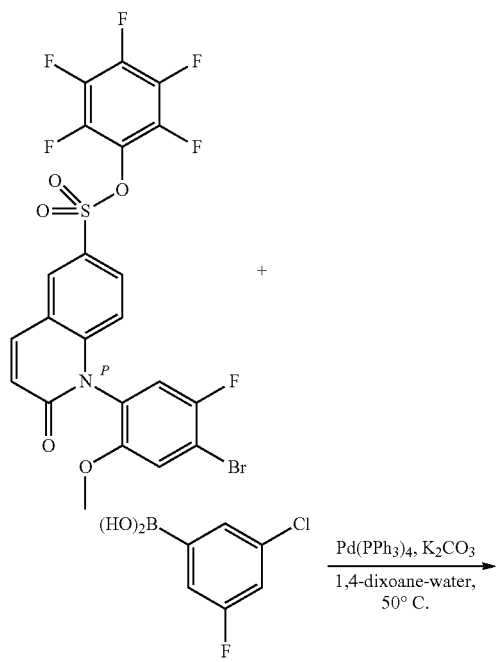

A RBF was charged with perfluorophenyl 1-(4-bromo-5-fluoro-2-methoxyphenyl)-2-oxo-1,2-dihydroquinoline-6-sulfonate, (3-chloro-5-fluorophenyl)boronic acid (1.310 g, 7.52 mmol), PdCl$_2$(dppf)-CH$_2$Cl$_2$ adduct (0.307 g, 0.376 mmol), and potassium carbonate (2.60 g, 18.79 mmol). The flask was flushed with Ar (g), then 1,4-dioxane (14.09 ml) and water (4.70 ml) were added. A reflux condenser was attached, and the flask was heated for 50° C. for 1.5 h. The mixture was cooled, diluted with water, and extracted with EtOAc (3×). The combined organic extracts were concentrated. The residue was purified by chromatography on silica gel (80-g Redi-Sep Gold column, 25-g silica gel loading column, 0-50% EtOAc/Heptane). Several mixed fractions were discarded, and the resulting fractions containing product were combined and concentrated to give a tan solid. The solid was concentrated from DCM, then taken up in DCM and filtered. The filtrate was concentrated to give perfluorophenyl 1-(3'-chloro-2,5'-difluoro-5-methoxy-[1,1'-biphenyl]-4-yl)-2-oxo-1,2-dihydroquinoline-6-sulfonate (1.646 g, 2.56 mmol, 68.0% yield) as a tan solid. $^1$H NMR (400 MHz, DMSO-d$_6$)=8.62 (d, J=2.3 Hz, 1H), 8.28 (d, J=9.6 Hz, 1H), 8.00 (dd, J=2.3, 9.1 Hz, 1H), 7.72-7.57 (m, 4H), 7.52 (d, J=6.8 Hz, 1H), 6.93 (dd, J=9.4, 10.4 Hz, 2H), 3.78 (s, 3H).

Intermediate AT: 1-(2-bromo-4-chlorophenyl)-N-(isoxazol-3-yl)-2-oxo-1,2-dihydroquinoline-6-sulfonamide

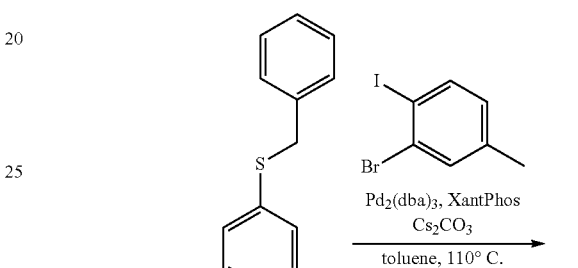

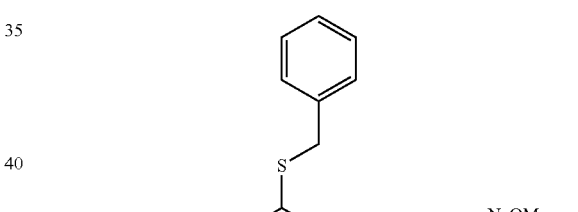

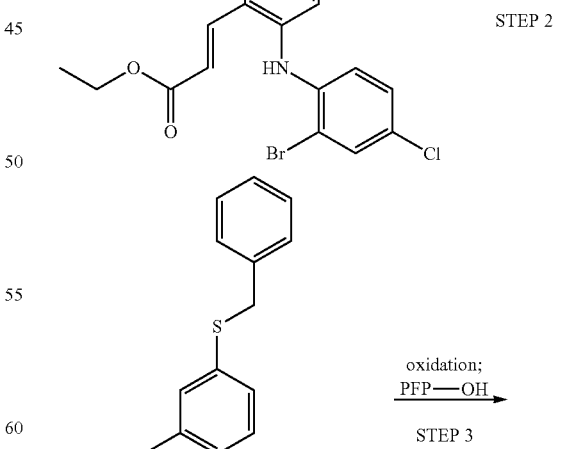

-continued

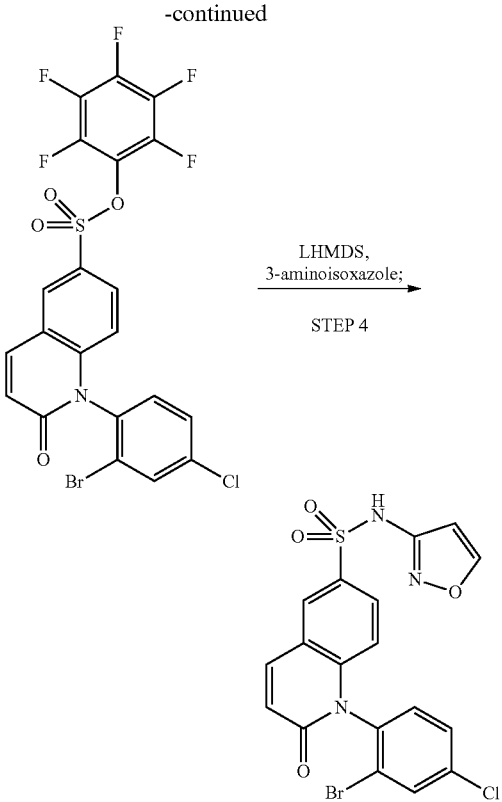

Step 1: (E)-ethyl 3-(5-(benzylthio)-2-((2-bromo-4-chlorophenyl)amino)phenyl)acrylate A RBF was charged with (E)-ethyl 3-(2-amino-5-(benzylthio)phenyl)acrylate (8.25 g, 26.3 mmol, made via Method 42, Steps 1-2), 2-bromo-4-chloro-1-iodobenzene (10.02 g, 31.6 mmol), Xantphos (0.762 g, 1.316 mmol), $Pd_2(dba)_3$ (0.603 g, 0.658 mmol), and cesium carbonate (21.44 g, 65.8 mmol) were added. A reflux condenser was attached and the flask was lowered into a 110° C. heating bath for 1 h. The mixture was cooled to room temperature then filtered through celite with the aid of toluene. The filtrate was concentrated. The residue was taken up in 2-PrOH and concentrated to give a yellow solid with some tan chunks. The mixture was taken up in 2-PrOH and the resulting slurry was heated to boiling for 5 min to give a brown solution (after breaking up some solid with a spatula). The resulting solution was allowed to cool to RT while being stirred. The mixture became a thick slurry that was diluted with 2-PrOH and filtered. The collected solid was washed with 2-PrOH (3×), then dried under a stream of $N_2$ (g) to give (E)-ethyl 3-(5-(benzylthio)-2-((2-bromo-4-chlorophenyl)amino)phenyl)acrylate (10.473 g, 20.83 mmol, 79% yield) as a bright-yellow solid. $^1$H NMR (400 MHz, DMSO-$d_6$)=7.76-7.61 (m, 4H), 7.38-7.27 (m, 5H), 7.27-7.20 (m, 2H), 6.88 (d, J=8.4 Hz, 1H), 6.62-6.52 (m, 2H), 4.27 (s, 2H), 4.14 (q, J=7.1 Hz, 2H), 1.22 (t, J=7.1 Hz, 3H). m/z (ESI) 502.0 (M+H)+.

Step 2: 6-(benzylthio)-1-(2-bromo-4-chlorophenyl)quinolin-2(1H)-one

A 250-mL RBF was charged with (E)-ethyl 3-(5-(benzylthio)-2-((2-bromo-4-chlorophenyl)amino)phenyl)acrylate (10.4 g, 20.68 mmol) and MeOH (103 ml) to give a thick, yellow suspension. Sodium methoxide (25 wt % in MeOH) (0.894 ml, 4.14 mmol) was added. A reflux condenser was attached, and the flask was heated to 80° C. overnight. The mixture was cooled to room temperature. Acetic acid (1.776 ml, 31.0 mmol) was added, and the mixture was concentrated. The residue was taken up in 2-PrOH and heated to boiling to give a brown solution. The mixture was cooled to room temperature with stirring then was concentrated. The residue was taken up in DCM and loaded onto a 25-g silica gel loading column. The column was eluted directly onto a pre-equilibrated 120-g Redi-Sep silica gel column with 0-50% EtOAc/Heptane to give a solid. The solid was taken up in heptane and filtered. The filtered solid was washed with heptane and dried under a stream of $N_2$ (g) to give 6-(benzylthio)-1-(2-bromo-4-chlorophenyl)quinolin-2(1H)-one (5.816 g, 12.73 mmol, 61.6% yield) as a tan solid. $^1$H NMR (400 MHz, DMSO-$d_6$)=8.09 (d, J=2.3 Hz, 1H), 8.01 (d, J=9.5 Hz, 1H), 7.83 (d, J=2.2 Hz, 1H), 7.72 (dd, J=2.3, 8.4 Hz, 1H), 7.56 (d, J=8.4 Hz, 1H), 7.41 (dd, J=2.2, 8.8 Hz, 1H), 7.37-7.17 (m, 5H), 6.71 (d, J=9.6 Hz, 1H), 6.41 (d, J=8.8 Hz, 1H), 4.25 (s, 2H), 3.32 (s, 3H). m/z (ESI) 456.0 (M+H)+.

Step 3: Perfluorophenyl 1-(2-bromo-4-chlorophenyl)-2-oxo-1,2-dihydroquinoline-6-sulfonate A RBF was charged with 6-(benzylthio)-1-(2-bromo-4-chlorophenyl)quinolin-2(1H)-one (5.81 g, 12.72 mmol), acetonitrile (59.9 ml), acetic acid (2.245 ml), and water (1.496 ml) to give a solution. The flask was cooled in an ice-water bath for 10 min, then 1,3-dichloro-5,5-dimethyl-imidazolidine-2,4-dione (2.506 g, 12.72 mmol) was added in 4 portions over 5 min. After 15 min, an additional portion of oxidant (500 mg) was added. After another 10 min, an additional portion of oxidant (750 mg) was added. The mixture was stirred for 10 min, then 2,3,4,5,6-pentafluorophenol (3.51 g, 19.08 mmol) was added. After another minute, TEA (7.09 ml, 50.9 mmol) was added dropwise over 30 s. The mixture was stirred for 5 min then was diluted with EtOAc and brine and allowed to warm to RT. The mixture was diluted with water, and the layers were separated. The organic layer was dried over sodium sulfate, filtered, and concentrated. The residue was taken up in DCM. The resulting solution was loaded onto a dry 100-g SNAP Ultra column. The column was partially dried with a vacuum hose then the column was eluted with 0-50% EtOAc/Heptane to give 7.05 g of a light-yellow solid. LCMS looked clean but NMR showed an equivalent of 5,5-dimethylimidazolidine-2,4-dione (from the oxidant). This would be about 82 wt % pure. The mixture was taken up in heptane, and the resulting suspension was stirred for 2 h. The mixture was filtered, and the collected solid was washed with heptane (3×), dried under a flow of $N_2$ (g), then dried under vacuum to give 6.82 g of perfluorophenyl 1-(2-bromo-4-chlorophenyl)-2-oxo-1,2-dihydroquinoline-6-sulfonate as an off-white solid with a purity of ca. 82 wt %. m/z (ESI) 579.9 (M+H)+.

Step 4: 1-(2-bromo-4-chlorophenyl)-N-(isoxazol-3-yl)-2-oxo-1,2-dihydroquinoline-6-sulfonamide A RBF was charged with perfluorophenyl 1-(2-bromo-4-chlorophenyl)-2-oxo-1,2-dihydroquinoline-6-sulfonate (3.876 g, 6.67 mmol), isoxazol-3-amine (0.740 ml, 10.01 mmol) and THF (44.5 ml) to give a clear solution. The flask was cooled in an ice-water bath for 15 min, then lithium bis(trimethylsilyl)amide (1M in THF) (14.02 ml, 14.02 mmol) was added dropwise. After 30 min, an additional portion of LHMDS solution (6 mL) was added dropwise. The mixture was stirred for 15 min then diluted with EtOAc and washed with 1N aq. HCl. The aq. layer was extracted with EtOAc (2×). The combined organic extracts were dried over sodium sulfate, filtered, and concentrated. The residue was purified by chromatography (100-g SNAP Ultra column, 0-5% MeOH/DCM). The material was purified further by chromatography on a 100-g SNAP Ultra column with 15-60% EtOAc/Heptane). The fractions containing product were combined and concentrated to give 1-(2-bromo-4-chlorophenyl)-n-(isoxazol-3-yl)-2-oxo-1,2-dihydroquinoline-6-sulfonamide as a off-white solid. $^1$H NMR (400 MHz, DMSO-$d_6$)=11.67 (s, 1H), 8.74 (d, J=1.8 Hz, 1H), 8.41 (d, J=2.2 Hz, 1H), 8.27 (d, J=9.5 Hz, 1H), 8.11 (d, J=2.2 Hz, 1H), 7.86 (dd, J=2.2, 8.9 Hz, 1H), 7.74 (dd, J=2.3, 8.5 Hz, 1H), 7.63 (d, J=8.4 Hz, 1H), 6.84 (d, J=9.6 Hz, 1H), 6.74 (d, J=9.0 Hz, 1H), 6.45 (d, J=1.9 Hz, 1H). m/z (ESI) 479.9 (M+H)$^+$.

Intermediate AW: 1-(5,6-dichloro-2-methoxypyridin-3-yl)-N-(isoxazol-3-yl)-2-oxo-1,2-dihydroquinoline-6-sulfonamide

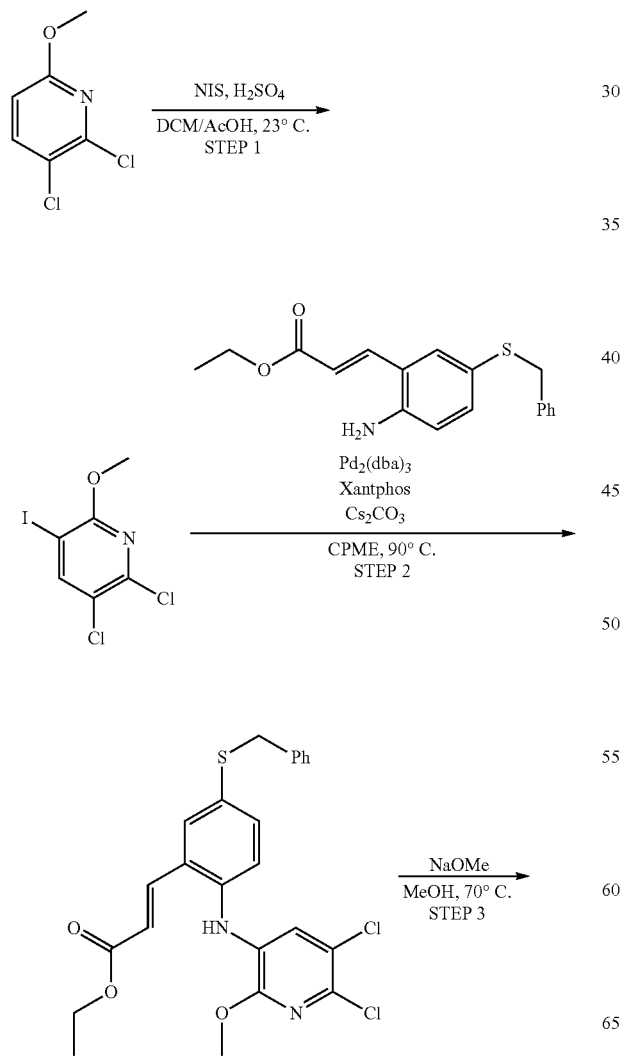
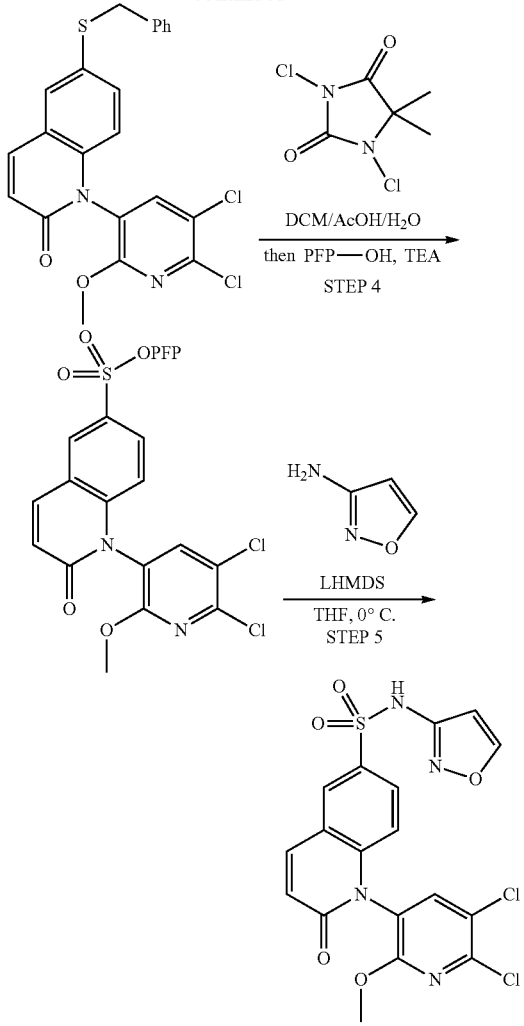

Step 1: 2,3-dichloro-5-iodo-6-methoxypyridine

A RBF was charged with 2,3-dichloro-6-methoxypyridine (4.84 g, 27.2 mmol, Accel Pharmtech), DCM (40.0 ml), AcOH (40.0 ml), and sulfuric acid (0.797 ml, 14.95 mmol) to give a clear solution. N-iodosuccinimide (6.12 g, 27.2 mmol) was added in one portion to give a maroon-colored solution. The reaction was stirred for three hours at RT. The mixture was diluted with ethyl acetate, washed with water, washed with 10% aq. sodium thiosulfate, washed with brine, dried over sodium sulfate, filtered, and concentrated. The residue was purified by chromatography on silica gel (80-g Redi-Sep Gold column, 0-15% Et2O/Heptane) to afford 2,3-dichloro-5-iodo-6-methoxypyridine (6.29 g, 20.70 mmol, 76% yield) as a white solid. m/z (ESI) 304.0 (M+H)$^+$.

Step 2: (E)-ethyl 3-(5-(benzylthio)-2-((5,6-dichloro-2-methoxypyridin-3-yl)amino)phenyl)acrylate A RBF was charged with (E)-ethyl 3-(2-amino-5-(benzylthio)phenyl)acrylate (2.0 g, 6.38 mmol)), 2,3-dichloro-5-iodo-6-methoxypyridine (2.327 g, 7.66 mmol)), xantphos (0.185 g, 0.319 mmol)), Pd2(dba)3 (0.146 g, 0.160 mmol)), and cesium carbonate (2.91 g, 8.93 mmol)) were added. A reflux condenser was attached and the flask was heated at 90° C. overnight. The mixture was cooled to RT, diluted with EtOAc, and filtered through celite with the aid of EtOAc. The filtrate was concentrated and i-PrOH was added. The mixture was heated to 110° C. until all the material dissolved, then the solution was allowed to cool to RT overnight causing a yellow solid to crash out of solution. The solids were filtered and washed with i-PrOH, then dried under a nitrogen blanket to afford (E)-ethyl 3-(5-(benzylthio)-2-((5,6-dichloro-2-methoxypyridin-3-yl)amino)phenyl)acrylate (2.54 g, 5.19 mmol, 81% yield) as a yellow solid. m/z (ESI) 491.1 (M+H)$^+$.

Step 3: 6-(benzylthio)-1-(5,6-dichloro-2-methoxypyridin-3-yl)quinolin-2(1H)-one

A RBF was charged with (E)-ethyl 3-(5-(benzylthio)-2-((5,6-dichloro-2-methoxypyridin-3-yl)amino)phenyl)acrylate (2.54 g, 5.19 mmol) and MeOH (25.9 ml) to give a yellow suspension. Sodium methoxide, 0.5M solution in methanol (4.15 ml, 2.076 mmol) was added. A reflux condenser was attached, and the reaction was heated to 70° C. and stirred overnight. The reaction was cooled to RT and filtered through a pad of Celite/silica gel and then washed with MeOH and then with DCM. The reaction was concentrated, dissolved in IPA, and heated to 110° C. The solution was filtered, cooled to RT, and concentrated to afford 6-(benzylthio)-1-(5,6-dichloro-2-methoxypyridin-3-yl)quinolin-2(1H)-one (2.10 g, 4.74 mmol, 91% yield) as a light yellow solid. m/z (ESI) 443.0 (M+H)$^+$.

Step 4: Perfluorophenyl 1-(5,6-dichloro-2-methoxypyridin-3-yl)-2-oxo-1,2-dihydroquinoline-6-sulfonate A RBF was charged with 6-(benzylthio)-1-(5,6-dichloro-2-methoxypyridin-3-yl)quinolin-2(1H)-one (2.10 g, 4.74 mmol), DCM (44.6 ml), acetic acid (1.672 ml), and water (1.115 ml) to give a thin suspension. The flask was cooled in an ice-bath for 10 min, then 1,3-dichloro-5,5-dimethylimidazolidine-2,4-dione (2.333 g, 11.84 mmol) was added in one portion, leading to a solution. The reaction was stirred for 15 minutes. 2,3,4,5,6-Pentafluorophenol (0.992 ml, 9.47 mmol) was added followed by dropwise addition of triethylamine (1.651 ml, 11.84 mmol). The reaction was stirred for 30 minutes. The reaction was concentrated and purified via column chromatography (RediSep Gold 40 g, gradient elution 0-50% EtOAc:Heptane) to afford perfluorophenyl 1-(5,6-dichloro-2-methoxypyridin-3-yl)-2-oxo-1,2-dihydroquinoline-6-sulfonate (1.97 g, 3.47 mmol, 73.3% yield) as an off-white solid. m/z (ESI) 568.0 (M+H)$^+$.

Step 5: 1-(5,6-dichloro-2-methoxypyridin-3-yl)-N-(isoxazol-3-yl)-2-oxo-1,2-dihydroquinoline-6-sulfonamide A RBF was charged with perfluorophenyl 1-(5,6-dichloro-2-methoxypyridin-3-yl)-2-oxo-1,2-dihydroquinoline-6-sulfonate (1.0 g, 1.763 mmol), isoxazol-3-amine (0.143 ml, 1.939 mmol), and THF (8.81 ml) to give a clear solution. The flask was cooled to 0° C. for 10 min, then lithium bis(trimethylsilyl)amide (1M in THF) (3.88 ml, 3.88 mmol) was added dropwise. The reaction was stirred for 30 minutes. The reaction was diluted with 1N aq. HCl and EtOAc. The aqueous layer was extracted with ethyl acetate, and the combined organic layers were washed with 1N aq. HCl, washed with brine, dried with sodium sulfate, filtered, and concentrated to afford crude 1-(5,6-dichloro-2-methoxypyridin-3-yl)-N-(isoxazol-3-yl)-2-oxo-1,2-dihydroquinoline-6-sulfonamide (1.10 g, 2.354 mmol, 100% yield) as an orange solid. m/z (ESI) 467.0 (M+H)$^+$.

Intermediate AY: 2-(4-bromo-2-methoxy-5-methylphenyl)-4,4,5,5-tetramethyl-1,3,2-dioxaborolane

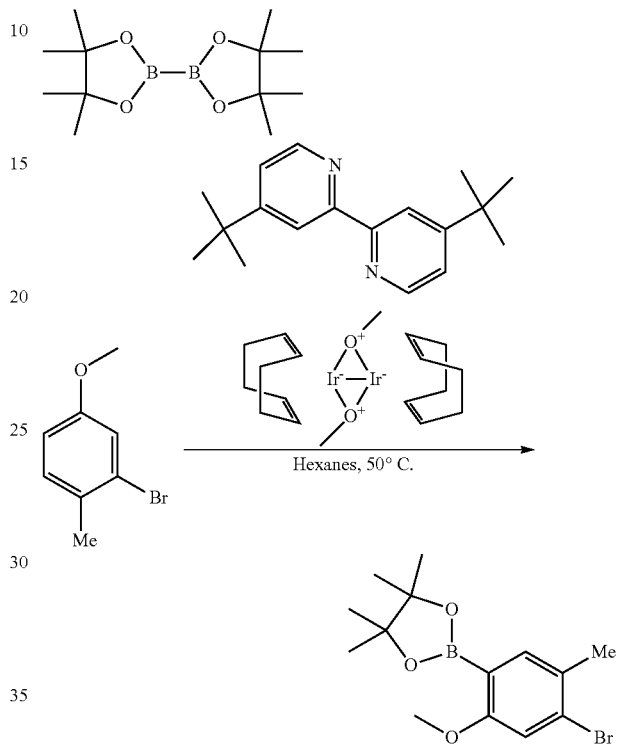

A RBF was charged with (1,5-cyclooctadiene)(methoxy)iridium(i) dimer (0.049 g, 0.075 mmol), 4,4'-di-tert-butyl-2,2'-dipyridyl (0.040 g, 0.149 mmol), and bis(pinacolato)diboron (1.339 g, 5.27 mmol). The flask was flushed with Ar (g), then hexane (15.30 ml) was added. A reflux condenser was attached to the flask, and the flask was heated to 50° C. for 10 minutes. 2-bromo-4-methoxy-1-methylbenzene (2.0 g, 9.95 mmol) was added and the reaction was stirred overnight at 50° C. The reaction was diluted with ethyl acetate and washed with water. The aqueous layer was extracted with ethyl acetate, and the combined organic layers were dried with sodium sulfate, filtered, and concentrated. The material was purified via column chromatography (RediSep Gold 80 g, gradient elution 0-50% EtOAc:Heptane) to afford 2-(4-bromo-2-methoxy-5-methylphenyl)-4,4,5,5-tetramethyl-1,3,2-dioxaborolane (0.694 g, 2.122 mmol, 21.33% yield) as an off-white oily solid. m/z (ESI) 329.1 (M+H)$^+$.

Intermediate AZ: 2-bromo-3-methoxynaphthalene

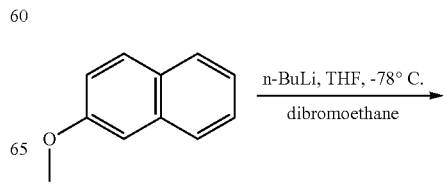

-continued

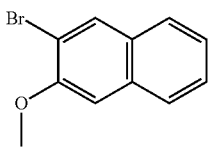

A RBF was charged 2-methoxynaphthalene (2.00 g, 12.64 mmol) and THF (30 mL) to give a clear solution. n-butyllithium (2.5M in hexanes) (5.66 mL, 14.16 mmol) was added dropwise. The flask was cooled in a dry ice-acetone bath for 10 min and 1,2-dibromoethane (1.634 mL, 18.96 mmol) was added dropwise. The reaction was warmed to room temperature and stirred for 16 hours. NaOH (1 M, 10 mL, 10 mmol0 was added and the reaction was heated to reflux for 1 hour. The mixture was cooled to room temperature and extracted with DCM (2×), and the combined organic extracts were dried over magnesium sulfate, filtered, and concentrated. The crude solid was recrystallized from heptane to give 2-bromo-3-methoxynaphthalene (1.75 g, 7.38 mmol, 58.4% yield) as an off-white solid. m/z (ESI) 237.1 (M+H)$^+$.

Intermediate BA: 4-bromo-5-fluoro-2-iodoaniline

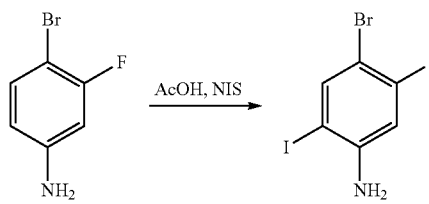

N-iodosuccinimide (2.90 ml, 28.9 mmol) was added to a solution of 4-bromo-3-fluoroaniline (5.00 g, 26.3 mmol) in AcOH (52.6 ml). The reaction was maintained at ambient temperature for 1.5 h, then diluted with 20 mL toluene and concentrated. The residue was dissolved in EtOAc and washed with 2 N aqueous NaOH. The organic phase was washed with brine, dried over sodium sulfate, filtered, and concentrated. The residue was purified by chromatography on silica gel (40-g Ultra SNAP column, 25-g silica gel loading column, 2-10% EtOAc/Heptane) to give 4-bromo-5-fluoro-2-iodoaniline (7.23 g, 22.89 mmol, 87% yield). $^1$H NMR (400 MHz, CHLOROFORM-d) δ 7.74-7.78 (m, 1H), 6.53-6.57 (m, 1H). m/z (ESI) 315.9 (M+H)$^+$.

Intermediate BB: 4-(1-bromoethyl)-1,2-dichlorobenzene

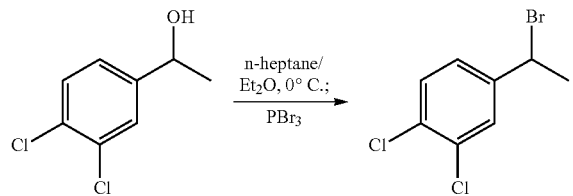

To a solution of 1-(3,4-dichlorophenyl)ethanol (0.87 g, 4.55 mmol) in n-heptane (5.00 mL) and Et$_2$O (0.500 mL) at 0° C. was added pyridine (1 drop) and phosphorous tribromide (0.214 mL, 2.277 mmol). The reaction mixture was warmed to RT and stirred for 2 h. The reaction was diluted with ether, washed with water (1×), saturated NaHCO$_3$ (1×), and brine (1×). The organic layer was dried over magnesium sulfate, filtered, and concentrated to give 4-(1-bromoethyl)-1,2-dichlorobenzene (0.985 g, 3.88 mmol, 85% yield). m/z (ESI) 249.0 (M+H)$^+$.

Intermediate BC: Perfluorophenyl 1-(2-chloro-3'-fluoro-5-methoxy-[1,1'-biphenyl]-4-yl)-2-oxo-1,2-dihydroquinoline-6-sulfonate

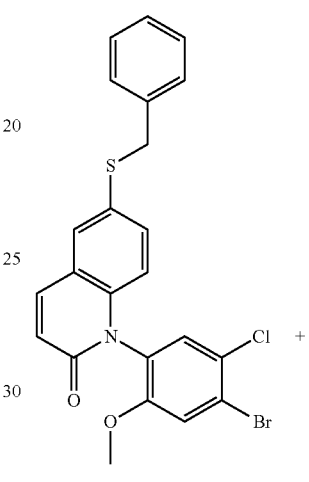

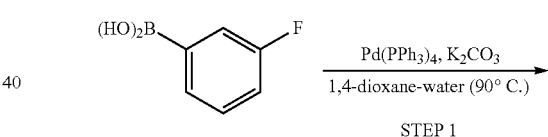

STEP 1

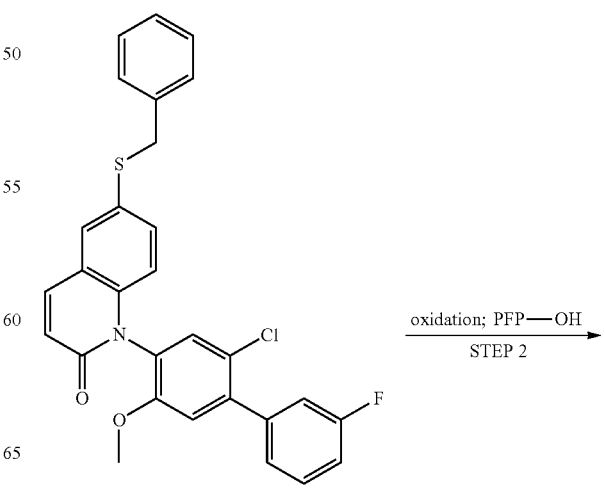

oxidation; PFP—OH
STEP 2

-continued

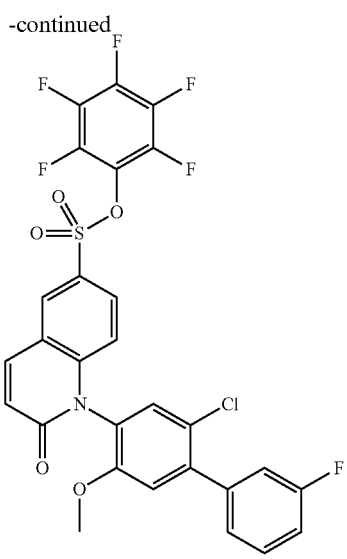

Step 1: 6-(benzylthio)-1-(2-chloro-3'-fluoro-5-methoxy-[1,1'-biphenyl]-4-yl)quinolin-2(1H)-one A screw cap vial was charged with 6-(benzylthio)-1-(4-bromo-5-chloro-2-methoxyphenyl)quinolin-2(1H)-one (1.22 g, 2.506 mmol), (3-fluorophenyl)boronic acid (0.526 g, 3.76 mmol), potassium carbonate (1.039 g, 7.52 mmol) and Pd(Ph$_3$P)$_4$ (0.290 g, 0.251 mmol). The vial was flushed with Ar (g), then 1,4-dioxane (9.4 ml) and water (3.1 ml) were added in sequence. The reaction was heated to 90° C. for 1 hour. The mixture was diluted with NH$_4$Cl and extracted with EtOAc (3×). The combined organic extracts were dried over magnesium sulfate, filtered, and concentrated. The residue was purified by chromatography on silica gel (40-g Ultra SNAP column, 25-g silica gel loading column, 0-50% EtOAc/Heptane) to give 6-(benzylthio)-1-(2-chloro-3'-fluoro-5-methoxy-[1,1'-biphenyl]-4-yl)quinolin-2(1H)-one (1.02 g, 2.03 mmol, 81% yield) as a cream-colored solid. m/z (ESI) 502.2 (M+H)$^+$.

Step 2: Perfluorophenyl 1-(2-chloro-3'-fluoro-5-methoxy-[1,1'-biphenyl]-4-yl)-2-oxo-1,2-dihydroquinoline-6-sulfonate A RBF was charged with 6-(benzylthio)-1-(2-chloro-3'-fluoro-5-methoxy-[1,1'-biphenyl]-4-yl)quinolin-2(1H)-one (1.00 g, 1.992 mmol), DCM (18.9 ml), acetic acid (0.47 ml), and water (0.47 ml) to give clear, orange solution. The flask was cooled in an ice-water bath for 10 min, then 1,3-dichloro-5,5-dimethylhydantoin (0.654 ml, 4.98 mmol) was added in one portion. After 30 min, 2,3,4,5,6-pentafluorophenol (0.417 ml, 3.98 mmol) and triethylamine (0.694 ml, 4.98 mmol) (dropwise) were added in sequence. After 2 hours, the mixture was diluted with water, then extracted with DCM (2×). The combined organic extracts were dried over magnesium sulfate, filtered, and concentrated. The residue was purified by chromatography on silica gel (40-g Redi-Sep Gold column, 25-g silica gel loading column, 0-50% EtOAc/Heptane) to give perfluorophenyl 1-(2-chloro-3'-fluoro-5-methoxy-[1,1'-biphenyl]-4-yl)-2-oxo-1,2-dihydroquinoline-6-sulfonate (0.600 g, 0.959 mmol, 48.1% yield) as an off-white solid. m/z (ESI) 626.1 (M+H)$^+$.

Intermediate BD: Perfluorophenyl 1-(4-bromo-5-chloro-2-methoxyphenyl)-2-oxo-1,2-dihydroquinoline-6-sulfonate

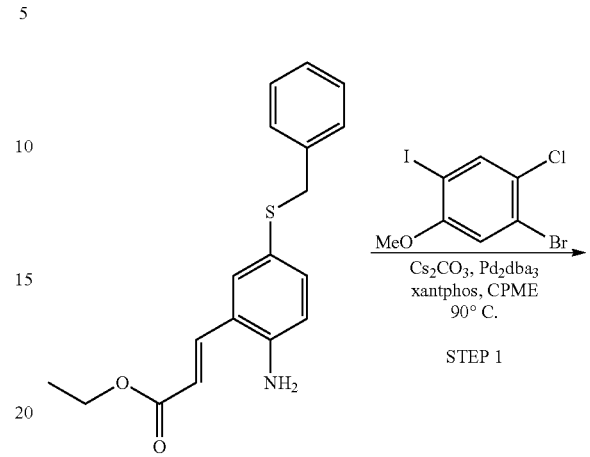
STEP 1

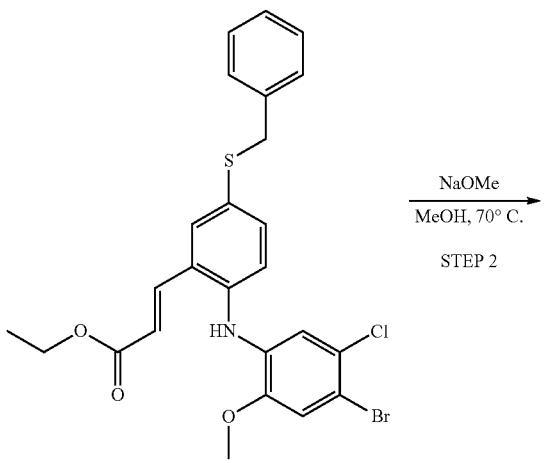
STEP 2

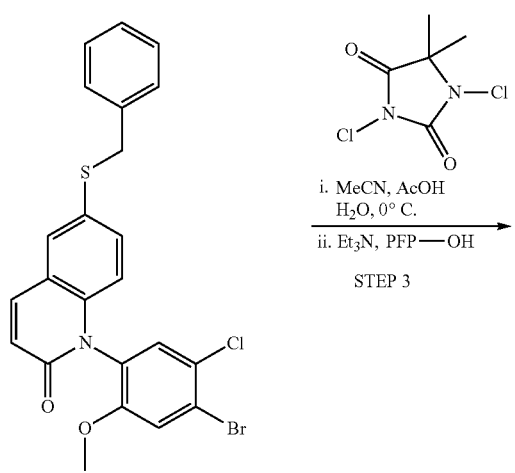
STEP 3

-continued

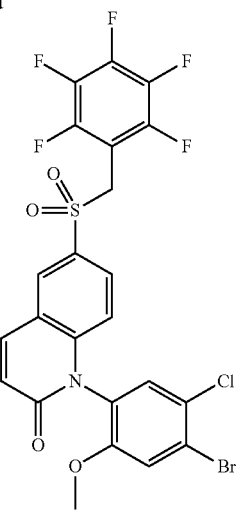

Step 1: (E)-ethyl 3-(5-(benzylthio)-2-((4-bromo-5-chloro-2-methoxyphenyl)amino)phenyl)acrylate A flask was charged with (E)-ethyl 3-(2-amino-5-(benzylthio)phenyl)acrylate (50.0 g, 160 mmol), 1-bromo-2-chloro-4-iodo-5-methoxybenzene (66.5 g, 191 mmol), xantphos (4.62 g, 7.98 mmol), $Pd_2(dba)_3$ (3.65 g, 3.99 mmol), and cesium carbonate (72.8 g, 223 mmol). A reflux condenser was attached and the reaction placed under nitrogen atmosphere. CPME (319 ml) was added and the reaction was heated at 90° C. for 36 h. The mixture was cooled to rt and partitioned between 1000 mL of EtOAc and 1000 mL of water. The layers were separated and the aqueous layer was extracted with 200 mL of EtOAc. The combined organic layers were poured through a silica plug to provide a brown solution. The solution was concentrated until about 100 mL of solvent was left, giving a heterogeneous brown sludge. Isopropanol (500 mL) was added to the solution and a yellow solid precipitated. The yellow solid was collected by vacuum filtration (rinsing with 200 mL isopropanol) to provide desired product (E)-ethyl 3-(5-(benzylthio)-2-((4-bromo-5-chloro-2-methoxyphenyl)amino)phenyl)acrylate (76.4 g, 143 mmol, 90% yield) as a yellow solid. m/z (ESI) 531.9 $(M-H)^-$.

Step 2: 6-(benzylthio)-1-(4-bromo-5-chloro-2-methoxyphenyl)quinolin-2(1H)-one

A flask was charged with (E)-ethyl 3-(5-(benzylthio)-2-((4-bromo-5-chloro-2-methoxyphenyl)amino)phenyl)acrylate (73.2 g, 137 mmol) and MeOH (687 ml) to give a yellow suspension. Sodium methoxide (25 wt % in MeOH) (15.01 ml, 54.9 mmol) was added and a reflux condenser was attached. The flask was lowered into a 70° C. heating bath and stirred at 70° C. for 18 h. The mixture was cooled to rt and poured through a 3 inch silica plug to remove black particulates. The product that was crashed out on the silica plug was washed through the plug with DCM. The mother liquor was concentrated to half its volume, then IPA (500 mL) was added and the solution concentrated again. An additional 500 mL of IPA was added and a tan solid precipitated. The tan solid was collected by vacuum filtration to give 6-(benzylthio)-1-(4-bromo-5-chloro-2-methoxyphenyl)quinolin-2(1H)-one (50.34 g, 103 mmol, 75% yield) as a dark tan powdery solid. m/z (ESI) 486.0 $(M+H)^+$.

Step 3: Perfluorophenyl 1-(4-bromo-5-chloro-2-methoxyphenyl)-2-oxo-1,2-dihydroquinoline-6-sulfonate A flask was charged with 6-(benzylthio)-1-(4-bromo-5-chloro-2-methoxyphenyl)quinolin-2(1H)-one (46.34 g, 95 mmol), acetonitrile (298 ml), acetic acid (11.34 ml), and water (7.46 ml). The solution was cooled to 0° C. To the solution was added 1,3-dichloro-5,5-dimethylimidazolidine-2,4-dione (18.75 g, 95 mmol) as a solid in a single portion and stirred for 10 min. An additional 0.3 equiv 1,3-dichloro-5,5-dimethylimidazolidine-2,4-dione (5.63 g, 28.6 mmol), then 0.2 eq. 1,3-dichloro-5,5-dimethylimidazolidine-2,4-dione (3.75 g, 19.04 mmol) was added until complete conversion to sulfonyl chloride 6-(benzylsulfinyl)-1-(4-bromo-5-chloro-2-methoxyphenyl)quinolin-2(1H)-one. At this time 2,3,4,5,6-pentafluorophenol (21.03 g, 114 mmol) was added as a warmed liquid (gooey solid at rt), using 10 mL of acetonitrile to aid in transfer from pre-tared vial containing the 2,3,4,5,6-pentafluorophenol. Then, TEA (53.1 ml, 381 mmol) was added from an addition funnel. During the addition, a white fume was produced. The solution was maintained at 0° C. for 30 min and then allowed to warm to rt and stir for 20 min. The reaction mixture was partitioned between 1:1 brine:water (500 mL) and EtOAc (700 mL) The layers were separated and the aqueous layer was extracted with EtOAc (2×400 mL). Both layers had suspended white solid. The combined organic layers were filtered to remove suspended solid and concentrated to give a brown sludge. The solid that was collected was clean product perfluorophenyl 1-(4-bromo-5-chloro-2-methoxyphenyl)-2-oxo-1,2-dihydroquinoline-6-sulfonate which was set aside. The remaining brown sludge was taken up in IPA (500 mL) and a tan solid precipitated, which was collected by vacuum filtration (rinsing with 200 mL IPA) to give an additional 19.961 g perfluorophenyl 1-(4-bromo-5-chloro-2-methoxyphenyl)-2-oxo-1,2-dihydroquinoline-6-sulfonate. The aqueous layer still had tan suspended solid, which was extracted with DCM (2×500 mL). The combined organic layers were concentrated to give 4.542 g perfluorophenyl 1-(4-bromo-5-chloro-2-methoxyphenyl)-2-oxo-1,2-dihydroquinoline-6-sulfonate as a tan solid. The three lots were combined to give 36.21 g, 59.3 mmol (62.3% yield) of perfluorophenyl 1-(4-bromo-5-chloro-2-methoxyphenyl)-2-oxo-1,2-dihydroquinoline-6-sulfonate. $^1$H NMR (400 MHz, DMSO-$d_6$) δ 8.60 (d, J=2.35 Hz, 1H), 8.19-8.31 (m, 1H), 7.96 (dd, J=2.30, 9.05 Hz, 1H), 7.82-7.89 (m, 1H), 7.74-7.80 (m, 1H), 6.92-6.98 (m, 1H), 6.84-6.91 (m, 1H), 3.71-3.80 (s, 3H). m/z (ESI) 609.9 $(M+H)^+$.

Intermediate BE: (3'-(difluoromethyl)-2,5'-difluoro-5-methoxy-[1,1'-biphenyl]-4-yl)boronic acid

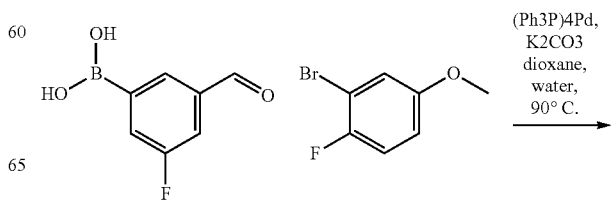

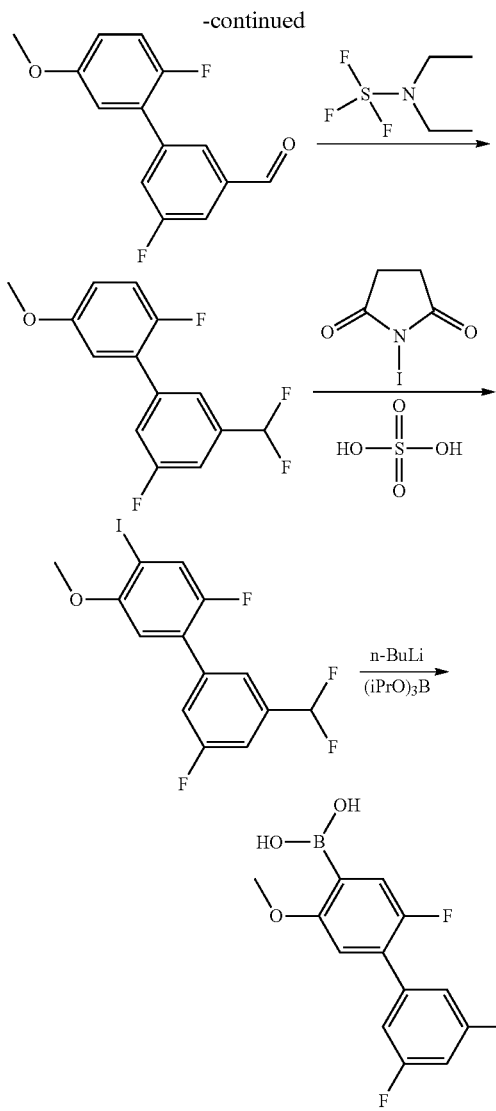

Step 1: 2',5-difluoro-5'-methoxy-[1,1'-biphenyl]-3-carbaldehyde

To a RBF was added 2-bromo-1-fluoro-4-methoxybenzene (1.850 mL, 9.02 mmol, Oakwood), 3-fluoro-5-formylphenylboronic acid (1667 mg, 9.93 mmol, Combi-blocks), tetrakis(triphenylphosphine)palladium (521 mg, 0.451 mmol) and potassium carbonate (3741 mg, 27.1 mmol). A condenser and septum was attached and 1,4-dioxane (24.100 mL) and water (6.03 mL) were added. The mixture was heated at 90° C. for 2 h, at which time the reaction mixture was diluted with water (50 mL) and extracted with EtOAc (2×50 mL). The organic extract was washed with brine (20 mL) and dried over MgSO$_4$. The solution was filtered and concentrated. The residue was absorbed onto a plug of silica gel and purified by chromatography through a 50 g silica column, eluting with a gradient of 0% to 30% EtOAc in Heptane, to provide 2',5-difluoro-5'-methoxy-[1,1'-biphenyl]-3-carbaldehyde (640 mg, 2.58 mmol, 28.6% yield) as white solid. $^1$H NMR (400 MHz, DMSO-d$_6$) δ 10.01-10.14 (m, 1H), 8.01 (q, J=1.56 Hz, 1H), 7.82 (tdd, J=1.41, 2.59, 9.76 Hz, 1H), 7.67-7.78 (m, 1H), 7.32 (dd, J=9.05, 10.42 Hz, 1H), 7.18 (dd, J=3.23, 6.46 Hz, 1H), 7.05 (td, J=3.57, 9.00 Hz, 1H), 3.83 (s, 3H).

Step 2: 3'-(difluoromethyl)-2,5'-difluoro-5-methoxy-1,1'-biphenyl

To a 250-mL RBF was added 2',5-difluoro-5'-methoxy-[1,1'-biphenyl]-3-carbaldehyde (640 mg, 2.58 mmol) followed by DCM (8.594 mL). The clear solution was cooled to −78° C., then (diethylamino)sulfur trifluoride (1.022 mL, 7.73 mmol) was added dropwise. After 3 min, the reaction flask was put in an ice-water bath. After 4 h, sat aqueous NaHCO$_3$ was carefully added to quench the reaction. The reaction mixture was extracted with EtOAc (2×20 mL). The organic layers were combined, dried (MgSO$_4$) and concentrated. The residue was absorbed onto a plug of silica gel and purified by silica gel chromatography through a Redi-Sep pre-packed silica gel column (12 g), eluting with a gradient of 0% to 40% EtOAc in hexane, to provide 3'-(difluoromethyl)-2,5'-difluoro-5-methoxy-1,1'-biphenyl (642 mg, 2.376 mmol, 92% yield) as colorless clear oil. $^1$H NMR (400 MHz, DMSO-d$_6$) δ 7.61-7.69 (m, 2H), 7.47-7.55 (m, 1H), 7.23-7.35 (m, 1H), 6.96-7.16 (m, 3H), 3.82 (s, 3H).

Step 3: 3'-(difluoromethyl)-2,5'-difluoro-4-iodo-5-methoxy-1,1'-biphenyl

To a 250-mL RBF was added 3'-(difluoromethyl)-2,5'-difluoro-5-methoxy-1,1'-biphenyl (642 mg, 2.376 mmol) and sulfuric acid (69.7 μl, 1.307 mmol). DCM (3960 μl) and AcOH (3960 μl) were added to give a colorless clear solution. To this solution was added n-iodosuccinimide (238 μl, 2.376 mmol) as a solid in a single portion to give a maroon-colored solution. After 3 h at rt, the mixture was diluted with DCM (30 mL), washed with water (10 mL), washed with saturated aq. sodium thiosulfate (10 mL, DCM was upper layer for separation), dried over sodium sulfate, filtered, and concentrated. The residue was purified by chromatography on silica gel (50-g silica gel column, 0-5% EtOAc/Heptane) to provide 3'-(difluoromethyl)-2,5'-difluoro-4-iodo-5-methoxy-1,1'-biphenyl (771 mg, 1.946 mmol, 82% yield) as a white solid. $^1$H NMR (400 MHz, DMSO-d$_6$) δ 7.80-7.87 (m, 1H), 7.67-7.73 (m, 1H), 7.63-7.67 (m, 1H), 7.48-7.57 (m, 1H), 7.08-7.18 (m, 2H), 3.91 (d, J=2.54 Hz, 3H)

Step 4: (3'-(difluoromethyl)-2,5'-difluoro-5-methoxy-[1,1'-biphenyl]-4-yl)boronic acid A RBF was charged with 3'-(difluoromethyl)-2,5'-difluoro-4-iodo-5-methoxy-1,1'-biphenyl (770 mg, 1.944 mmol), triisopropyl borate (0.580 mL, 2.53 mmol) and THF (9.719 mL). The flask was cooled to −78° C. for 10 min, then n-butyllithium solution, 2.5 m in hexanes (1.011 mL, 2.53 mmol) was added dropwise over 1 min. The colorless solution turned green then yellow. After 30 min at −78° C., 2N aq. NaOH (10 mL) was added. The resulting biphasic mixture was stirred for 10 min, and partitioned between water (20 mL) and ether (50 mL). The layers were separated, and the ethereal layer was extracted with water (2×10 mL). The combined aqueous extracts were washed with ether (10 mL), and then were acidified with 6N aq. HCl (10 mL). The resulting aq. mixture was extracted with DCM (3×20 mL). The combined DCM layers were dried over sodium sulfate, filtered, and concentrated to give (3'-(difluoromethyl)-2,5'- difluoro-5-methoxy-[1,1'-biphenyl]-4-yl)boronic acid (111 mg, 0.353 mmol, 18.18% yield) as white solid. m/z (ESI) 315.0 (M+H)+.

Intermediate BH: 6-(benzylthio)-1-(2,3'-difluoro-5-hydroxy-[1,1'-biphenyl]-4-yl)quinolin-2(1H)-one

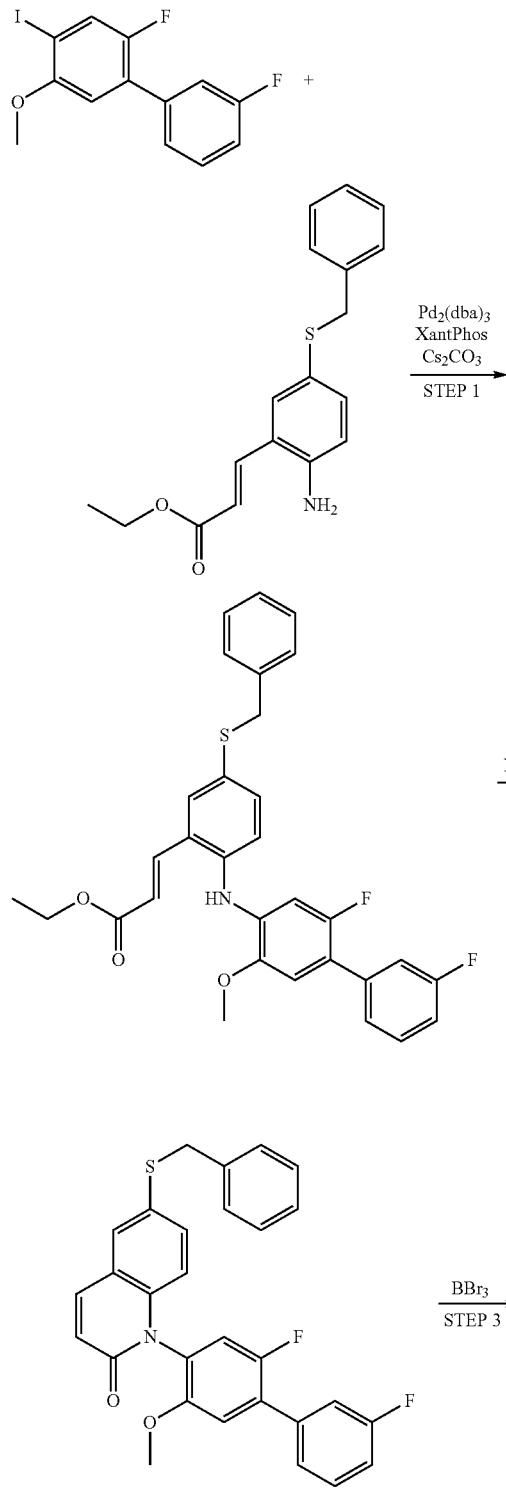

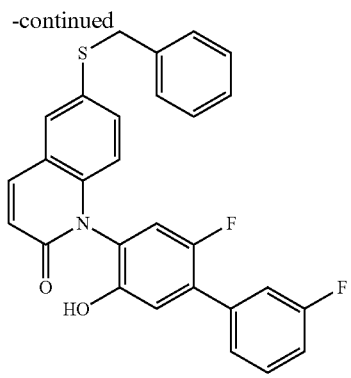

Step 1: Synthesis of (E)-ethyl 3-(5-(benzylthio)-2-((2,3'-difluoro-5-methoxy-[1,1'-biphenyl]-4-yl)amino)phenyl)acrylate A RBF was charged with (E)-ethyl 3-(2-amino-5-(benzylthio)phenyl)acrylate (2.0 g, 6.38 mmol), 2,3'-difluoro-4-iodo-5-methoxy-1,1'-biphenyl (2.65 g, 7.66 mmol), XantPhos (0.185 g, 0.319 mmol), Pd$_2$(dba)$_3$ (0.146 g, 0.160 mmol), and Cs$_2$CO$_3$ (4.16 g, 12.76 mmol).

A reflux condenser was attached and the reaction placed under nitrogen atmosphere. Toluene (12.76 mL) was added and the reaction was heated at 110° C. for 48 h. The whole was cooled to rt, poured through Celite, and washed with EtOAc. The crude residue was taken up in minimal DCM and absorbed directly onto a Biotage SNAP pre-packed silica gel column (100 g) and eluted using 90:10 heptane: EtOAc to 100% EtOAc gradient to afford (E)-ethyl 3-(5-(benzylthio)-2-((2,3'-difluoro-5-methoxy-[1,1'-biphenyl]-4-yl)amino)phenyl)acrylate (3.1 g, 92% yield) as a yellow foam. m/z (ESI−): [M−H]=530.1.

Step 2: Synthesis of 6-(benzylthio)-1-(2,3'-difluoro-5-methoxy-[1,1'-biphenyl]-4-yl)quinolin-2(1H)-one A RBF was charged with (E)-ethyl 3-(5-(benzylthio)-2-((2,3'-difluoro-5-methoxy-[1,1'-biphenyl]-4-yl)amino)phenyl)acrylate (6.2 g, 11.66 mmol), and MeOH (58.3 mL), then sodium methoxide (1.274 ml, 4.67 mmol). A reflux condenser was attached and the whole was heated at 70° C. for 18 h. The reaction was concentrated to dryness and then triturated with IPA (with heating) to provide 6-(benzylthio)-1-(2,3'-difluoro-5-methoxy-[1,1'-biphenyl]-4-yl)quinolin-2(1H)-one (5.15 g, 91% yield) as a tan solid. m/z (ESI): [M+Na]+=508.0.

Step 3: Synthesis of 6-(benzylthio)-1-(2,3'-difluoro-5-hydroxy-[1,1'-biphenyl]-4-yl)quinolin-2(1H)-one To a solution of 6-(benzylthio)-1-(2,3'-difluoro-5-methoxy-[1,1'-biphenyl]-4-yl)quinolin-2(1H)-one (1.700 g, 3.50 mmol) was added boron tribromide (1.0 M in DCM) (17.51 ml, 17.51 mmol) at rt to give a dark solution and stirred for 1 h. The whole was poured on to ice-water mixture. The product was extracted with DCM (3×30 mL). The organic layer was separated, combined, dried over MgSO$_4$, filtered, and concentrated to afford beige solid. The solid was triturated with a mixture of EtOAc/Et$_2$O. The solid was filtered with an aid of Et$_2$O. 1.32 g was obtained. A second batch was obtained from the filtrate. The filtrate was concentrated. The crude material was absorbed onto a plug of silica gel and purified by chromatography through a Redi-Sep pre-packed silica gel column (12 g), eluting with a gradient of 0% to 50% EtOAc in heptane, to provide 6-(benzylthio)-1-(2,3'-difluoro-5-hydroxy-[1,1'-biphenyl]-4-yl)quinolin-2(1H)-one (1.42 g, 80% yield) as light brown solid. m/z (ESI): [M+H]$^+$=472.0. $^1$H NMR (400 MHz, DMSO-d$_6$) ppm 4.24 (s, 2H) 6.63 (d, J8.80 Hz, 1H) 6.69 (d, J=9.59 Hz, 1H) 7.15 (d, J=7.34 Hz, 1H) 7.18-7.37 (m, 7H) 7.38-7.48 (m, 3H) 7.57 (dd, J=8.02, 6.06 Hz, 1H) 7.79 (d, J=2.15 Hz, 1H) 7.95 (d, J=9.49 Hz, 1H) 9.97 (s, 1H).

Intermediate BN: (P)-1-(4-bromo-5-fluoro-2-methoxyphenyl)-N-(isoxazol-3-yl)-2-oxo-1,2-dihydroquinoline-6-sulfonamide

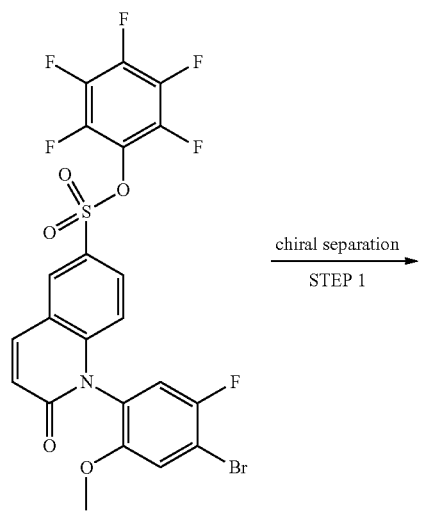

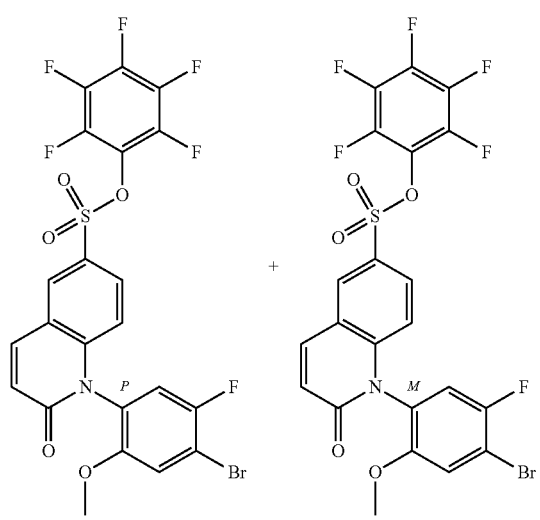

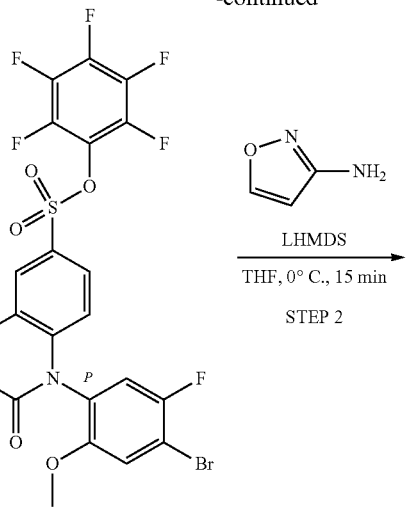

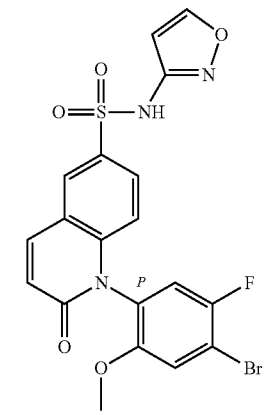

Step 1: (P)-perfluorophenyl 1-(4-bromo-5-fluoro-2-methoxyphenyl)-2-oxo-1,2-dihydroquinoline-6-sulfonate Racemic perfluorophenyl 1-(4-bromo-5-fluoro-2-methoxyphenyl)-2-oxo-1,2-dihydroquinoline-6-sulfonate (76.90 g) was separated via Chiralcel OJ column (40% MeOH/60% CO2) to give (P)-perfluorophenyl 1-(4-bromo-5-fluoro-2-methoxyphenyl)-2-oxo-1,2-dihydroquinoline-6-sulfonate and (M)-perfluorophenyl 1-(4-bromo-5-fluoro-2-methoxyphenyl)-2-oxo-1,2-dihydroquinoline-6-sulfonate as pale yellow flocculent solids. Data for peak 1: m/z (ESI) 594.0 (M+H)$^+$. Data for peak 2: m/z (ESI) 594.0 (M+H)$^+$.

Step 2: (P)-1-(4-bromo-5-fluoro-2-methoxyphenyl)-N-(isoxazol-3-yl)-2-oxo-1,2-dihydroquinoline-6-sulfonamide A THF (200 mL) solution of (P)-perfluorophenyl 1-(4-bromo-5-fluoro-2-methoxyphenyl)-2-oxo-1,2-dihydroquinoline-6-sulfonate (6.00 g, 10.10 mmol) and 3-aminoisoxazole (0.821 ml, 11.11 mmol) in a 250-mL round-bottom flask was cooled to 0° C., and lithium bis(trimethylsilyl)amide, 1.0 M solution in THF (21.20 ml, 21.20 mmol) was added dropwise. After stirring the yellow solution at 0° C. for 15 min, it was quenched at 0° C. with 1 N HCl and extracted thrice with EtOAc. The organic extracts were combined, dried over MgSO$_4$, filtered, and concentrated to a light tan residue. Et$_2$O was added, and the slurry was triturated and sonicated. Filtration afforded an off-white solid, which was washed twice with Et$_2$O and dried in vacuo to afford 3.88 g of product as an off-white solid. The filtrate was concentrated in vacuo and purified via column chromatography (12 g silica gel, 35% to 100% EtOAc/hept gradient) to afford an additional 1.36 g of product as a pale yellow flocculent solid. A total of 5.24 g of (P)-1-(4-bromo-5-fluoro-2-methoxyphenyl)-N-(isoxazol-3-yl)-2-oxo-1,2-dihydroquinoline-6-sulfonamide was afforded. m/z (ESI) 494.1 (M+H)$^+$.

Intermediate BO: 3-chloro-2-methyl-5-(4,4,5,5-tetramethyl-1,3,2-dioxaborolan-2-yl)pyridine

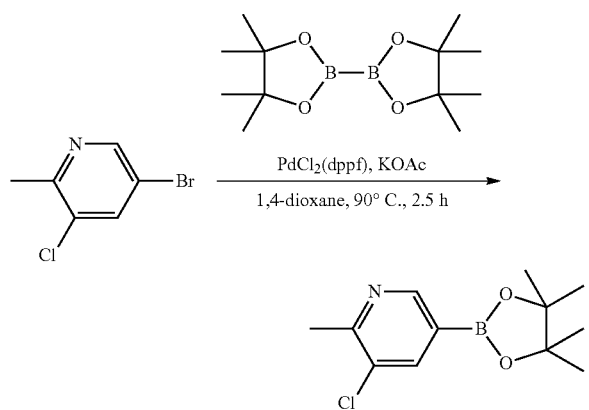

A 40-mL vial containing 5-bromo-3-chloro-2-methylpyridine (185 mg, 0.896 mmol, purchased from Synthonix Inc.), potassium acetate (264 mg, 2.69 mmol), bis(pinacolato)diboron (250 mg, 0.986 mmol), and 1,1'-bis(diphenylphosphino)ferrocene palladium(II)dichloride dichloromethane adduct (36.6 mg, 0.045 mmol) was flushed with N$_2$. Dioxane (4.5 mL) was added, and the orange slurry was stirred at 90° C. After 2.5 h, the resulting black slurry was cooled to rt, washed twice with brine, dried over Na$_2$SO$_4$, filtered, and concentrated in vacuo to afford 3-chloro-2-methyl-5-(4,4,5,5-tetramethyl-1,3,2-dioxaborolan-2-yl)pyridine as a black oil that was used with further purification. m/z (ESI) 254.1 (M+H)$^+$.

Intermediate BP: N-(4-methoxybenzyl)pyridazin-3-amine

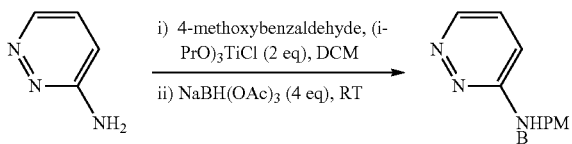

To a solution of pyridazin-3-ylamine (105 g, 1.1 mol, 1 eq) and 4-methoxybenzaldehyde (150 g, 1.1 mol, 1 eq) in DCM (3 L), was added titanium(IV) chloride triisopropoxide (572 g, 2.2 mol, 2 eq). The reaction mixture was stirred at RT for 8 h. The reaction mixture was cooled to 0° C. and sodium triacetoxyborohydride (933 g, 4.4 mol, 4 eq) was added. The reaction mixture was allowed to stir at RT 5 h. After completion of the reaction, the reaction mixture was cooled to 0° C., quenched with ice water and the solid was filtered through celite pad. The layers were separated and the aqueous layer extracted with DCM (1 L). The combined organic layer was dried over sodium sulfate, filtered and concentrated under reduced pressure. The crude mass was dissolved in minimum amount of DCM and the product was extracted in 1.5 N HCl thrice. The aqueous layer was basified with saturated NaHCO$_3$ solution; the precipitated product was filtered and dried. Then the solid obtained was washed with minimum amount of diethyl ether and dried to get 60 g of the title compound as pale pink solid (0.27 mol, 25% yield). MS (ESI pos. ion) m/z: (M+2)$^+$=216.7. $^1$H NMR (400 MHz, Chloroform-d) δ 8.56 (dd, J=1.20, 4.60 Hz, 1H), 7.31 (dd, J=2.80, 11.60 Hz, 2H), 7.15 (dd, J=4.40, 9.00 Hz, 1H), 6.89 (dd, J=2.80, 5.80 Hz, 2H), 6.63 (dd, J=1.20, 9.20 Hz, 1H), 5.15 (br. s, 1H), 4.55 (d, J=5.60 Hz, 2H), 3.81 (s, 3H).

Intermediate BQ: N-(4-methoxybenzyl)pyrimidin-2-amine

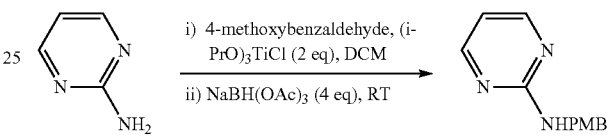

To a mixture of 2-aminopyrimidine (104.7 g, 1.1 mol, 1 eq) and 4-methoxybenzaldehyde (150 g, 1.1 mol, 1 eq) in DCM (3 L), was added titanium(IV) chloride triisopropoxide (572 g, 2.2 mol, 2 eq). The reaction mixture was stirred at room temperature for 8 h. The reaction mixture was cooled to 0° C. and sodium triacetoxyborohydride (933 g, 4.4 mol, 4 eq) was added portionwise and stirred overnight at RT. After completion of reaction, the reaction mixture was cooled to 0° C., quenched with ice water and the solid was filtered through celite pad. The layers were separated and the aqueous layer extracted in DCM (1 L). The organic layer was dried over sodium sulfate and concentrated under reduced pressure to get the crude material which was purified by column chromatography (Silica [60-120 mesh]; eluted with 20-35% EtOAc in hexane) to yield 125 g (0.58 mol, 52% yield) of the title compound as a white solid. MS (ESI pos. ion) m/z: (M+2)$^+$=216.2. $^1$H-NMR (400 MHz, DMSO-d$_6$) δ 8.26 (d, J=3.68 Hz, 2H), 7.63 (t, J=6.16 Hz, 1H), 7.23 (d, J=8.48 Hz, 2H), 6.86 (d, J=8.56 Hz, 2H), 6.56-6.54 (m, 1H), 4.42 (d, J=6.32 Hz, 2H), 3.71 (s, 3H).

Intermediate BU: 2,3'-dichloro-4-iodo-5-methoxy-1,1'-biphenyl

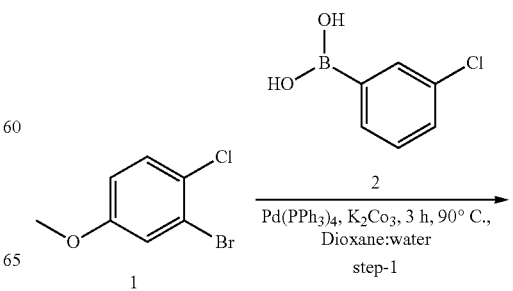

-continued

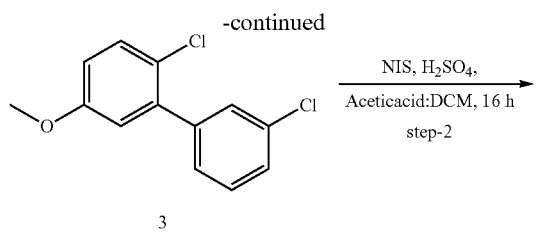

Step 1: 2,3'-dichloro-5-methoxy-1,1'-biphenyl

A solution of compound-1 (100 g, 0.45 mol, 1.0 equiv, F-Chemicals), compound-2 (84.72 g, 0.541 mol, 1.2 equiv, Combi-Blocks) and potassium carbonate (186.92 g, 1.35 mol, 3.0 equiv) in 1,4-dioxane (660 mL) and H$_2$O (180 mL) was degassed with nitrogen for 15 min. Pd(PPh$_3$)$_4$ (26.08 g, 0.0226 mol, 0.05 equiv) was added and the mixture was again degassed with nitrogen for 5 min. The reaction mixture was heated at 90° C. for 3 h. The reaction mass was cooled to RT, diluted with ethyl acetate (1.0 L) and washed with brine (750 mL). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (106 g, 93%). TLC solvent system: Heptane, Product R$_f$: 0.5. $^1$H NMR (400 MHz, DMSO-d$_6$) δ 7.51-7.37 (m, 5H), 7.00-6.96 (m, 2H), 3.78 (s, 3H).

Step 2: 2,3'-dichloro-4-iodo-5-methoxy-1,1'-biphenyl

To a solution of compound-3 (106 g, 0.418 mol, 1.0 equiv), in DCM (208 mL), AcOH (208 mL), and sulphuric acid (39 mL) was added N-iodosuccinimide (94.26 g, 0.418 mol, 1.0 equiv) in one portion. The reaction mass was stirred at RT for 16 h. The reaction mass was diluted with DCM (800 mL) and the organic layer was washed with water (800 mL) and saturated aqueous sodium thiosulfate (500 mL). The organic layer was dried over sodium sulphate, filtered and concentrated under reduced pressure to get the crude material which was purified by column chromatography (silica gel 60-120 mesh, elution 1% EtOAc/Hexane) to get liquid compound-4 (89.0 g, 56%). TLC solvent system: Heptane, Product's R$_f$: 0.6. $^1$H NMR (400 MHz, DMSO-d$_6$) δ 7.94 (s, 1H), 7.54-7.50 (m, 3H), 7.45-7.43 (m, 1H), 7.01 (s, 1H), 3.87 (s, 3H).

Intermediate BU: 2,3'-difluoro-4-iodo-5-methoxy-1,1'-biphenyl

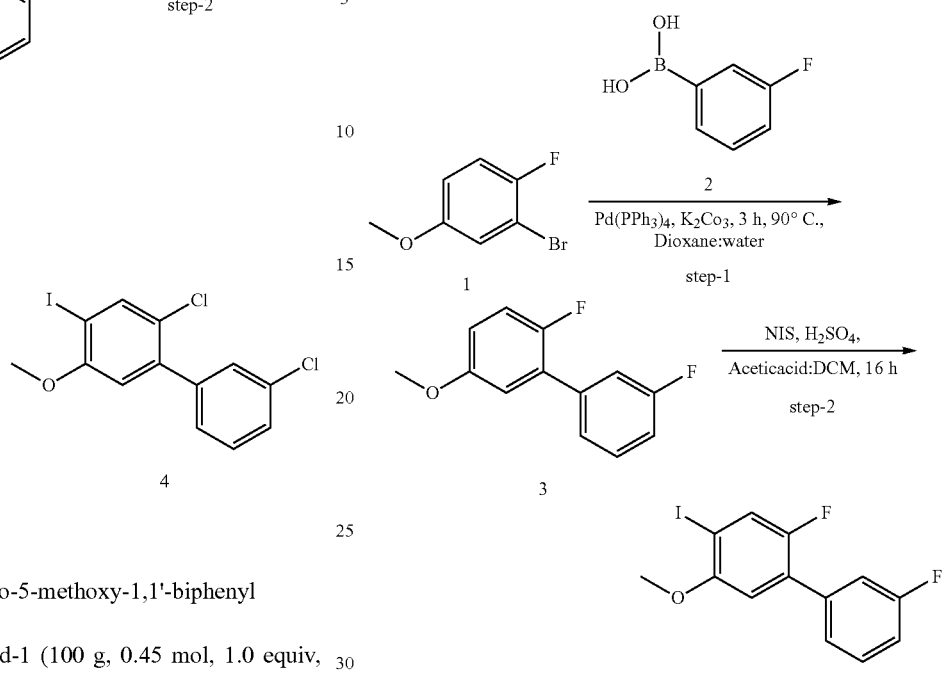

Step 1: 2,3'-difluoro-5-methoxy-1,1'-biphenyl

A solution of compound-1 (50 g, 0.24 mol, 1.0 equiv, F-Chemicals), compound-2 (101 g, 0.26 mol, 1.1 equiv, Combi-Blocks) and potassium carbonate (101 g, 0.73 mol, 2.0 equiv) in 1,4-dioxane (1.0 L) and H$_2$O (250 mL) was degassed with nitrogen for 15 min. Pd(PPh$_3$)$_4$ (15.2 g, 0.013 mol, 0.05 equiv) was added and the mixture was again degassed with nitrogen for 5 min. The reaction mixture was heated at 90° C. for 3 h. The reaction mass was cooled to room temperature, diluted with ethyl acetate (1.0 L) and washed with brine (750 mL). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (50 g, 93%). TLC solvent system: Heptane, Product R$_f$: 0.5. $^1$H NMR (400 MHz, Chloroform-d) δ 7.42 (td, J=7.9, 6.0 Hz, 1H), 7.36-7.31 (m, 1H), 7.29 (dd, J=2.5, 1.4 Hz, 1H), 7.12-7.05 (m, 2H), 6.94 (dd, J=6.2, 3.1 Hz, 1H), 6.87 (dt, J=8.9, 3.5 Hz, 1H), 3.84 (s, 3H).

Step 2: 2,3'-difluoro-4-iodo-5-methoxy-1,1'-biphenyl

To a solution of compound-3 (50 g, 0.23 mol, 1.0 equiv) in DCM (90 mL), AcOH (90 mL), and sulphuric acid (16.7 mL) was added N-iodosuccinimide (51.11 g, 0.227 mol, 1.0 equiv) in one portion. The reaction mass was stirred at room temperature for 16 h. The reaction mass was diluted with DCM (500 mL) and the organic layer was washed with water (500 mL) and saturated aqueous sodium thiosulfate (300 mL). The organic layer was dried over sodium sulphate, filtered and concentrated under reduced pressure to get the crude material which was purified by column chromatography (silica gel 60-120 mesh, elution 1% EtOAc/Hexane) to get compound-4 (45 g, 57.28%). TLC solvent system: Heptane, Product's $R_f$: 0.6. $^1$H NMR (400 MHz, Chloroform-d) δ 7.80 (d, J=9.7 Hz, 1H), 7.55-7.46 (m, 3H), 7.31-7.26 (m, 1H), 7.11 (d, J=6.6 Hz, 1H), 3.89 (s, 3H).

Intermediate BV: (3'-chloro-5-methoxy-2-methyl-[1,1'-biphenyl]-4-yl)boronic acid

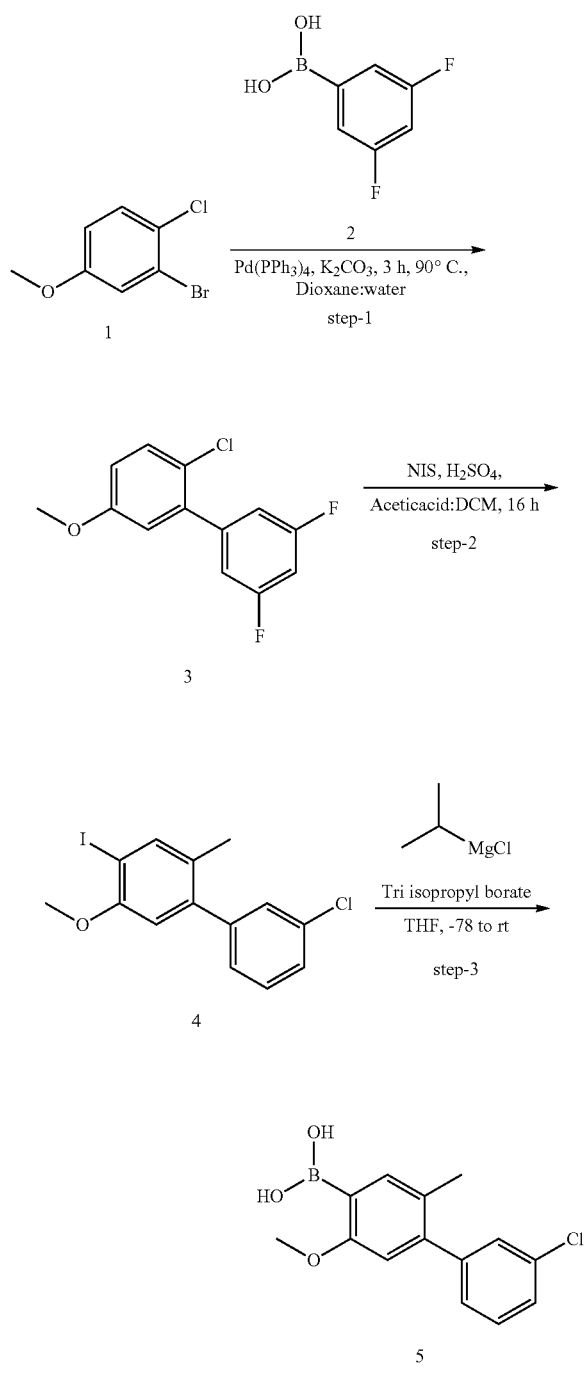

Step 1: 2-chloro-3',5'-difluoro-5-methoxy-1,1'-biphenyl

A solution of compound-1 (120 g, 0.59 mol, 1.0 equiv, F-chemicals), compound-2 (101.4 g, 0.65 mol, 1.1 equiv, combi blocks) and potassium carbonate (247.1 g, 1.79 mol, 3.0 equiv) in 1,4-dioxane (2.0 L) and H₂O (500 mL) was degassed with N₂ for 15 min. Pd(PPh₃)₄ (34.4 g, 0.029 mol, 0.05 equiv) was added and the mixture was again degassed with N₂ gas for 5 min. The reaction mixture was heated at 90° C. for 3 h. The reaction mass was cooled to RT, diluted with ethyl acetate (2.0 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (110 g, 79%). TLC solvent system: heptane, Product $R_f$: 0.5. $^1$H NMR (300 MHz, Chloroform-d) δ 7.40-7.29 (m, 3H), 7.26-7.14 (m, 2H), 6.85 (dd, J=8.4, 2.7 Hz, 1H), 6.77 (d, J=2.6 Hz, 1H), 3.81 (s, 3H), 2.19 (s, 3H).

Step 2: 3'-chloro-4-iodo-5-methoxy-2-methyl-1,1'-biphenyl

To a solution of compound-3 (110 g, 0.47 mol, 1.0 equiv) in DCM (750 mL), AcOH (750 mL), and sulphuric acid (15 mL) was added N-iodosuccinimide (106 g, 0.47 mol, 1.0 equiv) in one portion. The reaction mass was stirred at room temperature for 16 h. The reaction mass was diluted with DCM (1.0 L) and the organic layer was washed with water (1.0 L) and saturated aqueous sodium thiosulfate (500 mL). The organic layer was dried over sodium sulphate, filtered and concentrated under reduced pressure to get the crude material which was purified by column chromatography (silica gel 60-120 mesh, elution 1% EtOAc/Hexane) to get compound-4 (110 g, 65%). TLC solvent system: Heptane, Product's $R_f$: 0.6. $^1$H NMR (400 MHz, Chloroform-d) δ 7.70 (s, 1H), 7.39-7.34 (m, 2H), 7.30 (d, J=12.4 Hz, 1H), 7.21 (dd, J=5.1, 2.1 Hz, 1H), 6.66 (d, J=3.0 Hz, 1H), 3.88 (d, J=3.1 Hz, 3H), 2.17 (d, J=2.9 Hz, 3H).

Step 3: (3'-chloro-5-methoxy-2-methyl-[1,1'-biphenyl]-4-yl)boronic acid

A solution of compound-4 (60 g, 0.167 mol, 1.0 equiv) in THF (600 mL) was cooled to −78° C. under nitrogen atmosphere. Isopropyl magnesium chloride (2.0 M in THF, 126 mL, 0.251 mol, 1.5 equiv) was added dropwise for 30 mins. After addition the reaction mass was allowed warm to −55° C. and stirred for 1 h. Triisopropylborate (58.8 mL, 0.25 mol, 1.5 equiv) was added at −55° C. The reaction mass was allowed to warm to room temperature and stirred for 3 h. Saturated aqueous ammonium chloride solution (500 mL) was added slowly and the mixture was extracted with EtOAc (2×750 mL). The combined organic extract was washed with brine (500 mL), dried over sodium sulfate, filtered and concentrated under reduced pressure to get the crude material which was purified by stirring with EtOAc:Hexane (1:9, 200 mL) for 30 min and filtered to get compound-5 (25 g, 54%) as white solid. TLC solvent system: 20% Ethylacetate/Hexane Product's $R_f$: 0.5. $^1$H NMR (400 MHz, Chloroform-d) δ 7.72 (s, 2H), 7.49-7.44 (m, 3H), 7.43 (dd, J=5.2, 1.9 Hz, 1H), 7.33 (dt, J=7.2, 1.5 Hz, 1H), 6.79 (s, 1H), 3.81 (s, 3H), 2.14 (s, 3H).

Intermediate BW: 3'-chloro-2-fluoro-4-iodo-5-methoxy-1,1'-biphenyl

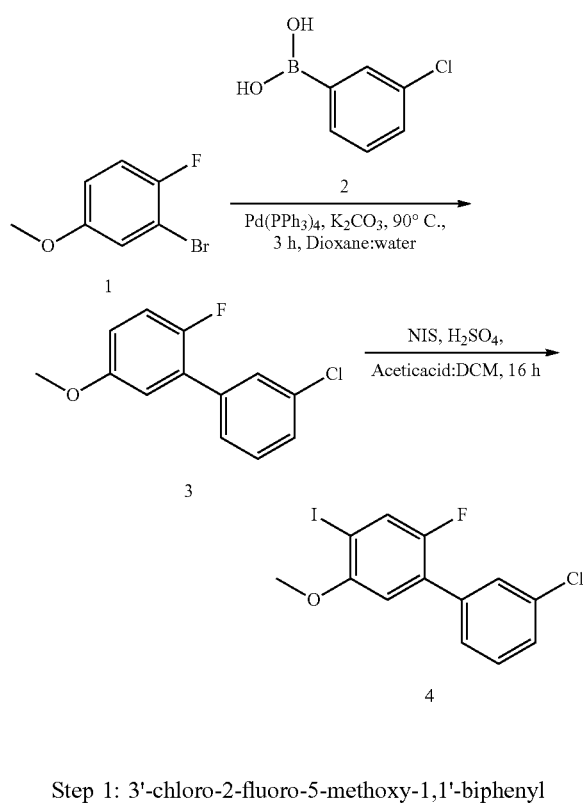

Step 1: 3'-chloro-2-fluoro-5-methoxy-1,1'-biphenyl

A solution of compound-1 (100 g, 0.487 mol, 1.0 equiv, F-Chemical), compound-2 (91.52 g, 0.585 mol, 1.2 equiv, combi-block) and potassium carbonate (201.92 g, 1.46 mol, 3.0 equiv) in 1,4-dioxane (660 mL) and $H_2O$ (180 mL) was degassed with nitrogen for 15 min. $Pd(PPh_3)_4$ (28.17.0 g, 0.024 mol, 0.05 equiv) was added and the mixture was again degassed with nitrogen for 5 min. The reaction mixture was heated at 90° C. for 3 h. The reaction mass was cooled to RT, diluted with ethyl acetate (2.0 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (92.5 g, 80%). TLC solvent system: Heptane, Product $R_f$: 0.5. $^1H$ NMR (400 MHz, DMSO-$d_6$) δ 7.60-7.47 (m, 4H), 7.27-7.21 (m, 1H), 7.06-6.94 (m, 2H), 3.78 (s, 3H).

Step 2: 3'-chloro-2-fluoro-4-iodo-5-methoxy-1,1'-biphenyl

To a solution of compound-3 (92.5 g, 0.39 mol, 1.0 equiv) in DCM (167 mL), AcOH (167 mL) and sulphuric acid (31 mL) was added N-iodosuccinimide (87.93 g, 0.39 mol, 1.0 equiv) in one portion. The reaction mass was stirred at RT for 16 h. The reaction mass was diluted with DCM (1.0 L) and the organic layer was washed with water (1.0 L) and saturated aqueous sodium thiosulfate (500 mL). The organic layer was dried over sodium sulphate, filtered and concentrated under reduced pressure to get the crude material which was purified by column chromatography (silica gel 60-120 mesh, elution 1% EtOAc/Hexane) to get compound-4 (53.0 g, 38.0%). TLC solvent system: Heptane, Product's $R_f$: 0.6. $^1H$ NMR (400 MHz, DMSO-$d_6$) δ 8.06 (d, J=8.0 Hz, 1H), 7.80 (s, 1H), 7.57-7.49 (m, 3H), 7.10 (d, J=8.0 Hz, 1H), 3.89 (s, 3H).

Intermediate BX: (2-fluoro-5-methoxy-3'-(trifluoromethyl)-[1,1'-biphenyl]-4-yl)boronic acid

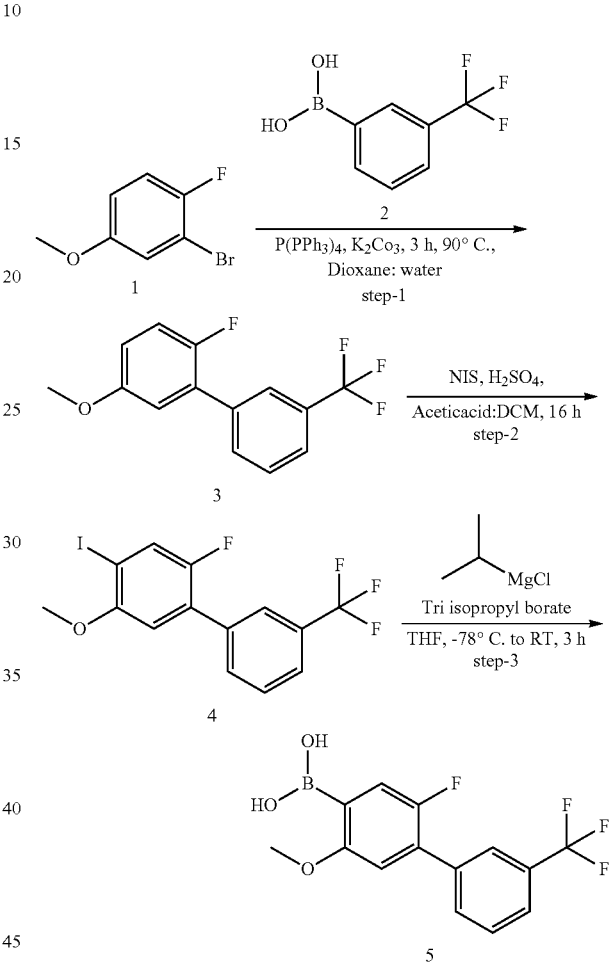

Step 1: 2-fluoro-5-methoxy-3'-(trifluoromethyl)-1,1'-biphenyl

A solution of compound-1 (70 g, 0.348 mol, 1.0 equiv, F-chemicals), compound-2 (72 g, 0.372 mol, 1.09 equiv, combi-blocks) and potassium carbonate (140 g, 1.044 mol, 3.0 quiv) in 1,4-dioxane (1.3 L) and $H_2O$ (500 mL) was degassed with nitrogen for 15 min. $Pd(PPh_3)_4$ (21 g, 0.017 mol, 0.05 equiv) was added and the mixture was again degassed with nitrogen for 5 min. The reaction mixture was heated at 90° C. for 3 h. The reaction mass was cooled to room temperature, diluted with ethyl acetate (1.5 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (76 g, 91%). TLC solvent system: Heptane, Product $R_f$: 0.5. $^1H$ NMR (400 MHz, Chloroform-d) δ 7.82 (s, 1H), 7.75 (d, J=7.6 Hz, 1H), 7.66 (d, J=7.8 Hz, 1H), 7.59 (t, J=7.8 Hz, 1H), 7.12 (t, J=9.4 Hz, 1H), 6.96 (dd, J=6.2, 3.1 Hz, 1H), 6.90 (dt, J=8.9, 3.4 Hz, 1H), 3.86 (s, 3H).

Step 2: 2-fluoro-4-iodo-5-methoxy-3'-(trifluoromethyl)-1,1'-biphenyl

To a solution of compound-3 (75 g, 0.28 mol, 1.0 equiv) in DCM (450 mL), AcOH (450 mL) and sulphuric acid (8.0 mL) was added N-iodosuccinimide (63 g, 0.0.28 mol, 1.0 equiv) in one portion. The reaction mass was stirred at room temperature for 16 h. The reaction mass was diluted with DCM (1.0 L) and the organic layer was washed with water (1.0 L) and saturated aqueous sodium thiosulfate (1 L). The organic layer was dried over sodium sulphate, filtered and concentrated under reduced pressure to get the crude material which was purified by column chromatography (silica gel 60-120 mesh, elution 1% EtOAc/Hexane) to get compound-4 (70 g, 63%). TLC solvent system: Heptane, Product's $R_f$: 0.6. $^1H$ NMR (400 MHz, Chloroform-d) δ 7.79 (s, 1H), 7.74 (d, J=7.7 Hz, 1H), 7.68 (d, J=7.8 Hz, 1H), 7.62 (dd, J=11.1, 8.5 Hz, 2H), 6.83 (d, J=6.4 Hz, 1H), 3.94 (s, 3H).

Step 3: (2-fluoro-5-methoxy-3'-(trifluoromethyl)-[1,1'-biphenyl]-4-yl)boronic acid A solution of compound-4 (70 g, 0.177 mol, 1.0 equiv) in THF (700 mL) was cooled to −78° C. under nitrogen atmosphere. Isopropyl magnesium chloride (2.0 M in THF, 140 mL, 0.265 mol, 1.5 equiv) was added drop-wise for 30 min. After addition the reaction mass was allowed warm to −55° C. and stirred for h. Triisopropylborate (63.1 ml, 0.265 mol, 1.5 equiv) was added at −55° C. The reaction mass was allowed to warm to room temperature and stirred for 3 h. Saturated aqueous ammonium chloride solution (700 mL) was added slowly and the mixture was extracted with EtOAc (1.5 L). The combined organic extract was washed with brine (1.0 L), dried over sodium sulfate, filtered and concentrated under reduced pressure to get the crude material which was purified by stirring with EtOAc:Hexane (1:9, 200 mL) for 30 min and filtered to get compound-5 (34 g, 60%) as white solid. TLC solvent system: 20% Ethylacetate/Hexane Product's $R_f$: 0.5. $^1H$ NMR (400 MHz, DMSO-d$_6$) δ 7.95 (s, 2H), 7.92 (d, J=6.5 Hz, 2H), 7.83-7.71 (m, 2H), 7.39 (d, J=10.8 Hz, 1H), 7.13 (d, J=6.0 Hz, 1H), 3.88 (s, 3H).

Intermediate BY: (5-methoxy-2-methyl-3'-(trifluoromethyl)-[1,1'-biphenyl]-4-yl)boronic acid

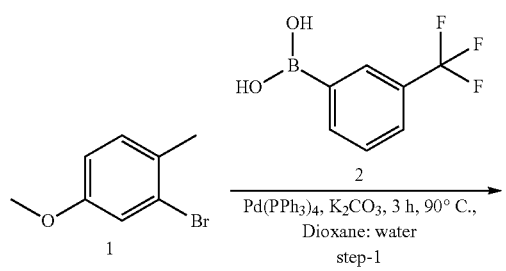

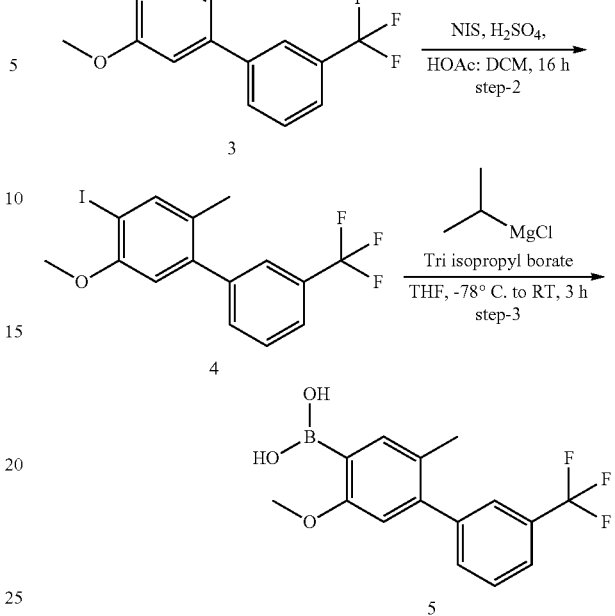

Step 1: 5-methoxy-2-methyl-3'-(trifluoromethyl)-1,1'-biphenyl

A solution of compound-1 (50.0 g, 0.248 mol, 1.0 equiv, F-chemicals), compound-2 (51.49 g, 0.265 mol, 1.1 equiv, combi-blocks) and potassium carbonate (100 g, 0.725 mol, 3.0 equiv) in 1,4-dioxane (1.0 L) and H$_2$O (250 mL) was degassed with nitrogen for 15 min. Pd(PPh$_3$)$_4$ (14.0 g, 0.0294 mol, 0.05 equiv) was added and the mixture was again degassed with nitrogen for 5 min. The reaction mixture was heated at 90° C. for 3 h. The reaction mass was cooled to RT, diluted with ethyl acetate (1.0 L) and washed with brine (500 mL). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (55 g, 89%). TLC solvent system: Heptane, Product $R_f$: 0.5. $^1H$ NMR (300 MHz, Chloroform-d) δ 7.62-7.53 (m, 4H), 7.27-7.19 (m, 1H), 6.88-6.78 (m, 2H), 3.82 (s, 3H), 2.19 (s, 3H).

Step 2: 4-iodo-5-methoxy-2-methyl-3'-(trifluoromethyl)-1,1'-biphenyl

To a solution of compound-3 (50.0 g, 0.188 mol, 1.0 equiv) in DCM (300 mL), AcOH (300 mL) and sulphuric acid (17 mL) was added N-iodosuccinimide (42.25 g, 0.188 mol, 1.0 equiv) in one portion. The reaction mass was stirred at RT for 16 h. The reaction mass was diluted with DCM (1.0 L) and the organic layer was washed with water (500 mL) and saturated aqueous thiosulfate (500 mL). The organic layer was dried over sodium sulphate, filtered and concentrated under reduced pressure to get the crude material which was purified by column chromatography (silica gel 60-120 mesh, elution 1% EtOAc/Hexane) to get compound-4 (32 g, 43.83%). TLC solvent system: Heptane, Product's $R_f$: 0.6. $^1H$ NMR (400 MHz, DMSO-d$_6$) δ 7.73-7.67 (m, 5H), 6.83 (s, 1H), 3.82 (s, 3H), 2.09 (s, 3H)

Step 3: (5-methoxy-2-methyl-3'-(trifluoromethyl)-[1,1'-biphenyl]-4-yl)boronic acid A solution of compound-4 (36 g, 0.0918 mol, 1.0 equiv) in THF (700 mL) was cooled to −78° C. under nitrogen atmosphere. Isopropyl magnesium chloride (2.0 M in THF, 69 mL, 0.137 mol, 1.5 equiv) was added drop-wise for 30 min. After addition the reaction mass was allowed warm to −55° C. and stirred for 1 h. Triisopropylborate (32 ml, 0.137 mol, 1.5 equiv) was added at −55° C. The reaction mass was allowed to warm to RT and stirred for 3 h. Saturated aqueous ammonium chloride solution (400 mL) was added slowly and the mixture was extracted with EtOAc (800 mL). The combined organic extract was washed with brine (500 mL), dried over sodium sulfate, filtered and concentrated under reduced pressure to get the crude material which was purified by stirring with EtOAc:Hexane (1:9, 200 mL) for 30 min and filtered to get compound-5 (25 g, 89%) as white solid. TLC solvent system: 20% Ethylacetate/Hexane Product's $R_f$: 0.5. $^1$H NMR (400 MHz, DMSO-$d_6$) δ 7.76-7.69 (m, 6H), 7.49 (s, 1H), 6.84 (s, 1H), 3.82 (s, 3H), 2.149 (s, 3H)

Intermediate BX: (3'-chloro-2,5'-difluoro-5-methoxy-[1,1'-biphenyl]-4-yl)boronic acid

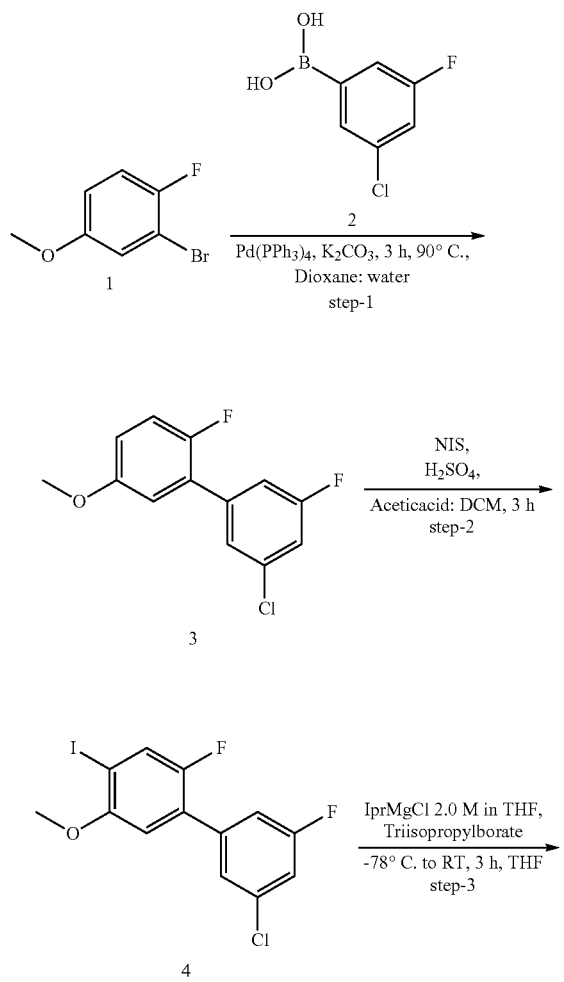

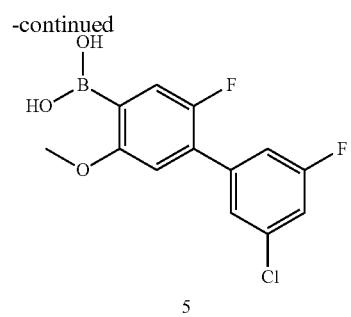

Step 1: 3'-chloro-2,5'-difluoro-5-methoxy-1,1'-biphenyl

A solution of compound-1 (50.0 g, 0.243 mol, 1.0 equiv, F-Chemical), compound-2 (46.2 g, 0.265 mol, 1.1 equiv, combi-blocks) and potassium carbonate (100 g, 0.729 mol, 3.0 equiv) in 1,4-dioxane (1.0 L) and $H_2O$ (250 mL) was degassed with nitrogen for 15 min. Pd(PPh$_3$)$_4$ (14.0 g, 0.0294 mol, 0.05 equiv) was added and the mixture was again degassed with nitrogen for 5 min. The reaction mixture was heated at 90° C. for 3 h. The reaction mass was cooled to room temperature, diluted with ethyl acetate (2.0 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-2 (60 g, 96%). TLC solvent system: Heptane, Product $R_f$: 0.5. $^1$H NMR (300 MHz, Chloroform-d) δ 7.34 (s, 1H), 7.22-7.14 (m, 1H), 7.09 (t, J=9.6 Hz, 2H), 6.88 (dd, J=11.2, 3.9 Hz, 2H), 3.83 (s, 3H).

Step 2: 3'-chloro-2,5'-difluoro-4-iodo-5-methoxy-1,1'-biphenyl

To a solution of compound-2 (76.0 g, 0.299 mol, 1.0 equiv) in DCM (750 mL), AcOH (750 mL) and sulphuric acid (15 mL) was added N-iodosuccinimide (113.4 g, 0.504 mol, 1.0 equiv) in one portion. The reaction mass was stirred at RT for 16 h. The reaction mass was diluted with DCM (1.0 L) and the organic layer was washed with water (1.0 L) and saturated aqueous sodium thiosulfate (1.0 L). The organic layer was dried over sodium sulphate, filtered and concentrated under reduced pressure to get the crude material which was purified by column chromatography (silica gel 60-120 mesh, elution 1% EtOAc/Hexane) to get compound-3 (80 g, 72%). TLC solvent system: Heptane, Product's $R_f$: 0.6. $^1$H NMR (400 MHz, Chloroform-d) δ 7.63 (d, J=9.3 Hz, 1H), 7.33 (s, 1H), 7.23-7.11 (m, 2H), 6.79 (d, J=6.4 Hz, 1H), 3.93 (s, 3H).

Step 3: (3'-chloro-2,5'-difluoro-5-methoxy-[1,1'-biphenyl]-4-yl)boronic acid A solution of compound-3 (30 g, 0.078 mol, 1.0 equiv) in THF (300 mL) was cooled to −78° C. under nitrogen atmosphere. Isopropyl magnesium chloride (2.0 M in THF, 59.1 mL, 1.5 equiv) was added drop-wise for 30 mins. After addition, the reaction mass was allowed warm to −55° C. and stirred for 1 h. Triisopropylborate (27.1 mL, 0.118 mol, 1.5 equiv) was added at −55° C. The reaction mass was allowed to warm to RT and stirred for 3 h. Saturated aqueous ammonium chloride solution (200 mL) was added slowly and the mixture was extracted with EtOAc (2×200 mL). The combined organic extract was washed with brine (200 mL), dried over sodium sulfate, filtered and concentrated under reduced pressure to get the crude material which was purified by stirring with EtOAc:Hexane (1:9, 200 mL) for 30 min and filtered to get compound-4 (13.2 g, 52.8%) as white solid. TLC solvent system: 20% Ethyl acetate/Hexane Product's $R_f$: 0.5. $^1$H NMR (400 MHz, Chloroform-d) δ 7.69 (d, J=10.4 Hz, 1H), 7.36 (d, J=1.2 Hz, 1H), 7.27-7.23 (m, 1H), 7.21-7.13 (m, 1H), 6.89 (d, J=5.6 Hz, 1H), 5.78 (s, 2H), 3.97 (s, 3H).

Intermediate BY: (4'-chloro-2-fluoro-5-methoxy-3'-methyl-[1,1'-biphenyl]-4-yl)boronic acid

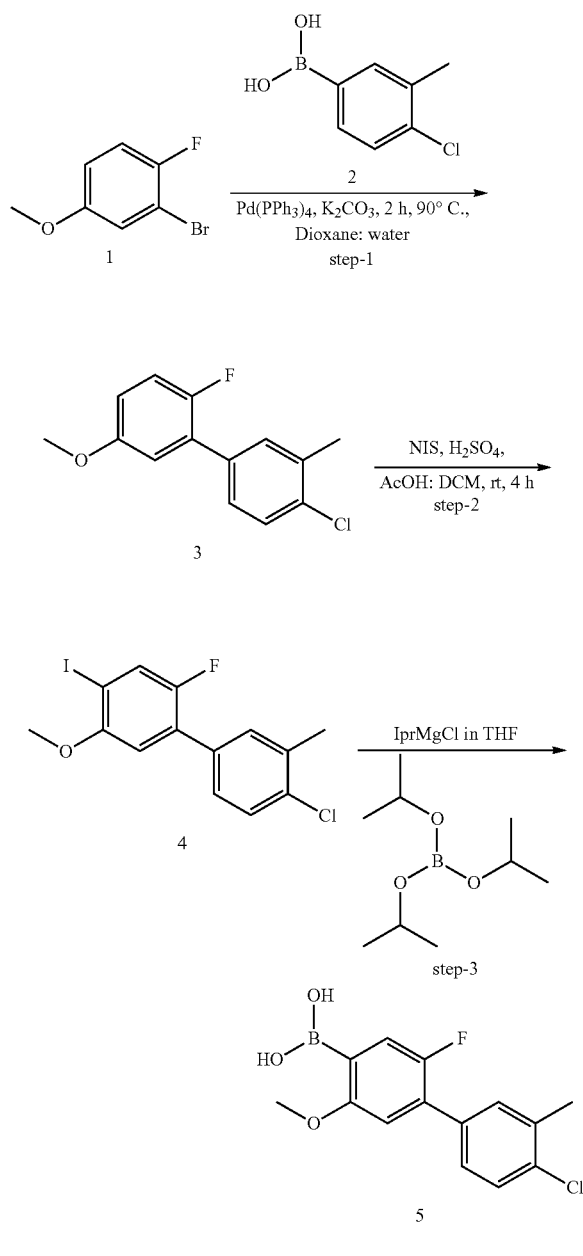

Step 1: 4'-chloro-2-fluoro-5-methoxy-3'-methyl-1,1'-biphenyl

A solution of compound-1 (100 g, 487.73 mmol, 1.0 equiv, F-chemicals), compound-2 (91.42 g, 536.50 mmol, 1.1 equiv, F-chemicals) and potassium carbonate (202.2 g, 1463.09 mmol, 3.0 equiv) in 1,4-dioxane (2.0 L) and $H_2O$ (500 mL) was degassed with nitrogen for 15 min. $Pd(PPh_3)_4$ (28.18 g, 24.38 mmol, 0.05 equiv) was added and the mixture was again degassed with nitrogen for 5 min. The reaction mixture was heated at 90° C. for 3 h. The reaction mass was cooled to room temperature, diluted with ethyl acetate (1.0 L) and washed with brine (200 mL). The organic layer was dried over sodium sulfate, filtered and concentrated under reduced pressure to get the crude material which was purified by column chromatography (silica gel 60-120 mesh, elution Hexane) to get the pure compound-3 (105 g, 86%). TLC solvent system: Heptane, Product $R_f$: 0.5. $^1$H NMR (400 MHz, Chloroform-d) δ 7.45-7.40 (m, 2H), 7.35-7.31 (m, 1H), 7.12-7.06 (m, 1H), 6.92 (dd, J=6.3, 3.1 Hz, 1H), 6.85 (dt, J=8.9, 3.5 Hz, 1H), 3.85 (s, 3H), 2.45 (s, 3H).

Step 2: 4'-chloro-2-fluoro-4-iodo-5-methoxy-3'-methyl-1,1'-biphenyl

To a solution of compound-3 (105 g, 418.82 mmol, 1.0 equiv) in DCM (500 mL), AcOH (500 mL) and sulphuric acid (22.59 g) was added N-iodosuccinimide (94.23 g, 418.82 mmol, 1.0 equiv) in one portion. The reaction mass was stirred at room temperature for 16 h. The reaction mass was diluted with DCM (4×600 mL) and the organic layer was washed with water (3×500 mL) and saturated aqueous sodium thiosulfate (1.0 L). The organic layer was dried over sodium sulphate, filtered and concentrated under reduced pressure to get the crude material which was purified by column chromatography (silica gel 230-400 mesh; elution Hexane) to get compound-4 (110 g, 70%). TLC solvent system: Heptane, Product's $R_f$: 0.6. $^1$H NMR (400 MHz, DMSO-$d_6$) δ 7.77 (d, J=9.7 Hz, 1H), 7.59 (s, 1H), 7.52 (d, J=8.3 Hz, 1H), 7.44 (t, J=10.0 Hz, 1H), 7.06 (t, J=6.6 Hz, 1H), 3.88 (s, 3H), 2.40 (s, 3H).

Step 3: (4'-chloro-2-fluoro-5-methoxy-3'-methyl-[1,1'-biphenyl]-4-yl)boronic acid A solution of compound-4 (60 g, 159.32 mmol, 1.0 equiv) in THF (600 mL) was cooled to −78° C. under nitrogen atmosphere. Isopropyl magnesium chloride (1.3 M in THF, 245.1 mL, 2.0 equiv) was added dropwise for 30 mins. After addition the reaction mass was allowed warm to −55° C. and stirred for h. Triisopropylborate (59.93 g, 318.65 mmol, 2.0 equiv) was added at −55° C. The reaction mass was allowed to warm to RT and stirred for 3 h. Saturated aqueous ammonium chloride solution (700 mL) was added slowly and the mixture was extracted with EtOAc (2×750 mL). The combined organic extract was washed with brine (400 mL), dried over sodium sulfate, filtered and concentrated under reduced pressure to get the crude material which was purified by stirring with Hexane and filtered to get compound-5 (36 g, 76%) as an off-white solid. TLC solvent system: 10% Ethylacetate/Hexane Product's $R_f$: 0.2. $^1$H NMR (400 MHz, DMSO-$d_6$) δ 7.90 (s, 2H), 7.59 (s, 1H), 7.51 (d, J=8.3 Hz, 1H), 7.43 (d, J=8.3 Hz, 1H), 7.35 (d, J=10.8 Hz, 1H), 7.03 (d, J=6.0 Hz, 1H), 3.85 (s, 3H), 2.39 (s, 3H).

Intermediate BZ: (2,3',5'-trifluoro-5-methoxy-[1,1'-biphenyl]-4-yl)boronic acid

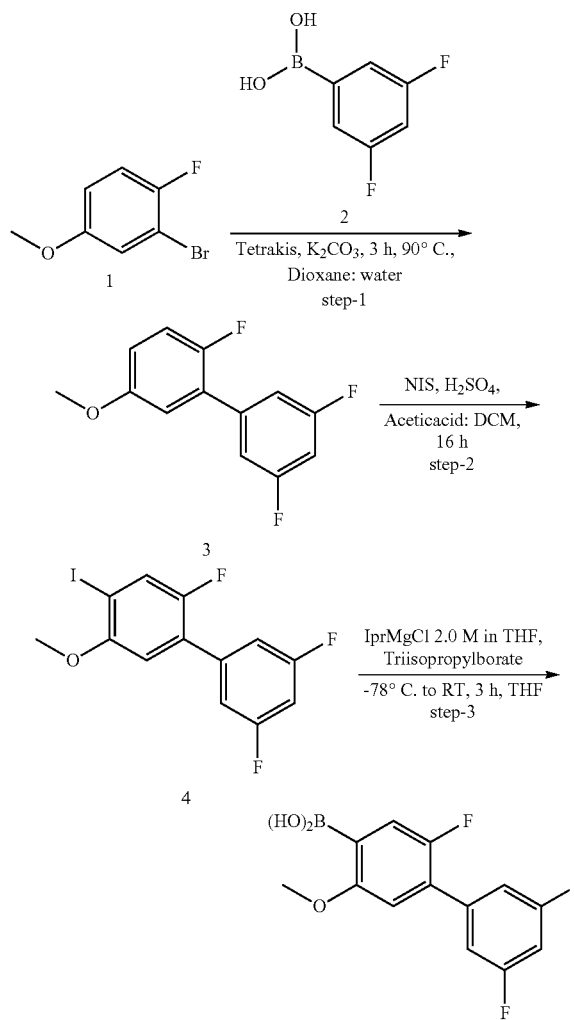

Step 1: 2,3',5'-trifluoro-5-methoxy-1,1'-biphenyl

A solution of compound-1 (120 g, 0.588 mol, 1.0 equiv, F-chemicals), compound-2 (101 g, 0.641 mol, 1.1 equiv, combi-blocks) and potassium carbonate (244 g, 1.164 mol, 2.0 equiv) in 1,4-dioxane (2.0 L) and $H_2O$ (500 mL) was degassed with nitrogen for 15 min. $Pd(PPh_3)_4$ (34.0 g, 0.0294 mol, 0.05 equiv) was added and the mixture was again degassed with nitrogen for 5 min. The reaction mixture was heated at 90° C. for 3 h. The reaction mass was cooled to room temperature, diluted with ethyl acetate (2.0 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (125 g, 89%). TLC solvent system: Heptane, Product $R_f$: 0.5. $^1$H NMR (400 MHz, Chloroform-d) δ 7.35-7.27 (m, 1H), 7.12-7.02 (m, 2H), 6.92-6.79 (m, 3H), 3.84 (s, 3H).

Step 2: 2,3',5'-trifluoro-4-iodo-5-methoxy-1,1'-biphenyl

To a solution of compound-3 (120 g, 0.504 mol, 1.0 equiv) in DCM (750 mL), AcOH (750 mL), and sulphuric acid (15 mL) was added N-iodosuccinimide (113.4 g, 0.504 mol, 1.0 equiv) in one portion. The reaction mass was stirred at room temperature for 16 h. The reaction mass was diluted with DCM (2.0 L) and the organic layer was washed with water (2.0 L) and saturated aqueous sodium thiosulfate (500 mL). The organic layer was dried over sodium sulphate, filtered and concentrated under reduced pressure to get the crude material which was purified by column chromatography (silica gel 60-120 mesh, elution 1% EtOAc/Hexane) to get compound-4 (142 g, 76%). TLC solvent system: Heptane, Product's $R_f$: 0.6. $^1$H NMR (400 MHz, Chloroform-d) δ 7.63 (dd, J=9.3, 1.0 Hz, 1H), 7.13-7.04 (m, 2H), 6.87 (tdd, J=8.8, 2.8, 1.7 Hz, 1H), 6.80 (d, J=6.4 Hz, 1H), 3.93 (d, J=0.9 Hz, 3H).

Step 3: (2,3',5'-trifluoro-5-methoxy-[1,1'-biphenyl]-4-yl)boronic acid

A solution of compound-4 (75.0 g, 0.21 mol, 1.0 equiv) in THF (750 mL) was cooled to −78° C. under nitrogen atmosphere. Isopropyl magnesium chloride (2.0 M in THF, 241 mL, 0.31 mol, 1.5 equiv) was added drop-wise for 30 mins. After addition the reaction mass was allowed warm to −55° C. and stirred for 1 h. Triisopropylborate (73 mL, 0.31 mol, 1.5 equiv) was added at −55° C. The reaction mass was allowed to warm to RT and stirred for 3 h. Saturated aqueous ammonium chloride solution (700 mL) was added slowly and the mixture was extracted with EtOAc (2×1.0 L). The combined organic extract was washed with brine (1.0 L), dried over sodium sulfate filtered and concentrated under reduced pressure to get the crude material which was purified by stirring with EtOAc:Hexane (1:9, 200 mL) for 30 min and filtered to get compound-5 (30 g, 50%) as white solid. TLC solvent system: 20% Ethylacetate/Hexane Product's $R_f$: 0.5. $^1$H NMR (400 MHz, DMSO-$d_6$) δ 7.97 (s, 2H), 7.58 (s, 1H), 7.36-7.31 (m, 1H), 7.25 (d, J=7.1 Hz, 2H), 7.02 (s, J=6.0 Hz, 1H), 3.83 (s, 3H).

Intermediate CA: 2-fluoro-4-iodo-5-methoxy-3'-(trifluoromethyl)-1,1'-biphenyl

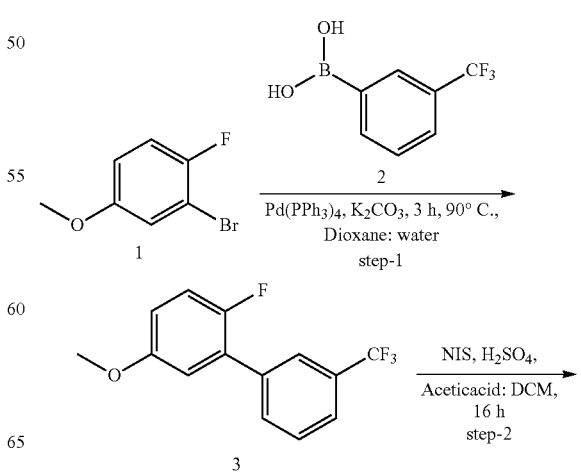

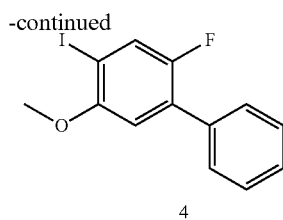

4

Step 1: 2-fluoro-5-methoxy-3'-(trifluoromethyl)-1,1'-biphenyl

A solution of compound-1 (50.0 g, 0.2438 mol, 1.0 equiv, Sozhoin sibica chemical), compound-2 (55.5 g, 0.29 mol, 1.2 equiv, F-chemicals) and potassium carbonate (100 g, 0.73 mol, 3.0 equiv) in 1,4-dioxane (380.0 mL) and H$_2$O (90 mL) was degassed with nitrogen for 15 min. Pd(PPh$_3$)$_4$ (14.5 g, 0.121 mol, 0.05 equiv) was added and the mixture was again degassed with nitrogen for 5 min. The reaction mixture was heated at 90° C. for 3 h. The reaction mass was cooled to RT, diluted with ethyl acetate (300 mL) and washed with brine (200 mL). The organic layer was dried over sodium sulfate, filtered and concentrated under reduced pressure to get the crude material which was purified by column chromatography (silica gel 60-120 mesh, elution 0.5% EtOAc/Hexane) to get the pure compound-3 (55 g, 83.7%) as white solid. TLC solvent system: Heptane, Product R$_f$: 0.5. $^1$H NMR (300 MHz, Chloroform-d) δ 7.80 (s, 1H), 7.74 (d, J=6.6 Hz, 1H), 7.60 (dt, J=14.9, 7.7 Hz, 2H), 7.15-7.03 (m, 1H), 6.96-6.85 (m, 2H), 3.84 (s, 3H).

Step 2: 2-fluoro-4-iodo-5-methoxy-3'-(trifluoromethyl)-1,1'-biphenyl

To a solution of compound-2 (55.0 g, 0.2037 mol, 1.0 equiv) in DCM (330 mL), AcOH (330 mL) and sulphuric acid (6.0 mL) was added N-iodosuccinimide (45.8 g, 0.203 mol, 1.0 equiv) in one portion. The reaction mass was stirred at room temperature for 16 h. The reaction mass was diluted with DCM (200 mL) and the organic layer was washed with water (500 mL) and saturated aqueous sodium thiosulfate (500 mL). The organic layer was dried over sodium sulphate, filtered and concentrated under reduced pressure to get the crude material which was purified by column chromatography (silica gel 60-120 mesh, elution 100% Hexane) to get compound-4 (45 g, 55.8%) as colourless liquid. TLC solvent system: Heptane, Product's R$_f$: 0.5. $^1$H NMR (400 MHz, Chloroform-d) δ 7.78 (s, 1H), 7.73 (d, J=7.7 Hz, 1H), 7.67 (d, J=7.8 Hz, 1H), 7.63 (d, J=9.2 Hz, 1H), 7.60 (d, J=7.7 Hz, 1H), 6.82 (d, J=6.4 Hz, 1H), 3.93 (s, 3H).

Intermediate CB: 2,3',5'-trifluoro-4-iodo-5-methoxy-1,1'-biphenyl

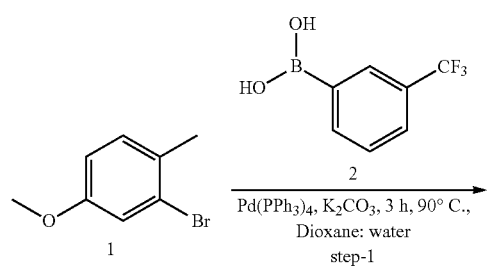

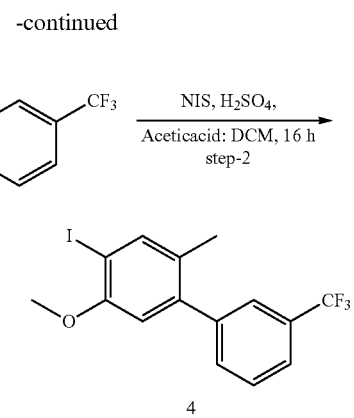

4

Step 1: 5-methoxy-2-methyl-3'-(trifluoromethyl)-1,1'-biphenyl

A solution of compound-1 (100 g, 0.49 mol, 1.0 equiv, Fchemicals), compound-2 (103 g, 0.54 mol, 1.1 equiv, combiblock) and potassium carbonate (206 g, 1.492 mol, 3.0 equiv) in 1,4-dioxane (2.0 L) and H$_2$O (500 mL) was degassed with nitrogen for 15 min. Pd(PPh$_3$)$_4$ (29 g, 0.029 mol, 0.05 equiv) was added and the mixture was again degassed with nitrogen for 5 min. The reaction mixture was heated at 90° C. for 3 h. The reaction mass was cooled to RT, diluted with ethyl acetate (2.0 L) and washed with brine (1.0 L). The organic layer was dried over sodium sulfate, filtered and concentrated under reduced pressure to get the crude material which was purified by column chromatography (silica gel 60-120 mesh, elution 1% EtOAc/Hexane) to get the pure compound-3 (100 g, 75%). TLC solvent system: Heptane, Product R$_f$: 0.5. $^1$H NMR (400 MHz, Chloroform-d) δ 7.66-7.59 (m, 2H), 7.59-7.47 (m, 2H), 7.21 (d, J=8.4 Hz, 1H), 6.87 (dd, J=8.4, 2.8 Hz, 1H), 6.79 (d, J=2.8 Hz, 1H), 3.83 (s, 3H), 2.19 (s, 3H).

Step 2: 2,3',5'-trifluoro-4-iodo-5-methoxy-1,1'-biphenyl

To a solution of compound-3 (75 g, 0.28 mol, 1.0 equiv) in DCM (475 mL), AcOH (475 mL) and sulphuric acid (8 mL) was added N-iodosuccinimide (63 g, 0.281 mol, 1.0 equiv) in one portion. The reaction mass was stirred at RT for 16 h. The reaction mass was diluted with DCM (1.0 L) and the organic layer was washed with water (1.0 L) and saturated aqueous sodium thiosulfate (1 L). The organic layer was dried over sodium sulphate, filtered and concentrated under reduced pressure to get the crude material which was purified by column chromatography (silica gel 60-120 mesh, elution 2% EtOAc/Hexane) to get compound-4 (66 g, 61%). TLC solvent system: Heptane, Product's R$_f$: 0.6. $^1$H NMR (400 MHz, Chloroform-d) δ 7.72 (s, 1H), 7.66-7.65 (m, 1H), 7.59-7.50 (m, 3H), 6.67 (s, 1H), 3.89 (s, 3H), 2.16 (s, 3H).

Table 2 provides analytical characterization and biological data for the examples 312-588, as representative compounds of the present invention. The compounds in the table are name by ACD software, version 12; while the compound names in the written examples presented herein were named using ChemDraw Ultra version 12; molecular weight measured (MW); the method by which the compound was made; the NMR of the representative example (for those compounds having no detailed written procedure above); and biological data including in-vitro Nav 1.7 PX data (IC$_{50}$ in uM) and Nav 1.5 PX data (IC$_{50}$ in uM), where available.

TABLE 2

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 312 | N-3-isoxazolyl-1-(4-methoxy-3'-(trifluoromethyl)-3-biphenylyl)-2-oxo-1,2-dihydro-6-quinolinesulfonamide | 542.2 | 115 | 0.022 | | |
| 482 | 1-(3'-fluoro-4-methoxy-3-biphenylyl)-N-3-isoxazolyl-2-oxo-1,2-dihydro-6-quinolinesulfonamide | 492.2 | 115 | 0.08 | | |
| 485 | 1-(5-(5-fluoro-3-pyridinyl)-2-methoxyphenyl)-N-3-isoxazolyl-2-oxo-1,2-dihydro-6-quinolinesulfonamide | 493.2 | 115 | 0.69 | | |
| 483 | (P)-1-(3'-fluoro-4-methoxy-3-biphenylyl)-N-3-isoxazolyl-2-oxo-1,2-dihydro-6-quinolinesulfonamide | 492.0 | 115 | 0.054 | | |
| 484 | (M)-1-(3'-fluoro-4-methoxy-3-biphenylyl)-N-3-isoxazolyl-2-oxo-1,2-dihydro-6-quinolinesulfonamide | 492.0 | 115 | 32.28 | | |
| 381 | (P)—N-3-isoxazolyl-1-(4-methoxy-3'-(trifluoromethyl)-3-biphenylyl)-2-oxo-1,2-dihydro-6-quinolinesulfonamide | 542.2 | 115 | 0.015 | | |
| 382 | (M)—N-3-isoxazolyl-1-(4-methoxy-3'-(trifluoromethyl)-3-biphenylyl)-2-oxo-1,2-dihydro-6-quinolinesulfonamide | 542.0 | 115 | 3.079 | | |
| 486 | N-3-isoxazolyl-1-(2-methoxy-5-(1-methyl-1H-pyrazol-4-yl)phenyl)-2-oxo-1,2-dihydro-6-quinolinesulfonamide | 478.1 | 115 | 27.14 | | |
| 487 | 1-(5-(6-fluoro-3-pyridinyl)-2-methoxyphenyl)-N-3-isoxazolyl-2-oxo-1,2-dihydro-6-quinolinesulfonamide | 492.3 | 115 | 0.902 | | |
| 488 | 1-(5-(5-fluoro-2-methoxy-3-pyridinyl)-2-methoxyphenyl)-N-3-isoxazolyl-2-oxo-1,2-dihydro-6-quinolinesulfonamide | 523.1 | 115 | 0.299 | | |
| 383 | N-3-isoxazolyl-1-(2-methoxy-5-(4-pyridinyl)phenyl)-2-oxo-1,2-dihydro-6-quinolinesulfonamide | 475.2 | 116 | | | |
| 489 | N-3-isoxazolyl-1-(2-methoxy-5-(5-pyrimidinyl)phenyl)-2-oxo-1,2-dihydro-6-quinolinesulfonamide | 474.0 | 116 | | | |
| 490 | N-3-isoxazolyl-1-(2-methoxy-5-(3-pyridinyl)phenyl)-2-oxo-1,2-dihydro-6-quinolinesulfonamide | 475.0 | 116 | | | |
| 384 | N-3-isoxazolyl-1-(2-methoxy-5-(2- | 475.1 | 117 | | | |

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | pyridinyl)phenyl)-2-oxo-1,2-dihydro-6-quinolinesulfonamide | | | | | |
| 385 | N-3-isoxazolyl-1-(2-methoxy-5-(1-methyl-1H-pyrazol-5-yl)phenyl)-2-oxo-1,2-dihydro-6-quinolinesulfonamide | 478.1 | 118 | 6.23 | | |
| 491 | 1-(5-(5-cyano-3-pyridinyl)-2-methoxyphenyl)-N-3-isoxazolyl-2-oxo-1,2-dihydro-6-quinolinesulfonamide | 500.1 | 118 | 2.073 | | |
| 492 | N-3-isoxazolyl-1-(2-methoxy-5-(5-(trifluoromethyl)-3-pyridinyl)phenyl)-2-oxo-1,2-dihydro-6-quinolinesulfonamide | 543.1 | 118 | 0.298 | | |
| 493 | 1-(3'-cyano-4-methoxy-3-biphenylyl)-N-3-isoxazolyl-2-oxo-1,2-dihydro-6-quinolinesulfonamide | 499.1 | 118 | 0.418 | | |
| 494 | 1-(5-(5-chloro-3-pyridinyl)-2-methoxyphenyl)-N-3-isoxazolyl-2-oxo-1,2-dihydro-6-quinolinesulfonamide | 509.1 | 118 | 0.682 | | |
| 495 | 1-(5-(2-fluoro-3-pyridinyl)-2-methoxyphenyl)-N-3-isoxazolyl-2-oxo-1,2-dihydro-6-quinolinesulfonamide | 493.1 | 118 | 2.448 | | |
| 496 | 1-(5-(2-fluoro-4-pyridinyl)-2-methoxyphenyl)-N-3-isoxazolyl-2-oxo-1,2-dihydro-6-quinolinesulfonamide | 493.1 | 118 | 2.768 | | |
| 312 | (P)-1-(3'-chloro-5-methoxy-2-methyl-4-biphenylyl)-N-3-isoxazolyl-2-oxo-1,2-dihydro-6-quinolinesulfonamide | 522.0 | 65 | 0.017 | | |
| 313 | (M)-1-(3'-chloro-5-methoxy-2-methyl-4-biphenylyl)-N-3-isoxazolyl-2-oxo-1,2-dihydro-6-quinolinesulfonamide | 522.0 | 65 | 0.799 | | |
| 417 | (P)-1-(3'-chloro-5'-fluoro-5-methoxy-2-methyl-4-biphenylyl)-N-3-isoxazolyl-2-oxo-1,2-dihydro-6-quinolinesulfonamide | 540.0 | 65 | 0.009 | | |
| 418 | (M)-1-(3'-chloro-5'-fluoro-5-methoxy-2-methyl-4-biphenylyl)-N-3-isoxazolyl-2-oxo-1,2-dihydro-6-quinolinesulfonamide | 540.0 | 65 | 0.309 | | |
| 419 | (P)—N-3-isoxazolyl-1-(5-methoxy-2-methyl-3'-(trifluoromethyl)-4-biphenylyl)-2-oxo-1,2-dihydro-6-quinolinesulfonamide | 556.2 | 65 | 0.01 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 420 | (M)—N-3-isoxazolyl-1-(5-methoxy-2-methyl-3'-(trifluoromethyl)-4-biphenylyl)-2-oxo-1,2-dihydro-6-quinolinesulfonamide | 556.2 | 65 | 3.845 | | |
| 533 | (P)-1-(2-chloro-5-methoxy-3'-(trifluoromethyl)-4-biphenylyl)-N-3-isoxazolyl-2-oxo-1,2-dihydro-6-quinolinesulfonamide | 576.0 | 65 | 0.004 | >30 | |
| 534 | (M)-1-(2-chloro-5-methoxy-3'-(trifluoromethyl)-4-biphenylyl)-N-3-isoxazolyl-2-oxo-1,2-dihydro-6-quinolinesulfonamide | 576.0 | 65 | 1.349 | | |
| 359 | (P)-1-(2-fluoro-5-methoxy-3'-(trifluoromethyl)-4-biphenylyl)-N-3-isoxazolyl-2-oxo-1,2-dihydro-6-quinolinesulfonamide | 558.0 | 99 | 0.009 | | |
| 360 | (M)-1-(2-fluoro-5-methoxy-3'-(trifluoromethyl)-4-biphenylyl)-N-3-isoxazolyl-2-oxo-1,2-dihydro-6-quinolinesulfonamide | 558.0 | 99 | 2.554 | | |
| 421 | (P)-1-(4'-chloro-5-methoxy-2,3'-dimethyl-4-biphenylyl)-N-3-isoxazolyl-2-oxo-1,2-dihydro-6-quinolinesulfonamide | 536.1 | 65 | 0.016 | | |
| 422 | (M)-1-(4'-chloro-5-methoxy-2,3'-dimethyl-4-biphenylyl)-N-3-isoxazolyl-2-oxo-1,2-dihydro-6-quinolinesulfonamide | 536.1 | 65 | 6.092 | | |
| 415 | (P)-1-(4-bromo-2-methoxy-5-methylphenyl)-N-3-isoxazolyl-2-oxo-1,2-dihydro-6-quinolinesulfonamide | 489.9 | Intermediate Synthesis | 0.269 | | |
| 416 | (M)-1-(4-bromo-2-methoxy-5-methylphenyl)-N-3-isoxazolyl-2-oxo-1,2-dihydro-6-quinolinesulfonamide | 489.9 | Intermediate Synthesis | | | |
| 423 | (P)-1-(3',5'-difluoro-5-methoxy-2-methyl-4-biphenylyl)-N-3-isoxazolyl-2-oxo-1,2-dihydro-6-quinolinesulfonamide | 524.1 | 65 | 0.022 | >30 | |
| 424 | (M)-1-(3',5'-difluoro-5-methoxy-2-methyl-4-biphenylyl)-N-3-isoxazolyl-2-oxo-1,2-dihydro-6-quinolinesulfonamide | 524.1 | 65 | 1.988 | | |
| 427 | (P)-1-(3'-fluoro-5-methoxy-2-methyl-4-biphenylyl)-N-3-isoxazolyl-2-oxo-1,2-dihydro- | 506.1 | 65 | 0.025 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 428 | (M)-1-(3'-fluoro-5-methoxy-2-methyl-4-biphenylyl)-N-3-isoxazolyl-2-oxo-1,2-dihydro-6-quinolinesulfonamide | 506.1 | 65 | 7.589 | | |
| 323 | (P)—N-3-isoxazolyl-1-(3-methoxy-3'-(trifluoromethyl)-4-biphenylyl)-2-oxo-1,2-dihydro-6-quinolinesulfonamide | 542.2 | 72 | 0.023 | | |
| 324 | (M)—N-3-isoxazolyl-1-(3-methoxy-3'-(trifluoromethyl)-4-biphenylyl)-2-oxo-1,2-dihydro-6-quinolinesulfonamide | 542.2 | 72 | 4.478 | | |
| 429 | (M)-1-(3'-chloro-5'-fluoro-3-methoxy-4-biphenylyl)-N-3-isoxazolyl-2-oxo-1,2-dihydro-6-quinolinesulfonamide | 526.1 | 72 | 1.591 | | |
| 430 | (P)-1-(3'-chloro-5'-fluoro-3-methoxy-4-biphenylyl)-N-3-isoxazolyl-2-oxo-1,2-dihydro-6-quinolinesulfonamide | 526.1 | 72 | 0.012 | | |
| 425 | (M)-1-(4-(5-fluoro-2-methoxy-3-pyridinyl)-2-methoxy-5-methylphenyl)-N-3-isoxazolyl-2-oxo-1,2-dihydro-6-quinolinesulfonamide | 537.2 | 65 | 20.09 | | |
| 426 | (P)-1-(4-(5-fluoro-2-methoxy-3-pyridinyl)-2-methoxy-5-methylphenyl)-N-3-isoxazolyl-2-oxo-1,2-dihydro-6-quinolinesulfonamide | 537.2 | 65 | 0.063 | | |
| 321 | (P)-1-(3'-chloro-5-methoxy-2-methyl-4-biphenylyl)-2-oxo-N-2-pyrimidinyl-1,2-dihydro-6-quinolinesulfonamide | 533.2 | 71 | 0.01 | | |
| 322 | (M)-1-(3'-chloro-5-methoxy-2-methyl-4-biphenylyl)-2-oxo-N-2-pyrimidinyl-1,2-dihydro-6-quinolinesulfonamide | 533.2 | 71 | 3.888 | | |
| 319 | (M)-1-(3'-chloro-3-fluoro-5-methoxy-4-biphenylyl)-N-3-isoxazolyl-2-oxo-1,2-dihydro-6-quinolinesulfonamide | 526.2 | 70 | 0.207 | | |
| 320 | (P)-1-(3'-chloro-3-fluoro-5-methoxy-4-biphenylyl)-N-3-isoxazolyl-2-oxo-1,2-dihydro-6-quinolinesulfonamide | 526.2 | 70 | 0.141 | | |
| 433 | (P)-1-(3'-chloro-2-cyano-5'-fluoro-5-methoxy-4-biphenylyl)-N-3-isoxazolyl-2-oxo-1,2-dihydro-6-quinolinesulfonamide | 551.2 | 72 | 0.01 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 434 | (M)-1-(3'-chloro-2-cyano-5'-fluoro-5-methoxy-4-biphenylyl)-N-3-isoxazolyl-2-oxo-1,2-dihydro-6-quinolinesulfonamide | 551.2 | 72 | 1.836 | | |
| 540 | (P)-1-(3'-chloro-2,5'-difluoro-5-methoxy-4-biphenylyl)-2-oxo-N-4-pyrimidinyl-1,2-dihydro-6-quinolinesulfonamide | 555.0 | 73 | 0.009 | | 1H NMR (400 MHz, DMSO-d6) d = 8.60 (s, 1 H), 8.42 (s, 1 H), 8.30 (br. s., 1 H), 8.24 (d, J = 9.6 Hz, 1 H), 7.92 (dd, J = 2.2, 9.0 Hz, 1 H), 7.67 (d, J = 1.5 Hz, 1 H), 7.64-7.53 (m, 3 H), 7.47 (d, J = 6.9 Hz, 1 H), 7.00 (br. s., 1 H), 6.86-6.74 (m, 2 H), 3.75 (s, 3 H). |
| 541 | (P)-1-(3'-chloro-2,5'-difluoro-5-methoxy-4-biphenylyl)-2-oxo-N-2-pyrimidinyl-1,2-dihydro-6-quinolinesulfonamide | 555.0 | 73 | 0.018 | | 1H NMR (400 MHz, DMSO-d6) d = 11.91 (br. s., 1 H), 8.57-8.45 (m, 3 H), 8.27 (d, J = 9.5 Hz, 1 H), 7.99 (dd, J = 2.2, 8.9 Hz, 1 H), 7.66 (d, J = 1.3 Hz, 1 H), 7.64-7.53 (m, 3 H), 7.47 (d, J = 6.8 Hz, 1 H), 7.05 (t, J = 4.9 Hz, 1 H), 6.88-6.75 (m, 2 H), 3.75 (s, 3 H). |
| 542 | (P)-1-(3'-chloro-2,5'-difluoro-5-methoxy-4-biphenylyl)-2-oxo-N-3-pyridazinyl-1,2-dihydro-6-quinolinesulfonamide | 555.0 | 73 | 0.007 | | 1H NMR (400 MHz, DMSO-d6) d = 14.48 (br. s., 1 H), 8.41-8.29 (m, 2 H), 8.21 (d, J = 9.6 Hz, 1 H), 7.98-7.80 (m, 2 H), 7.72-7.65 (m, 2 H), 7.64-7.52 (m, 3 H), 7.47 (d, J = 6.9 Hz, 1 H), 6.78 (dd, J = 3.9, 9.3 Hz, 2 H), 3.75 (s, 3 H). |
| 325 | (P)-1-(3'-chloro-2,5'-difluoro-5-methoxy-4-biphenylyl)-N-1,3-oxazol-2-yl-2-oxo-1,2-dihydro-6-quinolinesulfonamide | 544.1 | 73 | 0.014 | | |
| 326 | (P)-1-(3'-chloro-2,5'-difluoro-5-methoxy-4-biphenylyl)-N-1,2,4-oxadiazol-3-yl-2-oxo-1,2-dihydro-6-quinolinesulfonamide | 545.0 | 74 | 0.005 | | |
| 543 | (P)-1-(3'-chloro-2,5'-difluoro-5-methoxy-4-biphenylyl)-2-oxo-N-2-pyrazinyl-1,2-dihydro-6-quinolinesulfonamide | 555.0 | 73 | 0.013 | | 1H NMR (400 MHz, DMSO-d6) d = 11.64 (br. s., 1 H), 8.48 (d, J = 2.2 Hz, 1 H), 8.36 (d, J = 1.2 Hz, 1 H), 8.31-8.17 (m, 3 H), 7.95 (dd, J = 2.2, 9.0 Hz, 1 H), 7.66 (d, J = 1.3 Hz, 1 H), 7.63-7.53 (m, 3 H), 7.47 (d, J = 6.9 Hz, 1 H), 6.82 (dd, J = 9.3, 11.3 Hz, 2 H), 3.74 (s, 3 H). |
| 544 | (P)-1-(3'-chloro-2,5'-difluoro-5-methoxy-4-biphenylyl)-N-(5-fluoro-2-pyrimidinyl)-2-oxo-1,2-dihydro-6-quinolinesulfonamide | 573.0 | 73 | 0.014 | | 1H NMR (400 MHz, DMSO-d6) d = 11.98 (s, 1 H), 8.62 (d, J = 0.6 Hz, 2 H), 8.48 (d, J = 2.2 Hz, 1 H), 8.27 (d, J = 9.5 Hz, 1 H), 7.97 (dd, J = 2.2, 9.0 Hz, 1 H), 7.66 (d, J = 1.3 Hz, 1 H), 7.63-7.53 (m, 3 H), 7.48 (d, J = 6.9 Hz, 1 H), 6.86-6.76 (m, 2 H), 3.75 (s, 3 H). |
| 327 | 1-(3-((2R)-2,3-dihydroxypropyl)-3'-fluoro-4-biphenylyl)-N-3-isoxazolyl-2-oxo-1,2-dihydro-6-quinolinesulfonamide, 1-(3-((2S)-2,3-dihydroxypropyl)-3'-fluoro-4-biphenylyl)-N-3-isoxazolyl-2-oxo-1,2-dihydro-6-quinolinesulfonamide | 536.1 | 75 | 5.571 | | |
| 431 | (M)-1-(4'-chloro-3-methoxy-3'-methyl-4-biphenylyl)-N-3- | 522.0 | 72 | 5.053 | | |

TABLE 2-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | isoxazolyl-2-oxo-1,2-dihydro-6-quinolinesulfonamide | | | | | |
| 432 | (P)-1-(4'-chloro-3-methoxy-3'-methyl-4-biphenylyl)-N-3-isoxazolyl-2-oxo-1,2-dihydro-6-quinolinesulfonamide | 522.0 | 72 | 0.009 | | |
| 475 | (P)-1-(3'-chloro-2-fluoro-5-methoxy-4-biphenylyl)-N-3-isoxazolyl-2-oxo-1,2-dihydro-6-quinolinesulfonamide | 524.1 | 99 | 0.011 | >30 | |
| 463 | (P)-1-(2-methoxy-4-(trifluoromethyl)phenyl)-2-oxo-N-1,3-thiazol-2-yl-1,2-dihydro-6-quinolinesulfonamide | 482.2 | 42 | 0.241 | >30 | |
| 464 | (M)-1-(2-methoxy-4-(trifluoromethyl)phenyl)-2-oxo-N-1,3-thiazol-2-yl-1,2-dihydro-6-quinolinesulfonamide | 482.2 | 42 | 22.13 | >30 | |
| 353 | (P)-1-(2-chloro-3'-fluoro-5-methoxy-4-biphenylyl)-2-oxo-N-1,3,4-thiadiazol-2-yl-1,2-dihydro-6-quinolinesulfonamide | 544.0 | 94 | 0.012 | >30 | |
| 354 | (M)-1-(2-chloro-3'-fluoro-5-methoxy-4-biphenylyl)-2-oxo-N-1,3,4-thiadiazol-2-yl-1,2-dihydro-6-quinolinesulfonamide | 544.0 | 94 | 5.856 | | |
| 355 | (P)-1-(2-chloro-3'-fluoro-5-methoxy-4-biphenylyl)-2-oxo-N-2-pyrimidinyl-1,2-dihydro-6-quinolinesulfonamide | 537.0 | 95 | 0.031 | | |
| 356 | (M)-1-(2-chloro-3'-fluoro-5-methoxy-4-biphenylyl)-2-oxo-N-2-pyrimidinyl-1,2-dihydro-6-quinolinesulfonamide | 537.0 | 95 | | | |
| 455 | (P)-1-(2-chloro-3'-fluoro-5-methoxy-4-biphenylyl)-N-3-isoxazolyl-2-oxo-1,2-dihydro-6-quinolinesulfonamide | 526.0 | 65 | 0.014 | | |
| 456 | (M)-1-(2-chloro-3'-fluoro-5-methoxy-4-biphenylyl)-N-3-isoxazolyl-2-oxo-1,2-dihydro-6-quinolinesulfonamide | 526.0 | 65 | 0.548 | | |
| 457 | (P)-1-(2-chloro-3',5'-difluoro-5-methoxy-4-biphenylyl)-N-3-isoxazolyl-2-oxo-1,2-dihydro-6-quinolinesulfonamide | 544.1 | 65 | 0.009 | | |
| 458 | (M)-1-(2-chloro-3',5'-difluoro-5-methoxy-4-biphenylyl)-N-3-isoxazolyl-2-oxo-1,2-dihydro-6-quinolinesulfonamide | 544.1 | 65 | 0.889 | | |
| 459 | (P)-1-(2,3'-dichloro-5-methoxy-4-biphenylyl)-N-3-isoxazolyl-2-oxo- | 542.0 | 65 | 0.012 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 460 | 1,2-dihydro-6-quinolinesulfonamide (M)-1-(2,3'-dichloro-5-methoxy-4-biphenylyl)-N-3-isoxazolyl-2-oxo-1,2-dihydro-6-quinolinesulfonamide | 542.0 | 65 | 1.757 | | |
| 461 | (P)-1-(2,3'-dichloro-5'-fluoro-5-methoxy-4-biphenylyl)-N-3-isoxazolyl-2-oxo-1,2-dihydro-6-quinolinesulfonamide | 561.0 | 65 | 0.006 | >30 | |
| 462 | (M)-1-(2,3'-dichloro-5'-fluoro-5-methoxy-4-biphenylyl)-N-3-isoxazolyl-2-oxo-1,2-dihydro-6-quinolinesulfonamide | 561.0 | 65 | 0.193 | | |
| 471 | (P)-1-(2,4'-dichloro-5-methoxy-3'-methyl-4-biphenylyl)-N-3-isoxazolyl-2-oxo-1,2-dihydro-6-quinolinesulfonamide | 557.1 | 65 | 0.008 | | |
| 472 | (M)-1-(2,4'-dichloro-5-methoxy-3'-methyl-4-biphenylyl)-N-3-isoxazolyl-2-oxo-1,2-dihydro-6-quinolinesulfonamide | 557.1 | 65 | 0.786 | | |
| 466 | (M)-1-(2-chloro-3'-fluoro-5-methoxy-4-biphenylyl)-2-oxo-N-4-pyrimidinyl-1,2-dihydro-6-quinolinesulfonamide | 537.0 | 2, Step 1 | 4.317 | | |
| 468 | (M)-1-(2-chloro-3'-fluoro-5-methoxy-4-biphenylyl)-2-oxo-N-3-pyridazinyl-1,2-dihydro-6-quinolinesulfonamide | 537.0 | 2, Step 1 | 6.996 | | |
| 467 | (P)-1-(2-chloro-3'-fluoro-5-methoxy-4-biphenylyl)-2-oxo-N-3-pyridazinyl-1,2-dihydro-6-quinolinesulfonamide | 537.0 | 2, Step 1 | 0.013 | >30 | |
| 473 | (P)-1-(4-bromo-5-chloro-2-methoxyphenyl)-N-3-isoxazolyl-2-oxo-1,2-dihydro-6-quinolinesulfonamide | 511.0 | 97 | 0.178 | | |
| 474 | (M)-1-(4-bromo-5-chloro-2-methoxyphenyl)-N-3-isoxazolyl-2-oxo-1,2-dihydro-6-quinolinesulfonamide | 511.0 | 97 | | | |
| 357 | 1-(2-chloro-3'-fluoro-5-methoxy-4-biphenylyl)-7-fluoro-N-3-isoxazolyl-2-oxo-1,2-dihydro-6-quinolinesulfonamide | 544.1 | 96 | 0.04 | | |
| 545 | (P)-1-(2-chloro-3'-fluoro-5-methoxy-4-biphenylyl)-7-fluoro-N-3-isoxazolyl-2-oxo-1,2-dihydro-6-quinolinesulfonamide | 544.1 | 96 | 0.01 | | 1H NMR (400 MHz, DMSO-d6) δ = 12.02 (br. s., 1H), 8.74 (d, J = 1.76 Hz, 1H), 8.49 (d, J = 7.77 Hz, 1H), 8.21-8.30 (m, 1H), 7.66-7.71 (m, 1H), 7.54-7.63 (m, 1H), 7.42-7.49 (m, 2H), 7.28-7.37 (m, 2H), 6.79 (d, J = 9.64 Hz, 1H), 6.67 (d, J = 11.92 Hz, 1H), 6.40 (d, J = 1.76 Hz, 1H), 3.75 (s, 3H |
| 358 | (M)-1-(2-chloro-3'-fluoro-5-methoxy-4- | 544.1 | 96 | 4.665 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | biphenylyl)-7-fluoro-N-3-isoxazolyl-2-oxo-1,2-dihydro-6-quinolinesulfonamide | | | | | |
| 465 | (P)-1-(2-chloro-3'-fluoro-5-methoxy-4-biphenylyl)-2-oxo-N-4-pyrimidinyl-1,2-dihydro-6-quinolinesulfonamide | 537.0 | 2, step 1 | 0.017 | >30 | |
| 469 | (P)-1-(4'-chloro-2-fluoro-5-methoxy-3'-methyl-4-biphenylyl)-N-3-isoxazolyl-2-oxo-1,2-dihydro-6-quinolinesulfonamide | 540.0 | 65 | 0.006 | >30 | |
| 470 | (M)-1-(4'-chloro-2-fluoro-5-methoxy-3'-methyl-4-biphenylyl)-N-3-isoxazolyl-2-oxo-1,2-dihydro-6-quinolinesulfonamide | 540.0 | 65 | 1.462 | | |
| 477 | (P)-1-(3'-chloro-2,5'-difluoro-5-methoxy-4-biphenylyl)-N-3-isoxazolyl-2-oxo-1,2-dihydro-6-quinolinesulfonamide | 542.1 | 99 | 0.007 | >30 | |
| 478 | (M)-1-(3'-chloro-2,5'-difluoro-5-methoxy-4-biphenylyl)-N-3-isoxazolyl-2-oxo-1,2-dihydro-6-quinolinesulfonamide | 542.1 | 99 | 0.816 | | |
| 346 | (P)—N-3-isoxazolyl-2-oxo-1-(2-(1H-pyrazol-4-yl)-4-(trifluoromethyl)phenyl)-1,2-dihydro-6-quinolinesulfonamide | 502.1 | 90 | 0.648 | | |
| 347 | (M)—N-3-isoxazolyl-2-oxo-1-(2-(1H-pyrazol-4-yl)-4-(trifluoromethyl)phenyl)-1,2-dihydro-6-quinolinesulfonamide | 502.1 | 90 | 6.605 | | |
| 567 | 1-(2-chloro-3'-fluoro-5-methoxy-4-biphenylyl)-N-3-isoxazolyl-4-methyl-2-oxo-1,2-dihydro-6-quinolinesulfonamide | 540.1 | 91 | 0.162 | | 1H NMR (ACETONITRILE-d3) d: 8.36-8.40 (m, 1H), 8.27-8.30 (m, 1H), 7.81-7.87 (m, 1H), 7.50-7.58 (m, 1H), 7.43-7.45 (m, 1H), 7.38-7.43 (m, 1H), 7.33-7.38 (m, 1H), 7.19-7.27 (m, 2H), 6.85-6.90 (m, 1H), 6.66-6.70 (m, 1H), 6.46-6.50 (m, 1H), 3.70 (s, 3H), 2.56 (d, J = 1.2 Hz, 3H) |
| 568 | (P)-1-(3'-fluoro-5-methoxy-2-methyl-4-biphenylyl)-N-3-isoxazolyl-4-methyl-2-oxo-1,2-dihydro-6-quinolinesulfonamide | 520.2 | 91 | 0.092 | | 1H NMR (ACETONITRILE-d3) d: 8.37 (d, J = 1.8 Hz, 1H), 8.27 (d, J = 2.2 Hz, 1H), 7.82 (dd, J = 8.9, 2.2 Hz, 1H), 7.51 (td, J = 7.9, 6.1 Hz, 1H), 7.27-7.32 (m, 1H), 7.15-7.27 (m, 2H), 7.13 (s, 1H), 7.08 (s, 1H), 6.83 (d, J = 8.9 Hz, 1H), 6.67 (d, J = 1.2 Hz, 1H), 6.47 (d, J = 1.9 Hz, 1H), 3.66 (s, 3H), 2.55 (d, J = 1.2 Hz, 3H), 2.22 (s, 3H) |
| 569 | (M)-1-(3'-fluoro-5-methoxy-2-methyl-4-biphenylyl)-N-3-isoxazolyl-4-methyl-2-oxo-1,2-dihydro-6-quinolinesulfonamide | 520.2 | 91 | | | 1H NMR (ACETONITRILE-d3) d: 8.37 (d, J = 1.8 Hz, 1H), 8.27 (d, J = 2.2 Hz, 1H), 7.82 (dd, J = 8.9, 2.2 Hz, 1H), 7.51 (td, J = 7.9, 6.1 Hz, 1H), 7.27-7.32 (m, 1H), 7.15-7.27 (m, 2H), 7.13 (s, 1H), 7.08 (s, 1H), 6.83 (d, J = 8.9 Hz, 1H), 6.67 (d, J = 1.2 Hz, 1H), 6.47 (d, J = 1.9 Hz, 1H), 3.66 (s, 3H), 2.55 (d, J = 1.2 Hz, 3H), 2.22 (s, 3H) |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 570 | (P)-1-(3',5'-difluoro-5-methoxy-2-methyl-4-biphenylyl)-N-3-isoxazolyl-4-methyl-2-oxo-1,2-dihydro-6-quinolinesulfonamide | 538.2 | 91 | 0.067 | | 1H NMR (ACETONITRILE-d3) d: 8.37 (d, J = 1.8 Hz, 1H), 8.27 (d, J = 2.2 Hz, 1H), 7.82 (dd, J = 9.0, 2.2 Hz, 1H), 7.07-7.16 (m, 4H), 6.98-7.06 (m, 1H), 6.82 (d, J = 9.0 Hz, 1H), 6.67 (d, J = 1.2 Hz, 1H), 6.47 (d, J = 1.8 Hz, 1H), 3.67 (s, 3H), 2.55 (d, J = 1.3 Hz, 3H), 2.23 (s, 3H) |
| 571 | (M)-1-(3',5'-difluoro-5-methoxy-2-methyl-4-biphenylyl)-N-3-isoxazolyl-4-methyl-2-oxo-1,2-dihydro-6-quinolinesulfonamide | 538.2 | 91 | | | 1H NMR (ACETONITRILE-d3) d: 8.37 (d, J = 1.8 Hz, 1H), 8.27 (d, J = 2.2 Hz, 1H), 7.82 (dd, J = 9.0, 2.2 Hz, 1H), 7.07-7.16 (m, 4H), 6.98-7.06 (m, 1H), 6.82 (d, J = 9.0 Hz, 1H), 6.67 (d, J = 1.2 Hz, 1H), 6.47 (d, J = 1.8 Hz, 1H), 3.67 (s, 3H), 2.55 (d, J = 1.3 Hz, 3H), 2.23 (s, 3H) |
| 572 | (P)-1-(2,3'-difluoro-5-methoxy-4-biphenylyl)-N-3-isoxazolyl-4-methyl-2-oxo-1,2-dihydro-6-quinolinesulfonamide | 524.2 | 91 | 0.485 | | 1H NMR (ACETONITRILE-d3) d: 8.38 (d, J = 1.9 Hz, 1H), 8.28 (d, J = 2.2 Hz, 1H), 7.83 (dd, J = 8.9, 2.2 Hz, 1H), 7.50-7.59 (m, 2H), 7.43-7.50 (m, 1H), 7.31 (d, J = 6.8 Hz, 1H), 7.18-7.26 (m, 2H), 6.88 (d, J = 8.9 Hz, 1H), 6.68 (d, J = 1.3 Hz, 1H), 6.48 (d, J = 1.8 Hz, 1H), 3.72 (s, 3H), 2.55 (d, J = 1.2 Hz, 3H) |
| 573 | (M)-1-(2,3'-difluoro-5-methoxy-4-biphenylyl)-N-3-isoxazolyl-4-methyl-2-oxo-1,2-dihydro-6-quinolinesulfonamide | 524.2 | 91 | | | 1H NMR (ACETONITRILE-d3) d: 8.38 (d, J = 1.9 Hz, 1H), 8.28 (d, J = 2.2 Hz, 1H), 7.83 (dd, J = 8.9, 2.2 Hz, 1H), 7.50-7.59 (m, 2H), 7.43-7.50 (m, 1H), 7.31 (d, J = 6.8 Hz, 1H), 7.18-7.26 (m, 2H), 6.88 (d, J = 8.9 Hz, 1H), 6.68 (d, J = 1.3 Hz, 1H), 6.48 (d, J = 1.8 Hz, 1H), 3.72 (s, 3H), 2.55 (d, J = 1.2 Hz, 3H) |
| 349 | (M)-1-(2-chloro-3'-fluoro-5-methoxy-4-biphenylyl)-N-3-isoxazolyl-4-methyl-2-oxo-1,2-dihydro-6-quinolinesulfonamide | 540.1 | 91 | 10.56 | | |
| 348 | (P)-1-(2-chloro-3'-fluoro-5-methoxy-4-biphenylyl)-N-3-isoxazolyl-4-methyl-2-oxo-1,2-dihydro-6-quinolinesulfonamide | 540.1 | 91 | 0.159 | | |
| 574 | (P)-1-(4-bromo-2-methoxyphenyl)-N-3-isoxazolyl-2-oxo-1,2-dihydro-6-quinolinesulfonamide | 477.0 | 92 | 0.772 | | 1H NMR (ACETONITRILE-d3) d: 8.37 (d, J = 1.9 Hz, 1H), 8.23 (d, J = 2.3 Hz, 1H), 7.97 (d, J = 9.6 Hz, 1H), 7.78 (dd, J = 8.9, 2.2 Hz, 1H), 7.43 (d, J = 2.1 Hz, 1H), 7.34 (dd, J = 8.3, 2.1 Hz, 1H), 7.16 (d, J = 8.3 Hz, 1H), 6.71-6.79 (m, 2H), 6.45 (d, J = 1.8 Hz, 1H), 3.69 (s, 3H) |
| 575 | (M)-1-(3'-fluoro-3-methoxy-4'-methyl-4-biphenylyl)-N-3-isoxazolyl-2-oxo-1,2-dihydro-6-quinolinesulfonamide | 506.1 | 92 | | | 1H NMR (ACETONITRILE-d3) d: 8.37 (d, J = 1.8 Hz, 1H), 8.24 (d, J = 2.2 Hz, 1H), 7.99 (d, J = 9.5 Hz, 1H), 7.79 (dd, J = 9.0, 2.2 Hz, 1H), 7.44-7.52 (m, 3H), 7.35-7.44 (m, 2H), 7.30 (d, J = 8.0 Hz, 1H), 6.73-6.83 (m, 2H), 6.45 (d, J = 1.9 Hz, 1H), 3.77 (s, 3H), 2.34 (d, J = 1.7 Hz, 3H) |
| 576 | (P)-1-(3'-fluoro-3-methoxy-4'-methyl-4-biphenylyl)-N-3-isoxazolyl-2-oxo-1,2-dihydro-6-quinolinesulfonamide | 506.1 | 92 | 0.04 | | 1H NMR (ACETONITRILE-d3) d: 8.37 (d, J = 1.8 Hz, 1H), 8.24 (d, J = 2.2 Hz, 1H), 7.99 (d, J = 9.5 Hz, 1H), 7.79 (dd, J = 9.0, 2.2 Hz, 1H), 7.44-7.52 (m, 3H), 7.35-7.44 (m, 2H), 7.30 (d, J = 8.0 Hz, |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | | | | | | 1H), 6.73-6.83 (m, 2H), 6.45 (d, J = 1.9 Hz, 1H), 3.77 (s, 3H), 2.34 (d, J = 1.7 Hz, 3H) |
| 577 | (M)-1-(3'-chloro-4'-fluoro-3-methoxy-4-biphenylyl)-N-3-isoxazolyl-2-oxo-1,2-dihydro-6-quinolinesulfonamide | 526.1 | 92 | 7.135 | | 1H NMR (ACETONITRILE-d3) d: 8.37 (d, J = 1.8 Hz, 1H), 8.25 (d, J = 2.2 Hz, 1H), 7.99 (d, J = 9.6 Hz, 1H), 7.91 (dd, J = 7.1, 2.3 Hz, 1H), 7.80 (dd, J = 9.0, 2.2 Hz, 1H), 7.72 (ddd, J = 8.6, 4.6, 2.3 Hz, 1H), 7.35-7.45 (m, 3H), 7.28-7.34 (m, 1H), 6.78 (dd, J = 11.5, 9.4 Hz, 2H), 6.45 (d, J = 1.9 Hz, 1H), 3.77 (s, 3H) |
| 578 | (P)-1-(3'-chloro-4'-fluoro-3-methoxy-4-biphenylyl)-N-3-isoxazolyl-2-oxo-1,2-dihydro-6-quinolinesulfonamide | 526.1 | 92 | 0.016 | | 1H NMR (ACETONITRILE-d3) d: 8.37 (d, J = 1.8 Hz, 1H), 8.25 (d, J = 2.2 Hz, 1H), 7.99 (d, J = 9.6 Hz, 1H), 7.91 (dd, J = 7.1, 2.3 Hz, 1H), 7.80 (dd, J = 9.0, 2.2 Hz, 1H), 7.72 (ddd, J = 8.6, 4.6, 2.3 Hz, 1H), 7.35-7.45 (m, 3H), 7.28-7.34 (m, 1H), 6.78 (dd, J = 11.5, 9.4 Hz, 2H), 6.45 (d, J = 1.9 Hz, 1H), 3.77 (s, 3H) |
| 579 | (M)-1-(4'-chloro-3'-fluoro-3-methoxy-4-biphenylyl)-N-3-isoxazolyl-2-oxo-1,2-dihydro-6-quinolinesulfonamide | 526.1 | 92 | 4.31 | | 1H NMR (ACETONITRILE-d3) d: 8.37 (d, J = 1.8 Hz, 1H), 8.25 (d, J = 2.2 Hz, 1H), 7.99 (d, J = 9.7 Hz, 1H), 7.79 (dd, J = 9.0, 2.2 Hz, 1H), 7.68 (dd, J = 11.0, 1.9 Hz, 1H), 7.56-7.65 (m, 2H), 7.40-7.48 (m, 2H), 7.33 (d, J = 8.0 Hz, 1H), 6.78 (dd, J = 11.7, 9.3 Hz, 2H), 6.45 (d, J = 1.8 Hz, 1H), 3.78 (s, 3H) |
| 580 | (P)-1-(4'-chloro-3'-fluoro-3-methoxy-4-biphenylyl)-N-3-isoxazolyl-2-oxo-1,2-dihydro-6-quinolinesulfonamide | 526.1 | 92 | 0.011 | | 1H NMR (ACETONITRILE-d3) d: 8.37 (d, J = 1.8 Hz, 1H), 8.25 (d, J = 2.2 Hz, 1H), 7.99 (d, J = 9.7 Hz, 1H), 7.79 (dd, J = 9.0, 2.2 Hz, 1H), 7.68 (dd, J = 11.0, 1.9 Hz, 1H), 7.56-7.65 (m, 2H), 7.40-7.48 (m, 2H), 7.33 (d, J = 8.0 Hz, 1H), 6.78 (dd, J = 11.7, 9.3 Hz, 2H), 6.45 (d, J = 1.8 Hz, 1H), 3.78 (s, 3H) |
| 581 | (P)-1-(4-(5-fluoro-2-methoxy-3-pyridinyl)-2-methoxyphenyl)-N-3-isoxazolyl-2-oxo-1,2-dihydro-6-quinolinesulfonamide | 523.2 | 92 | 0.102 | >10 | 1H NMR (ACETONITRILE-d3) d: 8.37 (d, J = 1.8 Hz, 1H), 8.25 (d, J = 2.0 Hz, 1H), 8.09 (d, J = 3.0 Hz, 1H), 7.99 (d, J = 9.3 Hz, 1H), 7.82 (dd, J = 9.0, 2.2 Hz, 1H), 7.72 (dd, J = 8.7, 3.0 Hz, 1H), 7.47 (d, J = 1.9 Hz, 1H), 7.37-7.42 (m, 1H), 7.29 (d, J = 8.1 Hz, 1H), 6.74-6.81 (m, 2H), 6.45 (d, J = 1.9 Hz, 1H), 3.97 (s, 3H), 3.73 (s, 3H) |
| 582 | (M)-1-(4-(5-fluoro-2-methoxy-3-pyridinyl)-2-methoxyphenyl)-N-3-isoxazolyl-2-oxo-1,2-dihydro-6-quinolinesulfonamide | 523.2 | 92 | | | 1H NMR (ACETONITRILE-d3) d: 8.37 (d, J = 1.8 Hz, 1H), 8.25 (d, J = 2.0 Hz, 1H), 8.09 (d, J = 3.0 Hz, 1H), 7.99 (d, J = 9.3 Hz, 1H), 7.82 (dd, J = 9.0, 2.2 Hz, 1H), 7.72 (dd, J = 8.7, 3.0 Hz, 1H), 7.47 (d, J = 1.9 Hz, 1H), 7.37-7.42 (m, 1H), 7.29 (d, J = 8.1 Hz, 1H), 6.74-6.81 (m, 2H), 6.45 (d, J = 1.9 Hz, 1H), 3.97 (s, 3H), 3.73 (s, 3H) |
| 350 | (P)-1-(3'-chloro-3-methoxy-4-biphenylyl)-N-3-isoxazolyl-2-oxo-1,2-dihydro-6-quinolinesulfonamide | 508.1 | 92 | 0.026 | | |
| 351 | (M)-1-(3'-chloro-3-methoxy-4-biphenylyl)-N-3-isoxazolyl-2-oxo-1,2-dihydro-6-quinolinesulfonamide | 508.1 | 92 | 5.516 | | |

TABLE 2-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| 583 | (M)—N-3-isoxazolyl-1-(3-methoxy-3'-methyl-4-biphenylyl)-2-oxo-1,2-dihydro-6-quinolinesulfonamide | 488.1 | 92 | >10 | | 1H NMR (ACETONITRILE-d3) d: 8.37 (d, J = 1.9 Hz, 1H), 8.25 (d, J = 2.2 Hz, 1H), 7.99 (d, J = 9.6 Hz, 1H), 7.80 (dd, J = 9.0, 2.2 Hz, 1H), 7.60 (s, 1H), 7.55 (d, J = 7.7 Hz, 1H), 7.45 (d, J = 1.9 Hz, 1H), 7.36-7.43 (m, 2H), 7.24-7.31 (m, 2H), 6.79 (dd, J = 18.6, 9.4 Hz, 2H), 6.45 (d, J = 1.9 Hz, 1H), 3.77 (s, 3H), 2.44 (s, 3H) |
| 584 | (P)—N-3-isoxazolyl-1-(3-methoxy-3'-methyl-4-biphenylyl)-2-oxo-1,2-dihydro-6-quinolinesulfonamide | 488.1 | 92 | 0.013 | | 1H NMR (ACETONITRILE-d3) d: 8.37 (d, J = 1.9 Hz, 1H), 8.25 (d, J = 2.2 Hz, 1H), 7.99 (d, J = 9.6 Hz, 1H), 7.80 (dd, J = 9.0, 2.2 Hz, 1H), 7.60 (s, 1H), 7.55 (d, J = 7.7 Hz, 1H), 7.45 (d, J = 1.9 Hz, 1H), 7.36-7.43 (m, 2H), 7.24-7.31 (m, 2H), 6.79 (dd, J = 18.6, 9.4 Hz, 2H), 6.45 (d, J = 1.9 Hz, 1H), 3.77 (s, 3H), 2.44 (s, 3H) |
| 585 | (P)-1-(3'-chloro-3-methoxy-5'-methyl-4-biphenylyl)-N-3-isoxazolyl-2-oxo-1,2-dihydro-6-quinolinesulfonamide | 522.2 | 92 | 0.008 | | 1H NMR (ACETONITRILE-d3) d: 8.20-8.28 (m, 2H), 7.98 (d, J = 9.5 Hz, 1H), 7.79 (dd, J = 9.0, 2.1 Hz, 1H), 7.57-7.62 (m, 1H), 7.52-7.56 (m, 1H), 7.37-7.46 (m, 2H), 7.26-7.33 (m, 2H), 6.74 (dd, J = 9.3, 4.0 Hz, 2H), 6.37 (d, J = 1.8 Hz, 1H), 3.77 (s, 3H), 2.43 (d, J = 0.6 Hz, 3H) |
| 586 | (M)-1-(3'-chloro-3-methoxy-5'-methyl-4-biphenylyl)-N-3-isoxazolyl-2-oxo-1,2-dihydro-6-quinolinesulfonamide | 522.2 | 92 | >1.0 | | 1H NMR (ACETONITRILE-d3) d: 8.20-8.28 (m, 2H), 7.98 (d, J = 9.5 Hz, 1H), 7.79 (dd, J = 9.0, 2.1 Hz, 1H), 7.57-7.62 (m, 1H), 7.52-7.56 (m, 1H), 7.37-7.46 (m, 2H), 7.26-7.33 (m, 2H), 6.74 (dd, J = 9.3, 4.0 Hz, 2H), 6.37 (d, J = 1.8 Hz, 1H), 3.77 (s, 3H), 2.43 (d, J = 0.6 Hz, 3H) |
| 587 | (P)-1-(3'-chloro-3-methoxy-4'-methyl-4-biphenylyl)-N-3-isoxazolyl-2-oxo-1,2-dihydro-6-quinolinesulfonamide | 522.2 | 92 | 0.02 | | 1H NMR (ACETONITRILE-d3) d: 8.36 (s, 1H), 8.24 (d, J = 1.9 Hz, 1H), 7.98 (d, J = 9.6 Hz, 1H), 7.75-7.83 (m, 2H), 7.61 (dd, J = 7.8, 2.0 Hz, 1H), 7.33-7.47 (m, 3H), 7.30 (d, J = 8.0 Hz, 1H), 6.78 (dd, J = 13.2, 9.4 Hz, 2H), 6.44 (s, 1H), 3.77 (s, 3H), 2.44 (s, 3H) |
| 588 | (M)-1-(3'-chloro-3-methoxy-4'-methyl-4-biphenylyl)-N-3-isoxazolyl-2-oxo-1,2-dihydro-6-quinolinesulfonamide | 522.2 | 92 | 1.021 | | 1H NMR (ACETONITRILE-d3) d: 8.36 (s, 1H), 8.24 (d, J = 1.9 Hz, 1H), 7.98 (d, J = 9.6 Hz, 1H), 7.75-7.83 (m, 2H), 7.61 (dd, J = 7.8, 2.0 Hz, 1H), 7.33-7.47 (m, 3H), 7.30 (d, J = 8.0 Hz, 1H), 6.78 (dd, J = 13.2, 9.4 Hz, 2H), 6.44 (s, 1H), 3.77 (s, 3H), 2.44 (s, 3H) |
| 341 | 1-(5-chloro-6-(3-fluorophenyl)-2-methoxy-3-pyridinyl)-N-3-isoxazolyl-2-oxo-1,2-dihydro-6-quinolinesulfonamide | 527.1 | 84 | 0.168 | | |
| 447 | 1-(5-chloro-6-(3,5-difluorophenyl)-2-methoxy-3-pyridinyl)-N-3-isoxazolyl-2-oxo-1,2-dihydro-6-quinolinesulfonamide | 545.0 | 84 | 0.059 | | |
| 448 | 1-(5-chloro-6-(4-chloro-3-methylphenyl)-2-methoxy-3-pyridinyl)-N-3-isoxazolyl-2-oxo-1,2-dihydro-6-quinolinesulfonamide | 559.0 | 84 | 0.115 | | |
| 449 | 1-(5-chloro-6-(3-chloro-5-fluorophenyl)-2- | 563.0 | 84 | 0.085 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | methoxy-3-pyridinyl)-N-3-isoxazolyl-2-oxo-1,2-dihydro-6-quinolinesulfonamide | | | | | |
| 342 | 1-(5-chloro-6-(3,3-difluoro-1-azetidinyl)-2-methoxy-3-pyridinyl)-N-3-isoxazolyl-2-oxo-1,2-dihydro-6-quinolinesulfonamide | 524.0 | 85 | 1.642 | | |
| 387 | 1-(5-(cyanomethoxy)-2,3'-difluoro-4-biphenylyl)-N-3-isoxazolyl-2-oxo-1,2-dihydro-6-quinolinesulfonamide | 535.2 | 120 | 0.089 | | |
| 388 | (P)-1-(5-ethoxy-2,3'-difluoro-4-biphenylyl)-N-3-isoxazolyl-2-oxo-1,2-dihydro-6-quinolinesulfonamide | 524.1 | 121 | 0.048 | | |
| 389 | (M)-1-(5-ethoxy-2,3'-difluoro-4-biphenylyl)-N-3-isoxazolyl-2-oxo-1,2-dihydro-6-quinolinesulfonamide | 524.1 | 121 | 0.239 | | |
| 390 | (P)-1-(2,3'-difluoro-5-methyl-4-biphenylyl)-N-3-isoxazolyl-2-oxo-1,2-dihydro-6-quinolinesulfonamide | 494.1 | 122 | 0.1 | | |
| 391 | (M)-1-(2,3'-difluoro-5-methyl-4-biphenylyl)-N-3-isoxazolyl-2-oxo-1,2-dihydro-6-quinolinesulfonamide | 494.1 | 122 | | | |
| 363 | (P)—N-3-isoxazolyl-2-oxo-1-(2,3',5'-trifluoro-5-methoxy-4-biphenylyl)-1,2-dihydro-6-quinolinesulfonamide | 528.0 | 102 | 0.017 | | |
| 364 | (M)—N-3-isoxazolyl-2-oxo-1-(2,3',5'-trifluoro-5-methoxy-4-biphenylyl)-1,2-dihydro-6-quinolinesulfonamide | 528.0 | 102 | 5.809 | | |
| 476 | (M)-1-(3'-chloro-2-fluoro-5-methoxy-4-biphenylyl)-N-3-isoxazolyl-2-oxo-1,2-dihydro-6-quinolinesulfonamide | 524.1 | 99 | 2.288 | | |
| 365 | (P)-1-(3'-chloro-2,4'-difluoro-5-methoxy-4-biphenylyl)-N-3-isoxazolyl-2-oxo-1,2-dihydro-6-quinolinesulfonamide | 544.0 | 103 | 0.009 | | |
| 366 | (M)-1-(3'-chloro-2,4'-difluoro-5-methoxy-4-biphenylyl)-N-3-isoxazolyl-2-oxo-1,2-dihydro-6-quinolinesulfonamide | 544.0 | 103 | 1.255 | | |
| 367 | (P)-1-(2,4'-dichloro-5-methoxy-3'-methyl-4-biphenylyl)-2-oxo-N-4-pyrimidinyl-1,2-dihydro-6-quinolinesulfonamide | 567.0 | 104 | 0.003 | | |
| 368 | (M)-1-(2,4'-dichloro-5-methoxy-3'-methyl-4-biphenylyl)-2-oxo-N-4-pyrimidinyl-1,2-dihydro-6-quinolinesulfonamide | 567.0 | 104 | 0.677 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 369 | (P)-1-(3-methoxy-3'-(trifluoromethyl)-4-biphenylyl)-2-oxo-N-3-pyridazinyl-1,2-dihydro-6-quinolinesulfonamide | 552.9 | 105 | 0.016 | | |
| 370 | (M)-1-(3-methoxy-3'-(trifluoromethyl)-4-biphenylyl)-2-oxo-N-3-pyridazinyl-1,2-dihydro-6-quinolinesulfonamide | 552.9 | 105 | 2.428 | | |
| 480 | (P)-1-(3'-chloro-5'-fluoro-3-methoxy-4-biphenylyl)-2-oxo-N-3-pyridazinyl-1,2-dihydro-6-quinolinesulfonamide | 537.0 | 105 | 0.008 | | |
| 481 | (M)-1-(3'-chloro-5'-fluoro-3-methoxy-4-biphenylyl)-2-oxo-N-3-pyridazinyl-1,2-dihydro-6-quinolinesulfonamide | 537.0 | 105 | 3.074 | | |
| 371 | (M)-1-(4'-chloro-3-methoxy-3'-methyl-4-biphenylyl)-2-oxo-N-3-pyridazinyl-1,2-dihydro-6-quinolinesulfonamide | 532.8 | 106 | 4.364 | | |
| 372 | (P)-1-(4'-chloro-3-methoxy-3'-methyl-4-biphenylyl)-2-oxo-N-3-pyridazinyl-1,2-dihydro-6-quinolinesulfonamide | 532.8 | 106 | 0.029 | | |
| 404 | 1-(5-fluoro-2-methoxy-4-(3-pyridinyl)phenyl)-N-3-isoxazolyl-2-oxo-1,2-dihydro-6-quinolinesulfonamide | 493.2 | 133 | 4.296 | | |
| 498 | (P)-1-(3'-cyano-2-fluoro-5-methoxy-4-biphenylyl)-N-3-isoxazolyl-2-oxo-1,2-dihydro-6-quinolinesulfonamide | 517.1 | 133 | 0.034 | | |
| 499 | (M)-1-(3'-cyano-2-fluoro-5-methoxy-4-biphenylyl)-N-3-isoxazolyl-2-oxo-1,2-dihydro-6-quinolinesulfonamide | 517.1 | 133 | 24.85 | | |
| 500 | 1-(5-fluoro-2-methoxy-4-(6-methyl-3-pyridinyl)phenyl)-N-3-isoxazolyl-2-oxo-1,2-dihydro-6-quinolinesulfonamide | 507.2 | 133 | 2.84 | | |
| 501 | (P)-1-(3'-chloro-2-fluoro-5,5'-dimethoxy-4-biphenylyl)-N-3-isoxazolyl-2-oxo-1,2-dihydro-6-quinolinesulfonamide | 555.9 | 133 | 0.004 | | |
| 502 | (M)-1-(3'-chloro-2-fluoro-5,5'-dimethoxy-4-biphenylyl)-N-3-isoxazolyl-2-oxo-1,2-dihydro-6-quinolinesulfonamide | 555.9 | 133 | 1.229 | | |
| 405 | 1-(5-fluoro-2-methoxy-4-(1-methyl-1H-pyrazol-4-yl)phenyl)-N-3-isoxazolyl-2-oxo-1,2-dihydro-6-quinolinesulfonamide | 496.1 | 134 | 14.6 | | |
| 503 | (M)-1-(4'-chloro-2,3'-difluoro-5-methoxy-4-biphenylyl)-N-3- | 544.1 | 133 | 1.096 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | isoxazolyl-2-oxo-1,2-dihydro-6-quinolinesulfonamide | | | | | |
| 504 | (P)-1-(4'-chloro-2,3'-difluoro-5-methoxy-4-biphenylyl)-N-3-isoxazolyl-2-oxo-1,2-dihydro-6-quinolinesulfonamide | 544.1 | 133 | 0.008 | | |
| 505 | 1-(5-fluoro-2-methoxy-4-(4-pyridinyl)phenyl)-N-3-isoxazolyl-2-oxo-1,2-dihydro-6-quinolinesulfonamide | 493.0 | 133 | 1.8 | | |
| 406 | 1-(4-(3,3-difluoro-1-azetidinyl)-5-fluoro-2-methoxyphenyl)-N-3-isoxazolyl-2-oxo-1,2-dihydro-6-quinolinesulfonamide | 507.1 | 135 | 1.004 | | |
| 407 | 1-(4-(5-chloro-3-pyridinyl)-5-fluoro-2-methoxyphenyl)-N-3-isoxazolyl-2-oxo-1,2-dihydro-6-quinolinesulfonamide | 527.1 | 136 | 0.158 | | |
| 506 | (P)-1-(3'-chloro-2-fluoro-5-methoxy-5'-methyl-4-biphenylyl)-N-3-isoxazolyl-2-oxo-1,2-dihydro-6-quinolinesulfonamide | 540.0 | 133 | 0.008 | | |
| 507 | (M)-1-(3'-chloro-2-fluoro-5-methoxy-5'-methyl-4-biphenylyl)-N-3-isoxazolyl-2-oxo-1,2-dihydro-6-quinolinesulfonamide | 540.0 | 133 | 1.011 | | |
| 508 | (P)-1-(4'-chloro-3'-cyano-2-fluoro-5-methoxy-4-biphenylyl)-N-3-isoxazolyl-2-oxo-1,2-dihydro-6-quinolinesulfonamide | 550.8 | 133 | 0.007 | | |
| 509 | (M)-1-(4'-chloro-3'-cyano-2-fluoro-5-methoxy-4-biphenylyl)-N-3-isoxazolyl-2-oxo-1,2-dihydro-6-quinolinesulfonamide | 550.8 | 133 | 1.675 | | |
| 510 | (P)-1-(2,3'-difluoro-5-methoxy-4'-methyl-4-biphenylyl)-N-3-isoxazolyl-2-oxo-1,2-dihydro-6-quinolinesulfonamide | 523.8 | 133 | 0.017 | | |
| 511 | (M)-1-(2,3'-difluoro-5-methoxy-4'-methyl-4-biphenylyl)-N-3-isoxazolyl-2-oxo-1,2-dihydro-6-quinolinesulfonamide | 523.8 | 133 | 8.617 | | |
| 512 | (P)-1-(2,4'-difluoro-5-methoxy-3'-methyl-4-biphenylyl)-N-3-isoxazolyl-2-oxo-1,2-dihydro-6-quinolinesulfonamide | 524.1 | 133 | 0.011 | | |
| 513 | (M)-1-(2,4'-difluoro-5-methoxy-3'-methyl-4-biphenylyl)-N-3-isoxazolyl-2-oxo-1,2-dihydro-6-quinolinesulfonamide | 524.1 | 133 | 0.944 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 514 | (P)—N-3-isoxazolyl-2-oxo-1-(2,2',3',5'-tetrafluoro-5-methoxy-4-biphenylyl)-1,2-dihydro-6-quinolinesulfonamide | 546.0 | 133 | 0.018 | | |
| 515 | (M)—N-3-isoxazolyl-2-oxo-1-(2,2',3',5'-tetrafluoro-5-methoxy-4-biphenylyl)-1,2-dihydro-6-quinolinesulfonamide | 546.0 | 133 | 5.16 | | |
| 531 | (P)-1-(5-fluoro-4-(5-fluoro-2-methoxy-3-pyridinyl)-2-methoxyphenyl)-N-3-isoxazolyl-2-oxo-1,2-dihydro-6-quinolinesulfonamide | 541.1 | 136 | 0.342 | | |
| 532 | 1-(4-(5-chloro-6-methyl-3-pyridinyl)-5-fluoro-2-methoxyphenyl)-N-3-isoxazolyl-2-oxo-1,2-dihydro-6-quinolinesulfonamide | 541.1 | 136 | 0.282 | | |
| 530 | 1-(5-fluoro-2-methoxy-4-(3-(trifluoromethyl)-1-azetidinyl)phenyl)-N-3-isoxazolyl-2-oxo-1,2-dihydro-6-quinolinesulfonamide | 539.1 | 135 | 0.495 | | |
| 516 | (M)—N-3-isoxazolyl-2-oxo-1-(2,2',4',5'-tetrafluoro-5-methoxy-4-biphenylyl)-1,2-dihydro-6-quinolinesulfonamide | 546.9 | 133 | >10 | | |
| 517 | (P)—N-3-isoxazolyl-2-oxo-1-(2,2',4',5'-tetrafluoro-5-methoxy-4-biphenylyl)-1,2-dihydro-6-quinolinesulfonamide | 546.9 | 133 | 0.021 | | |
| 518 | (M)-1-(3'-chloro-5'-cyano-2-fluoro-5-methoxy-4-biphenylyl)-N-3-isoxazolyl-2-oxo-1,2-dihydro-6-quinolinesulfonamide | 551.1 | 133 | 2.005 | | |
| 519 | (P)-1-(3'-chloro-5'-cyano-2-fluoro-5-methoxy-4-biphenylyl)-N-3-isoxazolyl-2-oxo-1,2-dihydro-6-quinolinesulfonamide | 551.1 | 133 | 0.016 | | |
| 520 | (P)-1-(3'-chloro-4'-cyano-2-fluoro-5-methoxy-4-biphenylyl)-N-3-isoxazolyl-2-oxo-1,2-dihydro-6-quinolinesulfonamide | 551.2 | 133 | 0.026 | | |
| 521 | (M)-1-(3'-chloro-4'-cyano-2-fluoro-5-methoxy-4-biphenylyl)-N-3-isoxazolyl-2-oxo-1,2-dihydro-6-quinolinesulfonamide | 551.2 | 133 | >10 | | |
| 410 | (P)-1-(4'-cyano-2-fluoro-5-methoxy-3'-methyl-4-biphenylyl)-N-3-isoxazolyl-2-oxo-1,2-dihydro-6-quinolinesulfonamide | 531.2 | 137 | 0.091 | | |

TABLE 2-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 411 | 1-(5-fluoro-2-methoxy-4-(1-methyl-1H-imidazol-4-yl)phenyl)-N-3-isoxazolyl-2-oxo-1,2-dihydro-6-quinolinesulfonamide | 496.1 | 138 | | | |
| 522 | (P)-1-(2-fluoro-5-methoxy-3'-methyl-4-biphenylyl)-N-3-isoxazolyl-2-oxo-1,2-dihydro-6-quinolinesulfonamide | 506.1 | 133 | 0.009 | | |
| 523 | (M)-1-(2-fluoro-5-methoxy-3'-methyl-4-biphenylyl)-N-3-isoxazolyl-2-oxo-1,2-dihydro-6-quinolinesulfonamide | 506.1 | 133 | 4.738 | | |
| 524 | (P)-1-(3'-cyano-2-fluoro-5-methoxy-4'-methyl-4-biphenylyl)-N-3-isoxazolyl-2-oxo-1,2-dihydro-6-quinolinesulfonamide | 531.0 | 133 | 0.025 | | |
| 525 | (M)-1-(3'-cyano-2-fluoro-5-methoxy-4'-methyl-4-biphenylyl)-N-3-isoxazolyl-2-oxo-1,2-dihydro-6-quinolinesulfonamide | 531.0 | 133 | 4.844 | | |
| 408 | (M)-1-(4-(5-chloro-3-pyridinyl)-5-fluoro-2-methoxyphenyl)-N-3-isoxazolyl-2-oxo-1,2-dihydro-6-quinolinesulfonamide | 527.2 | 136 | 8.038 | | |
| 409 | (P)-1-(4-(5-chloro-3-pyridinyl)-5-fluoro-2-methoxyphenyl)-N-3-isoxazolyl-2-oxo-1,2-dihydro-6-quinolinesulfonamide | 527.2 | 136 | 0.06 | | |
| 526 | (P)-1-(3'-cyano-2-fluoro-5-methoxy-5'-methyl-4-biphenylyl)-N-3-isoxazolyl-2-oxo-1,2-dihydro-6-quinolinesulfonamide | 531.2 | 133 | 0.031 | | |
| 527 | (M)-1-(3'-cyano-2-fluoro-5-methoxy-5'-methyl-4-biphenylyl)-N-3-isoxazolyl-2-oxo-1,2-dihydro-6-quinolinesulfonamide | 531.2 | 133 | | | |
| 528 | (P)-1-(3'-chloro-2-fluoro-5-methoxy-4'-methyl-4-biphenylyl)-N-3-isoxazolyl-2-oxo-1,2-dihydro-6-quinolinesulfonamide | 540.2 | 133 | 0.007 | | |
| 529 | (M)-1-(3'-chloro-2-fluoro-5-methoxy-4'-methyl-4-biphenylyl)-N-3-isoxazolyl-2-oxo-1,2-dihydro-6-quinolinesulfonamide | 540.2 | 133 | 3.153 | | |
| 412 | (P)-1-(4'-chloro-2-fluoro-2',5-dimethoxy-4-biphenylyl)-N-3-isoxazolyl-2-oxo-1,2-dihydro-6-quinolinesulfonamide | 556.1 | 139 | 0.016 | | |
| 413 | (M)-1-(4'-chloro-2-fluoro-5-methoxy-3'- | 568.2 | 140 | 5.892 | | |

TABLE 2-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | methyl-4-biphenylyl)-N-3-isoxazolyl-3-methoxy-2-oxo-1,2-dihydro-6-quinolinesulfonamide | | | | | |
| 414 | (P)-1-(4'-chloro-2-fluoro-5-methoxy-3'-methyl-4-biphenylyl)-N-3-isoxazolyl-3-methoxy-2-oxo-1,2-dihydro-6-quinolinesulfonamide | 568.2 | 140 | | 0.013 | |

Example 589

(Method 141): (P)-2-oxo-N-3-pyridazinyl-1-(2,3',4'-trifluoro-5-methoxy-4-biphenylyl)-1,2-dihydro-6-quinolinesulfonamide

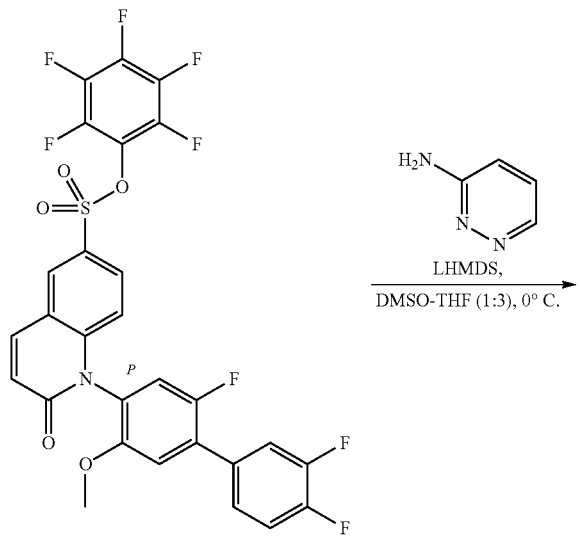

A RBF was charged with (P)-perfluorophenyl 2-oxo-1-(2,3',4'-trifluoro-5-methoxy-[1,1'-biphenyl]-4-yl)-1,2-dihydroquinoline-6-sulfonate (151.1 mg, 0.241 mmol) and pyridazin-3-amine (34.4 mg, 0.361 mmol). DMSO (602 µl) was added to give a solution which was then diluted with THF (1806 µl). The flask was cooled in an ice-water bath for 10 min, then lithium bis(trimethylsilyl)amide (1M in THF) (530 µl, 0.530 mmol) was added dropwise. After 15 min total, the mixture was diluted with 1N aq. HCl and EtOAc. The layers were separated, and the aq. layer was extracted with EtOAc (1×). The combined organic extracts were dried over sodium sulfate, filtered, and concentrated. The residue was taken up in MeOH and filtered through a 0.2 micron filter. The resulting solution was purified by reverse-phase HPLC (25-70% CH$_3$CN/H$_2$O with 0.1% TFA). Fractions containing the desired product were combined and lyophilized to give (P)-2-oxo-N-3-pyridazinyl-1-(2,3',4'-trifluoro-5-methoxy-4-biphenylyl)-1,2-dihydro-6-quinolinesulfonamide (55 mg, 0.102 mmol, 42.4% yield) as a white solid. $^1$H NMR (400 MHz, DMSO-d$_6$) δ=14.5 (br. s, 1H), 8.52-8.06 (m, 3H), 8.01-7.76 (m, 3H), 7.76-7.30 (m, 5H), 6.91-6.62 (m, 2H), 3.73 (br. s., 3H). m/z (ESI) 539.0 (M+H)$^+$.

Example 590

(Method 142): 1-(4-chloro-2-(1-methyl-1,2,3,6-tetrahydro-4-pyridinyl)phenyl)-N-3-isoxazolyl-2-oxo-1,2-dihydro-6-quinolinesulfonamide

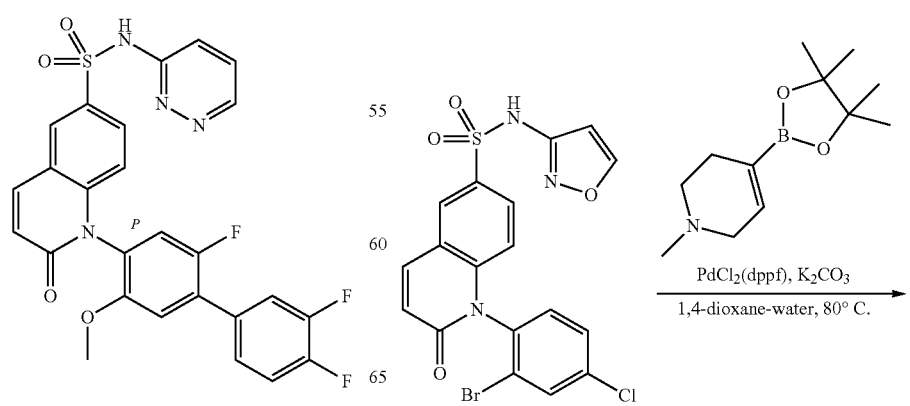

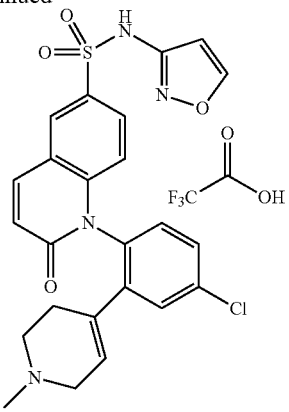

A vial was charged with 1-(2-bromo-4-chlorophenyl)-N-(isoxazol-3-yl)-2-oxo-1,2-dihydroquinoline-6-sulfonamide (147.5 mg, 0.233 mmol), 1-methyl-4-(4,4,5,5-tetramethyl-1,3,2-dioxaborolan-2-yl)-1,2,3,6-tetrahydropyridine (104 mg, 0.466 mmol), $PdCl_2(dppf)\cdot CH_2Cl_2$ (19.04 mg, 0.023 mmol), and potassium carbonate (161 mg, 1.166 mmol). The vial was flushed with Ar (g), then 1,4-dioxane (874 µl) and water (291 µl) were added in sequence. The vial was sealed and placed in an 80° C. heating bath for 30 min. The mixture was extracted with EtOAc (with a small amount of MeOH) (4×), and the combined organic extracts were concentrated. The residue was taken up in MeOH, and the resulting mixture was filtered through a 0.2 micron filter. The filtrate was purified by reverse-phase HPLC (5-50% $CH_3CN/H_2O$ with 0.1% TFA). Fractions containing product were combined and lyophilized to give 1-(4-chloro-2-(1-methyl-1,2,3,6-tetrahydro-4-pyridinyl)phenyl)-N-3-isoxazolyl-2-oxo-1,2-dihydro-6-quinolinesulfonamide 2,2,2-trifluoroacetate (105 mg, 0.172 mmol, 73.7% yield) as an off-white solid. $^1$H NMR (400 MHz, DMSO-d$_6$) δ=11.83-11.21 (m, 1H), 10.04-9.51 (m, 1H), 8.67 (d, J=1.8 Hz, 1H), 8.39-8.26 (m, 1H), 8.24-8.11 (m, 1H), 7.84-7.65 (m, 1H), 7.56 (s, 2H), 7.37 (s, 1H), 6.81-6.64 (m, 2H), 6.38 (d, J=1.8 Hz, 1H), 5.45-5.30 (m, 1H), 3.71-3.49 (m, 1H), 3.41-3.13 (m, 2H), 3.00-2.72 (m, 1H), 2.64-2.46 (m, 3H), 2.35-2.08 (m, 2H). m/z (ESI) 496.9 (M+H)$^+$.

Example 591

(Method 143): N-3-isoxazolyl-2-oxo-1-(3'-(trifluoromethyl)-4-biphenylyl)-1,2-dihydro-6-quinolinesulfonamide

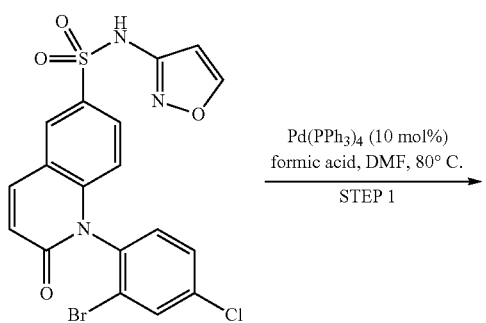

Step 1: 1-(4-chlorophenyl)-N-(isoxazol-3-yl)-2-oxo-1,2-dihydroquinoline-6-sulfonamide A vial was charged with 1-(2-bromo-4-chlorophenyl)-N-(isoxazol-3-yl)-2-oxo-1,2-dihydroquinoline-6-sulfonamide (202.5 mg, 0.320 mmol) and tetrakis(triphenylphosphine)palladium(0) (37.0 mg, 0.032 mmol). The vial was flushed with Ar (g), then DMF (1.6 mL) and formic acid (123 µl, 3.20 mmol) were added. The vial was sealed and placed in an 80° C. heating bath for 27 hrs. The mixture was cooled to rt and was loaded onto a 4-g silica gel loading column with the aid of MeOH/DCM, and the column was dried was dried under vacuum. The column was then eluted onto a 25-g SNAP Ultra column with 0-50% of a 3:1 EtOAc/EtOH in heptane with 10% DCM to give 166 mg of 1-(4-chlorophenyl)-N-(isoxazol-3-yl)-2-oxo-1,2-dihydroquinoline-6-sulfonamide contaminated with some DMF and starting material. m/z (ESI) 402.2 (M+H)$^+$.

Step 2: N-3-isoxazolyl-2-oxo-1-(3'-(trifluoromethyl)-4-biphenylyl)-1,2-dihydro-6-quinolinesulfonamide A vial was charged with (3-(trifluoromethyl)phenyl)boronic acid (188 mg, 0.991 mmol), S-Phos Precatalyst (25.1 mg, 0.033 mmol), and potassium phosphate (281 mg, 1.322 mmol). The vial was flushed with Ar (g), then a solution of 1-(4-chlorophenyl)-N-(isoxazol-3-yl)-2-oxo-1,2-dihydroquinoline-6-sulfonamide (166 mg, 0.330 mmol) in 1,4-dioxane (1322 µl) was added. Water (330 µl) was then added, and the vial was sealed and heated to 120° C. for 30 min in a Biotage Initiator microwave reactor. The mixture was extracted with EtOAc (3×). The combined organic extracts were concentrated. The residue was taken up in MeOH and filtered through a 0.2 micron filter. The resulting solution was purified by reverse-phase HPLC (25-70% $CH_3CN/H_2O$ with 0.1% TFA). Fractions containing product were combined and lyophilized to give N-3-isoxazolyl-2-oxo-1-(3'-(trifluoromethyl)-4-biphenylyl)-1,2-dihydro-6-quinolinesulfonamide (32.5 mg, 0.064 mmol, 19.23% yield) as an off-white powder. $^1$H NMR (400 MHz, DMSO-$d_6$) δ=11.62 (s, 1H), 8.69 (d, J=1.9 Hz, 1H), 8.35 (d, J=2.3 Hz, 1H), 8.21 (d, J=9.5 Hz, 1H), 8.10-8.01 (m, 2H), 7.99-7.94 (m, 2H), 7.83-7.70 (m, 3H), 7.52-7.41 (m, 2H), 6.78 (t, J=9.0 Hz, 2H), 6.40 (d, J=1.9 Hz, 1H). m/z (ESI) 511.9 (M+H)$^+$.

Example 592

(Method 144): 1-(4'-fluoro-3-(1-methyl-1,2,3,6-tetrahydro-4-pyridinyl)-4-biphenylyl)-N-3-isoxazolyl-2-oxo-1,2-dihydro-6-quinolinesulfonamide

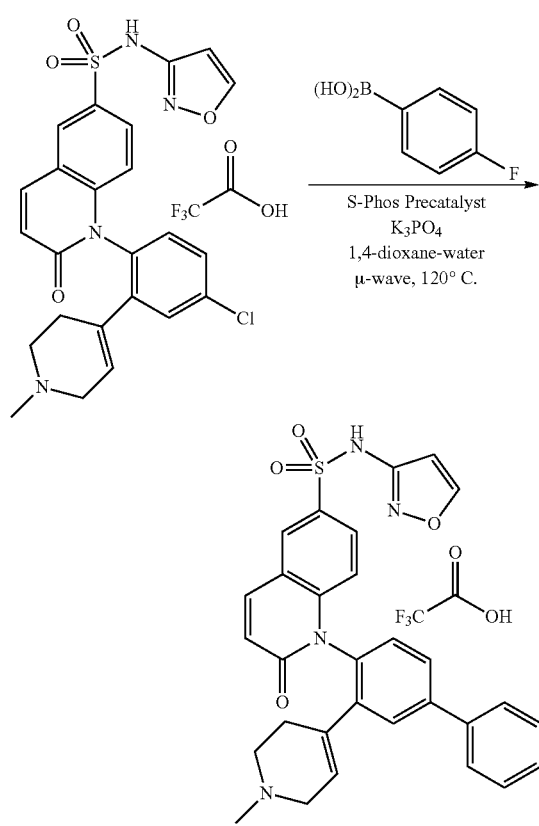

A vial was charged with 1-(4-chloro-2-(1-methyl-1,2,3,6-tetrahydro-4-pyridinyl)phenyl)-N-3-isoxazolyl-2-oxo-1,2-dihydro-6-quinolinesulfonamide 2,2,2-trifluoroacetate (90.6 mg, 0.148 mmol), S-Phos Precatalyst (11.28 mg, 0.015 mmol), and potassium phosphate (126 mg, 0.593 mmol). The vial was flushed with Ar (g), then a solution 1,4-dioxane (593 μl) and water (148 μl) were added in sequence. The vial was sealed and heated to 120° C. for 30 min in a Biotage Initiator microwave reactor. The mixture was extracted with 10% MeOH-EtOAc (3×). The combined organic extracts were concentrated. The residue was taken up in MeOH and filtered through a 0.2 micron filter. The resulting solution was purified by reverse-phase HPLC (25-70% CH$_3$CN/H$_2$O with 0.1% TFA). Fractions containing product were combined and lyophilized to give 1-(4'-fluoro-3-(1-methyl-1,2,3,6-tetrahydro-4-pyridinyl)-4-biphenylyl)-N-3-isoxazolyl-2-oxo-1,2-dihydro-6-quinolinesulfonamide 2,2,2-trifluoroacetate (48.9 mg, 0.073 mmol, 49.2% yield) as an off-white solid. $^1$H NMR (400 MHz, DMSO-$d_6$) δ=11.60 (br. s., 1H), 9.59 (br. s., 1H), 8.68 (d, J=2.1 Hz, 1H), 8.33 (s, 1H), 8.20 (d, J=9.6 Hz, 1H), 7.84-7.70 (m, 5H), 7.39-7.26 (m, 3H), 6.80-6.69 (m, 2H), 6.38 (s, 1H), 5.41 (br. s., 1H), 3.31 (d, J=19.9 Hz, 3H), 3.05-2.72 (m, 1H), 2.65-2.47 (m, 3H), 2.35 (br. s., 1H), 2.32-2.22 (m, 1H). m/z (ESI) 556.9 (M+H)$^+$.

Example 593

(Method 145): ((P)-1-(3'-chloro-2-fluoro-4',5-dimethoxy-4-biphenylyl)-N-3-isoxazolyl-2-oxo-1,2-dihydro-6-quinolinesulfonamide

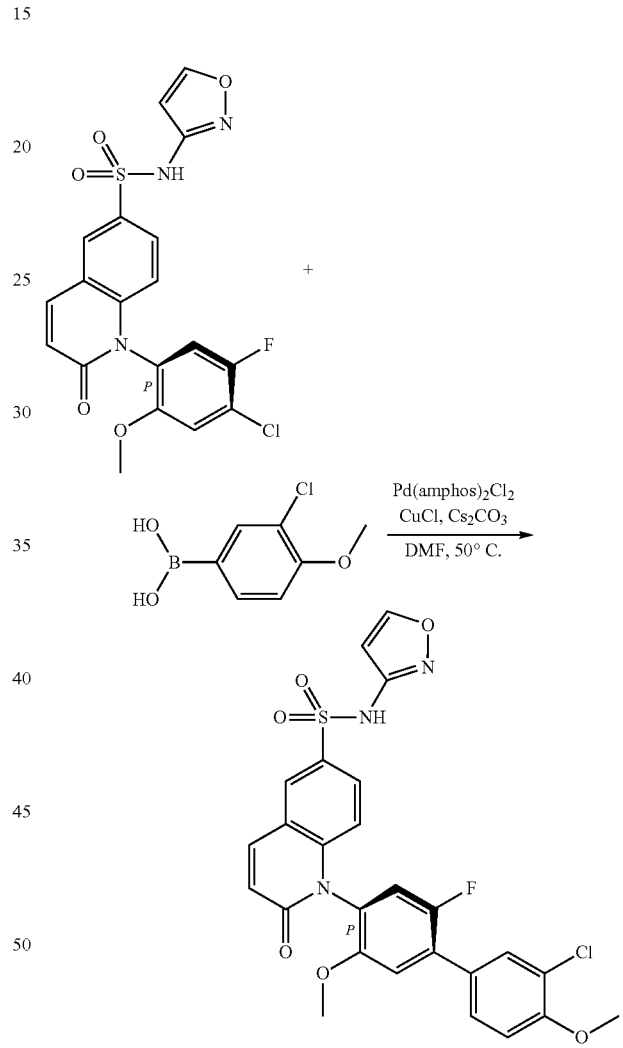

40-mL vial was charged with (P)-1-(4-bromo-5-fluoro-2-methoxyphenyl)-N-(isoxazol-3-yl)-2-oxo-1,2-dihydroquinoline-6-sulfonamide (175 mg, 0.354 mmol), (3-chloro-4-methoxyphenyl)boronic acid (198 mg, 1.062 mmol, Combi-Blocks, Inc.), cesium carbonate (461 mg, 1.416 mmol), copper(I) chloride (105 mg, 1.062 mmol), and 1,1-bis[(di-t-butyl-p-methylaminophenyl]palladium(II) chloride (50.1 mg, 0.071 mmol), flushed with N$_2$, and subsequently charged with DMF (3.5 mL). After stirring for 30 min, the reaction was quenched with 1 N HCl and extracted thrice with EtOAc. The organic extracts were combined, washed with 1 N HCl, passed through a short plug of SiO$_2$ (rinsing with EtOAc), and concentrated in vacuo to an oily yellow solid. Column chromatography (12 g Redisep Gold column, 0% to 100% [3:1 EtOAc:EtOH]/hept gradient with 10% DCM additive) afforded (P)-1-(3'-chloro-2-fluoro-4',5-dimethoxy-4-biphenylyl)-N-3-isoxazolyl-2-oxo-1,2-dihydro-6-quinolinesulfonamide (110.6 mg, 0.199 mmol, 56.2% yield) as a yellow crystalline solid. $^1$H NMR (400 MHz, DMSO-$d_6$) δ ppm 3.75 (s, 3H) 3.95 (s, 3H) 6.46 (s, 1H) 6.82 (d, J=9.64 Hz, 1H) 6.88 (d, J=9.02 Hz, 1H) 7.33 (d, J=8.81 Hz, 1H) 7.40 (d, J=7.05 Hz, 1H) 7.50 (d, J=10.47 Hz, 1H) 7.61-7.73 (m, 1H) 7.79 (s, 1H) 7.87 (dd, J=8.97, 2.23 Hz, 1H) 8.24 (d, J=9.64 Hz, 1H) 8.39 (d, J=2.18 Hz, 1H) 8.75 (s, 1H) 11.68 (s, 1H). m/z (ESI) 556.1 (M+H)$^+$.

Example 594

(Method 146): 1-(5-fluoro-2-methoxy-4-(2-pyridinyl)phenyl)-N-3-isoxazolyl-2-oxo-1,2-dihydro-6-quinolinesulfonamide

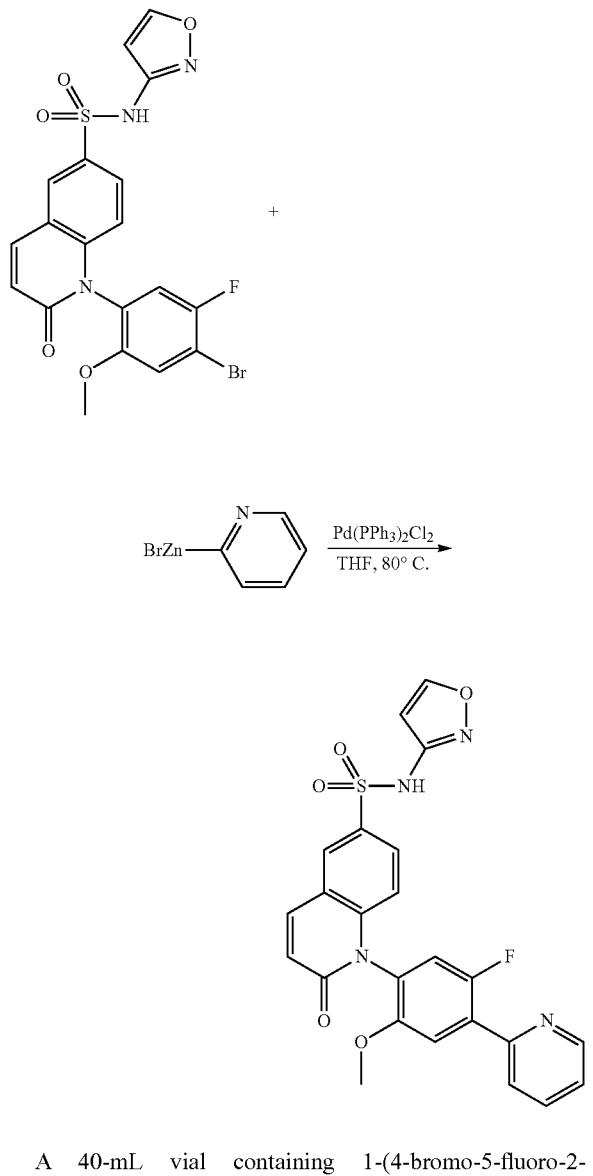

A 40-mL vial containing 1-(4-bromo-5-fluoro-2-methoxyphenyl)-N-(isoxazol-3-yl)-2-oxo-1,2-dihydroquinoline-6-sulfonamide (200 mg, 0.405 mmol) and bis(triphenylphosphine)palladium(II) dichloride (56.8 mg, 0.081 mmol) was flushed with $N_2$ and subsequently charged with 2-pyridylzinc bromide, 0.5M solution in tetrahydrofuran (4.0 ml, 2.023 mmol), and the black slurry was stirred at 80° C. for 30 min. The reaction was then cooled to rt, quenched with 1 N HCl, and extracted thrice with EtOAc. The organic extracts were combined, dried over $Na_2SO_4$, filtered, and concentrated in vacuo to a brown-black residue. Column chromatography (12 g Redisep gold column, 0% to 100% EtOAc/hept) afforded 1-(5-fluoro-2-methoxy-4-(2-pyridinyl)phenyl)-N-3-isoxazolyl-2-oxo-1,2-dihydro-6-quinolinesulfonamide (37.1 mg, 0.075 mmol, 18.62% yield) as a pale yellow amorphous solid. $^1$H NMR (400 MHz, DMSO-$d_6$) δ ppm 3.74 (s, 3H) 6.46 (s, 1H) 6.83 (d, J=9.64 Hz, 1H) 6.91 (d, J=9.02 Hz, 1H) 7.50 (ddd, J=7.44, 4.79, 1.24 Hz, 1H) 7.57 (d, J=10.88 Hz, 1H) 7.78 (d, J=6.95 Hz, 1H) 7.87 (dd, J=8.97, 2.12 Hz, 1H) 7.90-7.96 (m, 1H) 7.97-8.04 (m, 1H) 8.25 (d, J=9.64 Hz, 1H) 8.39 (d, J=2.18 Hz, 1H) 8.74 (s, 1H) 8.81 (d, J=4.90 Hz, 1H) 11.67 (s, 1H). m/z (ESI) 493.1 (M+H)$^+$.

Example 595

(Method 147): (P)-1-(3'-cyano-2-fluoro-4',5-dimethoxy-4-biphenylyl)-N-3-isoxazolyl-2-oxo-1,2-dihydro-6-quinolinesulfonamide

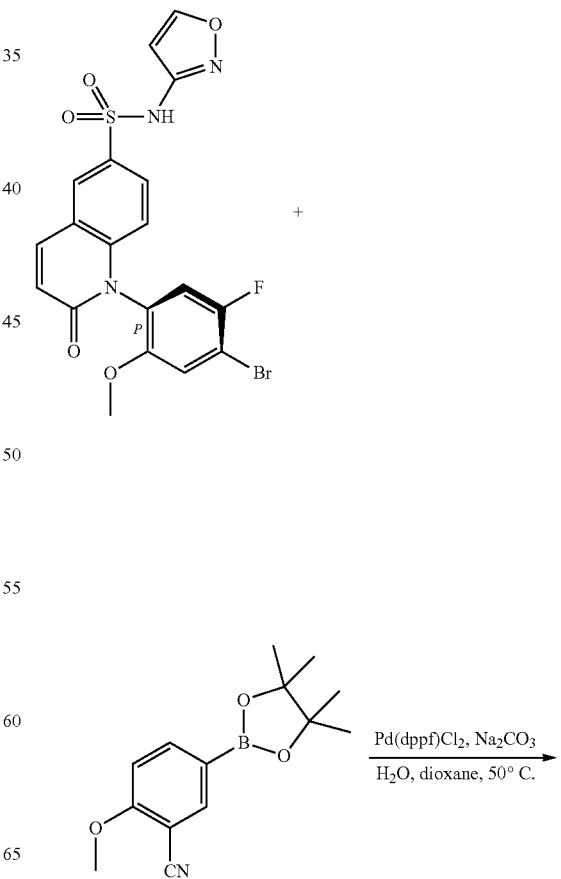

303

-continued

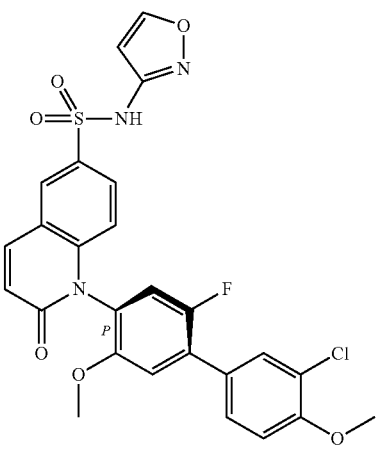

A 40-mL vial containing (P)-1-(4-bromo-5-fluoro-2-methoxyphenyl)-N-(isoxazol-3-yl)-2-oxo-1,2-dihydroquinoline-6-sulfonamide (175 mg, 0.354 mmol), 2-methoxy-5-(4,4,5,5-tetramethyl-1,3,2-dioxaborolan-2-yl)benzonitrile (315 mg, 1.214 mmol, Anichem, Inc.), and 1,1'-bis(diphenylphosphino)ferrocene palladium(II)dichloride dichloromethane adduct (57.8 mg, 0.071 mmol) was flushed with $N_2$ and subsequently charged with dioxane (4.6 mL) and 1.9 M $Na_2CO_3$ in $H_2O$ (1.5 mL). After stirring the reaction at 50° C. for 16 h, it was cooled to rt, quenched with 1 N HCl, and extracted thrice with EtOAc. The organic extracts were combined, washed with brine, filtered, and concentrated in vacuo to a brown oil. Preparatory HPLC (25% to 75% MeCN/$H_2O$ with 0.1% TFA) followed by column chromatography (25 g Snap Ultra column, 0-80% [3:1 EtOAc/EtOH]/hept gradient with 10% DCM) afforded (P)-1-(3'-cyano-2-fluoro-4',5-dimethoxy-4-biphenylyl)-N-3-isoxazolyl-2-oxo-1,2-dihydro-6-quinolinesulfonamide (60 mg, 0.110 mmol, 18.09% yield) as a white amorphous solid. $^1$H NMR (400 MHz, DMSO-$d_6$) δ ppm 3.75 (s, 3H) 4.01 (s, 3H) 6.46 (d, J=1.87 Hz, 1H) 6.82 (d, J=9.64 Hz, 1H) 6.88 (d, J=8.91 Hz, 1H) 7.41-7.48 (m, 2H) 7.53 (d, J=10.57 Hz, 1H) 7.87 (dd, J=8.97, 2.23 Hz, 1H) 8.02 (dd, J=8.81, 1.87 Hz, 1H) 8.12 (d, J=1.76 Hz, 1H) 8.24 (d, J=9.74 Hz, 1H) 8.39 (d, J=2.18 Hz, 1H) 8.74 (d, J=1.76 Hz, 1H) 11.67 (s, 1H). m/z (ESI) 547.2 (M+H)$^+$.

304

Example 596 (3141800)

(Method 148): (P)-1-(3'-(difluoromethyl)-2-fluoro-5-methoxy-4-biphenylyl)-N-3-isoxazolyl-2-oxo-1,2-dihydro-6-quinolinesulfonamide

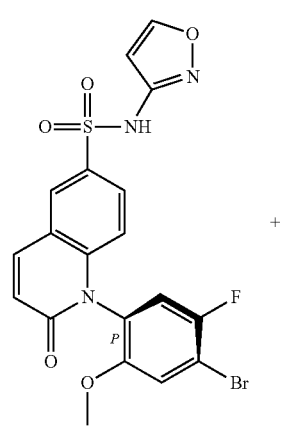

+

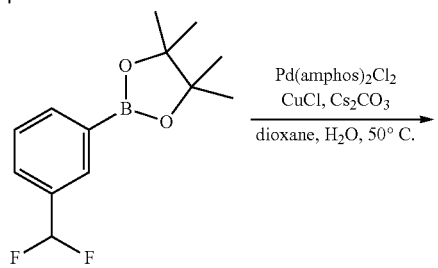

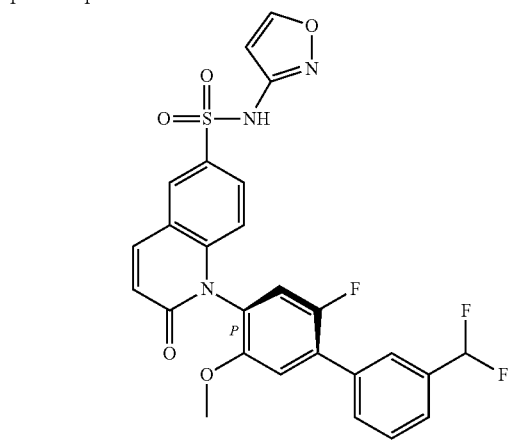

A 40-mL vial containing (P)-1-(4-bromo-5-fluoro-2-methoxyphenyl)-N-(isoxazol-3-yl)-2-oxo-1,2-dihydroquinoline-6-sulfonamide (200 mg, 0.405 mmol), cesium carbonate (659 mg, 2.023 mmol), copper(I) chloride (160 mg, 1.618 mmol), and 1,1-bis[(di-t-butyl-p-methylaminophenyl] palladium(II) chloride (57.3 mg, 0.081 mmol) was flushed with $N_2$ and subsequently charged with 2-(3-(difluoromethyl)phenyl)-4,4,5,5-tetramethyl-1,3,2-dioxaborolane (411 mg, 1.618 mmol, Milestone PharmTech USA, Inc.) and dioxane (2 mL). After stirring at 50° C. for 1 h, 0.1 mL $H_2O$ was added. After an additional hour, the reaction was cooled to rt, quenched with 1 N HCl, and extracted thrice with EtOAc. The organic extracted were combined, washed with brine, dried over $Na_2SO_4$, filtered, and concentrated in vacuo to a brown oil. Column chromatography (12 g Redisep Gold column, 0-80% [3:1 EtOAc/EtOH]/hept gradient with 10% DCM) afforded (P)-1-(3'-(difluoromethyl)-2-fluoro-5-methoxy-4-biphenylyl)-N-3-isoxazolyl-2-oxo-1,2-dihydro-6-quinolinesulfonamide (115 mg, 0.212 mmol, 52.5% yield) as a yellow amorphous solid. $^1$H NMR (400 MHz, DMSO-$d_6$) δ ppm 3.75 (s, 3H) 6.46 (s, 1H) 6.83 (d, J=9.64 Hz, 1H) 6.90 (d, J=9.02 Hz, 1H) 6.99-7.31 (m, 1H) 7.44 (d, J=6.95 Hz, 1H) 7.55 (d, J=10.37 Hz, 1H) 7.65-7.77 (m, 2H) 7.85-7.93 (m, 3H) 8.24 (d, J=9.74 Hz, 1H) 8.39 (d, J=2.18 Hz, 1H) 8.74 (d, J=4.91 Hz, 1H) 11.67 (s, 1H). m/z (ESI) 542.2 (M+H)$^+$.

Example 597

(Method 149): (P)-1-(2,3'-difluoro-5-methoxy-5'-methyl-4-biphenylyl)-N-3-isoxazolyl-2-oxo-1,2-dihydro-6-quinolinesulfonamide

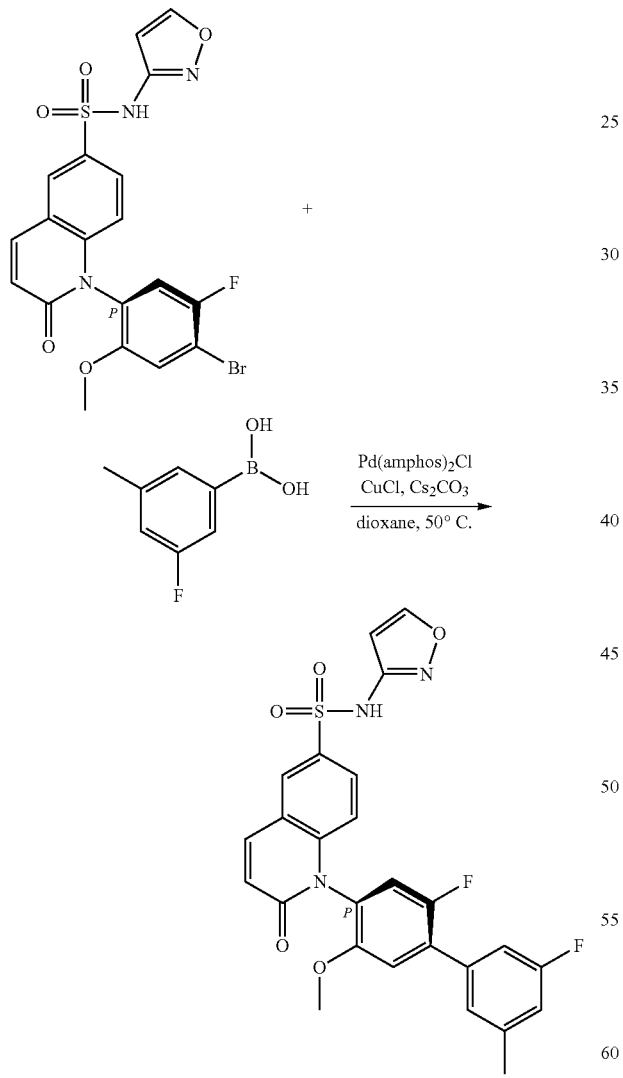

A 40-mL vial containing (P)-1-(4-bromo-5-fluoro-2-methoxyphenyl)-N-(isoxazol-3-yl)-2-oxo-1,2-dihydroquinoline-6-sulfonamide (200 mg, 0.405 mmol), (3-fluoro-5-methylphenyl)boronic acid (249 mg, 1.618 mmol), cesium carbonate (659 mg, 2.023 mmol), copper(I) chloride (160 mg, 1.618 mmol), and 1,1-bis[(di-t-butyl-p-methylaminophenyl]palladium(II) chloride (57.3 mg, 0.081 mmol) was flushed with $N_2$ and subsequently charged with dioxane (2 mL). After stirring for 1 h, the reaction was cooled to rt, quenched with 1 N HCl, and extracted thrice with EtOAc. The organic extracts were combined, washed with brine, dried over $Na_2SO_4$, filtered, and concentrated in vacuo to an orange oil. Column chromatography (12 g Redisep Gold column, 0-80% [3:1 EtOAc/EtOH]/hept gradient with 10% DCM) afforded (P)-1-(2,3'-difluoro-5-methoxy-5'-methyl-4-biphenylyl)-N-3-isoxazolyl-2-oxo-1,2-dihydro-6-quinolinesulfonamide (46 mg, 0.088 mmol, 21.72% yield) as a white amorphous solid. $^1$H NMR (400 MHz, DMSO-$d_6$) δ ppm 2.44 (s, 3H) 3.75 (s, 3H) 6.46 (d, J=1.76 Hz, 1H) 6.82 (d, J=9.64 Hz, 1H) 6.88 (d, J=8.91 Hz, 1H) 7.14-7.21 (m, 1H) 7.32-7.43 (m, 3H) 7.53 (d, J=10.37 Hz, 1H) 7.87 (dd, J=8.97, 2.23 Hz, 1H) 8.24 (d, J=9.64 Hz, 1H) 8.39 (d, J=2.28 Hz, 1H) 8.74 (d, J=1.76 Hz, 1H) 11.67 (s, 1H). m/z (ESI) 524.2 (M+H)$^+$.

Example 598

(Method 150): (P)-1-(4'-chloro-2-fluoro-5-methoxy-4-biphenylyl)-2-oxo-N-2-pyrimidinyl-1,2-dihydro-6-quinolinesulfonamide

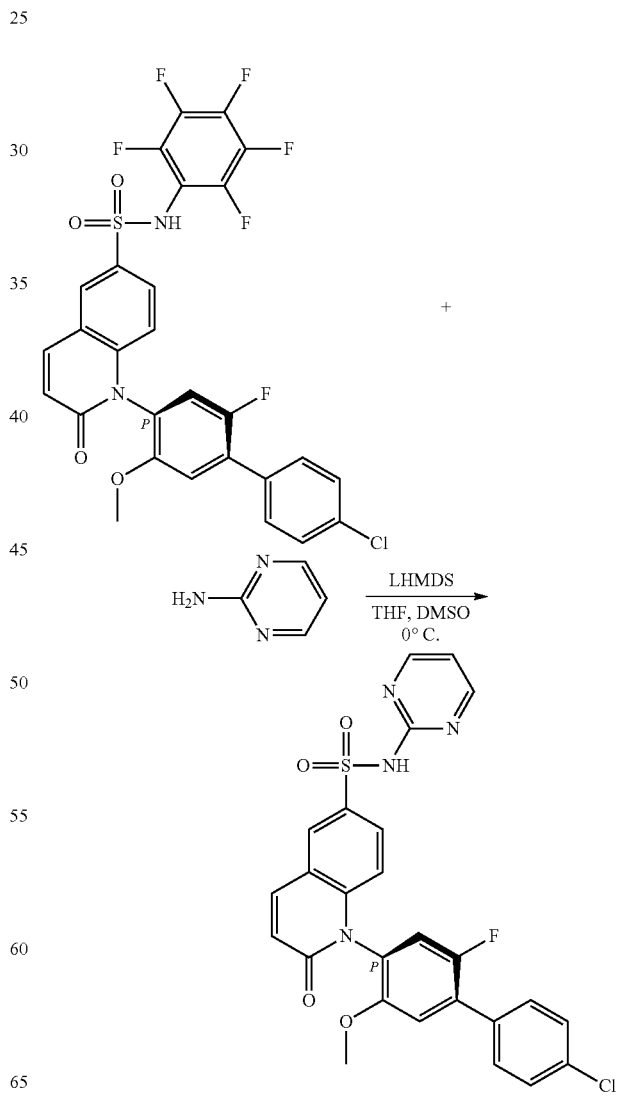

A 40-mL vial containing (P)-perfluorophenyl 1-(4'-chloro-2-fluoro-5-methoxy-[1,1'-biphenyl]-4-yl)-2-oxo-1,2-dihydroquinoline-6-sulfonate (150 mg, 0.240 mmol) and 2-aminopyrimidine (34.2 mg, 0.359 mmol) was flushed with $N_2$ and then sequentially charged with DMSO (0.6 mL) and THF (1.8 mL). After stirring to homogeneity, the solution was cooled to 0° C., and lithium bis(trimethylsilyl)amide, 1.0M solution in THF (0.53 mL, 0.527 mmol) was added down the side of the vial. The resulting red-orange solution was stirred at 0° C. for 20 min and subsequently quenched at 0° C. with 1 N HCl and extracted thrice with EtOAc. The organic extracts were combined, washed with brine, dried over $Na_2SO_4$, filtered, and concentrated in vacuo to a yellow oil. Column chromatography (55 g Interchim C18 PuriFlash column, 10-100% MeCN/$H_2O$ with 0.1% $NH_4OH$) afforded 1-(4'-chloro-2-fluoro-5-methoxy-4-biphenylyl)-2-oxo-N-2-pyrimidinyl-1,2-dihydro-6-quinolinesulfonamide (45.0 mg, 0.084 mmol, 35.0% yield) as an off-white amorphous solid. $^1$H NMR (400 MHz, DMSO-$d_6$) δ ppm 3.73 (s, 3H) 6.74 (d, J=9.74 Hz, 3H) 7.39 (d, J=6.95 Hz, 1H) 7.50 (d, J=10.47 Hz, 1H) 7.62 (d, J=7.93 Hz, 2H) 7.75 (dd, J=8.45, 1.30 Hz, 2H) 7.92 (dd, J=8.86, 2.13 Hz, 1H) 8.21 (d, J=9.64 Hz, 1H) 8.26-8.38 (m, 3H) 11.53-12.39 (m, 1H). m/z (ESI) 537.2 (M+H)$^+$.

Example 599

(Method 151): 1-(5-fluoro-2-methoxy-4-(4-methyl-2-oxo-1(2H)-pyridinyl)phenyl)-N-3-isoxazolyl-2-oxo-1,2-dihydro-6-quinolinesulfonamide 1-(5-Fluoro-2-methoxy-4-(4-methyl-2-oxopyridin-1(2H)-yl)phenyl)-N-(isoxazol-3-yl)-N-(4-methoxybenzyl)-2-oxo-1,2-dihydroquinoline-6-sulfonamide (18 mg, 0.028 mmol) was taken up in TFA (2 mL) in a microwave vial and irradiated to 70° C. for 1 h. Concentration under a stream of $N_2$ followed by column chromatography (5 g Redisep gold column, 0-80% [3:1 EtOAc/EtOH]/hept gradient with 10% DCM) afforded 1-(5-fluoro-2-methoxy-4-(4-methyl-2-oxo-1(2H)-pyridinyl)phenyl)-N-3-isoxazolyl-2-oxo-1,2-dihydro-6-quinolinesulfonamide (0.24 mg, 0.459 μmol, 1.640% yield) as a colorless residue. $^1$H NMR (400 MHz, CHLOROFORM-d) δ ppm 2.55 (s, 3H) 3.72 (s, 3H) 6.64 (d, J=1.76 Hz, 1H) 6.88 (d, J=9.74 Hz, 1H) 6.98-7.02 (m, 2H) 7.11 (d, J=6.84 Hz, 1H) 7.32 (d, J=1.35 Hz, 2 H) 7.80-7.90 (m, 2H) 8.15 (d, J=2.07 Hz, 1H) 8.23 (d, J=5.39 Hz, 1H) 8.29 (d, J=1.66 Hz, 1H). m/z (ESI) 523.0 (M+H)$^+$.

Example 600

(Method 152): (P)-1-(4'-chloro-3-methoxy-4-biphenylyl)-2-oxo-N-2-pyrimidinyl-1,2-dihydro-6-quinolinesulfonamide

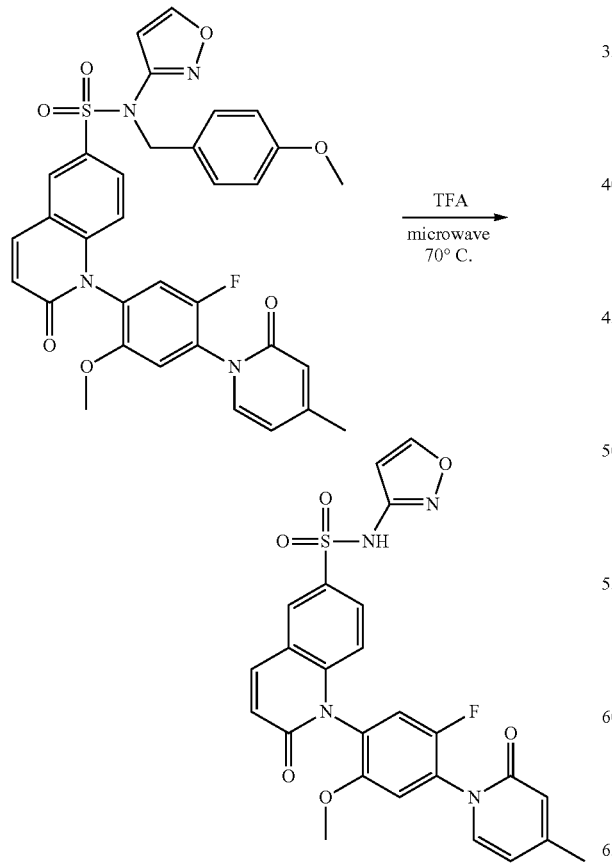

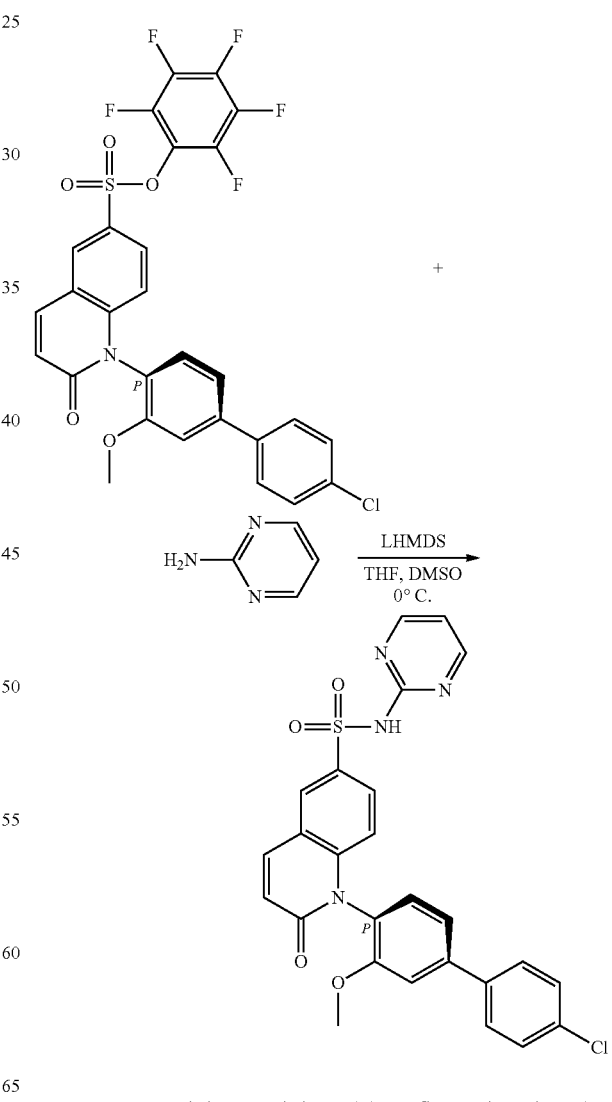

A 40-mL vial containing (P)-perfluorophenyl 1-(4'-chloro-3-methoxy-[1,1'-biphenyl]-4-yl)-2-oxo-1,2-dihydroquinoline-6-sulfonate (150 mg, 0.247 mmol) and 2-aminopyrimidine (35.2 mg, 0.370 mmol) was flushed with N₂ and then sequentially charged with DMSO (0.6 mL) and THF (1.8 mL). After stirring to homogeneity, the solution was cooled to 0° C., and lithium bis(trimethylsilyl)amide, 1.0M solution in THF (543 µl, 0.543 mmol) was added down the side of the vial. The resulting red-orange solution was stirred at 0° C. for 20 min and subsequently quenched at 0° C. with 1 N HCl and extracted thrice with EtOAc. The organic extracts were combined, washed twice with H₂O and once with brine, dried over Na₂SO₄, filtered, and concentrated in vacuo to a yellow oil. Column chromatography (25 g Snap Ultra column, 0-100% [3:1 EtOAc/EtOH]/hept gradient with 10% DCM) afforded (P)-1-(4'-chloro-3-methoxy-4-biphenylyl)-2-oxo-N-2-pyrimidinyl-1,2-dihydro-6-quinolinesulfonamide (62.4 mg, 0.120 mmol, 48.7% yield) as an amorphous white solid. ¹H NMR (400 MHz, DMSO-d₆) δ ppm 3.77 (s, 3H) 6.79 (dd, J=9.33, 6.32 Hz, 2H) 7.06 (t, J=5.43 Hz, 1H) 7.37-7.42 (m, 1H) 7.42-7.48 (m, 1H) 7.52-7.64 (m, 3H) 7.87 (d, J=7.67 Hz, 2H) 7.98 (dd, J=8.97, 2.12 Hz, 1H) 8.26 (d, J=9.64 Hz, 1H) 8.46-8.56 (m, 3H) 11.61-11.95 (m, 1H). m/z (ESI) 519.0 (M+H)⁺.

Examples 601, 602 & 603

(Method 153): 1-(6-(3-fluorophenyl)-4-methoxy-3-pyridinyl)-N-3-isoxazolyl-2-oxo-1,2-dihydro-6-quinolinesulfonamide, (P)-1-(6-(3-fluorophenyl)-4-methoxy-3-pyridinyl)-N-3-isoxazolyl-2-oxo-1,2-dihydro-6-quinolinesulfonamide (602), and (M)-1-(6-(3-fluorophenyl)-4-methoxy-3-pyridinyl)-N-3-isoxazolyl-2-oxo-1,2-dihydro-6-quinolinesulfonamide (603)

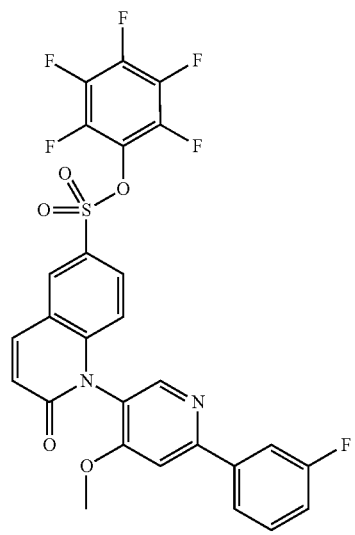

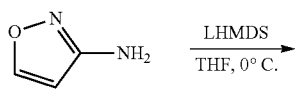

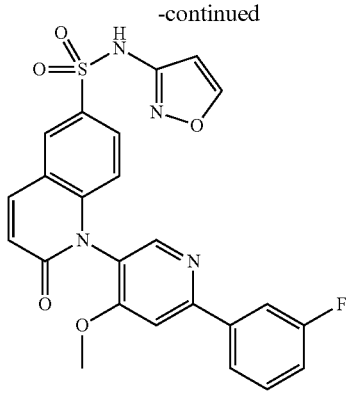

601

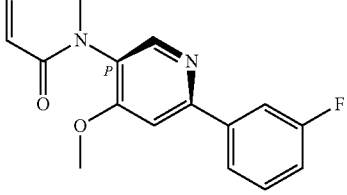

602

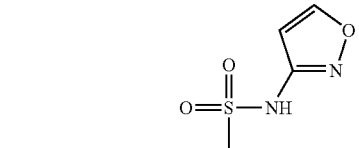

603

A THF (2.4 mL) solution of perfluorophenyl 1-(6-(3-fluorophenyl)-4-methoxypyridin-3-yl)-2-oxo-1,2-dihydroquinoline-6-sulfonate (140 mg, 0.236 mmol) and 3-aminoisoxazole (19.20 µl, 0.260 mmol) in a 40-mL vial was cooled to 0° C. and subsequently treated with lithium bis(trimethylsilyl)amide, 1.0M solution in THF (496 µl, 0.496 mmol). After stirring the yellow solution at 0° C. for 20 min, the reaction was quenched at 0° C. with 1 N HCl and extracted thrice with EtOAc. The organic extracts were combined, washed with brine, dried over Na₂SO₄, filtered, and concentrated in vacuo to a yellow residue. Column chromatography (25 g Snap Ultra column, 0-80% [3:1 EtOAc/EtOH]/hept gradient with 10% DCM) afforded racemic 1-(6-(3-fluorophenyl)-4-methoxy-3-pyridinyl)-N-3- isoxazolyl-2-oxo-1,2-dihydro-6-quinolinesulfonamide (76.6 mg, 0.156 mmol, 65.8% yield) as an amorphous white solid. $^1$H NMR (400 MHz, DMSO-$d_6$) δ ppm 3.92 (s, 3H) 6.46 (d, J=5.48 Hz, 1H) 6.84 (d, J=9.64 Hz, 1H) 6.92 (d, J=9.02 Hz, 1H) 7.36 (d, J=8.22 Hz, 1H) 7.61 (dd, J=7.98, 1.76 Hz, 1H) 7.86 (dd, J=8.91, 2.28 Hz, 1H) 7.92 (s, 1H) 8.05-8.15 (m, 2H) 8.27 (d, J=14.13 Hz, 1H) 8.40 (d, J=2.18 Hz, 1H) 8.50 (s, 1H) 8.74 (d, J=1.76 Hz, 1H) 11.67 (s, 1H). m/z (ESI) 493.0 (M+H)$^+$. A portion of the racemic product was separated via Chiralpak AS-H (30% MeOH/70% $CO_2$) to afford (P)-1-(6-(3-fluorophenyl)-4-methoxy-3-pyridinyl)-N-3-isoxazolyl-2-oxo-1,2-dihydro-6-quinolinesulfonamide (27 mg) and (M)-1-(6-(3-fluorophenyl)-4-methoxy-3-pyridinyl)-N-3-isoxazolyl-2-oxo-1,2-dihydro-6-quinolinesulfonamide (28 mg) as white amorphous solids. Data for peak 1: $^1$H NMR (400 MHz, DMSO-$d_6$) δ ppm 3.92 (s, 3H) 6.40 (d, J=1.45 Hz, 1H) 6.82 (d, J=9.64 Hz, 1H) 6.88 (d, J=9.02 Hz, 1H) 7.36 (t, J=8.03 Hz, 1H) 7.57-7.65 (m, 1H) 7.84 (dd, J=8.97, 2.13 Hz, 1H) 7.92 (s, 1H) 8.07 (dd, J=10.42, 2.02 Hz, 1H) 8.11 (d, J=8.09 Hz, 1H) 8.25 (d, J=9.74 Hz, 1H) 8.36 (d, J=1.76 Hz, 1H) 8.50 (s, 1H) 8.65 (s, 1H) 11.50-11.82 (m, 1H). m/z (ESI) 493.2 (M+H)$^+$. Data for peak 2: $^1$H NMR (400 MHz, DMSO-$d_6$) δ ppm 3.92 (s, 3H) 6.38 (d, J=1.35 Hz, 1H) 6.81 (d, J=9.64 Hz, 1H) 6.86 (d, J=8.81 Hz, 1H) 7.35 (t, J=8.20 Hz, 1H) 7.61 (dd, J=7.93, 1.81 Hz, 1H) 7.83 (dd, J=8.97, 2.02 Hz, 1H) 7.92 (s, 1H) 8.07 (dd, J=10.42, 2.02 Hz, 1H) 8.11 (d, J=7.98 Hz, 1H) 8.24 (d, J=9.64 Hz, 1H) 8.34 (d, J=1.97 Hz, 1H) 8.49 (s, 1H) 8.61 (s, 1H) 11.50-11.79 (m, 1H). m/z (ESI) 493.2 (M+H)$^+$.

Example 604

(Method 154): (P)-1-(2,4'-difluoro-5-methoxy-4-biphenylyl)-2-oxo-N-2-pyrimidinyl-1,2-dihydro-6-quinolinesulfonamide

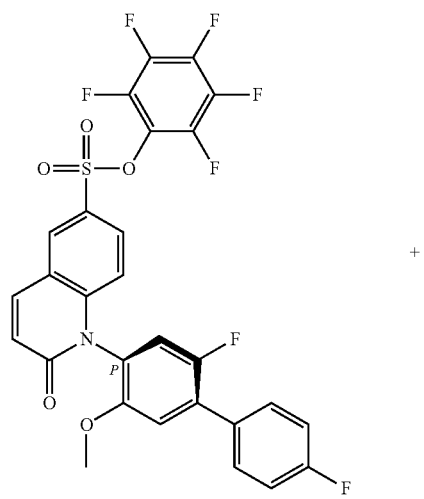

+

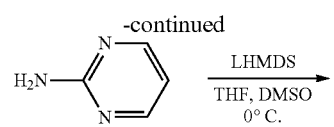

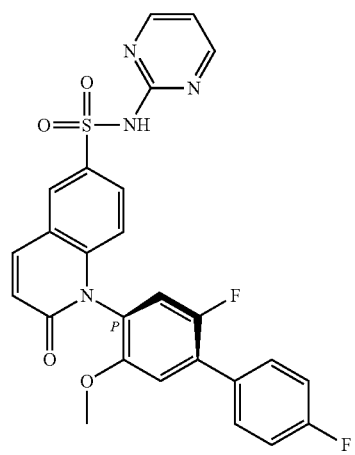

A 40-mL vial containing (P)-perfluorophenyl 1-(2,4'-difluoro-5-methoxy-[1,1'-biphenyl]-4-yl)-2-oxo-1,2-dihydroquinoline-6-sulfonate (95 mg, 0.156 mmol) and 2-aminopyrimidine (22.24 mg, 0.234 mmol) was flushed with $N_2$ and then sequentially charged with DMSO (0.6 mL) and THF (1.8 mL). After stirring to homogeneity, the solution was cooled to 0° C., and lithium bis(trimethylsilyl)amide, 1.0M solution in THF (343 μl, 0.343 mmol) was added down the side of the vial. The resulting red-orange solution was stirred at 0° C. for 30 min and subsequently quenched at 0° C. with 1 N HCl and extracted thrice with EtOAc. The organic extracts were combined, washed with brine, dried over Na2SO4, filtered, and concentrated in vacuo to a yellow residue. Purification was done with 0.1% TFA in MeCN and water as mobile phase to afford (P)-1-(2,4'-difluoro-5-methoxy-4-biphenylyl)-2-oxo-N-2-pyrimidinyl-1,2-dihydro-6-quinolinesulfonamide (26.26 mg, 0.050 mmol, 32.4% yield) as a white amorphous solid. $^1$H NMR (500 MHz, DMSO-$d_6$) δ ppm 3.73 (s, 3H) 6.80 (d, J=9.67 Hz, 1H) 6.85 (d, J=8.95 Hz, 1H) 7.05 (t, J=4.64 Hz, 1H) 7.34-7.42 (m, 3H) 7.49 (d, J=10.38 Hz, 1H) 7.75 (t, J=6.72 Hz, 2H) 8.00 (dd, J=8.92, 1.98 Hz, 1H) 8.26 (d, J=9.73 Hz, 1H) 8.46-8.53 (m, 3H) 11.47-12.12 (m, 1H). m/z (ESI) 521.2 (M+H)$^+$.

Example 605

(Method 155): (P)-1-(4-(5-chloro-2-methoxy-3-pyridinyl)-5-fluoro-2-methoxyphenyl)-2-oxo-N-2-pyrimidinyl-1,2-dihydro-6-quinolinesulfonamide

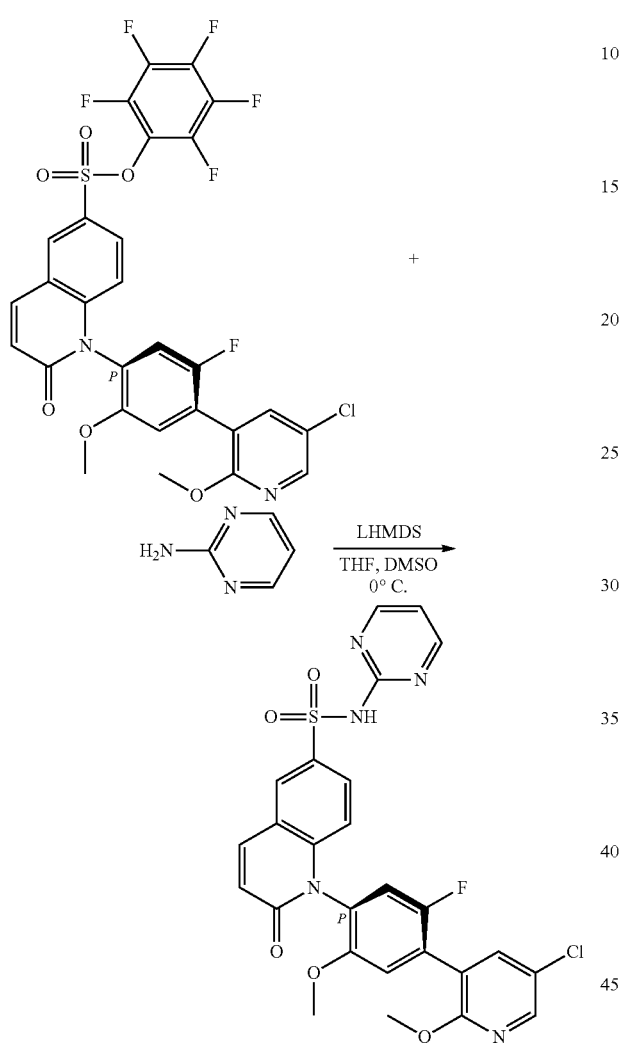

A 40-mL vial containing (P)-perfluorophenyl 1-(4-(5-chloro-2-methoxypyridin-3-yl)-5-fluoro-2-methoxyphenyl)-2-oxo-1,2-dihydroquinoline-6-sulfonate (115 mg, 0.175 mmol) and 2-aminopyrimidine (24.97 mg, 0.263 mmol) was flushed with $N_2$ and then sequentially charged with DMSO (0.6 mL) and THF (1.8 mL). After stirring to homogeneity, the solution was cooled to 0° C., and lithium bis(trimethylsilyl)amide, 1.0M solution in THF (385 µl, 0.385 mmol) was added down the side of the vial. The resulting red-orange solution was stirred at 0° C. for 30 min and subsequently quenched at 0° C. with 1 N HCl and extracted thrice with EtOAc. The organic extracts were combined, washed with brine, dried over $Na_2SO_4$, filtered, and concentrated in vacuo to a yellow residue. Purification was done with 0.1% TFA in MeCN and water as mobile phase to afford (P)-1-(4-(5-chloro-2-methoxy-3-pyridinyl)-5-fluoro-2-methoxyphenyl)-2-oxo-N-2-pyrimidinyl-1,2-dihydro-6-quinolinesulfonamide (41.1 mg, 0.072 mmol, 41.3% yield) as a white amorphous solid. $^1$H NMR (500 MHz, DMSO-$d_6$) δ ppm 3.74 (s, 3H) 4.03 (s, 3H) 6.80 (d, J=9.09 Hz, 1H) 6.84 (d, J=8.11 Hz, 1H) 7.02-7.09 (m, 1H) 7.39-7.57 (m, 2H) 7.99 (d, J=8.15 Hz, 1H) 8.23-8.36 (m, 2H) 8.50 (dd, J=8.50, 4.35 Hz, 4H) 11.62-12.08 (m, 1H). m/z (ESI) 568.1 (M+H)$^+$.

Example 606

(Method 156): (P)-1-(3'-fluoro-4-methoxy-3-biphenylyl)-2-oxo-N-2-pyrimidinyl-1,2-dihydro-6-quinolinesulfonamide

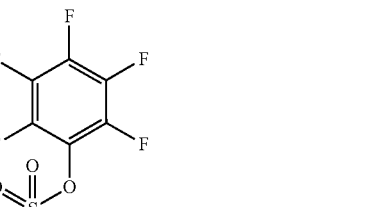

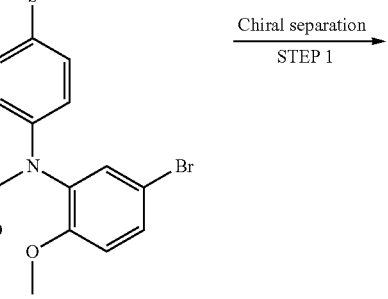

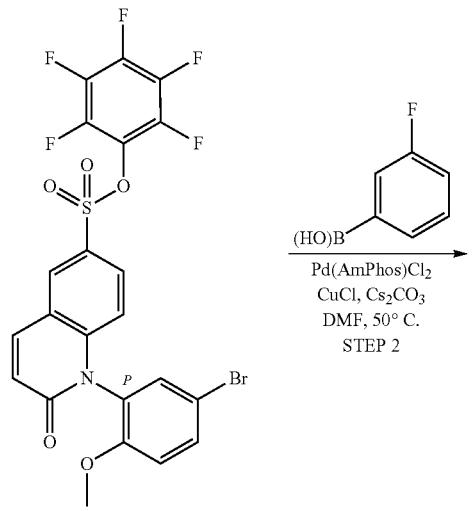

-continued

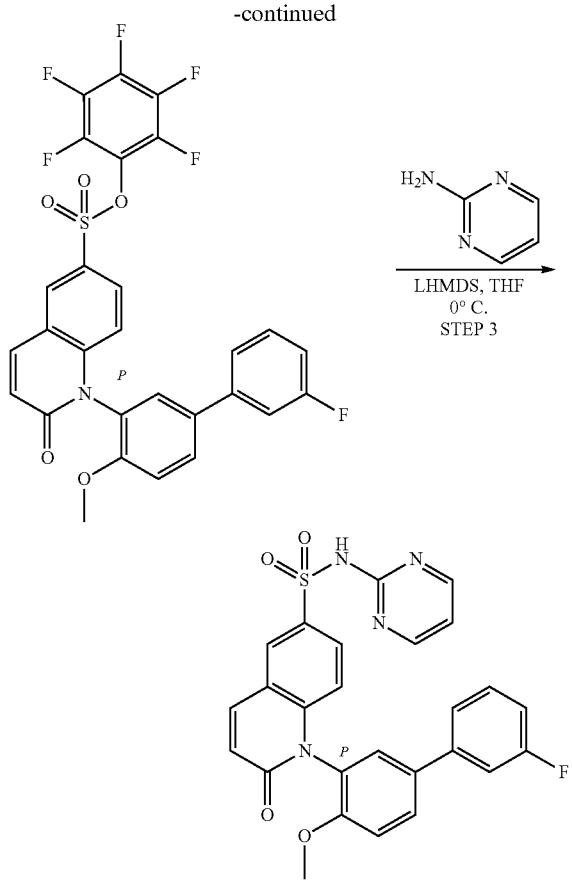

Step 1: (P)-perfluorophenyl 1-(5-bromo-2-methoxy-phenyl)-2-oxo-1,2-dihydroquinoline-6-sulfonate Perfluorophenyl 1-(5-bromo-2-methoxyphenyl)-2-oxo-1,2-dihydroquinoline-6-sulfonate (from Step 3 of Method 115) underwent chiral separation via SFC (Column: (S,S) Whelk-O; Eluent: 50% isopropanol/CO$_2$). Peak 1 ((P)-perfluorophenyl 1-(5-bromo-2-methoxyphenyl)-2-oxo-1,2-dihydroquinoline-6-sulfonate) was returned with >99% ae as a white solid. m/z (ESI) 576.0 (M+H)$^+$.

Step 2: (P)-perfluorophenyl 1-(3'-fluoro-4-methoxy-[1,1'-biphenyl]-3-yl)-2-oxo-1,2-dihydroquinoline-6-sulfonate A RBF was charged with (P)-perfluorophenyl 1-(5-bromo-2-methoxyphenyl)-2-oxo-1,2-dihydroquinoline-6-sulfonate (0.100 g, 0.174 mmol), (3-fluorophenyl)boronic acid (0.073 g, 0.521 mmol), copper(i) chloride (0.052 g, 0.521 mmol), cesium carbonate (0.226 g, 0.694 mmol) and Pd(AmPhos)Cl$_2$ (0.025 g, 0.035 mmol). The flask was flushed with Ar (g), and then DMF (0.868 ml) was added. The reaction was heated to 50° C. for 30 minutes. The reaction was diluted with ethyl acetate and washed (×3) with water containing excess EDTA. The organics were then washed with water, brine and dried over sodium sulfate, filtered and concentrated in vacuo. The material was then purified via MPLC, eluting with 0-100% ethyl acetate in heptane to yield (P)-perfluorophenyl 1-(3'-fluoro-4-methoxy-[1,1'-biphenyl]-3-yl)-2-oxo-1,2-dihydroquinoline-6-sulfonate (0.051 g, 0.086 mmol, 49.7% yield) as a light orange solid. m/z (ESI) 592.0 (M+H)$^+$.

Step 3: (P)-1-(3'-fluoro-4-methoxy-3-biphenylyl)-2-oxo-N-2-pyrimidinyl-1,2-dihydro-6-quinolinesulfonamide A RBF was charged with pyrimidin-2-amine (10.66 mg, 0.112 mmol) and (P)-perfluorophenyl 1-(3'-fluoro-4-methoxy-[1,1'-biphenyl]-3-yl)-2-oxo-1,2-dihydroquinoline-6-sulfonate (0.051 g, 0.086 mmol), and DMF (0.862 ml) was added. The flask was cooled in an ice bath, then lithium bis(trimethylsilyl)amide, 1.0M in THF (0.198 ml, 0.198 mmol) was added drop wise. After 10 minutes, the reaction was diluted with 1N aq. HCl and ethyl acetate. The layers were separated, and the aqueous was extracted (×2) with ethyl acetate. The combined organics were dried over sodium sulfate, filtered and concentrated in vacuo. The crude material was purified via MPLC, eluting with 0-100% ethyl acetate in heptanes to yield (P)-1-(3'-fluoro-4-methoxy-3-biphenylyl)-2-oxo-N-2-pyrimidinyl-1,2-dihydro-6-quinolinesulfonamide as an off-white solid. $^1$H NMR (400 MHz, DMSO-d$_6$) δ ppm 3.72 (s, 3H) 6.79 (t, J=8.00 Hz, 2H) 7.05 (br. s., 1H) 7.14 (t, J=8.71 Hz, 1H) 7.40 (d, J=8.71 Hz, 1H) 7.42-7.49 (m, 1H) 7.56 (d, J=8.21 Hz, 2H) 7.77 (d, J=2.38 Hz, 1H) 7.94-7.98 (m, 2H) 8.26 (d, J=9.64 Hz, 1H) 8.45-8.54 (m, 3H) 11.84 (br. s., 1H). m/z (ESI) 503.2 (M+H)$^+$.

Example 607, 608, and 609

(Method 157): 1-(6-chloro-3'-fluoro-4-methoxy-3-biphenylyl)-N-3-isoxazolyl-2-oxo-1,2-dihydro-6-quinolinesulfonamide, (P)-1-(6-chloro-3'-fluoro-4-methoxy-3-biphenylyl)-N-3-isoxazolyl-2-oxo-1,2-dihydro-6-quinolinesulfonamide (608) and (M)-1-(6-chloro-3'-fluoro-4-methoxy-3-biphenylyl)-N-3-isoxazolyl-2-oxo-1,2-dihydro-6-quinolinesulfonamide (609)

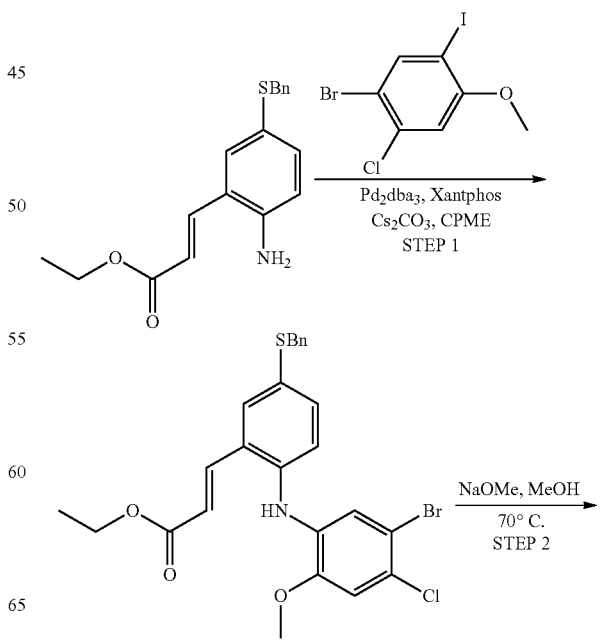

-continued

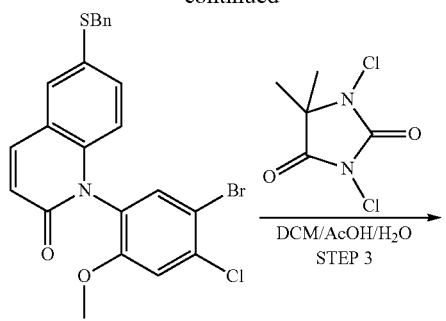

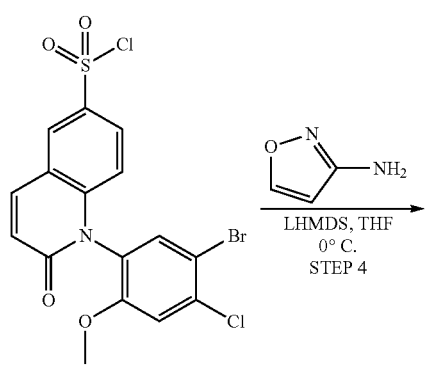

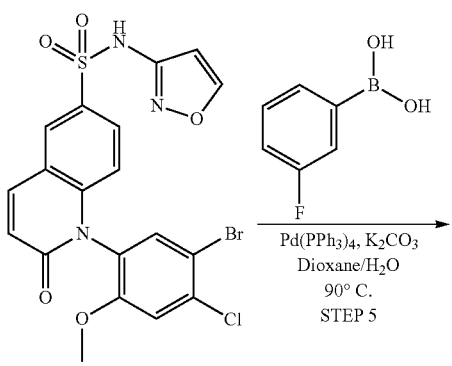

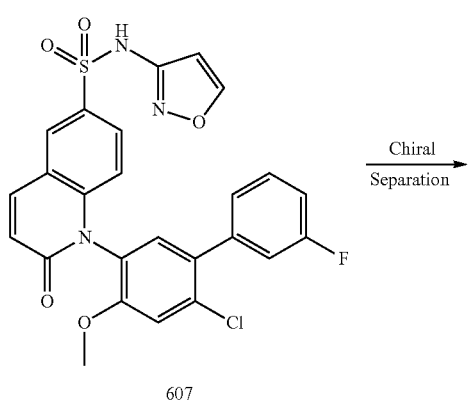

607

-continued

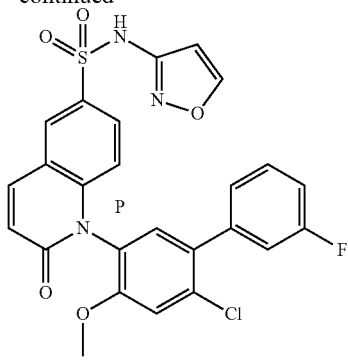

608

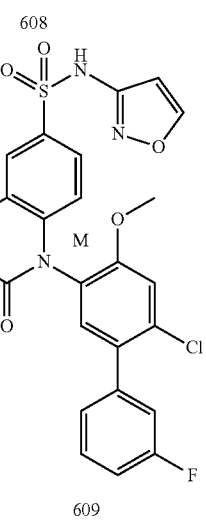

609

Step 1: (E)-ethyl 3-(5-(benzylthio)-2-((5-bromo-4-chloro-2-methoxyphenyl)amino)phenyl)acrylate 1-Bromo-2-chloro-5-iodo-4-methoxybenzene (6.65 g, 19.14 mmol), (E)-ethyl 3-(2-amino-5-(benzylthio)phenyl)acrylate (4.000 g, 12.76 mmol), $Pd_2(dba)_3$ (0.292 g, 0.319 mmol), Xantphos (0.369 g, 0.638 mmol) and cesium carbonate (5.82 g, 17.87 mmol) were combined in CPME (25.5 ml) and the reaction was heated to 90° C. overnight. The reaction was cooled to RT, diluted with EtOAc and filtered over a pad of Celite (washing well with EtOAc). The filtrate was concentrated in vacuo and the crude oil was then taken up in DCM and purified via MPLC, eluting with 0-20% ethyl acetate in heptanes to yield (E)-ethyl 3-(5-(benzylthio)-2-((5-bromo-4-chloro-2-methoxyphenyl)amino)phenyl)acrylate as a yellow solid. m/z (ESI) 534.0 $(M+H)^+$.

Step 2: 6-(benzylthio)-1-(5-bromo-4-chloro-2-methoxyphenyl)quinolin-2(1H)-one

A RBF was charged with (E)-ethyl 3-(5-(benzylthio)-2-((5-bromo-4-chloro-2-methoxyphenyl)amino)phenyl)acrylate (6.80 g, 12.76 mmol) and MeOH (63.8 ml) to give a yellow suspension. Sodium methoxide, 25 wt % solution in methanol (10.21 ml, 5.10 mmol) was added, the RBF was fitted with a reflux condenser and the reaction was heated at 70° C. overnight. The reaction was cooled to RT and concentrated in vacuo. The crude material was concentrated onto silica gel and purified via MPLC, eluting with 50% ethyl acetate in heptanes (with 10% DCM additive) (isocratic). The impure material retrieved from column chromatography was dissolved in DCM and further purified via SCX column (product eluted with the methanol wash). The methanol filtrate was concentrated in vacuo and then the solids were triturated in IPA, filtered over a frit washing with minimal IPA to yield 6-(benzylthio)-1-(5-bromo-4-chloro-2-methoxyphenyl)quinolin-2(1H)-one (2.71 g, 5.57 mmol, 43.6% yield) as a beige solid. m/z (ESI) 486.0 (M+H)$^+$.

Step 3: 1-(5-bromo-4-chloro-2-methoxyphenyl)-2-oxo-1,2-dihydroquinoline-6-sulfonyl chloride A solution of 6-(benzylthio)-1-(5-bromo-4-chloro-2-methoxyphenyl)quinolin-2(1H)-one (0.508 g, 1.044 mmol) in DCM (4.91 ml)/AcOH (0.187 ml)/water (0.123 ml) was treated with 1,3-dichloro-5,5-dimethylimidazolidine-2,4-dione (0.411 g, 2.087 mmol) and was allowed to stir for 15 minutes. The reaction was diluted with DCM and washed with sat. aq. ammonium chloride. An emulsion formed, and all layers were concentrated together. The crude solid was triturated in IPA, the solids were filtered and dried onto silica gel. The crude material was purified via MPLC, eluting with 0-100% ethyl acetate in heptanes, to yield 1-(5-bromo-4-chloro-2-methoxyphenyl)-2-oxo-1,2-dihydroquinoline-6-sulfonyl chloride (0.254 g, 0.548 mmol, 52.6% yield) as a white solid. m/z (ESI) 463.8 (M+H)$^+$.

Step 4: 1-(5-bromo-4-chloro-2-methoxyphenyl)-N-(isoxazol-3-yl)-2-oxo-1,2-dihydroquinoline-6-sulfonamide A solution of 3-aminoisoxazole (0.041 ml, 0.548 mmol) and 1-(5-bromo-4-chloro-2-methoxyphenyl)-2-oxo-1,2-dihydroquinoline-6-sulfonyl chloride (0.254 g, 0.548 mmol) in THF (5.48 ml) was cooled to 0° C., at which point LiHMDS, 1.0M in THF (1.152 ml, 1.152 mmol) was added drop wise. After 40 minutes in the ice bath, the reaction was complete and ammonium chloride (sat aq) was added and the product was extracted with ethyl acetate (×3). The combined organics were dried over magnesium sulfate, filtered and concentrated in vacuo. The crude material was purified via MPLC, eluting with 0-100% ethyl acetate in heptane to yield 1-(5-bromo-4-chloro-2-methoxyphenyl)-N-(isoxazol-3-yl)-2-oxo-1,2-dihydroquinoline-6-sulfonamide (0.096 g, 0.188 mmol, 34.3% yield) as a light-yellow solid. m/z (ESI) 510.0 (M+H)$^+$.

Step 5: 1-(6-chloro-3'-fluoro-4-methoxy-3-biphenylyl)-N-3-isoxazolyl-2-oxo-1,2-dihydro-6-quinolinesulfonamide 1-(5-Bromo-4-chloro-2-methoxyphenyl)-N-(isoxazol-3-yl)-2-oxo-1,2-dihydroquinoline-6-sulfonamide (0.096 g, 0.188 mmol), (3-fluorophenyl)boronic acid (0.039 g, 0.282 mmol), potassium carbonate (0.078 g, 0.564 mmol), and Pd(PPh$_3$)$_4$ (0.022 g, 0.019 mmol) were combined in 1,4-dioxane (0.705 ml) and water (0.235 ml). The reaction was heated to 90° C. for 2 h. The reaction was cooled to RT and sat. aq. ammonium chloride was added. The organics were extracted (×3) with DCM, dried through a Radley's phase separator, and concentrated in vacuo. The crude material was purified via MPLC, eluting with 0-100% ethyl acetate in heptanes, to yield 1-(6-chloro-3'-fluoro-4-methoxy-[1,1'-biphenyl]-3-yl)-N-(isoxazol-3-yl)-2-oxo-1,2-dihydroquinoline-6-sulfonamide (0.025 g, 0.048 mmol, 25.3% yield) as a white solid. m/z (ESI) 526.0 (M+H)$^+$. $^1$H NMR (400 MHz, DMSO-d$_6$) δ ppm 3.76 (s, 3H) 6.44 (d, J=1.76 Hz, 1H) 6.80 (d, J=9.54 Hz, 1H) 6.93 (d, J=9.12 Hz, 1H) 7.21-7.36 (m, 3H) 7.54 (d, J=12.96 Hz, 2H) 7.85 (dd, J=8.97, 2.13 Hz, 1H) 8.22 (d, J=9.64 Hz, 1H) 8.36 (d, J=1.97 Hz, 1H) 8.72 (s, 1H) 11.49-11.64 (m, 1H) 11.67 (s, 1H). 1-(6-chloro-3'-fluoro-4-methoxy-[1,1'-biphenyl]-3-yl)-N-(isoxazol-3-yl)-2-oxo-1,2-dihydroquinoline-6-sulfonamide was separated by chiral SFC on a (S,S) Whelk-O column, eluting with 40% methanol to yield (P)-1-(6-chloro-3'-fluoro-4-methoxy-3-biphenylyl)-N-3-isoxazolyl-2-oxo-1,2-dihydro-6-quinolinesulfonamide as peak 1 and (M)-1-(6-chloro-3'-fluoro-4-methoxy-3-biphenylyl)-N-3-isoxazolyl-2-oxo-1,2-dihydro-6-quinolinesulfonamide as peak 2. Data for peak 1: m/z (ESI) 526.0 (M+H)$^+$. $^1$H NMR (400 MHz, DMSO-d$_6$) δ ppm 3.75 (s, 3H) 6.14 (d, J=0.93 Hz, 1H) 6.69 (d, J=9.64 Hz, 1H) 6.73 (d, J=8.81 Hz, 1H) 7.18-7.26 (m, 1H) 7.29-7.34 (m, 2H) 7.43-7.55 (m, 3H) 7.74 (dd, J=8.81, 1.97 Hz, 1H) 8.09-8.29 (m, 4H). Data for peak 2: m/z (ESI) 526.0 (M+H)$^+$. $^1$H NMR (400 MHz, DMSO-d$_6$) δ ppm 3.75 (s, 3H) 6.08-6.15 (m, 1H) 6.68 (d, J=9.64 Hz, 1H) 6.72 (d, J=8.71 Hz, 1H) 7.16-7.26 (m, 1H) 7.27-7.35 (m, 2H) 7.41-7.55 (m, 3H) 7.73 (dd, J=8.71, 1.97 Hz, 1H) 8.08-8.25 (m, 4H).

Example 610, 611 and 612

(Method 158): 1-(3'-chloro-5'-fluoro-4-methoxy-3-biphenylyl)-2-oxo-N-4-pyrimidinyl-1,2-dihydro-6-quinolinesulfonamide, (P)-1-(3'-chloro-5'-fluoro-4-methoxy-3-biphenylyl)-2-oxo-N-4-pyrimidinyl-1,2-dihydro-6-quinolinesulfonamide (611) and (M)-1-(3'-chloro-5'-fluoro-4-methoxy-3-biphenylyl)-2-oxo-N-4-pyrimidinyl-1,2-dihydro-6-quinolinesulfonamide (612)

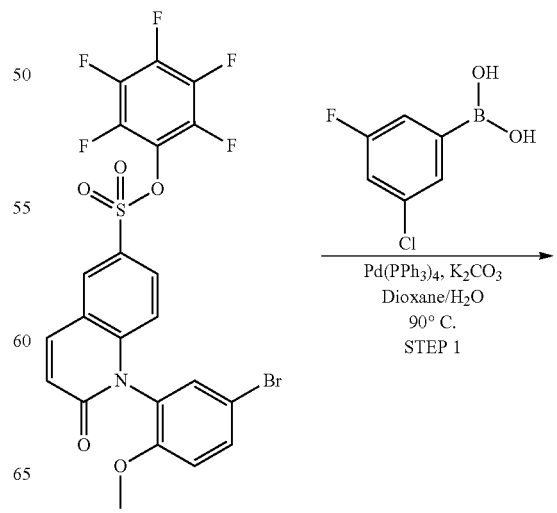

-continued

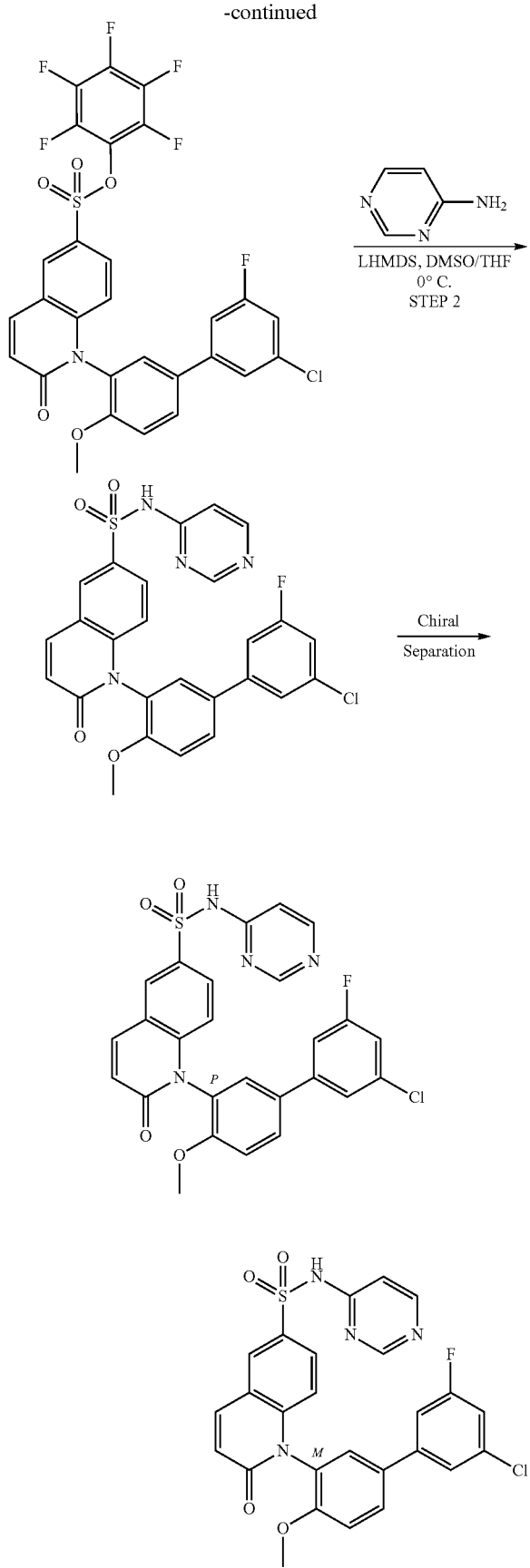

Step 1: Perfluorophenyl 1-(3'-chloro-5'-fluoro-4-methoxy-[1,1'-biphenyl]-3-yl)-2-oxo-1,2-dihydro-quinoline-6-sulfonate Perfluorophenyl 1-(5-bromo-2-methoxyphenyl)-2-oxo-1,2-dihydroquinoline-6-sulfonate (15.00 g, 26.0 mmol), (3-chloro-5-fluorophenyl)boronic acid (4.99 g, 28.6 mmol), potassium carbonate (10.79 g, 78 mmol), and Pd(PPh$_3$)$_4$ (3.01 g, 2.60 mmol) were combined in 1,4-dioxane (98 ml) and water (32.5 ml). The reaction was heated to 90° C. for 2.5 h. After cooling to room temperature, the reaction was diluted with DCM and washed with water. The organics were dried via phase separator and concentrated in vacuo. The crude oil was dry loaded onto silica gel and purified via MPLC, eluting with 0-100% ethyl acetate (with a 10% DCM additive) to yield perfluorophenyl 1-(3'-chloro-5'-fluoro-4-methoxy-[1,1'-biphenyl]-3-yl)-2-oxo-1,2-dihydroquinoline-6-sulfonate (6.20 g, 9.91 mmol, 38.1% yield) as a beige solid. m/z (ESI) 626.0 (M+H)$^+$.

Step 2: 1-(3'-chloro-5'-fluoro-4-methoxy-3-biphenylyl)-2-oxo-N-4-pyrimidinyl-1,2-dihydro-6-quinoline-sulfonamide 4-Aminopyrimidine (0.099 g, 1.038 mmol) was dissolved in dimethyl sulfoxide (1.997 ml), and perfluorophenyl 1-(3'-chloro-5'-fluoro-4-methoxy-[1,1'-biphenyl]-3-yl)-2-oxo-1,2-dihydroquinoline-6-sulfonate (0.500 g, 0.799 mmol) in tetrahydrofuran (5.99 ml) was added as a solution. The reaction was cooled to 0° C. and LHMDS, 1.0M in THF (1.837 ml, 1.837 mmol) was added drop wise. The reaction mixture was diluted with EtOAc and 1N HCl (aq). The layers were separated, and the aqueous was washed (×1) with EtOAc. The combined organics were dried over magnesium sulfate, filtered and concentrated in vacuo. The crude material was purified via MPLC, eluting with 0-100% ethyl acetate in heptane (with a 10% DCM additive), to yield 1-(3'-chloro-5'-fluoro-4-methoxy-[1,1'-biphenyl]-3-yl)-2-oxo-N-(pyrimidin-4-yl)-1,2-dihydroquinoline-6-sulfonamide (0.210 g, 0.391 mmol, 49.0% yield) as a white solid. m/z (ESI) 537.0 (M+H)$^+$. $^1$H NMR (400 MHz, DMSO-d$_6$) δ ppm 3.73 (s, 3H) 6.75 (d, J=8.91 Hz, 1H) 6.80 (d, J=9.64 Hz, 1H) 7.00 (br. s., 1H) 7.34-7.42 (m, 2H) 7.59-7.64 (m, 1H) 7.68 (t, J=1.61 Hz, 1H) 7.86 (d, J=2.49 Hz, 1H) 7.89 (dd, J=8.97, 2.02 Hz, 1H) 8.02 (dd, J=8.76, 2.44 Hz, 1H) 8.24 (d, J=9.54 Hz, 1H) 8.27-8.34 (m, 1H) 8.43 (s, 1H) 8.60 (s, 1H). 1-(3'-chloro-5'-fluoro-4-methoxy-[1,1'-biphenyl]-3-yl)-2-oxo-N-(pyrimidin-4-yl)-1,2-dihydroquinoline-6-sulfonamide was separated by chiral SFC on a Chiralpak AD with 30% isopropanol to give (P)-1-(3'-chloro-5'-fluoro-4-methoxy-3-biphenylyl)-2-oxo-N-4-pyrimidinyl-1,2-dihydro-6-quinolinesulfonamide as peak 1 and (M)-1-(3'-chloro-5'-fluoro-4-methoxy-3-biphenylyl)-2-oxo-N-4-pyrimidinyl-1,2-dihydro-6-quinolinesulfonamide as peak 2. Data for peak 1: m/z (ESI) 537.0 (M+H)$^+$. $^1$H NMR (400 MHz, DMSO-d$_6$) δ ppm 3.73 (s, 3H) 6.75 (d, J=8.81 Hz, 1H) 6.79 (d, J=9.64 Hz, 1H) 6.98 (br. s., 1H) 7.34-7.41 (m, 2H) 7.62 (dt, J=7.63 Hz, 1H) 7.68 (t, J=1.61 Hz, 1H) 7.86 (d, J=2.38 Hz, 1H) 7.87-7.91 (m, 1H) 8.02 (dd, J=8.76, 2.44 Hz, 1H) 8.23 (d, J=9.54 Hz, 1H) 8.26-8.31 (m, 1H) 8.40-8.44 (m, 1H) 8.59 (s, 1H). Data for peak 2: m/z (ESI) 537.0 (M+H)$^+$. $^1$H NMR (400 MHz, DMSO-d$_6$) δ ppm 3.73 (s, 3H) 6.75 (d, J=9.02 Hz, 1H) 6.79 (d, J=9.64 Hz, 1H) 7.00 (br. s., 1H) 7.35-7.41 (m, 2H) 7.61 (dt, J=6.43 Hz, 1H) 7.68 (t, J=1.55 Hz, 1H) 7.86 (d, J=2.49 Hz, 1H) 7.87-7.91 (m, 1H) 8.02 (dd, J=8.71, 2.49 Hz, 1H) 8.24 (d, J=9.64 Hz, 1H) 8.29 (br. s., 1H) 8.41-8.44 (m, 1H) 8.59 (s, 1H). The sulfonamide —NH was not observed in the NMR spectra of the three compounds.

Example 613, 614 and 615

(Method 159): 1-(3',6-dichloro-5'-fluoro-4-methoxy-3-biphenylyl)-N-3-isoxazolyl-2-oxo-1,2-dihydro-6-quinolinesulfonamide, (P)-1-(3',6-dichloro-5'-fluoro-4-methoxy-3-biphenylyl)-N-3-isoxazolyl-2-oxo-1,2-dihydro-6-quinolinesulfonamide (614) and (M)-1-(3',6-dichloro-5'-fluoro-4-methoxy-3-biphenylyl)-N-3-isoxazolyl-2-oxo-1,2-dihydro-6-quinolinesulfonamide (615)

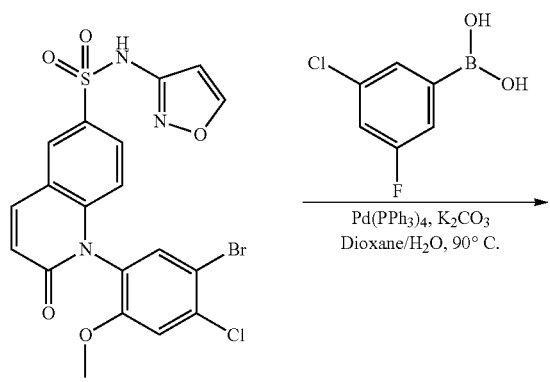

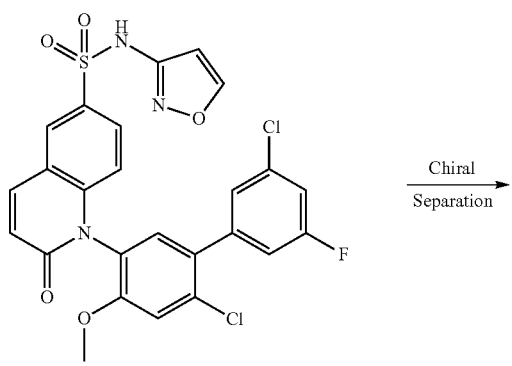

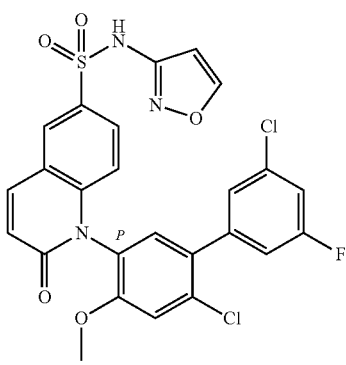 [SMILES: COc1cnc(-c2cc(F)cc(Cl)c2)cc1-n1c(=O)ccc2cc(S(=O)(=O)Nc3ccon3)ccc21]

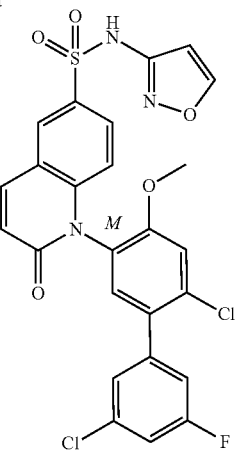

1-(5-Bromo-4-chloro-2-methoxyphenyl)-N-(isoxazol-3-yl)-2-oxo-1,2-dihydroquinoline-6-sulfonamide (0.484 g, 0.948 mmol), (3-chloro-5-fluorophenyl)boronic acid (0.248 g, 1.421 mmol), potassium carbonate (0.393 g, 2.84 mmol), and Pd(PPh$_3$)$_4$ (0.110 g, 0.095 mmol) were combined in 1,4-dioxane (3.55 ml) and water (1.185 ml). The reaction was heated to 90° C. for 2 h. The reaction was cooled to RT and sat. aq. ammonium chloride was added. The organics were extracted (×3) with DCM, dried via phase separator, and concentrated in vacuo. The crude material was purified via MPLC, eluting with 0-100% ethyl acetate in heptanes, to yield 1-(3',6-dichloro-5'-fluoro-4-methoxy-[1,1'-biphenyl]-3-yl)-N-(isoxazol-3-yl)-2-oxo-1,2-dihydroquinoline-6-sulfonamide (0.344 g, 0.614 mmol, 64.8% yield). m/z (ESI) 562.0 (M+H)$^+$. $^1$H NMR (400 MHz, DMSO-d$_6$) δ ppm 3.76 (s, 3H) 6.45 (d, J=1.76 Hz, 1H) 6.79 (d, J=9.64 Hz, 1H) 6.93 (d, J=9.02 Hz, 1H) 7.35 (ddd, J=9.59, 2.38, 1.50 Hz, 1H) 7.39-7.41 (m, 1H) 7.49 (dt, J=8.73, 2.11 Hz, 1H) 7.57 (d, J=5.08 Hz, 2H) 7.84 (dd, J=9.02, 2.28 Hz, 1H) 8.22 (d, J=9.54 Hz, 1H) 8.37 (d, J=2.18 Hz, 1H) 8.72 (d, J=1.76 Hz, 1H) 11.66 (s, 1H). The material was separated by chiral SFC on a Chiralpak AD with 45% isopropanol to give (P)-1-(3',6-dichloro-5'-fluoro-4-methoxy-3-biphenylyl)-N-3-isoxazolyl-2-oxo-1,2-dihydro-6-quinolinesulfonamide as peak 1 and (M)-1-(3',6-dichloro-5'-fluoro-4-methoxy-3-biphenylyl)-N-3-isoxazolyl-2-oxo-1,2-dihydro-6-quinolinesulfonamide as peak 2. Data for peak 1: m/z (ESI) 560.0 (M+H)$^+$. $^1$H NMR (400 MHz, DMSO-d$_6$) δ ppm 3.76 (s, 3H) 6.45 (d, J=1.76 Hz, 1H) 6.79 (d, J=9.64 Hz, 1H) 6.93 (d, J=8.91 Hz, 1H) 7.35 (d, J=9.51 Hz, 1H) 7.40 (s, 1H) 7.49 (dt, J=8.76, 2.15 Hz, 1H) 7.57 (d, J=5.18 Hz, 2H) 7.84 (dd, J=9.02, 2.28 Hz, 1H) 8.22 (d, J=9.43 Hz, 1H) 8.37 (d, J=2.28 Hz, 1H) 8.72 (d, J=1.76 Hz, 1H) 11.66 (s, 1H). Data for peak 2: m/z (ESI) 560.0 (M+H)$^+$. $^1$H NMR (400 MHz, DMSO-d$_6$) δ ppm 3.76 (s, 3H) 6.45 (d, J=1.76 Hz, 1H) 6.79 (d, J=9.64 Hz, 1H) 6.93 (d, J=8.91 Hz, 1H) 7.35 (ddd, J=9.61, 2.36, 1.50 Hz, 1H) 7.39-7.41 (m, 1H) 7.49 (dt, J=8.71 Hz, 1H) 7.57 (d, J=5.18 Hz, 2H) 7.84 (dd, J=8.97, 2.23 Hz, 1H) 8.22 (d, J=9.54 Hz, 1H) 8.37 (d, J=2.18 Hz, 1H) 8.72 (d, J=1.76 Hz, 1H) 11.66 (s, 1H).

Example 616

(Method 160): (P)-1-(4'-chloro-3'-cyano-2-fluoro-5-methoxy-4-biphenylyl)-2-oxo-N-3-pyridazinyl-1,2-dihydro-6-quinolinesulfonamide

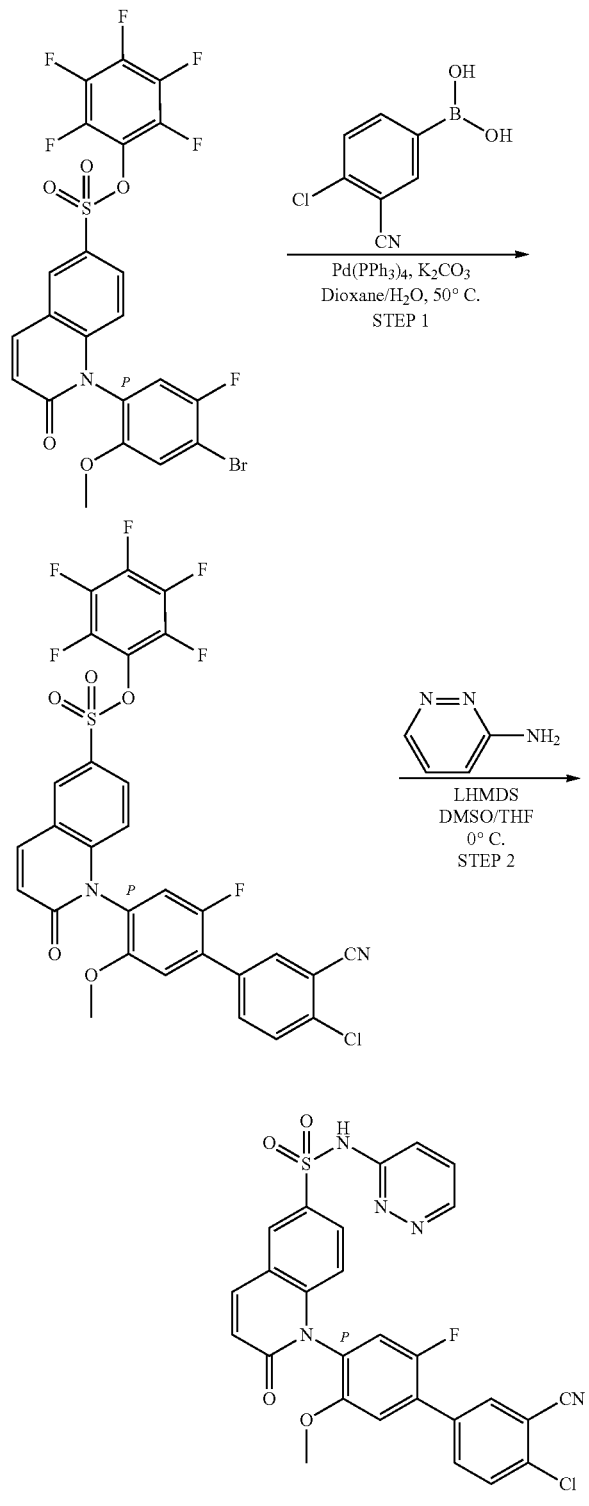

Step 1: (P)-perfluorophenyl 1-(4'-chloro-3'-cyano-2-fluoro-5-methoxy-[1,1'-biphenyl]-4-yl)-2-oxo-1,2-dihydroquinoline-6-sulfonate (P)-perfluorophenyl 1-(4-bromo-5-fluoro-2-methoxyphenyl)-2-oxo-1,2-dihydroquinoline-6-sulfonate (5.66 g, 9.52 mmol), (4-chloro-3-cyanophenyl)boronic acid (1.900 g, 10.48 mmol), potassium carbonate (3.95 g, 28.6 mmol), and Pd(PPh$_3$)$_4$ (1.101 g, 0.952 mmol) were combined in 1,4-dioxane (35.7 ml) and water (11.91 ml). The reaction was heated to 50° C. overnight at which point it was cooled to RT and water was added. The product was extracted with DCM (×3), dried via phase separator and concentrated in vacuo. The crude material was purified via MPLC, eluting with 0-100% ethyl acetate in heptanes (with a 10% DCM additive) to yield product as a dark brown oily solid. To remove some of the impurities, the material was dissolved in DCM and loaded onto a 50-g SCX-2 column. (P)-perfluorophenyl 1-(4'-chloro-3'-cyano-2-fluoro-5-methoxy-[1,1'-biphenyl]-4-yl)-2-oxo-1,2-dihydroquinoline-6-sulfonate (2.95 g, 4.53 mmol, 47.6% yield) eluted off with the methanol wash as a light yellow solid after concentration in vacuo. m/z (ESI) 651.0 (M+H)$^+$.

Step 2: (P)-1-(4'-chloro-3'-cyano-2-fluoro-5-methoxy-4-biphenylyl)-2-oxo-N-3-pyridazinyl-1,2-dihydro-6-quinolinesulfonamide Pyridazin-3-amine (0.047 g, 0.499 mmol) was dissolved in dimethyl sulfoxide (0.960 ml), and (P)-perfluorophenyl 1-(4'-chloro-3'-cyano-2-fluoro-5-methoxy-[1,1'-biphenyl]-4-yl)-2-oxo-1,2-dihydroquinoline-6-sulfonate (0.250 g, 0.384 mmol) in tetrahydrofuran (2.88 ml) was added as a solution. The resulting reaction was cooled to 0° C. and LHMDS, 1.0M in THF (0.883 ml, 0.883 mmol) was added drop wise. After 15 minutes, the reaction mixture was diluted with EtOAc and 1N HCl (aq). The layers were separated, and the aqueous was washed (×1) with EtOAc. The combined organics were dried over magnesium sulfate, filtered and concentrated in vacuo. The crude material was purified by reverse-phase preparative HPLC using an XBridge Prep C18 column (10 micron OBD, 19×100 mm), 0.1% TFA in CH$_3$CN/H$_2$O, gradient 25% to 95% over 12 minutes to provide 1-(4'-chloro-3'-cyano-2-fluoro-5-methoxy-[1,1'-biphenyl]-4-yl)-2-oxo-N-(pyridazin-3-yl)-1,2-dihydroquinoline-6-sulfonamide as a white solid. To quantify the ae %, a small sample of product (in DMSO) was heated to 100° C. overnight; Method developed on racemate—Whelk-O (S,S) 60% methanol. Sample contains 6.8% minor atropisomer (ee>86%). m/z (ESI) 561.9 (M+H)+. $^1$H NMR (400 MHz, DMSO-d$_6$) δ ppm 3.75 (s, 3H) 6.75-6.83 (m, 2H) 7.49-7.58 (m, 2H) 7.69 (dd, J=9.48, 4.20 Hz, 1H) 7.84-7.98 (m, 3H) 8.07 (dt, J=5.96 Hz, 1H) 8.21 (d, J=9.54 Hz, 1H) 8.25-8.34 (m, 1H) 8.34-8.38 (m, 2H) 14.50 (br. s., 1H).

Examples 617 and 618

(Method 161): 1-(2-chloro-5-methoxy-4-pyridinyl)-N-3-isoxazolyl-2-oxo-1,2-dihydro-6-quinolinesulfonamide (617) and 1-(2-(3-chloro-5-fluorophenyl)-5-methoxy-4-pyridinyl)-N-3-isoxazolyl-2-oxo-1,2-dihydro-6-quinolinesulfonamide (618)

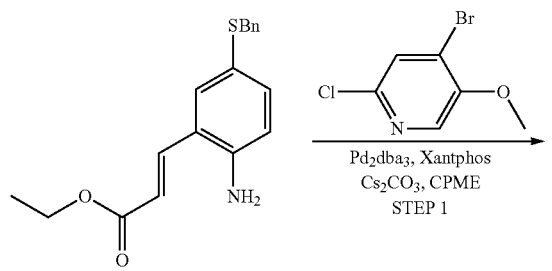

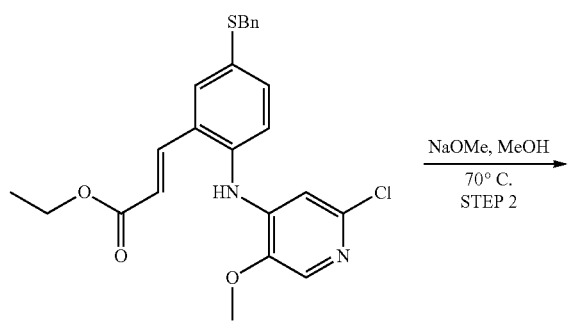

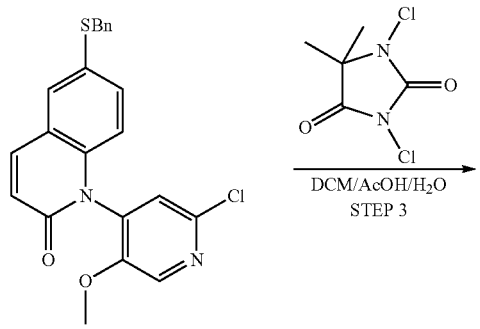

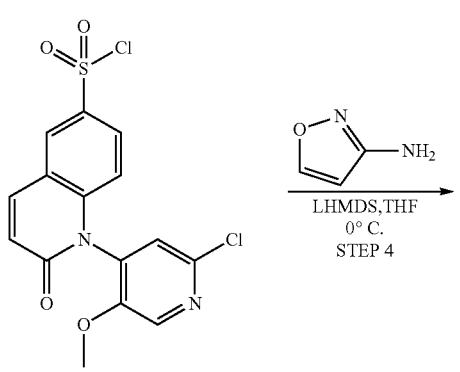

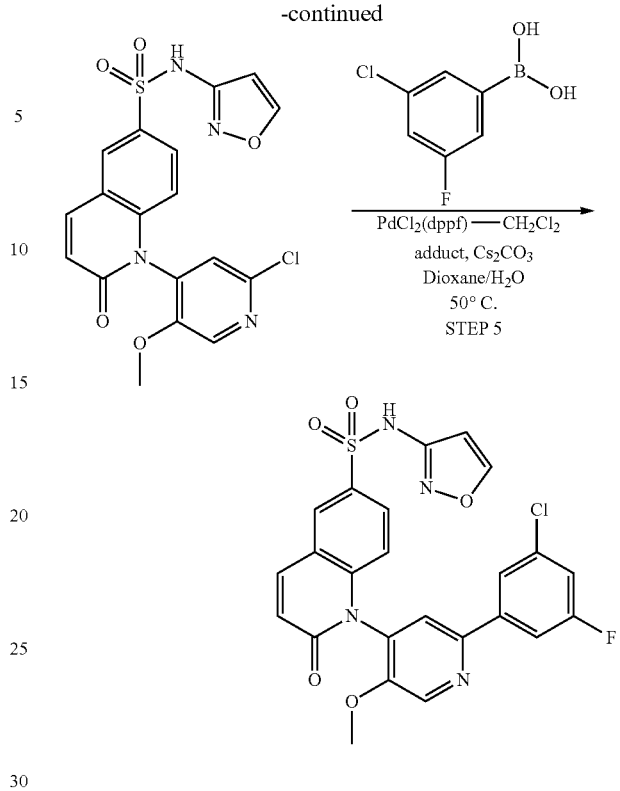

Step 1: (E)-ethyl 3-(5-(benzylthio)-2-((2-chloro-5-methoxypyridin-4-yl)amino)phenyl)acrylate (E)-ethyl 3-(5-(benzylthio)-2-((2-chloro-5-methoxypyridin-4-yl)amino)phenyl)acrylate was synthesized in a manner similar to Step 1 in Method 157, using 4-bromo-2-chloro-5-methoxypyridine (Combi-Blocks) instead of 1-bromo-2-chloro-5-iodo-4-methoxybenzene. m/z (ESI) 455.2 (M+H)+.

Step 2: 6-(benzylthio)-1-(2-chloro-5-methoxypyridin-4-yl)quinolin-2(1H)-one 6-(Benzylthio)-1-(2-chloro-5-methoxypyridin-4-yl)quinolin-2(1H)-one was synthesized in a manner similar to Step 2 in Method 157. m/z (ESI) 409.2 (M+H)+.

Step 3: 1-(2-chloro-5-methoxypyridin-4-yl)-2-oxo-1,2-dihydroquinoline-6-sulfonyl chloride 1-(2-Chloro-5-methoxypyridin-4-yl)-2-oxo-1,2-dihydroquinoline-6-sulfonyl chloride was synthesized in a manner similar to Step 3 in Method 157. m/z (ESI) 385.0 (M+H)+.

Step 4: 1-(2-chloro-5-methoxy-4-pyridinyl)-N-3-isoxazolyl-2-oxo-1,2-dihydro-6-quinolinesulfonamide The title compound was synthesized in a manner similar to Step 4 in Method 157. m/z (ESI) 433.0 (M+H)+. ¹H NMR (400 MHz, DMSO-d$_6$) δ ppm 3.80-3.83 (m, 3H) 6.45 (d, J=1.76 Hz, 1H) 6.82 (d, J=9.74 Hz, 1H) 6.90 (d, J=9.02 Hz, 1H) 7.76 (s, 1H) 7.84 (dd, J=8.97, 2.23 Hz, 1H) 8.25 (d, J=9.54 Hz, 1H) 8.39 (d, J=2.18 Hz, 1H) 8.53 (s, 1H) 8.74 (d, J=1.76 Hz, 1H) 11.68 (s, 1H).

Step 5: 1-(2-(3-chloro-5-fluorophenyl)-5-methoxy-pyridin-4-yl)-N-(isoxazol-3-yl)-2-oxo-1,2-dihydro-quinoline-6-sulfonamide 1-(2-Chloro-5-methoxy-4-pyridinyl)-N-3-isoxazolyl-2-oxo-1,2-dihydro-6-quinolinesulfonamide (0.100 g, 0.231 mmol), (3-chloro-5-fluorophenyl)boronic acid (0.081 g, 0.462 mmol), PdCl$_2$(dppf)-CH$_2$Cl$_2$ adduct (0.038 g, 0.046 mmol), and cesium carbonate (0.301 g, 0.924 mmol) were combined in a mixture of 1,4-dioxane (0.616 ml) and water (0.154 ml) and the reaction mixture was heated to 50° C. overnight. The reaction was diluted with ethyl acetate and 1N HCl was added. The layers were separated, and the aqueous was washed (×2) with ethyl acetate. The combined organics were dried over magnesium sulfate, filtered and concentrated in vacuo. The crude material was purified by reverse-phase preparative HPLC (XBridge Prep C18 OBD column, 10 micron, 19×100 mm) 0.1% TFA in CH$_3$CN/H$_2$O, gradient 25% to 95% over 12 min to provide 1-(2-(3-chloro-5-fluorophenyl)-5-methoxypyridin-4-yl)-N-(isoxazol-3-yl)-2-oxo-1,2-dihydroquinoline-6-sulfonamide (0.034 g, 0.065 mmol, 27.9% yield) as an off-white solid. m/z (ESI) 527.0 (M+H)+. $^1$H NMR (400 MHz, DMSO-d$_6$) δ ppm 3.89 (s, 3H) 6.45 (d, J=1.87 Hz, 1H) 6.85 (d, J=9.64 Hz, 1H) 6.91 (d, J=9.02 Hz, 1H) 7.45-7.50 (m, 1H) 7.84 (dd, J=8.91, 2.18 Hz, 1H) 7.88-7.93 (m, 1H) 8.02 (t, J=1.55 Hz, 1H) 8.27-8.32 (m, 2H) 8.42 (d, J=2.18 Hz, 1H) 8.73 (d, J=1.76 Hz, 1H) 8.81 (s, 1H) 11.68 (s, 1H).

Example 619

(Method 162): (P)-1-(3',4'-difluoro-3-methoxy-4-biphenylyl)-N-(5-fluoro-2-pyrimidinyl)-2-oxo-1,2-dihydro-6-quinolinesulfonamide

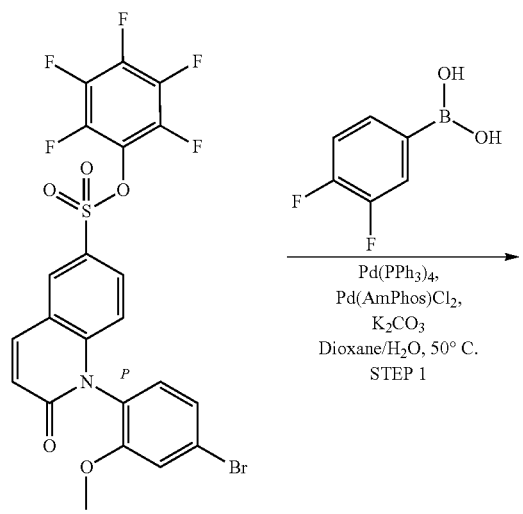

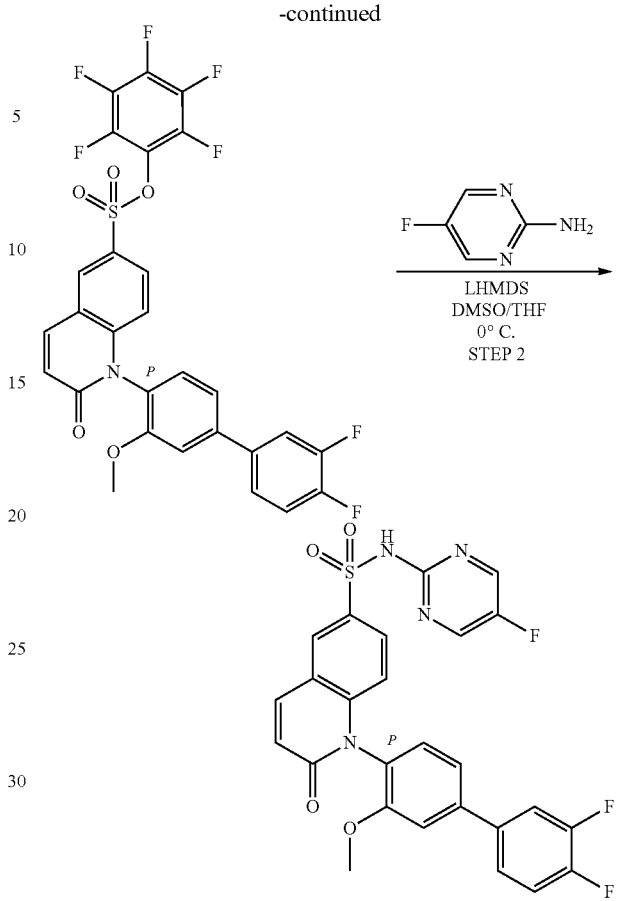

Step 1: Perfluorophenyl (P)-1-(3',4'-difluoro-3-methoxy-[1,1'-biphenyl]-4-yl)-2-oxo-1,2-dihydro-quinoline-6-sulfonate (P)-perfluorophenyl 1-(4-bromo-2-methoxyphenyl)-2-oxo-1,2-dihydroquinoline-6-sulfonate (5.41 g, 9.39 mmol), (3,4-difluorophenyl)boronic acid (1.631 g, 10.33 mmol), potassium carbonate (3.89 g, 28.2 mmol), and Pd(PPh$_3$)$_4$ (1.085 g, 0.939 mmol) were combined in 1,4-dioxane (35.2 ml) and water (11.73 ml). The reaction was heated to 50° C. overnight. About 60% conversion was observed by LC/MS, so Pd(AmPhos)Cl$_2$ (0.665 g, 0.939 mmol) was added and heating continued for 2 h. The reaction was cooled to RT and sat. aq. ammonium chloride solution (to pH neutral) was added. The product was extracted with DCM (×3), dried via phase separator and concentrated in vacuo. The crude material was purified via MPLC, eluting with 0-100% ethyl acetate in heptanes (with a 10% DCM additive) to yield impure product as a dark brown oily solid. The material was then dissolved in DCM and loaded onto a 70-g SCX column. (P)-perfluorophenyl 1-(3',4'-difluoro-3-methoxy-[1,1'-biphenyl]-4-yl)-2-oxo-1,2-dihydroquinoline-6-sulfonate eluted off with the methanol wash as a light yellow solid after concentration in vacuo. m/z (ESI) 527.0 (M+H)+.

Step 2: 1-(3',4'-difluoro-3-methoxy-4-biphenylyl)-N-(5-fluoro-2-pyrimidinyl)-2-oxo-1,2-dihydro-6-quinolinesulfonamide 5-Fluoropyrimidin-2-amine (0.060 g, 0.533 mmol) was dissolved in dimethyl sulfoxide (1.025 ml), and (P)-perfluorophenyl 1-(3',4'-difluoro-3-methoxy-[1,1'-biphenyl]-4-yl)-2-oxo-1,2-dihydroquinoline-6-sulfonate (0.250 g, 0.410 mmol) in tetrahydrofuran (3.08 ml) was added as a solution. The resulting reaction was cooled to 0° C. and LHMDS, 1.0M in THF (0.943 ml, 0.943 mmol) was added drop wise. After 10 minutes, the reaction mixture was diluted with EtOAc and 1N HCl (aq). The layers were separated, and the aqueous was washed (×1) with EtOAc. The combined organics were dried over magnesium sulfate, filtered and concentrated in vacuo. The crude material was loaded onto a 2-g SCX-2 column, eluting with the methanol wash to yield impure material. The crude material was further purified by reverse-phase preparative HPLC (XBridge Prep C18 column, 10 micron OBD, 19×100 mm) 0.1% TFA in CH₃CN/H₂O, gradient 25% to 95% over 12 min to provide (P)-1-(3',4'-difluoro-3-methoxy-[1,1'-biphenyl]-4-yl)-N-(5-fluoropyrimidin-2-yl)-2-oxo-1,2-dihydroquinoline-6-sulfonamide as a light-yellow solid. To quantify the ae %, a small sample of product (in DMSO) was heated to 100° C. overnight; method developed on racemate—Whelk-O (S,S) 40% methanol. Sample contains 7.6% minor atropisomer (ee~85%). m/z (ESI) 539.0 (M+H)+. ¹H NMR (400 MHz, DMSO-d₆) δ ppm 3.77 (s, 3H) 6.77 (d, J=9.02 Hz, 1H) 6.80 (d, J=9.64 Hz, 1H) 7.39 (d, J=8.09 Hz, 1H) 7.45-7.49 (m, 1H) 7.55-7.62 (m, 2H) 7.68-7.73 (m, 1H) 7.94-8.01 (m, 2H) 8.25 (d, J=9.43 Hz, 1H) 8.47 (d, J=2.18 Hz, 1H) 8.62 (d, J=0.73 Hz, 2H) 11.96 (s, 1H)

Example 620

(Method 163): N-3-isoxazolyl-1-(2-methoxy-5-(tetrahydro-2H-pyran-4-yl)phenyl)-2-oxo-1,2-dihydro-6-quinolinesulfonamide

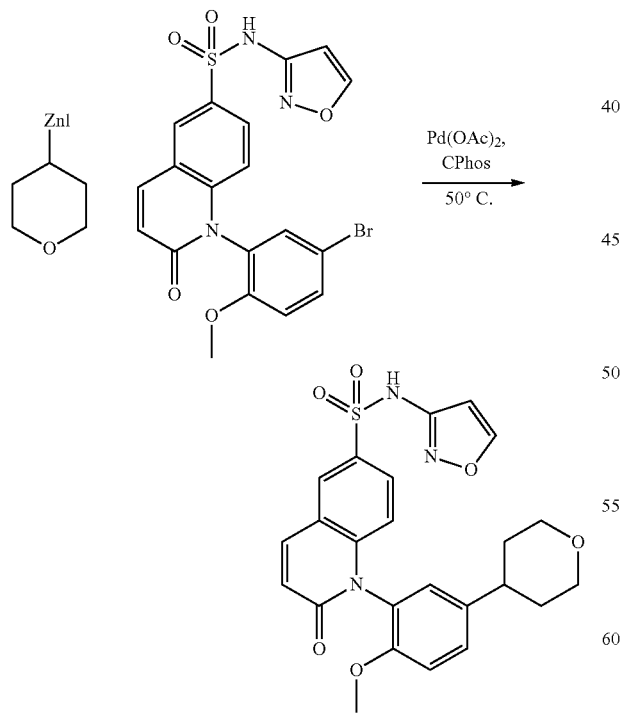

A vial was charged with palladium(ii) acetate (2.83 mg, 0.013 mmol), CPhos (0.011 g, 0.025 mmol) and 1-(5-bromo-2-methoxyphenyl)-N-(isoxazol-3-yl)-2-oxo-1,2-dihydroquinoline-6-sulfonamide (0.100 g, 0.210 mmol). (Tetrahydro-2H-pyran-4-yl)zinc(II) iodide (0.26M in THF) (2.423 ml, 0.630 mmol) was added and the reaction was stirred at 50° C. for 1 h. The reaction was diluted with ethyl acetate and washed (×2) with 1N HCl solution. The organics were washed with brine, dried over sodium sulfate, filtered and concentrated in vacuo. The crude material was purified by reverse-phase preparative HPLC using an XBridge Prep C18 column, 10 micron OBD, 19×100 mm, 0.1% TFA in CH₃CN/H₂O, gradient 25% to 95% over 12 min to provide N-(isoxazol-3-yl)-1-(2-methoxy-5-(tetrahydro-2H-pyran-4-yl)phenyl)-2-oxo-1,2-dihydroquinoline-6-sulfonamide (0.039 g, 0.081 mmol, 38.6% yield) as a white solid. m/z (ESI) 482.2 (M+H)+.

Example 621

(Method 164): Tert-butyl 2-(3-(6-(N-(isoxazol-3-yl)sulfamoyl)-2-oxoquinolin-1 (2H)-yl)-4-methoxyphenyl)acetate

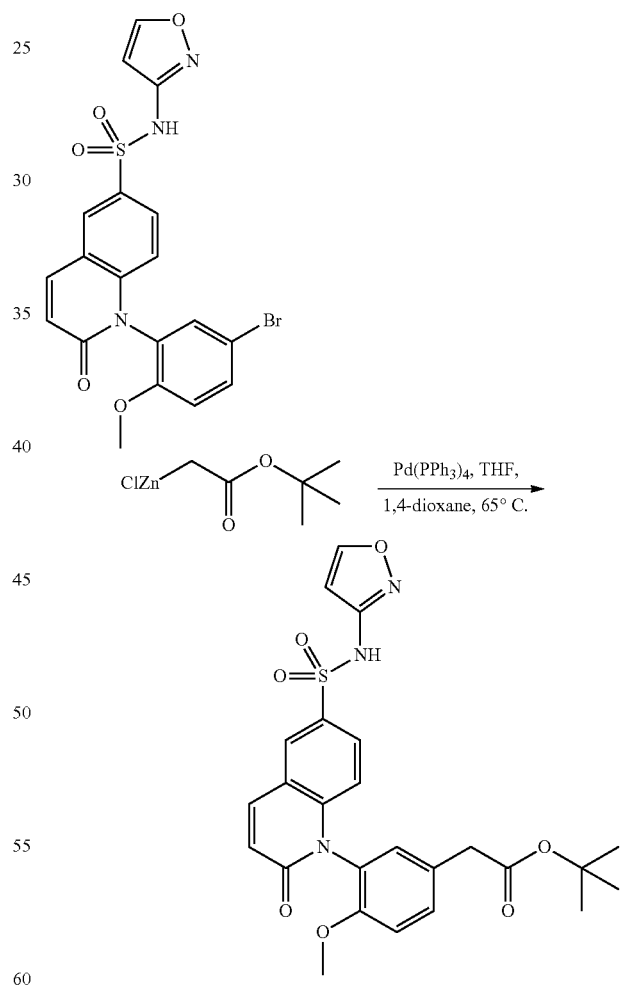

To a heterogeneous solution of 1-(5-bromo-2-methoxyphenyl)-N-(isoxazol-3-yl)-2-oxo-1,2-dihydroquinoline-6-sulfonamide (0.075 g, 0.157 mmol) in 1,4-dioxane (0.394 ml) and THF (0.394 ml) was added palladiumtetrakis (0.018 g, 0.016 mmol) followed by (2-(tert-butoxy)-2-oxoethyl)zinc(II) chloride (0.5 M solution in ether) (0.630 ml, 0.315 mmol). The resulting solution was heated to 65° C. and stirred overnight. After 2 days, minor conversion to desired product was observed by LCMS. Additional palladiumtetrakis (0.018 g, 0.016 mmol) and (2-(tert-butoxy)-2-oxoethyl)zinc(II) chloride (0.5 M solution in ether) (0.630 ml, 0.315 mmol) was added and the reaction temperature was increased to 80° C. This mixture was stirred overnight and cooled to room temperature. The solution was then dissolved in 1.5 ml of DMSO and passed through a 0.20 micron filter. An additional 0.5 ml was used to rinse the reaction vial and the solution was passed through the same filter. The resulting DMSO solution was purified by reverse-phase HPLC (Waters XBridge Prep Shield RP18 10 μm OBD 19×100 mm) gradient, 5 to 30% MeCN in water (containing 0.1% trifluoroacetic acid as an additive), flow rate 40 mL/min to yield tert-butyl 2-(3-(6-(N-(isoxazol-3-yl)sulfamoyl)-2-oxoquinolin-1(2H)-yl)-4-methoxyphenyl)acetate (5.1 mgs, 6.3% yield). 1H NMR (500 MHz, DMSO-d6)=ppm 1.32-1.42 (m, 10H) 3.51-3.60 (m, 3H) 3.65 (s, 3H) 3.70 (br. s., 2H) 6.41 (br. s., 1H) 6.65 (d, J=8.10 Hz, 1H) 6.78 (d, J=9.80 Hz, 1H) 6.97 (br. s., 1H) 7.07 (br. s., 1H) 7.15 (s, 2H) 7.24 (d, J=8.63 Hz, 1H) 7.42 (d, J=8.26 Hz, 1H) 7.80 (d, J=8.64 Hz, 1H) 8.19 (d, J=9.67 Hz, 1H) 8.33 (br. s., 1H) 8.68 (br. s., 1H). m/z (ESI) 512.2 (M+H)$^+$.

Example 622

(Method 165): 1-(4'-chloro-5-(cyanomethoxy)-2-fluoro-3'-methyl-[1,1'-biphenyl]-4-yl)-N-(isoxazol-3-yl)-2-oxo-1,2-dihydroquinoline-6-sulfonamide To a solution of 1-(4-bromo-2-(cyanomethoxy)-5-fluorophenyl)-N-(isoxazol-3-yl)-2-oxo-1,2-dihydroquinoline-6-sulfonamide (0.020 g, 0.039 mmol) and (4-chloro-3-methylphenyl)boronic acid (9.84 mg, 0.058 mmol) in DMF (0.154 ml) and water (0.039 ml) was added potassium carbonate (0.016 g, 0.116 mmol) followed by PdCl$_2$dppf, DCM adduct (1.409 mg, 1.926 μmol). The resulting mixture was heated to 50° C. and stirred for 3.5 hours. The solution was then cooled to RT, dissolved in 1.5 ml of DMSO and passed through a 0.20 micron filter. An additional 0.5 ml was used to rinse the reaction vial and the solution was passed through the same filter. The resulting DMSO solution was purified by reverse-phase HPLC (Waters XBridge Prep Shield RP18 10 μm OBD 19×100 mm) gradient, 30 to 95% MeCN in water (containing 0.1% trifluoroacetic acid as an additive), flow rate 40 mL/min to yield 1-(4'-chloro-5-(cyanomethoxy)-2-fluoro-3'-methyl-[1,1'-biphenyl]-4-yl)-N-(isoxazol-3-yl)-2-oxo-1,2-dihydroquinoline-6-sulfonamide (5.7 mgs, 26% yield). $^1$H NMR (500 MHz, DMSO-d6)=ppm 2.45 (s, 3H) 5.17-5.27 (m, 2H) 6.79-6.91 (m, 1H) 7.00 (br. s., 1H) 7.10 (br. s., 1H) 7.20 (br. s., 1H) 7.54 (d, J=8.04 Hz, 2H) 7.58-7.66 (m, 2H) 7.69 (br. s., 1H) 7.87 (d, J=8.89 Hz, 1H) 8.25 (d, J=7.98 Hz, 1H) 8.39 (s, 1H) 8.72 (s, 1H). m/z (ESI) 565.0 (M+H)$^+$.

Example 623

(Method 166): 1-(4-bromo-2-(cyanomethoxy)-5-fluorophenyl)-N-(isoxazol-3-yl)-2-oxo-1,2-dihydroquinoline-6-sulfonamide

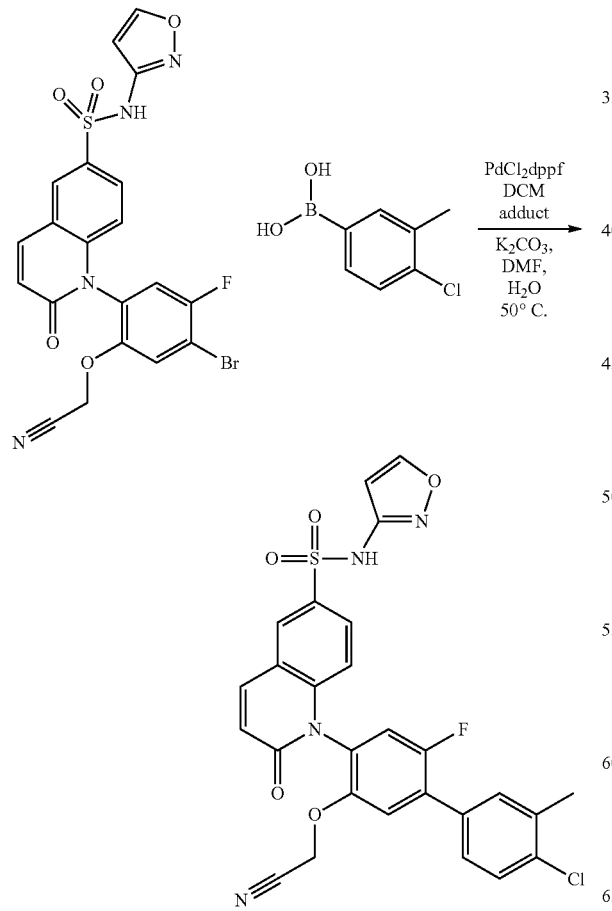

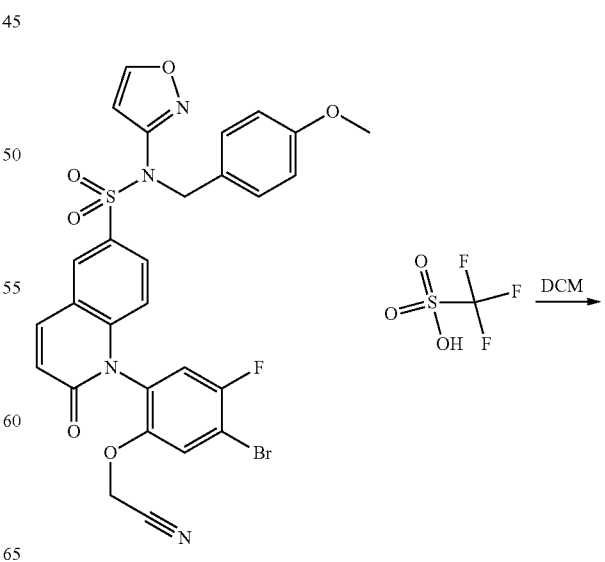

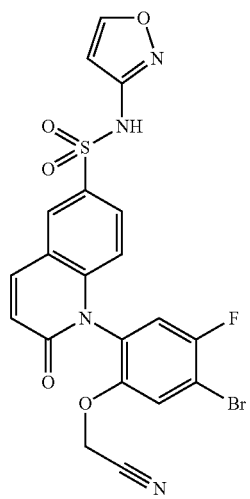

To a solution of 1-(4-bromo-2-(cyanomethoxy)-5-fluorophenyl)-N-(isoxazol-3-yl)-N-(4-methoxybenzyl)-2-oxo-1,2-dihydroquinoline-6-sulfonamide (53.1 mg, 0.083 mmol) in DCM (830 μl) at RT was added trifluoromethanesulfonic acid (22.11 μl, 0.249 mmol). The resulting solution was stirred for 2.5 hours and LCMS indicated that the reaction had not proceeded. Additional 0.010 mL was then added and the resulting mixture stirred for 16 hr. The reaction mixture was concentrated by sending a stream of $N_2$ gas into the uncapped reaction vial. The residue was then dissolved in 1 ml of DMSO and 0.050 mL of saturated $NaHCO_3$ was added and the resulting mixture was stirred for 5 minutes. The solution was then passed through a 0.20 micron filter. An additional 0.5 ml was used to rinse the reaction vial and the solution was passed through the same filter. The DMSO solution was purified by reverse-phase HPLC (Waters XBridge Prep Shield RP18 10 μm OBD 19×100 mm) gradient, 5 to 30% MeCN in water (containing 0.1% ammonium hydroxide as an additive), flow rate 40 mL/min to yield 1-(4-bromo-2-(cyanomethoxy)-5-fluorophenyl)-N-(isoxazol-3-yl)-2-oxo-1,2-dihydroquinoline-6-sulfonamide (5.2 mgs, 12% yield). $^1$H NMR (500 MHz, DMSO-d6)=ppm 5.13-5.22 (m, 2H) 6.22 (s, 1H) 6.73 (dd, J=9.21, 4.41 Hz, 2H) 7.70 (d, J=8.56 Hz, 1H) 7.75 (dd, J=8.92, 1.85 Hz, 1H) 7.89 (d, J=6.10 Hz, 1H) 8.18 (d, J=9.27 Hz, 1H) 8.20-8.23 (m, 1H) 8.37 (s, 1H). m/z (ESI) 518.9 (M+H)$^+$.

Example 624

(Method 167): N-(isoxazol-3-yl)-2-oxo-1-(2,3',5'-trifluoro-5-hydroxy-[1,1'-biphenyl]-4-yl)-1,2-dihydroquinoline-6-sulfonamide

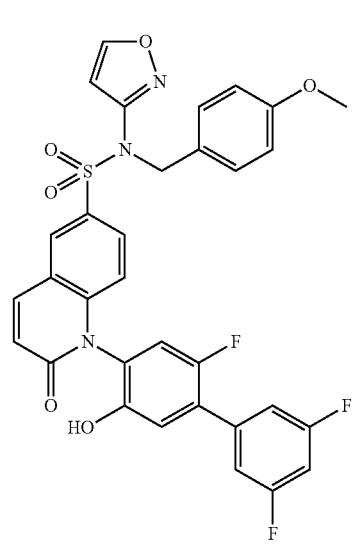
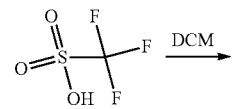
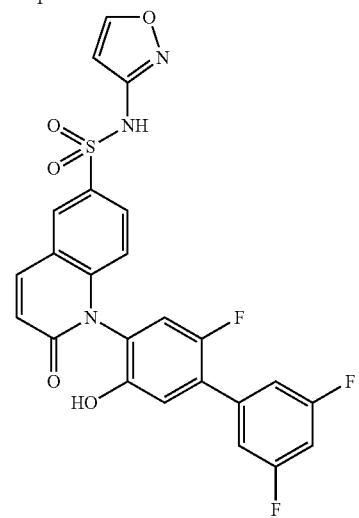

To a solution of N-(isoxazol-3-yl)-N-(4-methoxybenzyl)-2-oxo-1-(2,3',5'-trifluoro-5-hydroxy-[1,1'-biphenyl]-4-yl)-1,2-dihydroquinoline-6-sulfonamide (39.3 mg, 0.062 mmol) in DCM (620 μl) at room temperature was added trifluoromethanesulfonic acid (16.52 μl, 0.186 mmol). The resulting solution was stirred for 1 hour. The solution was then dissolved in 1.5 ml of DMSO and passed through a 0.20 micron filter. An additional 0.5 ml was used to rinse the reaction vial and the solution was passed through the same filter. The resulting DMSO solution was purified by reverse-phase HPLC (Waters XBridge Prep Shield RP18 10 μm OBD 19×100 mm) gradient, 5 to 50% MeCN in water (containing 0.1% ammonium hydroxide as an additive), flow rate 40 mL/min to yield N-(isoxazol-3-yl)-2-oxo-1-(2,3',5'-trifluoro-5-hydroxy-[1,1'-biphenyl]-4-yl)-1,2-dihydroquinoline-6-sulfonamide (10.2 mgs, 32% yield over two steps). $^1$H NMR (500 MHz, DMSO-d6)=ppm 6.37 (s, 1H) 6.78 (d, J=9.17 Hz, 1H) 6.83 (d, J=8.45 Hz, 1H) 7.17 (d, J=7.20 Hz, 1H) 7.30-7.43 (m, 4H) 7.84 (dd, J=8.95, 2.01 Hz, 1H) 8.19

(d, J=7.88 Hz, 1H) 8.31 (s, J=8.04 Hz, 1H) 8.59 (s, 1H) 10.06 (br. s., 1H). m/z (ESI) 513.9 (M+H)+.

Example 625

(Method 168): 1-(4-bromo-5-fluoro-2-(pyrrolidin-3-yloxy)phenyl)-N-(isoxazol-3-yl)-2-oxo-1,2-dihydroquinoline-6-sulfonamide

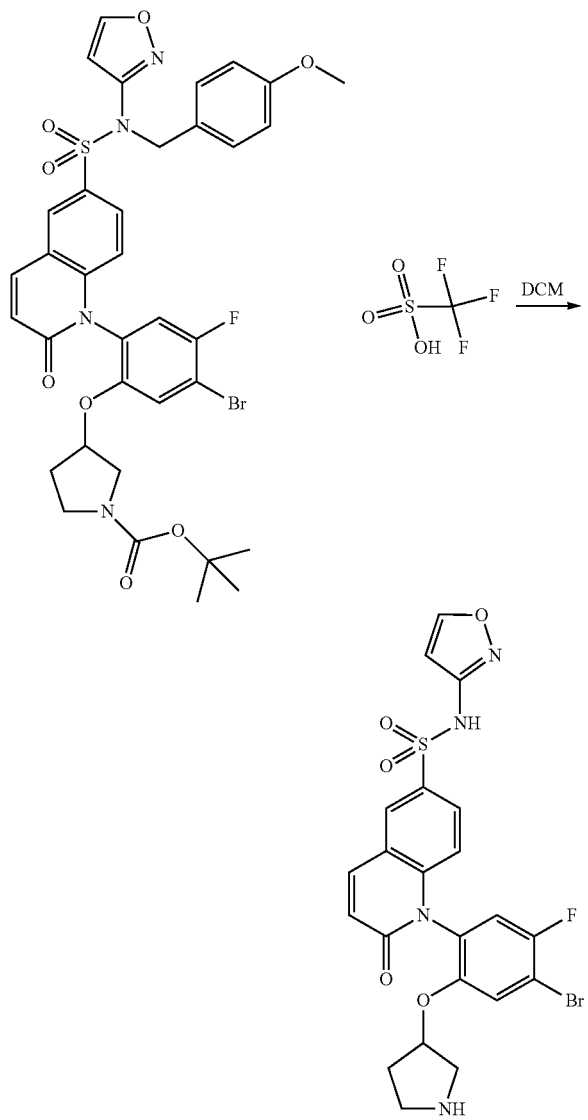

To a solution of tert-butyl 3-(5-bromo-4-fluoro-2-(6-(N-(isoxazol-3-yl)-N-(4-methoxybenzyl)sulfamoyl)-2-oxoquinolin-1(2H)-yl)phenoxy)pyrrolidine-1-carboxylate (74.7 mg, 0.097 mmol) in DCM (970 µl) at RT was added trifluoromethanesulfonic acid (25.8 µl, 0.291 mmol). The resulting solution was stirred overnight. LCMS indicated that the reaction was not complete. 0.012 mL of triflic acid was added and the solution stirred 16 hr. LCMS indicated that product was generated but there was a significant amount of PMB protected material. Another equivalent of triflic acid was added and the resulting solution was stirred for 48 hr. The reaction mixture was concentrated by sending a stream of N2 gas into the uncapped reaction vial. The residue was then dissolved in 1 ml of DMSO and 0.050 mL of saturated NaHCO3 was added and the mixture stirred for 5 minutes. The solution was then passed through a 0.20 micron filter. An additional 0.5 ml was used to rinse the reaction vial and the solution was passed through the same filter. The DMSO solution was purified by reverse-phase HPLC (Waters XBridge Prep Shield RP18 10 µm OBD 19×100 mm) gradient, 5 to 30% MeCN in water (containing 0.1% ammonium hydroxide as an additive), flow rate 40 mL/min to yield 1-(4-bromo-5-fluoro-2-(pyrrolidin-3-yloxy)phenyl)-N-(isoxazol-3-yl)-2-oxo-1,2-dihydroquinoline-6-sulfonamide (5.5 mgs, 10% yield for two steps). 1H NMR (500 MHz, DMSO-d6) δ=ppm 1.22-1.36 (m, 1H) 1.82-2.01 (m, 2H) 2.61-2.81 (m, 1H) 2.84-3.06 (m, 2H) 3.30 (br. s., 7H) 5.13 (br. s., 1H) 6.09 (d, J=11.67 Hz, 1H) 6.61-6.71 (m, 2H) 7.60 (t, J=8.19 Hz, 1H) 7.71 (t, J=8.01 Hz, 1H) 7.78 (t, J=7.13 Hz, 1H) 8.07-8.18 (m, 3H). m/z (ESI) 548.8.

Example 626

(Method 173): (P)-1-(4'-chloro-3-methoxy-4-biphenylyl)-N-3-isoxazolyl-2-oxo-1,2-dihydro-6-quinolinesulfonamide

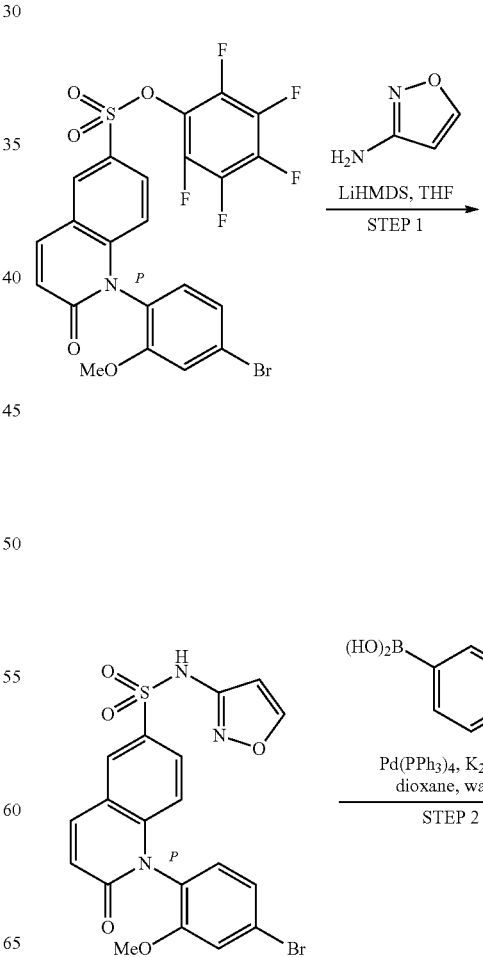

-continued

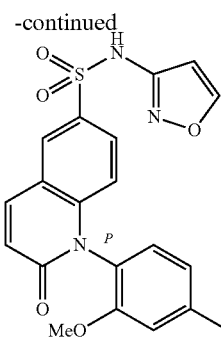

Step 1: (P)-1-(4-bromo-2-methoxyphenyl)-N-(isoxazol-3-yl)-2-oxo-1,2-dihydroquinoline-6-sulfonamide A solution of 3-aminoisoxazole (0.494 ml, 6.68 mmol) and (P)-perfluorophenyl 1-(4-bromo-2-methoxyphenyl)-2-oxo-1,2-dihydroquinoline-6-sulfonate (3.500 g, 6.07 mmol) in 50 mL THF, was cooled to 0° C. LHMDS 1N in THF (12.75 ml, 12.75 mmol) was added dropwise. After stirring for an hour, the reaction mixture was poured into 1N HCl and was extracted with DCM. The organics were dried over $MgSO_4$ and concentrated yielding (P)-1-(4-bromo-2-methoxyphenyl)-N-(isoxazol-3-yl)-2-oxo-1,2-dihydroquinoline-6-sulfonamide (4.30 g, 9.03 mmol, 149% yield) with minor impurities. m/z (ESI) 476.1 (M+H)$^+$.

Step 2: (P)-1-(4'-chloro-3-methoxy-4-biphenylyl)-N-3-isoxazolyl-2-oxo-1,2-dihydro-6-quinolinesulfonamide A vial charged with Pd(PPh3)4 (74.5 mg, 0.064 mmol), (4-chlorophenyl)boronic acid (198 mg, 1.289 mmol), (P)-1-(4-bromo-2-methoxyphenyl)-N-(isoxazol-3-yl)-2-oxo-1,2-dihydroquinoline-6-sulfonamide (307 mg, 0.645 mmol), potassium carbonate (356 mg, 2.58 mmol) and 3 mL dioxane 1 mL water was heated to 50° C. for 4 hours. The reaction mixture was allowed to cool to RT and HCl 4N in dioxane (1611 µl, 6.45 mmol) was added. The reaction mixture was then concentrated. Purification of the crude residue by reverse phase column chromatography [puriflash C18, 10-100% (0.1% $NH_4OH$ in MeOH)/(0.1% $NH_4OH$ in water)] gave (P)-1-(4'-CHLORO-3-METHOXY-4-BIPHENYLYL)-N-3-ISOXAZOLYL-2-OXO-1,2-DIHYDRO-6-QUINOLINESULFONAMIDE (0.017 g, 0.033 mmol, 10.6%). $^1$H NMR (ACETONITRILE-d3) δ: 8.37 (d, J=1.9 Hz, 1H), 8.26 (d, J=2.2 Hz, 1H), 7.99 (d, J=9.4 Hz, 1H), 7.73-7.83 (m, 3H), 7.49-7.59 (m, 2H), 7.45 (s, 1H), 7.40-7.43 (m, 1H), 7.31 (d, J=8.1 Hz, 1H), 6.70-6.85 (m, 2H), 6.46 (d, J=1.9 Hz, 1H), 3.77 (s, 3H). m/z (ESI) 508.1 (M+H)$^+$.

Example 627 (3142240)

(Method 174): (P)-1-(4'-chloro-3,3'-dimethoxy-4-biphenylyl)-2-oxo-N-2-pyrimidinyl-1,2-dihydro-6-quinolinesulfonamide

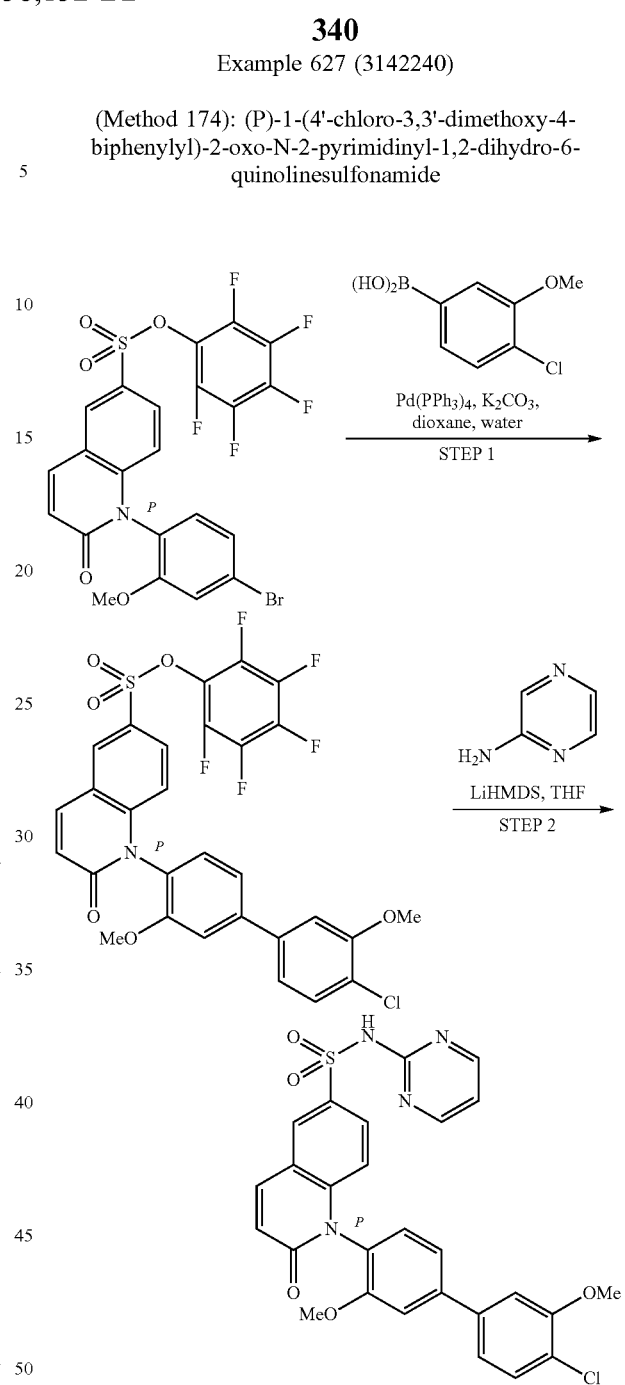

Step 1: (P)-perfluorophenyl 1-(4'-chloro-3,3'-dimethoxy-[1,1'-biphenyl]-4-yl)-2-oxo-1,2-dihydroquinoline-6-sulfonate A solution of Pd(Ph3P)4 (0.201 g, 0.174 mmol), (4-chloro-3-methoxyphenyl)boronic acid (0.356 g, 1.909 mmol), (P)-perfluorophenyl 1-(4-bromo-2-methoxyphenyl)-2-oxo-1,2-dihydroquinoline-6-sulfonate (1.000 g, 1.735 mmol), and potassium carbonate (0.959 g, 6.94 mmol) in 6 ml dioxane 2 mL water was heated to 50° C. for 3 hours. The reaction mixture was then diluted with DCM and washed with water. The organics were dried over $MgSO_4$ and concentrated. Purification of the crude residue by silica gel column chromatography (0-70% EtOAc/heptane) gave (P)-perfluorophenyl 1-(4'-chloro-3,3'-dimethoxy-[1,1'-biphenyl]-4-yl)-2-oxo-1,2-dihydroquinoline-6-sulfonate (0.600 g, 0.941 mmol, 54.2% yield). m/z (ESI) 638.0 (M+H)⁺.

Step 2: (P)-1-(4'-chloro-3,3'-dimethoxy-4-biphenylyl)-2-oxo-N-2-pyrimidinyl-1,2-dihydro-6-quinolinesulfonamide A solution of pyrimidin-2-amine (0.056 g, 0.588 mmol) and (P)-perfluorophenyl 1-(4'-chloro-3,3'-dimethoxy-[1,1'-biphenyl]-4-yl)-2-oxo-1,2-dihydroquinoline-6-sulfonate (0.125 g, 0.196 mmol) in 3 mL THF was cooled to 0° C. and was treated with LHMDS 1N in THF (0.490 ml, 0.490 mmol). The cooling bath was removed and the reaction mixture was allowed to stir for one hour. TFA (0.151 ml, 1.959 mmol) was added, and the reaction mixture was concentrated. Purification of the crude residue by reverse phase column chromatography [Puriflash C18, 10-100% (0.1% NH4OH in MeOH)/(0.1% NH4OH in water)] gave 1-(4'-chloro-3,3'-dimethoxy-[1,1'-biphenyl]-4-yl)-2-oxo-N-(pyrimidin-2-yl)-1,2-dihydroquinoline-6-sulfonamide (0.067 g, 0.122 mmol, 62.3% yield). $^1$H NMR (ACETONITRILE-d3) δ: 8.40-8.46 (m, 3H), 7.96-8.05 (m, 2H), 7.42-7.52 (m, 4H), 7.28-7.35 (m, 2H), 6.95 (t, J=4.9 Hz, 1H), 6.72-6.80 (m, 2H), 4.00 (s, 3H), 3.77 (s, 3H). m/z (ESI) 549.0 (M+H)⁺.

Example 628

(Method 175): (P)-1-(4'-chloro-2-fluoro-3',5-dimethoxy-4-biphenylyl)-2-oxo-N-3-pyridazinyl-1,2-dihydro-6-quinolinesulfonamide

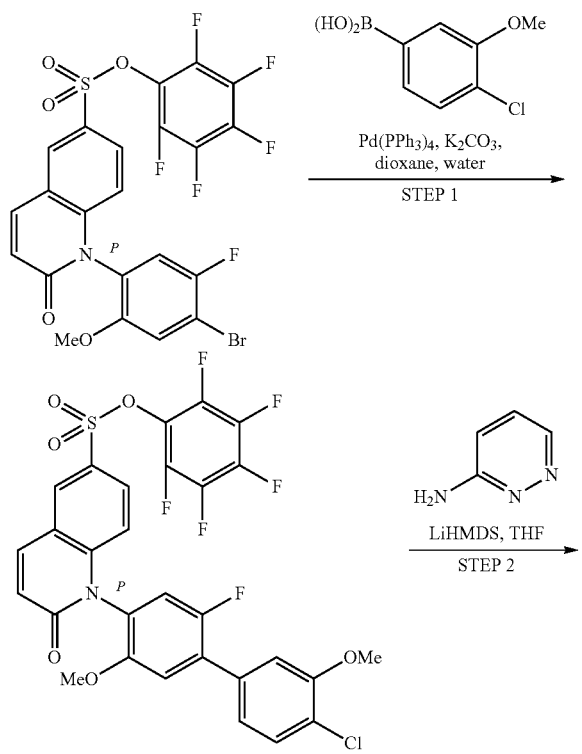

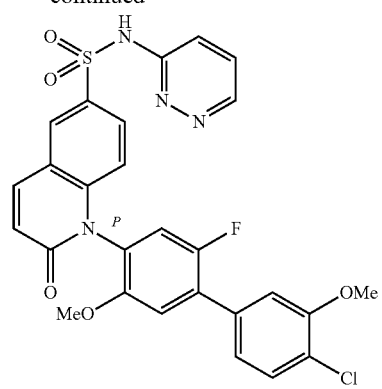

Step 1: (P)-perfluorophenyl 1-(4'-chloro-2-fluoro-3',5-dimethoxy-[1,1'-biphenyl]-4-yl)-2-oxo-1,2-dihydroquinoline-6-sulfonate A solution of Pd(Ph₃P)₄ (0.194 g, 0.168 mmol), (4-chloro-3-methoxyphenyl)boronic acid (0.345 g, 1.851 mmol), (P)-perfluorophenyl 1-(4-bromo-5-fluoro-2-methoxyphenyl)-2-oxo-1,2-dihydroquinoline-6-sulfonate (1.000 g, 1.683 mmol), and potassium carbonate (0.930 g, 6.73 mmol) in 6 ml dioxane 2 mL water was heated to 50° C. for 3 hours. The reaction mixture was diluted with DCM and washed with water. The organics were dried over MgSO4 and concentrated. Purification of the crude residue by silica gel column chromatography (0-70% EtOAc/heptane) gave (P)-perfluorophenyl 1-(4'-chloro-2-fluoro-3',5-dimethoxy-[1,1'-biphenyl]-4-yl)-2-oxo-1,2-dihydroquinoline-6-sulfonate (0.468 g, 0.713 mmol, 42.4% yield). m/z (ESI) 656.0 (M+H)⁺.

Step 2: (P)-1-(4'-chloro-2-fluoro-3',5-dimethoxy-4-biphenylyl)-2-oxo-N-3-pyridazinyl-1,2-dihydro-6-quinolinesulfonamide A solution of 3-aminopyridazine (0.017 g, 0.175 mmol) and (P)-perfluorophenyl 1-(4'-chloro-2-fluoro-3',5-dimethoxy-[1,1'-biphenyl]-4-yl)-2-oxo-1,2-dihydroquinoline-6-sulfonate (0.115 g, 0.175 mmol) in 3 mL THF was cooled to 0° C. and was treated with LHMDS 1N in THF (0.351 ml, 0.351 mmol). The cooling bath was removed and the reaction mixture was allowed to stir for one hour. TFA (0.068 ml, 0.877 mmol) was added, and the reaction mixture was concentrated. Purification of the crude residue by reverse phase column chromatography [Puriflash C18, 10-100% (0.1% NH₄OH in MeOH)/(0.1% NH₄OH in water)] gave (P)-1-(4'-chloro-2-fluoro-3',5-dimethoxy-[1,1'-biphenyl]-4-yl)-2-oxo-N-(pyridazin-3-yl)-1,2-dihydroquinoline-6-sulfonamide (0.065 g, 0.115 mmol, 65.4% yield). $^1$H NMR (ACETONITRILE-d3) δ: 8.27 (d, J=2.2 Hz, 1H), 8.18 (dd, J=4.1, 1.5 Hz, 1H), 8.00 (d, J=9.6 Hz, 1H), 7.85 (dd, J=8.9, 2.1 Hz, 1H), 7.71 (dd, J=9.6, 1.5 Hz, 1H), 7.45-7.55 (m, 2H), 7.30-7.37 (m, 2H), 7.18-7.27 (m, 2H), 6.83 (d, J=8.8 Hz, 1H), 6.75 (d, J=9.6 Hz, 1H), 3.97 (s, 3H), 3.74 (s, 3H). m/z (ESI) 567.0 (M+H)⁺.

Example 629

(Method 176): (P)-1-(3-cyclopropyl-3',5'-difluoro-4-biphenylyl)-N-3-isoxazolyl-2-oxo-1,2-dihydro-6-quinolinesulfonamide

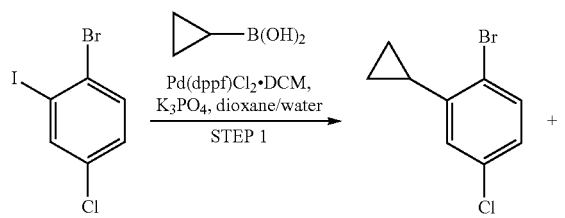

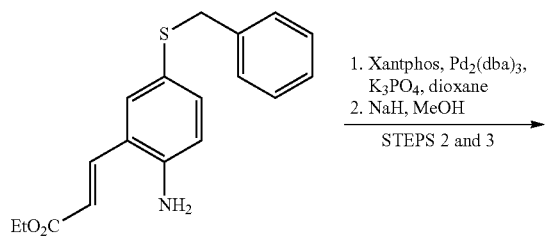

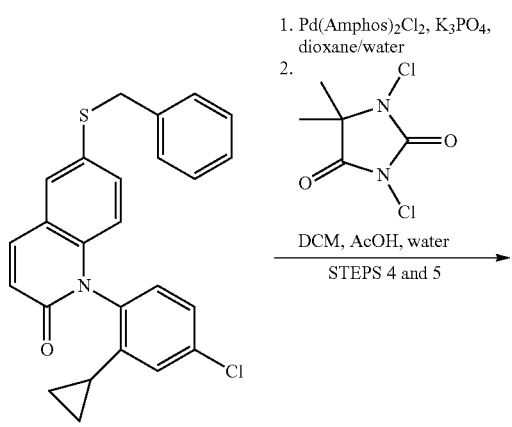

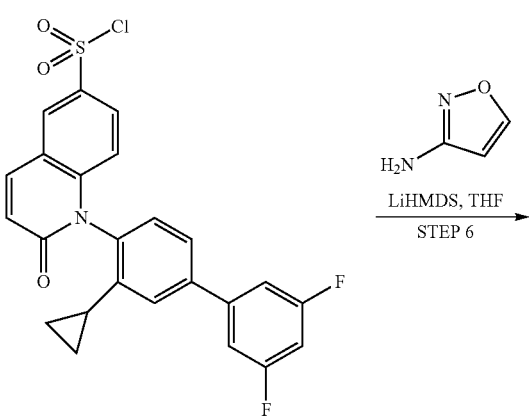

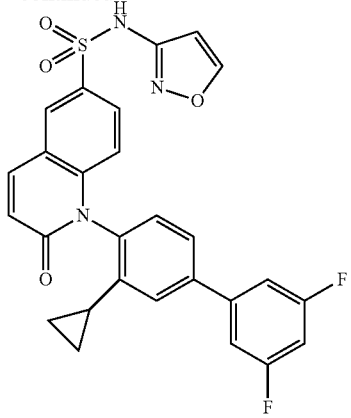

Step 1: 1-bromo-4-chloro-2-cyclopropylbenzene

A solution of cyclopropyl boronic acid (2.104 g, 24.49 mmol), 1-bromo-4-chloro-2-iodobenzene (5.700 g, 17.96 mmol), potassium phosphate (13.86 g, 65.3 mmol), and $PdCl_2$(dppf)-DCM adduct (0.667 g, 0.816 mmol) in 18 mL dioxane and 6 mL water was heated to 100° C. overnight. The reaction mixture was then diluted with DCM and washed with water. The organics were dried over $MgSO_4$ and concentrated. The crude residue was used in the next step without purification. m/z (ESI) does not ionize in H+ mode.

Step 2: (E)-ethyl 3-(5-(benzylthio)-2-((4-chloro-2-cyclopropylphenyl)amino)phenyl)acrylate The crude residue from the previous step was dissolved in 18 mL dioxane and was treated with xantphos (0.945 g, 1.633 mmol), pd2(dba)3 (0.374 g, 0.408 mmol), potassium phosphate (13.86 g, 65.3 mmol), and (E)-ethyl 3-(2-amino-5-(benzylthio)phenyl)acrylate (5.12 g, 16.33 mmol) and was heated to 100° C. overnight. The reaction mixture was then diluted with DCM and was washed with saturated $NH_4Cl$ solution. The organics were dried over MgSO4 and concentrated. The crude residue was used in the following step without purification. m/z (ESI) 464.2 $(M+H)^+$.

Step 3: 6-(benzylthio)-1-(4-chloro-2-cyclopropylphenyl)quinolin-2(1H)-one

The crude residue was dissolved in 18 mL MeOH and was cooled to 0° C. Sodium hydride 60% (1.306 g, 32.7 mmol) was added, and the reaction mixture was allowed to stir for 30 minutes. The reaction mixture was then heated to reflux overnight. The reaction mixture was poured into saturated $NH_4Cl$ solution and was extracted with DCM. The organics were dried over $MgSO_4$ and concentrated. Purification of the crude residue by silica gel column chromatography (0-70% EtOAc/heptane) gave 6-(benzylthio)-1-(4-chloro-2-cyclopropylphenyl)quinolin-2(1H)-one (3.03 g, 7.25 mmol, 44.4% yield). m/z (ESI) 418.2 $(M+H)^+$.

Step 4: 6-(benzylthio)-1-(3-cyclopropyl-3',5'-difluoro-[1,1'-biphenyl]-4-yl)quinolin-2(1H)-one A microwave vial charged with 1,1-bis[(di-t-butyl-p-methylaminophenyl]palladium(ii) chloride (0.254 g, 0.359 mmol), (3,5-difluorophenyl)boronic acid (1.133 g, 7.18 mmol), 6-(benzylthio)-1-(4-chloro-2-cyclopropylphenyl)quinolin-2(1H)-one (1.500 g, 3.59 mmol), potassium phosphate (2.285 g, 10.77 mmol) and 10 ml and dioxane 3 ml water was heated to 150° C. in a Biotage Initiator microwave reactor for 30 minutes. The organic layer was removed and concentrated. The crude residue was used in the following step without purification. m/z (ESI) 496.2 (M+H)+.

Step 5: 1-(3-cyclopropyl-3',5'-difluoro-[1,1'-biphenyl]-4-yl)-2-oxo-1,2-dihydroquinoline-6-sulfonyl chloride The crude residue from the previous step was dissolved in 10 mL DCM, was treated with 2 mL (1.5:1 HOAc/water) and was cooled to 0° C. 1,3-dichloro-5,5-dimethylhydantoin (0.943 ml, 7.18 mmol) was added and the cooling bath was removed. After stirring for 30 minutes, the reaction mixture was diluted with DCM and was dried over MgSO$_4$. The organics were then concentrated. The crude residue was purified by silica gel column chromatography (0-70% EtOAc/heptane) yielding 1-(3-cyclopropyl-3',5'-difluoro-[1,1'-biphenyl]-4-yl)-2-oxo-1,2-dihydroquinoline-6-sulfonyl chloride (1.58 g, 3.35 mmol, 93% yield) with minor impurities. m/z (ESI) 472.0 (M+H)+.

Step 6: 1-(3-cyclopropyl-3',5'-difluoro-[1,1'-biphenyl]-4-yl)-N-(isoxazol-3-yl)-2-oxo-1,2-dihydroquinoline-6-sulfonamide A solution of 3-aminoisoxazole (0.070 ml, 0.954 mmol) and 1-(3-cyclopropyl-3',5'-difluoro-[1,1'-biphenyl]-4-yl)-2-oxo-1,2-dihydroquinoline-6-sulfonyl chloride (0.150 g, 0.318 mmol) in 3 mL THF was cooled to 0° C. and was treated with LiHMDS 1N in THF (0.636 ml, 0.636 mmol). The cooling bath was removed and the reaction mixture was allowed to stir for one hour. TFA (0.122 ml, 1.589 mmol) was then added, and the reaction mixture was concentrated. Purification of the crude residue by reverse phase column chromatography [Puriflash C18, 10-100% (0.1% NH4OH in MeOH)/(0.1% NH4OH in water)] gave 1-(3-cyclopropyl-3',5'-difluoro-[1,1'-biphenyl]-4-yl)-N-(isoxazol-3-yl)-2-oxo-1,2-dihydroquinoline-6-sulfonamide (0.06, 0.115 mmol, 36.3% yield). m/z (ESI) 520.1 (M+H)+. The atropisomers were separated using supercritical fluid chromatography (SFC). The column used was Chiralpak OJ-H. The mobile phase was run under isocratic conditions; CO$_2$ with 25% Methanol to afford product as an off-white solid. First atropisomer (peak 1): (M)-1-(3-cyclopropyl-3',5'-difluoro-[1,1'-biphenyl]-4-yl)-N-(isoxazol-3-yl)-2-oxo-1,2-dihydroquinoline-6-sulfonamide (0.015 g, 0.029 mmol, 9.08% yield). $^1$H NMR (ACETONITRILE-d3): 8.22 (d, J=2.1 Hz, 1H), 8.17 (d, J=1.8 Hz, 1H), 8.01 (d, J=9.6 Hz, 1H), 7.80 (dd, J=8.9, 2.1 Hz, 1H), 7.65 (dd, J=8.2, 2.2 Hz, 1H), 7.35-7.42 (m, 3H), 7.30 (d, J=8.2 Hz, 1H), 6.95-7.04 (m, 1H), 6.76 (d, J=9.6 Hz, 1H), 6.66 (d, J=8.9 Hz, 1H), 6.30 (d, J=1.8 Hz, 1H), 1.42-1.53 (m, 1H), 0.69-0.88 (m, 2H), 0.51-0.65 (m, 2H). m/z (ESI) 472.0 (M+H)+. Second atropisomer (peak 2): (P)-1-(3-cyclopropyl-3',5'-difluoro-[1,1'-biphenyl]-4-yl)-N-(isoxazol-3-yl)-2-oxo-1,2-dihydroquinoline-6-sulfonamide (0.016 g, 0.031 mmol, 9.69% yield). $^1$H NMR (ACETONITRILE-d3): 8.22 (d, J=2.1 Hz, 1H), 8.17 (d, J=1.8 Hz, 1H), 8.01 (d, J=9.6 Hz, 1H), 7.80 (dd, J=8.9, 2.1 Hz, 1H), 7.65 (dd, J=8.2, 2.2 Hz, 1H), 7.35-7.42 (m, 3H), 7.30 (d, J=8.2 Hz, 1H), 6.95-7.04 (m, 1H), 6.76 (d, J=9.6 Hz, 1H), 6.66 (d, J=8.9 Hz, 1H), 6.30 (d, J=1.8 Hz, 1H), 1.42-1.53 (m, 1H), 0.69-0.88 (m, 2H), 0.51-0.65 (m, 2H). m/z (ESI) 520.2 (M+H)+.

Example 630

(Method 177): (P)-1-(5'-chloro-3-methoxy-2'-methyl-4-biphenylyl)-2-oxo-N-2-pyrimidinyl-1,2-dihydro-6-quinolinesulfonamide

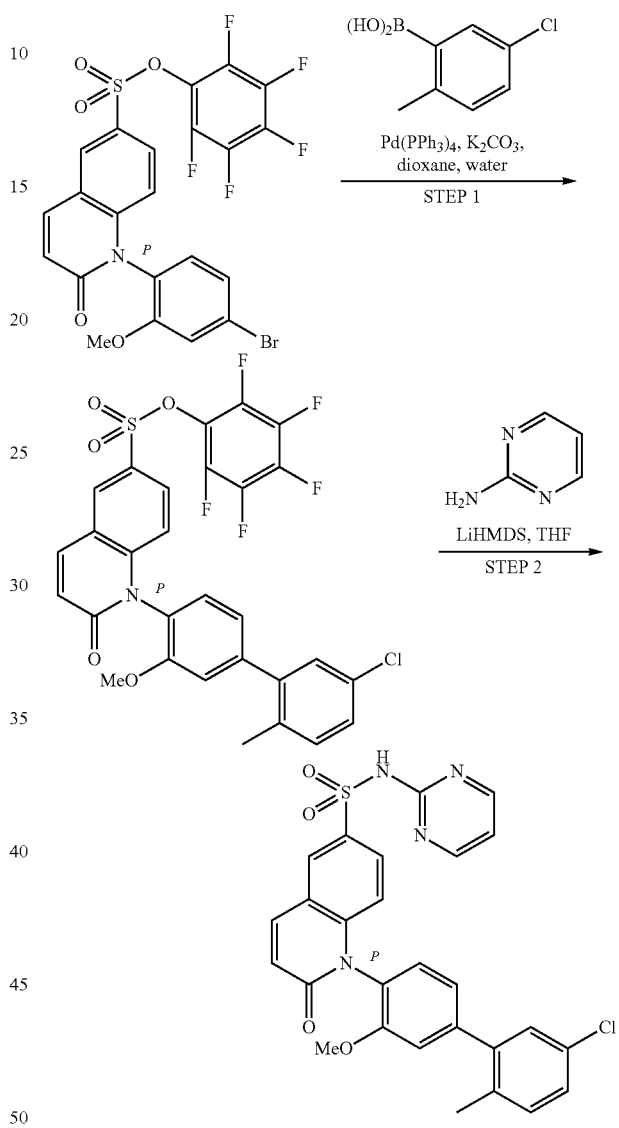

Step 1: (P)-1-(5'-chloro-3-methoxy-2'-methyl-[1,1'-biphenyl]-4-yl)-2-oxo-N-(perfluorophenyl)-1,2-dihydroquinoline-6-sulfonamide A solution of potassium phosphate (0.243 ml, 4.51 mmol), Pd(Ph$_3$P)$_4$ (0.130 g, 0.113 mmol), (5-chloro-2-methylphenyl)boronic acid (0.384 g, 2.256 mmol), and (P)-perfluorophenyl 1-(4-bromo-2-methoxyphenyl)-2-oxo-1,2-dihydroquinoline-6-sulfonate (0.650 g, 1.128 mmol) in 3 mL dioxane and 1 mL water was heated to 50° C. for 30 minutes. The reaction mixture was then poured into water and was extracted with DCM. The organics were dried over MgSO$_4$ and concentrated. Purification of the crude residue by silica gel column chromatography (0-70% EtOAc/heptane) gave (P)-1-(5'-chloro-3-methoxy-2'-methyl-[1,1'-biphenyl]-4-yl)-

2-oxo-N-(perfluorophenyl)-1,2-dihydroquinoline-6-sulfonamide (0.345 g, 0.556 mmol, 49.3% yield). m/z (ESI) 622.0 (M+H)+.

Step 2: (p)-1-(5'-chloro-3-methoxy-2'-methyl-4-biphenylyl)-2-oxo-N-2-pyrimidinyl-1,2-dihydro-6-quinolinesulfonamide A solution of pyrimidin-2-amine (0.026 g, 0.277 mmol) in 1 mL DMF was treated with a solution of (P)-perfluorophenyl 1-(5'-chloro-3-methoxy-2'-methyl-[1,1'-biphenyl]-4-yl)-2-oxo-1,2-dihydroquinoline-6-sulfonate (0.115 g, 0.185 mmol) in 4 mL THF and was cooled to 0° C. LiHMDS 1N in THF (0.407 ml, 0.407 mmol) was added, and the reaction mixture was allowed to stir for 20 minutes. The reaction mixture was then treated with TFA (0.085 ml, 1.109 mmol) and was concentrated. Purification of the crude residue by reverse phase column chromatography [Puriflash C18, 10-100% (0.1% NH$_4$OH in MeOH)/(0.1% NH$_4$OH in water)] gave (P)-1-(5'-chloro-3-methoxy-2'-methyl-[1,1'-biphenyl]-4-yl)-2-oxo-N-(pyrimidin-2-yl)-1,2-dihydroquinoline-6-sulfonamide (0.080 g, 0.150 mmol, 81% yield). $^1$H NMR (ACETONITRILE-d3): 8.40-8.44 (m, 3H), 7.95-8.06 (m, 2H), 7.38-7.42 (m, 1H), 7.34 (d, J=1.5 Hz, 2H), 7.29 (d, J=8.0 Hz, 1H), 7.19 (d, J=1.8 Hz, 1H), 7.13 (dd, J=8.0, 1.8 Hz, 1H), 6.95 (t, J=4.9 Hz, 1H), 6.72-6.81 (m, 2H), 3.70 (s, 3H), 2.34 (s, 3H). m/z (ESI) 533.2 (M+H)+.

Example 631

(Method 179): (P)-1-(3'-ethoxy-3-methoxy-4-biphenylyl)-N-3-isoxazolyl-2-oxo-1,2-dihydro-6-quinolinesulfonamide

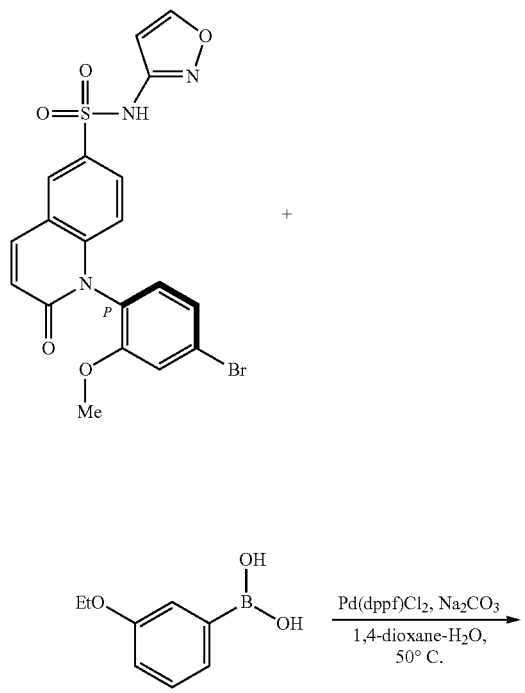

-continued

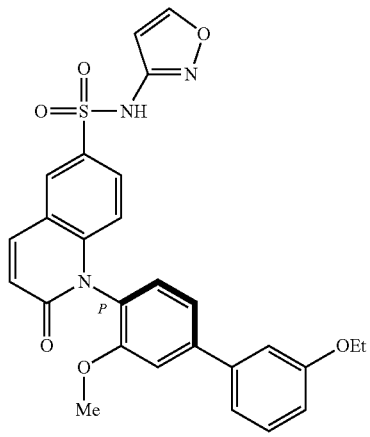

A 20-mL vial was charged with (P)-1-(4-bromo-2-methoxyphenyl)-N-(isoxazol-3-yl)-2-oxo-1,2-dihydroquinoline-6-sulfonamide (300 mg, 0.630 mmol), (3-ethoxyphenyl)boronic acid (314 mg, 1.890 mmol), and (1,1'-bis(diphenylphosphino)ferrocene)dichloropalladium(II) (92 mg, 0.126 mmol) then purged with nitrogen. The reaction vessel was then sequentially charged with dioxane (4.7 mL) and an aqueous solution of sodium carbonate (1.6 mL, 1.9 M) via syringe. The vial was sealed with a PTFE line cap and the resultant red reaction mixture was heated to 50° C. After 14 h, the reaction mixture was allowed to cool to ambient temperature and an aqueous solution of 1.0 N HCL (5 mL) was added and the mixture diluted with EtOAc (5 mL). The layers were separated and the aqueous layer was extracted with EtOAc (3×5 mL). The combined organic layers were washed with brine (25 mL), dried over anhydrous sodium sulfate, filtered, and concentrated under reduced pressure to furnish a tan oil, which was purified by flash column chromatography (25-g Biotage column, eluent: gradient, 0 to 100% EtOAc in heptane with 10% CH$_2$Cl$_2$ as an additive) to afford (P)-1-(3'-ethoxy-3-methoxy-4-biphenylyl)-N-3-isoxazolyl-2-oxo-1,2-dihydro-6-quinolinesulfonamide (123 mg, 0.238 mmol, 37.7% yield) as a white amorphous solid. $^1$H NMR (400 MHz, DMSO-d$_6$) δ=11.70 (br. s., 1H), 8.78 (d, J=1.8 Hz, 1H), 8.42 (d, J=2.2 Hz, 1H), 8.27 (d, J=9.6 Hz, 1H), 7.91 (dd, J=2.2, 9.0 Hz, 1H), 7.56 (d, J=1.3 Hz, 1H), 7.50-7.35 (m, 5H), 7.03 (dd, J=1.6, 8.0 Hz, 1H), 6.86 (d, J=9.6 Hz, 2H), 6.51 (d, J=1.8 Hz, 1H), 4.18 (q, J=6.9 Hz, 2H), 3.82 (s, 3H), 2.59-2.50 (m, 1H), 1.42 (t, J=7.0 Hz, 3H). m/z (ESI) 518.2 (M+H)+.

Example 632

(Method 180): (P)-1-(3'-(difluoromethoxy)-2-fluoro-5-methoxy-4-biphenylyl)-N-3-isoxazolyl-2-oxo-1,2-dihydro-6-quinolinesulfonamide

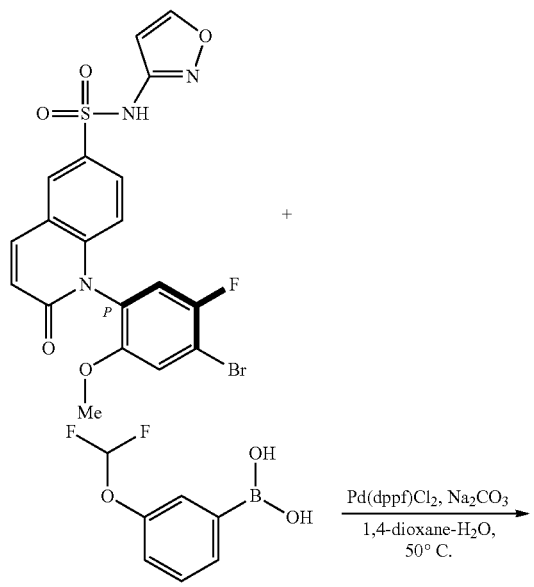

A 20-mL vial was charged with (P)-1-(4-bromo-5-fluoro-2-methoxyphenyl)-N-(isoxazol-3-yl)-2-oxo-1,2-dihydro-quinoline-6-sulfonamide (250 mg, 0.506 mmol), 3-(difluoromethoxy)phenylboronic acid (285 mg, 1.517 mmol) (purchased from Combi-Blocks Inc.), and (1,1'-bis(diphenylphosphino)ferrocene)dichloropalladium(II) (83 mg, 0.101 mmol) then purged with nitrogen. The reaction vessel was then sequentially charged with dioxane (3.8 mL) and an aqueous solution of sodium carbonate (1.3 mL, 1.9 M) via syringe. The vial was sealed with a PTFE line cap and the resultant red reaction mixture was heated to 50° C. After 16 h, the reaction mixture was allowed to cool to ambient temperature and an aqueous solution of 1.0 N HCL (5 mL) was added and the mixture diluted with EtOAc (5 mL). The layers were separated and the aqueous layer was extracted with EtOAc (3×5 mL). The combined organic layers were washed with brine (25 mL), dried over anhydrous sodium sulfate, filtered, and concentrated under reduced pressure to furnish a tan oil, which was purified by flash column chromatography (25-g Biotage column, eluent: gradient, 0 to 100% EtOAc in heptane with 10% $CH_2Cl_2$ as an additive) to afford (P)-1-(3'-(difluoromethoxy)-2-fluoro-5-methoxy-4-biphenylyl)-N-3-isoxazolyl-2-oxo-1,2-dihydro-6-quinolinesulfonamide (128 mg, 0.230 mmol, 45.4% yield) as a white amorphous solid. $^1$H NMR (400 MHz, DMSO-$d_6$) δ=11.67 (br. s., 1H), 8.73 (d, J=1.7 Hz, 1H), 8.38 (d, J=2.0 Hz, 1H), 8.24 (d, J=9.6 Hz, 1H), 7.87 (dd, J=2.1, 9.0 Hz, 1H), 7.69-7.48 (m, 5H), 7.42 (d, J=6.8 Hz, 1H), 7.30 (d, J=7.4 Hz, 1H), 6.89 (d, J=9.0 Hz, 1H), 6.82 (d, J=9.6 Hz, 1H), 6.45 (d, J=1.7 Hz, 1H), 3.75 (s, 3H). m/z (ESI) 558.0 (M+H)$^+$.

Example 633 and 634

(Method 181): (P)-1-(4'-chloro-2-fluoro-5-methoxy-4-biphenylyl)-N-3-isoxazolyl-2-oxo-1,2-dihydro-6-quinolinesulfonamide (633) and (P)-1-(4''-chloro-2-fluoro-5-methoxy-1,1':4',1''-terphenyl-4-yl)-N-3-isoxazolyl-2-oxo-1,2-dihydro-6-quinolinesulfonamide (634)

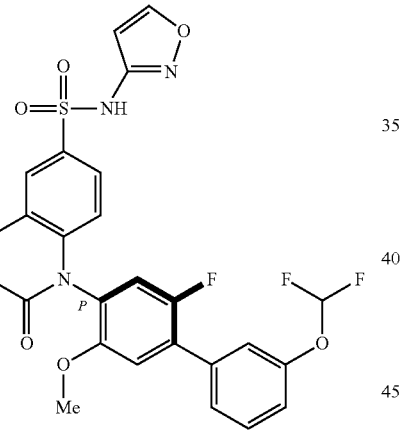

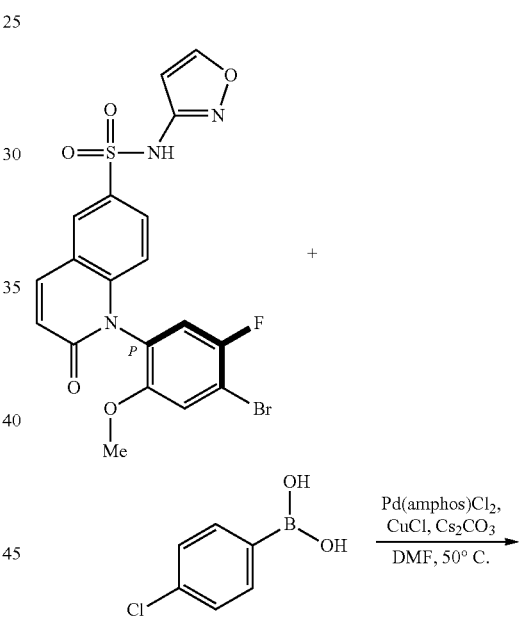

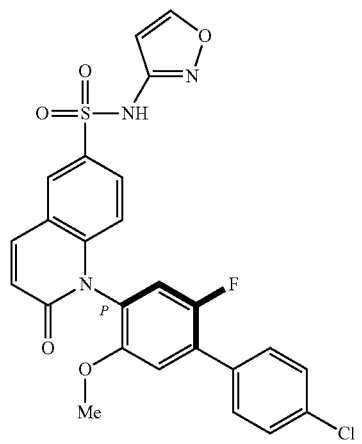

-continued

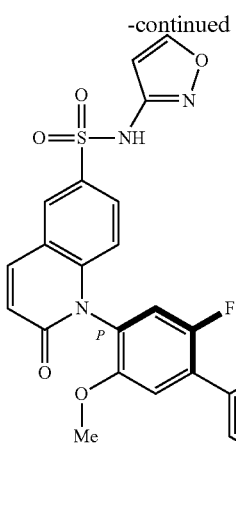

A 100-mL RBF was charged with (P)-1-(4-bromo-5-fluoro-2-methoxyphenyl)-N-(isoxazol-3-yl)-2-oxo-1,2-dihydroquinoline-6-sulfonamide (1.5 g, 3.03 mmol) 4-chlorophenylboronic acid (1.424 g, 9.10 mmol), copper (I) chloride (0.255 ml, 9.10 mmol), cesium carbonate (0.971 ml, 12.14 mmol), and 1,1-bis[(di-t-butyl-p-methylaminophenyl]palladium(II) chloride (0.430 g, 0.607 mmol) then purged with nitrogen. DMF (30.3 ml) was introduced and the resultant green reaction mixture was heated to 50° C. After 4 h, the brown reaction mixture was allowed to cool to ambient temperature and poured into a separatory funnel containing 1.0 N HCl (50 mL) and diluted with EtOAc (50 mL). The layers were separated and the aqueous layer was extracted with EtOAc (3×50 mL). The combined organic layers were washed with a saturated aqueous solution of ethylenediaminetetraacetic acid (3×50 mL), dried over anhydrous sodium sulfate, filtered, and concentrated under reduced pressure to furnish a tan oil, which was purified by flash column chromatography (100-g Biotage column, eluent: gradient, 0 to 100% EtOAc in heptane with 10% $CH_2Cl_2$ as an additive) to afford a mixture of (P)-1-(4'-chloro-2-fluoro-5-methoxy-4-biphenylyl)-N-3-isoxazolyl-2-oxo-1,2-dihydro-6-quinolinesulfonamide and (P)-1-(4''-chloro-2-fluoro-5-methoxy-1,1':4',1''-terphenyl-4-yl)-N-3-isoxazolyl-2-oxo-1,2-dihydro-6-quinolinesulfonamide as a tan solid, which was further purified. The residue was dissolved in MeCN (ca. 2.0 mL and purified by reverse-phase column chromatography (120-g Biotage Snap Cartridge, KP-C18-HS eluent: gradient, 30 to 100% MeCN in water (containing 0.1% formic acid as an additive). The fractions containing product were combined and concentrated via lyophilization in a 500-mL round-bottomed flask to afford (P)-1-(4'-chloro-2-fluoro-5-methoxy-4-biphenylyl)-N-3-isoxazolyl-2-oxo-1,2-dihydro-6-quinolinesulfonamide (304 mg, 0.580, 19.1% yield) as a white amorphous solid. $^1$H NMR (400 MHz, DMSO-$d_6$) δ=11.67 (s, 1H), 8.74 (d, J=1.8 Hz, 1H), 8.39 (d, J=2.2 Hz, 1H), 8.24 (d, J=9.4 Hz, 1H), 7.91-7.78 (m, 8H), 7.59-7.57 (m, 1H), 7.57-7.55 (m, 1H), 7.53 (d, J=10.5 Hz, 1H), 7.44 (d, J=7.0 Hz, 1H), 6.91 (d, J=9.0 Hz, 1H), 6.83 (d, J=9.6 Hz, 1H), 6.46 (d, J=1.9 Hz, 1H), 3.75 (s, 3H). m/z (ESI) 526.1 $(M+H)^+$. (P)-1-(4''-chloro-2-fluoro-5-methoxy-1,1':4',1''-terphenyl-4-yl)-N-3-isoxazolyl-2-oxo-1,2-dihydro-6-quinolinesulfonamide (68.6 mg, 0.114 mmol, 3.8% yield) was also isolated as a white amorphous solid. $^1$H NMR (400 MHz, DMSO-$d_6$) δ=11.67 (s, 1H), 8.74 (d, J=1.8 Hz, 1H), 8.39 (d, J=2.2 Hz, 1H), 8.24 (d, J=9.5 Hz, 1H), 7.90-7.78 (m, 7H), 7.61-7.50 (m, 3H), 7.44 (d, J=6.9 Hz, 1H), 6.91 (d, J=8.9 Hz, 1H), 6.83 (d, J=9.6 Hz, 1H), 6.46 (d, J=1.9 Hz, 1H), 3.75 (s, 3H). m/z (ESI) 603.2 $(M+H)^+$.

Example 635

(Method 182): (P)-1-(5-fluoro-2-methoxy-4-(2-pyridinyl)phenyl)-N-3-isoxazolyl-2-oxo-1,2-dihydro-6-quinolinesulfonamide

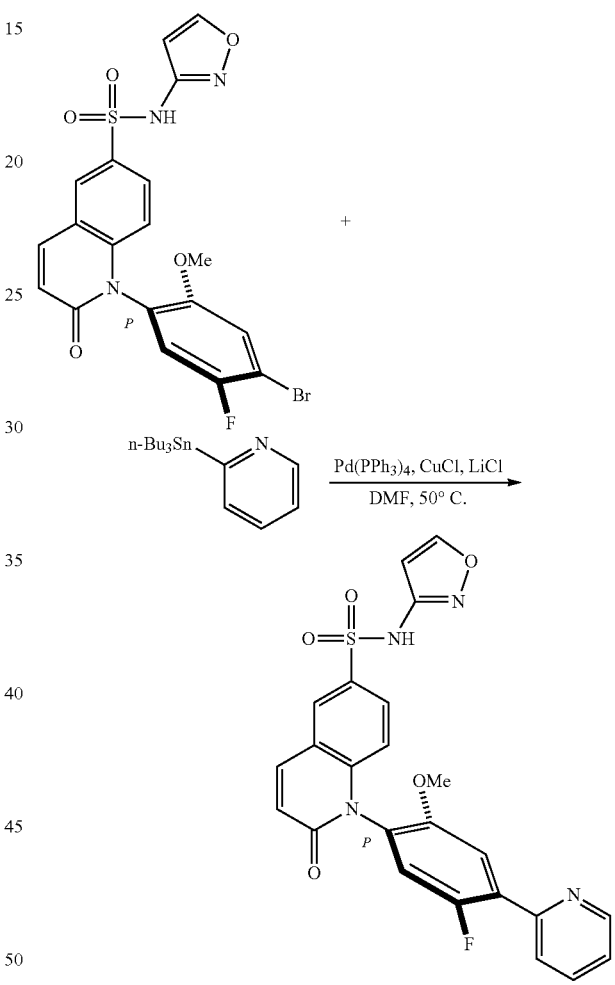

A 20-mL vial was sequentially charged with (P)-1-(4-bromo-5-fluoro-2-methoxyphenyl)-N-(isoxazol-3-yl)-2-oxo-1,2-dihydroquinoline-6-sulfonamide (250 mg, 0.506 mmol), 2-(tributylstannyl)pyridine (328 μl, 1.012 mmol), N,N-dimethylformamide (3.4 mL), lithium chloride (193 mg, 1.012 mmol) then sparged with nitrogen for 15 min. Copper (I) chloride (100 mg, 1.012 mmol) and tetrakis (triphenylphosphine)palladium (29.3 mg, 0.101 mmol) were then introduced under a stream of nitrogen and the reaction vessel was sealed with a PTFE lined cap. The stirred reaction mixture was then warmed to 50° C. After 12 h, the reaction mixture was allowed to cool to ambient temperature and filtered through a pad of celite, which was washed with EtOAc (3×25 mL). The filtrate was concentrated and the residue purified by reverse-phase HPLC (Waters XBridge Prep Shield RP18 10 μm OBD 19×100 mm) gradient, 35 to 85% MeCN in water (containing 0.1% formic acid as an additive). The fractions containing product were combined and concentrated via lyophilization to afford (P)-1-(5-fluoro-2-methoxy-4-(2-pyridinyl)phenyl)-N-3-isoxazolyl-2-oxo-1,2-dihydro-6-quinolinesulfonamide (101 mg, 0.205 mmol, 40.5% yield) a green tinted amorphous solid. $^1$H NMR (400 MHz, ACETONITRILE-d$_3$) δ ppm 8.95 (br. s., 1H) 8.38 (d, J=1.45 Hz, 1H) 8.27 (d, J=1.66 Hz, 1H) 8.01 (d, J=9.74 Hz, 1H) 7.82 (d, J=7.46 Hz, 1H) 7.31 (d, J=10.05 Hz, 1H) 6.89 (d, J=8.60 Hz, 1H) 6.78 (d, J=9.64 Hz, 1H) 6.46 (d, J=1.24 Hz, 1H) 3.78 (br. s., 3H). m/z (ESI) 493.0 (M+H)$^+$.

Example 636

(Method 183): (P)-1-(2-fluoro-5-methoxy-4'-(trifluoromethyl)-4-biphenylyl)-N-1,3-oxazol-2-yl-2-oxo-1,2-dihydro-6-quinolinesulfonamide

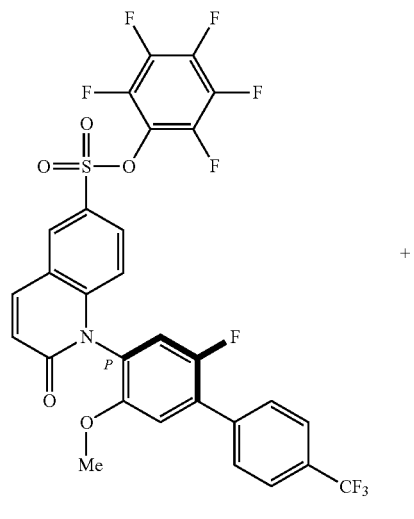

+

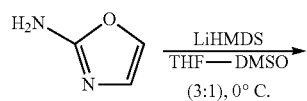

A 10-mL RBF was charged with (P)-perfluorophenyl 1-(2-fluoro-5-methoxy-4'-(trifluoromethyl)-[1,1'-biphenyl]-4-yl)-2-oxo-1,2-dihydroquinoline-6-sulfonate (200 mg, 0.303 mmol) and 1,3-oxazol-2-amine (38.2 mg, 0.455 mmol) then purged with nitrogen. Tetrahydrofuran (3.17 mL) and dimethyl sulfoxide (1.056 mL) were introduced, and the resultant brown solution cooled to 0° C. A solution of lithium bis(trimethylsilyl)amide in tetrahydrofuran (1.0 M, 0.667 mL, 0.667 mmol) was added dropwise via syringe to the stirred reaction mixture over 3 min. After 15 min, 1.0 N HCl (5 mL) was introduced and the resultant reaction mixture was allowed to warm to ambient temperature. The mixture was diluted with and EtOAc (10 mL) and the layers were separated, and the aqueous layer was further extracted with EtOAc (3×10 mL). The combined organic layers were then washed with brine (20 mL), dried over anhydrous magnesium sulfate, filtered, and concentrated under reduced pressure to furnish a yellow oil, which was dissolved in DMSO (2 mL) filtered through a 0.2 micron filter and purified by reverse-phase HPLC (Waters XBridge Prep Shield RP18 10 μm OBD 19×100 mm) gradient, 35 to 95% MeCN in water (containing 0.1% formic acid as an additive). The fractions containing product were combined and concentrated via lyophilization to yield (P)-1-(2-fluoro-5-methoxy-4'-(trifluoromethyl)-[1,1'-biphenyl]-4-yl)-N-(oxazol-2-yl)-2-oxo-1,2-dihydroquinoline-6-sulfonamide (50.1 mg, 0.090 mmol, 29.5% yield) as a white amorphous solid. $^1$H NMR (400 MHz, ACETONITRILE-d$_3$) δ=8.23 (d, J=2.07 Hz, 1H) 8.00 (d, J=9.64 Hz, 1H) 7.80-7.92 (m, 5H) 7.34 (d, J=6.84 Hz, 1H) 7.24 (d, J=10.16 Hz, 1H) 7.19 (d, J=1.76 Hz, 1H) 6.94 (d, J=1.76 Hz, 1H) 6.83 (d, J=8.91 Hz, 1H) 6.75 (d, J=9.64 Hz, 1H) 3.74 (s, 3H). m/z (ESI) 559.8 (M+H)$^+$.

Example 637

(Method 184): (P)-1-(5-fluoro-2-methoxy-4-(5-(trifluoromethyl)-2-pyridinyl)phenyl)-N-3-isoxazolyl-2-oxo-1,2-dihydro-6-quinolinesulfonamide

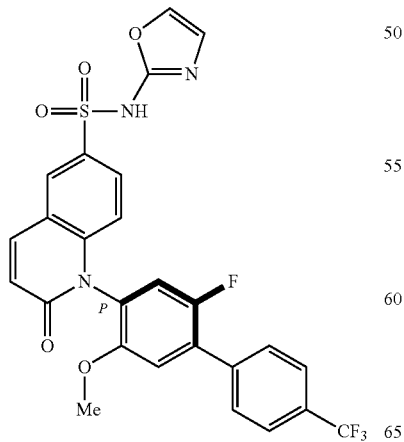

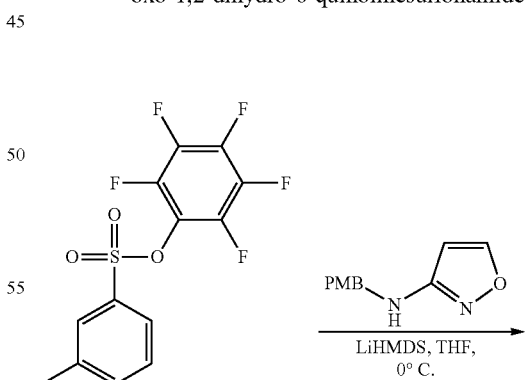

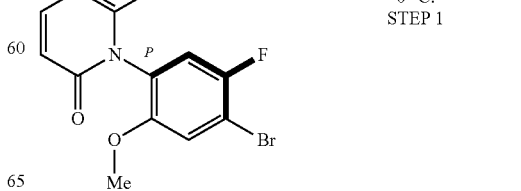

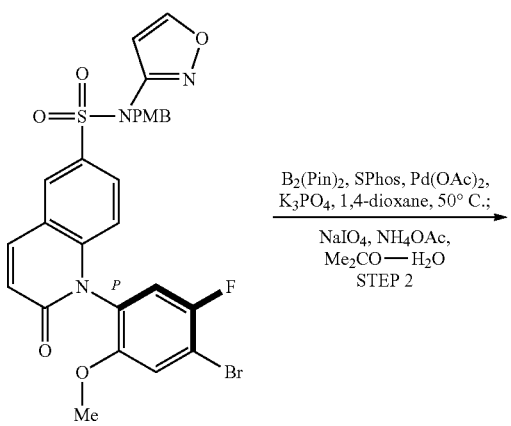

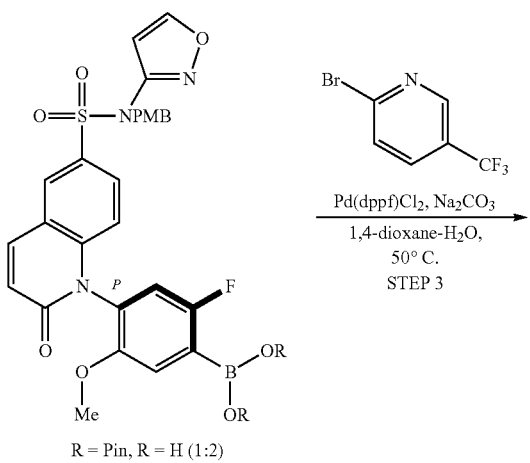

R = Pin, R = H (1:2)

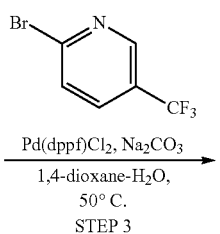

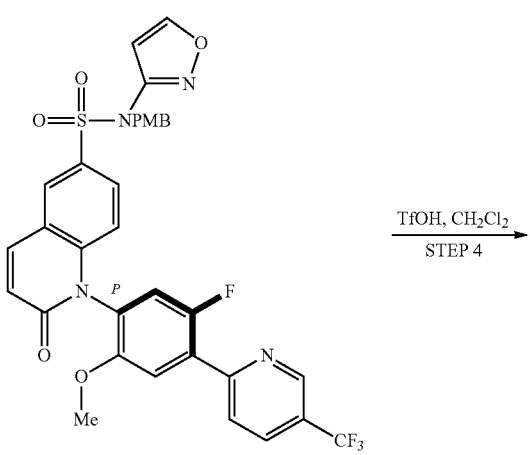

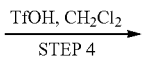

Step 1: (P)-1-(4-bromo-5-fluoro-2-methoxyphenyl)-N-(isoxazol-3-yl)-N-(4-methoxybenzyl)-2-oxo-1,2-dihydroquinoline-6-sulfonamide A 250-mL round-bottomed flask was charged with (P)-perfluorophenyl 1-(4-bromo-5-fluoro-2-methoxyphenyl)-2-oxo-1,2-dihydroquinoline-6-sulfonate (11.34 g, 19.08 mmol), and N-(4-methoxybenzyl)isoxazol-3-amine (4.09 g, 20.04 mmol), then purged with nitrogen. Tetrahydrofuran (191 mL) was introduced, and the resultant brown solution cooled to 0° C. A solution of lithium bis(trimethylsilyl)amide in THF (1.0 M, 21.0 mL, 21.0 mmol) was added dropwise via syringe to the stirred reaction mixture over 10 min. After 15 min, 1.0 N HCl (100 mL) was introduced and the resultant reaction mixture was allowed to warm to RT. The mixture was diluted with and EtOAc (100 mL) and the layers were separated, and the aqueous layer was further extracted with EtOAc (2×100 mL). The combined organic layers were then washed with brine (100 mL), dried over anhydrous sodium sulfate, filtered, and concentrated under reduced pressure. The residue was then purified by flash column chromatography (100-g Biotage column, eluent: gradient, 0 to 100% EtOAc in heptane with 10% CH$_2$C2 as an additive) to afford (P)-1-(4-bromo-5-fluoro-2-methoxyphenyl)-N-(isoxazol-3-yl)-N-(4-methoxybenzyl)-2-oxo-1,2-dihydroquinoline-6-sulfonamide (9.54 g, 15.53 mmol, 81% yield) as a white amorphous solid. $^1$H NMR (400 MHz, DMSO-d$_6$) δ=8.82 (d, J=2.0 Hz, 1H), 8.38 (d, J=2.3 Hz, 1H), 8.17 (d, J=9.4 Hz, 1H), 7.76 (t, J=5.1 Hz, 1H), 7.68 (d, J=6.1 Hz, 1H), 7.63 (d, J=8.5 Hz, 1H), 7.26 (d, J=7.9 Hz, 2H), 6.91-6.78 (m, 4H), 6.74 (d, J=2.0 Hz, 1H), 4.92 (s, 2H), 3.73-3.69 (m, 6H), 3.32 (s, 1H). m/z (ESI) 615.1 (M+H)$^+$.

Step 2: (P)-(2-fluoro-4-(6-(N-(isoxazol-3-yl)-N-(4-methoxybenzyl)sulfamoyl)-2-oxoquinolin-1(2H)-yl)-5-methoxyphenyl)boronic acid and (P)-1-(5-fluoro-2-methoxy-4-(4,4,5,5-tetramethyl-1,3,2-dioxaborolan-2-yl)phenyl)-N-(isoxazol-3-yl)-N-(4-methoxybenzyl)-2-oxo-1,2-dihydroquinoline-6-sulfonamide A 100-mL RBF was charged with (P)-1-(4-bromo-5-fluoro-2-methoxyphenyl)-N-(isoxazol-3-yl)-N-(4-methoxybenzyl)-2-oxo-1,2-dihydroquinoline-6-sulfonamide (3 g, 4.88 mmol), 2-dicyclohexylphosphino-2',6'-dimethoxy-1'1'-biphenyl (0.251 g, 0.610 mmol), potassium phosphate (3.11 g, 14.65 mmol), 4,4,5,5-tetramethyl-2-(4,4,5,5-tetramethyl- 1,3,2-dioxaborolan-2-yl)-1,3,2-dioxaborolane (3.72 g, 14.65 mmol), and 1,4-dioxane (45.0 ml). The resultant solution was sparged with nitrogen for 15 min. Palladium (II) acetate (0.055 g, 0.244 mmol) was introduced, and the reaction mixture was warmed to 50° C. After 20 h, the green slurry was allowed to cool to RT, filtered through a pad of celite, and washed with EtOAc (2×50 mL). The filtrate was diluted with water (100 mL) and the layers were separated. The aqueous layer was further extracted with EtOAc (3×50 mL) and the combined organic layers were washed with brine (100 mL), dried over anhydrous magnesium sulfate, filtered, and concentrated under reduced pressure in a 100-mL round-bottomed flask. Acetone (45 ml) and an aqueous ammonium acetate solution (22.5 ml, 22.5 mmol, 1.0 M) were sequentially introduced and the resultant milky white suspension was stirred vigorously at ambient temperature. After 24 h, the solvent were removed under reduced pressure and the residue redissolved in water (250 mL) and dichloromethane (250 mL). The layers were separated and the aqueous layer extracted with dichloromethane (2×150 mL). The combined organic layers were washed with brine (100 mL), dried over magnesium sulfate, filtered and concentrated under reduced pressure to provide 3 g of a green foam, which was used without further purification. The product contained both (P)-(2-fluoro-4-(6-(N-(isoxazol-3-yl)-N-(4-methoxybenzyl)sulfamoyl)-2-oxoquinolin-1(2H)-yl)-5-methoxyphenyl)boronic acid (m/z (ESI) 580.0 (M+H)$^+$) and (P)-1-(5-fluoro-2-methoxy-4-(4,4,5,5-tetramethyl-1,3,2-dioxaborolan-2-yl)phenyl)-N-(isoxazol-3-yl)-N-(4-methoxybenzyl)-2-oxo-1,2-dihydroquinoline-6-sulfonamide (m/z (ESI) 662.3 (M+H)$^+$) in a 2:1 ratio based on $^1$H NMR. The yield based on this ratio was quantitative.

Step 3: (P)-1-(5-fluoro-2-methoxy-4-(5-(trifluoromethyl)pyridin-2-yl)phenyl)-N-(isoxazol-3-yl)-N-(4-methoxybenzyl)-2-oxo-1,2-dihydroquinoline-6-sulfonamide A 20-mL vial was charged with a mixture of (P)-1-(5-fluoro-2-methoxy-4-(4,4,5,5-tetramethyl-1,3,2-dioxaborolan-2-yl)phenyl)-N-(isoxazol-3-yl)-N-(4-methoxybenzyl)-2-oxo-1,2-dihydroquinoline-6-sulfonamide and (P)-(2-fluoro-4-(6-(N-(isoxazol-3-yl)-N-(4-methoxybenzyl)sulfamoyl)-2-oxoquinolin-1(2H)-yl)-5-methoxyphenyl) boronic (300 mg), 2-bromo-5-(trifluoromethyl)pyridine (351 mg, 1.553 mmol), and (1,1'-bis(diphenylphosphino)ferrocene)dichloropalladium(II) (85 mg, 0.104 mmol) then purged with nitrogen. The reaction vessel was then sequentially charged with dioxane (3.9 mL) and an aqueous solution of sodium carbonate (1.3 mL, 1.9 M) via syringe. The vial was sealed with a PTFE line cap and the resultant red reaction mixture was heated to 50° C. After 16 h the reaction mixture was allowed to cool to RT and an aqueous solution of 1.0 N HCL (5 mL) was added and the mixture diluted with EtOAc (5 mL). The layers were separated and the aqueous layer was extracted with EtOAc (3×5 mL). The combined organic layers were washed with brine (25 mL), dried over anhydrous sodium sulfate, filtered, and concentrated under reduced pressure to furnish a brown oil, which was dissolved in DMSO (2 mL) filtered through a 0.2 micron filter and purified by reverse-phase HPLC (Waters XBridge Prep Shield RP18 10 μm OBD 19×100 mm) gradient, 50 to 95% MeCN in water (containing 0.1% formic acid as an additive). The fractions containing product were combined and concentrated via lyophilization to yield (P)-1-(5-fluoro-2-methoxy-4-(5-(trifluoromethyl)pyridin-2-yl)phenyl)-N-(isoxazol-3-yl)-N-(4-methoxybenzyl)-2-oxo-1,2-dihydroquinoline-6-sulfonamide (91 mg, 0.134 mmol, 25.8% yield) as a tan solid. $^1$H NMR (400 MHz, DMSO-d$_6$) δ=9.24-9.16 (m, 1H), 8.81 (d, J=1.8 Hz, 1H), 8.42 (dd, J=2.2, 8.6 Hz, 1H), 8.39 (d, J=2.3 Hz, 1H), 8.19 (d, J=9.6 Hz, 1H), 8.15 (d, J=7.8 Hz, 1H), 7.82 (d, J=6.7 Hz, 1H), 7.80 (dd, J=2.2, 8.9 Hz, 1H), 7.65 (d, J=10.7 Hz, 1H), 7.32-7.22 (m, 2H), 6.91-6.82 (m, 4H), 6.74 (d, J=1.9 Hz, 1H), 4.92 (s, 2H), 3.76 (s, 2H), 3.71 (s, 3H). m/z (ESI) 681.1 (M+H)$^+$.

Step 4: (P)-1-(5-fluoro-2-methoxy-4-(5-(trifluoromethyl)-2-pyridinyl)phenyl)-N-3-isoxazolyl-2-oxo-1,2-dihydro-6-quinolinesulfonamide A 5-mL vial was charged with (P)-1-(5-fluoro-2-methoxy-4-(5-(trifluoromethyl)pyridin-2-yl)phenyl)-N-(isoxazol-3-yl)-N-(4-methoxybenzyl)-2-oxo-1,2-dihydroquinoline-6-sulfonamide (91 mg, 0.134 mmol) evacuated and back-filled with nitrogen (×3). CH$_2$Cl$_2$ (1.3 mL) was introduced and triflic acid (35.6 μL, 0.401 mmol) was added dropwise via syringe to the yellow reaction mixture at ambient temperature. The reaction immediate turned purple. After 34 min, water (2.5 mL) was added and the mixture stirred until the purple color had dissipated. The layers were separated and the aqueous layer was extracted with CH$_2$Cl$_2$ (2×5 mL). The combined organic layers were dried over magnesium sulfate, filtered, concentrated and purified by flash column chromatography (12-g Biotage column, eluent: gradient, 35→100% EtOAc in heptane with 10% CH$_2$Cl$_2$ as an additive) to yield (P)-1-(5-fluoro-2-methoxy-4-(5-(trifluoromethyl)-2-pyridinyl)phenyl)-N-3-isoxazolyl-2-oxo-1,2-dihydro-6-quinolinesulfonamide (61 mg, 0.109 mmol, 81% yield) as a white amorphous solid. $^1$H NMR (400 MHz, DMSO-d$_6$) δ=11.67 (br. s., 1H), 9.20 (br. s., 1H), 8.74 (br. s., 1H), 8.47-8.34 (m, 2H), 8.25 (d, J=9.2 Hz, 1H), 8.15 (d, J=7.3 Hz, 1H), 7.94-7.76 (m, 2H), 7.64 (d, J=10.3 Hz, 1H), 6.91 (d, J=8.4 Hz, 1H), 6.83 (d, J=9.3 Hz, 1H), 6.45 (br. s., 1H), 3.75 (br. s., 3H). m/z (ESI) 560.8 (M+H)$^+$.

Example 638

(Method 185): 1-(5-chloro-6-(cyclopropylmethoxy)-2-methoxy-3-pyridinyl)-N-3-isoxazolyl-2-oxo-1,2-dihydro-6-quinolinesulfonamide

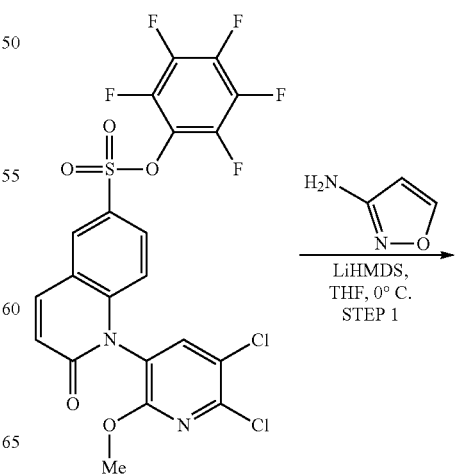

Step 1: 1-(5,6-dichloro-2-methoxypyridin-3-yl)-N-(isoxazol-3-yl)-2-oxo-1,2-dihydroquinoline-6-sulfonamide A 100-mL RBF was charged with perfluorophenyl 1-(5,6-dichloro-2-methoxypyridin-3-yl)-2-oxo-1,2-dihydroquinoline-6-sulfonate (3.0 g, 5.29 mmol) then purged with nitrogen. THF (191 mL) and 3-aminoisoxazole (4.89 g, 5.82 mmol) were introduced and the resultant tan solution cooled to 0° C. A solution of lithium bis(trimethylsilyl)amide in tetrahydrofuran (1.0 M, 11.1 mL, 11.1 mmol) was added dropwise via syringe to the stirred reaction mixture over 5 min. After 15 min, 1.0 N HCl (25 mL) was introduced and the resultant reaction mixture was allowed to warm to RT. The mixture was diluted with and EtOAc (25 mL) and the layers were separated, and the aqueous layer was further extracted with EtOAc (3×25 mL). The combined organic layers were then washed with brine (100 mL), dried over anhydrous sodium sulfate, filtered, and concentrated under reduced pressure. The residue was then purified by flash column chromatography (100-g Biotage column, eluent: gradient, 0 to 100% EtOAc in heptane with 10% $CH_2Cl_2$ as an additive) to afford 1-(5,6-dichloro-2-methoxypyridin-3-yl)-N-(isoxazol-3-yl)-2-oxo-1,2-dihydroquinoline-6-sulfonamide (1.97 g, 4.22 mmol, 80% yield) as a white amorphous solid. $^1$H NMR (400 MHz, DMSO-$d_6$) δ=8.62 (d, J=2.3 Hz, 1H), 8.47 (s, 1H), 8.28 (d, J=9.6 Hz, 1H), 7.94 (dd, J=2.3, 9.1 Hz, 1H), 7.19 (d, J=9.0 Hz, 1H), 6.91 (d, J=9.7 Hz, 1H), 3.82 (s, 3H). m/z (ESI) 468.9 (M+H)$^+$.

Step 2: 1-(5-chloro-6-(cyclopropylmethoxy)-2-methoxy-3-pyridinyl)-N-3-isoxazolyl-2-oxo-1,2-dihydro-6-quinolinesulfonamide A 5-mL vial was sequentially charged with 1-(5,6-dichloro-2-methoxypyridin-3-yl)-N-(isoxazol-3-yl)-2-oxo-1,2-dihydroquinoline-6-sulfonamide (300 mg, 0.642 mmol), cesium carbonate (154 µl, 1.926 mmol), dimethyl sulfoxide (2.1 mL), and (hydroxymethyl) cyclopropane (130 µL, 1.605 mmol). The vial was sealed with a PTFE lined cap and heated to 90° C. After 16 h, the brown reaction mixture was allowed to cool to RT, then diluted with IPA (3 mL) and filtered through a pad of celite. The pad was rinsed with IPA (2×5 mL) and the filtrate was concentrated under reduced pressure to furnish a brown oil, which was dissolved in DMSO (2 mL) filtered through a 0.2 micron filter and purified by reverse-phase HPLC (Waters XBridge Prep Shield RP18 10 µm OBD 19×100 mm) gradient, 20 to 75% MeCN in water (containing 0.1% trifluoroacetic acid as an additive), flow rate 40 mL/min to afford 1-(5-chloro-6-(cyclopropylmethoxy)-2-methoxy-3-pyridinyl)-N-3-isoxazolyl-2-oxo-1,2-dihydro-6-quinolinesulfonamide (180 mg, 0.358 mmol, 55.7% yield) as a tan amorphous solid. $^1$H NMR (500 MHz, DMSO-$d_6$) δ=11.65 (br. s., 1H) 8.72 (s, 1H) 8.36 (s, 1H) 8.21 (d, J=9.67 Hz, 1H) 8.04 (s, 1H) 7.85 (dd, J=8.95, 1.75 Hz, 1H) 7.00 (d, J=9.02 Hz, 1H) 6.79 (d, J=9.67 Hz, 1H) 6.45 (d, J=1.10 Hz, 1H) 4.23-4.40 (m, 2H) 3.78 (s, 3H) 1.30-1.43 (m, 1H) 0.62 (d, J=7.66 Hz, 2H) 0.41 (br. s., 2H). m/z (ESI) 503.3 (M+H)$^+$.

Example 639

(Method 186): 1-(4-bromo-5-fluoro-2-methoxyphenyl)-N-(4,5-dimethyl-3-isoxazolyl)-2-oxo-1,2-dihydro-6-quinolinesulfonamide

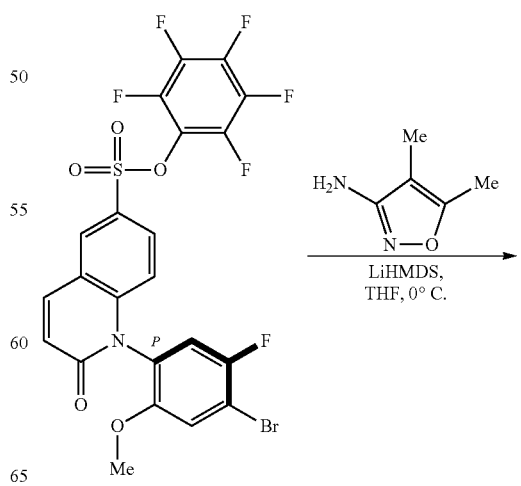

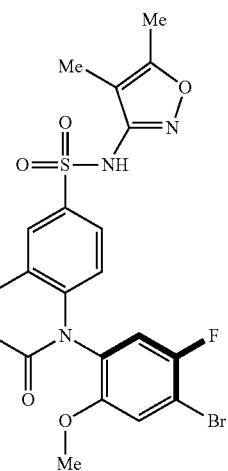

A 10-mL RBF was charged with (P)-perfluorophenyl perfluorophenyl 1-(4-bromo-5-fluoro-2-methoxyphenyl)-2-oxo-1,2-dihydroquinoline-6-sulfonate (58 mg, 0.098 mmol) and 4,5-dimethylisoxazol-3-amine (16.4 mg, 0.146 mmol) then purged with nitrogen. Tetrahydrofuran (732 µL) and dimethyl sulfoxide (244 µL) were introduced, and the resultant brown solution cooled to 0° C. A solution of lithium bis(trimethylsilyl)amide in tetrahydrofuran (1.0 M, 215 µL, 0.215 mmol) was added dropwise via syringe to the stirred reaction mixture over 3 min. After 15 min, 1.0 N HCl (5 mL) was introduced and the resultant reaction mixture was allowed to warm to ambient temperature. The mixture was diluted with and EtOAc (10 mL) and the layers were separated, and the aqueous layer was further extracted with EtOAc (3×10 mL). The combined organic layers were then washed with brine (20 mL), dried over anhydrous magnesium sulfate, filtered, and concentrated under reduced pressure to furnish a yellow oil, which was dissolved in DMSO (2 mL) filtered through a 0.2 micron filter and purified by reverse-phase HPLC (Waters XBridge Prep Shield RP18 10 µm OBD 19×100 mm) gradient, 20 to 75% MeCN in water (containing 0.1% trifluoroacetic acid as an additive), flow rate 40 mL/min to afford (P)-1-(4-bromo-5-fluoro-2-methoxyphenyl)-N-(4,5-dimethyl-3-isoxazolyl)-2-oxo-1,2-dihydro-6-quinolinesulfonamide (29.0 mg, 0.056 mmol, 56.9% yield) as a white amorphous solid. $^1$H NMR (500 MHz, DMSO-$d_6$) δ ppm 10.79 (br. s., 1H) 8.32 (d, J=2.01 Hz, 1H) 8.23 (d, J=9.67 Hz, 1H) 7.85 (dd, J=8.99, 2.04 Hz, 1H) 7.67 (d, J=6.23 Hz, 1H) 7.62 (d, J=8.56 Hz, 1H) 6.86 (d, J=8.95 Hz, 1H) 6.79 (d, J=9.67 Hz, 1H) 3.70 (s, 3H) 2.21 (s, 3H) 1.80 (s, 3H). m/z (ESI) 522.0 (M+H)$^+$.

Example 640

(Method 187): 1-(5-chloro-6-cyclopropyl-2-methoxy-3-pyridinyl)-N-3-isoxazolyl-2-oxo-1,2-dihydro-6-quinolinesulfonamide

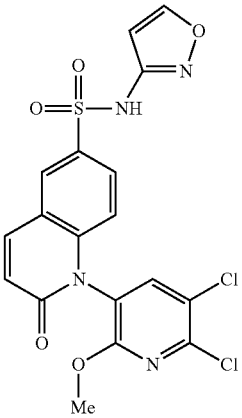

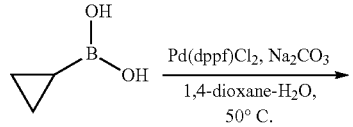

A 20-mL vial was charged with 1-(5,6-dichloro-2-methoxypyridin-3-yl)-N-(isoxazol-3-yl)-2-oxo-1,2-dihydroquinoline-6-sulfonamide (200 mg, 0.428 mmol), cyclopropyl boronic acid (66.2 µl, 0.856 mmol), and (1,1'-bis(diphenylphosphino)ferrocene)dichloropalladium(II) (62.6 mg, 0.086 mmol) then purged with nitrogen. The reaction vessel was then sequentially charged with dioxane (3.2 mL) and an aqueous solution of sodium carbonate (1.1 mL, 1.9 M) via syringe. The vial was sealed with a PTFE line cap and the resultant red reaction mixture was heated to 50° C. After 12 h, the reaction mixture was allowed to cool to ambient temperature and an aqueous solution of 1.0 N HCL (5 mL) was added and the mixture diluted with EtOAc (5 mL). The layers were separated and the aqueous layer was extracted with EtOAc (3×5 mL). The combined organic layers were washed with brine (25 mL), dried over anhydrous sodium sulfate, filtered, and concentrated under reduced pressure to furnish a brown oil, which was dissolved in DMSO (2 mL) filtered through a 0.2 micron filter and purified by reverse-phase HPLC (Waters XBridge Prep Shield RP18 10 µm OBD 19×100 mm) gradient, 20 to 75%

MeCN in water (containing 0.1% trifluoroacetic acid as an additive), flow rate 40 mL/min to afford 1-(5-chloro-6-cyclopropyl-2-methoxy-3-pyridinyl)-N-3-isoxazolyl-2-oxo-1,2-dihydro-6-quinolinesulfonamide (85 mg, 0.180 mmol, 42.0% yield) as a white amorphous solid. $^1$H NMR (400 MHz, CHLOROFORM-d) δ ppm 8.23 (d, J=1.76 Hz, 1H) 8.13 (d, J=1.97 Hz, 1H) 7.74-7.80 (m, 2H) 7.46 (s, 1H) 6.82 (d, J=9.64 Hz, 1H) 6.75 (d, J=9.02 Hz, 1H) 6.56 (d, J=0.66 Hz, 1H) 3.76 (s, 3H) 2.41-2.61 (m, 1H) 1.14-1.23 (m, 2H) 1.09 (dd, J=8.09, 3.21 Hz, 2H). m/z (ESI) 473.0 (M+H)$^+$.

Example 641

(Method 188): (P)-1-(4-(cyclohexylmethyl)-5-fluoro-2-methoxyphenyl)-2-oxo-N-2-pyrimidinyl-1,2-dihydro-6-quinolinesulfonamide

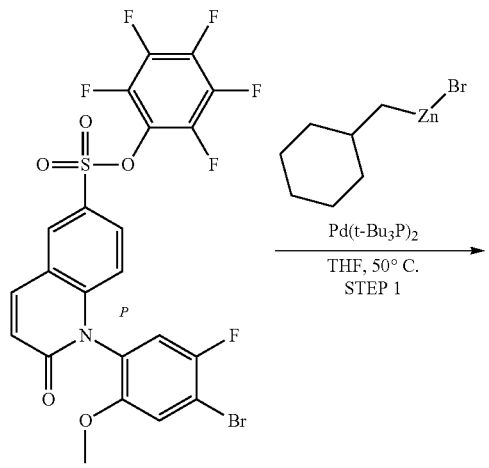

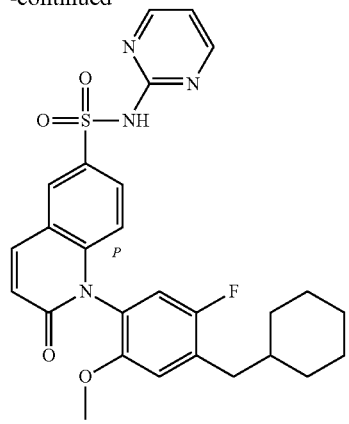

Step 1: (P)-perfluorophenyl 1-(4-(cyclohexylmethyl)-5-fluoro-2-methoxyphenyl)-2-oxo-1,2-dihydroquinoline-6-sulfonate A RBF was charged with (P)-perfluorophenyl 1-(4-bromo-5-fluoro-2-methoxyphenyl)-2-oxo-1,2-dihydroquinoline-6-sulfonate (2.017 g, 3.39 mmol), (cyclohexylmethyl)zinc(II) bromide (21.04 ml, 10.52 mmol), and bis(tri-t-butylphosphine)palladium(0) (0.260 g, 0.509 mmol) The vial was flushed with Ar (g), then THF (16.97 ml) was added. The reaction mixture was heated to 50° C. and stirred for one hour. The reaction was brought to RT and then diluted with ethyl acetate and 1N Aq. HCl solution. The organic layer was washed with brine, dried with sodium sulfate, filtered, and concentrated. The material was purified via column chromatography (RediSep Gold 80 g, gradient elution 10-75% [3:1 EtOAc/EtOH]:Heptane) to give perfluorophenyl 1-(4-(cyclohexylmethyl)-5-fluoro-2-methoxyphenyl)-2-oxo-1,2-dihydroquinoline-6-sulfonate (1.1 g, 1.799 mmol, 53.0% yield) as a light yellow solid. m/z (ESI) 611.9 (M+H)$^+$.

Step 2: (P)-1-(4-(cyclohexylmethyl)-5-fluoro-2-methoxyphenyl)-2-oxo-N-2-pyrimidinyl-1,2-dihydro-6-quinolinesulfonamide A RBF was charged with (P)-perfluorophenyl 1-(4-(cyclohexylmethyl)-5-fluoro-2-methoxyphenyl)-2-oxo-1,2-dihydroquinoline-6-sulfonate (0.130 g, 0.213 mmol) and pyrimidin-2-amine (0.026 g, 0.276 mmol). DMSO (0.55 ml) was added to give a solution which was then diluted with THF (1.66 ml). The flask was cooled in an ice-water bath for 15 min, then lithium bis(trimethylsilyl)amide (1M in THF) (0.489 ml, 0.489 mmol) was added dropwise, slowly over 2 min. After 15 min, the mixture was diluted with 1N aq. HCl and EtOAc. The layers were separated, and the aq. layer was extracted with EtOAc (2×). The combined organic extracts were dried over sodium sulfate, filtered, and concentrated. The residue was purified by chromatography on silica gel (50-g SNAP Ultra column, 10-70% of a 3:1 EtOAc/EtOH solution in heptane with 10% DCM as additive). Fractions containing pure product were combined and concentrated to give (P)-1-(4-(cyclohexylmethyl)-5-fluoro-2-methoxyphenyl)-2-oxo-N-(pyrimidin-2-yl)-1,2-dihydroquinoline-6-sulfonamide (60 mg, 0.115 mmol, 54.0% yield) as an off-white solid. $^1$H NMR (500 MHz, DMSO-d6) δ ppm 11.56 (s, 1H) 8.44-8.52 (m, 3H) 8.23 (d, J=9.73 Hz, 1H) 7.97 (dd, J=8.99, 2.04 Hz, 1H) 7.24 (d, J=9.47 Hz, 1H) 7.12-7.20 (m, 1H)

6.97-7.10 (m, 1H) 6.70-6.80 (m, 2H) 3.63 (s, 3H) 2.54-2.74 (m, 2H) 1.58-1.85 (m, 7H) 1.12-1.30 (m, 4H). m/z (ESI) 523.2 (M+H)+.

Example 642

(Method 189): (P)-1-(4-(cyclohexylmethyl)-5-fluoro-2-methoxyphenyl)-N-1,2,4-oxadiazol-3-yl-2-oxo-1,2-dihydro-6-quinolinesulfonamide

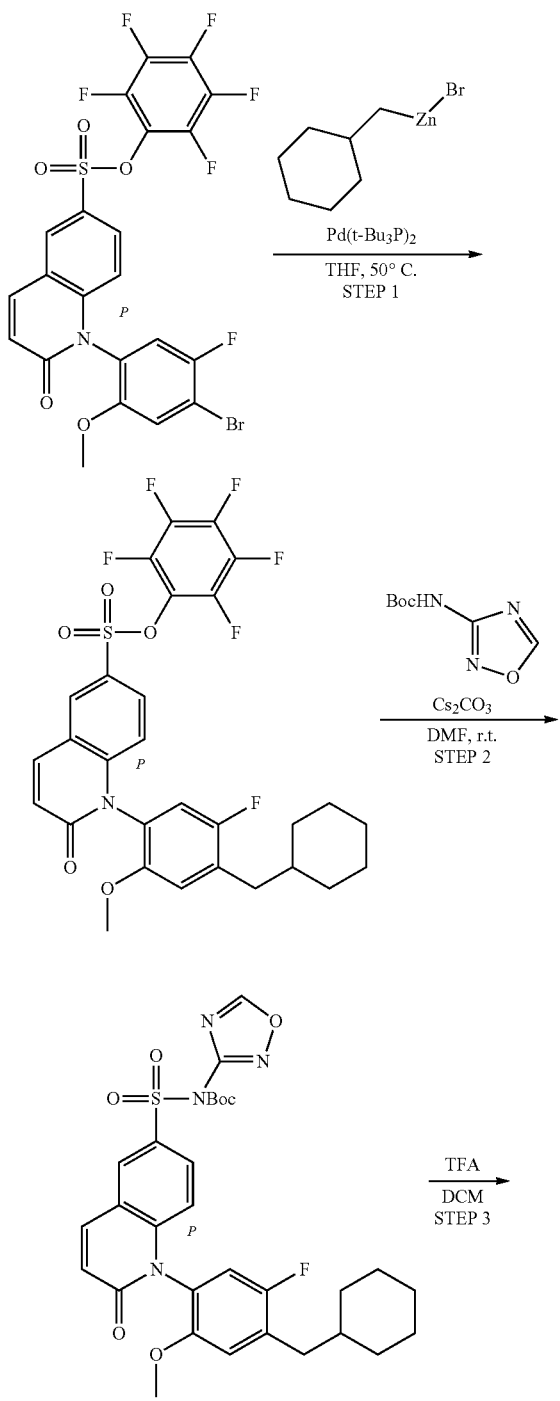

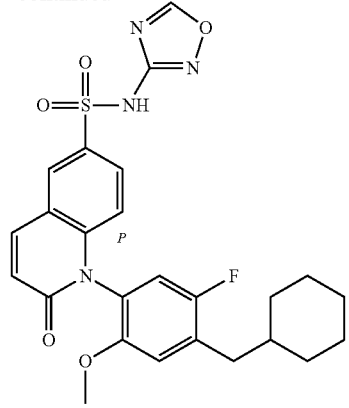

Step 1: (P)-perfluorophenyl 1-(4-(cyclohexylmethyl)-5-fluoro-2-methoxyphenyl)-2-oxo-1,2-dihydroquinoline-6-sulfonate A RBF was charged with (P)-perfluorophenyl 1-(4-bromo-5-fluoro-2-methoxyphenyl)-2-oxo-1,2-dihydroquinoline-6-sulfonate (2.017 g, 3.39 mmol), (cyclohexylmethyl)zinc(II) bromide (21.04 ml, 10.52 mmol), and bis(tri-t-butylphosphine)palladium(0) (0.260 g, 0.509 mmol) The vial was flushed with Ar (g), then THF (16.97 ml) was added. The reaction mixture was heated to 50° C. and stirred for one hour. The reaction was brought to RT and then diluted with ethyl acetate and 1N Aq. HCl solution. The organic layer was washed with brine, dried with sodium sulfate, filtered, and concentrated. The material was purified via column chromatography (RediSep Gold 80 g, gradient elution 10-75% [3:1 EtOAc/EtOH]:Heptane) to give perfluorophenyl 1-(4-(cyclohexylmethyl)-5-fluoro-2-methoxyphenyl)-2-oxo-1,2-dihydroquinoline-6-sulfonate (1.1 g, 1.799 mmol, 53.0% yield) as a light yellow solid. m/z (ESI) 611.9 (M+H)+.

Step 2: (P)-tert-butyl (1-(4-(cyclohexylmethyl)-5-fluoro-2-methoxyphenyl)-2-oxo-1,2-dihydroquinolin-6-yl)sulfonyl(1,2,4-oxadiazol-3-yl)carbamate A RBF was charged with perfluorophenyl (P)-1-(4-(cyclohexylmethyl)-5-fluoro-2-methoxyphenyl)-2-oxo-1,2-dihydroquinoline-6-sulfonate (0.19 g, 0.311 mmol), tert-butyl 1,2,4-oxadiazol-3-ylcarbamate (0.115 g, 0.621 mmol), and cesium carbonate (0.152 g, 0.466 mmol). The vial was flushed with Ar (g) and then DMF (1.553 ml) was added. The reaction was stirred for 24 hours at room temperature. The mixture was diluted with water and extracted with EtOAc (3×). The combined organic extracts were washed with brine, dried over sodium sulfate, filtered, and concentrated. The material was purified via column chromatography (RediSep Gold 40 g, gradient elution 0-100% EtOAc:Heptane) to afford (P)-tert-butyl (1-(4-(cyclohexylmethyl)-5-fluoro-2-methoxyphenyl)-2-oxo-1,2-dihydroquinolin-6-yl)sulfonyl(1,2,4-oxadiazol-3-yl)carbamate (48 mg, 0.078 mmol, 25.2% yield). m/z (ESI) 613.2 (M+H)+.

Step 3: (P)-1-(4-(cyclohexylmethyl)-5-fluoro-2-methoxyphenyl)-N-1,2,4-oxadiazol-3-yl-2-oxo-1,2-dihydro-6-quinolinesulfonamide (P)-Tert-butyl (1-(4-(cyclohexylmethyl)-5-fluoro-2-methoxyphenyl)-2-oxo-1,2-dihydroquinolin-6-yl)sulfonyl (1,2,4-oxadiazol-3-yl)carbamate (48 mg, 0.078 mmol) was suspended in TFA (1 mL) and stirred for one hour at room temperature. The mixture was then concentrated and partitioned between water and DCM. The organic portion was concentrated and purified via silica gel (40-g Redi-Sep Gold column, 10-50% of a 3:1 EtOAc/EtOH solution in heptane with 10% DCM as additive) to give (P)-1-(4-(cyclohexyl-methyl)-5-fluoro-2-methoxyphenyl)-N-1,2,4-oxadiazol-3-yl-2-oxo-1,2-dihydro-6-quinolinesulfonamide (39 mg, 0.076 mmol, 97.4% yield). $^1$H NMR (500 MHz, DMSO-d$_6$) δ ppm 12.41 (br. s., 1H) 9.19 (s., 1H) 8.35 (s, 1H) 8.21 (d, J=9.60 Hz, 1H) 7.89 (d, J=8.64 Hz, 1H) 7.24 (d, J=9.54 Hz, 1H) 7.16 (d, J=6.55 Hz, 1H) 6.74 (m, 2H) 3.65 (s, 3H) 2.59 (m, 2H) 1.53-1.80 (m, 7H) 1.12-1.32 (m, 4H). m/z (ESI) 513.2 (M+H)$^+$.

Example 643

(Method 190): (P)-1-(4-(cyclopentylethynyl)-5-fluoro-2-methoxyphenyl)-N-3-isoxazolyl-2-oxo-1,2-dihydro-6-quinolinesulfonamide

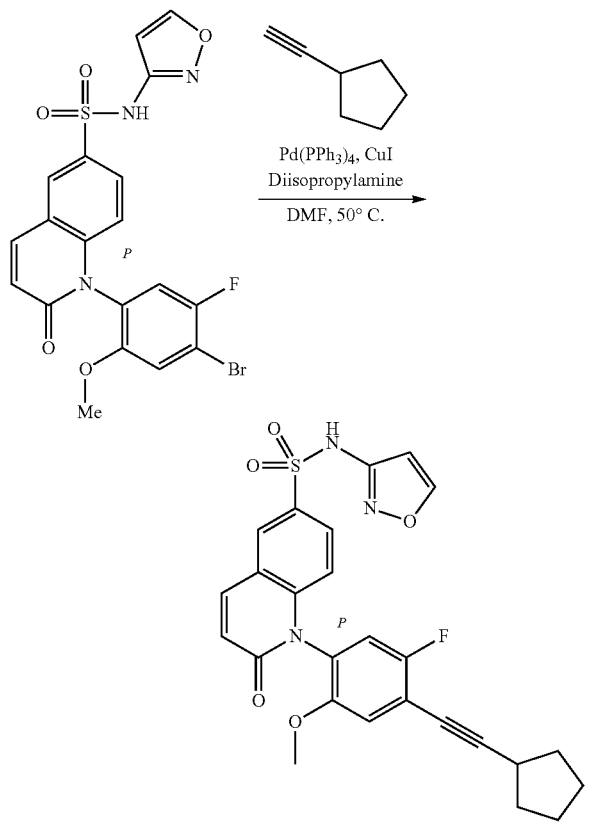

A RBF was charged with (P)-1-(4-bromo-5-fluoro-2-methoxyphenyl)-N-(isoxazol-3-yl)-2-oxo-1,2-dihydroquinoline-6-sulfonamide (234 mg, 0.272 mmol), Tetrakis(triphenylphosphine)palladium(0) (31.5 mg, 0.027 mmol), copper(i) iodide (1.384 μl, 0.041 mmol), diisopropylamine (582 μl, 4.08 mmol), 3,3-dimethylbut-1-yne (112 mg, 1.361 mmol) and DMF (1.36 ml). The reaction was stirred at 50° C. for 3 hrs. The mixture was diluted with water and Ethyl Acetate. The organic portion was collected, dried with sodium sulfate, filtered, and concentrated. The crude material was purified via column chromatography (RediSep Gold 40 g, gradient elution 10-75% [3:1 EtOAc/EtOH]:Heptane to give (P)-1-(4-(cyclopentylethynyl)-5-fluoro-2-methoxyphenyl)-N-(isoxazol-3-yl)-2-oxo-1,2-dihydroquinoline-6-sulfonamide (45 mg, 0.089 mmol, 32.6% yield) as an off-white solid. $^1$H NMR (400 MHz, DMSO-d$_6$) δ ppm 11.60 (br. s, 1H) 8.67 (d, J=1.81 Hz, 1H) 8.30-8.38 (m, 1H) 8.15 (d, J=9.69 Hz, 1H) 7.76 (dd, J=8.97, 2.23 Hz, 1H) 7.39 (d, J=9.17 Hz, 1H) 7.26 (d, J=6.38 Hz, 1H) 6.70-6.79 (m, 2H) 6.39 (d, J=1.76 Hz, 1H) 3.60 (s, 3H) 2.85-2.89 (m, 1H) 1.91-1.99 (m, 2H) 1.51-1.73 (m, 6H). m/z (ESI) 508.0 (M+H)$^+$.

Example 644

(Method 191): 1-(5-fluoro-2-methoxy-4-(3,3,3-trifluoro-1-propyn-1-yl)phenyl)-N-3-isoxazolyl-2-oxo-1,2-dihydro-6-quinolinesulfonamide

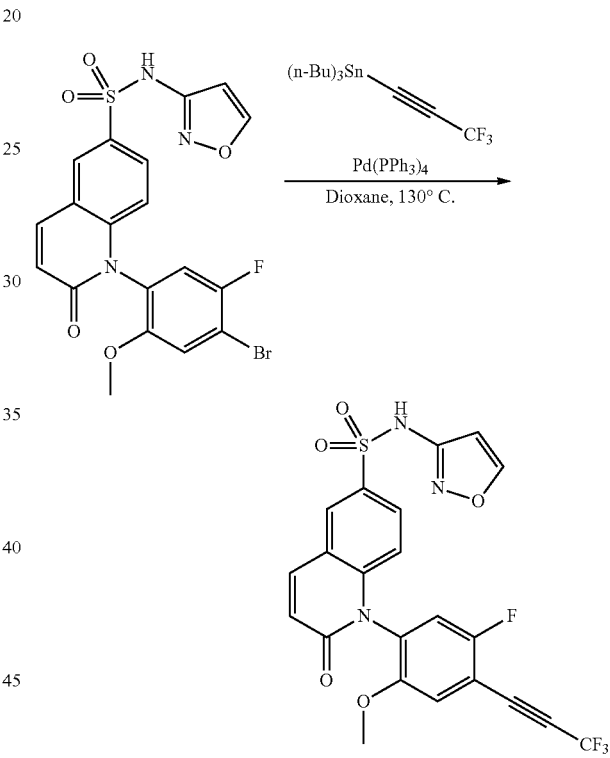

A microwave vial was charged with (P)-1-(4-bromo-5-fluoro-2-methoxyphenyl)-N-(isoxazol-3-yl)-2-oxo-1,2-dihydroquinoline-6-sulfonamide (83 mg, 0.168 mmol), Tetrakis(triphenylphosphine)palladium(0) (38.8 mg, 0.034 mmol), tributyl(3,3,3-trifluoroprop-1-yn-1-yl)stannane (129 mg, 0.336 mmol) and 1,4-dioxane. The vial was sealed and heated to 130° C. for 2 hrs in a Biotage Initiator microwave reactor. The reaction mixture was brought to ambient temperature and then diluted with 1N HCl and Ethyl Acetate. The organic portion was concentrated and purified in 10-100% EtOAc/Heptanes to give (P)-1-(5-fluoro-2-methoxy-4-(3,3,3-trifluoro-1-propyn-1-yl)phenyl)-N-3-isoxazolyl-2-oxo-1,2-dihydro-6-quinolinesulfonamide (10 mg, 0.020 mmol, 11.74% yield) as a tan solid. $^1$H NMR (400 MHz, DMSO-d$_6$) δ ppm 11.67 (br. s, 1H) 8.64-8.72 (m, 1H) 8.34-8.38 (m, 1H) 8.24 (d, J=9.74 Hz, 1H) 7.77-7.83 (m, 2H) 7.72 (d, J=9.23 Hz, 1H) 6.77-6.87 (m, 2H) 6.38-6.44 (m, 1H) 3.71 (s, 3H). m/z (ESI) 507.8 (M+H)$^+$.

Example 645

(Method 192): (P)-1-(4-(cyclopentylethynyl)-5-fluoro-2-methoxyphenyl)-2-oxo-N-3-pyridazinyl-1,2-dihydro-6-quinolinesulfonamide

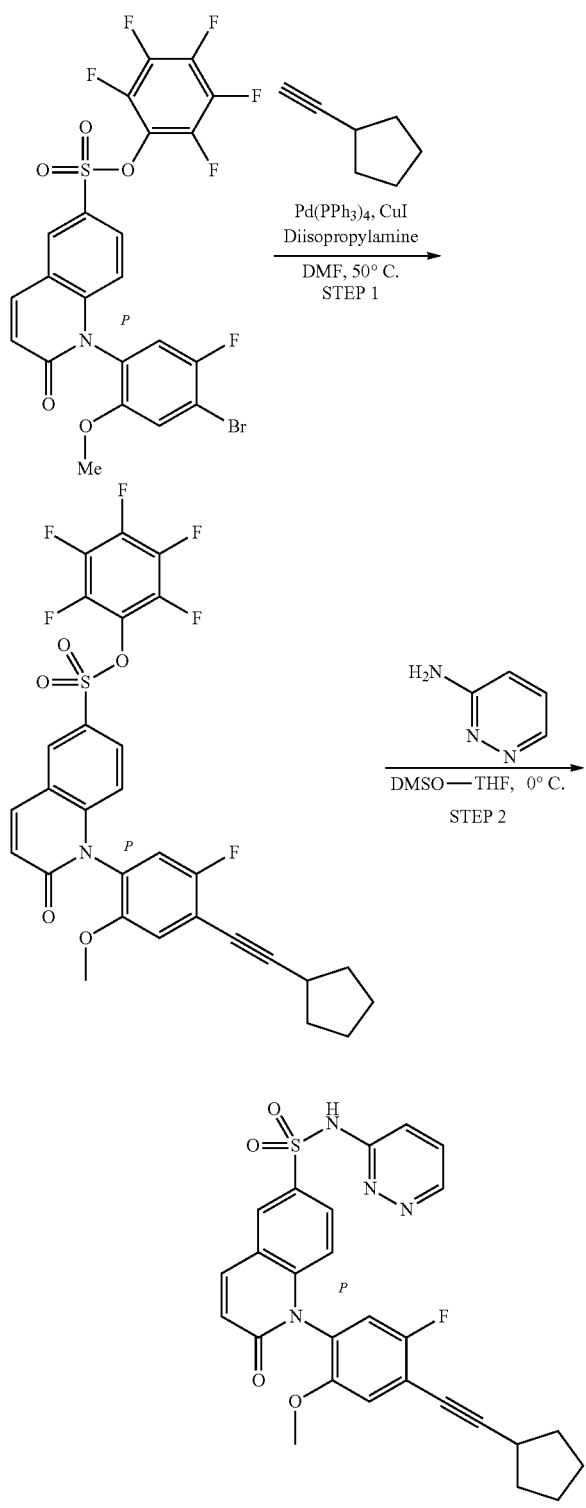

Step 1: (P)-perfluorophenyl 1-(4-(cyclopentylethynyl)-5-fluoro-2-methoxyphenyl)-2-oxo-1,2-dihydroquinoline-6-sulfonate A RBF was charged with (P)-perfluorophenyl 1-(4-bromo-5-fluoro-2-methoxyphenyl)-2-oxo-1,2-dihydroquinoline-6-sulfonate (2 g, 3.37 mmol), ethynylcyclopentane (1.584 g, 16.83 mmol), diisopropylamine (2.398 ml, 16.83 mmol), copper(i) iodide (0.064 g, 0.337 mmol), Tetrakis(triphenylphosphine)palladium(0) (0.389 g, 0.337 mmol), and DMF (16.83 ml). The reaction was stirred at 50° C. for 3 hrs. The mixture was diluted with water and Ethyl Acetate. The organic portion was collected, dried with sodium sulfate, filtered, and concentrated. The crude material was purified via column chromatography (RediSep Gold 40 g, gradient elution 10-75% [3:1 EtOAc/EtOH]:Heptane to give (P)-perfluorophenyl 1-(4-(cyclopentylethynyl)-5-fluoro-2-methoxyphenyl)-2-oxo-1,2-dihydroquinoline-6-sulfonate (1.25 g, 2.058 mmol, 61.1% yield) as an off-white solid. m/z (ESI) 608.0 (M+H)$^+$.

Step 2: (P)-1-(4-(cyclopentylethynyl)-5-fluoro-2-methoxyphenyl)-2-oxo-N-3-pyridazinyl-1,2-dihydro-6-quinolinesulfonamide A RBF was charged with (P)-perfluorophenyl 1-(4-(cyclopentylethynyl)-5-fluoro-2-methoxyphenyl)-2-oxo-1,2-dihydroquinoline-6-sulfonate (179 mg, 0.295 mmol) and pyridazin-3-amine (36.4 mg, 0.383 mmol). DMSO (0.76 ml) was added to give a solution which was then diluted with THF (2.21 ml). The flask was cooled in an ice-water bath for 15 min, then lithium bis(trimethylsilyl)amide (1M in THF) (678 µl, 0.678 mmol) was added dropwise, slowly over 2 min. After 15 min, the mixture was diluted with 1N aq. HCl and EtOAc. The layers were separated, and the aq. layer was extracted with EtOAc (2×). The combined organic extracts were dried over sodium sulfate, filtered, and concentrated. The residue was purified by chromatography on silica gel (50-g SNAP Ultra column, 10-70% of a 3:1 EtOAc/EtOH solution in heptane with 10% DCM as additive). Fractions containing pure product were combined and concentrated to give (P)-1-(4-(cyclopentylethynyl)-5-fluoro-2-methoxyphenyl)-2-oxo-N-(pyridazin-3-yl)-1,2-dihydroquinoline-6-sulfonamide (60 mg, 0.116 mmol, 39.3% yield) as an off-white solid. $^1$H NMR (400 MHz, DMSO-d$_6$) δ ppm 14.46 (br. s., 1H) 8.25-8.38 (m, 2H) 8.19 (d, J=9.64 Hz, 1H) 7.90-7.97 (m, 1H) 7.82 (dd, J=8.81, 1.76 Hz, 1H) 7.69 (dd, J=9.54, 4.25 Hz, 1H) 7.43 (d, J=9.23 Hz, 1H) 7.32 (d, J=6.43 Hz, 1H) 6.70-6.77 (m, 2H) 3.66 (s, 3H) 2.95-3.01 (m, 1H) 1.98-2.08 (m, 2H) 1.58-1.79 (m, 6H). m/z (ESI) 519.0 (M+H)$^+$.

Example 646

(Method 193): 1-(5-chloro-6-(cyclopentylethynyl)-2-methoxy-3-pyridinyl)-2-oxo-N-3-pyridazinyl-1,2-dihydro-6-quinolinesulfonamide

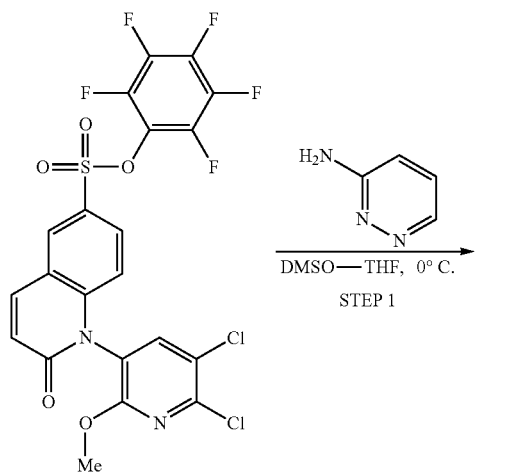

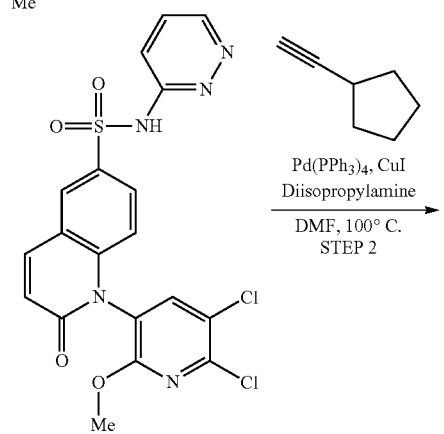

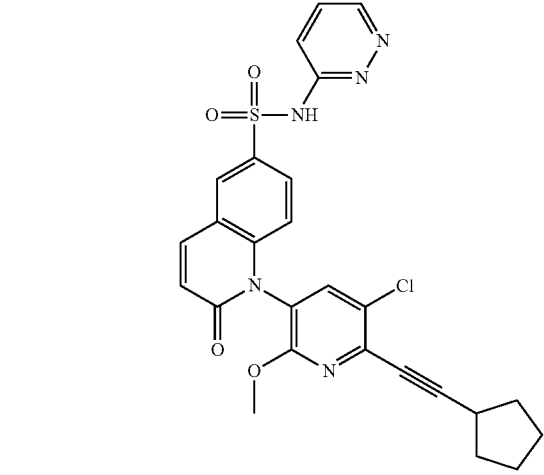

Step 1: 1-(5,6-dichloro-2-methoxypyridin-3-yl)-2-oxo-N-(pyridazin-3-yl)-1,2-dihydroquinoline-6-sulfonamide A RBF was charged with perfluorophenyl 1-(5,6-dichloro-2-methoxypyridin-3-yl)-2-oxo-1,2-dihydroquinoline-6-sulfonate (0.68 g, 1.199 mmol) and pyridazin-3-amine (0.137 g, 1.438 mmol). DMSO (2.2 ml) was added to give a solution which was then diluted with THF (7.14 ml). The flask was cooled in an ice-water bath for 15 min, then lithium bis(trimethylsilyl)amide (1M in THF) (2.64 ml, 2.64 mmol) was added dropwise, slowly over 2 min. After 15 min, the mixture was diluted with 1N aq. HCl and EtOAc. The layers were separated, and the aq. layer was extracted with EtOAc (2×). The combined organic extracts were dried over sodium sulfate, filtered, and concentrated. The residue was purified by chromatography on silica gel (100-g SNAP Ultra column, 10-70% of a 3:1 EtOAc/EtOH solution in heptane with 10% DCM as additive). Fractions containing pure product were combined and concentrated to give 1-(5,6-dichloro-2-methoxypyridin-3-yl)-2-oxo-N-(pyridazin-3-yl)-1,2-dihydroquinoline-6-sulfonamide (0.25 g, 0.523 mmol, 43.6% yield) as an off-white solid. m/z (ESI) 478.0 (M+H)$^+$.

Step 2: 1-(5-chloro-6-(cyclopentylethynyl)-2-methoxy-3-pyridinyl)-2-oxo-N-3-pyridazinyl-1,2-dihydro-6-quinolinesulfonamide A RBF was charged with 1-(5,6-dichloro-2-methoxypyridin-3-yl)-2-oxo-N-(pyridazin-3-yl)-1,2-dihydroquinoline-6-sulfonamide (0.075 g, 0.157 mmol), ethynylcyclopentane (0.074 ml, 0.784 mmol), diisopropylamine (0.134 ml, 0.941 mmol), copper(i) iodide (2.66 µl, 0.078 mmol), tetrakis(triphenylphosphine)palladium(0) (0.018 g, 0.016 mmol), and DMF (0.784 ml). The reaction was stirred at 100° C. for 18 hrs. The mixture was diluted with water and Ethyl Acetate. The organic portion was collected, dried with sodium sulfate, filtered, and concentrated. The crude material was purified via column chromatography (RediSep Gold 40 g, gradient elution 10-75% [3:1 EtOAc/EtOH]:Heptane to give 1-(5-chloro-6-(cyclopentylethynyl)-2-methoxy-3-pyridinyl)-2-oxo-N-3-pyridazinyl-1,2-dihydro-6-quinolinesulfonamide (55 mg, 0.103 mmol, 65.4% yield) as an off-white solid. m/z (ESI) 536.0 (M+H)$^+$.

Example 647

(Method 194): (P)-1-(5-fluoro-2-methoxy-4-(3-methoxy-3-methyl-1-butyn-1-yl)phenyl)-N-3-isoxazolyl-2-oxo-1,2-dihydro-6-quinolinesulfonamide

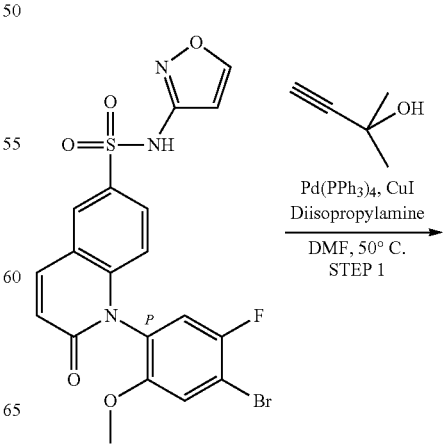

-continued

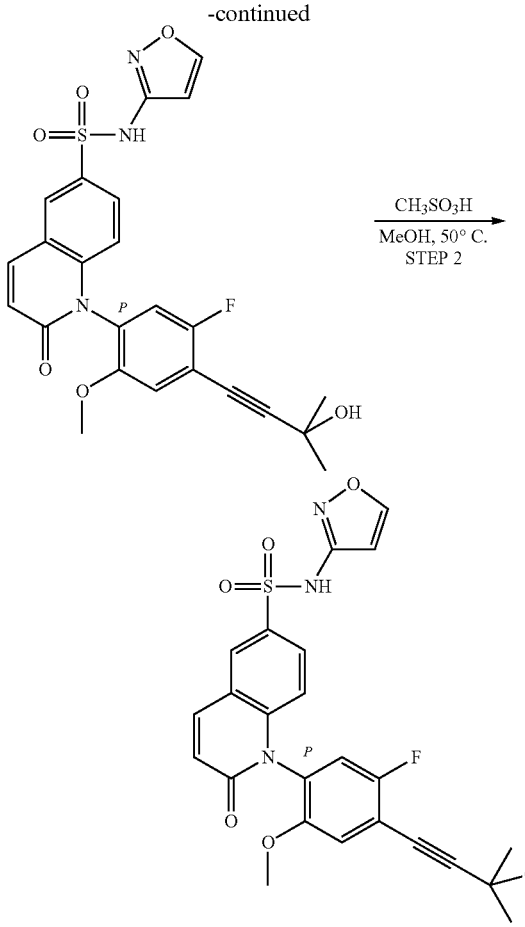

Step 1: (P)-1-(5-fluoro-4-(3-hydroxy-3-methyl-1-butyn-1-yl)-2-methoxyphenyl)-N-3-isoxazolyl-2-oxo-1,2-dihydro-6-quinolinesulfonamide A RBF was charged with (P)-1-(4-bromo-5-fluoro-2-methoxyphenyl)-N-(isoxazol-3-yl)-2-oxo-1,2-dihydroquinoline-6-sulfonamide (204 mg, 0.413 mmol), 2-methylbut-3-yn-2-ol (139 mg, 1.651 mmol), diisopropylamine (294 μl, 2.064 mmol), copper(i) iodide (7.86 mg, 0.041 mmol), tetrakis(triphenylphosphine)palladium(0) (47.7 mg, 0.041 mmol), and DMF (2.06 ml). The reaction was stirred at 50° C. for 3 hrs. The mixture was diluted with water and Ethyl Acetate. The organic portion was collected, dried with sodium sulfate, filtered, and concentrated. The crude material was purified via column chromatography (RediSep Gold 40 g, gradient elution 10-75% [3:1 EtOAc/EtOH]:Heptane to give (P)-1-(5-fluoro-4-(3-hydroxy-3-methylbut-1-yn-1-yl)-2-methoxyphenyl)-N-(isoxazol-3-yl)-2-oxo-1,2-dihydroquinoline-6-sulfonamide (150 mg, 0.302 mmol, 73.1% yield) as a yellow solid. m/z (ESI) 498.0 (M+H)+.

Step 2: (P)-1-(5-fluoro-2-methoxy-4-(3-methoxy-3-methyl-1-butyn-1-yl)phenyl)-N-3-isoxazolyl-2-oxo-1,2-dihydro-6-quinolinesulfonamide A pressure-resistant vessel was charged with (P)-1-(5-fluoro-4-(3-hydroxy-3-methylbut-1-yn-1-yl)-2-methoxyphenyl)-N-(isoxazol-3-yl)-2-oxo-1,2-dihydroquinoline-6-sulfonamide (135 mg, 0.271 mmol), methanesulfonic acid (132 μl, 2.035 mmol) and methanol (2196 μl, 54.3 mmol). The resulting mixture was stirred at 55° C. for 48 hrs. The reaction was then concentrated and the residue was partitioned between Aq. 1N HCl solution and EtOAc. The layers were separated, and the aq. layer was extracted with EtOAc (2×). The combined organic extracts were dried over sodium sulfate, filtered, and concentrated. The residue was purified by chromatography on silica gel (100-g SNAP Ultra column, 10-70% of a 3:1 EtOAc/EtOH solution in heptane with 10% DCM as additive). Fractions containing pure product were combined and concentrated to give 1-(5-fluoro-2-methoxy-4-(3-methoxy-3-methylbut-1-yn-1-yl)phenyl)-N-(isoxazol-3-yl)-2-oxo-1,2-dihydroquinoline-6-sulfonamide (80 mg, 0.156 mmol, 57.6% yield) as an off-white solid. $^1$H NMR (400 MHz, DMSO-$d_6$) δ ppm 11.66 (br. s, 1H) 8.74 (d, J=1.81 Hz, 1H) 8.37 (d, J=2.13 Hz, 1H) 8.23 (d, J=9.69 Hz, 1H) 7.83 (dd, J=8.97, 2.23 Hz, 1H) 7.52 (d, J=9.17 Hz, 1H) 7.40 (d, J=6.27 Hz, 1H) 6.85 (d, J=8.97 Hz, 1H) 6.80 (d, J=9.64 Hz, 1H) 6.46 (d, J=1.76 Hz, 1H) 3.69 (s, 3H) 3.37 (s, 3H) 1.54 (s, 6H). m/z (ESI) 511.8 (M+H)+.

Example 648

(Method 195): 1-(5-chloro-6-(cyclopentylamino)-2-methoxy-3-pyridinyl)-N-3-isoxazolyl-2-oxo-1,2-dihydro-6-quinolinesulfonamide

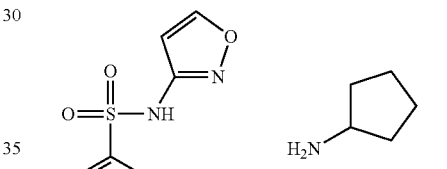

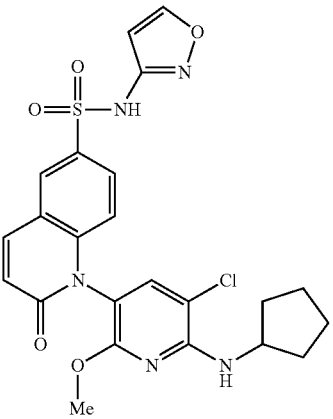

A microwave vessel was charged 1-(5,6-dichloro-2-methoxypyridin-3-yl)-N-(isoxazol-3-yl)-2-oxo-1,2-dihydroquinoline-6-sulfonamide (50 mg, 0.107 mmol), cyclopentanamine (456 μl, 5.35 mmol), hunig's base (93 μl, 0.535 mmol) and DMSO (1070 μl). The vial was sealed and heated to 130° C. for 2 hrs in a Biotage Initiator microwave reactor. The reaction mixture was brought to ambient temperature and then diluted with 1N HCl and Ethyl Acetate. The layers were separated, and the aq. layer was extracted with EtOAc (2×). The combined organic extracts were dried over sodium sulfate, filtered, and concentrated. The crude residue was purified by chromatography on silica gel (100-g SNAP Ultra column, 10-100% EtOAc/Heptanes) to give 1-(5-chloro-6-(cyclopentylamino)-2-methoxypyridin-3-yl)-N-(isoxazol-3-yl)-2-oxo-1,2-dihydroquinoline-6-sulfonamide (30 mg, 0.058 mmol, 54.3% yield) as a light yellow solid. $^1$H NMR (400 MHz, DMSO-d$_6$) δ ppm 11.66 (br. s, 1H) 8.72 (d, J=1.71 Hz, 1H) 8.32-8.35 (m, 1H) 8.18 (d, J=9.59 Hz, 1H) 7.86 (dd, J=8.97, 2.23 Hz, 1H) 7.66 (s, 1H) 7.00 (d, J=9.02 Hz, 1H) 6.77 (d, J=9.64 Hz, 1H) 6.46 (d, J=6.79 Hz, 1H) 5.57 (br. s., 1H) 4.30-4.37 (m, 1H) 3.72 (s, 3H) 1.99-2.03 (m, 2H) 1.47-1.85 (m, 6H). m/z (ESI) 516.0 (M+H)$^+$.

Example 649 and 650

(Method 196): (P)-1-(4'-chloro-2-fluoro-3',5-dimethyl-4-biphenylyl)-2-oxo-N-2-pyrimidinyl-1,2-dihydro-6-quinolinesulfonamide and (M)-1-(4'-chloro-2-fluoro-3',5-dimethyl-4-biphenylyl)-2-oxo-N-2-pyrimidinyl-1,2-dihydro-6-quinolinesulfonamide

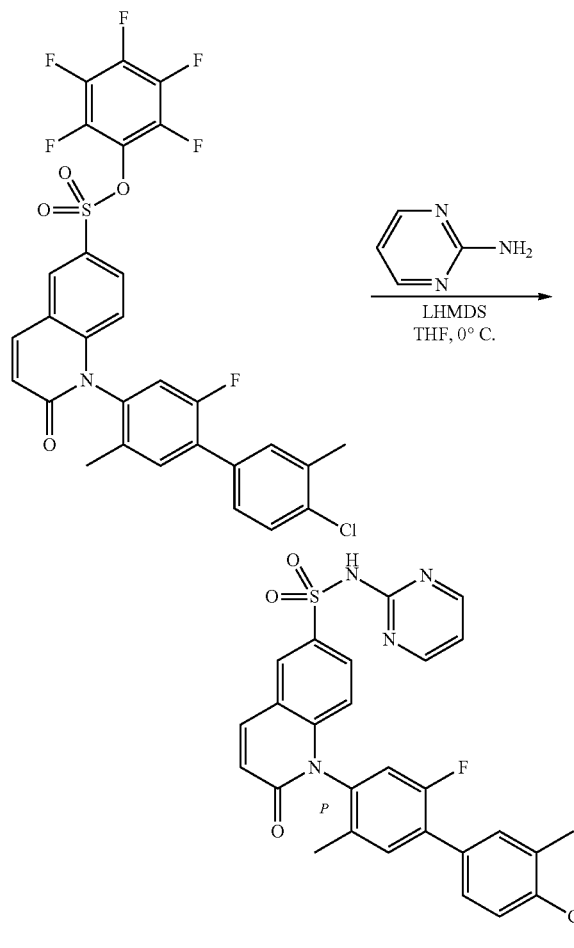

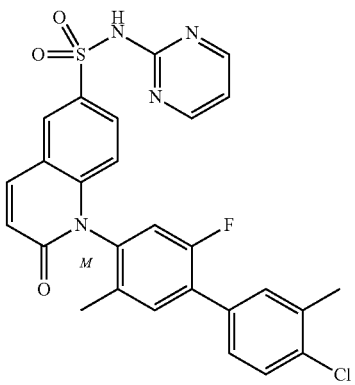

To a RBF was added perfluorophenyl 1-(4'-chloro-2-fluoro-3',5-dimethyl-[1,1'-biphenyl]-4-yl)-2-oxo-1,2-dihydroquinoline-6-sulfonate (0.250 g, 0.401 mmol), and THF (4.01 ml). To this, was added pyrimidin-2-amine (0.057 g, 0.601 mmol) and the reaction was cooled to 0° C. Lithium bis(trimethylsilyl)amide, 1.0 m solution in THF (0.881 ml, 0.881 mmol) was added dropwise and allowed to stir at 0° C. After 1 hour, the mixture was diluted with 1N aq. HCl and EtOAc. The layers were separated, and the aq. layer was extracted with EtOAc (2×). The combined organic extracts were dried over sodium sulfate, filtered, and concentrated. The residue was purified by chromatography on silica gel (40-g Redi-Sep Gold column, 10-50% of a 3:1 EtOAc/EtOH solution in heptane) 1-(4'-chloro-2-fluoro-3',5-dimethyl-[1,1'-biphenyl]-4-yl)-2-oxo-N-(pyrimidin-2-yl)-1,2-dihydroquinoline-6-sulfonamide (0.059 g, 0.110 mmol, 27.5% yield) as an off white solid. The racemic mixture was separated using SFC chiral chromatography (S,S) Whelk-O column, 55% methanol in CO$_2$. Peak 1: $^1$H NMR (400 MHz, DMSO-d6) δ 11.92 (br. s., 1H), 8.47-8.55 (m, 3H), 8.32 (d, J=9.64 Hz, 1H), 8.02 (dd, J=2.12, 8.97 Hz, 1H), 7.62-7.74 (m, 2H), 7.54-7.60 (m, 1H), 7.49-7.52 (m, 1H), 7.45 (d, J=11.05 Hz, 1H), 7.03 (t, J=4.87 Hz, 1H), 6.84 (d, J=9.64 Hz, 1H), 6.76 (d, J=9.02 Hz, 1H), 2.43 (s, 3H), 1.91 (s, 3H). m/z (ESI) 536.2 (M+H)$^+$. Peak 2: $^1$H NMR (400 MHz, DMSO-d6) δ 11.92 (br. s., 1H), 8.48-8.55 (m, 3H), 8.32 (d, J=9.64 Hz, 1H), 8.02 (d, J=8.89 Hz, 1H), 7.62-7.75 (m, 2H), 7.54-7.60 (m, 1H), 7.37-7.54 (m, 2H), 7.04 (t, J=5.08 Hz, 1H), 6.84 (d, J=9.64 Hz, 1H), 6.76 (d, J=8.91 Hz, 1H), 2.43 (s, 3H), 1.89-1.94 (m, 3H). m/z (ESI) 536.2 (M+H)$^+$.

Example 651

(Method 197): (P)-1-(4-bromo-5-fluoro-2-methoxy-phenyl)-N-(2-methylpyrimidin-4-yl)-2-oxo-1,2-dihydroquinoline-6-sulfonamide

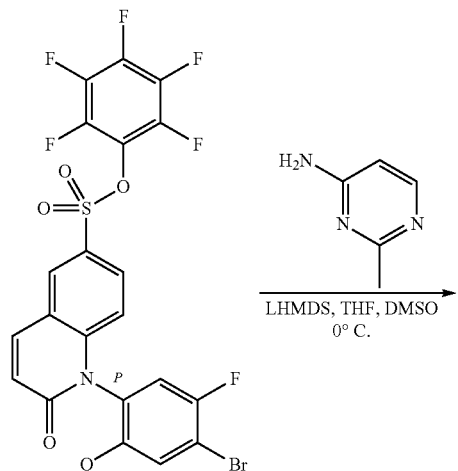

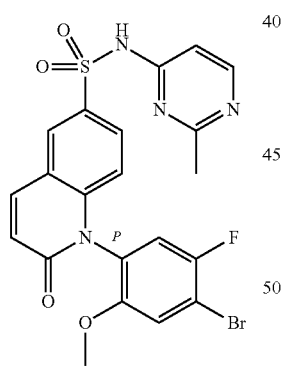

This compound was synthesized via method 186, using the following purification technique: The compound was purified using column chromatography (RediSep Gold 40 g, gradient elution 10-75% [3:1 EtOAc/EtOH]:Heptane) to afford 1-(4-bromo-5-fluoro-2-methoxyphenyl)-N-(2-methylpyrimidin-4-yl)-2-oxo-1,2-dihydroquinoline-6-sulfonamide (0.043 g, 0.083 mmol, 49.2% yield) as an off-white solid. $^1$H NMR (400 MHz, DMSO-d6) δ 8.24 (d, J=2.18 Hz, 1H), 8.08 (d, J=9.54 Hz, 1H), 7.98 (d, J=6.63 Hz, 1H), 7.72 (dd, J=2.12, 8.97 Hz, 1H), 7.52 (d, J=6.22 Hz, 1H), 7.45 (d, J=8.60 Hz, 1H), 6.74 (s, 1H), 6.63 (dd, J=5.08, 9.33 Hz, 2H), 3.54 (s, 3H), 2.23 (s, 3H). m/z (ESI) 520.0 (M+H)$^+$.

Example 652, 653 and 654

(Method 198): 1-(4'-chloro-2-fluoro-5-methoxy-3'-methyl-[1,1'-biphenyl]-4-yl)-N-(isoxazol-3-yl)-2-oxo-1,2-dihydroquinoxaline-6-sulfonamide (652), (P)-1-(4'-chloro-2-fluoro-5-methoxy-3'-methyl-[1,1'-biphenyl]-4-yl)-N-(isoxazol-3-yl)-2-oxo-1,2-dihydroquinoxaline-6-sulfonamide (653) and (M)-1-(4'-chloro-2-fluoro-5-methoxy-3'-methyl-[1,1'-biphenyl]-4-yl)-N-(isoxazol-3-yl)-2-oxo-1,2-dihydroquinoxaline-6-sulfonamide (654)

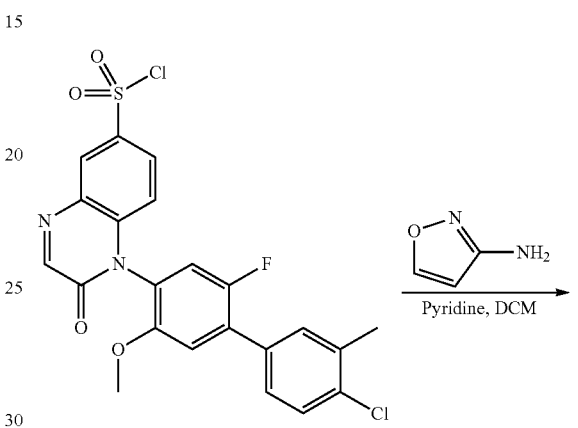

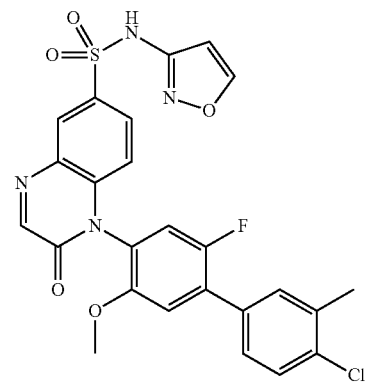

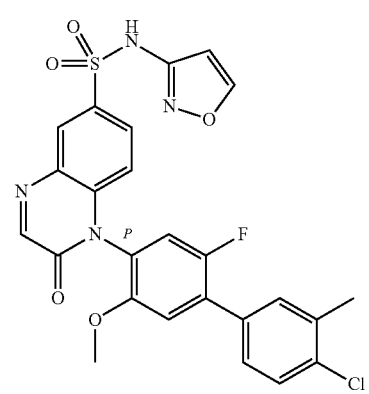

-continued

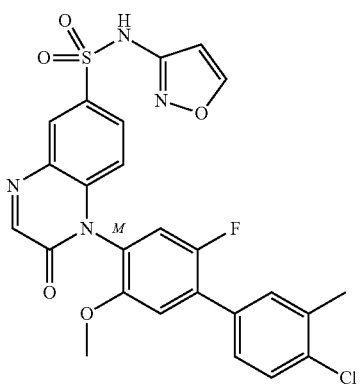

To a RBF was added, 3-aminoisoxazole (0.037 ml, 0.507 mmol) and pyridine (2.53 ml). This was cooled to 0° C. and 1-(4'-chloro-2-fluoro-5-methoxy-3'-methyl-[1,1'-biphenyl]-4-yl)-2-oxo-1,2-dihydroquinoxaline-6-sulfonyl chloride (0.250 g, 0.507 mmol) in 1 mL DCM was added dropwise. The ice bath was removed and allowed to warm up to RT. Let stir overnight. Removed solvent in vaccuo and took residue up in small amount of DCM and purified on Biotage, eluting with 0-50% EtOAc/Heptane. Collected fractions and removed solvent in vaccuo to yield 1-(4'-chloro-2-fluoro-5-methoxy-3'-methyl-[1,1'-biphenyl]-4-yl)-N-(isoxazol-3-yl)-2-oxo-1,2-dihydroquinoxaline-6-sulfonamide (0.182 g, 0.336 mmol, 66% yield) as an off-white solid. $^1$H NMR (400 MHz, DMSO-d6) δ 11.81 (s, 1H), 8.81 (d, J=1.87 Hz, 1H), 8.55 (s, 1H), 8.38 (d, J=2.18 Hz, 1H), 8.01 (dd, J=2.18, 8.81 Hz, 1H), 7.76 (s, J=5.42 Hz, 1H), 7.57-7.68 (m, 3H), 7.49 (t, J=6.97 Hz, 1H), 7.05 (d, J=8.91 Hz, 1H), 6.55 (d, J=1.76 Hz, 1H), 3.82-3.87 (m, 3H), 2.50 (s, 3H). m/z (ESI) 542.0 (M+H)$^+$. The remaining solid was purified using SFC chiral chromatography using a Regis Whelk-O (s,s) column, and 45% methanol in CO$_2$. Peak 1: $^1$H NMR (400 MHz, DMSO-d6) δ 11.76 (br. s., 1H), 8.75 (d, J=1.76 Hz, 1H), 8.50 (s, 1H), 8.32 (d, J=2.18 Hz, 1H), 7.95 (dd, J=2.12, 8.86 Hz, 1H), 7.71 (s, 1H), 7.52-7.62 (m, 3H), 7.44 (d, J=6.84 Hz, 1H), 7.00 (d, J=8.91 Hz, 1H), 6.49 (d, J=1.87 Hz, 1H), 3.78 (s, 3H), 2.45 (s, 3H). m/z (ESI) 542.0 (M+H)$^+$. $^1$H NMR (400 MHz, DMSO-d6) Shift 11.76 (br. s., 1H), 8.75 (d, J=1.76 Hz, 1H), 8.50 (s, 1H), 8.32 (d, J=2.18 Hz, 1H), 7.95 (dd, J=2.18, 8.91 Hz, 1H), 7.71 (s, 1H), 7.52-7.62 (m, 3H), 7.44 (d, J=6.84 Hz, 1H), 7.00 (d, J=8.91 Hz, 1H), 6.49 (d, J=1.76 Hz, 1H), 3.78 (s, 3H), 2.45 (s, 3H). m/z (ESI) 542.0 (M+H)$^+$ Example 655

(Method 199): 1-(5-chloro-6-(3-fluorophenyl)-2-oxo-1,2-dihydropyridin-3-yl)-N-(isoxazol-3-yl)-2-oxo-1,2-dihydroquinoline-6-sulfonamide 2,2,2-trifluoroacetate

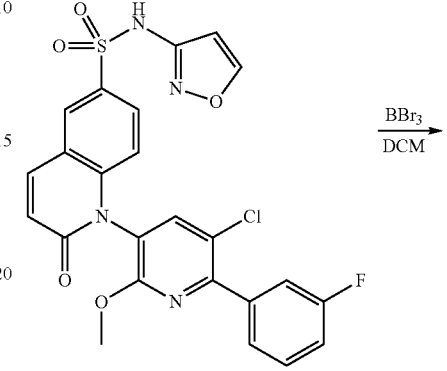

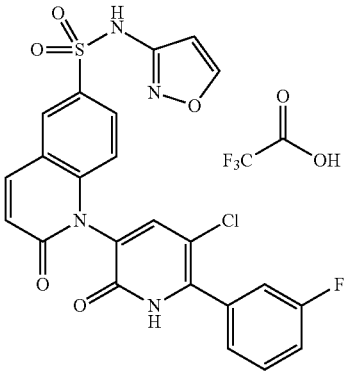

1-(5-Chloro-6-(3-fluorophenyl)-2-methoxypyridin-3-yl)-N-(isoxazol-3-yl)-2-oxo-1,2-dihydroquinoline-6-sulfonamide (20.00 mg, 0.038 mmol) was dissolved in DCM (380 µl) and cooled to 0° C. and stirred for 10 minutes. Boron tribromide (114 µl, 0.114 mmol) was added dropwise and the reaction was stirred for 30 minutes. The reaction mixture was warmed to rt and was stirred for 2 days. The reaction mixture was filtered. The crude material was purified by reverse-phase preparative HPLC using 0.1% TFA in CH$_3$CN/H$_2$O, gradient 10% to 90% over 20 min to provide 1-(5-chloro-6-(3-fluorophenyl)-2-oxo-1,2-dihydropyridin-3-yl)-N-(isoxazol-3-yl)-2-oxo-1,2-dihydroquinoline-6-sulfonamide 2,2,2-trifluoroacetate as a white solid. (4.48 mg, 0.007 mmol, 19% yield) as white solid. m/z (ESI) 513.9 [M+1]. $^1$H NMR (500 MHz, DMSO-d6) δ 11.65 (br. s., 1H), 8.72 (d, J=1.69 Hz, 1H), 8.38 (d, J=1.75 Hz, 1H), 8.23 (d, J=9.73 Hz, 1H), 7.89 (dd, J=2.08, 9.02 Hz, 1H), 7.45-7.67 (m, 4H), 7.39 (br. s., 1H), 6.82 (d, J=9.73 Hz, 1H), 6.45 (d, J=1.69 Hz, 1H).

Example 656 & 657

(Method 200): (P)-1-(5-chloro-2-methoxy-4-(trifluoromethyl)phenyl)-2-oxo-N-(pyrimidin-4-yl)-1,2-dihydroquinoline-6-sulfonamide (656) and (M)-1-(5-chloro-2-methoxy-4-(trifluoromethyl)phenyl)-2-oxo-N-(pyrimidin-4-yl)-1,2-dihydroquinoline-6-sulfonamide (657)

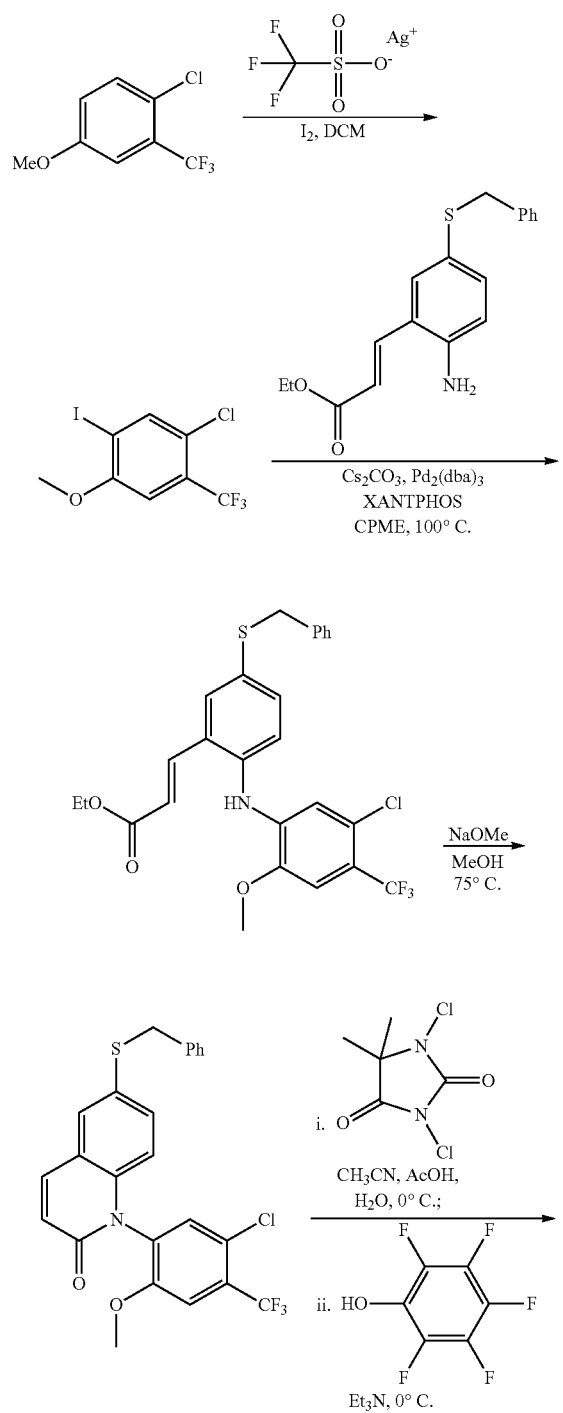

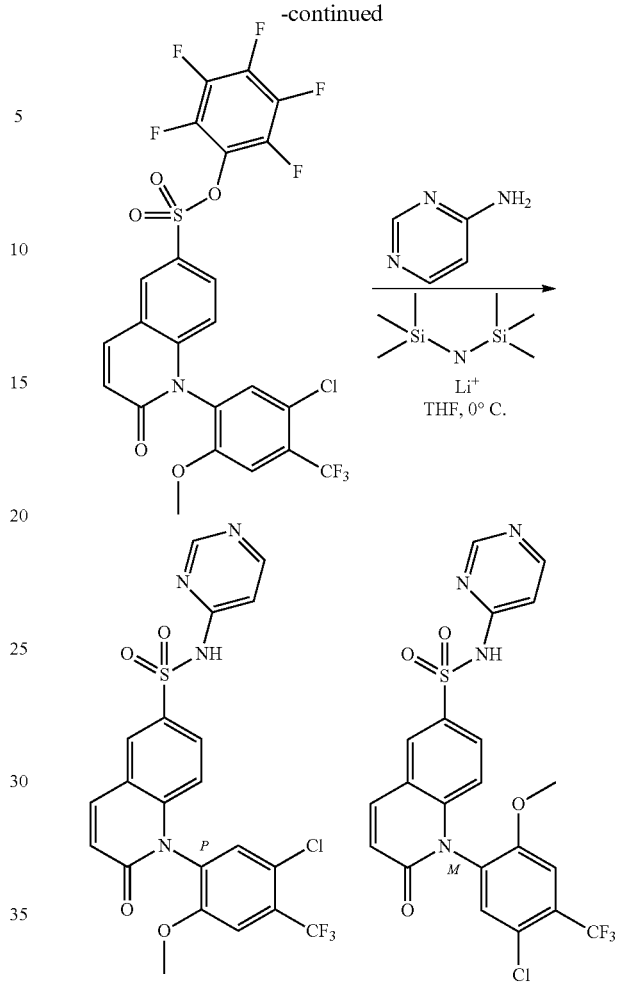

Step 1: 1-chloro-5-iodo-4-methoxy-2-(trifluoromethyl)benzene

A flask was charged with DCM (95 mL) and 1-chloro-4-methoxy-2-(trifluoromethyl)benzene (5 g, 23.74 mmol) to form a clear solution. Iodine (6.63 g, 26.1 mmol) was added, followed by silver trifluoromethanesulfonate (7.32 g, 28.5 mmol). The reaction was allowed to stir at RT under nitrogen atmosphere. The reaction was stopped at 1.5 h and filtered through Celite, eluting with DCM until the eluent was no longer purple. The purple filtrate was extracted with saturated aqueous sodium thiosulfate (50 mL) until the mixture was all light yellow. The biphasic mixture was diluted with water (100 mL) and the layers were separated. The aqueous layer was extracted with DCM (2×50 mL). The combined organics were dried with sodium sulfate, filtered and concentrated by rotovap to give 9.01 g crude brown liquid containing fine needle crystals. The mixture was purified by Biotage, 100 g SNAP Ultra silica col, loaded in minimal DCM directly onto dry column and eluted with 0-3% EtOAc/heptane. Fractions containing desired product were concentrated to provide 1-chloro-5-iodo-4-methoxy-2-(trifluoromethyl)benzene (6.6687 g, 19.82 mmol, 83% yield) as a white crystalline solid, a single peak by LCMS but parent ion does not show up. $^1$H NMR (400 MHz, CDCl$_3$) δ 7.93 (s, 1H), 7.06 (s, 1H), 3.94 (s, 3H).

Step 2: (E)-ethyl 3-(5-(benzylthio)-2-((5-chloro-2-methoxy-4-(trifluoromethyl)phenyl)amino)phenyl) acrylate A flask was charged with (E)-ethyl 3-(2-amino-5-(benzylthio)phenyl)acrylate (Bellen Chemistry Co., 3.2 g, 10.21 mmol), 1-chloro-5-iodo-4-methoxy-2-(trifluoromethyl)benzene (4.12 g, 12.25 mmol), cesium carbonate (4.66 g, 14.29 mmol), $Pd_2(dba)_3$ (0.234 g, 0.255 mmol), and (9,9-dimethyl-9H-xanthene-4,5-diyl)bis(diphenylphosphine) (0.295 g, 0.511 mmol) (XANTPHOS). The flask was flushed with nitrogen and a reflux condenser was added. CPME (20.42 mL) was added and the flask was heated to 100° C. with vigorous stirring. The reaction was stopped at 24 h and cooled to RT. Water and EtOAc were added (30 mL each), and the layers were separated. The aqueous layer was extracted again with EtOAc (50 mL). The combined organics were passed through a plug of Celite/silica to remove Pd, and the orange filtrate was concentrated. The residue was triturated with isopropanol, filtered through a medium glass frit, and the solid was dried under high vac to provide (E)-ethyl 3-(5-(benzylthio)-2-((5-chloro-2-methoxy-4-(trifluoromethyl)phenyl)amino)phenyl)acrylate (5.48 g, 10.50 mmol, 103% yield). m/z (ESI) 520.2 (M−H)⁻.

Step 3: 6-(benzylthio)-1-(5-chloro-2-methoxy-4-(trifluoromethyl)phenyl)quinolin-2(1H)-one A flask was charged with (E)-ethyl 3-(5-(benzylthio)-2-((5-chloro-2-methoxy-4-(trifluoromethyl)phenyl)amino)phenyl)acrylate (5.33 g, 10.21 mmol) and MeOH (102 mL), followed by sodium methoxide (8.17 ml, 4.08 mmol) under nitrogen atmosphere. A reflux condenser was added, and the flask was lowered into an oil bath at 75° C. At 18 h the reaction was cooled to RT and filtered through a silica plug to remove black particulates. The product was eluted with MeOH and concentrated down to about 50 mL, followed by filtration through a medium glass frit, washing the solid with MeOH. The solid precipitate was dried under high vac to provide 6-(benzylthio)-1-(5-chloro-2-methoxy-4-(trifluoromethyl)phenyl)quinolin-2(1H)-one (3.257 g, 6.84 mmol, 67.0% yield). m/z (ESI) 475.8 (M+H)⁺.

Step 4: Perfluorophenyl 1-(5-chloro-2-methoxy-4-(trifluoromethyl)phenyl)-2-oxo-1,2-dihydroquinoline-6-sulfonate A flask was charged with 6-(benzylthio)-1-(5-chloro-2-methoxy-4-(trifluoromethyl)phenyl)quinolin-2(1H)-one (1.63 g, 3.43 mmol), MeCN (16.11 ml), AcOH (0.612 ml), and water (0.403 ml). The heterogeneous mixture was cooled to 0° C. for 10 min. 1,3-dichloro-5,5-dimethylimidazolidine-2,4-dione (0.675 g, 3.43 mmol) was added portionwise (5 portions 0.135 g each, each portion added over 5 min., 20-30 min apart). After 3.5 h the reaction was not complete by LCMS, so another 0.25 equiv (0.1688 g) of hydantoin was added, followed by another 0.25 equiv. hydantoin at 4 h. With the reaction still at 0° C., 2,3,4,5,6-pentafluorophenol (0.757 g, 4.11 mmol) was added to the reaction flask, along with MeCN (2 mL). After 10 minutes, triethylamine (1.910 ml, 13.70 mmol) was added dropwise over 1 min. The reaction was allowed to stir at 0° C. After for 30 min, 1:1 brine:water (20 mL) was added, then EtOAc (20 mL). The layers were separated and the aqueous layer was extracted again with 20 mL EtOAc. The combined organics were dried with sodium sulfate, filtered and concentrated to give a brown sticky solid, which was taken up in 75 mL iPrOH (with 10 min sonication), then let stand for 20 min. A white powdery solid crashed out and was collected by filtration through a medium glass frit, the solid washed with iPrOH and dried under high vac. The filtrate was also concentrated to dryness and purified by Biotage, 100 g SNAP Ultra silica col, loaded in minimal DCM onto dry column and purified with a gradient from 2-50% EtOAc/heptane. Fractions with product were combined with the filtered crystals and concentrated under high vac to provide perfluorophenyl 1-(5-chloro-2-methoxy-4-(trifluoromethyl)phenyl)-2-oxo-1,2-dihydroquinoline-6-sulfonate (1.7957 g, 2.99 mmol, 87% yield). m/z (ESI) 600.0 (M+H)⁺.

Step 5: (P)-1-(5-chloro-2-methoxy-4-(trifluoromethyl)phenyl)-2-oxo-N-(pyrimidin-4-yl)-1,2-dihydroquinoline-6-sulfonamide and (M)-1-(5-chloro-2-methoxy-4-(trifluoromethyl)phenyl)-2-oxo-N-(pyrimidin-4-yl)-1,2-dihydroquinoline-6-sulfonamide A flask was charged with perfluorophenyl 1-(5-chloro-2-methoxy-4-(trifluoromethyl)phenyl)-2-oxo-1,2-dihydroquinoline-6-sulfonate (1.7957 g, 2.99 mmol) and pyrimidin-4-amine (0.342 g, 3.59 mmol). The flask was flushed with nitrogen, and THF (29.9 mL) was added. The solution was cooled to 0° C. for 10 min., then lithium bis(trimethylsilyl) amide (6.29 ml, 6.29 mmol) was added dropwise over 5 min. The reaction was stopped at 1 h. While still cold, 1N HCl (30 mL) and EtOAc (25 mL) were added and the layers separated. The organic layer was washed again with 1N HCl (20 mL). The combined aqueous layers were extracted with EtOAc (2×30 mL). All combined organic layers were dried with sodium sulfate, filtered and concentrated to give 3 g of a light yellow sticky solid, which was purified by Biotage, 120 g Redi-Sep silica col, 40-100% EtOAc/heptane plus 5% DCM, solid loading. Fractions containing product were concentrated to provide 0.557 g white solid (36%), which was subjected to chiral separation, SFC, Chiralpak AD, 30% ethanol, to give (P)-1-(5-chloro-2-methoxy-4-(trifluoromethyl)phenyl)-2-oxo-N-(pyrimidin-4-yl)-1,2-dihydroquinoline-6-sulfonamide as peak 1 (234.3 mg, 15% yield), and (M)-1-(5-chloro-2-methoxy-4-(trifluoromethyl)phenyl)-2-oxo-N-(pyrimidin-4-yl)-1,2-dihydroquinoline-6-sulfonamide as peak 2 (242.0 mg, 16% yield). Data for peak 1: $^1$H NMR (400 MHz, DMSO-$d_6$) δ 8.61 (s, 1H), 8.45 (br. s, 1H), 8.30 (br. s, 1H), 8.26 (d, J=8.0 Hz, 1H), 7.92 (m, 2H), 7.69 (s, 1H), 7.02 (br. s, 1H), 6.80 (m, 2H), 3.80 (s, 3H). m/z (ESI) 510.9 (M+H)⁺. Data for peak 2: $^1$H NMR (400 MHz, DMSO-$d_6$) δ 8.62 (s, 1H), 8.45 (s, 1H), 8.30 (br. s, 1H), 8.26 (d, J=8.0 Hz, 1H), 7.92 (m, 2H), 7.69 (s, 1H), 7.02 (br. s, 1H), 6.80 (m, 2H), 3.80 (s, 3H). m/z (ESI) 510.9 (M+H)⁺.

Example 658

(Method 201): (P)-1-(4'-chloro-3-methoxy-3'-methyl-4-biphenylyl)-2-oxo-N-2-pyrazinyl-1,2-dihydro-6-quinolinesulfonamide

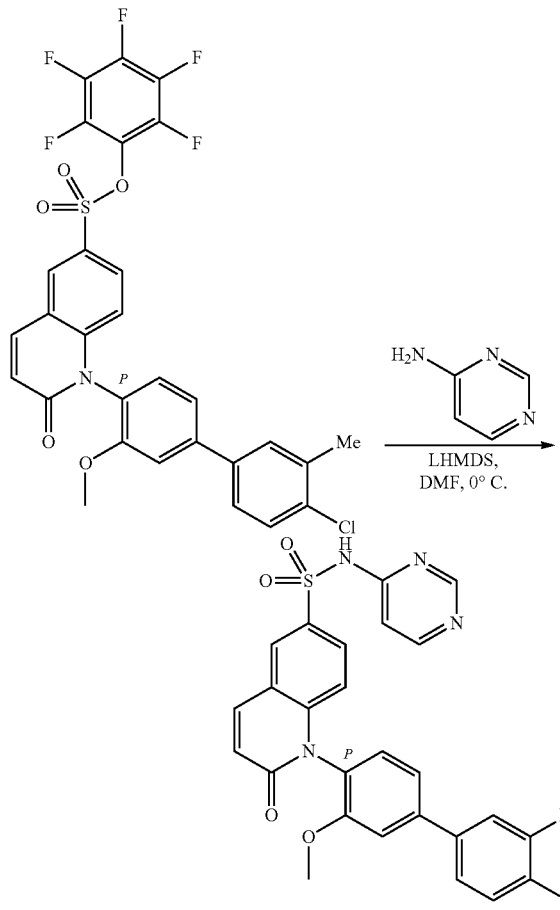

A flask was charged with pyrimidin-4-amine (0.071 g, 0.744 mmol) and (P)-perfluorophenyl 1-(4'-chloro-3-methoxy-3'-methyl-[1,1'-biphenyl]-4-yl)-2-oxo-1,2-dihydroquinoline-6-sulfonate (0.356 g, 0.572 mmol). The flask was sealed with a septum and DMF (2.86 ml) was added to generate a homogeneous solution. The flask was cooled in an ice-bath for 5 min, then a THF solution of lithium bis(trimethylsilyl)amide (1.316 ml, 1.316 mmol, 1M) was added dropwise. After 10 min total, the mixture was diluted with 1N aq. HCl (15 mL) and EtOAc (20 mL). The layers were separated, there was some solid that was not dissolved remaining in the flask. The material in the flask and the aq. layer were taken up in DCM (20 mL) with about 1 mL of MeOH in the sep. funnel. The layers were separated (all solids dissolved) and the aqueous layer was extracted an additional time with DCM (10 mL). The combined organic extracts were dried over sodium sulfate, filtered, and concentrated. The residue was purified by chromatography on silica gel (40-g Redi-Sep column with) to give (P)-1-(4'-chloro-3-methoxy-3'-methyl-4-biphenylyl)-2-oxo-N-4-pyrimidinyl-1,2-dihydro-6-quinolinesulfonamide (0.125 g, 0.235 mmol, 41.0% yield) as a white amorphous solid. $^1$H NMR (400 MHz, DMSO-$d_6$) δ 8.61 (s, 1H), 8.42 (d, J=2.07 Hz, 1H), 8.30 (d, J=5.91 Hz, 1H), 8.23 (d, J=9.54 Hz, 1H), 7.92 (dd, J=2.18, 8.91 Hz, 1H), 7.84 (d, J=1.97 Hz, 1H), 7.61-7.72 (m, 1H), 7.51-7.59 (m, 2H), 7.41-7.48 (m, 1H), 7.34-7.40 (m, 1H), 7.01 (d, J=6.01 Hz, 1H), 6.77-6.82 (m, 1H), 6.73-6.77 (m, 1H), 3.78 (s, 3H), 2.45 (s, 3H); LCMS m/z (ESI) 532.8 (M+H)$^+$.

Example 659

(Method 202): 1-(4'-chloro-3-methoxy-3'-methyl-4-biphenylyl)-2-oxo-N-2-pyrazinyl-1,2-dihydro-6-quinolinesulfonamide

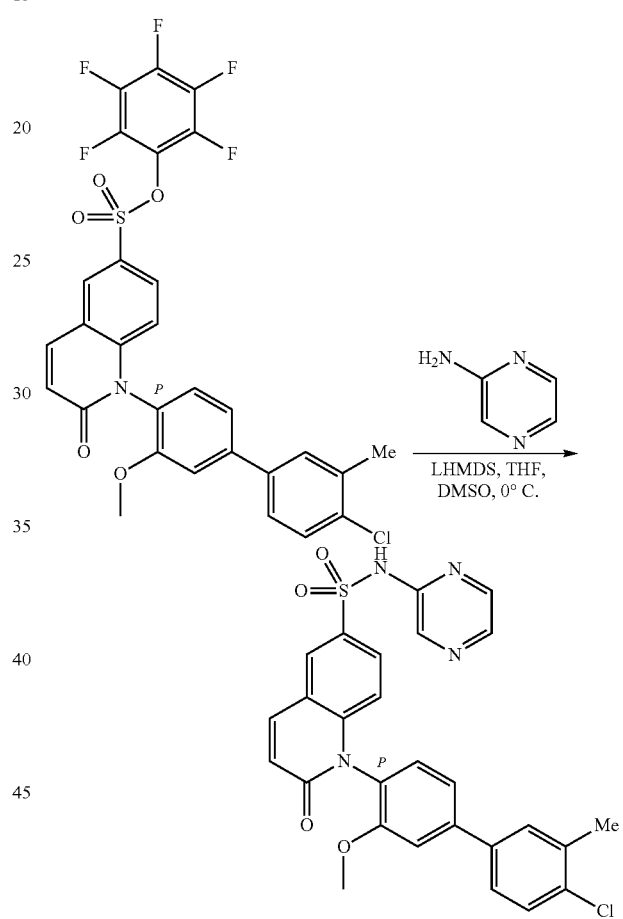

A flask was charged with pyrazin-2-amine (0.041 g, 0.431 mmol) and (P)-perfluorophenyl 1-(4'-chloro-3-methoxy-3'-methyl-[1,1'-biphenyl]-4-yl)-2-oxo-1,2-dihydroquinoline-6-sulfonate (0.206 g, 0.331 mmol). The flask was sealed with a septum and THF (2.84 ml) and DMSO (0.473 ml) were added to generate a homogeneous solution. The flask was cooled in an ice-bath for 5 min, then a THF solution of lithium bis(trimethylsilyl)amide (0.762 ml, 0.762 mmol, 1M) was added dropwise. After 10 min, the mixture was diluted with 1N aq. HCl (10 mL) and EtOAc (20 mL). The layers were separated, and the aqueous layer was extracted with EtOAc (2×20 mL). The combined organic extracts were dried over sodium sulfate, filtered, and concentrated. The residue was purified by chromatography on silica gel (40-g Redi-Sep column with 10-70% of a 3:1 EtOAc/EtOH solution in heptane) to give (P)-1-(4'-chloro-3-methoxy-3'- methyl-4-biphenylyl)-2-oxo-N-2-pyrazinyl-1,2-dihydro-6-quinolinesulfonamide (0.063 g, 0.118 mmol, 35.7% yield) as a white amorphous solid. $^1$H NMR (400 MHz, DMSO-$d_6$) δ 11.63 (br. s., 1H), 8.47 (d, J=2.18 Hz, 1H), 8.31-8.41 (m, 1H), 8.19-8.27 (m, 3H), 7.95 (dd, J=2.23, 8.97 Hz, 1H), 7.83 (s, 1H), 7.60-7.72 (m, 1H), 7.51-7.57 (m, 2H), 7.41-7.46 (m, 1H), 7.35-7.40 (m, 1H), 6.80 (d, J=7.67 Hz, 1H), 6.78 (d, J=7.15 Hz, 1H), 3.76 (s, 3H), 2.44 (s, 3H); LCMS m/z (ESI) 532.8 (M+H)$^+$.

Example 660

(Method 203): (P)-1-(4'-chloro-3-methoxy-3'-methyl-4-biphenylyl)-N-1,3-oxazol-2-yl-2-oxo-1,2-dihydro-6-quinolinesulfonamide

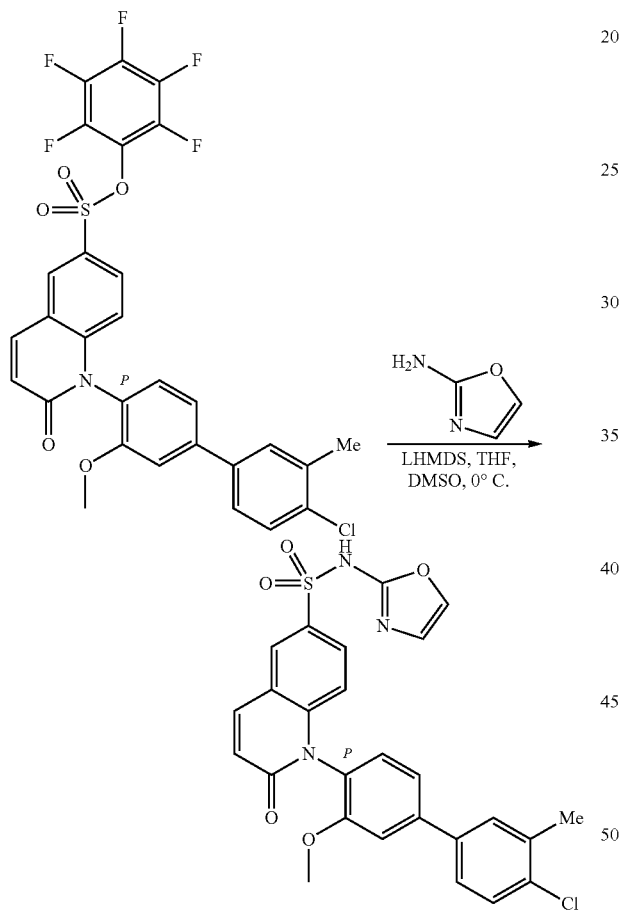

A flask was charged with oxazol-2-amine (0.036 g, 0.428 mmol, Astatech) and (P)-perfluorophenyl 1-(4'-chloro-3-methoxy-3'-methyl-[1,1'-biphenyl]-4-yl)-2-oxo-1,2-dihydroquinoline-6-sulfonate (0.205 g, 0.330 mmol). The flask was sealed with a septum, flushed with $N_2$ and THF (2.83 ml) was added, followed by DMSO (0.471 ml) to generate a homogeneous solution. The flask was cooled in an ice-bath for 5 min, then a THF solution of lithium bis(trimethylsilyl)amide (0.758 ml, 0.758 mmol. 1M) was added dropwise. After 10 min, the mixture was diluted with 1N aq. HCl (10 mL) and EtOAc (20 mL). The layers were separated, and the aqueous layer was extracted with EtOAc (2×20 mL). The combined organic extracts were dried over sodium sulfate, filtered, and concentrated. The residue was purified by chromatography on silica gel (40-g Redi-Sep column with 10-70% of a 3:1 EtOAc/EtOH solution in heptane) to give (P)-1-(4'-chloro-3-methoxy-3'-methyl-4-biphenylyl)-N-1,3-oxazol-2-yl-2-oxo-1,2-dihydro-6-quinolinesulfonamide (0.042 g, 0.080 mmol, 24.41% yield) as a white amorphous solid. $^1$H NMR (400 MHz, DMSO-$d_6$) δ 12.15 (br. s., 1H), 8.32 (d, J=2.18 Hz, 1H), 8.14-8.23 (m, 1H), 7.81-7.88 (m, 2H), 7.63-7.71 (m, 1H), 7.57-7.62 (m, 1H), 7.50-7.57 (m, 2H), 7.41-7.47 (m, 1H), 7.34-7.40 (m, 1H), 7.25 (d, J=1.66 Hz, 1H), 6.75-6.81 (m, 1H), 6.72 (d, J=8.91 Hz, 1H), 3.74-3.81 (m, 3H), 2.44 (s, 3H); LCMS m/z (ESI) 522.0 (M+H)$^+$.

Example 661

(Method 204): (P)-1-(4'-chloro-3-methoxy-3'-methyl-4-biphenylyl)-N-1,2,4-oxadiazol-3-yl-2-oxo-1,2-dihydro-6-quinolinesulfonamide

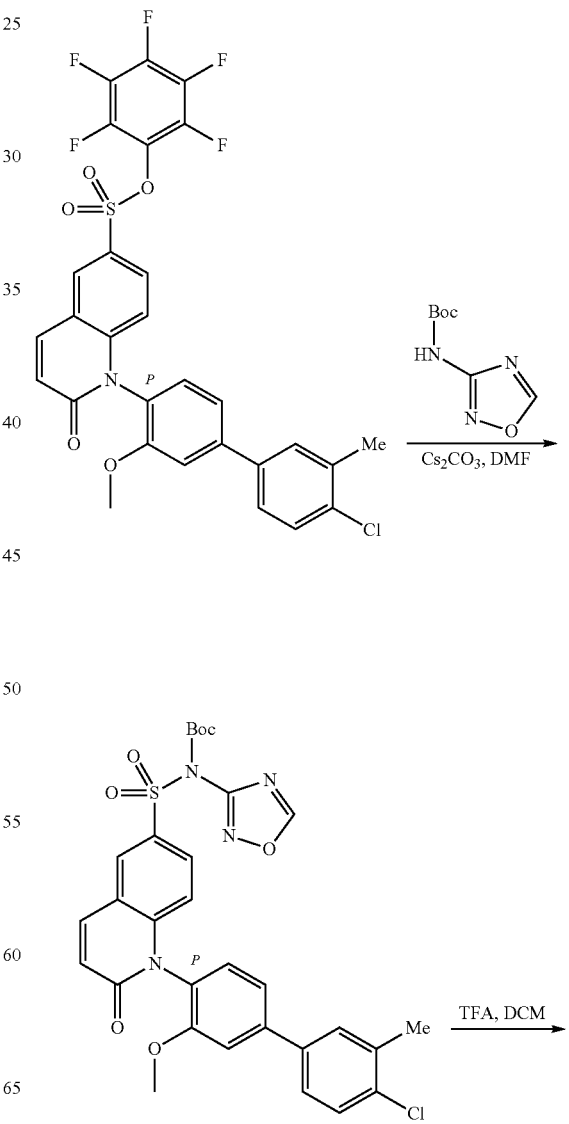

389

-continued

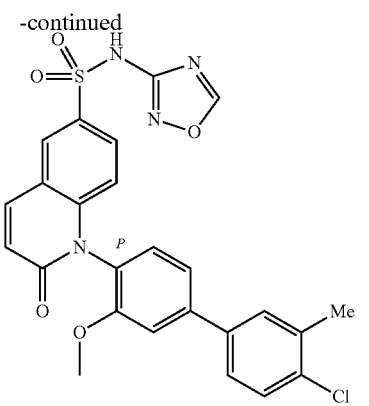

Step 1: (P)-tert-butyl (1-(4'-chloro-3-methoxy-3'-methyl-[1,1'-biphenyl]-4-yl)-2-oxo-1,2-dihydroquinolin-6-yl)sulfonyl(1,2,4-oxadiazol-3-yl)carbamate A flask was charged with (P)-perfluorophenyl 1-(4'-chloro-3-methoxy-3'-methyl-[1,1'-biphenyl]-4-yl)-2-oxo-1,2-dihydroquinoline-6-sulfonate (0.356 g, 0.572 mmol), tert-butyl 1,2,4-oxadiazol-3-ylcarbamate (0.159 g, 0.859 mmol), and cesium carbonate (0.410 g, 1.259 mmol). DMF (2.86 ml) was and the mixture was stirred at rt for 18 h. Additional tert-butyl 1,2,4-oxadiazol-3-ylcarbamate (0.159 g, 0.859 mmol) and tert-butyl (1-(4'-chloro-3-methoxy-3'-methyl-[1,1'-biphenyl]-4-yl)-2-oxo-1,2-dihydroquinolin-6-yl)sulfonyl (1,2,4-oxadiazol-3-yl)carbamate were added and the mixture was maintained additional 48 h at rt. The mixture was diluted with 1 N HCl (10 mL) and extracted with EtOAc (3×10 mL). The combined organic extracts were dried over sodium sulfate, filtered, and concentrated to provide (P)-tert-butyl (1-(4'-chloro-3-methoxy-3'-methyl-[1,1'-biphenyl]-4-yl)-2-oxo-1,2-dihydroquinolin-6-yl)sulfonyl(1,2,4-oxadiazol-3-yl)carbamate as a crude residue, which was taken to the next step without purification. LCMS m/z (ESI) 623.1 (M+H)$^+$.

Step 2: (P)-1-(4'-chloro-3-methoxy-3'-methyl-4-biphenylyl)-N-1,2,4-oxadiazol-3-yl-2-oxo-1,2-dihydro-6-quinolinesulfonamide The crude residue from Step 1, (P)-tert-butyl (1-(4'-chloro-3-methoxy-3'-methyl-[1,1'-biphenyl]-4-yl)-2-oxo-1,2-dihydroquinolin-6-yl)sulfonyl(1,2,4-oxadiazol-3-yl)carbamate, was was taken up in DCM (5 mL) and TFA (5 mL) was added. After 5 minutes, the solution was concentrated for purification by MPLC (Biotage Isolera). The crude residue was taken up in minimal DCM and absorbed onto a 5 g loading cartridge and passed through a Redi-Sep® Gold pre-packed silica gel column (40 g) using 90:10 Heptane/3:1 EtOAc:EtOH to 20:80 Heptane/3:1 EtOAc:EtOH gradient with 10% DCM constant additive to afford (P)-1-(4'-chloro-3-methoxy-3'-methyl-4-biphenylyl)-N-1,2,4-oxadiazol-3-yl-2-oxo-1,2-dihydro-6-quinolinesulfonamide (0.020 g, 0.038 mmol, 6.68% yield) as a white amorphous solid. $^1$H NMR (500 MHz, DMSO-d$_6$) δ 12.06-12.68 (br. s, 1H), 9.35 (s, 1H), 8.43 (d, J=1.95 Hz, 1H), 8.26 (d, J=9.67 Hz, 1H), 7.88-8.02 (m, 1H), 7.83 (s, 1H), 7.67 (dd, J=1.85, 8.27 Hz, 1H), 7.50-7.59 (m, 2H), 7.42-7.48 (m, 1H), 7.33-7.42 (m, 1H), 6.82 (dd, J=4.77, 9.31 Hz, 2H), 3.78 (s, 3H), 2.45 (s, 3H); LCMS m/z (ESI) 522.9 (M+H)$^+$.

390

Example 662

(Method 205): (P)-1-(4'-chloro-2-fluoro-5-methoxy-3'-methyl-4-biphenylyl)-2-oxo-N-4-pyrimidinyl-1,2-dihydro-6-quinolinesulfonamide

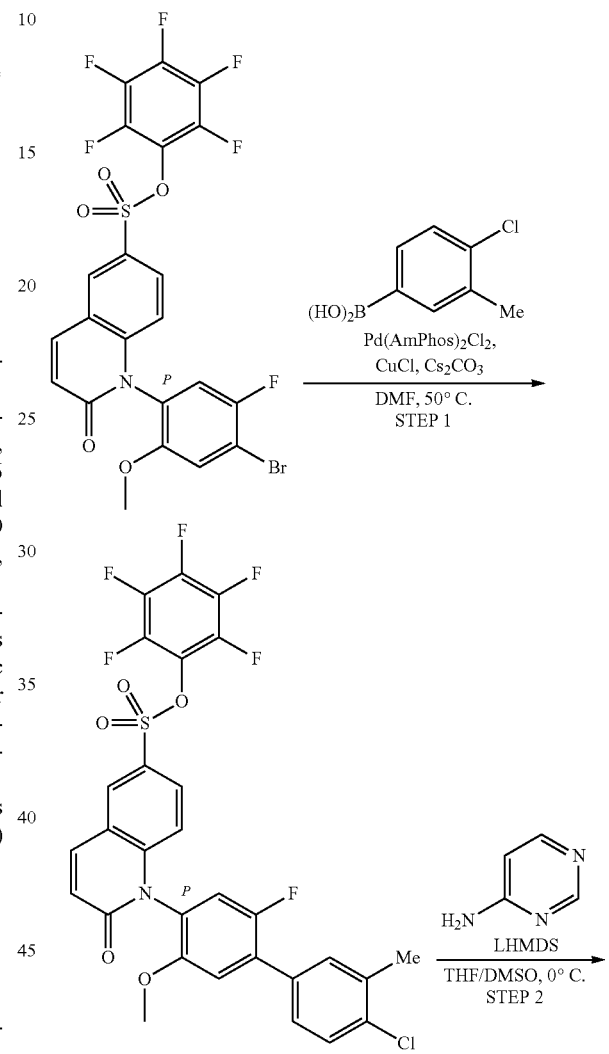

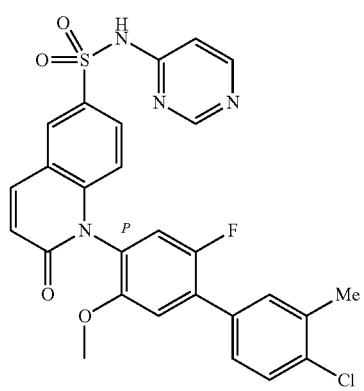

Step 1: Perfluorophenyl 1-(4'-chloro-2-fluoro-5-methoxy-3'-methyl-[1,1'-biphenyl]-4-yl)-2-oxo-1,2-dihydroquinoline-6-sulfonate A RBF was charged with (P)-perfluorophenyl 1-(4'-chloro-2-fluoro-5-methoxy-3'-methyl-[1,1'-biphenyl]-4-yl)-2-oxo-1,2-dihydroquinoline-6-sulfonate (2.26 g, 3.53 mmol, 70.0% yield), (4-chloro-3-methylphenyl)boronic acid (2.58 g, 15.14 mmol), copper(i) chloride (1.499 g, 15.14 mmol), cesium carbonate (6.58 g, 20.19 mmol), and bis(di-tert-butyl(4-dimethylaminophenyl)phosphine)-dichloropalladium(ii) (0.036 g, 0.05 mmol). The flask was flushed with Ar (g), then DMF (25.2 ml) was added. The reaction was heated to 50° C. and stirred for one hour. The reaction was diluted with ethyl acetate and washed three times with water containing excess n-(2-hydroxyethyl)ethylenediaminetriacetic acid, trisodium salt hydrate. The organic layer was washed with water, washed with brine, dried with sodium sulfate, filtered, and concentrated. The material was purified via column chromatography (RediSep Gold 120 g, gradient elution 0-35% EtOAc:Heptane) to afford (P)-perfluorophenyl 1-(4'-chloro-2-fluoro-5-methoxy-3'-methyl-[1,1'-biphenyl]-4-yl)-2-oxo-1,2-dihydroquinoline-6-sulfonate (2.26 g, 3.53 mmol, 70.0% yield) as an off-white solid. m/z (ESI) 640.8 (M+H)$^+$.

Step 2: 1-(4'-chloro-2-fluoro-5-methoxy-3'-methyl-4-biphenylyl)-2-oxo-N-4-pyrimidinyl-1,2-dihydro-6-quinolinesulfonamide A RBF was charged with pyrimidin-4-amine (0.039 g, 0.406 mmol) and DMSO (0.781 ml) to give a solution. (P)-perfluorophenyl 1-(4'-chloro-2-fluoro-5-methoxy-3'-methyl-[1,1'-biphenyl]-4-yl)-2-oxo-1,2-dihydroquinoline-6-sulfonate (0.200 g, 0.313 mmol) and perfluorophenyl 1-(4'-chloro-2-fluoro-5-methoxy-3'-methyl-[1,1'-biphenyl]-4-yl)-2-oxo-1,2-dihydroquinoline-6-sulfonate (0.200 g, 0.313 mmol) were added, and the mixture remained a solution. The flask was cooled in an ice-bath for 5 min, then lithium bis(trimethylsilyl)amide (1M in THF) (0.719 ml, 0.719 mmol) was added dropwise. The reaction was stirred for 15 minutes. the reaction was diluted with ethyl acetate and washed twice with 1N HCl solution. The organic layers was washed with brine, dried with sodium sulfate, filtered, and concentrated. The material was purified via column chromatography (RediSep Gold 40 g, gradient elution 10-75% [3:1 EtOAc/EtOH]:Heptane). The material was repurified via reverse phase MPLC (10-100% MeOH:H$_2$O w/0.1% NH$_4$OH modifier). The product fractions were concentrated to a minimal volume and partitioned between ethyl acetate and 1N HCl aqueous solution. The organic layer was washed with brine, dried with sodium sulfate, filtered, and concentrated to afford (P)-1-(4'-chloro-2-fluoro-5-methoxy-3'-methyl-[1,1'-biphenyl]-4-yl)-2-oxo-N-(pyrimidin-4-yl)-1,2-dihydroquinoline-6-sulfonamide (0.070 g, 0.127 mmol, 40.7% yield) as a white solid. $^1$H NMR (400 MHz, DMSO-d$_6$) δ=8.62 (br. s., 1H), 8.43 (br. s., 1H), 8.37-8.18 (m, 2H), 7.93 (d, J=8.9 Hz, 1H), 7.70 (br. s., 1H), 7.63-7.45 (m, 3H), 7.38 (d, J=6.8 Hz, 1H), 7.03 (br. s., 1H), 6.81 (t, J=9.1 Hz, 2H), 3.73 (s, 3H), 2.44 (s, 3H). m/z (ESI) 551.2 (M+H)$^+$.

Example 663

(Method 206): (P)-1-(4'-chloro-2-fluoro-5-methoxy-3'-methyl-4-biphenylyl)-N-1,2,4-oxadiazol-3-yl-2-oxo-1,2-dihydro-6-quinolinesulfonamide

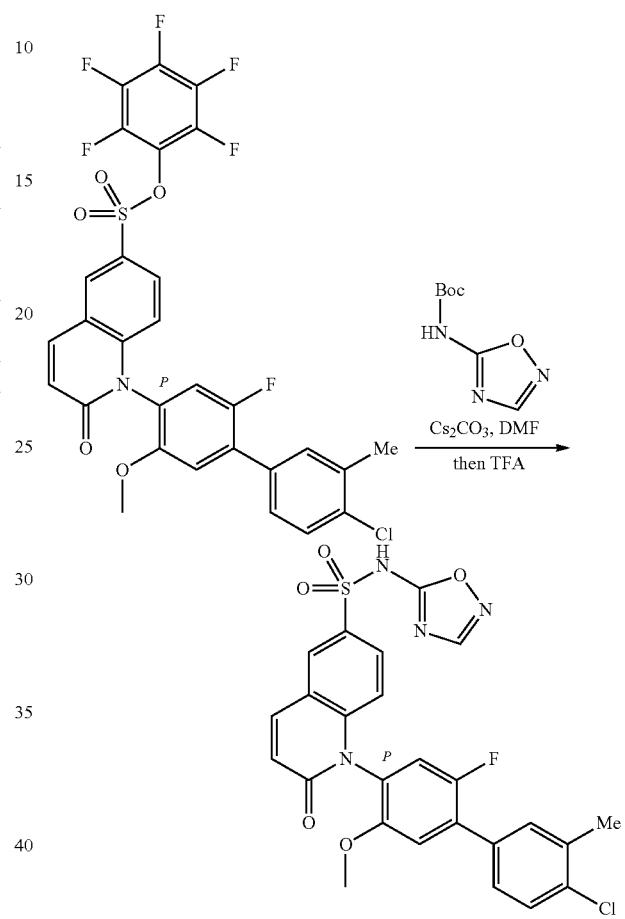

A vial was charged with (P)-perfluorophenyl 1-(4'-chloro-2-fluoro-5-methoxy-3'-methyl-[1,1'-biphenyl]-4-yl)-2-oxo-1,2-dihydroquinoline-6-sulfonate (0.400 g, 0.625 mmol) (as described in Method 205, Step 1), tert-butyl 1,2,4-oxadiazol-3-ylcarbamate (0.231 g, 1.250 mmol), and cesium carbonate (0.305 g, 0.938 mmol). The vial was flushed with Ar (g), then DMF (3.13 ml) was added. The reaction was stirred for 24 hours at room temperature. The mixture was diluted with water and extracted with EtOAc (3×). The combined organic extracts were washed with brine, dried over sodium sulfate, filtered, and concentrated. The material was purified via column chromatography (RediSep Gold 40 g, gradient elution 0-100% EtOAc:Heptane) to afford (P)-tert-butyl (1-(4'-chloro-2-fluoro-5-methoxy-3'-methyl-[1,1'-biphenyl]-4-yl)-2-oxo-1,2-dihydroquinolin-6-yl)sulfonyl(1,2,4-oxadiazol-3-yl)carbamate. The material was taken up in TFA (1 mL) and stirred for one hour at room temperature. The mixture was concentrated and purified via column chromatography (RediSep Gold 40 g, gradient elution 10-75% [3:1 EtOAc/EtOH]:Heptane) to afford (P)-1-(4'-chloro-2-fluoro-5-methoxy-3'-methyl-[1,1'-biphenyl]-4-yl)-N-(1,2,4-oxadiazol-3-yl)-2-oxo-1,2-dihydroquinoline-6-sulfonamide (0.124 g, 0.229 mmol, 36.7% yield) as a white solid. $^1$H NMR (400 MHz, DMSO-d$_6$) δ=9.32 (s, 1H), 8.43 (d, J=2.3 Hz, 1H), 8.27 (d, J=9.5 Hz, 1H), 7.94 (dd, J=2.2, 9.0 Hz, 1H), 7.70 (s, 1H), 7.60-7.49 (m, 3H), 7.39 (d, J=6.9 Hz, 1H), 6.89 (d, J=8.9 Hz, 1H), 6.82 (d, J=9.6 Hz, 1H), 3.74 (s, 3H), 2.44 (s, 3H). m/z (ESI) 541.1 (M+H)$^+$.

Example 664

(Method 207): (P)-1-(4-cyclopentyl-5-fluoro-2-methoxyphenyl)-N-3-isoxazolyl-2-oxo-1,2-dihydro-6-quinolinesulfonamide

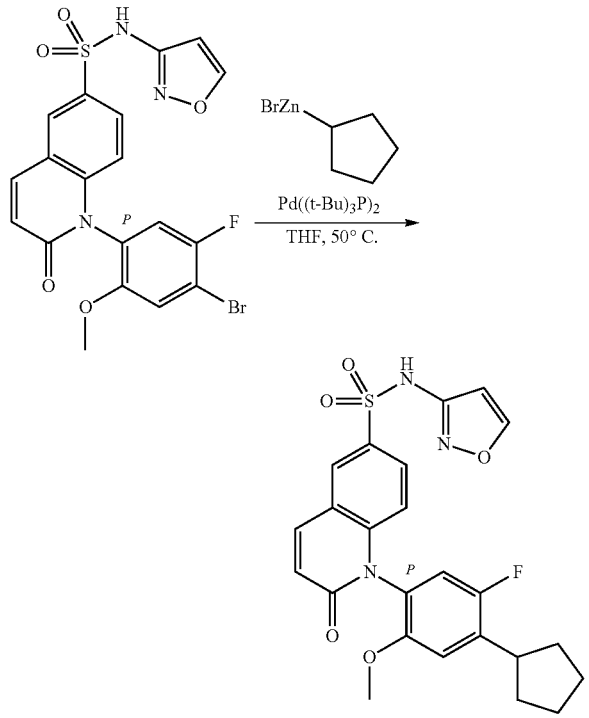

A vial was charged with (P)-1-(4-bromo-5-fluoro-2-methoxyphenyl)-N-(isoxazol-3-yl)-2-oxo-1,2-dihydroquinoline-6-sulfonamide (0.100 g, 0.202 mmol) and bis(tri-t-butylphosphine)palladium(0) (0.016 g, 0.030 mmol) (4.14 mg used). The vial was flushed with Ar (g), then THF (1.012 ml) and cyclopentylzinc bromide, 0.5M solution in THF (1.618 ml, 0.809 mmol) were added. The reaction was heated to 50° C. and stirred for one hour. The reaction was diluted with ethyl acetate and washed twice with 1N HCl solution. The organic layer was washed with brine, dried with sodium sulfate, filtered, and concentrated. The material was purified via column chromatography (RediSep Gold 40 g, gradient elution 10-75% [3:1 EtOAc/EtOH]:Heptane) to afford (P)-1-(4-cyclopentyl-5-fluoro-2-methoxyphenyl)-N-(isoxazol-3-yl)-2-oxo-1,2-dihydroquinoline-6-sulfonamide (0.037 g, 0.077 mmol, 37.8% yield) as a white solid. $^1$H NMR (400 MHz, DMSO-d$_6$) δ=11.65 (s, 1H), 8.73 (d, J=1.8 Hz, 1H), 8.35 (d, J=2.1 Hz, 1H), 8.20 (d, J=9.6 Hz, 1H), 7.85 (dd, J=2.2, 9.0 Hz, 1H), 7.27 (d, J=10.2 Hz, 1H), 7.19 (d, J=6.6 Hz, 1H), 6.78 (dd, J=2.7, 9.3 Hz, 2H), 6.44 (d, J=1.8 Hz, 1H), 3.66 (s, 3H), 3.29-3.20 (m, 1H), 2.07 (d, J=4.2 Hz, 2H), 1.85 (br. s., 2H), 1.71 (br. s., 4H). m/z (ESI) 484.1 (M+H)$^+$.

Example 665 & 666

(Method 208): (P)-1-(5-chloro-6-(3,5-difluorophenyl)-2-methoxy-3-pyridinyl)-N-3-isoxazolyl-2-oxo-1,2-dihydro-6-quinolinesulfonamide (665) & (M)-1-(5-chloro-6-(3,5-difluorophenyl)-2-methoxy-3-pyridinyl)-N-3-isoxazolyl-2-oxo-1,2-dihydro-6-quinolinesulfonamide (666)

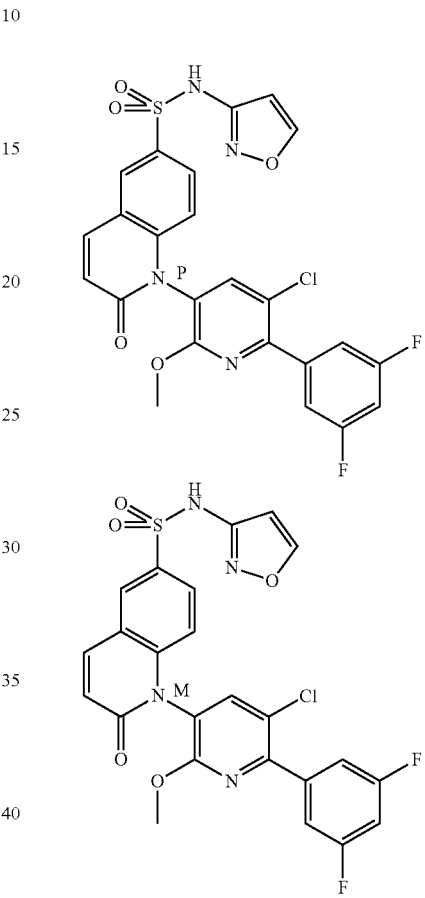

The title compound was prepared via method 84 except that (3,5-difluorophenyl)boronic acid was used instead of (3-fluorophenyl)boronic acid to afford racemic 1-(5-chloro-6-(3,5-difluorophenyl)-2-methoxy-3-pyridinyl)-N-3-isoxazolyl-2-oxo-1,2-dihydro-6-quinolinesulfonamide. The atropisomers were separated by chiral SFC: whelk-O (s,s) 50% MeOH/CO$_2$, yielding (P)-1-(5-chloro-6-(3,5-difluorophenyl)-2-methoxy-3-pyridinyl)-N-3-isoxazolyl-2-oxo-1,2-dihydro-6-quinolinesulfonamide (Peak 1) & (M)-1-(5-chloro-6-(3,5-difluorophenyl)-2-methoxy-3-pyridinyl)-N-3-isoxazolyl-2-oxo-1,2-dihydro-6-quinolinesulfonamide (Peak 2) as off-white solids. P: $^1$H NMR (400 MHz, DMSO-d$_6$) δ=11.68 (br. s., 1H), 8.74 (d, J=1.5 Hz, 1H), 8.41 (d, J=1.7 Hz, 1H), 8.33 (s, 1H), 8.27 (d, J=9.7 Hz, 1H), 7.87 (dd, J=2.0, 8.9 Hz, 1H), 7.59 (d, J=6.3 Hz, 2H), 7.45 (t, J=9.3 Hz, 1H), 7.03 (d, J=9.0 Hz, 1H), 6.85 (d, J=9.7 Hz, 1H), 6.46 (d, J=1.5 Hz, 1H), 3.84 (s, 3H). m/z (ESI) 545.2 (M+H)$^+$. M: $^1$H NMR (400 MHz, DMSO-d$_6$) δ=11.67 (br. s., 1H), 8.72 (s, 1H), 8.40 (br. s., 1H), 8.33 (s, 1H), 8.27 (d, J=9.7 Hz, 1H), 7.86 (d, J=8.7 Hz, 1H), 7.59 (d, J=6.4 Hz, 2H), 7.45 (t, J=9.0 Hz, 1H), 7.02 (d, J=8.9 Hz, 1H), 6.84 (d, J=9.7 Hz, 1H), 6.45 (s, 1H), 3.84 (s, 3H). m/z (ESI) 545.2 (M+H)$^+$.

Example 667

(Method 209): (P)-1-(4-(cyclopentylmethyl)-5-fluoro-2-methoxyphenyl)-N-3-isoxazolyl-2-oxo-1,2-dihydro-6-quinolinesulfonamide

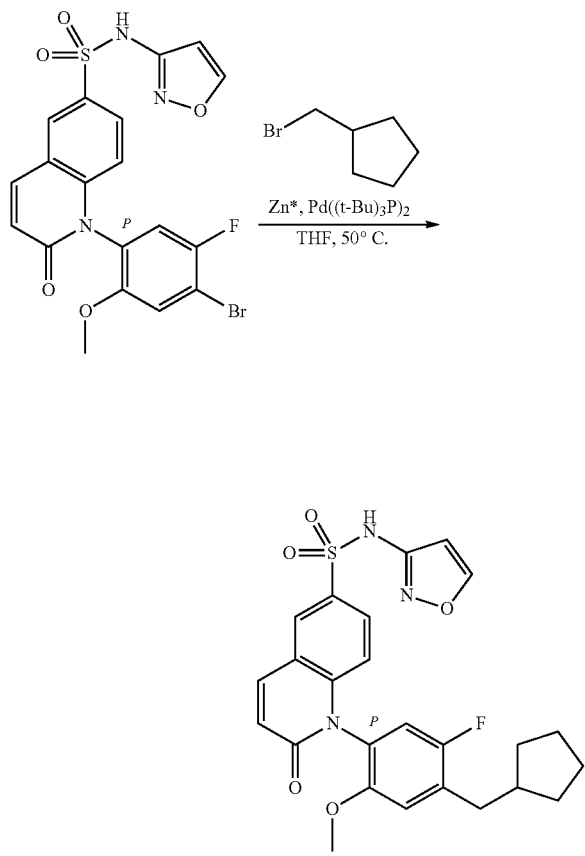

A vial was charged with (bromomethyl)cyclopentane (0.152 ml, 1.214 mmol) and THF (0.607 ml). Zinc activated (Rieke zinc) (2.383 ml, 1.821 mmol) was added and the reaction was stirred overnight at room temperature. Bis(tri-t-butylphosphine)palladium(0) (0.023 g, 0.046 mmol) and (P)-1-(4-bromo-5-fluoro-2-methoxyphenyl)-N-(isoxazol-3-yl)-2-oxo-1,2-dihydroquinoline-6-sulfonamide (0.150 g, 0.303 mmol) were added and the reaction was stirred for one hour at 50° C. The reaction was diluted with ethyl acetate and washed twice with 1N HCl solution. The organic layer was washed with brine, dried with sodium sulfate, filtered, and concentrated. The material was purified via column chromatography (RediSep Gold 40 g, gradient elution 0-50% [3:1 EtOAc:EtOH]:Heptane) to afford (P)-1-(4-(cyclopentylmethyl)-5-fluoro-2-methoxyphenyl)-N-(isoxazol-3-yl)-2-oxo-1,2-dihydroquinoline-6-sulfonamide (0.059 g, 0.119 mmol, 39.1% yield) as a white solid. $^1$H NMR (400 MHz, DMSO-$d_6$) δ=11.65 (s, 1H), 8.72 (d, J=1.8 Hz, 1H), 8.35 (d, J=2.1 Hz, 1H), 8.20 (d, J=9.7 Hz, 1H), 7.84 (dd, J=2.2, 9.0 Hz, 1H), 7.27 (d, J=9.6 Hz, 1H), 7.20 (d, J=6.6 Hz, 1H), 6.77 (dd, J=9.4, 10.9 Hz, 2H), 6.44 (d, J=1.8 Hz, 1H), 3.64 (s, 3H), 2.70 (d, J=6.6 Hz, 2H), 2.19 (td, J=7.6, 15.1 Hz, 1H), 1.80-1.62 (m, 4H), 1.54 (dd, J=4.6, 7.0 Hz, 2H), 1.32-1.21 (m, 5H). m/z (ESI) 498.2 (M+H)$^+$.

Example 668

(Method 210): (P)-1-(5-fluoro-2-methoxy-4-(tetrahydro-2H-pyran-4-yl)phenyl)-N-3-isoxazolyl-2-oxo-1,2-dihydro-6-quinolinesulfonamide

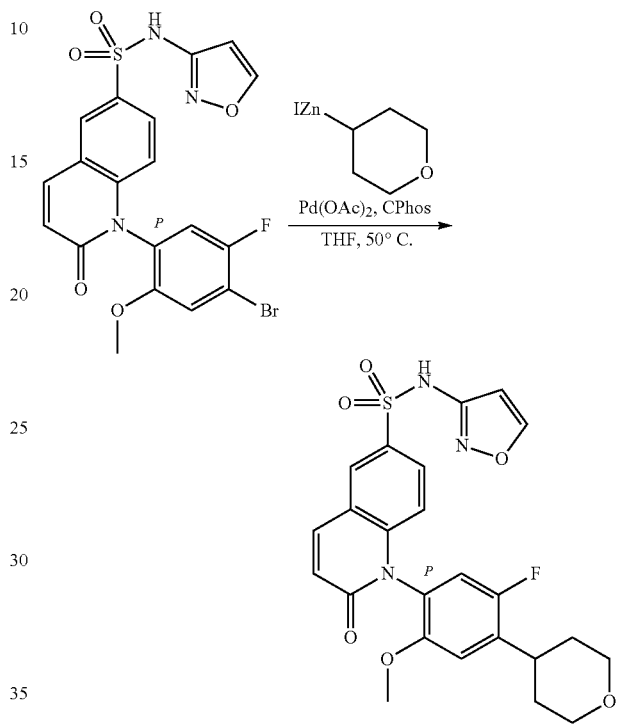

A vial was charged with palladium(ii) acetate (4.09 mg, 0.018 mmol), 2'-(dicyclohexylphosphino)-N2,N2,N6,N6-tetramethyl-[1,1'-biphenyl]-2,6-diamine (CPhos) (0.016 g, 0.036 mmol), and (P)-1-(4-bromo-5-fluoro-2-methoxyphenyl)-N-(isoxazol-3-yl)-2-oxo-1,2-dihydroquinoline-6-sulfonamide (0.150 g, 0.303 mmol). (tetrahydro-2H-pyran-4-yl)zinc(II) iodide (0.26M in THF) (3.25 ml, 0.910 mmol) was added and the reaction was stirred for one hour at 50° C. The reaction was diluted with ethyl acetate and washed twice with 1N HCl solution. The organic layer was washed with brine, dried with sodium sulfate, filtered, and concentrated. The material was purified via column chromatography (RediSep Gold 40 g, gradient elution 0-50% [3:1 EtOAc:EtOH]:Heptane) but the isolated material was not clean. The material was repurified via Gilson HPLC (45-70% MeCN:H2O w/0.1% TFA modifier). The product fractions were combined, frozen in a dry ice/acetone bath, and lyophilized for three days to afford (P)-1-(5-fluoro-2-methoxy-4-(tetrahydro-2H-pyran-4-yl)phenyl)-N-(isoxazol-3-yl)-2-oxo-1,2-dihydroquinoline-6-sulfonamide (0.067 g, 0.134 mmol, 44.2% yield) as a white solid. $^1$H NMR (400 MHz, DMSO-$d_6$) δ=11.65 (s, 1H), 8.73 (d, J=1.8 Hz, 1H), 8.36 (d, J=2.2 Hz, 1H), 8.21 (d, J=9.6 Hz, 1H), 7.85 (dd, J=2.2, 9.0 Hz, 1H), 7.31 (d, J=10.2 Hz, 1H), 7.22 (d, J=6.6 Hz, 1H), 6.77 (dd, J=9.3, 11.4 Hz, 2H), 6.44 (d, J=1.8 Hz, 1H), 4.06-3.94 (m, 2H), 3.68 (s, 3H), 3.51 (t, J=11.1 Hz, 2H), 3.23-3.11 (m, 1H), 2.00-1.82 (m, 2H), 1.74 (d, J=12.9 Hz, 2H). m/z (ESI) 500.2 (M+H)$^+$.

Example 669 (3140531)

(Method 211): (P)-1-(3'-fluoro-3-methoxy-5'-(trifluoromethyl)-4-biphenylyl)-2-oxo-N-2-pyrazinyl-1,2-dihydro-6-quinolinesulfonamide

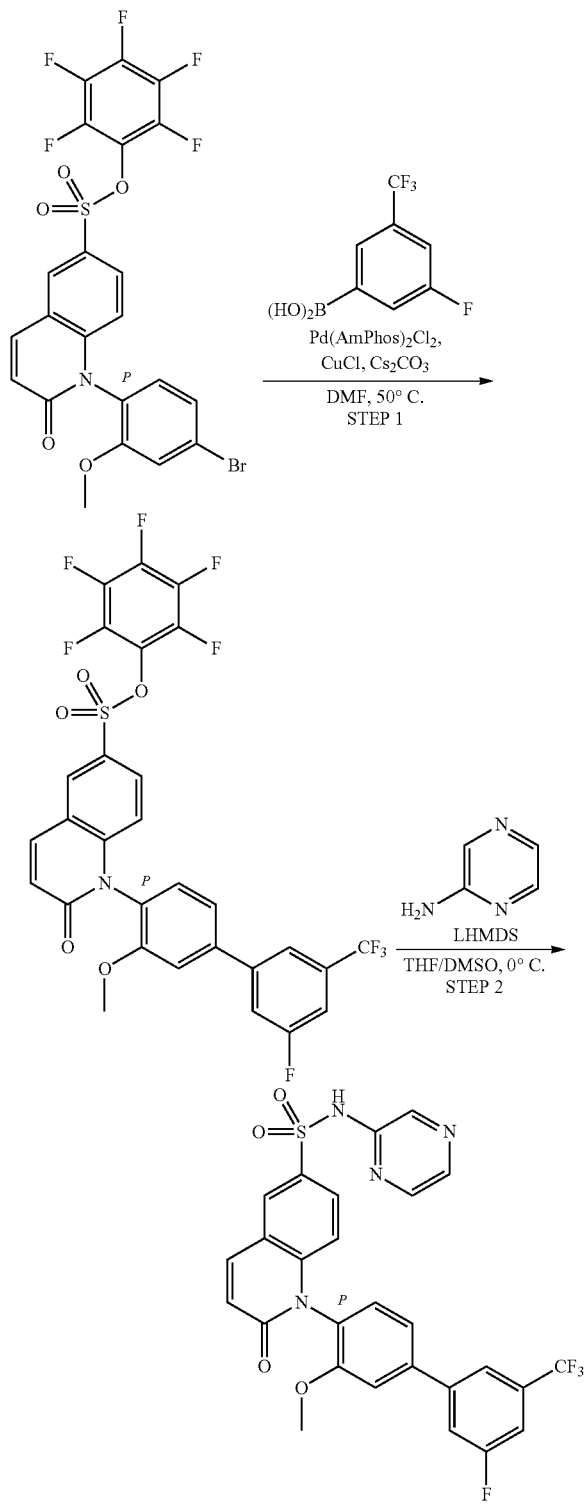

Step 1: Perfluorophenyl 1-(4'-chloro-2-fluoro-5-methoxy-3'-methyl-[1,1'-biphenyl]-4-yl)-2-oxo-1,2-dihydroquinoline-6-sulfonate A RBF was charged with (P)-perfluorophenyl 1-(4'-chloro-2-fluoro-5-methoxy-3'-methyl-[1,1'-biphenyl]-4-yl)-2-oxo-1,2-dihydroquinoline-6-sulfonate (2.26 g, 3.53 mmol, 70.0% yield), (4-chloro-3-methylphenyl)boronic acid (2.58 g, 15.14 mmol), copper(i) chloride (1.499 g, 15.14 mmol), cesium carbonate (6.58 g, 20.19 mmol), and bis(di-tert-butyl (4-dimethylaminophenyl)phosphine)-dichloropalladium(ii) (0.036 g, 0.05 mmol). The flask was flushed with Ar (g), then DMF (25.2 ml) was added. The reaction was heated to 50° C. and stirred for one hour. The reaction was diluted with ethyl acetate and washed three times with water containing excess n-(2-hydroxyethyl)ethylenediaminetriacetic acid, trisodium salt hydrate. The organic layer was washed with water, washed with brine, dried with sodium sulfate, filtered, and concentrated. The material was purified via column chromatography (RediSep Gold 120 g, gradient elution 0-35% EtOAc:Heptane) to afford (P)-perfluorophenyl 1-(4'-chloro-2-fluoro-5-methoxy-3'-methyl-[1,1'-biphenyl]-4-yl)-2-oxo-1,2-dihydroquinoline-6-sulfonate (2.26 g, 3.53 mmol, 70.0% yield) as an off-white solid. m/z (ESI) 640.8 (M+H)$^+$.

Step 2: 1-(3'-fluoro-3-methoxy-5'-(trifluoromethyl)-4-biphenylyl)-2-oxo-N-2-pyrazinyl-1,2-dihydro-6-quinolinesulfonamide A RBF was charged with pyrazin-2-amine (0.047 g, 0.493 mmol) and DMSO (0.948 ml) to give a solution. Perfluorophenyl 1-(3'-fluoro-3-methoxy-5'-(trifluoromethyl)-[1,1'-biphenyl]-4-yl)-2-oxo-1,2-dihydroquinoline-6-sulfonate (0.250 g, 0.379 mmol) and THF (2.84 ml) were added, and the mixture remained a solution. The flask was cooled in an ice-bath for 5 min, then lithium bis(trimethylsilyl)amide (1M in THF) (0.872 ml, 0.872 mmol) was added dropwise. The reaction was stirred for 15 minutes. The reaction was diluted with ethyl acetate and washed twice with 1N HCl solution. The organic layers was washed with brine, dried with sodium sulfate, filtered, and concentrated. The material was purified via column chromatography (RediSep Gold 40 g, gradient elution 0-50% [3:1 EtOAc/EtOH]:Heptane) to afford 1-(3'-fluoro-3-methoxy-5'-(trifluoromethyl)-[1,1'-biphenyl]-4-yl)-2-oxo-N-(pyrazin-2-yl)-1,2-dihydroquinoline-6-sulfonamide (0.153 g, 0.268 mmol, 70.7% yield) as an off-white solid. $^1$H NMR (400 MHz, DMSO-d$_6$) δ=11.62 (br. s., 1H), 8.47 (d, J=2.2 Hz, 1H), 8.36 (d, J=1.1 Hz, 1H), 8.29-8.19 (m, 3H), 8.09 (d, J=9.9 Hz, 1H), 8.03 (s, 1H), 7.94 (dd, J=2.2, 9.0 Hz, 1H), 7.75 (d, J=8.6 Hz, 1H), 7.66 (d, J=1.8 Hz, 1H), 7.58 (dd, J=1.9, 8.1 Hz, 1H), 7.44 (d, J=8.1 Hz, 1H), 6.79 (dd, J=9.3, 13.7 Hz, 2H), 3.80 (s, 3H). m/z (ESI) 571.1 (M+H)$^+$.

Example 670

(Method 212): 1-(5-(azetidin-3-yloxy)-2,3',5'-trifluoro-[1,1'-biphenyl]-4-yl)-N-(isoxazol-3-yl)-2-oxo-1,2-dihydroquinoline-6-sulfonamide 2,2,2-trifluoroacetate

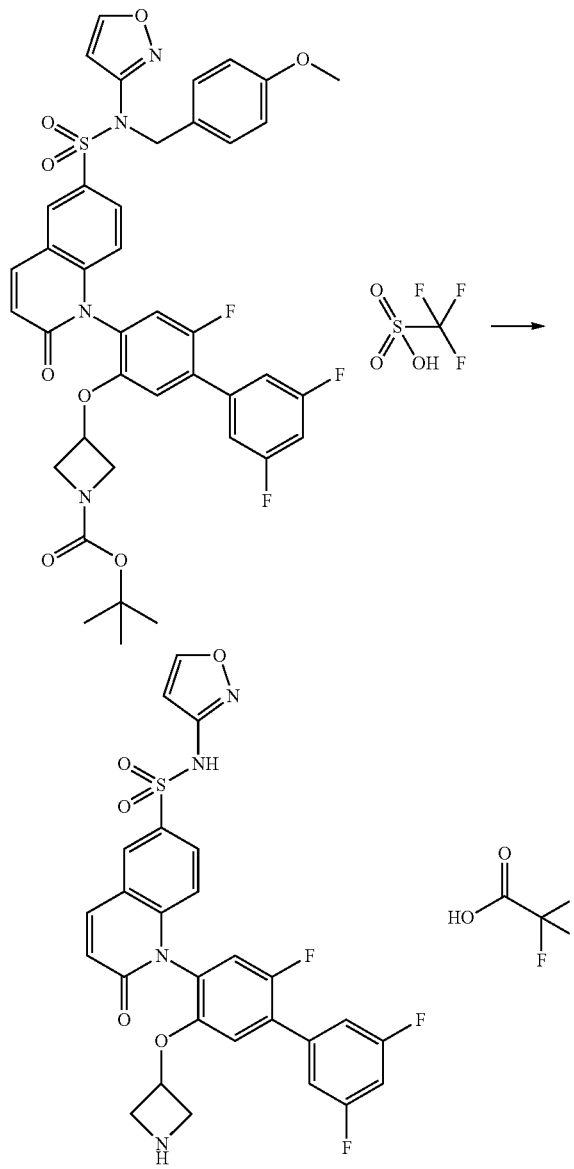

Tert-butyl 3-((3',5',6-trifluoro-4-(6-(N-(isoxazol-3-yl)-N-(4-methoxybenzyl)sulfamoyl)-2-oxoquinolin-1(2H)-yl)-[1,1'-biphenyl]-3-yl)oxy)azetidine-1-carboxylate (34.7 mg, 0.044 mmol) was then taken up in DCM (440 µl) and trifluoromethanesulfonic acid (23.44 µl, 0.264 mmol) was added dropwise very slowly. The resulting mixture was then stirred for 45 minutes. LCMS indicated that the starting material was completely converted. The solution was then dissolved in 1.5 ml of DMSO and passed through a 0.20 micron filter. An additional 0.5 ml was used to rinse the reaction vial and the solution was passed through the same filter. The DMSO solution was purified by reverse-phase HPLC (Waters XBridge Prep Shield RP18 10 µm OBD 19×100 mm) gradient, 15→75% MeCN in water (containing 0.1% trifluoroacetic acid as an additive), flow rate 40 mL/min to yield 1-(5-(azetidin-3-yloxy)-2,3',5'-trifluoro-[1,1'-biphenyl]-4-yl)-N-(isoxazol-3-yl)-2-oxo-1,2-dihydroquinoline-6-sulfonamide 2,2,2-trifluoroacetate (5.7 mgs, 19% yield over two steps). $^1$H NMR (500 MHz, DMSO-d6)=ppm 3.64-3.77 (m, 2H) 4.23-4.31 (m, 1H) 4.32-4.38 (m, 1H) 5.19-5.26 (m, 1H) 6.46 (s, 1H) 6.85 (d, J=8.28 Hz, 1H) 6.94 (d, J=9.08 Hz, 1H) 7.31 (d, J=6.62 Hz, 1H) 7.37-7.48 (m, 3H) 7.66 (d, J=9.60 Hz, 1H) 7.87 (d, J=8.74 Hz, 1H) 8.29 (d, J=9.67 Hz, 1H) 8.42 (s, 1H) 8.73 (s, 1H) 8.79 (br. s., 1H). m/z (ESI) 568.9.

Example 671

(P)-1-(3-methoxy-3'-(trifluoromethyl)-4-biphenylyl)-2-oxo-N-4-pyrimidinyl-1,2-dihydro-6-quinolinesulfonamide

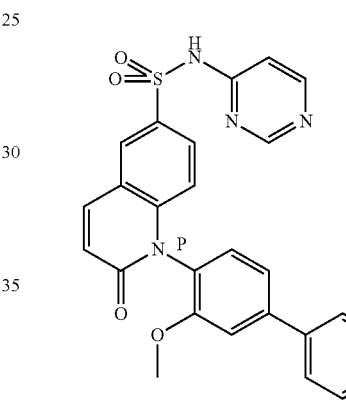

This compound was synthesized via Method 73. A round-bottom flask was charged with (P)-perfluorophenyl 1-(3-methoxy-3'-(trifluoromethyl)-[1,1'-biphenyl]-4-yl)-2-oxo-1,2-dihydroquinoline-6-sulfonate (194.2 mg, 0.303 mmol) and pyrimidin-4-amine (43.2 mg, 0.454 mmol). DMSO (757 µl) was added to give a solution which was then diluted with THF (2271 µl). The flask was cooled in an ice-water bath for 15 min, then lithium bis(trimethylsilyl)amide (1M in THF) (666 µl, 0.666 mmol) was added dropwise, slowly over 2 min. After 15 min, the mixture was diluted with 1N aq. HCl and EtOAc. The layers were separated, and the aq. layer was extracted with EtOAc (2×). The combined organic extracts were dried over sodium sulfate, filtered, and concentrated. The residue was purified by chromatography on silica gel (25-g SNAP Ultra column, 20-70% of a 3:1 EtOAc/EtOH solution in heptane with 10% DCM as additive). Fractions containing pure product were combined and concentrated to give (P)-1-(3-methoxy-3'-(trifluoromethyl)-4-biphenylyl)-2-oxo-N-4-pyrimidinyl-1,2-dihydro-6-quinolinesulfonamide (61.08 mg, 0.111 mmol, 36.5% yield) as a light-yellow solid. $^1$H NMR (400 MHz, DMSO-d$_6$) δ=8.62-8.51 (m, 1H), 8.42-8.33 (m, 1H), 8.32-8.14 (m, 2H), 8.08 (s, 2H), 7.91-7.81 (m, 1H), 7.78-7.67 (m, 2H), 7.56 (d, J=1.8 Hz, 1H), 7.50-7.43 (m, 1H), 7.38 (s, 1H), 7.02-6.91 (m, 1H), 6.77-6.66 (m, 2H), 3.74 (s, 3H). m/z (ESI) 553.1 (M+H)$^+$.

Example 672

(P)-1-(3-methoxy-3'-(trifluoromethyl)-4-biphenylyl)-2-oxo-N-2-pyrimidinyl-1,2-dihydro-6-quinolinesulfonamide

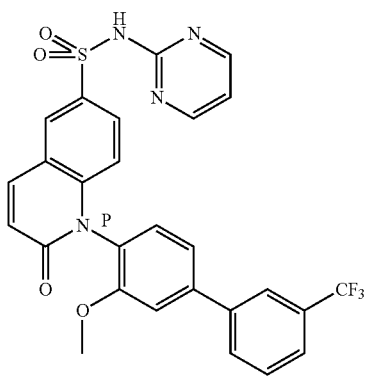

This compound was synthesized via Method 73. A round-bottom flask was charged with (P)-perfluorophenyl 1-(3-methoxy-3'-(trifluoromethyl)-[1,1'-biphenyl]-4-yl)-2-oxo-1,2-dihydroquinoline-6-sulfonate (154.5 mg, 0.241 mmol) and pyrimidin-2-amine (34.4 mg, 0.361 mmol). DMSO (602 µl) was added to give a solution which was then diluted with THF (1806 µl). The flask was cooled in an ice-water bath for 10 min, then lithium bis(trimethylsilyl)amide (1M in THF) (530 µl, 0.530 mmol) was added dropwise. After 15 min, the mixture was diluted with 1N aq. HCl and EtOAc. The layers were separated, and the aq. layer was extracted with EtOAc (1×). The combined organic extracts were dried over sodium sulfate, filtered, and concentrated. The residue was purified by chromatography on silica gel (40-g Redi-Sep Gold column, 10-50% of a 3:1 EtOAc/EtOH solution in heptane with 10% DCM as additive) to give (P)-1-(3-methoxy-3'-(trifluoromethyl)-4-biphenylyl)-2-oxo-N-2-pyrimidinyl-1,2-dihydro-6-quinolinesulfonamide (49.61 mg, 0.090 mmol, 37.3% yield) as an off-white foam.

$^1$H NMR (400 MHz, DMSO-$d_6$) δ=12.04-11.74 (br s, 1H), 8.53-8.46 (m, 3H), 8.26 (d, J=9.5 Hz, 1H), 8.15-8.11 (m, 2H), 7.97 (dd, J=2.2, 9.0 Hz, 1H), 7.83-7.74 (m, 2H), 7.61 (d, J=1.9 Hz, 1H), 7.51 (d, J=7.8 Hz, 1H), 7.42 (d, J=8.1 Hz, 1H), 7.05 (t, J=4.8 Hz, 1H), 6.78 (t, J=8.9 Hz, 2H), 3.79 (s, 3H), 2.52-2.47 (m, 8H), 1.17 (s, 1H). m/z (ESI) 553.1 (M+H)$^+$.

Example 673

(P)-1-(2-fluoro-5-methoxy-4'-(trifluoromethyl)-4-biphenylyl)-N-3-isoxazolyl-2-oxo-1,2-dihydro-6-quinolinesulfonamide

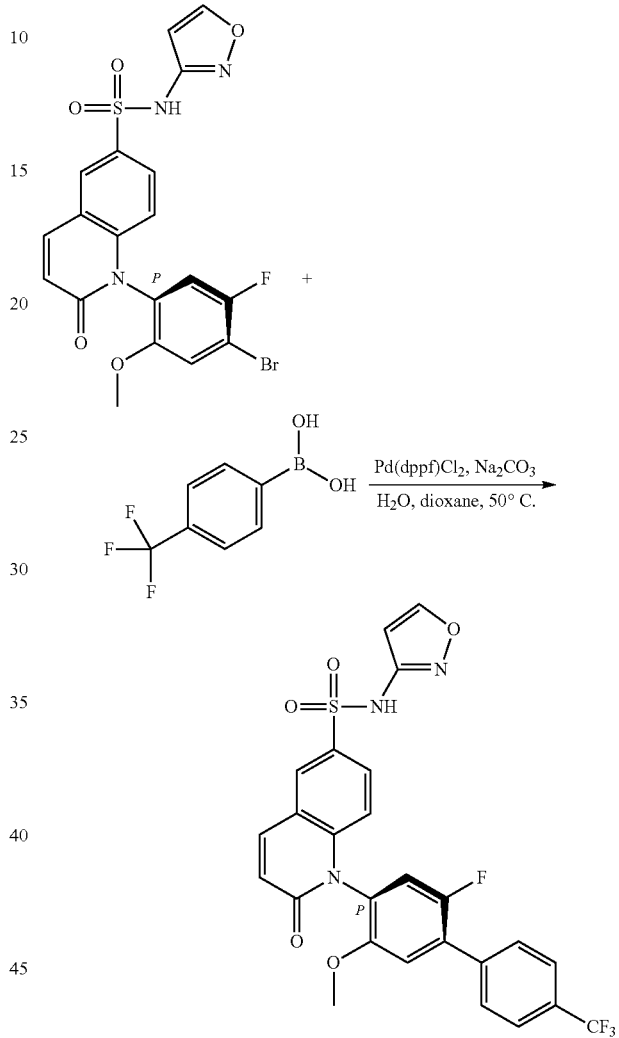

This compound was synthesized via Method 139. A 40-mL vial containing (P)-1-(4-bromo-5-fluoro-2-methoxyphenyl)-N-(isoxazol-3-yl)-2-oxo-1,2-dihydroquinoline-6-sulfonamide (175 mg, 0.354 mmol), 4-(trifluoromethyl)benzeneboronic acid (231 mg, 1.214 mmol, purchased from Frontier Scientific, Inc.), and 1,1'-bis(diphenylphosphino)ferrocene palladium(II)dichloride dichloromethane adduct (57.8 mg, 0.071 mmol) was flushed with $N_2$ and subsequently charged with dioxane (2.7 mL) and 1.9 M $Na_2CO_3$ in $H_2O$ (0.9 mL). After stirring the reaction at 50° C. for 16 h, it was cooled to rt, quenched with 1 N HCl, and extracted thrice with EtOAc. The organic extracts were combined, washed with brine, filtered through a plug of $SiO_2$, rinsing with EtOAc, and concentrated in vacuo to a brown oil. Column chromatography (12 g silica gel, 40% to 100% EtOAc/hept gradient) afforded (P)-1-(2-fluoro-5-methoxy-4'-(trifluoromethyl)-4-biphenylyl)-N-2-isoxazolyl-2-oxo-1,2-dihydro-6-quinolinesulfonamide (138.3 mg, 0.247 mmol, 40.7% yield) as a pale yellow crystalline solid. $^1$H NMR (400 MHz, DMSO-d$_6$) δ ppm 3.75 (s, 3H) 6.46 (s, 1H) 6.83 (d, J=9.64 Hz, 1H) 6.91 (d, J=9.02 Hz, 1H) 7.47 (d, J=6.95 Hz, 1H) 7.58 (d, J=10.37 Hz, 1H) 7.88 (dd, J=8.91, 2.18 Hz, 1H) 7.90-7.98 (m, 4H) 8.25 (d, J=9.54 Hz, 1H) 8.39 (d, J=2.07 Hz, 1H) 8.74 (s, 1H) 11.67 (s, 1H). m/z (ESI) 560.2 (M+H)$^+$.

Example 674

(P)—N-3-isoxazolyl-2-oxo-1-(2,3',4'-trifluoro-5-methoxy-4-biphenylyl)-1,2-dihydro-6-quinolinesulfonamide

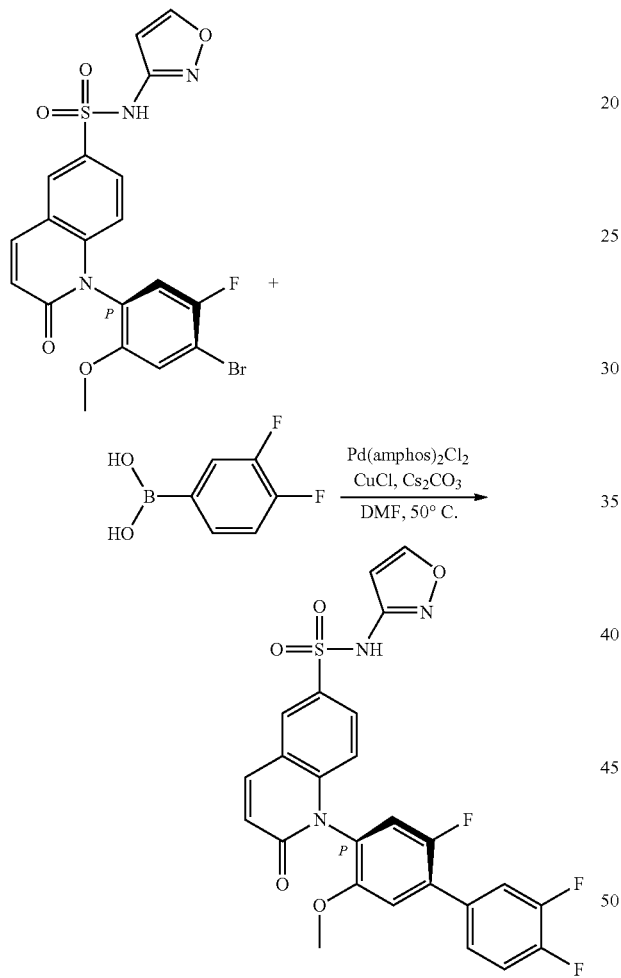

This compound was synthesized via Method 145. A 40-mL vial was charged with (P)-1-(4-bromo-5-fluoro-2-methoxyphenyl)-N-(isoxazol-3-yl)-2-oxo-1,2-dihydroquinoline-6-sulfonamide (175 mg, 0.354 mmol), (3,4-difluorophenyl)boronic acid (168 mg, 1.062 mmol), cesium carbonate (461 mg, 1.416 mmol), copper(I) chloride (105 mg, 1.062 mmol), and 1,1-bis[(di-t-butyl-p-methylaminophenyl]palladium(II) chloride (50.1 mg, 0.071 mmol), flushed with N$_2$, and subsequently charged with DMF (3.5 mL). After stirring for 2.5 h, the reaction was quenched with 1 N HCl and extracted thrice with EtOAc. The organic extracts were combined, washed with 1 N HCl, passed through a short plug of SiO$_2$ (rinsing with EtOAc), and concentrated in vacuo to an oily yellow solid. Column chromatography (12 g Redisep Gold column, 0% to 100% [3:1 EtOAc:EtOH]/hept gradient with 10% DCM additive) afforded (P)—N-3-isoxazolyl-2-oxo-1-(2,3',4'-trifluoro-5-methoxy-4-biphenylyl)-1,2-dihydro-6-quinolinesulfonamide (93 mg, 0.176 mmol, 49.8% yield) as an off-white amorphous solid. $^1$H NMR (400 MHz, DMSO-d$_6$) δ ppm 3.75 (s, 3H) 6.46 (s, 1H) 6.82 (d, J=9.64 Hz, 1H) 6.88 (d, J=8.91 Hz, 1H) 7.43 (d, J=7.15 Hz, 1H) 7.52-7.67 (m, 3H) 7.81-7.89 (m, 2H) 8.24 (d, J=9.54 Hz, 1H) 8.39 (d, J=2.18 Hz, 1H) 8.74 (s, 1H) 11.67 (s, 1H). m/z (ESI) 528.2 (M+H)$^+$.

Example 675

(P)-1-(4'-chloro-2-fluoro-5-methoxy-4-biphenylyl)-N-3-isoxazolyl-2-oxo-1,2-dihydro-6-quinolinesulfonamide

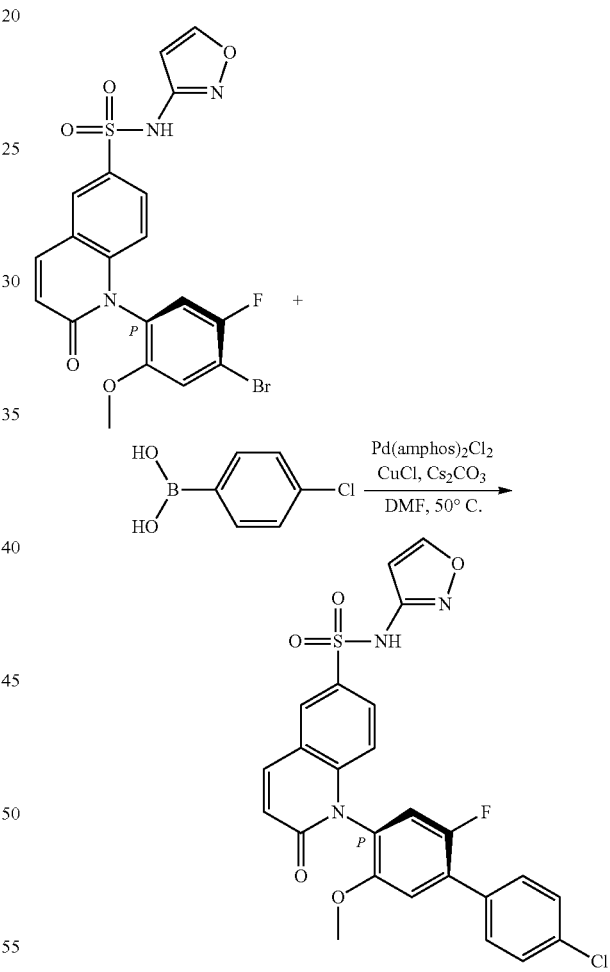

This compound was synthesized via Method 145. A 40-mL vial was charged with (P)-1-(4-bromo-5-fluoro-2-methoxyphenyl)-N-(isoxazol-3-yl)-2-oxo-1,2-dihydroquinoline-6-sulfonamide (175 mg, 0.354 mmol), cesium carbonate (461 mg, 1.416 mmol), copper(i) chloride (105 mg, 1.062 mmol), and 1,1-bis[(di-t-butyl-p-methylaminophenyl] palladium(II) chloride (50.1 mg, 0.071 mmol), flushed with N$_2$, and subsequently charged with DMF (3.5 mL). After stirring for 30 min, the reaction was quenched with 1 N HCl and extracted thrice with EtOAc. The organic extracts were combined, washed with H₂O, passed through a short plug of SiO₂ (rinsing with EtOAc), and concentrated in vacuo to an oily yellow solid. Column chromatography (12 g Redisep Gold column, 0% to 100% [3:1 EtOAc:EtOH]/hept gradient with 10% DCM additive) afforded 1-(4'-chloro-2-fluoro-5-methoxy-4-biphenylyl)-N-3-isoxazolyl-2-oxo-1,2-dihydro-6-quinolinesulfonamide (92.3 mg, 0.175 mmol, 49.6% yield) as a pale yellow amorphous solid. ¹H NMR (400 MHz, DMSO-d₆) δ ppm 3.73 (s, 3H) 6.45 (s, 1H) 6.82 (d, J=9.33 Hz, 1H) 6.88 (d, J=9.02 Hz, 1H) 7.40 (d, J=6.84 Hz, 1H) 7.53 (d, J=10.26 Hz, 1H) 7.62 (m, J=8.19 Hz, 2H) 7.74 (m, J=8.29 Hz, 2H) 7.86 (d, J=8.60 Hz, 1H) 8.24 (d, J=9.64 Hz, 1H) 8.38 (s, 1H) 8.73 (s, 1H) 11.68 (s, 1H). m/z (ESI) 526.1 (M+H)⁺.

Example 676

(P)-1-(4-(5-chloro-2-methoxy-3-pyridinyl)-5-fluoro-2-methoxyphenyl)-N-3-isoxazolyl-2-oxo-1,2-dihydro-6-quinolinesulfonamide

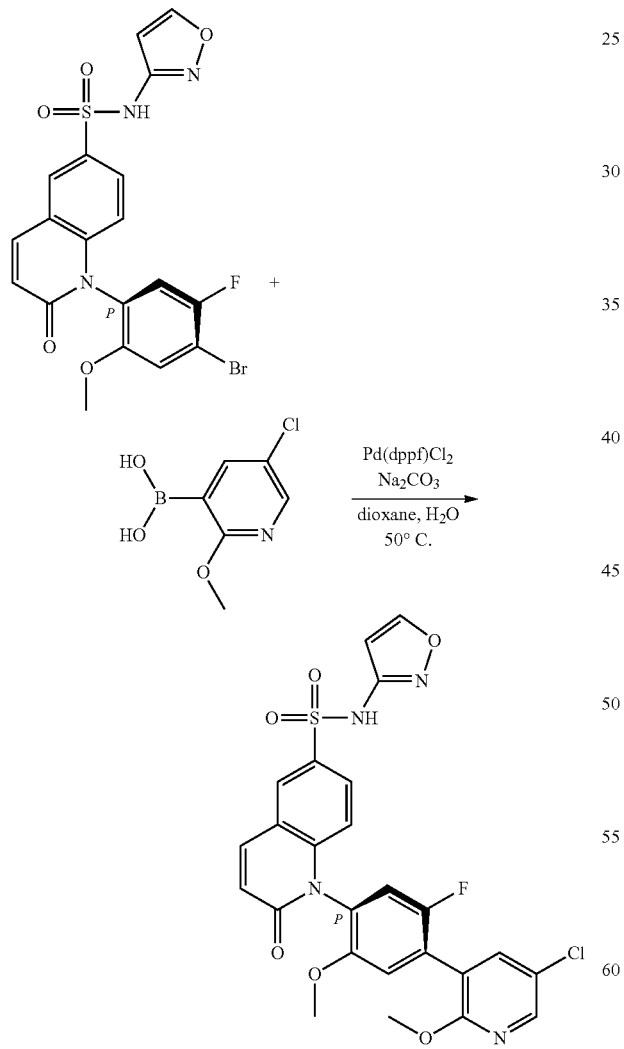

This compound was synthesized via Method 139. A 40-mL vial containing (P)-1-(4-bromo-5-fluoro-2-methoxyphenyl)-N-(isoxazol-3-yl)-2-oxo-1,2-dihydroquinoline-6-sulfonamide (200 mg, 0.405 mmol), (5-chloro-2-methoxypyridin-3-yl)boronic acid (152 mg, 0.809 mmol, purchased from Combi-Blocks, Inc.), and 1,1'-bis(diphenylphosphino)ferrocene palladium(II)dichloride dichloromethane adduct (66.1 mg, 0.081 mmol) was flushed with N₂ and subsequently charged with dioxane (1.5 mL) and 1.9 M Na₂CO₃ in H₂O (0.5 mL). After stirring vigorously overnight (18 h) at 50° C., the reaction was cooled to rt, quenched with 1 N HCl, diluted with EtOAc, and filtered through a plug of celite. The layers of the filtrate were separated, and the aqueous fraction was extracted twice with EtOAc. The organic extracts were combined, washed with brine, dried over Na₂SO₄, filtered, and concentrated in vacuo to an orange oil. Column chromatography (12 g Redisep Gold column, 0-80% [3:1 EtOAc/EtOH]/hept gradient with 10% DCM) followed by preparatory HPLC (50% to 100% MeCN/H₂O with 0.1% TFA) afforded (P)-1-(4-(5-chloro-2-methoxy-3-pyridinyl)-5-fluoro-2-methoxyphenyl)-N-3-isoxazolyl-2-oxo-1,2-dihydro-6-quinolinesulfonamide (52.1 mg, 0.094 mmol, 23.12% yield) as an amorphous white solid. ¹H NMR (400 MHz, DMSO-d₆) δ ppm 3.75 (s, 3H) 4.04 (s, 3H) 6.08 (d, J=1.90 Hz, 1H) 6.63 (d, J=8.81 Hz, 1H) 6.69 (d, J=9.54 Hz, 1H) 7.44-7.52 (m, 2H) 7.72 (d, J=8.84 Hz, 1H) 8.09-8.17 (m, 3H) 8.29 (s, 1H) 8.50 (t, J=1.92 Hz, 1H). m/z (ESI) 557.0 (M+H)⁺.

Example 677

(P)-1-(2,4'-difluoro-5-methoxy-4-biphenylyl)-N-3-isoxazolyl-2-oxo-1,2-dihydro-6-quinolinesulfonamide

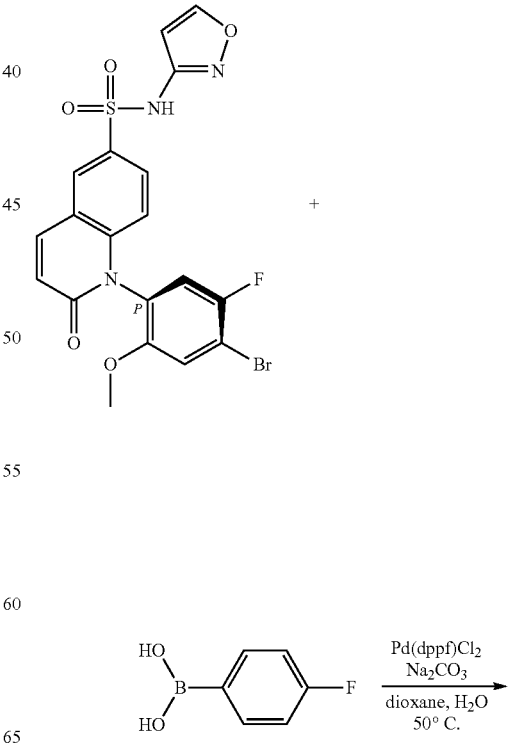

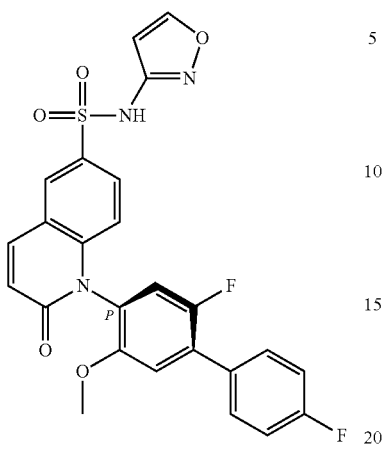

This compound was synthesized via Method 139. A 40-mL vial containing (P)-1-(4-bromo-5-fluoro-2-methoxyphenyl)-N-(isoxazol-3-yl)-2-oxo-1,2-dihydroquinoline-6-sulfonamide (200 mg, 0.405 mmol), 4-fluorobenzeneboronic acid (113 mg, 0.809 mmol), and 1,1'-bis(diphenylphosphino)ferrocene palladium(II)dichloride dichloromethane adduct (66.1 mg, 0.081 mmol) was flushed with $N_2$ and subsequently charged with dioxane (3 mL) and 1.9 M $Na_2CO_3$ in H2O (1 mL). After stirring the reaction at 50° C. overnight (18 h), the reaction was cooled to rt, quenched with 1 N HCl, and extracted thrice with EtOAc. The organic extracts were combined, washed with brine, dried over $Na_2SO_4$, filtered, and concentrated in vacuo to a black oil. Column chromatography (25 g Snap Ultra column, 0-80% [3:1 EtOAc/EtOH]/hept gradient with 10% DCM) followed by column chromatography (55 g Interchim C18 PuriFlash column, 10-100% MeCN/$H_2O$ with 0.1% $NH_4OH$) afforded 1-(2,4'-difluoro-5-methoxy-4-biphenylyl)-N-3-isoxazolyl-2-oxo-1,2-dihydro-6-quinolinesulfonamide (63.0 mg, 0.124 mmol, 30.6% yield) as a white amorphous solid. $^1H$ NMR (400 MHz, DMSO-$d_6$) δ ppm 3.74 (s, 3H) 6.46 (d, J=1.66 Hz, 1H) 6.82 (d, J=9.64 Hz, 1H) 6.89 (d, J=9.02 Hz, 1H) 7.34-7.45 (m, 3H) 7.52 (d, J=10.47 Hz, 1H) 7.76 (dd, J=7.26, 5.49 Hz, 2H) 7.87 (dd, J=8.97, 2.12 Hz, 1H) 8.24 (d, J=9.64 Hz, 1H) 8.38 (d, J=2.18 Hz, 1H) 8.74 (d, J=1.66 Hz, 1H) 11.67 (s, 1H). m/z (ESI) 510.2 $(M+H)^+$.

Example 678

(P)-1-(3'-(difluoromethoxy)-2,5'-difluoro-5-methoxy-4-biphenylyl)-N-3-isoxazolyl-2-oxo-1,2-dihydro-6-quinolinesulfonamide

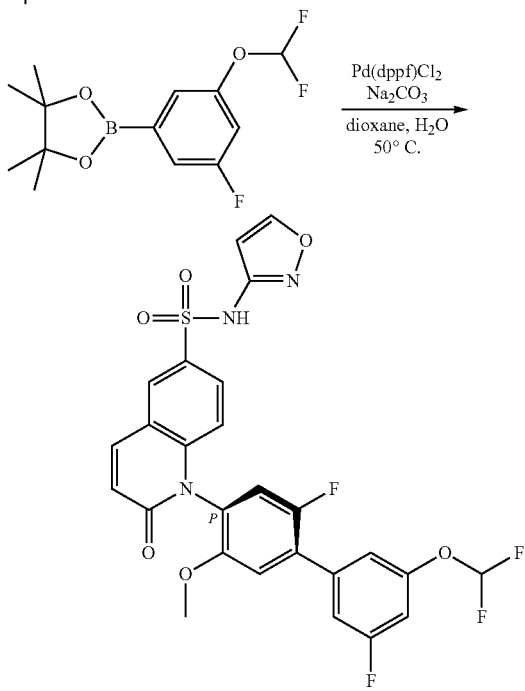

This compound was synthesized via 3140525. A 40-mL vial containing (P)-1-(4-bromo-5-fluoro-2-methoxyphenyl)-N-(isoxazol-3-yl)-2-oxo-1,2-dihydroquinoline-6-sulfonamide (192 mg, 0.389 mmol), 2-(3-(difluoromethoxy)-5-fluorophenyl)-4,4,5,5-tetramethyl-1,3,2-dioxaborolane (224.3 mg, 0.779 mmol), and 1,1'-bis(diphenylphosphino)ferrocene palladium(II)dichloride dichloromethane adduct (63.6 mg, 0.078 mmol) was flushed with $N_2$ and subsequently charged with dioxane (3 mL) and 1.9 M $Na_2CO_3$ in $H_2O$ (1 mL). After stirring overnight (18 h) at 50° C., the black slurry was cooled to rt, quenched with 1 N HCl, and extracted thrice with EtOAc. The organic extracts were combined, washed with brine, dried over $Na_2SO_4$, filtered, and concentrated in vacuo to a black oil. Column chromatography (55 g Interchim C18 PuriFlash column, 0-100% MeCN/$H_2O$ with 0.1% $NH_4OH$) followed by column chromatography (25 g Snap Ultra column, 0-80% [3:1 EtOAc/ EtOH]/hept gradient with 10% DCM) afforded 1-(3'-(difluoromethoxy)-2,5'-difluoro-5-methoxy-4-biphenylyl)-N-3-isoxazolyl-2-oxo-1,2-dihydro-6-quinolinesulfonamide (34.5 mg, 0.060 mmol, 15.40% yield) as a white amorphous solid. ¹H NMR (400 MHz, DMSO-d₆) δ ppm 3.76 (s, 3H) 6.46 (d, J=1.76 Hz, 1H) 6.85 (dd, J=19.02, 9.28 Hz, 2H) 7.21-7.64 (m, 6H) 7.87 (dd, J=8.97, 2.23 Hz, 1H) 8.24 (d, J=9.74 Hz, 1H) 8.39 (d, J=2.18 Hz, 1H) 8.74 (d, J=1.66 Hz, 1H) 11.67 (s, 1H). m/z (ESI) 576.0 (M+H)⁺.

Example 679

(M)-1-(3'-fluoro-4-methoxy-3-biphenylyl)-2-oxo-N-2-pyrimidinyl-1,2-dihydro-6-quinolinesulfonamide The title compound was prepared according to Method 156, instead using (M)-perfluorophenyl 1-(5-bromo-2-methoxyphenyl)-2-oxo-1,2-dihydroquinoline-6-sulfonate (peak 2 from chiral separation) in Step 1. ¹H NMR (400 MHz, DMSO-d₆) δ ppm 3.72 (s, 3H) 6.79 (dd, J=9.33, 6.63 Hz, 2H) 7.05 (t, J=5.48 Hz, 1H) 7.14 (t, J=8.23 Hz, 1H) 7.40 (d, J=8.81 Hz, 1H) 7.43-7.49 (m, 1H) 7.52-7.59 (m, 2H) 7.77 (d, J=2.38 Hz, 1H) 7.94-7.98 (m, 2H) 8.27 (d, J=9.54 Hz, 1H) 8.47-8.52 (m, 3H) 11.83 (br. s., 1H). m/z (ESI) 503.0 (M+H)⁺.

Example 680

1-(4-bromo-2-(1-cyanoethoxy)-5-fluorophenyl)-N-(isoxazol-3-yl)-2-oxo-1,2-dihydroquinoline-6-sulfonamide

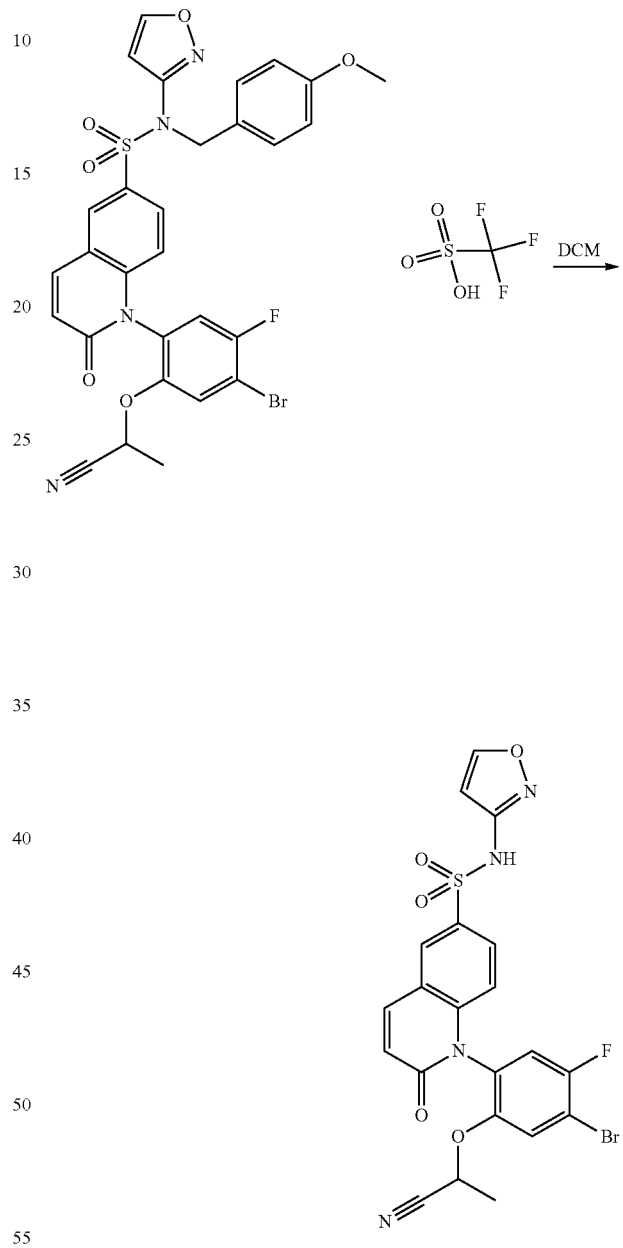

This compound was made in an analogous fashion to 1-(4-bromo-2-(cyanomethoxy)-5-fluorophenyl)-N-(isoxazol-3-yl)-2-oxo-1,2-dihydroquinoline-6-sulfonamide via Method 166 except employing 2-bromopropanenitrile in the first step to alkylate the phenol. The yield of the desired product after HPLC purification was 5.3 mgs (14% yield). ¹H NMR (500 MHz, DMSO-d6)=ppm 1.36 (d, J=6.62 Hz, 2H) 3.02-3.11 (m, 1H) 3.17 (s, 1H) 5.43-5.51 (m, 1H) 6.16-6.22 (m, 1H) 6.72 (d, J=9.73 Hz, 2H) 7.67-7.78 (m, 2H) 7.84-7.94 (m, 1H) 8.15-8.24 (m, 2H) 8.35 (br. s., 1H). m/z (ESI) 530.9 (M−H).

411

Example 681

1-(5-(1-cyanoethoxy)-2,3',5'-trifluoro-[1,1'-biphenyl]-4-yl)-N-(isoxazol-3-yl)-2-oxo-1,2-dihydroquinoline-6-sulfonamide

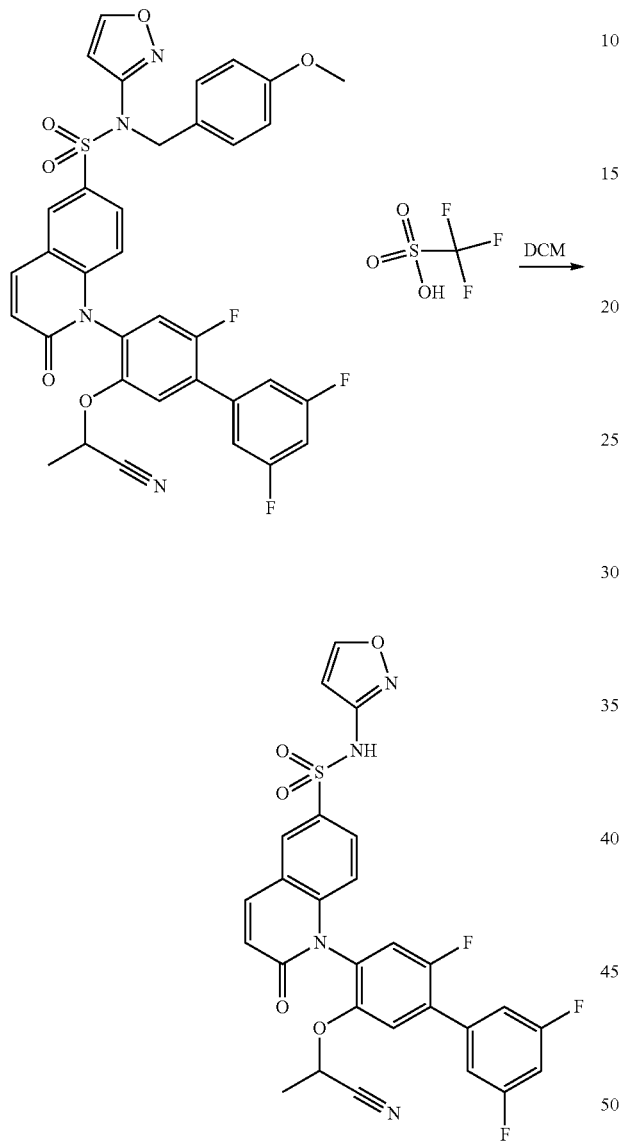

This compound was made using Method 166. The compound was purified by reverse-phase HPLC (Waters XBridge Prep Shield RP18 10 μm OBD 19×100 mm) gradient, 25 to 85% MeCN in water (containing 0.1% trifluoroacetic acid as an additive), flow rate 40 mL/min to yield 1-(5-(1-cyanoethoxy)-2,3',5'-trifluoro-[1,1'-biphenyl]-4-yl)-N-(isoxazol-3-yl)-2-oxo-1,2-dihydroquinoline-6-sulfonamide (5.7 mgs, 9.7% yield over two steps). $^{1}$H NMR (500 MHz, DMSO-d6)=ppm 1.29 (d, J=6.68 Hz, 1H) 1.33-1.46 (m, 2H) 5.54-5.64 (m, 1H) 6.40-6.46 (m, 1H) 6.84 (d, J=9.17 Hz, 1H) 6.88 (d, J=8.86 Hz, 1H) 7.39-7.53 (m, 3H) 7.69 (d, J=9.17 Hz, 1H) 7.70-7.75 (m, 1H) 7.78-7.93 (m, 1H) 8.22-8.31 (m, 1H) 8.34-8.45 (m, 1H) 8.71 (s, 1H) 11.65 (br. s., 1H). m/z (ESI) 567.1 (M+H)$^{+}$.

412

Example 682

(P)-1-(3'-chloro-3,5'-dimethoxy-4-biphenylyl)-N-3-isoxazolyl-2-oxo-1,2-dihydro-6-quinolinesulfonamide

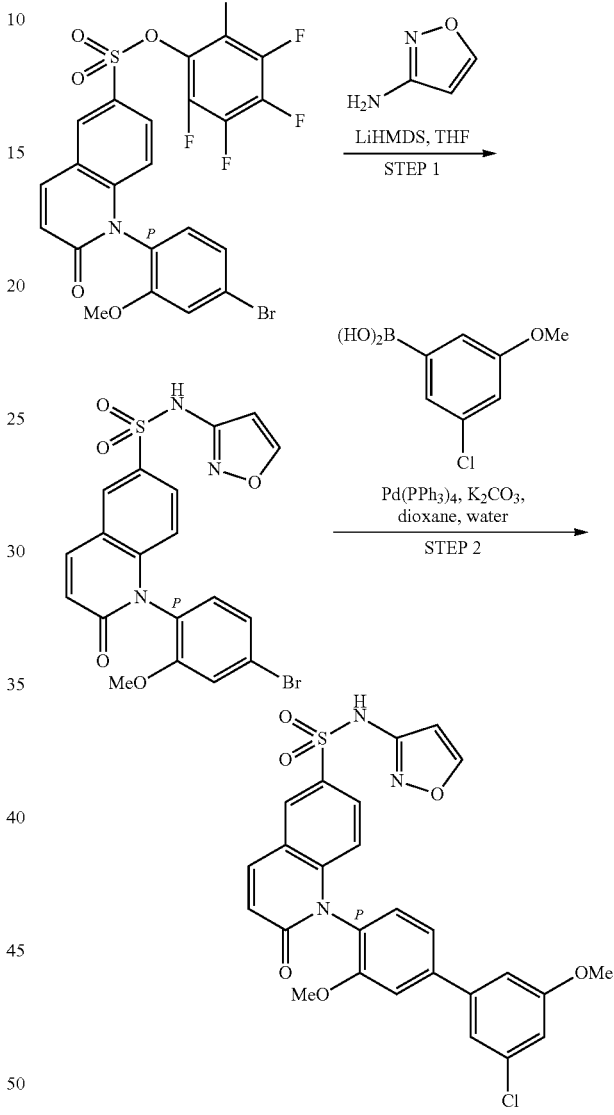

This compound was synthesized via Method 173.

Step 1: (P)-1-(4-bromo-2-methoxyphenyl)-N-(isoxazol-3-yl)-2-oxo-1,2-dihydroquinoline-6-sulfonamide A solution of 3-aminoisoxazole (0.494 ml, 6.68 mmol) and (P)-perfluorophenyl 1-(4-bromo-2-methoxyphenyl)-2-oxo-1,2-dihydroquinoline-6-sulfonate (3.500 g, 6.07 mmol) in 50 mL THF, was cooled to 0° C. LiHMDS 1N in THF (12.75 ml, 12.75 mmol) was added dropwise. After stirring for an hour, the reaction mixture was poured into 1N HCl and was extracted with DCM. The organics were dried over MgSO$_{4}$ and concentrated yielding (P)-1-(4-bromo-2-methoxyphenyl)-N-(isoxazol-3-yl)-2-oxo-1,2-dihydroquinoline-6-sulfonamide (4.30 g, 9.03 mmol, 149% yield) with minor impurities. m/z (ESI) 476.1 (M+H)+.

Step 2: (P)-1-(3'-chloro-3,5'-dimethoxy-4-biphenylyl)-N-3-isoxazolyl-2-oxo-1,2-dihydro-6-quinoline-sulfonamide A vial charged with Pd(PPh$_3$)$_4$ (74.5 mg, 0.064 mmol), (3-chloro-5-methoxyphenyl)boronic acid (235 mg, 1.26 mmol), (P)-1-(4-bromo-2-methoxyphenyl)-N-(isoxazol-3-yl)-2-oxo-1,2-dihydroquinoline-6-sulfonamide (307 mg, 0.645 mmol), potassium carbonate (356 mg, 2.58 mmol) and 3 mL dioxane and 1 mL water was heated to 50° C. for 4 hours. The reaction mixture was allowed to cool to room temperature and HCl 4N in dioxane (1611 μl, 6.45 mmol) was added. The reaction mixture was then concentrated. Purification of the crude residue by reverse phase column chromatography [puriflash C18, 10-100%0 (0.1% NH$_4$OH in MeOH)/(0.1% NH$_4$OH in water)] gave (P)-1-(3'-chloro-3,5'-dimethoxy-4-biphenylyl)-n-3-isoxazolyl-2-oxo-1,2-dihydro-6-quinolinesulfonamide (0.092 g, 0.17 mmol, 54.4%). $^1$H NMR (ACETONITRILE-d3): 8.35 (d, J=1.8 Hz, 1H), 8.25 (d, J=2.2 Hz, 1H), 7.98 (d, J=9.5 Hz, 1H), 7.80 (dd, J=9.0, 2.2 Hz, 1H), 7.36-7.47 (m, 3H), 7.30 (d, J=8.1 Hz, 1H), 7.23 (dd, J=2.4, 1.6 Hz, 1H), 7.01-7.07 (m, 1H), 6.73-6.81 (m, 2H), 6.42-6.46 (m, 1H), 3.88 (s, 3H), 3.77 (s, 3H). m/z (ESI) 538.2 (M+H)+.

Example 683

(P)-1-(4'-chloro-3-methoxy-3'-methyl-4-biphenylyl)-2-oxo-N-2-pyrimidinyl-1,2-dihydro-6-quinolinesulfonamide

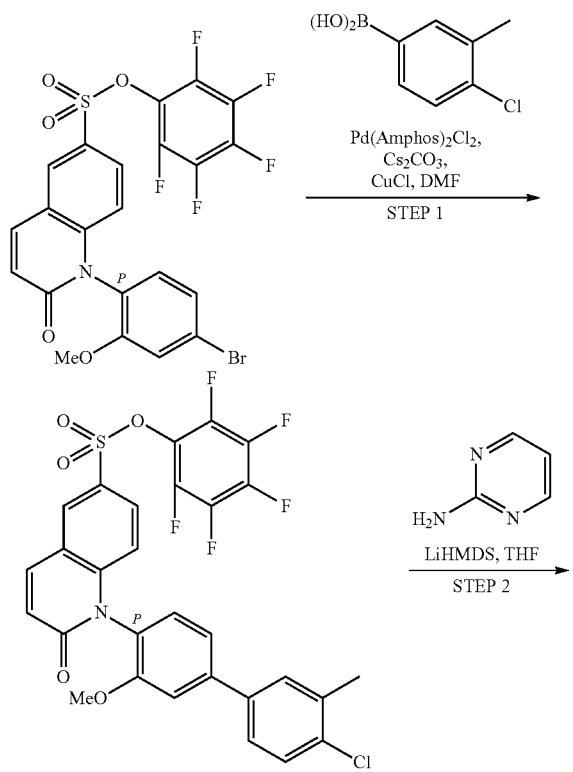

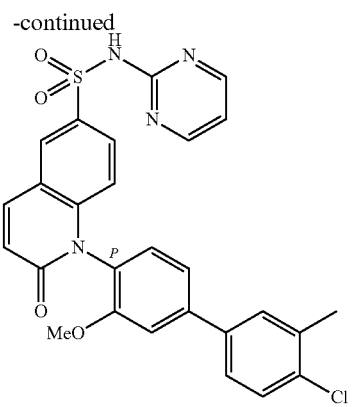

This compound was synthesized via Method 174.

Step 1: (P)-perfluorophenyl 1-(4'-chloro-3-methoxy-3'-methyl-[1,1'-biphenyl]-4-yl)-2-oxo-1,2-dihydroquinoline-6-sulfonate A RBF was charged with (P)-perfluorophenyl 1-(4-bromo-2-methoxyphenyl)-2-oxo-1,2-dihydroquinoline-6-sulfonate (3.14 g, 5.45 mmol), (4-chloro-3-methylphenyl)boronic acid (2.79 g, 16.35 mmol), copper(i) chloride (1.618 g, 16.35 mmol), cesium carbonate (7.10 g, 21.79 mmol), and bis(di-tert-butyl(4-dimethylaminophenyl)phosphine)-dichloropalladium(ii) (0.772 g, 1.090 mmol). A septum was attached and DMF (27.2 ml) was added. The solution was sparged with N$_2$ for 3 min, then a reflux condenser was attached and the solution was heated at 50° C. for 1 hour. The reaction mixture was decanted into a separatory funnel containing saturated aqueous n-(2-hydroxyethyl)ethylenediaminetriacetic acid, trisodium salt hydrate and EtOAc leaving behind black solid that was rinsed several times with EtOAc. The entire solution was filtered through a plug of celite, rinsing with EtOAc. The organic layer was extracted with saturated aqueous n-(2-hydroxyethyl)ethylenediaminetriacetic acid, trisodium salt hydrate (200 mL) and then washed with brine, dried over Na$_2$SO$_4$ and was concentrated. Purification of the crude residue by silica gel column chromatography (98:2 Heptane/EtOAc to 40:60 Heptane/EtOAc) (P)-perfluorophenyl 1-(4'-chloro-3-methoxy-3'-methyl-[1,1'-biphenyl]-4-yl)-2-oxo-1,2-dihydroquinoline-6-sulfonate (3.80 g, 6.11 mmol, 112% yield) as a white amorphous solid. m/z (ESI) 621.9 (M+H)+.

Step 2: (P)-1-(4'-chloro-3-methoxy-3'-methyl-4-biphenylyl)-2-oxo-N-2-pyrimidinyl-1,2-dihydro-6-quinolinesulfonamide A solution of pyrimidin-2-amine (0.287 g, 3.01 mmol) and (P)-perfluorophenyl 1-(4'-chloro-3-methoxy-3'-methyl-[1,1'-biphenyl]-4-yl)-2-oxo-1,2-dihydroquinoline-6-sulfonate (1.250 g, 2.010 mmol) in 5 mL DMF was diluted with 15 mL THF and was cooled to 0° C. The reaction mixture was treated with a dropwise addition of lihmds 1N in THF (4.42 ml, 4.42 mmol). After stirring for 20 minutes the reaction mixture was treated with 1N aqueous HCl then was poured into water. The aqueous was extracted with DCM, the organics dried over MgSO$_4$ and concentrated. The crude residue was purified by silica gel column chromatography (0-97% EtOAc/heptane 3% MeOH) yielding (P)-1-(4'-chloro-3-methoxy-3'-methyl-[1,1'-biphenyl]-4-yl)-2-oxo-N-(pyrimidin-2-yl)-1,2-dihydroquinoline-6-sulfonamide (0.672 g, 1.261 mmol, 62.7% yield). ¹H NMR (ACETONITRILE-d3): 8.43-8.50 (m, 3H), 7.96-8.08 (m, 2H), 7.73 (d, J=1.8 Hz, 1H), 7.56-7.62 (m, 1H), 7.49-7.54 (m, 1H), 7.39-7.47 (m, 2H), 7.31 (d, J=8.0 Hz, 1H), 7.01 (t, J=4.9 Hz, 1H), 6.74-6.82 (m, 2H), 3.77 (s, 3H), 2.48 (s, 3H). m/z (ESI) 533.2 (M+H)⁺.

Example 684

(P)-1-(3',5'-difluoro-3-methoxy-4-biphenylyl)-N-3-isoxazolyl-2-oxo-1,2-dihydro-6-quinolinesulfonamide

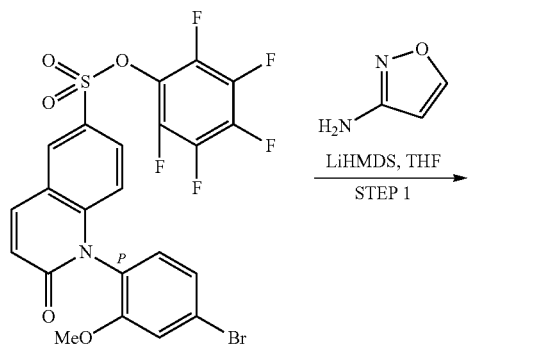

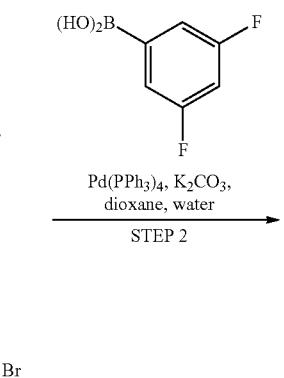

This compound was synthesized via Method 173.

Step 1: (P)-1-(4-bromo-2-methoxyphenyl)-N-(isoxazol-3-yl)-2-oxo-1,2-dihydroquinoline-6-sulfonamide A solution of 3-aminoisoxazole (0.494 ml, 6.68 mmol) and (P)-perfluorophenyl 1-(4-bromo-2-methoxyphenyl)-2-oxo-1,2-dihydroquinoline-6-sulfonate (3.500 g, 6.07 mmol) in 50 mL THF, was cooled to 0° C. LiHMDS 1N in THF (12.75 ml, 12.75 mmol) was added dropwise. After stirring for an hour, the reaction mixture was poured into 1N HCl and was extracted with DCM. The organics were dried over MgS₄ and concentrated yielding (P)-1-(4-bromo-2-methoxyphenyl)-N-(isoxazol-3-yl)-2-oxo-1,2-dihydroquinoline-6-sulfonamide (4.30 g, 9.03 mmol, 149% yield) with minor impurities. m/z (ESI) 476.1 (M+H)⁺.

Step 2: (P)-1-(3'-chloro-3,5'-dimethoxy-4-biphenylyl)-N-3-isoxazolyl-2-oxo-1,2-dihydro-6-quinolinesulfonamide A vial charged with Pd(PPh₃)₄ (74.5 mg, 0.064 mmol), (3,5-difluorophenyl)boronic acid (199 mg, 1.26 mmol), (P)-1-(4-bromo-2-methoxyphenyl)-N-(isoxazol-3-yl)-2-oxo-1, 2-dihydroquinoline-6-sulfonamide (307 mg, 0.645 mmol), potassium carbonate (356 mg, 2.58 mmol) and 3 mL dioxane and 1 mL water was heated to 50° C. for 4 hours. The reaction mixture was allowed to cool to RT and HCl 4N in dioxane (1611 ml, 6.45 mmol) was added. The reaction mixture was then concentrated. Purification of the crude residue by reverse phase column chromatography [puriflash C18, 10-100% (0.1% NH₄OH in MeOH)/(0.1% NH₄OH in water)] gave (P)-1-(3',5'-difluoro-3-methoxy-4-biphenylyl)-n-3-isoxazolyl-2-oxo-1,2-dihydro-6-quinolinesulfonamide (0.043 g, 0.08 mmol, 26.8%). ¹H NMR (ACETONITRILE-d3): 8.35 (d, J=1.8 Hz, 1H), 8.25 (d, J=2.2 Hz, 1H), 7.99 (d, J=9.6 Hz, 1H), 7.80 (dd, J=9.0, 2.2 Hz, 1H), 7.38-7.49 (m, 4H), 7.33 (d, J=8.1 Hz, 1H), 6.97-7.06 (m, 1H), 6.77 (t, J=9.2 Hz, 2H), 6.44 (d, J=1.8 Hz, 1H), 3.78 (s, 3H). m/z (ESI) 510.1 (M+H)⁺.

Example 685

(P)-1-(4'-chloro-2-fluoro-3',5-dimethoxy-4-biphenylyl)-2-oxo-N-2-pyrimidinyl-1,2-dihydro-6-quinolinesulfonamide

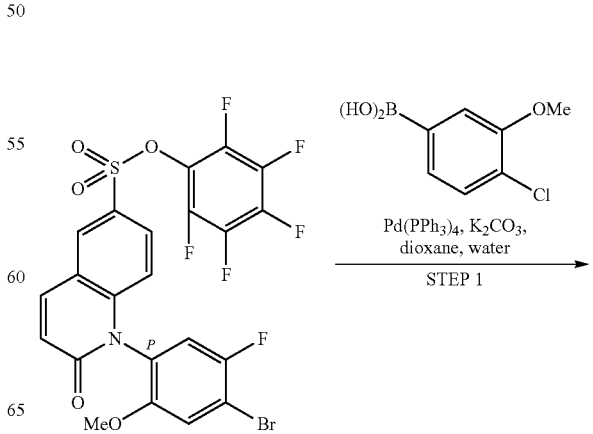

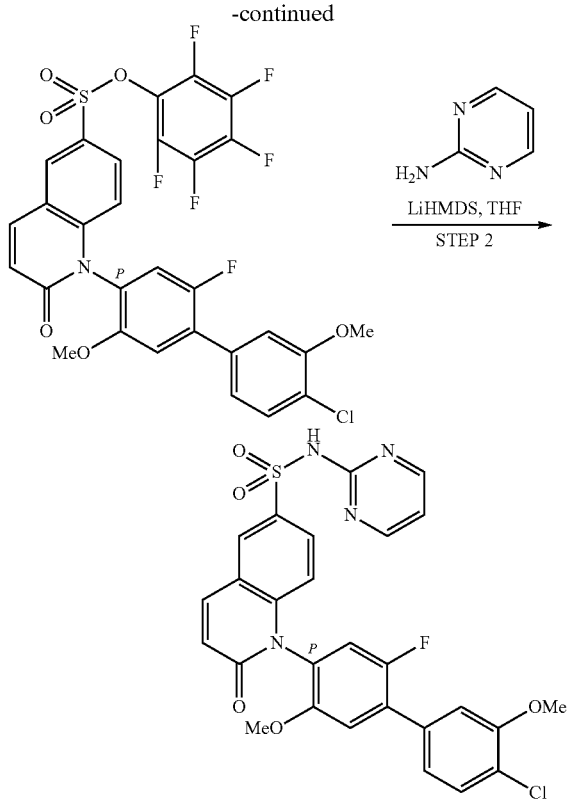

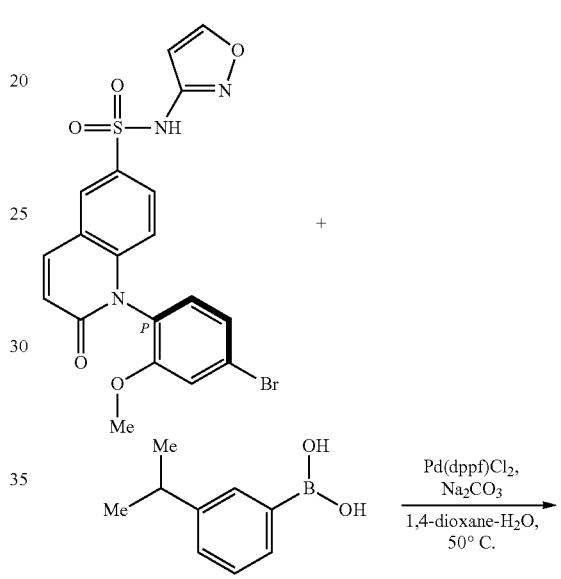

This compound was synthesized via Method 175.

Step 1: (P)-perfluorophenyl 1-(4'-chloro-2-fluoro-3',5-dimethoxy-[1,1'-biphenyl]-4-yl)-2-oxo-1,2-dihydroquinoline-6-sulfonate A solution of Pd(Ph₃P)₄ (0.194 g, 0.168 mmol), (4-chloro-3-methoxyphenyl)boronic acid (0.345 g, 1.851 mmol), (P)-perfluorophenyl 1-(4-bromo-5-fluoro-2-methoxyphenyl)-2-oxo-1,2-dihydroquinoline-6-sulfonate (1.000 g, 1.683 mmol), and potassium carbonate (0.930 g, 6.73 mmol) in 6 ml dioxane 2 mL water was heated to 50° C. for 3 hours. The reaction mixture was diluted with DCM and washed with water. The organics were dried over MgSO₄ and concentrated. Purification of the crude residue by silica gel column chromatography (0-70% EtOAc/heptane) gave (P)-perfluorophenyl 1-(4'-chloro-2-fluoro-3',5-dimethoxy-[1,1'-biphenyl]-4-yl)-2-oxo-1,2-dihydroquinoline-6-sulfonate (0.468 g, 0.713 mmol, 42.4% yield). m/z (ESI) 656.0 (M+H)⁺.

Step 2: (P)-1-(4'-chloro-2-fluoro-3',5-dimethoxy-4-biphenylyl)-2-oxo-N-2-pyrimidinyl-1,2-dihydro-6-quinolinesulfonamide A solution of pyrimidin-2-amine (0.033 g, 0.351 mmol) and (P)-perfluorophenyl 1-(4'-chloro-2-fluoro-3',5-dimethoxy-[1,1'-biphenyl]-4-yl)-2-oxo-1,2-dihydroquinoline-6-sulfonate (0.115 g, 0.175 mmol) in 3 mL THF was cooled to 0° C. and was treated with LiHMDS 1N in THF (0.351 ml, 0.351 mmol). The cooling bath was removed and the reaction mixture was allowed to stir for one hour. TFA (0.068 ml, 0.877 mmol) was added, and the reaction mixture was concentrated. Purification of the crude residue by reverse phase column chromatography [Puriflash C18, 10-100% (0.1% NH₄OH in MeOH)/(0.1% NH₄OH in water)] gave 1-(4'-chloro-2-fluoro-3',5-dimethoxy-[1,1'-biphenyl]-4-yl)-2-oxo-N-(pyrimidin-2-yl)-1,2-dihydroquinoline-6-sulfonamide (0.062 g, 0.109 mmol, 62.4% yield). ¹H NMR (ACETONITRILE-d3): 8.41-8.47 (m, 3H), 7.97-8.07 (m, 2H), 7.52 (d, J=8.2 Hz, 1H), 7.29-7.36 (m, 2H), 7.18-7.26 (m, 2H), 7.00 (t, J=4.9 Hz, 1H), 6.84 (d, J=9.0 Hz, 1H), 6.75 (d, J=9.7 Hz, 1H), 3.96 (s, 3H), 3.72 (s, 3H). m/z (ESI) 567.0 (M+H)⁺.

Example 686

(P)-1-(3,3'-dimethoxy-4'-methyl-4-biphenylyl)-N-3-isoxazolyl-2-oxo-1,2-dihydro-6-quinolinesulfonamide

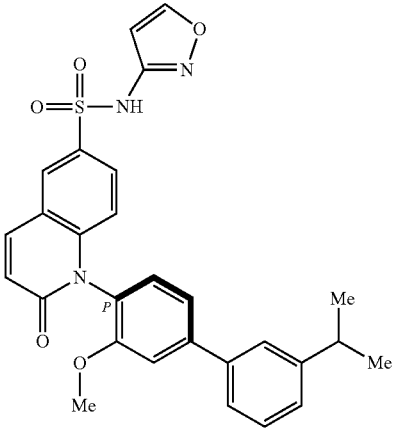

This compound was synthesized via Method 179. A 20-mL vial was charged with (P)-1-(4-bromo-2-methoxyphenyl)-N-(isoxazol-3-yl)-2-oxo-1,2-dihydroquinoline-6-sulfonamide (250 mg, 0.525 mmol), (3-isopropylphenyl)boronic acid (258 mg, 1.575 mmol), and (1,1'-bis(diphenylphosphino)ferrocene)dichloropalladium(II) (77 mg, 0.105 mmol) and purged with nitrogen. The reaction vessel was then sequentially charged with dioxane (3.7 mL) and an aqueous solution of sodium carbonate (1.3 mL, 1.9 M) via syringe. The vial was sealed with a PTFE line cap and the resultant brown reaction mixture was heated to 50°

C. After 14 h the reaction mixture was allowed to cool to ambient temperature and an aqueous solution of 1.0 N HCL (5 mL) was added and the mixture diluted with EtOAc (5 mL). The layers were separated and the aqueous layer was extracted with EtOAc (3×5 mL). The combined organic layers were washed with brine (25 mL), dried over anhydrous sodium sulfate, filtered, and concentrated under reduced pressure to furnish a tan oil, which was purified by flash column chromatography (25-g Biotage column, eluent: gradient, 0 to 100% EtOAc in heptane with 10% $CH_2Cl_2$ as an additive) to afford (P)-1-(3,3'-dimethoxy-4'-methyl-4-biphenylyl)-N-3-isoxazolyl-2-oxo-1,2-dihydro-6-quinolinesulfonamide (122 mg, 0.237 mmol, 45.1% yield) as a white amorphous solid. $^1$H NMR (400 MHz, DMSO-$d_6$) δ=11.70 (br. s., 1H), 8.78 (d, J=1.8 Hz, 1H), 8.42 (d, J=2.2 Hz, 1H), 8.27 (d, J=9.6 Hz, 1H), 7.91 (dd, J=2.2, 9.0 Hz, 1H), 7.56 (d, J=1.3 Hz, 1H), 7.50-7.35 (m, 5H), 7.03 (dd, J=1.6, 8.0 Hz, 1H), 6.86 (d, J=9.6 Hz, 2H), 6.51 (d, J=1.8 Hz, 1H), 4.18 (q, J=6.9 Hz, 2H), 3.82 (s, 3H), 2.59-2.50 (m, 1H), 1.42 (t, =7.0 Hz, 3H). m/z (ESI) 516.2 (M+H)$^+$.

Example 687

(P)-1-(2-fluoro-3',5,5'-trimethoxy-4-biphenylyl)-N-3-isoxazolyl-2-oxo-1,2-dihydro-6-quinolinesulfonamide

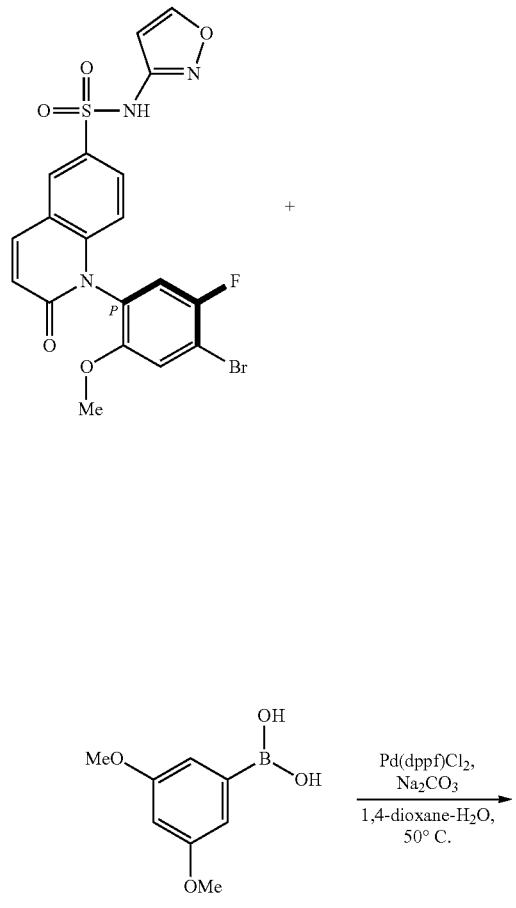

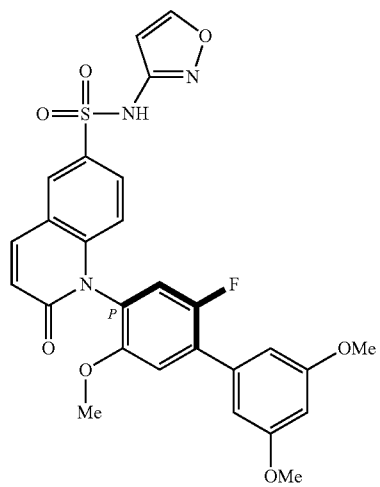

This compound was synthesized via Method 180. A 20-mL vial was charged with (P)-1-(4-bromo-5-fluoro-2-methoxyphenyl)-N-(isoxazol-3-yl)-2-oxo-1,2-dihydroquinoline-6-sulfonamide (250 mg, 0.506 mmol), 3,5-dimethoxyphenylboronic acid (276 mg, 1.517 mmol) (purchased from Combi-Blocks Inc.), and (1,1'-bis(diphenylphosphino)ferrocene)dichloropalladium(II) (83 mg, 0.101 mmol) then purged with nitrogen. The reaction vessel was then sequentially charged with dioxane (3.8 mL) and an aqueous solution of sodium carbonate (1.3 mL, 1.9 M) via syringe. The vial was sealed with a PTFE line cap and the resultant brown reaction mixture was heated to 50° C. After 16 h the reaction mixture was allowed to cool to ambient temperature and an aqueous solution of 1.0 N HCL (5 mL) was added and the mixture diluted with EtOAc (5 mL). The layers were separated and the aqueous layer was extracted with EtOAc (3×5 mL). The combined organic layers were washed with brine (25 mL), dried over anhydrous sodium sulfate, filtered, and concentrated under reduced pressure to furnish a tan oil, which was purified by flash column chromatography (25-g Biotage column, eluent: gradient, 0 to 100% EtOAc in heptane with 10% $CH_2Cl_2$ as an additive) to afford (P)-1-(2-fluoro-3',5,5'-trimethoxy-4-biphenylyl)-N-3-isoxazolyl-2-oxo-1,2-dihydro-6-quinolinesulfonamide (143 mg, 0.259 mmol, 51.3% yield) as a white amorphous solid. $^1$H NMR (400 MHz, DMSO-$d_6$) δ=11.66 (s, 1H), 8.74 (d, J=1.8 Hz, 1H), 8.38 (d, J=2.2 Hz, 1H), 8.23 (d, J=9.5 Hz, 1H), 7.87 (dd, J=2.3, 9.0 Hz, 1H), 7.49 (d, J=10.3 Hz, 1H), 7.37 (d, J=6.8 Hz, 1H), 6.88 (d, J=8.9 Hz, 1H), 6.85-6.79 (m, 3H), 6.62 (t, J=2.2 Hz, 1H), 6.46 (d, J=1.8 Hz, 1H), 3.83 (s, 7H), 3.73 (s, 3H). m/z (ESI) 516.0 (M+H)$^+$.

Example 688

(P)-1-(2-fluoro-5-methoxy-3'-(trifluoromethyl)-4-biphenylyl)-N-(6-methyl-4-pyrimidinyl)-2-oxo-1,2-dihydro-6-quinolinesulfonamide

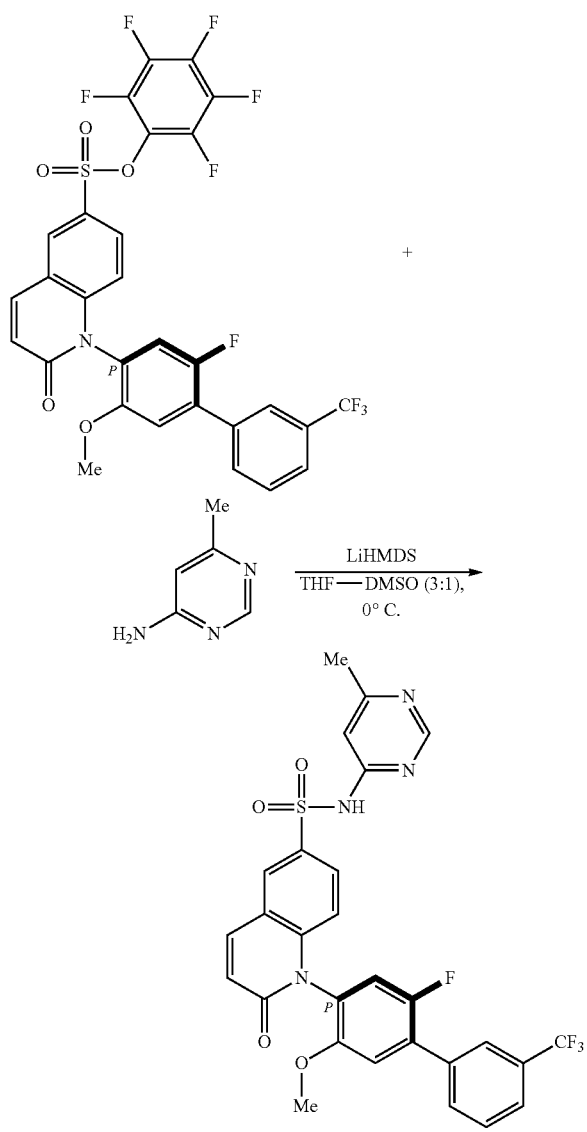

This compound was synthesized via Method 183. A 10-mL round-bottomed flask was charged with (P)-perfluorophenyl 1-(2-fluoro-5-methoxy-3'-(trifluoromethyl)-[1,1'-biphenyl]-4-yl)-2-oxo-1,2-dihydroquinoline-6-sulfonate (250 mg, 0.379 mmol) and 6-methylpyrimidin-4-amine (62.1 mg, 0.569 mmol) then purged with nitrogen. Tetrahydrofuran (2.8 mL) and dimethyl sulfoxide (0.95 mL) were introduced, and the resultant brown solution cooled to 0° C. A solution of lithium bis(trimethylsilyl)amide in tetrahydrofuran (1.0 M, 0.834 mL, 0.834 mmol) was added dropwise via syringe to the stirred reaction mixture over 3 min. After 15 min, 1.0 N HCl (5 mL) was introduced and the resultant reaction mixture was allowed to warm to ambient temperature. The mixture was diluted with and EtOAc (10 mL) and the layers were separated, and the aqueous layer was further extracted with EtOAc (3×10 mL). The combined organic layers were then washed with brine (20 mL), dried over anhydrous magnesium sulfate, filtered, and concentrated under reduced pressure to furnish a yellow oil, which was dissolved in DMSO (2 mL) filtered through a 0.2 micron filter and purified by reverse-phase HPLC (Waters XBridge Prep Shield RP18 10 μm OBD 19×100 mm) gradient, 35 to 95% MeCN in water (containing 0.1% formic acid as an additive). The fractions containing product were combined and concentrated via lyophilization to yield 1-(2-fluoro-5-methoxy-3'-(trifluoromethyl)-4-biphenylyl)-N-(6-methyl-4-pyrimidinyl)-2-oxo-1,2-dihydro-6-quinolinesulfonamide (69.0 mg, 0.118 mmol, 31.1% yield) as a white amorphous solid. $^1$H NMR (400 MHz, ACETONITRILE-$d_3$) δ ppm 8.54 (d, J=0.93 Hz, 1H) 8.39 (d, J=2.18 Hz, 1H) 8.03 (d, J=9.54 Hz, 1H) 7.95-8.01 (m, 1H) 7.93 (dd, J=8.97, 2.12 Hz, 1H) 7.77-7.82 (m, 1H) 7.70-7.76 (m, 1H) 7.35 (d, J=6.84 Hz, 1H) 7.23 (d, J=10.16 Hz, 1H) 6.99 (s, 1H) 6.86 (d, J=9.02 Hz, 1H) 6.78 (d, J=9.64 Hz, 1H) 6.13 (br. s., 1H) 3.73 (s, 3H) 2.41 (s, 3H). m/z (ESI) 585.0 (M+H)$^+$.

Example 689

(P)-1-(4'-chloro-3-methoxy-3'-methyl-4-biphenylyl)-N-(5-fluoro-2-pyridinyl)-2-oxo-1,2-dihydro-6-quinolinesulfonamide

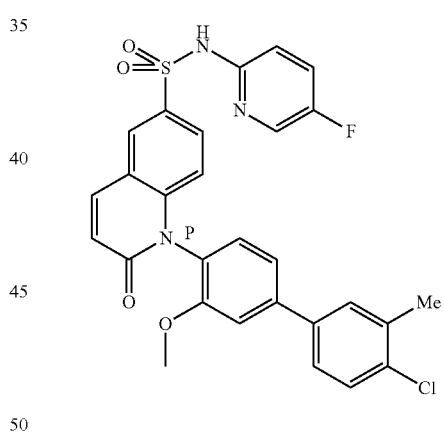

(P)-1-(4'-Chloro-3-methoxy-3'-methyl-4-biphenylyl)-N-(5-fluoro-2-pyridinyl)-2-oxo-1,2-dihydro-6-quinolinesulfonamide was prepared from (P)-perfluorophenyl 1-(4'-chloro-3-methoxy-3'-methyl-[1,1'-biphenyl]-4-yl)-2-oxo-1,2-dihydroquinoline-6-sulfonate and 5-fluoropyridin-2-amine according to the method described in Method 202. Data for (P)-1-(4'-chloro-3-methoxy-3'-methyl-4-biphenylyl)-N-(5-fluoro-2-pyridinyl)-2-oxo-1,2-dihydro-6-quinolinesulfonamide: $^1$H NMR (400 MHz, DMSO-$d_6$) δ 11.17 (br. s., 1H), 8.40 (d, J=2.18 Hz, 1H), 8.22 (d, J=9.54 Hz, 1H), 8.17 (d, J=3.11 Hz, 1H), 7.89 (dd, J=2.18, 9.02 Hz, 1H), 7.83 (d, J=1.97 Hz, 1H), 7.62-7.70 (m, 2H), 7.51-7.57 (m, 2H), 7.41-7.46 (m, 1H), 7.35-7.40 (m, 1H), 7.11 (dd, J=3.73, 9.12 Hz, 1H), 6.79 (d, J=9.64 Hz, 1H), 6.74-6.77 (m, 1H), 3.77 (s, 3H), 2.44 (s, 3H); LCMS m/z (ESI) 549.9 (M+H)$^+$.

Example 690

(P)-1-(4'-chloro-3-methoxy-3'-methyl-4-biphenylyl)-N-(5-fluoro-2-pyrimidinyl)-2-oxo-1,2-dihydro-6-quinolinesulfonamide

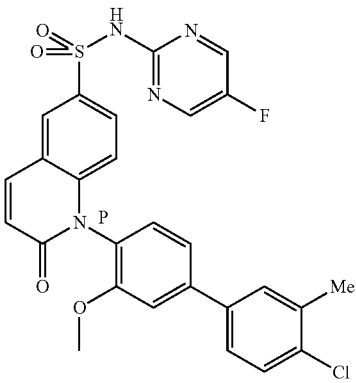

(P)-1-(4'-Chloro-3-methoxy-3'-methyl-4-biphenylyl)-N-(5-fluoro-2-pyrimidinyl)-2-oxo-1,2-dihydro-6-quinolinesulfonamide was prepared from (P)-perfluorophenyl 1-(4'-chloro-3-methoxy-3'-methyl-[1,1'-biphenyl]-4-yl)-2-oxo-1,2-dihydroquinoline-6-sulfonate and 5-fluoropyrimidin-2-amine (Oakwood) according to the method described in Method 202. Data for (P)-1-(4'-chloro-3-methoxy-3'-methyl-4-biphenylyl)-N-(5-fluoro-2-pyrimidinyl)-2-oxo-1,2-dihydro-6-quinolinesulfonamide: $^1$H NMR (400 MHz, DMSO-$d_6$) δ 11.96 (br. s., 1H), 8.62 (s, 2H), 8.47 (d, J=2.07 Hz, 1H), 8.25 (d, J=9.64 Hz, 1H), 7.97 (dd, J=2.18, 8.91 Hz, 1H), 7.81-7.87 (m, 1H), 7.63-7.70 (m, 1H), 7.51-7.57 (m, 2H), 7.42-7.48 (m, 1H), 7.34-7.40 (m, 1H), 6.79 (t, J=9.28 Hz, 2H), 3.73-3.83 (m, 3H), 2.44 (s, 3H); LCMS m/z (ESI) 550.8 (M+H)$^+$.

Example 691

(P)-1-(4'-chloro-2-fluoro-5-methoxy-3'-methyl-4-biphenylyl)-2-oxo-N-2-pyrazinyl-1,2-dihydro-6-quinolinesulfonamide

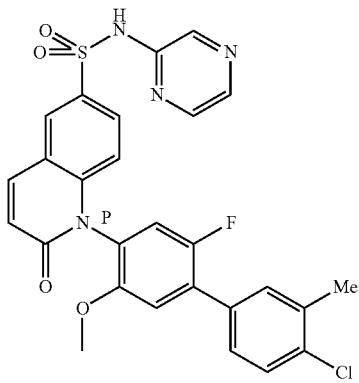

This compound was synthesized via Method 205. A round bottom flask was charged with pyrazin-2-amine (0.039 g, 0.406 mmol) and DMSO (0.781 ml) to give a solution. (P)-perfluorophenyl 1-(4'-chloro-2-fluoro-5-methoxy-3'-methyl-[1,1'-biphenyl]-4-yl)-2-oxo-1,2-dihydroquinoline-6-sulfonate (0.200 g, 0.313 mmol) and THF (2.344 ml) were added, and the mixture remained a solution. The flask was cooled in an ice-bath for 5 min, then lithium bis(trimethylsilyl)amide (1M in THF) (0.719 ml, 0.719 mmol) was added dropwise. The reaction was stirred for 15 minutes. The reaction was diluted with ethyl acetate and washed twice with 1N HCl solution. The organic layers was washed with brine, dried with sodium sulfate, filtered, and concentrated. The material was purified via column chromatography (RediSep Gold 40 g, gradient elution 10-75% [3:1 EtOAc/EtOH]:Heptane) to afford (P)-1-(4'-chloro-2-fluoro-5-methoxy-3'-methyl-[1,1'-biphenyl]-4-yl)-2-oxo-N-(pyrazin-2-yl)-1,2-dihydroquinoline-6-sulfonamide (0.109 g, 0.198 mmol, 63.3% yield) as a light pink solid. $^1$H NMR (400 MHz, DMSO-$d_6$) δ=11.64 (br. s., 1H), 8.47 (d, J=2.1 Hz, 1H), 8.36 (d, J=1.0 Hz, 1H), 8.29-8.19 (m, 3H), 7.96 (dd, J=2.2, 9.0 Hz, 1H), 7.69 (s, 1H), 7.61-7.47 (m, 3H), 7.38 (d, J=6.9 Hz, 1H), 6.83 (dd, J=9.3, 18.1 Hz, 2H), 3.72 (s, 3H), 2.44 (s, 3H). m/z (ESI) 551.2 (M+H)$^+$.

Example 692

(P)-1-(4'-chloro-2-fluoro-5-methoxy-3'-methyl-4-biphenylyl)-N-(5-fluoro-2-pyrimidinyl)-2-oxo-1,2-dihydro-6-quinolinesulfonamide

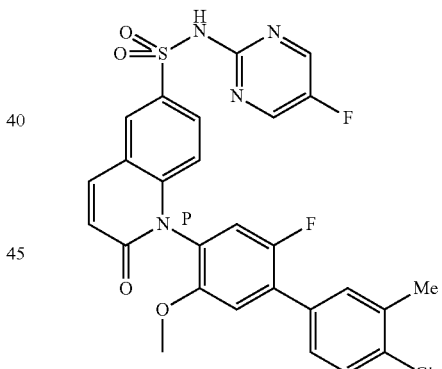

The title compound was prepared via Method 205 except that 5-fluoropyrimidin-2-amine was used instead of pyrimidin-4-amine in Step 2 to afford (P)-1-(4'-chloro-2-fluoro-5-methoxy-3'-methyl-[1,1'-biphenyl]-4-yl)-N-(5-fluoropyrimidin-2-yl)-2-oxo-1,2-dihydroquinoline-6-sulfonamide (0.137 g, 0.241 mmol, 51.4% yield) as an off-white solid. $^1$H NMR (400 MHz, DMSO-$d_6$) δ=11.98 (s, 1H), 8.62 (s, 2H), 8.48 (d, J=2.1 Hz, 1H), 8.26 (d, J=9.7 Hz, 1H), 7.98 (dd, J=2.2, 9.0 Hz, 1H), 7.70 (s, 1H), 7.61-7.47 (m, 3H), 7.39 (d, J=6.9 Hz, 1H), 6.83 (dd, J=9.3, 15.9 Hz, 2H), 3.73 (s, 3H), 2.44 (s, 3H). m/z (ESI) 569.2 (M+H)$^+$.

Example 693

(P)-1-(4'-chloro-2-fluoro-5-methoxy-3'-methyl-4-biphenylyl)-N-(5-fluoro-2-pyridinyl)-2-oxo-1,2-dihydro-6-quinolinesulfonamide

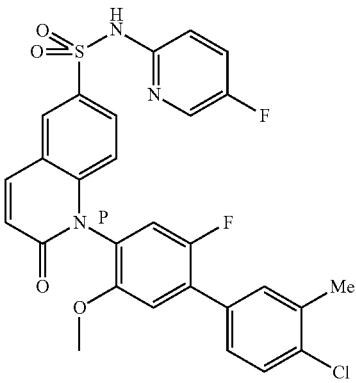

The title compound was prepared via Method 205 except that 5-fluoropyridin-2-amine was used instead of pyrimidin-4-amine in Step 2 to afford (P)-1-(4'-chloro-2-fluoro-5-methoxy-3'-methyl-[1,1'-biphenyl]-4-yl)-N-(5-fluoropyridin-2-yl)-2-oxo-1,2-dihydroquinoline-6-sulfonamide (0.173 g, 0.305 mmol, 65.0% yield) as a light yellow solid. $^1$H NMR (400 MHz, DMSO-$d_6$) δ=11.18 (br. s., 1H), 8.41 (d, J=2.1 Hz, 1H), 8.23 (d, J=9.6 Hz, 1H), 8.18 (d, J=3.1 Hz, 1H), 7.90 (dd, J=2.2, 9.0 Hz, 1H), 7.72-7.63 (m, 2H), 7.61-7.47 (m, 3H), 7.38 (d, J=6.9 Hz, 1H), 7.11 (dd, J=3.7, 9.1 Hz, 1H), 6.82 (dd, J=9.3, 13.8 Hz, 2H), 3.73 (s, 3H), 2.44 (s, 3H). m/z (ESI) 568.1 (M+H)$^+$.

Example 694

(P)-1-(4'-chloro-2-fluoro-5-methoxy-3'-methyl-4-biphenylyl)-N-1,3-oxazol-2-yl-2-oxo-1,2-dihydro-6-quinolinesulfonamide

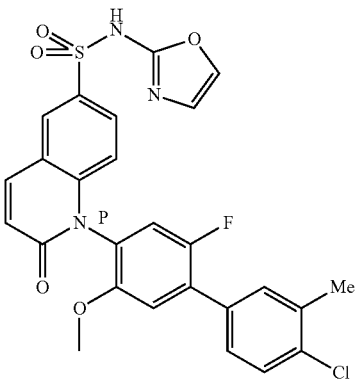

The title compound was prepared via method 205 except that oxazol-2-amine was used instead of pyrimidin-4-amine in Step 2 to afford (P)-1-(4'-chloro-2-fluoro-5-methoxy-3'-methyl-[1,1'-biphenyl]-4-yl)-N-(oxazol-2-yl)-2-oxo-1,2-dihydroquinoline-6-sulfonamide (0.138 g, 0.256 mmol, 40.9% yield) as a light yellow solid. $^1$H NMR (400 MHz, DMSO-$d_6$) δ=12.17 (br. s., 1H), 8.33 (d, J=2.1 Hz, 1H), 8.20 (d, J=9.5 Hz, 1H), 7.87 (dd, J=2.2, 8.9 Hz, 1H), 7.70 (s, 1H), 7.61-7.52 (m, 3H), 7.50 (d, J=10.5 Hz, 1H), 7.39 (d, J=7.0 Hz, 1H), 7.25 (d, J=1.7 Hz, 1H), 6.78 (dd, J=1.5, 9.2 Hz, 2H), 3.74 (s, 3H), 2.44 (s, 3H). m/z (ESI) 540.0 (M+H)$^+$.

Example 695

(P)-1-(4'-chloro-2-fluoro-5-methoxy-3'-methyl-4-biphenylyl)-2-oxo-N-3-pyridazinyl-1,2-dihydro-6-quinolinesulfonamide

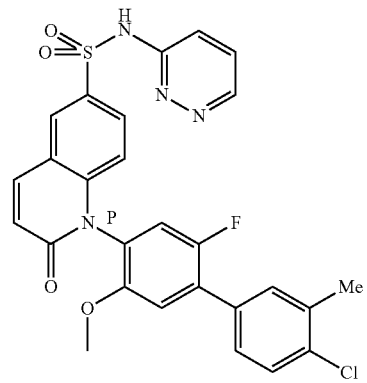

This compound was synthesized via Method 205. A RBF was charged with pyridazin-3-amine (0.039 g, 0.406 mmol) and DMSO (0.781 ml) to give a solution. (P)-perfluorophenyl 1-(4'-chloro-2-fluoro-5-methoxy-3'-methyl-[1,1'-biphenyl]-4-yl)-2-oxo-1,2-dihydroquinoline-6-sulfonate (0.200 g, 0.313 mmol) and THF (2.344 ml) were added, and the mixture remained a solution. The flask was cooled in an ice-bath for 5 min, then lithium bis(trimethylsilyl)amide (1M in THF) (0.719 ml, 0.719 mmol) was added dropwise. The reaction was stirred for 15 minutes. The reaction was diluted with ethyl acetate and washed twice with 1N HCl solution. The organic layers was washed with brine, dried with sodium sulfate, filtered, and concentrated. The material was purified via column chromatography (RediSep Gold 40 g, gradient elution 10-75% [3:1 EtOAc/EtOH]:Heptane) to afford (P)-1-(4'-chloro-2-fluoro-5-methoxy-3'-methyl-[1,1'-biphenyl]-4-yl)-2-oxo-N-(pyridazin-3-yl)-1,2-dihydroquinoline-6-sulfonamide (0.108 g, 0.196 mmol, 62.7% yield) as an off-white solid. $^1$H NMR (400 MHz, DMSO-$d_6$) δ=14.52 (br. s., 1H), 8.51-8.19 (m, 3H), 7.93 (d, J=8.6 Hz, 2H), 7.76 (br. s., 2H), 7.69-7.51 (m, 3H), 7.45 (d, J=5.7 Hz, 1H), 6.86 (d, J=7.6 Hz, 2H), 3.80 (br. s., 3H), 2.50 (br. s., 3H). m/z (ESI) 551.2 (M+H)$^+$.

Example 696

(P)-1-(4'-chloro-2-fluoro-5-methoxy-3'-methyl-4-biphenylyl)-2-oxo-N-2-pyrimidinyl-1,2-dihydro-6-quinolinesulfonamide

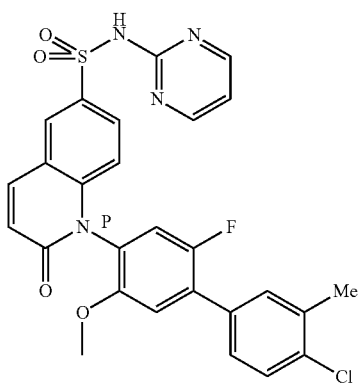

This compound was synthesized via Method 205. A RBF was charged with pyridazin-3-amine (0.039 g, 0.406 mmol) and DMSO (0.781 ml) to give a solution. (P)-perfluorophenyl 1-(4'-chloro-2-fluoro-5-methoxy-3'-methyl-[1,1'-biphenyl]-4-yl)-2-oxo-1,2-dihydroquinoline-6-sulfonate (0.200 g, 0.313 mmol) and THF (2.344 ml) were added, and the mixture remained a solution. The flask was cooled in an ice-bath for 5 min, then lithium bis(trimethylsilyl)amide (1M in THF) (0.719 ml, 0.719 mmol) was added dropwise. The reaction was stirred for 15 minutes. The reaction was diluted with ethyl acetate and washed twice with 1N HCl solution. The organic layers was washed with brine, dried with sodium sulfate, filtered, and concentrated. The material was purified via column chromatography (RediSep Gold 40 g, gradient elution 10-75% [3:1 EtOAc/EtOH]:Heptane) to afford (P)-1-(4'-chloro-2-fluoro-5-methoxy-3'-methyl-[1,1'-biphenyl]-4-yl)-2-oxo-N-(pyridazin-3-yl)-1,2-dihydroquinoline-6-sulfonamide (0.108 g, 0.196 mmol, 62.7% yield) as an off-white solid. $^1$H NMR (400 MHz, DMSO-d$_6$) δ=14.52 (br. s., 1H), 8.51-8.19 (m, 3H), 7.93 (d, J=8.6 Hz, 2H), 7.76 (br. s., 2H), 7.69-7.51 (m, 2H), 7.45 (d, J=5.7 Hz, 1H), 6.86 (d, J=7.6 Hz, 2H), 3.80 (br. s., 3H), 2.50 (br. s., 3H). m/z (ESI) 551.2 (M+H)$^+$.

Example 697

(P)-1-(3'-fluoro-3-methoxy-5'-(trifluoromethyl)-4-biphenylyl)-N-3-isoxazolyl-2-oxo-1,2-dihydro-6-quinolinesulfonamide

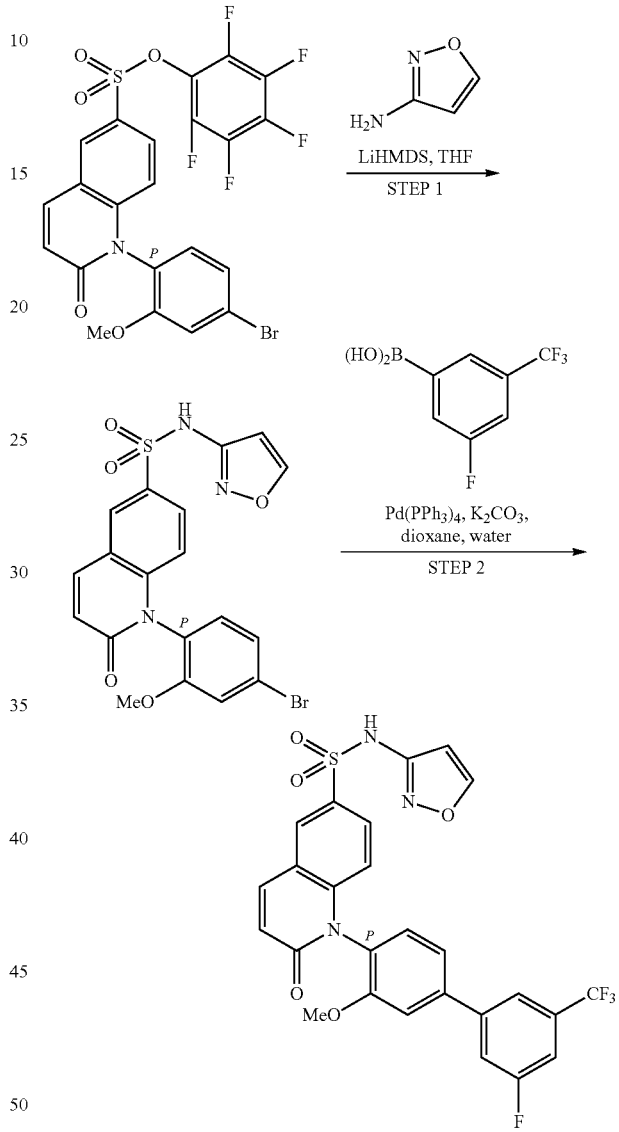

This compound was made via Method 173.

Step 1: (P)-1-(4-bromo-2-methoxyphenyl)-N-(isoxazol-3-yl)-2-oxo-1,2-dihydroquinoline-6-sulfonamide A solution of 3-aminoisoxazole (0.494 ml, 6.68 mmol) and (P)-perfluorophenyl 1-(4-bromo-2-methoxyphenyl)-2-oxo-1,2-dihydroquinoline-6-sulfonate (3.500 g, 6.07 mmol) in 50 mL THF, was cooled to 0° C. LHMDS 1N in THF (12.75 ml, 12.75 mmol) was added dropwise. After stirring for an hour, the reaction mixture was poured into 1N HCl and was extracted with DCM. The organics were dried over MgSO$_4$ and concentrated yielding (P)-1-(4-bromo-2-methoxyphenyl)-N-(isoxazol-3-yl)-2-oxo-1,2-dihydroquinoline-6-sulfonamide (4.30 g, 9.03 mmol, 149% yield) with minor impurities. m/z (ESI) 476.1 (M+H)⁺.

Step 2: (P)-1-(3'-fluoro-3-methoxy-5'-(trifluoromethyl)-4-biphenylyl)-N-3-isoxazolyl-2-oxo-1,2-dihydro-6-quinolinesulfonamide A solution of Pd(Ph₃P)₄ (63 mg, 0.054 mmol), (3-fluoro-5-trifluoromethylphenyl)boronic acid (226 mg, 1.09 mmol), (P)-1-(4-bromo-2-methoxyphenyl)-N-(isoxazol-3-yl)-2-oxo-1,2-dihydroquinoline-6-sulfonamide (288 mg, 0.605 mmol), and potassium carbonate (301 mg, 2.18 mmol) in 3 mL dioxane 1 mL water was heated to 50° C. for 3 hours. The reaction mixture was then treated with 1 mL TFA and was concentrated. Purification of the crude residue by reverse phase column chromatography [Puriflash C18, 10-100% (0.1% NH4OH in MeOH)/(0.1% NH4OH in water)] gave (P)-1-(3'-FLUORO-3-METHOXY-5'-(TRIFLUOROMETHYL)-4-BIPHENYLYL)-N-3-ISOXAZOLYL-2-oxo-1,2-DIHYDRO-6-QUINOLINESULFONAMIDE (0.090 g, 0.161 mmol, 29.6%). ¹H NMR (ACETONITRILE-d3): 8.34-8.38 (m, 1H), 8.23-8.28 (m, 1H), 8.00 (dd, J=9.7, 2.1 Hz, 1H), 7.92 (s, 1H), 7.78-7.85 (m, 2H), 7.44-7.57 (m, 3H), 7.33-7.39 (m, 1H), 6.73-6.82 (m, 2H), 6.42-6.47 (m, 1H), 3.79 (d, J=2.5 Hz, 3H). m/z (ESI) 560.2 (M+H)⁺.

Example 698 (3140704)

(P)-1-(2-fluoro-3',5-dimethoxy-4'-methyl-4-biphenylyl)-N-3-isoxazolyl-2-oxo-1,2-dihydro-6-quinolinesulfonamide This compound was prepared via method 139 using 3-methoxy-4-methylphenylboronic acid (purchased from Cuschem, Inc.) as the boronic acid. ¹H NMR (400 MHz, DMSO-d₆) δ ppm 2.23 (s, 3H) 3.74 (s, 3H) 3.89 (s, 3H) 6.46 (d, J=4.68 Hz, 1H) 6.83 (d, J=9.64 Hz, 1H) 6.90 (d, J=9.12 Hz, 1H) 7.13-7.24 (m, 2H) 7.30 (d, J=7.77 Hz, 1H) 7.38 (d, J=6.95 Hz, 1H) 7.49 (d, J=10.37 Hz, 1H) 7.88 (dd, J=8.91, 2.28 Hz, 1H) 8.24 (d, J=9.74 Hz, 1H) 8.39 (d, J=2.07 Hz, 1H) 8.75 (d, J=4.71 Hz, 1H) 11.68 (s, 1H). m/z (ESI) 536.2 (M+H)⁺.

Example 699 (3137256)

(P)-1-(2'-chloro-2-fluoro-4',5-dimethoxy-4-biphenylyl)-N-3-isoxazolyl-2-oxo-1,2-dihydro-6-quinolinesulfonamide This compound was prepared via method 139 using 2-chloro-4-methoxyphenylboronic acid (purchased from Combi-Blocks, Inc.) as the boronic acid. ¹H NMR (400 MHz, DMSO-d₆) δ ppm 3.69 (s, 3H) 3.86 (s, 3H) 6.46 (s, 1H) 6.83 (dd, J=9.23, 1.87 Hz, 2H) 7.10 (d, J=7.97 Hz, 1H) 7.22-7.27 (m, 2H) 7.49 (d, J=9.23 Hz, 2H) 7.90 (dd, J=8.91, 2.18 Hz, 1H) 8.24 (d, J=9.64 Hz, 1H) 8.39 (d, J=2.18 Hz, 1H) 8.74 (d, J=4.97 Hz, 1H) 11.68 (s, 1H). m/z (ESI) 556.1 (M+H)⁺.

Example 700 (3140310)

(P)-1-(4'-chloro-2-fluoro-3',5-dimethoxy-4-biphenylyl)-N-3-isoxazolyl-2-oxo-1,2-dihydro-6-quinolinesulfonamide This compound was prepared via method 139 using 4-chloro-3-methoxyphenylboronic acid (purchased from Combi-Blocks, Inc.) as the boronic acid. ¹H NMR (400 MHz, DMSO-d₆) δ ppm 3.75 (s, 3H) 3.97 (s, 3H) 6.46 (s, 1H) 6.83 (d, J=9.64 Hz, 1H) 6.89 (d, J=9.02 Hz, 1H) 7.28 (d, J=7.75 Hz, 1H) 7.41 (d, J=9.73 Hz, 1H) 7.43 (d, J=6.38 Hz, 1H) 7.53 (d, J=10.37 Hz, 1H) 7.60 (d, J=8.19 Hz, 1H) 7.87 (dd, J=8.91, 2.28 Hz, 1H) 8.24 (d, J=9.64 Hz, 1H) 8.39 (d, J=2.18 Hz, 1H) 8.74 (d, J=1.76 Hz, 1H) 11.67 (s, 1H). m/z (ESI) 556.1 (M+H)⁺.

Example 701 (3140524)

(P)-1-(2-fluoro-5-methoxy-4-biphenylyl)-N-3-isoxazolyl-2-oxo-1,2-dihydro-6-quinolinesulfonamide This compound was prepared via method 139 using benzeneboronic acid as the boronic acid. ¹H NMR (400 MHz, DMSO-d₆) δ ppm 3.74 (s, 3H) 6.46 (d, J=1.76 Hz, 1H) 6.83 (d, J=9.64 Hz, 1H) 6.90 (d, J=8.91 Hz, 1H) 7.39 (d, J=6.95 Hz, 1H) 7.46-7.61 (m, 4H) 7.70 (d, J=6.97 Hz, 1H) 7.72 (d, J=6.97 Hz, 1H) 7.88 (dd, J=8.91, 2.18 Hz, 1H) 8.24 (d, J=9.74 Hz, 1H) 8.39 (d, J=2.18 Hz, 1H) 8.74 (s, 1H) 11.67 (s, 1H). m/z (ESI) 492.2 (M+H)⁺.

Example 702 (3140526)

(P)-1-(2,2'-difluoro-4',5-dimethoxy-4-biphenylyl)-N-3-isoxazolyl-2-oxo-1,2-dihydro-6-quinolinesulfonamide This compound was prepared via method 139 using 2-fluoro-5-methoxyphenylboronic acid as the boronic acid. ¹H NMR (400 MHz, DMSO-d₆) δ ppm 3.72 (s, 3H) 3.84 (s, 3H) 6.46 (s, 1H) 6.83 (d, J=9.64 Hz, 1H) 6.87 (d, J=9.02 Hz, 1H) 7.05-7.12 (m, 1H) 7.15 (dd, J=5.86, 3.16 Hz, 1H) 7.32 (t, J=9.23 Hz, 1H) 7.38 (d, J=6.43 Hz, 1H) 7.53 (d, J=9.54 Hz, 1H) 7.89 (dd, J=9.02, 2.18 Hz, 1H) 8.25 (d, J=9.74 Hz, 1H) 8.39 (d, J=2.07 Hz, 1H) 8.74 (s, 1H) 11.68 (s, 1H). m/z (ESI) 540.2 (M+H)⁺.

Example 703 (3140527)

(P)-1-(3'-chloro-2,2'-difluoro-5-methoxy-4-biphenylyl)-N-3-isoxazolyl-2-oxo-1,2-dihydro-6-quinolinesulfonamide This compound was prepared via method 139 using 3-chloro-2-fluorobenzeneboronic acid as the boronic acid. ¹H NMR (400 MHz, DMSO-d₆) δ ppm 3.72 (s, 3H) 6.46 (d, J=5.40 Hz, 1H) 6.83 (d, J=9.64 Hz, 1H) 6.88 (d, J=8.91 Hz, 1H) 7.37-7.48 (m, 2H) 7.56-7.68 (m, 2H) 7.76 (t, J=7.07 Hz, 1H) 7.89 (dd, J=8.91, 2.28 Hz, 1H) 8.25 (d, J=9.64 Hz, 1H) 8.40 (d, J=10.50 Hz, 1H) 8.74 (s, 1H) 11.68 (s, 1H). m/z (ESI) 544.0 (M+H)⁺.

Example 704 (3140703)

(P)-1-(2-fluoro-5-methoxy-3',4'-dimethyl-4-biphenylyl)-N-3-isoxazolyl-2-oxo-1,2-dihydro-6-quinolinesulfonamide This compound was prepared via method 139 using 3,4-dimethylbenzeneboronic acid (purchased from Lancaster Synthesis, Ltd.) as the boronic acid. ¹H NMR (400 MHz, DMSO-d₆) δ ppm 2.31 (s, 3H) 2.33 (s, 3H) 3.73 (s, 3H) 6.46 (s, 1H) 6.82 (d, J=9.64 Hz, 1H) 6.89 (d, J=8.91 Hz, 1H) 7.32 (dd, J=13.22, 7.52 Hz, 2H) 7.41 (d, J=7.77 Hz, 1H) 7.44-7.50 (m, 2H) 7.87 (dd, J=9.07, 2.23 Hz, 1H) 8.24 (d, J=9.54 Hz, 1H) 8.38 (d, J=2.28 Hz, 1H) 8.74 (s, 1H) 11.68 (s, 1H). m/z (ESI) 520.3 (M+H)+.

Example 705 (3140705)

(P)-1-(2,3'-difluoro-4',5-dimethoxy-4-biphenylyl)-N-3-isoxazolyl-2-oxo-1,2-dihydro-6-quinolinesulfonamide This compound was prepared via method 145 using 3-fluoro-4-methoxyphenylboronic acid as the boronic acid. $^1$H NMR (400 MHz, DMSO-d$_6$) δ ppm 3.74 (s, 3H) 3.93 (s, 3H) 6.46 (d, J=2.04 Hz, 1H) 6.82 (d, J=9.64 Hz, 1H) 6.88 (d, J=9.02 Hz, 1H) 7.34 (d, J=8.92 Hz, 1H) 7.39 (d, J=9.60 Hz, 1H) 7.48-7.55 (m, 2H) 7.61 (d, J=12.41 Hz, 1H) 7.87 (dd, J=8.97, 2.23 Hz, 1H) 8.24 (d, J=9.54 Hz, 1H) 8.39 (d, J=2.18 Hz, 1H) 8.74 (s, 1H) 11.68 (s, 1H). m/z (ESI) 540.2 (M+H)+.

Example 706 (3140706)

(P)-1-(2-fluoro-5-methoxy-3',5'-dimethyl-4-biphenylyl)-N-3-isoxazolyl-2-oxo-1,2-dihydro-6-quinolinesulfonamide This compound was prepared via method 139 using 3,5-dimethylbenzeneboronic acid as the boronic acid. $^1$H NMR (400 MHz, DMSO-d$_6$) δ ppm 2.38 (s, 6H) 3.73 (s, 3H) 6.46 (s, 1H) 6.82 (d, J=9.54 Hz, 1H) 6.88 (d, J=9.02 Hz, 1H) 7.11 (s, 1H) 7.29 (s, 2H) 7.34 (d, J=6.95 Hz, 1H) 7.48 (d, J=10.26 Hz, 1H) 7.88 (dd, J=6.72 Hz, 1H) 8.24 (d, J=9.64 Hz, 1H) 8.39 (d, J=2.18 Hz, 1H) 8.75 (d, J=4.34 Hz, 1H) 11.68 (s, 1H). m/z (ESI) 520.3 (M+H)+.

Example 707 (3140707)

(P)-1-(5'-chloro-2,2'-difluoro-5-methoxy-4-biphenylyl)-N-3-isoxazolyl-2-oxo-1,2-dihydro-6-quinolinesulfonamide This compound was prepared via method 145 using 5-chloro-2-fluorophenylboronic acid as the boronic acid. $^1$H NMR (400 MHz, DMSO-d$_6$) δ ppm 3.73 (s, 3H) 6.46 (s, 1H) 6.85 (t, J=9.43 Hz, 2H) 7.42-7.52 (m, 2H) 7.57 (d, J=9.64 Hz, 1H) 7.64 (ddd, J=8.84, 4.33, 2.70 Hz, 1H) 7.75 (dd, J=6.27, 2.75 Hz, 1H) 7.88 (dd, J=8.97, 2.23 Hz, 1H) 8.25 (d, J=9.64 Hz, 1H) 8.40 (d, J=2.18 Hz, 1H) 8.75 (s, 1H) 11.69 (s, 1H). m/z (ESI) 544.0 (M+H)+.

Example 708 (3140708)

(P)-1-(2-fluoro-3',5-dimethoxy-5'-methyl-4-biphenylyl)-N-3-isoxazolyl-2-oxo-1,2-dihydro-6-quinolinesulfonamide This compound was prepared via method 139 using 3-methoxy-5-methylphenylboronic acid (purchased from Combi-Blocks, Inc.) as the boronic acid. $^1$H NMR (400 MHz, DMSO-d$_6$) δ ppm 3.73 (s, 3H) 3.82 (s, 3H) 6.46 (s, 1H) 6.82 (d, J=9.64 Hz, 1H) 6.86-6.92 (m, 2H) 7.02 (s, 1H) 7.07 (s, 1H) 7.36 (d, J=6.95 Hz, 1H) 7.49 (d, J=10.37 Hz, 1H) 7.87 (dd, J=8.97, 2.23 Hz, 1H) 8.24 (d, J=9.64 Hz, 1H) 8.39 (d, J=2.07 Hz, 1H) 8.75 (d, J=1.76 Hz, 1H) 11.69 (s, 1H). m/z (ESI) 536.3 (M+H)+.

Example 709 (3140767)

(P)-1-(2-fluoro-3',5-dimethoxy-4-biphenylyl)-N-3-isoxazolyl-2-oxo-1,2-dihydro-6-quinolinesulfonamide This compound was prepared via method 139 using 3-methoxyphenylboronic acid as the boronic acid. $^1$H NMR (400 MHz, DMSO-d$_6$) δ ppm 3.74 (s, 3H) 3.85 (s, 3H) 6.46 (d, J=2.07 Hz, 1H) 6.83 (d, J=9.64 Hz, 1H) 6.90 (d, J=8.91 Hz, 1H) 7.05 (d, J=8.40 Hz, 1H) 7.23 (d, J=9.58 Hz, 1H) 7.26 (d, J=8.52 Hz, 1H) 7.39 (d, J=6.84 Hz, 1H) 7.46 (d, J=7.98 Hz, 1H) 7.50 (d, J=10.37 Hz, 1H) 7.88 (dd, J=8.97, 2.23 Hz, 1H) 8.24 (d, J=9.64 Hz, 1H) 8.39 (d, J=2.18 Hz, 1H) 8.75 (s, 1H) 11.67 (s, 1H). m/z (ESI) 522.0 (M+H)+.

Example 710 (3140768)

(P)-1-(2,3'-difluoro-5,5'-dimethoxy-4-biphenylyl)-N-3-isoxazolyl-2-oxo-1,2-dihydro-6-quinolinesulfonamide This compound was prepared via method 139 using (3-fluoro-5-methoxyphenyl)boronic acid (purchased from Synthonix, Inc.) as the boronic acid. $^1$H NMR (400 MHz, DMSO-d$_6$) δ ppm 3.75 (s, 3H) 3.87 (s, 3H) 6.46 (d, J=1.96 Hz, 1H) 6.83 (d, J=9.64 Hz, 1H) 6.88 (d, J=9.02 Hz, 1H) 6.94-7.00 (m, 1H) 7.11 (d, J=9.52 Hz, 1H) 7.11-7.15 (m, 1H) 7.42 (d, J=6.84 Hz, 1H) 7.53 (d, J=10.47 Hz, 1H) 7.87 (d, J=9.02 Hz, 1H) 8.24 (d, J=9.54 Hz, 1H) 8.39 (d, J=2.18 Hz, 1H) 8.75 (d, J=2.08 Hz, 1H) 11.67 (s, 1H). m/z (ESI) 540.0 (M+H)+.

Example 711 (3140779)

(P)-1-(2,3'-difluoro-5-methoxy-5'-(trifluoromethyl)-4-biphenylyl)-N-3-isoxazolyl-2-oxo-1,2-dihydro-6-quinolinesulfonamide This compound was prepared via method 139 using 3-fluoro-5-trifluoromethylphenylboronic acid (purchased from Combi-Blocks, Inc.) as the boronic acid. $^1$H NMR (400 MHz, DMSO-d$_6$) δ ppm 3.77 (s, 3H) 6.46 (s, 1H) 6.83 (d, J=9.64 Hz, 1H) 6.88 (d, J=9.02 Hz, 1H) 7.53 (d, J=6.95 Hz, 1H) 7.60 (d, J=10.47 Hz, 1H) 7.83-7.88 (m, 2H) 7.94-7.99 (m, 2H) 8.25 (d, J=9.64 Hz, 1H) 8.39 (d, J=2.28 Hz, 1H) 8.74 (d, J=0.87 Hz, 1H) 11.67 (s, 1H). m/z (ESI) 578.2 (M+H)+.

Example 712 (3140781)

(P)-1-(3'-chloro-2-fluoro-5-methoxy-2'-methyl-4-biphenylyl)-N-3-isoxazolyl-2-oxo-1,2-dihydro-6-quinolinesulfonamide This compound was prepared via method 139 using (3-chloro-2-methylphenyl)boronic acid (purchased from Combi-Blocks, Inc.) as the boronic acid. $^1$H NMR (400 MHz, DMSO-d$_6$) δ ppm 3.69 (s, 3H) 6.45 (d, J=1.76 Hz, 1H) 6.83 (d, J=9.64 Hz, 1H) 6.90 (d, J=8.71 Hz, 1H) 7.26 (d, J=6.63 Hz, 1H) 7.35-7.42 (m, 2H) 7.52 (d, J=9.43 Hz, 1H) 7.55-7.60 (m, 1H) 7.88 (dd, J=8.91, 2.18 Hz, 1H) 8.24 (d,

Example 713 (3140787)

(P)-1-(2,4'-difluoro-3',5-dimethoxy-4-biphenylyl)-N-3-isoxazolyl-2-oxo-1,2-dihydro-6-quinolinesulfonamide This compound was prepared via method 139 using (4-fluoro-3-methoxyphenyl)boronic acid (purchased from Combi-Blocks, Inc.) as the boronic acid. $^1$H NMR (400 MHz, DMSO-$d_6$) δ ppm 3.75 (s, 3H) 3.95 (s, 3H) 6.46 (d, J=1.76 Hz, 1H) 6.83 (d, J=9.74 Hz, 1H) 6.89 (d, J=8.91 Hz, 1H) 7.21-7.30 (m, 1H) 7.35-7.48 (m, 3H) 7.52 (d, J=10.37 Hz, 1H) 7.85-7.91 (m, 1H) 8.24 (d, J=9.64 Hz, 1H) 8.39 (d, J=2.18 Hz, 1H) 8.75 (d, J=1.76 Hz, 1H) 11.67 (s, 1H). m/z (ESI) 540.0 (M+H)$^+$.

Example 714 (3140845)

(P)-1-(2-fluoro-2',5-dimethoxy-5'-methyl-4-biphenylyl)-N-3-isoxazolyl-2-oxo-1,2-dihydro-6-quinolinesulfonamide This compound was prepared via method 139 using 2-methoxy-5-methylphenylboronic acid (purchased from Combi-Blocks, Inc.) as the boronic acid. $^1$H NMR (400 MHz, DMSO-$d_6$) δ ppm 2.33 (s, 3H) 3.68 (s, 3H) 3.79 (s, 3H) 6.45 (s, 1H) 6.83 (dd, J=9.33, 5.91 Hz, 2H) 7.07 (d, J=8.40 Hz, 1H) 7.17-7.29 (m, 3H) 7.39 (d, J=9.54 Hz, 1H) 7.89 (dd, J=9.02, 2.18 Hz, 1H) 8.24 (d, J=9.64 Hz, 1H) 8.38 (d, J=2.18 Hz, 1H) 8.73 (d, J=1.76 Hz, 1H) 11.67 (s, 1H). m/z (ESI) 536.2 (M+H)$^+$.

Example 715 (3140846)

(P)-1-(5-fluoro-2-methoxy-4-(2-methoxy-5-methyl-3-pyridinyl)phenyl)-N-3-isoxazolyl-2-oxo-1,2-dihydro-6-quinolinesulfonamide This compound was prepared via method 139 using 2-methoxy-5-methylpyridine-3-boronic acid (purchased from Combi-Blocks, Inc.) as the boronic acid. $^1$H NMR (400 MHz, DMSO-$d_6$) δ ppm 2.32 (s, 3H) 3.69 (s, 3H) 3.89 (s, 3H) 6.46 (d, J=1.76 Hz, 1H) 6.84 (dd, J=9.23, 5.49 Hz, 2H) 7.32 (d, J=6.43 Hz, 1H) 7.45 (d, J=9.54 Hz, 1H) 7.69 (d, J=2.28 Hz, 1H) 7.90 (dd, J=8.97, 2.23 Hz, 1H) 8.11 (d, J=1.56 Hz, 1H) 8.24 (d, J=9.74 Hz, 1H) 8.39 (d, J=2.07 Hz, 1H) 8.74 (d, J=1.76 Hz, 1H) 11.67 (s, 1H). m/z (ESI) 537.2 (M+H)$^+$.

Example 716 (3141084)

(P)-1-(2'-chloro-2-fluoro-5-methoxy-5'-methyl-4-biphenylyl)-N-3-isoxazolyl-2-oxo-1,2-dihydro-6-quinolinesulfonamide This compound was prepared via method 139 using (2-chloro-5-methyl)benzeneboronic acid (purchased from Combi-Blocks, Inc.) as the boronic acid. $^1$H NMR (400 MHz, DMSO-$d_6$) δ ppm 2.39 (s, 3H) 3.69 (s, 3H) 6.47 (s, 1H) 6.82 (s, 1H) 6.85 (s, 1H) 7.28 (d, J=6.43 Hz, 1H) 7.31-7.36 (m, 1H) 7.37-7.42 (m, 1H) 7.51 (d, J=8.76, 6.38 Hz, 2H) 7.90 (dd, J=8.97, 2.23 Hz, 1H) 8.25 (d, J=9.64 Hz, 1H) 8.40 (d, J=2.18 Hz, 1H) 8.74 (s, 1H) 11.68 (s, 1H). m/z (ESI) 540.0 (M+H)$^+$.

Example 717 (3141085)

(P)-1-(5'-cyano-2-fluoro-5-methoxy-2'-methyl-4-biphenylyl)-N-3-isoxazolyl-2-oxo-1,2-dihydro-6-quinolinesulfonamide This compound was prepared via method 139 using (5-cyano-2-methylphenyl)boronic acid (purchased from Combi-Blocks, Inc.) as the boronic acid. $^1$H NMR (400 MHz, DMSO-$d_6$) δ ppm 2.36 (s, 3H) 3.70 (s, 3H) 6.46 (s, 1H) 6.84 (d, J=9.64 Hz, 1H) 6.88 (d, J=8.81 Hz, 1H) 7.31 (d, J=6.41 Hz, 1H) 7.54 (d, J=9.23 Hz, 1H) 7.62 (d, J=7.98 Hz, 1H) 7.84-7.91 (m, 3H) 8.25 (d, J=9.74 Hz, 1H) 8.39 (d, J=2.18 Hz, 1H) 8.74 (d, J=5.32 Hz, 1H) 11.68 (s, 1H). m/z (ESI) 531.0 (M+H)$^+$.

Example 718 (3141086)

(P)-1-(5'-cyano-2-fluoro-2',5-dimethoxy-4-biphenylyl)-N-3-isoxazolyl-2-oxo-1,2-dihydro-6-quinolinesulfonamide This compound was prepared via method 139 using 5-cyano-2-methoxyphenylboronic acid (purchased from Combi-Blocks, Inc.) as the boronic acid. $^1$H NMR (400 MHz, DMSO-$d_6$) δ ppm 3.69 (s, 3H) 3.93 (s, 3H) 6.46 (d, J=1.55 Hz, 1H) 6.83 (d, J=9.43 Hz, 2H) 7.33 (d, J=6.43 Hz, 1H) 7.38 (d, J=8.81 Hz, 1H) 7.46 (d, J=9.43 Hz, 1H) 7.85-7.93 (m, 2H) 7.98 (dd, J=8.55, 2.13 Hz, 1H) 8.24 (d, J=9.64 Hz, 1H) 8.39 (d, J=1.97 Hz, 1H) 8.74 (d, J=1.55 Hz, 1H) 11.68 (s, 1H). m/z (ESI) 547.1 (M+H)$^+$.

Example 719 (3141087)

(P)-1-(2,2'-difluoro-5-methoxy-3'-methyl-4-biphenylyl)-N-3-isoxazolyl-2-oxo-1,2-dihydro-6-quinolinesulfonamide This compound was prepared via method 139 using 2-fluoro-3-methylphenylboronic acid (purchased from Combi-Blocks, Inc.) as the boronic acid. $^1$H NMR (400 MHz, DMSO-$d_6$) δ ppm 2.35 (d, J=1.76 Hz, 3H) 3.71 (s, 3H) 6.46 (d, J=1.76 Hz, 1H) 6.83 (d, J=9.64 Hz, 1H) 6.87 (d, J=9.02 Hz, 1H) 7.24-7.31 (m, 1H) 7.34 (d, J=6.43 Hz, 1H) 7.43 (t, J=7.00 Hz, 2H) 7.53 (d, J=9.54 Hz, 1H) 7.90 (dd, J=8.97, 2.23 Hz, 1H) 8.25 (d, J=9.54 Hz, 1H) 8.39 (d, J=2.18 Hz, 1H) 8.74 (d, J=1.87 Hz, 1H) 11.68 (s, 1H). m/z (ESI) 524.2 (M+H)$^+$.

Example 720 (3141088)

(P)-1-(4'-cyano-2-fluoro-3',5-dimethoxy-4-biphenylyl)-N-3-isoxazolyl-2-oxo-1,2-dihydro-6-quinolinesulfonamide This compound was prepared via method 139 using (4-cyano-3-methoxyphenyl)boronic acid (purchased from Combi-Blocks, Inc.) as the boronic acid. $^1$H NMR (400 MHz, DMSO-$d_6$) δ ppm 3.71-3.82 (m, 3H) 4.00-4.07 (m, 3H) 6.46 (s, 1H) 6.83 (dd, J=9.64, 1.97 Hz, 1H) 6.89 (d, J=9.02 Hz, 1H) 7.42 (d, J=7.77 Hz, 1H) 7.46-7.53 (m, 2H) 7.59 (dd, J=10.31, 1.92 Hz, 1H) 7.84-7.94 (m, 2H) 8.25 (d, J=9.59 Hz, 1H) 8.40 (s, 1H) 8.74 (s, 1H) 11.67 (s, 1H). m/z (ESI) 547.1 (M+H)$^+$.

Example 721 (3141090)

(P)-1-(5-fluoro-2-methoxy-4-(5-(trifluoromethyl)-3-pyridinyl)phenyl)-N-3-isoxazolyl-2-oxo-1,2-dihydro-6-quinolinesulfonamide This compound was prepared via method 139 using (5-trifluoromethylpyridin-3-yl)boronic acid (purchased from Combi-Blocks, Inc.) as the boronic acid. $^1$H NMR (400 MHz, DMSO-$d_6$) δ ppm 3.78 (s, 3H) 6.47 (d, J=1.76 Hz, 1H) 6.84 (d, J=9.64 Hz, 1H) 6.89 (d, J=9.02 Hz, 1H) 7.60-7.66 (m, 2H) 7.87 (dd, J=8.97, 2.23 Hz, 1H) 8.25 (d, J=9.54 Hz, 1H) 8.40 (d, J=2.18 Hz, 1H) 8.54 (s, 1H) 8.75 (d, J=1.87 Hz, 1H) 9.10 (d, J=1.24 Hz, 1H) 9.23 (s, 1H) 11.67 (s, 1H). m/z (ESI) 561.2 (M+H)$^+$.

Example 722 (3141091)

(P)-1-(5-fluoro-4-(6-fluoro-5-methyl-3-pyridinyl)-2-methoxyphenyl)-N-3-isoxazolyl-2-oxo-1,2-dihydro-6-quinolinesulfonamide This compound was prepared via method 139 using (6-fluoro-5-methylpyridin-3-yl)boronic acid (purchased from Combi-Blocks, Inc.) as the boronic acid. $^1$H NMR (400 MHz, DMSO-$d_6$) δ ppm 2.37 (s, 3H) 3.75 (s, 3H) 6.46 (d, J=1.76 Hz, 1H) 6.83 (d, J=9.64 Hz, 1H) 6.88 (d, J=9.02 Hz, 1H) 7.48 (d, J=6.95 Hz, 1H) 7.56 (s, 1H) 7.59 (s, 1H) 7.87 (dd, J=8.97, 2.23 Hz, 1H) 8.20 (d, J=9.54 Hz, 1H) 8.25 (d, J=9.54 Hz, 1H) 8.39 (d, J=2.07 Hz, 2H) 8.75 (d, J=1.87 Hz, 1H) 11.67 (s, 1H). m/z (ESI) 525.0 (M+H)$^+$.

Example 723 (3141709)

(P)-1-(3''-chloro-2-fluoro-5,5',5''-trimethoxy-1,1':3',1''-terphenyl-4-yl)-N-3-isoxazolyl-2-oxo-1,2-dihydro-6-quinolinesulfonamide This compound was prepared via method 139 using (3-chloro-5-methoxyphenyl)boronic acid (purchased from Aurum Pharmatech, Inc.) as the boronic acid. $^1$H NMR (400 MHz, DMSO-$d_6$) δ ppm 3.76 (s, 3H) 3.88 (s, 3H) 3.93 (s, 3H) 6.47 (s, 1H) 6.83 (d, J=9.64 Hz, 1H) 6.90 (d, J=9.02 Hz, 1H) 7.08 (s, 1H) 7.24-7.36 (m, 3H) 7.43 (t, J=1.61 Hz, 1H) 7.46-7.56 (m, 3H) 7.88 (dd, J=8.91, 2.18 Hz, 1H) 8.25 (d, J=9.64 Hz, 1H) 8.39 (d, J=2.18 Hz, 1H) 8.75 (d, J=6.17 Hz, 1H) 11.67 (s, 1H). m/z (ESI) 662.2 (M+H)$^+$.

Example 724 (3141822)

(P)-1-(2-fluoro-5,5'-dimethoxy-2'-methyl-4-biphenylyl)-N-3-isoxazolyl-2-oxo-1,2-dihydro-6-quinolinesulfonamide This compound was prepared via method 148 using 2-(5-methoxy-2-methylphenyl)-4,4,5,5-tetramethyl-1,3,2-dioxaborolane as the boronic ester. $^1$H NMR (400 MHz, DMSO-$d_6$) δ ppm 2.19 (s, 3H) 3.69 (s, 3H) 3.80 (s, 3H) 6.46 (s, 1H) 6.83 (d, J=9.64 Hz, 1H) 6.89 (d, J=9.02 Hz, 1H) 6.92-7.00 (m, 2H) 7.21 (d, J=6.63 Hz, 1H) 7.29 (d, J=8.60 Hz, 1H) 7.47 (d, J=9.54 Hz, 1H) 7.89 (dd, J=8.91, 2.18 Hz, 1H) 8.24 (d, J=9.64 Hz, 1H) 8.39 (d, J=2.07 Hz, 1H) 8.74 (d, J=1.76 Hz, 1H) 11.68 (s, 1H). m/z (ESI) 536.0 (M+H)$^+$.

Example 725 (3141823)

(P)-1-(2'-chloro-2-fluoro-5-methoxy-4'-methyl-4-biphenylyl)-N-3-isoxazolyl-2-oxo-1,2-dihydro-6-quinolinesulfonamide This compound was prepared via method 139 using 2-chloro-4-methylphenylboronic acid as the boronic acid. $^1$H NMR (400 MHz, DMSO-$d_6$) δ ppm 2.40 (s, 3H) 3.68 (s, 3H) 6.46 (s, 1H) 6.84 (dd, J=9.33, 1.87 Hz, 2H) 7.26 (d, J=6.63 Hz, 1H) 7.33 (d, J=7.36 Hz, 1H) 7.45 (d, J=7.88 Hz, 1H) 7.48-7.54 (m, 2H) 7.90 (dd, J=9.02, 2.28 Hz, 1H) 8.25 (d, J=9.64 Hz, 1H) 8.39 (d, J=2.18 Hz, 1H) 8.74 (s, 1H) 11.68 (s, 1H). m/z (ESI) 540.2 (M+H)$^+$.

Example 726 (3141868)

(P)-1-(2'-chloro-2-fluoro-5,5'-dimethoxy-4-biphenylyl)-N-3-isoxazolyl-2-oxo-1,2-dihydro-6-quinolinesulfonamide This compound was prepared via method 149 using 2-chloro-5-methoxyphenyl boronic acid (purchased from Combi-Blocks, Inc.) as the boronic acid. $^1$H NMR (400 MHz, DMSO-$d_6$) δ ppm 3.70 (s, 3H) 3.84 (s, 3H) 6.45 (d, J=5.04 Hz, 1H) 6.83 (d, J=9.64 Hz, 2H) 7.09 (d, J=8.93 Hz, 1H) 7.13-7.15 (m, 1H) 7.30 (d, J=6.53 Hz, 1H) 7.51 (d, J=9.43 Hz, 1H) 7.54 (d, J=8.81 Hz, 1H) 7.89 (dd, J=8.91, 2.07 Hz, 1H) 8.25 (d, J=9.54 Hz, 1H) 8.39 (d, J=2.07 Hz, 1H) 8.72 (d, J=1.66 Hz, 1H) 11.68 (s, 1H). m/z (ESI) 556.0 (M+H)$^+$.

Example 727 (3142065)

(P)-1-(3'-ethoxy-2-fluoro-5-methoxy-4-biphenylyl)-N-3-isoxazolyl-2-oxo-1,2-dihydro-6-quinolinesulfonamide This compound was prepared via method 139 using 3-ethoxyphenylboronic acid as the boronic acid. $^1$H NMR (400 MHz, DMSO-$d_6$) δ ppm 1.33-1.43 (m, 3H) 3.74 (s, 3H) 4.13 (q, J=6.81 Hz, 2H) 6.44-6.47 (m, 1H) 6.82 (dd, J=9.64, 1.66 Hz, 1H) 6.89 (d, J=8.71 Hz, 1H) 7.04 (d, J=8.09 Hz, 1H) 7.20-7.27 (m, 2H) 7.37-7.52 (m, 3H) 7.87 (d, J=9.12 Hz, 1H) 8.24 (d, J=9.64 Hz, 1H) 8.38 (s, 1H) 8.73 (s, 1H) 11.67 (s, 1H). m/z (ESI) 536.0 (M+H)$^+$.

Example 728 (3142077)

(P)-1-(2-fluoro-5-methoxy-3'-(trifluoromethoxy)-4-biphenylyl)-N-3-isoxazolyl-2-oxo-1,2-dihydro-6-quinolinesulfonamide This compound was prepared via method 139 using 3-(trifluoromethoxy)phenylboronic acid (purchased from Matrix Scientific) as the boronic acid. $^1$H NMR (400 MHz, DMSO-$d_6$) δ ppm 3.76 (s, 3H) 6.46 (d, J=1.76 Hz, 1H) 6.83 (d, J=9.54 Hz, 1H) 6.90 (d, J=8.81 Hz, 1H) 7.45 (d, J=6.84 Hz, 1H) 7.51 (d, J=7.77 Hz, 1H) 7.56 (d, J=10.37 Hz, 1H) 7.67-7.79 (m, 3H) 7.87 (dd, J=8.91, 2.18 Hz, 1H) 8.25 (d, J=9.54 Hz, 1H) 8.39 (d, J=1.97 Hz, 1H) 8.75 (d, J=1.76 Hz, 1H) 11.67 (s, 1H). m/z (ESI) 576.0 (M+H)$^+$.

Example 729 (3142078)

(P)-1-(5-fluoro-2-methoxy-4-(6-methoxy-3-pyridinyl)phenyl)-N-3-isoxazolyl-2-oxo-1,2-dihydro-6-quinolinesulfonamide This compound was prepared via method 139 using 2-methoxy-5-pyridineboronic acid as the boronic acid. $^1$H NMR (400 MHz, DMSO-$d_6$) δ ppm 3.74 (s, 3H) 3.94 (s, 3H) 6.46 (d, J=1.76 Hz, 1H) 6.82 (d, J=9.64 Hz, 1H) 6.89 (d, J=9.02 Hz, 1H) 7.01 (d, J=8.71 Hz, 1H) 7.44 (d, J=6.84 Hz, 1H) 7.53 (d, J=10.37 Hz, 1H) 7.87 (dd, J=8.91, 2.28 Hz, 1H) 8.06 (d, J=8.60 Hz, 1H) 8.24 (d, J=9.74 Hz, 1H) 8.38 (d, J=2.18 Hz, 1H) 8.53 (s, 1H) 8.74 (d, J=1.76 Hz, 1H) 11.67 (s, 1H). m/z (ESI) 523.0 (M+H)$^+$.

Example 730 (3142104)

(p)-1-(5-fluoro-4-(5-fluoro-3-pyridinyl)-2-methoxyphenyl)-N-3-isoxazolyl-2-oxo-1,2-dihydro-6-quinolinesulfonamide This compound was prepared via method 139 using 5-fluoropyridine-3-boronic acid (purchased from Combi-Blocks, Inc.) as the boronic acid. $^1$H NMR (400 MHz, DMSO-$d_6$) δ ppm 3.77 (s, 3H) 6.46 (d, J=1.76 Hz, 1H) 6.83 (d, J=9.64 Hz, 1H) 6.89 (d, J=9.02 Hz, 1H) 7.56 (d, J=6.43 Hz, 1H) 7.62 (d, J=10.47 Hz, 1H) 7.78-7.94 (m, 1H) 8.15 (d, J=9.74 Hz, 1H) 8.25 (d, J=9.64 Hz, 1H) 8.40 (d, J=2.07 Hz, 1H) 8.71 (d, J=2.49 Hz, 1H) 8.75 (d, J=1.97 Hz, 1H) 8.82 (br. s., 1H) 11.67 (br. s., 1H). m/z (ESI) 511.0 (M+H)$^+$.

Example 731 (3142106)

(P)-1-(2'-chloro-2-fluoro-3',5-dimethoxy-4-biphenylyl)-N-3-isoxazolyl-2-oxo-1,2-dihydro-6-quinolinesulfonamide This compound was prepared via method 149 using 2-chloro-3-methoxyphenylboronic acid (purchased from Combi-Blocks, Inc.) as the boronic acid. $^1$H NMR (400 MHz, DMSO-$d_6$) δ ppm 3.68 (s, 3H) 3.94 (s, 3H) 6.46 (s, 1H) 6.79-6.89 (m, 2H) 7.13 (dd, J=7.67, 1.35 Hz, 1H) 7.23-7.31 (m, 2H) 7.44-7.54 (m, 2H) 7.91 (dd, J=8.91, 1.97 Hz, 1H) 8.25 (d, J=9.64 Hz, 1H) 8.39 (d, J=2.18 Hz, 1H) 8.74 (s, 1H) 11.68 (s, 1H). m/z (ESI) 556.0 (M+H)$^+$.

Example 732 (3142107)

(P)-1-(2,2'-difluoro-5,5'-dimethoxy-4-biphenylyl)-N-3-isoxazolyl-2-oxo-1,2-dihydro-6-quinolinesulfonamide This compound was prepared via method 139 using 2-fluoro-5-methoxyphenylboronic acid as the boronic acid. $^1$H NMR (400 MHz, DMSO-$d_6$) δ ppm 3.72 (s, 3H) 3.84 (s, 3H) 6.46 (d, J=4.72 Hz, 1H) 6.83 (d, J=9.64 Hz, 1H) 6.87 (d, J=9.02 Hz, 1H) 7.05-7.12 (m, 1H) 7.15 (dd, J=5.91, 3.21 Hz, 1H) 7.32 (t, J=9.23 Hz, 1H) 7.38 (d, J=6.43 Hz, 1H) 7.53 (m, J=9.64 Hz, 1H) 7.89 (dd, J=8.97, 2.23 Hz, 1H) 8.25 (m, J=9.74 Hz, 1H) 8.39 (d, J=2.18 Hz, 1H) 8.74 (d, J=4.32 Hz, 1H) 11.68 (s, 1H). m/z (ESI) 540.0 (M+H)$^+$.

Example 733 (3142274)

(P)-1-(4'-chloro-2,2'-difluoro-5-methoxy-4-biphenylyl)-N-3-isoxazolyl-2-oxo-1,2-dihydro-6-quinolinesulfonamide This compound was prepared via method 139 using 4-chloro-2-fluorophenylboronic acid (purchased from Combi-Blocks, Inc.) as the boronic acid. $^1$H NMR (400 MHz, DMSO-$d_6$) δ ppm 3.63 (s, 3H) 6.16 (s, 1H) 6.62-6.71 (m, 2H) 7.29 (d, J=6.53 Hz, 1H) 7.38-7.50 (m, 2H) 7.54-7.67 (m, 2H) 7.72 (dd, J=8.81, 2.07 Hz, 1H) 8.11 (d, J=9.74 Hz, 1H) 8.15 (s, 1H) 8.32 (br. s., 1H) 11.59 (br. s., 1H). m/z (ESI) 544.0 (M+H)$^+$.

Example 734 (3142373)

(P)-1-(2,2'-difluoro-3',5-dimethoxy-4-biphenylyl)-N-3-isoxazolyl-2-oxo-1,2-dihydro-6-quinolinesulfonamide This compound was prepared via method 139 using 2-fluoro-3-methoxyphenylboronic acid as the boronic acid. $^1$H NMR (400 MHz, DMSO-$d_6$) δ ppm 3.71 (s, 3H) 3.92 (s, 3H) 6.46 (d, J=1.76 Hz, 1H) 6.83 (d, J=9.64 Hz, 1H) 6.88 (d, J=8.91 Hz, 1H) 7.10-7.18 (m, 1H) 7.28-7.39 (m, 3H) 7.53 (d, J=9.54 Hz, 1H) 7.90 (dd, J=8.97, 2.23 Hz, 1H) 8.25 (d, J=9.64 Hz, 1H) 8.39 (d, J=2.18 Hz, 1H) 8.74 (d, J=1.76 Hz, 1H) 11.68 (s, 1H). m/z (ESI) 540.0 (M+H)$^+$.

Example 735 (3142375)

(P)-1-(2-fluoro-3',5-dimethoxy-2'-methyl-4-biphenylyl)-N-3-isoxazolyl-2-oxo-1,2-dihydro-6-quinolinesulfonamide This compound was prepared via method 139 using (3-methoxy-2-methylphenyl)boronic acid (purchased from SynQuest Laboratories) as the boronic acid. $^1$H NMR (400 MHz, DMSO-$d_6$) δ ppm 2.09 (s, 3H) 3.68 (s, 3H) 3.87 (s, 3H) 6.46 (d, J=4.29 Hz, 1H) 6.83 (d, J=9.64 Hz, 1H) 6.89 (d, J=8.91 Hz, 1H) 6.97 (d, J=7.46 Hz, 1H) 7.08 (d, J=8.09 Hz, 1H) 7.18 (d, J=6.02 Hz, 1H) 7.26-7.40 (m, 1H) 7.47 (d, J=9.43 Hz, 1H) 7.89 (dd, J=9.07, 2.23 Hz, 1H) 8.24 (d, J=9.64 Hz, 1H) 8.39 (d, J=2.18 Hz, 1H) 8.74 (s, 1H) 11.68 (s, 1H). m/z (ESI) 536.2 (M+H)$^+$.

Example 736 (3142790)

(P)-1-(5-fluoro-2-methoxy-4-(2-methyl-4-pyridinyl)phenyl)-N-3-isoxazolyl-2-oxo-1,2-dihydro-6-quinolinesulfonamide This compound was prepared via method 139 using (2-methylpyridin-4-yl)boronic acid (purchased from Combi-Blocks, Inc.) as the boronic acid. $^1$H NMR (400 MHz, DMSO-$d_6$) δ ppm 2.51 (s, 3H) 3.68 (s, 3H) 6.24 (s, 1H) 6.67-6.74 (m, 2H) 7.38 (d, J=6.84 Hz, 1H) 7.45 (d, J=5.08 Hz, 1H) 7.48 (d, J=10.47 Hz, 1H) 7.53 (s, 1H) 7.74 (dd, J=8.81, 2.07 Hz, 1H) 8.13 (d, J=9.85 Hz, 1H) 8.20 (s, 1H) 8.44 (br. s., 1H) 8.53 (d, J=5.18 Hz, 1H). m/z (ESI) 507.0 (M+H)$^+$.

Example 737 (3142826)

(P)-1-(5-fluoro-2-methoxy-4-(2-methyl-3-pyridinyl)phenyl)-N-3-isoxazolyl-2-oxo-1,2-dihydro-6-quinolinesulfonamide This compound was prepared via method 139 using 2-methylpyridine-3-boronic acid (purchased from Combi-Blocks, Inc.) as the boronic acid. $^1$H NMR (400 MHz, DMSO-d$_6$) δ ppm 2.53 (s, 3H) 3.63 (s, 3H) 6.39 (d, J=2.03 Hz, 1H) 6.77 (d, J=9.64 Hz, 1H) 6.85 (d, J=9.02 Hz, 1H) 7.32 (d, J=6.53 Hz, 1H) 7.54 (d, J=9.54 Hz, 1H) 7.66 (dd, J=7.67, 5.39 Hz, 1H) 7.81 (dd, J=8.97, 2.23 Hz, 1H) 8.13 (d, J=6.84 Hz, 1H) 8.18 (d, J=9.64 Hz, 1H) 8.33 (d, J=2.18 Hz, 1H) 8.67 (d, J=7.27 Hz, 1H) 8.68-8.71 (m, 1H) 11.42-11.85 (m, 1H). m/z (ESI) 507.0 (M+H)$^+$.

Example 738 (3142857)

(P)-1-(5-fluoro-2-methoxy-4-(5-methoxy-3-pyridinyl)phenyl)-N-3-isoxazolyl-2-oxo-1,2-dihydro-6-quinolinesulfonamide This compound was prepared via method 139 using 5-methoxypyridine-3-boronic acid (purchased from Combi-Blocks, Inc.) as the boronic acid. $^1$H NMR (400 MHz, DMSO-d$_6$) δ ppm 3.76 (s, 3H) 3.94-3.97 (m, 3H) 6.46 (d, J=4.74 Hz, 1H) 6.83 (d, J=9.64 Hz, 1H) 6.89 (d, J=9.02 Hz, 1H) 7.51 (d, J=6.95 Hz, 1H) 7.59 (d, J=10.37 Hz, 1H) 7.75 (br. s., 1H) 7.88 (dd, J=8.91, 2.28 Hz, 1H) 8.25 (d, J=9.54 Hz, 1H) 8.39 (d, J=2.18 Hz, 1H) 8.44 (d, J=6.18 Hz, 1H) 8.53 (s, 1H) 8.75 (d, J=6.70 Hz, 1H) 11.67 (s, 1H). m/z (ESI) 523.0 (M+H)$^+$.

Example 739 (3142859)

(P)-1-(5-fluoro-2-methoxy-4-(2-methoxy-4-pyridinyl)phenyl)-N-3-isoxazolyl-2-oxo-1,2-dihydro-6-quinolinesulfonamide This compound was prepared via method 139 using 2-methoxypyridine-4-boronic acid (purchased from Combi-Blocks, Inc.) as the boronic acid. $^1$H NMR (400 MHz, DMSO-d$_6$) δ ppm 3.75 (s, 3H) 3.94 (s, 3H) 6.46 (d, J=2.03 Hz, 1H) 6.83 (d, J=9.64 Hz, 1H) 6.89 (d, J=9.02 Hz, 1H) 7.16 (s, 1H) 7.33 (d, J=5.31 Hz, 1H) 7.48 (d, J=6.84 Hz, 1H) 7.58 (d, J=10.47 Hz, 1H) 7.87 (dd, J=8.58 Hz, 1H) 8.25 (d, J=9.54 Hz, 1H) 8.33 (dd, J=5.34, 0.67 Hz, 1H) 8.39 (d, J=2.28 Hz, 1H) 8.74 (d, J=2.08 Hz, 1H) 11.67 (s, 1H). m/z (ESI) 523.0 (M+H)$^+$.

Example 740 (3143093)

(P)-1-(4-(5-chloro-6-methoxy-3-pyridinyl)-5-fluoro-2-methoxyphenyl)-N-3-isoxazolyl-2-oxo-1,2-dihydro-6-quinolinesulfonamide This compound was prepared via method 145 using 3-chloro-2-methoxypyridine-5-boronic acid (purchased from Combi-Blocks, Inc.) as the boronic acid. $^1$H NMR (400 MHz, DMSO-d$_6$) δ ppm 3.70 (s, 3H) 3.94 (s, 3H) 6.46 (d, J=1.76 Hz, 1H) 6.77-6.90 (m, 2H) 7.41 (d, J=6.43 Hz, 1H) 7.50 (d, J=9.54 Hz, 1H) 7.89 (dd, J=8.97, 2.23 Hz, 1H) 8.02 (d, J=2.58 Hz, 1H) 8.25 (d, J=9.64 Hz, 1H) 8.37 (d, J=2.59 Hz, 1H) 8.39 (d, J=2.18 Hz, 1H) 8.74 (s, 1H) 11.68 (br. s., 1H). m/z (ESI) 557.0 (M+H)$^+$.

Example 741 (3143548)

(P)-1-(2,4'-difluoro-2',5-dimethoxy-4-biphenylyl)-N-3-isoxazolyl-2-oxo-1,2-dihydro-6-quinolinesulfonamide This compound was prepared via method 145 using 4-fluoro-2-methoxyphenylboronic acid as the boronic acid. $^1$H NMR (400 MHz, DMSO-d$_6$) δ ppm 3.67 (s, 3H) 3.85 (s, 3H) 6.38 (s, 1H) 6.80 (d, J=9.43 Hz, 2H) 6.95 (t, J=8.26 Hz, 1H) 7.11 (dd, J=1.61, 2.49 Hz, 1H) 7.23 (d, J=6.53 Hz, 1H) 7.38-7.46 (m, 2H) 7.86 (dd, J=8.97, 2.02 Hz, 1H) 8.22 (d, J=9.85 Hz, 1H) 8.33 (s, 1H) 8.62 (br. s., 1H) 11.57-11.80 (m, 1H). m/z (ESI) 540.0 (M+H)$^+$.

Example 742 (3143549)

(P)-1-(4'-chloro-2-fluoro-5-methoxy-2'-methyl-4-biphenylyl)-N-3-isoxazolyl-2-oxo-1,2-dihydro-6-quinolinesulfonamide This compound was prepared via method 145 using (4-chloro-2-methylphenyl)boronic acid (purchased from Indofine Chemical Company, Inc.) as the boronic acid. $^1$H NMR (400 MHz, DMSO-d$_6$) δ ppm 2.28 (s, 3H) 3.68 (s, 3H) 6.46 (s, 1H) 6.83 (d, J=9.64 Hz, 1H) 6.89 (d, J=8.91 Hz, 1H) 7.23 (d, J=6.53 Hz, 1H) 7.36-7.46 (m, 2H) 7.47-7.54 (m, 2H) 7.88 (dd, J=8.97, 2.23 Hz, 1H) 8.24 (d, J=9.54 Hz, 1H) 8.39 (d, J=2.18 Hz, 1H) 8.74 (s, 1H) 11.68 (s, 1H). m/z (ESI) 540.0 (M+H)$^+$.

Example 743 (3143557)

(P)-1-(5'-chloro-2-fluoro-5-methoxy-2'-methyl-4-biphenylyl)-N-3-isoxazolyl-2-oxo-1,2-dihydro-6-quinolinesulfonamide This compound was prepared via method 145 using (5-chloro-2-methylphenyl)boronic acid (purchased from Synthonix, Inc.) as the boronic acid. $^1$H NMR (400 MHz, DMSO-d$_6$) δ ppm 3.69 (s, 3H) 6.46 (s, 1H) 6.81-6.91 (m, 2H) 7.26 (d, J=6.53 Hz, 1H) 7.40-7.47 (m, 3H) 7.51 (d, J=9.43 Hz, 1H) 7.87 (dd, J=8.97, 2.23 Hz, 1H) 8.25 (d, J=9.64 Hz, 1H) 8.39 (d, J=2.18 Hz, 1H) 8.74 (s, 1H) 11.68 (s, 1H). m/z (ESI) 540.0 (M+H)$^+$.

Example 744 (3143558)

(P)-1-(5'-chloro-2-fluoro-2',5-dimethoxy-4-biphenylyl)-N-3-isoxazolyl-2-oxo-1,2-dihydro-6-quinolinesulfonamide This compound was prepared via method 145 using 5-chloro-2-methoxyphenylboronic acid (purchased from Combi-Blocks, Inc.) as the boronic acid. $^1$H NMR (400 MHz, DMSO-d$_6$) δ ppm 3.69 (s, 3H) 3.84 (s, 3H) 6.46 (s, 1H) 6.84 (dd, J=9.28, 5.13 Hz, 2H) 7.22 (d, J=9.02 Hz, 1H) 7.29 (d, J=6.43 Hz, 1H) 7.39-7.47 (m, 2H) 7.52 (dd, J=8.86, 2.75 Hz, 1H) 7.88 (dd, J=9.02, 2.18 Hz, 1H) 8.24 (d, J=9.64 Hz, 1H) 8.39 (d, J=2.18 Hz, 1H) 8.74 (d, J=5.43 Hz, 1H) 11.67 (s, 1H). m/z (ESI) 556.0 (M+H)$^+$.

Example 745 (3143767)

(P)-1-(4-(3-chloro-2-methoxy-4-pyridinyl)-5-fluoro-2-methoxyphenyl)-N-3-isoxazolyl-2-oxo-1,2-dihydro-6-quinolinesulfonamide This compound was prepared via method 145 using 3-chloro-2-methoxypyridine-4-boronic acid as the boronic acid. ¹H NMR (400 MHz, DMSO-d₆) δ ppm 3.69 (s, 3H) 4.03 (s, 3H) 6.46 (d, J=2.02 Hz, 1H) 6.82-6.84 (m, 1H) 6.85 (s, 1H) 7.23 (d, J=5.08 Hz, 1H) 7.36 (d, J=6.43 Hz, 1H) 7.59 (d, J=9.54 Hz, 1H) 7.90 (d, J=8.53 Hz, 1H) 8.25 (d, J=9.54 Hz, 1H) 8.29 (d, J=5.08 Hz, 1H) 8.40 (d, J=2.18 Hz, 1H) 8.74 (d, J=1.96 Hz, 1H) 11.68 (br. s., 1H). m/z (ESI) 557.0 (M+H)⁺.

Example 746 (3143784)

(P)-1-(4'-chloro-2-fluoro-5-methoxy-4-biphenylyl)-2-oxo-N-3-pyridazinyl-1,2-dihydro-6-quinolinesulfonamide This compound was prepared via method 150 using 3-aminopyridazine as the amine. ¹H NMR (400 MHz, DMSO-d₆) δ ppm 3.74 (s, 3H) 6.76-6.82 (m, 2H) 7.40 (d, J=6.74 Hz, 1H) 7.50 (d, J=10.37 Hz, 1H) 7.58-7.67 (m, 3H) 7.75 (d, J=8.29 Hz, 3H) 7.86 (d, J=8.91 Hz, 1H) 8.20 (d, J=9.64 Hz, 1H) 8.35 (br. s., 2H) 13.93-14.65 (m, 1H). m/z (ESI) 537.0 (M+H)⁺.

Example 747 (3143785)

(P)-1-(3'-chloro-2-fluoro-2',5-dimethoxy-4-biphenylyl)-N-3-isoxazolyl-2-oxo-1,2-dihydro-6-quinolinesulfonamide This compound was prepared via method 145 using 3-chloro-2-methoxyphenylboronic acid (purchased from Combi-Blocks, Inc.) as the boronic acid. ¹H NMR (400 MHz, DMSO-d₆) δ ppm 3.66 (s, 3H) 3.69 (s, 3H) 6.46 (s, 1H) 6.84 (dd, J=9.33, 4.46 Hz, 2H) 7.28-7.38 (m, 2H) 7.45 (dd, J=7.62, 1.30 Hz, 1H) 7.52 (d, J=9.43 Hz, 1H) 7.63 (d, J=7.63 Hz, 1H) 7.90 (dd, J=8.97, 2.23 Hz, 1H) 8.25 (d, J=9.64 Hz, 1H) 8.39 (d, J=2.18 Hz, 1H) 8.74 (s, 1H) 11.68 (s, 1H). m/z (ESI) 556.0 (M+H)⁺.

Example 748 (3143934)

(P)-1-(4-(3-chloro-4-pyridinyl)-5-fluoro-2-methoxyphenyl)-N-3-isoxazolyl-2-oxo-1,2-dihydro-6-quinolinesulfonamide This compound was prepared via method 145 using 3-chloro-4-pyridineboronic acid (purchased from Frontier Scientific, Inc.) as the boronic acid. ¹H NMR (400 MHz, DMSO-d₆) δ ppm 3.70 (s, 3H) 6.46 (d, J=2.15 Hz, 1H) 6.83 (d, J=3.52 Hz, 1H) 6.86 (d, J=2.80 Hz, 1H) 7.41 (d, J=6.43 Hz, 1H) 7.62 (d, J=9.54 Hz, 1H) 7.67 (d, J=4.87 Hz, 1H) 7.90 (d, J=9.01 Hz, 1H) 8.26 (d, J=9.54 Hz, 1H) 8.40 (d, J=2.18 Hz, 1H) 8.71 (d, J=4.87 Hz, 1H) 8.74 (d, J=1.87 Hz, 1H) 8.85 (s, J=5.54 Hz, 1H) 11.68 (s, 1H). m/z (ESI) 527.0 (M+H)⁺.

Example 749 (3143935)

(P)-1-(2-fluoro-4',5-dimethoxy-3'-methyl-4-biphenylyl)-N-3-isoxazolyl-2-oxo-1,2-dihydro-6-quinolinesulfonamide This compound was prepared via method 145 using 4-methoxy-3-methylphenylboronic acid (purchased from Combi-Blocks, Inc.) as the boronic acid. ¹H NMR (400 MHz, DMSO-d₆) δ ppm 2.25 (s, 3H) 3.73 (s, 3H) 3.87 (s, 3H) 6.46 (d, J=4.40 Hz, 1H) 6.82 (d, J=9.64 Hz, 1H) 6.89 (d, J=8.91 Hz, 1H) 7.10 (d, J=8.40 Hz, 1H) 7.33 (d, J=7.05 Hz, 1H) 7.45 (d, J=10.47 Hz, 1H) 7.48-7.56 (m, 2H) 7.88 (dd, J=9.02, 2.18 Hz, 1H) 8.23 (d, J=9.54 Hz, 1H) 8.38 (d, J=2.18 Hz, 1H) 8.74 (d, J=4.52 Hz, 1H) 11.67 (br. s., 1H). m/z (ESI) 536.0 (M+H)⁺.

Example 750 (3143936)

(P)-1-(4'-chloro-2-fluoro-5-methoxy-4-biphenylyl)-N-(5-fluoro-2-pyrimidinyl)-2-oxo-1,2-dihydro-6-quinolinesulfonamide This compound was prepared via method 150 using 2-amino-5-fluoropyrimidine (purchased from Oakwood Products, Inc.) as the amine. ¹H NMR (400 MHz, DMSO-d₆) δ ppm 3.74 (s, 3H) 6.77 (dd, J=9.28, 4.09 Hz, 2H) 7.40 (d, J=6.95 Hz, 1H) 7.50 (d, J=10.37 Hz, 1H) 7.60-7.65 (m, 2H) 7.75 (dd, J=8.55, 1.40 Hz, 2H) 7.92 (dd, J=8.91, 2.07 Hz, 1H) 8.22 (d, J=9.54 Hz, 1H) 8.37 (d, J=2.07 Hz, 1H) 8.42 (s, 2H) 11.47-12.48 (m, 1H). m/z (ESI) 555.0 (M+H)⁺.

Example 751 (3143938)

(P)-1-(4'-chloro-2-fluoro-5-methoxy-4-biphenylyl)-N-(2-methyl-4-pyrimidinyl)-2-oxo-1,2-dihydro-6-quinolinesulfonamide This compound was prepared via method 150 using 2-methyl-4-pyrimidinamine (purchased from J & W Pharm-Lab, LLC) as the amine. ¹H NMR (400 MHz, DMSO-d₆) δ ppm 2.36 (s, 3H) 3.74 (s, 3H) 6.73-6.86 (m, 3H) 7.41 (d, J=7.05 Hz, 1H) 7.51 (d, J=10.37 Hz, 1H) 7.59-7.66 (m, 2H) 7.70-7.79 (m, 2H) 7.89 (dd, J=8.91, 2.18 Hz, 1H) 8.06 (d, J=6.63 Hz, 1H) 8.23 (d, J=9.43 Hz, 1H) 8.38 (d, J=2.18 Hz, 1H) 12.39-14.20 (m, 1H). m/z (ESI) 551.0 (M+H)⁺.

Example 752 (3143939)

(P)-1-(4'-chloro-2-fluoro-5-methoxy-4-biphenylyl)-N-(6-methyl-4-pyrimidinyl)-2-oxo-1,2-dihydro-6-quinolinesulfonamide This compound was prepared via method 150 using 6-methyl-4-pyrimidinamine (purchased from ChemBridge Corporation) as the amine. ¹H NMR (400 MHz, DMSO-d₆) δ ppm 2.34 (s, 3H) 3.74 (s, 3H) 6.81 (d, J=9.64 Hz, 1H) 6.83 (d, J=9.02 Hz, 1H) 6.94 (s, 1H) 7.41 (d, J=6.95 Hz, 1H) 7.52 (d, J=10.37 Hz, 1H) 7.59-7.66 (m, 2H) 7.69-7.80 (m, 2H) 7.93 (dd, J=8.91, 2.18 Hz, 1H) 8.25 (d, J=9.54 Hz, 1H) 8.45 (d, J=2.18 Hz, 1H) 8.54 (s, 1H). m/z (ESI) 551.2 (M+H)⁺.

Example 753 (3143940)

(P)-1-(4'-chloro-2-fluoro-5-methoxy-4-biphenylyl)-N-1,3-oxazol-2-yl-2-oxo-1,2-dihydro-6-quinolinesulfonamide This compound was prepared via method 150 using 2-aminooxazole (purchased from Astatech, Inc.) as the amine. ¹H NMR (400 MHz, DMSO-d₆) δ ppm 3.75 (s, 3H) 6.80 (t, J=7.69 Hz, 2H) 7.29 (d, J=1.55 Hz, 1H) 7.41 (d, J=6.47 Hz, 1H) 7.52 (d, J=10.37 Hz, 1H) 7.59-7.66 (m, 3H) 7.75 (d, J=7.26 Hz, 2H) 7.87 (d, J=8.98 Hz, 1H) 8.21 (d, J=7.51 Hz, 1H) 8.34 (d, J=2.07 Hz, 1H) 12.18 (br. s., 1H). m/z (ESI) 526.0 (M+H)⁺.

Example 754 (3143945)

(P)-1-(4'-cyano-2-fluoro-5-methoxy-4-biphenylyl)-N-3-isoxazolyl-2-oxo-1,2-dihydro-6-quinolinesulfonamide This compound was prepared via method 139 using 4-cyanophenylboronic acid (purchased from Combi-Blocks, Inc.) as the boronic acid. $^1$H NMR (400 MHz, DMSO-$d_6$) δ ppm 3.75 (s, 3H) 4.04 (s, 3H) 6.08 (d, J=1.76 Hz, 1H) 6.63 (d, J=8.81 Hz, 1H) 6.69 (d, J=9.54 Hz, 1H) 7.45-7.53 (m, 2H) 7.72 (dd, J=8.76, 2.02 Hz, 1H) 8.09-8.17 (m, 3H) 8.29 (dd, J=2.12, 1.09 Hz, 1H) 8.50 (t, J=1.92 Hz, 1H). m/z (ESI) 517.0 (M+H)$^+$.

Example 755 (3144021)

(P)-4-chloro-2'-fluoro-4'-(6-(3-isoxazolylsulfamoyl)-2-oxo-1(2H)-quinolinyl)-5'-methoxy-2-biphenylcarboxamide This compound was prepared via method 139 using (4-chloro-2-cyanophenyl)boronic acid (purchased from Combi-Blocks, Inc.) as the boronic acid. $^1$H NMR (400 MHz, DMSO-$d_6$) δ ppm 3.68 (s, 3H) 6.47 (d, J=1.76 Hz, 1H) 6.76 (d, J=9.02 Hz, 1H) 6.83 (d, J=9.64 Hz, 1H) 7.27 (d, J=6.74 Hz, 1H) 7.41 (d, J=9.64 Hz, 1H) 7.49 (s, 1H) 7.57 (d, J=8.09 Hz, 1H) 7.62-7.72 (m, 2H) 7.80-7.94 (m, 2H) 8.24 (d, J=9.64 Hz, 1H) 8.39 (d, J=2.28 Hz, 1H) 8.74 (d, J=1.76 Hz, 1H) 11.67 (s, 1H). m/z (ESI) 569.2 (M+H)$^+$.

Example 756 (3144300)

(P)-1-(2-fluoro-5-methoxy-4'-methyl-4-biphenylyl)-N-3-isoxazolyl-2-oxo-1,2-dihydro-6-quinolinesulfonamide This compound was prepared via method 145 using p-tolylboronic acid as the boronic acid. $^1$H NMR (400 MHz, DMSO-$d_6$) δ ppm 2.39 (s, 3H) 3.73 (s, 3H) 6.45 (s, 1H) 6.82 (d, J=9.64 Hz, 1H) 6.89 (d, J=9.02 Hz, 1H) 7.35 (dd, J=7.41, 3.06 Hz, 3H) 7.48 (d, J=10.47 Hz, 1H) 7.59 (d, J=6.74 Hz, 2H) 7.87 (d, J=9.02 Hz, 1H) 8.23 (d, J=9.54 Hz, 1H) 8.38 (d, J=2.18 Hz, 1H) 8.74 (d, J=5.56 Hz, 1H). m/z (ESI) 506.1 (M+H)$^+$.

Example 757 (3144301)

(P)-1-(4'-cyclopropyl-2-fluoro-5-methoxy-4-biphenylyl)-N-3-isoxazolyl-2-oxo-1,2-dihydro-6-quinolinesulfonamide This compound was prepared via method 145 using 4-cyclopropylphenylboronic acid (purchased from Combi-Blocks, Inc.) as the boronic acid. $^1$H NMR (400 MHz, DMSO-$d_6$) δ ppm 0.70-0.82 (m, 2H) 0.96-1.08 (m, 2H) 1.97-2.05 (m, 1H) 3.73 (s, 3H) 6.46 (d, J=1.76 Hz, 1H) 6.82 (d, J=9.64 Hz, 1H) 6.89 (d, J=9.02 Hz, 1H) 7.25 (d, J=8.29 Hz, 2H) 7.35 (d, J=6.95 Hz, 1H) 7.48 (d, J=10.47 Hz, 1H) 7.58 (d, J=6.74 Hz, 2H) 7.88 (dd, J=8.97, 2.12 Hz, 1H) 8.24 (d, J=9.74 Hz, 1H) 8.38 (d, J=2.07 Hz, 1H) 8.74 (d, J=1.66 Hz, 1H) 11.67 (s, 1H). m/z (ESI) 532.2 (M+H)$^+$.

Example 758 (3144302)

(P)-1-(5'-chloro-2'-cyano-2-fluoro-5-methoxy-4-biphenylyl)-N-3-isoxazolyl-2-oxo-1,2-dihydro-6-quinolinesulfonamide This compound was prepared via method 145 using 5-chloro-2-cyanophenylboronic acid (purchased from Combi-Blocks, Inc.) as the boronic acid. $^1$H NMR (400 MHz, DMSO-$d_6$) δ ppm 3.74 (s, 3H) 6.47 (d, J=2.04 Hz, 1H) 6.83 (dd, J=10.88, 9.33 Hz, 2H) 7.52 (d, J=6.53 Hz, 1H) 7.65 (d, J=9.85 Hz, 1H) 7.82 (dd, J=8.40, 2.18 Hz, 1H) 7.89 (dd, J=8.97, 2.23 Hz, 1H) 7.93 (d, J=2.07 Hz, 1H) 8.11 (d, J=8.05 Hz, 1H) 8.26 (d, J=9.54 Hz, 1H) 8.41 (d, J=2.18 Hz, 1H) 8.74 (s, 1H) 11.68 (s, 1H). m/z (ESI) 551.1 (M+H)$^+$.

Example 759 (3144303)

(P)-1-(4-(5-chloro-2-methoxy-4-pyridinyl)-5-fluoro-2-methoxyphenyl)-N-3-isoxazolyl-2-oxo-1,2-dihydro-6-quinolinesulfonamide This compound was prepared via method 145 using (5-chloro-2-methoxypyridin-4-yl)boronic acid (purchased from Aurum Pharmatech, LLC) as the boronic acid. $^1$H NMR (400 MHz, DMSO-$d_6$) δ ppm 3.70 (s, 3H) 3.94 (s, 3H) 6.46 (d, J=1.97 Hz, 1H) 6.83 (dd, J=9.28, 3.99 Hz, 2H) 7.12 (s, 1H) 7.38 (d, J=6.43 Hz, 1H) 7.59 (d, J=9.54 Hz, 1H) 7.89 (d, J=8.98 Hz, 1H) 8.25 (d, J=9.54 Hz, 1H) 8.40 (d, J=2.18 Hz, 1H) 8.43 (s, 1H) 8.74 (d, J=1.99 Hz, 1H) 11.68 (s, 1H). m/z (ESI) 557.1 (M+H)$^+$.

Example 760 (3144633)

(P)-1-(2-fluoro-5-methoxy-4'-(trifluoromethoxy)-4-biphenylyl)-N-3-isoxazolyl-2-oxo-1,2-dihydro-6-quinolinesulfonamide This compound was prepared via method 145 using 4-trifluoromethoxyphenylboronic acid (purchased from Combi-Blocks, Inc.) as the boronic acid. $^1$H NMR (400 MHz, DMSO-$d_6$) δ ppm 3.74 (s, 3H) 6.46 (s, 1H) 6.83 (d, J=9.64 Hz, 1H) 6.89 (d, J=8.91 Hz, 1H) 7.44 (d, J=7.05 Hz, 1H) 7.52-7.60 (m, 3H) 7.81-7.90 (m, 3H) 8.24 (d, J=9.54 Hz, 1H) 8.39 (d, J=2.18 Hz, 1H) 8.74 (s, 1H) 11.67 (s, 1H). m/z (ESI) 576.0 (M+H)$^+$.

Example 761 (3144634)

(P)-1-(5-fluoro-2-methoxy-4-(6-(trifluoromethyl)-3-pyridinyl)phenyl)-N-3-isoxazolyl-2-oxo-1,2-dihydro-6-quinolinesulfonamide This compound was prepared via method 145 using 2-(trifluoromethyl)pyridine-5-boronic acid (purchased from Combi-Blocks, Inc.) as the boronic acid. $^1$H NMR (400 MHz, DMSO-$d_6$) δ ppm 3.77 (s, 3H) 6.46 (d, J=4.84 Hz, 1H) 6.84 (d, J=9.74 Hz, 1H) 6.91 (d, J=9.02 Hz, 1H) 7.61 (d, J=6.84 Hz, 1H) 7.65 (d, J=10.26 Hz, 1H) 7.88 (dd, J=8.97, 2.23 Hz, 1H) 8.12 (d, J=8.19 Hz, 1H) 8.26 (d, J=9.64 Hz, 1H) 8.40 (d, J=2.18 Hz, 1H) 8.44 (d, J=8.09 Hz, 1H) 8.75 (d, J=4.98 Hz, 1H) 9.12 (s, 1H) 11.67 (s, 1H). m/z (ESI) 561.0 (M+H)$^+$.

Example 762 (3144635)

(P)-1-(5-fluoro-2-methoxy-4-(2-(trifluoromethyl)-4-pyridinyl)phenyl)-N-3-isoxazolyl-2-oxo-1,2-dihydro-6-quinolinesulfonamide This compound was prepared via method 145 using 2-(trifluoromethyl)pyridine-4-boronic acid (purchased from Combi-Blocks, Inc.) as the boronic acid. $^1$H NMR (400 MHz, DMSO-$d_6$) δ ppm 3.78 (s, 3H) 6.46 (d, J=4.94 Hz, 1H) 6.83 (d, J=9.64 Hz, 1H) 6.89 (d, J=8.91 Hz, 1H) 7.62 (d, J=8.92 Hz, 1H) 7.66 (d, J=9.55 Hz, 1H) 7.86 (dd, J=8.97, 2.23 Hz, 1H) 8.08 (d, J=4.98 Hz, 1H) 8.22 (s, 1H) 8.23-8.27 (m, 1H) 8.40 (d, J=2.28 Hz, 1H) 8.74 (d, J=7.03 Hz, 1H) 8.95 (d, J=5.18 Hz, 1H) 11.67 (s, 1H). m/z (ESI) 561.0 (M+H)$^+$.

Example 763 (3144636)

(P)-1-(4'-(difluoromethoxy)-2-fluoro-5-methoxy-4-biphenylyl)-N-3-isoxazolyl-2-oxo-1,2-dihydro-6-quinolinesulfonamide This compound was prepared via method 145 using 4-(difluoromethoxy)phenylboronic acid (purchased from Combi-Blocks, Inc.) as the boronic acid. $^1$H NMR (400 MHz, DMSO-$d_6$) δ ppm 3.74 (s, 3H) 6.46 (d, J=2.03 Hz, 1H) 6.83 (d, J=9.64 Hz, 1H) 6.90 (d, J=9.02 Hz, 1H) 7.32-7.43 (m, 4H) 7.50-7.55 (m, 1H) 7.77 (d, J=7.98 Hz, 2H) 7.88 (dd, J=9.05 Hz, 1H) 8.24 (d, J=9.54 Hz, 1H) 8.39 (d, J=2.28 Hz, 1H) 8.74 (d, J=1.99 Hz, 1H) 11.67 (s, 1H). m/z (ESI) 558.0 (M+H)$^+$.

Example 764 (3144638)

(P)-1-(4'-chloro-3-methoxy-4-biphenylyl)-N-(5-fluoro-2-pyrimidinyl)-2-oxo-1,2-dihydro-6-quinolinesulfonamide This compound was prepared via method 152 using 2-amino-5-fluoropyrimidine (purchased from Oakwood Products, Inc.) as the amine. $^1$H NMR (400 MHz, DMSO-$d_6$) δ ppm 3.78 (s, 3H) 6.80 (dd, J=9.28, 7.62 Hz, 2H) 7.36-7.42 (m, 1H) 7.43-7.49 (m, 1H) 7.53-7.63 (m, 3H) 7.86 (s, 1H) 7.87-7.89 (m, 1H) 7.97 (dd, J=9.02, 2.18 Hz, 1H) 8.48 (d, J=2.18 Hz, 1H) 8.62 (s, 2H) 11.97 (s, 1H). m/z (ESI) 537.0 (M+H)$^+$.

Example 765 (3144639)

(P)-1-(4'-chloro-3-methoxy-4-biphenylyl)-2-oxo-N-3-pyridazinyl-1,2-dihydro-6-quinolinesulfonamide This compound was prepared via method 152 using 3-aminopyridazine as the amine. $^1$H NMR (400 MHz, DMSO-$d_6$) δ ppm 3.78 (s, 3H) 6.74 (d, J=9.02 Hz, 1H) 6.79 (d, J=9.64 Hz, 1H) 7.36-7.41 (m, 1H) 7.43-7.48 (m, 1H) 7.54 (d, J=1.76 Hz, 1H) 7.57-7.62 (m, 2H) 7.69 (dd, J=9.48, 4.09 Hz, 1H) 7.82-7.90 (m, 3H) 7.93 (br. s., 1H) 8.20 (d, J=9.74 Hz, 1H) 8.29 (br. s., 1H) 8.35 (br. s., 1H) 14.49 (br. s., 1H). m/z (ESI) 519.0 (M+H)$^+$.

Example 766 (3144640)

(P)-1-(4'-chloro-3-methoxy-4-biphenylyl)-N-1,3-oxazol-2-yl-2-oxo-1,2-dihydro-6-quinolinesulfonamide This compound was prepared via method 152 using 2-aminooxazole (purchased from Astatech, Inc.) as the amine. $^1$H NMR (400 MHz, DMSO-$d_6$) δ ppm 3.79 (s, 3H) 6.73 (d, J=8.91 Hz, 1H) 6.78 (d, J=9.64 Hz, 1H) 7.25 (d, J=1.45 Hz, 1H) 7.37-7.42 (m, 1H) 7.42-7.49 (m, 1H) 7.54 (d, J=1.76 Hz, 1H) 7.56-7.65 (m, 3H) 7.81-7.92 (m, 3H) 8.19 (d, J=9.54 Hz, 1H) 8.33 (d, J=2.07 Hz, 1H) 12.04-12.29 (m, 1H). m/z (ESI) 508.0 (M+H)$^+$.

Example 767 (3144646)

(P)-1-(4'-chloro-3-methoxy-4-biphenylyl)-N-(6-methyl-4-pyrimidinyl)-2-oxo-1,2-dihydro-6-quinolinesulfonamide This compound was prepared via method 152 using 6-methyl-4-pyrimidinamine (purchased from ChemBridge Corporation) as the amine. $^1$H NMR (400 MHz, DMSO-$d_6$) δ ppm 2.32 (s, 3H) 3.78 (s, 3H) 6.72-6.83 (m, 2H) 6.92 (br. s., 1H) 7.37-7.42 (m, 1H) 7.42-7.48 (m, 1H) 7.52-7.63 (m, 3H) 7.83-7.93 (m, 3H) 8.23 (d, J=9.64 Hz, 1H) 8.43 (br. s., 1H) 8.49 (s, 1H) 12.06-13.37 (m, 1H). m/z (ESI) 533.0 (M+H)$^+$.

Example 768 (3144647)

(P)-1-(4'-chloro-3-methoxy-4-biphenylyl)-N-(2-methyl-4-pyrimidinyl)-2-oxo-1,2-dihydro-6-quinolinesulfonamide This compound was prepared via method 152 using 2-methyl-4-pyrimidinamine (purchased from J & W Pharm-Lab, LLC) as the amine. $^1$H NMR (400 MHz, DMSO-$d_6$) δ ppm 2.37 (s, 3H) 3.75-3.81 (m, 3H) 6.69-6.99 (m, 3H) 7.37-7.43 (m, 1H) 7.43-7.48 (m, 1H) 7.53-7.63 (m, 3H) 7.87 (dd, J=8.60, 2.49 Hz, 3H) 8.10 (br. s., 1H) 8.22 (d, J=9.54 Hz, 1H) 8.38 (br. s., 1H) 12.69-14.07 (m, 1H). m/z (ESI) 533.0 (M+H)$^+$.

Example 769 (3145452)

(P)-1-(2,4'-difluoro-5-methoxy-4-biphenylyl)-N-(5-fluoro-2-pyrimidinyl)-2-oxo-1,2-dihydro-6-quinolinesulfonamide This compound was prepared via method 154 using 2-amino-5-fluoropyrimidine (purchased from Oakwood Products, Inc.) as the amine. $^1$H NMR (500 MHz, DMSO-$d_6$) δ ppm 3.73 (s, 3H) 6.81 (d, J=9.67 Hz, 1H) 6.86 (d, J=8.95 Hz, 1H) 7.35-7.42 (m, 3H) 7.49 (d, J=8.37 Hz, 1H) 7.70-7.81 (m, 2H) 7.98 (dd, J=9.02, 2.08 Hz, 1H) 8.26 (d, J=9.67 Hz, 1H) 8.48 (d, J=1.95 Hz, 1H) 8.62 (s, 2H) 11.96 (br. s., 1H). m/z (ESI) 539.2 (M+H)$^+$.

Example 770 (3145453)

(P)-1-(2,4'-difluoro-5-methoxy-4-biphenylyl)-2-oxo-N-3-pyridazinyl-1,2-dihydro-6-quinolinesulfonamide This compound was prepared via method 154 using 3-aminopyridazine as the amine. $^1$H NMR (500 MHz, DMSO-$d_6$) δ ppm 3.73 (s, 3H) 6.79 (t, =8.92 Hz, 2H) 7.34-7.43 (m, 1H) 7.48 (d, J=10.32 Hz, 1H) 7.66-7.71 (m, 1H) 7.72-7.80 (m, 2H) 7.86 (d, J=8.56 Hz, 1H) 7.93 (d, J=7.46 Hz, 1H) 8.20 (d, J=9.73 Hz, 1H) 8.27 (br. s., 1H) 8.35 (br. s., 1H) 14.31-14.61 (m, 1H). m/z (ESI) 521.2 (M+H)$^+$.

Example 771 (3145454)

(P)-1-(2,4'-difluoro-5-methoxy-4-biphenylyl)-N-1,3-oxazol-2-yl-2-oxo-1,2-dihydro-6-quinolinesulfonamide This compound was prepared via method 154 using 2-aminooxazole (purchased from Astatech, Inc.) as the amine. $^1$H NMR (500 MHz, DMSO-$d_6$) δ ppm 3.74 (s, 3H) 6.80 (t, J=9.24 Hz, 2H) 7.26-7.29 (m, 1H) 7.36-7.43 (m, 3H) 7.49 (d, J=10.25 Hz, 1H) 7.60 (d, J=1.49 Hz, 1H) 7.76 (dd, J=7.33, 5.58 Hz, 2H) 7.87 (dd, J=8.82, 2.01 Hz, 1H) 8.20 (d, J=9.67 Hz, 1H) 8.33 (d, J=1.82 Hz, 1H) 12.06-12.35 (m, 1H). m/z (ESI) 510.0 (M+H)$^+$.

Example 772 (3145455)

(P)-1-(2,4'-difluoro-5-methoxy-4-biphenylyl)-N-(6-methyl-4-pyrimidinyl)-2-oxo-1,2-dihydro-6-quinolinesulfonamide This compound was prepared via method 154 using 6-methyl-4-pyrimidinamine (purchased from ChemBridge Corporation) as the amine. $^1$H NMR (500 MHz, DMSO-$d_6$) δ ppm 2.32 (s, 3H) 3.73 (s, 3H) 6.80 (d, J=11.54 Hz, 1H) 6.82 (d, J=11.80 Hz, 1H) 6.92 (d, J=8.06 Hz, 1H) 7.37-7.43 (m, 3H) 7.49 (d, J=10.38 Hz, 1H) 7.74-7.80 (m, 2H) 7.92 (d, J=8.04 Hz, 1H) 8.23 (d, J=9.73 Hz, 1H) 8.43 (s, J=8.78 Hz, 1H) 8.50 (s, J=8.24, 8.24 Hz, 1H). m/z (ESI) 535.2 (M+H)$^+$.

Example 773 (3145456)

(P)-1-(2,4'-difluoro-5-methoxy-4-biphenylyl)-N-(2-methyl-4-pyrimidinyl)-2-oxo-1,2-dihydro-6-quinolinesulfonamide This compound was prepared via method 154 using 2-methyl-4-pyrimidinamine (purchased from J & W PharmLab, LLC) as the amine. $^1$H NMR (500 MHz, DMSO-$d_6$) δ ppm 2.38 (s, 3H) 3.73 (s, 3H) 6.80 (dd, J=12.49, 9.31 Hz, 3H) 7.36-7.42 (m, 3H) 7.48 (d, J=10.32 Hz, 1H) 7.73-7.80 (m, 2H) 7.90 (d, J=8.49 Hz, 1H) 8.12 (d, J=7.86 Hz, 1H) 8.23 (d, J=8.38 Hz, 1H) 8.39 (s, J=8.49, 8.49 Hz, 1H). m/z (ESI) 535.2 (M+H)$^+$.

Example 774 (3145744)

(P)-1-(4-(5-chloro-2-methoxy-3-pyridinyl)-5-fluoro-2-methoxyphenyl)-N-(5-fluoro-2-pyrimidinyl)-2-oxo-1,2-dihydro-6-quinolinesulfonamide This compound was prepared via method 155 using 2-amino-5-fluoropyrimidine (purchased from Oakwood Products, Inc.) as the amine. $^1$H NMR (500 MHz, DMSO-$d_6$) δ ppm 3.74 (s, 3H) 4.03 (s, 3H) 6.81 (d, J=8.44 Hz, 1H) 6.84 (d, J=7.94 Hz, 1H) 7.39-7.57 (m, 2H) 7.95-8.04 (m, 1H) 8.23-8.36 (m, 2H) 8.49 (d, J=8.76 Hz, 2H) 8.62 (s, 2H) 11.96 (br. s., 1H). m/z (ESI) 586.2 (M+H)$^+$.

Example 775 (3145745)

(P)-1-(4-(5-chloro-2-methoxy-3-pyridinyl)-5-fluoro-2-methoxyphenyl)-2-oxo-N-3-pyridazinyl-1,2-dihydro-6-quinolinesulfonamide This compound was prepared via method 155 using 3-aminopyridazine as the amine. $^1$H NMR (500 MHz, DMSO-$d_6$) δ ppm 3.75 (s, 3H) 4.03 (s, 3H) 6.79 (d, J=9.73 Hz, 2H) 7.38-7.57 (m, 2H) 7.61-7.76 (m, 1H) 7.86 (d, J=8.55 Hz, 1H) 7.93 (d, J=8.63 Hz, 1H) 8.20 (d, J=8.36 Hz, 1H) 8.28 (br. s., 2H) 8.36 (br. s., 1H) 8.50 (s, 1H) 14.31-14.63 (m, 1H). m/z (ESI) 568.1 (M+H)$^+$.

Example 776 (3145746)

(P)-1-(4-(5-chloro-2-methoxy-3-pyridinyl)-5-fluoro-2-methoxyphenyl)-N-1,3-oxazol-2-yl-2-oxo-1,2-dihydro-6-quinolinesulfonamide This compound was prepared via method 155 using 2-aminooxazole (purchased from Astatech, Inc.) as the amine. $^1$H NMR (500 MHz, DMSO-$d_6$) δ ppm 3.75 (s, 3H) 4.04 (s, 3H) 6.79 (dd, J=9.24, 2.37 Hz, 2H) 7.28 (s, 1H) 7.39-7.57 (m, 2H) 7.61 (s, 1H) 7.87 (d, J=8.39 Hz, 1H) 8.20 (d, J=9.67 Hz, 1H) 8.28 (s, 1H) 8.31-8.38 (m, 1H) 8.50 (s, 1H) 11.95-12.40 (m, 1H). m/z (ESI) 557.0 (M+H)$^+$.

Example 777 (3145747)

(P)-1-(4-(5-chloro-2-methoxy-3-pyridinyl)-5-fluoro-2-methoxyphenyl)-N-(6-methyl-4-pyrimidinyl)-2-oxo-1,2-dihydro-6-quinolinesulfonamide This compound was prepared via method 155 using 6-methyl-4-pyrimidinamine (purchased from ChemBridge Corporation) as the amine. $^1$H NMR (500 MHz, DMSO-$d_6$) δ ppm 2.32 (s, 3H) 3.74 (s, 3H) 4.03 (s, 3H) 6.80 (t, J=8.34 Hz, 2H) 6.91 (br. s., 1H) 7.39-7.57 (m, 2H) 7.92 (d, J=7.40 Hz, 1H) 8.21-8.35 (m, 2H) 8.43 (s, J=21.99, 21.99 Hz, 1H) 8.50 (s, 2H) 11.11-11.59 (m, 1H). m/z (ESI) 582.2 (M+H)$^+$.

Example 778 (3145748)

(P)-1-(4-(5-chloro-2-methoxy-3-pyridinyl)-5-fluoro-2-methoxyphenyl)-N-(2-methyl-4-pyrimidinyl)-2-oxo-1,2-dihydro-6-quinolinesulfonamide This compound was prepared via method 155 using 2-methyl-4-pyrimidinamine (purchased from J & W PharmLab, LLC) as the amine. $^1$H NMR (500 MHz, DMSO-$d_6$) δ ppm 2.39 (s, 3H) 3.75 (s, 3H) 4.03 (s, 3H) 6.79 (t, J=8.39 Hz, 2H) 6.90 (br. s., 1H) 7.39-7.54 (m, 2H) 7.90 (d, J=8.02 Hz, 1H) 8.13 (d, J=6.80 Hz, 1H) 8.20-8.31 (m, 2H) 8.40 (s, 1H) 8.50 (s, 1H) 11.18-11.54 (m, 1H). m/z (ESI) 582.1 (M+H)$^+$.

Example 779 (3142926)

(P)-1-(3'-ethoxy-3-methoxy-4-biphenylyl)-N-3-isoxazolyl-2-oxo-1,2-dihydro-6-quinolinesulfonamide This compound was prepared via method 179 using (3-ethoxyphenyl)boronic acid as the boronic acid. $^1$H NMR (400 MHz, DMSO-$d_6$) δ=11.70 (br. s., 1H), 8.78 (d, J=1.8 Hz, 1H), 8.42 (d, J=2.2 Hz, 1H), 8.27 (d, J=9.6 Hz, 1H), 7.91 (dd, J=2.2, 9.0 Hz, 1H), 7.56 (d, J=1.3 Hz, 1H), 7.50-7.35 (m, 5H), 7.03 (dd, J=1.6, 8.0 Hz, 1H), 6.86 (d, J=9.6 Hz, 2H), 6.51 (d, J=0.8 Hz, 1H), 4.18 (q, J=6.9 Hz, 2H), 3.82 (s, 3H), 2.59-2.50 (m, 1H), 1.42 (t, J=7.0 Hz, 3H). m/z (ESI) 518.2 (M+H)$^+$.

Example 780 (3142927)

(P)—N-3-isoxazolyl-1-(3-methoxy-3'-(1-methyl-ethoxy)-4-biphenylyl)-2-oxo-1,2-dihydro-6-quinolinesulfonamide This compound was prepared via method 179 using 3-isopropoxyphenylboronic acid as the boronic acid. $^1$H NMR (400 MHz, DMSO-d$_6$) δ=11.69 (br. s., 1H), 8.77 (d, J=1.8 Hz, 1H), 8.42 (d, J=2.2 Hz, 1H), 8.26 (d, J=9.6 Hz, 1H), 7.90 (dd, J=2.2, 9.0 Hz, 1H), 7.54 (d, J=1.6 Hz, 1H), 7.49-7.32 (m, 5H), 7.03 (dd, J=1.8, 8.1 Hz, 1H), 6.85 (d, J=9.6 Hz, 2H), 6.50 (d, J=1.8 Hz, 1H), 4.80 (td, J=6.0, 12.0 Hz, 1H), 3.82 (s, 3H), 1.36 (s, 3H), 1.35 (s, 3H). m/z (ESI) 532.3 (M+H)$^+$.

Example 781 (3142928)

(P)—N-3-isoxazolyl-1-(3-methoxy-3'-(trifluoromethoxy)-4-biphenylyl)-2-oxo-1,2-dihydro-6-quinolinesulfonamide This compound was prepared via method 179 using 3-(trifluoromethoxy)phenylboronic acid as the boronic acid. $^1$H NMR (400 MHz, DMSO-d$_6$) δ=11.69 (br. s., 1H), 8.77 (d, J=1.8 Hz, 1H), 8.42 (d, J=2.2 Hz, 1H), 8.27 (d, J=9.6 Hz, 1H), 7.95-7.85 (m, 3H), 7.70 (t, J=8.0 Hz, 1H), 7.63 (d, J=0.8 Hz, 1H), 7.56-7.44 (m, 3H), 6.85 (dd, J=1.5, 9.3 Hz, 2H), 6.50 (d, J=1.8 Hz, 1H), 3.83 (s, 3H), 3.37 (br. s., 1H). m/z (ESI) 558.1 (M+H)$^+$.

Example 782 (3142929)

(P)-1-(2'-chloro-3,3'-dimethoxy-4-biphenylyl)-N-3-isoxazolyl-2-oxo-1,2-dihydro-6-quinolinesulfonamide This compound was prepared via method 179 using 2-chloro-3-methoxyphenylboronic acid (purchased from Combi-Blocks, Inc.) as the boronic acid. $^1$H NMR (400 MHz, DMSO-d$_6$) δ=11.71 (br. s., 1H), 8.78 (d, J=1.8 Hz, 1H), 8.43 (d, J=2.2 Hz, 1H), 8.28 (d, J=9.6 Hz, 1H), 7.94 (dd, J=2.2, 9.0 Hz, 1H), 7.51-7.45 (m, 1H), 7.43 (d, J=8.0 Hz, 1H), 7.35 (d, J=1.8 Hz, 1H), 7.27 (dd, J=1.3, 8.4 Hz, 1H), 7.24 (dd, J=1.8, 8.0 Hz, 1H), 7.17 (dd, J=1.3, 7.7 Hz, 1H), 6.87 (d, J=9.6 Hz, 1H), 6.82 (d, J=8.9 Hz, 1H), 6.50 (d, J=1.8 Hz, 1H), 3.97 (s, 3H), 3.75 (s, 3H). m/z (ESI) 538.1 (M+H)$^+$.

Example 783 (3142930)

(P)—N-3-isoxazolyl-1-(3-methoxy-3'-(1-methylethyl)-4-biphenylyl)-2-oxo-1,2-dihydro-6-quinolinesulfonamide This compound was prepared via method 179 using (3-isopropylphenyl)boronic acid as the boronic acid. $^1$H NMR (400 MHz, DMSO-d$_6$) δ=11.65 (s, 1H), 8.74 (d, J=1.8 Hz, 1H), 8.38 (d, J=2.2 Hz, 1H), 8.23 (d, J=9.5 Hz, 1H), 7.86 (dd, J=2.3, 9.0 Hz, 1H), 7.63 (t, J=1.6 Hz, 1H), 7.60 (td, J=1.2, 8.0 Hz, 1H), 7.49 (d, J=1.8 Hz, 1H), 7.44 (t, J=7.7 Hz, 1H), 7.42 (dd, J=1.8, 8.1 Hz, 1H), 7.37 (d, J=8.0 Hz, 1H), 7.31 (d, J=7.7 Hz, 1H), 6.82 (d, J=9.6 Hz, 2H), 6.46 (d, J=1.8 Hz, 1H), 3.78 (s, 3H), 1.30 (s, 3H), 1.28 (s, 3H). m/z (ESI) 516.2 (M+H)+.

Example 784 (3142932)

(P)-1-(3,3'-dimethoxy-5'-methyl-4-biphenylyl)-N-3-isoxazolyl-2-oxo-1,2-dihydro-6-quinolinesulfonamide This compound was prepared via method 179 using 3-methoxy-5-methylphenylboronic acid (purchased from Combi-Blocks, Inc.) as the boronic acid. $^1$H NMR (400 MHz, DMSO-d$_6$) δ=11.65 (br. s., 1H), 8.73 (d, J=1.9 Hz, 1H), 8.37 (d, J=2.2 Hz, 1H), 8.22 (d, J=9.4 Hz, 1H), 7.86 (dd, J=2.3, 9.0 Hz, 1H), 7.49 (d, J=1.8 Hz, 1H), 7.42 (dd, J=1.8, 8.1 Hz, 1H), 7.36 (d, J=8.2 Hz, 1H), 7.19 (s, 1H), 7.12 (t, J=1.7 Hz, 1H), 6.85-6.83 (m, 1H), 6.81 (dd, J=2.3, 9.3 Hz, 2H), 6.45 (d, J=1.9 Hz, 1H), 3.84 (s, 3H), 3.77 (s, 3H), 2.39 (s, 3H). m/z (ESI) 518.2 (M+H)+.

Example 785 (3142933)

(P)-1-(2'-fluoro-3,3'-dimethoxy-4-biphenylyl)-N-3-isoxazolyl-2-oxo-1,2-dihydro-6-quinolinesulfonamide This compound was prepared via method 179 using 2-fluoro-3-methoxyphenylboronic acid as the boronic acid. $^1$H NMR (400 MHz, DMSO-d$_6$) δ=11.66 (br. s., 1H), 8.73 (d, J=1.8 Hz, 1H), 8.38 (d, J=2.3 Hz, 1H), 8.23 (d, J=9.5 Hz, 1H), 7.88 (dd, J=2.3, 9.0 Hz, 1H), 7.44-7.39 (m, 2H), 7.31 (td, J=1.5, 8.1 Hz, 1H), 7.29-7.18 (m, 3H), 6.83 (d, J=2.7 Hz, 1H), 6.80 (d, J=2.0 Hz, 1H), 6.46 (d, J=1.8 Hz, 1H), 3.91 (s, 3H), 3.73 (s, 3H). m/z (ESI) 522.1 (M+H)+.

Example 786 (3142934)

(P)-1-(3'-(difluoromethoxy)-3-methoxy-4-biphenylyl)-N-3-isoxazolyl-2-oxo-1,2-dihydro-6-quinolinesulfonamide This compound was prepared via method 179 using 3-(difluoromethoxy)phenylboronic acid (purchased from Combi-Blocks, Inc.) as the boronic acid. $^1$H NMR (400 MHz, DMSO-d$_6$) δ=11.65 (s, 1H), 8.73 (d, J=1.8 Hz, 1H), 8.37 (d, J=2.3 Hz, 1H), 8.23 (d, J=9.5 Hz, 1H), 7.86 (dd, J=2.3, 9.0 Hz, 1H), 7.70 (ddd, J=0.9, 1.8, 7.8 Hz, 1H), 7.61 (t, J=2.0 Hz, 1H), 7.59 (d, J=7.8 Hz, 1H), 7.57 (d, J=5.2 Hz, 1H), 7.56 (d, J=1.9 Hz, 1H), 7.47 (dd, J=1.9, 8.0 Hz, 1H), 7.41 (d, J=13.7 Hz, 1H), 7.25 (dd, J=2.1, 8.0 Hz, 1H), 6.82 (d, J=3.2 Hz, 1H), 6.80 (d, J=2.7 Hz, 1H), 6.45 (d, J=1.8 Hz, 1H), 3.79 (s, 3H). m/z (ESI) 540.2 (M+H)+.

Example 787 (3142935)

(P)-1-(3,3'-dimethoxy-2'-methyl-4-biphenylyl)-N-3-isoxazolyl-2-oxo-1,2-dihydro-6-quinolinesulfonamide This compound was prepared via method 179 using 3-(difluoromethoxy)phenylboronic acid (purchased from Synquest Laboratories) as the boronic acid. $^1$H NMR (400 MHz, DMSO-d$_6$) δ=11.65 (s, 1H), 8.73 (d, J=1.9 Hz, 1H), 8.37 (d, J=2.2 Hz, 1H), 8.23 (d, J=9.5 Hz, 1H), 7.88 (dd, J=2.2, 9.0 Hz, 1H), 7.34 (d, J=8.0 Hz, 1H), 7.29 (t, J=7.8 Hz, 1H), 7.19 (d, J=1.8 Hz, 1H), 7.07 (dd, J=1.8, 7.9 Hz, 1H), 7.03 (d, J=7.9 Hz, 1H), 6.96 (dd, J=0.7, 7.7 Hz, 1H), 6.83 (d, J=3.1 Hz, 1H), 6.80 (d, J=2.4 Hz, 1H), 6.45 (d, J=1.8 Hz, 1H), 3.85 (s, 3H), 3.69 (s, 3H), 2.17 (s, 3H). m/z (ESI) 518.2 (M+H)+.

Example 788 (3142936)

(P)-1-(3'-cyclopropyl-3-methoxy-4-biphenylyl)-N-3-isoxazolyl-2-oxo-1,2-dihydro-6-quinolinesulfonamide This compound was prepared via method 179 using 2-(3-cyclopropylphenyl)-4,4,5,5-tetramethyl-[1,3,2]dioxaborolane (purchased from Green Chempharm, Inc.) as the boronic ester. $^1$H NMR (400 MHz, DMSO-d$_6$) δ=11.65 (s, 1H), 8.73 (d, J=1.8 Hz, 1H), 8.37 (d, J=2.3 Hz, 1H), 8.22 (d, J=9.5 Hz, 1H), 7.86 (dd, J=2.3, 9.0 Hz, 1H), 7.54 (ddd, J=1.0, 1.7, 7.7 Hz, 1H), 7.49 (d, J=1.8 Hz, 1H), 7.47 (t, J=1.7 Hz, 1H), 7.44-7.35 (m, 3H), 7.13 (td, J=1.2, 7.7 Hz, 1H), 6.82 (d, J=1.7 Hz, 1H), 6.80 (d, J=1.0 Hz, 1H), 6.45 (d, J=1.8 Hz, 1H), 3.77 (s, 3H), 2.08-1.99 (m, 1H), 1.04-0.95 (m, 2H), 0.86-0.74 (m, 2H). m/z (ESI) 514.2 (M+H)+.

Example 789 (3142937)

(P)-1-(4-(2,3-dihydro-1-benzofuran-7-yl)-2-methoxyphenyl)-N-3-isoxazolyl-2-oxo-1,2-dihydro-6-quinolinesulfonamide This compound was prepared via method 179 using 2,3-dihydro-1-benzofuran-7-ylboronic acid (purchased from ChemBridge Corporation) as the boronic ester. $^1$H NMR (400 MHz, DMSO-d$_6$) δ=11.65 (s, 1H), 8.73 (d, J=1.9 Hz, 1H), 8.37 (d, J=2.2 Hz, 1H), 8.22 (d, J=9.5 Hz, 1H), 7.87 (dd, J=2.2, 9.0 Hz, 1H), 7.54 (d, J=1.8 Hz, 1H), 7.51-7.43 (m, 2H), 7.34 (d, J=8.1 Hz, 1H), 7.29 (qd, J=1.0, 7.3 Hz, 1H), 6.99 (t, J=7.6 Hz, 1H), 6.82 (d, J=1.2 Hz, 1H), 6.80 (d, J=2.0 Hz, 1H), 6.45 (d, J=1.8 Hz, 1H), 4.62 (t, J=8.9 Hz, 2H), 3.72 (s, 3H), 3.28 (t, J=8.7 Hz, 2H). m/z (ESI) 516.2 (M+H)+.

Example 790 (3142938)

(P)-1-(3'-cyclopropyl-2-fluoro-5-methoxy-4-biphenylyl)-N-3-isoxazolyl-2-oxo-1,2-dihydro-6-quinolinesulfonamide This compound was prepared via method 180 using 2-(3-cyclopropylphenyl)-4,4,5,5-tetramethyl-[1,3,2]dioxaborolane (purchased from Green Chempharm, Inc.) as the boronic ester. $^1$H NMR (400 MHz, DMSO-d$_6$) δ=11.66 (s, 1H), 8.74 (d, J=1.8 Hz, 1H), 8.38 (d, J=2.1 Hz, 1H), 8.23 (d, J=9.7 Hz, 1H), 7.87 (dd, J=2.2, 9.0 Hz, 1H), 7.48 (d, J=10.4 Hz, 1H), 7.46-7.33 (m, 4H), 7.16 (td, J=1.6, 6.8 Hz, 1H), 6.88 (d, J=9.0 Hz, 1H), 6.82 (d, J=9.6 Hz, 1H), 6.45 (d, J=1.9 Hz, 1H), 3.73 (s, 3H), 2.03 (tt, J=5.0, 8.4 Hz, 1H), 1.04-0.97 (m, 2H), 0.81-0.74 (m, 2H). m/z (ESI) 532.1 (M+H)+.

Example 791 (3142939)

(P)-1-(3'-ethyl-2-fluoro-5-methoxy-4-biphenylyl)-N-3-isoxazolyl-2-oxo-1,2-dihydro-6-quinolinesulfonamide This compound was prepared via method 180 using 3-ethylbenzyl-boronic acid (purchased from Combi-Blocks Inc.) as the boronic acid. $^1$H NMR (400 MHz, DMSO-d$_6$) δ=11.67 (s, 1H), 8.74 (d, J=1.9 Hz, 1H), 8.38 (d, J=2.3 Hz, 1H), 8.23 (d, J=9.5 Hz, 1H), 7.87 (dd, J=2.3, 9.0 Hz, 1H), 7.55-7.41 (m, 4H), 7.36 (d, J=6.9 Hz, 1H), 7.32 (td, J=1.5, 7.3 Hz, 1H), 6.89 (d, J=8.9 Hz, 1H), 6.82 (d, J=9.6 Hz, 1H), 6.46 (d, J=1.8 Hz, 1H), 3.73 (s, 3H), 2.72 (d, J=7.6 Hz, 2H), 1.25 (t, J=7.6 Hz, 3H). m/z (ESI) 520.1 (M+H)+.

Example 792 (3142940)

(P)-1-(2-fluoro-2',5-dimethoxy-3'-methyl-4-biphenylyl)-N-3-isoxazolyl-2-oxo-1,2-dihydro-6-quinolinesulfonamide This compound was prepared via method 180 using 2-methoxy-3-methylphenyl boronic acid (purchased from Combi-Blocks Inc.) as the boronic acid. $^1$H NMR (400 MHz, DMSO-d$_6$) δ=11.67 (s, 1H), 8.73 (d, J=1.8 Hz, 1H), 8.39 (d, J=2.2 Hz, 1H), 8.24 (d, J=9.6 Hz, 1H), 7.90 (dd, J=2.2, 9.0 Hz, 1H), 7.46 (d, J=9.4 Hz, 1H), 7.33 (qd, J=0.8, 7.4 Hz, 1H), 7.30-7.23 (m, 2H), 7.18 (d, J=7.5 Hz, 1H), 6.84 (d, J=4.5 Hz, 1H), 6.82 (d, J=5.0 Hz, 1H), 6.46 (d, J=1.9 Hz, 1H), 3.67 (s, 3H), 3.51 (s, 3H), 2.33 (s, 3H). m/z (ESI) 536.2 (M+H)+.

Example 793 (3142941)

1-(2-fluoro-2',5-dimethoxy-4'-methyl-4-biphenylyl)-N-3-isoxazolyl-2-oxo-1,2-dihydro-6-quinolinesulfonamide This compound was prepared via method 180 using (2-methoxy-4-methylphenyl)boronic acid (purchased from AOBChem) as the boronic acid. $^1$H NMR (400 MHz, DMSO-d$_6$) δ=11.67 (s, 1H), 8.73 (d, J=1.8 Hz, 1H), 8.38 (d, J=2.3 Hz, 1H), 8.23 (d, J=9.5 Hz, 1H), 7.90 (dd, J=2.2, 9.0 Hz, 1H), 7.38 (d, J=9.5 Hz, 1H), 7.26 (d, J=7.6 Hz, 1H), 7.20 (d, J=6.5 Hz, 1H), 7.01 (s, 1H), 6.91 (qd, J=0.7, 7.7 Hz, 1H), 6.85 (d, J=8.9 Hz, 1H), 6.82 (d, J=9.6 Hz, 1H), 6.46 (d, J=1.8 Hz, 1H), 3.81 (s, 3H), 3.66 (s, 3H), 2.39 (s, 3H). m/z (ESI) 536.2 (M+H)+.

Example 794 (3143112)

(P)-1-(5-fluoro-2-methoxy-4-(6-(trifluoromethyl)-2-pyridinyl)phenyl)-N-3-isoxazolyl-2-oxo-1,2-dihydro-6-quinolinesulfonamide This compound was prepared via method 180 using 6-(trifluoromethyl)pyridine-2-boronic acid (purchased from Combi-Blocks Inc.) as the boronic acid. $^1$H NMR (400 MHz, DMSO-d$_6$) δ=11.67 (s, 1H), 8.74 (d, J=1.8 Hz, 1H), 8.39 (d, J=2.0 Hz, 1H), 8.34-8.17 (m, 3H), 8.01 (d, J=7.7 Hz, 1H), 7.85 (dd, J=2.2, 8.9 Hz, 1H), 7.69 (d, J=6.7 Hz, 1H), 7.62 (d, J=10.5 Hz, 1H), 6.93 (d, J=9.0 Hz, 1H), 6.83 (d, J=9.7 Hz, 1H), 6.45 (d, J=1.8 Hz, 1H), 3.74 (s, 3H). m/z (ESI) 561.2 (M+H)$^+$.

Example 795 (3143927)

(P)-1-(2-fluoro-5-methoxy-4'-(trifluoromethyl)-4-biphenylyl)-2-oxo-N-3-pyridazinyl-1,2-dihydro-6-quinolinesulfonamide This compound was prepared via method 183 using 3-aminopyridazine as the amine. $^1$H NMR (400 MHz, DMSO-d$_3$) δ ppm 8.36 (s, 1H) 8.31 (br. s, 1H) 8.21 (d, J=9.64 Hz, 1H) 7.83-8.02 (m, 5H) 7.68 (dd, J=9.80, 4.09 Hz, 1H) 7.55 (d, J=10.47 Hz, 1H) 7.46 (d, J=6.95 Hz, 1H) 6.76-6.87 (m, 2H) 3.74 (s, 3H). m/z (ESI) 571.2 (M+H)$^+$.

Example 796 (3143928)

(P)-1-(2-fluoro-5-methoxy-4'-(trifluoromethyl)-4-biphenylyl)-N-(5-fluoro-2-pyrimidinyl)-2-oxo-1,2-dihydro-6-quinolinesulfonamide This compound was prepared via method 183 using 2-amino-5-fluoropyrimidine as the amine. $^1$H NMR (400 MHz, ACETONITRILE-$d_3$) δ=9.22 (br. s., 1H), 8.44 (d, J=2.2 Hz, 1H), 8.40 (d, J=0.6 Hz, 2H), 8.05 (d, J=9.6 Hz, 1H), 8.00 (dd, J=2.2, 9.0 Hz, 1H), 7.91-7.83 (m, 4H), 7.34 (d, J=6.8 Hz, 1H), 7.24 (d, J=10.2 Hz, 1H), 6.86 (d, J=9.0 Hz, 1H), 6.77 (d, J=9.7 Hz, 1H), 3.73 (s, 3H). m/z (ESI) 589.2 (M+H)$^+$.

Example 797 (3143932)

(P)-1-(2-fluoro-5-methoxy-4'-(trifluoromethyl)-4-biphenylyl)-2-oxo-N-2-pyrimidinyl-1,2-dihydro-6-quinolinesulfonamide This compound was prepared via method 183 using 2-aminopyrimidine as the amine. $^1$H NMR (400 MHz, DMSO-$d_6$) δ ppm 11.85 (br. s., 1H) 8.44-8.59 (m, 3H) 8.28 (d, J=9.74 Hz, 1H) 7.89-8.05 (m, 5H) 7.57 (d, J=10.26 Hz, 1H) 7.47 (d, J=6.84 Hz, 1H) 7.01-7.12 (m, 1H) 6.87 (d, J=8.71 Hz, 1H) 6.81 (d, J=9.64 Hz, 1H) 3.74 (s, 3H). m/z (ESI) 571.2 (M+H)$^+$.

Example 798 (3143933)

(P)-1-(2-fluoro-5-methoxy-4'-(trifluoromethyl)-4-biphenylyl)-N-(6-methyl-4-pyrimidinyl)-2-oxo-1,2-dihydro-6-quinolinesulfonamide This compound was prepared via method 183 using 6-methylpyrimidin-4-amine as the amine. $^1$H NMR (400 MHz, ACETONITRILE-$d_3$) δ ppm 8.52 (d, J=1.04 Hz, 1H) 8.38 (d, J=2.18 Hz, 1H) 8.03 (d, J=9.54 Hz, 1H) 7.93 (dd, J=8.97, 2.23 Hz, 1H) 7.86 (m, J=3.80 Hz, 5H) 7.34 (d, J=6.84 Hz, 1H) 7.24 (d, J=10.16 Hz, 1H) 6.98 (s, 1H) 6.87 (d, J=9.02 Hz, 1H) 6.77 (d, J=9.64 Hz, 1H) 3.73 (s, 4H) 2.40 (s, 3H). m/z (ESI) 585.0 (M+H)$^+$.

Example 799 (3143937)

(P)-1-(2-fluoro-5-methoxy-4'-(trifluoromethyl)-4-biphenylyl)-N-(2-methyl-4-pyrimidinyl)-2-oxo-1,2-dihydro-6-quinolinesulfonamide This compound was prepared via method 183 using 2-methyl-4-pyrimidinamine as the amine. $^1$H NMR (400 MHz, ACETONITRILE-$d_3$) δ ppm 8.35 (d, J=2.07 Hz, 1H) 8.11 (d, J=6.43 Hz, 1H) 8.09-8.13 (m, 1H) 8.03 (d, J=9.64 Hz, 1H) 7.83-7.95 (m, 5H) 7.34 (d, J=6.84 Hz, 1H) 7.24 (d, J=10.16 Hz, 1H) 6.94 (d, J=6.53 Hz, 1H) 6.86 (d, J=8.91 Hz, 1H) 6.76 (d, J=9.64 Hz, 1H) 3.73 (s, 3H) 2.45 (s, 3H). m/z (ESI) 585.2 (M+H)+.

Example 800 (3143950)

(P)-1-(4-(5-chloro-2-pyridinyl)-5-fluoro-2-methoxyphenyl)-N-3-isoxazolyl-2-oxo-1,2-dihydro-6-quinolinesulfonamide This compound was prepared via method 182 using 5-chloro-2-(tributylstannyl)pyridine (purchased from Combi-Blocks Inc.) as the organostannane. $^1$H NMR (400 MHz, ACETONITRILE-$d_3$) δ ppm 8.80-8.95 (m, 1H) 8.75 (t, J=1.71 Hz, 1H) 8.37 (d, J=1.87 Hz, 1H) 8.25 (d, J=2.18 Hz, 1H) 8.00 (d, J=9.64 Hz, 1H) 7.90-7.95 (m, 2H) 7.76-7.84 (m, 2H) 7.24 (d, J=10.78 Hz, 1H) 6.88 (d, J=9.02 Hz, 2H) 6.77 (d, J=9.74 Hz, 1H) 6.45 (d, J=1.87 Hz, 1H) 3.74 (s, 3H). m/z (ESI) 526.8 (M+H)$^+$.

Example 801 (3143956)

(P)-1-(4-(4-chloro-2-pyridinyl)-5-fluoro-2-methoxyphenyl)-N-3-isoxazolyl-2-oxo-1,2-dihydro-6-quinolinesulfonamide This compound was prepared via method 182 using 4-chloro-2-(tributylstannyl)pyridine (purchased from Synthonix) as the organostannane. $^1$H NMR (400 MHz, DMSO-$d_6$) δ ppm 11.66 (br. s., 1H) 8.65-8.94 (m, 2H) 8.39 (br. s., 1H) 8.24 (d, J=9.74 Hz, 1H) 8.00 (br. s., 1H) 7.86 (d, J=7.98 Hz, 1H) 7.77 (d, J=6.63 Hz, 1H) 7.66 (d, J=3.94 Hz, 1H) 7.53-7.65 (m, 2H) 6.88 (d, J=8.81 Hz, 1H) 6.82 (d, J=9.43 Hz, 1H) 6.45 (s, 1H) 3.74 (s, 3H). m/z (ESI) 527.8 (M+H)$^+$.

Example 802 (3143972)

(P)-1-(2-fluoro-5-methoxy-3'-(trifluoromethyl)-4-biphenylyl)-N-(5-fluoro-2-pyrimidinyl)-2-oxo-1,2-dihydro-6-quinolinesulfonamide This compound was prepared via method 183 using 2-amino-5-fluoropyrimidine as the amine. $^1$H NMR (400 MHz, ACETONITRILE-$d_3$) δ ppm 9.15 (br. s., 1H) 8.44 (d, J=2.18 Hz, 1H) 8.39 (d, J=0.62 Hz, 2H) 8.05 (d, J=9.64 Hz, 1H) 7.98-8.02 (m, 2H) 7.96 (d, J=8.09 Hz, 1H) 7.77-7.81 (m, 1H) 7.71-7.76 (m, 1H) 7.35 (d, J=6.84 Hz, 1H) 7.23 (d, J=10.26 Hz, 1H) 6.86 (d, J=9.02 Hz, 1H) 6.77 (d, J=9.64 Hz, 1H) 3.73 (s, 3H). m/z (ESI) 588.9 (M+H)$^+$.

Example 803 (3143974)

(P)-1-(2-fluoro-5-methoxy-3'-(trifluoromethyl)-4-biphenylyl)-2-oxo-N-2-pyrimidinyl-1,2-dihydro-6-quinolinesulfonamide This compound was prepared via method 183 using 2-aminopyrimidine as the amine. $^1$H NMR (400 MHz, ACETONITRILE-$d_3$) δ ppm 8.44-8.49 (m, 2H) 8.05 (d, J=9.54 Hz, 1H) 8.02 (dd, J=9.02, 2.28 Hz, 1H) 7.96 (d, J=7.57 Hz, 1H) 7.77-7.83 (m, 1H) 7.70-7.77 (m, 1H) 7.36 (d, J=6.84 Hz, 1H) 7.24 (d, J=10.16 Hz, 1H) 7.01 (t, J=4.92 Hz, 1H) 6.86 (d, J=9.02 Hz, 1H) 6.77 (d, J=9.64 Hz, 1H) 3.74 (s, 3H). m/z (ESI) 571.9 (M+H)$^+$.

Example 804 (3143977)

(P)-1-(2-fluoro-5-methoxy-3'-(trifluoromethyl)-4-biphenylyl)-N-(2-methyl-4-pyrimidinyl)-2-oxo-1,2-dihydro-6-quinolinesulfonamide This compound was prepared via method 183 using 2-methyl-4-pyrimidinamine as the amine. $^1$H NMR (400 MHz, ACETONITRILE-$d_3$) δ ppm 8.40 (d, J=2.07 Hz, 1H) 8.22 (d, J=6.74 Hz, 1H) 8.04 (d, J=9.54 Hz, 1H) 8.00 (s, 1H) 7.95 (dd, J=8.97, 2.12 Hz, 2H) 7.77-7.82 (m, 1H) 7.70-7.76 (m, 1H) 7.35 (d, J=6.95 Hz, 1H) 7.23 (d, J=10.16 Hz, 1H)

7.02 (d, J=6.74 Hz, 1H) 6.87 (d, J=8.91 Hz, 1H) 6.78 (d, J=9.74 Hz, 1H) 3.73 (s, 3H) 2.51 (s, 3H). m/z (ESI) 585.1 (M+H)$^+$.

Example 805 (3144291)

(P)-1-(5-fluoro-2-methoxy-4-(6-methoxy-2-pyridinyl)phenyl)-N-3-isoxazolyl-2-oxo-1,2-dihydro-6-quinolinesulfonamide This compound was prepared via method 182 using 2-methoxy-6-(tributylstannyl)pyridine (purchased from Synthonix Inc.) as the organostannane. $^1$H NMR (400 MHz, DMSO-d$_6$) δ ppm 11.67 (s, 1H) 8.74 (d, J=1.76 Hz, 1H) 8.38 (d, J=2.28 Hz, 1H) 8.24 (d, J=9.54 Hz, 1H) 7.81-7.93 (m, 3H) 7.49-7.57 (m, 2H) 6.93 (d, J=0.52 Hz, 1H) 6.91 (d, J=0.62 Hz, 1H) 6.82 (d, J=9.64 Hz, 1H) 6.45 (d, J=1.87 Hz, 1H) 3.99 (s, 3H) 3.75 (s, 3H). m/z (ESI) 523.0 (M+H)$^+$.

Example 806 (3144363)

(P)-1-(2-fluoro-5-methoxy-3'-(trifluoromethyl)-4-biphenylyl)-N-1,3-oxazol-2-yl-2-oxo-1,2-dihydro-6-quinolinesulfonamide (3144363)

This compound was prepared via method 183 using 2-aminooxazole as the amine. $^1$H NMR (400 MHz, DMSO-d$_6$) δ ppm 12.18 (br. s., 1H) 8.34 (d, J=2.07 Hz, 1H) 8.21 (d, J=9.54 Hz, 1H) 8.03 (br. s., 2H) 7.75-7.90 (m, 3H) 7.61 (d, J=1.66 Hz, 1H) 7.55 (d, J=10.37 Hz, 1H) 7.48 (d, J=6.95 Hz, 1H) 7.28 (d, J=1.66 Hz, 1H) 6.81 (d, J=8.81 Hz, 1H) 6.79 (d, J=9.64 Hz, 1H) 3.76 (s, 3H) 3.73-3.79 (m, 3H). m/z (ESI) 559.8 (M+H)$^+$.

Example 807 (3144366)

(P)-1-(4-(5-chloro-6-methyl-2-pyridinyl)-5-fluoro-2-methoxyphenyl)-N-3-isoxazolyl-2-oxo-1,2-dihydro-6-quinolinesulfonamide This compound was prepared via method 184 using 6-bromo-3-chloro-2-methylpyridine as the aryl bromide in step 3 (purchased from Combi-Blocks Inc.). $^1$H NMR (400 MHz, DMSO-d$_6$) δ=11.67 (s, 1H), 8.73 (d, J=1.9 Hz, 1H), 8.38 (d, J=2.3 Hz, 1H), 8.24 (d, J=9.5 Hz, 1H), 8.05 (d, J=8.4 Hz, 1H), 7.86 (dd, J=2.2, 9.0 Hz, 1H), 7.76 (dd, J=1.6, 8.4 Hz, 1H), 7.72 (d, J=6.8 Hz, 1H), 7.56 (d, J=10.8 Hz, 1H), 6.90 (d, J=9.0 Hz, 1H), 6.82 (d, J=9.6 Hz, 1H), 6.45 (d, J=1.8 Hz, 1H), 3.73 (s, 3H), 2.67 (s, 3H). m/z (ESI) 541.0 (M+H)$^+$.

Example 808 (3144643)

(P)-1-(5-fluoro-2-methoxy-4-(4-methoxy-2-pyrimidinyl)phenyl)-N-3-isoxazolyl-2-oxo-1,2-dihydro-6-quinolinesulfonamide This compound was prepared via method 184 using 2-chloro-4-methoxypyrimidine as the aryl bromide in step 3. $^1$H NMR (500 MHz, DMSO-d6) δ=11.65 (br. s., 1H), 8.72 (d, J=5.8 Hz, 1H), 8.71 (d, J=1.4 Hz, 1H), 8.37 (d, J=1.9 Hz, 1H), 8.24 (d, J=9.7 Hz, 1H), 7.92-7.82 (m, 2H), 7.55 (d, J=10.4 Hz, 1H), 7.01 (d, J=5.8 Hz, 1H), 6.90 (d, J=9.0 Hz, 1H), 6.82 (d, J=9.7 Hz, 1H), 6.44 (d, J=1.6 Hz, 1H), 4.04 (s, 3H), 3.74 (s, 3H). m/z (ESI) 523.9 (M+H)$^+$.

Example 809 (3144951)

(P)-1-(4-(2,3-dihydro-1-benzofuran-6-yl)-2-methoxyphenyl)-N-3-isoxazolyl-2-oxo-1,2-dihydro-6-quinolinesulfonamide This compound was prepared via method 179 using 2-(2,3-dihydrobenzofuran-6-yl)-4,4,5,5-tetramethyl-1,3,2-dioxaborolane (purchased from Ark Pharm, Inc.) as the boronic ester. $^1$H NMR (500 MHz, DMSO-d$_6$) δ=2.54 (s, 3H), 3.10-3.20 (m, 1H), 3.24 (t, J=8.50 Hz, 1H), 3.76 (s, 2H), 4.60 (t, J=8.66 Hz, 1H), 6.45 (d, J=1.49 Hz, 1H), 6.81 (dd, J=9.28, 3.76 Hz, 1H), 7.09-7.29 (m, 2H), 7.30-7.42 (m, 2H), 7.44-7.52 (m, 1H), 7.52-7.69 (m, 1H), 7.86 (dd, J=9.02, 1.95 Hz, 1H), 8.21 (d, J=9.67 Hz, 1H), 8.36 (d, J=1.82 Hz, 1H), 8.69-8.76 (m, 1H), 11.63 (br. s., 1H). m/z (ESI) 516.1 (M+H)$^+$.

Example 810 (3144953)

(P)-1-(3'-ethyl-3-methoxy-4-biphenylyl)-N-3-isoxazolyl-2-oxo-1,2-dihydro-6-quinolinesulfonamide This compound was prepared via method 179 using 3-ethylbenzyl-boronic acid (purchased from Combi-Blocks Inc.) as the boronic ester. $^1$H NMR (500 MHz, DMSO-d$_6$) δ=1.26 (t, J=7.59 Hz, 3H), 2.72 (q, J=7.53 Hz, 2H), 3.77 (s, 3H), 6.45 (d, J=1.49 Hz, 1H), 6.80 (s, 1H), 6.82 (s, 1H), 7.28 (d, J=7.33 Hz, 1H), 7.34-7.47 (m, 3H), 7.47-7.66 (m, 2H), 7.86 (dd, J=8.99, 1.91 Hz, 1H), 8.22 (d, J=9.67 Hz, 1H), 8.37 (d, J=1.82 Hz, 1H), 8.73 (s, 1H), 11.63 (br. s., 1H). m/z (ESI) 502.3 (M+H)$^+$.

Example 811 (3144954)

(P)—N-3-isoxazolyl-2-oxo-1-(3,3',5'-trimethoxy-4-biphenylyl)-1,2-dihydro-6-quinolinesulfonamide This compound was prepared via method 179 using 3,5-dimethoxyphenylboronic acid (purchased from Combi-Blocks Inc.) as the boronic ester. $^1$H NMR (500 MHz, DMSO-d$_6$) δ=3.77 (s, 3H), 3.80 (s, 3H), 3.84 (s, 3H), 6.45 (d, J=1.56 Hz, 1H), 6.50 (s, J=7.09 Hz, 1H), 6.58 (s, J=6.62 Hz, 1H), 6.72-6.86 (m, 2H), 6.92 (d, J=2.01 Hz, 1H), 7.37 (d, J=8.04 Hz, 1H), 7.44 (d, J=8.08 Hz, 1H), 7.50 (s, 1H), 7.86 (dd, J=8.99, 1.98 Hz, 1H), 8.22 (d, J=9.67 Hz, 1H), 8.37 (d, J=1.75 Hz, 1H), 8.73 (d, J=1.43 Hz, 1H), 11.63 (br. s., 1H). m/z (ESI) 534.1 (M+H)$^+$.

Example 812 (3144959)

(P)—N-3-isoxazolyl-1-(3-methoxy-3',4'-dimethyl-4-biphenylyl)-2-oxo-1,2-dihydro-6-quinolinesulfonamide This compound was prepared via method 179 using 3,4-dimethylbenzeneboronic acid (purchased from Lancaster Synthesis Ltd.) as the boronic ester. $^1$H NMR (500 MHz, DMSO-d$_6$) δ=2.29 (s, 3H), 2.33 (s, 3H), 3.77 (s, 3H), 6.45 (d, J=7.47 Hz, 1H), 6.74-6.87 (m, 2H), 7.27 (d, J=7.78 Hz, 1H), 7.34 (d, J=7.80 Hz, 1H), 7.40 (d, J=7.99 Hz, 1H), 7.46-7.56 (m, 2H), 7.59 (s, 1H), 7.85 (dd, J=8.99, 1.98 Hz, 1H), 8.21 (d, J=9.67 Hz, 1H), 8.36 (d, J=1.82 Hz, 1H), 8.65-8.81 (m, 1H), 11.63 (br. s., 1H). m/z (ESI) 502.3 (M+H)$^+$.

Example 813 (3144960)

(P)-1-(4-(5-chloro-2-methoxy-3-pyridinyl)-2-methoxyphenyl)-N-3-isoxazolyl-2-oxo-1,2-dihydro-6-quinolinesulfonamide This compound was prepared via method 179 using (5-chloro-2-methoxypyridin-3-yl)boronic acid (purchased from Combi-Blocks Inc.) as the boronic ester. $^1$H NMR (500 MHz, DMSO-d$_6$) δ=11.63 (br. s., 1H) 8.73 (s, 1H) 8.63 (d, J=1.82 Hz, 1H) 8.42 (d, J=1.82 Hz, 1H) 8.37 (d, J=1.75 Hz, 1H) 8.22 (d, J=9.67 Hz, 1H) 7.85 (dd, J=8.99, 1.85 Hz, 1H) 7.60 (s, 1H) 7.50 (d, J=6.75 Hz, 1H) 7.40 (d, J=7.98 Hz, 1H) 6.81 (d, J=4.09 Hz, 1H) 6.79 (d, J=3.44 Hz, 1H) 6.45 (d, J=1.36 Hz, 1H) 4.02 (s, 3H) 3.78 (s, 3H). m/z (ESI) 538.9 (M+H)$^+$.

Example 814 (3144974)

(P)-1-(4-(5-chloro-6-methoxy-3-pyridinyl)-2-methoxyphenyl)-N-3-isoxazolyl-2-oxo-1,2-dihydro-6-quinolinesulfonamide This compound was prepared via method 179 using 3-chloro-2-methoxypyridine-5-boronic acid (purchased from Combi-Blocks Inc.) as the boronic ester. $^1$H NMR (500 MHz, DMSO-d$_6$) δ=11.64 (br. s., 1H) 8.73 (d, J=1.49 Hz, 1H) 8.37 (d, J=1.88 Hz, 1H) 8.29 (d, J=2.40 Hz, 1H) 8.22 (d, J=9.73 Hz, 1H) 8.06 (d, J=2.40 Hz, 1H) 7.87 (dd, J=8.99, 1.98 Hz, 1H) 7.50 (s, 1H) 7.41 (dd, J=7.91, 1.30 Hz, 1H) 7.38 (d, J=7.98 Hz, 1H) 6.81 (d, J=9.60 Hz, 1H) 6.78 (d, J=9.02 Hz, 1H) 6.45 (d, J=1.56 Hz, 1H) 3.95 (s, 3H) 3.73 (s, 3H). m/z (ESI) 538.9 (M+H)$^+$.

Example 815 (3144975)

(P)-1-(3'-chloro-2',3-dimethoxy-4-biphenylyl)-N-3-isoxazolyl-2-oxo-1,2-dihydro-6-quinolinesulfonamide This compound was prepared via method 179 using 3-chloro-2-methoxyphenylboronic acid (purchased from Combi-Blocks Inc.) as the boronic ester. $^1$H NMR (500 MHz, DMSO-d$_6$) δ=11.64 (br. s., 1H) 8.73 (d, J=1.49 Hz, 1H) 8.37 (d, J=1.82 Hz, 1H) 8.23 (d, J=9.67 Hz, 1H) 7.87 (dd, J=8.99, 1.91 Hz, 1H) 7.56 (d, J=6.81 Hz, 1H) 7.51 (d, J=7.59 Hz, 1H) 7.43 (s, 1H) 7.40 (d, J=7.98 Hz, 1H) 7.27-7.34 (m, 2H) 6.82 (d, J=9.60 Hz, 1H) 6.78 (d, J=8.95 Hz, 1H) 6.45 (d, J=1.43 Hz, 1H) 3.72 (s, 3H) 3.62 (s, 3H). m/z (ESI) 538.0 (M+H)$^+$.

Example 816 (3144976)

(P)-1-(4'-chloro-2',3-dimethoxy-4-biphenylyl)-N-3-isoxazolyl-2-oxo-1,2-dihydro-6-quinolinesulfonamide This compound was prepared via method 179 using (4-chloro-2-methoxyphenyl)boronic acid (purchased from Combi-Blocks Inc.) as the boronic ester. $^1$H NMR (500 MHz, DMSO-d$_6$) δ=11.64 (br. s., 1H) 8.72 (d, J=1.49 Hz, 1H) 8.37 (d, J=1.88 Hz, 1H) 8.22 (d, J=9.67 Hz, 1H) 7.87 (dd, J=9.02, 2.01 Hz, 1H) 7.48 (d, J=8.11 Hz, 1H) 7.36 (d, J=0.10 Hz, 1H) 7.31-7.35 (m, 1H) 7.23-7.29 (m, 2H) 7.15 (dd, J=8.11, 1.75 Hz, 1H) 6.80 (t, J=9.28 Hz, 2H) 6.45 (d, J=1.49 Hz, 1H) 3.88 (s, 3H) 3.70 (s, 3H). m/z (ESI) 538.0 (M+H)$^+$.

Example 817 (3145504)

(P)-((1-(2-fluoro-5-methoxy-3'-(trifluoromethyl)-4-biphenylyl)-2-oxo-1,2-dihydro-6-quinolinyl)sulfonyl)(1-pyridiniumyl)azanide This compound was prepared via method 183 using 1-aminopyridinium iodide as the amine. $^1$H NMR (500 MHz, DMSO-d$_6$) δ=8.51 (d, J=5.77 Hz, 2H) 8.22 (t, J=7.75 Hz, 1H) 8.12 (d, J=9.67 Hz, 1H) 8.01-8.06 (m, 2H) 7.76-7.88 (m, 3H) 7.62 (dd, J=8.82, 1.88 Hz, 1H) 7.50 (d, J=10.25 Hz, 1H) 7.48 (d, J=7.01 Hz, 1H) 6.75 (d, J=4.15 Hz, 1H) 6.73 (d, J=3.31 Hz, 1H) 3.76 (s, 3H). m/z (ESI) 570.2 (M+H)+.

Example 818 (3145512)

(P)-1-(3'-fluoro-3-methoxy-4-biphenylyl)-N-3-isoxazolyl-2-oxo-1,2-dihydro-6-quinolinesulfonamide This compound was prepared via method 179 using (3-fluorophenyl)boronic acid as the boronic ester. $^1$H NMR (500 MHz, DMSO-d$_6$) δ=11.63 (br. s., 1H) 8.73 (d, J=1.56 Hz, 1H) 8.37 (d, J=1.95 Hz, 1H) 8.22 (d, J=9.67 Hz, 1H) 7.86 (dd, J=8.99, 1.98 Hz, 1H) 7.64-7.74 (m, 2H) 7.53-7.62 (m, 3H) 7.48 (dd, J=8.04, 1.49 Hz, 1H) 7.40 (d, J=7.98 Hz, 1H) 7.27 (t, J=8.43 Hz, 1H) 6.82 (d, J=3.83 Hz, 1H) 6.80 (d, J=3.11 Hz, 1H) 6.45 (d, J=1.56 Hz, 1H) 3.78 (s, 3H). m/z (ESI) 492.2 (M+H)$^+$.

Example 819 (3145680)

1-(5-chloro-6-(cyclopropylmethoxy)-2-methoxy-3-pyridinyl)-N-3-isoxazolyl-2-oxo-1,2-dihydro-6-quinolinesulfonamide This compound was prepared via method 185. $^1$H NMR (500 MHz, DMSO-d$_6$) δ=11.63 (br. s., 1H) 8.73 (d, J=1.56 Hz, 1H) 8.37 (d, J=1.95 Hz, 1H) 8.22 (d, J=9.67 Hz, 1H) 7.86 (dd, J=8.99, 1.98 Hz, 1H) 7.64-7.74 (m, 2H) 7.53-7.62 (m, 3H) 7.48 (dd, J=8.04, 1.49 Hz, 1H) 7.40 (d, J=7.98 Hz, 1H) 7.27 (t, J=8.43 Hz, 1H) 6.82 (d, J=3.83 Hz, 1H) 6.80 (d, J=3.11 Hz, 1H) 6.45 (d, J=1.56 Hz, 1H) 3.78 (s, 3H). m/z (ESI) 503.3 (M+H)$^+$.

Example 820 (3145681)

(P)-1-(2-fluoro-5-methoxy-3'-(trifluoromethyl)-4-biphenylyl)-2-oxo-N-3-pyridazinyl-1,2-dihydro-6-quinolinesulfonamide This compound was prepared via method 183 using 3-aminopyridazine as the amine. $^1$H NMR (500 MHz, DMSO-d$_6$) δ=14.51 (br. s., 1H) 8.37 (d, J=1.97 Hz, 1H) 8.22 (d, J=9.54 Hz, 1H) 8.03 (br. s., 2H) 7.84-7.89 (m, 2H) 7.82 (d, J=7.57 Hz, 1H) 7.70 (dd, J=9.59, 4.20 Hz, 1H) 7.55 (d, J=10.37 Hz, 1H) 7.49 (d, J=7.05 Hz, 1H) 6.82 (d, J=8.81 Hz, 1H) 6.80 (d, J=9.54 Hz, 1H) 3.76 (s, 3H). m/z (ESI) 571.0 (M+H)$^+$.

Example 821 (3145682)

1-(5-chloro-6-(cyclobutyloxy)-2-methoxy-3-pyridinyl)-N-3-isoxazolyl-2-oxo-1,2-dihydro-6-quinolinesulfonamide This compound was prepared via method 185 using cyclobutanol as the alcohol. $^1$H NMR (500 MHz, DMSO-$d_6$) δ=11.65 (br. s., 1H) 8.72 (d, J=1.17 Hz, 1H) 8.36 (d, J=1.56 Hz, 1H) 8.21 (d, J=9.67 Hz, 1H) 8.04 (s, 1H) 7.85 (dd, J=8.95, 1.69 Hz, 1H) 6.98 (d, J=8.95 Hz, 1H) 6.79 (d, J=9.67 Hz, 1H) 6.44 (d, J=1.17 Hz, 1H) 5.25 (t, J=7.36 Hz, 1H) 3.77 (s, 3H) 2.09-2.28 (m, 2H) 1.85 (q, J=10.23 Hz, 1H) 1.63-1.78 (m, 1H). m/z (ESI) 503.0 (M+H)$^+$.

Example 822 (3145727)

1-(5-chloro-2-methoxy-6-((1-methylcyclopropyl)methoxy)-3-pyridinyl)-N-3-isoxazolyl-2-oxo-1,2-dihydro-6-quinolinesulfonamide This compound was prepared via method 185 using 1-methylcyclopropanemethanol as the alcohol. $^1$H NMR (500 MHz, DMSO-$d_6$) δ=11.64 (br. s., 1H) 8.72 (d, J=1.10 Hz, 1H) 8.36 (d, J=1.56 Hz, 1H) 8.21 (d, J=9.67 Hz, 1H) 8.04 (s, 1H) 7.84 (dd, J=8.99, 1.72 Hz, 1H) 7.00 (d, J=8.95 Hz, 1H) 6.79 (d, J=9.73 Hz, 1H) 6.45 (d, J=1.17 Hz, 1H) 4.27 (q, J=10.96 Hz, 2H) 3.77 (s, 3H) 1.23 (s, 3H) 0.61 (br. s., 2H) 0.45 (br. s., 2H). m/z (ESI) 517.0 (M+H)$^+$.

Example 823 (3145728)

(P)-1-(2-fluoro-5-methoxy-3'-(1-methylethoxy)-4-biphenylyl)-N-3-isoxazolyl-2-oxo-1,2-dihydro-6-quinolinesulfonamide This compound was prepared via method 180 using 3-isopropoxyphenylboronic acid as the boronic ester. $^1$H NMR (500 MHz, DMSO-$d_6$) δ=$^1$H NMR (500 MHz, DMSO-$d_6$) δ ppm 11.65 (br. s., 1H) 8.73 (d, J=1.56 Hz, 1H) 8.38 (d, J=1.82 Hz, 1H) 8.23 (d, J=9.67 Hz, 1H) 7.87 (dd, J=9.02, 1.95 Hz, 1H) 7.48 (d, J=10.25 Hz, 1H) 7.43 (t, J=7.95 Hz, 1H) 7.37 (d, J=6.88 Hz, 1H) 7.33 (t, J=7.91 Hz, 1H) 7.15-7.24 (m, 3H) 7.12 (s, 1H) 7.02 (d, J=8.17 Hz, 1H) 6.86-6.94 (m, 2H) 6.82 (d, J=9.60 Hz, 1H) 6.45 (d, J=1.49 Hz, 1H) 4.61-4.81 (m, 2H) 3.74 (s, 3H) 1.31 (d, J=6.03 Hz, 6H). m/z (ESI) 550.2 (M+H)$^+$.

Example 824 (3145730)

1-(5-chloro-6-(cyclopentylmethoxy)-2-methoxy-3-pyridinyl)-N-3-isoxazolyl-2-oxo-1,2-dihydro-6-quinolinesulfonamide This compound was prepared via method 185 using cyclopentanemethanol as the alcohol. $^1$H NMR (500 MHz, DMSO-$d_6$) δ=11.64 (br. s., 1H) 8.72 (s, 1H) 8.36 (s, 1H) 8.21 (d, J=9.67 Hz, 1H) 8.03 (s, 1H) 7.84 (d, J=8.95 Hz, 1H) 7.00 (d, J=8.89 Hz, 1H) 6.79 (d, J=9.67 Hz, 1H) 6.44 (s, 1H) 4.26-4.45 (m, 2H) 3.78 (s, 3H) 2.41 (quin, J=7.46 Hz, 1H) 1.81 (d, J=7.27 Hz, 2H) 1.52-1.72 (m, 4H) 1.40 (dd, J=12.39, 6.81 Hz, 2H). m/z (ESI) 531.2 (M+H)$^+$.

Example 825 (314573)

1-(5-chloro-6-(cyclopentyloxy)-2-methoxy-3-pyridinyl)-N-3-isoxazolyl-2-oxo-1,2-dihydro-6-quinolinesulfonamide This compound was prepared via method 185 using cyclopentanol as the alcohol. $^1$H NMR (500 MHz, DMSO-$d_6$) δ=11.64 (br. s., 1H) 8.72 (s, 1H) 8.35 (s, 1H) 8.21 (d, J=9.73 Hz, 1H) 8.01 (s, 1H) 7.84 (d, J=9.08 Hz, 1H) 6.99 (d, J=8.95 Hz, 1H) 6.79 (d, J=9.60 Hz, 1H) 6.44 (s, 1H) 5.48 (br. s., 1H) 3.79 (s, 3H) 2.05 (d, J=7.14 Hz, 2H) 1.72-1.94 (m, 4H) 1.65 (br. s., 2H). m/z (ESI) 517.2 (M+H)$^+$.

Example 826 (3146192)

(P)-1-(3-methoxy-3'-(1-methylethoxy)-4-biphenylyl)-N-1,3-oxazol-2-yl-2-oxo-1,2-dihydro-6-quinolinesulfonamide This compound was prepared via method 183 using 2-aminooxazole as the amine. $^1$H NMR (500 MHz, DMSO-$d_6$) δ=12.14 (br. s., 1H) 8.32 (d, J=1.95 Hz, 1H) 8.19 (d, J=9.60 Hz, 1H) 7.86 (dd, J=8.92, 1.98 Hz, 1H) 7.60 (d, J=1.49 Hz, 1H) 7.50 (d, J=1.36 Hz, 1H) 7.39-7.46 (m, 2H) 7.26-7.38 (m, 4H) 6.99 (dd, J=8.08, 1.46 Hz, 1H) 6.78 (d, J=9.67 Hz, 1H) 6.73 (d, J=8.89 Hz, 1H) 4.77 (dt, =12.00, 6.00 Hz, 1H) 3.78 (s, 3H) 1.32 (s, 3H) 1.31 (s, 3H). m/z (ESI) 532.2 (M+H)$^+$.

Example 827 (3146240)

(P)—N-(5-fluoro-2-pyrimidinyl)-1-(3-methoxy-3'-(1-methylethoxy)-4-biphenylyl)-2-oxo-1,2-dihydro-6-quinolinesulfonamide This compound was prepared via method 183 using 2-amino-5-fluoropyrimidine as the amine. $^1$H NMR (500 MHz, DMSO-$d_6$) δ=11.94 (s, 1H) 8.62 (s, 2H) 8.47 (d, J=1.95 Hz, 1H) 8.25 (d, J=9.73 Hz, 1H) 7.97 (dd, J=8.99, 2.04 Hz, 1H) 7.50 (d, J=1.30 Hz, 1H) 7.39-7.45 (m, 2H) 7.28-7.38 (m, 3H) 6.99 (dd, J=8.11, 1.88 Hz, 1H) 6.79 (t, J=8.99 Hz, 2 H) 4.76 (dt, =12.00, 6.00 Hz, 1H) 3.77 (s, 3H) 1.32 (s, 3H) 1.31 (s, 3H). m/z (ESI) 561.2 (M+H)$^+$.

Example 828 (3146241)

(P)-1-(3-methoxy-3'-(1-methylethoxy)-4-biphenylyl)-2-oxo-N-2-pyrimidinyl-1,2-dihydro-6-quinolinesulfonamide (3146241)

This compound was prepared via method 183 using 2-aminopyrimidine as the amine. $^1$H NMR (500 MHz, DMSO-$d_6$) δ=11.86 (br. s., 1H) 8.42-8.63 (m, 3H) 8.25 (d, J=9.67 Hz, 1H) 7.98 (dd, J=8.95, 2.01 Hz, 1H) 7.49 (d, J=1.30 Hz, 1H) 7.38-7.45 (m, 2H) 7.35 (d, J=8.04 Hz, 1H) 7.33 (d, J=7.91 Hz, 1H) 7.27-7.30 (m, 1H) 7.05 (t, J=4.74 Hz, 1H) 6.98 (dd, J=8.11, 1.82 Hz, 1H) 6.79 (d, J=9.54 Hz, 1H) 6.77 (d, J=8.69 Hz, 1H) 4.76 (dt, J=11.99, 5.98 Hz, 1H) 3.76 (s, 3H) 1.32 (s, 3H) 1.31 (s, 3H). m/z (ESI) 543.2 (M+H)$^+$.

Example 829 (3146246)

(P)-1-(4-bromo-5-fluoro-2-methoxyphenyl)-N-(4,5-dimethyl-3-isoxazolyl)-2-oxo-1,2-dihydro-6-quinolinesulfonamide This compound was prepared via method 186 using 4,5-dimethylisoxazol-3-amine as the amine. $^1$H NMR (500

MHz, DMSO-d$_6$) δ=10.79 (br. s., 1H) 8.32 (d, J=2.01 Hz, 1H) 8.23 (d, J=9.67 Hz, 1H) 7.85 (dd, 1=8.99, 2.04 Hz, 1H) 7.67 (d, J=6.23 Hz, 1H) 7.62 (d, J=8.56 Hz, 1H) 6.86 (d, J=8.95 Hz, 1H) 6.79 (d, J=9.67 Hz, 1H) 3.70 (s, 3H) 2.21 (s, 3H) 1.80 (s, 3H). m/z (ESI) 522.0 (M+H)$^+$.

Example 830 (3146247)

1-(5-chloro-6-cyclopropyl-2-methoxy-3-pyridinyl)-N-3-isoxazolyl-2-oxo-1,2-dihydro-6-quinolinesulfonamide This compound was prepared via method 187 using cyclopropyl boronic acid as the boronic acid. $^1$H NMR (400 MHz, CHLOROFORM-d) δ ppm 8.23 (d, J=1.76 Hz, 1H) 8.13 (d, J=1.97 Hz, 1H) 7.74-7.80 (m, 2H) 7.46 (s, 1H) 6.82 (d, J=9.64 Hz, 1H) 6.75 (d, J=9.02 Hz, 1H) 6.56 (d, J=1.66 Hz, 1H) 3.76 (s, 3H) 2.41-2.61 (m, 1H) 1.14-1.23 (m, 2H) 1.09 (dd, J=8.09, 3.21 Hz, 2H). m/z (ESI) 473.0 (M+H)$^+$.

Example 831 (3146248)

1-(5-chloro-2-methoxy-6-(3-methoxypropoxy)-3-pyridinyl)-N-3-isoxazolyl-2-oxo-1,2-dihydro-6-quinolinesulfonamide This compound was prepared via method 185 using 3-methoxy-1-propanol as the alcohol. $^1$H NMR (500 MHz, DMSO-d$_6$) δ=11.65 (br. s., 1H) 8.72 (d, J=1.69 Hz, 1H) 8.33-8.41 (m, 1H) 8.17-8.28 (m, 1H) 8.04 (s, 1H) 7.84 (dd, J=8.95, 2.08 Hz, 1H) 6.96-7.11 (m, 1H) 6.76-6.84 (m, 1H) 6.45 (d, J=1.69 Hz, 1H) 4.46-4.56 (m, 2H) 3.79 (s, 3H) 3.52 (t, J=6.23 Hz, 2H) 3.28 (s, 3H) 2.05 (quin, J=6.31 Hz, 2H). m/z (ESI) 521.0 (M+H)$^+$.

Example 832 (3146249)

1-(5-chloro-2-methoxy-6-(2,2,3,3,3-pentafluoropropoxy)-3-pyridinyl)-N-3-isoxazolyl-2-oxo-1,2-dihydro-6-quinolinesulfonamide This compound was prepared via method 185 using 1,1-dihydropentafluoropropanol as the alcohol. $^1$H NMR (500 MHz, DMSO-d$_6$) δ=11.65 (br. s., 1H) 8.73 (d, J=1.69 Hz, 1H) 8.37 (d, J=1.95 Hz, 1H) 8.23 (d, J=9.67 Hz, 1H) 8.19 (s, 1H) 7.85 (dd, J=8.95, 2.08 Hz, 1H) 7.00 (d, J=8.95 Hz, 1H) 6.80 (d, J=9.67 Hz, 1H) 6.45 (d, J=1.69 Hz, 1H) 5.16-5.40 (m, 2H) 3.84 (s, 3H). m/z (ESI) 580.9 (M+H)$^+$.

Example 833 (3146250)

1-(5-chloro-2-methoxy-6-(2,2,2-trifluoroethoxy)-3-pyridinyl)-N-3-isoxazolyl-2-oxo-1,2-dihydro-6-quinolinesulfonamide This compound was prepared via method 185 using 2,2,2-trifluoroethanol as the alcohol. $^1$H NMR (500 MHz, DMSO-d$_6$) δ=11.65 (br. s., 1H) 8.73 (d, J=1.69 Hz, 1H) 8.38 (d, J=2.01 Hz, 1H) 8.23 (d, J=9.73 Hz, 1H) 8.19 (s, 1H) 7.85 (dd, J=8.95, 2.08 Hz, 1H) 7.01 (s, 1H) 6.81 (d, J=9.67 Hz, 1H) 6.45 (d, J=1.69 Hz, 1H) 5.11-5.30 (m, 2H) 3.83 (s, 3H). m/z (ESI) 530.8 (M+H)$^+$.

Table 3 provides data for examples 589-1139, as representative compounds of the present invention, as follows: compound name (as named by ACD software, version 12; while the compound names in the written examples presented herein were named using ChemDraw Ultra version 12); molecular weight measured (MW); the method by which the compound was made; the NMR of the representative example; and biological data including in-vitro Nav 1.7 PX data (IC$_{50}$ in uM) and Nav 1.5 PX data (IC$_{50}$ in uM), where available.

TABLE 3

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 834 | 1-(3'-cyano-4'-fluoro-4-methoxy-3-biphenylyl)-N-3-isoxazolyl-2-oxo-1,2-dihydro-6-quinolinesulfonamide | 517.1 | 118 | 0.294 | | 1H NMR (400 MHz, DMSO-d6) δ ppm 3.74 (s, 3 H) 6.45 (d, J = 1.76 Hz, 1 H) 6.82 (d, J = 9.43 Hz, 2 H) 7.42 (d, J = 8.71 Hz, 1 H) 7.58 (t, J = 9.26 Hz, 1 H) 7.83-7.86 (m, 2 H) 7.99 (d, J = 8.69 Hz, 1 H) 8.11-8.15 (m, 1 H) 8.24 (d, J = 9.43 Hz, 1 H) 8.29-8.32 (m, 1 H) 8.38 (d, J = 2.28 Hz, 1 H) 8.73 (d, J = 1.87 Hz, 1 H) 11.66 (s, 1 H) |
| 835 | 1-(3',5'-difluoro-4-methoxy-3-biphenylyl)-N-3-isoxazolyl-2-oxo-1,2-dihydro-6-quinolinesulfonamide | 510.1 | 118 | 0.027 | | 1H NMR (400 MHz, DMSO-d6) δ ppm 3.74 (s, 3 H) 6.45 (d, J = 1.76 Hz, 1 H) 6.81 (dd, J = 9.33, 2.49 Hz, 2 H) 7.13-7.20 (m, 1 H) 7.40 (d, J = 8.91 Hz, 1 H) 7.50 (dd, J = 6.73 Hz, 2 H) 7.82-7.89 (m, 2 H) 8.02 (dd, J = 8.71, 2.49 Hz) 8.23 (d, J = 9.64 Hz, 1 H) 8.38 (d, J = 2.28 Hz, 1 H) 8.73 (d, J = 1.76 Hz, 1 H) 11.66 (s, 1 H) |
| 836 | 1-(2'-fluoro-4-methoxy-3-biphenylyl)-N-3-isoxazolyl-2-oxo-1,2-dihydro-6-quinolinesulfonamide | 492.1 | 118 | 0.12 | | 1H NMR (400 MHz, DMSO-d6) δ ppm 3.73 (s, 3 H) 6.45 (d, J = 1.76 Hz, 1 H) 6.81 (dd, J = 9.33, 5.91 Hz, 2 H) 7.25-7.32 (m, 2 H) 7.36-7.43 (m, 2 H) 7.52-7.58 (m, 2 H) 7.76-7.80 (m, 1 H) 7.86 (dd, J = 8.91, 2.28 Hz, 1 H) 8.22 (d, J = 9.43 Hz, 1 H) 8.37 (d, J = 2.28 Hz, 1 H) 8.73 (d, J = 1.76 Hz, 1 H) 11.65 (s, 1 H) |
| 837 | 1-(2',4'-difluoro-4-methoxy-3-biphenylyl)-N-3-isoxazolyl-2-oxo-1,2-dihydro-6-quinolinesulfonamide | 510.1 | 118 | 0.178 | | 1H NMR (400 MHz, DMSO-d6) δ ppm 3.73 (s, 3 H) 6.45 (d, J = 1.76 Hz, 1 H) 6.81 (dd, J = 9.43, 3.73 Hz, 2 H) 7.17 (td, J = 8.42, 2.95 Hz, 1 H) 7.31-7.38 (m, 1 H) 7.41 (d, J = 8.91 Hz, 1 H) 7.50-7.54 (m, 1 H) 7.61 (m, J = 8.97, 8.97, 6.53 Hz, 1 H) 7.75 (dt, J = 8.58, 2.09 Hz, 1 H) |

TABLE 3-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | | | | | | 7.85 (dd, J = 8.97, 2.23 Hz, 1 H) 8.22 (d, J = 9.54 Hz, 1 H) 8.37 (d, J = 2.07 Hz, 1 H) 8.73 (d, J = 1.76 Hz, 1 H) 11.65 (s, 1 H) |
| 838 | 1-(3'-fluoro-4,5'-dimethoxy-3-biphenylyl)-N-3-isoxazolyl-2-oxo-1,2-dihydro-6-quinolinesulfonamide | 522.0 | 118 | 0.069 | | 1H NMR (400 MHz, DMSO-d6) δ ppm 3.72 (s, 3 H) 3.81 (s, 3 H) 6.45 (d, J = 1.87 Hz, 1 H) 6.77 (dt, J = 10.83, 2.20 Hz, 1 H) 6.81 (dd, J = 9.28, 2.33 Hz, 2 H) 7.09 (t, J = 1.76 Hz, 1 H) 7.11-7.16 (m, 1 H) 7.38 (d, J = 8.81 Hz, 1 H) 7.80 (d, J = 2.38 Hz, 1 H) 7.85 (dd, J = 9.02, 2.28 Hz, 1 H) 7.96 (dd, J = 8.71, 2.49 Hz, 1 H) 8.23 (d, J = 9.43 Hz, 1 H) 8.37 (d, J = 2.18 Hz, 1 H) 8.73 (d, J = 1.76 Hz, 1 H) 11.65 (s, 1 H) |
| 839 | 1-(3',4'-difluoro-4-methoxy-3-biphenylyl)-N-3-isoxazolyl-2-oxo-1,2-dihydro-6-quinolinesulfonamide | 510.0 | 118 | 0.113 | | 1H NMR (400 MHz, DMSO-d6) δ ppm 3.72 (s, 3 H) 6.45 (d, J = 1.76 Hz, 1 H) 6.81 (d, J = 9.43 Hz, 2 H) 7.39 (d, J = 8.81 Hz, 1 H) 7.43-7.52 (m, 1 H) 7.54-7.60 (m, 1 H) 7.76-7.82 (m, 2 H) 7.85 (dd, J = 8.97, 2.23 Hz, 1 H) 7.94 (dd, J = 8.71, 2.49 Hz, 1 H) 8.23 (d, J = 9.54 Hz, 1 H) 8.38 (d, J = 2.18 Hz, 1 H) 8.73 (d, J = 1.76 Hz, 1 H) 11.65 (s, 1 H) |
| 840 | 1-(2',5'-difluoro-4-methoxy-3-biphenylyl)-N-3-isoxazolyl-2-oxo-1,2-dihydro-6-quinolinesulfonamide | 510.2 | 118 | 0.163 | | 1H NMR (400 MHz, DMSO-d6) δ ppm 3.73 (s, 3 H) 6.45 (d, J = 1.76 Hz, 1 H) 6.81 (dd, J = 9.33, 3.42 Hz, 2 H) 7.19-7.28 (m, 1 H) 7.32-7.48 (m, 3 H) 7.61 (dd, J = 2.28, 1.14 Hz, 1 H) 7.80-7.89 (m, 2 H) 8.22 (d, J = 9.54 Hz, 1 H) 8.37 (d, J = 2.18 Hz, 1 H) 8.73 (d, J = 1.76 Hz, 1 H) 11.65 (s, 1 H) |
| 841 | 1-(3'-chloro-4-methoxy-3-biphenylyl)-N-3-isoxazolyl-2-oxo-1,2-dihydro-6-quinolinesulfonamide | 508.1 | 118 | 0.027 | | 1H NMR (400 MHz, DMSO-d6) δ ppm 3.73 (s, 3 H) 6.45 (d, J = 1.76 Hz, 1 H) 6.82 (dd, J = 9.33, 1.45 Hz, 2 H) 7.36-7.47 (m, 3 H) 7.66-7.70 (m, 1 H) 7.77 (t, J = 1.81 Hz, 1 H) 7.80 (d, J = 2.38 Hz, 1 H) 7.83-7.87 (m, 1 H) 7.96 (dd, J = 8.76, 2.44 Hz, 1 H) 8.23 (d, J = 9.54 Hz, 1 H) 8.37 (d, J = 2.28 Hz, 1 H) 8.73 (d, J = 1.76 Hz, 1 H) 11.65 (s, 1 H) |
| 842 | 1-(2'-chloro-4-methoxy-3-biphenylyl)-N-3-isoxazolyl-2-oxo-1,2-dihydro-6-quinolinesulfonamide | 507.9 | 118 | 0.072 | | 1H NMR (400 MHz, DMSO-d6) δ ppm 3.73 (s, 3 H) 6.46 (d, J = 1.76 Hz, 1 H) 6.81 (dd, J = 12.75, 9.33 Hz, 2 H) 7.36-7.48 (m, 5 H) 7.56 (d, J = 7.27 Hz, 1 H) 7.65 (dd, J = 8.60, 2.28 Hz, 1 H) 7.88 (dd, J = 9.02, 2.28 Hz, 1 H) 8.21 (d, J = 9.43 Hz, 1 H) 8.37 (d, J = 2.18 Hz, 1 H) 8.73 (d, J = 1.76 Hz, 1 H) 11.64 (s, 1 H) |
| 843 | N-3-isoxazolyl-1-(4-methoxy-4'-(trifluoromethyl)-3-biphenylyl)-2-oxo-1,2-dihydro-6-quinolinesulfonamide | 542.2 | 118 | 0.023 | | 1H NMR (400 MHz, DMSO-d6) δ ppm 3.74 (s, 3 H) 6.45 (d, J = 1.76 Hz, 1 H) 6.83 (dd, J = 9.33, 5.18 Hz, 2 H) 7.44 (d, J = 8.81 Hz, 1 H) 7.77 (d, J = 8.40 Hz, 2 H) 7.81-7.87 (m, 2 H) 7.92 (d, J = 8.19 Hz, 2 H) 8.00 (dd, J = 8.76, 2.44 Hz, 1 H) 8.24 (d, J = 9.54 Hz, 1 H) 8.38 (d, J = 2.28 Hz, 1 H) 8.73 (d, J = 1.87 Hz, 1 H) 11.65 (s, 1 H) |
| 844 | 1-(4'-fluoro-4-methoxy-3-biphenylyl)-N-3-isoxazolyl-2-oxo-1,2-dihydro-6-quinolinesulfonamide | 492.2 | 118 | 0.215 | | 1H NMR (400 MHz, DMSO-d6) δ ppm 3.72 (s, 3 H) 6.45 (d, J = 1.76 Hz, 1 H) 6.82 (dd, J = 9.33, 3.52 Hz, 2 H) 7.25 (t, J = 8.22 Hz, 2 H) 7.39 (d, J = 8.81 Hz, 1 H) 7.67-7.76 (m, 3 H) 7.86 (ddd, J = 12.88, 8.84, 2.33 Hz, 2 H) 8.23 (d, J = 9.43 Hz, 1 H) 8.37 (d, J = 2.18 Hz, 1 H) 8.73 (d, J = 1.76 Hz, 1 H) 11.65 (s, 1 H) |
| 845 | 1-(4'-chloro-4-methoxy-3-biphenylyl)-N-3-isoxazolyl-2-oxo-1,2-dihydro-6-quinolinesulfonamide | 507.9 | 118 | 0.057 | | 1H NMR (400 MHz, DMSO-d6) δ ppm 3.72 (s, 3 H) 6.45 (d, J = 1.87 Hz, 1 H) 6.82 (dd, J = 9.33, 3.11 Hz, 2 H) 7.40 (d, J = 8.81 Hz, 1 H) 7.48 (d, J = 7.39 Hz, 2 H) 7.65-7.78 (m, 3 H) 7.84 (dd, J = 8.97, 2.23 Hz, 1 H) 7.91 (dd, J = 8.71, 2.38 Hz, 1 H) 8.23 (d, J = 9.54 Hz, 1 H) 8.37 (d, J = 2.18 Hz, 1 H) 8.73 (d, J = 1.76 Hz, 1 H) 11.65 (s, 1 H) |
| 846 | 1-(4'-chloro-4-methoxy-3'-methyl-3-biphenylyl)-N-3-isoxazolyl-2-oxo-1,2-dihydro-6-quinolinesulfonamide | 522.0 | 118 | 0.025 | | 1H NMR (400 MHz, DMSO-d6) δ ppm 2.36 (s, 3 H) 3.72 (s, 3 H) 6.45 (d, J = 1.76 Hz, 1 H) 6.81 (d, J = 9.68 Hz, 2 H) 7.39 (d, J = 8.76 Hz, 1 H) 7.44 (d, J = 8.52 Hz, 1 H) 7.55 (dd, J = 8.45, 2.23 Hz, 1 H) 7.72 (d, J = 5.10 Hz, 2 H) 7.85 (d, J = 9.06 Hz, 1 H) 7.92 (d, J = 8.83 Hz, 1 H) 8.23 (d, J = 9.64 Hz, 1 H) 8.38 (d, J = 2.18 Hz, 1 H) 8.73 (d, J = 1.76 Hz, 1 H) 11.68 (s, 1 H) |
| 847 | 1-(3',4-dimethoxy-3-biphenylyl)-N-3-isoxazolyl-2-oxo-1,2- | 504.0 | | 0.403 | | 1H NMR (400 MHz, DMSO-d6) δ ppm 3.72 (s, 3 H) 3.79 (s, 3 H) 6.45 (d, J = 1.76 Hz, 1 H) 6.82 (d, J = 9.33 Hz, 2 H) 6.89 (dd, J = 7.98, 1.97 Hz, 1 |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | dihydro-6-quinolinesulfonamide | | | | | H) 7.19-7.29 (m, 2 H) 7.29-7.41 (m, 2 H) 7.73 (d, J = 3.79 Hz, 1 H) 7.83-7.93 (m, 2 H) 8.23 (d, J = 9.66 Hz, 1 H) 8.38 (d, J = 1.87 Hz, 1 H) 8.73 (d, J = 1.66 Hz, 1 H) 11.67 (s, 1 H) |
| 848 | 1-(2',3'-difluoro-4-methoxy-3-biphenylyl)-N-3-isoxazolyl-2-oxo-1,2-dihydro-6-quinolinesulfonamide | 510.1 | 118 | 0.118 | | 1H NMR (400 MHz, DMSO-d6) δ ppm 3.74 (s, 3 H) 6.45 (d, J = 1.87 Hz, 1 H) 6.82 (dd, J = 9.28, 3.27 Hz, 2 H) 7.21-7.31 (m, 1 H) 7.35-7.48 (m, 3 H) 7.55-7.64 (m, 1 H) 7.81 (dt, J = 8.71, 1.87 Hz, 1 H) 7.86 (dd, J = 8.97, 2.23 Hz, 1 H) 8.23 (d, J = 9.54 Hz, 1 H) 8.38 (d, J = 2.18 Hz, 1 H) 8.73 (d, J = 1.76 Hz, 1 H) 11.68 (s, 1 H) |
| 849 | 1-(3'-chloro-5'-fluoro-4-methoxy-3-biphenylyl)-N-3-isoxazolyl-2-oxo-1,2-dihydro-6-quinolinesulfonamide | 526.1 | 118 | 0.017 | | 1H NMR (400 MHz, DMSO-d6) δ ppm 3.74 (s, 3 H) 6.45 (d, J = 1.87 Hz, 1 H) 6.81 (dd, J = 9.33, 3.11 Hz, 2 H) 7.35-7.42 (m, 2 H) 7.62 (dt, J = 10.42, 2.00 Hz, 1 H) 7.69 (t, J = 1.66 Hz, 1 H) 7.85 (dd, J = 8.97, 2.23 Hz, 1 H) 7.88 (d, J = 2.38 Hz, 1 H) 8.03 (dd, J = 8.81, 2.49 Hz, 1 H) 8.24 (d, J = 9.54 Hz, 1 H) 8.38 (d, J = 2.28 Hz, 1 H) 8.73 (d, J = 1.76 Hz, 1 H) 11.68 (s, 1 H) |
| 850 | N-3-isoxazolyl-1-(4-methoxy-2'-(trifluoromethyl)-3-biphenylyl)-2-oxo-1,2-dihydro-6-quinolinesulfonamide | 542.2 | 118 | 0.141 | | 1H NMR (400 MHz, DMSO-d6) δ ppm 3.73 (s, 3 H) 6.47 (d, J = 1.76 Hz, 1 H) 6.75 (d, J = 8.91 Hz, 1 H) 6.79 (d, J = 9.54 Hz, 1 H) 7.28 (d, J = 2.18 Hz, 1 H) 7.38 (d, J = 8.60 Hz, 1 H) 7.43-7.55 (m, 2 H) 7.60 (t, J = 7.54 Hz, 1 H) 7.72 (t, J = 7.69 Hz, 1 H) 7.82 (d, J = 7.57 Hz, 1 H) 7.86 (dd, J = 8.97, 2.23 Hz, 1 H) 8.21 (d, J = 9.54 Hz, 1 H) 8.37 (d, J = 2.18 Hz, 1 H) 8.74 (d, J = 1.87 Hz, 1 H) 11.65 (s, 1 H) |
| 851 | 1-(5-bromo-2-methoxyphenyl)-N-3-isoxazolyl-2-oxo-1,2-dihydro-6-quinolinesulfonamide | 476.0 | step 4, 115 | 0.371 | | 1H NMR (400 MHz, DMSO-d6) δ ppm 3.69 (s, 3 H) 6.44 (d, J = 1.76 Hz, 1 H) 6.73-6.82 (m, 2 H) 7.28 (d, J = 9.02 Hz, 1 H) 7.63 (d, J = 2.49 Hz, 1 H) 7.74 (dd, J = 8.91, 2.49 Hz, 1 H) 7.85 (dd, J = 8.91, 2.28 Hz, 1 H) 8.21 (d, J = 9.54 Hz, 1 H) 8.36 (d, J = 2.18 Hz, 1 H) 8.73 (d, J = 1.76 Hz, 1 H) 11.66 (s, 1 H) |
| 852 | 1-(3'-chloro-4-methoxy-3-biphenylyl)-N-3-isoxazolyl-2-oxo-1,2-dihydro-6-quinolinesulfonamide | 508.1 | 118 | 0.022 | | 1H NMR (400 MHz, DMSO-d6) δ ppm 3.73 (s, 3 H) 6.43 (d, J = 1.76 Hz, 1 H) 6.81 (d, J = 9.54 Hz, 2 H) 7.33-7.49 (m, 3 H) 7.63-7.73 (m, 1 H) 7.74-7.81 (m, 2 H) 7.82-7.87 (m, 1 H) 7.95 (dd, J = 8.71, 2.49 Hz, 1 H) 8.22 (d, J = 9.54 Hz, 1 H) 8.37 (d, J = 2.18 Hz, 1 H) 8.71 (d, J = 1.76 Hz, 1 H) 11.65 (br. s., 1 H) |
| 853 | 1-(3'-fluoro-4,5'-dimethoxy-3-biphenylyl)-N-3-isoxazolyl-2-oxo-1,2-dihydro-6-quinolinesulfonamide | 522.0 | 118 | 0.06 | | 1H NMR (400 MHz, DMSO-d6) δ ppm 3.69-3.76 (m, 3 H) 3.81 (s, 3 H) 6.41 (d, J = 1.66 Hz, 1 H) 6.76-6.84 (m, 3 H) 7.09 (t, J = 1.87 Hz, 1 H) 7.14 (dt, J = 10.29, 1.85 Hz, 1 H) 7.37 (d, J = 8.81 Hz, 1 H) 7.79 (d, J = 2.49 Hz, 1 H) 7.83 (dd, J = 8.97, 2.23 Hz, 1 H) 7.96 (dd, J = 8.71, 2.38 Hz, 1 H) 8.19-8.24 (m, 1 H) 8.34 (d, J = 2.18 Hz, 1 H) 8.66 (s, 1 H) 11.65 (br. s., 1 H) |
| 854 | N-3-isoxazolyl-1-(4-methoxy-4'-(trifluoromethyl)-3-biphenylyl)-2-oxo-1,2-dihydro-6-quinolinesulfonamide | 542.2 | 118 | | | |
| 855 | 1-(4'-chloro-4-methoxy-3-biphenylyl)-N-3-isoxazolyl-2-oxo-1,2-dihydro-6-quinolinesulfonamide | 508.3 | 118 | | | |
| 606 | 1-(3'-fluoro-4-methoxy-3-biphenylyl)-2-oxo-N-2-pyrimidinyl-1,2-dihydro-6-quinolinesulfonamide | 503.2 | 156 | 0.159 | | 1H NMR (400 MHz, DMSO-d6) δ ppm 3.72 (s, 3 H) 6.79 (t, J = 8.00 Hz, 2 H) 7.05 (br. s., 1 H) 7.14 (t, J = 8.71 Hz, 1 H) 7.40 (d, J = 8.71 Hz, 1 H) 7.42-7.49 (m, 1 H) 7.56 (d, J = 8.21 Hz, 2 H) 7.77 (d, J = 2.38 Hz, 1 H) 7.94-7.98 (m, 2 H) 8.26 (d, J = 9.64 Hz, 1 H) 8.45-8.54 (m, 3 H) 11.84 (br. s., 1 H) |
| 856 | N-3-isoxazolyl-1-(4-methoxy-4'-(trifluoromethyl)-3-biphenylyl)-2-oxo-1,2-dihydro-6- | 542.2 | 118 | 0.035 | | 1H NMR (400 MHz, DMSO-d6) δ ppm 3.74 (s, 3 H) 6.44 (d, J = 1.87 Hz, 1 H) 6.82 (dd, J = 9.28, 4.41 Hz, 2 H) 7.44 (d, J = 8.81 Hz, 1 H) 7.77 (d, J = 8.29 Hz, 2 H) 7.81-7.87 (m, 2 H) 7.92 (d, J = 8.19 Hz, 2 H) 8.00 (dd, J = 8.71, 2.49 Hz, 1 H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | quinolinesulfonamide | | | | | 8.23 (d, J = 9.64 Hz, 1 H) 8.37 (d, J = 2.28 Hz, 1 H) 8.72 (d, J = 6.92 Hz, 1 H) 11.65 (br. s., 1 H) |
| 679 | 1-(3'-fluoro-4-methoxy-3-biphenylyl)-2-oxo-N-2-pyrimidinyl-1,2-dihydro-6-quinolinesulfonamide | 503.0 | 156 | | | |
| 857 | 1-(4'-chloro-4-methoxy-3-biphenylyl)-N-3-isoxazolyl-2-oxo-1,2-dihydro-6-quinolinesulfonamide | 508.2 | 118 | 0.02 | | 1H NMR (400 MHz, DMSO-d6) δ ppm 3.72 (s, 3 H) 6.44 (d, J = 1.76 Hz, 1 H) 6.81 (dd, J = 9.28, 2.44 Hz, 2 H) 7.40 (d, J = 8.81 Hz, 1 H) 7.45-7.49 (m, 2 H) 7.70-7.74 (m, 3 H) 7.84 (dd, J = 8.97, 2.23 Hz, 1 H) 7.91 (dd, J = 8.71, 2.49 Hz, 1 H) 8.22 (d, J = 9.54 Hz, 1 H) 8.37 (d, J = 2.28 Hz, 1 H) 8.72 (d, J = 1.76 Hz, 1 H) 11.64 (br. s., 1 H) |
| 607 | 1-(6-chloro-3'-fluoro-4-methoxy-3-biphenylyl)-N-3-isoxazolyl-2-oxo-1,2-dihydro-6-quinolinesulfonamide | 526.0 | 157 | 0.027 | | 1H NMR (400 MHz, DMSO-d6) δ ppm 3.76 (s, 3 H) 6.44 (d, J = 1.76 Hz, 1 H) 6.80 (d, J = 9.54 Hz, 1 H) 6.93 (d, J = 9.12 Hz, 1 H) 7.21-7.36 (m, 3 H) 7.54 (d, J = 12.96 Hz, 2 H) 7.85 (dd, J = 8.97, 2.13 Hz, 1 H) 8.22 (d, J = 9.64 Hz, 1 H) 8.36 (d, J = 1.97 Hz, 1 H) 8.72 (s, 1 H) 11.49-11.64 (m, 1 H) 11.67 (s, 1 H) |
| 858 | 1-(3'-chloro-5'-fluoro-4-methoxy-3-biphenylyl)-N-3-isoxazolyl-2-oxo-1,2-dihydro-6-quinolinesulfonamide | 526.0 | 118 | 0.025 | | 1H NMR (400 MHz, DMSO-d6) δ ppm 3.74 (s, 3 H) 6.42 (d, J = 1.76 Hz, 1 H) 6.80 (dd, J = 9.28, 5.13 Hz, 2 H) 7.34-7.43 (m, 2 H) 7.62 (dt, J = 10.16, 2.12 Hz, 1 H) 7.66-7.71 (m, 1 H) 7.83 (dd, J = 8.97, 2.23 Hz, 1 H) 7.87 (d, J = 2.49 Hz, 1 H) 8.02 (dd, J = 8.81, 2.49 Hz, 1 H) 8.22 (d, J = 9.54 Hz, 1 H) 8.36 (d, J = 2.18 Hz, 1 H) 8.68 (d, J = 1.66 Hz, 1 H) 11.66 (br. s., 1 H) |
| 859 | 1-(3'-chloro-5'-fluoro-4-methoxy-3-biphenylyl)-N-3-isoxazolyl-2-oxo-1,2-dihydro-6-quinolinesulfonamide | 526.0 | 118 | 0.675 | | 1H NMR (400 MHz, DMSO-d6) δ ppm 3.74 (d, J = 2.28 Hz, 3 H) 6.39 (s, 1 H) 6.70-6.88 (m, 2 H) 7.31-7.47 (m, 2 H) 7.62 (d, J = 10.47 Hz, 1 H) 7.69 (s, 1 H) 7.80-7.89 (m, 2 H) 8.02 (d, J = 6.00 Hz, 1 H) 8.22 (d, J = 9.72 Hz, 1 H) 8.34 (s, 1 H) 8.64 (br. s., 1 H) 11.65 (br. s., 1 H) |
| 608 | 1-(6-chloro-3'-fluoro-4-methoxy-3-biphenylyl)-N-3-isoxazolyl-2-oxo-1,2-dihydro-6-quinolinesulfonamide | 526.0 | 157 | 0.012 | | 1H NMR (400 MHz, DMSO-d6) δ ppm 3.75 (s, 3 H) 6.14 (d, J = 0.93 Hz, 1 H) 6.69 (d, J = 9.64 Hz, 1 H) 6.73 (d, J = 8.81 Hz, 1 H) 7.18-7.26 (m, 1 H) 7.29-7.34 (m, 2 H) 7.43-7.55 (m, 3 H) 7.74 (dd, J = 8.81, 1.97 Hz, 1 H) 8.09-8.29 (m, 4 H) |
| 609 | 1-(6-chloro-3'-fluoro-4-methoxy-3-biphenylyl)-N-3-isoxazolyl-2-oxo-1,2-dihydro-6-quinolinesulfonamide | 526.0 | 157 | 10.09 | | |
| 613 | 1-(3',6-dichloro-5'-fluoro-4-methoxy-3-biphenylyl)-N-3-isoxazolyl-2-oxo-1,2-dihydro-6-quinolinesulfonamide | 562.0 | 115 | 0.018 | | 1H NMR (400 MHz, DMSO-d6) δ ppm 3.76 (s, 3 H) 6.45 (d, J = 1.76 Hz, 1 H) 6.79 (d, J = 9.64 Hz, 1 H) 6.93 (d, J = 9.02 Hz, 1 H) 7.35 (ddd, J = 9.59, 2.38, 1.50 Hz, 1 H) 7.39-7.41 (m, 1 H) 7.49 (dt, J = 8.73, 2.11 Hz, 1 H) 7.57 (d, J = 5.08 Hz, 2 H) 7.84 (dd, J = 9.02, 2.28 Hz, 1 H) 8.22 (d, J = 9.54 Hz, 1 H) 8.37 (d, J = 2.18 Hz, 1 H) 8.72 (d, J = 1.76 Hz, 1 H) 11.66 (s, 1 H) |
| 610 | 1-(3'-chloro-5'-fluoro-4-methoxy-3-biphenylyl)-2-oxo-N-4-pyrimidinyl-1,2-dihydro-6-quinolinesulfonamide | 537.0 | 158 | 0.013 | | 1H NMR (400 MHz, DMSO-d6) δ ppm 3.73 (s, 3 H) 6.75 (d, J = 8.91 Hz, 1 H) 6.80 (d, J = 9.64 Hz, 1 H) 7.00 (br. s., 1 H) 7.34-7.42 (m, 2 H) 7.59-7.64 (m, 1 H) 7.68 (t, J = 1.61 Hz, 1 H) 7.86 (d, J = 2.49 Hz, 1 H) 7.89 (dd, J = 8.97, 2.02 Hz, 1 H) 8.02 (dd, J = 8.76, 2.44 Hz, 1 H) 8.24 (d, J = 9.54 Hz, 1 H) 8.27-8.34 (m, 1 H) 8.43 (s, 1 H) 8.60 (s, 1 H) |
| 860 | 1-(3'-chloro-5'-fluoro-4-methoxy-3-biphenylyl)-2-oxo-N-2-pyrazinyl-1,2-dihydro-6-quinolinesulfonamide | 537.0 | 158 | 0.251 | | 1H NMR (400 MHz, DMSO-d6) δ ppm 3.73 (s, 3 H) 6.80 (t, J = 8.76 Hz, 2 H) 7.34-7.42 (m, 2 H) 7.61 (dt, J = 10.16, 2.07 Hz, 1 H) 7.68 (t, J = 1.61 Hz, 1 H) 7.87 (d, J = 2.49 Hz, 1 H) 7.93 (dd, J = 8.97, 2.23 Hz, 1 H) 8.02 (dd, J = 8.76, 2.54 Hz, 1 H) 8.20-8.28 (m, 3 H) 8.36 (d, J = 1.04 Hz, 1 H) 8.48 (d, J = 2.18 Hz, 1 H) 11.63 (br. s., 1 H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 861 | 1-(3'-chloro-5'-fluoro-4-methoxy-3-biphenylyl)-2-oxo-N-3-pyridazinyl-1,2-dihydro-6-quinolinesulfonamide | 537.2 | 158 | 0.038 | | 1H NMR (400 MHz, DMSO-d6) δ ppm 3.73 (s, 3 H) 6.73 (d, J = 8.91 Hz, 1 H) 6.79 (d, J = 9.64 Hz, 1 H) 7.34-7.42 (m, 2 H) 7.61 (dt, J = 10.13, 2.09 Hz, 1 H) 7.65-7.71 (m, 2 H) 7.81-7.95 (m, 3 H) 8.01 (dd, J = 8.71, 2.49 Hz, 1 H) 8.21 (d, J = 9.64 Hz, 1 H) 8.25-8.38 (m, 2 H) 14.48 (br. s., 1 H) |
| 862 | 1-(3'-chloro-4',5'-dimethoxy-3-biphenylyl)-N-3-isoxazolyl-2-oxo-1,2-dihydro-6-quinolinesulfonamide | 538.0 | 115 | 0.019 | | 1H NMR (400 MHz, DMSO-d6) δ ppm 3.73 (s, 3 H) 3.82 (s, 3 H) 6.44 (d, J = 1.76 Hz, 1 H) 6.81 (dd, J = 9.23, 2.80 Hz, 2 H) 6.97 (t, J = 2.02 Hz, 1 H) 7.21 (s, 1 H) 7.34 (t, J = 1.66 Hz, 1 H) 7.38 (d, J = 8.33 Hz, 1 H) 7.82 (d, J = 2.49 Hz, 1 H) 7.82-7.87 (m, 1 H) 7.96 (dd, J = 8.71, 2.49 Hz, 1 H) 8.23 (d, J = 9.54 Hz, 1 H) 8.37 (d, J = 2.18 Hz, 1 H) 8.71 (d, J = 1.76 Hz, 1 H) 11.65 (s, 1 H) |
| 863 | 1-(3'-chloro-4',5'-dimethoxy-3-biphenylyl)-N-3-isoxazolyl-2-oxo-1,2-dihydro-6-quinolinesulfonamide | 537.9 | 115 | | | |
| 864 | 1-(3'-chloro-5'-fluoro-4-methoxy-3-biphenylyl)-N-1,3-oxazol-2-yl-2-oxo-1,2-dihydro-6-quinolinesulfonamide | 526.0 | 158 | 0.043 | | 1H NMR (400 MHz, DMSO-d6) δ ppm 3.74 (s, 3 H) 6.73 (d, J = 9.09 Hz, 1 H) 6.79 (d, J = 9.55 Hz, 1 H) 7.28 (d, J = 1.66 Hz, 1 H) 7.34-7.44 (m, 2 H) 7.59-7.65 (m, 2 H) 7.69 (t, J = 1.50 Hz, 1 H) 7.82-7.86 (m, 1 H) 7.86 (s, 1 H) 8.02 (d, J = 8.84 Hz, 1 H) 8.20 (d, J = 9.54 Hz, 1 H) 8.33 (d, J = 2.18 Hz, 1 H) 12.16 (br. s., 1 H) |
| 865 | 1-(3',5'-difluoro-4-methoxy-3-biphenylyl)-N-3-isoxazolyl-2-oxo-1,2-dihydro-6-quinolinesulfonamide | 510.0 | 115 | 0.053 | | 1H NMR (400 MHz, DMSO-d6) δ ppm 3.74 (s, 3 H) 6.43 (d, J = 1.87 Hz, 1 H) 6.81 (dd, J = 9.28, 3.47 Hz, 2 H) 7.17 (tt, J = 9.21, 2.24 Hz, 1 H) 7.40 (d, J = 8.81 Hz, 1 H) 7.47-7.53 (m, 2 H) 7.82-7.88 (m, 2 H) 8.02 (dd, J = 8.76, 2.44 Hz, 1 H) 8.23 (d, J = 9.54 Hz, 1 H) 8.37 (d, J = 2.18 Hz, 1 H) 8.71 (d, J = 1.76 Hz, 1 H) 11.66 (s, 1 H) |
| 866 | 1-(3',5'-difluoro-4-methoxy-3-biphenylyl)-N-3-isoxazolyl-2-oxo-1,2-dihydro-6-quinolinesulfonamide | 510.0 | 115 | | | |
| 867 | 1-(3'-chloro-4-methoxy-5'-methyl-3-biphenylyl)-N-3-isoxazolyl-2-oxo-1,2-dihydro-6-quinolinesulfonamide | 522.2 | 115 | 0.016 | | 1H NMR (400 MHz, DMSO-d6) δ ppm 2.34 (s, 3 H) 3.73 (s, 3 H) 6.44 (d, J = 1.76 Hz, 1 H) 6.81 (dd, J = 9.33, 3.11 Hz, 2 H) 7.21 (s, 1 H) 7.38 (d, J = 8.81 Hz, 1 H) 7.50-7.58 (m, 2 H) 7.77 (d, J = 2.38 Hz, 1 H) 7.84 (dd, J = 8.97, 2.23 Hz, 1 H) 7.94 (dd, J = 8.71, 2.38 Hz, 1 H) 8.23 (d, J = 9.54 Hz, 1 H) 8.37 (d, J = 2.18 Hz, 1 H) 8.72 (d, J = 1.76 Hz, 1 H) 11.65 (s, 1 H) |
| 868 | 1-(3'-chloro-4-methoxy-5'-methyl-3-biphenylyl)-N-3-isoxazolyl-2-oxo-1,2-dihydro-6-quinolinesulfonamide | 522.0 | 115 | | | |
| 869 | 1-(4'-chloro-3',4-dimethoxy-3-biphenylyl)-N-3-isoxazolyl-2-oxo-1,2-dihydro-6-quinolinesulfonamide | 538.0 | 115 | | | |
| 870 | 1-(4'-chloro-3',4-dimethoxy-3-biphenylyl)-N-3-isoxazolyl-2-oxo-1,2-dihydro-6-quinolinesulfonamide | 538.0 | 115 | 0.023 | | 1H NMR (400 MHz, DMSO-d6) δ ppm 3.72 (s, 3 H) 3.91 (s, 3 H) 6.44 (d, J = 1.87 Hz, 1 H) 6.80 (s, 1 H) 6.83 (s, 1 H) 7.28 (dd, J = 8.29, 2.07 Hz, 1 H) 7.33-7.41 (m, 2 H) 7.45 (d, J = 8.29 Hz, 1 H) 7.80 (d, J = 2.38 Hz, 1 H) 7.85 (dd, J = 8.97, 2.23 Hz, 1 H) 7.95 (dd, J = 8.71, 2.38 Hz, 1 H) 8.23 (d, J = 9.54 Hz, 1 H) 8.37 (d, J = 2.18 Hz, 1 H) 8.71 (d, J = 1.76 Hz, 1 H) 11.65 (s, 1 H) |
| 614 | 1-(3',6-dichloro-5'-fluoro-4-methoxy-3-biphenylyl)-N-3-isoxazolyl-2-oxo-1,2-dihydro-6-quinolinesulfonamide | 560.0 | 159 | 0.009 | | 1H NMR (400 MHz, DMSO-d6) δ ppm 3.76 (s, 3 H) 6.45 (d, J = 1.76 Hz, 1 H) 6.79 (d, J = 9.64 Hz, 1 H) 6.93 (d, J = 8.91 Hz, 1 H) 7.35 (d, J = 9.51 Hz, 1 H) 7.40 (s, 1 H) 7.49 (dt, J = 8.76, 2.15 Hz, 1 H) 7.57 (d, J = 5.18 Hz, 2 H) 7.84 (dd, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | quinolinesulfonamide | | | | | J = 9.02, 2.28 Hz, 1 H) 8.22 (d, J = 9.43 Hz, 1 H) 8.37 (d, J = 2.28 Hz, 1 H) 8.72 (d, J = 1.76 Hz, 1 H) 11.66 (s, 1 H) |
| 615 | 1-(3',6-dichloro-5'-fluoro-4-methoxy-3-biphenylyl)-N-3-isoxazolyl-2-oxo-1,2-dihydro-6-quinolinesulfonamide | 560.0 | 159 | 10.77 | | |
| 616 | 1-(4'-chloro-3'-cyano-2-fluoro-5-methoxy-4-biphenylyl)-2-oxo-N-3-pyridazinyl-1,2-dihydro-6-quinolinesulfonamide | 561.9 | 160 | 0.017 | | 1H NMR (400 MHz, DMSO-d6) δ ppm 3.75 (s, 3 H) 6.75-6.83 (m, 2 H) 7.49-7.58 (m, 2 H) 7.69 (dd, J = 9.48, 4.20 Hz, 1 H) 7.84-7.98 (m, 3 H) 8.07 (dt, J = 5.96 Hz, 1 H) 8.21 (d, J = 9.54 Hz, 1 H) 8.25-8.34 (m, 1 H) 8.34-8.38 (m, 2 H) 14.50 (br. s., 1 H) |
| 871 | 1-(4'-chloro-3'-cyano-2-fluoro-5-methoxy-4-biphenylyl)-2-oxo-N-2-pyrimidinyl-1,2-dihydro-6-quinolinesulfonamide | 561.9 | 160 | 0.044 | | 1H NMR (400 MHz, DMSO-d6) δ ppm 3.75 (s, 3 H) 6.78-6.85 (m, 2 H) 7.03-7.09 (m, 1 H) 7.52 (d, J = 7.05 Hz, 1 H) 7.58 (d, J = 10.47 Hz, 1 H) 7.93 (d, J = 8.60 Hz, 1 H) 7.99 (dd, J = 8.97, 2.23 Hz, 1 H) 8.07 (dt, J = 8.58, 2.03 Hz, 1 H) 8.27 (d, J = 9.54 Hz, 1 H) 8.37 (d, J = 2.07 Hz, 1 H) 8.48-8.55 (m, 3 H) 11.84 (s, 1 H) |
| 872 | 1-(4'-chloro-4-methoxy-3'-methyl-3-biphenylyl)-N-3-isoxazolyl-2-oxo-1,2-dihydro-6-quinolinesulfonamide | 522.0 | 115 | 11.55 | | |
| 873 | 1-(4'-chloro-3'-fluoro-4-methoxy-3-biphenylyl)-N-3-isoxazolyl-2-oxo-1,2-dihydro-6-quinolinesulfonamide | 526.0 | 115 | | | |
| 874 | 1-(4'-chloro-3'-fluoro-4-methoxy-3-biphenylyl)-N-3-isoxazolyl-2-oxo-1,2-dihydro-6-quinolinesulfonamide | 526.0 | 115 | 0.033 | | 1H NMR (400 MHz, DMSO-d6) δ ppm 3.73 (s, 3 H) 6.42 (d, J = 1.76 Hz, 1 H) 6.80 (dd, J = 9.28, 2.33 Hz, 2 H) 7.40 (d, J = 8.81 Hz, 1 H) 7.58-7.64 (m, 2 H) 7.76-7.85 (m, 3 H) 7.98 (dd, J = 8.71, 2.49 Hz, 1 H) 8.22 (d, J = 9.54 Hz, 1 H) 8.36 (d, J = 2.18 Hz, 1 H) 8.69 (d, J = 1.76 Hz, 1 H) 11.65 (br. s., 1 H) |
| 875 | 1-(4'-chloro-4-methoxy-3'-methyl-3-biphenylyl)-N-3-isoxazolyl-2-oxo-1,2-dihydro-6-quinolinesulfonamide | 522.0 | 115 | 0.015 | | 1H NMR (400 MHz, DMSO-d6) δ ppm 2.36 (s, 3 H) 3.72 (s, 3 H) 6.44 (d, J = 1.87 Hz, 1 H) 6.79-6.83 (m, 2 H) 7.39 (d, J = 8.71 Hz, 1 H) 7.44 (d, J = 8.40 Hz, 1 H) 7.55 (dd, J = 8.40, 1.97 Hz, 1 H) 7.70-7.73 (m, 2 H) 7.85 (dd, J = 9.02, 2.28 Hz, 1 H) 7.91 (dd, J = 8.66, 2.44 Hz, 1 H) 8.23 (d, J = 9.54 Hz, 1 H) 8.37 (d, J = 2.28 Hz, 1 H) 8.72 (d, J = 1.76 Hz, 1 H) 11.65 (br. s., 1 H) |
| 876 | 1-(3'-chloro-5'-fluoro-4-methoxy-3-biphenylyl)-2-oxo-N-2-pyrazinyl-1,2-dihydro-6-quinolinesulfonamide | 537.1 | 158 | 0.206 | | 1H NMR (400 MHz, DMSO-d6) δ ppm 3.73 (s, 3 H) 6.76-6.83 (m, 2 H) 7.34-7.42 (m, 2 H) 7.61 (dt, J = 10.13, 2.09 Hz, 1 H) 7.68 (t, J = 1.61 Hz, 1 H) 7.87 (d, J = 2.49 Hz, 1 H) 7.93 (dd, J = 9.02, 2.18 Hz, 1 H) 8.02 (dd, J = 8.76, 2.54 Hz, 1 H) 8.20-8.23 (m, 2 H) 8.26 (d, J = 9.54 Hz, 1 H) 8.35 (d, J = 0.93 Hz, 1 H) 8.48 (d, J = 2.18 Hz, 1 H) 11.63 (br. s., 1 H) |
| 877 | 1-(3'-chloro-5'-fluoro-4-methoxy-3-biphenylyl)-2-oxo-N-2-pyrazinyl-1,2-dihydro-6-quinolinesulfonamide | 537.1 | 158 | | | |
| 878 | 1-(4'-fluoro-4-methoxy-3'-methyl-3-biphenylyl)-N-3-isoxazolyl-2-oxo-1,2-dihydro-6-quinolinesulfonamide | 506.2 | 115 | 0.021 | | 1H NMR (400 MHz, DMSO-d6) δ ppm 2.26 (d, J = 1.66 Hz, 3 H) 3.71 (s, 3 H) 6.43 (d, J = 1.76 Hz, 1 H) 6.78-6.83 (m, 2 H) 7.14-7.21 (m, 1 H) 7.37 (d, J = 8.81 Hz, 1 H) 7.50-7.56 (m, 1 H) 7.62 (dd, J = 7.31, 1.92 Hz, 1 H) 7.67 (d, J = 2.38 Hz, 1 H) 7.81-7.89 (m, 2 H) 8.22 (d, J = 9.74 Hz, 1 H) 8.36 (d, J = 2.07 Hz, 1 H) 8.70 (d, J = 1.76 Hz, 1 H) 11.66 (br. s., 1 H) |
| 879 | 1-(4'-fluoro-4-methoxy-3'-methyl-3-biphenylyl)-N-3- | 506.2 | 115 | | | |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | isoxazolyl-2-oxo-1,2-dihydro-6-quinolinesulfonamide | | | | | |
| 880 | 1-(5'-chloro-2'-fluoro-4-methoxy-3-biphenylyl)-N-3-isoxazolyl-2-oxo-1,2-dihydro-6-quinolinesulfonamide | 525.9 | 115 | 0.032 | | 1H NMR (400 MHz, DMSO-d6) δ ppm 3.73 (s, 3 H) 6.43 (d, J = 1.76 Hz, 1 H) 6.78-6.83 (m, 2 H) 7.31-7.45 (m, 3 H) 7.62 (d, J = 2.38 Hz, 2 H) 7.79-7.87 (m, 2 H) 8.22 (d, J = 9.64 Hz, 1 H) 8.36 (s, J = 4.64 Hz, 1 H) 8.69 (s, J = 5.12 Hz, 1 H) 11.65 (br. s., 1 H) |
| 881 | 1-(5'-chloro-2'-fluoro-4-methoxy-3-biphenylyl)-N-3-isoxazolyl-2-oxo-1,2-dihydro-6-quinolinesulfonamide | 525.9 | 115 | | | |
| 882 | 1-(3'-chloro-4-methoxy-4'-methyl-3-biphenylyl)-N-3-isoxazolyl-2-oxo-1,2-dihydro-6-quinolinesulfonamide | 522.0 | 115 | | | |
| 883 | 1-(3'-chloro-4,4'-dimethoxy-3-biphenylyl)-N-3-isoxazolyl-2-oxo-1,2-dihydro-6-quinolinesulfonamide | 537.9 | 115 | | | |
| 884 | 1-(3'-chloro-4,4'-dimethoxy-3-biphenylyl)-N-3-isoxazolyl-2-oxo-1,2-dihydro-6-quinolinesulfonamide | 537.9 | 115 | 0.035 | | 1H NMR (400 MHz, DMSO-d6) δ ppm 3.71 (s, 3 H) 3.88 (s, 3 H) 6.42 (d, J = 1.76 Hz, 1 H) 6.76-6.83 (m, 2 H) 7.19 (d, J = 8.81 Hz, 1 H) 7.35 (d, J = 8.81 Hz, 1 H) 7.65 (dd, J = 8.66, 2.33 Hz, 1 H) 7.72 (d, J = 2.49 Hz, 1 H) 7.77 (d, J = 2.38 Hz, 1 H) 7.81-7.90 (m, 2 H) 8.21 (d, J = 9.74 Hz, 1 H) 8.35 (d, J = 2.07 Hz, 1 H) 8.68 (d, J = 1.76 Hz, 1 H) 11.65 (br. s., 1 H) |
| 885 | 1-(3'-chloro-4-methoxy-4'-methyl-3-biphenylyl)-N-3-isoxazolyl-2-oxo-1,2-dihydro-6-quinolinesulfonamide | 522.0 | 115 | 0.012 | | 1H NMR (400 MHz, DMSO-d6) δ ppm 2.34 (s, 3 H) 3.72 (s, 3 H) 6.45 (d, J = 1.87 Hz, 1 H) 6.79-6.83 (m, 2 H) 7.35-7.43 (m, 2 H) 7.59 (dd, J = 7.88, 1.97 Hz, 1 H) 7.75 (d, J = 1.87 Hz, 1 H) 7.77 (d, J = 2.38 Hz, 1 H) 7.85 (dd, J = 9.02, 2.28 Hz, 1 H) 7.93 (dd, J = 8.71, 2.49 Hz, 1 H) 8.23 (d, J = 9.54 Hz, 1 H) 8.37 (d, J = 2.18 Hz, 1 H) 8.73 (d, J = 1.76 Hz, 1 H) 11.65 (s, 1 H) |
| 886 | 1-(3'-chloro-2'-fluoro-4-methoxy-3-biphenylyl)-N-3-isoxazolyl-2-oxo-1,2-dihydro-6-quinolinesulfonamide | 526.0 | 115 | | | |
| 887 | 1-(3'-chloro-2'-fluoro-4-methoxy-3-biphenylyl)-N-3-isoxazolyl-2-oxo-1,2-dihydro-6-quinolinesulfonamide | 526.0 | 115 | 0.03 | | 1H NMR (400 MHz, DMSO-d6) δ ppm 3.74 (s, 3 H) 6.44 (d, J = 1.87 Hz, 1 H) 6.81 (dd, J = 9.28, 3.78 Hz, 2 H) 7.29 (td, J = 7.74 Hz, 1 H) 7.43 (d, J = 8.81 Hz, 1 H) 7.49-7.63 (m, 3 H) 7.79 (dt, J = 8.73, 1.96 Hz, 1 H) 7.85 (dd, J = 8.97, 2.23 Hz, 1 H) 8.22 (d, J = 9.54 Hz, 1 H) 8.36 (d, J = 2.18 Hz, 1 H) 8.71 (d, J = 1.87 Hz, 1 H) 11.65 (br. s., 1 H) |
| 888 | 1-(4'-fluoro-3',4-dimethoxy-3-biphenylyl)-N-3-isoxazolyl-2-oxo-1,2-dihydro-6-quinolinesulfonamide | 522.1 | 115 | | | |
| 889 | 1-(4'-fluoro-3',4-dimethoxy-3-biphenylyl)-N-3-isoxazolyl-2-oxo-1,2-dihydro-6-quinolinesulfonamide | 522.1 | 115 | 0.184 | | 1H NMR (400 MHz, DMSO-d6) δ ppm 3.72 (s, 3 H) 3.89 (s, 3 H) 6.43 (d, J = 1.87 Hz, 1 H) 6.79-6.84 (m, 2 H) 7.23-7.27 (m, 2 H) 7.35-7.42 (m, 2 H) 7.75 (d, J = 2.38 Hz, 1 H) 7.85 (dd, J = 9.02, 2.18 Hz, 1 H) 7.91 (dd, J = 8.76, 2.44 Hz, 1 H) 8.23 (d, J = 9.54 Hz, 1 H) 8.37 (d, J = 2.28 Hz, 1 H) 8.71 (d, J = 1.76 Hz, 1 H) 11.65 (s, 1 H) |
| 611 | 1-(3'-chloro-5'-fluoro-4-methoxy-3-biphenylyl)-2-oxo-N-4-pyrimidinyl-1,2- | 537.0 | 158 | 0.029 | | 1H NMR (400 MHz, DMSO-d6) δ ppm 3.73 (s, 3 H) 6.75 (d, J = 8.81 Hz, 1 H) 6.79 (d, J = 9.64 Hz, 1 H) 6.98 (br. s., 1 H) 7.34-7.41 (m, 2 H) 7.62 (dt, J = 7.63 Hz, 1 H) 7.68 (t, J = 1.61 Hz, 1 |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | dihydro-6-quinolinesulfonamide | | | | | H) 7.86 (d, J = 2.38 Hz, 1 H) 7.87-7.91 (m, 1 H) 8.02 (dd, J = 8.76, 2.44 Hz, 1 H) 8.23 (d, J = 9.54 Hz, 1 H) 8.26-8.31 (m, 1 H) 8.40-8.44 (m, 1 H) 8.59 (s, 1 H) |
| 612 | 1-(3'-chloro-5'-fluoro-4-methoxy-3-biphenylyl)-2-oxo-N-4-pyrimidinyl-1,2-dihydro-6-quinolinesulfonamide | 537.0 | 158 | 0.355 | | 1H NMR (400 MHz, DMSO-d6) δ ppm 3.73 (s, 3 H) 6.75 (d, J = 9.02 Hz, 1 H) 6.79 (d, J = 9.64 Hz, 1 H) 7.00 (br. s., 1 H) 7.35-7.41 (m, 2 H) 7.61 (dt, J = 6.43 Hz, 1 H) 7.68 (t, J = 1.55 Hz, 1 H) 7.86 (d, J = 2.49 Hz, 1 H) 7.87-7.91 (m, 1 H) 8.02 (dd, J = 8.71, 2.49 Hz, 1 H) 8.24 (d, J = 9.64 Hz, 1 H) 8.29 (br. s., 1 H) 8.41-8.44 (m, 1 H) 8.59 (s, 1 H) |
| 617 | 1-(2-chloro-5-methoxy-4-pyridinyl)-N-3-isoxazolyl-2-oxo-1,2-dihydro-6-quinolinesulfonamide | 433.0 | 161 | 3.877 | | |
| 890 | 1-(4'-chloro-3'-cyano-2-fluoro-5-methoxy-4-biphenylyl)-N-1,3-oxazol-2-yl-2-oxo-1,2-dihydro-6-quinolinesulfonamide | 551.1 | 160 | 0.084 | | 1H NMR (500 MHz, DMSO-d6) δ ppm 3.76 (s, 3 H) 6.74-6.82 (m, 2 H) 7.24-7.33 (m, 1 H) 7.49-7.58 (m, 2 H) 7.61 (d, J = 1.49 Hz, 1 H) 7.86 (dd, J = 8.92, 1.98 Hz, 1 H) 7.92 (d, J = 8.50 Hz, 1 H) 8.04-8.11 (m, 1 H) 8.20 (d, J = 9.67 Hz, 1 H) 8.27-8.44 (m, 1 H) 12.16 (br. s., 1 H) |
| 891 | 1-(3'-chloro-4-methoxy-2'-methyl-3-biphenylyl)-N-3-isoxazolyl-2-oxo-1,2-dihydro-6-quinolinesulfonamide | 522.0 | 115 | 0.02 | | 1H NMR (400 MHz, DMSO-d6) δ ppm 2.28-2.31 (m, 3 H) 3.72 (s, 3 H) 6.42 (d, J = 1.76 Hz, 1 H) 6.79 (d, J = 9.64 Hz, 1 H) 6.83 (d, J = 8.91 Hz, 1 H) 7.23-7.30 (m, 2 H) 7.34 (d, J = 2.28 Hz, 1 H) 7.38 (d, J = 8.71 Hz, 1 H) 7.41-7.45 (m, 1 H) 7.54 (dd, J = 8.50, 2.28 Hz, 1 H) 7.85 (dd, J = 8.97, 2.23 Hz, 1 H) 8.20 (d, J = 9.54 Hz, 1 H) 8.34 (d, J = 2.07 Hz, 1 H) 8.68 (d, J = 6.55 Hz, 1 H) 11.64 (br. s., 1 H) |
| 892 | 1-(4'-chloro-3'-cyano-2-fluoro-5-methoxy-4-biphenylyl)-N-(2-methyl-4-pyrimidinyl)-2-oxo-1,2-dihydro-6-quinolinesulfonamide | 576.2 | 160 | 0.051 | | 1H NMR (500 MHz, DMSO-d6) δ ppm 2.38 (s, 3 H) 3.75 (s, 3 H) 6.73-6.83 (m, 2 H) 6.89 (br. s., 1 H) 7.51-7.67 (m, 2 H) 7.84-7.95 (m, 2 H) 8.06-8.15 (m, 2 H) 8.23 (d, J = 9.60 Hz, 1 H) 8.38 (d, J = 12.39 Hz, 2 H) 11.37 (br. s., 1 H) |
| 893 | 1-(4'-chloro-3'-cyano-2-fluoro-5-methoxy-4-biphenylyl)-N-(5-fluoro-2-pyrimidinyl)-2-oxo-1,2-dihydro-6-quinolinesulfonamide | 580.0 | 160 | 0.013 | | 1H NMR (500 MHz, DMSO-d6) δ ppm 3.75 (s, 3 H) 6.74-6.90 (m, 2 H) 7.46-7.61 (m, 2 H) 7.92 (d, J = 8.56 Hz, 1 H) 7.98 (dd, J = 8.99, 2.04 Hz, 1 H) 8.04-8.10 (m, 1 H) 8.26 (d, J = 9.67 Hz, 1 H) 8.32-8.41 (m, 1 H) 8.48 (d, J = 1.95 Hz, 1 H) 8.62 (s, 2 H) 11.96 (s, 1 H) |
| 619 | 1-(3',4'-difluoro-3-methoxy-4-biphenylyl)-N-(5-fluoro-2-pyrimidinyl)-2-oxo-1,2-dihydro-6-quinolinesulfonamide | 539.0 | 162 | 0.076 | | 1H NMR (400 MHz, DMSO-d6) δ ppm 3.77 (s, 3 H) 6.77 (d, J = 9.02 Hz, 1 H) 6.80 (d, J = 9.64 Hz, 1 H) 7.39 (d, J = 8.09 Hz, 1 H) 7.45-7.49 (m, 1 H) 7.55-7.62 (m, 2 H) 7.68-7.73 (m, 1 H) 7.94-8.01 (m, 2 H) 8.25 (d, J = 9.43 Hz, 1 H) 8.47 (d, J = 2.18 Hz, 1 H) 8.62 (d, J = 0.73 Hz, 2 H) 11.96 (s, 1 H) |
| 894 | 1-(3',4'-difluoro-3-methoxy-4-biphenylyl)-N-1,3-oxazol-2-yl-2-oxo-1,2-dihydro-6-quinolinesulfonamide | 510.0 | 162 | 0.083 | | 1H NMR (400 MHz, DMSO-d6) δ ppm 3.79 (s, 3 H) 6.72 (d, J = 8.91 Hz, 1 H) 6.78 (d, J = 9.64 Hz, 1 H) 7.27-7.30 (m, 1 H) 7.39 (d, J = 8.05 Hz, 1 H) 7.45-7.49 (m, 1 H) 7.55-7.62 (m, 3 H) 7.68-7.74 (m, 1 H) 7.83-7.87 (m, 1 H) 7.95-8.01 (m, 1 H) 8.19 (dd, J = 9.90, 0.47 Hz, 1 H) 8.33 (d, J = 2.18 Hz, 1 H) 12.15 (br. s., 1 H) |
| 895 | 1-(3'-chloro-4-methoxy-2'-methyl-3-biphenylyl)-N-3-isoxazolyl-2-oxo-1,2-dihydro-6-quinolinesulfonamide | 522.0 | 115 | 1.842 | | |
| 896 | 1-(3',4'-difluoro-3-methoxy-4-biphenylyl)-2-oxo-N-3-pyridazinyl-1,2-dihydro-6-quinolinesulfonamide | 521.1 | 162 | 0.047 | | 1H NMR (400 MHz, DMSO-d6) δ ppm 3.78 (s, 3 H) 6.72 (d, J = 9.02 Hz, 1 H) 6.78 (d, J = 9.54 Hz, 1 H) 7.38 (d, J = 8.28 Hz, 1 H) 7.47 (dd, J = 8.14, 1.92 Hz, 1 H) 7.54-7.61 (m, 2 H) 7.66-7.73 (m, 1 H) 7.84 (d, J = 4.54 Hz, 1 H) 7.90-8.01 (m, 2 H) 8.20 (d, J = 9.58 Hz, 1 H) 8.28 (br. s., 1 H) 8.34 (s, J = 4.80, 4.80 Hz, 1 H) 14.48 (s, 1 H) |
| 897 | 1-(3',4'-difluoro-3-methoxy-4- | 521.0 | 162 | 0.1 | | 1H NMR (400 MHz, DMSO-d6) δ ppm 3.77 (s, 3 H) 6.74-6.82 (m, 2 H) 7.01-7.08 (m, 1 H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
|  | biphenylyl)-2-oxo-N-2-pyrimidinyl-1,2-dihydro-6-quinolinesulfonamide |  |  |  |  | 7.39 (d, J = 8.09 Hz, 1 H) 7.44-7.49 (m, 1 H) 7.54-7.62 (m, 2 H) 7.70 (br. s., 1 H) 7.94-8.01 (m, 2 H) 8.26 (d, J = 9.54 Hz, 1 H) 8.46-8.54 (m, 3 H) 11.81 (s, 1 H) |
| 898 | 1-(4'-chloro-3'-cyano-2-fluoro-5-methoxy-4-biphenylyl)-N-(6-methyl-4-pyrimidinyl)-2-oxo-1,2-dihydro-6-quinolinesulfonamide | 576.0 | 160 | 0.044 |  | 1H NMR (400 MHz, DMSO-d6) δ ppm 2.32 (s, 3 H) 3.72-3.79 (m, 3 H) 6.78-6.82 (m, 2 H) 7.50-7.63 (m, 3 H) 7.89-7.95 (m, 2 H) 8.07 (dt, J = 8.66, 2.00 Hz, 1 H) 8.24 (d, J = 9.64 Hz, 1 H) 8.37 (d, J = 5.31 Hz, 1 H) 8.43 (d, J = 1.76 Hz, 1 H) 8.50 (s, 1 H) 11.40 (s, 1 H) |
| 899 | 1-(3',4'-difluoro-3-methoxy-4-biphenylyl)-N-(6-methyl-4-pyrimidinyl)-2-oxo-1,2-dihydro-6-quinolinesulfonamide | 535.2 | 162 | 0.107 |  | 1H NMR (400 MHz, DMSO-d6) δ ppm 2.32 (s, 3 H) 3.78 (s, 3 H) 6.74 (d, J = 8.87 Hz, 1 H) 6.79 (d, J = 9.77 Hz, 1 H) 6.88-6.93 (m, 1 H) 7.39 (d, J = 8.09 Hz, 1 H) 7.47 (dd, J = 8.09, 1.87 Hz, 1 H) 7.54-7.60 (m, 2 H) 7.67-7.73 (m, 1 H) 7.91 (dd, J = 8.91, 2.18 Hz, 1 H) 7.97 (ddd, J = 12.18, 7.83, 2.18 Hz, 1 H) 8.23 (d, J = 9.43 Hz, 1 H) 8.42 (d, J = 2.07 Hz, 1 H) 8.50 (s, 1 H) |
| 900 | 1-(3',4'-difluoro-3-methoxy-4-biphenylyl)-N-(2-methyl-4-pyrimidinyl)-2-oxo-1,2-dihydro-6-quinolinesulfonamide | 535.2 | 162 | 0.285 |  | 1H NMR (400 MHz, DMSO-d6) δ ppm 2.38 (s, 3 H) 3.78 (s, 3 H) 6.73 (d, J = 9.12 Hz, 1 H) 6.78 (d, J = 9.54 Hz, 1 H) 6.84-6.93 (m, 1 H) 7.38 (d, J = 8.09 Hz, 1 H) 7.45-7.49 (m, 1 H) 7.55-7.62 (m, 2 H) 7.67-7.73 (m, 1 H) 7.88 (dd, J = 9.02, 2.18 Hz, 1 H) 7.98 (ddd, J = 12.23, 7.72, 2.44 Hz, 1 H) 8.12 (d, J = 5.71 Hz, 1 H) 8.22 (d, J = 9.64 Hz, 1 H) 8.39 (d, J = 2.07 Hz, 1 H) |
| 901 | 1-(3'-chloro-5'-fluoro-4-methoxy-3-biphenylyl)-2-oxo-N-3-pyridazinyl-1,2-dihydro-6-quinolinesulfonamide | 537.2 | 158 |  |  |  |
| 618 | 1-(2-(3-chloro-5-fluorophenyl)-5-methoxy-4-pyridinyl)-N-3-isoxazolyl-2-oxo-1,2-dihydro-6-quinolinesulfonamide | 527.0 | 161 | 0.605 |  | 1H NMR (400 MHz, DMSO-d6) δ ppm 3.89 (s, 3 H) 6.45 (d, J = 1.87 Hz, 1 H) 6.85 (d, J = 9.64 Hz, 1 H) 6.91 (d, J = 9.02 Hz, 1 H) 7.45-7.50 (m, 1 H) 7.84 (dd, J = 8.91, 2.18 Hz, 1 H) 7.88-7.93 (m, 1 H) 8.02 (t, J = 1.55 Hz, 1 H) 8.27-8.32 (m, 2 H) 8.42 (d, J = 2.18 Hz, 1 H) 8.73 (d, J = 1.76 Hz, 1 H) 8.81 (s, 1 H) 11.68 (s, 1 H) |
| 902 | 1-(3'-chloro-5'-fluoro-4-methoxy-3-biphenylyl)-2-oxo-N-3-pyridazinyl-1,2-dihydro-6-quinolinesulfonamide | 537.0 | 158 | 0.077 |  | 1H NMR (400 MHz, DMSO-d6) δ ppm 3.73 (s, 3 H) 6.73 (d, J = 9.04 Hz, 1 H) 6.79 (d, J = 9.56 Hz, 1 H) 7.33-7.43 (m, 2 H) 7.59-7.72 (m, 3 H) 7.81-7.93 (m, 3 H) 8.01 (dd, J = 8.81, 2.49 Hz, 1 H) 8.20 (d, J = 9.54 Hz, 1 H) 8.28-8.38 (m, 2 H) |
| 620 | N-3-isoxazolyl-1-(2-methoxy-5-(tetrahydro-2H-pyran-4-yl)phenyl)-2-oxo-1,2-dihydro-6-quinolinesulfonamide | 482.2 | 163 | 8.103 |  |  |
| 903 | 1-(2-fluoro-3',5,5'-trimethoxy-4-biphenylyl)-2-oxo-N-2-pyrimidinyl-1,2-dihydro-6-quinolinesulfonamide | 561 | 141 | 0.064 |  | $^1$H NMR (400 MHz, DMSO-d$_6$) δ ppm 3.67 (s, 3 H) 3.78 (s, 6 H) 6.56 (t, J = 2.23 Hz, 1 H) 6.68-6.87 (m, 3 H) 7.01 (br. s., 1 H) 7.26-7.37 (m, 1 H) 7.43 (d, J = 10.37 Hz, 1 H) 7.95 (dd, J = 8.97, 2.13 Hz, 1 H) 8.22 (d, J = 9.64 Hz, 1 H) 8.39-8.56 (m, 3 H) 11.78 (br. s., 1 H) |
| 904 | N-(5-fluoro-2-pyrimidinyl)-1-(2-fluoro-3',5,5'-trimethoxy-4-biphenylyl)-2-oxo-1,2-dihydro-6-quinolinesulfonamide | 579 | 141 | 0.033 |  | 1H NMR (400 MHz, DMSO-d6) δ ppm 3.72 (s, 3 H) 3.82 (s, 6 H) 6.61 (t, J = 2.23 Hz, 1 H) 6.78-6.83 (m, 3 H) 6.85 (d, J = 8.91 Hz, 1 H) 7.37 (d, J = 6.95 Hz, 1 H) 7.48 (d, J = 10.37 Hz, 1 H) 7.98 (dd, J = 8.97, 2.23 Hz, 1 H) 8.26 (d, J = 9.54 Hz, 1 H) 8.47 (d, J = 2.28 Hz, 1 H) 8.62 (d, J = 0.62 Hz, 2 H) 11.97 (s, 1 H) |
| 905 | 1-(2-fluoro-3',5,5'-trimethoxy-4-biphenylyl)-2-oxo-N-3-pyridazinyl-1,2-dihydro-6-quinolinesulfonamide | 561 | 141 | 0.083 |  | 1H NMR (400 MHz, DMSO-d6) δ ppm 3.73 (s, 3 H) 3.82 (s, 7 H) 6.61 (t, J = 2.23 Hz, 1 H) 6.76-6.83 (m, 4 H) 7.37 (d, J = 6.84 Hz, 1 H) 7.46 (d, J = 10.37 Hz, 1 H) 7.68 (dd, J = 9.59, 4.20 Hz, 1 H) 7.86 (dd, J = 9.12, 2.18 Hz, 1 H) 8.20 (d, J = 9.54 Hz, 1 H) 8.35 (d, J = 2.07 Hz, 1 H) 14.49 (s, 1 H) |
| 906 | 1-(3'-(difluoromethoxy)-2- | 567 | 141 | 0.023 |  | 1H NMR (500 MHz, DMSO-d6) δ ppm 3.74 (s, 3 H) 6.80 (d, J = 9.67 Hz, 1 H) 6.85 (d, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | fluoro-5-methoxy-4-biphenylyl)-2-oxo-N-2-pyrimidinyl-1,2-dihydro-6-quinolinesulfonamide | | | | | J = 8.95 Hz, 1 H) 7.06 (br. s., 1 H) 7.23-7.23 (m, 1 H) 7.30 (d, J = 7.14 Hz, 1 H) 7.35 (t, J = 73.96 Hz, 1 H) 7.42 (d, J = 6.94 Hz, 1 H) 7.48-7.55 (m, 2 H) 7.56-7.66 (m, 2 H) 7.94-8.05 (m, 1 H) 8.27 (d, J = 9.67 Hz, 1 H) 8.39-8.62 (m, 3 H) 11.84 (br. s., 1 H) |
| 907 | 1-(3'-(difluoromethoxy)-2-fluoro-5-methoxy-4-biphenylyl)-N-(5-fluoro-2-pyrimidinyl)-2-oxo-1,2-dihydro-6-quinolinesulfonamide | 585 | 141 | 0.191 | | 1H NMR (500 MHz, DMSO-d6) δ ppm 3.74 (s, 3 H) 3.84-3.84 (m, 1 H) 6.81 (d, J = 9.67 Hz, 1 H) 6.86 (d, J = 8.95 Hz, 1 H) 7.29 (d, J = 7.46 Hz, 1 H) 7.35 (t, J = 73.96 Hz, 1 H) 7.39-7.67 (m, 6 H) 7.98 (dd, J = 9.02, 2.14 Hz, 1 H) 8.26 (d, J = 9.73 Hz, 1 H) 8.48 (d, J = 1.95 Hz, 1 H) 8.62 (s, 2 H) 11.96 (br. s., 1 H) |
| 908 | 1-(3,3'-dimethoxy-4'-methyl-4-biphenylyl)-2-oxo-N-2-pyrimidinyl-1,2-dihydro-6-quinolinesulfonamide | 527 | 141 | 0.243 | | 1H NMR (500 MHz, DMSO-d6) δ ppm 2.21 (s, 3 H) 3.77 (s, 3 H) 3.92 (s, 3 H) 6.79 (d, J = 9.47 Hz, 2 H) 7.05 (br. s., 1 H) 7.25-7.31 (m, 3 H) 7.35 (d, J = 7.98 Hz, 1 H) 7.44 (d, J = 8.04 Hz, 1 H) 7.50 (s, 1 H) 7.99 (dd, J = 8.99, 1.85 Hz, 1 H) 8.25 (d, J = 9.73 Hz, 1 H) 8.41-8.57 (m, 3 H) 11.83 (br. s., 1 H) |
| 909 | 1-(3,3'-dimethoxy-4'-methyl-4-biphenylyl)-N-(5-fluoro-2-pyrimidinyl)-2-oxo-1,2-dihydro-6-quinolinesulfonamide | 545 | 141 | 0.166 | | 1H NMR (500 MHz, DMSO-d6) δ ppm 2.21 (s, 3 H) 3.77 (s, 3 H) 3.92 (s, 3 H) 6.80 (d, J = 9.41 Hz, 2 H) 7.23-7.31 (m, 3 H) 7.35 (d, J = 8.04 Hz, 1 H) 7.40-7.47 (m, 1 H) 7.50 (d, J = 1.30 Hz, 1 H) 7.97 (dd, J = 9.02, 2.08 Hz, 1 H) 8.24 (d, J = 9.67 Hz, 1 H) 8.47 (d, J = 1.95 Hz, 1 H) 8.61 (s, 2 H) 11.94 (br. s., 1 H) |
| 910 | 1-(3,3'-dimethoxy-4'-methyl-4-biphenylyl)-2-oxo-N-3-pyridazinyl-1,2-dihydro-6-quinolinesulfonamide | 527 | 141 | 0.143 | | 1H NMR (500 MHz, DMSO-d6) δ ppm 2.21 (s, 3 H) 3.77 (s, 3 H) 3.92 (s, 3 H) 6.75 (d, J = 9.08 Hz, 1 H) 6.78 (d, J = 9.60 Hz, 1 H) 7.24-7.32 (m, 3 H) 7.34 (d, J = 7.98 Hz, 1 H) 7.44 (d, J = 8.04 Hz, 1 H) 7.50 (s, 1 H) 7.68 (d, J = 6.03 Hz, 1 H) 7.85 (d, J = 7.07 Hz, 1 H) 8.19 (d, J = 9.67 Hz, 1 H) 8.34 (br. s., 1 H) 14.48 (br. s., 1 H) |
| 911 | 1-(3,3'-dimethoxy-4'-methyl-4-biphenylyl)-N-(2-methyl-4-pyrimidinyl)-2-oxo-1,2-dihydro-6-quinolinesulfonamide | 541 | 141 | 0.296 | | 1H NMR (400 MHz, DMSO-d6) δ ppm 2.21 (s, 3 H) 2.37 (s, 3 H) 3.77 (s, 3 H) 3.92 (s, 3 H) 6.71-6.82 (m, 2 H) 7.24-7.30 (m, 3 H) 7.34 (d, J = 7.98 Hz, 1 H) 7.40-7.47 (m, 1 H) 7.50 (d, J = 1.76 Hz, 1 H) 7.88 (d, J = 10.88 Hz, 1 H) 8.21 (d, J = 9.64 Hz, 1 H) 8.38 (s, 1 H) |
| 912 | 1-(3,3'-dimethoxy-4'-methyl-4-biphenylyl)-N-(6-methyl-4-pyrimidinyl)-2-oxo-1,2-dihydro-6-quinolinesulfonamide | 541 | 141 | 0.198 | | 1H NMR (400 MHz, DMSO-d6) δ ppm 2.21 (s, 3 H) 2.31 (s, 3 H) 3.76 (s, 3 H) 3.92 (s, 3 H) 6.73-6.82 (m, 2 H) 6.90 (br. s., 1 H) 7.25-7.30 (m, 3 H) 7.35 (d, J = 8.09 Hz, 1 H) 7.41-7.46 (m, 1 H) 7.49 (d, J = 1.76 Hz, 1 H) 7.91 (dd, J = 8.97, 2.12 Hz, 1 H) 8.22 (d, J = 9.64 Hz, 1 H) 8.41 (s, 1 H) 8.49 (s, 1 H) |
| 913 | 1-(3'-(difluoromethoxy)-2-fluoro-5-methoxy-4-biphenylyl)-N-(2-methyl-4-pyrimidinyl)-2-oxo-1,2-dihydro-6-quinolinesulfonamide | 581 | 141 | 0.028 | | 1H NMR (400 MHz, DMSO-d6) δ ppm 2.31 (s, 3 H) 3.68 (s, 3 H) 6.72 (d, J = 9.64 Hz, 1 H) 6.74 (d, J = 8.71 Hz, 1 H) 7.21-7.25 (m, 1 H) 7.29 (t, J = 74.01 Hz, 1 H) 7.35 (d, J = 7.05 Hz, 1 H) 7.42-7.59 (m, 4 H) 7.83 (dd, J = 8.81, 1.87 Hz, 1 H) 8.05 (br. s., 1 H) 8.17 (d, J = 9.64 Hz, 1 H) 8.32 (s, 1 H) |
| 914 | 1-(2-fluoro-3',5,5'-trimethoxy-4-biphenylyl)-N-(6-methyl-4-pyrimidinyl)-2-oxo-1,2-dihydro-6-quinolinesulfonamide | 575 | 141 | | | 1H NMR (400 MHz, DMSO-d6) δ ppm 1.75 (s, 3 H) 3.73 (s, 3 H) 3.83 (s, 6 H) 6.61 (t, J = 2.23 Hz, 1 H) 6.74-6.85 (m, 4 H) 7.27 (br. s., 1 H) 7.37 (d, J = 6.89 Hz, 1 H) 7.46 (d, J = 10.31 Hz, 1 H) 7.89 (dd, J = 8.91, 2.07 Hz, 1 H) 8.12 (d, J = 5.96 Hz, 1 H) 8.23 (d, J = 9.64 Hz, 1 H) 8.39 (d, J = 1.87 Hz, 1 H) |
| 698 | 1-(2-fluoro-3',5-dimethoxy-4'-methyl-4-biphenylyl)-N-3-isoxazolyl-2-oxo-1,2-dihydro-6-quinolinesulfonamide | 536.2 | 139 | 0.014 | >10.0 | $^1$H NMR (400 MHz, DMSO-d$_6$) δ ppm 2.23 (s, 3 H) 3.74 (s, 3 H) 3.89 (s, 3 H) 6.46 (d, J = 4.68 Hz, 1 H) 6.83 (d, J = 9.64 Hz, 1 H) 6.90 (d, J = 9.12 Hz, 1 H) 7.13-7.24 (m, 2 H) 7.30 (d, J = 7.77 Hz, 1 H) 7.38 (d, J = 6.95 Hz, 1 H) 7.49 (d, J = 10.37 Hz, 1 H) 7.88 (dd, J = 8.91, 2.28 Hz, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | | | | | | 1 H) 8.24 (d, J = 9.74 Hz, 1 H) 8.39 (d, J = 2.07 Hz, 1 H) 8.75 (d, J = 4.71 Hz, 1 H) 11.68 (s, 1 H). |
| 656 | 1-(5-chloro-2-methoxy-4-(trifluoromethyl)phenyl)-2-oxo-N-4-pyrimidinyl-1,2-dihydro-6-quinolinesulfonamide | 510.9 | 200 | 0.123 | | : $^1$H NMR (400 MHz, DMSO-d$_6$) δ 8.61 (s, 1H), 8.45 (br. s, 1H), 8.30 (br. s, 1H), 8.26 (d, J = 8.0 Hz, 1H), 7.92 (m, 2H), 7.69 (s, 1H), 7.02 (br. s, 1H), 6.80 (m, 2H), 3.80 (s, 3H). m/z (ESI) 510.9 (M + H)$^+$. |
| 657 | 1-(5-chloro-2-methoxy-4-(trifluoromethyl)phenyl)-2-oxo-N-4-pyrimidinyl-1,2-dihydro-6-quinolinesulfonamide | 510.9 | 200 | | | $^1$H NMR (400 MHz, DMSO-d$_6$) δ 8.62 (s, 1H), 8.45 (s, 1H), 8.30 (br. s, 1H), 8.26 (d, J = 8.0 Hz, 1H), 7.92 (m, 2H), 7.69 (s, 1H), 7.02 (br. s, 1H), 6.80 (m, 2H), 3.80 (s, 3H). m/z (ESI) 510.9 (M + H)$^+$. |
| 658 | 1-(4'-chloro-3-methoxy-3'-methyl-4-biphenylyl)-2-oxo-N-4-pyrimidinyl-1,2-dihydro-6-quinolinesulfonamide | 532.8 | 201 | 0.01 | | 1H NMR (400 MHz, DMSO-d6) δ 8.61 (s, 1H), 8.42 (d, J = 2.07 Hz, 1H), 8.30 (d, J = 5.91 Hz, 1H), 8.23 (d, J = 9.54 Hz, 1H), 7.92 (dd, J = 2.18, 8.91 Hz, 1H), 7.84 (d, J = 1.97 Hz, 1H), 7.61-7.72 (m, 1H), 7.51-7.59 (m, 2H), 7.41-7.48 (m, 1H), 7.34-7.40 (m, 1H), 7.01 (d, J = 6.01 Hz, 1H), 6.77-6.82 (m, 1H), 6.73-6.77 (m, 1H), 3.78 (s, 3H), 2.45 (s, 3H). |
| 671 | 1-(3-methoxy-3'-(trifluoromethyl)-4-biphenylyl)-2-oxo-N-4-pyrimidinyl-1,2-dihydro-6-quinolinesulfonamide | 553.1 | 73 | 0.011 | | $^1$H NMR (400 MHz, DMSO-d$_6$) δ = 8.62-8.51 (m, 1 H), 8.42-8.33 (m, 1 H), 8.32-8.14 (m, 2 H), 8.08 (s, 2 H), 7.91-7.81 (m, 1 H), 7.78-7.67 (m, 2 H), 7.56 (d, J = 1.8 Hz, 1 H), 7.50-7.43 (m, 1 H), 7.38 (s, 1 H), 7.02-6.91 (m, 1 H), 6.77-6.66 (m, 2 H), 3.74 (s, 3 H). |
| 915 | 1-(3-methoxy-3'-(trifluoromethyl)-4-biphenylyl)-2-oxo-N-2-pyrazinyl-1,2-dihydro-6-quinolinesulfonamide | 553.1 | 73 | 0.031 | | $^1$H NMR (400 MHz, DMSO-d$_6$) δ = 11.83-11.38 (m, 1 H), 8.52-8.45 (m, 1 H), 8.40-8.32 (m, 1 H), 8.29-8.21 (m, 3 H), 8.16-8.09 (m, 2 H), 8.00-7.88 (m, 1 H), 7.85-7.71 (m, 2 H), 7.64-7.58 (m, 1 H), 7.56-7.48 (m, 1 H), 7.47-7.37 (m, 1 H), 6.90-6.72 (m, 2 H), 3.79 (s, 3 H). |
| 916 | 1-(3-methoxy-3'-(trifluoromethyl)-4-biphenylyl)-N-1,3-oxazol-2-yl-2-oxo-1,2-dihydro-6-quinolinesulfonamide | 542.2 | 73 | 0.05 | | $^1$H NMR (400 MHz, DMSO-d$_6$) δ = 12.16 (br. s., 1 H), 8.32 (d, J = 2.1 Hz, 1 H), 8.21-8.09 (m, 3 H), 7.87-7.74 (m, 3 H), 7.63-7.50 (m, 3 H), 7.42 (d, J = 8.1 Hz, 1 H), 7.24 (d, J = 1.7 Hz, 1 H), 6.81-6.70 (m, 2 H), 4.02 (q, J = 7.2 Hz, 1 H), 3.80 (s, 3 H), 3.31 (s, 3 H), 2.51-2.48 (m, 7 H), 1.98 (s, 1 H), 1.17 (t, J = 7.1 Hz, 1 H). |
| 917 | N-(5-fluoro-2-pyrimidinyl)-1-(3-methoxy-3'-(trifluoromethyl)-4-biphenylyl)-2-oxo-1,2-dihydro-6-quinolinesulfonamide | 571.1 | 73 | 0.031 | | $^1$H NMR (400 MHz, DMSO-d$_6$) δ = 11.97 (s, 1 H), 8.63 (d, J = 1.9 Hz, 2 H), 8.48 (s, 1 H), 8.27 (dd, J = 1.8, 9.8 Hz, 1 H), 8.14 (d, J = 5.5 Hz, 2 H), 8.14 (s, 1 H), 7.97 (d, J = 9.1 Hz, 1 H), 7.84-7.75 (m, 2 H), 7.62 (s, 1 H), 7.53 (d, J = 8.4 Hz, 1 H), 7.43 (d, J = 7.7 Hz, 1 H), 6.80 (t, J = 9.7 Hz, 2 H), 3.80 (s, 3 H). |
| 918 | N-(5-fluoro-2-pyridinyl)-1-(3-methoxy-3'-(trifluoromethyl)-4-biphenylyl)-2-oxo-1,2-dihydro-6-quinolinesulfonamide | 570.2 | 73 | 0.093 | | $^1$H NMR (400 MHz, DMSO-d$_6$) δ = 11.19 (br. s., 1 H), 8.41 (d, J = 2.2 Hz, 1 H), 8.26-8.09 (m, 4 H), 7.90 (dd, J = 2.2, 9.0 Hz, 1 H), 7.84-7.75 (m, 2 H), 7.70-7.60 (m, 2 H), 7.52 (d, J = 7.7 Hz, 1 H), 7.43 (d, J = 8.1 Hz, 1 H), 7.11 (dd, J = 3.6, 9.0 Hz, 1 H), 6.81 (d, J = 9.6 Hz, 1 H), 6.78 (d, J = 8.9 Hz, 1 H), 3.80 (s, 3 H). |
| 919 | 1-(3-methoxy-3'-(trifluoromethyl)-4-biphnylyl)-N-1,2,4-oxadiazol-3-yl-2-oxo-1,2-dihydro-6-quinolinesulfonamide | 543.0 | 74 | 0.022 | | $^1$H NMR (400 MHz, DMSO-d$_6$) δ = 8.45 (d, J = 2.2 Hz, 1 H), 8.28 (d, J = 9.5 Hz, 1 H), 8.15 (d, J = 5.6 Hz, 2 H), 8.14 (s, 1 H), 8.01-7.89 (m, 2 H), 7.85-7.75 (m, 2 H), 7.63 (d, J = 1.8 Hz, 1 H), 7.53 (dd, J = 1.9, 8.1 Hz, 1 H), 7.45 (d, J = 8.1 Hz, 1 H), 6.83 (dd, J = 3.2, 9.3 Hz, 2 H), 3.81 (s, 3 H). |
| 920 | 1-(3'-chloro-2,5'-difluoro-5-methoxy-4-biphenylyl)-N-(5-fluoro-2-pyridinyl)-2-oxo-1,2-dihydro-6-quinolinesulfonamide | 572.0 | 73 | 0.06 | | $^1$H NMR (400 MHz, DMSO-d$_6$) δ = 11.19 (br. s., 1 H), 8.41 (s, 1 H), 8.24 (d, J = 9.6 Hz, 1 H), 8.18 (s, 1 H), 7.90 (d, J = 9.1 Hz, 1 H), 7.69-7.53 (m, 5 H), 7.47 (d, J = 6.6 Hz, 1 H), 7.14-7.09 (m, 1 H), 6.84-6.79 (m, 2 H), 5.76 (d, J = 2.2 Hz, 1 H), 3.75 (s, 3 H). |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 921 | 1-(3'-chloro-2,5'-difluoro-5-methoxy-4-biphenylyl)-N-3-isothiazolyl-2-oxo-1,2-dihydro-6-quinolinesulfonamide | 560.1 | 73 | 0.037 | | $^1$H NMR (400 MHz, DMSO-d$_6$) δ = 11.19 (br. s., 1 H), 8.41 (s, 1 H), 8.24 (d, J = 9.6 Hz, 1 H), 8.18 (s, 1 H), 7.90 (d, J = 9.1 Hz, 1 H), 7.69-7.53 (m, 5 H), 7.47 (d, J = 6.6 Hz, 1 H), 7.14-7.09 (m, 1 H), 6.84-6.79 (m, 2 H), 5.76 (d, J = 2.2 Hz, 1 H), 3.75 (s, 3 H). |
| 922 | 1-(3'-chloro-2,5'-difluoro-5-methoxy-4-biphenylyl)-2-oxo-N-1,2,5-thiadiazol-3-yl-1,2-dihydro-6-quinolinesulfonamide | 561.0 | 73 | 0.004 | | $^1$H NMR (400 MHz, DMSO-d$_6$) δ = 11.19 (br. s., 1 H), 8.41 (s, 1 H), 8.24 (d, J = 9.6 Hz, 1 H), 8.18 (s, 1 H), 7.90 (d, J = 9.1 Hz, 1 H), 7.69-7.53 (m, 5 H), 7.47 (d, J = 6.6 Hz, 1 H), 7.14-7.09 (m, 1 H), 6.84-6.79 (m, 2 H), 5.76 (d, J = 2.2 Hz, 1 H), 3.75 (s, 3 H). |
| 923 | 1-(3'-chloro-3,5'-dimethoxy-4-biphenylyl)-N-2-pyrimidinyl-1,2-dihydro-6-quinolinesulfonamide | 549.2 | 73 | 0.012 | | $^1$H NMR (400 MHz, DMSO-d$_6$) δ = 11.19 (br. s., 1 H), 8.41 (s, 1 H), 8.24 (d, J = 9.6 Hz, 1 H), 8.18 (s, 1 H), 7.90 (d, J = 9.1 Hz, 1 H), 7.69-7.53 (m, 5 H), 7.47 (d, J = 6.6 Hz, 1 H), 7.14-7.09 (m, 1 H), 6.84-6.79 (m, 2 H), 5.76 (d, J = 2.2 Hz, 1 H), 3.75 (s, 3 H). |
| 924 | 1-(3'-chloro-2-fluoro-5,5'-dimethoxy-4-biphenylyl)-2-oxo-N-2-pyrimidinyl-1,2-dihydro-6-quinolinesulfonamide | 567.2 | 73 | 0.014 | >10.0 | $^1$H NMR (400 MHz, DMSO-d$_6$) δ = 11.19 (br. s., 1 H), 8.41 (s, 1 H), 8.24 (d, J = 9.6 Hz, 1 H), 8.18 (s, 1 H), 7.90 (d, J = 9.1 Hz, 1 H), 7.69-7.53 (m, 5 H), 7.47 (d, J = 6.6 Hz, 1 H), 7.14-7.09 (m, 1 H), 6.84-6.79 (m, 2 H), 5.76 (d, J = 2.2 Hz, 1 H), 3.75 (s, 3 H). |
| 925 | 1-(3'-chloro-3,5'-dimethoxy-4-biphenylyl)-N-1,3-oxazol-2-yl-2-oxo-1,2-dihydro-6-quinolinesulfonamide | 538.1 | 73 | 0.022 | | $^1$H NMR (400 MHz, DMSO-d$_6$) δ = 12.16 (br. s., 1 H), 8.33 (d, J = 2.2 Hz, 1 H), 8.19 (d, J = 9.5 Hz, 1 H), 7.86 (dd, J = 2.1, 8.9 Hz, 1 H), 7.62-7.53 (m, 2 H), 7.48 (s, 1 H), 7.49 (d, J = 6.9 Hz, 2 H), 7.39 (d, J = 8.2 Hz, 1 H), 7.33 (s, 1 H), 7.25 (d, J = 1.7 Hz, 1 H), 7.11 (s, 1 H), 6.78 (d, J = 9.6 Hz, 1 H), 6.72 (d, J = 8.9 Hz, 1 H), 3.89 (s, 3 H), 3.80 (s, 3 H). |
| 926 | 1-(3'-chloro-2-fluoro-5,5'-dimethoxy-4-biphenylyl)-N-1,3-oxazol-2-yl-2-oxo-1,2-dihydro-6-quinolinesulfonamide | 556.1 | 73 | 0.006 | | $^1$H NMR (400 MHz, DMSO-d$_6$) δ = 12.18 (br. s., 1 H), 8.34 (s, 1 H), 8.20 (d, J = 9.5 Hz, 1 H), 7.87 (d, J = 9.0 Hz, 1 H), 7.59 (s, 1 H), 7.52 (dd, J = 2.0, 10.3 Hz, 1 H), 7.43 (d, J = 6.6 Hz, 1 H), 7.34 (s, 1 H), 7.24 (t, J = 4.8 Hz, 2 H), 7.16 (d, J = 4.6 Hz, 1 H), 6.79 (d, J = 9.4 Hz, 2 H), 3.88 (d, J = 2.1 Hz, 3 H), 3.78-3.73 (m, 3 H). |
| 927 | 1-(3'-chloro-3,5'-dimethoxy-4-biphenylyl)-N-(5-fluoro-2-pyrimidinyl)-2-oxo-1,2-dihydro-6-quinolinesulfonamide | 567.0 | 73 | 0.015 | | $^1$H NMR (400 MHz, DMSO-d$_6$) δ = 11.97 (s, 1 H), 8.62 (s, 2 H), 8.48 (d, J = 2.2 Hz, 1 H), 8.26 (d, J = 9.5 Hz, 1 H), 7.97 (dd, J = 2.2, 9.0 Hz, 1 H), 7.56 (d, J = 1.9 Hz, 1 H), 7.50-7.46 (m, 2 H), 7.41-7.37 (m, 1 H), 7.33 (s, 1 H), 7.11 (t, J = 2.1 Hz, 1 H), 6.81 (d, J = 9.6 Hz, 1 H), 6.78 (d, J = 9.0 Hz, 1 H), 3.89 (s, 3 H), 3.79 (s, 3 H). |
| 928 | 1-(3'-chloro-3,5'-dimethoxy-4-biphenylyl)-2-oxo-N-3-pyridazinyl-1,2-dihydro-6-quinolinesulfonamide | 549.2 | 73 | 0.008 | | $^1$H NMR (400 MHz, DMSO-d$_6$) δ = 14.46 (br. s., 1 H), 8.42-8.27 (m, 2 H), 8.20 (d, J = 9.5 Hz, 1 H), 7.95-7.81 (m, 2 H), 7.69 (dd, J = 4.1, 9.5 Hz, 1 H), 7.56-7.45 (m, 3 H), 7.42-7.29 (m, 2 H), 7.11 (t, J = 2.0 Hz, 1 H), 6.81-6.70 (m, 2 H), 3.89 (s, 3 H), 3.79 (s, 3 H). |
| 929 | 1-(3'-chloro-2-fluoro-5,5'-dimethoxy-4-biphenylyl)-N-(5-fluoro-2-pyrimidinyl)-2-oxo-1,2-dihydro-6-quinolinesulfonamide | 585.2 | 73 | 0.023 | | $^1$H NMR (400 MHz, DMSO-d$_6$) δ = 8.20-8.11 (m, 4 H), 7.81 (dd, J = 2.0, 8.8 Hz, 1 H), 7.49-7.33 (m, 3 H), 7.23 (s, 1 H), 7.15 (s, 1 H), 6.69 (d, J = 9.6 Hz, 1 H), 6.62 (d, J = 9.1 Hz, 1 H), 3.88 (s, 3 H), 3.74 (s, 3 H). |
| 930 | 1-(3'-chloro-2-fluoro-5,5'-dimethoxy-4-biphenylyl)-2-oxo-N-3-pyridazinyl-1,2-dihydro-6-quinolinesulfonamide | 567.0 | 73 | 0.014 | | $^1$H NMR (400 MHz, DMSO-d$_6$) δ = 14.30 (br. s., 1H), 8.40-8.29 (m, 2H), 8.20 (d, J = 9.5 Hz, 1H), 7.92-7.83 (m, 2H), 7.68 (dd, J = 4.1, 9.6 Hz, 1H), 7.52-7.31 (m, 3H), 7.24-7.19 (m, 1H), 7.15 (s, 1H), 6.78 (d, J = 9.3 Hz, 2H), 3.86 (s, 3H), 3.74 (s, 3H). |
| 931 | 1-(4'-chloro-2-fluoro-5-methoxy-3'-methyl-4-biphenylyl)-N-(5-methyl-3-isoxazolyl)-2-oxo-1,2-dihydro-6-quinolinesulfonamide | 554.2 | 73 | 0.128 | | $^1$H NMR (400 MHz, DMSO-d$_6$) δ = 11.52 (s, 1 H), 8.36 (d, J = 2.2 Hz, 1 H), 8.24 (d, J = 9.5 Hz, 1 H), 7.86 (dd, J = 2.2, 9.0 Hz, 1 H), 7.70 (s, 1 H), 7.61-7.50 (m, 3 H), 7.39 (d, J = 6.9 Hz, 1 H), 6.88 (d, J = 9.0 Hz, 1 H), 6.83 (d, J = 9.6 Hz, 1 H), 6.16 (s, 1 H), 3.75 (s, 3 H), 2.45 (s, 3 H), 2.30 (d, J = 0.8 Hz, 3 H). |
| 932 | 1-(4'-chloro-2-fluoro-5-methoxy-3'-methyl-4-biphenylyl)-2-oxo- | 556.1 | 73 | 0.078 | | $^1$H NMR (400 MHz, DMSO-d$_6$) δ = 11.17 (s, 1 H), 8.88 (d, J = 2.2 Hz, 1 H), 8.33 (d, J = 2.2 Hz, 1 H), 8.20 (d, J = 9.5 Hz, 1 H), 7.85 (dd, J = 2.2, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | N-1,3-thiazol-4-yl-1,2-dihydro-6-quinolinesulfonamide | | | | | 9.0 Hz, 1 H), 7.70 (s, 1 H), 7.62-7.48 (m, 3 H), 7.39 (d, J = 6.9 Hz, 1 H), 7.08 (d, J = 2.1 Hz, 1 H), 6.84 (d, J = 8.9 Hz, 1 H), 6.80 (d, J = 9.5 Hz, 1 H), 3.74 (s, 3 H), 2.45 (s, 3 H). |
| 933 | 1-(3'-chloro-2,5'-difluoro-5-methoxy-4-biphenylyl)-N-(6-methyl-4-pyrimidinyl)-2-oxo-1,2-dihydro-6-quinolinesulfonamide | 569.2 | 73 | 0.008 | | $^1$H NMR (400 MHz, DMSO-d$_6$) δ = 8.49 (br. s., 1H), 8.43 (br. s., 1H), 8.24 (d, J = 9.8 Hz, 1H), 7.91 (d, J = 7.5 Hz, 1H), 7.68-7.52 (m, 4H), 7.48 (d, J = 6.9 Hz, 1H), 6.83-6.72 (m, 2H), 3.80-3.71 (m, 3H), 2.32 (br. s., 3H). |
| 934 | 1-(3'-chloro-2,5'-difluoro-5-methoxy-4-biphenylyl)-N-(2-methyl-4-pyrimidinyl)-2-oxo-1,2-dihydro-6-quinolinesulfonamide | 569.2 | 73 | 0.006 | | $^1$H NMR (400 MHz, DMSO-d$_6$) δ = 8.48-8.31 (m, 1H), 8.22 (d, J = 9.5 Hz, 1H), 8.11 (br. s., 1H), 7.88 (dd, J = 2.1, 8.9 Hz, 1H), 7.68-7.42 (m, 5H), 6.88 (br. s., 1H), 6.78 (d, J = 9.7 Hz, 2H), 5.74 (s, 1H), 3.74 (s, 3H), 2.36 (s, 3H) |
| 935 | 2-oxo-N-2-pyrimidinyl-1-(2,3',4'-trifluoro-5-methoxy-4-biphenylyl)-1,2-dihydro-6-quinolinesulfonamide | 539.1 | 141 | 0.022 | | $^1$H NMR (400 MHz, DMSO-d$_6$) δ = 12.26-10.98 (m, 1H), 8.49 (br. s., 3H), 8.37-8.18 (m, 1H), 8.08-7.91 (m, 1H), 7.90-7.75 (m, J = 17.9 Hz, 1H), 7.71-7.33 (m, 4H), 7.16-6.97 (m, 1H), 6.94-6.59 (m, 2H), 3.73 (br. s., 5H). |
| 589 | 2-oxo-N-3-pyridazinyl-1-(2,3',4'-trifluoro-5-methoxy-4-biphenylyl)-1,2-dihydro-6-quinolinesulfonamide | 539.0 | 141 | 0.016 | | $^1$H NMR (400 MHz, DMSO-d$_6$) δ = 14.5 (br. s, 1H), 8.52-8.06 (m, 3H), 8.01-7.76 (m, 3H), 7.76-7.30 (m, 5H), 6.91-6.62 (m, 2H), 3.73 (br. s., 3H). |
| 936 | N-1,3-oxazol-2-yl-2-oxo-1-(2,3',4'-trifluoro-5-methoxy-4-biphenylyl)-1,2-dihydro-6-quinolinesulfonamide | 528.0 | 141 | 0.041 | | $^1$H NMR (400 MHz, DMSO-d$_6$) δ = 12.42-11.86 (m, 1H), 8.46-8.29 (m, 1H), 8.27-8.16 (m, 1H), 7.98-7.75 (m, 2H), 7.74-7.38 (m, 5H), 7.35-7.19 (m, 1H), 6.93-6.60 (m, 2H), 3.76 (br. s., 3H). |
| 937 | N-(5-fluoro-2-pyrimidinyl)-2-oxo-1-(2,3',4'-trifluoro-5-methoxy-4-biphenylyl)-1,2-dihydro-6-quinolinesulfonamide | 557.0 | 141 | 0.029 | | $^1$H NMR (400 MHz, DMSO-d$_6$) δ = 11.94 (br. s., 1H), 8.58 (s, 2H), 8.48-8.37 (m, 1H), 8.27-8.12 (m, 1H), 8.01-7.85 (m, 1H), 7.84-7.67 (m, 1H), 7.65-7.46 (m, 3H), 7.45-7.33 (m, 1H), 6.85-6.65 (m, 2H), 3.75 (m, 3H). |
| 938 | N-(6-methyl-4-pyrimidinyl)-2-oxo-1-(2,3',4'-trifluoro-5-methoxy-4-biphenylyl)-1,2-dihydro-6-quinolinesulfonamide | 553.2 | 141 | 0.047 | | $^1$H NMR (400 MHz, DMSO-d$_6$) δ = 8.63-8.38 (m, 2H), 8.28-8.18 (m, 1H), 7.99-7.79 (m, 2H), 7.74-7.30 (m, 5H), 6.82 (br. s., 3H), 3.75 (br. s., 3H), 2.34 (br. s., 3H). |
| 939 | N-(2-methyl-4-pyrimidinyl)-2-oxo-1-(2,3',4'-trifluoro-5-methoxy-4-biphenylyl)-1,2-dihydro-6-quinolinesulfonamide | 553.0 | 141 | 0.041 | | $^1$H NMR (400 MHz, DMSO-d$_6$) δ = 8.72-8.08 (m, 4H), 8.02-7.78 (m, 2H), 7.75-7.37 (m, 4H), 7.15-6.63 (m, 3H), 3.75 (br. s., 3H), 2.39 (br. s., 3H). |
| 940 | 1-(2,4'-difluoro-5-methoxy-3'-methyl-4-biphenylyl)-2-oxo-N-2-pyrimidinyl-1,2-dihydro-6-quinolinesulfonamide | 535.0 | 141 | 0.034 | | $^1$H NMR (400 MHz, DMSO-d$_6$) δ = 8.72-8.08 (m, 4H), 8.02-7.78 (m, 2H), 7.75-7.37 (m, 4H), 7.15-6.63 (m, 3H), 3.75 (br. s., 3H), 2.39 (br. s., 3H). |
| 941 | 1-(2,4'-difluoro-5-methoxy-3'-methyl-4-biphenylyl)-2-oxo-N-3-pyridazinyl-1,2-dihydro-6-quinolinesulfonamide | 535.0 | 141 | 0.017 | | $^1$H NMR (400 MHz, DMSO-d$_6$) δ = 14.51 (br. s., 1H), 8.44 (br. s., 1H), 8.36 (br. s., 1H), 8.32-8.09 (m, 2H), 8.04-7.78 (m, 2H), 7.77-7.60 (m, 2H), 7.55 (br. s., 1H), 7.49 (s, J = 4.7, 4.7 Hz, 1H), 7.46 (s, 1H), 7.42-7.25 (m, 2H), 7.01-6.85 (m, 1H), 6.80 (d, J = 7.8 Hz, 1H), 3.74 (br. s., 3H), 3.40 (br. s., 6H), 2.76 (br. s., 1H), 2.51 (br. s., 4H), 2.35 (br. s., 3H). |
| 942 | 1-(2,4'-difluoro-5-methoxy-3'-methyl-4-biphenylyl)-N-(5-fluoro-2-pyrimidinyl)-2-oxo-1,2-dihydro-6-quinolinesulfonamide | 553.0 | 141 | 0.031 | | $^1$H NMR (400 MHz, DMSO-d$_6$) δ = 12.14-11.76 (m, 1H), 8.63 (s, 2H), 8.55-8.44 (m, 1H), 8.32-8.21 (m, 1H), 8.06-7.93 (m, 1H), 7.67-7.60 (m, 1H), 7.59-7.52 (m, 1H), 7.52-7.46 (m, 1H), 7.41-7.36 (m, 1H), 7.35-7.26 (m, |

TABLE 3-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | quinolinesulfonamide | | | | | 1H), 6.90-6.77 (m, 2H), 3.73 (s, 4H), 2.35 (s, 3H). |
| 943 | 1-(2,4'-difluoro-5-methoxy-3'-methyl-4-biphenylyl)-N-1,3-oxazol-2-yl-2-oxo-1,2-dihydro-6-quinolinesulfonamide | 523.9 | 141 | 0.013 | | $^1$H NMR (400 MHz, DMSO-d$_6$) δ = 12.42-11.74 (m, 1H), 8.36-8.32 (m, 1H), 8.25-8.16 (m, 1H), 7.93-7.82 (m, 1H), 7.67-7.63 (m, 1H), 7.62-7.61 (m, 1H), 7.59-7.53 (m, 1H), 7.50-7.45 (m, 1H), 7.40-7.35 (m, 1H), 7.35-7.30 (m, 1H), 7.29 (d, J = 1.7 Hz, 1H), 6.83-6.74 (m, 2H), 3.75 (s, 3H), 2.37-2.31 (m, 3H). |
| 944 | 1-(2,4'-difluoro-5-methoxy-3'-methyl-4-biphenylyl)-N-(2-methyl-4-pyrimidinyl)-2-oxo-1,2-dihydro-6-quinolinesulfonamide | 549.1 | 141 | 0.027 | | $^1$H NMR (400 MHz, DMSO-d$_6$) δ = 11.62-11.11 (m, 1H), 8.40 (d, J = 2.1 Hz, 1H), 8.23 (d, J = 9.5 Hz, 1H), 8.16-8.09 (m, 1H), 8.03-7.98 (m, 1H), 7.95-7.84 (m, 1H), 7.68-7.60 (m, 1H), 7.59-7.51 (m, 1H), 7.51-7.45 (m, 1H), 7.40-7.34 (m, 1H), 7.34-7.26 (m, 1H), 7.00-6.85 (m, 1H), 6.79 (d, J = 9.5 Hz, 2H), 6.71-6.55 (m, 1H), 3.73 (s, 4H), 2.42-2.37 (m, 3H), 2.36-2.29 (m, 4H). |
| 945 | 1-(2,4'-difluoro-5-methoxy-3'-methyl-4-biphenylyl)-N-(6-methyl-4-pyrimidinyl)-2-oxo-1,2-dihydro-6-quinolinesulfonamide | 549.2 | 141 | 0.034 | | $^1$H NMR (400 MHz, DMSO-d$_6$) δ = 8.51 (s, 1H), 8.45-8.41 (m, 1H), 8.23 (d, J = 9.5 Hz, 1H), 7.95-7.89 (m, 1H), 7.65-7.61 (m, 1H), 7.58-7.50 (m, 1H), 7.48 (d, J = 10.4 Hz, 1H), 7.41-7.34 (m, 1H), 7.34-7.27 (m, 1H), 6.96-6.89 (m, 1H), 6.80 (dd, J = 5.9, 9.3 Hz, 2H), 3.73 (s, 3H), 2.36-2.33 (m, 3H), 2.33-2.30 (m, 3H). |
| 946 | 1-(3-methoxy-3'-(trifluoromethyl)-4-biphenylyl)-N-(6-methyl-4-pyrimidinyl)-2-oxo-1,2-dihydro-6-quinolinesulfonamide | 567.1 | 141 | 0.024 | | $^1$H NMR (400 MHz, DMSO-d$_6$) δ = 8.51 (s, 1H), 8.43 (d, J = 2.0 Hz, 1H), 8.24 (d, J = 9.4 Hz, 1H), 8.16-8.13 (m, 2H), 7.91 (dd, J = 2.2, 8.9 Hz, 1H), 7.83-7.75 (m, 2H), 7.62 (d, J = 1.9 Hz, 1H), 7.53 (d, J = 8.3 Hz, 1H), 7.43 (d, J = 7.7 Hz, 1H), 6.91 (br. s., 1H), 6.82-6.74 (m, 2H), 3.80 (s, 3H), 2.53-2.49 (m, 45H), 2.33 (s, 3H). |
| 947 | 1-(3-methoxy-3'-(trifluoromethyl)-4-biphenylyl)-N-(2-methyl-4-pyrimidinyl)-2-oxo-1,2-dihydro-6-quinolinesulfonamide | 567.1 | 141 | 0.051 | | $^1$H NMR (400 MHz, DMSO-d$_6$) δ = 8.40 (d, J = 2.1 Hz, 1H), 8.29-8.21 (m, 1H), 8.19-8.08 (m, 3H), 7.93-7.86 (m, 1H), 7.85-7.74 (m, 2H), 7.67-7.58 (m, 1H), 7.56-7.48 (m, 1H), 7.47-7.31 (m, 1H), 6.83-6.73 (m, 2H), 6.71-6.66 (m, 1H), 3.80 (s, 3H), 2.39 (s, 3H). |
| 948 | 1-(2,4'-difluoro-5-methoxy-3'-methyl-4-biphenylyl)-N-(5-methyl-1,3,4-thiadiazol-2-yl)-2-oxo-1,2-dihydro-6-quinolinesulfonamide | 555.1 | 141 | 0.1 | | $^1$H NMR (400 MHz, DMSO-d$_6$) δ = 14.11-13.81 (m, 1H), 8.31-8.27 (m, 1H), 8.27-8.16 (m, 1H), 7.87-7.78 (m, 1H), 7.66-7.60 (m, 1H), 7.59-7.52 (m, 1H), 7.51-7.44 (m, 1H), 7.39-7.35 (m, 1H), 7.35-7.27 (m, 1H), 6.86-6.73 (m, 2H), 3.74 (s, 3H), 2.47 (s, 3H), 2.37-2.32 (m, 3H). |
| 590 | 1-(4-chloro-2-(1-methyl-1,2,3,6-tetrahydro-4-pyridinyl)phenyl)-N-3-isoxazolyl-2-oxo-1,2-dihydro-6-quinolinesulfonamide | 496.9 | 142 | | | $^1$H NMR (400 MHz, DMSO-d$_6$) δ = 11.83-11.21 (m, 1H), 10.04-9.51 (m, 1H), 8.67 (d, J = 1.8 Hz, 1H), 8.39-8.26 (m, 1H), 8.24-8.11 (m, 1H), 7.84-7.65 (m, 1H), 7.56 (s, 2H), 7.37 (s, 1H), 6.81-6.64 (m, 2H), 6.38 (d, J = 1.8 Hz, 1H), 5.45-5.30 (m, 1H), 3.71-3.49 (m, 1H), 3.41-3.13 (m, 2H), 3.00-2.72 (m, 1H), 2.64-2.46 (m, 3H), 2.35-2.08 (m, 2H). |
| 949 | 1-(3-methoxy-3'-(trifluoromethyl)-4-biphenylyl)-N-(5-methyl-2-pyrazinyl)-2-oxo-1,2-dihydro-6-quinolinesulfonamide | 567.1 | 141 | 1.24 | | $^1$H NMR (400 MHz, DMSO-d$_6$) δ = 11.38 (br. s., 1H), 8.44 (d, J = 2.2 Hz, 1H), 8.30-8.23 (m, 2H), 8.17-8.11 (m, 3H), 7.91 (dd, J = 2.2, 9.0 Hz, 1H), 7.83-7.75 (m, 2H), 7.62 (d, J = 1.8 Hz, 1H), 7.52 (d, J = 7.7 Hz, 1H), 7.43 (d, J = 8.1 Hz, 1H), 6.80 (t, J = 9.7 Hz, 2H), 3.80 (s, 3H), 2.36 (s, 3H). |
| 950 | 1-(3-methoxy-3'-(trifluoromethyl)-4-biphenylyl)-N-(6-methyl-2-pyrazinyl)-2-oxo-1,2-dihydro-6-quinolinesulfonamide | 567.1 | 141 | 0.099 | | $^1$H NMR (400 MHz, DMSO-d$_6$) δ = 11.49 (br. s., 1H), 8.51 (d, J = 2.2 Hz, 1H), 8.27 (d, J = 9.4 Hz, 1H), 8.19-8.12 (m, 4H), 7.96 (d, J = 9.0 Hz, 1H), 7.84-7.75 (m, 2H), 7.62 (d, J = 1.9 Hz, 1H), 7.53 (d, J = 7.9 Hz, 1H), 7.43 (d, J = 8.2 Hz, 1H), 6.81 (dd, J = 4.1, 9.3 Hz, 2H), 3.79 (s, 3H), 2.34 (s, 3H). |
| 591 | N-3-isoxazolyl-2-oxo-1-(3'-(trifluoromethyl)-4-biphenylyl)-1,2-dihydro-6-quinolinesulfonamide | 511.9 | 143 | 0.732 | | $^1$H NMR (400 MHz, DMSO-d$_6$) δ = 11.62 (s, 1H), 8.69 (d, J = 1.9 Hz, 1H), 8.35 (d, J = 2.3 Hz, 1H), 8.21 (d, J = 9.5 Hz, 1H), 8.10-8.01 (m, 2H), 7.99-7.94 (m, 2H), 7.83-7.70 (m, 3H), 7.52-7.41 (m, 2H), 6.78 (t, J = 9.0 Hz, 2H), 6.40 (d, J = 1.9 Hz, 1H). |

TABLE 3-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| 592 | 1-(4'-fluoro-3-(1-methyl-1,2,3,6-tetrahydro-4-pyridinyl)-4-biphenylyl)-N-3-isoxazolyl-2-oxo-1,2-dihydro-6-quinolinesulfonamide | 556.9 | 144 | | | $^1$H NMR (400 MHz, DMSO-d$_6$) δ = 11.60 (br. s., 1H), 9.59 (br. s., 1H), 8.68 (d, J = 2.1 Hz, 1H), 8.33 (s, 1H), 8.20 (d, J = 9.6 Hz, 1H), 7.84-7.70 (m, 5H), 7.39-7.26 (m, 3H), 6.80-6.69 (m, 2H), 6.38 (s, 1H), 5.41 (br. s., 1H), 3.31 (d, J = 19.9 Hz, 3H), 3.05-2.72 (m, 1H), 2.65-2.47 (m, 3H), 2.35 (br. s., 1H), 2.32-2.22 (m, 1H). |
| 672 | 1-(3-methoxy-3'-(trifluoromethyl)-4-biphenylyl)-2-oxo-N-2-pyrimidinyl-1,2-dihydro-6-quinolinesulfonamide | 553.1 | 73 | 0.023 | | $^1$H NMR (400 MHz, DMSO-d$_6$) δ = 12.04-11.74 (br s, 1 H), 8.53-8.46 (m, 3 H), 8.26 (d, J = 9.5 Hz, 1 H), 8.15-8.11 (m, 2 H), 7.97 (dd, J = 2.2, 9.0 Hz, 1 H), 7.83-7.74 (m, 2 H), 7.61 (d, J = 1.9 Hz, 1 H), 7.51 (d, J = 7.8 Hz, 1 H), 7.42 (d, J = 8.1 Hz, 1 H), 7.05 (t, J = 4.8 Hz, 1 H), 6.78 (t, J = 8.9 Hz, 2 H), 3.79 (s, 3 H), 2.52-2.47 (m, 8H), 1.17 (s, 1 H). |
| 951 | 1-(2,2'-difluoro-5-methoxy-4-biphenylyl)-N-3-isoxazolyl-2-oxo-1,2-dihydro-6-quinolinesulfonamide | 510.0 | 139 | 0.09 | | 1H NMR (400 MHz, DMSO-d6) Shift 11.68 (s, 1H), 8.74 (d, J = 1.76 Hz, 1H), 8.39 (d, J = 2.18 Hz, 1H), 8.25 (d, J = 9.54 Hz, 1H), 7.90 (dd, J = 2.28, 9.02 Hz, 1H), 7.63 (s, 1H), 7.54 (d, J = 9.64 Hz, 2H), 7.35-7.44 (m, 3H), 6.88 (d, J = 9.02 Hz, 1H), 6.83 (d, J = 9.64 Hz, 1H), 6.46 (d, J = 1.87 Hz, 1H), 3.72 (s, 3H) |
| 952 | 1-(2'-chloro-2-fluoro-5-methoxy-4-biphenylyl)-N-3-isoxazolyl-2-oxo-1,2-dihydro-6-quinolinesulfonamide | 526.1 | 139 | 0.062 | | 1H NMR (400 MHz, DMSO-d6) Shift 11.68 (br. s., 1H), 8.74 (s, 1H), 8.39 (s, 1H), 8.25 (t, J = 17.60 Hz, 1H), 7.90 (d, J = 9.08 Hz, 1H), 7.66 (t, J = 5.60 Hz, 1H), 7.47-7.61 (m, 4H), 7.30 (d, J = 6.10 Hz, 1H), 6.81-6.86 (m, 2H), 6.46 (s, 1H), 3.66-3.72 (s, 3H) |
| 953 | 1-(2-fluoro-5-methoxy-2'-methyl-4-biphenylyl)-N-3-isoxazolyl-2-oxo-1,2-dihydro-6-quinolinesulfonamide | 506.1 | 139 | 0.026 | | 1H NMR (400 MHz, DMSO-d6) Shift 11.68 (s, 1H), 8.74 (d, J = 1.87 Hz, 1H), 8.39 (d, J = 2.28 Hz, 1H), 8.24 (d, J = 9.54 Hz, 1H), 7.89 (dd, J = 2.23, 8.97 Hz, 1H), 7.48 (d, J = 9.43 Hz, 1H), 7.32-7.41 (m, 4H), 7.21 (d, J = 6.63 Hz, 1H), 6.81-6.91 (m, 2H), 6.46 (d, J = 1.76 Hz, 1H), 3.68 (s, 3H), 3.32 (s, 3H) |
| 954 | 1-(2-fluoro-4',5-dimethoxy-4-biphenylyl)-N-3-isoxazolyl-2-oxo-1,2-dihydro-6-quinolinesulfonamide | 522.2 | 139 | 0.071 | | 1H NMR (400 MHz, DMSO-d6) Shift 11.64 (br. s., 1H), 8.72 (s, 1H), 8.36 (s, 1H), 8.21 (d, J = 9.74 Hz, 1H), 7.85 (d, J = 8.81 Hz, 1H), 7.63 (d, J = 7.26 Hz, 1H), 7.46 (s, 1H), 7.32 (d, J = 7.05 Hz, 2H), 7.09 (d, J = 8.81 Hz, 2H), 6.87 (d, J = 9.12 Hz, 1H), 6.80 (d, J = 9.43 Hz, 1H), 6.43 (s, 1H), 3.83 (s, 3H), 3.71 (s, 3H) |
| 955 | 1-(2-fluoro-5-methoxy-2'-(trifluoromethyl)-4-biphenylyl)-N-3-isoxazolyl-2-oxo-1,2-dihydro-6-quinolinesulfonamide | 560.2 | 145 | 0.069 | | 1H NMR (400 MHz, DMSO-d6) Shift 11.68 (br. s., 1H), 8.70 (s, 1H), 8.38 (s, 1H), 8.23 (d, J = 9.43 Hz, 1H), 7.94 (d, J = 7.77 Hz, 2H), 7.84 (t, J = 7.36 Hz, 2H), 7.67-7.77 (m, 2H), 7.62 (d, J = 7.57 Hz, 1H), 7.51 (s, 1H), 7.27 (s, 1H), 6.83 (d, J = 9.64 Hz, 2H), 6.45 (s, 1H), 3.63 (s, 3H) |
| 956 | 1-(2-fluoro-2',5-dimethoxy-4-biphenylyl)-N-3-isoxazolyl-2-oxo-1,2-dihydro-6-quinolinesulfonamide | 522.2 | 145 | 0.099 | | 1H NMR (400 MHz, DMSO-d6) Shift 11.68 (br. s., 1H), 8.67 (s, 1H), 8.35 (d, J = 2.07 Hz, 1H), 8.20 (d, J = 9.74 Hz, 1H), 7.89 (dd, J = 2.23, 8.97 Hz, 1H), 7.38-7.49 (m, 3H), 7.24 (d, J = 6.53 Hz, 1H), 7.19 (d, J = 7.98 Hz, 1H), 7.11 (t, J = 7.44 Hz, 1H), 6.71-6.87 (m, 2H), 6.42 (d, J = 1.66 Hz, 1H), 3.83 (s, 3H), 3.67 (s, 3H) |
| 957 | 1-(3'-fluoro-5,5'-dimethoxy-2-methyl-4-biphenylyl)-2-oxo-N-2-pyrimidinyl-1,2-dihydro-6-quinolinesulfonamide | 547.1 | 147 | 0.023 | | 1H NMR (400 MHz, DMSO-d6) Shift 11.92 (br. s., 1H), 8.47-8.55 (m, 3H), 8.26 (d, J = 9.64 Hz, 1H), 7.95-8.05 (m, 1H), 7.24 (s, 1H), 7.14 (s, 1H), 7.06 (t, J = 5.00 Hz, 1H), 6.84-6.95 (m, 3H), 6.75-6.84 (m, 2H), 3.85 (s, 3H), 3.68 (s, 3H), 2.22 (s, 3H) |
| 958 | 1-(3',4'-difluoro-5-methoxy-2-methyl-4-biphenylyl)-2-oxo-N-2-pyrimidinyl-1,2-dihydro-6-quinolinesulfonamide | 535.1 | 147 | 0.028 | | $^1$H NMR (400 MHz, DMSO-d6) δ 11.92 (br. s., 1H), 8.44-8.57 (m, 3H), 8.26 (d, J = 9.64 Hz, 1H), 8.00 (dd, J = 2.18, 9.02 Hz, 1H), 7.47-7.72 (m, 2H), 7.30-7.43 (m, 1H), 7.25 (s, 1H), 7.15 (s, 1H), 7.06 (t, J = 4.82 Hz, 1H), 6.79 (dd, J = 4.66, 9.23 Hz, 2H), 3.62-3.73 (m, 3H), 2.22 (s, 3H) |
| 595 | 1-(4'-chloro-5-methoxy-2,3'- | 548.2 | 147 | 0.029 | | 1H NMR (400 MHz, DMSO-d6) Shift 11.94 (br. s., 1H), 8.45-8.56 (m, 3H), 8.26 (d, |

TABLE 3-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | dimethyl-4-biphenylyl)-2-oxo-N-2-pyrimidinyl-1,2-dihydro-6-quinolinesulfonamide | | | | | J = 9.64 Hz, 1H), 8.01 (dd, J = 2.18, 8.91 Hz, 1H), 7.43-7.62 (m, 2H), 7.34 (dd, J = 1.92, 8.14 Hz, 1H), 7.24 (s, 1H), 6.94-7.15 (m, 2H), 6.80 (dd, J = 1.71, 9.28 Hz, 2H), 3.67 (s, 3H), 2.43 (s, 3H), 2.20 (s, 3H) |
| 960 | 1-(4'-fluoro-3',5-dimethoxy-2-methyl-4-biphenylyl)-2-oxo-N-2-pyrimidinyl-1,2-dihydro-6-quinolinesulfonamide | 547.2 | 147 | 0.036 | | $^1$H NMR (400 MHz, DMSO-d$_6$) δ 11.94 (br. s., 1H), 8.46-8.56 (m, 3H), 8.26 (d, J = 9.64 Hz, 1H), 8.01 (dd, J = 2.18, 9.02 Hz, 1H), 7.33 (dd, J = 8.24, 11.56 Hz, 1H), 7.24-7.23 (m, J = 7.65 Hz, 2H), 7.14 (s, 1H), 6.92-7.09 (m, 2H), 6.80 (dd, J = 3.06, 9.28 Hz, 2H), 3.92 (s, 3H), 3.68 (s, 3H), 2.22 (s, 3H) |
| 961 | 1-(2'-chloro-5-methoxy-2,3'-dimethyl-4-biphenylyl)-2-oxo-N-2-pyrimidinyl-1,2-dihydro-6-quinolinesulfonamide | 548.2 | 139 | 0.056 | | $^1$H NMR (400 MHz, DMSO-d$_6$) δ 11.94 (br. s., 1H), 8.46-8.56 (m, 3H), 8.27 (dd, J = 2.85, 9.59 Hz, 1H), 8.02 (ddd, J = 2.18, 9.02, 17.31 Hz, 1H), 7.34-7.49 (m, 2H), 7.19-7.30 (m, 2H), 6.94-7.10 (m, 2H), 6.72-6.92 (m, 2H), 3.62 (s, 3H), 2.45 (d, J = 2.28 Hz, 3H), 1.96-2.06 (m, 3H) |
| 962 | 1-(3'-chloro-5-methoxy-2,2'-dimethyl-4-biphenylyl)-2-oxo-N-2-pyrimidinyl-1,2-dihydro-6-quinolinesulfonamide | 548.2 | 139 | 0.017 | | $^1$H NMR (400 MHz, DMSO-d$_6$) δ 11.92 (br. s., 1H), 8.46-8.56 (m, 3H), 8.26 (dd, 7 = 1.97, 9.64 Hz, 1H), 8.01 (t, 7 = 4.89 Hz, 1H), 7.52 (d, J = 7.98 Hz, 1H), 7.35 (dt, J = 3.68, 7.64 Hz, 1H), 7.25 (s, 1H), 7.22 (s, 1H), 6.98-7.11 (m, 2H), 6.81 (s, 1H), 6.79 (s, 1H), 3.54-3.72 (m, 3H), 2.18 (d, J = 17.93 Hz, 3H), 1.97 (s, 3H) |
| 963 | 1-(3'-ethoxy-5-methoxy-2-methyl-4-biphenylyl)-2-oxo-N-2-pyrimidinyl-1,2-dihydro-6-quinolinesulfonamide | 543.2 | 139 | 0.027 | | $^1$H NMR (400 MHz, DMSO-d$_6$) δ 11.94 (br. s., 1H), 8.47-8.55 (m, 3H), 8.26 (d, J = 9.64 Hz, 1H), 8.01 (dd, J = 2.18, 9.02 Hz, 1H), 7.40 (t, J = 7.35 Hz, 1H), 7.22 (s, 1H), 6.93-7.13 (m, 5H), 6.80 (dd, J = 2.44, 9.28 Hz, 2H), 4.11 (q, J = 6.95 Hz, 2H), 3.67 (s, 3H), 2.21 (s, 3H), 1.37 (t, J = 6.95 Hz, 3H) |
| 964 | 1-(2'-fluoro-3',5-dimethoxy-2-methyl-4-biphenylyl)-2-oxo-N-2-pyrimidinyl-1,2-dihydro-6-quinolinesulfonamide | 547.1 | 139 | 0.246 | | $^1$H NMR (400 MHz, DMSO-d$_6$) δ 11.94 (br. s., 1H), 8.45-8.57 (m, 3H), 8.27 (d, J = 9.74 Hz, 1H), 8.03 (dd, J = 2.12, 8.97 Hz, 1H), 7.19-7.34 (m, 3H), 6.92-7.17 (m, 3H), 6.79 (t, J = 8.86 Hz, 2H), 3.91 (s, 3H), 3.60-3.71 (m, 3H), 2.10 (s, 3H) |
| 965 | 1-(2'-fluoro-5,5'-dimethoxy-2-methyl-4-biphenylyl)-2-oxo-N-2-pyrimidinyl-1,2-dihydro-6-quinolinesulfonamide | 547.2 | 139 | 0.074 | | $^1$H NMR (400 MHz, DMSO-d$_6$) δ 11.94 (br. s., 1H), 8.47-8.55 (m, 3H), 8.27 (d, J = 9.54 Hz, 1H), 8.02 (dd, J = 2.23, 8.97 Hz, 1H), 7.24-7.31 (m, 2H), 7.15 (s, 1H), 6.94-7.09 (m, 3H), 6.74-6.86 (m, 2H), 3.82 (s, 3H), 3.66 (s, 3H), 2.12 (s, 3H) |
| 966 | 1-(3',5-dimethoxy-2,4'-dimethyl-4-biphenylyl)-2-oxo-N-2-pyrimidinyl-1,2-dihydro-6-quinolinesulfonamide | 543.2 | 139 | 0.064 | | $^1$H NMR (400 MHz, DMSO-d$_6$) δ 11.94 (br. s., 1H), 8.47-8.55 (m, 3H), 8.26 (d, J = 9.64 Hz, 1H), 8.02 (dd, J = 2.18, 9.02 Hz, 1H), 7.17-7.34 (m, 2H), 6.92-7.14 (m, 4H), 6.81 (t, J = 8.76 Hz, 2H), 3.87 (s, 3H), 3.67 (s, 3H), 2.22 (s, 6H) |
| 967 | 1-(3',5-dimethoxy-2,5'-dimethyl-4-biphenylyl)-2-oxo-N-2-pyrimidinyl-1,2-dihydro-6-quinolinesulfonamide | 543.2 | 139 | 0.014 | | $^1$H NMR (400 MHz, DMSO-d$_6$) δ 11.94 (br. s., 1H), 8.47-8.55 (m, 3H), 8.26 (d, J = 9.54 Hz, 1H), 8.01 (dd, J = 2.23, 8.97 Hz, 1H), 7.21 (s, 1H), 7.03-7.12 (m, 2H), 6.78-6.86 (m, 5H), 3.81 (s, 3H), 3.66 (s, 3H), 2.37 (s, 3H), 2.20 (s, 3H) |
| 968 | 1-(3',5-dimethoxy-2,2'-dimethyl-4-biphenylyl)-2-oxo-N-2-pyrimidinyl-1,2-dihydro-6-quinolinesulfonamide | 543.2 | 139 | 0.057 | | $^1$H NMR (400 MHz, DMSO-d$_6$) δ 11.94 (br. s., 1H), 8.47-8.55 (m, 3H), 8.26 (dd, J = 2.23, 9.59 Hz, 1H), 7.96-8.07 (m, 1H), 7.28 (dt, J = 1.66, 7.88 Hz, 1H), 7.21 (s, 1H), 6.92-7.11 (m, 3H), 6.75-6.87 (m, 3H), 3.86 (d, J = 2.38 Hz, 3H), 3.61 (s, 3H), 2.00 (d, J = 3.52 Hz, 3H), 1.90-1.98 (m, 3H) |
| 969 | 1-(3'-chloro-5,5'-dimethoxy-2-methyl-4-biphenylyl)-2-oxo-N-2-pyrimidinyl-1,2-dihydro-6-quinolinesulfonamide | 564.2 | 139 | 0.005 | | $^1$H NMR (400 MHz, DMSO-d$_6$) δ 11.94 (br. s., 1H), 8.47-8.55 (m, 3H), 8.26 (d, J = 9.64 Hz, 1H), 8.00 (dd, J = 2.18, 8.91 Hz, 1H), 7.24 (s, 1H), 6.99-7.17 (m, 5H), 6.79 (dd, J = 3.37, 9.28 Hz, 2H), 3.86 (s, 3H), 3.68 (s, 3H), 2.21 (s, 3H) |
| 970 | 1-(2'-fluoro-5-methoxy-2,5'-dimethyl-4-biphenylyl)-2-oxo-N-2-pyrimidinyl-1,2- | 531.2 | 139 | 0.024 | | $^1$H NMR (400 MHz, DMSO-d$_6$) δ 11.92 (br. s., 1H), 8.48-8.55 (m, 3H), 8.27 (d, J = 9.54 Hz, 1H), 8.02 (dd, J = 2.18, 9.02 Hz, 1H), 7.19-7.33 (m, 4H), 7.12 (s, 1H), 7.06 (t, J = 4.87 Hz, 1H), 6.80 (d, J = 9.64 Hz, 1H), 6.78 (d, J = 9.02 Hz, 1H), 3.66 (s, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | dihydro-6-quinolinesulfonamide | | | | | 3H), 2.38 (s, 3H), 2.10 (s, 3H) |
| 649 | 1-(4'-chloro-2-fluoro-3',5-dimethyl-4-biphenylyl)-2-oxo-N-2-pyrimidinyl-1,2-dihydro-6-quinolinesulfonamide | 536.2 | 196 | 0.049 | | $^1$H NMR (400 MHz, DMSO-d$_6$) δ 11.92 (br. s., 1H), 8.47-8.55 (m, 3H), 8.32 (d, J = 9.64 Hz, 1H), 8.02 (dd, J = 2.12, 8.97 Hz, 1H), 7.62-7.74 (m, 2H), 7.54-7.60 (m, 1H), 7.49-7.52 (m, 1H), 7.45 (d, J = 11.05 Hz, 1H), 7.03 (t, J = 4.87 Hz, 1H), 6.84 (d, J = 9.64 Hz, 1H), 6.76 (d, J = 9.02 Hz, 1H), 2.43 (s, 3H), 1.91 (s, 3H) |
| 650 | 1-(4'-chloro-2-fluoro-3',5-dimethyl-4-biphenylyl)-2-oxo-N-2-pyrimidinyl-1,2-dihydro-6-quinolinesulfonamide | 536.2 | 196 | 3.801 | | $^1$H NMR (400 MHz, DMSO-d$_6$) δ 11.92 (br. s., 1H), 8.48-8.55 (m, 3H), 8.32 (d, J = 9.64 Hz, 1H), 8.02 (d, J = 8.89 Hz, 1H), 7.62-7.75 (m, 2H), 7.54-7.60 (m, 1H), 7.37-7.54 (m, 2H), 7.04 (t, J = 5.08 Hz, 1H), 6.84 (d, J = 9.64 Hz, 1H), 6.76 (d, J = 8.91 Hz, 1H), 2.43 (s, 3H), 1.89-1.94 (m, 3H) |
| 971 | 1-(4'-chloro-2-fluoro-3',5-dimethyl-4-biphenylyl)-2-oxo-N-4-pyrimidinyl-1,2-dihydro-6-quinolinesulfonamide | 536.2 | 196 | 0.019 | | $^1$H NMR (400 MHz, DMSO-d$_6$) δ δ 12.52 (br. s., 1H), 8.60 (s, 1H), 8.46 (d, J = 2.07 Hz, 1H), 8.22-8.36 (m, 2H), 7.95 (dd, J = 2.18, 8.91 Hz, 1H), 7.70 (d, J = 8.63 Hz, 1H), 7.65-7.68 (m, 1H), 7.42-7.60 (m, 3H), 7.00 (d, J = 6.32 Hz, 1H), 6.84 (d, J = 9.64 Hz, 1H), 6.74 (d, J = 8.91 Hz, 1H), 2.43 (s, 3H), 1.92 (s, 3H) |
| 972 | 1-(4'-chloro-2-fluoro-3',5-dimethyl-4-biphenylyl)-2-oxo-N-4-pyrimidinyl-1,2-dihydro-6-quinolinesulfonamide | 536.2 | 196 | 0.684 | | $^1$H NMR (400 MHz, DMSO-d$_6$) δ 12.52 (br. s., 1H), 8.58 (s, 1H), 8.45 (d, J = 2.07 Hz, 1H), 8.19-8.35 (m, 2H), 7.94 (dd, J = 2.18, 8.91 Hz, 1H), 7.63-7.75 (m, 2H), 7.41-7.61 (m, 3H), 6.97 (d, J = 6.32 Hz, 1H), 6.83 (d, J = 9.64 Hz, 1H), 6.73 (d, J = 9.02 Hz, 1H), 2.43 (s, 3H), 1.91 (s, 3H) |
| 973 | 1-(4'-chloro-2-fluoro-3',5-dimethyl-4-biphenylyl)-2-oxo-N-3-pyridazinyl-1,2-dihydro-6-quinolinesulfonamide | 536.2 | 196 | 0.09 | | $^1$H NMR (400 MHz, DMSO-d$_6$) δ 14.32 (br. s., 1H), 8.40 (d, J = 2.07 Hz, 1H), 8.31-8.37 (m, 1H), 8.26 (d, J = 9.74 Hz, 1H), 7.80-7.99 (m, 2H), 7.63-7.75 (m, 3H), 7.41-7.60 (m, 3H), 6.83 (d, J = 9.64 Hz, 1H), 6.72 (d, J = 8.91 Hz, 1H), 2.43 (s, 3H), 1.92 (s, 3H) |
| 974 | 1-(4'-chloro-2-fluoro-3',5-dimethyl-4-biphenylyl)-2-oxo-N-3-pyridazinyl-1,2-dihydro-6-quinolinesulfonamide | 536.2 | 196 | | | $^1$H NMR (400 MHz, DMSO-d$_6$) δ 14.32 (br. s., 1H), 8.37-8.43 (m, 1H), 8.34 (br. s., 1H), 8.26 (dd, J = 1.87, 9.74 Hz, 1H), 7.89 (t, J = 5.64 Hz, 2H), 7.64-7.73 (m, 3H), 7.41-7.60 (m, 3H), 6.83 (dd, J = 2.23, 9.59 Hz, 1H), 6.72 (d, J = 8.91 Hz, 1H), 2.43 (s, 3H), 1.92 (s, 3H) |
| 975 | 1-(4'-chloro-2-fluoro-3',5-dimethyl-4-biphenylyl)-N-1,3-oxazol-2-yl-2-oxo-1,2-dihydro-6-quinolinesulfonamide | 525.0 | 196 | 0.05 | | $^1$H NMR (400 MHz, DMSO-d$_6$) δ 12.18 (br. s., 1H), 8.38 (d, J = 2.07 Hz, 1H), 8.26 (d, J = 9.54 Hz, 1H), 7.89 (dd, J = 2.18, 8.91 Hz, 1H), 7.49-7.72 (m, 5H), 7.45 (d, J = 10.88 Hz, 1H), 7.29 (d, J = 1.66 Hz, 1H), 6.83 (d, J = 9.54 Hz, 1H), 6.72 (d, J = 8.91 Hz, 1H), 2.44 (s, 3H), 1.93 (s, 3H) |
| 976 | 1-(4'-chloro-2-fluoro-3',5-dimethyl-4-biphenylyl)-N-1,3-oxazol-2-yl-2-oxo-1,2-dihydro-6-quinolinesulfonamide | 525.0 | 196 | 3.518 | | $^1$H NMR (400 MHz, DMSO-d$_6$) δ 12.42 (br. s., 1H), 8.37 (d, J = 2.07 Hz, 1H), 8.25 (d, J = 9.54 Hz, 1H), 7.89 (dd, J = 2.18, 8.91 Hz, 1H), 7.71 (d, J = 8.61 Hz, 1H), 7.66-7.67 (m, 1H), 7.42-7.60 (m, 4H), 7.22 (d, J = 1.55 Hz, 1H), 6.83 (d, J = 9.64 Hz, 1H), 6.71 (d, J = 8.81 Hz, 1H), 2.44 (s, 3H), 1.93 (s, 3H) |
| 977 | 1-(4'-chloro-2-fluoro-5-methoxy-3'-methyl-4-biphenylyl)-7-fluoro-N-3-isoxazolyl-2-oxo-1,2-dihydro-6-quinolinesulfonamide | 559.2 | 139 | 0.013 | | 1H NMR (400 MHz, DMSO-d6) Shift 12.01 (br. s., 1H), 8.67-8.74 (m, 1H), 8.47 (d, J = 7.67 Hz, 1H), 8.25 (d, J = 9.74 Hz, 1H), 7.70 (s, 1H), 7.47-7.62 (m, 3H), 7.37 (d, J = 6.95 Hz, 1H), 6.77 (d, J = 9.64 Hz, 1H), 6.63 (d, J = 11.82 Hz, 1H), 6.38 (d, J = 1.76 Hz, 1H), 3.76 (s, 3H), 2.44 (s, 3H) |
| 652 | 1-(4'-chloro-2-fluoro-5-methoxy-3'-methyl-4-biphenylyl)-N-3-isoxazolyl-2-oxo-1,2-dihydro-6-quinoxalinesulfonamide | 542.0 | 198 | 0.048 | | $^1$H NMR (400 MHz, DMSO-d$_6$) δ 11.81 (s, 1H), 8.81 (d, J = 1.87 Hz, 1H), 8.55 (d, J = 2.18 Hz, 1H), 8.38 (d, J = 2.18 Hz, 1H), 8.01 (dd, J = 2.18, 8.81 Hz, 1H), 7.76 (s, J = 5.42 Hz, 1H), 7.57-7.68 (m, 3H), 7.49 (t, J = 6.97 Hz, 1H), 7.05 (d, J = 8.91 Hz, 1H), 6.55 (d, J = 1.76 Hz, 1H), 3.82-3.87 (m, 3H), 2.50 (s, 3H) |
| 978 | 1-(4'-chloro-2-fluoro-5-methoxy-3'-methyl-4-biphenylyl)-2-oxo-N-2-pyrimidinyl-1,2-dihydro-6-quinoxalinesulfonamide | 553.0 | 198 | 0.023 | | $^1$H NMR (400 MHz, DMSO-d$_6$) δ 11.97 (s, 1H), 8.43-8.57 (m, 4H), 8.07 (dd, J = 2.12, 8.97 Hz, 1H), 7.71 (s, 1H), 7.53-7.61 (m, 3H), 7.44 (d, J = 6.79 Hz, 1H), 7.07 (br. s., 1H), 6.96 (d, J = 8.81 Hz, 1H), 3.74 (s, 3H), 2.42 (s, 3H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 979 | 1-(3'-chloro-2-fluoro-5-methoxy-4'-methyl-4-biphenylyl)-7-fluoro-N-3-isoxazolyl-2-oxo-1,2-dihydro-6-quinolinesulfonamide | 560.2 | 139 | 0.021 | | $^1$H NMR (400 MHz, DMSO-d$_6$) δ 12.01 (s, 1H), 8.45 (t, J = 5.98 Hz, 1H), 8.24 (d, J = 9.74 Hz, 1H), 8.15 (s, 1H), 7.74-7.83 (m, 3H), 7.26-7.44 (m, 3H), 6.77 (d, J = 9.54 Hz, 1H), 6.62 (d, J = 11.92 Hz, 1H), 3.71-3.81 (s, 3H), 2.42 (s, 3H) |
| 980 | 7-fluoro-1-(2-fluoro-5-methoxy-3'-(trifluoromethyl)-4-biphenylyl)-N-3-isoxazolyl-2-oxo-1,2-dihydro-6-quinolinesulfonamide | 578.2 | 139 | 0.022 | | $^1$H NMR (400 MHz, DMSO-d$_6$) δ 12.01 (s, 1H), 8.45 (t, J = 5.98 Hz, 1H), 8.24 (d, J = 9.74 Hz, 1H), 8.15 (s, 1H), 7.74-7.83 (m, 3H), 7.26-7.44 (m, 3H), 6.77 (d, J = 9.54 Hz, 1H), 6.62 (d, J = 11.92 Hz, 1H), 3.71 (s, 3H), 2.42 (s, 3H) |
| 981 | 1-(2,4'-difluoro-5-methoxy-3'-methyl-4-biphenylyl)-7-fluoro-N-3-isoxazolyl-2-oxo-1,2-dihydro-6-quinolinesulfonamide | 542.2 | 139 | 0.014 | 0.496 | $^1$H NMR (400 MHz, DMSO-d$_6$) δ 12.01 (s, 1H), 8.45 (t, J = 5.98 Hz, 1H), 8.24 (d, J = 9.74 Hz, 1H), 8.15 (s, 1H), 7.74-7.83 (m, 3H), 7.26-7.44 (m, 3H), 6.77 (d, J = 9.54 Hz, 1H), 6.62 (d, J = 11.92 Hz, 1H), 3.71 (s, 3H), 2.42 (s, 3H) |
| 982 | 7-fluoro-1-(3-methoxy-3'-(trifluoromethyl)-4-biphenylyl)-2-oxo-N-2-pyrimidinyl-1,2-dihydro-6-quinolinesulfonamide | 571.0 | 139 | 0.038 | | $^1$H NMR (400 MHz, DMSO-d$_6$) δ 12.41 (s, 1H), 8.46-8.57 (m, 3H), 8.30 (d, J = 9.74 Hz, 1H), 8.13 (s, 2H), 7.70-7.88 (m, 2H), 7.60 (d, J = 1.76 Hz, 1H), 7.42-7.54 (m, 2H), 7.05 (s, 1H), 6.77 (d, J = 9.64 Hz, 1H), 6.43 (d, J = 12.13 Hz, 1H), 3.81 (s, 3H) |
| 651 | 1-(4-bromo-5-fluoro-2-methoxyphenyl)-N-(2-methyl-4-pyrimidinyl)-2-oxo-1,2-dihydro-6-quinolinesulfonamide | 520.0 | 197 | 3.012 | | $^1$H NMR (400 MHz, DMSO-d$_6$) δ 8.24 (d, J = 2.18 Hz, 1H), 8.08 (d, J = 9.54 Hz, 1H), 7.98 (d, J = 6.63 Hz, 1H), 7.72 (dd, J = 2.12, 8.97 Hz, 1H), 7.52 (d, J = 6.22 Hz, 1H), 7.45 (d, J = 8.60 Hz, 1H), 6.74 (s, 1H), 6.63 (dd, J = 5.08, 9.33 Hz, 2H), 3.54 (s, 3H), 2.23 (s, 3H) |
| 983 | 1-(4-bromo-5-fluoro-2-methoxyphenyl)-N-(6-methyl-4-pyrimidinyl)-2-oxo-1,2-dihydro-6-quinolinesulfonamide | 520.0 | 197 | 1.038 | | $^1$H NMR (400 MHz, DMSO-d$_6$) δ 8.35 (s, 1H), 8.27 (d, J = 2.07 Hz, 1H), 8.08 (d, J = 9.43 Hz, 1H), 7.73 (dd, J = 2.18, 8.91 Hz, 1H), 7.52 (d, J = 6.15 Hz, 1H), 7.45 (d, J = 8.22 Hz, 1H), 6.76 (br. s., 1H), 6.64 (dd, J = 5.44, 9.28 Hz, 2H), 3.53 (s, 3H), 2.18 (s, 3H) |
| 984 | 1-(4-bromo-5-fluoro-2-methoxyphenyl)-N-(2-methoxy-4-pyrimidinyl)-2-oxo-1,2-dihydro-6-quinolinesulfonamide | 536.0 | 197 | | | $^1$H NMR (400 MHz, DMSO-d$_6$) δ 8.31 (d, J = 2.18 Hz, 1H), 7.97-8.17 (m, 2H), 7.76 (dd, J = 2.23, 8.97 Hz, 1H), 7.52 (d, J = 9.60 Hz, 1H), 7.47 (d, J = 9.02 Hz, 1H), 6.70 (d, J = 9.02 Hz, 1H), 6.65 (d, J = 9.60 Hz, 1H), 6.46 (d, J = 5.70 Hz, 1H), 3.61 (s, 3H), 3.54 (s, 3H) |
| 985 | 1-(4-bromo-5-fluoro-2-methoxyphenyl)-N-(6-(methoxymethyl)-4-pyrimidinyl)-2-oxo-1,2-dihydro-6-quinolinesulfonamide | 550.0 | 197 | 4.528 | | $^1$H NMR (400 MHz, DMSO-d$_6$) δ 8.40 (s, 1H), 8.27 (s, 1H), 8.09 (d, J = 9.64 Hz, 1H), 7.73 (dd, J = 2.07, 8.91 Hz, 1H), 7.52 (d, J = 6.09 Hz, 1H), 7.46 (d, J = 8.69 Hz, 1H), 7.23-7.36 (m, 1H), 6.96 (br. s., 1H), 6.62-6.70 (m, 2H), 4.22 (s, 2H), 3.54 (s, 3H) |
| 986 | 1-(4-bromo-5-fluoro-2-methoxyphenyl)-N-(6-methoxy-4-pyrimidinyl)-2-oxo-1,2-dihydro-6-quinolinesulfonamide | 536.0 | 197 | 0.312 | | $^1$H NMR (400 MHz, DMSO-d$_6$) δ 8.37-8.47 (m, 2H), 8.25 (d, J = 9.54 Hz, 1H), 7.87 (d, J = 8.50 Hz, 1H), 7.58-7.70 (m, 2H), 6.76-6.86 (m, 2H), 6.38 (s, 1H), 3.85 (s, 3H), 3.69 (s, 3H) |
| 987 | 1-(4-bromo-5-fluoro-2-methoxyphenyl)-N-(1-methyl-2-oxo-1,2-dihydro-4-pyridinyl)-2-oxo-1,2-dihydro-6-quinolinesulfonamide | 535.0 | 197 | | | $^1$H NMR (400 MHz, DMSO-d$_6$) δ 10.97 (s, 1H), 8.40 (d, J = 2.18 Hz, 1H), 8.25 (d, J = 9.54 Hz, 1H), 7.81 (dd, J = 2.23, 8.97 Hz, 1H), 7.61-7.69 (m, 2H), 7.54 (d, J = 7.36 Hz, 1H), 6.89 (d, J = 8.91 Hz, 1H), 6.81 (d, J = 9.64 Hz, 1H), 5.95-6.05 (m, 2H), 3.70 (s, 3H), 3.25 (s, 3H) |
| 988 | 1-(4-bromo-5-fluoro-2-methoxyphenyl)-N-(2-ethyl-4-pyrimidinyl)-2-oxo-1,2-dihydro-6-quinolinesulfonamide | 534.0 | 197 | 0.124 | | $^1$H NMR (400 MHz, DMSO-d$_6$) δ 8.39 (d, J = 15.38 Hz, 1H), 8.14-8.25 (m, 2H), 7.86 (d, J = 8.34 Hz, 1H), 7.67 (d, J = 6.22 Hz, 1H), 7.60 (d, J = 8.53 Hz, 1H), 6.78 (dd, J = 3.32, 9.23 Hz, 3H), 3.69 (s, 3H), 2.64 (q, J = 7.53 Hz, 2H), 1.11 (t, J = 7.57 Hz, 3H) |
| 989 | 1-(4-bromo-5-fluoro-2-methoxyphenyl)-N-(6-methyl-2-pyridinyl)-2-oxo-1,2-dihydro-6-quinolinesulfonamide | 520.0 | 197 | 8.613 | | $^1$H NMR (400 MHz, DMSO-d$_6$) δ 8.34 (d, J = 2.07 Hz, 1H), 8.21 (d, J = 9.54 Hz, 1H), 7.83 (dd, J = 2.13, 8.86 Hz, 1H), 7.57-7.68 (m, 3H), 7.05 (d, J = 8.60 Hz, 1H), 6.76 (dd, J = 4.66, 9.23 Hz, 2H), 6.66 (d, J = 7.26 Hz, 1H), 3.69 (s, 3H), 2.31 (s, 3H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 990 | 1-(4-bromo-5-fluoro-2-methoxyphenyl)-N-(4-methyl-2-pyrimidinyl)-2-oxo-1,2-dihydro-6-quinolinesulfonamide | 520.0 | 197 | 1.564 | | $^1$H NMR (400 MHz, DMSO-d$_6$) δ 11.42 (s, 1H), 8.48 (d, J = 2.18 Hz, 1H), 8.32 (d, J = 5.32 Hz, 1H), 8.26 (d, J = 8.66 Hz, 1H), 7.96 (dd, J = 2.18, 8.91 Hz, 1H), 7.67 (d, J = 6.03 Hz, 1H), 7.61 (d, J = 8.66 Hz, 1H), 6.91 (d, J = 5.18 Hz, 1H), 6.75-6.85 (m, 2H), 3.69 (s, 3H), 2.33 (s, 3H) |
| 991 | 1-(4-bromo-5-fluoro-2-methoxyphenyl)-N-(2,6-dimethyl-4-pyrimidinyl)-2-oxo-1,2-dihydro-6-quinolinesulfonamide | 534.0 | 197 | | | $^1$H NMR (400 MHz, DMSO-d$_6$) δ 8.41 (d, J = 2.07 Hz, 1H), 8.23 (d, J = 9.43 Hz, 1H), 7.87 (dd, J = 2.18, 8.91 Hz, 1H), 7.67 (d, J = 6.22 Hz, 1H), 7.60 (d, J = 8.71 Hz, 1H), 6.72-6.84 (m, 3H), 3.70 (s, 3H), 2.37 (s, 3H), 2.30 (s, 3H) |
| 992 | 1-(4-bromo-5-fluoro-2-methoxyphenyl)-N-(6-methoxy-2-pyridinyl)-2-oxo-1,2-dihydro-6-quinolinesulfonamide | 535.0 | 197 | | | $^1$H NMR (400 MHz, DMSO-d$_6$) δ 11.10 (br. s., 1H), 8.44 (s, 1H), 8.23 (d, J = 9.74 Hz, 1H), 7.90 (d, J = 8.91 Hz, 1H), 7.52-7.70 (m, 3H), 6.75-6.89 (m, 2H), 6.53 (d, J = 7.77 Hz, 1H), 6.36 (d, J = 7.98 Hz, 1H), 3.69 (s, 3H), 3.61 (s, 3H) |
| 993 | 1-(4-bromo-5-fluoro-2-methoxyphenyl)-N-(2-cyano-4-pyridinyl)-2-oxo-1,2-dihydro-6-quinolinesulfonamide | 530.0 | 197 | | | $^1$H NMR (400 MHz, DMSO-d$_6$) δ 11.69 (br. s., 1H), 8.48-8.53 (m, 2H), 8.23 (dd, J = 2.02, 9.69 Hz, 1H), 7.86 (d, J = 9.12 Hz, 1H), 7.67 (dd, J = 2.44, 6.27 Hz, 1H), 7.60 (d, J = 8.66 Hz, 1H), 7.55-7.56 (m, 1H), 7.36-7.39 (m, 1H), 6.80-6.89 (m, 2H), 3.68 (d, J = 2.38 Hz, 3H) |
| 994 | 1-(4-bromo-5-fluoro-2-methoxyphenyl)-N-(4,6-dimethyl-2-pyridinyl)-2-oxo-1,2-dihydro-6-quinolinesulfonamide | 533.0 | 197 | | | $^1$H NMR (400 MHz, DMSO-d$_6$) δ 13.05 (br. s., 1H), 8.39 (br. s., 1H), 8.27 (d, J = 9.74 Hz, 1H), 7.87 (d, J = 7.57 Hz, 1H), 7.72 (d, J = 6.03 Hz, 1H), 7.65 (d, J = 8.08 Hz, 1H), 7.04 (br. s., 1H), 6.81 (d, J = 9.64 Hz, 2H), 6.53 (br. s., 1H), 3.75 (s, 3H), 2.31 (s, 3H), 2.26 (s, 3H) |
| 995 | 1-(4-bromo-5-fluoro-2-methoxyphenyl)-N-(2-(methoxymethyl)-4-pyrimidinyl)-2-oxo-1,2-dihydro-6-quinolinesulfonamide | 550.0 | 197 | | | $^1$H NMR (400 MHz, DMSO-d$_6$) δ 8.54 (br. s., 1H), 8.28 (d, J = 9.64 Hz, 2H), 7.98 (d, J = 8.60 Hz, 1H), 7.73 (d, J = 6.22 Hz, 1H), 7.66 (d, J = 8.60 Hz, 1H), 6.79-6.98 (m, 3H), 4.44 (s, 2H), 3.74 (s, 3H), 3.36 (s, 3H) |
| 996 | 1-(3'-fluoro-3,5'-dimethoxy-4-biphenylyl)-2-oxo-N-2-pyrimidinyl-1,2-dihydro-6-quinolinesulfonamide | 533.2 | 73 | 0.052 | | $^1$H NMR (400 MHz, DMSO-d$_6$) δ 11.62 (br. s., 1H), 8.39-8.45 (m, 3H), 8.18 (d, J = 9.64 Hz, 1H), 7.91 (dd, J = 2.18, 9.02 Hz, 1H), 7.48 (d, J = 1.76 Hz, 1H), 7.41 (dd, J = 1.87, 8.09 Hz, 1H), 7.31 (d, J = 7.98 Hz, 1H), 7.20 (d, J = 9.66 Hz, 1H), 7.13-7.16 (m, 1H), 6.96 (t, J = 5.10 Hz, 1H), 6.84 (td, J = 2.24, 10.96 Hz, 1H), 6.72 (d, J = 9.64 Hz, 1H), 6.69 (d, J = 9.02 Hz, 1H), 3.81 (s, 3H), 3.71 (s, 3H) |
| 997 | 1-(3'-fluoro-3,5'-dimethoxy-4-biphenylyl)-2-oxo-N-3-pyridazinyl-1,2-dihydro-6-quinolinesulfonamide | 533.2 | 73 | 0.066 | | $^1$H NMR (400 MHz, DMSO-d$_6$) δ 14.21 (br. s., 1H), 8.21-8.33 (m, 2H), 8.13 (d, J = 9.54 Hz, 1H), 7.74-7.85 (m, 2H), 7.60 (d, J = 4.15, 9.54 Hz, 1H), 7.47 (d, J = 1.87 Hz, 1H), 7.41 (d, J = 7.74 Hz, 1H), 7.30 (d, J = 8.09 Hz, 1H), 7.13-7.22 (m, 2H), 6.84 (d, J = 10.85 Hz, 1H), 6.71 (d, J = 9.56 Hz, 1H), 6.65 (d, J = 8.98 Hz, 1H), 3.81 (s, 3H), 3.71 (s, 3H) |
| 998 | 1-(3'-fluoro-3,5'-dimethoxy-4-biphenylyl)-N-(5-fluoro-2-pyrimidinyl)-2-oxo-1,2-dihydro-6-quinolinesulfonamide | 551.2 | 73 | 0.089 | | $^1$H NMR (400 MHz, DMSO-d$_6$) δ 11.97 (br. s., 1H), 8.60 (s, 2H), 8.46 (d, J = 2.18 Hz, 1H), 8.25 (d, J = 9.64 Hz, 1H), 7.97 (dd, J = 2.18, 9.02 Hz, 1H), 7.55 (d, J = 1.76 Hz, 1H), 7.49 (d, J = 7.72 Hz, 1H), 7.39 (d, J = 8.09 Hz, 1H), 7.28 (d, J = 9.74 Hz, 1H), 7.21-7.24 (m, 1H), 6.91 (d, J = 10.53 Hz, 1H), 6.80 (d, J = 9.64 Hz, 1H), 6.77 (d, J = 9.02 Hz, 1H), 3.88 (s, 3H), 3.78 (s, 3H) |
| 999 | 1-(3'-chloro-2,5'-difluoro-5-methoxy-4-biphenylyl)-N-(2-ethyl-4-pyrimidinyl)-2-oxo-1,2-dihydro-6-quinolinesulfonamide | 584.2 | 73 | 7.922 | | $^1$H NMR (400 MHz, DMSO-d$_6$) δ 13.01 (br. s., 1H), 8.45 (d, J = 1.76 Hz, 1H), 8.29 (d, J = 9.74 Hz, 1H), 8.19 (d, J = 5.39 Hz, 1H), 7.94 (dd, J = 2.02, 8.97 Hz, 1H), 7.52-7.75 (m, 5H), 6.81-6.94 (m, 3H), 3.81 (s, 3H), 2.69 (q, J = 7.60 Hz, 2H), 1.17 (t, J = 7.52 Hz, 3H) |
| 1000 | 1-(3'-chloro-2,5'-difluoro-5-methoxy-4-biphenylyl)-N-(6-methoxy-4-pyrimidinyl)-2-oxo-1,2-dihydro-6-quinolinesulfonamide | 586.0 | 73 | 0.049 | | $^1$H NMR (400 MHz, DMSO-d$_6$) δ 12.25 (br. s., 1H), 8.30-8.42 (m, 2H), 8.19 (d, J = 9.64 Hz, 1H), 7.84 (dd, J = 2.12, 8.97 Hz, 1H), 7.45-7.62 (m, 4H), 7.41 (d, J = 6.95 Hz, 1H), 6.75 (t, J = 8.63 Hz, 2H), 6.31 (d, J = 0.73 Hz, 1H), 3.78 (s, 3H), 3.68 (s, 3H) |

TABLE 3-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| 653 | 1-(4'-chloro-2-fluoro-5-methoxy-3'-methyl-4-biphenylyl)-N-3-isoxazolyl-2-oxo-1,2-dihydro-6-quinoxalinesulfonamide | 542.0 | 198 | 0.005 | | $^1$H NMR (400 MHz, DMSO-d$_6$) δ 11.76 (br. s., 1H), 8.75 (d, J = 1.76 Hz, 1H), 8.50 (s, 1H), 8.32 (d, J = 2.18 Hz, 1H), 7.95 (dd, J = 2.12, 8.86 Hz, 1H), 7.71 (s, 1H), 7.52-7.62 (m, 3H), 7.44 (d, J = 6.84 Hz, 1H), 7.00 (d, J = 8.91 Hz, 1H), 6.49 (d, J = 1.87 Hz, 1H), 3.78 (s, 3H), 2.45 (s, 3H) |
| 654 | 1-(4'-chloro-2-fluoro-5-methoxy-3'-methyl-4-biphenylyl)-N-3-isoxazolyl-2-oxo-1,2-dihydro-6-quinoxalinesulfonamide | 542.0 | 198 | 0.109 | | 1H NMR (400 MHz, DMSO-d6) Shift 11.76 (br. s., 1H), 8.75 (d, J = 1.76 Hz, 1H), 8.50 (s, 1H), 8.32 (d, J = 2.18 Hz, 1H), 7.95 (dd, J = 2.18, 8.91 Hz, 1H), 7.71 (s, 1H), 7.52-7.62 (m, 3H), 7.44 (d, J = 6.84 Hz, 1H), 7.00 (d, J = 8.91 Hz, 1H), 6.49 (d, J = 1.76 Hz, 1H), 3.78 (s, 3H), 2.45 (s, 3H) |
| 1001 | 1-(4'-chloro-2-fluoro-5-methoxy-3'-methyl-4-biphenylyl)-2-oxo-N-2-pyrimidinyl-1,2-dihydro-6-quinoxalinesulfonamide | 553.2 | 198 | 0.006 | | $^1$H NMR (400 MHz, DMSO-d$_6$) δ 12.01 (br. s., 1H), 8.46-8.55 (m, 3H), 8.43 (s, 1H), 8.06 (t, J = 6.73 Hz, 1H), 7.71 (s, 1H), 7.52-7.62 (m, 3H), 7.43 (d, J = 6.72 Hz, 1H), 7.04 (br. s., 1H), 6.95 (d, J = 8.81 Hz, 1H), 3.77 (s, 3H), 2.45 (s, 3H) |
| 1002 | 1-(4'-chloro-2-fluoro-5-methoxy-3'-methyl-4-biphenylyl)-2-oxo-N-2-pyrimidinyl-1,2-dihydro-6-quinoxalinesulfonamide | 553.2 | 198 | 0.236 | | $^1$H NMR (400 MHz, DMSO-d$_6$) δ 12.01 (br. s., 1H), 8.46-8.55 (m, 3H), 8.43 (s, 1H), 8.06 (t, J = 6.73 Hz, 1H), 7.71 (s, 1H), 7.52-7.62 (m, 3H), 7.43 (d, J = 6.72 Hz, 1H), 7.04 (br. s., 1H), 6.95 (d, J = 8.81 Hz, 1H), 3.77 (s, 3H), 2.45 (s, 3H) |
| 1003 | 1-(3'-fluoro-3,5'-dimethoxy-4-biphenylyl)-N-(2-methyl-4-pyrimidinyl)-2-oxo-1,2-dihydro-6-quinolinesulfonamide | 547.2 | 73 | 1.258 | | $^1$H NMR (400 MHz, DMSO-d$_6$) δ 8.31 (s, 1H), 8.15 (d, J = 9.54 Hz, 1H), 8.04 (br. s., 1H), 7.81 (dd, J = 2.07, 9.02 Hz, 1H), 7.48 (d, J = 1.87 Hz, 1H), 7.41 (dd, J = 1.92, 8.03 Hz, 1H), 7.31 (d, J = 8.09 Hz, 1H), 7.20 (d, J = 9.70 Hz, 1H), 7.14-7.15 (m, 1H), 6.85 (t, J = 5.59 Hz, 1H), 6.82 (t, J = 2.28 Hz, 1H), 6.69-6.73 (m, 1H), 6.66 (d, J = 8.98 Hz, 1H), 3.81 (s, 3H), 3.71 (s, 3H), 2.30 (s, 3H) |
| 1004 | 1-(3'-fluoro-3,5'-dimethoxy-4-biphenylyl)-N-(6-methyl-4-pyrimidinyl)-2-oxo-1,2-dihydro-6-quinolinesulfonamide | 547.2 | 73 | 0.219 | | $^1$H NMR (400 MHz, DMSO-d$_6$) δ 8.41 (s, 1H), 8.34 (d, J = 1.87 Hz, 1H), 8.15 (d, J = 9.64 Hz, 1H), 7.83 (dd, J = 2.13, 8.97 Hz, 1H), 7.47 (d, J = 1.76 Hz, 1H), 7.41 (dd, J = 1.81, 8.14 Hz, 1H), 7.31 (d, J = 7.98 Hz, 1H), 7.20 (d, J = 9.84 Hz, 1H), 7.14-7.15 (m, 1H), 6.77-6.89 (m, 2H), 6.72 (d, J = 9.64 Hz, 1H), 6.67 (d, J = 8.91 Hz, 1H), 3.81 (s, 3H), 3.71 (s, 3H), 2.24 (s, 3H) |
| 1005 | 1-(3'-fluoro-3,5'-dimethoxy-4-biphenylyl)-N-1,3-oxazol-2-yl-2-oxo-1,2-dihydro-6-quinolinesulfonamide | 522.2 | 73 | 0.268 | | $^1$H NMR (400 MHz, DMSO-d$_6$) δ 8.31 (s, 1H), 8.18 (d, J = 9.63 Hz, 1H), 7.86 (d, J = 9.08 Hz, 1H), 7.45-7.61 (m, 3H), 7.38 (dd, J = 2.38, 7.98 Hz, 1H), 7.20-7.30 (m, 2H), 7.14 (br. s., 1H), 6.91 (d, J = 10.12 Hz, 1H), 6.77 (d, J = 9.55 Hz, 1H), 6.70 (d, J = 8.93 Hz, 1H), 3.89 (d, J = 2.38 Hz, 3H), 3.73-3.84 (m, 3H) |
| 1006 | 1-(2',4'-difluoro-3',5-dimethoxy-4-biphenylyl)-2-oxo-N-2-pyrimidinyl-1,2-dihydro-6-quinolinesulfonamide | 551.2 | 73 | 0.076 | | $^1$H NMR (400 MHz, DMSO-d$_6$) δ 8.48-8.54 (m, 3H), 8.28 (d, J = 9.54 Hz, 1H), 8.01 (dd, J = 2.18, 8.91 Hz, 1H), 7.36-7.53 (m, 4H), 7.26 (ddd, J = 1.92, 4.25, 8.45 Hz, 1H), 7.07 (t, J = 4.87 Hz, 1H), 6.86 (d, J = 9.02 Hz, 1H), 6.81 (d, J = 9.64 Hz, 1H), 3.95 (s, 3H), 3.74 (s, 3H) |
| 1007 | 1-(2',4'-difluoro-3',5-dimethoxy-4-biphenylyl)-2-oxo-N-3-pyridazinyl-1,2-dihydro-6-quinolinesulfonamide | 551.2 | 73 | 0.131 | | $^1$H NMR (400 MHz, DMSO-d$_6$) δ 8.21-8.37 (m, 2H), 8.14 (d, J = 9.59 Hz, 1H), 7.78-7.88 (m, 2H), 7.62 (dd, J = 4.15, 9.54 Hz, 1H), 7.28-7.47 (m, 4H), 7.18 (td, J = 2.14, 4.12 Hz, 1H), 6.73 (dd, J = 4.77, 9.23 Hz, 2H), 3.85-3.89 (m, 3H), 3.65-3.69 (m, 3H) |
| 1008 | 1-(2',4'-difluoro-3',5-dimethoxy-4-biphenylyl)-N-(2-methyl-4-pyrimidinyl)-2-oxo-1,2-dihydro-6-quinolinesulfonamide | 565.2 | 73 | 0.21 | | $^1$H NMR (400 MHz, DMSO-d$_6$) δ 11.42 (br. s., 1H), 8.34 (d, J = 2.07 Hz, 1H), 8.17 (d, J = 9.54 Hz, 1H), 8.08 (d, J = 6.55 Hz, 1H), 7.84 (dd, J = 2.07, 8.91 Hz, 1H), 7.28-7.46 (m, 4H), 7.16-7.22 (m, 1H), 6.84 (d, J = 6.32 Hz, 1H), 6.71-6.77 (m, 2H), 3.88 (s, 3H), 3.67 (s, 3H) |
| 1009 | 1-(2',4'-difluoro-3',5-dimethoxy-4-biphenylyl)-N-(6-methyl-4-pyrimidinyl)-2-oxo-1,2-dihydro-6-quinolinesulfonamide | 565.2 | 73 | 0.151 | | $^1$H NMR (400 MHz, DMSO-d$_6$) δ 11.47 (br. s., 1H), 8.52 (s, 1H), 8.44 (s, 1H), 8.25 (dd, J = 1.87, 9.74 Hz, 1H), 7.92-7.96 (m, 1H), 7.36-7.52 (m, 4H), 7.23-7.28 (m, 1H), 6.92 (br. s., 1H), 6.82 (t, J = 9.01 Hz, 2H), 3.95 (d, J = 2.38 Hz, 3H), 3.75 (d, J = 2.28 Hz, 3H), 2.31-2.35 (m, 3H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 1010 | 1-(2,4'-difluoro-3',5-dimethoxy-4-biphenylyl)-N-(5-fluoro-2-pyrimidinyl)-2-oxo-1,2-dihydro-6-quinolinesulfonamide | 569.2 | 73 | 0.074 | | $^1$H NMR (400 MHz, DMSO-d$_6$) δ 11.98 (br. s., 1H), 8.63 (d, J = 0.73 Hz, 2H), 8.49 (d, J = 2.18 Hz, 1H), 8.27 (d, J = 9.54 Hz, 1H), 7.99 (dd, J = 2.23, 8.97 Hz, 1H), 7.36-7.53 (m, 4H), 7.26 (ddd, J = 2.02, 4.22, 8.37 Hz, 1H), 6.86 (d, J = 9.02 Hz, 1H), 6.82 (d, J = 9.64 Hz, 1H), 3.95 (s, 3H), 3.74 (s, 3H) |
| 1011 | 1-(2,4'-difluoro-3',5-dimethoxy-4-biphenylyl)-N-1,3-oxazol-2-yl-2-oxo-1,2-dihydro-6-quinolinesulfonamide | 540.0 | 73 | 0.207 | | $^1$H NMR (400 MHz, DMSO-d$_6$) δ 11.98 (br. s., 1H), 8.63 (d, J = 0.73 Hz, 2H), 8.49 (d, J = 2.18 Hz, 1H), 8.27 (d, J = 9.54 Hz, 1H), 7.99 (dd, J = 2.23, 8.97 Hz, 1H), 7.36-7.53 (m, 4H), 7.26 (ddd, J = 2.02, 4.22, 8.37 Hz, 1H), 6.86 (d, J = 9.02 Hz, 1H), 6.82 (d, J = 9.64 Hz, 1H), 3.95 (s, 3H), 3.74 (s, 3H) |
| 697 | 1-(3'-fluoro-3-methoxy-5'-trifluoromethyl)-4-biphenylyl)-N-3-isoxazolyl-2-oxo-1,2-dihydro-6-quinolinesulfonamide | 560.2 | 173 | 0.009 | | $^1$H NMR (ACETONITRILE-d3) δ: 8.34-8.38 (m, 1H), 8.23-8.28 (m, 1H), 8.00 (dd, J = 9.7, 2.1 Hz, 1H), 7.92 (s, 1H), 7.78-7.85 (m, 2H), 7.44-7.57 (m, 3H), 7.33-7.39 (m, 1H), 6.73-6.82 (m, 2H), 6.42-6.47 (m, 1H), 3.79 (d, J = 2.5 Hz, 3H). |
| 695 | 1-(4'-chloro-2-fluoro-5-methoxy-3'-methyl-4-biphenylyl)-2-oxo-N-3-pyridazinyl-1,2-dihydro-6-quinolinesulfonamide | 551.2 | 205 | 0.012 | | $^1$H NMR (400 MHz, DMSO-d$_6$) δ = 14.52 (br. s., 1H), 8.51-8.19 (m, 3H), 7.93 (d, J = 8.6 Hz, 2H), 7.76 (br. s., 2H), 7.69-7.51 (m, 3H), 7.45 (d, J = 5.7 Hz, 1H), 6.86 (d, J = 7.6 Hz, 2H), 3.80 (br. s., 3H), 2.50 (br. s., 3H) |
| 696 | 1-(4'-chloro-2-fluoro-5-methoxy-3'-methyl-4-biphenylyl)-2-oxo-N-2-pyrimidinyl-1,2-dihydro-6-quinolinesulfonamide | 551.2 | 205 | 0.012 | | $^1$H NMR (400 MHz, DMSO-d$_6$) δ = 14.52 (br. s., 1H), 8.51-8.19 (m, 3H), 7.93 (d, J = 8.6 Hz, 2H), 7.76 (br. s., 2H), 7.69-7.51 (m, 3H), 7.45 (d, J = 5.7 Hz, 1H), 6.86 (d, J = 7.6 Hz, 2H), 3.80 (br. s., 3H), 2.50 (br. s., 3H) |
| 1012 | 1-(5-chloro-6-(3-fluorophenyl)-2-oxo-1,2-dihydro-3-pyridinyl)-N-3-isoxazolyl-2-oxo-1,2-dihydro-6-quinolinesulfonamide | 513.9 | 199 | | | 1H NMR (500 MHz, DMSO-d6) δ 11.65 (br. s., 1H), 8.72 (d, J = 1.69 Hz, 1H), 8.38 (d, J = 1.75 Hz, 1H), 8.23 (d, J = 9.73 Hz, 1H), 7.89 (dd, J = 2.08, 9.02 Hz, 1H), 7.45-7.67 (m, 4H), 7.39 (br. s., 1H), 6.82 (d, J = 9.73 Hz, 1H), 6.45 (d, J = 1.69 Hz, 1H). |
| 626 | 1-(4'-chloro-3-methoxy-4-biphenylyl)-N-3-isoxazolyl-2-oxo-1,2-dihydro-6-quinolinesulfonamide | 508.1 | 173 | 0.022 | | 1H NMR (ACETONITRILE-d3) δ: 8.37 (d, J = 1.9 Hz, 1H), 8.26 (d, J = 2.2 Hz, 1H), 7.99 (d, J = 9.4 Hz, 1H), 7.73-7.83 (m, 3H), 7.49-7.59 (m, 2H), 7.45 (s, 1H), 7.40-7.43 (m, 1H), 7.31 (d, J = 8.1 Hz, 1H), 6.70-6.85 (m, 2H), 6.46 (d, J = 1.9 Hz, 1H), 3.77 (s, 3H) |
| 1013 | N-3-isoxazolyl-1-(3-methoxy-4'-(trifluoromethyl)-4-biphenylyl)-2-oxo-1,2-dihydro-6-quinolinesulfonamide | 542.2 | 173 | 0.019 | | 1H NMR (ACETONITRILE-d3) δ: 8.36 (d, J = 1.9 Hz, 1H), 8.25 (d, J = 2.2 Hz, 1H), 7.92-8.02 (m, 3H), 7.77-7.90 (m, 2H), 7.44-7.53 (m, 2H), 7.35 (d, J = 8.0 Hz, 1H), 6.73-6.90 (m, 3H), 6.44 (d, J = 1.9 Hz, 1H), 3.77-3.80 (m, 3H) |
| 1014 | 1-(3',4'-difluoro-3-methoxy-4-biphenylyl)-N-3-isoxazolyl-2-oxo-1,2-dihydro-6-quinolinesulfonamide | 510.1 | 173 | 0.053 | | 1H NMR (ACETONITRILE-d3) δ: 8.37 (d, J = 1.8 Hz, 1H), 8.25 (d, J = 2.2 Hz, 1H), 7.99 (d, J = 9.7 Hz, 1H), 7.80 (dd, J = 9.0, 2.2 Hz, 1H), 7.70 (ddd, J = 12.1, 7.7, 2.2 Hz, 1H), 7.57 (dddd, J = 8.6, 4.2, 2.5, 1.4 Hz, 1H), 7.36-7.46 (m, 3H), 7.28-7.34 (m, 1H), 6.78 (dd, J = 12.6, 9.4 Hz, 2H), 6.42-6.48 (m, 1H), 3.77 (s, 3H) |
| 1015 | 1-(3'-fluoro-3-methoxy-5'-methyl-4-biphenylyl)-N-3-isoxazolyl-2-oxo-1,2-dihydro-6-quinolinesulfonamide | 506.1 | 173 | 0.012 | | 1H NMR (ACETONITRILE-d3) δ: 8.34 (d, J = 1.9 Hz, 1H), 8.25 (d, J = 2.1 Hz, 1H), 7.98 (d, J = 9.6 Hz, 1H), 7.80 (dd, J = 9.0, 2.2 Hz, 1H), 7.39-7.47 (m, 3H), 7.28-7.35 (m, 2H), 6.98-7.07 (m, 1H), 6.77 (dd, J = 11.7, 9.4 Hz, 2H), 6.43 (d, J = 1.9 Hz, 1H), 3.77 (s, 3H), 2.44 (s, 3H) |
| 1016 | N-3-isoxazolyl-1-(3-methoxy-3',5'-dimethyl-4-biphenylyl)-2-oxo-1,2-dihydro-6-quinolinesulfonamide | 502.3 | 173 | 0.011 | | 1H NMR (ACETONITRILE-d3) δ: 8.37 (d, J = 1.8 Hz, 1H), 8.25 (d, J = 2.2 Hz, 1H), 7.98 (d, J = 9.5 Hz, 1H), 7.80 (dd, J = 9.0, 2.2 Hz, 1H), 7.36-7.46 (m, 4H), 7.27 (d, J = 8.1 Hz, 1H), 7.07-7.11 (m, 1H), 6.79 (dd, J = 17.6, 9.4 Hz, 2H), 6.45 (d, J = 1.9 Hz, 1H), 3.77 (s, 3H), 2.39 (s, J = 0.6 Hz, 6H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 1017 | 1-(4'-fluoro-3,3'-dimethoxy-4-biphenylyl)-N-3-isoxazolyl-2-oxo-1,2-dihydro-6-quinolinesulfonamide | 522.2 | 173 | 0.08 | | 1H NMR (ACETONITRILE-d3) δ: 8.37 (d, J = 1.8 Hz, 1H), 8.25 (d, J = 2.2 Hz, 1H), 7.99 (d, J = 9.7 Hz, 1H), 7.80 (dd, J = 9.0, 2.2 Hz 1H), 7.38-7.46 (m, 3H), 7.21-7.32 (m, 3H), 6.79 (dd, J = 17.3, 9.3 Hz, 2H), 6.45 (d, J = 1.8 Hz, 1H), 3.98 (s, 3H), 3.78 (s, 3H) |
| 1018 | 1-(3'-fluoro-3,5'-dimethoxy-4-biphenylyl)-N-3-isoxazolyl-2-oxo-1,2-dihydro-6-quinolinesulfonamide | 522.2 | 173 | 0.013 | | 1H NMR (ACETONITRILE-d3) δ: 8.35-8.38 (m, 1H), 8.23-8.27 (m, 1H), 7.96-8.02 (m, 1H), 7.77-7.83 (m, 1H), 7.41-7.48 (m, 2H), 7.28-7.35 (m, 1H), 7.09-7.17 (m, 2H), 6.74-6.83 (m, 3H), 6.43-6.47 (m, 1H), 3.89 (d, J = 1.9 Hz, 3H), 3.78 (d, J = 1.8 Hz, 3H) |
| 1019 | 1-(3'-cyano-3-methoxy-4-biphenylyl)-N-3-isoxazolyl-2-oxo-1,2-dihydro-6-quinolinesulfonamide | 499.1 | 173 | 0.098 | | 1H NMR (ACETONITRILE-d3) δ: 8.34-8.38 (m, 1H), 8.25 (d, J = 2.2 Hz, 1H), 8.15 (t, J = 1.8 Hz, 1H), 8.03-8.08 (m, 1H), 7.99 (d, J = 9.4 Hz, 1H), 7.76-7.82 (m, 2H), 7.64-7.71 (m, 1H), 7.49 (d, J = 1.9 Hz, 1H), 7.43-7.47 (m, 1H), 7.35 (d, J = 8.0 Hz, 1H), 6.74-6.82 (m, 2H), 6.42-6.46 (m, 1H), 3.78 (s, 3H) |
| 1020 | 1-(3'-cyano-4'-fluoro-3-methoxy-4-biphenylyl)-N-3-isoxazolyl-2-oxo-1,2-dihydro-6-quinolinesulfonamide | 517.1 | 173 | 0.082 | | 1H NMR (ACETONITRILE-d3) δ: 8.34-8.38 (m, 1H), 8.25 (d, J = 2.2 Hz, 1H), 8.16 (dd, J = 6.1, 2.4 Hz, 1H), 8.08 (ddd, J = 8.9, 5.1, 2.5 Hz, 1H), 7.99 (d, J = 9.6 Hz, 1H), 7.80 (dd, J = 9.0, 2.2 Hz, 1H), 7.39-7.51 (m, 3H), 7.31-7.36 (m, 1H), 6.77 (dd, J = 9.3, 8.0 Hz, 2H), 6.42-6.45 (m, 1H), 3.77 (s, 3H) |
| 1021 | 1-(3'-cyano-5'-fluoro-3-methoxy-4-biphenylyl)-N-3-isoxazolyl-2-oxo-1,2-dihydro-6-quinolinesulfonamide | 517.2 | 173 | 0.105 | | 1H NMR (ACETONITRILE-d3) δ: 8.33-8.37 (m, 1H), 8.25 (d, J = 2.2 Hz, 1H), 7.96-8.04 (m, 2H), 7.77-7.88 (m, 2H), 7.55-7.62 (m, 1H), 7.44-7.52 (m, 2H), 7.36 (d, J = 8.1 Hz, 1H), 6.77 (dd, J = 9.4, 5.3 Hz, 2H), 6.44 (d, J = 1.8 Hz, 1H), 3.78 (s, 3H) |
| 1022 | N-3-isoxazolyl-1-(2-methoxy-4-(2-methoxy-5-methyl-3-pyridinyl)phenyl)-2-oxo-1,2-dihydro-6-quinolinesulfonamide | | | | | 1H NMR (ACETONITRILE-d3) δ: 8.37 (d, J = 1.8 Hz, 1H), 8.25 (d, J = 2.1 Hz, 1H), 7.96-8.04 (m, 2H), 7.81 (dd, J = 9.0, 2.2 Hz, 1H), 7.65-7.70 (m, 1H), 7.44 (d, J = 1.8 Hz, 1H), 7.33-7.39 (m, 1H), 7.26 (d, J = 8.1 Hz, 1H), 6.78 (dd, J = 13.1, 9.3 Hz, 2H), 6.45 (d, J = 1.9 Hz, 1H), 3.94 (s, 3H), 3.72 (s, 3H), 2.32 (s, 3H) |
| 1023 | 1-(3',5'-dichloro-3-methoxy-4-biphenylyl)-N-3-isoxazolyl-2-oxo-1,2-dihydro-6-quinolinesulfonamide | 544.0 | 173 | 0.009 | | 1H NMR (ACETONITRILE-d3) δ: 8.36 (d, J = 1.9 Hz, 1H), 8.25 (d, J = 2.2 Hz, 1H), 7.99 (d, J = 9.6 Hz, 1H), 7.79 (dd, J = 9.0, 2.2 Hz, 1H), 7.75 (d, J = 1.9 Hz, 2H), 7.52 (t, J = 1.9 Hz, 1H), 7.39-7.48 (m, 2H), 7.33 (d, J = 8.0 Hz, 1H), 6.74-6.82 (m, 2H), 6.45 (d, J = 1.8 Hz, 1H), 3.78 (s, 3H) |
| 1024 | N-3-isoxazolyl-2-oxo-1-(2',4',5'-trifluoro-3-methoxy-4-biphenylyl)-1,2-dihydro-6-quinolinesulfonamide | 528.2 | 173 | 0.062 | | 1H NMR (ACETONITRILE-d3) δ: 8.36 (d, J = 1.9 Hz, 1H), 8.25 (d, J = 2.2 Hz, 1H), 7.99 (d, J = 9.5 Hz, 1H), 7.81 (dd, J = 9.0, 2.2 Hz, 1H), 7.60 (ddd, J = 11.2, 8.9, 7.2 Hz, 1H), 7.37 (d, J = 1.0 Hz, 1H), 7.25-7.34 (m, 3H), 6.74-6.81 (m, 2H), 6.44 (d, J = 1.9 Hz, 1H), 3.74 (s, 3H) |
| 1025 | N-3-isoxazolyl-2-oxo-1-(2',3',5'-trifluoro-3-methoxy-4-biphenylyl)-1,2-dihydro-6-quinolinesulfonamide | 528.2 | 173 | 0.027 | | 1H NMR (ACETONITRILE-d3) δ: 8.36 (d, J = 1.9 Hz, 1H), 8.26 (d, J = 2.1 Hz, 1H), 7.99 (d, J = 9.5 Hz, 1H), 7.81 (dd, J = 9.0, 2.2 Hz, 1H), 7.41 (d, J = 0.8 Hz, 1H), 7.34-7.38 (m, 2H), 7.16-7.29 (m, 2H), 6.74-6.81 (m, 2H), 6.42-6.46 (m, 1H), 3.74 (s, 3H) |
| 1026 | 1-(3'-chloro-3,4'-dimethoxy-4-biphenylyl)-N-3-isoxazolyl-2-oxo-1,2-dihydro-6-quinolinesulfonamide | 538.1 | 173 | 0.059 | | 1H NMR (ACETONITRILE-d3) δ: 8.31 (d, J = 1.8 Hz, 1H), 8.23 (d, J = 2.1 Hz, 1H), 7.96 (d, J = 9.5 Hz, 1H), 7.76-7.83 (m, 2H), 7.68 (dd, J = 8.6, 2.3 Hz, 1H), 7.34-7.42 (m, 2H), 7.26 (d, J = 8.0 Hz, 1H), 7.18 (d, J = 8.6 Hz, 1H), 6.83-6.92 (m, 1H), 6.68-6.79 (m, 2H), 3.94 (s, 3H), 3.75 (s, 3H) |
| 1027 | 1-(4'-chloro-3,3'-dimethoxy-4-biphenylyl)-N-3-isoxazolyl-2-oxo-1,2-dihydro-6-quinolinesulfonamide | 538.1 | 173 | 0.032 | | 1H NMR (ACETONITRILE-d3) δ: 8.32 (d, J = 1.9 Hz, 1H), 8.24 (d, J = 2.2 Hz, 1H), 7.98 (d, J = 9.5 Hz, 1H), 7.80 (dd, J = 9.0, 2.2 Hz, 1H), 7.50 (d, J = 8.2 Hz, 1H), 7.38-7.46 (m, 3H), 7.30 (dt, J = 8.1, 1.1 Hz, 2H), 6.77 (dd, J = 12.6, 9.3 Hz, 2H), 6.41 (d, J = 1.8 Hz, 1H), 4.00 (s, 3H), 3.78 (s, 3H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 1028 | 1-(3'-chloro-3-methoxy-2'-methyl-4-biphenylyl)-N-3-isoxazolyl-2-oxo-1,2-dihydro-6-quinolinesulfonamide | 522.2 | 173 | 0.018 | | 1H NMR (ACETONITRILE-d3) δ: 8.37 (d, J = 1.8 Hz, 1H), 8.25 (d, J = 2.2 Hz, 1H), 7.99 (d, J = 9.5 Hz, 1H), 7.81 (dd, J = 9.0, 2.3 Hz, 1H), 7.44-7.49 (m, 1H), 7.26-7.33 (m, 3H), 7.14-7.19 (m, 1H), 7.10 (dd, J = 7.9, 1.8 Hz, 1H), 6.83 (d, J = 9.0 Hz, 1H), 6.77 (d, J = 9.7 Hz, 1H), 6.46 (d, J = 1.9 Hz, 1H), 3.67-3.72 (m, 3H), 2.38 (s, 3H) |
| 1029 | 1-(5'-chloro-3-methoxy-2'-methyl-4-biphenylyl)-N-3-isoxazolyl-2-oxo-1,2-dihydro-6-quinolinesulfonamide | 522.2 | 173 | 0.003 | | 1H NMR (ACETONITRILE-d3) δ: 8.35 (d, J = 1.9 Hz, 1H), 8.25 (d, J = 2.2 Hz, 1H), 7.99 (d, J = 9.5 Hz, 1H), 7.80 (dd, J = 9.0, 2.2 Hz, 1H), 7.39 (t, J = 1.2 Hz, 1H), 7.33 (d, J = 1.5 Hz, 2H), 7.29 (d, J = 8.0 Hz, 1H), 7.18 (d, J = 1.7 Hz, 1H), 7.12 (dd, J = 8.0, 1.8 Hz, 1H), 6.78 (dd, J = 14.7, 9.3 Hz, 2H), 6.44 (d, J = 1.9 Hz, 1H), 3.70 (s, 3H), 2.33 (s, 3H) |
| 1030 | 1-(2'-chloro-3-methoxy-5'-methyl-4-biphenylyl)-N-3-isoxazolyl-2-oxo-1,2-dihydro-6-quinolinesulfonamide | 522.1 | 173 | 0.012 | | 1H NMR (ACETONITRILE-d3) δ: 8.35 (d, J = 1.8 Hz, 1H), 8.25 (d, J = 2.2 Hz, 1H), 7.99 (d, J = 9.6 Hz, 1H), 7.81 (dd, J = 9.0, 2.2 Hz, 1H), 7.44 (d, J = 8.2 Hz, 1H), 7.36 (dd, J = 1.9, 0.6 Hz, 1H), 7.27-7.32 (m, 2H), 7.20-7.25 (m, 2H), 6.74-6.82 (m, 2H), 6.44 (d, J = 1.9 Hz, 1H), 3.71 (s, 3H), 2.39 (s, 3H) |
| 1031 | 1-(2'-chloro-3,5'-dimethoxy-4-biphenylyl)-N-3-isoxazolyl-2-oxo-1,2-dihydro-6-quinolinesulfonamide | 538.2 | 173 | 0.025 | | 1H NMR (ACETONITRILE-d3) δ: 8.36 (d, J = 1.8 Hz, 1H), 8.25 (d, J = 2.1 Hz, 1H), 7.99 (d, J = 9.5 Hz, 1H), 7.81 (dd, J = 9.0, 2.2 Hz, 1H), 7.47 (d, J = 8.8 Hz, 1H), 7.22-7.32 (m, 3H), 7.08 (d, J = 3.0 Hz, 1H), 6.98 (dd, J = 8.8, 3.0 Hz, 1H), 6.78 (dd, J = 9.3, 7.8 Hz, 2H), 6.44 (d, J = 1.8 Hz, 1H), 3.85 (s, 3H), 3.72 (s, 3H) |
| 1032 | 1-(2'-fluoro-3-methoxy-5'-methyl-4-biphenylyl)-N-3-isoxazolyl-2-oxo-1,2-dihydro-6-quinolinesulfonamide | 506.2 | 173 | 0.049 | | 1H NMR (ACETONITRILE-d3) δ: 8.35 (d, J = 1.9 Hz, 1H), 8.25 (d, J = 2.1 Hz, 1H), 7.98 (d, J = 9.5 Hz, 1H), 7.81 (dd, J = 9.0, 2.2 Hz, 1H), 7.42-7.47 (m, 1H), 7.39 (t, J = 1.3 Hz, 1H), 7.21-7.35 (m, 3H), 7.15 (dd, J = 10.9, 8.4 Hz, 1H), 6.78 (dd, J = 14.4, 9.3 Hz, 2H), 6.44 (d, J = 1.8 Hz, 1H), 3.73 (s, 3H), 2.39 (s, 3H) |
| 1033 | 1-(2'-fluoro-3,5'-dimethoxy-4-biphenylyl)-N-3-isoxazolyl-2-oxo-1,2-dihydro-6-quinolinesulfonamide | 522.0 | 173 | 0.064 | | 1H NMR (ACETONITRILE-d3) δ: 8.35 (d, J = 1.8 Hz, 1H), 8.26 (d, J = 2.2 Hz, 1H), 7.99 (d, J = 9.6 Hz, 1H), 7.82 (dd, J = 9.0, 2.2 Hz, 1H), 7.41 (t, J = 1.3 Hz, 1H), 7.30-7.39 (m, 2H), 7.18-7.24 (m, 1H), 7.13-7.17 (m, 1H), 6.98 (dt, J = 9.0, 3.5 Hz, 1H), 6.79 (dd, J = 13.3, 9.3 Hz, 2H), 6.44 (d, J = 1.9 Hz, 1H), 3.85 (s, 3H), 3.74 (s, 3H) |
| 1034 | 1-(5'-chloro-2'-fluoro-3-methoxy-4-biphenylyl)-N-3-isoxazolyl-2-oxo-1,2-dihydro-6-quinolinesulfonamide | 526.1 | 173 | 0.01 | | 1H NMR (ACETONITRILE-d3) δ: 8.35 (d, J = 1.9 Hz, 1H), 8.25 (d, J = 2.2 Hz, 1H), 7.99 (d, J = 9.5 Hz, 1H), 7.81 (dd, J = 9.0, 2.2 Hz, 1H), 7.67 (dd, J = 6.7, 2.7 Hz, 1H), 7.45 (ddd, J = 8.8, 4.3, 2.7 Hz, 1H), 7.40 (s, 1H), 7.25-7.37 (m, 3H), 6.74-6.81 (m, 2H), 6.44 (d, J = 1.8 Hz, 1H), 3.74 (s, 3H) |
| 1035 | 1-(5'-chloro-2',3-dimethoxy-4-biphenylyl)-N-3-isoxazolyl-2-oxo-1,2-dihydro-6-quinolinesulfonamide | 538.2 | 173 | 0.019 | | 1H NMR (ACETONITRILE-d3) δ: 8.35 (d, J = 1.9 Hz, 1H), 8.25 (d, J = 2.2 Hz, 1H), 7.98 (d, J = 9.5 Hz, 1H), 7.81 (dd, J = 9.0, 2.2 Hz, 1H), 7.47 (d, J = 2.7 Hz, 1H), 7.36-7.41 (m, 2H), 7.27-7.32 (m, 1H), 7.23-7.26 (m, 1H), 7.11 (d, J = 8.9 Hz, 1H), 6.74-6.81 (m, 2H), 6.44 (d, J = 1.8 Hz, 1H), 3.84-3.87 (m, 3H), 3.71 (s, 3H) |
| 1036 | 1-(2',3-dimethoxy-5'-methyl-4-biphenylyl)-N-3-isoxazolyl-2-oxo-1,2-dihydro-6-quinolinesulfonamide | 518.1 | 173 | 0.02 | | 1H NMR (ACETONITRILE-d3) δ: 8.36 (d, J = 1.9 Hz, 1H), 8.25 (d, J = 2.2 Hz, 1H), 7.98 (d, J = 9.5 Hz, 1H), 7.82 (dd, J = 9.0, 2.2 Hz, 1H), 7.38 (d, J = 1.8 Hz, 1H), 7.26-7.31 (m, 2H), 7.18-7.25 (m, 2H), 7.02 (d, J = 8.4 Hz, 1H), 6.79 (dd, J = 16.0, 9.4 Hz, 2H), 6.45 (d, J = 1.8 Hz, 1H), 3.82 (s, 3H), 3.69-3.73 (m, 3H), 2.34 (s, 3H) |
| 1037 | 1-(3',5'-dimethoxy-2'-methyl-4-biphenylyl)-N-3-isoxazolyl-2-oxo-1,2-dihydro-6-quinolinesulfonamide | 518.2 | 173 | 0.024 | | 1H NMR (ACETONITRILE-d3) δ: 8.32 (d, J = 1.8 Hz, 1H), 8.25 (d, J = 2.1 Hz, 1H), 7.97 (d, J = 9.5 Hz, 1H), 7.81 (dd, J = 9.0, 2.2 Hz, 1H), 7.23-7.28 (m, 2H), 7.18 (d, J = 1.7 Hz, |

TABLE 3-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | quinolinesulfonamide | | | | | 1H), 7.12 (dd, J = 7.9, 1.8 Hz, 1H), 6.87-6.99 (m, 2H), 6.78 (dd, J = 16.3, 9.3 Hz, 2H), 6.42 (d, J = 1.8 Hz, 1H), 3.79-3.83 (m, 3H), 3.70 (s, 3H), 2.28 (s, 3H) |
| 627 | 1-(4'-chloro-3,3'-dimethoxy-4-biphenylyl)-2-oxo-N-2-pyrimidinyl-1,2-dihydro-6-quinolinesulfonamide | 549.0 | 174 | 0.021 | | 1H NMR (ACETONITRILE-d3) δ: 8.40-8.46 (m, 3H), 7.96-8.05 (m, 2H), 7.42-7.52 (m, 4H), 7.28-7.35 (m, 2H), 6.95 (t, J = 4.9 Hz, 1H), 6.72-6.80 (m, 2H), 4.00 (s, 3H), 3.77 (s, 3H) |
| 1038 | 1-(4'-chloro-3,3'-dimethoxy-4-biphenylyl)-2-oxo-N-3-pyridazinyl-1,2-dihydro-6-quinolinesulfonamide | 549.2 | 174 | 0.058 | | 1H NMR (ACETONITRILE-d3) δ: 8.26 (d, J = 2.2 Hz, 1H), 8.18 (dd, J = 4.1, 1.5 Hz, 1H), 7.97 (d, J = 9.5 Hz, 1H), 7.83 (dd, J = 8.9, 2.2 Hz, 1H), 7.67 (dd, J = 9.5, 1.5 Hz, 1H), 7.38-7.52 (m, 5H), 7.27-7.32 (m, 2H), 6.75 (dd, J = 9.3, 4.2 Hz, 2H), 3.97-4.02 (m, 3H), 3.74-3.79 (m, 3H) |
| 1039 | 1-(4'-chloro-3,3'-dimethoxy-4-biphenylyl)-N-1,3-oxazol-2-yl-2-oxo-1,2-dihydro-6-quinolinesulfonamide | 538.0 | 174 | 0.149 | | 1H NMR (ACETONITRILE-d3) δ: 8.23 (d, J = 2.2 Hz, 1H), 7.99 (d, J = 9.6 Hz, 1H), 7.81 (dd, J = 8.9, 2.1 Hz, 1H), 7.39-7.54 (m, 4H), 7.30-7.35 (m, 2H), 7.19 (d, J = 1.8 Hz, 1H), 6.94 (d, J = 1.8 Hz, 1H), 6.76 (dd, J = 9.3, 5.9 Hz, 2H), 4.01 (s, 3H), 3.79 (s, 3H) |
| 628 | 1-(4'-chloro-2-fluoro-3',5-dimethoxy-4-biphenylyl)-2-oxo-N-3-pyridazinyl-1,2-dihydro-6-quinolinesulfonamide | 567.0 | 175 | 0.01 | >10.0 | 1H NMR (ACETONITRILE-d3) δ: 8.27 (d, J = 2.2 Hz, 1H), 8.18 (dd, J = 4.1, 1.5 Hz, 1H), 8.00 (d, J = 9.6 Hz, 1H), 7.85 (dd, J = 8.9, 2.1 Hz, 1H), 7.71 (dd, J = 9.6, 1.5 Hz, 1H), 7.45-7.55 (m, 2H), 7.30-7.37 (m, 2H), 7.18-7.27 (m, 2H), 6.83 (d, J = 8.8 Hz, 1H), 6.75 (d, J = 9.6 Hz, 1H), 3.97 (s, 3H), 3.74 (s, 3H) |
| 1040 | 1-(4'-chloro-2-fluoro-3',5-dimethoxy-4-biphenylyh-N-1,3-oxazol-2-yl-2-oxo-1,2-dihydro-6-quinolinesulfonamide | 556.0 | 175 | 0.031 | | 1H NMR (ACETONITRILE-d3) δ: 8.22-8.27 (m, 1H), 8.01 (dd, J = 9.6, 1.8 Hz, 1H), 7.81-7.87 (m, 1H), 7.53 (dd, J = 8.2, 2.3 Hz, 1H), 7.30-7.39 (m, 2H), 7.18-7.28 (m, 3H), 6.95 (t, J = 2.1 Hz, 1H), 6.83 (dd, J = 9.1, 1.8 Hz, 1H), 6.76 (dd, J = 9.7, 2.2 Hz, 1H), 3.98 (d, J = 2.2 Hz, 3H), 3.73-3.78 (m, 3H) |
| 1041 | 1-(3-cyclopropyl-3',5'-difluoro-4-biphenylyl)-N-3-isoxazolyl-2-oxo-1,2-dihydro-6-quinolinesulfonamide | 520.1 | 176 | | | 1H NMR (ACETONITRILE-d3) δ: 8.22 (d, J = 2.1 Hz, 1H), 8.17 (d, J = 1.8 Hz, 1H), 8.01 (d, J = 9.6 Hz, 1H), 7.80 (dd, J = 8.9, 2.1 Hz, 1H), 7.65 (dd, J = 8.2, 2.2 Hz, 1H), 7.35-7.42 (m, 3H), 7.30 (d, J = 8.2 Hz, 1H), 6.95-7.04 (m, 1H), 6.76 (d, J = 9.6 Hz, 1H), 6.66 (d, J = 8.9 Hz, 1H), 6.30 (d, J = 1.8 Hz, 1H), 1.42-1.53 (m, 1H), 0.69-0.88 (m, 2H), 0.51-0.65 (m, 2H) |
| 629 | 1-(3-cyclopropyl-3',5'-difluoro-4-biphenylyl)-N-3-isoxazolyl-2-oxo-1,2-dihydro-6-quinolinesulfonamide | 520.2 | 176 | 0.127 | | 1H NMR (ACETONITRILE-d3) δ: 8.22 (d, J = 2.1 Hz, 1H), 8.17 (d, J = 1.8 Hz, 1H), 8.01 (d, J = 9.6 Hz, 1H), 7.80 (dd, J = 8.9, 2.1 Hz, 1H), 7.65 (dd, J = 8.2, 2.2 Hz, 1H), 7.35-7.42 (m, 3H), 7.30 (d, J = 8.2 Hz, 1H), 6.95-7.04 (m, 1H), 6.76 (d, J = 9.6 Hz, 1H), 6.66 (d, J = 8.9 Hz, 1H), 6.30 (d, J = 1.8 Hz, 1H), 1.42-1.53 (m, 1H), 0.69-0.88 (m, 2H), 0.51-0.65 (m, 2H) |
| 1042 | 1-(3-cyclopropyl-3',5'-difluoro-4-biphenylyl)-2-oxo-N-3-pyridazinyl-1,2-dihydro-6-quinolinesulfonamide | 531.1 | 176 | 0.195 | | 1H NMR (ACETONITRILE-d3) δ: 8.29 (d, J = 2.1 Hz, 1H), 8.18 (dd, J = 4.1, 1.5 Hz, 1H), 8.03 (d, J = 9.4 Hz, 1H), 7.84 (dd, J = 8.9, 2.2 Hz, 1H), 7.68 (ddd, J = 17.4, 8.9, 1.8 Hz, 2H), 7.48 (dd, J = 9.6, 4.1 Hz, 1H), 7.35-7.43 (m, 3H), 7.30 (d, J = 8.1 Hz, 1H), 7.00 (tt, J = 9.2, 2.3 Hz, 1H), 6.79 (d, J = 9.6 Hz, 1H), 6.70 (d, J = 8.9 Hz, 1H), 1.42-1.53 (m, 1H), 0.70-0.88 (m, 2H), 0.54-0.65 (m, 2H) |
| 1043 | 1-(3-cyclopropyl-3',5'-difluoro-4-biphenylyl)-2-oxo-N-3-pyridazinyl-1,2-dihydro-6-quinolinesulfonamide | 531.0 | 176 | | | 1H NMR (ACETONITRILE-d3) δ: 8.29 (d, J = 2.1 Hz, 1H), 8.18 (dd, J = 4.1, 1.5 Hz, 1H), 8.03 (d, J = 9.4 Hz, 1H), 7.84 (dd, J = 8.9, 2.2 Hz, 1H), 7.68 (ddd, J = 17.4, 8.9, 1.8 Hz, 2H), 7.48 (dd, J = 9.6, 4.1 Hz, 1H), 7.35-7.43 (m, 3H), 7.30 (d, J = 8.1 Hz, 1H), 7.00 (tt, J = 9.2, 2.3 Hz, 1H), 6.79 (d, J = 9.6 Hz, 1H), 6.70 (d, J = 8.9 Hz, 1H), 1.42-1.53 (m, 1H), 0.70-0.88 (m, 2H), 0.54-0.65 (m, 2H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 1044 | 1-(3-cyclopropyl-3',5'-difluoro-4-biphenylyl)-2-oxo-N-2-pyrazinyl-1,2-dihydro-6-quinolinesulfonamide | 531.2 | 176 | 2.951 | | 1H NMR (ACETONITRILE-d3) δ: 8.46 (d, J = 1.3 Hz, 1H), 8.38 (d, J = 2.2 Hz, 1H), 8.23 (d, J = 2.5 Hz, 1H), 8.12-8.16 (m, 1H), 8.02-8.08 (m, 1H), 7.90 (dd, J = 9.0, 2.2 Hz, 1H), 7.67 (dd, J = 8.1, 2.2 Hz, 1H), 7.35-7.43 (m, 3H), 7.30 (d, J = 8.1 Hz, 1H), 7.01 (tt, J = 9.2, 2.3 Hz, 1H), 6.81 (d, J = 9.6 Hz, 1H), 6.73 (d, J = 9.0 Hz, 1H), 1.39-1.48 (m, 1H), 0.69-0.90 (m, 2H), 0.48-0.65 (m, 2H) |
| 1045 | 1-(3-cyclopropyl-3',5'-difluoro-4-biphenylyl)-2-oxo-N-2-pyrazinyl-1,2-dihydro-6-quinolinesulfonamide | 531.0 | 176 | | | 1H NMR (ACETONITRILE-d3) δ: 8.46 (d, J = 1.3 Hz, 1H), 8.38 (d, J = 2.2 Hz, 1H), 8.23 (d, J = 2.5 Hz, 1H), 8.12-8.16 (m, 1H), 8.02-8.08 (m, 1H), 7.90 (dd, J = 9.0, 2.2 Hz, 1H), 7.67 (dd, J = 8.1, 2.2 Hz, 1H), 7.35-7.43 (m, 3H), 7.30 (d, J = 8.1 Hz, 1H), 7.01 (tt, J = 9.2, 2.3 Hz, 1H), 6.81 (d, J = 9.6 Hz, 1H), 6.73 (d, J = 9.0 Hz, 1H), 1.39-1.48 (m, 1H), 0.69-0.90 (m, 2H), 0.48-0.65 (m, 2H) |
| 1046 | 1-(3-cyclopropyl-3',5'-difluoro-4-biphenylyl)-2-oxo-N-1,3,4-thiadiazol-2-yl-1,2-dihydro-6-quinolinesulfonamide | 537.0 | 176 | 0.112 | | 1H NMR (ACETONITRILE-d3) δ: 8.36 (s, 1H), 8.22 (d, J = 2.1 Hz, 1H), 8.02 (d, J = 9.4 Hz, 1H), 7.77 (dd, J = 8.9, 2.2 Hz, 1H), 7.64 (dd, J = 8.1, 2.1 Hz, 1H), 7.33-7.41 (m, 3H), 7.29 (d, J = 8.1 Hz, 1H), 6.98 (tt, J = 9.2, 2.4 Hz, 1H), 6.78 (d, J = 9.6 Hz, 1H), 6.69 (d, J = 8.9 Hz, 1H), 1.42-1.52 (m, 1H), 0.69-0.88 (m, 3H), 0.54-0.64 (m, 2H) |
| 1047 | 1-(3-cyclopropyl-3',5'-difluoro-4-biphenylyl)-2-oxo-N-1,3,4-thiadiazol-2-yl-1,2-dihydro-6-quinolinesulfonamide | 537.0 | 176 | | 6.5 | 1H NMR (ACETONITRILE-d3) δ: 8.36 (s, 1H), 8.22 (d, J = 2.1 Hz, 1H), 8.02 (d, J = 9.4 Hz, 1H), 7.77 (dd, J = 8.9, 2.2 Hz, 1H), 7.64 (dd, J = 8.1, 2.1 Hz, 1H), 7.33-7.41 (m, 3H), 7.29 (d, J = 8.1 Hz, 1H), 6.98 (tt, J = 9.2, 2.4 Hz, 1H), 6.78 (d, J = 9.6 Hz, 1H), 6.69 (d, J = 8.9 Hz, 1H), 1.42-1.52 (m, 1H), 0.69-0.88 (m, 3H), 0.54-0.64 (m, 2H) |
| 1048 | 1-(3-cyclopropyl-3',5'-difluoro-4-biphenylyl)-2-oxo-N-1,2,4-thiadiazol-5-yl-1,2-dihydro-6-quinolinesulfonamide | 537.2 | 176 | 0.015 | | 1H NMR (ACETONITRILE-d3) δ: 8.23 (s, 1H), 8.03 (d, J = 9.6 Hz, 1H), 7.90 (s, 1H), 7.81 (d, J = 8.0 Hz, 1H), 7.65 (dd, J = 8.1, 1.9 Hz, 1H), 7.34-7.43 (m, 3H), 7.30 (d, J = 8.2 Hz, 1H), 6.95-7.04 (m, 1H), 6.75 (d, J = 9.7 Hz, 1H), 6.66 (d, J = 8.8 Hz, 1H), 1.44-1.54 (m, 1H), 0.69-0.91 (m, 2H), 0.55-0.66 (m, 2H) |
| 1049 | 1-(3-cyclopropyl-3',5'-difluoro-4-biphenylyl)-2-oxo-N-1,2,4-thiadiazol-5-yl-1,2-dihydro-6-quinolinesulfonamide | 537.0 | 176 | | 0.912 | 1H NMR (ACETONITRILE-d3) δ: 8.23 (s, 1H), 8.03 (d, J = 9.6 Hz, 1H), 7.90 (s, 1H), 7.81 (d, J = 8.0 Hz, 1H), 7.65 (dd, J = 8.1, 1.9 Hz, 1H), 7.34-7.43 (m, 3H), 7.30 (d, J = 8.2 Hz, 1H), 6.95-7.04 (m, 1H), 6.75 (d, J = 9.7 Hz, 1H), 6.66 (d, J = 8.8 Hz, 1H), 1.44-1.54 (m, 1H), 0.69-0.91 (m, 2H), 0.55-0.66 (m, 2H) |
| 1050 | 1-(4-bromo-2-methoxyphenyl)-2-oxo-N-3-pyridazinyl-1,2-dihydro-6-quinolinesulfonamide | 489.0 | 105 | 1.433 | | 1H NMR (ACETONITRILE-d3) δ: 8.25 (d, J = 2.0 Hz, 1H), 8.19 (d, J = 4.0 Hz, 1H), 7.99 (d, J = 9.6 Hz, 1H), 7.82 (dd, J = 8.9, 2.1 Hz, 1H), 7.70 (dd, J = 9.6, 1.5 Hz, 1H), 7.49 (dd, J = 9.6, 4.1 Hz, 1H), 7.44 (d, J = 2.1 Hz, 1H), 7.35 (dd, J = 8.2, 2.0 Hz, 1H), 7.17 (d, J = 8.2 Hz, 1H), 6.73 (dd, J = 9.3, 2.2 Hz, 2H), 3.69-3.73 (m, 3H) |
| 1051 | 1-(4-bromo-2-methoxyphenyl)-2-oxo-N-3-pyridazinyl-1,2-dihydro-6-quinolinesulfonamide | 489.0 | 105 | | | 1H NMR (ACETONITRILE-d3) δ: 8.25 (d, J = 2.0 Hz, 1H), 8.19 (d, J = 4.0 Hz, 1H), 7.99 (d, J = 9.6 Hz, 1H), 7.82 (dd, J = 8.9, 2.1 Hz, 1H), 7.70 (dd, J = 9.6, 1.5 Hz, 1H), 7.49 (dd, J = 9.6, 4.1 Hz, 1H), 7.44 (d, J = 2.1 Hz, 1H), 7.35 (dd, J = 8.2, 2.0 Hz, 1H), 7.17 (d, J = 8.2 Hz, 1H), 6.73 (dd, J = 9.3, 2.2 Hz, 2H), 3.69-3.73 (m, 3H) |
| 1052 | N-3-isoxazolyl-1-(3-methoxy-2'-(trifluoromethyl)-4-biphenylyl)-2-oxo-1,2-dihydro-6-quinolinesulfonamide | 542.0 | 173 | 0.054 | | 1H NMR (ACETONITRILE-d3) δ: 8.83 (s, 1H), 8.39 (d, J = 1.8 Hz, 1H), 8.27 (d, J = 2.2 Hz, 1H), 8.01 (d, J = 9.5 Hz, 1H), 7.80-7.91 (m, 2H), 7.71-7.78 (m, 1H), 7.60-7.67 (m, 1H), 7.55 (d, J = 7.6 Hz, 1H), 7.30 (d, J = 7.9 Hz, 1H), 7.22 (d, J = 1.7 Hz, 1H), 7.15 (dd, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | | | | | | J = 7.9, 1.2 Hz, 1H), 6.78 (dd, J = 9.4, 3.7 Hz, 2H), 6.47 (d, J = 1.8 Hz, 1H), 3.66-3.72 (m, 3H) |
| 1053 | N-3-isoxazolyl-1-(3-methoxy-2'-methyl-5'-(trifluoromethyl)-4-biphenylyl)-2-oxo-1,2-dihydro-6-quinolinesulfonamide | 556.2 | 173 | 0.004 | | 1H NMR (ACETONITRILE-d3) δ: 8.82 (s, 1H), 8.38 (d, J = 1.8 Hz, 1H), 8.26 (d, J = 2.3 Hz, 1H), 8.00 (d, J = 9.7 Hz, 1H), 7.81 (dd, J = 9.0, 2.3 Hz, 1H), 7.62-7.70 (m, 2H), 7.55 (d, J = 8.5 Hz, 1H), 7.32 (d, J = 7.9 Hz, 1H), 7.22 (d, J = 1.8 Hz, 1H), 7.15 (dd, J = 7.9, 1.8 Hz, 1H), 6.81 (dd, J = 18.7, 9.3 Hz, 2H), 6.47 (d, J = 1.8 Hz, 1H), 3.72 (s, 3H), 2.44 (s, 3H) |
| 1054 | 1-(4'-fluoro-3-methoxy-3'-methyl-4-biphenylyl)-N-3-isoxazolyl-2-oxo-1,2-dihydro-6-quinolinesulfonamide | 506.2 | 173 | 0.016 | | 1H NMR (ACETONITRILE-d3) δ: 8.82 (s, 1H), 8.37 (d, J = 1.9 Hz, 1H), 8.25 (d, J = 2.0 Hz, 1H), 7.99 (d, J = 9.4 Hz, 1H), 7.79 (dd, J = 9.0, 2.2 Hz, 1H), 7.66 (dd, J = 7.4, 1.8 Hz, 1H), 7.55-7.62 (m, 1H), 7.35-7.44 (m, 2H), 7.28 (d, J = 8.0 Hz, 1H), 7.14-7.22 (m, 1H), 6.79 (dd, J = 16.7, 9.4 Hz, 2H), 6.45 (d, J = 1.8 Hz, 1H), 3.76-3.80 (m, 3H), 2.37 (d, J = 1.9 Hz, 3H) |
| 1055 | N-3-isoxazolyl-1-(3-methoxy-2',5'-dimethyl-4-biphenylyl)-2-oxo-1,2-dihydro-6-quinolinesulfonamide | 502.2 | 173 | 0.016 | | 1H NMR (ACETONITRILE-d3) δ: 8.82 (s, 1H), 8.38 (d, J = 1.8 Hz, 1H), 8.25 (d, J = 2.0 Hz, 1H), 8.00 (d, J = 9.4 Hz, 1H), 7.81 (dd, J = 9.0, 2.3 Hz, 1 H), 7.08-7.30 (m, 6H), 6.80 (dd, J = 19.7, 9.3 Hz, 2H), 6.47 (d, J = 1.8 Hz, 1H), 3.71 (s, 3H), 2.37 (s, 3H), 2.33 (s, 3H) |
| 1056 | N-3-isoxazolyl-1-(3-methoxy-2',3'-dimethyl-4-biphenylyl)-2-oxo-1,2-dihydro-6-quinolinesulfonamide | 502.2 | 173 | 0.025 | | 1H NMR (ACETONITRILE-d3) δ: 8.83 (s, 1H), 8.38 (d, J = 1.8 Hz, 1H), 8.26 (d, J = 2.3 Hz, 1H), 8.00 (d, J = 9.6 Hz, 1H), 7.81 (dd, J = 9.0, 2.2 Hz, 1H), 7.14-7.29 (m, 5H), 7.09 (dd, J = 7.9, 1.8 Hz, 1 H), 6.85 (d, J = 8.9 Hz, 1H), 6.78 (d, J = 9.7 Hz, 1H), 6.47 (d, J = 1.8 Hz, 1H), 3.70 (s, 3H), 2.37 (s, 3H), 2.27 (s, 3H) |
| 1057 | 1-(3'-chloro-2'-fluoro-3-methoxy-4-biphenylyl)-N-3-isoxazolyl-2-oxo-1,2-dihydro-6-quinolinesulfonamide | 526.0 | 173 | 0.011 | | 1H NMR (ACETONITRILE-d3) δ: 8.82 (s, 1H), 8.38 (d, J = 1.9 Hz, 1H), 8.25 (d, J = 2.2 Hz, 1H), 8.00 (d, J = 9.6 Hz, 1H), 7.81 (dd, J = 9.0, 2.2 Hz, 1H), 7.51-7.61 (m, 2H), 7.41 (s, 1H), 7.27-7.36 (m, 3H), 6.79 (dd, J = 14.2, 9.3 Hz, 2H), 6.46 (d, J = 1.8 Hz, 1H), 3.74 (s, 3H) |
| 1058 | 1-(2'-chloro-3'-fluoro-3-methoxy-4-biphenylyl)-N-3-isoxazolyl-2-oxo-1,2-dihydro-6-quinolinesulfonamide | 526.0 | 173 | 0.038 | | 1H NMR (ACETONITRILE-d3) δ: 8.83 (s, 1H), 8.38 (d, J = 1.9 Hz, 1H), 8.26 (d, J = 2.3 Hz, 1H), 8.01 (d, J = 9.6 Hz, 1H), 7.82 (dd, J = 9.0, 2.3 Hz, 1H), 7.42-7.51 (m, 1H), 7.31-7.40 (m, 4H), 7.23-7.29 (m, 1H), 6.80 (dd, J = 11.1, 9.3 Hz, 2H), 6.47 (d, J = 1.9 Hz, 1H), 3.72 (s, 3H) |
| 1059 | 1-(2'-chloro-3-methoxy-3'-methyl-4-biphenylyl)-N-3-isoxazolyl-2-oxo-1,2-dihydro-6-quinolinesulfonamide | 522.0 | 173 | 0.032 | | 1H NMR (ACETONITRILE-d3) δ: 8.83 (s, 1H), 8.38 (d, J = 1.8 Hz, 1H), 8.26 (d, J = 2.3 Hz, 1H), 8.00 (d, J = 9.3 Hz, 1H), 7.82 (dd, J = 9.0, 2.2 Hz, 1H), 7.17-7.45 (m, 6H), 6.75-6.83 (m, 2H), 6.47 (d, J = 1.9 Hz, 1H), 3.69-3.73 (m, 3H), 2.49 (s, 3H) |
| 1060 | 1-(2'-chloro-3-methoxy-4'-methyl-4-biphenylyl)-N-3-isoxazolyl-2-oxo-1,2-dihydro-6-quinolinesulfonamide | 522.1 | 173 | 0.028 | | 1H NMR (ACETONITRILE-d3) δ: 8.83 (s, 1H), 8.39 (d, J = 1.8 Hz, 1H), 8.26 (d, J = 2.2 Hz, 1H), 8.01 (d, J = 9.6 Hz, 1H), 7.82 (dd, J = 9.0, 2.2 Hz, 1H), 7.40-7.46 (m, 2H), 7.21-7.33 (m, 4H), 6.80 (dd, J = 11.0, 9.4 Hz, 2H), 6.47 (d, J = 1.8 Hz, 1H), 3.72 (s, 3H), 2.42 (s, 3H) |
| 1061 | 1-(2'-chloro-3,4'-dimethoxy-4-biphenylyl)-N-3-isoxazolyl-2-oxo-1,2-dihydro-6-quinolinesulfonamide | 538.2 | 173 | 0.061 | | 1H NMR (ACETONITRILE-d3) δ: 8.83 (s, 1H), 8.38 (d, J = 1.8 Hz, 1H), 8.26 (d, J = 2.2 Hz, 1H), 8.00 (d, J = 9.4 Hz, 1H), 7.82 (dd, J = 9.0, 2.2 Hz, 1H), 7.39-7.45 (m, 2H), 7.21-7.33 (m, 4H), 6.79 (dd, J = 11.0, 9.4 Hz, 2H), 6.46 (d, J = 1.8 Hz, 1H), 3.72 (s, 3H), 2.41 (s, 3H) |
| 1062 | 1-(4'-chloro-2'-fluoro-3-methoxy-4-biphenylyl)-N-3-isoxazolyl-2-oxo-1,2-dihydro-6-quinolinesulfonamide | 526.0 | 173 | 0.019 | | 1H NMR (ACETONITRILE-d3) δ: 8.83 (s, 1H), 8.39 (d, J = 1.9 Hz, 1H), 8.26 (d, J = 2.2 Hz, 1H), 8.01 (d, J = 9.6 Hz, 1H), 7.82 (dd, J = 9.0, 2.2 Hz, 1H), 7.61-7.68 (m, 1H), 7.31-7.43 (m, 5H), 6.80 (dd, J = 13.8, 9.3 Hz, 2H), 6.47 (d, J = 1.9 Hz, 1H), 3.74 (s, 3H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 1063 | 1-(2',3-dimethoxy-4'-methyl-4-biphenylyl)-N-3-isoxazolyl-2-oxo-1,2-dihydro-6-quinolinesulfonamide | 518.0 | 173 | 0.098 | | 1H NMR (ACETONITRILE-d3) δ: 8.88 (s, 1H), 8.37 (d, J = 1.8 Hz, 1H), 8.25 (d, J = 2.2 Hz, 1H), 7.99 (d, J = 9.6 Hz, 1H), 7.81 (dd, J = 9.0, 2.3 Hz, 1H), 7.38 (d, J = 1.8 Hz, 1H), 7.26-7.35 (m, 2H), 7.19-7.24 (m, 1H), 6.98 (s, 1H), 6.88-6.93 (m, 1H), 6.79 (dd, J = 18.5, 9.4 Hz, 2H), 6.46 (d, J = 1.9 Hz, 1H), 3.85 (s, 3H), 3.71 (s, 3H), 2.41 (s, 3H) |
| 1064 | 1-(4',5'-difluoro-3-methoxy-2'-methyl-4-biphenylyl)-N-3-isoxazolyl-2-oxo-1,2-dihydro-6-quinolinesulfonamide | 524.0 | 173 | 0.013 | | 1H NMR (ACETONITRILE-d3) δ: 8.82 (s, 1H), 8.35-8.41 (m, 1H), 8.26 (d, J = 2.3 Hz, 1H), 8.00 (d, J = 9.4 Hz, 1H), 7.80 (dd, J = 8.9, 2.3 Hz, 1H), 7.28-7.31 (m, 2H), 7.16-7.19 (m, 1H), 7.12 (dd, J = 8.0, 1.8 Hz, 1H), 7.04 (dd, J = 11.1, 8.2 Hz, 1H), 6.80 (dd, J = 14.2, 9.3 Hz, 2H), 6.46 (d, J = 1.9 Hz, 1H), 3.68-3.73 (m, 3H), 2.33 (s, 3H) |
| 1065 | 1-(2',4'-difluoro-3-methoxy-5'-methyl-4-biphenylyl)-N-3-isoxazolyl-2-oxo-1,2-dihydro-6-quinolinesulfonamide | 524.1 | 173 | 0.009 | | 1H NMR (ACETONITRILE-d3) δ: 8.36 (d, J = 1.9 Hz, 1H), 8.24 (d, J = 2.2 Hz, 1H), 7.98 (d, J = 9.7 Hz, 1H), 7.79 (dd, J = 9.0, 2.3 Hz, 1H), 7.45-7.55 (m, 1H), 7.35 (s, 1 H), 7.27-7.33 (m, 2H), 6.98-7.10 (m, 1H), 6.77 (dd, J = 13.5, 9.3 Hz, 2H), 6.44 (d, J = 1.8 Hz, 1H), 3.72 (s, 3H), 2.28-2.33 (m, 3H) |
| 630 | 1-(5'-chloro-3-methoxy-2'-methyl-4-biphenylyl)-2-oxo-N-2-pyrimidinyl-1,2-dihydro-6-quinolinesulfonamide | 533.2 | 177 | 0.012 | | 1H NMR (ACETONITRILE-d3) δ: 8.40-8.44 (m, 3H), 7.95-8.06 (m, 2H), 7.38-7.42 (m, 1H), 7.34 (d, J = 1.5 Hz, 2H), 7.29 (d, J = 8.0 Hz, 1H), 7.19 (d, J = 1.8 Hz, 1H), 7.13 (dd, J = 8.0, 1.8 Hz, 1H), 6.95 (t, J = 4.9 Hz, 1H), 6.72-6.81 (m, 2H), 3.70 (s, 3H), 2.34 (s, 3H) |
| 1066 | 1-(5'-chloro-3-methoxy-2'-methyl-4-biphenylyl)-2-oxo-N-3-pyridazinyl-1,2-dihydro-6-quinolinesulfonamide | 533.0 | 177 | 0.019 | | 1H NMR (ACETONITRILE-d3) δ: 8.26 (d, J = 2.0 Hz, 1H), 8.19 (dd, J = 4.1, 1.5 Hz, 1H), 8.00 (d, J = 9.5 Hz, 1H), 7.84 (dd, J = 8.9, 2.2 Hz, 1H), 7.70 (dd, J = 9.6, 1.5 Hz, 1H), 7.48 (dd, J = 9.5, 4.1 Hz, 1H), 7.40 (t, J = 1.1 Hz, 1H), 7.34 (d, J = 1.6 Hz, 2H), 7.30 (d, J = 7.9 Hz, 1H), 7.19 (d, J = 1.8 Hz, 1H), 7.13 (dd, J = 7.9, 1.8 Hz, 1H), 6.76 (dd, J = 9.3, 6.6 Hz, 2H), 3.71 (s, 3H), 2.33-2.36 (m, 3H) |
| 1067 | 1-(5'-chloro-3-methoxy-2'-methyl-4-biphenylyl)-N-1,3-oxazol-2-yl-2-oxo-1,2-dihydro-6-quinolinesulfonamide | 522.1 | 177 | 0.006 | | 1H NMR (ACETONITRILE-d3) δ: 8.23 (d, J = 2.0 Hz, 1H), 8.00 (d, J = 9.6 Hz, 1H), 7.81 (dd, J = 8.9, 2.2 Hz, 1H), 7.41 (t, J = 1.1 Hz, 1H), 7.35 (d, J = 1.6 Hz, 2H), 7.31 (d, J = 8.0 Hz, 1H), 7.18-7.21 (m, 2H), 7.13 (dd, J = 7.9, 1.8 Hz, 1H), 6.94 (d, J = 1.8 Hz, 1H), 6.77 (dd, J = 9.3, 6.3 Hz, 2H), 3.70-3.74 (m, 3H), 2.33-2.37 (m, 3H) |
| 1068 | 1-(3'-(difluoromethyl)-5'-fluoro-3-methoxy-4-biphenylyl)-N-3-isoxazolyl-2-oxo-1,2-dihydro-6-quinolinesulfonamide | 542.2 | 173 | 0.075 | | 1H NMR (Acetone) δ: 8.54 (s, 1H), 8.33 (s, 1H), 8.11 (d, J = 9.5 Hz, 1H), 7.84-7.92 (m, 2H), 7.78 (d, J = 10.1 Hz, 1H), 7.64 (s, 1H), 7.50-7.56 (m, 1H), 7.40-7.47 (m, 2H), 6.88-7.19 (m, 1H), 6.73-6.87 (m, 2H), 6.52-6.60 (m, 1H), 3.83 (s, 3H) |
| 1069 | 1-(4'-fluoro-3-methoxy-4-biphenylyl)-N-3-isoxazolyl-2-oxo-1,2-dihydro-6-quinolinesulfonamide | 492.2 | 173 | 0.071 | | 1H NMR (ACETONITRILE-d3) δ: 8.35 (d, J = 1.8 Hz, 1H), 8.25 (d, J = 2.2 Hz, 1H), 7.98 (d, J = 9.5 Hz, 1H), 7.73-7.84 (m, 3H), 7.42 (s, 1 H), 7.38 (d, J = 7.6 Hz, 1H), 7.23-7.32 (m, 3H), 6.72-6.83 (m, 2H), 6.44 (d, J = 2.0 Hz, 1H), 3.76 (s, 3H) |
| 682 | 1-(3'-chloro-3,5'-dimethoxy-4-biphenylyl)-N-3-isoxazolyl-2-oxo-1,2-dihydro-6-quinolinesulfonamide | 538.2 | 173 | 0.01 | | 1H NMR (ACETONITRILE-d3) δ: 8.35 (d, J = 1.8 Hz, 1H), 8.25 (d, J = 2.2 Hz, 1H), 7.98 (d, J = 9.5 Hz, 1H), 7.80 (dd, J = 9.0, 2.2 Hz, 1H), 7.36-7.47 (m, 3H), 7.30 (d, J = 8.1 Hz, 1H), 7.23 (dd, J = 2.4, 1.6 Hz, 1H), 7.01-7.07 (m, 1 H), 6.73-6.81 (m, 2H), 6.42-6.46 (m, 1H), 3.88 (s, 3H), 3.77 (s, 3H) |
| 683 | 1-(4'-chloro-3-methoxy-3'-methyl-4-biphenylyl)-2-oxo-N-2-pyrimidinyl-1,2-dihydro-6-quinolinesulfonamide | 533.2 | 174 | 0.017 | | 1H NMR (ACETONITRILE-d3) δ: 8.43-8.50 (m, 3H), 7.96-8.08 (m, 2H), 7.73 (d, J = 1.8 Hz, 1H), 7.56-7.62 (m, 1H), 7.49-7.54 (m, 1H), 7.39-7.47 (m, 2H), 7.31 (d, J = 8.0 Hz, 1H), 7.01 (t, J = 4.9 Hz, 1H), 6.74-6.82 (m, 2H), 3.77 (s, 3H), 2.48 (s, 3H) |
| 684 | 1-(3',5'-difluoro-3-methoxy-4-biphenylyl)-N-3- | 510.1 | 173 | 0.027 | | 1H NMR (ACETONITRILE-d3) δ: 8.35 (d, J = 1.8 Hz, 1H), 8.25 (d, J = 2.2 Hz, 1H), 7.99 (d, J = 9.6 Hz, 1H), 7.80 (dd, J = 9.0, 2.2 Hz, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
|  | isoxazolyl-2-oxo-1,2-dihydro-6-quinolinesulfonamide |  |  |  |  | 1H), 7.38-7.49 (m, 4H), 7.33 (d, J = 8.1 Hz, 1H), 6.97-7.06 (m, 1H), 6.77 (t, J = 9.2 Hz, 2H), 6.44 (d, J = 1.8 Hz, 1H), 3.78 (s, 3H) |
| 685 | 1-(4'-chloro-2-fluoro-3',5-dimethoxy-4-biphenylyl)-2-oxo-N-2-pyrimidinyl-1,2-dihydro-6-quinolinesulfonamide | 567.0 | 175 | 0.02 | >10.0 | 1H NMR (ACETONITRILE-d3) δ: 8.41-8.47 (m, 3H), 7.97-8.07 (m, 2H), 7.52 (d, J = 8.2 Hz, 1H), 7.29-7.36 (m, 2H), 7.18-7.26 (m, 2H), 7.00 (t, J = 4.9 Hz, 1H), 6.84 (d, J = 9.0 Hz, 1H), 6.75 (d, J = 9.7 Hz, 1H), 3.96 (s, 3H), 3.72 (s, 3H) |
| 621 | tert-butyl (3-(6-(3-isoxazolylsulfamoyl)-2-oxo-1(2H)-quinolinyl)-4-methoxyphenyl)acetate | 512.2 | 164 | 1.98 |  | 1H NMR (400 MHz, DMSO-d6) δ = 1.32-1.42 (m, 10 H) 3.51-3.60 (m, 3 H) 3.65 (s, 3 H) 3.70 (br. s., 2 H) 6.41 (br. s., 1 H) 6.65 (d, J = 8.10 Hz, 1 H) 6.78 (d, J = 9.80 Hz, 1 H) 6.97 (br. s., 1 H) 7.07 (br. s., 1 H) 7.15 (s, 2 H) 7.24 (d, J = 8.63 Hz, 1 H) 7.42 (d, J = 8.26 Hz, 1 H) 7.80 (d, J = 8.64 Hz, 1 H) 8.19 (d, J = 9.67 Hz, 1 H) 8.33 (br. s., 1 H) 8.68 (br. s., 1 H). |
| 622 | 1-(4'-chloro-5-(cyanomethoxy)-2-fluoro-3'-methyl-4-biphenylyl)-N-3-isoxazolyl-2-oxo-1,2-dihydro-6-quinolinesulfonamide | 565.0 | 165 | 0.312 |  | 1H NMR (400 MHz, DMSO-d6) δ = 2.45 (s, 3 H), 5.17-5.27 (m, 2 H) 6.79-6.91 (m, 1 H) 7.00 (br. s., 1 H) 7.10 (br. s., 1 H) 7.20 (br. s., 1 H) 7.54 (d, J = 8.04 Hz, 2 H) 7.58-7.66 (m, 2 H) 7.69 (br. s., 1 H) 7.87 (d, J = 8.89 Hz, 1 H) 8.25 (d, J = 7.98 Hz, 1 H) 8.39 (s, 1 H) 8.72 (s, 1 H) |
| 624 | N-3-isoxazolyl-2-oxo-1-(2,3',5'-trifluoro-5-hydroxy-4-biphenylyl)-1,2-dihydro-6-quinolinesulfonamide | 513.9 | 167 | 1.726 |  | 1H NMR (400 MHz, DMSO-d6) δ = 6.37 (s, 1 H) 6.78 (d, J = 9.17 Hz, 1 H) 6.83 (d, J = 8.45 Hz, 1 H) 7.17 (d, J = 7.20 Hz, 1 H) 7.30-7.43 (m, 4 H) 7.84 (dd, J = 8.95, 2.01 Hz, 1 H) 8.19 (d, J = 7.88 Hz, 1 H) 8.31 (s, J = 8.04 Hz, 1 H) 8.59 (s, 1 H) 10.06 (br. s., 1 H). |
| 680 | 1-(4-bromo-2-((1R)-1-cyanoethoxy)-5-fluorophenyl)-N-3-isoxazolyl-2-oxo-1,2-dihydro-6-quinolinesulfonamide, 1-(4-bromo-2-((1S)-1-cyanoethoxy)-5-fluorophenyl)-N-3-isoxazolyl-2-oxo-1,2-dihydro-6-quinolinesulfonamide | 530.9 | 166 | 25.41 |  | $^1$H NMR (500 MHz, DMSO-d6) δ = ppm 1.36 (d, J = 6.62 Hz, 2 H) 3.02-3.11 (m, 1 H) 3.17 (s, 1 H) 5.43-5.51 (m, 1 H) 6.16-6.22 (m, 1 H) 6.72 (d, J = 9.73 Hz, 2 H) 7.67-7.78 (m, 2 H) 7.84-7.94 (m, 1 H) 8.15-8.24 (m, 2 H) 8.35 (br. s., 1 H). m/z (ESI) 530.9 (M − H). |
| 623 | 1-(4-bromo-2-(cyanomethoxy)-5-fluorophenyl)-N-3-isoxazolyl-2-oxo-1,2-dihydro-6-quinolinesulfonamide | 518.9 | 166 | 7.781 |  | 1H NMR (400 MHz, DMSO-d6) δ = 5.13-5.22 (m, 2 H) 6.22 (s, 1 H) 6.73 (dd, J = 9.21, 4.41 Hz, 2 H) 7.70 (d, J = 8.56 Hz, 1 H) 7.75 (dd, J = 8.92, 1.85 Hz, 1 H) 7.89 (d, J = 6.10 Hz, 1 H) 8.18 (d, J = 9.27 Hz, 1 H) 8.20-8.23 (m, 1 H) 8.37 (s, 1 H). |
| 625 | 1-(4-bromo-5-fluoro-2-((3R)-3-pyrrolidinyloxy)phenyl)-N-3-isoxazolyl-2-oxo-1,2-dihydro-6-quinolinesulfonamide, 1-(4-bromo-5-fluoro-2-((3S)-3-pyrrolidinyloxy)phenyl)-N-3-isoxazolyl-2-oxo-1,2-dihydro-6-quinolinesulfonamide | 548.8 | 168 | 5.609 |  | 1H NMR (400 MHz, DMSO-d6) δ = 1.22-1.36 (m, 1 H) 1.82-2.01 (m, 2 H) 2.61-2.81 (m, 1 H) 2.84-3.06 (m, 2 H) 3.30 (br. s., 7 H) 5.13 (br. s., 1 H) 6.09 (d, J = 11.67 Hz, 1 H) 6.61-6.71 (m, 2 H) 7.60 (t, J = 8.19 Hz, 1 H) 7.71 (t, J = 8.01 Hz, 1 H) 7.78 (t, J = 7.13 Hz, 1 H) 8.07-8.18 (m, 3 H). |
| 681 | 1-(5-((1R)-1-cyanoethoxy)-2,3',5'-trifluoro-4-biphenylyl)-N-3-isoxazolyl-2-oxo-1,2-dihydro-6-quinolinesulfonamide, 1-(5-((1S)-1-cyanoethoxy)-2,3',5'-trifluoro-4-biphenylyl)-N-3-isoxazolyl-2-oxo-1,2-dihydro-6-quinolinesulfonamide | 567.1 | 166 | 0.458 |  | 1H NMR (400 MHz, DMSO-d6) δ = 1.29 (d, J = 6.68 Hz, 1 H) 1.33-1.46 (m, 2 H) 5.54-5.64 (m, 1H) 6.40-6.46 (m, 1 H) 6.84 (d, J = 9.17 Hz, 1 H) 6.88 (d, J = 8.86 Hz, 1 H) 7.39-7.53 (m, 3 H) 7.69 (d, J = 9.17 Hz, 1 H) 7.70-7.75 (m, 3 H) 7.78-7.93 (m, 1 H) 8.22-8.31 (m, 1 H) 8.34-8.45 (m, 1 H) 8.71 (s, 1 H) 11.65 (br. s., 1 H) |
| 670 | 1-(5-(3-azetidinyloxy)-2,3',5'- | 568.9 | 212 | 0.039 |  | $^1$H NMR (500 MHz, DMSO-d6) δ = ppm 3.64-3.77 (m, 2 H) 4.23-4.31 (m, 1 H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | trifluoro-4-biphenylyl)-N-3-isoxazolyl-2-oxo-1,2-dihydro-6-quinolinesulfonamide | | | | | 4.32-4.38 (m, 1 H) 5.19-5.26 (m, 1 H) 6.46 (s, 1 H) 6.85 (d, J = 8.28 Hz, 1 H) 6.94 (d, J = 9.08 Hz, 1 H) 7.31 (d, J = 6.62 Hz, 1 H) 7.37-7.48 (m, 3 H) 7.66 (d, J = 9.60 Hz, 1 H) 7.87 (d, J = 8.74 Hz, 1 H) 8.29 (d, J = 9.67 Hz, 1 H) 8.42 (s, 1 H) 8.73 (s, 1 H) 8.79 (br. s., 1 H) |
| 662 | 1-(4'-chloro-2-fluoro-5-methoxy-3'-methyl-4-biphenylyl)-2-oxo-N-4-pyrimidinyl-1,2-dihydro-6-quinolinesulfonamide | 551.2 | 205 | 0.005 | | $^1$H NMR (400 MHz, DMSO-d$_6$) δ = 8.62 (br. s., 1H), 8.43 (br. s., 1H), 8.37-8.18 (m, 2H), 7.93 (d, J = 8.9 Hz, 1H), 7.70 (br. s., 1H), 7.63-7.45 (m, 3H), 7.38 (d, J = 6.8 Hz, 1H), 7.03 (br. s., 1H), 6.81 (t, J = 9.1 Hz, 2H), 3.73 (s, 3H), 2.44 (s, 3H) |
| 691 | 1-(4'-chloro-2-fluoro-5-methoxy-3'-methyl-4-biphenylyl)-2-oxo-N-2-pyrazinyl-1,2-dihydro-6-quinolinesulfonamide | 551.2 | 205 | 0.015 | | $^1$H NMR (400 MHz, DMSO-d$_6$) δ = 11.64 (br. s., 1H), 8.47 (d, J = 2.1 Hz, 1H), 8.36 (d, J = 1.0 Hz, 1H), 8.29-8.19 (m, 3H), 7.96 (dd, J = 2.2, 9.0 Hz, 1H), 7.69 (s, 1H), 7.61-7.47 (m, 3H), 7.38 (d, J = 6.9 Hz, 1H), 6.83 (dd, J = 9.3, 18.1 Hz, 2H), 3.72 (s, 3H), 2.44 (s, 3H) |
| 692 | 1-(4'-chloro-2-fluoro-5-methoxy-3'-methyl-4-biphenylyl)-N-(5-fluoro-2-pyrimidinyl)-2-oxo-1,2-dihydro-6-quinolinesulfonamide | 569.2 | 205 | 0.03 | | $^1$H NMR (400 MHz, DMSO-d$_6$) δ = 11.98 (s, 1H), 8.62 (s, 2H), 8.48 (d, J = 2.1 Hz, 1H), 8.26 (d, J = 9.7 Hz, 1H), 7.98 (dd, J = 2.2, 9.0 Hz, 1H), 7.70 (s, 1H), 7.61-7.47 (m, 3H), 7.39 (d, J = 6.9 Hz, 1H), 6.83 (dd, J = 9.3, 15.9 Hz, 2H), 3.73 (s, 3H), 2.44 (s, 3H) |
| 693 | 1-(4'-chloro-2-fluoro-5-methoxy-3'-methyl-4-biphenylyl)-N-(5-fluoro-2-pyridinyl)-2-oxo-1,2-dihydro-6-quinolinesulfonamide | 568.1 | 205 | 0.186 | | $^1$H NMR (400 MHz, DMSO-d$_6$) δ = 11.18 (br. s., 1H), 8.41 (d, J = 2.1 Hz, 1H), 8.23 (d, J = 9.6 Hz, 1H), 8.18 (d, J = 3.1 Hz, 1H), 7.90 (dd, J = 2.2, 9.0 Hz, 1H), 7.72-7.63 (m, 2H), 7.61-7.47 (m, 3H), 7.38 (d, J = 6.9 Hz, 1H), 7.11 (dd, J = 3.7, 9.1 Hz, 1H), 6.82 (dd, J = 9.3, 13.8 Hz, 2H), 3.73 (s, 3H), 2.44 (s, 3H) |
| 665 | 1-(5-chloro-6-(3,5-difluorophenyl)-2-methoxy-3-pyridinyl)-N-3-isoxazolyl-2-oxo-1,2-dihydro-6-quinolinesulfonamide | 545.2 | 208 | 0.015 | | $^1$H NMR (400 MHz, DMSO-d$_6$) δ = 11.68 (br. s., 1H), 8.74 (d, J = 1.5 Hz, 1H), 8.41 (d, J = 1.7 Hz, 1H), 8.33 (s, 1H), 8.27 (d, J = 9.7 Hz, 1H), 7.87 (dd, J = 2.0, 8.9 Hz, 1H), 7.59 (d, J = 6.3 Hz, 2H), 7.45 (t, J = 9.3 Hz, 1H), 7.03 (d, J = 9.0 Hz, 1H), 6.85 (d, J = 9.7 Hz, 1H), 6.46 (d, J = 1.5 Hz, 1H), 3.84 (s, 3H) |
| 666 | 1-(5-chloro-6-(3,5-difluorophenyl)-2-methoxy-3-pyridinyl)-N-3-isoxazolyl-2-oxo-1,2-dihydro-6-quinolinesulfonamide | 545.2 | 208 | 1.058 | | $^1$H NMR (400 MHz, DMSO-d$_6$) δ = 11.67 (br. s., 1H), 8.72 (s, 1H), 8.40 (br. s., 1H), 8.33 (s, 1H), 8.27 (d, J = 9.7 Hz, 1H), 7.86 (d, J = 8.7 Hz, 1H), 7.59 (d, J = 6.4 Hz, 2H), 7.45 (t, J = 9.0 Hz, 1H), 7.02 (d, J = 8.9 Hz, 1H), 6.84 (d, J = 9.7 Hz, 1H), 6.45 (s, 1H), 3.84 (s, 3H) |
| 1070 | 1-(5-chloro-6-(3-chloro-5-fluorophenyl)-2-methoxy-3-pyridinyl)-N-3-isoxazolyl-2-oxo-1,2-dihydro-6-quinolinesulfonamide | 561.0 | 208 | 0.012 | | $^1$H NMR (400 MHz, DMSO-d$_6$) δ = 11.67 (br. s., 1H), 8.72 (br. s., 1H), 8.40 (br. s., 1H), 8.33 (s, 1H), 8.27 (d, J = 9.8 Hz, 1H), 7.86 (d, J = 8.2 Hz, 1H), 7.76 (br. s., 1H), 7.73-7.59 (m, 2H), 7.01 (d, J = 8.8 Hz, 1H), 6.84 (d, J = 9.5 Hz, 1H), 6.45 (br. s., 1H), 3.83 (s, 3H) |
| 1071 | 1-(5-chloro-6-(3-chloro-5-fluorophenyl)-2-methoxy-3-pyridinyl)-N-3-isoxazolyl-2-oxo-1,2-dihydro-6-quinolinesulfonamide | 561.0 | 208 | 0.348 | | $^1$H NMR (400 MHz, DMSO-d$_6$) δ = 11.68 (br. s., 1H), 8.73 (d, J = 1.8 Hz, 1H), 8.41 (d, J = 2.1 Hz, 1H), 8.33 (s, 1H), 8.27 (d, J = 9.7 Hz, 1H), 7.86 (dd, J = 2.2, 8.9 Hz, 1H), 7.76 (s, 1H), 7.73-7.68 (m, J = 1.9, 1.9, 9.5 Hz, 1H), 7.64 (td, J = 2.1, 8.7 Hz, 1H), 7.02 (d, J = 9.0 Hz, 1H), 6.84 (d, J = 9.7 Hz, 1H), 6.46 (d, J = 1.8 Hz, 1H), 3.83 (s, 3H) |
| 694 | 1-(4'-chloro-2-fluoro-5-methoxy-3'-methyl-4-biphenylyl)-N-1,3-oxazol-2-yl-2-oxo-1,2-dihydro-6-quinolinesulfonamide | 540.0 | 205 | 0.027 | | $^1$H NMR (400 MHz, DMSO-d$_6$) δ = 12.17 (br. s., 1H), 8.33 (d, J = 2.1 Hz, 1H), 8.20 (d, J = 9.5 Hz, 1H), 7.87 (dd, J = 2.2, 8.9 Hz, 1H), 7.70 (s, 1H), 7.61-7.52 (m, 3H), 7.50 (d, J = 10.5 Hz, 1H), 7.39 (d, J = 7.0 Hz, 1H), 7.25 (d, J = 1.7 Hz, 1H), 6.78 (dd, J = 1.5, 9.2 Hz, 2H), 3.74 (s, 3H), 2.44 (s, 3H) |
| 663 | 1-(4'-chloro-2-fluoro-5-methoxy-3'-methyl-4-biphenylyl)-N-1,2,4-oxadiazol-3-yl-2-oxo-1,2-dihydro-6-quinolinesulfonamide | 541.1 | 206 | 0.006 | | $^1$H NMR (400 MHz, DMSO-d$_6$) δ = 9.32 (s, 1H), 8.43 (d, J = 2.3 Hz, 1H), 8.27 (d, J = 9.5 Hz, 1H), 7.94 (dd, J = 2.2, 9.0 Hz, 1H), 7.70 (s, 1H), 7.60-7.49 (m, 3H), 7.39 (d, J = 6.9 Hz, 1H), 6.89 (d, J = 8.9 Hz, 1H), 6.82 (d, J = 9.6 Hz, 1H), 3.74 (s, 3H), 2.44 (s, 3H) |
| 1072 | 1-(4'-chloro-2-fluoro-5-methoxy-3'-methyl-4-biphenylyl)-2-oxo- | 557.0 | 205 | 0.018 | | $^1$H NMR (400 MHz, DMSO-d$_6$) δ = 12.27 (br. s., 1H), 8.52-8.39 (m, 2H), 8.25 (d, J = 9.7 Hz, 1H), 7.94 (dd, J = 1.9, 8.9 Hz, 1H), 7.69 (s, 1H), |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 1073 | N-1,2,5-thiadiazol-3-yl-1,2-dihydro-6-quinolinesulfonamide 1-(4'-chloro-2-fluoro-5-methoxy-3'-methyl-4-biphenylyl)-N-3-isothiazolyl-2-oxo-1,2-dihydro-6-quinolinesulfonamide | 556.1 | 205 | 0.023 | | 7.61-7.46 (m, 3H), 7.39 (d, J = 6.9 Hz, 1H), 6.87 (d, J = 9.0 Hz, 1H), 6.82 (d, J = 9.6 Hz, 1H), 3.73 (s, 3H), 2.43 (s, 3H) $^1$H NMR (400 MHz, DMSO-d$_6$) δ = 11.65 (s, 1H), 8.91 (d, J = 4.8 Hz, 1H), 8.40 (d, J = 2.2 Hz, 1H), 8.23 (d, J = 9.6 Hz, 1H), 7.89 (dd, J = 2.2, 9.0 Hz, 1H), 7.69 (s, 1H), 7.60-7.48 (m, 3H), 7.38 (d, J = 6.9 Hz, 1H), 7.00 (d, J = 4.8 Hz, 1H), 6.85 (d, J = 9.0 Hz, 1H), 6.80 (d, J = 9.6 Hz, 1H), 3.73 (s, 3H), 2.44 (s, 3H) |
| 1074 | 1-(4'-chloro-2-fluoro-5-methoxy-3'-methyl-4-biphenylyl)-2-oxo-N-1,3,4-thiadiazol-2-yl-1,2-dihydro-6-quinolinesulfonamide | 557.1 | 205 | 0.003 | | $^1$H NMR (400 MHz, DMSO-d$_6$) δ = 14.35 (br. s., 1H), 8.75 (s, 1H), 8.29 (d, J = 2.2 Hz, 1H), 8.22 (d, J = 9.5 Hz, 1H), 7.81 (dd, J = 2.2, 8.9 Hz, 1H), 7.70 (s, 1H), 7.60-7.52 (m, 2H), 7.49 (d, J = 10.4 Hz, 1H), 7.38 (d, J = 7.0 Hz, 1H), 6.80 (dd, J = 6.7, 9.3 Hz, 2H), 3.74 (s, 3H), 2.44 (s, 3H) |
| 1075 | 1-(4'-chloro-2-fluoro-5-methoxy-3'-methyl-4-biphenylyl)-2-oxo-N-1,2,4-thiadiazol-5-yl-1,2-dihydro-6-quinolinesulfonamide | 557.1 | 205 | 0.004 | >10.0 | $^1$H NMR (400 MHz, DMSO-d$_6$) δ = 8.33 (s, 1H), 8.29 (d, J = 2.1 Hz, 1H), 8.23 (d, J = 9.7 Hz, 1H), 7.82 (dd, J = 2.1, 8.9 Hz, 1H), 7.70 (s, 1H), 7.61-7.52 (m, 2H), 7.49 (d, J = 10.4 Hz, 1H), 7.38 (d, J = 7.0 Hz, 1H), 6.79 (dd, J = 6.2, 9.3 Hz, 2H), 3.74 (s, 3H), 2.44 (s, 3H) |
| 664 | 1-(4-cyclopentyl-5-fluoro-2-methoxyphenyl)-N-3-isoxazolyl-2-oxo-1,2-dihydro-6-quinolinesulfonamide | 484.1 | 207 | 0.088 | | $^1$H NMR (400 MHz, DMSO-d$_6$) δ = 11.65 (s, 1H), 8.73 (d, J = 1.8 Hz, 1H), 8.35 (d, J = 2.1 Hz, 1H), 8.20 (d, J = 9.6 Hz, 1H), 7.85 (dd, J = 2.2, 9.0 Hz, 1H), 7.27 (d, J = 10.2 Hz, 1H), 7.19 (d, J = 6.6 Hz, 1H), 6.78 (dd, J = 2.7, 9.3 Hz, 2H), 6.44 (d, J = 1.8 Hz, 1H), 3.66 (s, 3H), 3.29-3.20 (m, 1H), 2.07 (d, J = 4.2 Hz, 2H), 1.85 (br. s., 2H), 1.71 (br. s., 4H) |
| 1076 | 1-(4-(2,2-dimethylpropyl)-5-fluoro-2-methoxyphenyl)-N-3-isoxazolyl-2-oxo-1,2-dihydro-6-quinolinesulfonamide | 486.2 | 207 | 0.064 | | $^1$H NMR (400 MHz, DMSO-d$_6$) δ = 11.65 (br. s., 1H), 8.71 (d, J = 1.3 Hz, 1H), 8.35 (d, J = 2.1 Hz, 1H), 8.20 (d, J = 9.6 Hz, 1H), 7.85 (dd, J = 2.2, 9.0 Hz, 1H), 7.29 (d, J = 9.5 Hz, 1H), 7.10 (d, J = 6.6 Hz, 1H), 6.85-6.71 (m, 2H), 6.43 (d, J = 1.8 Hz, 1H), 3.64 (s, 3H), 2.62 (s, 2H), 0.99 (s, 9H) |
| 1077 | 1-(4-cyclohexyl-5-fluoro-2-methoxyphenyl)-N-3-isoxazolyl-2-oxo-1,2-dihydro-6-quinolinesulfonamide | 498.2 | 207 | 0.038 | | $^1$H NMR (400 MHz, DMSO-d$_6$) δ = 11.65 (br. s., 1H), 8.73 (br. s., 1H), 8.35 (br. s., 1H), 8.20 (d, J = 9.4 Hz, 1H), 7.85 (d, J = 8.5 Hz, 1H), 7.27 (d, J = 9.8 Hz, 1H), 7.17 (d, J = 5.3 Hz, 1H), 6.77 (dd, J = 9.5, 13.9 Hz, 2H), 6.44 (br. s., 1H), 3.66 (br. s., 3H), 2.89 (br. s., 1H), 1.85 (d, J = 9.3 Hz, 4H), 1.68-1.56 (m, 2H), 1.28 (d, J = 11.9 Hz, 4H) |
| 1078 | 1-(4-(cyclobutylmethyl)-5-fluoro-2-methoxyphenyl)-N-3-isoxazolyl-2-oxo-1,2-dihydro-6-quinolinesulfonamide | 484.1 | 207 | 0.069 | | $^1$H NMR (400 MHz, DMSO-d$_6$) δ = 11.65 (s, 1H), 8.73 (d, J = 1.5 Hz, 1H), 8.35 (d, J = 1.8 Hz, 1H), 8.20 (d, J = 9.7 Hz, 1H), 7.84 (dd, J = 1.9, 8.9 Hz, 1H), 7.27 (d, J = 9.5 Hz, 1H), 7.16 (d, J = 6.5 Hz, 1H), 6.76 (dd, J = 9.3, 17.8 Hz, 2H), 6.44 (d, J = 1.5 Hz, 1H), 3.64 (s, 3H), 2.89-2.73 (m, 2H), 2.65 (td, J = 7.5, 15.1 Hz, 1H), 2.07 (br. s., 2H), 1.92-1.75 (m, 4H) |
| 1079 | 1-(4-(cyclohexylmethyl)-5-fluoro-2-methoxyphenyl)-N-3-isoxazolyl-2-oxo-1,2-dihydro-6-quinolinesulfonamide | 512.2 | 207 | 0.017 | | $^1$H NMR (400 MHz, DMSO-d$_6$) δ = 11.65 (s, 1H), 8.73 (d, J = 1.8 Hz, 1H), 8.35 (d, J = 2.2 Hz, 1H), 8.20 (d, J = 9.6 Hz, 1H), 7.85 (dd, J = 2.2, 9.0 Hz, 1H), 7.27 (d, J = 9.5 Hz, 1H), 7.16 (d, J = 6.6 Hz, 1H), 6.77 (dd, J = 7.0, 9.3 Hz, 2H), 6.44 (d, J = 1.8 Hz, 1H), 3.64 (s, 3H), 2.59 (d, J = 3.7 Hz, 2H), 1.75-1.59 (m, 7H), 1.25 (d, J = 11.5 Hz, 4H) |
| 1080 | 1-(5-chloro-6-(3,5-difluorophenyl)-2-methoxy-3-pyridinyl)-2-oxo-N-2-pyrimidinyl-1,2-dihydro-6-quinolinesulfonamide | 556.1 | 208 | 0.021 | | $^1$H NMR (400 MHz, DMSO-d$_6$) δ = 11.93 (br. s., 1H), 8.51 (d, J = 4.9 Hz, 3H), 8.35-8.28 (m, 2H), 7.99 (dd, J = 2.1, 9.0 Hz, 1H), 7.60 (dd, J = 2.2, 8.3 Hz, 2H), 7.45 (tt, J = 2.3, 9.3 Hz, 1H), 7.05 (t, J = 4.8 Hz, 1H), 6.98 (d, J = 9.0 Hz, 1H), 6.83 (d, J = 9.6 Hz, 1H), 3.83 (s, 3H) |
| 1081 | 1-(5-chloro-6-(3,5-difluorophenyl)-2-methoxy-3-pyridinyl)-2-oxo-N-2- | 556.1 | 208 | 4.151 | | $^1$H NMR (400 MHz, DMSO-d$_6$) δ = 11.93 (br. s., 1H), 8.51 (d, J = 4.8 Hz, 3H), 8.36-8.28 (m, 2H), 7.99 (dd, J = 2.1, 9.0 Hz, 1H), 7.65-7.55 (m, 2H), 7.45 (tt, J = 2.3, 9.3 Hz, 1H), 7.05 (t, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | pyrimidinyl-1,2-dihydro-6-quinolinesulfonamide | | | | | J = 4.8 Hz, 1H), 6.98 (d, J = 9.0 Hz, 1H), 6.83 (d, J = 9.6 Hz, 1H), 3.83 (s, 3H) |
| 667 | 1-(4-(cyclopentylmethyl)-5-fluoro-2-methoxyphenyl)-N-3-isoxazolyl-2-oxo-1,2-dihydro-6-quinolinesulfonamide | 498.2 | 209 | 0.011 | | $^1$H NMR (400 MHz, DMSO-d$_6$) δ = 11.65 (s, 1H), 8.72 (d, J = 1.8 Hz, 1H), 8.35 (d, J = 2.1 Hz, 1H), 8.20 (d, J = 9.7 Hz, 1H), 7.84 (dd, J = 2.2, 9.0 Hz, 1H), 7.27 (d, J = 9.6 Hz, 1H), 7.20 (d, J = 6.6 Hz, 1H), 6.77 (dd, J = 9.4, 10.9 Hz, 2H), 6.44 (d, J = 1.8 Hz, 1H), 3.64 (s, 3H), 2.70 (d, J = 6.6 Hz, 2H), 2.19 (td, J = 7.6, 15.1 Hz, 1H), 1.80-1.62 (m, 4H), 1.54 (dd, J = 4.6, 7.0 Hz, 2H), 1.32-1.21 (m, 5H) |
| 1082 | 1-(4-((1R,2R,4R)-bicyclo[2.2.1]hept-2-ylmethyl)-5-fluoro-2-methoxyphenyl)-N-3-isoxazolyl-2-oxo-1,2-dihydro-6-quinolinesulfonamide, 1-(4-((1R,2R,4S)-bicyclo[2.2.1]hept-2-ylmethyl)-5-fluoro-2-methoxyphenyl)-N-3-isoxazolyl-2-oxo-1,2-dihydro-6-quinolinesulfonamide, 1-(4-((1R,2S,4R)-bicyclo[2.2.1]hept-2-ylmethyl)-5-fluoro-2-methoxyphenyl)-N-3-isoxazolyl-2-oxo-1,2-dihydro-6-quinolinesulfonamide, 1-(4-((1R,2S,4S)-bicyclo[2.2.1]hept-2-ylmethyl)-5-fluoro-2-methoxyphenyl)-N-3-isoxazolyl-2-oxo-1,2-dihydro-6-quinolinesulfonamide, 1-(4-((1S,2R,4R)-bicyclo[2.2.1]hept-2-ylmethyl)-5-fluoro-2-methoxyphenyl)-N-3-isoxazolyl-2-oxo-1,2-dihydro-6-quinolinesulfonamide, 1-(4-((1S,2R,4S)-bicyclo[2.2.1]hept-2-ylmethyl)-5-fluoro-2-methoxyphenyl)-N-3-isoxazolyl-2-oxo-1,2-dihydro-6-quinolinesulfonamide, 1-(4-((1S,2S,4R)-bicyclo[2.2.1]hept-2-ylmethyl)-5-fluoro-2-methoxyphenyl)-N-3-isoxazolyl-2-oxo-1,2-dihydro-6-quinolinesulfonamide, 1-(4-((1S,2S,4S)-bicyclo[2.2.1]hept-2-ylmethyl)-5-fluoro-2-methoxyphenyl)-N-3-isoxazolyl-2-oxo-1,2-dihydro-6-quinolinesulfonamide | 524.2 | 209 | 0.009 | | $^1$H NMR (400 MHz, DMSO-d$_6$) δ = 11.65 (s, 1H), 8.73 (d, J = 1.8 Hz, 1H), 8.35 (d, J = 2.1 Hz, 1H), 8.20 (d, J = 9.7 Hz, 1H), 7.84 (dd, J = 2.2, 8.9 Hz, 1H), 7.30-7.24 (m, 1H), 7.20 (dd, J = 2.4, 6.6 Hz, 1H), 6.77 (dd, J = 9.3, 13.4 Hz, 2H), 6.44 (d, J = 1.8 Hz, 1H), 3.66-3.62 (m, 3H), 2.72 (d, J = 7.7 Hz, 2H), 2.30-2.16 (m, 2H), 1.74 (dt, J = 3.5, 7.5 Hz, 2H), 1.58-1.44 (m, 2H), 1.29-1.17 (m, 5H), 0.90-0.76 (m, 4H) |
| 1083 | 1-(5-fluoro-2-methoxy-4-(cis-4-methylcyclohexyl)phenyl)-N-3-isoxazolyl-2-oxo-1,2-dihydro-6-quinolinesulfonamide, | 512.2 | 209 | 0.01 | | $^1$H NMR (400 MHz, DMSO-d$_6$) δ = 11.65 (br. s., 1H), 8.73 (br. s., 1H), 8.35 (br. s., 1H), 8.20 (d, J = 9.1 Hz, 1H), 7.85 (d, J = 8.3 Hz, 1H), 7.26 (d, J = 9.4 Hz, 1H), 7.17 (br. s., 1H), 6.87-6.68 (m, 2H), 6.44 (br. s., 1H), 3.66 (br. s., 4H), 2.93 (br. s., 1H), 1.83 (br. s., 4H), 1.18-1.04 (m, 4H), |

TABLE 3-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
|  | 1-(5-fluoro-2-methoxy-4-(trans-4-methylcyclohexyl)phenyl)-N-3-isoxazolyl-2-oxo-1,2-dihydro-6-quinolinesulfonamide |  |  |  |  | 0.95 (br. s., 4H) |
| 1084 | 1-(5-chloro-6-(4-chloro-3-methylphenyl)-2-methoxy-3-pyridinyl)-N-3-isoxazolyl-2-oxo-1,2-dihydro-6-quinolinesulfonamide | 557.1 | 208 | 0.019 |  | $^1$H NMR (400 MHz, DMSO-d$_6$) δ = 11.69 (s, 1H), 8.74 (d, J = 1.7 Hz, 1H), 8.41 (d, J = 2.0 Hz, 1H), 8.32-8.23 (m, 2H), 7.87 (dd, J = 2.2, 9.0 Hz, 1H), 7.82 (d, J = 1.4 Hz, 1H), 7.70 (dd, J = 1.8, 8.3 Hz, 1H), 7.62-7.56 (m, 1H), 7.04 (d, J = 9.0 Hz, 1H), 6.84 (d, J = 9.6 Hz, 1H), 6.46 (d, J = 1.8 Hz, 1H), 3.82 (s, 3H), 2.44 (s, 3H) |
| 1085 | 1-(5-chloro-6-(4-chloro-3-methylphenyl)-2-methoxy-3-pyridinyl)-N-3-isoxazolyl-2-oxo-1,2-dihydro-6-quinolinesulfonamide | 557.1 | 208 | 3.438 |  | $^1$H NMR (400 MHz, DMSO-d$_6$) δ = 11.69 (s, 1H), 8.74 (d, J = 1.8 Hz, 1H), 8.41 (d, J = 2.1 Hz, 1H), 8.32-8.21 (m, 2H), 7.87 (dd, J = 2.2, 9.0 Hz, 1H), 7.82 (d, J = 1.6 Hz, 1H), 7.70 (dd, J = 1.9, 8.2 Hz, 1H), 7.63-7.58 (m, 1H), 7.04 (d, J = 9.0 Hz, 1H), 6.84 (d, J = 9.7 Hz, 1H), 6.46 (d, J = 1.7 Hz, 1H), 3.82 (s, 3H), 2.44 (s, 3H) |
| 668 | 1-(5-fluoro-2-methoxy-4-(tetrahydro-2H-pyran-4-yl)phenyl)-N-3-isoxazolyl-2-oxo-1,2-dihydro-6-quinolinesulfonamide | 500.2 | 210 | 3.07 |  | $^1$H NMR (400 MHz, DMSO-d$_6$) δ = 11.65 (s, 1H), 8.73 (d, J = 1.8 Hz, 1H), 8.36 (d, J = 2.2 Hz, 1H), 8.21 (d, J = 9.6 Hz, 1H), 7.85 (dd, J = 2.2, 9.0 Hz, 1H), 7.31 (d, J = 10.2 Hz, 1H), 7.22 (d, J = 6.6 Hz, 1H), 6.77 (dd, J = 9.3, 11.4 Hz, 2H), 6.44 (d, J = 1.8 Hz, 1H), 4.06-3.94 (m, 2H), 3.68 (s, 3H), 3.51 (t, J = 11.1 Hz, 2H), 3.23-3.11 (m, 1H), 2.00-1.82 (m, 2H), 1.74 (d, J = 12.9 Hz, 2H) |
| 1086 | 1-(5-fluoro-2-methoxy-4-(cis-4-methoxycyclohexyl)phenyl)-N-3-isoxazolyl-2-oxo-1,2-dihydro-6-quinolinesulfonamide, 1-(5-fluoro-2-methoxy-4-(trans-4-methoxycyclohexyl)phenyl)-N-3-isoxazolyl-2-oxo-1,2-dihydro-6-quinolinesulfonamide | 528.2 | 210 | 3.909 |  | $^1$H NMR (400 MHz, DMSO-d$_6$) δ = 11.66 (s, 1H), 8.73 (d, J = 1.8 Hz, 1H), 8.36 (d, J = 2.2 Hz, 1H), 8.21 (d, J = 9.6 Hz, 1H), 7.85 (dd, J = 2.2, 9.0 Hz, 1H), 7.28 (d, J = 10.1 Hz, 1H), 7.19 (d, J = 6.5 Hz, 1H), 6.77 (dd, J = 9.3, 14.8 Hz, 2H), 6.45 (d, J = 1.8 Hz, 1H), 3.66 (s, 3H), 3.29 (s, 3H), 3.26-3.18 (m, 1H), 2.94-2.80 (m, 1H), 2.16 (d, J = 10.1 Hz, 2H), 1.94-1.83 (m, 3H), 1.78-1.62 (m, 3H), 1.38-1.23 (m, 3H) |
| 1087 | 1-(5-fluoro-2-methoxy-4-((1R,2R,4S)-7-oxabicyclo[2.2.1]hept-2-ylmethyl)phenyl)-N-3-isoxazolyl-2-oxo-1,2-dihydro-6-quinolinesulfonamide, 1-(5-fluoro-2-methoxy-4-((1S,2S,4R)-7-oxabicyclo[2.2.1]hept-2-ylmethyl)phenyl)-N-3-isoxazolyl-2-oxo-1,2-dihydro-6-quinolinesulfonamide | 526.2 | 210 | 1.732 |  | $^1$H NMR (400 MHz, DMSO-d$_6$) δ = 11.65 (s, 1H), 8.72 (d, J = 1.7 Hz, 1H), 8.35 (d, J = 2.0 Hz, 1H), 8.20 (d, J = 9.7 Hz, 1H), 7.84 (d, J = 8.9 Hz, 1H), 7.29 (d, J = 9.6 Hz, 1H), 7.21 (d, J = 6.5 Hz, 1H), 6.77 (dd, J = 9.4, 12.6 Hz, 2H), 6.44 (d, J = 1.7 Hz, 1H), 4.55 (br. s., 1H), 4.26 (dd, J = 4.5, 10.7 Hz, 1H), 2.82-2.69 (m, 1H), 2.16 (dd, J = 3.7, 7.7 Hz, 1H), 1.71-1.62 (m, 1H), 1.61-1.50 (m, 3H), 1.48-1.37 (m, 2H), 1.33 (br. s., 1H), 1.25 (br. s., 1H), 0.90-0.80 (m, 2H) |
| 1088 | 1-(5-chloro-2-methoxy-6-(3-methylphenyl)-3-pyridinyl)-N-3-isoxazolyl-2-oxo-1,2-dihydro-6-quinolinesulfonamide | 523.0 | 208 | 0.047 |  | $^1$H NMR (400 MHz, DMSO-d$_6$) δ = 11.69 (s, 1H), 8.74 (d, J = 1.8 Hz, 1H), 8.41 (d, J = 2.2 Hz, 1H), 8.32-8.19 (m, 2H), 7.88 (dd, J = 2.2, 9.0 Hz, 1H), 7.67-7.59 (m, 2H), 7.49-7.41 (m, 1H), 7.33 (d, J = 7.9 Hz, 1H), 7.04 (d, J = 9.0 Hz, 1H), 6.84 (d, J = 9.6 Hz, 1H), 6.46 (d, J = 1.8 Hz, 1H), 3.82 (s, 3H), 2.42 (s, 3H) |
| 1089 | 1-(5-chloro-2-methoxy-6-(3-methylphenyl)-3-pyridinyl)-N-3-isoxazolyl-2-oxo-1,2-dihydro-6-quinolinesulfonamide | 523.0 | 208 | 3.241 |  | $^1$H NMR (400 MHz, DMSO-d$_6$) δ = 11.69 (s, 1H), 8.74 (d, J = 1.8 Hz, 1H), 8.41 (d, J = 2.2 Hz, 1H), 8.30-8.23 (m, 2H), 7.88 (dd, J = 2.2, 8.9 Hz, 1H), 7.67-7.60 (m, 2H), 7.44 (t, J = 8.0 Hz, 1H), 7.33 (d, J = 7.8 Hz, 1H), 7.04 (d, J = 9.0 Hz, 1H), 6.84 (d, J = 9.7 Hz, 1H), 6.46 (d, J = 1.8 Hz, 1H), 3.82 (s, 3H), 2.42 (s, 3H) |
| 1090 | 1-(5-chloro-6-(3-cyanophenyl)-2-methoxy-3-pyridinyl)- | 534.0 | 208 | 0.201 |  | $^1$H NMR (400 MHz, DMSO-d$_6$) δ = 11.69 (s, 1H), 8.74 (d, J = 1.8 Hz, 1H), 8.41 (d, J = 2.2 Hz, 1H), 8.34 (s, 1H), 8.31-8.25 (m, 2H), 8.21 (td, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | N-3-isoxazolyl-2-oxo-1,2-dihydro-6-quinolinesulfonamide | | | | | J = 1.3, 8.1 Hz, 1H), 8.01 (td, J = 1.3, 7.8 Hz, 1H), 7.87 (dd, J = 2.2, 9.0 Hz, 1H), 7.82-7.76 (m, 1H), 7.04 (d, J = 9.0 Hz, 1H), 6.85 (d, J = 9.6 Hz, 1H), 6.46 (d, J = 1.8 Hz, 1H), 3.84 (s, 3H) |
| 1091 | 1-(5-chloro-6-(3-cyanophenyl)-2-methoxy-3-pyridinyl)-N-3-isoxazolyl-2-oxo-1,2-dihydro-6-quinolinesulfonamide | 534.0 | 208 | 20.33 | | $^1$H NMR (400 MHz, DMSO-d$_6$) δ = 11.69 (s, 1H), 8.74 (d, J = 1.8 Hz, 1H), 8.41 (d, J = 2.2 Hz, 1H), 8.34 (s, 1H), 8.31-8.25 (m, 2H), 8.21 (td, J = 1.3, 8.1 Hz, 1H), 8.01 (td, J = 1.3, 7.8 Hz, 1H), 7.87 (dd, J = 2.2, 9.0 Hz, 1H), 7.79 (t, J = 7.9 Hz, 1H), 7.04 (d, J = 9.0 Hz, 1H), 6.85 (d, J = 9.6 Hz, 1H), 6.46 (d, J = 1.8 Hz, 1H), 3.84 (s, 3H) |
| 1092 | 1-(5-chloro-2-methoxy-6-(3-methoxyphenyl)-3-pyridinyl)-N-3-isoxazolyl-2-oxo-1,2-dihydro-6-quinolinesulfonamide | 539.0 | 208 | 0.048 | | $^1$H NMR (400 MHz, DMSO-d$_6$) δ = 11.68 (br. s., 1H), 8.72 (s, 1H), 8.40 (s, 1H), 8.30-8.21 (m, 2H), 7.87 (d, J = 9.2 Hz, 1H), 7.51-7.39 (m, 2H), 7.37 (s, 1H), 7.10 (d, J = 7.0 Hz, 1H), 7.04 (d, J = 9.0 Hz, 1H), 6.84 (d, J = 9.6 Hz, 1H), 6.45 (s, 1H), 3.84 (s, 3H), 3.82 (s, 3H) |
| 1093 | 1-(5-chloro-2-methoxy-6-(3-methoxyphenyl)-3-pyridinyl)-N-3-isoxazolyl-2-oxo-1,2-dihydro-6-quinolinesulfonamide | 539.0 | 208 | 4.945 | | $^1$H NMR (400 MHz, DMSO-d$_6$) δ = 11.68 (br. s., 1H), 8.72 (d, J = 1.7 Hz, 1H), 8.40 (d, J = 2.2 Hz, 1H), 8.29-8.20 (m, 2H), 7.87 (dd, J = 2.2, 8.9 Hz, 1H), 7.50-7.45 (m, 1H), 7.44-7.36 (m, 2H), 7.10 (ddd, J = 1.1, 2.6, 8.1 Hz, 1H), 7.03 (d, J = 8.9 Hz, 1H), 6.84 (d, J = 9.6 Hz, 1H), 6.45 (d, J = 1.8 Hz, 1H), 3.84 (s, 3H), 3.82 (s, 3H) |
| 1094 | 1-(3'-fluoro-3-methoxy-5'-(trifluoromethyl)-4-biphenylyl)-2-oxo-N-2-pyrazinyl-1,2-dihydro-6-quinolinesulfonamide | 571.1 | 211 | 0.069 | | $^1$H NMR (400 MHz, DMSO-d$_6$) δ = 11.62 (br. s., 1H), 8.47 (d, J = 2.2 Hz, 1H), 8.36 (d, J = 1.1 Hz, 1H), 8.29-8.19 (m, 3H), 8.09 (d, J = 9.9 Hz, 1H), 8.03 (s, 1H), 7.94 (dd, J = 2.2, 9.0 Hz, 1H), 7.75 (d, J = 8.6 Hz, 1H), 7.66 (d, J = 1.8 Hz, 1H), 7.58 (dd, J = 1.9, 8.1 Hz, 1H), 7.44 (d, J = 8.1 Hz, 1H), 6.79 (dd, J = 9.3, 13.7 Hz, 2H), 3.80 (s, 3H) |
| 1095 | 1-(3'-fluoro-3-methoxy-5'-(trifluoromethyl)-4-biphenylyl)-2-oxo-N-3-pyridazinyl-1,2-dihydro-6-quinolinesulfonamide | 571.2 | 211 | 0.006 | | $^1$H NMR (400 MHz, DMSO-d$_6$) δ = 14.48 (br. s., 1H), 8.35 (d, J = 1.5 Hz, 1H), 8.31 (br. s., 1H), 8.20 (d, J = 9.7 Hz, 1H), 8.09 (d, J = 9.9 Hz, 1H), 8.04 (s, 1H), 7.91 (br. s., 1H), 7.85 (dd, J = 1.8, 8.9 Hz, 1H), 7.75 (d, J = 8.6 Hz, 1H), 7.71-7.63 (m, 2H), 7.58 (dd, J = 1.7, 8.1 Hz, 1H), 7.43 (d, J = 8.1 Hz, 1H), 6.78 (d, J = 9.6 Hz, 1H), 6.72 (d, J = 8.9 Hz, 1H), 3.80 (s, 3H) |
| 1096 | 1-(4-((4R)-2,2-dimethyltetrahydro-2H-pyran-4-yl)-5-fluoro-2-methoxyphenyl)-N-3-isoxazolyl-2-oxo-1,2-dihydro-6-quinolinesulfonamide, 1-(4-((4S)-2,2-dimethyltetrahydro-2H-pyran-4-yl)-5-fluoro-2-methoxyphenyl)-N-3-isoxazolyl-2-oxo-1,2-dihydro-6-quinolinesulfonamide | 528.2 | 210 | 1.122 | | $^1$H NMR (400 MHz, DMSO-d$_6$) δ = 11.64 (s, 1H), 8.72 (d, J = 1.8 Hz, 1H), 8.35 (d, J = 2.2 Hz, 1H), 8.20 (d, J = 9.6 Hz, 1H), 7.84 (td, J = 2.4, 9.0 Hz, 1H), 7.29 (d, J = 10.2 Hz, 1H), 7.20 (d, J = 6.2 Hz, 1H), 6.78 (d, J = 9.7 Hz, 1H), 6.74 (dd, J = 2.5, 9.0 Hz, 1H), 6.44 (d, J = 1.8 Hz, 1H), 3.75 (d, J = 7.0 Hz, 2H), 3.67 (s, 3H), 3.33 (br. s., 1H), 1.70 (br. s., 2H), 1.29 (s, 3H), 1.21 (d, J = 5.6 Hz, 3H) |
| 1097 | 1-(3'-fluoro-3-methoxy-5'-(trifluoromethyl)-4-biphenylyl)-2-oxo-N-2-pyrimidinyl-1,2-dihydro-6-quinolinesulfonamide | 569.0 | 211 | 0.05 | | $^1$H NMR (500 MHz, DMSO-d6) δ ppm 3.80 (s, 3 H) 6.76 (d, J = 9.02 Hz, 1 H) 6.79 (d, J = 9.60 Hz, 1 H) 7.05 (t, J = 4.64 Hz, 1 H) 7.42 (d, J = 8.01 Hz, 1 H) 7.55-7.69 (m, 2 H) 7.75 (d, J = 8.43 Hz, 1 H) 7.96-8.05 (m, 2 H) 8.08 (d, J = 10.32 Hz, 1 H) 8.26 (d, J = 9.67 Hz, 1 H) 8.46-8.55 (m, 2 H) 11.90 (br. s., 1 H) |
| 1098 | 1-(3'-fluoro-3-methoxy-5'-(trifluoromethyl)-4-biphenylyl)-N-1,3-oxazol-2-yl-2-oxo-1,2-dihydro-6-quinolinesulfonamide | 559.0 | 211 | 0.037 | | $^1$H NMR (500 MHz, DMSO-d6) δ ppm 3.81 (s, 4 H) 6.72 (d, J = 8.95 Hz, 1 H) 6.78 (d, J = 9.54 Hz, 1 H) 7.26 (s, 1 H) 7.44 (d, J = 7.98 Hz, 1 H) 7.56-7.62 (m, 2 H) 7.66 (s, 1 H) 7.75 (d, J = 8.82 Hz, 1 H) 7.85 (d, J = 9.02 Hz, 1 H) 8.00-8.06 (m, 1 H) 8.09 (d, J = 9.73 Hz, 1 H) 8.19 (d, J = 9.73 Hz, 1 H) 8.33 (s, 1 H) |
| 1099 | 1-(3'-fluoro-3-methoxy-5'-(trifluoromethyl)-4-biphenylyl)-N-(5- | 588.0 | 211 | 0.035 | | $^1$H NMR (500 MHz, DMSO-d6) δ ppm 3.80 (s, 3 H) 6.77 (d, J = 9.02 Hz, 1 H) 6.80 (d, J = 9.67 Hz, 1 H) 7.42 (d, J = 7.91 Hz, 1 H) 7.56-7.64 (m, 1 H) 7.66 (s, 1 H) 7.75 (d, J = 8.56 Hz, 1 H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | fluoro-2-pyrimidinyl)-2-oxo-1,2-dihydro-6-quinolinesulfonamide | | | | | 7.94-8.05 (m, 2 H) 8.05-8.16 (m, 1 H) 8.25 (d, J = 9.67 Hz, 1 H) 8.47 (s, 1 H) 8.61 (s, 1 H) 11.95 (br. s., 1 H) |
| 1100 | 1-(3'-fluoro-3-methoxy-5'-(trifluoromethyl)-4-biphenylyl)-N-(2-methyl-4-pyrimidinyl)-2-oxo-1,2-dihydro-6-quinolinesulfonamide | 585.2 | 211 | 0.037 | | $^1$H NMR (500 MHz, DMSO-d6) δ ppm 2.37 (s, 2 H) 3.80 (s, 3 H) 6.72 (d, J = 8.89 Hz, 1 H) 6.78 (d, J = 8.48 Hz, 1 H) 6.90 (br. s., 1 H) 7.43 (d, J = 7.98 Hz, 1 H) 7.59 (d, J = 7.79 Hz, 1 H) 7.66 (s, 1 H) 7.75 (d, J = 8.76 Hz, 1 H) 7.87 (d, J = 8.89 Hz, 1 H) 8.03 (s, 1 H) 8.09 (d, J = 9.54 Hz, 2 H) 8.22 (d, J = 9.60 Hz, s.,1 1 H) |
| 1101 | 1-(3'-fluoro-3-methoxy-5'-(trifluoromethyl)-4-biphenylyl)-N-(6-methyl-4-pyrimidinyl)-2-oxo-1,2-dihydro-6-quinolinesulfonamide | 585.0 | 211 | 0.041 | | $^1$H NMR (500 MHz, DMSO-d6) δ ppm 2.31 (s, 3 H) 3.65 (br. s., 1 H) 3.80 (s, 3 H) 6.73 (d, J = 8.95 Hz, 1 H) 6.79 (d, J = 9.60 Hz, 1 H) 6.90 (br. s., 1 H) 7.43 (d, J = 8.04 Hz, 1 H) 7.56-7.64 (m, 1 H) 7.66 (s, 1 H) 7.75 (d, J = 8.24 Hz, 1 H) 7.90 (d, J = 8.11 Hz, 1 H) 8.00-8.05 (m, 1 H) 8.09 (d, J = 9.93 Hz, 1 H) 8.23 (d, J = 9.67 Hz, 1 H) 8.42 (br. s., 1 H) 8.48 (s, 1 H) |
| 1102 | 1-(4-(4,4-difluorocyclohexyl)-5-fluoro-2-methoxyphenyl)-N-3-isoxazolyl-2-oxo-1,2-dihydro-6-quinolinesulfonamide | 534.2 | 210 | 0.237 | | $^1$H NMR (400 MHz, DMSO-d6) δ = 11.66 (s, 1H), 8.74 (d, J = 1.8 Hz, 1H), 8.36 (d, J = 2.2 Hz, 1H), 8.21 (d, J = 9.5 Hz, 1H), 7.85 (dd, J = 2.3, 8.9 Hz, 1H), 7.32 (d, J = 10.2 Hz, 1H), 7.20 (d, J = 6.5 Hz, 1H), 6.78 (dd, J = 9.3, 13.7 Hz, 2H), 6.45 (d, J = 1.9 Hz, 1H), 3.68 (s, 3H), 3.09 (br. s., 1H), 2.24-2.07 (m, 3H), 2.02-1.84 (m, 5H), |
| 673 | 1-(2-fluoro-5-methoxy-4'-(trifluoromethyl)-4-biphenylyl)-N-3-isoxazolyl-2-oxo-1,2-dihydro-6-quinolinesulfonamide | 560.2 | 139 | 0.019 | | $^1$H NMR (400 MHz, DMSO-d6) δ ppm 3.75 (s, 3 H) 6.46 (s, 1 H) 6.83 (d, J = 9.64 Hz, 1 H) 6.91 (d, J = 9.02 Hz, 1 H) 7.47 (d, J = 6.95 Hz, 1 H) 7.58 (d, J = 10.37 Hz, 1 H) 7.88 (dd, J = 8.91, 2.18 Hz, 1 H) 7.90-7.98 (m, 4 H) 8.25 (d, J = 9.54 Hz, 1 H) 8.39 (d, J = 2.07 Hz, 1 H) 8.74 (s, 1 H) 11.67 (s, 1 H). |
| 631/779 | 1-(3'-ethoxy-3-methoxy-4-biphenylyl)-N-3-isoxazolyl-2-oxo-1,2-dihydro-6-quinolinesulfonamide | 518.2 | 179 | 0.024 | | $^1$H NMR (400 MHz, DMSO-d6) δ = 11.70 (br. s., 1H), 8.78 (d, J = 1.8 Hz, 1H), 8.42 (d, J = 2.2 Hz, 1H), 8.27 (d, J = 9.6 Hz, 1H), 7.91 (dd, J = 2.2, 9.0 Hz, 1H), 7.56 (d, J = 1.3 Hz, 1H), 7.50-7.35 (m, 5H), 7.03 (dd, J = 1.6, 8.0 Hz, 1H), 6.86 (d, J = 9.6 Hz, 2H), 6.51 (d, J = 1.8 Hz, 1H), 4.18 (q, J = 6.9 Hz, 2H), 3.82 (s, 3H), 2.59-2.50 (m, 1H), 1.42 (t, J = 7.0 Hz, 3H). |
| 780 | N-3-isoxazolyl-1-(3-methoxy-3'-(1-methylethoxy)-4-biphenylyl)-2-oxo-1,2-dihydro-6-quinolinesulfonamide | 532.3 | 179 | 0.026 | | $^1$H NMR (400 MHz, DMSO-d6) δ = 11.69 (br. s., 1H), 8.77 (d, J = 1.8 Hz, 1H), 8.42 (d, J = 2.2 Hz, 1H), 8.26 (d, J = 9.6 Hz, 1H), 7.90 (dd, J = 2.2, 9.0 Hz, 1H), 7.54 (d, J = 1.6 Hz, 1H), 7.49-7.32 (m, 5H), 7.03 (dd, J = 1.8, 8.1 Hz, 1H), 6.85 (d, J = 9.6 Hz, 2H), 6.50 (d, J = 1.8 Hz, 1H), 4.80 (td, J = 6.0, 12.0 Hz, 1H), 3.82 (s, 3H), 1.36 (s, 3H), 1.35 (s, 3H). |
| 781 | N-3-isoxazolyl-1-(3-methoxy-3'-(trifluoromethoxy)-4-biphenylyl)-2-oxo-1,2-dihydro-6-quinolinesulfonamide | 558.1 | 179 | 0.01 | | $^1$H NMR (400 MHz, DMSO-d$_6$) δ = 11.69 (br. s., 1H), 8.77 (d, J = 1.8 Hz, 1H), 8.42 (d, J = 2.2 Hz, 1H), 8.27 (d, J = 9.6 Hz, 1H), 7.95-7.85 (m, 3H), 7.70 (t, J = 8.0 Hz, 1H), 7.63 (d, J = 1.8 Hz, 1H), 7.56-7.44 (m, 3H), 6.85 (dd, J = 1.5, 9.3 Hz, 2H), 6.50 (d, J = 1.8 Hz, 1H), 3.83 (s, 3H), 3.37 (br. s., 1H). |
| 782 | 1-(2'-chloro-3,3'-dimethoxy-4-biphenylyl)-N-3-isoxazolyl-2-oxo-1,2-dihydro-6-quinolinesulfonamide | 538.1 | 179 | 0.087 | | $^1$H NMR (400 MHz, DMSO-d$_6$) δ = 11.71 (br. s., 1H), 8.78 (d, J = 1.8 Hz, 1H), 8.43 (d, J = 2.2 Hz, 1H), 8.28 (d, J = 9.6 Hz, 1H), 7.94 (dd, J = 2.2, 9.0 Hz, 1H), 7.51-7.45 (m, 1H), 7.43 (d, J = 8.0 Hz, 1H), 7.35 (d, J = 1.8 Hz, 1H), 7.27 (dd, J = 1.3, 8.4 Hz, 1H), 7.24 (dd, J = 1.8, 8.0 Hz, 1H), 7.17 (dd, J = 1.3, 7.7 Hz, 1H), 6.87 (d, J = 9.6 Hz, 1H), 6.82 (d, J = 8.9 Hz, 1H), 6.50 (d, J = 1.8 Hz, 1H), 3.97 (s, 3H), 3.75 (s, 3H). |
| 783 | N-3-isoxazolyl-1-(3-methoxy-3'-(1-methylethyl)-4-biphenylyl)-2-oxo-1,2-dihydro-6-quinolinesulfonamide | 516.2 | 179 | 0.009 | | $^1$H NMR (400 MHz, DMSO-d$_6$) δ = 11.65 (s, 1H), 8.74 (d, J = 1.8 Hz, 1H), 8.38 (d, J = 2.2 Hz, 1H), 8.23 (d, J = 9.5 Hz, 1H), 7.86 (dd, J = 2.3, 9.0 Hz, 1H), 7.63 (t, J = 1.6 Hz, 1H), 7.60 (td, J = 1.2, 8.0 Hz, 1H), 7.49 (d, J = 1.8 Hz, 1H), 7.44 (t, J = 7.7 Hz, 1H), 7.42 (dd, J = 1.8, 8.1 Hz, 1H), 7.37 (d, J = 8.0 Hz, 1H), 7.31 (d, J = 7.7 Hz, 1H), 6.82 (d, J = 9.6 Hz, 2H), 6.46 (d, J = 1.8 Hz, 1H), 3.78 (s, 3H), 1.30 (s, 3H), 1.28 (s, 3H). |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 686 | 1-(3,3'-dimethoxy-4'-methyl-4-biphenylyl)-N-3-isoxazolyl-2-oxo-1,2-dihydro-6-quinolinesulfonamide | 518.2 | 179 | 0.015 | | $^1$H NMR (400 MHz, DMSO-d$_6$) δ = 11.70 (br. s., 1H), 8.78 (d, J = 1.8 Hz, 1H), 8.42 (d, J = 2.2 Hz, 1H), 8.27 (d, J = 9.6 Hz, 1H), 7.91 (dd, J = 2.2, 9.0 Hz, 1H), 7.56 (d, J = 1.3 Hz, 1H), 7.50-7.35 (m, 5H), 7.03 (dd, J = 1.6, 8.0 Hz, 1H), 6.86 (d, J = 9.6 Hz, 2H), 6.51 (d, J = 1.8 Hz, 1H), 4.18 (q, J = 6.9 Hz, 2H), 3.82 (s, 3H), 2.59-2.50 (m, 1H), 1.42 (t, J = 7.0 Hz, 3H). |
| 784 | 1-(3,3'-dimethoxy-5'-methyl-4-biphenylyl)-N-3-isoxazolyl-2-oxo-1,2-dihydro-6-quinolinesulfonamide | 518.2 | 179 | 0.02 | | $^1$H NMR (400 MHz, DMSO-d$_6$) δ = 11.65 (br. s., 1H), 8.73 (d, J = 1.9 Hz, 1H), 8.37 (d, J = 2.2 Hz, 1H), 8.22 (d, J = 9.4 Hz, 1H), 7.86 (dd, J = 2.3, 9.0 Hz, 1H), 7.49 (d, J = 1.8 Hz, 1H), 7.42 (dd, J = 1.8, 8.1 Hz, 1H), 7.36 (d, J = 8.2 Hz, 1H), 7.19 (s, 1H), 7.12 (t, J = 1.7 Hz, 1H), 6.85-6.83 (m, 1H), 6.81 (dd, J = 2.3, 9.3 Hz, 2H), 6.45 (d, J = 1.9 Hz, 1H), 3.84 (s, 3H), 3.77 (s, 3H), 2.39 (s, 3H). |
| 785 | 1-(2'-fluoro-3,3'-dimethoxy-4-biphenylyl)-N-3-isoxazolyl-2-oxo-1,2-dihydro-6-quinolinesulfonamide | 522.1 | 179 | 0.066 | | $^1$H NMR (400 MHz, DMSO-d$_6$) δ = 11.66 (br. s., 1H), 8.73 (d, J = 1.8 Hz, 1H), 8.38 (d, J = 2.3 Hz, 1H), 8.23 (d, J = 9.5 Hz, 1H), 7.88 (dd, J = 2.3, 9.0 Hz, 1H), 7.44-7.39 (m, 2H), 7.31 (td, J = 1.5, 8.1 Hz, 1H), 7.29-7.18 (m, 3H), 6.83 (d, J = 2.7 Hz, 1H), 6.80 (d, J = 2.0 Hz, 1H), 6.46 (d, J = 1.8 Hz, 1H), 3.91 (s, 3H), 3.73 (s, 3H). |
| 786 | 1-(3'-(difluoromethoxy)-3-methoxy-4-biphenylyl)-N-3-isoxazolyl-2-oxo-1,2-dihydro-6-quinolinesulfonamide | 540.2 | 179 | 0.048 | | $^1$H NMR (400 MHz, DMSO-d$_6$) δ = 11.65 (s, 1H), 8.73 (d, J = 1.8 Hz, 1H), 8.37 (d, J = 2.3 Hz, 1H), 8.23 (d, J = 9.5 Hz, 1H), 7.86 (dd, J = 2.3, 9.0 Hz, 1H), 7.70 (ddd, J = 0.9, 1.8, 7.8 Hz, 1H), 7.61 (t, J = 2.0 Hz, 1H), 7.59 (d, J = 7.8 Hz, 1H), 7.57 (d, J = 5.2 Hz, 1H), 7.56 (d, J = 1.9 Hz, 1H), 7.47 (dd, J = 1.9, 8.0 Hz, 1H), 7.41 (d, J = 13.7 Hz, 1H), 7.25 (dd, J = 2.1, 8.0 Hz, 1H), 6.82 (d, J = 3.2 Hz, 1H), 6.80 (d, J = 2.7 Hz, 1H), 6.45 (d, J = 1.8 Hz, 1H), 3.79 (s, 3H). |
| 787 | 1-(3,3'-dimethoxy-2'-methyl-4-biphenylyl)-N-3-isoxazolyl-2-oxo-1,2-dihydro-6-quinolinesulfonamide | 518.2 | 179 | 0.052 | | $^1$H NMR (400 MHz, DMSO-d$_6$) δ = 11.65 (s, 1H), 8.73 (d, J = 1.9 Hz, 1H), 8.37 (d, J = 2.2 Hz, 1H), 8.23 (d, J = 9.5 Hz, 1H), 7.88 (dd, J = 2.2, 9.0 Hz, 1H), 7.34 (d, J = 8.0 Hz, 1H), 7.29 (t, J = 7.8 Hz, 1H), 7.19 (d, J = 1.8 Hz, 1H), 7.07 (dd, J = 1.8, 7.9 Hz, 1H), 7.03 (d, J = 7.9 Hz, 1H), 6.96 (dd, J = 0.7, 7.7 Hz, 1H), 6.83 (d, J = 3.1 Hz, 1H), 6.80 (d, J = 2.4 Hz, 1H), 6.45 (d, J = 1.8 Hz, 1H), 3.85 (s, 3H), 3.69 (s, 3H), 2.17 (s, 3H). |
| 788 | 1-(3'-cyclopropyl-3-methoxy-4-biphenylyl)-N-3-isoxazolyl-2-oxo-1,2-dihydro-6-quinolinesulfonamide | #### | 179 | 0.006 | | $^1$H NMR (400 MHz, DMSO-d$_6$) δ = 11.65 (s, 1H), 8.73 (d, J = 1.8 Hz, 1H), 8.37 (d, J = 2.3 Hz, 1H), 8.22 (d, J = 9.5 Hz, 1H), 7.86 (dd, J = 2.3, 9.0 Hz, 1H), 7.54 (ddd, J = 1.0, 1.7, 7.7 Hz, 1H), 7.49 (d, J = 1.8 Hz, 1H), 7.47 (t, J = 1.7 Hz, 1H), 7.44-7.35 (m, 3H), 7.13 (td, J = 1.2, 7.7 Hz, 1H), 6.82 (d, J = 1.7 Hz, 1H), 6.80 (d, J = 1.0 Hz, 1H), 6.45 (d, J = 1.8 Hz, 1H), 3.77 (s, 3H), 2.08-1.99 (m, 1H), 1.04-0.95 (m, 2H), 0.86-0.74 (m, 2H). |
| 789 | 1-(4-(2,3-dihydro-1-benzofuran-7-yl)-2-methoxyphenyl)-N-3-isoxazolyl-2-oxo-1,2-dihydro-6-quinolinesulfonamide | 516.2 | 179 | 0.089 | | $^1$H NMR (400 MHz, DMSO-d$_6$) δ = 11.65 (s, 1H), 8.73 (d, J = 1.9 Hz, 1H), 8.37 (d, J = 2.2 Hz, 1H), 8.22 (d, J = 9.5 Hz, 1H), 7.87 (dd, J = 2.2, 9.0 Hz, 1H), 7.54 (d, J = 1.8 Hz, 1H), 7.51-7.43 (m, 2H), 7.34 (d, J = 8.1 Hz, 1H), 7.29 (qd, J = 1.0, 7.3 Hz, 1H), 6.99 (t, J = 7.6 Hz, 1H), 6.82 (d, J = 1.2 Hz, 1H), 6.80 (d, J = 2.0 Hz, 1H), 6.45 (d, J = 1.8 Hz, 1H), 4.62 (t, J = 8.9 Hz, 2H), 3.72 (s, 3H), 3.28 (t, J = 8.7 Hz, 2H). |
| 790 | 1-(3'-cyclopropyl-2-fluoro-5-methoxy-4-biphenylyl)-N-3-isoxazolyl-2-oxo-1,2-dihydro-6-quinolinesulfonamide | 532.1 | 180 | 0.005 | | $^1$H NMR (400 MHz, DMSO-d$_6$) δ = 11.66 (s, 1H), 8.74 (d, J = 1.8 Hz, 1H), 8.38 (d, J = 2.1 Hz, 1H), 8.23 (d, J = 9.7 Hz, 1H), 7.87 (dd, J = 2.2, 9.0 Hz, 1H), 7.48 (d, J = 10.4 Hz, 1H), 7.46-7.33 (m, 4H), 7.16 (td, J = 1.6, 6.8 Hz, 1H), 6.88 (d, J = 9.0 Hz, 1H), 6.82 (d, J = 9.6 Hz, 1H), 6.45 (d, J = 1.9 Hz, 1H), 3.73 (s, 3H), 2.03 (tt, J = 5.0, 8.4 Hz, 1H), 1.04-0.97 (m, 2H), 0.81-0.74 (m, 2H). |
| 791 | 1-(3'-ethyl-2-fluoro-5-methoxy-4-biphenylyl)-N-3-isoxazolyl-2-oxo-1,2- | 520.1 | 180 | 0.009 | | $^1$H NMR (400 MHz, DMSO-d$_6$) δ = 11.67 (s, 1H), 8.74 (d, J = 1.9 Hz, 1H), 8.38 (d, J = 2.3 Hz, 1H), 8.23 (d, J = 9.5 Hz, 1H), 7.87 (dd, J = 2.3, 9.0 Hz, 1H), 7.55-7.41 (m, 4H), 7.36 (d, J = 6.9 Hz, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | dihydro-6-quinolinesulfonamide | | | | | 1H), 7.32 (td, J = 1.5, 7.3 Hz, 1H), 6.89 (d, J = 8.9 Hz, 1H), 6.82 (d, J = 9.6 Hz, 1H), 6.46 (d, J = 1.8 Hz, 1H), 3.73 (s, 3H), 2.72 (d, J = 7.6 Hz, 2H), 1.25 (t, J = 7.6 Hz, 3H). |
| 792 | 1-(2-fluoro-2',5-dimethoxy-3'-methyl-4-biphenylyl)-N-3-isoxazolyl-2-oxo-1,2-dihydro-6-quinolinesulfonamide | 536.2 | 180 | 0.038 | | $^1$H NMR (400 MHz, DMSO-d$_6$) δ = 11.67 (s, 1H), 8.73 (d, J = 1.8 Hz, 1H), 8.39 (d, J = 2.2 Hz, 1H), 8.24 (d, J = 9.6 Hz, 1H), 7.90 (dd, J = 2.2, 9.0 Hz, 1H), 7.46 (d, J = 9.4 Hz, 1H), 7.33 (qd, J = 0.8, 7.4 Hz, 1H), 7.30-7.23 (m, 2H), 7.18 (d, J = 7.5 Hz, 1H), 6.84 (d, J = 4.5 Hz, 1H), 6.82 (d, J = 5.0 Hz, 1H), 6.46 (d, J = 1.9 Hz, 1H), 3.67 (s, 3H), 3.51 (s, 3H), 2.33 (s, 3H). |
| 793 | 1-(2-fluoro-2',5-dimethoxy-4'-methyl-4-biphenylyl)-N-3-isoxazolyl-2-oxo-1,2-dihydro-6-quinolinesulfonamide | 536.2 | 180 | 0.048 | | $^1$H NMR (400 MHz, DMSO-d$_6$) δ = 11.67 (s, 1H), 8.73 (d, J = 1.8 Hz, 1H), 8.38 (d, J = 2.3 Hz, 1H), 8.23 (d, J = 9.5 Hz, 1H), 7.90 (dd, J = 2.2, 9.0 Hz, 1H), 7.38 (d, J = 9.5 Hz, 1H), 7.26 (d, J = 7.6 Hz, 1H), 7.20 (d, J = 6.5 Hz, 1H), 7.01 (s, 1H), 6.91 (qd, J = 0.7, 7.7 Hz, 1H), 6.85 (d, J = 8.9 Hz, 1H), 6.82 (d, J = 9.6 Hz, 1H), 6.46 (d, J = 1.8 Hz, 1H), 3.81 (s, 3H), 3.66 (s, 3H), 2.39 (s, 3H). |
| 632 | 1-(3'-(difluoromethoxy)-2-fluoro-5-methoxy-4-biphenylyl)-N-3-isoxazolyl-2-oxo-1,2-dihydro-6-quinolinesulfonamide | 558.0 | 180 | 0.009 | | $^1$H NMR (400 MHz, DMSO-d$_6$) δ = 11.67 (br. s., 1H), 8.73 (d, J = 1.7 Hz, 1H), 8.38 (d, J = 2.0 Hz, 1H), 8.24 (d, J = 9.6 Hz, 1H), 7.87 (dd, J = 2.1, 9.0 Hz, 1H), 7.69-7.48 (m, 5H), 7.42 (d, J = 6.8 Hz, 1H), 7.30 (d, J = 7.4 Hz, 1H), 6.89 (d, J = 9.0 Hz, 1H), 6.82 (d, J = 9.6 Hz, 1H), 6.45 (d, J = 1.7 Hz, 1H), 3.75 (s, 3H). |
| 687 | 1-(2-fluoro-3',5,5'-trimethoxy-4-biphenylyl)-N-3-isoxazolyl-2-oxo-1,2-dihydro-6-quinolinesulfonamide | #### | 180 | 0.012 | | $^1$H NMR (400 MHz, DMSO-d$_6$) δ = 11.66 (s, 1H), 8.74 (d, J = 1.8 Hz, 1H), 8.38 (d, J = 2.2 Hz, 1H), 8.23 (d, J = 9.5 Hz, 1H), 7.87 (dd, J = 2.3, 9.0 Hz, 1H), 7.49 (d, J = 10.3 Hz, 1H), 7.37 (d, J = 6.8 Hz, 1H), 6.88 (d, J = 8.9 Hz, 1H), 6.85-6.79 (m, 3H), 6.62 (t, J = 2.2 Hz, 1H), 6.46 (d, J = 1.8 Hz, 1H), 3.83 (s, 7H), 3.73 (s, 3H). |
| 794 | 1-(5-fluoro-2-methoxy-4-(6-(trifluoromethyl)-2-pyridinyl)phenyl)-N-3-isoxazolyl-2-oxo-1,2-dihydro-6-quinolinesulfonamide | #### | 180 | 0.096 | | $^1$H NMR (400 MHz, DMSO-d$_6$) δ = 11.67 (s, 1H), 8.74 (d, J = 1.8 Hz, 1H), 8.39 (d, J = 2.0 Hz, 1H), 8.34-8.17 (m, 3H), 8.01 (d, J = 7.7 Hz, 1H), 7.85 (dd, J = 2.2, 8.9 Hz, 1H), 7.69 (d, J = 6.7 Hz, 1H), 7.62 (d, J = 10.5 Hz, 1H), 6.93 (d, J = 9.0 Hz, 1H), 6.83 (d, J = 9.7 Hz, 1H), 6.45 (d, J = 1.8 Hz, 1H), 3.74 (s, 3H). |
| 633 | 1-(4''-chloro-2-fluoro-5-methoxy-1,1':4',1''-terphenyl-4-yl)-N-3-isoxazolyl-2-oxo-1,2-dihydro-6-quinolinesulfonamide | #### | 181 | 0.007 | | $^1$H NMR (400 MHz, DMSO-d$_6$) δ = 11.67 (s, 1H), 8.74 (d, J = 1.8 Hz, 1H), 8.39 (d, J = 2.2 Hz, 1H), 8.24 (d, J = 9.5 Hz, 1H), 7.90-7.78 (m, 7H), 7.61-7.50 (m, 3H), 7.44 (d, J = 6.9 Hz, 1H), 6.91 (d, J = 8.9 Hz, 1H), 6.83 (d, J = 9.6 Hz, 1H), 6.46 (d, J = 1.9 Hz, 1H), 3.75 (s, 3H). |
| 635 | 1-(5-fluoro-2-methoxy-4-(2-pyridinyl)phenyl)-N-3-isoxazolyl-2-oxo-1,2-dihydro-6-quinolinesulfonamide | 493.0 | 182 | 0.888 | | $^1$H NMR (400 MHz, ACETONITRILE-d$_3$) δ ppm 8.95 (br. s., 1 H) 8.38 (d, J = 1.45 Hz, 1 H) 8.27 (d, J = 1.66 Hz, 1 H) 8.01 (d, J = 9.74 Hz, 1 H) 7.82 (d, J = 7.46 Hz, 1 H) 7.31 (d, J = 10.05 Hz, 1 H) 6.89 (d, J = 8.60 Hz, 1 H) 6.78 (d, J = 9.64 Hz, 1 H) 6.46 (d, J = 1.24 Hz, 1 H) 3.78 (br. s., 3 H). |
| 636 | 1-(2-fluoro-5-methoxy-4'-(trifluoromethyl)-4-biphenylyl)-N-1,3-oxazol-2-yl-2-oxo-1,2-dihydro-6-quinolinesulfonamide | 559.8 | 183 | 0.031 | | $^1$H NMR (400 MHz, ACETONITRILE-d$_3$) δ = 8.23 (d, J = 2.07 Hz, 1 H) 8.00 (d, J = 9.64 Hz, 1 H) 7.80-7.92 (m, 5 H) 7.34 (d, J = 6.84 Hz, 1 H) 7.24 (d, J = 10.16 Hz, 1 H) 7.19 (d, J = 1.76 Hz, 1 H) 6.94 (d, J = 1.76 Hz, 1 H) 6.83 (d, J = 8.91 Hz, 1 H) 6.75 (d, J = 9.64 Hz, 1 H) 3.74 (s, 3 H). |
| 795 | 1-(2-fluoro-5-methoxy-4'-(trifluoromethyl)-4-biphenylyl)-2-oxo-N-3-pyridazinyl-1,2-dihydro-6-quinolinesulfonamide | 571.2 | 183 | 0.031 | | $^1$H NMR (400 MHz, DMSO-d$_3$) δ ppm 8.36 (s, 1 H) 8.31 (br. s, 1 H) 8.21 (d, J = 9.64 Hz, 1 H) 7.83-8.02 (m, 5 H) 7.68 (dd, J = 9.80, 4.09 Hz, 1 H) 7.55 (d, J = 10.47 Hz, 1 H) 7.46 (d, J = 6.95 Hz, 1 H) 6.76-6.87 (m, 2 H) 3.74 (s, 3 H). |
| 796 | 1-(2-fluoro-5-methoxy-4'-(trifluoromethyl)-4-biphenylyl)-N-(5-fluoro-2-pyrimidinyl)- | #### | 183 | 0.033 | | $^1$H NMR (400 MHz, ACETONITRILE-d$_3$) δ = 9.22 (br. s., 1H), 8.44 (d, J = 2.2 Hz, 1H), 8.40 (d, J = 0.6 Hz, 2H), 8.05 (d, J = 9.6 Hz, 1H), 8.00 (dd, J = 2.2, 9.0 Hz, 1H), 7.91-7.83 (m, 4H), 7.34 (d, J = 6.8 Hz, 1H), 7.24 (d, J = 10.2 Hz, 1H), |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 797 | 1-(2-fluoro-5-methoxy-4'-(trifluoromethyl)-4-biphenylyl)-2-oxo-N-2-pyrimidinyl-1,2-dihydro-6-quinolinesulfonamide | #### | 183 | 0.043 | | 6.86 (d, J = 9.0 Hz, 1H), 6.77 (d, J = 9.7 Hz, 1H), 3.73 (s, 3H). $^1$H NMR (400 MHz, DMSO-d$_6$) δ ppm 11.85 (br. s., 1 H) 8.44-8.59 (m, 3 H) 8.28 (d, J = 9.74 Hz, 1 H) 7.89-8.05 (m, 5 H) 7.57 (d, J = 10.26 Hz, 1 H) 7.47 (d, J = 6.84 Hz, 1 H) 7.01-7.12 (m, 1 H) 6.87 (d, J = 8.71 Hz, 1 H) 6.81 (d, J = 9.64 Hz, 1 H) 3.74 (s, 3 H). |
| 798 | 1-(2-fluoro-5-methoxy-4'-(trifluoromethyl)-4-biphenylyl)-N-(6-methyl-4-pyrimidinyl)-2-oxo-1,2-dihydro-6-quinolinesulfonamide | 585.0 | 183 | 0.049 | | $^1$H NMR (400 MHz, ACETONITRILE-d$_3$) δ ppm 8.52 (d, J = 1.04 Hz, 1 H) 8.38 (d, J = 2.18 Hz, 1 H) 8.03 (d, J = 9.54 Hz, 1 H) 7.93 (dd, J = 8.97, 2.23 Hz, 1 H) 7.86 (m, J = 3.80 Hz, 5 H) 7.34 (d, J = 6.84 Hz, 1 H) 7.24 (d, J = 10.16 Hz, 1 H) 6.98 (s, 1 H) 6.87 (d, J = 9.02 Hz, 1 H) 6.77 (d, J = 9.64 Hz, 1 H) 3.73 (s, 4 H) 2.40 (s, 3 H). |
| 799 | 1-(2-fluoro-5-methoxy-4'-(trifluoromethyl)-4-biphenylyl)-N-(2-methyl-4-pyrimidinyl)-2-oxo-1,2-dihydro-6-quinolinesulfonamide | #### | 183 | 0.059 | | $^1$H NMR (400 MHz, ACETONITRILE-d$_3$) δ ppm 8.35 (d, J = 2.07 Hz, 1 H) 8.11 (d, J = 6.43 Hz, 1 H) 8.09-8.13 (m, 1 H) 8.03 (d, J = 9.64 Hz, 1 H) 7.83-7.95 (m, 5 H) 7.34 (d, J = 6.84 Hz, 1 H) 7.24 (d, J = 10.16 Hz, 1 H) 6.94 (d, J = 6.53 Hz, 1 H) 6.86 (d, J = 8.91 Hz, 1 H) 6.76 (d, J = 9.64 Hz, 1 H) 3.73 (s, 3 H) 2.45 (s, 3 H). |
| 800 | 1-(4-(5-chloro-2-pyridinyl)-5-fluoro-2-methoxyphenyl)-N-3-isoxazolyl-2-oxo-1,2-dihydro-6-quinolinesulfonamide | 526.8 | 182 | 0.253 | | $^1$H NMR (400 MHz, ACETONITRILE-d$_3$) δ ppm 8.80-8.95 (m, 1 H) 8.75 (t, J = 1.71 Hz, 1 H) 8.37 (d, J = 1.87 Hz, 1 H) 8.25 (d, J = 2.18 Hz, 1 H) 8.00 (d, J = 9.64 Hz, 1 H) 7.90-7.95 (m, 2 H) 7.76-7.84 (m, 2 H) 7.24 (d, J = 10.78 Hz, 1 H) 6.88 (d, J = 9.02 Hz, 2 H) 6.77 (d, J = 9.74 Hz, 1 H) 6.45 (d, J = 1.87 Hz, 1 H) 3.74 (s, 3 H). |
| 801 | 1-(4-(4-chloro-2-pyridinyl)-5-fluoro-2-methoxyphenyl)-N-3-isoxazolyl-2-oxo-1,2-dihydro-6-quinolinesulfonamide | 527.8 | 182 | 0.093 | | $^1$H NMR (400 MHz, DMSO-d$_6$) δ ppm 11.66 (br. s., 1 H) 8.65-8.94 (m, 2 H) 8.39 (br. s., 1 H) 8.24 (d, J = 9.74 Hz, 1 H) 8.00 (br. s., 1 H) 7.86 (d, J = 7.98 Hz, 1 H) 7.77 (d, J = 6.63 Hz, 1 H) 7.66 (d, J = 3.94 Hz, 1 H) 7.53-7.65 (m, 2 H) 6.88 (d, J = 8.81 Hz, 1 H) 6.82 (d, J = 9.43 Hz, 1 H) 6.45 (s, 1 H) 3.74 (s, 3 H). |
| 802 | 1-(2-fluoro-5-methoxy-3'-(trifluoromethyl)-4-biphenylyl)-N-(5-fluoro-2-pyrimidinyl)-2-oxo-1,2-dihydro-6-quinolinesulfonamide | 588.9 | 183 | 0.021 | | $^1$H NMR (400 MHz, ACETONITRILE-d$_3$) δ ppm 9.15 (br. s., 1 H) 8.44 (d, J = 2.18 Hz, 1 H) 8.39 (d, J = 0.62 Hz, 2 H) 8.05 (d, J = 9.64 Hz, 1 H) 7.98-8.02 (m, 2 H) 7.96 (d, J = 8.09 Hz, 1 H) 7.77-7.81 (m, 1 H) 7.71-7.76 (m, 1 H) 7.35 (d, J = 6.84 Hz, 1 H) 7.23 (d, J = 10.26 Hz, 1 H) 6.86 (d, J = 9.02 Hz, 1 H) 6.77 (d, J = 9.64 Hz, 1 H) 3.73 (s, 3 H). |
| 803 | 1-(2-fluoro-5-methoxy-3'-(trifluoromethyl)-4-biphenylyl)-2-oxo-N-2-pyrimidinyl-1,2-dihydro-6-quinolinesulfonamide | 571.9 | 183 | 0.01 | | $^1$H NMR (400 MHz, ACETONITRILE-d$_3$) δ ppm 8.44-8.49 (m, 2 H) 8.05 (d, J = 9.54 Hz, 1 H) 8.02 (dd, J = 9.02, 2.28 Hz, 1 H) 7.96 (d, J = 7.57 Hz, 1 H) 7.77-7.83 (m, 1 H) 7.70-7.77 (m, 1 H) 7.36 (d, J = 6.84 Hz, 1 H) 7.24 (d, J = 10.16 Hz, 1 H) 7.01 (t, J = 4.92 Hz, 1 H) 6.86 (d, J = 9.02 Hz, 1 H) 6.77 (d, J = 9.64 Hz, 1 H) 3.74 (s, 3 H). |
| 688 | 1-(2-fluoro-5-methoxy-3'-(trifluoromethyl)-4-biphenylyl)-N-(6-methyl-4-pyrimidinyl)-2-oxo-1,2-dihydro-6-quinolinesulfonamide | 585.0 | 183 | 0.01 | | $^1$H NMR (400 MHz, ACETONITRILE-d$_3$) δ ppm 8.54 (d, J = 0.93 Hz, 1 H) 8.39 (d, J = 2.18 Hz, 1 H) 8.03 (d, J = 9.54 Hz, 1 H) 7.95-8.01 (m, 1 H) 7.93 (dd, J = 8.97, 2.12 Hz, 1 H) 7.77-7.82 (m, 1 H) 7.70-7.76 (m, 1 H) 7.35 (d, J = 6.84 Hz, 1 H) 7.23 (d, J = 10.16 Hz, 1 H) 6.99 (s, 1 H) 6.86 (d, J = 9.02 Hz, 1 H) 6.78 (d, J = 9.64 Hz, 1 H) 6.13 (br. s., 1 H) 3.73 (s, 3 H) 2.41 (s, 3 H). |
| 804 | 1-(2-fluoro-5-methoxy-3'-(trifluoromethyl)-4-biphenylyl)-N-(2-methyl-4-pyrimidinyl)-2-oxo-1,2-dihydro-6-quinolinesulfonamide | 585.1 | 183 | 0.014 | | $^1$H NMR (400 MHz, ACETONITRILE-d$_3$) δ ppm 8.40 (d, J = 2.07 Hz, 1 H) 8.22 (d, J = 6.74 Hz, 1 H) 8.04 (d, J = 9.54 Hz, 1 H) 8.00 (s, 1 H) 7.95 (dd, J = 8.97, 2.12 Hz, 2 H) 7.77-7.82 (m, 1 H) 7.70-7.76 (m, 1 H) 7.35 (d, J = 6.95 Hz, 1 H) 7.23 (d, J = 10.16 Hz, 1 H) 7.02 (d, J = 6.74 Hz, 1 H) 6.87 (d, J = 8.91 Hz, 1 H) 6.78 (d, J = 9.74 Hz, 1 H) 3.73 (s, 3 H) 2.51 (s, 3 H). |
| 805 | 1-(5-fluoro-2-methoxy-4-(6-methoxy-2-pyridinyl)phenyl)-N-3- | 523.0 | 182 | 0.07 | | $^1$H NMR (400 MHz, DMSO-d$_6$) δ = ppm 11.67 (s, 1 H) 8.74 (d, J = 1.76 Hz, 1 H) 8.38 (d, J = 2.28 Hz, 1 H) 8.24 (d, J = 9.54 Hz, 1 H) 7.81-7.93 (m, 3 H) 7.49-7.57 (m, 2 H) 6.93 (d, J = 0.52 Hz, |

TABLE 3-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | isoxazolyl-2-oxo-1,2-dihydro-6-quinolinesulfonamide | | | | | 1 H) 6.91 (d, J = 0.62 Hz, 1 H) 6.82 (d, J = 9.64 Hz, 1 H) 6.45 (d, J = 1.87 Hz, 1 H) 3.99 (s, 3 H) 3.75 (s, 3 H). |
| 806 | 1-(2-fluoro-5-methoxy-3'-(trifluoromethyl)-4-biphenylyl)-N-1,3-oxazol-2-yl-2-oxo-1,2-dihydro-6-quinolinesulfonamide | 559.8 | 183 | 0.028 | | $^1$H NMR (400 MHz, DMSO-d$_6$) δ = ppm 12.18 (br. s., 1 H) 8.34 (d, J = 2.07 Hz, 1 H) 8.21 (d, J = 9.54 Hz, 1 H) 8.03 (br. s., 2 H) 7.75-7.90 (m, 3 H) 7.61 (d, J = 1.66 Hz, 1 H) 7.55 (d, J = 10.37 Hz, 1 H) 7.48 (d, J = 6.95 Hz, 1 H) 7.28 (d, J = 1.66 Hz, 1 H) 6.81 (d, J = 8.81 Hz, 1 H) 6.79 (d, J = 9.64 Hz, 1 H) 3.76 (s, 3 H) 3.73-3.79 (m, 3 H). |
| 637 | 1-(5-fluoro-2-methoxy-4-(5-(trifluoromethyl)-2-pyridinyl)phenyl)-N-3-isoxazolyl-2-oxo-1,2-dihydro-6-quinolinesulfonamide | 560.8 | 184 | | | $^1$H NMR (400 MHz, DMSO-d$_6$) δ = 11.67 (br. s., 1H), 9.20 (br. s., 1H), 8.74 (br. s., 1H), 8.47-8.34 (m, 2H), 8.25 (d, J = 9.2 Hz, 1H), 8.15 (d, J = 7.3 Hz, 1H), 7.94-7.76 (m, 2H), 7.64 (d, J = 10.3 Hz, 1H), 6.91 (d, J = 8.4 Hz, 1H), 6.83 (d, J = 9.3 Hz, 1H), 6.45 (br. s., 1H), 3.75 (br. s., 3H). |
| 807 | 1-(4-(5-chloro-6-methyl-2-pyridinyl)-5-fluoro-2-methoxyphenyl)-N-3-isoxazolyl-2-oxo-1,2-dihydro-6-quinolinesulfonamide | 541.0 | 184 | | | $^1$H NMR (400 MHz, DMSO-d$_6$) δ = 11.67 (s, 1H), 8.73 (d, J = 1.9 Hz, 1H), 8.38 (d, J = 2.3 Hz, 1H), 8.24 (d, J = 9.5 Hz, 1H), 8.05 (d, J = 8.4 Hz, 1H), 7.86 (dd, J = 2.2, 9.0 Hz, 1H), 7.76 (dd, J = 1.6, 8.4 Hz, 1H), 7.72 (d, J = 6.8 Hz, 1H), 7.56 (d, J = 10.8 Hz, 1H), 6.90 (d, J = 9.0 Hz, 1H), 6.82 (d, J = 9.6 Hz, 1H), 6.45 (d, J = 1.8 Hz, 1H), 3.73 (s, 3H), 2.67 (s, 3H). |
| 808 | 1-(5-fluoro-2-methoxy-4-(4-methoxy-2-pyrimidinyl)phenyl)-N-3-isoxazolyl-2-oxo-1,2-dihydro-6-quinolinesulfonamide | 523.9 | 184 | 3.071 | | $^1$H NMR (500 MHz, DMSO-d$_6$) δ = 11.65 (br. s., 1H), 8.72 (d, J = 5.8 Hz, 1H), 8.71 (d, J = 1.4 Hz, 1H), 8.37 (d, J = 1.9 Hz, 1H), 8.24 (d, J = 9.7 Hz, 1H), 7.92-7.82 (m, 2H), 7.55 (d, J = 10.4 Hz, 1H), 7.01 (d, J = 5.8 Hz, 1H), 6.90 (d, J = 9.0 Hz, 1H), 6.82 (d, J = 9.7 Hz, 1H), 6.44 (d, J = 1.6 Hz, 1H), 4.04 (s, 3H), 3.74 (s, 3H). |
| 809 | 1-(4-(2,3-dihydro-1-benzofuran-6-yl)-2-methoxyphenyl)-N-3-isoxazolyl-2-oxo-1,2-dihydro-6-quinolinesulfonamide | 516.1 | 179 | 0.122 | | $^1$H NMR (500 MHz, DMSO-d$_6$) δ = 2.54 (s, 3 H), 3.10-3.20 (m, 1 H), 3.24 (t, J = 8.50 Hz, 1 H), 3.76 (s, 2 H), 4.60 (t, J = 8.66 Hz, 1 H), 6.45 (d, J = 1.49 Hz, 1 H), 6.81 (dd, J = 9.28, 3.76 Hz, 1 H), 7.09-7.29 (m, 2 H), 7.30-7.42 (m, 2 H), 7.44-7.52 (m, 1 H), 7.52-7.69 (m, 1 H), 7.86 (dd, J = 9.02, 1.95 Hz, 1 H), 8.21 (d, J = 9.67 Hz, 1 H), 8.36 (d, J = 1.82 Hz, 1 H), 8.69-8.76 (m, 1 H), 11.63 (br. s., 1 H). |
| 810 | 1-(3'-ethyl-3-methoxy-4-biphenylyl)-N-3-isoxazolyl-2-oxo-1,2-dihydro-6-quinolinesulfonamide | 502.3 | 179 | 0.015 | | $^1$H NMR (500 MHz, DMSO-d$_6$) δ = 1.26 (t, J = 7.59 Hz, 3 H), 2.72 (q, J = 7.53 Hz, 2 H), 3.77 (s, 3 H), 6.45 (d, J = 1.49 Hz, 1 H), 6.80 (s, 1 H), 6.82 (s, 1 H), 7.28 (d, J = 7.33 Hz, 1 H), 7.34-7.47 (m, 3 H), 7.47-7.66 (m, 2 H), 7.86 (dd, J = 8.99, 1.91 Hz, 1 H), 8.22 (d, J = 9.67 Hz, 1 H), 8.37 (d, J = 1.82 Hz, 1 H), 8.73 (s, 1 H), 11.63 (br. s., 1 H). |
| 811 | N-3-isoxazolyl-2-oxo-1-(3,3',5'-trimethoxy-4-biphenylyl)-1,2-dihydro-6-quinolinesulfonamide | 534.1 | 179 | 0.066 | | $^1$H NMR (500 MHz, DMSO-d$_6$) δ = 3.77 (s, 3 H), 3.80 (s, 3 H), 3.84 (s, 3 H), 6.45 (d, J = 1.56 Hz, 1 H), 6.50 (s, J = 7.09 Hz, 1 H), 6.58 (s, J = 6.62 Hz, 1 H), 6.72-6.86 (m, 2 H), 6.92 (d, J = 2.01 Hz, 1 H), 7.37 (d, J = 8.04 Hz, 1 H), 7.44 (d, J = 8.08 Hz, 1 H), 7.50 (s, 1 H), 7.86 (dd, J = 8.99, 1.98 Hz, 1 H), 8.22 (d, J = 9.67 Hz, 1 H), 8.37 (d, J = 1.75 Hz, 1 H), 8.73 (d, J = 1.43 Hz, 1 H), 11.63 (br. s., 1 H). |
| 812 | N-3-isoxazolyl-1-(3-methoxy-3',4'-dimethyl-4-biphenylyl)-2-oxo-1,2-dihydro-6-quinolinesulfonamide | 502.3 | 179 | 0.073 | | $^1$H NMR (500 MHz, DMSO-d$_6$) δ = 2.29 (s, 3 H), 2.33 (s, 3 H), 3.77 (s, 3 H), 6.45 (d, J = 7.47 Hz, 1 H), 6.74-6.87 (m, 2 H), 7.27 (d, J = 7.78 Hz, 1 H), 7.34 (d, J = 7.80 Hz, 1 H), 7.40 (d, J = 7.99 Hz, 1 H), 7.46-7.56 (m, 2 H), 7.59 (s, 1 H), 7.85 (dd, J = 8.99, 1.98 Hz, 1 H), 8.21 (d, J = 9.67 Hz, 1 H), 8.36 (d, J = 1.82 Hz, 1 H), 8.65-8.81 (m, 1 H), 11.63 (br. s., 1 H). |
| 813 | 1-(4-(5-chloro-2-methoxy-3-pyridinyl)-2-methoxyphenyl)-N-3-isoxazolyl-2-oxo-1,2-dihydro-6-quinolinesulfonamide | 538.9 | 179 | 0.101 | | $^1$H NMR (500 MHz, DMSO-d$_6$) δ = 11.63 (br. s., 1 H) 8.73 (s, 1 H) 8.63 (d, J = 1.82 Hz, 1 H) 8.42 (d, J = 1.82 Hz, 1 H) 8.37 (d, J = 1.75 Hz, 1 H) 8.22 (d, J = 9.67 Hz, 1 H) 7.85 (dd, J = 8.99, 1.85 Hz, 1 H) 7.60 (s, 1 H) 7.50 (d, J = 6.75 Hz, 1 H) 7.40 (d, J = 7.98 Hz, 1 H) 6.81 (d, J = 4.09 Hz, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | | | | | | 1 H) 6.79 (d, J = 3.44 Hz, 1 H) 6.45 (d, J = 1.36 Hz, 1 H) 4.02 (s, 3 H) 3.78 (s, 3 H). |
| 814 | 1-(4-(5-chloro-6-methoxy-3-pyridinyl)-2-methoxyphenyl)-N-3-isoxazolyl-2-oxo-1,2-dihydro-6-quinolinesulfonamide | 538.9 | 179 | 0.035 | | $^1$H NMR (500 MHz, DMSO-d$_6$) δ = 11.64 (br. s., 1 H) 8.73 (d, J = 1.49 Hz, 1 H) 8.37 (d, J = 1.88 Hz, 1 H) 8.29 (d, J = 2.40 Hz, 1 H) 8.22 (d, J = 9.73 Hz, 1 H) 8.06 (d, J = 2.40 Hz, 1 H) 7.87 (dd, J = 8.99, 1.98 Hz, 1 H) 7.50 (s, 1 H) 7.41 (dd, J = 7.91, 1.30 Hz, 1 H) 7.38 (d, J = 7.98 Hz, 1 H) 6.81 (d, J = 9.60 Hz, 1 H) 6.78 (d, J = 9.02 Hz, 1 H) 6.45 (d, J = 1.56 Hz, 1 H) 3.95 (s, 3 H) 3.73 (s, 3 H). |
| 815 | 1-(3'-chloro-2',3-dimethoxy-4-biphenylyl)-N-3-isoxazolyl-2-oxo-1,2-dihydro-6-quinolinesulfonamide | 538.0 | 179 | 0.056 | | $^1$H NMR (500 MHz, DMSO-d$_6$) δ = 11.64 (br. s., 1 H) 8.73 (d, J = 1.49 Hz, 1 H) 8.37 (d, J = 1.82 Hz, 1 H) 8.23 (d, J = 9.67 Hz, 1 H) 7.87 (dd, J = 8.99, 1.91 Hz, 1 H) 7.56 (d, J = 6.81 Hz, 1 H) 7.51 (d, J = 7.59 Hz, 1 H) 7.43 (s, 1 H) 7.40 (d, J = 7.98 Hz, 1 H) 7.27-7.34 (m, 2 H) 6.82 (d, J = 9.60 Hz, 1 H) 6.78 (d, J = 8.95 Hz, 1 H) 6.45 (d, J = 1.43 Hz, 1 H) 3.72 (s, 3 H) 3.62 (s, 3 H). |
| 816 | 1-(4'-chloro-2',3-dimethoxy-4-biphenylyl)-N-3-isoxazolyl-2-oxo-1,2-dihydro-6-quinolinesulfonamide | 538.0 | 179 | 0.027 | | $^1$H NMR (500 MHz, DMSO-d$_6$) δ = 11.64 (br. s., 1 H) 8.72 (d, J = 1.49 Hz, 1 H) 8.37 (d, J = 1.88 Hz, 1 H) 8.22 (d, J = 9.67 Hz, 1 H) 7.87 (dd, J = 9.02, 2.01 Hz, 1 H) 7.48 (d, J = 8.11 Hz, 1 H) 7.36 (d, J = 1.10 Hz, 1 H) 7.31-7.35 (m, 1 H) 7.23-7.29 (m, 2 H) 7.15 (dd, J = 8.11, 1.75 Hz, 1 H) 6.80 (t, J = 9.28 Hz, 2 H) 6.45 (d, J = 1.49 Hz, 1 H) 3.88 (s, 3 H) 3.70 (s, 3 H). |
| 817 | ((1-(2-fluoro-5-methoxy-3'-(trifluoromethyl)-4-biphenylyl)-2-oxo-1,2-dihydro-6-quinolinyl)sulfonyl)(1-pyridiniumyl)azanide | 570.2 | 183 | 4.533 | | $^1$H NMR (500 MHz, DMSO-d$_6$) δ = 8.51 (d, J = 5.77 Hz, 2 H) 8.22 (t, J = 7.75 Hz, 1 H) 8.12 (d, J = 9.67 Hz, 1 H) 8.01-8.06 (m, 2 H) 7.76-7.88 (m, 3 H) 7.62 (dd, J = 8.82, 1.88 Hz, 1 H) 7.50 (d, J = 10.25 Hz, 1 H) 7.48 (d, J = 7.01 Hz, 1 H) 6.75 (d, J = 4.15 Hz, 1 H) 6.73 (d, J = 3.31 Hz, 1 H) 3.76 (s, 3 H). |
| 818 | 1-(3'-fluoro-3-methoxy-4-biphenylyl)-N-3-isoxazolyl-2-oxo-1,2-dihydro-6-quinolinesulfonamide | 492.2 | 179 | 0.038 | | $^1$H NMR (500 MHz, DMSO-d$_6$) δ = 11.63 (br. s., 1 H) 8.73 (d, J = 1.56 Hz, 1 H) 8.37 (d, J = 1.95 Hz, 1 H) 8.22 (d, J = 9.67 Hz, 1 H) 7.86 (dd, J = 8.99, 1.98 Hz, 1 H) 7.64-7.74 (m, 2 H) 7.53-7.62 (m, 3 H) 7.48 (dd, J = 8.04, 1.49 Hz, 1 H) 7.40 (d, J = 7.98 Hz, 1 H) 7.27 (t, J = 8.43 Hz, 1 H) 6.82 (d, J = 3.83 Hz, 1 H) 6.80 (d, J = 3.11 Hz, 1 H) 6.45 (d, J = 1.56 Hz, 1 H) 3.78 (s, 3 H). |
| 638/819 | 1-(5-chloro-6-(cyclopropylmethoxy)-2-methoxy-3-pyridinyl)-N-3-isoxazolyl-2-oxo-1,2-dihydro-6-quinolinesulfonamide | 503.3 | 185 | 0.825 | | $^1$H NMR (500 MHz, DMSO-d$_6$) δ = 11.63 (br. s., 1 H) 8.73 (d, J = 1.56 Hz, 1 H) 8.37 (d, J = 1.95 Hz, 1 H) 8.22 (d, J = 9.67 Hz, 1 H) 7.86 (dd, J = 8.99, 1.98 Hz, 1 H) 7.64-7.74 (m, 2 H) 7.53-7.62 (m, 3 H) 7.48 (dd, J = 8.04, 1.49 Hz, 1 H) 7.40 (d, J = 7.98 Hz, 1 H) 7.27 (t, J = 8.43 Hz, 1 H) 6.82 (d, J = 3.83 Hz, 1 H) 6.80 (d, J = 3.11 Hz, 1 H) 6.45 (d, J = 1.56 Hz, 1 H) 3.78 (s, 3 H). |
| 820 | 1-(2-fluoro-5-methoxy-3'-(trifluoromethyl)-4-biphenylyl)-2-oxo-N-3-pyridazinyl-1,2-dihydro-6-quinolinesulfonamide | 571.0 | 183 | 0.018 | | $^1$H NMR (500 MHz, DMSO-d$_6$) δ = 14.51 (br. s., 1 H) 8.37 (d, J = 1.97 Hz, 1 H) 8.22 (d, J = 9.54 Hz, 1 H) 8.03 (br. s., 2 H) 7.84-7.89 (m, 2 H) 7.82 (d, J = 7.57 Hz, 1 H) 7.70 (dd, J = 9.59, 4.20 Hz, 1 H) 7.55 (d, J = 10.37 Hz, 1 H) 7.49 (d, J = 7.05 Hz, 1 H) 6.82 (d, J = 8.81 Hz, 1 H) 6.80 (d, J = 9.54 Hz, 1 H) 3.76 (s, 3 H). |
| 821 | 1-(5-chloro-6-(cyclobutyloxy)-2-methoxy-3-pyridinyl)-N-3-isoxazolyl-2-oxo-1,2-dihydro-6-quinolinesulfonamide | 503.0 | 185 | 4.66 | | $^1$H NMR (500 MHz, DMSO-d$_6$) δ = 11.65 (br. s., 1 H) 8.72 (d, J = 1.17 Hz, 1 H) 8.36 (d, J = 1.56 Hz, 1 H) 8.21 (d, J = 9.67 Hz, 1 H) 8.04 (s, 1 H) 7.85 (dd, J = 8.95, 1.69 Hz, 1 H) 6.98 (d, J = 8.95 Hz, 1 H) 6.79 (d, J = 9.67 Hz, 1 H) 6.44 (d, J = 1.17 Hz, 1 H) 5.25 (t, J = 7.36 Hz, 1 H) 3.77 (s, 3 H) 2.09-2.28 (m, 2 H) 1.85 (q, J = 10.23 Hz, 1 H) 1.63-1.78 (m, 1 H). |
| 822 | 1-(5-chloro-2-methoxy-6-((1-methylcyclopropyl)methoxy)-3-pyridinyl)-N-3-isoxazolyl-2-oxo-1,2-dihydro-6-quinolinesulfonamide | 517.0 | 185 | 0.46 | | $^1$H NMR (500 MHz, DMSO-d$_6$) δ 11.64 (br. s., 1 H) 8.72 (d, J = 1.10 Hz, 1 H) 8.36 (d, J = 1.56 Hz, 1 H) 8.21 (d, J = 9.67 Hz, 1 H) 8.04 (s, 1 H) 7.84 (dd, J = 8.99, 1.72 Hz, 1 H) 7.00 (d, J = 8.95 Hz, 1 H) 6.79 (d, J = 9.73 Hz, 1 H) 6.45 (d, J = 1.17 Hz, 1 H) 4.27 (q, J = 10.96 Hz, 2 H) 3.77 (s, 3 H) 1.23 (s, 3 H) 0.61 (br. s., 2 H) 0.45 (br. s., 2 H). |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 823 | 1-(2-fluoro-5-methoxy-3'-(1-methylethoxy)-4-biphenylyl)-N-3-isoxazolyl-2-oxo-1,2-dihydro-6-quinolinesulfonamide | 550.2 | 180 | 0.025 | | $^1$H NMR (500 MHz, DMSO-d$_6$) δ = $^1$H NMR (500 MHz, DMSO-d$_6$) δ ppm 11.65 (br. s., 1 H) 8.73 (d, J = 1.56 Hz, 1 H) 8.38 (d, J = 1.82 Hz, 1 H) 8.23 (d, J = 9.67 Hz, 1 H) 7.87 (dd, J = 9.02, 1.95 Hz, 1 H) 7.48 (d, J = 10.25 Hz, 1 H) 7.43 (t, J = 7.95 Hz, 1 H) 7.37 (d, J = 6.88 Hz, 1 H) 7.33 (t, J = 7.91 Hz, 1 H) 7.15-7.24 (m, 3 H) 7.12 (s, 1 H) 7.02 (d, J = 8.17 Hz, 1 H) 6.86-6.94 (m, 2 H) 6.82 (d, J = 9.60 Hz, 1 H) 6.45 (d, J = 1.49 Hz, 1 H) 4.61-4.81 (m, 2 H) 3.74 (s, 3 H) 1.31 (d, J = 6.03 Hz, 6 H). |
| 824 | 1-(5-chloro-6-(cyclopentylmethoxy)-2-methoxy-3-pyridinyl)-N-3-isoxazolyl-2-oxo-1,2-dihydro-6-quinolinesulfonamide | 531.2 | 185 | 0.217 | | $^1$H NMR (500 MHz, DMSO-d$_6$) δ = 11.64 (br. s., 1 H) 8.72 (s, 1 H) 8.36 (s, 1 H) 8.21 (d, J = 9.67 Hz, 1 H) 8.03 (s, 1 H) 7.84 (d, J = 8.95 Hz, 1 H) 7.00 (d, J = 8.89 Hz, 1 H) 6.79 (d, J = 9.67 Hz, 1 H) 6.44 (s, 1 H) 4.26-4.45 (m, 2 H) 3.78 (s, 3 H) 2.41 (quin, J = 7.46 Hz, 1 H) 1.81 (d, J = 7.27 Hz, 2 H) 1.52-1.72 (m, 4 H) 1.40 (dd, J = 12.39, 6.81 Hz, 2 H). |
| 825 | 1-(5-chloro-6-(cyclopentyloxy)-2-methoxy-3-pyridinyl)-N-isoxazolyl-2-oxo-1,2-dihydro-6-quinolinesulfonamide | 517.2 | 185 | 0.33 | | $^1$H NMR (500 MHz, DMSO-d$_6$) δ = 11.64 (br. s., 1 H) 8.72 (s, 1 H) 8.35 (s, 1 H) 8.21 (d, J = 9.73 Hz, 1 H) 8.01 (s, 1 H) 7.84 (d, J = 9.08 Hz, 1H) 6.99 (d, J = 8.95 Hz, 1 H) 6.79 (d, J = 9.60 Hz, 1 H) 6.44 (s, 1 H) 5.48 (br. s., 1 H) 3.79 (s, 3 H) 2.05 (d, J = 7.14 Hz, 2 H) 1.72-1.94 (m, 4 H) 1.65 (br. s., 2 H). |
| 826 | 1-(3-methoxy-3'-(1-methylethoxy)-4-biphenylyl)-N-1,3-oxazol-2-yl-2-oxo-1,2-dihydro-6-quinolinesulfonamide | 532.2 | 183 | 0.14 | | $^1$H NMR (500 MHz, DMSO-d$_6$) δ ppm 12.14 (br. s., 1 H) 8.32 (d, J = 1.95 Hz, 1 H) 8.19 (d, J = 9.60 Hz, 1 H) 7.86 (dd, J = 8.92, 1.98 Hz, 1 H) 7.60 (d, J = 1.49 Hz, 1 H) 7.50 (d, J = 1.36 Hz, 1 H) 7.39-7.46 (m, 2 H) 7.26-7.38 (m, 4 H) 6.99 (dd, J = 8.08, 1.46 Hz, 1 H) 6.78 (d, J = 9.67 Hz, 1 H) 6.73 (d, J = 8.89 Hz, 1 H) 4.77 (dt, J = 12.00, 6.00 Hz, 1 H) 3.78 (s, 3 H) 1.32 (s, 3 H) 1.31 (s, 3 H). |
| 827 | N-(5-fluoro-2-pyrimidinyl)-1-(3-methoxy-3'-(1-methylethoxy)-4-biphenylyl)-2-oxo-1,2-dihydro-6-quinolinesulfonamide | 561.2 | 183 | 0.177 | | $^1$H NMR (500 MHz, DMSO-d$_6$) δ = 11.94 (s, 1 H) 8.62 (s, 2 H) 8.47 (d, J = 1.95 Hz, 1 H) 8.25 (d, J = 9.73 Hz, 1 H) 7.97 (dd, J = 8.99, 2.04 Hz, 1 H) 7.50 (d, J = 1.30 Hz, 1 H) 7.39-7.45 (m, 2 H) 7.28-7.38 (m, 3 H) 6.99 (dd, J = 8.11, 1.88 Hz, 1 H) 6.79 (t, J = 8.99 Hz, 2 H) 4.76 (dt, J = 12.00, 6.00 Hz, 1 H) 3.77 (s, 3 H) 1.32 (s, 3 H) 1.31 (s, 3 H). |
| 828 | 1-(3-methoxy-3'-(1-methylethoxy)-4-biphenylyl)-2-oxo-N-2-pyrimidinyl-1,2-dihydro-6-quinolinesulfonamide | 543.2 | 183 | 0.613 | | $^1$H NMR (500 MHz, DMSO-d$_6$) δ = 11.86 (br. s., 1 H) 8.42-8.63 (m, 3 H) 8.25 (d, J = 9.67 Hz, 1 H) 7.98 (dd, J = 8.95, 2.01 Hz, 1 H) 7.49 (d, J = 1.30 Hz, 1 H) 7.38-7.45 (m, 2 H) 7.35 (d, J = 8.04 Hz, 1 H) 7.33 (d, J = 7.91 Hz, 1 H) 7.27-7.30 (m, 1 H) 7.05 (t, J = 4.74 Hz, 1 H) 6.98 (dd, J = 8.11, 1.82 Hz, 1 H) 6.79 (d, J = 9.54 Hz, 1 H) 6.77 (d, J = 8.69 Hz, 1 H) 4.76 (dt, J = 11.99, 5.98 Hz, 1 H) 3.76 (s, 3 H) 1.32 (s, 3 H) 1.31 (s, 3 H). |
| 639/829 | 1-(4-bromo-5-fluoro-2-methoxyphenyl)-N-(4,5-dimethyl-3-isoxazolyl)-2-oxo-1,2-dihydro-6-quinolinesulfonamide | 522.0 | 186 | | | $^1$H NMR (500 MHz, DMSO-d$_6$) δ = 10.79 (br. s., 1 H) 8.32 (d, J = 2.01 Hz, 1 H) 8.23 (d, J = 9.67 Hz, 1 H) 7.85 (dd, J = 8.99, 2.04 Hz, 1 H) 7.67 (d, J = 6.23 Hz, 1 H) 7.62 (d, J = 8.56 Hz, 1 H) 6.86 (d, J = 8.95 Hz, 1 H) 6.79 (d, J = 9.67 Hz, 1 H) 3.70 (s, 3 H) 2.21 (s, 3 H) 1.80 (s, 3 H). |
| 640/830 | 1-(5-chloro-6-cyclopropyl-2-methoxy-3-pyridinyl)-N-3-isoxazolyl-2-oxo-1,2-dihydro-6-quinolinesulfonamide | 473.0 | 187 | 0.038 | | $^1$H NMR (400 MHz, CHLOROFORM-d) δ ppm 8.23 (d, J = 1.76 Hz, 1 H) 8.13 (d, J = 1.97 Hz, 1 H) 7.74-7.80 (m, 1 H) 7.46 (s, 1 H) 6.82 (d, J = 9.64 Hz, 1 H) 6.75 (d, J = 9.02 Hz, 1 H) 6.56 (d, J = 1.66 Hz, 1 H) 3.76 (s, 3 H) 2.41-2.61 (m, 1 H) 1.14-1.23 (m, 2 H) 1.09 (dd, J = 8.09, 3.21 Hz, 2 H). |
| 831 | 1-(5-chloro-2-methoxy-6-(3-methoxypropoxy)-3-pyridinyl)-N-3-isoxazolyl-2-oxo-1,2-dihydro-6-quinolinesulfonamide | 521.0 | 185 | 3.814 | | $^1$H NMR (500 MHz, DMSO-d$_6$) δ = 11.65 (br. s., 1 H) 8.72 (d, J = 1.69 Hz, 1 H) 8.33-8.41 (m, 1 H) 8.17-8.28 (m, 1 H) 8.04 (s, 1 H) 7.84 (dd, J = 8.95, 2.08 Hz, 1 H) 6.96-7.11 (m, 1 H) 6.76-6.84 (m, 1 H) 6.45 (d, J = 1.69 Hz, 1 H) 4.46-4.56 (m, 2 H) 3.79 (s, 3 H) 3.52 (t, J = 6.23 Hz, 2 H) 3.28 (s, 3 H) 2.05 (quin, J = 6.31 Hz, 2 H). |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 832 | 1-(5-chloro-2-methoxy-6-(2,2,3,3,3-pentafluoropropoxy)-3-pyridinyl)-N-3-isoxazolyl-2-oxo-1,2-dihydro-6-quinolinesulfonamide | 580.9 | 185 | 0.161 | | $^1$H NMR (500 MHz, DMSO-d$_6$) δ = 11.65 (br. s., 1 H) 8.73 (d, J = 1.69 Hz, 1 H) 8.37 (d, J = 1.95 Hz, 1 H) 8.23 (d, J = 9.67 Hz, 1 H) 8.19 (s, 1 H) 7.85 (dd, J = 8.95, 2.08 Hz, 1 H) 7.00 (d, J = 8.95 Hz, 1 H) 6.80 (d, J = 9.67 Hz, 1 H) 6.45 (d, J = 1.69 Hz, 1 H) 5.16-5.40 (m, 2 H) 3.84 (s, 3 H). |
| 833 | 1-(5-chloro-2-methoxy-6-(2,2,2-trifluoroethoxy)-3-pyridinyl)-N-3-isoxazolyl-2-oxo-1,2-dihydro-6-quinolinesulfonamide | 530.8 | 185 | 0.565 | | $^1$H NMR (500 MHz, DMSO-d$_6$) δ = 11.65 (br. s., 1 H) 8.73 (d, J = 1.69 Hz, 1 H) 8.38 (d, J = 2.01 Hz, 1 H) 8.23 (d, J = 9.73 Hz, 1 H) 8.19 (s, 1 H) 7.85 (dd, J = 8.95, 2.08 Hz, 1 H) 7.01 (s, 1 H) 6.81 (d, J = 9.67 Hz, 1 H) 6.45 (d, J = 1.69 Hz, 1 H) 5.11-5.30 (m, 2 H) 3.83 (s, 3 H). |
| 674 | N-3-isoxazolyl-2-oxo-1-(2,3',4'-trifluoro-5-methoxy-4-biphenylyl)-1,2-dihydro-6-quinolinesulfonamide | 528.2 | 145 | 0.015 | | $^1$H NMR (400 MHz, DMSO-d$_6$) δ ppm 3.75 (s, 3 H) 6.46 (s, 1 H) 6.82 (d, J = 9.64 Hz, 1 H) 6.88 (d, J = 8.91 Hz, 1 H) 7.43 (d, J = 7.15 Hz, 1 H) 7.52-7.67 (m, 3 H) 7.81-7.89 (m, 2 H) 8.24 (d, J = 9.54 Hz, 1 H) 8.39 (d, J = 2.18 Hz, 1 H) 8.74 (s, 1 H) 11.67 (s, 1 H). |
| 634/675 | 1-(4'-chloro-2-fluoro-5-methoxy-4-biphenylyl)-N-3-isoxazolyl-2-oxo-1,2-dihydro-6-quinolinesulfonamide | 526.1 | 145 | 0.013 | | $^1$H NMR (400 MHz, DMSO-d$_6$) δ ppm 3.73 (s, 3 H) 6.45 (s, 1 H) 6.82 (d, J = 9.33 Hz, 1 H) 6.88 (d, J = 9.02 Hz, 1 H) 7.40 (d, J = 6.84 Hz, 1 H) 7.53 (d, J = 10.26 Hz, 1 H) 7.62 (m, J = 8.19 Hz, 2 H) 7.74 (m, J = 8.29 Hz, 2 H) 7.86 (d, J = 8.60 Hz, 1 H) 8.24 (d, J = 9.64 Hz, 1 H) 8.38 (s, 1 H) 8.73 (s, 1 H) 11.68 (s, 1 H). |
| 659 | 1-(4'-chloro-3-methoxy-3'-methyl-4-biphenylyl)-2-oxo-N-2-pyrazinyl-1,2-dihydro-6-quinolinesulfonamide | 532.8 | 202 | 0.035 | | 1H NMR (400 MHz, DMSO-d6) Shift 11.63 (br. s., 1H), 8.47 (d, J = 2.18 Hz, 1H), 8.31-8.41 (m, 1H), 8.19-8.27 (m, 3H), 7.95 (dd, J = 2.23, 8.97 Hz, 1H), 7.83 (s, 1H), 7.60-7.72 (m, 1 H), 7.51-7.57 (m, 2H), 7.41-7.46 (m, 1H), 7.35-7.40 (m, 1H), 6.80 (d, J = 7.67 Hz, 1H), 6.78 (d, J = 7.15 Hz, 1H), 3.76 (s, 3H), 2.44 (s, 3H) |
| 689 | 1-(4'-chloro-3-methoxy-3'-methyl-4-biphenylyl)-N-(5-fluoro-2-pyridinyl)-2-oxo-1,2-dihydro-6-quinolinesulfonamide | 549.9 | 202 | 0.05 | | 1H NMR (400 MHz, DMSO-d6) Shift 11.17 (br. s., 1H), 8.40 (d, J = 2.18 Hz, 1H), 8.22 (d, J = 9.54 Hz, 1H), 8.17 (d, J = 3.11 Hz, 1H), 7.89 (dd, J = 2.18, 9.02 Hz, 1H), 7.83 (d, J = 1.97 Hz, 1H), 7.62-7.70 (m, 1H), 7.51-7.57 (m, 2H), 7.41-7.46 (m, 1H), 7.35-7.40 (m, 1H), 7.11 (dd, J = 3.73, 9.12 Hz, 1H), 6.79 (d, J = 9.64 Hz, 1H), 6.74-6.77 (m, 1 H), 3.77 (s, 3H), 2.44 (s, 3H) |
| 690 | 1-(4'-chloro-3-methoxy-3'-methyl-4-biphenylyl)-N-(5-fluoro-2-pyrimidinyl)-2-oxo-1,2-dihydro-6-quinolinesulfonamide | 550.8 | 202 | 0.049 | | 1H NMR (400 MHz, DMSO-d6) Shift 11.96 (br. s., 1H), 8.62 (s, 2H), 8.47 (d, J = 2.07 Hz, 1 H), 8.25 (d, J = 9.64 Hz, 1H), 7.97 (dd, J = 2.18, 8.91 Hz, 1H), 7.81-7.87 (m, 1H), 7.63-7.70 (m, 1 H), 7.51-7.57 (m, 2H), 7.42-7.48 (m, 1 H), 7.34-7.40 (m, 1H), 6.79 (t, J = 9.28 Hz, 2H), 3.73-3.83 (m, 3H), 2.44 (s, 3H) |
| 660 | 1-(4'-chloro-3-methoxy-3'-methyl-4-biphenylyl)-N-1,3-oxazol-2-yl-2-oxo-1,2-dihydro-6-quinolinesulfonamide | 522.0 | 203 | 0.009 | | 1H NMR (400 MHz, DMSO-d6) Shift 12.15 (br. s., 1H), 8.32 (d, J = 2.18 Hz, 1H), 8.14-8.23 (m, 1H), 7.81-7.88 (m, 2H), 7.63-7.71 (m, 1H), 7.57-7.62 (m, 1H), 7.50-7.57 (m, 2H), 7.41-7.47 (m, 1H), 7.34-7.40 (m, 1H), 7.25 (d, J = 1.66 Hz, 1H), 6.75-6.81 (m, 1H), 6.72 (d, J = 8.91 Hz, 1H), 3.74-3.81 (m, 3H), 2.44 (s, 3H) |
| 661 | 1-(4'-chloro-3-methoxy-3'-methyl-4-biphenylyl)-N-1,2,4-oxadiazol-3-yl-2-oxo-1,2-dihydro-6-quinolinesulfonamide | 522.9 | 204 | 0.03 | | $^1$H NMR (500 MHz, DMSO-d$_6$) δ 12.06-12.68 (br.s, 1H), 9.35 (s, 1H), 8.43 (d, J = 1.95 Hz, 1H), 8.26 (d, J = 9.67 Hz, 1H), 7.88-8.02 (m, 1H), 7.83 (s, 1H), 7.67 (dd, J = 1.85, 8.27 Hz, 1H), 7.50-7.59 (m, 2H), 7.42-7.48 (m, 1H), 7.33-7.42 (m, 1H), 6.82 (dd, J = 4.77, 9.31 Hz, 2H), 3.78 (s, 3H), 2.45 (s, 3H) |
| 1103 | 1-(4-bromo-5-fluoro-2-methoxyphenyl)-N-3-isoxazolyl-2-oxo-1,2-dihydro-6-quinolinesulfonamide | 494.0 | Intermediate Prep | | | $^1$H NMR (400 MHz, DMSO-d$_6$) δ ppm 3.70 (s, 3 H) 6.45 (s, 1 H) 6.80 (d, J = 9.64 Hz, 1 H) 6.87 (d, J = 9.02 Hz, 1 H) 7.62 (d, J = 8.71 Hz, 1 H) 7.67 (d, J = 6.22 Hz, 1 H) 7.83 (dd, J = 9.02, 2.18 Hz, 1 H) 8.23 (d, J = 9.64 Hz, 1 H) 8.37 (d, J = 2.18 Hz, 1 H) 8.74 (s, 1 H) 11.66 (s, 1 H). |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 1104 | 1-(4-bromo-5-fluoro-2-methoxyphenyl)-2-oxo-N-2-pyrimidinyl-1,2-dihydro-6-quinolinesulfonamide | 505.2 | Intermediate Prep | | | $^1$H NMR (400 MHz, DMSO-d$_6$) δ 11.81 (s, 1H), 8.56-8.42 (m, 3H), 8.26 (d, J = 9.6 Hz, 1H), 7.95 (dd, J = 8.9, 2.1 Hz, 1H), 7.66 (d, J = 6.2 Hz, 1H), 7.61 (d, J = 8.6 Hz, 1H), 7.05 (s, 1H), 6.79 (dd, J = 16.1, 9.3 Hz, 2H), 3.68 (s, 3H) |
| 1105 | 1-(4-bromo-5-fluoro-2-methoxyphenyl)-N-3-isoxazolyl-2-oxo-1,2-dihydro-6-quinolinesulfonamide | 494.0 | Intermediate Prep | 0.307 | | $^1$H NMR (400 MHz, DMSO-d$_6$) δ ppm 3.70 (s, 3 H) 6.45 (s, 1 H) 6.80 (d, J = 9.64 Hz, 1 H) 6.87 (d, J = 9.02 Hz, 1 H) 7.62 (d, J = 8.71 Hz, 1 H) 7.67 (d, J = 6.22 Hz, 1 H) 7.83 (dd, J = 9.02, 2.18 Hz, 1 H) 8.23 (d, J = 9.64 Hz, 1 H) 8.37 (d, J = 2.18 Hz, 1 H) 8.74 (s, 1 H) 11.66 (s, 1 H). |
| 1106 | 1-(2-fluoro-5-methoxy-3'-methyl-4-biphenylyl)-N-1,3-oxazol-2-yl-2-oxo-1,2-dihydro-6-quinolinesulfonamide | 506.0 | 73 | 0.024 | | 1H NMR (400 MHz, DMSO-d6) δ ppm 12.13 (br. s., 1 H), 8.27 (d, J = 2.07 Hz, 1 H), 8.14 (d, J = 9.64 Hz, 1 H), 7.82 (dd, J = 8.91, 2.13 Hz, 1 H), 7.35-7.53 (m, 5 H), 7.31 (d, J = 7.00 Hz, 1 H), 7.24 (d, J = 7.19 Hz, 1 H), 7.14 (br. s, 1 H), 6.72 (m, 2 H), 3.69 (s, 3 H), 2.37 (s, 3 H). |
| 1107 | 1-(2-fluoro-5-methoxy-3'-methyl-4-biphenylyl)-2-oxo-N-2-pyrimidinyl-1,2-dihydro-6-quinolinesulfonamide | 517.0 | 73 | 0.032 | | 1H NMR (400 MHz, DMSO-d6) δ ppm 11.86 (br. s., 1 H), 8.47-8.54 (m, 3 H), 8.27 (d, J = 9.74 Hz, 1 H), 7.99-8.02 (m, 1 H), 7.40-7.53 (m, 4 H), 7.36 (d, J = 6.95 Hz, 1 H), 7.26-7.32 (m, 1 H), 7.02-7.09 (m, 1 H), 6.78-6.88 (m, 2 H), 3.73 (s, 3 H), 2.41 (s, 3 H). |
| 1108 | 1-(2-fluoro-5-methoxy-3'-methyl-4-biphenylyl)-2-oxo-N-3-pyrimidinyl-1,2-dihydro-6-quinolinesulfonamide | 517.0 | 73 | 0.021 | | 1H NMR (400 MHz, DMSO-d6) δ ppm 14.48 (br. s., 1 H), 8.27-8.41 (m, 2 H), 8.21 (d, J = 9.54 Hz, 1 H), 7.85-7.97 (m, 2 H), 7.69 (dd, J = 9.54, 4.15 Hz, 1 H), 7.40-7.55 (m, 4 H), 7.36 (d, J = 6.95 Hz, 1 H), 7.29 (d, J = 8.40 Hz, 1 H), 6.76-6.84 (m, 2 H), 3.74 (s, 3 H), 2.42 (s, 3 H). |
| 1109 | 1-(2-fluoro-5-methoxy-3'-methyl-4-biphenylyl)-N-(5-fluoro-2-pyrimidinyl)-2-oxo-1,2-dihydro-6-quinolinesulfonamide | 535.0 | 73 | 0.02 | | 1H NMR (500 MHz, DMSO-d6) δ ppm 11.96 (s, 1 H) 8.62 (s, 2 H) 8.47 (d, J = 2.01 Hz, 1 H) 8.25 (d, J = 9.67 Hz, 1 H) 7.98 (dd, J = 8.95, 2.08 Hz, 1 H) 7.40-7.55 (m, 4 H) 7.36 (d, J = 6.94 Hz, 1 H) 7.28 (d, J = 7.40 Hz, 1 H) 6.79-6.99 (m, 2 H) 3.72 (s, 3 H) 2.41 (s, 3 H) |
| 641 | 1-(4-(cyclohexylmethyl)-5-fluoro-2-methoxyphenyl)-2-oxo-N-2-pyrimidinyl-1,2-dihydro-6-quinolinesulfonamide | 523.2 | 188 | 0.039 | | 1H NMR (500 MHz, DMSO-d6) δ ppm 11.56 (s, 1 H) 8.44-8.52 (m, 3 H) 8.23 (d, J = 9.73 Hz, 1 H) 7.97 (dd, J = 8.99, 2.04 Hz, 1 H) 7.24 (d, J = 9.47 Hz, 1 H) 7.12-7.20 (m, 1 H) 6.97-7.10 (m, 1 H) 6.70-6.80 (m, 2 H) 3.63 (s, 3 H) 2.54-2.74 (m, 2 H) 1.58-1.85 (m, 7 H) 1.12-1.30 (m, 4 H) |
| 1110 | 1-(4-(cyclohexylmethyl)-5-fluoro-2-methoxyphenyl)-N-1,3-oxazol-2-yl-2-oxo-1,2-dihydro-6-quinolinesulfonamide | 512.2 | 188 | 0.052 | | 1H NMR (500 MHz, DMSO-d6) δ ppm 12.20 (br s, 1 H) 8.30 (d, J = 1.88 Hz, 1 H) 8.16 (d, J = 9.67 Hz, 1 H) 7.85 (dd, J = 8.92, 2.04 Hz, 1 H) 7.60 (d, J = 1.56 Hz, 1 H) 7.21-7.31 (m, 2 H) 7.08-7.20 (m, 1 H) 6.75 (d, J = 9.60 Hz, 1 H) 6.68 (d, J = 8.95 Hz, 1 H) 3.64 (s, 3 H) 2.55-2.74 (m, 2 H) 1.66-1.78 (m, 7 H) 1.09-1.32 (m, 4 H) |
| 1111 | 1-(4-(cyclohexylmethyl)-5-fluoro-2-methoxyphenyl)-N-(5-fluoro-2-pyrimidinyl)-2-oxo-1,2-dihydro-6-quinolinesulfonamide | 541.0 | 188 | 0.088 | | 1H NMR (400 MHz, DMSO-d6) δ ppm 11.96 (br. s, 1 H) 8.60 (s, 2 H) 8.40-8.52 (m, 1 H) 8.22 (d, J = 9.64 Hz, 1 H) 7.95 (dd, J = 8.97, 2.18 Hz, 1 H) 7.24 (d, J = 9.48 Hz, 1 H) 7.16 (d, J = 6.63 Hz, 1 H) 6.71-6.76 (m, 2 H) 3.62 (s, 3 H) 2.53-2.62 (m, 2 H) 1.58-1.74 (m, 7 H) 1.16-1.30 (m, 4 H) |
| 1112 | 1-(4-(cyclohexylmethyl)-5-fluoro-2-methoxyphenyl)-2-oxo-N-3-pyridazinyl-1,2-dihydro-6-quinolinesulfonamide | 523.0 | 188 | 0.025 | | 1H NMR (400 MHz, DMSO-d6) δ ppm 14.31 (br. s., 1 H) 8.09-8.21 (m, 2 H) 8.00 (d, J = 9.64 Hz, 1 H) 7.62-7.79 (m, 2 H) 7.51 (dd, J = 9.54, 4.15 Hz, 1 H) 6.95-7.16 (m, 2 H) 6.49-6.61 (m, 2 H) 3.48 (s, 3 H) 2.38-2.47 (m, 2 H) 1.42-1.67 (m, 7 H) 1.01-1.15 (m, 4 H) |
| 1113 | 1-(3-methoxy-3'-methyl-4-biphenylyl)-N-1,3-oxazol-2-yl-2- | 488.0 | 73 | 0.044 | | 1H NMR (400 MHz, DMSO-d6) δ ppm 12.16 (br. s., 1 H) 8.31-8.34 (m, 1 H) 8.19 (d, J = 9.49 Hz, 1 H) 7.83-7.88 (m, 1 H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | oxo-1,2-dihydro-6-quinolinesulfonamide | | | | | 7.58-7.65 (m, 3 H) 7.50-7.53 (m, 1 H) 7.35-7.44 (m, 3 H) 7.23-7.31 (m, 2 H) 6.71-6.80 (m, 2 H) 3.78 (s, 3 H) 2.43 (s, 3 H) |
| 1114 | 1-(2-fluoro-5-methoxy-3'-methyl-4-biphenylyl)-N-1,2,4-oxadiazol-3-yl-2-oxo-1,2-dihydro-6-quinolinesulfonamide | 506.9 | 189 | 0.035 | | 1H NMR (500 MHz, DMSO-d6) δ ppm 9.07 (br. s., 1 H) 8.33 (s., 1 H) 8.22 (d, J = 9.60 Hz, 1 H) 7.89 (d, J = 9.02 Hz, 1 H) 7.40-7.55 (m, 5 H) 7.35 (d, J = 6.88 Hz, 1 H) 7.29 (d, J = 7.20 Hz, 1 H) 6.75-6.84 (m, 2 H) 3.73 (s, 3 H) 2.42 (s, 3 H) |
| 642 | 1-(4-(cyclohexylmethyl)-5-fluoro-2-methoxyphenyl)-N-1,2,4-oxadiazol-3-yl-2-oxo-1,2-dihydro-6-quinolinesulfonamide | 513.2 | 188 | 0.03 | | 1H NMR (500 MHz, DMSO-d6) δ ppm 12.41 (br. s., 1 H) 9.19 (s., 1 H) 8.35 (s, 1 H) 8.21 (d, J = 9.60 Hz, 1 H) 7.89 (d, J = 8.64 Hz, 1 H) 7.24 (d, J = 9.54 Hz, 1 H) 7.16 (d, J = 6.55 Hz, 1 H) 6.70-6.76 (m, 2 H) 3.65 (s, 3 H) 2.52-2.58 (m, 2 H) 1.53-1.80 (m, 7 H) 1.12-1.32 (m, 4 H) |
| 1115 | 1-(4-(cyclohexylmethyl)-5-fluoro-2-methoxyphenyl)-2-oxo-N-4-pyrimidinyl-1,2-dihydro-6-quinolinesulfonamide | 523.2 | 188 | 0.081 | | 1H NMR (500 MHz, DMSO-d6) δ ppm 12.11 (br. s., 1 H) 8.57 (s, 1 H) 8.32-8.36 (m, 1 H) 8.26 (d, J = 6.16 Hz, 1 H) 8.19 (d, J = 9.60 Hz, 1 H) 7.90 (dd, J = 8.95, 2.01 Hz, 1 H) 7.24 (d, J = 9.47 Hz, 1 H) 7.16 (d, J = 6.55 Hz, 1 H) 6.96 (d, J = 6.16 Hz, 1 H) 6.76 (d, J = 9.00 Hz, 1 H) 6.70 (d, J = 8.74 Hz, 1 H) 3.64 (s, 3 H) 2.55-2.59 (m, 2 H) 1.57-1.81 (m, 7 H) 1.12-1.30 (m, 4 H) |
| 1116 | 1-(4-(cyclohexylmethyl)-5-fluoro-2-methoxyphenyl)-2-oxo-N-2-pyrazinyl-1,2-dihydro-6-quinolinesulfonamide | 523.2 | 188 | 0.03 | | 1H NMR (500 MHz, DMSO-d6) δ ppm 11.61 (br. s., 1 H) 8.44 (d, J = 2.01 Hz, 1 H) 8.34 (s, 1 H) 8.17-8.24 (m, 3 H) 7.94 (dd, J = 8.99, 2.11 Hz, 1 H) 7.24 (d, J = 8.89 Hz, 1 H) 7.16 (d, J = 6.55 Hz, 1 H) 6.70-6.79 (m, 2 H) 3.63 (s, 3 H) 2.52-2.66 (m, 2 H) 1.54-1.84 (m, 7 H) 1.12-1.34 (m, 4 H) |
| 1117 | 1-(3-methoxy-3'-methyl-4-biphenylyl)-2-oxo-N-2-pyrimidinyl-1,2-dihydro-6-quinolinesulfonamide | 499.2 | 73 | 0.059 | | 1H NMR (400 MHz, DMSO-d6) δ ppm 11.81 (br. s., 1 H) 8.45-8.54 (m, 3 H) 8.25 (d, J = 9.64 Hz, 1 H) 7.98 (dd, J = 8.99, 2.15 Hz, 1 H) 7.55-7.66 (m, 2 H) 7.49 (d, J = 1.71 Hz, 1 H) 7.34-7.43 (m, 3 H) 7.23-7.30 (m, 1 H) 7.01-7.09 (m, 1 H) 6.75-6.81 (m, 2 H) 3.76 (s, 3 H) 2.42 (s, 3 H) |
| 1118 | 1-(5-fluoro-2-methoxy-4-((3R)-tetrahydro-2H-pyran-3-ylmethyl)phenyl)-N-3-isoxazolyl-2-oxo-1,2-dihydro-6-quinolinesulfonamide, 1-(5-fluoro-2-methoxy-4-((3S)-tetrahydro-2H-pyran-3-ylmethyl)phenyl)-N-3-isoxazolyl-2-oxo-1,2-dihydro-6-quinolinesulfonamide | 514.1 | 209 | 1.484 | | |
| 1119 | N-(5-fluoro-2-pyrimidinyl)-1-(3-methoxy-3'-methyl-4-biphenylyl)-2-oxo-1,2-dihydro-6-quinolinesulfonamide | 517.0 | 73 | 0.04 | | 1H NMR (500 MHz, DMSO-d6) δ ppm 11.95 (br. s., 1 H) 8.61 (s, 2 H) 8.47 (d, J = 1.95 Hz, 1 H) 8.24 (d, J = 9.67 Hz, 1 H) 7.97 (dd, J = 9.02, 2.01 Hz, 1 H) 7.55-7.67 (m, 2 H) 7.46-7.54 (m, 1 H) 7.33-7.45 (m, 3 H) 7.24 (d, J = 7.27 Hz, 1 H) 6.72-6.80 (m, 2 H) 3.78 (s, 3 H) 2.42 (s, 3 H) |
| 1120 | 1-(3-methoxy-3'-methyl-4-biphenylyl)-2-oxo-N-3-pyridazinyl-1,2-dihydro-6-quinolinesulfonamide | 499.0 | 73 | 0.108 | | 1H NMR (500 MHz, DMSO-d6) δ ppm 14.49 (br. s., 1 H) 8.27-8.43 (m, 2 H) 8.19 (d, J = 9.67 Hz, 1 H) 7.81-7.99 (m, 2 H) 7.55-7.73 (m, 3 H) 7.50 (s, 1 H) 7.33-7.45 (m, 3 H) 7.25 (d, J = 9.67 Hz, 1 H) 6.72-6.85 (m, 2 H) 3.78 (s, 3 H) 2.42 (s, 3 H) |
| 1121 | 1-(5-fluoro-2-methoxy-4-(tetrahydro-2H-pyran-4-ylmethyl)phenyl)-N-3-isoxazolyl-2-oxo-1,2-dihydro-6-quinolinesulfonamide | 514.0 | 209 | 0.694 | | 1H NMR (400 MHz, DMSO-d6) δ ppm 11.60 (br. s, 1 H) 8.67 (d, J = 1.50 Hz, 1 H) 8.30 (d, J = 2.12 Hz, 1 H) 8.15 (d, J = 9.64 Hz, 1 H) 7.79 (dd, J = 8.97, 2.23 Hz, 1 H) 7.23 (d, J = 9.54 Hz, 1 H) 7.15 (d, J = 6.58 Hz, 1 H) 6.70-6.79 (m, 2 H) 6.39 (d, J = 1.76 Hz, 1 H) 3.59 (s, 3 H) 3.21-3.27 (m, 4H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 643 | 1-(4-(cyclopentylethynyl)-5-fluoro-2-methoxyphenyl)-N-3-isoxazolyl-2-oxo-1,2-dihydro-6-quinolinesulfonamide | 508.0 | 190 | 0.022 | | 2.55-2.64 (m, 2 H) 1.45-1.55 (m, 3 H) 1.17-1.32 (m, 2 H) 1H NMR (400 MHz, DMSO-d6) δ ppm 11.60 (br. s, 1 H) 8.67 (d, J = 1.81 Hz, 1 H) 8.30-8.38 (m, 1 H) 8.15 (d, J = 9.69 Hz, 1 H) 7.76 (dd, J = 8.97, 2.23 Hz, 1 H) 7.39 (d, J = 9.17 Hz, 1 H) 7.26 (d, J = 6.38 Hz, 1 H) 6.70-6.79 (m, 2 H) 6.39 (d, J = 1.76 Hz, 1 H) 3.60 (s, 3 H) 2.85-2.89 (m, 1 H) 1.91-1.99 (m, 2 H) 1.51-1.73 (m, 6 H) |
| 1122 | 1-(4-(3,3-dimethyl-1-butyn-1-yl)-5-fluoro-2-methoxyphenyl)-N-3-isoxazolyl-2-oxo-1,2-dihydro-6-quinolinesulfonamide | 496.0 | 190 | 0.08 | | 1H NMR (400 MHz, DMSO-d6) δ ppm 11.60 (br. s, 1 H) 8.67 (d, J = 1.71 Hz, 1 H) 8.22-8.28 (m, 1 H) 8.16 (d, J = 9.69 Hz, 1 H) 7.76 (dd, J = 8.97, 2.18 Hz, 1 H) 7.39 (d, J = 9.23 Hz, 1 H) 7.23 (d, J = 6.32 Hz, 1 H) 6.68-6.77 (m, 2 H) 6.39 (d, J = 1.76 Hz, 1 H) 3.61 (s, 3 H) 1.29 (s, 9 H) |
| 1123 | 1-(5-fluoro-2-methoxy-4-((3R)-tetrahydro-3-furanylmethyl)phenyl)-N-3-isoxazolyl-2-oxo-1,2-dihydro-6-quinolinesulfonamide, 1-(5-fluoro-2-methoxy-4-((3S)-tetrahydro-3-furanylmethyl)phenyl)-N-3-isoxazolyl-2-oxo-1,2-dihydro-6-quinolinesulfonamide | 500.0 | 209 | 1.602 | | |
| 1124 | 1-(2,3'-difluoro-5-methoxy-4'-methyl-4-biphenylyl)-N-(2-methyl-4-pyrimidinyl)-2-oxo-1,2-dihydro-6-quinolinesulfonamide | 549.0 | 73 | 0.106 | | 1H NMR (400 MHz, DMSO-d6) δ ppm 8.39-8.45 (m, 1 H) 8.27 (d, J = 9.69 Hz, 1 H) 7.88-8.18 (m, 2 H) 7.44-7.59 (m, 6 H) 6.80-6.92 (m, 3 H) 3.78 (s, 3 H) 2.55 (s, 3 H) 2.39 (s, 3 H) |
| 644 | 1-(5-fluoro-2-methoxy-4-(3,3,3-trifluoro-1-propyn-1-yl)phenyl)-N-3-isoxazolyl-2-oxo-1,2-dihydro-6-quinolinesulfonamide | 507.8 | 191 | 0.387 | | 1H NMR (400 MHz, DMSO-d6) δ ppm 11.67 (br. s, 1 H) 8.64-8.72 (m, 1 H) 8.34-8.38 (m, 1 H) 8.24 (d, J = 9.74 Hz, 1 H) 7.77-7.83 (m, 2 H) 7.72 (d, J = 9.23 Hz, 1 H) 6.77-6.87 (m, 2 H) 6.38-6.44 (m, 1 H) 3.71 (s, 3 H) |
| 1125 | 1-(2,3'-difluoro-5-methoxy-4'-methyl-4-biphenylyl)-N-1,3-oxazol-2-yl-2-oxo-1,2-dihydro-6-quinolinesulfonamide | 524.0 | 73 | 0.081 | | 1H NMR (400 MHz, DMSO-d6) δ ppm 12.12 (br. s., 1 H) 8.27 (d, J = 2.07 Hz, 1 H) 8.14 (d, J = 9.59 Hz, 1 H) 7.81 (dd, J = 8.89, 2.15 Hz, 1 H) 7.34-7.53 (m, 6 H) 7.17 (br. s, 1 H) 6.73-6.85 (m, 2 H) 3.69 (s, 3 H) 2.27 (s, 3 H) |
| 1126 | 1-(2,3'-difluoro-5-methoxy-4'-methyl-4-biphenylyl)-2-oxo-N-2-pyrimidinyl-1,2-dihydro-6-quinolinesulfonamide | 535.0 | 73 | 0.057 | | 1H NMR (400 MHz, DMSO-d6) δ ppm 11.91 (br. s., 1 H) 8.47-8.52 (m, 3 H) 8.27 (d, J = 9.64 Hz, 1 H) 7.99 (dd, J = 8.91, 2.18 Hz, 1 H) 7.45-7.57 (m, 4 H) 7.41 (d, J = 6.95 Hz, 1 H) 7.01-7.07 (m, 1 H) 6.79-6.86 (m, 2 H) 3.74 (s, 3 H) 2.33 (s, 3 H) |
| 1127 | 1-(2,3'-difluoro-5-methoxy-4'-methyl-4-biphenylyl)-N-(5-fluoro-2-pyrimidinyl)-2-oxo-1,2-dihydro-6-quinolinesulfonamide | 553.0 | 73 | 0.034 | | 1H NMR (400 MHz, DMSO-d6) δ ppm 11.99 (br. s, 1 H) 8.62 (s, 2 H) 8.48 (d, J = 2.18 Hz, 1 H) 8.27 (d, J = 9.54 Hz, 1 H) 7.98 (dd, J = 8.97, 2.23 Hz, 1 H) 7.40-7.54 (m, 5 H) 6.86 (d, J = 9.02 Hz, 1 H) 6.82 (d, J = 9.64 Hz, 1 H) 3.74 (s, 3 H) 2.33 (s, 3 H) |
| 1128 | 1-(2,3'-difluoro-5-methoxy-4'-methyl-4-biphenylyl)-2-oxo-N-3-pyridazinyl-1,2-dihydro-6-quinolinesulfonamide | 535.0 | 73 | 0.036 | | 1H NMR (400 MHz, DMSO-d6) δ ppm 14.48 (br. s, 1 H) 8.28-8.40 (m, 2 H) 8.21 (d, J = 9.64 Hz, 1 H) 7.85-7.96 (m, 2 H) 7.65-7.72 (m, 1 H) 7.45-7.54 (m, 4 H) 7.41 (d, J = 7.05 Hz, 1 H) 6.77-6.82 (m, 2 H) 3.74 (s, 3 H) 2.33 (s, 3 H) |
| 1129 | 1-(2,3'-difluoro-5-methoxy-4'-methyl-4-biphenylyl)-N-(6-methyl-4-pyrimidinyl)-2-oxo-1,2-dihydro-6-quinolinesulfonamide | 549.0 | 73 | 0.08 | | 1H NMR (400 MHz, DMSO-d6) δ ppm 8.51 (s, 1 H) 8.44 (d, J = 1.87 Hz, 1 H) 8.24 (d, J = 9.54 Hz, 1 H) 7.92 (dd, J = 8.91, 2.18 Hz, 1 H) 7.43-7.54 (m, 4 H) 7.41 (d, J = 6.95 Hz, 1 H) 6.88-6.96 (m, 1 H) 6.79-6.85 (m, 2 H) 3.74 (s, 3 H) 2.33 (s, 6 H) |

TABLE 3-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| 1130 | 1-(4-(cyclopropylethynyl)-5-fluoro-2-methoxyphenyl)-N-3-isoxazolyl-2-oxo-1,2-dihydro-6-quinolinesulfonamide | 480.0 | 190 | 0.209 | | 1H NMR (400 MHz, DMSO-d6) δ ppm 11.66 (br. s, 1 H) 8.74 (d, J = 1.76 Hz, 1 H) 8.36 (d, J = 2.18 Hz, 1 H) 8.22 (d, J = 9.64 Hz, 1 H) 7.83 (dd, J = 8.97, 2.23 Hz, 1 H) 7.45 (d, J = 9.33 Hz, 1 H) 7.33 (d, J = 6.43 Hz, 1 H) 6.80 (t, J = 9.67 Hz, 2 H) 6.45 (d, J = 1.76 Hz, 1 H) 3.65 (s, 3 H) 1.63-1.70 (m, 1 H) 0.94-1.02 (m, 2 H) 0.78-0.87 (m, 2 H) |
| 1131 | 1-(3-methoxy-3'-methyl-4-biphenylyl)-N-(6-methyl-4-pyrimidinyl)-2-oxo-1,2-dihydro-6-quinolinesulfonamide | 513.0 | 73 | 0.155 | | 1H NMR (400 MHz, DMSO-d6) δ ppm 11.40 (br. s., 1 H) 8.50 (br. s, 1 H) 8.42 (br. s, 1 H) 8.23 (d, J = 9.54 Hz, 1 H) 7.91 (d, J = 9.08 Hz, 1 H) 7.58-7.64 (m, 2 H) 7.51 (d, J = 1.76 Hz, 1 H) 7.36-7.46 (m, 3 H) 7.26 (d, J = 7.57 Hz, 1 H) 6.87-6.95 (m, 1 H) 6.74-6.81 (m, 2 H) 3.77 (s, 3 H) 2.43 (s, 3 H) 2.33 (s, 3 H) |
| 1132 | 1-(3-methoxy-3'-methyl-4-biphenylyl)-N-(2-methyl-4-pyrimidinyl)-2-oxo-1,2-dihydro-6-quinolinesulfonamide | 513.0 | 73 | 0.192 | | 1H NMR (400 MHz, DMSO-d6) δ ppm 11.39 (br. s., 1 H) 8.39 (d, J = 1.76 Hz, 1 H) 8.23 (d, J = 9.43 Hz, 1 H) 8.12 (d, J = 6.01 Hz, 1 H) 7.89 (dd, J = 8.97, 2.13 Hz, 1 H) 7.58-7.65 (m, 2 H) 7.51 (d, J = 1.76 Hz, 1 H) 7.34-7.44 (m, 3 H) 7.26 (d, J = 7.57 Hz, 1 H) 6.85-6.96 (m, 1 H) 6.79 (d, J = 9.54 Hz, 1 H) 6.74 (d, J = 9.02 Hz, 1 H) 3.78 (s, 3 H) 2.43 (s, 3 H) 2.38 (s, 3 H) |
| 1133 | 1-(5-fluoro-2-methoxy-4-((2R)-tetrahydro-2H-pyran-2-ylmethyl)phenyl)-N-3-isoxazolyl-2-oxo-1,2-dihydro-6-quinolinesulfonamide, 1-(5-fluoro-2-methoxy-4-((2S)-tetrahydro-2H-pyran-2-ylmethyl)phenyl)-N-3-isoxazolyl-2-oxo-1,2-dihydro-6-quinolinesulfonamide | 514.0 | 209 | 2.261 | | |
| 1134 | 1-(4-(cyclopentylethynyl)-5-fluoro-2-methoxyphenyl)-2-oxo-N-2-pyrimidinyl-1,2-dihydro-6-quinolinesulfonamide | 519.0 | 192 | 0.026 | | 1H NMR (400 MHz, DMSO-d6) δ ppm 11.82 (br. s, 1 H) 8.46-8.53 (m, 3 H) 8.25 (d, J = 9.64 Hz, 1 H) 7.95 (dd, J = 8.91, 2.18 Hz, 1 H) 7.44 (d, J = 9.23 Hz, 1 H) 7.32 (d, J = 6.43 Hz, 1 H) 7.04-7.12 (m, 1 H) 6.78 (d, J = 9.52 Hz, 2 H) 3.66 (s, 3 H) 2.94-3.01 (m, 1 H) 1.98-2.07 (m, 2 H) 1.58-1.79 (m, 6 H) |
| 1135 | 1-(4-(cyclopentylethynyl)-5-fluoro-2-methoxyphenyl)-N-(5-fluoro-2-pyrimidinyl)-2-oxo-1,2-dihydro-6-quinolinesulfonamide | 537.0 | 192 | 0.114 | | 1H NMR (400 MHz, DMSO-d6) δ ppm 11.97 (br. s, 1 H) 8.62 (s, 2 H) 8.47 (d, J = 2.18 Hz, 1 H) 8.25 (d, J = 9.43 Hz, 1 H) 7.94 (dd, J = 8.97, 2.23 Hz, 1 H) 7.44 (d, J = 9.23 Hz, 1 H) 7.33 (d, J = 6.32 Hz, 1 H) 6.76-6.80 (m, 2 H) 3.66 (s, 3 H) 2.88-3.05 (m, 1 H) 1.95-2.11 (m, 2 H) 1.54-1.84 (m, 6 H) |
| 1136 | 1-(4-(cyclopentylethynyl)-5-fluoro-2-methoxyphenyl)-N-1,3-oxazol-2-yl-2-oxo-1,2-dihydro-6-quinolinesulfonamide | 508.0 | 192 | 0.048 | | 1H NMR (400 MHz, DMSO-d6) δ ppm 12.09 (br. s, 1 H) 8.31 (d, J = 2.18 Hz, 1 H) 8.18 (d, J = 9.54 Hz, 1 H) 7.83 (dd, J = 8.91, 2.18 Hz, 1 H) 7.59 (d, J = 1.66 Hz, 1 H) 7.44 (d, J = 9.23 Hz, 1 H) 7.32 (d, J = 6.43 Hz, 1 H) 7.26 (d, J = 1.55 Hz, 1 H) 6.76 (d, J = 9.54 Hz, 1 H) 6.73 (d, J = 8.91 Hz, 1 H) 3.67 (s, 3 H) 2.95-3.01 (m, 1 H) 1.98-2.08 (m, 2 H) 1.58-1.79 (m, 6 H) |
| 1137 | 1-(3-methoxy-3'-(trifluoromethyl)-4-biphenylyl)-N-(5-methyl-3-pyridazinyl)-2-oxo-1,2-dihydro-6-quinolinesulfonamide | 567.0 | 73 | 0.036 | | 1H NMR (400 MHz, DMSO-d6) δ ppm 14.13 (br. s., 1 H) 8.37 (d, J = 6.34 Hz, 1 H) 8.13-8.29 (m, 4 H) 7.71-7.90 (m, 4 H) 7.62 (d, J = 5.90 Hz, 1 H) 7.53 (dd, J = 6.74 Hz, 1 H) 7.42 (d, J = 6.17 Hz, 1 H) 6.77-6.81 (m, 1 H) 6.73 (d, J = 8.90 Hz, 1 H) 3.81 (s, 3 H) 2.31 (s, 3 H) |
| 645 | 1-(4-(cyclopentylethynyl)-5-fluoro-2- | 519.0 | 192 | 0.008 | | 1H NMR (400 MHz, DMSO-d6) δ ppm 14.46 (br. s., 1 H) 8.25-8.38 (m, 2 H) 8.19 (d, J = 9.64 Hz, 1 H) 7.90-7.97 (m, 1 H) |

TABLE 3-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | methoxyphenyl)-2-oxo-N-3-pyridazinyl-1,2-dihydro-6-quinolinesulfonamide | | | | | 7.82 (dd, J = 8.81, 1.76 Hz, 1 H) 7.69 (dd, J = 9.54, 4.25 Hz, 1 H) 7.43 (d, J = 9.23 Hz, 1 H) 7.32 (d, J = 6.43 Hz, 1 H) 6.70-6.77 (m, 2 H) 3.66 (s, 3 H) 2.95-3.01 (m, 1 H) 1.98-2.08 (m, 2 H) 1.58-1.79 (m, 6 H) |
| 1138 | 1-(3-methoxy-3'-(trifluoromethyl)-4-biphenylyl)-N-(6-methyl-3-pyridazinyl)-2-oxo-1,2-dihydro-6-quinolinesulfonamide | 567.0 | 73 | 0.146 | | 1H NMR (400 MHz, DMSO-d6) δ ppm 14.22 (br. s., 1 H) 8.33 (d, J = 1.97 Hz, 1 H) 8.12-8.21 (m, 3 H) 7.74-7.91 (m, 4 H) 7.58-7.64 (m, 2 H) 7.52 (dd, J = 8.09, 1.87 Hz, 1 H) 7.41 (d, J = 8.03 Hz, 1 H) 6.70-6.80 (m, 2 H) 3.79 (s, 3 H) 2.33 (s, 3 H) |
| 646 | 1-(5-chloro-6-(cyclopentylethynyl)-2-methoxy-3-pyridinyl)-2-oxo-N-3-pyridazinyl-1,2-dihydro-6-quinolinesulfonamide | 536.0 | 193 | 1.1 | | |
| 647 | 1-(5-fluoro-2-methoxy-4-(3-methoxy-3-methyl-1-butyn-1-yl)phenyl)-N-3-isoxazolyl-2-oxo-1,2-dihydro-6-quinolinesulfonamide | 512.0 | 194 | 0.373 | | 1H NMR (400 MHz, DMSO-d6) δ ppm 11.66 (br. s, 1 H) 8.74 (d, J = 1.81 Hz, 1 H) 8.37 (d, J = 2.13 Hz, 1 H) 8.23 (d, J = 9.69 Hz, 1 H) 7.83 (dd, J = 8.97, 2.23 Hz, 1 H) 7.52 (d, J = 9.17 Hz, 1 H) 7.40 (d, J = 6.27 Hz, 1 H) 6.85 (d, J = 8.97 Hz, 1 H) 6.80 (d, J = 9.64 Hz, 1 H) 6.46 (d, J = 1.76 Hz, 1 H) 3.69 (s, 3 H) 3.37 (s, 3 H) 1.54 (s, 6 H) |
| 1139 | 1-(5-fluoro-4-(3-hydroxy-3-methyl-1-butyn-1-yl)-2-methoxyphenyl)-N-3-isoxazolyl-2-oxo-1,2-dihydro-6-quinolinesulfonamide | 498.0 | 190 | 7.377 | | |
| 648 | 1-(5-chloro-6-(cyclopentylamino)-2-methoxy-3-pyridinyl)-N-3-isoxazolyl-2-oxo-1,2-dihydro-6-quinolinesulfonamide | 516.0 | 195 | 0.984 | | 1H NMR (400 MHz, DMSO-d6) δ ppm 11.66 (br. s, 1 H) 8.72 (d, J = 1.71 Hz, 1 H) 8.32-8.35 (m, 1 H) 8.18 (d, J = 9.59 Hz, 1 H) 7.86 (dd, J = 8.97, 2.23 Hz, 1 H) 7.66 (s, 1 H) 7.00 (d, J = 9.02 Hz, 1 H) 6.77 (d, J = 9.64 Hz, 1 H) 6.46 (d, J = 6.79 Hz, 1 H) 5.57 (br. s., 1 H) 4.30-4.37 (m, 1 H) 3.72 (s, 3 H) 1.99-2.03 (m, 2 H) 1.47-1.85 (m, 6 H) |
| 699 | 1-(2'-chloro-2-fluoro-4',5-dimethoxy-4-biphenylyl)-N-3-isoxazolyl-2-oxo-1,2-dihydro-6-quinolinesulfonamide | 556.1 | 139 | 0.037 | | $^{1}$H NMR (400 MHz, DMSO-d$_{6}$) δ ppm 3.69 (s, 3 H) 3.86 (s, 3 H) 6.46 (s, 1 H) 6.83 (dd, J = 9.23, 1.87 Hz, 2 H) 7.10 (d, J = 7.97 Hz, 1 H) 7.22-7.27 (m, 2 H) 7.49 (d, J = 9.23 Hz, 2 H) 7.90 (dd, J = 8.91, 2.18 Hz, 1 H) 8.24 (d, J = 9.64 Hz, 1 H) 8.39 (d, J = 2.18 Hz, 1 H) 8.74 (d, J = 4.97 Hz, 1 H) 11.68 (s, 1 H). |
| 700 | 1-(4'-chloro-2-fluoro-3',5-dimethoxy-4-biphenylyl)-N-3-isoxazolyl-2-oxo-1,2-dihydro-6-quinolinesulfonamide | 556.1 | 139 | 0.005 | | $^{1}$H NMR (400 MHz, DMSO-d$_{6}$) δ ppm 3.75 (s, 3 H) 3.97 (s, 3 H) 6.46 (s, 1 H) 6.83 (d, J = 9.64 Hz, 1 H) 6.89 (d, J = 9.02 Hz, 1 H) 7.28 (d, J = 7.75 Hz, 1 H) 7.41 (d, J = 9.73 Hz, 1 H) 7.43 (d, J = 6.38 Hz, 1 H) 7.53 (d, J = 10.37 Hz, 1 H) 7.60 (d, J = 8.19 Hz, 1 H) 7.87 (dd, J = 8.91, 2.28 Hz, 1 H) 8.24 (d, J = 9.64 Hz, 1 H) 8.39 (d, J = 2.18 Hz, 1 H) 8.74 (d, J = 1.76 Hz, 1 H) 11.67 (s, 1 H). |
| 701 | 1-(2-fluoro-5-methoxy-4-biphenylyl)-N-3-isoxazolyl-2-oxo-1,2-dihydro-6-quinolinesulfonamide | 492.2 | 139 | 0.104 | | $^{1}$H NMR (400 MHz, DMSO-d$_{6}$) δ ppm 3.74 (s, 3 H) 6.46 (d, J = 1.76 Hz, 1 H) 6.83 (d, J = 9.64 Hz, 1 H) 6.90 (d, J = 8.91 Hz, 1 H) 7.39 (d, J = 6.95 Hz, 1 H) 7.46-7.61 (m, 4 H) 7.70 (d, J = 6.97 Hz, 1 H) 7.72 (d, J = 6.97 Hz, 1 H) 7.88 (dd, J = 8.91, 2.18 Hz, 1 H) 8.24 (d, J = 9.74 Hz, 1 H) 8.39 (d, J = 2.18 Hz, 1 H) 8.74 (s, 1 H) 11.67 (s, 1 H). |
| 702 | 1-(2,2'-difluoro-4',5-dimethoxy-4-biphenylyl)-N-3-isoxazolyl-2-oxo-1,2-dihydro-6-quinolinesulfonamide | 540.2 | 139 | 0.022 | | $^{1}$H NMR (400 MHz, DMSO-d$_{6}$) δ ppm 3.72 (s, 3 H) 3.84 (s, 3 H) 6.46 (s, 1 H) 6.83 (d, J = 9.64 Hz, 1 H) 6.87 (d, J = 9.02 Hz, 1 H) 7.05-7.12 (m, 1 H) 7.15 (dd, J = 5.86, 3.16 Hz, 1 H) 7.32 (t, J = 9.23 Hz, 1 H) 7.38 (d, J = 6.43 Hz, 1 H) 7.53 (d, J = 9.54 Hz, 1 H) 7.89 (dd, J = 9.02, 2.18 Hz, 1 H) 8.25 (d, J = 9.74 Hz, 1 H) 8.39 (d, J = 2.07 Hz, 1 H) 8.74 (s, 1 H) 11.68 (s, 1 H). |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 703 | 1-(3'-chloro-2,2'-difluoro-5-methoxy-4-biphenylyl)-N-3-isoxazolyl-2-oxo-1,2-dihydro-6-quinolinesulfonamide | 544.0 | 139 | 0.005 | | $^1$H NMR (400 MHz, DMSO-d$_6$) δ ppm 3.72 (s, 3 H) 6.46 (d, J = 5.40 Hz, 1 H) 6.83 (d, J = 9.64 Hz, 1 H) 6.88 (d, J = 8.91 Hz, 1 H) 7.37-7.48 (m, 2 H) 7.56-7.68 (m, 2 H) 7.76 (t, J = 7.07 Hz, 1 H) 7.89 (dd, J = 8.91, 2.28 Hz, 1 H) 8.25 (d, J = 9.64 Hz, 1 H) 8.40 (d, J = 10.50 Hz, 1 H) 8.74 (s, 1 H) 11.68 (s, 1 H). |
| 593 | 1-(3'-chloro-2-fluoro-4',5-dimethoxy-4-biphenylyl)-N-3-isoxazolyl-2-oxo-1,2-dihydro-6-quinolinesulfonamide | 556.1 | 145 | 0.025 | | $^1$H NMR (400 MHz, DMSO-d$_6$) δ ppm 3.75 (s, 3 H) 3.95 (s, 3 H) 6.46 (s, 1 H) 6.82 (d, J = 9.64 Hz, 1 H) 6.88 (d, J = 9.02 Hz, 1 H) 7.33 (d, J = 8.81 Hz, 1 H) 7.40 (d, J = 7.05 Hz, 1 H) 7.50 (d, J = 10.47 Hz, 1 H) 7.61-7.73 (m, 1 H) 7.79 (s, 1 H) 7.87 (dd, J = 8.97, 2.23 Hz, 1 H) 8.24 (d, J = 9.64 Hz, 1 H) 8.39 (d, J = 2.18 Hz, 1 H) 8.75 (s, 1 H) 11.68 (s, 1 H). |
| 704 | 1-(2-fluoro-5-methoxy-3',4'-dimethyl-4-biphenylyl)-N-3-isoxazolyl-2-oxo-1,2-dihydro-6-quinolinesulfonamide | 520.3 | 139 | 0.016 | | $^1$H NMR (400 MHz, DMSO-d$_6$) δ ppm 2.31 (s, 3 H) 2.33 (s, 3 H) 3.73 (s, 3 H) 6.46 (s, 1 H) 6.82 (d, J = 9.64 Hz, 1 H) 6.89 (d, J = 8.91 Hz, 1 H) 7.32 (dd, J = 13.22, 7.52 Hz, 2 H) 7.41 (d, J = 7.77 Hz, 1 H) 7.44-7.50 (m, 2 H) 7.87 (dd, J = 9.07, 2.23 Hz, 1 H) 8.24 (d, J = 9.54 Hz, 1 H) 8.38 (d, J = 2.28 Hz, 1 H) 8.74 (s, 1 H) 11.68 (s, 1 H). |
| 705 | 1-(2,3'-difluoro-4',5-dimethoxy-4-biphenylyl)-N-3-isoxazolyl-2-oxo-1,2-dihydro-6-quinolinesulfonamide | 540.2 | 145 | 0.041 | | $^1$H NMR (400 MHz, DMSO-d$_6$) δ ppm 3.74 (s, 3 H) 3.93 (s, 3 H) 6.46 (d, J = 2.04 Hz, 1 H) 6.82 (d, J = 9.64 Hz, 1 H) 6.88 (d, J = 9.02 Hz, 1 H) 7.34 (d, J = 8.92 Hz, 1 H) 7.39 (d, J = 9.60 Hz, 1 H) 7.48-7.55 (m, 2 H) 7.61 (d, J = 12.41 Hz, 1 H) 7.87 (dd, J = 8.97, 2.23 Hz, 1 H) 8.24 (d, J = 9.54 Hz, 1 H) 8.39 (d, J = 2.18 Hz, 1 H) 8.74 (s, 1 H) 11.68 (s, 1 H). |
| 706 | 1-(2-fluoro-5-methoxy-3',5'-dimethyl-4-biphenylyl)-N-3-isoxazolyl-2-oxo-1,2-dihydro-6-quinolinesulfonamide | 520.3 | 139 | 0.014 | | $^1$H NMR (400 MHz, DMSO-d$_6$) δ ppm 2.38 (s, 6 H) 3.73 (s, 3 H) 6.46 (s, 1 H) 6.82 (d, J = 9.54 Hz, 1 H) 6.88 (d, J = 9.02 Hz, 1 H) 7.11 (s, 1 H) 7.29 (s, 2 H) 7.34 (d, J = 6.95 Hz, 1 H) 7.48 (d, J = 10.26 Hz, 1 H) 7.88 (dd, J = 6.72 Hz, 1 H) 8.24 (d, J = 9.64 Hz, 1 H) 8.39 (d, J = 2.18 Hz, 1 H) 8.75 (d, J = 4.34 Hz, 1 H) 11.68 (s, 1 H). |
| 707 | 1-(5'-chloro-2,2'-difluoro-5-methoxy-4-biphenylyl)-N-3-isoxazolyl-2-oxo-1,2-dihydro-6-quinolinesulfonamide | 544.0 | 145 | 0.012 | | $^1$H NMR (400 MHz, DMSO-d$_6$) δ ppm 3.73 (s, 3 H) 6.46 (s, 1 H) 6.85 (t, J = 9.43 Hz, 2 H) 7.42-7.52 (m, 2 H) 7.57 (d, J = 9.64 Hz, 1 H) 7.64 (ddd, J = 8.84, 4.33, 2.70 Hz, 1 H) 7.75 (dd, J = 6.27, 2.75 Hz, 1 H) 7.88 (dd, J = 8.97, 2.23 Hz, 1 H) 8.25 (d, J = 9.64 Hz, 1 H) 8.40 (d, J = 2.18 Hz, 1 H) 8.75 (s, 1 H) 11.69 (s, 1 H). |
| 708 | 1-(2-fluoro-3',5-dimethoxy-5'-methyl-4-biphenylyl)-N-3-isoxazolyl-2-oxo-1,2-dihydro-6-quinolinesulfonamide | 536.3 | 139 | 0.01 | | $^1$H NMR (400 MHz, DMSO-d$_6$) δ ppm 3.73 (s, 3 H) 3.82 (s, 3 H) 6.46 (s, 1 H) 6.82 (d, J = 9.64 Hz, 1 H) 6.86-6.92 (m, 2 H) 7.02 (s, 1 H) 7.07 (s, 1 H) 7.36 (d, J = 6.95 Hz, 1 H) 7.49 (d, J = 10.37 Hz, 1 H) 7.87 (dd, J = 8.97, 2.23 Hz, 1 H) 8.24 (d, J = 9.64 Hz, 1 H) 8.39 (d, J = 2.07 Hz, 1 H) 8.75 (d, J = 1.76 Hz, 1 H) 11.69 (s, 1 H). |
| 709 | 1-(2-fluoro-3',5-dimethoxy-4-biphenylyl)-N-3-isoxazolyl-2-oxo-1,2-dihydro-6-quinolinesulfonamide | 522.0 | 139 | 0.047 | | $^1$H NMR (400 MHz, DMSO-d$_6$) δ ppm 3.74 (s, 3 H) 3.85 (s, 3 H) 6.46 (d, J = 2.07 Hz, 1 H) 6.83 (d, J = 9.64 Hz, 1 H) 6.90 (d, J = 8.91 Hz, 1 H) 7.05 (d, J = 8.40 Hz, 1 H) 7.23 (d, J = 9.58 Hz, 1 H) 7.26 (d, J = 8.52 Hz, 1 H) 7.39 (d, J = 6.84 Hz, 1 H) 7.46 (d, J = 7.98 Hz, 1 H) 7.50 (d, J = 10.37 Hz, 1 H) 7.88 (dd, J = 8.97, 2.23 Hz, 1 H) 8.24 (d, J = 9.64 Hz, 1 H) 8.39 (d, J = 2.18 Hz, 1 H) 8.75 (s, 1 H) 11.67 (s, 1 H). |
| 710 | 1-(2,3'-difluoro-5,5'-dimethoxy-4-biphenylyl)-N-3-isoxazolyl-2-oxo-1,2-dihydro-6-quinolinesulfonamide | 540.0 | 139 | 0.014 | | $^1$H NMR (400 MHz, DMSO-d$_6$) δ ppm 3.75 (s, 3 H) 3.87 (s, 3 H) 6.46 (d, J = 1.96 Hz, 1 H) 6.83 (d, J = 9.64 Hz, 1 H) 6.88 (d, J = 9.02 Hz, 1 H) 6.94-7.00 (m, 1 H) 7.11 (d, J = 9.52 Hz, 1 H) 7.11-7.15 (m, 1 H) 7.42 (d, J = 6.84 Hz, 1 H) 7.53 (d, J = 10.47 Hz, 1 H) 7.87 (d, J = 9.02 Hz, 1 H) 8.24 (d, J = 9.54 Hz, 1 H) 8.39 (d, J = 2.18 Hz, 1 H) 8.75 (d, J = 2.08 Hz, 1 H) 11.67 (s, 1 H). |
| 594 | 1-(5-fluoro-2-methoxy-4-(2-pyridinyl)phenyl)-N-3-isoxazolyl-2-oxo-1,2-dihydro-6- | 493.1 | 146 | 1.658 | | $^1$H NMR (400 MHz, DMSO-d$_6$) δ ppm 3.74 (s, 3 H) 6.46 (s, 1 H) 6.83 (d, J = 9.64 Hz, 1 H) 6.91 (d, J = 9.02 Hz, 1 H) 7.50 (ddd, J = 7.44, 4.79, 1.24 Hz, 1 H) 7.57 (d, J = 10.88 Hz, 1 H) 7.78 (d, J = 6.95 Hz, 1 H) 7.87 (dd, J = 8.97, 2.12 Hz, 1 H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | quinolinesulfonamide | | | | | 7.90-7.96 (m, 1 H) 7.97-8.04 (m, 1 H) 8.25 (d, J = 9.64 Hz, 1 H) 8.39 (d, J = 2.18 Hz, 1 H) 8.74 (s, 1 H) 8.81 (d, J = 4.90 Hz, 1 H) 11.67 (s, 1 H). |
| 711 | 1-(2,3'-difluoro-5-methoxy-5'-(trifluoromethyl)-4-biphenylyl)-N-3-isoxazolyl-2-oxo-1,2-dihydro-6-quinolinesulfonamide | 578.2 | 139 | 0.009 | | $^1$H NMR (400 MHz, DMSO-d$_6$) δ ppm 3.77 (s, 3 H) 6.46 (s, 1 H) 6.83 (d, J = 9.64 Hz, 1 H) 6.88 (d, J = 9.02 Hz, 1 H) 7.53 (d, J = 6.95 Hz, 1 H) 7.60 (d, J = 10.47 Hz, 1 H) 7.83-7.88 (m, 2 H) 7.94-7.99 (m, 2 H) 8.25 (d, J = 9.64 Hz, 1 H) 8.39 (d, J = 2.28 Hz, 1 H) 8.74 (d, J = 1.87 Hz, 1 H) 11.67 (s, 1 H). |
| 712 | 1-(3'-chloro-2-fluoro-5-methoxy-2'-methyl-4-biphenylyl)-N-3-isoxazolyl-2-oxo-1,2-dihydro-6-quinolinesulfonamide | 540.0 | 139 | 0.006 | | $^1$H NMR (400 MHz, DMSO-d$_6$) δ ppm 3.69 (s, 3 H) 6.45 (d, J = 1.76 Hz, 1 H) 6.83 (d, J = 9.64 Hz, 1 H) 6.90 (d, J = 8.71 Hz, 1 H) 7.26 (d, J = 6.63 Hz, 1 H) 7.35-7.42 (m, 2 H) 7.52 (d, J = 9.43 Hz, 1 H) 7.55-7.60 (m, 1 H) 7.88 (dd, J = 8.91, 2.18 Hz, 1 H) 8.24 (d, J = 9.54 Hz, 1 H) 8.38 (d, J = 2.18 Hz, 1 H) 8.72 (d, J = 1.66 Hz, 1 H) 11.68 (br. s., 1 H). |
| 713 | 1-(2,4'-difluoro-3',5-dimethoxy-4-biphenylyl)-N-3-isoxazolyl-2-oxo-1,2-dihydro-6-quinolinesulfonamide | 540.0 | 139 | 0.015 | | $^1$H NMR (400 MHz, DMSO-d$_6$) δ ppm 3.75 (s, 3 H) 3.95 (s, 3 H) 6.46 (d, J = 1.76 Hz, 1 H) 6.83 (d, J = 9.74 Hz, 1 H) 6.89 (d, J = 8.91 Hz, 1 H) 7.21-7.30 (m, 1 H) 7.35-7.48 (m, 3 H) 7.52 (d, J = 10.37 Hz, 1 H) 7.85-7.91 (m, 1H) 8.24 (d, J = 9.64 Hz, 1 H) 8.39 (d, J = 2.18 Hz, 1 H) 8.75 (d, J = 1.76 Hz, 1 H) 11.67 (s, 1 H). |
| 714 | 1-(2-fluoro-2',5-dimethoxy-5'-methyl-4-biphenylyl)-N-3-isoxazolyl-2-oxo-1,2-dihydro-6-quinolinesulfonamide | 536.2 | 139 | 0.048 | | $^1$H NMR (400 MHz, DMSO-d$_6$) δ ppm 2.33 (s, 3 H) 3.68 (s, 3 H) 3.79 (s, 3 H) 6.45 (s, 1 H) 6.83 (dd, J = 9.33, 5.91 Hz, 2 H) 7.07 (d, J = 8.40 Hz, 1 H) 7.17-7.29 (m, 3 H) 7.39 (d, J = 9.54 Hz, 1 H) 7.89 (dd, J = 9.02, 2.18 Hz, 1 H) 8.24 (d, J = 9.64 Hz, 1 H) 8.38 (d, J = 2.18 Hz, 1 H) 8.73 (d, J = 1.76 Hz, 1 H) 11.67 (s, 1 H). |
| 715 | 1-(5-fluoro-2-methoxy-4-(2-methoxy-5-methyl-3-pyridinyl)phenyl)-N-3-isoxazolyl-2-oxo-1,2-dihydro-6-quinolinesulfonamide | 537.2 | 139 | 0.151 | | $^1$H NMR (400 MHz, DMSO-d$_6$) δ ppm 2.32 (s, 3 H) 3.69 (s, 3 H) 3.89 (s, 3 H) 6.46 (d, J = 1.76 Hz, 1 H) 6.84 (dd, J = 9.23, 5.49 Hz, 2 H) 7.32 (d, J = 6.43 Hz, 1 H) 7.45 (d, J = 9.54 Hz, 1 H) 7.69 (d, J = 2.28 Hz, 1 H) 7.90 (dd, J = 8.97, 2.23 Hz, 1 H) 8.11 (d, J = 1.56 Hz, 1 H) 8.24 (d, J = 9.74 Hz, 1 H) 8.39 (d, J = 2.07 Hz, 1 H) 8.74 (d, J = 1.76 Hz, 1 H) 11.67 (s, 1 H). |
| 716 | 1-(2'-chloro-2-fluoro-5-methoxy-5'-methyl-4-biphenylyl)-N-3-isoxazolyl-2-oxo-1,2-dihydro-6-quinolinesulfonamide | 540.0 | 139 | 0.006 | | $^1$H NMR (400 MHz, DMSO-d$_6$) δ ppm 2.39 (s, 3 H) 3.69 (s, 3 H) 6.47 (s, 1 H) 6.82 (s, 1 H) 6.85 (s, 1 H) 7.28 (d, J = 6.43 Hz, 1 H) 7.31-7.36 (m, 1 H) 7.37-7.42 (m, 1 H) 7.51 (dd, J = 8.76, 6.38 Hz, 2 H) 7.90 (dd, J = 8.97, 2.23 Hz, 1 H) 8.25 (d, J = 9.64 Hz, 1 H) 8.40 (d, J = 2.18 Hz, 1 H) 11.68 (s, 1 H). |
| 717 | 1-(5'-cyano-2-fluoro-5-methoxy-2'-methyl-4-biphenylyl)-N-3-isoxazolyl-2-oxo-1,2-dihydro-6-quinolinesulfonamide | 531.0 | 139 | 0.019 | | $^1$H NMR (400 MHz, DMSO-d$_6$) δ ppm 2.36 (s, 3 H) 3.70 (s, 3 H) 6.46 (s, 1 H) 6.84 (d, J = 9.64 Hz, 1 H) 6.88 (d, J = 8.81 Hz, 1 H) 7.31 (d, J = 6.41 Hz, 1 H) 7.54 (d, J = 9.23 Hz, 1 H) 7.62 (d, J = 7.98 Hz, 1 H) 7.84-7.91 (m, 3 H) 8.25 (d, J = 9.74 Hz, 1 H) 8.39 (d, J = 2.18 Hz, 1 H) 8.74 (d, J = 5.32 Hz, 1 H) 11.68 (s, 1 H). |
| 718 | 1-(5'-cyano-2-fluoro-2',5-dimethoxy-4-biphenylyl)-N-3-isoxazolyl-2-oxo-1,2-dihydro-6-quinolinesulfonamide | 547.1 | 139 | 0.153 | | $^1$H NMR (400 MHz, DMSO-d$_6$) δ ppm 3.69 (s, 3 H) 3.93 (s, 3 H) 6.46 (d, J = 1.55 Hz, 1 H) 6.83 (d, J = 9.43 Hz, 2 H) 7.33 (d, J = 6.43 Hz, 1 H) 7.38 (d, J = 8.81 Hz, 1 H) 7.46 (d, J = 9.43 Hz, 1 H) 7.85-7.93 (m, 2 H) 7.98 (dd, J = 8.55, 2.13 Hz, 1 H) 8.24 (d, J = 9.64 Hz, 1 H) 8.39 (d, J = 1.97 Hz, 1 H) 8.74 (d, J = 1.55 Hz, 1 H) 11.68 (s, 1 H). |
| 719 | 1-(2,2'-difluoro-5-methoxy-3'-methyl-4-biphenylyl)-N-3-isoxazolyl-2-oxo-1,2-dihydro-6-quinolinesulfonamide | 524.2 | 139 | 0.049 | | $^1$H NMR (400 MHz, DMSO-d$_6$) δ ppm 2.35 (d, J = 1.76 Hz, 3 H) 3.71 (s, 3 H) 6.46 (d, J = 1.76 Hz, 1 H) 6.83 (d, J = 9.64 Hz, 1 H) 6.87 (d, J = 9.02 Hz, 1 H) 7.24-7.31 (m, 1 H) 7.34 (d, J = 6.43 Hz, 1 H) 7.43 (t, J = 7.00 Hz, 2 H) 7.53 (d, J = 9.54 Hz, 1 H) 7.90 (dd, J = 8.97, 2.23 Hz, 1 H) 8.25 (d, J = 9.54 Hz, 1 H) 8.39 (d, J = 2.18 Hz, 1 H) 8.74 (d, J = 1.87 Hz, 1 H) 11.68 (s, 1 H). |
| 720 | 1-(4'-cyano-2-fluoro-3',5-dimethoxy-4-biphenylyl)-N-3- | 547.1 | 139 | 0.054 | | $^1$H NMR (400 MHz, DMSO-d$_6$) δ ppm 3.71-3.82 (m, 3 H) 4.00-4.07 (m, 3 H) 6.46 (s, 1 H) 6.83 (dd, J = 9.64, 1.97 Hz, 1 H) 6.89 (d, J = 9.02 Hz, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | isoxazolyl-2-oxo-1,2-dihydro-6-quinolinesulfonamide | | | | | 1 H) 7.42 (d, J = 7.77 Hz, 1 H) 7.46-7.53 (m, 2 H) 7.59 (dd, J = 10.31, 1.92 Hz, 1 H) 7.84-7.94 (m, 2 H) 8.25 (d, J = 9.59 Hz, 1 H) 8.40 (s, 1 H) 8.74 (s, 1 H) 11.67 (s, 1 H). |
| 595 | 1-(3'-cyano-2-fluoro-4',5-dimethoxy-4-biphenylyl)-N-3-isoxazolyl-2-oxo-1,2-dihydro-6-quinolinesulfonamide | 547.2 | 147 | 0.353 | | $^1$H NMR (400 MHz, DMSO-d$_6$) δ ppm 3.75 (s, 3 H) 4.01 (s, 3 H) 6.46 (d, J = 1.87 Hz, 1 H) 6.82 (d, J = 9.64 Hz, 1 H) 6.88 (d, J = 8.91 Hz, 1 H) 7.41-7.48 (m, 2 H) 7.53 (d, J = 10.57 Hz, 1 H) 7.87 (dd, J = 8.97, 2.23 Hz, 1 H) 8.02 (dd, J = 8.81, 1.87 Hz, 1 H) 8.12 (d, J = 1.76 Hz, 1 H) 8.24 (d, J = 9.74 Hz, 1 H) 8.39 (d, J = 2.18 Hz, 1 H) 8.74 (d, J = 1.76 Hz, 1 H) 11.67 (s, 1 H). |
| 721 | 1-(5-fluoro-2-methoxy-4-(5-(trifluoromethyl)-3-pyridinyl)phenyl)-N-3-isoxazolyl-2-oxo-1,2-dihydro-6-quinolinesulfonamide | 561.2 | 139 | 0.032 | | $^1$H NMR (400 MHz, DMSO-d$_6$) ε ppm 3.78 (s, 3 H) 6.47 (d, J = 1.76 Hz, 1 H) 6.84 (d, J = 9.64 Hz, 1 H) 6.89 (d, J = 9.02 Hz, 1 H) 7.60-7.66 (m, 2 H) 7.87 (dd, J = 8.97, 2.23 Hz, 1 H) 8.25 (d, J = 9.54 Hz, 1 H) 8.40 (d, J = 2.18 Hz, 1 H) 8.54 (s, 1 H) 8.75 (d, J = 1.87 Hz, 1 H) 9.10 (d, J = 1.24 Hz, 1 H) 9.23 (s, 1 H) 11.67 (s, 1 H). |
| 722 | 1-(5-fluoro-4-(6-fluoro-5-methyl-3-pyridinyl)-2-methoxyphenyl)-N-3-isoxazolyl-2-oxo-1,2-dihydro-6-quinolinesulfonamide | 525.0 | 139 | 0.178 | | $^1$H NMR (400 MHz, DMSO-d$_6$) δ ppm 2.37 (s, 3 H) 3.75 (s, 3 H) 6.46 (d, J = 1.76 Hz, 1 H) 6.83 (d, J = 9.64 Hz, 1 H) 6.88 (d, J = 9.02 Hz, 1 H) 7.48 (d, J = 6.95 Hz, 1 H) 7.56 (s, 1 H) 7.59 (s, 1 H) 7.87 (dd, J = 8.97, 2.23 Hz, 1 H) 8.20 (d, J = 9.54 Hz, 1 H) 8.25 (d, J = 9.54 Hz, 1 H) 8.39 (d, J = 2.07 Hz, 2 H) 8.75 (d, J = 1.87 Hz, 1 H) 11.67 (s, 1 H). |
| 723 | 1-(3''-chloro-2-fluoro-5,5''-trimethoxy-1,1':3',1''-terphenyl-4-yl)-N-3-isoxazolyl-2-oxo-1,2-dihydro-6-quinolinesulfonamide | 662.2 | 145 | 0.007 | | $^1$H NMR (400 MHz, DMSO-d$_6$) δ ppm 3.76 (s, 3 H) 3.88 (s, 3 H) 3.93 (s, 3 H) 6.47 (s, 1 H) 6.83 (d, J = 9.64 Hz, 1 H) 6.90 (d, J = 9.02 Hz, 1 H) 7.08 (s, 1 H) 7.24-7.36 (m, 3 H) 7.43 (t, J = 1.61 Hz, 1 H) 7.46-7.56 (m, 3 H) 7.88 (dd, J = 8.91, 2.18 Hz, 1 H) 8.25 (d, J = 9.64 Hz, 1 H) 8.39 (d, J = 2.18 Hz, 1 H) 8.75 (d, J = 6.17 Hz, 1 H) 11.67 (s, 1 H). |
| 596 | 1-(3'-(difluoromethyl)-2-fluoro-5-methoxy-4-biphenylyl)-N-3-isoxazolyl-2-oxo-1,2-dihydro-6-quinolinesulfonamide | 542.2 | 148 | 0.035 | | $^1$H NMR (400 MHz, DMSO-d$_6$) δ ppm 3.75 (s, 3 H) 6.46 (s, 1 H) 6.83 (d, J = 9.64 Hz, 1 H) 6.90 (d, J = 9.02 Hz, 1 H) 6.99-7.31 (m, 1 H) 7.44 (d, J = 6.95 Hz, 1 H) 7.55 (d, J = 10.37 Hz, 1 H) 7.65-7.77 (m, 2 H) 7.85-7.93 (m, 3 H) 8.24 (d, J = 9.74 Hz, 1 H) 8.39 (d, J = 2.18 Hz, 1 H) 8.74 (d, J = 4.91 Hz, 1 H) 11.67 (s, 1 H). |
| 597 | 1-(2,3'-difluoro-5-methoxy-5'-methyl-4-biphenylyl)-N-3-isoxazolyl-2-oxo-1,2-dihydro-6-quinolinesulfonamide | 524.2 | 149 | 0.008 | | $^1$H NMR (400 MHz, DMSO-d$_6$) δ ppm 2.44 (s, 3 H) 3.75 (s, 3 H) 6.46 (d, J = 1.76 Hz, 1 H) 6.82 (d, J = 9.64 Hz, 1 H) 6.88 (d, J = 8.91 Hz, 1 H) 7.14-7.21 (m, 1 H) 7.32-7.43 (m, 3 H) 7.53 (d, J = 10.37 Hz, 1 H) 7.87 (dd, J = 8.97, 2.23 Hz, 1 H) 8.24 (d, J = 9.64 Hz, 1 H) 8.39 (d, J = 2.28 Hz, 1 H) 8.74 (d, J = 1.76 Hz, 1 H) 11.67 (s, 1 H). |
| 724 | 1-(2-fluoro-5,5'-dimethoxy-2'-methyl-4-biphenylyl)-N-3-isoxazolyl-2-oxo-1,2-dihydro-6-quinolinesulfonamide | 536.0 | 148 | 0.017 | | $^1$H NMR (400 MHz, DMSO-d$_6$) δ ppm 2.19 (s, 3 H) 3.69 (s, 3 H) 3.80 (s, 3 H) 6.46 (s, 1 H) 6.83 (d, J = 9.64 Hz, 1 H) 6.89 (d, J = 9.02 Hz, 1 H) 6.92-7.00 (m, 2 H) 7.21 (d, J = 6.63 Hz, 1 H) 7.29 (d, J = 8.60 Hz, 1 H) 7.47 (d, J = 9.54 Hz, 1 H) 7.89 (dd, J = 8.91, 2.18 Hz, 1 H) 8.24 (d, J = 9.64 Hz, 1 H) 8.39 (d, J = 2.07 Hz, 1 H) 8.74 (d, J = 1.76 Hz, 1 H) 11.68 (s, 1 H). |
| 725 | 1-(2'-chloro-2-fluoro-5-methoxy-4'-methyl-4-biphenylyl)-N-3-isoxazolyl-2-oxo-1,2-dihydro-6-quinolinesulfonamide | 540.2 | 139 | 0.012 | | $^1$H NMR (400 MHz, DMSO-d$_6$) δ ppm 2.40 (s, 3 H) 3.68 (s, 3 H) 6.46 (s, 1 H) 6.84 (dd, J = 9.33, 1.87 Hz, 2 H) 7.26 (d, J = 6.63 Hz, 1 H) 7.33 (d, J = 7.36 Hz, 1 H) 7.45 (d, J = 7.88 Hz, 1 H) 7.48-7.54 (m, 2 H) 7.90 (dd, J = 9.02, 2.28 Hz, 1 H) 8.25 (d, J = 9.64 Hz, 1 H) 8.39 (d, J = 2.18 Hz, 1 H) 8.74 (s, 1 H) 11.68 (s, 1 H). |
| 726 | 1-(2'-chloro-2-fluoro-5,5'-dimethoxy-4-biphenylyl)-N-3-isoxazolyl-2-oxo-1,2-dihydro-6-quinolinesulfonamide | 556.0 | 149 | 0.019 | | $^1$H NMR (400 MHz, DMSO-d$_6$) δ ppm 3.70 (s, 3 H) 3.84 (s, 3 H) 6.45 (d, J = 5.04 Hz, 1 H) 6.83 (d, J = 9.64 Hz, 2 H) 7.09 (d, J = 8.93 Hz, 1 H) 7.13-7.15 (m, 1 H) 7.30 (d, J = 6.53 Hz, 1 H) 7.51 (d, J = 9.43 Hz, 1 H) 7.54 (d, J = 8.81 Hz, 1 H) 7.89 (dd, J = 8.91, 2.07 Hz, 1 H) 8.25 (d, J = 9.54 Hz, 1 H) 8.39 (d, J = 2.07 Hz, 1 H) 8.72 (d, J = 1.66 Hz, 1 H) 11.68 (s, 1 H). |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 727 | 1-(3'-ethoxy-2-fluoro-5-methoxy-4-biphenylyl)-N-3-isoxazolyl-2-oxo-1,2-dihydro-6-quinolinesulfonamide | 536.0 | 139 | 0.025 | | $^1$H NMR (400 MHz, DMSO-d$_6$) δ ppm 1.33-1.43 (m, 3 H) 3.74 (s, 3 H) 4.13 (q, J = 6.81 Hz, 2 H) 6.44-6.47 (m, 1 H) 6.82 (dd, J = 9.64, 1.66 Hz, 1 H) 6.89 (d, J = 8.71 Hz, 1 H) 7.04 (d, J = 8.09 Hz, 1 H) 7.20-7.27 (m, 2 H) 7.37-7.52 (m, 3 H) 7.87 (d, J = 9.12 Hz, 1 H) 8.24 (d, J = 9.64 Hz, 1 H) 8.38 (s, 1 H) 8.73 (s, 1 H) 11.67 (s, 1 H). |
| 728 | 1-(2-fluoro-5-methoxy-3'-(trifluoromethoxy)-4-biphenylyl)-N-3-isoxazolyl-2-oxo-1,2-dihydro-6-quinolinesulfonamide | 576.0 | 139 | 0.008 | | $^1$H NMR (400 MHz, DMSO-d$_6$) δ ppm 3.76 (s, 3 H) 6.46 (d, J = 1.76 Hz, 1 H) 6.83 (d, J = 9.54 Hz, 1 H) 6.90 (d, J = 8.81 Hz, 1 H) 7.45 (d, J = 6.84 Hz, 1 H) 7.51 (d, J = 7.77 Hz, 1 H) 7.56 (d, J = 10.37 Hz, 1 H) 7.67-7.79 (m, 3 H) 7.87 (dd, J = 8.91, 2.18 Hz, 1 H) 8.25 (d, J = 9.54 Hz, 1 H) 8.39 (d, J = 1.97 Hz, 1 H) 8.75 (d, J = 1.76 Hz, 1 H) 11.67 (s, 1 H). |
| 729 | 1-(5-fluoro-2-methoxy-4-(6-methoxy-3-pyridinyl)phenyl)-N-3-isoxazolyl-2-oxo-1,2-dihydro-6-quinolinesulfonamide | 523.0 | 139 | 0.598 | | $^1$H NMR (400 MHz, DMSO-d$_6$) δ ppm 3.74 (s, 3 H) 3.94 (s, 3 H) 6.46 (d, J = 1.76 Hz, 1 H) 6.82 (d, J = 9.64 Hz, 1 H) 6.89 (d, J = 9.02 Hz, 1 H) 7.01 (d, J = 8.71 Hz, 1 H) 7.44 (d, J = 6.84 Hz, 1 H) 7.53 (d, J = 10.37 Hz, 1 H) 7.87 (dd, J = 8.91, 2.28 Hz, 1 H) 8.06 (d, J = 8.60 Hz, 1 H) 8.24 (d, J = 9.74 Hz, 1 H) 8.38 (d, J = 2.18 Hz, 1 H) 8.53 (s, 1 H) 8.74 (d, J = 1.76 Hz, 1 H) 11.67 (s, 1 H). |
| 730 | 1-(5-fluoro-4-(5-fluoro-3-pyridinyl)-2-methoxyphenyl)-N-3-isoxazolyl-2-oxo-1,2-dihydro-6-quinolinesulfonamide | 511.0 | 139 | 0.795 | | $^1$H NMR (400 MHz, DMSO-d$_6$) δ ppm 3.77 (s, 3 H) 6.46 (d, J = 1.76 Hz, 1 H) 6.83 (d, J = 9.64 Hz, 1 H) 6.89 (d, J = 9.02 Hz, 1 H) 7.56 (d, J = 6.43 Hz, 1 H) 7.62 (d, J = 10.47 Hz, 1 H) 7.78-7.94 (m, 1 H) 8.15 (d, J = 9.74 Hz, 1 H) 8.25 (d, J = 9.64 Hz, 1 H) 8.40 (d, J = 2.07 Hz, 1 H) 8.71 (d, J = 2.49 Hz, 1 H) 8.75 (d, J = 1.97 Hz, 1 H) 8.82 (br. s., 1 H) 11.67 (br. s., 1 H). |
| 731 | 1-(2'-chloro-2-fluoro-3',5-dimethoxy-4-biphenylyl)-N-3-isoxazolyl-2-oxo-1,2-dihydro-6-quinolinesulfonamide | 556.0 | 149 | 0.142 | | $^1$H NMR (400 MHz, DMSO-d$_6$) δ ppm 3.68 (s, 3 H) 3.94 (s, 3 H) 6.46 (s, 1 H) 6.79-6.89 (m, 2 H) 7.13 (dd, J = 7.67, 1.35 Hz, 1 H) 7.23-7.31 (m, 2 H) 7.44-7.54 (m, 2 H) 7.91 (dd, J = 8.91, 1.97 Hz, 1 H) 8.25 (d, J = 9.64 Hz, 1 H) 8.39 (d, J = 2.18 Hz, 1 H) 8.74 (s, 1 H) 11.68 (s, 1 H). |
| 732 | 1-(2,2'-difluoro-5,5'-dimethoxy-4-biphenylyl)-N-3-isoxazolyl-2-oxo-1,2-dihydro-6-quinolinesulfonamide | 540.0 | 139 | 0.056 | | $^1$H NMR (400 MHz, DMSO-d$_6$) δ ppm 3.72 (s, 3 H) 3.84 (s, 3 H) 6.46 (d, J = 4.72 Hz, 1 H) 6.83 (d, J = 9.64 Hz, 1 H) 6.87 (d, J = 9.02 Hz, 1 H) 7.05-7.12 (m, 1 H) 7.15 (dd, J = 5.91, 3.21 Hz, 1 H) 7.32 (t, J = 9.23 Hz, 1 H) 7.38 (d, J = 6.43 Hz, 1 H) 7.53 (d, J = 9.64 Hz, 1 H) 7.89 (dd, J = 8.97, 2.23 Hz, 1 H) 8.25 (m, J = 9.74 Hz, 1 H) 8.39 (d, J = 2.18 Hz, 1 H) 8.74 (d, J = 4.32 Hz, 1 H) 11.68 (s, 1 H). |
| 733 | 1-(4'-chloro-2,2'-difluoro-5-methoxy-4-biphenylyl)-N-3-isoxazolyl-2-oxo-1,2-dihydro-6-quinolinesulfonamide | 544.0 | 139 | 0.02 | | $^1$H NMR (400 MHz, DMSO-d$_6$) δ ppm 3.63 (s, 3 H) 6.16 (s, 1 H) 6.62-6.71 (m, 2 H) 7.29 (d, J = 6.53 Hz, 1 H) 7.38-7.50 (m, 2 H) 7.54-7.67 (m, 2 H) 7.72 (dd, J = 8.81, 2.07 Hz, 1 H) 8.11 (d, J = 9.74 Hz, 1 H) 8.15 (s, 1 H) 8.32 (br. s., 1 H) 11.59 (br. s., 1 H). |
| 676 | 1-(4-(5-chloro-2-methoxy-3-pyridinyl)-5-fluoro-2-methoxyphenyl)-N-3-isoxazolyl-2-oxo-1,2-dihydro-6-quinolinesulfonamide | 557.0 | 139 | 0.024 | | $^1$H NMR (400 MHz, DMSO-d$_6$) δ ppm 3.75 (s, 3 H) 4.04 (s, 3 H) 6.08 (d, J = 1.90 Hz, 1 H) 6.63 (d, J = 8.81 Hz, 1 H) 6.69 (d, J = 9.54 Hz, 1 H) 7.44-7.52 (m, 3 H) 7.72 (d, J = 8.84 Hz, 1 H) 8.09-8.17 (m, 3 H) 8.29 (s, 1 H) 8.50 (t, J = 1.92 Hz, 1 H). |
| 734 | 1-(2,2'-difluoro-3',5-dimethoxy-4-biphenylyl)-N-3-isoxazolyl-2-oxo-1,2-dihydro-6-quinolinesulfonamide | 540.0 | 139 | 0.081 | | $^1$H NMR (400 MHz, DMSO-d$_6$) δ ppm 3.71 (s, 3 H) 3.92 (s, 3 H) 6.46 (d, J = 1.76 Hz, 1 H) 6.83 (d, J = 9.64 Hz, 1 H) 6.88 (d, J = 8.91 Hz, 1 H) 7.10-7.18 (m, 1 H) 7.28-7.39 (m, 3 H) 7.53 (d, J = 9.54 Hz, 1 H) 7.90 (dd, J = 8.97, 2.23 Hz, 1 H) 8.25 (d, J = 9.64 Hz, 1 H) 8.39 (d, J = 2.18 Hz, H) 8.74 (d, J = 1.76 Hz, 1 H) 11.68 (s, 1 H). |
| 735 | 1-(2-fluoro-3',5-dimethoxy-2'-methyl-4-biphenylyl)-N-3-isoxazolyl-2-oxo-1,2-dihydro-6-quinolinesulfonamide | 536.2 | 139 | 0.054 | | $^1$H NMR (400 MHz, DMSO-d$_6$) δ ppm 2.09 (s, 3 H) 3.68 (s, 3 H) 3.87 (s, 3 H) 6.46 (d, J = 4.29 Hz, 1 H) 6.83 (d, J = 9.64 Hz, 1 H) 6.89 (d, J = 8.91 Hz, 1 H) 6.97 (d, J = 7.46 Hz, 1 H) 7.08 (d, J = 8.09 Hz, 1 H) 7.18 (d, J = 6.02 Hz, 1 H) 7.26-7.40 (m, 1 H) 7.47 (d, J = 9.43 Hz, 1 H) 7.89 (dd, J = 9.07, 2.23 Hz, 1 H) 8.24 (d, J = 9.64 Hz, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | | | | | | 1 H) 8.39 (d, J = 2.18 Hz, 1 H) 8.74 (s, 1 H) 11.68 (s, 1 H). |
| 736 | 1-(5-fluoro-2-methoxy-4-(2-methyl-4-pyridinyl)phenyl)-N-3-isoxazolyl-2-oxo-1,2-dihydro-6-quinolinesulfonamide | 507.0 | 139 | 2.812 | | $^1$H NMR (400 MHz, DMSO-d$_6$) δ ppm 2.51 (s, 3 H) 3.68 (s, 3 H) 6.24 (s, 1 H) 6.67-6.74 (m, 2 H) 7.38 (d, J = 6.84 Hz, 1 H) 7.45 (d, J = 5.08 Hz, 1 H) 7.48 (d, J = 10.47 Hz, 1 H) 7.53 (s, 1 H) 7.74 (dd, J = 8.81, 2.07 Hz, 1 H) 8.13 (d, J = 9.85 Hz, 1 H) 8.20 (s, 1 H) 8.44 (br. s., 1 H) 8.53 (d, J = 5.18 Hz, 1 H). |
| 737 | 1-(5-fluoro-2-methoxy-4-(2-methyl-3-pyridinyl)phenyl)-N-3-isoxazolyl-2-oxo-1,2-dihydro-6-quinolinesulfonamide | 507.0 | 139 | 1.248 | | $^1$H NMR (400 MHz, DMSO-d$_6$) δ ppm 2.53 (s, 3 H) 3.63 (s, 3 H) 6.39 (d, J = 2.03 Hz, 1 H) 6.77 (d, J = 9.64 Hz, 1 H) 6.85 (d, J = 9.02 Hz, 1 H) 7.32 (d, J = 6.53 Hz, 1 H) 7.54 (d, J = 9.54 Hz, 1 H) 7.66 (dd, J = 7.67, 5.39 Hz, 1 H) 7.81 (dd, J = 8.97, 2.23 Hz, 1 H) 8.13 (d, J = 6.84 Hz, 1 H) 8.18 (d, J = 9.64 Hz, 1 H) 8.33 (d, J = 2.18 Hz, 1 H) 8.67 (d, J = 7.27 Hz, 1 H) 8.68-8.71 (m, 1 H) 11.42-11.85 (m, 1 H). |
| 738 | 1-(5-fluoro-2-methoxy-4-(5-methoxy-3-pyridinyl)phenyl)-N-3-isoxazolyl-2-oxo-1,2-dihydro-6-quinolinesulfonamide | 523.0 | 139 | 1.232 | | $^1$H NMR (400 MHz, DMSO-d$_6$) δ ppm 3.76 (s, 3 H) 3.94-3.97 (m, 3 H) 6.46 (d, J = 4.74 Hz, 1 H) 6.83 (d, J = 9.64 Hz, 1 H) 6.89 (d, J = 9.02 Hz, 1 H) 7.51 (d, J = 6.95 Hz, 1 H) 7.59 (d, J = 10.37 Hz, 1 H) 7.75 (br. s., 1 H) 7.88 (dd, J = 8.91, 2.28 Hz, 1 H) 8.25 (d, J = 9.54 Hz, 1 H) 8.39 (d, J = 2.18 Hz, 1 H) 8.44 (d, J = 6.18 Hz, 1 H) 8.53 (s, 1 H) 8.75 (d, J = 6.70 Hz, 1 H) 11.67 (s, 1 H). |
| 739 | 1-(5-fluoro-2-methoxy-4-(2-methoxy-4-pyridinyl)phenyl)-N-3-isoxazolyl-2-oxo-1,2-dihydro-6-quinolinesulfonamide | 523.0 | 139 | 0.224 | | $^1$H NMR (400 MHz, DMSO-d$_6$) δ ppm 3.75 (s, 3 H) 3.94 (s, 3 H) 6.46 (d, J = 2.03 Hz, 1 H) 6.83 (d, J = 9.64 Hz, 1 H) 6.89 (d, J = 9.02 Hz, 1 H) 7.16 (s, 1 H) 7.33 (d, J = 5.31 Hz, 1 H) 7.48 (d, J = 6.84 Hz, 1 H) 7.58 (d, J = 10.47 Hz, 1 H) 7.87 (dd, J = 8.58 Hz, 1 H) 8.25 (d, J = 9.54 Hz, 1 H) 8.33 (dd, J = 5.34, 0.67 Hz, 1 H) 8.39 (d, J = 2.28 Hz, 1 H) 8.74 (d, J = 2.08 Hz, 1 H) 11.67 (s, 1 H). |
| 740 | 1-(4-(5-chloro-6-methoxy-3-pyridinyl)-5-fluoro-2-methoxyphenyl)-N-3-isoxazolyl-2-oxo-1,2-dihydro-6-quinolinesulfonamide | 557.0 | 145 | 0.009 | | $^1$H NMR (400 MHz, DMSO-d$_6$) δ ppm 3.70 (s, 3 H) 3.94 (s, 3 H) 6.46 (d, J = 1.76 Hz, 1 H) 6.77-6.90 (m, 2 H) 7.41 (d, J = 6.43 Hz, 1 H) 7.50 (d, J = 9.54 Hz, 1 H) 7.89 (dd, J = 8.97, 2.23 Hz, 1 H) 8.02 (d, J = 2.58 Hz, 1 H) 8.25 (d, J = 9.64 Hz, 1 H) 8.37 (d, J = 2.59 Hz, 1 H) 8.39 (d, J = 2.18 Hz, 1 H) 8.74 (s, 1 H) 11.68 (br. s., 1 H). |
| 741 | 1-(2,4'-difluoro-2',5-dimethoxy-4-biphenylyl)-N-3-isoxazolyl-2-oxo-1,2-dihydro-6-quinolinesulfonamide | 540.0 | 145 | 0.071 | | $^1$H NMR (400 MHz, DMSO-d$_6$) δ ppm 3.67 (s, 3 H) 3.85 (s, 3 H) 6.38 (s, 1 H) 6.80 (d, J = 9.43 Hz, 2 H) 6.95 (t, J = 8.26 Hz, 1 H) 7.11 (dd, J = 11.61, 2.49 Hz, 1 H) 7.23 (d, J = 6.53 Hz, 1 H) 7.38-7.46 (m, 2 H) 7.86 (dd, J = 8.97, 2.02 Hz, 1 H) 8.22 (d, J = 9.85 Hz, 1 H) 8.33 (s, 1 H) 8.62 (br. s., 1 H) 11.57-11.80 (m, 1 H). |
| 742 | 1-(4'-chloro-2-fluoro-5-methoxy-2'-methyl-4-biphenylyl)-N-3-isoxazolyl-2-oxo-1,2-dihydro-6-quinolinesulfonamide | 540.0 | 145 | 0.007 | | $^1$H NMR (400 MHz, DMSO-d$_6$) δ ppm 2.28 (s, 3 H) 3.68 (s, 3 H) 6.46 (s, 1 H) 6.83 (d, J = 9.64 Hz, 1 H) 6.89 (d, J = 8.91 Hz, 1 H) 7.23 (d, J = 6.53 Hz, 1 H) 7.36-7.46 (m, 2 H) 7.47-7.54 (m, 2 H) 7.88 (dd, J = 8.97, 2.23 Hz, 1 H) 8.24 (d, J = 9.54 Hz, 1 H) 8.39 (d, J = 2.18 Hz, 1 H) 8.74 (s, 1 H) 11.68 (s, 1 H). |
| 743 | 1-(5'-chloro-2-fluoro-5-methoxy-2'-methyl-4-biphenylyl)-N-3-isoxazolyl-2-oxo-1,2-dihydro-6-quinolinesulfonamide | 540.0 | 145 | 0.005 | | $^1$H NMR (400 MHz, DMSO-d$_6$) δ ppm 3.69 (s, 3 H) 6.46 (s, 1 H) 6.81-6.91 (m, 2 H) 7.26 (d, J = 6.53 Hz, 1 H) 7.40-7.47 (m, 3 H) 7.51 (d, J = 9.43 Hz, 1 H) 7.87 (dd, J = 8.97, 2.23 Hz, 1 H) 8.25 (d, J = 9.64 Hz, 1 H) 8.39 (d, J = 2.18 Hz, 1 H) 8.74 (s, 1 H) 11.68 (s, 1 H). |
| 744 | 1-(5'-chloro-2-fluoro-2',5-dimethoxy-4-biphenylyl)-N-3-isoxazolyl-2-oxo-1,2-dihydro-6-quinolinesulfonamide | 556.0 | 145 | 0.007 | | $^1$H NMR (400 MHz, DMSO-d$_6$) δ ppm 3.69 (s, 3 H) 3.84 (s, 3 H) 6.46 (s, 1 H) 6.84 (dd, J = 9.28, 5.13 Hz, 2 H) 7.22 (d, J = 9.02 Hz, 1 H) 7.29 (d, J = 6.43 Hz, 1 H) 7.39-7.47 (m, 2 H) 7.52 (dd, J = 8.86, 2.75 Hz, 1 H) 7.88 (dd, J = 9.02, 2.18 Hz, 1 H) 8.24 (d, J = 9.64 Hz, 1 H) 8.39 (d, J = 2.18 Hz, 1 H) 8.74 (d, J = 5.43 Hz, 1 H) 11.67 (s, 1 H). |
| 745 | 1-(4-(3-chloro-2-methoxy-4-pyridinyl)-5-fluoro-2-methoxyphenyl)-N-3- | 557.0 | 145 | 0.051 | | $^1$H NMR (400 MHz, DMSO-d$_6$) δ ppm 3.69 (s, 3 H) 4.03 (s, 3 H) 6.46 (d, J = 2.02 Hz, 1 H) 6.82-6.84 (m, 1 H) 6.85 (s, 1 H) 7.23 (d, J = 5.08 Hz, 1 H) 7.36 (d, J = 6.43 Hz, 1 H) 7.59 (d, J = 9.54 Hz, |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | isoxazolyl-2-oxo-1,2-dihydro-6-quinolinesulfonamide | | | | | 1 H) 7.90 (d, J = 8.53 Hz, 1 H) 8.25 (d, J = 9.54 Hz, 1 H) 8.29 (d, J = 5.08 Hz, 1 H) 8.40 (d, J = 2.18 Hz, 1 H) 8.74 (d, J = 1.96 Hz, 1 H) 11.68 (br. s., 1 H). |
| 598 | 1-(4'-chloro-2-fluoro-5-methoxy-4-biphenylyl)-2-oxo-N-2-pyrimidinyl-1,2-dihydro-6-quinolinesulfonamide | 537.2 | 150 | 0.028 | | $^{1}$H NMR (400 MHz, DMSO-d$_{6}$) δ ppm 3.73 (s, 3 H) 6.74 (d, J = 9.74 Hz, 3 H) 7.39 (d, J = 6.95 Hz, 1 H) 7.50 (d, J = 10.47 Hz, 1 H) 7.62 (d, J = 7.93 Hz, 2 H) 7.75 (dd, J = 8.45, 1.30 Hz, 2 H) 7.92 (dd, J = 8.86, 2.13 Hz, 1 H) 8.21 (d, J = 9.64 Hz, 1 H) 8.26-8.38 (m, 3 H) 11.53-12.39 (m, 1 H). |
| 746 | 1-(4'-chloro-2-fluoro-5-methoxy-4-biphenylyl)-2-oxo-N-3-pyridazinyl-1,2-dihydro-6-quinolinesulfonamide | 537.0 | 150 | 0.024 | | $^{1}$H NMR (400 MHz, DMSO-d$_{6}$) δ ppm 3.74 (s, 3 H) 6.76-6.82 (m, 2 H) 7.40 (d, J = 6.74 Hz, 1 H) 7.50 (d, J = 10.37 Hz, 1 H) 7.58-7.67 (m, 3 H) 7.75 (d, J = 8.29 Hz, 3 H) 7.86 (d, J = 8.91 Hz, 1 H) 8.20 (d, J = 9.64 Hz, 1 H) 8.35 (br. s., 2 H) 13.93-14.65 (m, 1 H). |
| 747 | 1-(3'-chloro-2-fluoro-2',5-dimethoxy-4-biphenylyl)-N-3-isoxazolyl-2-oxo-1,2-dihydro-6-quinolinesulfonamide | 556.0 | 145 | 0.016 | | $^{1}$H NMR (400 MHz, DMSO-d$_{6}$) δ ppm 3.66 (s, 3 H) 3.69 (s, 3 H) 6.46 (s, 1 H) 6.84 (dd, J = 9.33, 4.46 Hz, 2 H) 7.28-7.38 (m, 2 H) 7.45 (dd, J = 7.62, 1.30 Hz, 1 H) 7.52 (d, J = 9.43 Hz, 1 H) 7.63 (d, J = 7.63 Hz, 1 H) 7.90 (dd, J = 8.97, 2.23 Hz, 1 H) 8.25 (d, J = 9.64 Hz, 1 H) 8.39 (d, J = 2.18 Hz, 1 H) 8.74 (s, 1 H) 11.68 (s, 1 H). |
| 599 | 1-(5-fluoro-2-methoxy-4-(4-methyl-2-oxo-1(2H)-pyridinyl)phenyl)-N-3-isoxazolyl-2-oxo-1,2-dihydro-6-quinolinesulfonamide | 523.0 | 151 | | | $^{1}$H NMR (400 MHz, CHLOROFORM-d) δ ppm 2.55 (s, 3 H) 3.72 (s, 3 H) 6.64 (d, J = 1.76 Hz, 1 H) 6.88 (d, J = 9.74 Hz, 1 H) 6.98-7.02 (m, 2 H) 7.11 (d, J = 6.84 Hz, 1 H) 7.32 (d, J = 1.35 Hz, 2 H) 7.80-7.90 (m, 2 H) 8.15 (d, J = 2.07 Hz, 1 H) 8.23 (d, J = 5.39 Hz, 1 H) 8.29 (d, J = 1.66 Hz, 1 H). |
| 748 | 1-(4-(3-chloro-4-pyridinyl)-5-fluoro-2-methoxyphenyl)-N-3-isoxazolyl-2-oxo-1,2-dihydro-6-quinolinesulfonamide | 527.0 | 145 | 0.573 | | $^{1}$H NMR (400 MHz, DMSO-d$_{6}$) δ ppm 3.70 (s, 3 H) 6.46 (d, J = 2.15 Hz, 1 H) 6.83 (d, J = 3.52 Hz, 1 H) 6.86 (d, J = 2.80 Hz, 1 H) 7.41 (d, J = 6.43 Hz, 1 H) 7.62 (d, J = 9.54 Hz, 1 H) 7.67 (d, J = 4.87 Hz, 1 H) 7.90 (d, J = 9.01 Hz, 1 H) 8.26 (d, J = 9.54 Hz, 1 H) 8.40 (d, J = 2.18 Hz, 1 H) 8.71 (d, J = 4.87 Hz, 1 H) 8.74 (d, J = 1.87 Hz, 1 H) 8.85 (s, J = 5.54 Hz, 1 H) 11.68 (s, 1 H). |
| 749 | 1-(2-fluoro-4',5-dimethoxy-3'-methyl-4-biphenylyl)-N-3-isoxazolyl-2-oxo-1,2-dihydro-6-quinolinesulfonamide | 536.0 | 145 | 0.048 | | $^{1}$H NMR (400 MHz, DMSO-d$_{6}$) δ ppm 2.25 (s, 3 H) 3.73 (s, 3 H) 3.87 (s, 3 H) 6.46 (d, J = 4.40 Hz, 1 H) 6.82 (d, J = 9.64 Hz, 1 H) 6.89 (d, J = 8.91 Hz, 1 H) 7.10 (d, J = 8.40 Hz, 1 H) 7.33 (d, J = 7.05 Hz, 1 H) 7.45 (d, J = 10.47 Hz, 1 H) 7.48-7.56 (m, 2 H) 7.88 (dd, J = 9.02, 2.18 Hz, 1 H) 8.23 (d, J = 9.54 Hz, 1 H) 8.38 (d, J = 2.18 Hz, 1 H) 8.74 (d, J = 4.52 Hz, 1 H) 11.67 (br. s., 1 H). |
| 750 | 1-(4'-chloro-2-fluoro-5-methoxy-4-biphenylyl)-N-(5-fluoro-2-pyrimidinyl)-2-oxo-1,2-dihydro-6-quinolinesulfonamide | 555.0 | 150 | 0.01 | | $^{1}$H NMR (400 MHz, DMSO-d$_{6}$) δ ppm 3.74 (s, 3 H) 6.77 (dd, J = 9.28, 4.09 Hz, 2 H) 7.40 (d, J = 6.95 Hz, 1 H) 7.50 (d, J = 10.37 Hz, 1 H) 7.60-7.65 (m, 2 H) 7.75 (dd, J = 8.55, 1.40 Hz, 2 H) 7.92 (dd, J = 8.91, 2.07 Hz, 1 H) 8.22 (d, J = 9.54 Hz, 1 H) 8.37 (d, J = 2.07 Hz, 1 H) 8.42 (s, 2 H) 11.47-12.48 (m, 1 H). |
| 751 | 1-(4'-chloro-2-fluoro-5-methoxy-4-biphenylyl)-N-(2-methyl-4-pyrimidinyl)-2-oxo-1,2-dihydro-6-quinolinesulfonamide | 551.0 | 150 | 0.067 | | $^{1}$H NMR (400 MHz, DMSO-d$_{6}$) δ ppm 2.36 (s, 3 H) 3.74 (s, 3 H) 6.73-6.86 (m, 3 H) 7.41 (d, J = 7.05 Hz, 1 H) 7.51 (d, J = 10.37 Hz, 1 H) 7.59-7.66 (m, 2 H) 7.70-7.79 (m, 2 H) 7.89 (dd, J = 8.91, 2.18 Hz, 1 H) 8.06 (d, J = 6.63 Hz, 1 H) 8.23 (d, J = 9.43 Hz, 1 H) 8.38 (d, J = 2.18 Hz, 1 H) 12.39-14.20 (m, 1 H). |
| 752 | 1-(4'-chloro-2-fluoro-5-methoxy-4-biphenylyl)-N-(6-methyl-4-pyrimidinyl)-2-oxo-1,2-dihydro-6-quinolinesulfonamide | 551.2 | 150 | 0.02 | | $^{1}$H NMR (400 MHz, DMSO-d$_{6}$) δ ppm 2.34 (s, 3 H) 3.74 (s, 3 H) 6.81 (d, J = 9.64 Hz, 1 H) 6.83 (d, J = 9.02 Hz, 1 H) 6.94 (s, 1 H) 7.41 (d, J = 6.95 Hz, 1 H) 7.52 (d, J = 10.37 Hz, 1 H) 7.59-7.66 (m, 2 H) 7.69-7.80 (m, 2 H) 7.93 (dd, J = 8.91, 2.18 Hz, 1 H) 8.25 (d, J = 9.54 Hz, 1 H) 8.45 (d, J = 2.18 Hz, 1 H) 8.54 (s, 1 H). |
| 753 | 1-(4'-chloro-2-fluoro-5-methoxy-4-biphenylyl)-N-1,3-oxazol-2-yl-2-oxo-1,2-dihydro-6- | 526.0 | 150 | 0.037 | | $^{1}$H NMR (400 MHz, DMSO-d$_{6}$) δ ppm 3.75 (s, 3 H) 6.80 (t, J = 7.69 Hz, 2 H) 7.29 (d, J = 1.55 Hz, 1 H) 7.41 (d, J = 6.47 Hz, 1 H) 7.52 (d, J = 10.37 Hz, 1 H) 7.59-7.66 (m, 3 H) 7.75 (d, J = 7.26 Hz, 2 H) 7.87 (d, J = 8.98 Hz, 1 H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | quinolinesulfonamide | | | | | 8.21 (d, J = 7.51 Hz, 1 H) 8.34 (d, J = 2.07 Hz, 1 H) 12.18 (br. s., 1 H). |
| 677 | 1-(2,4'-difluoro-5-methoxy-4-biphenylyl)-N-3-isoxazolyl-2-oxo-1,2-dihydro-6-quinolinesulfonamide | 510.2 | 139 | 0.009 | | $^1$H NMR (400 MHz, DMSO-d$_6$) δ ppm 3.74 (s, 3 H) 6.46 (d, J = 1.66 Hz, 1 H) 6.82 (d, J = 9.64 Hz, 1 H) 6.89 (d, J = 9.02 Hz, 1 H) 7.34-7.45 (m, 3 H) 7.52 (d, J = 10.47 Hz, 1 H) 7.76 (dd, J = 7.26, 5.49 Hz, 2 H) 7.87 (dd, J = 8.97, 2.12 Hz, 1 H) 8.24 (d, J = 9.64 Hz, 1 H) 8.38 (d, J = 2.18 Hz, 1 H) 8.74 (d, J = 1.66 Hz, 1 H) 11.67 (s, 1 H). |
| 754 | 1-(4'-cyano-2-fluoro-5-methoxy-4-biphenylyl)-N-3-isoxazolyl-2-oxo-1,2-dihydro-6-quinolinesulfonamide | 517.0 | 139 | 0.132 | | $^1$H NMR (400 MHz, DMSO-d$_6$) δ ppm 3.75 (s, 3 H) 4.04 (s, 3 H) 6.08 (d, J = 1.76 Hz, 1 H) 6.63 (d, J = 8.81 Hz, 1 H) 6.69 (d, J = 9.54 Hz, 1 H) 7.45-7.53 (m, 2 H) 7.72 (dd, J = 8.76, 2.02 Hz, 1 H) 8.09-8.17 (m, 3 H) 8.29 (dd, J = 2.12, 1.09 Hz, 1 H) 8.50 (t, J = 1.92 Hz, 1 H). |
| 755 | 4-chloro-2'-fluoro-4'-(6-(3-isoxazolylsulfamoyl)-2-oxo-1(2H)-quinolinyl)-5'-methoxy-2-biphenylcarboxamide | 569.2 | 139 | 0.351 | | $^1$H NMR (400 MHz, DMSO-d$_6$) δ ppm 3.68 (s, 3 H) 6.47 (d, J = 1.76 Hz, 1 H) 6.76 (d, J = 9.02 Hz, 1 H) 6.83 (d, J = 9.64 Hz, 1 H) 7.27 (d, J = 6.74 Hz, 1 H) 7.41 (d, J = 9.64 Hz, 1 H) 7.49 (s, 1 H) 7.57 (d, J = 8.09 Hz, 1 H) 7.62-7.72 (m, 2 H) 7.80-7.94 (m, 2 H) 8.24 (d, J = 9.64 Hz, 1 H) 8.39 (d, J = 2.28 Hz, 1 H) 8.74 (d, J = 1.76 Hz, 1 H) 11.67 (s, 1 H). |
| 678 | 1-(3'-(difluoromethoxy)-2,5'-difluoro-5-methoxy-4-biphenylyl)-N-3-isoxazolyl-2-oxo-1,2-dihydro-6-quinolinesulfonamide | 576.0 | 147 | 0.011 | | $^1$H NMR (400 MHz, DMSO-d$_6$) δ ppm 3.76 (s, 3 H) 6.46 (d, J = 1.76 Hz, 1 H) 6.85 (dd, J = 19.02, 9.28 Hz, 2 H) 7.21-7.64 (m, 6 H) 7.87 (dd, J = 8.97, 2.23 Hz, 1 H) 8.24 (d, J = 9.74 Hz, 1 H) 8.39 (d, J = 2.18 Hz, 1 H) 8.74 (d, J = 1.66 Hz, 1 H) 11.67 (s, 1 H). |
| 756 | 1-(2-fluoro-5-methoxy-4'-methyl-4-biphenylyly)-N-3-isoxazolyl-2-oxo-1,2-dihydro-6-quinolinesulfonamide | 506.1 | 145 | 0.055 | | $^1$H NMR (400 MHz, DMSO-d$_6$) δ ppm 2.39 (s, 3 H) 3.73 (s, 3 H) 6.45 (s, 1 H) 6.82 (d, J = 9.64 Hz, 1 H) 6.89 (d, J = 9.02 Hz, 1 H) 7.35 (dd, J = 7.41, 3.06 Hz, 3 H) 7.48 (d, J = 10.47 Hz, 1 H) 7.59 (d, J = 6.74 Hz, 2 H) 7.87 (d, J = 9.02 Hz, 1 H) 8.23 (d, J = 9.54 Hz, 1 H) 8.38 (d, J = 2.18 Hz, 1 H) 8.74 (d, J = 5.56 Hz, 1 H). |
| 757 | 1-(4'-cyclopropyl-2-fluoro-5-methoxy-4-biphenylyl)-N-3-isoxazolyl-2-oxo-1,2-dihydro-6-quinolinesulfonamide | 532.2 | 145 | 0.035 | | $^1$H NMR (400 MHz, DMSO-d$_6$) δ ppm 0.70-0.82 (m, 2 H) 0.96-1.08 (m, 2 H) 1.97-2.05 (m, 1 H) 3.73 (s, 3 H) 6.46 (d, J = 1.76 Hz, 1 H) 6.82 (d, J = 9.64 Hz, 1 H) 6.89 (d, J = 9.02 Hz, 1 H) 7.25 (d, J = 8.29 Hz, 2 H) 7.35 (d, J = 6.95 Hz, 1 H) 7.48 (d, J = 10.47 Hz, 1 H) 7.58 (d, J = 6.74 Hz, 2 H) 7.88 (dd, J = 8.97, 2.12 Hz, 1 H) 8.24 (d, J = 9.74 Hz, 1 H) 8.38 (d, J = 2.07 Hz, 1 H) 8.74 (d, J = 1.66 Hz, 1 H) 11.67 (s, 1 H). |
| 758 | 1-(5'-chloro-2'-cyano-2-fluoro-5-methoxy-4-biphenylyl)-N-3-isoxazolyl-2-oxo-1,2-dihydro-6-quinolinesulfonamide | 551.1 | 145 | 0.02 | | $^1$H NMR (400 MHz, DMSO-d$_6$) δ ppm 3.74 (s, 3 H) 6.47 (d, J = 2.04 Hz, 1 H) 6.83 (dd, J = 10.88, 9.33 Hz, 2 H) 7.52 (d, J = 6.53 Hz, 1 H) 7.65 (d, J = 9.85 Hz, 1 H) 7.82 (dd, J = 8.40, 2.18 Hz, 1 H) 7.89 (dd, J = 8.97, 2.23 Hz, 1 H) 7.93 (d, J = 2.07 Hz, 1 H) 8.11 (d, J = 8.05 Hz, 1 H) 8.26 (d, J = 9.54 Hz, 1 H) 8.41 (d, J = 2.18 Hz, 1 H) 8.74 (s, 1 H) 11.68 (s, 1 H). |
| 759 | 1-(4-(5-chloro-2-methoxy-4-pyridinyl)-5-fluoro-2-methoxyphenyl)-N-3-isoxazolyl-2-oxo-1,2-dihydro-6-quinolinesulfonamide | 557.1 | 145 | 0.1 | | $^1$H NMR (400 MHz, DMSO-d$_6$) δ ppm 3.70 (s, 3 H) 3.94 (s, 3 H) 6.46 (d, J = 1.97 Hz, 1 H) 6.83 (dd, J = 9.28, 3.99 Hz, 2 H) 7.12 (s, 1 H) 7.38 (d, J = 6.43 Hz, 1 H) 7.59 (d, J = 9.54 Hz, 1 H) 7.89 (d, J = 8.98 Hz, 1 H) 8.25 (d, J = 9.54 Hz, 1 H) 8.40 (d, J = 2.18 Hz, 1 H) 8.43 (s, 1 H) 8.74 (d, J = 1.99 Hz, 1 H) 11.68 (s, 1 H). |
| 760 | 1-(2-fluoro-5-methoxy-4'-(trifluoromethoxy)-4-biphenylyl)-N-3-isoxazolyl-2-oxo-1,2-dihydro-6-quinolinesulfonamide | 576.0 | 145 | 0.015 | | $^1$H NMR (400 MHz, DMSO-d$_6$) δ ppm 3.74 (s, 3 H) 6.46 (s, 1 H) 6.83 (d, J = 9.64 Hz, 1 H) 6.89 (d, J = 8.91 Hz, 1 H) 7.44 (d, J = 7.05 Hz, 1 H) 7.52-7.60 (m, 3 H) 7.81-7.90 (m, 3 H) 8.24 (d, J = 9.54 Hz, 1 H) 8.39 (d, J = 2.18 Hz, 1 H) 8.74 (s, 1 H) 11.67 (s, 1 H). |
| 761 | 1-(5-fluoro-2-methoxy-4-(6-(trifluoromethyl)-3-pyridinyl)phenyl)-N-3- | 561.0 | 145 | 0.12 | | $^1$H NMR (400 MHz, DMSO-d$_6$) δ ppm 3.77 (s, 3 H) 6.46 (d, J = 4.84 Hz, 1 H) 6.84 (d, J = 9.74 Hz, 1 H) 6.91 (d, J = 9.02 Hz, 1 H) 7.61 (d, J = 6.84 Hz, 1 H) 7.65 (d, J = 10.26 Hz, 1 H) |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | isoxazolyl-2-oxo-1,2-dihydro-6-quinolinesulfonamide | | | | | 7.88 (dd, J = 8.97, 2.23 Hz, 1 H) 8.12 (d, J = 8.19 Hz, 1 H) 8.26 (d, J = 9.64 Hz, 1 H) 8.40 (d, J = 2.18 Hz, 1 H) 8.44 (d, J = 8.09 Hz, 1 H) 8.75 (d, J = 4.98 Hz, 1 H) 9.12 (s, 1 H) 11.67 (s, 1 H). |
| 762 | 1-(5-fluoro-2-methoxy-4-(2-(trifluoromethyl)-4-pyridinyl)phenyl)-N-3-isoxazolyl-2-oxo-1,2-dihydro-6-quinolinesulfonamide | 561.0 | 145 | 0.041 | | $^1$H NMR (400 MHz, DMSO-d$_6$) δ ppm 3.78 (s, 3 H) 6.46 (d, J = 4.94 Hz, 1 H) 6.83 (d, J = 9.64 Hz, 1 H) 6.89 (d, J = 8.91 Hz, 1 H) 7.62 (d, J = 8.92 Hz, 1 H) 7.66 (d, J = 9.55 Hz, 1 H) 7.86 (dd, J = 8.97, 2.23 Hz, 1 H) 8.08 (d, J = 4.98 Hz, 1 H) 8.22 (s, 1 H) 8.23-8.27 (m, 1 H) 8.40 (d, J = 2.28 Hz, 1 H) 8.74 (d, J = 7.03 Hz, 1 H) 8.95 (d, J = 5.18 Hz, 1 H) 11.67 (s, 1 H). |
| 763 | 1-(4'-(difluoromethoxy)-2-fluoro-5-methoxy-4-biphenylyl)-N-3-isoxazolyl-2-oxo-1,2-dihydro-6-quinolinesulfonamide | 558.0 | 145 | 0.03 | | $^1$H NMR (400 MHz, DMSO-d$_6$) δ ppm 3.74 (s, 3 H) 6.46 (d, J = 2.03 Hz, 1 H) 6.83 (d, J = 9.64 Hz, 1 H) 6.90 (d, J = 9.02 Hz, 1 H) 7.32-7.43 (m, 4 H) 7.50-7.55 (m, 1 H) 7.77 (d, J = 7.98 Hz, 2 H) 7.88 (dd, J = 9.05 Hz, 1 H) 8.24 (d, J = 9.54 Hz, 1 H) 8.39 (d, J = 2.28 Hz, 1 H) 8.74 (d, J = 1.99 Hz, 1 H) 11.67 (s, 1 H). |
| 600 | 1-(4'-chloro-3-methoxy-4-biphenylyl)-2-oxo-N-2-pyrimidinyl-1,2-dihydro-6-quinolinesulfonamide | 519.0 | 152 | 0.095 | | $^1$H NMR (400 MHz, DMSO-d$_6$) δ ppm 3.77 (s, 3 H) 6.79 (dd, J = 9.33, 6.32 Hz, 2 H) 7.06 (t, J = 5.43 Hz, 1 H) 7.37-7.42 (m, 1 H) 7.42-7.48 (m, 1 H) 7.52-7.64 (m, 3 H) 7.87 (d, J = 7.67 Hz, 2 H) 7.98 (dd, J = 8.97, 2.12 Hz, 1 H) 8.26 (d, J = 9.64 Hz, 1 H) 8.46-8.56 (m, 3 H) 11.61-11.95 (m, 1 H). |
| 764 | 1-(4'-chloro-3-methoxy-4-biphenylyl)-N-(5-fluoro-2-pyrimidinyl)-2-oxo-1,2-dihydro-6-quinolinesulfonamide | 537.0 | 152 | 0.04 | | $^1$H NMR (400 MHz, DMSO-d$_6$) δ ppm 3.78 (s, 3 H) 6.80 (dd, J = 9.28, 7.62 Hz, 2 H) 7.36-7.42 (m, 1 H) 7.43-7.49 (m, 1 H) 7.53-7.63 (m, 3 H) 7.86 (s, 1 H) 7.87-7.89 (m, 1 H) 7.97 (dd, J = 9.02, 2.18 Hz, 1 H) 8.48 (d, J = 2.18 Hz, 1 H) 8.62 (s, 2 H) 11.97 (s, 1 H). |
| 765 | 1-(4'-chloro-3-methoxy-4-biphenylyl)-2-oxo-N-3-pyridazinyl-1,2-dihydro-6-quinolinesulfonamide | 519.0 | 152 | 0.112 | | $^1$H NMR (400 MHz, DMSO-d$_6$) δ ppm 3.78 (s, 3 H) 6.74 (d, J = 9.02 Hz, 1 H) 6.79 (d, J = 9.64 Hz, 1 H) 7.36-7.41 (m, 1 H) 7.43-7.48 (m, 1 H) 7.54 (d, J = 1.76 Hz, 1 H) 7.57-7.62 (m, 2 H) 7.69 (d, J = 9.48, 4.09 Hz, 1 H) 7.82-7.90 (m, 3 H) 7.93 (br. s., 1 H) 8.20 (d, J = 9.74 Hz, 1 H) 8.29 (br. s., 1 H) 8.35 (br. s., 1 H) 14.49 (br. s., 1 H). |
| 766 | 1-(4'-chloro-3-methoxy-4-biphenylyl)-N-1,3-oxazol-2-yl-2-oxo-1,2-dihydro-6-quinolinesulfonamide | 508.0 | 152 | 0.037 | | $^1$H NMR (400 MHz, DMSO-d$_6$) δ ppm 3.79 (s, 3 H) 6.73 (d, J = 8.91 Hz, 1 H) 6.78 (d, J = 9.64 Hz, 1 H) 7.25 (d, J = 1.45 Hz, 1 H) 7.37-7.42 (m, 1 H) 7.42-7.49 (m, 1 H) 7.54 (d, J = 1.76 Hz, 1 H) 7.56-7.65 (m, 3 H) 7.81-7.92 (m, 3 H) 8.19 (d, J = 9.54 Hz, 1 H) 8.33 (d, J = 2.07 Hz, 1 H) 12.04-12.29 (m, 1 H). |
| 601 | 1-(6-(3-fluorophenyl)-4-methoxy-3-pyridinyl)-N-3-isoxazolyl-2-oxo-1,2-dihydro-6-quinolinesulfonamide | 493.0 | 153 | 1.77 | | $^1$H NMR (400 MHz, DMSO-d$_6$) δ ppm 3.92 (s, 3 H) 6.46 (d, J = 5.48 Hz, 1 H) 6.84 (d, J = 9.64 Hz, 1 H) 6.92 (d, J = 9.02 Hz, 1 H) 7.36 (d, J = 8.22 Hz, 1 H) 7.61 (dd, J = 7.98, 1.76 Hz, 1 H) 7.86 (dd, J = 8.91, 2.28 Hz, 1 H) 7.92 (s, 1 H) 8.05-8.15 (m, 2 H) 8.27 (d, J = 14.13 Hz, 1 H) 8.40 (d, J = 2.18 Hz, 1 H) 8.50 (s, 1 H) 8.74 (d, J = 1.76 Hz, 1 H) 11.67 (s, 1 H). |
| 767 | 1-(4'-chloro-3-methoxy-4-biphenylyl)-N-(6-methyl-4-pyrimidinyl)-2-oxo-1,2-dihydro-6-quinolinesulfonamide | 533.0 | 152 | 0.054 | | $^1$H NMR (400 MHz, DMSO-d$_6$) δ ppm 2.32 (s, 3 H) 3.78 (s, 3 H) 6.72-6.83 (m, 2 H) 6.92 (br. s., 1 H) 7.37-7.42 (m, 1 H) 7.42-7.48 (m, 1 H) 7.52-7.63 (m, 3 H) 7.83-7.93 (m, 3 H) 8.23 (d, J = 9.64 Hz, 1 H) 8.43 (br. s., 1 H) 8.49 (s, 1 H) 12.06-13.37 (m, 1 H). |
| 768 | 1-(4'-chloro-3-methoxy-4-biphenylyl)-N-(2-methyl-4-pyrimidinyl)-2-oxo-1,2-dihydro-6-quinolinesulfonamide | 533.0 | 152 | 0.052 | | $^1$H NMR (400 MHz, DMSO-d$_6$) δ ppm 2.37 (s, 3 H) 3.75-3.81 (m, 3 H) 6.69-6.99 (m, 3 H) 7.37-7.43 (m, 1 H) 7.43-7.48 (m, 1 H) 7.53-7.63 (m, 3 H) 7.87 (dd, J = 8.60, 2.49 Hz, 3 H) 8.10 (br. s., 1 H) 8.22 (d, J = 9.54 Hz, 1 H) 8.38 (br. s., 1 H) 12.69-14.07 (m, 1 H). |
| 603 | 1-(6-(3-fluorophenyl)-4-methoxy-3-pyridinyl)-N-3-isoxazolyl-2-oxo-1,2-dihydro-6-quinolinesulfonamide | 493.2 | 153 | | | $^1$H NMR (400 MHz, DMSO-d$_6$) δ ppm 3.92 (s, 3 H) 6.40 (d, J = 1.45 Hz, 1 H) 6.82 (d, J = 9.64 Hz, 1 H) 6.88 (d, J = 9.02 Hz, 1 H) 7.36 (t, J = 8.03 Hz, 1 H) 7.57-7.65 (m, 1 H) 7.84 (dd, J = 8.97, 2.13 Hz, 1 H) 7.92 (s, 1 H) 8.07 (dd, J = 10.42, 2.02 Hz, 1 H) 8.11 (d, J = 8.09 Hz, 1 H) 8.25 (d, J = 9.74 Hz, 1 H) 8.36 (d, J = 1.76 Hz, 1 |

TABLE 3-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | | | | | | H) 8.50 (s, 1 H) 8.65 (s, 1 H) 11.50-11.82 (m, 1 H). |
| 602 | 1-(6-(3-fluorophenyl)-4-methoxy-3-pyridinyl)-N-3-isoxazolyl-2-oxo-1,2-dihydro-6-quinolinesulfonamide | 493.2 | 153 | 0.709 | | $^1$H NMR (400 MHz, DMSO-d$_6$) δ ppm 3.92 (s, 3 H) 6.38 (d, J = 1.35 Hz, 1 H) 6.81 (d, J = 9.64 Hz, 1 H) 6.86 (d, J = 8.81 Hz, 1 H) 7.35 (t, J = 8.20 Hz, 1 H) 7.61 (dd, J = 7.93, 1.81 Hz, 1 H) 7.83 (dd, J = 8.97, 2.02 Hz, 1 H) 7.92 (s, 1 H) 8.07 (dd, J = 10.42, 2.02 Hz, 1 H) 8.11 (d, J = 7.98 Hz, 1 H) 8.24 (d, J = 9.64 Hz, 1 H) 8.34 (d, J = 1.97 Hz, 1 H) 8.49 (s, 1 H) 8.61 (s, 1 H) 11.50-11.79 (m, 1 H). |
| 604 | 1-(2,4'-difluoro-5-methoxy-4-biphenylyl)-2-oxo-N-2-pyrimidinyl-1,2-dihydro-6-quinolinesulfonamide | 521.2 | 154 | 0.193 | | $^1$H NMR (500 MHz, DMSO-d$_6$) δ ppm 3.73 (s, 3 H) 6.80 (d, J = 9.67 Hz, 1 H) 6.85 (d, J = 8.95 Hz, 1 H) 7.05 (t, J = 4.64 Hz, 1 H) 7.34-7.42 (m, 3 H) 7.49 (d, J = 10.38 Hz, 1 H) 7.75 (t, J = 6.72 Hz, 2 H) 8.00 (dd, J = 8.92, 1.98 Hz, 1 H) 8.26 (d, J = 9.73 Hz, 1 H) 8.46-8.53 (m, 3 H) 11.47-12.12 (m, 1 H). |
| 769 | 1-(2,4'-difluoro-5-methoxy-4-biphenylyl)-N-(5-fluoro-2-pyrimidinyl)-2-oxo-1,2-dihydro-6-quinolinesulfonamide | 539.2 | 154 | 0.1 | | $^1$H NMR (500 MHz, DMSO-d$_6$) δ ppm 3.73 (s, 3 H) 6.81 (d, J = 9.67 Hz, 1 H) 6.86 (d, J = 8.95 Hz, 1 H) 7.35-7.42 (m, 3 H) 7.49 (d, J = 8.37 Hz, 1 H) 7.70-7.81 (m, 2 H) 7.98 (dd, J = 9.02, 2.08 Hz, 1 H) 8.26 (d, J = 9.67 Hz, 1 H) 8.48 (d, J = 1.95 Hz, 1 H) 8.62 (s, 2 H) 11.96 (br. s., 1 H). |
| 770 | 1-(2,4'-difluoro-5-methoxy-4-biphenylyl)-2-oxo-N-3-pyridazinyl-1,2-dihydro-6-quinolinesulfonamide | 521.2 | 154 | 0.033 | | $^1$H NMR (500 MHz, DMSO-d$_6$) δ ppm 3.73 (s, 3 H) 6.79 (t, J = 8.92 Hz, 2 H) 7.34-7.43 (m, 3 H) 7.48 (d, J = 10.32 Hz, 1 H) 7.66-7.71 (m, 1 H) 7.72-7.80 (m, 2 H) 7.86 (d, J = 8.56 Hz, 1 H) 7.93 (d, J = 7.46 Hz, 1 H) 8.20 (d, J = 9.73 Hz, 1 H) 8.27 (br. s., 1 H) 8.35 (br. s., 1 H) 14.31-14.61 (m, 1 H). |
| 771 | 1-(2,4'-difluoro-5-methoxy-4-biphenylyl)-N-1,3-oxazol-2-yl-2-oxo-1,2-dihydro-6-quinolinesulfonamide | 510.0 | 154 | 0.053 | | $^1$H NMR (500 MHz, DMSO-d$_6$) δ ppm 3.74 (s, 3 H) 6.80 (t, J = 9.24 Hz, 2 H) 7.26-7.29 (m, 1 H) 7.36-7.43 (m, 3 H) 7.49 (d, J = 10.25 Hz, 1 H) 7.60 (d, J = 1.49 Hz, 1 H) 7.76 (dd, J = 7.33, 5.58 Hz, 2 H) 7.87 (dd, J = 8.82, 2.01 Hz, 1 H) 8.20 (d, J = 9.67 Hz, 1 H) 8.33 (d, J = 1.82 Hz, 1 H) 12.06-12.35 (m, 1 H). |
| 772 | 1-(2,4'-difluoro-5-methoxy-4-biphenylyl)-N-(6-methyl-4-pyrimidinyl)-2-oxo-1,2-dihydro-6-quinolinesulfonamide | 535.2 | 154 | 0.232 | | $^1$H NMR (500 MHz, DMSO-d$_6$) δ ppm 2.32 (s, 3 H) 3.73 (s, 3 H) 6.80 (d, J = 11.54 Hz, 1 H) 6.82 (d, J = 11.80 Hz, 1 H) 6.92 (d, J = 8.06 Hz, 1 H) 7.37-7.43 (m, 3 H) 7.49 (d, J = 10.38 Hz, 1 H) 7.74-7.80 (m, 2 H) 7.92 (d, J = 8.04 Hz, 1 H) 8.23 (d, J = 9.73 Hz, 1 H) 8.43 (s, J = 8.78 Hz, 1 H) 8.50 (s, J = 8.24, 8.24 Hz, 1 H). |
| 773 | 1-(2,4'-difluoro-5-methoxy-4-biphenylyl)-N-(2-methyl-4-pyrimidinyl)-2-oxo-1,2-dihydro-6-quinolinesulfonamide | 535.2 | 154 | 0.274 | | $^1$H NMR (500 MHz, DMSO-d$_6$) δ ppm 2.38 (s, 3 H) 3.73 (s, 3 H) 6.80 (dd, J = 12.49, 9.31 Hz, 3 H) 7.36-7.42 (m, 3 H) 7.48 (d, J = 10.32 Hz, 1 H) 7.73-7.80 (m, 2 H) 7.90 (d, J = 8.49 Hz, 1 H) 8.12 (d, J = 7.86 Hz, 1 H) 8.23 (d, J = 8.38 Hz, 1 H) 8.39 (s, J = 8.49, 8.49 Hz, 1 H). |
| 605 | 1-(4-(5-chloro-2-methoxy-3-pyridinyl)-5-fluoro-2-methoxyphenyl)-2-oxo-N-2-pyrimidinyl-1,2-dihydro-6-quinolinesulfonamide | 568.1 | 155 | 0.072 | | $^1$H NMR (500 MHz, DMSO-d$_6$) δ ppm 3.74 (s, 3 H) 4.03 (s, 3 H) 6.80 (d, J = 9.09 Hz, 1 H) 6.84 (d, J = 8.11 Hz, 1 H) 7.02-7.09 (m, 1 H) 7.39-7.57 (m, 2 H) 7.99 (d, J = 8.15 Hz, 1 H) 8.23-8.36 (m, 2 H) 8.50 (dd, J = 8.50, 4.35 Hz, 4 H) 11.62-12.08 (m, 1 H). |
| 774 | 1-(4-(5-chloro-2-methoxy-3-pyridinyl)-5-fluoro-2-methoxyphenyl)-N-(5-fluoro-2-pyrimidinyl)-2-oxo-1,2-dihydro-6-quinolinesulfonamide | 586.2 | 155 | 0.048 | | $^1$H NMR (500 MHz, DMSO-d$_6$) δ ppm 3.74 (s, 3 H) 4.03 (s, 3 H) 6.81 (d, J = 8.44 Hz, 1 H) 6.84 (d, J = 7.94 Hz, 1 H) 7.39-7.57 (m, 2 H) 7.95-8.04 (m, 1 H) 8.23-8.36 (m, 2 H) 8.49 (d, J = 8.76 Hz, 2 H) 8.62 (s, 2 H) 11.96 (br. s., 1 H). |
| 775 | 1-(4-(5-chloro-2-methoxy-3-pyridinyl)-5-fluoro-2-methoxyphenyl)-2-oxo-N-3-pyridazinyl-1,2-dihydro-6-quinolinesulfonamide | 568.1 | 155 | 0.047 | | $^1$H NMR (500 MHz, DMSO-d$_6$) δ ppm 3.75 (s, 3 H) 4.03 (s, 3 H) 6.79 (d, J = 9.73 Hz, 2 H) 7.38-7.57 (m, 2 H) 7.61-7.76 (m, 1 H) 7.86 (d, J = 8.55 Hz, 1 H) 7.93 (d, J = 8.63 Hz, 1 H) 8.20 (d, J = 8.36 Hz, 1 H) 8.28 (br. s., 2 H) 8.36 (br. s., 1 H) 8.50 (s, 1 H) 14.31-14.63 (m, 1 H). |
| 776 | 1-(4-(5-chloro-2-methoxy-3-pyridinyl)- | 557.0 | 155 | 0.054 | | $^1$H NMR (500 MHz, DMSO-d$_6$) δ ppm 3.75 (s, 3 H) 4.04 (s, 3 H) 6.79 (dd, J = 9.24, 2.37 Hz, 2 |

TABLE 3-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | 5-fluoro-2-methoxyphenyl)-N-1,3-oxazol-2-yl-2-oxo-1,2-dihydro-6-quinolinesulfonamide | | | | | H) 7.28 (s, 1 H) 7.39-7.57 (m, 2 H) 7.61 (s, 1 H) 7.87 (d, J = 8.39 Hz, 1 H) 8.20 (d, J = 9.67 Hz, 1 H) 8.28 (s, 1 H) 8.31-8.38 (m, 1 H) 8.50 (s, 1 H) 11.95-12.40 (m, 1 H). |
| 777 | 1-(4-(5-chloro-2-methoxy-3-pyridinyl)-5-fluoro-2-methoxyphenyl)-N-(6-methyl-4-pyrimidinyl)-2-oxo-1,2-dihydro-6-quinolinesulfonamide | 582.2 | 155 | 0.103 | | $^1$H NMR (500 MHz, DMSO-d$_6$) δ ppm 2.32 (s, 3 H) 3.74 (s, 3 H) 4.03 (s, 3 H) 6.80 (t, J = 8.34 Hz, 2 H) 6.91 (br. s., 1 H) 7.39-7.57 (m, 2 H) 7.92 (d, J = 7.40 Hz, 1 H) 8.21-8.35 (m, 2 H) 8.43 (s, J = 21.99, 21.99 Hz, 1 H) 8.50 (s, 2 H) 11.11-11.59 (m, 1 H). |
| 778 | 1-(4-(5-chloro-2-methoxy-3-pyridinyl)-5-fluoro-2-methoxyphenyl)-N-(2-methyl-4-pyrimidinyl)-2-oxo-1,2-dihydro-6-quinolinesulfonamide | 582.1 | 155 | 0.111 | | $^1$H NMR (500 MHz, DMSO-d$_6$) δ ppm 2.39 (s, 3 H) 3.75 (s, 3 H) 4.03 (s, 3 H) 6.79 (t, J = 8.39 Hz, 2 H) 6.90 (br. s., 1 H) 7.39-7.54 (m, 2 H) 7.90 (d, J = 8.02 Hz, 1 H) 8.13 (d, J = 6.80 Hz, 1 H) 8.20-8.31 (m, 2 H) 8.40 (s, 1 H) 8.50 (s, 1 H) 11.18-11.54 (m, 1 H). |

Additional Examples Representative of the Present Invention

Example 1140

(Method 213): 8-(2-chloro-3'-fluoro-5-methoxy-[1,1'-biphenyl]-4-yl)-N-(isoxazol-3-yl)-7-oxo-7,8-dihydro-1,8-naphthyridine-3-sulfonamide

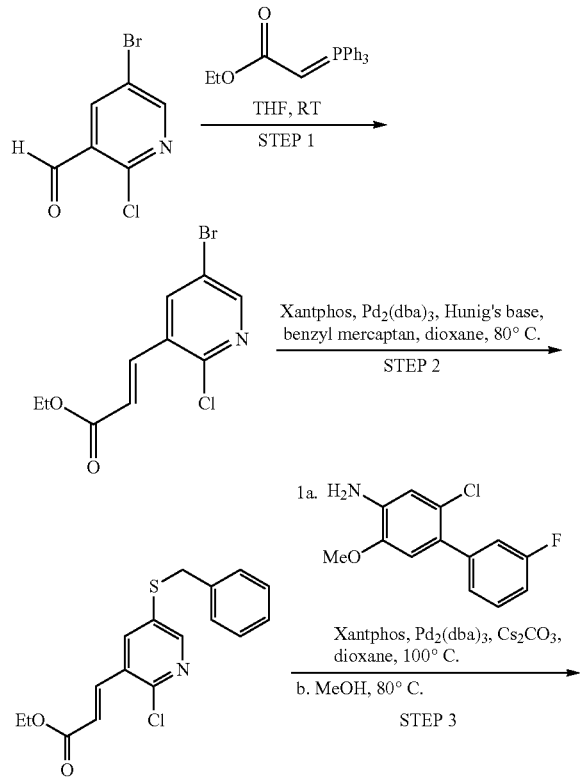

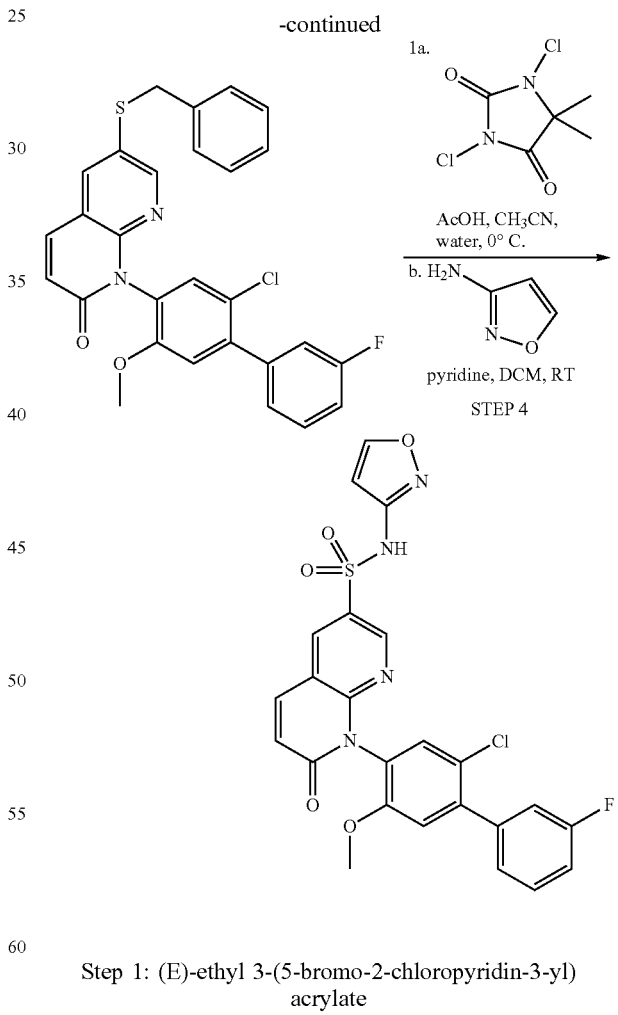

Step 1: (E)-ethyl 3-(5-bromo-2-chloropyridin-3-yl) acrylate

A vial was charged with 5-bromo-2-chloronicotinaldehyde (500 mg, 2.268 mmol, Small Molecules, Inc.) and THF (9072 µl). (Carbethoxymethylene)triphenylphosphorane (830 mg, 2.381 mmol) was added to the solution, and the mixture was stirred at RT for 1.5 h. The crude mixture was loaded onto silica gel and purified using a gradient of 0-50% EtOAc/heptane to provide (E)-ethyl 3-(5-bromo-2-chloropyridin-3-yl)acrylate (660 mg, 2.272 mmol, 100% yield) as a white solid. m/z (ESI) 291.8 (M+H)+.

Step 2: (E)-ethyl 3-(5-(benzylthio)-2-chloropyridin-3-yl)acrylate

A vial was charged with (E)-ethyl 3-(5-bromo-2-chloropyridin-3-yl)acrylate (660 mg, 2.272 mmol), phenylmethanethiol (296 mg, 2.385 mmol), Xantphos (131 mg, 0.227 mmol), Pd$_2$(dba)$_3$ (104 mg, 0.114 mmol), 1,4-dioxane (9086 µl), and Hunig's base (793 µl, 4.54 mmol). The vial was purged with argon and the mixture was heated at 80° C. for 1 h. Water and EtOAc were added, and the layers were separated. The organic portion was dried, filtered and concentrated. The crude material was purified by silica gel chromatography, 0-50% EtOAc/heptane to provide (E)-ethyl 3-(5-(benzylthio)-2-chloropyridin-3-yl)acrylate (790 mg, 2.366 mmol, 104% yield) as a yellow oil. m/z (ESI) 334.0 (M+H)+.

Step 3: 6-(benzylthio)-1-(2-chloro-3'-fluoro-5-methoxy-[1,1'-biphenyl]-4-yl)-1,8-naphthyridin-2(1H)-one A vial was charged with 2-chloro-3'-fluoro-5-methoxy-[1,1'-biphenyl]-4-amine (302 mg, 1.198 mmol), (E)-ethyl 3-(5-(benzylthio)-2-chloropyridin-3-yl)acrylate (400 mg, 1.198 mmol), Xantphos (69.3 mg, 0.120 mmol), Pd$_2$dba$_3$ (54.9 mg, 0.060 mmol), cesium carbonate (781 mg, 2.396 mmol) and 1,4-dioxane (4793 µl). The mixture was purged with argon, the vial was sealed, and the reaction was heated at 100° C. for 5 h. Upon cooling to RT, 10 mL methanol was added, and the mixture was heated at 80° C. for 2 h. Upon cooling to RT the mixture was loaded onto silica gel and purified using 0-50% EtOAc/heptane to provide 6-(benzylthio)-1-(2-chloro-3'-fluoro-5-methoxy-[1,1'-biphenyl]-4-yl)-1,8-naphthyridin-2(1H)-one (410 mg, 0.815 mmol, 68.0% yield) as a light orange foamy solid. m/z (ESI) 503.0 (M+H)+.

Step 4: 8-(2-chloro-3'-fluoro-5-methoxy-[1,1'-biphenyl]-4-yl)-N-(isoxazol-3-yl)-7-oxo-7,8-dihydro-1,8-naphthyridine-3-sulfonamide A vial was charged with 6-(benzylthio)-1-(2-chloro-3'-fluoro-5-methoxy-[1,1'-biphenyl]-4-yl)-1,8-naphthyridin-2(1H)-one (100 mg, 0.199 mmol), acetonitrile (935 µl), acetic acid (35.5 dl) and water (23.38 µl). The solution was cooled to 0° C. and 1,3-dichloro-5,5-dimethylimidazolidine-2,4-dione (50.9 mg, 0.258 mmol) was added. After 30 min, LCMS showed trace sulfoxide remained and the majority was desired sulfonyl chloride. Another 20 mg hydantoin was added, and after 20 min conversion was complete. Solid sodium bisulfite was added, followed by water and EtOAc. After stirring for 5 min, the layers were separated. The aqueous portion was extracted with EtOAc, and the combined organic portions were dried with sodium sulfate, filtered and concentrated. The crude material was taken up in 1 mL DCM. Isoxazol-3-amine (33.4 mg, 0.398 mmol) and then pyridine (80 µl, 0.994 mmol) were added, and the mixture was stirred at RT overnight. EtOAc and 1N HCl were added, and the layers were separated. The aqueous portion was extracted with additional EtOAc, and the combined organics were dried with sodium sulfate, filtered and concentrated. The crude material was purified by reverse phase chromatography, 20-70% 0.1% TFA/ACN in water to provide 8-(2-chloro-3'-fluoro-5-methoxy-[1,1'-biphenyl]-4-yl)-N-(isoxazol-3-yl)-7-oxo-7,8-dihydro-1,8-naphthyridine-3-sulfonamide (25 mg, 0.047 mmol, 23.86% yield) as a white solid after lyophilization. $^1$H NMR (400 MHz, DMSO-d$_6$) δ ppm 3.70 (s, 3H) 6.47-6.52 (m, 1H) 6.88-6.95 (m, 1H) 7.25-7.28 (m, 1H) 7.28-7.34 (m, 1H) 7.41-7.47 (m, 2H) 7.54-7.61 (m, 1H) 7.63 (s, 1H) 8.23-8.31 (m, 1H) 8.78 (d, J=1.87 Hz, 2H) 8.84-8.88 (m, 1H) 11.88 (br s, 1H). m/z (ESI) 525.0 (M−H)−.

Example 1141

(Method 214): 1-(2,4'-difluoro-5-methoxy-4-biphenylyl)-N-3-isoxazolyl-2-oxo-1,2-dihydro-6-quinoxalinesulfonamide

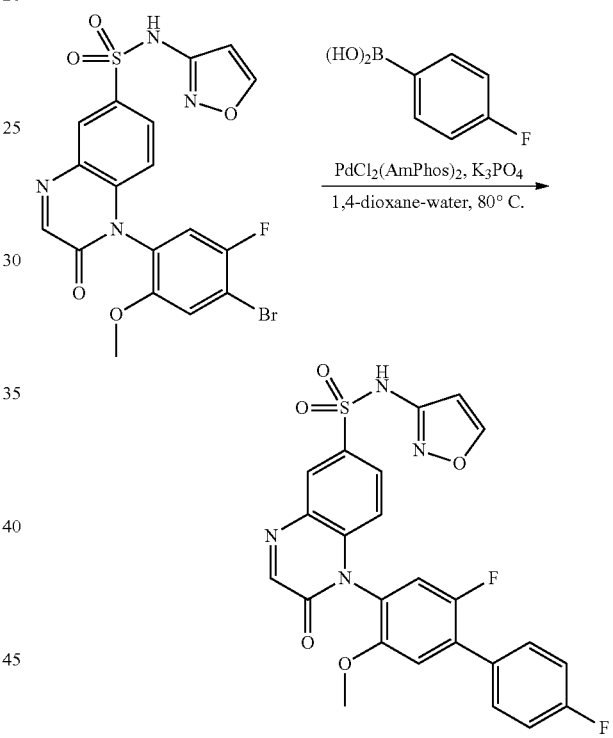

A vial was charged with 1-(4-bromo-5-fluoro-2-methoxyphenyl)-N-(isoxazol-3-yl)-2-oxo-1,2-dihydroquinoxaline-6-sulfonamide (201.5 mg, 0.407 mmol), (4-fluorophenyl)boronic acid (114 mg, 0.814 mmol), 1,1-bis[(di-t-butyl-p-methylaminophenyl]palladium(ii) chloride (28.8 mg, 0.041 mmol), and potassium phosphate (259 mg, 1.221 mmol). The vial was flushed with Ar (g), then 1,4-dioxane (1627 µl) and water (407 µl) were added. The vial was sealed and heated to 80° C. for 30 min. The mixture was cooled, the layers were separated, and the aq. layer was extracted with EtOAc. The combined organic extracts were dried over sodium sulfate, filtered, and concentrated. The residue was dissolved in MeOH and filtered through a 0.2 micron filter. The filtrate was purified by reverse-phase HPLC (25-70% CH$_3$CN/H$_2$O with 0.1% TFA). Fractions containing clean desired product were combined and lyophilized to give 1-(2,4'-difluoro-5-methoxy-4-biphenylyl)-N-3-isoxazolyl-2-oxo-1,2-dihydro-6-quinoxalinesulfonamide (107 mg, 82% yield) as an off-white solid. $^1$H NMR (400 MHz, DMSO-$d_6$) δ=11.76 (s, 1H), 8.76 (d, J=1.9 Hz, 1H), 8.50 (s, 1H), 8.32 (d, J=2.2 Hz, 1H), 7.95 (dd, J=2.3, 8.9 Hz, 1H), 7.76 (ddd, J=1.5, 5.4, 8.8 Hz, 2H), 7.56 (d, J=10.3 Hz, 1H), 7.46-7.37 (m, 3H), 7.01 (d, J=8.9 Hz, 1H), 6.49 (d, J=2.0 Hz, 1H), 3.80 (s, 3H). m/z (ESI) 511.0 (M+H)$^+$.

Example 1142

(Method 215): 1-(4-(cyclopentylethynyl)-5-fluoro-2-methoxyphenyl)-N-3-isoxazolyl-2-oxo-1,2-dihydro-6-quinoxalinesulfonamide

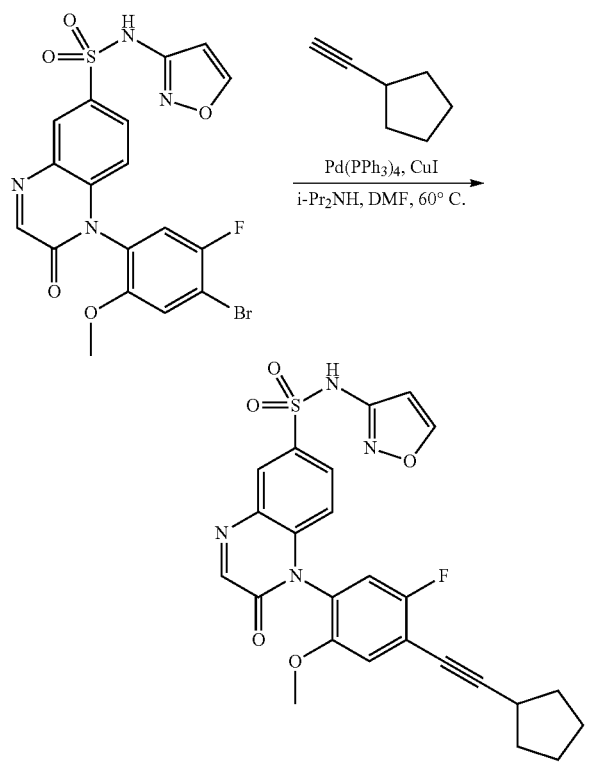

A vial was charged with 1-(4-bromo-5-fluoro-2-methoxyphenyl)-N-(isoxazol-3-yl)-2-oxo-1,2-dihydroquinoxaline-6-sulfonamide (147.0 mg, 0.297 mmol), copper(i) iodide (8.48 mg, 0.045 mmol), and Pd(PPh$_3$)$_4$ (34.3 mg, 0.030 mmol). The vial was flushed with Ar (g), then DMF (1484 μl), N,N-diisopropylamine (423 μl, 2.97 mmol), and ethynylcyclopentane (140 mg, 1.484 mmol) were added in sequence. The vial was sealed and heated to 60° C. for 1 h. The mixture was cooled, diluted with EtOAc, washed with 2N aq. HCl (2x), dried over sodium sulfate, filtered, and concentrated. The residue was taken up in DMSO-MeOH and filtered through a 0.2 micron filter. The filtrate was purified by reverse-phase HPLC (25-75 CH$_3$CN/H$_2$O with 0.1% TFA). Fractions containing desired product were combined and lyophilized to give 1-(4-(cyclopentylethynyl)-5-fluoro-2-methoxyphenyl)-N-3-isoxazolyl-2-oxo-1,2-dihydro-6-quinoxalinesulfonamide (98.2 mg, 65%) as a yellow solid. $^1$H NMR (400 MHz, DMSO-$d_6$) δ=11.74 (s, 1H), 8.75 (d, J=2.0 Hz, 1H), 8.47 (s, 1H), 8.30 (d, J=2.3 Hz, 1H), 7.90 (dd, J=2.2, 8.8 Hz, 1H), 7.48 (d, J=9.1 Hz, 1H), 7.38 (d, J=6.3 Hz, 1H), 6.95 (d, J=8.9 Hz, 1H), 6.49 (d, J=2.0 Hz, 1H), 3.67 s, 3H), 2.98 (t, J=7.3 Hz, 1H), 2.09-1.98 (m, 2H), 1.80-1.58 (m, 6H). m/z (ESI) 509.2 (M+H)$^+$.

Example 1143

(Method 216): 1-((1R,3R)-3-(3-fluorophenyl)cyclopentyl)-N-3-isoxazolyl-2-oxo-1,2-dihydro-6-quinolinesulfonamide, 1-((1R,3S)-3-(3-fluorophenyl)cyclopentyl)-N-3-isoxazolyl-2-oxo-1,2-dihydro-6-quinolinesulfonamide, 1-((1S,3R)-3-(3-fluorophenyl)cyclopentyl)-N-3-isoxazolyl-2-oxo-1,2-dihydro-6-quinolinesulfonamide, 1-((1S,3S)-3-(3-fluorophenyl)cyclopentyl)-N-3-isoxazolyl-2-oxo-1,2-dihydro-6-quinolinesulfonamide

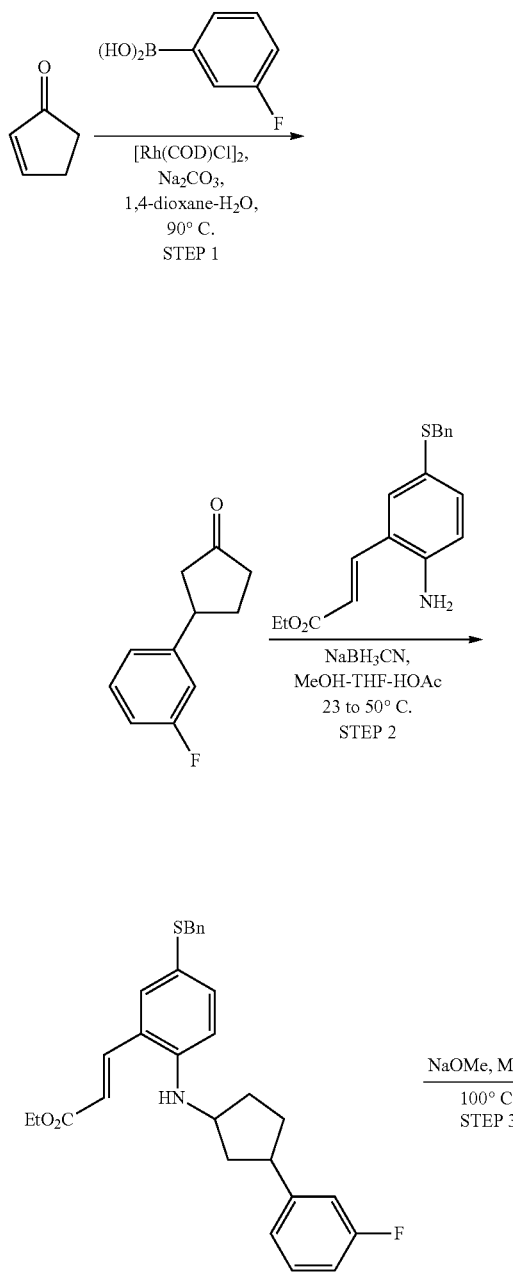

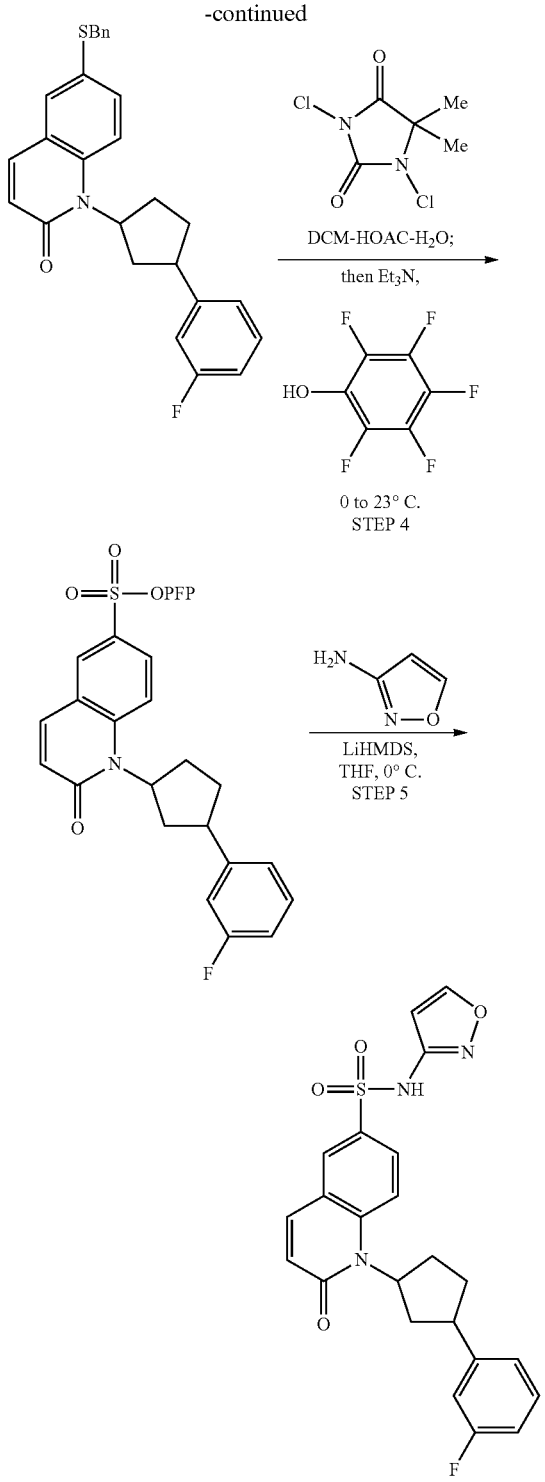

Step 1: 3-(3-fluorophenyl)cyclopentanone

A 40 mL vial was charged with (3-fluorophenyl)boronic acid (1.278 g, 9.14 mmol) and purged with nitrogen for 10 min. The reaction vessel was then sequentially charged with dioxane (15.2 mL), an aqueous solution of sodium carbonate (5.1 mL, 1.9 M), and 2-cyclopenten-1-one (0.510 ml, 6.09 mmol) via syringe. Chloro(1,5-cyclooctadiene)rhodium (I) dimer (0.090 g, 0.183 mmol) was introduced in a single portion. The vial was sealed with a PTFE line cap and the resultant reaction mixture was heated to 90° C. After 2 h, the reaction mixture was allowed to cool to RT and poured into a mixture of water (30 mL) and EtOAc (30 mL). The layers were separated and the aqueous layer was extracted with EtOAc (2×30 mL). The combined organic layers were dried over anhydrous magnesium sulfate, filtered, and concentrated under reduced pressure. The residue was purified by flash column chromatography (50-g Biotage column, eluent: gradient, 0 to 100% EtOAc in heptane with 10% $CH_2Cl_2$ as an additive) to afford 3-(3-fluorophenyl)cyclopentanone (668 mg, 3.75 mmol, 61.6% yield) as a clear oil. $^1$H NMR (400 MHz, CHLOROFORM-d) δ=7.37-7.23 (m, 1H), 7.08-6.99 (m, 1H), 6.99-6.89 (m, 1H), 3.50-3.33 (m, 1H), 2.68 (dd, J=7.7, 18.3 Hz, 1H), 2.53-2.40 (m, 2H), 2.39-2.25 (m, 2H), 2.05-1.90 (m, 1H). m/z (ESI) 179.2 (+H)$^+$.

Step 2: (E)-ethyl 3-(5-(benzylthio)-2-((3-(3-fluorophenyl)cyclopentyl)amino)phenyl)acrylate A 40-mL vial was charged with (E)-ethyl 3-(2-amino-5-(benzylthio)phenyl)acrylate (1.2 g, 3.73 mmol) and 3-(3-fluorophenyl)cyclopentanone (665 mg, 3.73 mmol) then purged with nitrogen for 10 min. Methanol (16.0 ml), tetrahydrofuran (4.0 ml), and acetic acid (1.89 ml, 33.0 mmol) were sequentially introduced. Sodium cyanoborohydride (469 mg, 7.46 mmol) was then added in a single portion to the yellow reaction mixture. The vial was sealed with a PTFE line cap and the solution stirred vigorously at ambient temperature. After 16 h, the reaction mixture was heated to 50° C. After 22 h, the reaction mixture was allowed to cool to ambient temperature and carefully poured into a mixture of ice and a saturated aqueous solution of sodium bicarbonate. The mixture was stirred until it reached ambient temperature then it was diluted with EtOAc (30 mL) and the layers were separated. The aqueous layer was further extracted with EtOAc (3×50 mL). The combined organic layers were washed with saturated aqueous sodium bicarbonate solution (100 mL) and brine (100 mL), dried over anhydrous magnesium sulfate, filtered, and concentrated under reduced pressure. The residue was then purified by flash column chromatography (50-g Biotage column, eluent: gradient, 20 to 70% EtOAc in heptane with $CH_2Cl_2$ as a 10% additive) to afford (E)-ethyl 3-(5-(benzylthio)-2-((3-(3-fluorophenyl)cyclopentyl)amino)phenyl)acrylate (812 mg, 1.707 mmol, 45.8% yield) as a yellow solid. m/z (ESI) 476.2 (M+H)$^+$.

Step 3: 6-(benzylthio)-1-(3-(3-fluorophenyl)cyclopentyl)quinolin-2(1H)-one

A 25-mL pressure vessel was charged with (E)-ethyl 3-(5-(benzylthio)-2-((3-(3-fluorophenyl)cyclopentyl)amino)phenyl)acrylate (800 mg, 1.682 mmol), methanol (8.4 ml), and a solution of sodium methoxide in methanol (0.5 M, 3.4 mL, 1.682 mmol). The reaction vessel was sealed with a Teflon cap and the yellow reaction mixture was warmed to 100° C. After 36 h, additional solution of sodium methoxide in methanol (0.5 M, 3.4 mL, 1.682 mmol) was added and the reaction vessel was sealed and warmed to 100° C. After 12 h, the reaction mixture was allowed to cool to ambient temperature and concentrated under reduced pressure to furnish a yellow residue, which was purified by flash column chromatography (50-g Biotage column, eluent: gradient, 20 to 30% EtOAc in heptane) to afford 6-(benzylthio)-1-(3-(3-fluorophenyl)cyclopentyl)quinolin-2(1H)-one (170 mg, 0.396 mmol, 23.53% yield). m/z (ESI) 430.1 (M+H)+.

Step 4: Perfluorophenyl 1-(3-(3-fluorophenyl)cyclopentyl)-2-oxo-1,2-dihydroquinoline-6-sulfonate A 10-mL RBF was charged with 6-(benzylthio)-1-(3-(3-fluorophenyl)cyclopentyl) quinolin-2(1H)-one (167 mg, 0.389 mmol), dichloromethane (3.7 mL), acetic acid (93 μl), and water (93 μl). The reaction mixture was cooled to 0° C. in an ice water bath for 10 minutes before 1,3-dichloro-5,5-dimethylhydantoin (191 mg, 0.972 mmol) was added in one portion. After 30 minutes, 2,3,4,5,6-pentafluorophenol (107 mg, 0.583 mmol) was added in one portion and the resultant solution stirred for 2 min before triethylamine (216 μl, 1.555 mmol) was added dropwise via syringe. The resultant solution was allowed to warm to ambient temperature. After 30 min, the reaction mixture was concentrated to ca. 1 mL under reduced pressure and purified by flash column chromatography (25-g Biotage column, eluent: gradient, 0 to 50% EtOAc in heptane) to afford perfluorophenyl 1-(3-(3-fluorophenyl)cyclopentyl)-2-oxo-1,2-dihydroquinoline-6-sulfonate (114 mg, 0.206 mmol, 53.0% yield) as a white solid. $^1$H NMR (400 MHz, DMSO-d$_6$) δ ppm 8.53 (d, J=2.28 Hz, 1H) 8.16 (ddd, J=9.12, 3.32, 2.38 Hz, 1H) 8.08-8.14 (m, 2H) 7.33-7.40 (m, 1H) 7.17-7.25 (m, 2H) 7.00-7.08 (m, 1H) 6.80 (dd, J=9.43, 0.83 Hz, 1H) 5.52-5.87 (m, 1H) 3.67-3.92 (m, 1H) 2.01-2.47 (m, 7H) 1.82 (qd, J=1.94, 6.48 Hz, 1H). m/z (ESI) 554.2 (M+H)+.

Step 5: 1-((1R,3R)-3-(3-fluorophenyl)cyclopentyl)-N-3-isoxazolyl-2-oxo-1,2-dihydro-6-quinolinesulfonamide, 1-((1R,3S)-3-(3-fluorophenyl)cyclopentyl)-N-3-isoxazolyl-2-oxo-1,2-dihydro-6-quinolinesulfonamide, 1-((1S,3R)-3-(3-fluorophenyl)cyclopentyl)-N-3-isoxazolyl-2-oxo-1,2-dihydro-6-quinolinesulfonamide, 1-((1S,3S)-3-(3-fluorophenyl)cyclopentyl)-N-3-isoxazolyl-2-oxo-1,2-dihydro-6-quinolinesulfonamide A 10-mL RBF was charged with perfluorophenyl 1-(3-(3-fluorophenyl)cyclopentyl)-2-oxo-1,2-dihydroquinoline-6-sulfonate (110 mg, 0.199 mmol) then purged with nitrogen for 10 min. Tetrahydrofuran (732 μL) and 3-aminoisoxazole (19.09 μl, 0.258 mmol) were sequentially introduced and the resultant solution cooled to 0° C. A solution of lithium bis(trimethylsilyl)amide in tetrahydrofuran (1.0 M, 457 μL, 0.457 mmol) was added dropwise via syringe to the stirred reaction mixture over 3 min. After 15 min, 1.0 N HCl (5 mL) was introduced and the resultant reaction mixture was allowed to warm to ambient temperature.

The mixture was diluted with and EtOAc (10 mL) and the layers were separated, and the aqueous layer was further extracted with EtOAc (3×10 mL). The combined organic layers were then washed with brine (20 mL), dried over anhydrous magnesium sulfate, filtered, concentrated under reduced pressure and purified by flash column chromatography (25-g Biotage Snap Ultra Column, eluent: gradient, 0 to 100% EtOAc in hexanes with CH$_2$Cl$_2$ as a 10% additive) to afford 1-((1R,3R)-3-(3-fluorophenyl)cyclopentyl)-N-3-isoxazolyl-2-oxo-1,2-dihydro-6-quinolinesulfonamide, 1-((1R,3S)-3-(3-fluorophenyl)cyclopentyl)-N-3-isoxazolyl-2-oxo-1,2-dihydro-6-quinolinesulfonamide, 1-((1S,3R)-3-(3-fluorophenyl)cyclopentyl)-N-3-isoxazolyl-2-oxo-1,2-dihydro-6-quinolinesulfonamide, 1-((1S,3S)-3-(3-fluorophenyl)cyclopentyl)-N-3-isoxazolyl-2-oxo-1,2-dihydro-6-quinolinesulfonamide (50 mg, 0.110 mmol, 55.5% yield)—one unassigned diastereomer was isolated, mixture of enantiomers (since unassigned stereochemistry—listing all the possible products). $^1$H NMR (400 MHz, DMSO-d6) δ ppm 11.65 (s, 1H) 8.73 (d, J=1.76 Hz, 1H) 8.32 (dd, J=6.22, 1.35 Hz, 1H) 8.08 (d, J=9.54 Hz, 1H) 8.01 (m, J=1.60 Hz, 2H) 7.31-7.42 (m, 1H) 7.14-7.24 (m, 2H) 6.97-7.08 (m, 1H) 6.71 (d, J=9.43 Hz, 1H) 6.47 (d, J=1.76 Hz, 1H) 5.88 (d, J=1.76 Hz, 1H) 5.51-5.71 (m, 1H) 3.70-3.91 (m, 1H) 3.16-3.29 (m, 1H) 2.01-2.47 (m, 5H) 1.70-1.87 (m, 1H). m/z (ESI) 454.0 (M+H)+.

Example 1144

(Method 217): (P)-1-(5-chloro-4-cyclopropyl-2-methoxyphenyl)-N-3-isoxazolyl-2-oxo-1,2-dihydro-6-quinolinesulfonamide

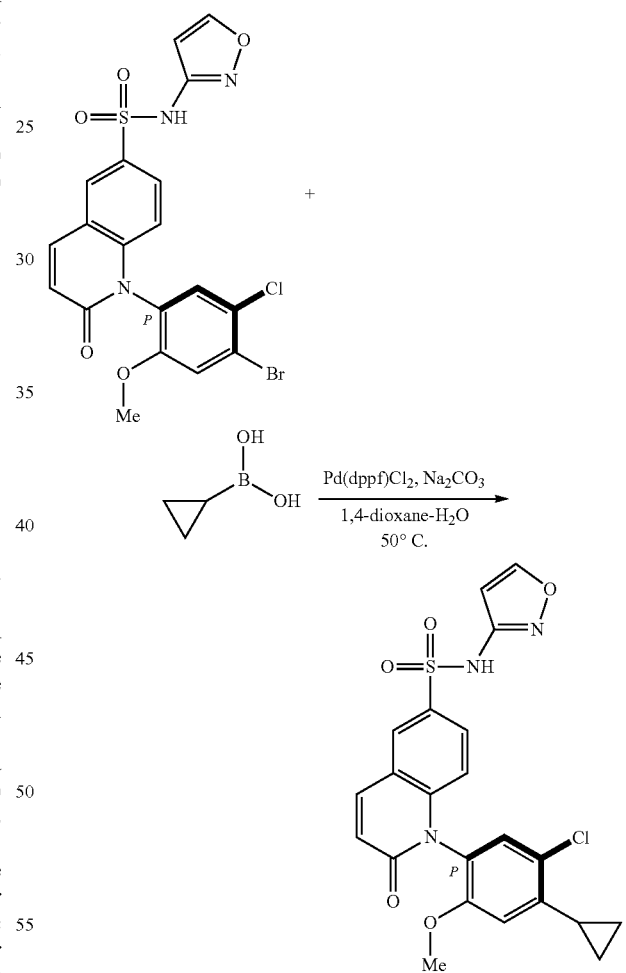

A 20-mL vial was charged with (P)-1-(4-bromo-5-chloro-2-methoxyphenyl)-N-(isoxazol-3-yl)-2-oxo-1,2-dihydroquinoline-6-sulfonamide (172 mg, 0.337 mmol), cyclopropyl boronic acid (52.1 μl, 0.674 mmol), and (1,1'-bis(diphenylphosphino) ferrocene)dichloropalladium(II) (123 mg, 0.168 mmol) then purged with nitrogen. The reaction vessel was then sequentially charged with dioxane (2.5 mL) and an aqueous solution of sodium carbonate (1.9 M, 0.84 mL) via syringe. The vial was sealed with a PTFE line cap and the resultant red reaction mixture was heated to 50° C. After 16 h, the reaction mixture was allowed to cool to ambient temperature and an aqueous solution of 1.0 N HCL (5 mL) was added and the mixture was diluted with EtOAc (5 mL). The layers were separated and the aqueous layer was extracted with EtOAc (3×5 mL). The combined organic layers were washed with brine (25 mL), dried over anhydrous sodium sulfate, filtered, and concentrated under reduced pressure to furnish a tan oil, which was purified by flash column chromatography (12-g Redi-Sep Gold column, eluent: gradient, 0 to 100% EtOAc in heptane with 10% $CH_2Cl_2$ as an additive) to afford (P)-1-(5-chloro-4-cyclopropyl-2-methoxyphenyl)-N-3-isoxazolyl-2-oxo-1,2-dihydro-6-quinolinesulfonamide (35.4 mg, 0.075 mmol, 22.27% yield) as a white amorphous solid. $^1$H NMR (400 MHz, DMSO-$d_6$) δ ppm 11.65 (s, 1H) 8.73 (d, J=1.76 Hz, 1H) 8.35 (d, J=2.18 Hz, 1H) 8.20 (d, J=9.54 Hz, 1H) 7.84 (dd, J=8.97, 2.23 Hz, 1H) 7.48 (s, 1H) 6.71-6.86 (m, 3H) 6.44 (d, J=1.76 Hz, 1H) 3.67 (s, 3H) 2.25 (tt, J=8.44, 5.25 Hz, 1H) 1.07-1.15 (m, 2H) 0.84-1.00 (m, 2H). m/z (ESI) 472.0 (M+H)$^+$.

Example 1145

(Method 218): (±)-1-((1S,2S)-2-methoxycyclohexyl)-2-oxo-N-1,2,4-thiadiazol-5-yl-1,2-dihydro-6-quinolinesulfonamide

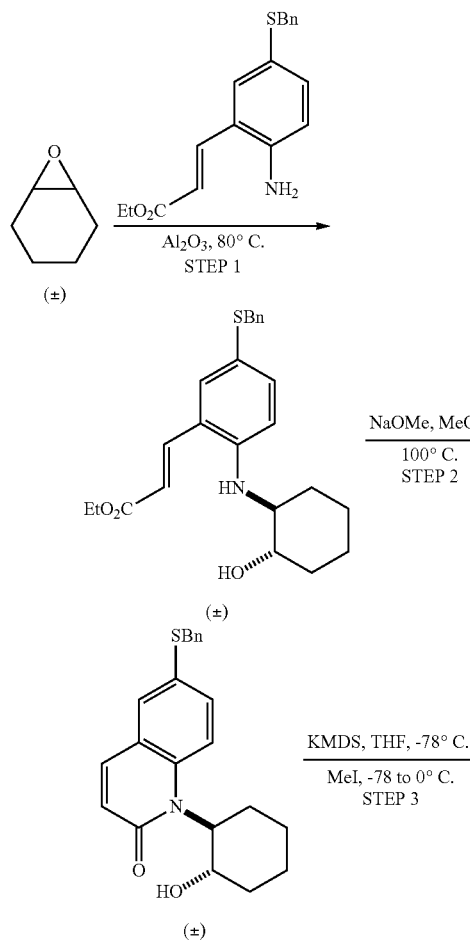

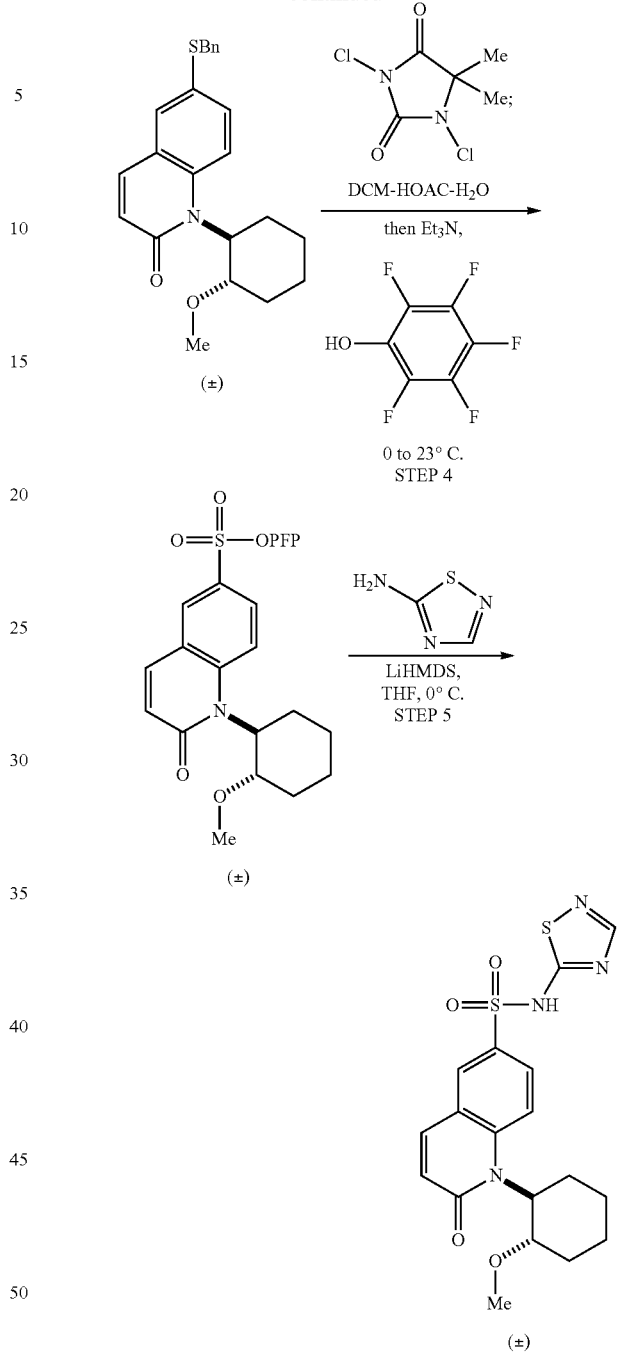

Step 1: (±)-(E)-ethyl 3-(5-(benzylthio)-2-((2-hydroxycyclohexyl)amino)phenyl)acrylate A 100-mL pressure vessel was charged with (E)-ethyl 3-(2-amino-5-(benzylthio)phenyl)acrylate (3 g, 9.57 mmol), toluene (31.9 ml), cyclohexene oxide (2.91 ml, 28.7 mmol), and activated $Al_2O_3$ (24 g, 9.57 mmol) (dried at 150° C. for 16 h). The reaction vessel was sealed with a Teflon cap and the yellow reaction mixture was warmed to 80° C. After 16 h, additional cyclohexene oxide (2.91 ml, 28.7 mmol) and activated $Al_2O_3$ (10 g, 3.98 mmol) was added and the reaction vessel was sealed with a Teflon cap and warmed to 80° C. After 48 h, the reaction mixture was allowed to cool to RT then filtered through a fritted funnel and the pad of Al₂O₃ was eluted with EtOAc (2×100 mL). The filtrate was concentrated under reduced pressure to furnish a yellow residue which was purified by flash column chromatography (100-g Biotage column, eluent: gradient, 0 to 50% EtOAc in heptane) to afford (±)-(E)-ethyl 3-(5-(benzylthio)-2-((2-hydroxycyclohexyl)amino)phenyl) acrylate (3.5 g, 8.50 mmol, 89% yield) as a yellow oil. ¹H NMR (400 MHz, DMSO-d6) δ=7.84 (d, J=15.7 Hz, 1H), 7.37 (d, J=2.3 Hz, 1H), 7.31-7.18 (m, 6H), 7.14 (dd, J=2.2, 8.7 Hz, 1H), 6.65 (d, J=8.9 Hz, 1H), 6.27 (d, J=15.5 Hz, 1H), 5.48 (d, J=6.8 Hz, 1H), 4.75 (d, J=5.0 Hz, 1H), 4.03 (s, 1H), 3.52-3.39 (m, 1H), 3.20-3.11 (m, 1H), 3.07 (d, J=8.9 Hz, 1H), 1.90 (d, J=9.7 Hz, 1H), 1.80 (d, J=2.5 Hz, 1H), 1.70-1.50 (m, 2H), 1.21-1.05 (m, 2H). m/z (ESI) 412.0 (M+H)⁺.

Step 2: (±)-6-(benzylthio)-1-((1R,2R)-2-hydroxycyclohexyl)quinolin-2(1H)-one

A 25-mL pressure vessel was charged with (E)-ethyl 3-(5-(benzylthio)-2-((2-hydroxycyclohexyl)amino)phenyl) acrylate (2.36 g, 5.73 mmol), methanol (10 ml), and a solution of sodium methoxide in methanol (25 wt. %, 2.64 mL, 11.47 mmol). The reaction vessel was sealed with a Teflon cap and the yellow reaction mixture was warmed to 70° C. After 16 h, additional solution of sodium methoxide in methanol (25 wt. %, 1.9 mL, 8.25 mmol) was added and the reaction vessel was sealed and warmed to 100° C. After 20 h, the reaction mixture was allowed to cool to ambient temperature and concentrated under reduced pressure to furnish a yellow residue which was purified by flash column chromatography (50-g Biotage column, eluent: gradient, 20 to 70% EtOAc in heptane) to afford 6-(benzylthio)-1-((1R,2R)-2-hydroxycyclohexyl)quinolin-2(1H)-one (469 mg, 1.283 mmol, 22.38% yield) as a yellow syrup. m/z (ESI) 366.1 (M+H)⁺.

Step 3: (±)-6-(benzylthio)-1-((1S,2S)-2-methoxycyclohexyl)quinolin-2(1H)-one

A 10-mL RBF was charged with 6-(benzylthio)-1-((1R,2R)-2-hydroxycyclohexyl)quinolin-2(1H)-one (150 mg, 0.410 mmol) and purged with nitrogen for 10 min. THF (2.1 mL) was introduced and the resultant solution cooled to −78° C. A solution of potassium bis(trimethylsilyl)amide in tetrahydrofuran (1.0 M, 451 µl, 0.451 mmol) was added dropwise to the stirred reaction mixture over 2 min via syringe to produce a dark purple solution. After 15 min, iodomethane (28.0 µl, 0.451 mmol) was added dropwise via syringe and the resultant reaction mixture was allowed to warm to 0° C. After 15 min, a solution of saturated aqueous ammonium chloride was added and the reaction mixture was allowed to warm to ambient temperature and diluted with EtOAc (10 mL). The layers were separated, and the aqueous layer was further extracted with EtOAc (3×10 mL). The combined organic layers were then washed with brine (20 mL), dried over anhydrous magnesium sulfate, filtered, and concentrated under reduced pressure. The residue was purified by flash column chromatography (25-g Biotage column, eluent: gradient, 0 to 20% EtOAc in heptane) to afford (±)-6-(benzylthio)-1-((1R,2R)-2-methoxycyclohexyl)quinolin-2(1H)-one (119 mg, 0.314 mmol, 76% yield) as a yellow solid. m/z (ESI) 380.2 (M+H)⁺.

Step 4: (±)-perfluorophenyl 1-((1S,2S)-2-methoxycyclohexyl)-2-oxo-1,2-dihydroquinoline-6-sulfonate A 10-mL RBF was charged with (±)-6-(benzylthio)-1-(3-(3-fluorophenyl)cyclopentyl)quinolin-2(1H)-one (119 mg, 0.314 mmol), dichloromethane (3.0 mL), acetic acid (74.7 µL), and water (74.7 µL). The reaction mixture was cooled to 0° C. in an ice water bath for 10 minutes before 1,3-dichloro-5,5-dimethylhydantoin (154 mg, 0.784 mmol) was added in one portion. After 30 minutes, 2,3,4,5,6-pentafluorophenol (87 mg, 0.470 mmol) was added in one portion and the resultant solution stirred for 2 min before triethylamine (174 µL, 1.25 mmol) was added dropwise via syringe. The resultant solution was allowed to warm to ambient temperature. After 30 min, the reaction mixture was concentrated to ca. 1 mL under reduced pressure and purified by flash column chromatography (25-g Biotage column, eluent: gradient, 0 to 50% EtOAc in heptane) to afford (±)-perfluorophenyl 1-(2-methoxycyclohexyl)-2-oxo-1,2-dihydroquinoline-6-sulfonate (131.7 mg, 0.262 mmol, 83% yield) as a white solid. m/z (ESI) 504.1 (M+H)⁺.

Step 5: (±)-1-((1S,2S)-2-methoxycyclohexyl)-2-oxo-N-1,2,4-thiadiazol-5-yl-1,2-dihydro-6-quinolinesulfonamide A 10-mL RBF was charged with (±)-perfluorophenyl 1-(2-methoxycyclohexyl)-2-oxo-1,2-dihydroquinoline-6-sulfonate (65 mg, 0.129 mmol), 5-amino-1,2,4-thiadiazole (19.6 mg, 0.194 mmol) then purged with nitrogen for 10 min. Tetrahydrofuran (323 µL) and dimethyl sulfoxide (990 µL) were sequentially introduced via syringe and the resultant solution cooled to 0° C. A solution of lithium bis(trimethylsilyl)amide in tetrahydrofuran (1.0 M, (871 µL, 0.871 mmol) was added dropwise via syringe to the stirred reaction mixture over 3 min. After 15 min, 1.0 N HCl (5 mL) was introduced and the resultant reaction mixture was allowed to warm to ambient temperature. The mixture was diluted with and EtOAc (10 mL) and the layers were separated, and the aqueous layer was further extracted with EtOAc (3×10 mL). The combined organic layers were then washed with brine (20 mL), dried over anhydrous magnesium sulfate, filtered, concentrated under reduced pressure. The residue was dissolved in DMSO (2 mL), filtered through a 0.2 micron filter, and purified by reverse-phase HPLC (Waters XBridge Prep Shield RP18 10 µm OBD 19×100 mm) gradient, 20 to 75% MeCN in water (containing 0.1% trifluoroacetic acid as an additive), flow rate 40 mL/min to afford 1-((1S,2S)-2-methoxycyclohexyl)-2-oxo-N-1,2,4-thiadiazol-5-yl-1,2-dihydro-6-quinolinesulfonamide (21 mg, 0.050 mmol, 38.7% yield, mixture of enantiomers) as a white solid. ¹H NMR (500 MHz, DMSO-d₆) δ ppm 8.44 (s, 1H) 8.20 (s, 1H) 8.04 (d, J=9.54 Hz, 1H) 7.90-7.96 (m, 1H) 7.84-7.90 (m, 1H) 6.61 (d, J=9.47 Hz, 1H) 4.41 (br. s., 2H) 3.03 (s, 3H) 2.90 (br. s., 1H) 2.22 (d, J=11.48 Hz, 1H) 1.61-1.85 (m, 3H) 1.38-1.57 (m, 1H) 1.07-1.37 (m, 2H). m/z (ESI) 421.2 (M+H)⁺.

Example 1146

(Method 219): 1-(5-(cyanomethyl)-2-methoxyphenyl)-N-3-isoxazolyl-2-oxo-1,2-dihydro-6-quinolinesulfonamide

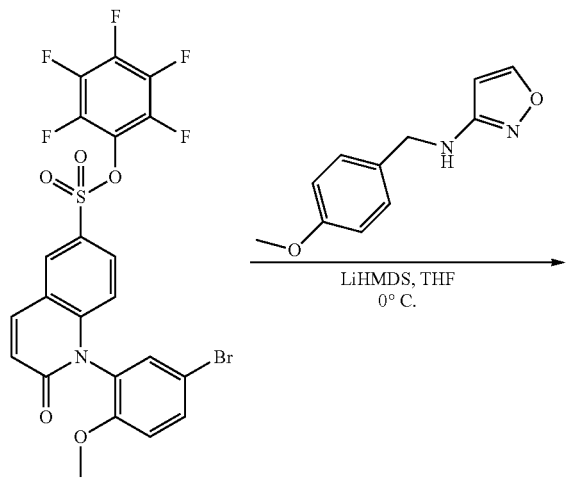

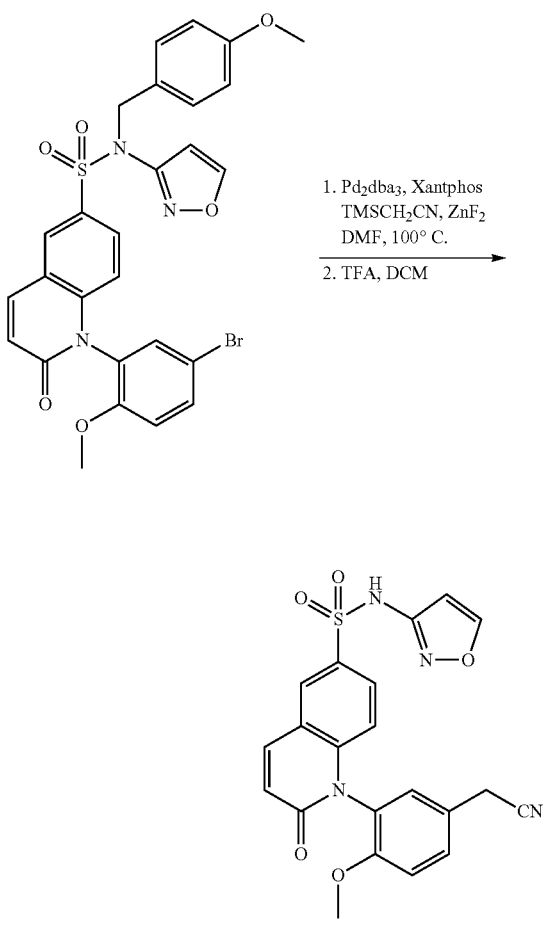

Step 1: 1-(5-bromo-2-methoxyphenyl)-N-(isoxazol-3-yl)-N-(4-methoxybenzyl)-2-oxo-1,2-dihydroquinoline-6-sulfonamide A flask containing perfluorophenyl 1-(5-bromo-2-methoxyphenyl)-2-oxo-1,2-dihydroquinoline-6-sulfonate (3.65 g, 6.33 mmol) and N-(4-methoxybenzyl)isoxazol-3-amine (1.358 g, 6.65 mmol) was flushed with nitrogen and then charged with THF (63.3 ml) and cooled to 0° C. Lithium bis(trimethylsilyl)amide (1.0M in THF) (6.97 ml, 6.97 mmol) was added slowly, and the solution was stirred at 0° C. for 45 minutes until complete consumption of starting material. The reaction was quenched with water and extracted (×3) with EtOAc. The combined organics were washed with brine, dried over sodium sulfate, filtered and concentrated in vacuo. The crude solid was triturated in IPA and filtered, washing well with IPA, to yield 1-(5-bromo-2-methoxyphenyl)-N-(isoxazol-3-yl)-N-(4-methoxybenzyl)-2-oxo-1,2-dihydroquinoline-6-sulfonamide (2.65 g, 4.44 mmol, 70.1% yield) as a white solid. m/z (ESI) 596.0 (M+H)$^+$.

Step 2: 1-(5-(cyanomethyl)-2-methoxyphenyl)-N-3-isoxazolyl-2-oxo-1,2-dihydro-6-quinolinesulfonamide To a mixture of Xantphos (0.049 g, 0.084 mmol), Pd$_2$(dba)$_3$ (0.077 g, 0.084 mmol) and 1-(5-bromo-2-methoxyphenyl)-N-(isoxazol-3-yl)-N-(4-methoxybenzyl)-2-oxo-1,2-dihydroquinoline-6-sulfonamide (0.500 g, 0.838 mmol) in N,N-dimethylformamide (0.838 ml) was added (trimethylsilyl)acetonitrile (0.138 ml, 1.006 mmol) followed by zinc difluoride (0.061 g, 0.587 mmol). The flask was sealed under an atmosphere of nitrogen and heated at 100° C. overnight. The reaction was diluted with water and extracted with DCM (×2). The combined organics were washed with brine, dried over sodium sulfate, filtered and concentrated in vacuo. The crude material was taken up in DCM and purified via MPLC, eluting with 0-100% ethyl acetate in heptanes with a 5% DCM additive, followed by reverse-phase preparative HPLC (XBridge Prep C18 column, 10 micron OBD, 19×100 mm), 0.1% TFA in CH$_3$CN/H$_2$O, gradient 25% to 95% over 12 min to provide 1-(5-(cyanomethyl)-2-methoxyphenyl)-N-(isoxazol-3-yl)-N-(4-methoxybenzyl)-2-oxo-1,2-dihydroquinoline-6-sulfonamide (0.092 g, 0.165 mmol, 19.72% yield) as a light-yellow solid. 1-(5-(cyanomethyl)-2-methoxyphenyl)-N-(isoxazol-3-yl)-N-(4-methoxybenzyl)-2-oxo-1,2-dihydroquinoline-6-sulfonamide (92 mg) was taken up in 2.5 mL of DCM and 2.5 mL of TFA and was heated under microwave irradiation for 1 h at 70° C. until complete deprotection. The reaction mixture was concentrated in vacuo. The crude material was purified by reverse-phase preparative HPLC (XBridge Prep C18 column, 10 micron OBD, 19×100 mm), 0.1% TFA in CH$_3$CN/H$_2$O, gradient 25% to 70% over 12 min to provide 1-(5-(cyanomethyl)-2-methoxyphenyl)-N-(isoxazol-3-yl)-2-oxo-1,2-dihydroquinoline-6-sulfonamide (0.011 g, 0.025 mmol, 3.01% yield) as a white solid. MS (ESI, pos. ion) m/z: [M+1] 437.0. $^1$H NMR (400 MHz, DMSO-d$_6$) δ ppm 3.68 (s, 3H) 4.03 (s, 2H) 6.44 (d, J=1.76 Hz, 1H) 6.71 (d, J=9.02 Hz, 1H) 6.79 (d, J=9.64 Hz, 1H) 7.30 (d, J=2.28 Hz, 1H) 7.34 (d, J=8.60 Hz, 1H) 7.55 (dd, J=8.60, 2.28 Hz, 1H) 7.84 (dd, J=8.97, 2.23 Hz, 1H) 8.22 (d, J=9.74 Hz, 1H) 8.36 (d, J=2.18 Hz, 1H) 8.73 (d, J=1.87 Hz, 1H) 11.64 (s, 1H).

Example 1147, 1148 & 1149

(Method 220): 1-(5-(cyclopentylethynyl)-2-methoxyphenyl)-N-3-isoxazolyl-2-oxo-1,2-dihydro-6-quinolinesulfonamide (1147), (P)-1-(5-(cyclopentylethynyl)-2-methoxyphenyl)-N-3-isoxazolyl-2-oxo-1,2-dihydro-6-quinolinesulfonamide (1148) and (M)-1-(5-(cyclopentylethynyl)-2-methoxyphenyl)-N-3-isoxazolyl-2-oxo-1,2-dihydro-6-quinolinesulfonamide (1149)

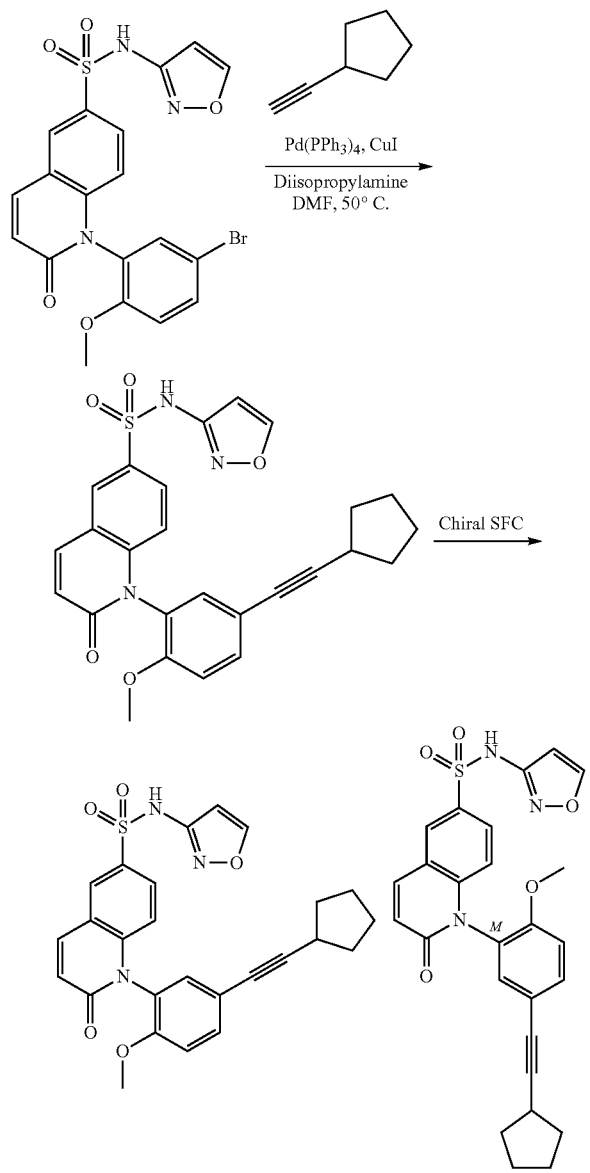

A mixture of 1-(5-bromo-2-methoxyphenyl)-N-(isoxazol-3-yl)-2-oxo-1,2-dihydroquinoline-6-sulfonamide (0.110 g, 0.231 mmol), Pd(PPh₃)₄ (0.027 g, 0.023 mmol), copper(i) iodide (6.60 mg, 0.035 mmol) and diisopropylamine (0.494 ml, 3.46 mmol) in N,N-dimethylformamide (1.155 ml) was treated with ethynylcyclopentane (0.134 ml, 1.155 mmol). The resulting reaction was heated to 50° C. for 10 hours. The reaction was cooled and diluted with ethyl acetate. 1N HCl was added and the layers separated. The organics were dried over magnesium sulfate, filtered and concentrated in vacuo. The crude material was purified by reverse-phase preparative HPLC (XBridge Prep C18 column, 10 micron OBD, 19×100 mm), 0.1% TFA in CH₃CN/H₂O, gradient 25% to 95% over 12 min to provide 1-(5-(cyclopentylethynyl)-2-methoxyphenyl)-N-(isoxazol-3-yl)-2-oxo-1,2-dihydroquinoline-6-sulfonamide (0.067 g, 0.137 mmol, 59.3% yield) as a white solid. MS (ESI, pos. ion) m/z: [M+1] 490.2. $^1$H NMR (400 MHz, DMSO-d₆) δ ppm 1.52-1.72 (m, 6H) 1.88-1.99 (m, 2H) 2.79-2.87 (m, 1H) 3.67 (s, 3H) 6.44 (d, J=1.87 Hz, 1H) 6.73 (d, J=9.02 Hz, 1H) 6.78 (d, J=9.54 Hz, 1H) 7.25 (d, J=8.71 Hz, 1H) 7.35 (d, J=2.07 Hz, 1H) 7.55 (dd, J=8.66, 2.13 Hz, 1H) 7.83 (dd, J=8.97, 2.23 Hz, 1H) 8.20 (d, J=9.64 Hz, 1H) 8.35 (d, J=2.28 Hz, 1H) 8.73 (d, J=1.76 Hz, 1H) 11.65 (s, 1H).

1-(5-(cyclopentylethynyl)-2-methoxyphenyl)-N-3-isoxazolyl-2-oxo-1,2-dihydro-6-quinolinesulfonamide was then subjected to chiral separation via chiral SFC ((S,S) Whelk-O, 45% methanol) to yield (P)-1-(5-(cyclopentylethynyl)-2-methoxyphenyl)-N-3-isoxazolyl-2-oxo-1,2-dihydro-6-quinolinesulfonamide as peak 1 and (M)-1-(5-(cyclopentylethynyl)-2-methoxyphenyl)-N-3-isoxazolyl-2-oxo-1,2-dihydro-6-quinolinesulfonamide as peak 2. Data for peak 1: MS (ESI, pos. ion) m/z: [M+1] 490.2. $^1$H NMR (400 MHz, DMSO-d₆) δ ppm 1.51-1.73 (m, 6H) 1.88-1.99 (m, 2H) 2.79-2.87 (m, 1H) 3.67 (s, 3H) 6.43 (d, J=1.87 Hz, 1H) 6.72 (d, J=8.91 Hz, 1H) 6.77 (d, J=9.54 Hz, 1H) 7.25 (d, J=8.71 Hz, 1H) 7.34 (d, J=2.07 Hz, 1H) 7.54 (dd, J=8.66, 2.12 Hz, 1H) 7.83 (dd, J=8.97, 2.23 Hz, 1H) 8.19 (d, J=9.54 Hz, 1H) 8.34 (d, J=2.28 Hz, 1H) 8.70 (d, J=1.76 Hz, 1H) 11.64 (br. s., 1H). Data for peak 2: MS (ESI, pos. ion) m/z: [M+1] 490.2. $^1$H NMR (400 MHz, DMSO-d₆) δ ppm 1.51-1.74 (m, 6H) 1.82-2.00 (m, 2H) 2.79-2.87 (m, 1H) 3.67 (s, 3H) 6.43 (d, J=1.76 Hz, 1H) 6.73 (d, J=8.91 Hz, 1H) 6.77 (d, J=9.64 Hz, 1H) 7.25 (d, J=8.71 Hz, 1H) 7.34 (d, J=2.18 Hz, 1H) 7.54 (dd, J=8.60, 2.18 Hz, 1H) 7.83 (dd, J=8.97, 2.23 Hz, 1H) 8.19 (d, J=9.54 Hz, 1H) 8.34 (d, J=2.18 Hz, 1H) 8.71 (d, J=1.87 Hz, 1H) 11.65 (br. s., 1H).

Example 1148

(Method 221): (P)-1-(4-(5-chloro-6-methoxy-3-pyridinyl)-5-fluoro-2-methoxyphenyl)-2-oxo-N-2-pyrimidinyl-1,2-dihydro-6-quinolinesulfonamide

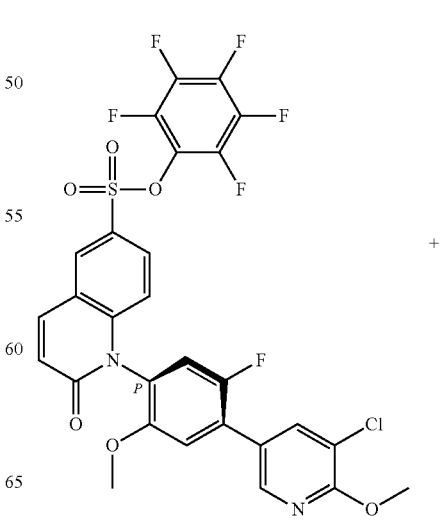

-continued

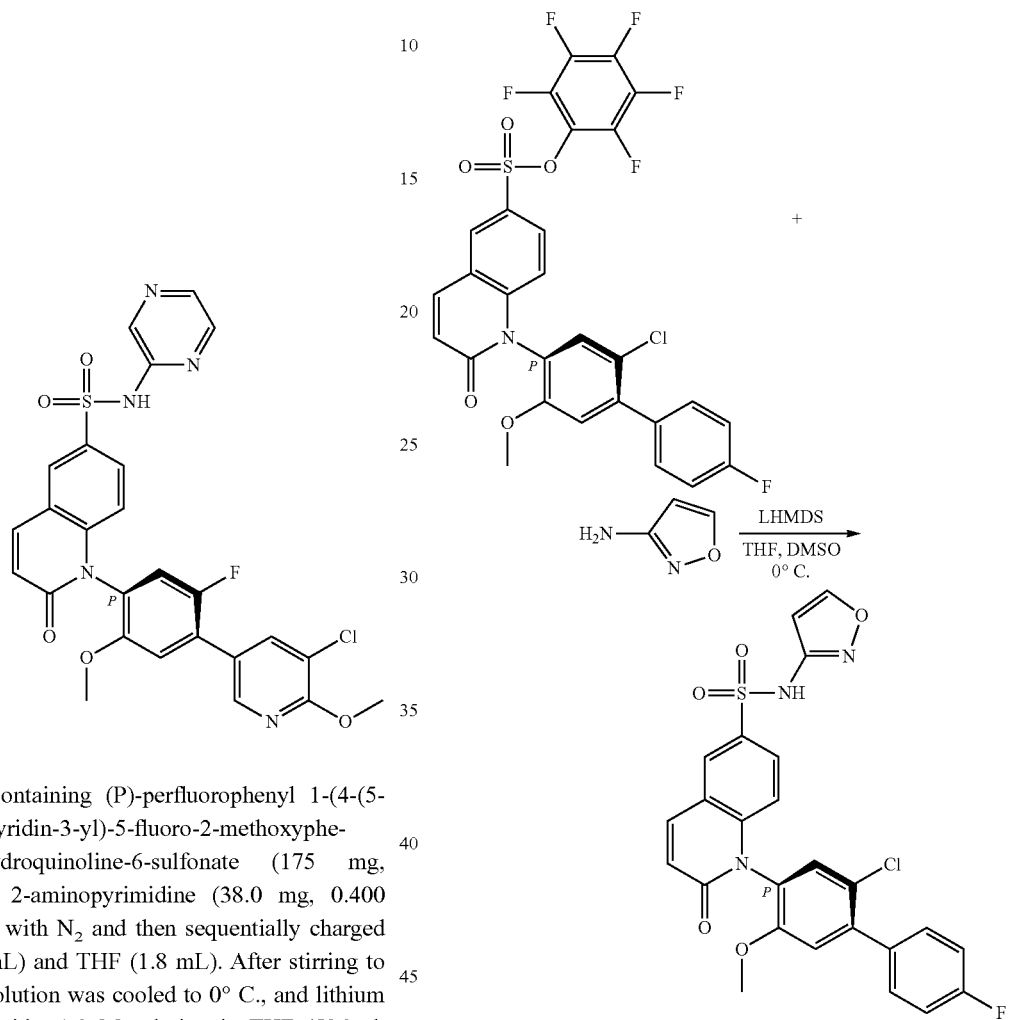

A 40-mL vial containing (P)-perfluorophenyl 1-(4-(5-chloro-6-methoxypyridin-3-yl)-5-fluoro-2-methoxyphenyl)-2-oxo-1,2-dihydroquinoline-6-sulfonate (175 mg, 0.266 mmol) and 2-aminopyrimidine (38.0 mg, 0.400 mmol) was flushed with $N_2$ and then sequentially charged with DMSO (0.6 mL) and THF (1.8 mL). After stirring to homogeneity, the solution was cooled to 0° C., and lithium bis(trimethylsilyl)amide, 1.0 M solution in THF (586 μl, 0.586 mmol) was added down the side of the vial. The resulting red-orange solution was stirred at 0° C. for 30 min and subsequently quenched at 0° C. with 1 N HCl and extracted thrice with EtOAc. The organic extracts were combined, washed with brine, dried over $Na_2SO_4$, filtered, and concentrated in vacuo to a yellow residue. Purification was done with 0.1% TFA in MeCN and water as mobile phase to afford (P)-1-(4-(5-chloro-6-methoxy-3-pyridinyl)-5-fluoro-2-methoxyphenyl)-2-oxo-N-2-pyrimidinyl-1,2-dihydro-6-quinolinesulfonamide (66.3 mg, 0.117 mmol, 43.8% yield) as a tan amorphous solid. $^1$H NMR (500 MHz, DMSO-$d_6$) δ ppm 3.68 (s, 3H) 3.93 (s, 3H) 6.80 (dd, J=9.28, 2.40 Hz, 2H) 7.05 (t, J=4.74 Hz, 1H) 7.40 (d, J=8.10 Hz, 1H) 7.47 (d, J=8.86 Hz, 1H) 7.96-8.07 (m, 2H) 8.27 (d, J=9.67 Hz, 1H) 8.35 (d, J=2.53 Hz, 1H) 8.42-8.58 (m, 3H) 11.58-12.24 (m, 1H). m/z (ESI) 568.2 (M+H)$^+$.

Example 1149

(Method 222): (P)-1-(2-chloro-4'-fluoro-5-methoxy-4-biphenylyl)-N-3-isoxazolyl-2-oxo-1,2-dihydro-6-quinolinesulfonamide A 40-mL vial containing (P)-perfluorophenyl 1-(2-chloro-4'-fluoro-5-methoxy-[1,1'-biphenyl]-4-yl)-2-oxo-1,2-dihydroquinoline-6-sulfonate (150 mg, 0.240 mmol) and 3-aminoisoxazole (26.6 μl, 0.359 mmol) was flushed with $N_2$ and then charged with THF (2.4 mL). The solution was cooled to 0° C., and lithium bis(trimethylsilyl)amide, 1.0 M solution in THF (527 μl, 0.527 mmol) was added down the side of the vial. The resulting viscous yellow slurry was stirred at 0° C. for 30 min and subsequently quenched at 0° C. with 1 N HCl and extracted thrice with EtOAc. The organic extracts were combined, washed with brine, dried over $Na_2SO_4$, filtered, and concentrated in vacuo to a viscous yellow oil. Purification was done with 0.1% TFA in MeCN and water as mobile phase to afford (P)-1-(2-chloro-4'-fluoro-5-methoxy-4-biphenylyl)-N-3-isoxazolyl-2-oxo-1,2-dihydro-6-quinolinesulfonamide (76.2 mg, 0.145 mmol, 60.5% yield) as a white amorphous solid. $^1$H NMR (500 MHz, DMSO-$d_6$) δ ppm 3.72 (s, 3H) 6.46 (d, J=1.69 Hz, 1H) 6.82 (d, J=9.18 Hz, 1H) 6.89 (d, J=8.95 Hz, 1H) 7.32 (s, 1H)

7.37 (t, J=8.82 Hz, 2H) 7.63 (dd, J=8.56, 5.51 Hz, 2H) 7.67 (s, 1H) 7.88 (dd, J=8.95, 2.08 Hz, 1H) 8.23 (d, J=9.67 Hz, 1H) 8.38 (d, J=1.95 Hz, 1H) 8.73 (d, J=1.69 Hz, 1H) 11.49-11.83 (m, 1H). m/z (ESI) 526.2 (M+H)$^+$.

Example 1150

(Method 223): (P)-1-(3'-(difluoromethoxy)-2,4'-difluoro-5-methoxy-4-biphenylyl)-N-3-isoxazolyl-2-oxo-1,2-dihydro-6-quinolinesulfonamide

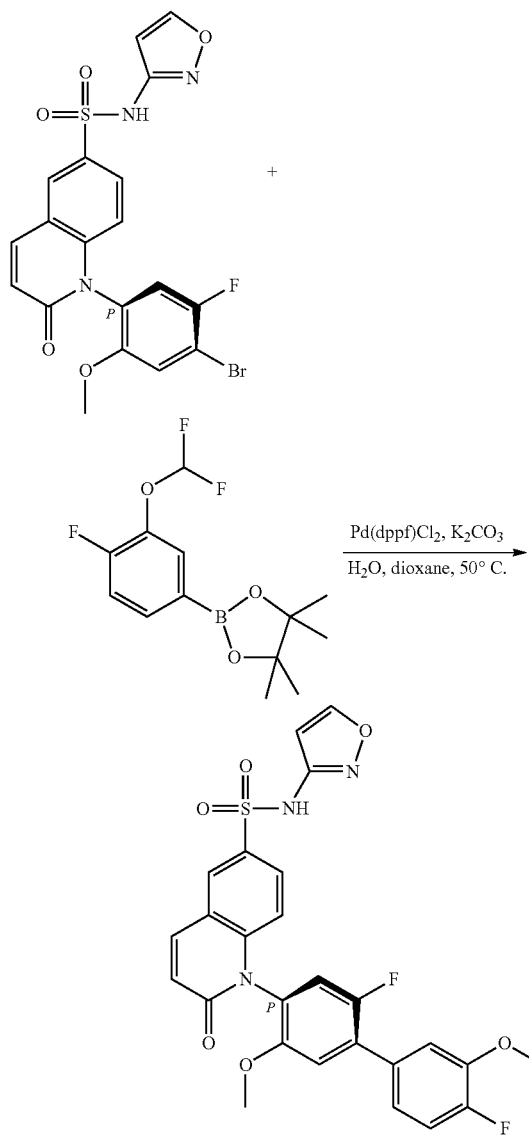

A 40-mL vial containing (P)-1-(4-bromo-5-fluoro-2-methoxyphenyl)-N-(isoxazol-3-yl)-2-oxo-1,2-dihydroquinoline-6-sulfonamide (151 mg, 0.305 mmol), 2-(3-(difluoromethoxy)-4-fluorophenyl)-4,4,5,5-tetramethyl-1,3,2-dioxaborolane (176 mg, 0.611 mmol), potassium carbonate (211 mg, 1.527 mmol), and 1,1'-bis(diphenylphosphino)ferrocene palladium(II)dichloride dichloromethane adduct (24.95 mg, 0.031 mmol) was flushed with N$_2$ and subsequently charged with dioxane (1.2 mL) and H$_2$O (0.4 mL). After at 50° C. for 30 min, the reaction was cooled to rt and extracted thrice with EtOAc. The organic extracts were combined, washed with brine, dried over Na$_2$SO$_4$, filtered, and concentrated in vacuo to a brown-black oil. Purification was done with 0.1% TFA in MeCN and water as mobile phase to afford (P)-1-(3'-(difluoromethoxy)-2,4'-difluoro-5-methoxy-4-biphenylyl)-N-3-isoxazolyl-2-oxo-1,2-dihydro-6-quinolinesulfonamide (35.2 mg, 0.061 mmol, 20.02% yield) as a yellow film. $^1$H NMR (500 MHz, DMSO-d$_6$) δ ppm 3.74 (s, 3H) 6.45 (d, J=1.69 Hz, 1H) 6.81 (d, J=9.67 Hz, 1H) 6.88 (d, J=8.95 Hz, 1H) 7.16-7.50 (m, 2H) 7.53 (d, J=10.32 Hz, 1H) 7.56-7.67 (m, 2H) 7.70 (d, J=7.27 Hz, 1H) 7.86 (dd, J=8.99, 2.04 Hz, 1H) 8.23 (d, J=9.73 Hz, 1H) 8.38 (d, J=1.95 Hz, 1H) 8.73 (d, J=1.69 Hz, 1H) 11.64 (br. s., 1H). m/z (ESI) 576.2 (M+H)$^+$.

Example 1151

(Method 224): (P)-1-(4-(4-fluorophenoxy)-2-methoxyphenyl)-N-3-isoxazolyl-2-oxo-1,2-dihydro-6-quinolinesulfonamide

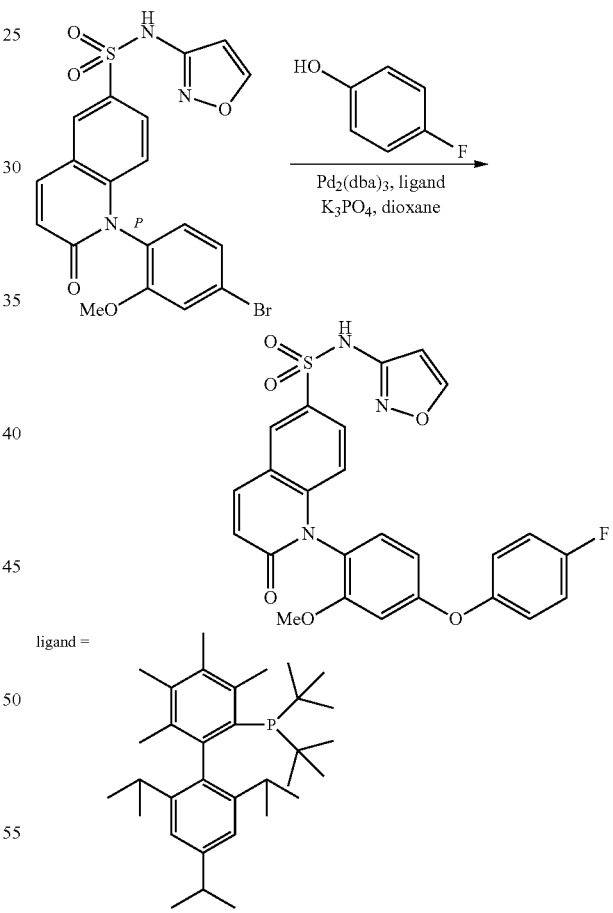

A solution of 2-di-i-butylphosphino-3,4,5,6-tetramethyl-2',4',6'-tri-i-propylbiphenyl (0.040 g, 0.084 mmol), Pd$_2$(dba)$_3$ (0.019 g, 0.021 mmol), 4-fluorophenol (0.094 g, 0.840 mmol), (P)-1-(4-bromo-2-methoxyphenyl)-N-(isoxazol-3-yl)-2-oxo-1,2-dihydroquinoline-6-sulfonamide (0.200 g, 0.420 mmol), and potassium phosphate (0.267 g, 1.260 mmol) in 1 mL dioxane was heated to 80° C. overnight. The reaction mixture was poured into water and was extracted with DCM. The organics were then concentrated. Purification of the crude residue by silica gel column chromatography (0-100% EtOAc/heptane) gave 1-(4-(4-fluorophenoxy)-2-methoxyphenyl)-N-(isoxazol-3-yl)-2-oxo-1,2-dihydroquinoline-6-sulfonamide (0.066 g, 0.13 mmol, 30.9%). m/z (ESI) 508.0 (M+H)$^+$. Chiral purification was performed by SFC: (Chiralpak AS, 45% isopropanol) yielding (peak 1) (P)-1-(4-(4-fluorophenoxy)-2-methoxyphenyl)-N-(isoxazol-3-yl)-2-oxo-1,2-dihydroquinoline-6-sulfonamide (0.016 g, 0.032 mmol, 7.51% yield) $^1$H NMR (Acetone): 8.54 (d, J=1.7 Hz, 1H), 8.30 (d, J=2.1 Hz, 1H), 8.08 (d, J=9.6 Hz, 1H), 7.88 (dd, J=9.0, 2.2 Hz, 1H), 7.20-7.28 (m, 5H), 6.93 (d, J=2.6 Hz, 1H), 6.85 (d, J=9.0 Hz, 1H), 6.75 (d, J=9.6 Hz, 1H), 6.67 (dd, J=8.5, 2.6 Hz, 1H), 6.57 (d, J=1.8 Hz, 1H), 3.68 (s, 3H). m/z (ESI) 508.0 (M+H)$^+$ and (peak 2) (M)-1-(4-(4-fluorophenoxy)-2-methoxyphenyl)-N-(isoxazol-3-yl)-2-oxo-1,2-dihydroquinoline-6-sulfonamide (0.011 g, 0.022 mmol, 5.16% yield). $^1$H NMR (Acetone): 8.54 (d, J=1.7 Hz, 1H), 8.30 (d, J=2.1 Hz, 1H), 8.08 (d, J=9.6 Hz, 1H), 7.88 (dd, J=9.0, 2.2 Hz, 1H), 7.20-7.28 (m, 5H), 6.93 (d, J=2.6 Hz, 1H), 6.85 (d, J=9.0 Hz, 1H), 6.75 (d, J=9.6 Hz, 1H), 6.67 (dd, J=8.5, 2.6 Hz, 1H), 6.57 (d, J=1.8 Hz, 1H), 3.68 (s, 3H). m/z (ESI) 508.0 (M+H)$^+$.

Example 1152

(Method 225): (P)-1-(5-fluoro-2-methoxy-4-((3-methyl-3-oxetanyl)ethynyl)phenyl)-N-3-isoxazolyl-2-oxo-1,2-dihydro-6-quinolinesulfonamide

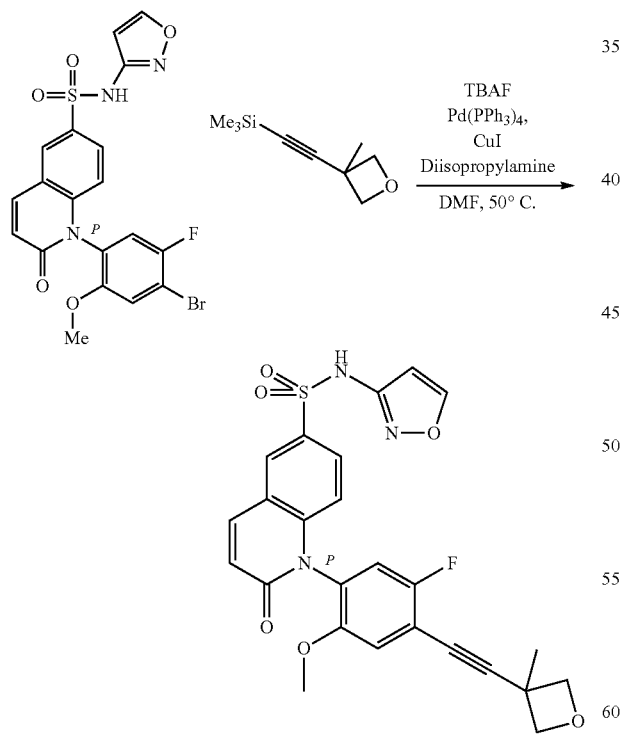

A RBF was charged with (P)-1-(4-bromo-5-fluoro-2-methoxyphenyl)-N-(isoxazol-3-yl)-2-oxo-1,2-dihydroquinoline-6-sulfonamide (76 mg, 0.154 mmol), trimethyl((3-methyloxetan-3-yl)ethynyl)silane (51.8 mg, 0.308 mmol), TBAF (1M in THF; 0.34 mL, 0.338 mmol), copper(i) iodide (2.93 mg, 0.015 mmol), tetrakis(triphenylphosphine)palladium(0) (17.77 mg, 0.015 mmol), diisopropylamine (0.11 mL, 0.769 mmol) and DMF (1 mL). The reaction was stirred at 50° C. for 3 hrs. The mixture was diluted with water and Ethyl Acetate. The organic portion was collected, dried with sodium sulfate, filtered, and concentrated. The crude material was purified via column chromatography (RediSep Gold 40 g, gradient elution 10-75% [3:1 EtOAc/EtOH]:Heptane to give (P)-1-(5-fluoro-2-methoxy-4-((3-methyl-3-oxetanyl)ethynyl)phenyl)-N-3-(isoxazolyl-2-oxo-1,2-dihydro-6-quinolinesulfonamide (55 mg, 0.108 mmol, 70.2% yield) as an off-white solid. m/z (ESI) 510.0 (M+H)$^+$.

Example 1153

(Method 226): (P)-1-(5-fluoro-4-((1-fluorocyclopentyl)ethynyl)-2-methoxyphenyl)-N-3-isoxazolyl-2-oxo-1,2-dihydro-6-quinolinesulfonamide

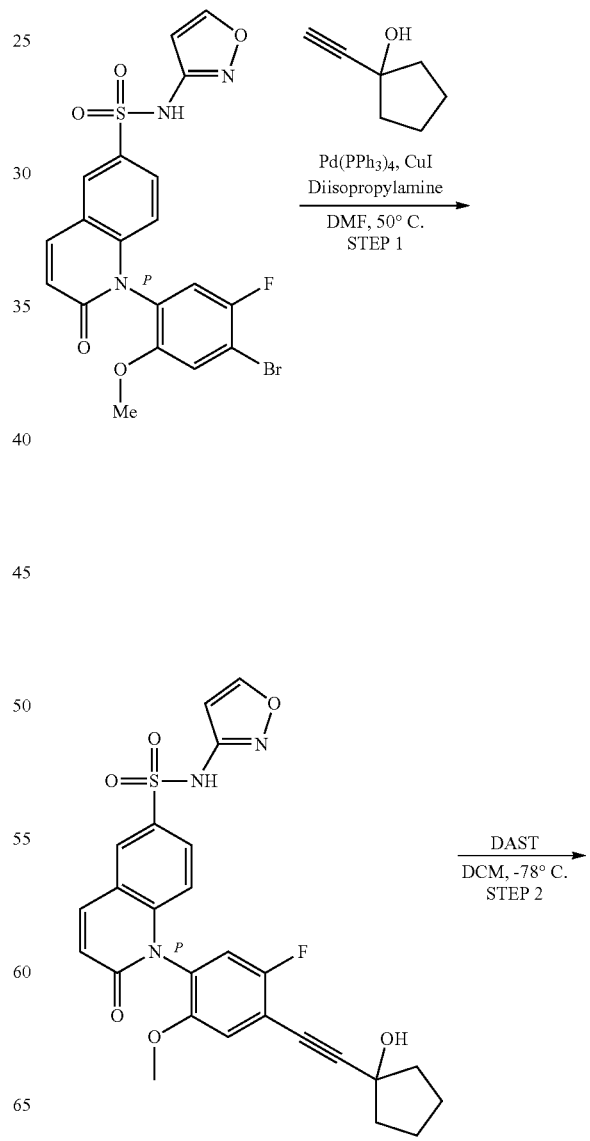

595

-continued

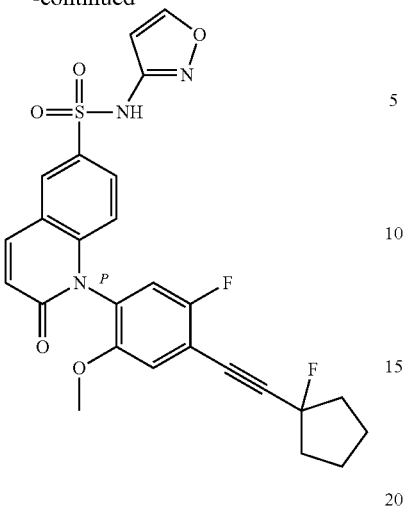

Step 1: (P)-1-(5-fluoro-4-((1-hydroxycyclopentyl)ethynyl)-2-methoxyphenyl)-N-3-isoxazolyl-2-oxo-1,2-dihydro-6-quinolinesulfonamide A RBF was charged with (P)-1-(4-bromo-5-fluoro-2-methoxyphenyl)-N-(isoxazol-3-yl)-2-oxo-1,2-dihydroquinoline-6-sulfonamide (308 mg, 0.623 mmol), 1-ethynylcyclopentanol (343 mg, 3.12 mmol, Sigma-Aldrich), diisopropylamine (0.44 mL, 3.12 mmol), copper(i) iodide (17.80 mg, 0.093 mmol), Tetrakis(triphenylphosphine)palladium(0) (108 mg, 0.093 mmol), and N, N-dimethylformamide (3.11 mL). The reaction was stirred at 50° C. for 3 hrs. The mixture was diluted with water and Ethyl Acetate. The organic portion was collected, dried with sodium sulfate, filtered, and concentrated. The crude material was purified via column chromatography (RediSep Gold 80 g, gradient elution 10-60% [3:1 EtOAc/EtOH]:Heptane to give (P)-1-(5-fluoro-4-((1-hydroxycyclopentyl)ethynyl)-2-methoxyphenyl)-N-3-isoxazolyl-2-oxo-1,2-dihydro-6-quinolinesulfonamide (228 mg, 0.436 mmol, 70.0% yield) as an off-white solid. m/z (ESI) 524.0 (M+H)$^+$.

Step 2: (P)-1-(5-fluoro-4-((1-fluorocyclopentyl)ethynyl)-2-methoxyphenyl)-N-3-isoxazolyl-2-oxo-1,2-dihydro-6-quinolinesulfonamide A RBF was charged with (P)-1-(5-fluoro-4-((1-hydroxycyclopentyl)ethynyl)-2-methoxyphenyl)-N-3-isoxazolyl-2-oxo-1,2-dihydro-6-quinolinesulfonamide (102 mg, 0.195 mmol) and dichloromethane (1.95 mL). The reaction mixture was cooled to −78° C. and DAST (51.5 µl, 0.390 mmol) was then added dropwise. The mixture was stirred for 25 minutes and then treated with a solution of Aq. NaHCO$_3$ until pH reached 7. The product was extracted with DCM. The organic portion was collected, dried with sodium sulfate, filtered, and concentrated. The crude material was purified via column chromatography (RediSep Gold 40 g, gradient elution 10-60% [3:1 EtOAc/EtOH]:Heptane to give (P)-1-(5-fluoro-4-((1-fluorocyclopentyl)ethynyl)-2-methoxyphenyl)-N-3-isoxazolyl-2-oxo-1,2-dihydro-6-quinolinesulfonamide (20 mg, 0.038 mmol, 19.53% yield) as an off-white solid. $^1$H NMR (400 MHz, DMSO-d$_6$) δ ppm 11.60 (br. s, 1H) 8.66 (d, J=1.76 Hz, 1H) 8.30 (d, J=2.13 Hz, 1H) 8.16 (d, J=9.64 Hz, 1H) 7.74-7.79 (m, 1H) 7.49 (d, J=9.17 Hz, 1H) 7.40 (d, J=8.46 Hz, 1H) 6.77 (d, J=8.61 Hz, 1H) 6.73 (d, J=9.64 Hz, 1H) 6.38 (d, J=1.81 Hz, 1H) 3.62 (s, 3H) 2.23-2.35 (m, 2H) 1.96-2.15 (m, 2H) 1.70-1.78 (m, 4H). m/z (ESI) 526.0 (M+H)$^+$.

Example 1154

(Method 227): N-(isoxazol-3-yl)-1-(2-methoxyphenyl)-2-oxo-1,2-dihydroquinoline-6-sulfonamide 597
-continued

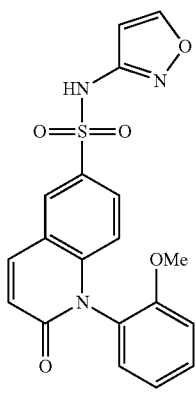

Step 1:
Ethyl-3-(5-(benzylthio)-2-iodophenyl)acrylate

To a solution of (E)-ethyl 3-(2-amino-5-(benzylthio)phenyl)acrylate (150 g, 479 mmol, 1.0 equiv) in acetonitrile (2.0 L) was added para-toluenesulfonic acid monohydrate (273.16 g, 1437 mmol, 3.0 equiv, Spectrochem). The reaction mixture was cooled to 0° C. and a solution of sodium nitrite (66.03 g, 958 mmol, 2.0 equiv, Spectrochem) and potassium iodide (185.7 g, 1198 mmol, 2.5 equiv, Spectrochem) in water (450 mL) was added drop wise keeping temperature below 5° C. The reaction mixture was stirred at 0° C. for 5 h. The mixture was then diluted with ethyl acetate (5.0 L) and quenched with 2M aqueous sodium thiosulfate solution (5.0 L). The layers were separated and the organic layer was washed with saturated aqueous sodium bicarbonate solution (3.0 L). The organic layer was dried over sodium sulfate, filtered and concentrated under reduced pressure to obtain the crude material which was purified by column chromatography (silica gel; mesh size 60-120, elution 0-5% ethyl acetate in hexane) to yield ethyl-3-(5-(benzylthio)-2-iodophenyl)acrylate (130 g, 64%) as light brown solid. TLC solvent system: 20% ethyl acetate in hexane. Product's $R_f$: 0.6. MS (ESI, positive ion) m/z; 425.0 (M+1)

Step 2: (E)-ethyl-3-(2-iodo-5-(N-(isoxazol-3-yl)sulfamoyl)phenyl)-acrylate (E)-Ethyl 3-(5-(benzylthio)-2-iodophenyl)acrylate (0.225 g, 0.265 mmol) was added to a vial and dissolved in acetonitrile (2.494 ml). Acetic acid (0.095 ml) and water (0.062 ml) were added and the vial was cooled to 0° C. 1,3-dichloro-5,5-dimethylhydantoin (0.057 g, 0.292 mmol) was then added as a solid in one portion while 0° C. was maintained. After 20 min. LC/MS showed mass corresponding to sulfoxide (mono-oxidation) along with sulfonyl chloride. After 1 hr. an additional 0.2 equiv (10 mg) of hydantoin was added. After an additional 20 min. the oxidation was complete. Solid sodium bisulfite was added and the reaction was diluted with EtOAc and water and stirred for 5 min. The organic layer was separated, the aq. re-extracted 2x with EtOAc, and the organic layers combined. After washing with brine, drying with $Na_2SO_4$, and concentrating, the crude residue was brought up in 1.5 mL of DCM and treated with 3-aminoisoxazole (0.039 ml, 0.530 mmol) and pyridine (0.107 ml, 1.326 mmol) After 45 min, the reaction was poured into 1N HCl and extracted 2x with EtOAc. The combined organics were washed with brine, dried over

598

$Na_2SO_4$, and concentrated to give an orange solid that was purified by MPLC (25 g puriflash, 25-85% EtOAC:Heptanes) to give (E)-ethyl 3-(2-iodo-5-(N-(isoxazol-3-yl)sulfamoyl)phenyl)acrylate (0.043 g, 0.096 mmol, 36.2% yield) as a white solid. m/z (ESI) 447.0 (M–H)⁻.

Step 3: N-(isoxazol-3-yl)-1-(2-methoxyphenyl)-2-oxo-1,2-dihydroquinoline-6-sulfonamide (E)-Ethyl 3-(2-iodo-5-(N-(isoxazol-3-yl)sulfamoyl)phenyl)acrylate (0.043 g, 0.096 mmol), xantphos (8.33 mg, 0.014 mmol), $Pd_2(dba)_3$ (4.39 mg, 4.80 µmol), and freshly ground potassium phosphate (0.061 g, 0.288 mmol) were added to a 1 dram vial and purged with $N_2$. 1,4-dioxane (0.5 ml) and 2-methoxyaniline (0.022 ml, 0.192 mmol) were added and the mixture was evacuated and backfilled with $N_2$ twice and then stirred at 80° C. for 4 hr. The reaction was then cooled to rt and diluted with 1.5 mL MeOH then heated to 80° C. overnight. The reaction was concentrated to remove MeOH, then diluted with EtOAc and 1N HCl. The aqueous layer was extracted twice with EtOAc, the combined organics were washed with brine, dried over $Na_2SO_4$, and concentrated. MPLC purification (12 g Snap, 40% [3:1 EtOAc:EtOH]:heptanes) provided N-(isoxazol-3-yl)-1-(2-methoxyphenyl)-2-oxo-1,2-dihydroquinoline-6-sulfonamide (24.8 mg, 0.062 mmol, 65.1% yield) as a light yellow solid. m/z (ESI) 396.0 (M–H)⁻.

Example 1155

(Method 228): 1-benzyl-N-(isoxazol-3-yl)-2-oxo-1,2-dihydroquinoline-6-sulfonamide

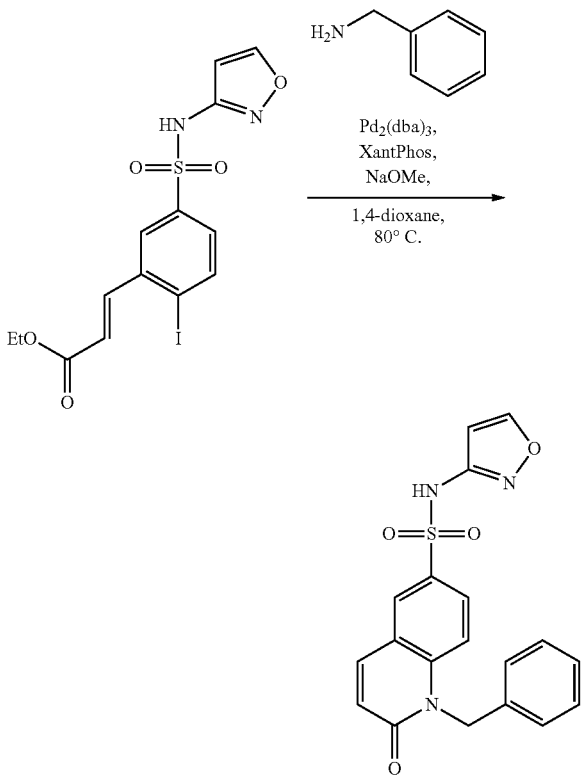

(E)-Ethyl 3-(2-iodo-5-(N-(isoxazol-3-yl)sulfamoyl)phenyl)acrylate (0.03 g, 0.067 mmol), xantphos (3.87 mg, 6.69 µmol), Pd$_2$(dba)$_3$ (3.06 mg, 3.35 mol), 1,4-dioxane (0.669 ml) and benzylamine (8.04 µl, 0.074 mmol) were added to a 2 dram vial and evacuated and backfilled with N$_2$. Sodium methoxide (0.045 ml, 0.201 mmol) was added and the mixture was evacuated and backfilled with N$_2$ twice and then stirred at 80° C. for 30 min. The reaction was cooled, diluted with EtOAc and 1M HCl was added. The aqueous layer was extracted 2× with EtOAc, combined, washed with brine, dried over Na$_2$SO$_4$ and concentrated. MPLC purification (12 g redi-sep, 30% [3:1 EtOAc:EtOH]:hep) gave 1-benzyl-N-(isoxazol-3-yl)-2-oxo-1,2-dihydroquinoline-6-sulfonamide (9.2 mg, 0.024 mmol, 36.0% yield) as a pale yellow solid. (ESI) 380.1 (M−H)$^−$.

Example 1156

(P)-1-(4-(5-chloro-6-methoxy-3-pyridinyl)-5-fluoro-2-methoxyphenyl)-N-(5-fluoro-2-pyrimidinyl)-2-oxo-1,2-dihydro-6-quinolinesulfonamide This compound was prepared via method 221 using 2-amino-5-fluoropyrimidine (purchased from Oakwood Products, Inc.) as the amine. $^1$H NMR (500 MHz, DMSO-d$_6$) δ ppm 3.69 (s, 3H) 3.93 (s, 3H) 6.81 (dd, J=9.31, 4.18 Hz, 2H) 7.41 (d, J=6.78 Hz, 1H) 7.48 (d, J=9.54 Hz, 1H) 8.01 (d, J=8.00 Hz, 2H) 8.26 (d, J=9.67 Hz, 1H) 8.36 (d, J=2.53 Hz, 1H) 8.48 (d, J=1.95 Hz, 1H) 8.62 (s, 2H) 11.88-12.02 (m, 1H). m/z (ESI) 586.2 (M+H)$^+$.

Example 1157

(P)-1-(4-(5-chloro-6-methoxy-3-pyridinyl)-5-fluoro-2-methoxyphenyl)-2-oxo-N-3-pyridazinyl-1,2-dihydro-6-quinolinesulfonamide This compound was prepared via method 221 using 3-aminopyridazine as the amine. $^1$H NMR (500 MHz, DMSO-d$_6$) δ ppm 3.69 (s, 3H) 3.90-3.97 (m, 3H) 6.79 (d, J=9.67 Hz, 2H) 7.40 (d, J=8.11 Hz, 1H) 7.46 (d, J=9.54 Hz, 1H) 7.69 (dd, J=9.34, 3.96 Hz, 1H) 8.02 (d, J=2.53 Hz, 3H) 8.17-8.47 (m, 4H) 14.35-14.65 (m, 1H). m/z (ESI) 568.2 (M+H)$^+$.

Example 1158

(P)-1-(4-(5-chloro-6-methoxy-3-pyridinyl)-5-fluoro-2-methoxyphenyl)-N-1,3-oxazol-2-yl-2-oxo-1,2-dihydro-6-quinolinesulfonamide This compound was prepared via method 221 using 2-aminooxazole (purchased from Astatech, Inc.) as the amine. $^1$H NMR (500 MHz, DMSO-d$_6$) δ ppm 3.70 (s, 3H) 3.93 (s, 3H) 6.78 (dd, J=18.00, 9.25 Hz, 2H) 7.28 (d, J=1.36 Hz, 1H) 7.40 (d, J=6.78 Hz, 1H) 7.47 (d, J=9.60 Hz, 1H) 7.61 (d, J=1.49 Hz, 1H) 7.89 (dd, J=8.89, 1.95 Hz, 1H) 8.02 (d, J=2.47 Hz, 1H) 8.20 (d, J=9.60 Hz, 1H) 8.35 (dd, J=7.85, 2.14 Hz, 2H) 12.05-12.30 (m, 1H). m/z (ESI) 557.2 (M+H)$^+$.

Example 1159

(P)-1-(4-(5-chloro-6-methoxy-3-pyridinyl)-5-fluoro-2-methoxyphenyl)-N-(6-methyl-4-pyrimidinyl)-2-oxo-1,2-dihydro-6-quinolinesulfonamide This compound was prepared via method 221 using 6-methyl-4-pyrimidinamine (purchased from ChemBridge Corporation) as the amine. $^1$H NMR (500 MHz, DMSO-d$_6$) δ ppm 2.32 (s, 3H) 3.69 (s, 3H) 3.93 (s, 3H) 6.78 (d, J=9.02 Hz, 1H) 6.80 (d, J=19.24 Hz, 1H) 6.92 (br. s., 1H) 7.40 (d, J=7.83 Hz, 1H) 7.47 (d, J=9.54 Hz, 1H) 7.94 (dd, J=7.90 Hz, 1H) 8.01 (d, J=8.23 Hz, 1H) 8.24 (d, J=7.97 Hz, 1H) 8.35 (d, J=7.13 Hz, 1H) 8.43 (s, 1H) 8.51 (s, 1H) 11.21-11.56 (m, 1H). m/z (ESI) 582.2 (M+H)$^+$.

Example 1160

(P)-1-(4-(5-chloro-6-methoxy-3-pyridinyl)-5-fluoro-2-methoxyphenyl)-N-(2-methyl-4-pyrimidinyl)-2-oxo-1,2-dihydro-6-quinolinesulfonamide This compound was prepared via method 221 using 2-methyl-4-pyrimidinamine (purchased from J & W Pharm-Lab, LLC) as the amine. $^1$H NMR (500 MHz, DMSO-d$_6$) δ ppm 2.39 (s, 3H) 3.69 (s, 3H) 3.93 (s, 3H) 6.77 (d, J=8.95 Hz, 1H) 6.79 (d, J=9.67 Hz, 1H) 6.90 (br. s., 1H) 7.40 (d, J=6.42 Hz, 1H) 7.46 (d, J=9.03 Hz, 1H) 7.91 (dd, J=8.86, 1.85 Hz, 1H) 8.02 (d, J=7.62 Hz, 1H) 8.13 (d, J=6.62 Hz, 1H) 8.24 (d, J=9.67 Hz, 1H) 8.35 (d, J=7.85 Hz, 1H) 8.38-8.43 (m, 1H) 11.17-11.61 (m, 1H). m/z (ESI) 582.2 (M+H)$^+$.

Example 1161

(P)-1-(4-(5-chloro-6-methoxy-3-pyridinyl)-5-fluoro-2-methoxyphenyl)-N-(5-fluoro-2-pyridinyl)-2-oxo-1,2-dihydro-6-quinolinesulfonamide This compound was prepared via method 221 using 2-amino-5-fluoropyridine as the amine. $^1$H NMR (500 MHz, DMSO-d$_6$) δ ppm 3.68 (s, 3H) 3.93 (s, 3H) 6.80 (t, J=8.59 Hz, 2H) 7.12 (dd, J=9.05, 3.67 Hz, 1H) 7.40 (d, J=6.36 Hz, 1H) 7.47 (d, J=9.54 Hz, 1H) 7.66 (td, J=8.68, 3.02 Hz, 1H) 7.92 (dd, J=8.92, 2.04 Hz, 1H) 8.01 (d, J=23.95 Hz, 1H) 8.17 (d, J=2.92 Hz, 1H) 8.23 (d, J=9.67 Hz, 1H) 8.35 (d, J=2.47 Hz, 1H) 8.41 (d, J=1.88 Hz, 1H) 11.04-11.36 (m, 1H). m/z (ESI) 585.2 (M+H)$^+$.

Example 1162

(P)-1-(4-(5-chloro-6-methoxy-3-pyridinyl)-5-fluoro-2-methoxyphenyl)-N-(6-fluoro-2-pyridinyl)-2-oxo-1,2-dihydro-6-quinolinesulfonamide This compound was prepared via method 221 using 2-amino-6-fluoropyridine as the amine. $^1$H NMR (500 MHz, DMSO-d$_6$) δ ppm 3.68 (s, 3H) 3.93 (s, 3H) 6.72 (dd, J=7.98, 2.01 Hz, 1H) 6.81 (d, J=9.80 Hz, 2H) 6.93-7.00 (m, 1H) 7.39 (d, J=6.42 Hz, 1H) 7.48 (d, J=9.54 Hz, 1H) 7.84 (q, J=8.17 Hz, 1H) 7.95 (dd, J=8.99, 2.04 Hz, 1H) 8.01 (d, J=16.70 Hz, 1H) 8.24 (d, J=9.67 Hz, 1H) 8.35 (d, J=2.47 Hz, 1H) 8.45 (d, J=1.95 Hz, 1H) 11.39-11.54 (m, 1H). m/z (ESI) 585.2 (M+H)$^+$.

Example 1163

(P)-1-(4'-chloro-2-fluoro-5-methoxy-4-biphenylyl)-N-(5-fluoro-2-pyridinyl)-2-oxo-1,2-dihydro-6-quinolinesulfonamide This compound was prepared via method 150 using 2-amino-5-fluoropyridine as the amine. $^1$H NMR (500 MHz, DMSO-d$_6$) δ ppm 3.73 (s, 3H) 6.80 (d, J=9.67 Hz, 1H) 6.85 (d, J=8.95 Hz, 1H) 7.12 (dd, J=8.99, 3.67 Hz, 1H) 7.40 (d, J=6.94 Hz, 1H) 7.51 (d, J=10.38 Hz, 1H) 7.61 (d, J=8.50 Hz, 2H) 7.66 (td, J=8.64, 3.08 Hz, 1H) 7.73 (d, J=7.33 Hz, 2H) 7.90 (dd, J=8.95, 2.01 Hz, 1H) 8.17 (d, J=2.92 Hz, 1H) 8.23 (d, J=9.67 Hz, 1H) 8.40 (d, J=1.88 Hz, 1H) 11.17 (br. s., 1H). m/z (ESI) 554.2 (M+H)$^+$.

Example 1164

(P)—N-3-isoxazolyl-2-oxo-1-(2,3',4',5'-tetrafluoro-5-methoxy-4-biphenylyl)-1,2-dihydro-6-quinoline-sulfonamide This compound was prepared via method 145 using (3,4,5-trifluorophenyl)boronic acid (purchased from Matrix Scientific) as the boronic acid. $^1$H NMR (500 MHz, DMSO-d$_6$) δ ppm 3.75 (s, 3H) 6.45 (d, J=1.69 Hz, 1H) 6.81 (d, J=10.02 Hz, 1H) 6.85 (d, J=9.02 Hz, 1H) 7.45 (d, J=6.94 Hz, 1H) 7.56 (d, J=9.58 Hz, 1H) 7.67-7.79 (m, 2H) 7.86 (dd, J=8.99, 2.11 Hz, 1H) 8.23 (d, J=9.67 Hz, 1H) 8.38 (d, J=1.95 Hz, 1H) 8.73 (d, J=1.62 Hz, 1H) 11.64 (br. s., 1H). m/z (ESI) 546.2 (M+H)$^+$.

Example 1165

(P)-1-(2-chloro-4'-fluoro-5-methoxy-[1,1'-biphenyl]-4-yl)-2-oxo-N-(pyrimidin-2-yl)-1,2-dihydroquinoline-6-sulfonamide This compound was prepared via method 222 using 2-aminopyrimidine as the amine. $^1$H NMR (500 MHz, DMSO-d$_6$) δ ppm 3.71 (s, 3H) 6.80 (d, J=9.60 Hz, 1H) 6.85 (d, J=9.02 Hz, 1H) 7.05 (t, J=4.77 Hz, 1H) 7.28-7.43 (m, 3H) 7.55-7.73 (m, 3H) 8.01 (dd, J=8.92, 1.98 Hz, 1H) 8.26 (d, J=9.67 Hz, 1H) 8.43-8.56 (m, 3H) 11.68-12.12 (m, 1H). m/z (ESI) 537.0 (M+H)$^+$.

Example 1166

(P)-1-(2-chloro-4'-fluoro-5-methoxy-[1,1'-biphenyl]-4-yl)-N-(5-fluoropyrimidin-2-yl)-2-oxo-1,2-dihydro-quinoline-6-sulfonamide This compound was prepared via method 222 using 2-amino-5-fluoropyrimidine (purchased from Oakwood Products, Inc.) as the amine. $^1$H NMR (500 MHz, DMSO-d$_6$) δ ppm 3.72 (s, 3H) 6.81 (d, J=9.67 Hz, 1H) 6.86 (d, J=8.95 Hz, 1H) 7.32 (s, 1H) 7.37 (t, J=8.86 Hz, 2H) 7.59-7.70 (m, 3H) 7.99 (dd, J=8.99, 2.04 Hz, 1H) 8.25 (d, J=9.67 Hz, 1H) 8.48 (d, J=1.88 Hz, 1H) 8.62 (s, 2H) 11.96 (br. s., 1H). m/z (ESI) 555.2 (M+H)$^+$.

Example 1167

(P)-1-(2-chloro-4'-fluoro-5-methoxy-[1,1'-biphenyl]-4-yl)-2-oxo-N-(pyridazin-3-yl)-1,2-dihydroquinoline-6-sulfonamide This compound was prepared via method 222 using 3-aminopyridazine as the amine. $^1$H NMR (500 MHz, DMSO-d$_6$) δ ppm 3.72 (s, 3H) 6.77-6.83 (m, 2H) 7.30-7.42 (m, 3H) 7.60-7.71 (m, 4H) 7.88 (d, J=8.37 Hz, 1H) 7.94 (d, J=8.82 Hz, 1H) 8.18-8.44 (m, 3H) 14.34-14.73 (m, 1H). m/z (ESI) 537.2 (M+H)$^+$.

Example 1168

(P)-1-(2-chloro-4'-fluoro-5-methoxy-[1,1'-biphenyl]-4-yl)-N-(oxazol-2-yl)-2-oxo-1,2-dihydroquinoline-6-sulfonamide This compound was prepared via method 222 using 2-aminooxazole (purchased from Astatech, Inc.) as the amine. $^1$H NMR (500 MHz, DMSO-d$_6$) δ ppm 3.73 (s, 3H) 6.79 (t, J=8.63 Hz, 2H) 7.25-7.30 (m, 1H) 7.30-7.41 (m, 3H) 7.57-7.70 (m, 4H) 7.88 (dd, J=8.92, 1.91 Hz, 1H) 8.19 (d, J=9.67 Hz, 1H) 8.33 (d, J=1.82 Hz, 1H) 11.98-12.40 (m, 1H). m/z (ESI) 526.1 (M+H)$^+$.

Additional Intermediates Used to Prepare Compounds of the Invention

Intermediate DX: 1-(4-bromo-5-fluoro-2-methoxy-phenyl)-2-oxo-1,2-dihydroquinoxaline-6-sulfonyl chloride

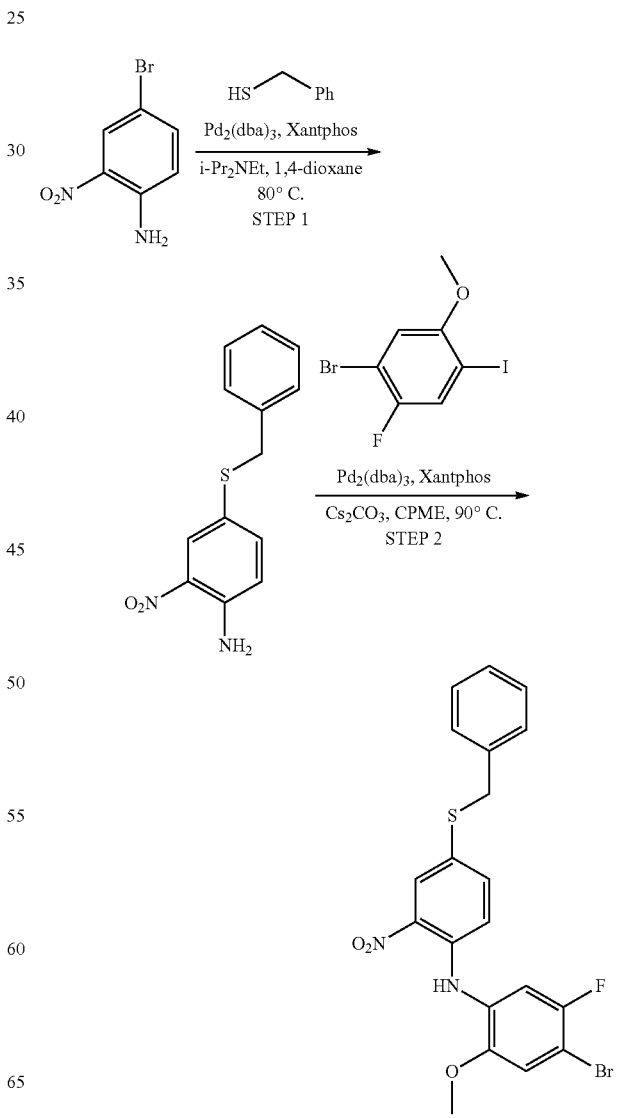

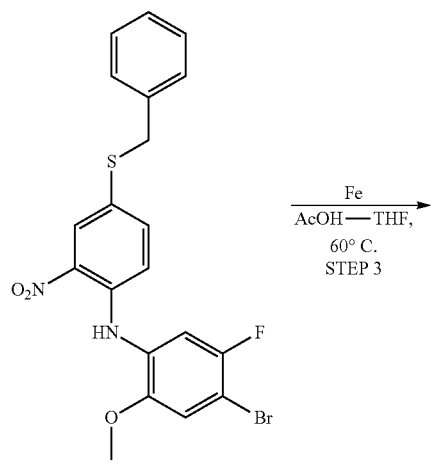

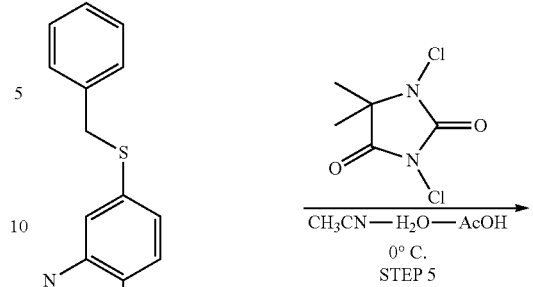

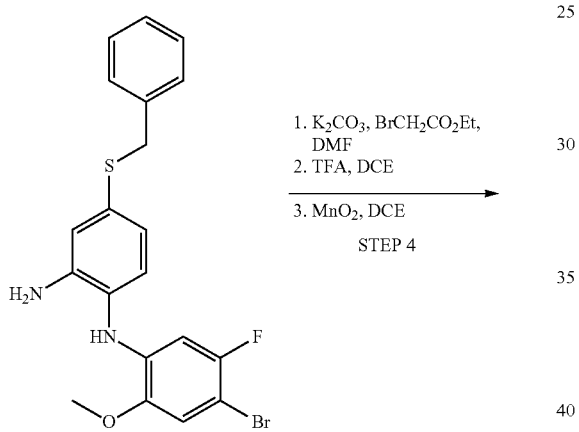

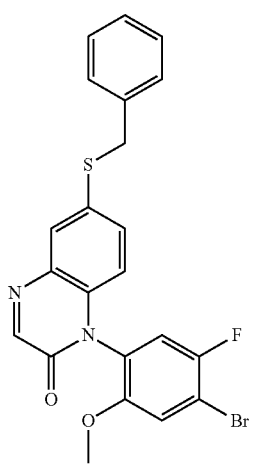

Step 1: 4-(benzylthio)-2-nitroaniline

A RBF was charged with 4-bromo-2-nitroaniline (21.698 g, 100 mmol), Xantphos (2.89 g, 5.00 mmol), tris(dibenzylideneacetone)dipalladium (0) (2.289 g, 2.500 mmol), 1,4-dioxane (100 ml), N,N-diisopropylethylamine (34.8 ml, 200 mmol), and benzyl mercaptan (12.42 ml, 105 mmol). The flask was fitted with a reflux condenser and lowered into an 80° C. heating bath. After 2 h, an additional portion of benzyl mercaptan (ca. 3 mL) was added After another 1 h, additional portions of Xantphos (1.45 g) and tris(dibenzylideneacetone)dipalladium (0) (1.15 g) were added. Finally, after an another hour, an additional portion of (12:15 μm). LCMS at 1 μm looked the same, so an additional portion of N,N-diisopropylethylamine (6 mL) was added. After 30 min, the mixture was diluted with water and extracted with EtOAc (3×). The combined organic extracts were dried over sodium sulfate and filtered through celite. The filtrate was concentrated. The mixture was taken up in DCM and filtered. The filtrate was concentrated. The residue was taken up in MeOH and filtered. The collected solid was washed with MeOH (2×), then dried under a stream of $N_2$ (g) for 1.5 h to give 10.97 g of an orange solid. The process was repeated with the filtrate to give an additional lot of product (2.84 g). The two materials were combined to give 4-(benzylthio)-2-nitroaniline (13.81 g, 53.1 mmol, 53.1% yield) as a rust-colored solid that was ~90% pure by LCMS. m/z (ESI) 261.0 $(M+H)^+$.

Step 2: N-(4-(benzylthio)-2-nitrophenyl)-4-bromo-5-fluoro-2-methoxyaniline

A RBF was charged with 4-(benzylthio)-2-nitroaniline (13.72 g, 47.4 mmol), 1-bromo-2-fluoro-4-iodo-5-methoxybenzene (17.27 g, 52.2 mmol), Xantphos (1.372 g, 2.372 mmol), Pd$_2$(dba)$_3$ (1.086 g, 1.186 mmol), CPME (95 ml) and cesium carbonate (23.18 g, 71.2 mmol) were added. A reflux condenser was attached and the flask was lowered into a 90° C. heating bath. The mixture was stirred overnight. In the morning, the solid was scraped of the bottom of the flask, and an additional portion of cesium carbonate (23.18 g, 71.2 mmol) was added. The flask was returned to the heat with vigorous stirring for 3 h. After cooling, the mixture was diluted with EtOAc and filtered through celite with the aid of EtOAc. The filtrate was concentrated, and the residue was dissolved in DCM and loaded onto a pre-equilibrated 340-g SNAP Ultra column. The column was eluted with 0-30% EtOAc/Heptane. The material crashed out on the column, so the elution was changed to 0-50% EtOAc/Heptane with 10% DCM. The eluent was raised to 100% EtOAc, 20% DCM. Fractions containing product were combined and concentrated to give 22.96 g (>100% yield) of N-(4-(benzylthio)-2-nitrophenyl)-4-bromo-5-fluoro-2-methoxyaniline as a red solid that was 80-90% pure by LCMS. m/z (ESI) 563.0 (M+H)$^+$.

Step 3: 4-(benzylthio)-N1-(4-bromo-5-fluoro-2-methoxyphenyl)benzene-1,2-diamine

A 3-neck 500-mL RBF was fitted with a mechanical stirrer, a reflux condenser, and an additional funnel. Acetic acid (100 mL) was added, followed by iron (31.4 g, 563 mmol). The flask was heated for 10 min in a 60° C. oil bath. Then a solution of N-(4-(benzylthio)-2-nitrophenyl)-4-bromo-5-fluoro-2-methoxyaniline (21.726 g, 37.5 mmol) in THF (75 mL) was added via the addition funnel over 25 min, and the addition funnel was washed with THF (2×). The mixture was cooled for 10 min, then filtered through celite. The filter cake was washed with THF (4×), then was removed from the filter and suspended in EtOAc. The suspension was filtered, and the filter cake was washed further with EtOAc (4×). All of the combined filtrates were concentrated. The material was dissolved in DCM (with a minimal amount of MeOH) and was loaded onto a 50-g SNAP Ultra column. The column was partially dried under vacuum then was eluted onto a pre-equilibrated 340-g SNAP Ultra column with 10-30% of a 3:1 EtOAc/EtOH mixture in heptane with 10% of DCM as co-eluent. Several mixed fractions were discarded, and the remainder containing product were combined and concentrated to give 4-(benzylthio)-N1-(4-bromo-5-fluoro-2-methoxyphenyl)benzene-1,2-diamine (13.49 g, 31.1 mmol, 83% yield) as a brown foam. $^1$H NMR (400 MHz, DMSO-d$_6$) δ=7.40-7.17 (m, 5H), 7.08 (d, J=6.5 Hz, 1H), 6.89 (s, 2H), 6.80-6.73 (m, 1H), 6.59-6.50 (m, 1H), 6.17-6.08 (m, 1H), 4.98-4.76 (m, 2H), 4.14 (s, 2H), 3.84 (s, 3H). m/z (ESI) 433.0 (M+H)$^+$.

Step 4: 6-(benzylthio)-1-(4-bromo-5-fluoro-2-methoxyphenyl)quinoxalin-2(1H)-one

A RBF was charged with 4-(benzylthio)-N1-(4-bromo-5-fluoro-2-methoxyphenyl)benzene-1,2-diamine (547.4 mg, 1.263 mmol) and potassium carbonate (210 mg, 1.516 mmol). The flask was flushed with Ar (g), then DMF (2526 µl) and ethyl bromoacetate (168 µl, 1.516 mmol) were added in sequence. The flask was heated to 50° C. for 6 h. The mixture was diluted with water and extracted with EtOAc (2×). The combined organic extracts were dried over sodium sulfate, filtered, and concentrated. The residue was taken up in DCE (5 mL) and trifluoroacetic acid (973 µl, 12.63 mmol). The flask was fitted with an air-cooled reflux condenser and heated to 50° C. overnight. The mixture was concentrated, and the residue was taken up in DCE (2.5 mL). Manganese dioxide (165 mg, 1.895 mmol) was added in one portion After 5 min, more DCE (2.5 mL) was added because the mixture was fairly thick. Following 30 min of stirring, the mixture was diluted with a small amount of DCM and filtered through celite with the aid of DCM. The filtrate was concentrated. The residue was taken up in DCM and loaded onto a 5-g silica gel loading column. The column was eluted onto a pre-equilibrated 50-g SNAP Ultra column with 10-60% EtOAc/Heptane to give 6-(benzylthio)-1-(4-bromo-5-fluoro-2-methoxyphenyl) quinoxalin-2(1H)-one (265.7 mg, 0.564 mmol, 44.6% yield) as a brown foam. $^1$H NMR (400 MHz, DMSO-d$_6$) δ=8.39-8.35 (m, 1H), 8.33 (s, 1H), 7.84-7.83 (m, 1H), 7.83-7.77 (m, 1H), 7.71-7.66 (m, 1H), 7.65-7.60 (m, 1H), 7.45-7.41 (m, 1H), 7.40-7.35 (m, 2H), 7.33-7.25 (m, 2H), 7.25-7.17 (m, 1H), 6.70-6.60 (m, 1H), 4.31 (s, 2H), 3.74-3.73 (m, 1H), 3.71 (s, 3H). m/z (ESI) 471.0.

Step 5: 1-(4-bromo-5-fluoro-2-methoxyphenyl)-2-oxo-1,2-dihydroquinoxaline-6-sulfonyl chloride A RBF was charged with 6-(benzylthio)-1-(4-bromo-5-fluoro-2-methoxyphenyl)quinoxalin-2(1H)-one (4.706 g, 9.98 mmol), acetonitrile (47.0 ml), acetic acid (1.762 ml), and water (1.175 ml) to give a thick suspension. The flask was cooled in an ice-water bath for 10 min, then 1,3-dichloro-5,5-dimethylimidazolidine-2,4-dione (0.649 g, 3.29 mmol) was added. After 5 min, another portion of 1,3-dichloro-5,5-dimethylimidazolidine-2,4-dione (0.649 g, 3.29 mmol) was added. This process was repeated three additional times, then stirred for 15 min. The mixture was diluted with EtOAc (50 mL), but the mixture remained a suspension. The mixture was concentrated to about ½ volume, then was filtered. The filter cake was washed with acetonitrile (1×), then dried under a nitrogen sweep to give 2.72 g of an off-white solid. The filtrate was again filtered, washed with acetonitrile (1×), and dried under a nitrogen sweep to give an additional portion of desired product. This process was repeated one additional time, and the three lots were combined to give 1-(4-bromo-5-fluoro-2-methoxyphenyl)-2-oxo-1,2-dihydroquinoxaline-6-sulfonyl chloride (3.945 g, 8.81 mmol, 88% yield) as an off-white solid. m/z (ESI) 447.0.

Intermediate DY: 1-(4-bromo-5-fluoro-2-methoxyphenyl)-N-(isoxazol-3-yl)-2-oxo-1,2-dihydroquinoxaline-6-sulfonamide

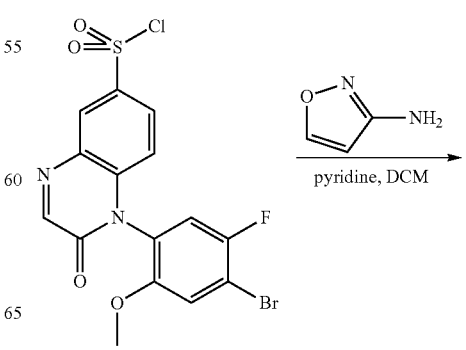

607
-continued

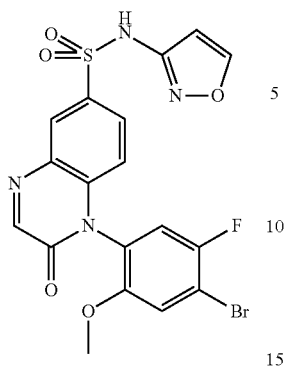

A RBF was charged with 1-(4-bromo-5-fluoro-2-methoxyphenyl)-2-oxo-1,2-dihydroquinoxaline-6-sulfonyl chloride (512.8 mg, 1.031 mmol), dichloromethane (1718 μl), and 3-aminoisoxazole (114 μl, 1.546 mmol) to give a thick suspension. Pyridine (3437 μl) was added relatively quickly, leading to thinner suspension. After 2 h, the mixture was concentrated in vacuo. The residue was partitioned between EtOAc and 2N aq. HCl. The layers were separated, and the aq. layer was extracted with EtOAc (2×). The combined organic extracts were dried over sodium sulfate, filtered, and concentrated. The residue was purified by chromatography on silica gel (50-g SNAP Ultra column, 0-50% 3:1 EtOAc/EtOH in heptane with 10% DCM) to give 1-(4-bromo-5-fluoro-2-methoxyphenyl)-N-(isoxazol-3-yl)-2-oxo-1,2-dihydroquinoxaline-6-sulfonamide (419.2 mg, 0.846 mmol, 82% yield) as a white foam. $^1$H NMR (400 MHz, DMSO-d$_6$) δ=11.74 (br. s., 1H), 8.74 (d, J=1.9 Hz, 1H), 8.47 (s, 1H), 8.29 (d, J=2.2 Hz, 1H), 7.90 (dd, J=2.2, 8.9 Hz, 1H), 7.72 (d, J=6.1 Hz, 1H), 7.62 (d, J=8.4 Hz, 1H), 6.98 (d, J=8.8 Hz, 1H), 6.48 (d, J=1.9 Hz, 1H), 3.74-3.71 (m, 3H), 3.32 (s, 3H). m/z (ESI) 495.0 (M+H)$^+$.

Intermediate DZ: 1-(4-bromo-5-fluoro-2-methoxyphenyl)-2-oxo-N-(pyridazin-3-yl)-1,2-dihydroquinoxaline-6-sulfonamide

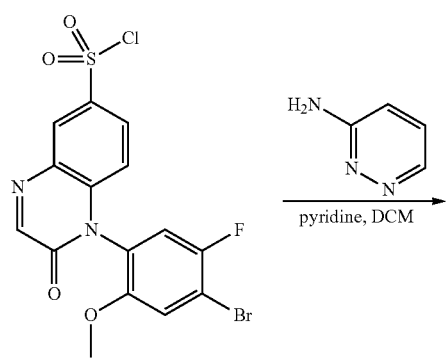

608
-continued

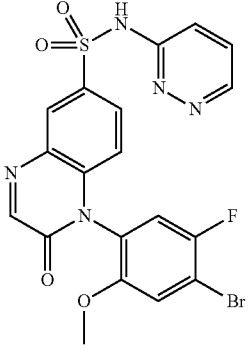

A RBF was charged with 1-(4-bromo-5-fluoro-2-methoxyphenyl)-2-oxo-1,2-dihydroquinoxaline-6-sulfonyl chloride (527.2 mg, 1.060 mmol), dichloromethane (1767 μl), and pyridazin-3-amine (151 mg, 1.590 mmol) to give a thick suspension. Pyridine (3533 μl) was added relatively quickly, and the mixture was stirred overnight. In the morning, the mixture was concentrated in vacuo, then taken up in 2N aq. HCl and MeOH/EtOAc. A solid formed that was slowly dissolved in the MeOH/EtOAc by repeated exposure. The layers were separated, and the aq. layer was extracted with MeOH/EtOAc (2×). The combined organic extracts were dried over sodium sulfate, filtered, and concentrated. The residue was purified by chromatography on silica gel (50-g SNAP Ultra column, 0-50% 3:1 EtOAc/EtOH in heptane with 10% DCM). The main peak was collected with a slightly lower-Rf peak to give 1-(4-bromo-5-fluoro-2-methoxyphenyl)-2-oxo-N-(pyridazin-3-yl)-1,2-dihydroquinoxaline-6-sulfonamide (119 mg, 0.235 mmol, 22.18% yield) as a yellow solid. m/z (ESI) 506.0 (M+H)+.

Intermediate EA: 6-(cyclopropylmethoxy)pyrimidin-4-amine

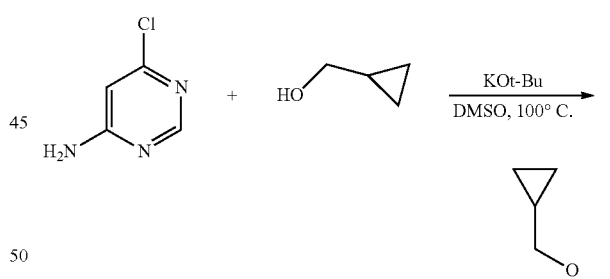

A vial was charged with 6-chloropyrimidin-4-amine (0.200 g, 1.544 mmol), potassium tert-butoxide (0.381 g, 3.40 mmol), cyclopropylmethanol (0.223 g, 3.09 mmol), and dimethyl sulfoxide (3.09 ml). The vial was capped and the reaction was heated to 100° C. After 3 hour, the mixture was diluted with water and EtOAc. The layers were separated, and the aq. layer was extracted with EtOAc (2×). The combined organic extracts were dried over magnesium sulfate, filtered, and concentrated. The residue was purified by chromatography on silica gel (40-g Redi-Sep Gold column, 0-50% of EtOAc/heptane to give 6-(cyclopropylmethoxy)pyrimidin-4-amine (0.189 g, 1.144 mmol, 74.1% yield) as a white solid. m/z (ESI) 166.2 (M+H)⁺.

Intermediate EB:
6-(cyclobutylmethoxy)pyrimidin-4-amine

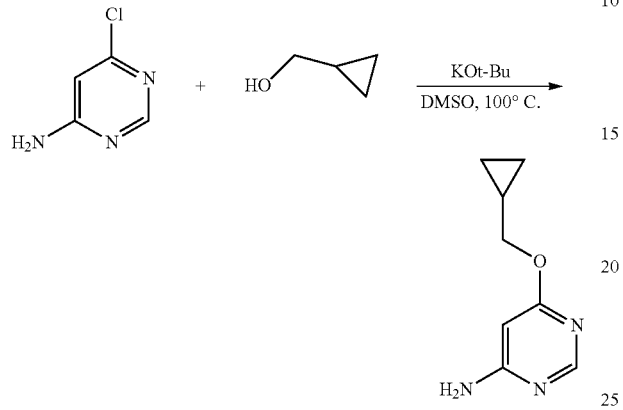

This was prepared in a manner analogous to 6-(cyclopropylmethoxy)pyrimidin-4-amine, where cyclobutylmethanol was used as the alcohol. 6-(cyclobutylmethoxy)pyrimidin-4-amine (0.245 g, 1.367 mmol, 89% yield) was obtained as a white solid. m/z (ESI) 180.2 (M+H)⁺.

Intermediate EC:
6-(cyclopentylmethoxy)pyrimidin-4-amine

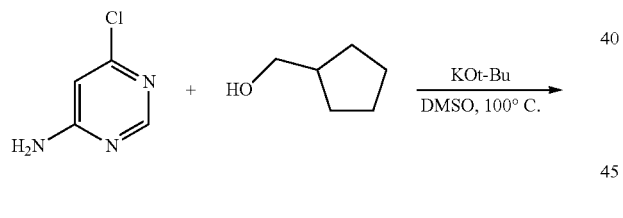

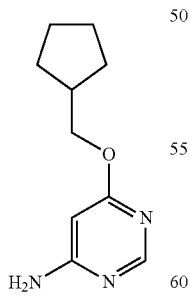

This was prepared in a manner analogous to 6-(cyclopropylmethoxy)pyrimidin-4-amine, where cyclopentylmethanol was used as the alcohol. 6-(cyclopentylmethoxy)pyrimidin-4-amine (0.266 g, 1.376 mmol, 89% yield) was obtained as a white solid. m/z (ESI) 194.2 (M+H)⁺.

Intermediate ED: 6-propoxypyrimidin-4-amine

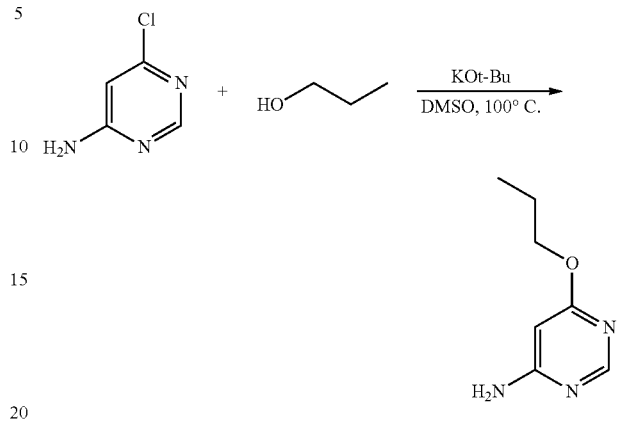

This was prepared in a manner analogous to 6-(cyclopropylmethoxy)pyrimidin-4-amine, where propan-1-ol was used as the alcohol. 6-propoxypyrimidin-4-amine (0.201 g, 1.312 mmol, 85% yield) was obtained as a white solid. m/z (ESI) 154.2 (M+H)⁺.

Intermediate EE: 6-isobutoxypyrimidin-4-amine

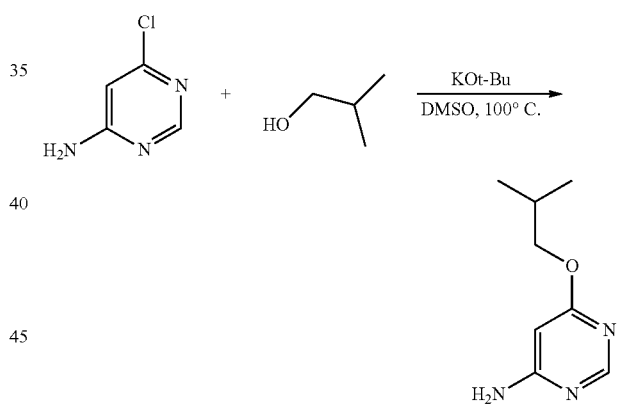

This was prepared in a manner analogous to 6-(cyclopropylmethoxy)pyrimidin-4-amine, where 2-methylpropan-1-ol was used as the alcohol. 6-isobutoxypyrimidin-4-amine (0.196 g, 1.172 mmol, 76% yield) was obtained as a white solid. m/z (ESI) 168.2 (M+H)⁺.

Intermediate EF: 6-cyclobutoxypyrimidin-4-amine

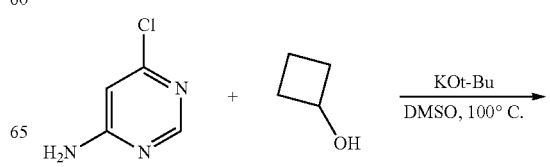

-continued

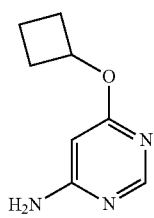

This was prepared in a manner analogous to 6-(cyclopropylmethoxy)pyrimidin-4-amine, where cyclobutanol was used as the alcohol. 6-cyclobutoxypyrimidin-4-amine (0.231 g, 1.398 mmol, 91% yield) was obtained as a white solid. m/z (ESI) 166.2 (M+H)⁺.

Intermediate EG:
6-((1-methylcyclopropyl)methoxy)pyrimidin-4-amine

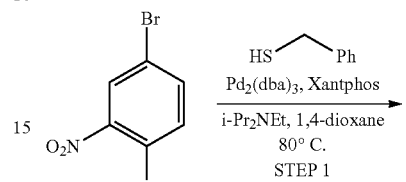

This was prepared in a manner analogous to 6-(cyclopropylmethoxy)pyrimidin-4-amine, where (1-methylcyclopropyl)methanol was used as the alcohol. 6-((1-methylcyclopropyl)methoxy)pyrimidin-4-amine (0.245 g, 1.367 mmol, 89% yield) was obtained as a white solid. m/z (ESI) 180.2 (M+H)⁺.

Intermediate EH:
6-(cyclopentyloxy)pyrimidin-4-amine

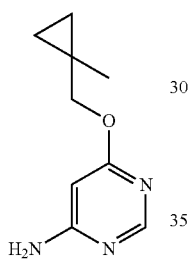

This was prepared in a manner analogous to 6-(cyclopropylmethoxy)pyrimidin-4-amine, where cyclopentanol was used as the alcohol. 6-(cyclopentyloxy)pyrimidin-4-amine (0.238 g, 1.328 mmol, 86% yield) was obtained as a white solid. m/z (ESI) 180.2 (M+H)⁺.

Intermediate EI: 1-(4-bromo-2-methoxyphenyl)-2-oxo-1,2-dihydroquinoxaline-6-sulfonyl chloride

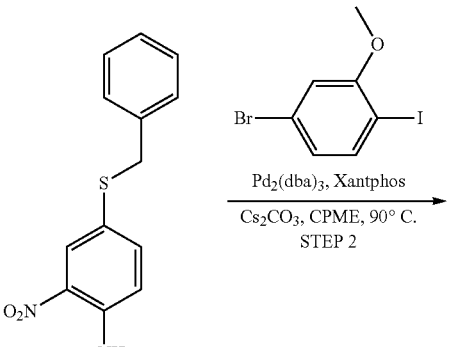

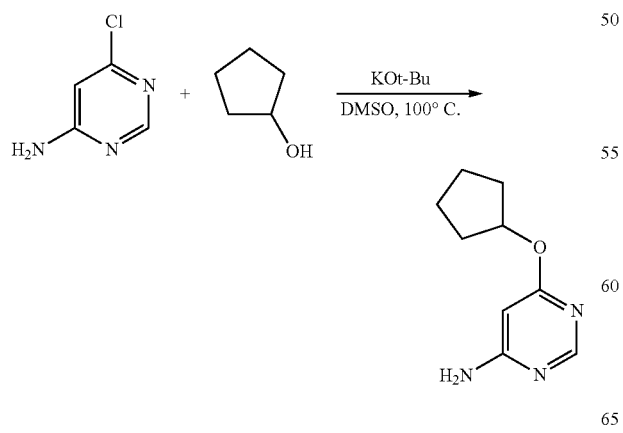

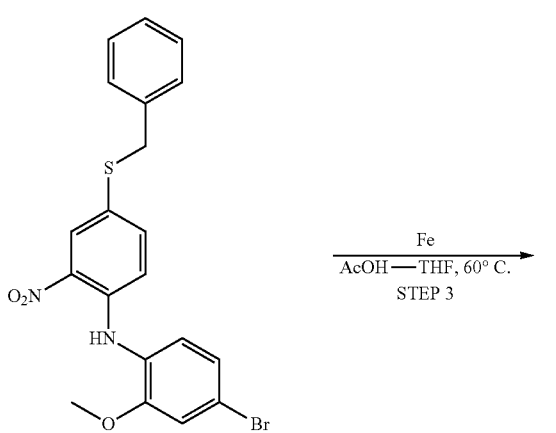

613
-continued

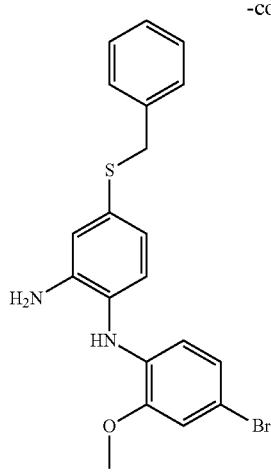

1. K₂CO₃, BrCH₂CO₂Et, DMF
2. TFA, DCE
3. MnO₂, DCE
STEP 4

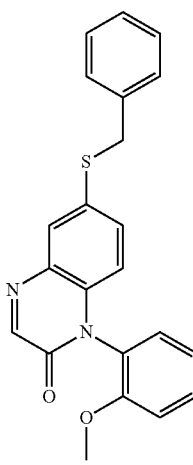

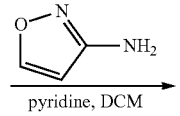
CH₃CN—H₂O—AcOH
0° C.
STEP 5

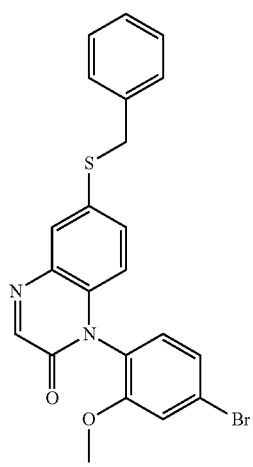

614
-continued

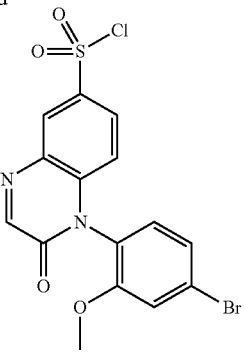

This intermediate was made in a similar manner to 1-(4-bromo-5-fluoro-2-methoxyphenyl)-2-oxo-1,2-dihydroquinoxaline-6-sulfonyl chloride with the exception that in step 2,4-bromo-1-iodo-2-methoxybenzene was used as the coupling partner. The remaining of the steps were identical, providing 1-(4-bromo-2-methoxyphenyl)-2-oxo-1,2-dihydroquinoxaline-6-sulfonyl chloride as an off white foam. m/z (ESI) 429.0 (M+H)⁺.

Intermediate EJ: 1-(4-bromo-2-methoxyphenyl)-N-(isoxazol-3-yl)-2-oxo-1,2-dihydroquinoxaline-6-sulfonamide

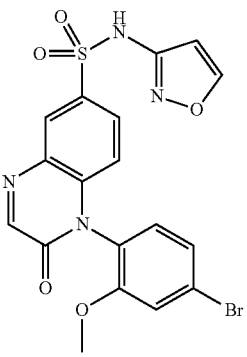

pyridine, DCM

A RBF was charged with 1-(4-bromo-2-methoxyphenyl)-2-oxo-1,2-dihydroquinoxaline-6-sulfonyl chloride (0.800 g, 1.862 mmol), DCM (3.12 ml), and 3-aminoisoxazole (0.206 ml, 2.79 mmol) to give a thick suspension. Pyridine (6.21 ml) was added relatively quickly, leading to thinner suspension. After 2 h, the mixture was concentrated in vacuo. The residue was partitioned between EtOAc and 2N aq. HCl. The layers were separated, and the aq. layer was extracted with EtOAc (2×). The combined organic extracts were dried over sodium sulfate, filtered, and concentrated. The residue was purified by chromatography on silica gel (50-g SNAP Ultra column, 0-50% 3:1 EtOAc/EtOH in heptane with 10% DCM) to give 1-(4-bromo-2-methoxyphenyl)-N-(isoxazol-3-yl)-2-oxo-1,2-dihydroquinoxaline-6-sulfonamide (0.751 g, 1.573 mmol, 85% yield) as a white foam. m/z (ESI) 478.9 (M+H)$^+$.

Intermediate EK: 1-(4-bromo-2-methoxyphenyl)-2-oxo-N-(pyrimidin-2-yl)-1,2-dihydroquinoxaline-6-sulfonamide

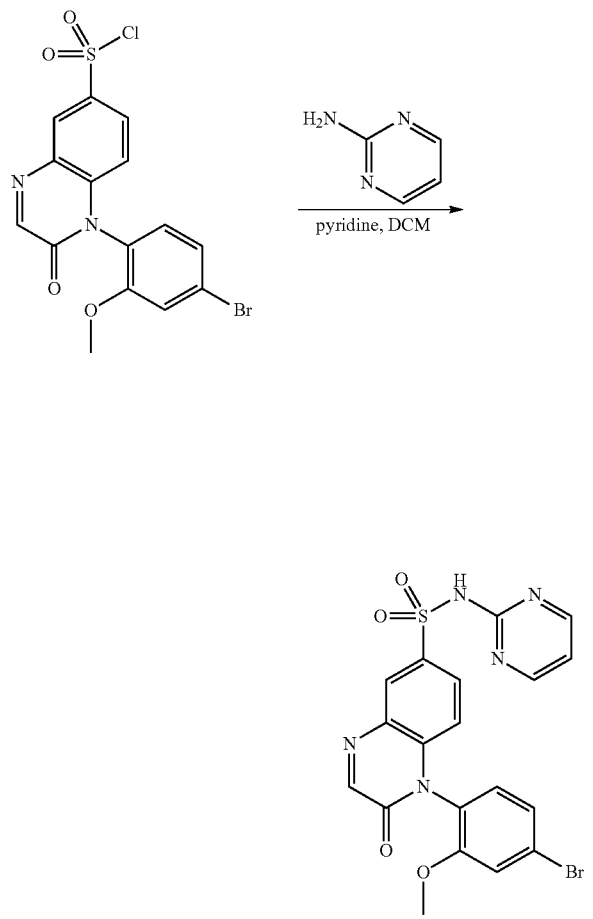

A RBF was charged with 1-(4-bromo-2-methoxyphenyl)-2-oxo-1,2-dihydroquinoxaline-6-sulfonyl chloride (500 mg, 1.164 mmol), dichloromethane (1939 µl), and pyrimidin-2-amine (166 mg, 1.746 mmol) to give a thick suspension. Pyridine (3879 µl) was added. After 3 h, the mixture was concentrated in vacuo, then taken up in 2N aq. HCl and EtOAc. The layers were separated, and the aq. layer was extracted with EtOAc (2×). The combined organic extracts were dried over sodium sulfate, filtered, and concentrated. The residue was purified by chromatography on silica gel (50-g SNAP Ultra column, 0-50% 3:1 EtOAc/EtOH in heptane with 10% DCM) to give 1-(4-bromo-2-methoxyphenyl)-2-oxo-N-(pyrimidin-2-yl)-1,2-dihydroquinoxaline-6-sulfonamide (0.300 g, 0.614 mmol, 52.8% yield) as a white foam. m/z (ESI) 489.0 (M+H)$^+$.

Intermediate EL: (P)-perfluorophenyl 1-(4-(5-chloro-6-methoxypyridin-3-yl)-5-fluoro-2-methoxyphenyl)-2-oxo-1,2-dihydroquinoline-6-sulfonate

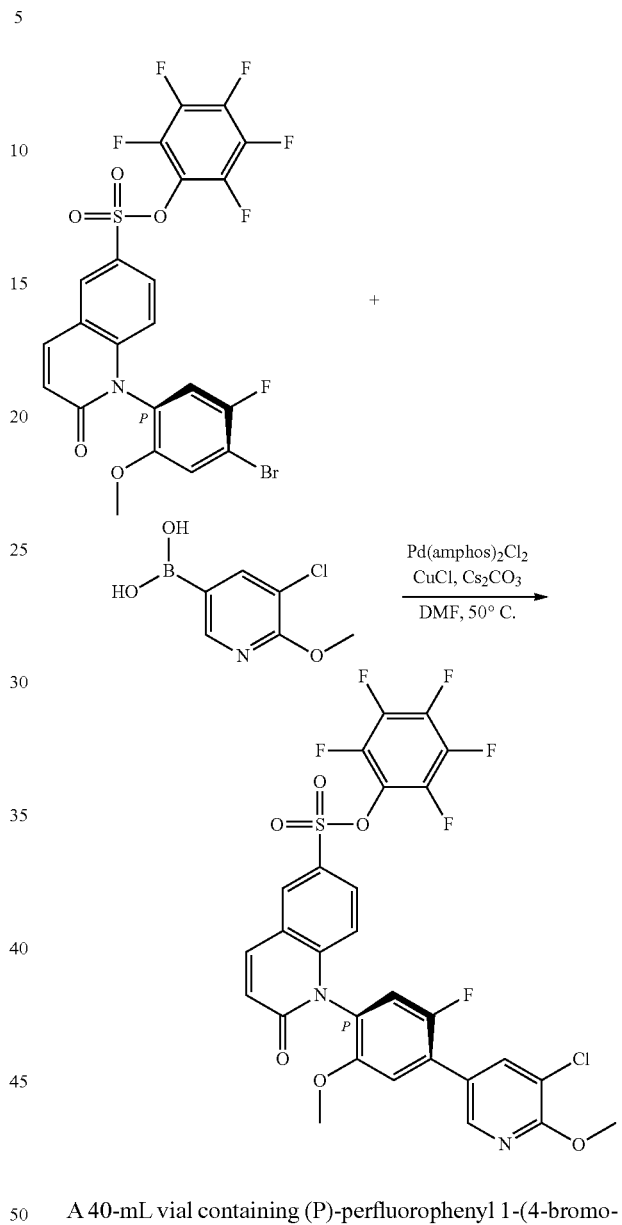

A 40-mL vial containing (P)-perfluorophenyl 1-(4-bromo-5-fluoro-2-methoxyphenyl)-2-oxo-1,2-dihydroquinoline-6-sulfonate (1.45 g, 2.440 mmol), 3-chloro-2-methoxypyridine-5-boronic acid (0.980 ml, 7.32 mmol) (purchased from Combi-Blocks, Inc.), cesium carbonate (3.18 g, 9.76 mmol), 1,1-bis[(di-t-butyl-p-methylaminophenyl]palladium(II) chloride (0.346 g, 0.488 mmol), and copper(I) chloride (0.725 g, 7.32 mmol) was flushed with N$_2$ and then charged with DMF (12 mL). The vial was stirred at 50° C. for 3 h. The brown slurry was cooled to rt, quenched with H$_2$O, diluted with ~1:1 EtOAc/hept, and filtered through a plug of celite. The layers of the filtrate were separated, and the aqueous layer was extracted twice more with ~1:1 EtOAc/hept. The organic extracts were combined, washed twice with H$_2$O and once with brine, dried over Na$_2$SO$_4$, filtered, and concentrated under a stream of N$_2$ to a brown oil. Column chromatography (50 g Snap Ultra column, 15% to 85% EtOAc/hept) afforded (P)-perfluorophenyl 1-(4-(5- chloro-6-methoxypyridin-3-yl)-5-fluoro-2-methoxyphenyl)-2-oxo-1,2-dihydroquinoline-6-sulfonate (1.252 g, 1.906 mmol, 78% yield) as an amber-colored amorphous solid. m/z (ESI) 657.0 (M+H)+.

Intermediate EM: (P)-perfluorophenyl 1-(2-chloro-4'-fluoro-5-methoxy-[1,1'-biphenyl]-4-yl)-2-oxo-1,2-dihydroquinoline-6-sulfonate

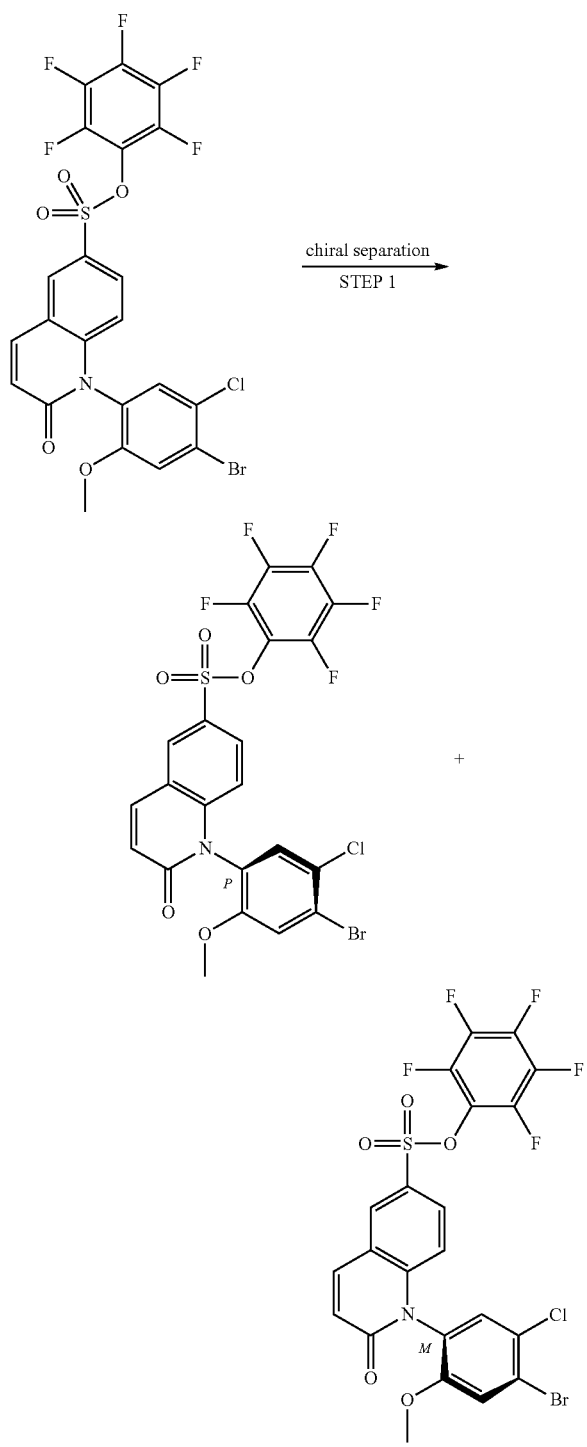

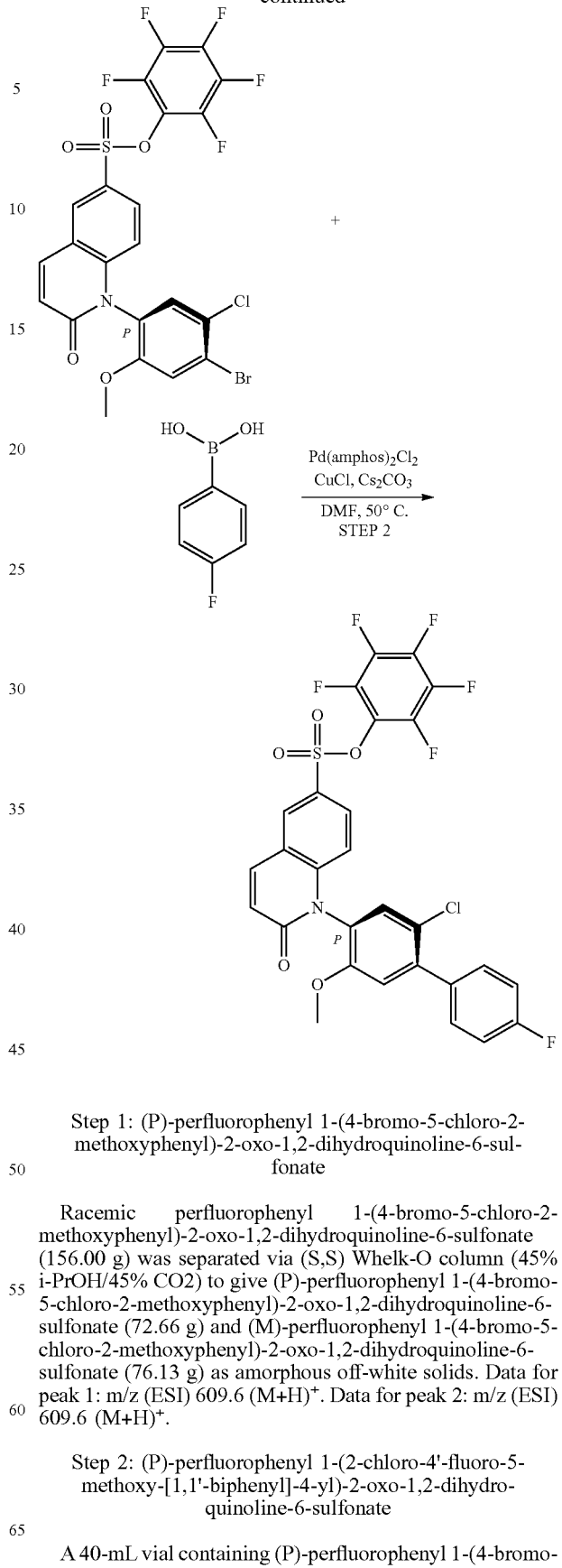

Step 1: (P)-perfluorophenyl 1-(4-bromo-5-chloro-2-methoxyphenyl)-2-oxo-1,2-dihydroquinoline-6-sulfonate Racemic perfluorophenyl 1-(4-bromo-5-chloro-2-methoxyphenyl)-2-oxo-1,2-dihydroquinoline-6-sulfonate (156.00 g) was separated via (S,S) Whelk-O column (45% i-PrOH/45% CO2) to give (P)-perfluorophenyl 1-(4-bromo-5-chloro-2-methoxyphenyl)-2-oxo-1,2-dihydroquinoline-6-sulfonate (72.66 g) and (M)-perfluorophenyl 1-(4-bromo-5-chloro-2-methoxyphenyl)-2-oxo-1,2-dihydroquinoline-6-sulfonate (76.13 g) as amorphous off-white solids. Data for peak 1: m/z (ESI) 609.6 (M+H)+. Data for peak 2: m/z (ESI) 609.6 (M+H)+.

Step 2: (P)-perfluorophenyl 1-(2-chloro-4'-fluoro-5-methoxy-[1,1'-biphenyl]-4-yl)-2-oxo-1,2-dihydroquinoline-6-sulfonate A 40-mL vial containing (P)-perfluorophenyl 1-(4-bromo-5-chloro-2-methoxyphenyl)-2-oxo-1,2-dihydroquinoline-6- sulfonate (1.45 g, 2.374 mmol), 4-fluorophenylboronic acid (0.997 g, 7.12 mmol), cesium carbonate (0.760 ml, 9.50 mmol), 1,1-bis[(di-t-butyl-p-methylaminophenyl]palladium (II) chloride (0.336 g, 0.475 mmol), and copper(I) chloride (0.705 g, 7.12 mmol) was flushed with $N_2$ and then charged with DMF (12 mL). The vial was stirred at 50° C. for 90 min. The brown slurry was cooled to rt, quenched with $H_2O$, diluted with ~1:1 EtOAc/hept, and filtered through a plug of celite. The layers of the filtrate were separated, and the aqueous layer was extracted twice more with ~1:1 EtOAc/hept. The organic extracts were combined, washed twice with $H_2O$ and once with brine, dried over $Na_2SO_4$, filtered, and concentrated under a stream of $N_2$ to a brown oil. Column chromatography (50 g Snap Ultra column, 15% to 85% EtOAc/hept) afforded (P)-perfluorophenyl 1-(2-chloro-4'-fluoro-5-methoxy-[1,1'-biphenyl]-4-yl)-2-oxo-1,2-dihydroquinoline-6-sulfonate (1.254 g, 2.003 mmol, 84% yield) as a pale yellow amorphous solid. m/z (ESI) 626.0 (M+H)$^+$.

Intermediate EN: 2-(3-(difluoromethoxy)-4-fluorophenyl)-4,4,5,5-tetramethyl-1,3,2-dioxaborolane

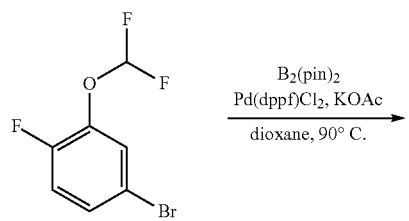

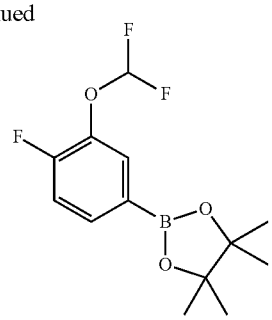

A 40-mL vial containing 4-bromo-2-(difluoromethoxy)-1-fluorobenzene (1.00 g, 4.15 mmol) (purchased from Combi-Blocks, Inc.), 1,1'-bis(diphenylphosphino)ferrocene palladium(II)dichloride dichloromethane adduct (0.169 g, 0.207 mmol), bis(pinacolato)diboron (1.159 g, 4.56 mmol), and potassium acetate (1.222 g, 12.45 mmol) was flushed with $N_2$ and subsequently charged with dioxane (4 mL). The slurry was stirred at 90° C. for 3.5 h. After cooling to rt, the reaction was quenched with $H_2O$ and extracted thrice with EtOAc. The organic extracts were combined, washed with brine, dried over $Na_2SO_4$, filtered, and concentrated in vacuo to a black oil. Column chromatography (25 g Snap Ultra column, 0% to 100% EtOAc/hept) afforded 2-(3-(difluoromethoxy)-4-fluorophenyl)-4,4,5,5-tetramethyl-1,3,2-dioxaborolane (178 mg, 0.618 mmol, 14.89% yield) as a brown-black oil. m/z (ESI) 289.2 (M+H)$^+$.

Table 4 provides data for examples 1140-1242, as representative compounds of the present invention, as follows: compound name (as named by ACD software, version 12; while the compound names in the written examples presented herein were named using ChemDraw Ultra version 12); molecular weight measured (MW); the method by which the compound was made; the NMR of the representative example; and biological data including in-vitro Nav 1.7 PX data (IC$_{50}$ in uM) and Nav 1.5 PX data (IC$_{50}$ in uM), where available.

TABLE 4

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| 1147 | 1-(5-(cyclopentylethynyl)-2-methoxyphenyl)-N-3-isoxazolyl-2-oxo-1,2-dihydro-6-quinolinesulfonamide | 490.2 | 220 | 0.121 | | 1H NMR (400 MHz, DMSO-d6) δ ppm 1.52-1.72 (m, 6 H) 1.88-1.99 (m, 2 H) 2.79-2.87 (m, 1 H) 3.67 (s, 3 H) 6.44 (d, J = 1.87 Hz, 1 H) 6.73 (d, J = 9.02 Hz, 1 H) 6.78 (d, J = 9.54 Hz, 1 H) 7.25 (d, J = 8.71 Hz, 1 H) 7.35 (d, J = 2.07 Hz, 1 H) 7.55 (dd, J = 8.66, 2.13 Hz, 1 H) 7.83 (dd, J = 8.97, 2.23 Hz, 1 H) 8.20 (d, J = 9.64 Hz, 1 H) 8.35 (d, J = 2.28 Hz, 1 H) 8.73 (d, J = 1.76 Hz, 1 H) 11.65 (s, 1 H) |
| 1146 | 1-(5-(cyanomethyl)-2-methoxyphenyl)-N-3-isoxazolyl-2-oxo-1,2-dihydro-6-quinolinesulfonamide | 437.0 | 219 | 3.594 | | |
| 1148 | (P)-1-(5-(cyclopentylethynyl)-2-methoxyphenyl)-N-3-isoxazolyl-2-oxo-1,2-dihydro-6-quinolinesulfonamide | 490.2 | 220 | 0.04 | | 1H NMR (400 MHz, DMSO-d6) δ ppm 1.51-1.73 (m, 6 H) 1.88-1.99 (m, 2 H) 2.79-2.87 (m, 1 H) 3.67 (s, 3 H) 6.43 (d, J = 1.87 Hz, 1 H) 6.72 (d, J = 8.91 Hz, 1 H) 6.77 (d, J = 9.54 Hz, 1 H) 7.25 (d, J = 8.71 Hz, 1 H) 7.34 (d, J = 2.07 Hz, 1 H) 7.54 (dd, J = 8.66, 2.12 Hz, 1 H) 7.83 (dd, J = 8.97, 2.23 Hz, 1 H) 8.19 (d, J = 9.54 Hz, 1 H) 8.34 (d, J = 2.28 Hz, |

TABLE 4-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | | | | | | 1 H) 8.70 (d, J = 1.76 Hz, 1 H) 11.64 (br. s., 1 H) |
| 1149 | (M)-1-(5-(cyclopentylethynyl)-2-methoxyphenyl)-N-3-isoxazolyl-2-oxo-1,2-dihydro-6-quinolinesulfonamide | 490.2 | 220 | | | |
| 1169 | 1-(2-(5-chloro-2-fluorophenyl)-5-methoxy-4-pyridinyl)-N-3-isoxazolyl-2-oxo-1,2-dihydro-6-quinolinesulfonamide | 527.0 | 161 | 0.805 | | 1H NMR (400 MHz, DMSO-d6) δ ppm 3.89 (s, 3 H) 6.22 (s, 1 H) 6.70-6.79 (m, 2 H) 7.39 (dd, J = 10.88, 8.81 Hz, 1 H) 7.51-7.56 (m, 1 H) 7.76 (dd, J = 10.32 Hz, 1 H) 7.87 (d, J = 1.24 Hz, 1 H) 8.00 (dd, J = 6.74, 2.80 Hz, 1 H) 8.18-8.24 (m, 2 H) 8.36 (s, J = 5.26, 5.26 Hz, 1 H) 8.84 (s, 1 H) |
| 1170 | 1-(2-(4-chloro-2-fluorophenyl)-5-methoxy-4-pyridinyl)-N-3-isoxazolyl-2-oxo-1,2-dihydro-6-quinolinesulfonamide | 527.0 | 161 | | | 1H NMR (400 MHz, DMSO-d6) δ ppm 3.88 (s, 3 H) 6.33 (s, 1 H) 6.73-6.84 (m, 2 H) 7.41-7.46 (m, 1 H) 7.53-7.59 (m, 1 H) 7.76-7.86 (m, 2 H) 8.01 (t, J = 8.39 Hz, 1 H) 8.22 (d, J = 9.69 Hz, 1 H) 8.31 (d, J = 1.87 Hz, 1 H) 8.54 (s, 1 H) 8.84 (s, 1 H) |
| 1154 | N-3-isoxazolyl-1-(2-methoxyphenyl)-2-oxo-1,2-dihydro-6-quinolinesulfonamide | 396.0 | 227 | 10.06 | | |
| 1171 | (P)-1-(2-fluoro-3',5,5'-trimethoxy-4-biphenylyl)-N-(2-methyl-4-pyrimidinyl)-2-oxo-1,2-dihydro-6-quinolinesulfonamide | 575.1 | 141 | 0.096 | | 1H NMR (400 MHz, DMSO-d6) δ ppm 2.39 (s, 3 H) 3.74 (s, 3 H) 3.83 (s, 6 H) 6.60-6.65 (m, 1 H) 6.76-6.84 (m, 4 H) 6.86-6.86 (m, 1 H) 7.38 (d, J = 6.84 Hz, 1 H) 7.47 (d, J = 10.26 Hz, 1 H) 7.90 (dd, J = 8.76, 2.02 Hz, 1 H) 8.13 (d, J = 5.91 Hz, 1 H) 8.24 (d, J = 9.64 Hz, 1 H) 8.40 (d, J = 1.76 Hz, 1 H) |
| 1172 | (P)-1-(3'-(difluoromethoxy)-2-fluoro-5-methoxy-4-biphenylyl)-2-oxo-N-3-pyridazinyl-1,2-dihydro-6-quinolinesulfonamide | 569.2 | 141 | 0.029 | | 1H NMR (400 MHz, DMSO-d6) δ ppm 3.75 (s, 3 H) 3.78-3.78 (m, 1 H) 6.78-6.85 (m, 2 H) 7.18 (s, 1 H) 7.21-7.21 (m, 1 H) 7.30 (t, J = 7.67 Hz, 1 H) 7.37 (s, 1 H) 7.42 (d, J = 6.84 Hz, 1 H) 7.50-7.65 (m, 4 H) 7.71 (s, 1 H) 7.87 (d, J = 6.53 Hz, 1 H) 8.22 (d, J = 9.74 Hz, 1 H) 8.36 (s, 1 H) |
| 1173 | (P)-1-(3'-(difluoromethoxy)-2-fluoro-5-methoxy-4-biphenylyl)-N-(6-methyl-4-pyrimidinyl)-2-oxo-1,2-dihydro-6-quinolinesulfonamide | 581.1 | 141 | 0.146 | | 1H NMR (400 MHz, DMSO-d6) δ ppm 2.32 (s, 3 H) 3.74 (s, 3 H) 6.77-6.85 (m, 2 H) 6.91 (s, 1 H) 7.29 (dt, J = 7.31, 2.15 Hz, 1 H) 7.36 (t, 73.91 Hz, 1 H) 7.42 (d, J = 6.95 Hz, 1 H) 7.48-7.65 (m, 4 H) 7.92 (dd, J = 8.97, 2.12 Hz, 1 H) 8.24 (d, J = 9.54 Hz, 1 H) 8.43 (d, J = 2.18 Hz, 1 H) 8.51 (s, 1 H) |
| 1155 | 1-benzyl-N-3-isoxazolyl-2-oxo-1,2-dihydro-6-quinolinesulfonamide | 380.1 | 228 | | | |
| 1174 | 1-(2,6-difluorophenyl)-N-3-isoxazolyl-2-oxo-1,2-dihydro-6-quinolinesulfonamide | 404.0 | 227 | | | |
| 1175 | 1-(2-fluorophenyl)-N-3-isoxazolyl-2-oxo-1,2-dihydro-6-quinolinesulfonamide | 386.2 | 227 | | | |
| 1176 | 1-(2-ethylphenyl)-N-3-isoxazolyl-2-oxo-1,2-dihydro-6-quinolinesulfonamide | 396.2 | 227 | | | |
| 1177 | 1-(2,3-dihydro-1-benzofuran-7-yl)-N-3-isoxazolyl-2-oxo-1,2- | 410.2 | 227 | | | |

TABLE 4-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| 1178 | dihydro-6-quinolinesulfonamide N-3-isoxazolyl-2-oxo-1-(2-phenylethyl)-1,2-dihydro-6-quinolinesulfonamide | 394.2 | 228 | | | |
| 1179 | N-3-isoxazolyl-2-oxo-1-(2,3',4'-trifluoro-5-methoxy-4-biphenylyl)-1,2-dihydro-6-quinoxalinesulfonamide | 529.2 | 214 | 0.062 | | $^1$H NMR (400 MHz, DMSO-d$_6$) δ = 11.76 (s, 1H), 8.76 (d, J = 2.0 Hz, 1H), 8.50 (s, 1H), 8.32 (d, J = 2.2 Hz, 1H), 7.95 (dd, J = 2.2, 8.9 Hz, 1H), 7.90-7.79 (m, 1H), 7.68-7.56 (m, 3H), 7.48 (d, J = 6.9 Hz, 1H), 6.99 (d, J = 8.8 Hz, 1H), 6.49 (d, J = 2.0 Hz, 1H), 3.81-3.77 (m, 4H). |
| 1141 | 1-(2,4'-difluoro-5-methoxy-4-biphenylyl)-N-3-isoxazolyl-2-oxo-1,2-dihydro-6-quinoxalinesulfonamide | 511.0 | 214 | 0.106 | | 1H NMR (400 MHz, DMSO-d6) δ = 11.76 (s, 1H), 8.76 (d, J = 1.9 Hz, 1H), 8.50 (s, 1H), 8.32 (d, J = 2.2 Hz, 1H), 7.95 (dd, J = 2.3, 8.9 Hz, 1H), 7.76 (ddd, J = 1.5, 5.4, 8.8 Hz, 2H), 7.56 (d, J = 10.3 Hz, 1H), 7.46-7.37 (m, 3H), 7.01 (d, J = 8.9 Hz, 1H), 6.49 (d, J = 2.0 Hz, 1H), 3.80 (s, 3H). |
| 1180 | 2-oxo-N-3-pyridazinyl-1-(2,3',4'-trifluoro-5-methoxy-4-biphenylyl)-1,2-dihydro-6-quinoxalinesulfonamide | 540.1 | 214 | 0.265 | | $^1$H NMR (400 MHz, DMSO-d$_6$) δ = 8.48 (s, 1H), 8.35 (br. s., 1H), 8.30 (d, J = 1.7 Hz, 1H), 7.94 (dd, J = 1.9, 8.5 Hz, 1H), 7.91-7.78 (m, 2H), 7.73-7.53 (m, 4H), 7.48 (d, J = 6.8 Hz, 1H), 6.90 (d, J = 8.7 Hz, 1H), 3.84-3.72 (m, 4H). |
| 1142 | 1-(4-(cyclopentylethynyl)-5-fluoro-2-methoxyphenyl)-N-3-isoxazolyl-2-oxo-1,2-dihydro-6-quinoxalinesulfonamide | 509.2 | 215 | 0.079 | | $^1$H NMR (400 MHz, DMSO-d$_6$) δ = 11.74 (s, 1H), 8.75 (d, J = 2.0 Hz, 1H), 8.47 (s, 1H), 8.30 (d, J = 2.3 Hz, 1H), 7.90 (dd, J = 2.2, 8.8 Hz, 1H), 7.48 (d, J = 9.1 Hz, 1H), 7.38 (d, J = 6.3 Hz, 1H), 6.95 (d, J = 8.9 Hz, 1H), 6.49 (d, J = 2.0 Hz, 1H), 3.67 s, 3H), 2.98 (t, J = 7.3 Hz, 1H), 2.09-1.98 (m, 2H), 1.80-1.58 (m, 6H). m/z (ESI) 509.2 (M + H)+. |
| 1181 | 1-(2-fluoro-5-methoxy-3'-(trifluoromethyl)-4-biphenylyl)-N-3-isoxazolyl-2-oxo-1,2-dihydro-6-quinoxalinesulfonamide | 561.0 | 214 | | | $^1$H NMR (400 MHz, DMSO-d$_6$) δ = 11.69 (s, 1H), 8.68 (d, J = 2.0 Hz, 1H), 8.43 (s, 1H), 8.25 (d, J = 2.3 Hz, 1H), 8.00-7.92 (m, 2H), 7.87 (t, J = 4.8 Hz, 1H), 7.80 (d, J = 6.6 Hz, 1H), 7.75 (d, J = 10.1 Hz, 1H), 7.53 (d, J = 10.1 Hz, 1H), 7.46 (d, J = 6.6 Hz, 1H), 6.94 (d, J = 8.9 Hz, 1H), 6.42 (d, J = 2.0 Hz, 1H), 3.72 (s, 3H). |
| 1182 | 1-(3'-chloro-2-fluoro-5,5'-dimethoxy-4-biphenylyl)-N-3-isoxazolyl-2-oxo-1,2-dihydro-6-quinoxalinesulfonamide | 557.0 | 214 | | | $^1$H NMR (400 MHz, DMSO-d$_6$) δ = 11.69 (s, 1H), 8.68 (d, J = 2.0 Hz, 1H), 8.43 (s, 1H), 8.25 (d, J = 2.3 Hz, 1H), 8.00-7.92 (m, 2H), 7.87 (t, J = 4.8 Hz, 1H), 7.80 (d, J = 6.6 Hz, 1H), 7.75 (d, J = 10.1 Hz, 1H), 7.53 (d, J = 10.1 Hz, 1H), 7.46 (d, J = 6.6 Hz, 1H), 6.94 (d, J = 8.9 Hz, 1H), 6.42 (d, J = 2.0 Hz, 1H), 3.72 (s, 3H). |
| 1183 | (P)-1-(4-bromo-5-fluoro-2-methoxyphenyl)-N-(6-(cyclopropylmethoxy)-4-pyrimidinyl)-2-oxo-1,2-dihydro-6-quinolinesulfonamide | 575.0 | 197 | 2.61 | | |
| 1184 | (P)-1-(4-bromo-5-fluoro-2-methoxyphenyl)-N-(6-(cyclobutylmethoxy)-4-pyrimidinyl)-2-oxo-1,2-dihydro-6-quinolinesulfonamide | 589.0 | 197 | 3.359 | | |
| 1185 | (P)-1-(4-bromo-5-fluoro-2-methoxyphenyl)-N-(6-(cyclopentylmethoxy)-4- | 603.0 | 197 | 6.643 | | |

TABLE 4-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | pyrimidinyl)-2-oxo-1,2-dihydro-6-quinolinesulfonamide | | | | | |
| 1186 | (P)-1-(4-bromo-5-fluoro-2-methoxyphenyl)-2-oxo-N-(6-propoxy-4-pyrimidinyl)-1,2-dihydro-6-quinolinesulfonamide | 563.0 | 197 | 0.246 | | 1H NMR (500 MHz, DMSO-d6) 8.36-8.45 (m, 2H), 8.24 (d, J = 9.73 Hz, 1H), 7.87 (d, J = 8.69 Hz, 1H), 7.66 (d, J = 6.16 Hz, 1H), 7.59 (d, J = 8.63 Hz, 1H), 6.75-6.86 (m, 2H), 6.35 (s, 1H), 4.19 (t, J = 6.62 Hz, 2H), 3.69 (s, 3H), 1.62-1.73 (m, 2H), 0.91 (t, J = 7.40 Hz, 3H) |
| 1187 | (P)-1-(4-bromo-5-fluoro-2-methoxyphenyl)-N-(6-(2-methylpropoxy)-4-pyrimidinyl)-2-oxo-1,2-dihydro-6-quinolinesulfonamide | 577.0 | 197 | 1.66 | | |
| 1188 | (P)-1-(4-bromo-5-fluoro-2-methoxyphenyl)-N-(6-(cyclobutyloxy)-4-pyrimidinyl)-2-oxo-1,2-dihydro-6-quinolinesulfonamide | 575.0 | 197 | 10.61 | | |
| 1189 | (P)-1-(4-bromo-5-fluoro-2-methoxyphenyl)-N-(6-((1-methylcyclopropyl)methoxy)-4-pyrimidinyl)-2-oxo-1,2-dihydro-6-quinolinesulfonamide | 589.0 | 197 | 8.358 | | |
| 1190 | (P)-1-(4-bromo-5-fluoro-2-methoxyphenyl)-N-(6-(cyclopentyloxy)-4-pyrimidinyl)-2-oxo-1,2-dihydro-6-quinolinesulfonamide | 589.0 | 197 | | | |
| 1191 | (P)-1-(4-bromo-5-fluoro-2-methoxyphenyl)-N-(1-methyl-1H-pyrazol-3-yl)-2-oxo-1,2-dihydro-6-quinolinesulfonamide | 507.0 | 197 | | | |
| 1192 | (P)-1-(4-bromo-5-fluoro-2-methoxyphenyl)-N-(1-ethyl-1H-pyrazol-3-yl)-2-oxo-1,2-dihydro-6-quinolinesulfonamide | 521.0 | 197 | | | |
| 1193 | 1-(3'-(difluoromethoxy)-2-fluoro-5-methoxy-4-biphenylyl)-N-3-isoxazolyl-2-oxo-1,2-dihydro-6-quinoxalinesulfonamide | 559.0 | 214 | 0.093 | | $^1$H NMR (400 MHz, DMSO-d$_6$) δ 11.69 (br. s, 1H), 8.68 (d, J = 1.87 Hz, 1H), 8.43 (s, 1H), 8.25 (d, J = 2.18 Hz, 1H), 7.88 (dd, J = 2.18, 8.91 Hz, 1H), 7.42-7.59 (m, 3H), 7.40 (d, J = 6.84 Hz, 1H), 7.20-7.31 (m, 2H), 7.11 (s, 1H), 6.93 (d, J = 8.81 Hz, 1H), 6.42 (d, J = 1.76 Hz, 1H), 3.71 (s, 3H) |
| 1194 | 1-(2,4'-difluoro-5-methoxy-3'-methyl-4-biphenylyl)-N-3-isoxazolyl-2-oxo-1,2-dihydro-6-quinoxalinesulfonamide | 525.1 | 214 | 0.056 | | $^1$H NMR (400 MHz, DMSO-d$_6$) δ 11.76 (br. s, 1H), 8.76 (d, J = 1.87 Hz, 1H), 8.50 (s, 1H), 8.32 (d, J = 2.18 Hz, 1H), 7.95 (dd, J = 2.18, 8.91 Hz, 1H), 7.64 (d, J = 7.46 Hz, 1H), 7.55 (s, J = 6.14 Hz, 1H), 7.53 (s, J = 3.61 Hz, 1H), 7.41 (d, J = 6.95 Hz, 1H), 7.32 (t, J = 9.06 Hz, 1H), 6.99 (d, J = 8.91 Hz, 1H), 6.49 (d, J = 1.87 Hz, 1H), 3.77 (s, 3H), 2.35 (d, J = 1.66 Hz, 3H) |
| 1195 | 1-(4'-chloro-3-methoxy-3'-methyl-4-biphenylyl)-N-3-isoxazolyl-2-oxo-1,2-dihydro-6- | 523.0 | 214 | 0.054 | | $^1$H NMR (400 MHz, DMSO-d$_6$) δ 11.74 (br. s, 1H), 8.75 (d, J = 1.76 Hz, 1H), 8.48 (s, 1H), 8.31 (d, J = 2.18 Hz, 1H), 7.94 (dd, J = 2.18, |

TABLE 4-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | quinoxalinesulfonamide | | | | | 8.91 Hz, 1H), 7.84 (d, J = 1.87 Hz, 1H), 7.68 (dd, J = 1.92, 8.34 Hz, 1H), 7.57 (s, 1H), 7.56 (d, J = 7.34 Hz, 2H), 7.49 (s, 2H), 6.91 (d, J = 8.81 Hz, 1H), 6.49 (d, J = 1.87 Hz, 1H), 3.81 (s, 3H), 2.45 (s, 3H) |
| 1196 | 1-(3'-chloro-3,5'-dimethoxy-4-biphenylyl)-N-3-isoxazolyl-2-oxo-1,2-dihydro-6-quinoxalinesulfonamide | 540.1 | 214 | 0.052 | | $^1$H NMR (400 MHz, DMSO-d$_6$) δ 11.75 (br.s, 1H), 8.75 (d, J = 1.76 Hz, 1H), 8.48 (s, 1H), 8.31 (d, J = 2.18 Hz, 1H), 7.94 (dd, J = 2.18, 8.91 Hz, 1H), 7.59 (d, J = 1.55 Hz, 1H), 7.45-7.54 (m, 3H), 7.33 (dd, J = 1.55, 2.28 Hz, 1H), 7.12 (s, 1H), 6.90 (d, J = 8.81 Hz, 1H), 6.49 (d, J = 1.87 Hz, 1H), 3.89 (s, 3H), 3.82 (s, 3H) |
| 1197 | 1-(3,3'-dimethoxy-4'-methyl-4-biphenylyl)-N-3-isoxazolyl-2-oxo-1,2-dihydro-6-quinoxalinesulfonamide | 519.1 | 214 | 0.146 | | $^1$H NMR (400 MHz, DMSO-d$_6$) δ 11.75 (br. s, 1H), 8.76 (d, J = 1.76 Hz, 1H), 8.48 (s, 1H), 8.31 (d, J = 2.18 Hz, 1H), 7.95 (dd, J = 2.23, 8.86 Hz, 1H), 7.54 (s, 1H), 7.44-7.51 (m, 2H), 7.25-7.34 (m, 3H), 6.93 (d, J = 9.02 Hz, 1H), 6.49 (d, J = 1.76 Hz, 1H), 3.93 (s, 3H), 3.81 (s, 3H), 2.22 (s, 3H) |
| 1198 | 1-(3'-chloro-4'-fluoro-3-methoxy-4-biphenylyl)-N-3-isoxazolyl-2-oxo-1,2-dihydro-6-quinoxalinesulfonamide | 526.9 | 214 | 0.039 | | $^1$H NMR (400 MHz, DMSO-d$_6$) δ 11.67 (br. s, 1H), 8.68 (d, J = 1.87 Hz, 1H), 8.41 (s, 1H), 8.24 (d, J = 2.18 Hz, 1H), 8.03 (dd, J = 2.28, 7.15 Hz, 1H), 7.87 (dd, J = 2.18, 8.81 Hz, 1H), 7.79 (ddd, J = 2.33, 4.66, 8.66 Hz, 1H), 7.48-7.55 (m, 2H), 7.41-7.46 (m, 2H), 6.83 (d, J = 8.71 Hz, 1H), 6.41 (d, J = 1.87 Hz, 1H), 3.74 (s, 3H) |
| 1199 | 1-(4'-chloro-3-methoxy-3'-methyl-4-biphenylyl)-2-oxo-N-2-pyrimidinyl-1,2-dihydro-6-quinoxalinesulfonamide | 534.1 | 214 | 0.127 | | $^1$H NMR (400 MHz, DMSO-d$_6$) δ 11.97 (br. s, 1H), 8.53 (d, J = 4.87 Hz, 2H), 8.47 (s, 1H), 8.43-8.44 (m, 1H), 8.06 (dd, J = 2.13, 8.86 Hz, 1H), 7.85 (d, J = 1.87 Hz, 1H), 7.68 (dd, J = 2.02, 8.24 Hz, 1H), 7.52-7.60 (m, 2H), 7.48 (s, J = 6.07 Hz, 2H), 7.07 (t, J = 5.03 Hz, 1H), 6.89 (d, J = 8.91 Hz, 1H), 3.80 (s, 3H), 2.52 (s, 3H) |
| 1200 | 1-(3-methoxy-3'-(trifluoromethyl)-4-biphenylyl)-2-oxo-N-2-pyrimidinyl-1,2-dihydro-6-quinoxalinesulfonamide | 554.2 | 214 | 0.078 | | $^1$H NMR (400 MHz, DMSO-d$_6$) δ 11.92 (br. s, 1H), 8.53 (d, J = 4.87 Hz, 2H), 8.41-8.50 (m, 1H), 8.11-8.20 (m, 2H), 8.06 (d, J = 8.96 Hz, 1H), 7.73-7.91 (m, 3H), 7.65 (d, J = 1.66 Hz, 1H), 7.48-7.62 (m, 2H), 7.08 (t, J = 5.18 Hz, 1H), 6.89 (d, J = 8.81 Hz, 1H), 3.83 (s, 3H) |
| 1201 | 1-(4'-chloro-2-fluoro-5',5-dimethoxy-4-biphenylyl)-2-oxo-N-2-pyrimidinyl-1,2-dihydro-6-quinoxalinesulfonamide | 568.0 | 214 | 0.11 | | $^1$H NMR (400 MHz, DMSO-d$_6$) δ 11.97 (br. s, 1H), 8.47-8.63 (m, 4H), 8.13 (dd, J = 2.18, 8.91 Hz, 1H), 7.58-7.71 (m, 2H), 7.45-7.57 (m, 2H), 7.34 (d, J = 8.49 Hz, 1H), 7.11 (t, J = 4.66 Hz, 1H), 7.02 (d, J = 8.81 Hz, 1H), 4.03 (s, 3H), 3.83 (s, 3H) |
| 1151 | (P)-1-(4-(4-fluorophenoxy)-2-methoxyphenyl)-N-3-isoxazolyl-2-oxo-1,2-dihydro-6-quinolinesulfonamide | 508.0 | 224 | 0.049 | | $^1$H NMR (Acetone): δ: 8.54 (d, J = 1.7 Hz, 1H), 8.30 (d, J = 2.1 Hz, 1H), 8.08 (d, J = 9.6 Hz, 1H), 7.88 (dd, J = 9.0, 2.2 Hz, 1H), 7.20-7.28 (m, 5H), 6.93 (d, J = 2.6 Hz, 1H), 6.85 (d, J = 9.0 Hz, 1H), 6.75 (d, J = 9.6 Hz, 1H), 6.67 (dd, J = 8.5, 2.6 Hz, 1H), 6.57 (d, J = 1.8 Hz, 1H), 3.68 (s, 3H) |
| 1202 | (M)-1-(4-(4-fluorophenoxy)-2-methoxyphenyl)-N-3-isoxazolyl-2-oxo-1,2-dihydro-6-quinolinesulfonamide | 508.0 | 224 | | | $^1$H NMR (Acetone): δ: 8.54 (d, J = 1.7 Hz, 1H), 8.30 (d, J = 2.1 Hz, 1H), 8.08 (d, J = 9.6 Hz, 1H), 7.88 (dd, J = 9.0, 2.2 Hz, 1H), 7.20-7.28 (m, 5H), 6.93 (d, J = 2.6 Hz, 1H), 6.85 (d, J = 9.0 Hz, 1H), 6.75 (d, J = 9.6 Hz, 1H), 6.67 (dd, J = 8.5, 2.6 Hz, 1H), 6.57 (d, J = 1.8 Hz, 1H), 3.68 (s, 3H) |
| 1203 | (P)-1-(5-chloro-6-(4-fluorophenyl)-2- | 527.0 | 208 | 0.187 | | $^1$H NMR (400 MHz, DMSO-d$_6$) δ = 11.68 (s, 1H), 8.74 (d, J = 1.8 Hz, |

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | methoxy-3-pyridinyl)-N-3-isoxazolyl-2-oxo-1,2-dihydro-6-quinolinesulfonamide | | | | | 1H), 8.40 (d, J = 2.1 Hz, 1H), 8.30-8.23 (m, 2H), 7.97-7.90 (m, 2H), 7.87 (dd, J = 2.2, 9.0 Hz, 1H), 7.44-7.36 (m, 2H), 7.05 (d, J = 9.0 Hz, 1H), 6.84 (d, J = 9.6 Hz, 1H), 6.46 (d, J = 1.8 Hz, 1H), 3.82 (s, 3H) |
| 1204 | (M)-1-(5-chloro-6-(4-fluorophenyl)-2-methoxy-3-pyridinyl)-N-3-isoxazolyl-2-oxo-1,2-dihydro-6-quinolinesulfonamide | 527.0 | 208 | | | $^1$H NMR (400 MHz, DMSO-d$_6$) δ = 11.68 (s, 1H), 8.74 (d, J = 1.8 Hz, 1H), 8.40 (d, J = 2.2 Hz, 1H), 8.32-8.22 (m, 2H), 7.98-7.90 (m, 2H), 7.87 (dd, J = 2.2, 9.0 Hz, 1H), 7.44-7.35 (m, 2H), 7.05 (d, J = 9.0 Hz, 1H), 6.84 (d, J = 9.7 Hz, 1H), 6.46 (d, J = 1.8 Hz, 1H), 3.82 (s, 3H) |
| 1143 | 1-((1R,3R)-3-(3-fluorophenyl)cyclopentyl)-N-3-isoxazolyl-2-oxo-1,2-dihydro-6-quinolinesulfonamide, 1-((1R,3S)-3-(3-fluorophenyl)cyclopentyl)-N-3-isoxazolyl-2-oxo-1,2-dihydro-6-quinolinesulfonamide, 1-((1S,3R)-3-(3-fluorophenyl)cyclopentyl)-N-3-isoxazolyl-2-oxo-1,2-dihydro-6-quinolinesulfonamide, 1-((1S,3S)-3-(3-fluorophenyl)cyclopentyl)-N-3-isoxazolyl-2-oxo-1,2-dihydro-6-quinolinesulfonamide | 454.0 | 216 | 8.914 | | $^1$H NMR (400 MHz, DMSO-d6) δ ppm 11.65 (s, 1 H) 8.73 (d, J = 1.76 Hz, 1 H) 8.32 (dd, J = 6.22, 1.35 Hz, 1 H) 8.08 (d, J = 9.54 Hz, 1 H) 8.01 (m, J = 1.60 Hz, 2 H) 7.31-7.42 (m, 1 H) 7.14-7.24 (m, 2 H) 6.97-7.08 (m, 1 H) 6.71 (d, J = 9.43 Hz, 1 H) 6.47 (d, J = 1.76 Hz, 1 H) 5.88 (d, J = 1.76 Hz, 1 H) 5.51-5.71 (m, 1 H) 3.70-3.91 (m, 1 H) 3.16-3.29 (m, 1 H) 2.01-2.47 (m, 5 H) 1.70-1.87 (m, 1 H). |
| 1205 | (P)-1-(3-methoxy-3'-(1-methylethoxy)-4-biphenylyl)-N-(6-methyl-4-pyrimidinyl)-2-oxo-1,2-dihydro-6-quinolinesulfonamide | 555.2 | 183 | 0.29 | | $^1$H NMR (500 MHz, DMSO-d$_6$) δ ppm 8.51 (s, 1 H) 8.42 (d, J = 1.69 Hz, 1 H) 8.22 (d, J = 9.67 Hz, 1 H) 7.91 (dd, J = 8.92, 1.91 Hz, 1 H) 7.50 (d, J = 1.30 Hz, 1 H) 7.38-7.47 (m, 2 H) 7.27-7.37 (m, 3 H) 6.98 (dd, J = 8.01, 1.78 Hz, 1 H) 6.79 (d, J = 9.67 Hz, 1 H) 6.76 (d, J = 8.95 Hz, 1 H) 4.76 (dt, J = 12.00, 5.94 Hz, 1 H) 3.77 (s, 3 H) 2.32 (s, 3 H) 1.31 (d, J = 5.97 Hz, 6H). |
| 1206 | (P)-1-(3-methoxy-3'-(1-methylethoxy)-4-biphenylyl)-N-(4-methyl-2-pyrimidinyl)-2-oxo-1,2-dihydro-6-quinolinesulfonamide | 555.2 | 183 | 0.59 | | $^1$H NMR (500 MHz, DMSO-d6) δ ppm 8.39 (d, J = 1.56 Hz, 1 H) 8.22 (d, J = 9.60 Hz, 1 H) 8.14 (d, J = 6.55 Hz, 1 H) 7.89 (dd, J = 8.95, 1.82 Hz, 1 H) 7.50 (d, J = 1.36 Hz, 1 H) 7.38-7.45 (m, 2 H) 7.28-7.37 (m, 3 H) 6.99 (dd, J = 8.01, 1.85 Hz, 1 H) 6.91 (br. s., 1 H) 6.78 (d, J = 9.60 Hz, 1 H) 6.75 (d, J = 8.95 Hz, 1 H) 4.76 (dt, J = 12.00, 6.00 Hz, 1 H) 2.38 (s, 3 H) 1.32 (s, 3H) 1.31 (s, 3H). |
| 1207 | (P)-1-(3-methoxy-3'-(1-methylethoxy)-4-biphenylyl)-2-oxo-N-3-pyridazinyl-1,2-dihydro-6-quinolinesulfonamide | 543.2 | 183 | 0.109 | | $^1$H NMR (400 MHz, CHLOROFORM-d) δ = 8.25 (d, J = 2.1 Hz, 1H), 8.12 (dd, J = 1.5, 3.6 Hz, 1H), 7.90 (dd, J = 2.1, 8.9 Hz, 1H), 7.83 (d, J = 9.6 Hz, 1H), 7.42-7.28 (m, 5H), 7.25-7.14 (m, 3H), 6.97-6.91 (m, 1H), 6.87 (d, J = 9.6 Hz, 1H), 6.83 (d, J = 8.9 Hz, 1H), 4.64 (td, J = 6.1, 12.1 Hz, 1H), 3.78 (s, 3H), 1.39 (d, J = 6.0 Hz, 6H). |
| 1208 | (P)-N-(6-fluoro-2-pyridinyl)-1-(3-methoxy-3'-(1-methylethoxy)-4-biphenylyl)-2-oxo-1,2-dihydro-6-quinolinesulfonamide | 560.2 | 183 | 0.258 | | $^1$H NMR (500 MHz, DMSO-d$_6$) δ = 11.44 (br. s., 1H), 8.44 (d, J = 2.0 Hz, 1H), 8.22 (d, J = 9.7 Hz, 1H), 7.93 (dd, J = 2.1, 9.0 Hz, 1H), 7.84 (q, J = 8.2 Hz, 1H), 7.49 (d, J = 1.3 Hz, 1H), 7.45-7.38 (m, 2H), 7.37-7.26 (m, 3H), 7.01-6.91 (m, 2H), 6.80 (dd, J = 3.1, 9.3 Hz, 2H), 6.73 (dd, J = 2.0, 7.9 Hz, 1H), 4.76 (td, J = 6.0, |

TABLE 4-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | | | | | | 12.0 Hz, 1H), 3.76 (s, 3H), 1.32 (s, 3H), 1.31 (s, 3H). |
| 1209 | (P)-1-(2-fluoro-5-methoxy-3'-(trifluoromethyl)-4-biphenylyl)-N-(6-fluoro-2-pyridinyl)-2-oxo-1,2-dihydro-6-quinolinesulfonamide | 588.0 | 183 | 0.075 | | $^1$H NMR (500 MHz, DMSO-d$_6$) δ = 11.45 (s, 1H), 8.45 (d, J = 2.0 Hz, 1H), 8.24 (d, J = 9.7 Hz, 1H), 8.02 (br. s., 2H), 7.93 (dd, J = 2.1, 9.0 Hz, 1H), 7.90-7.77 (m, 3H), 7.55 (d, J = 10.3 Hz, 1H), 7.48 (d, J = 6.9 Hz, 1H), 6.96 (dd, J = 1.5, 7.9 Hz, 1H), 6.89 (d, J = 9.0 Hz, 1H), 6.82 (d, J = 9.7 Hz, 1H), 6.73 (dd, J = 2.0, 8.0 Hz, 1H), 3.75 (s, 3H). |
| 1144 | (P)-1-(5-chloro-4-cyclopropyl-2-methoxyphenyl)-N-3-isoxazolyl-2-oxo-1,2-dihydro-6-quinolinesulfonamide | 472.0 | 217 | 0.481 | | $^1$H NMR (400 MHz, DMSO-d$_6$) δ ppm 11.65 (s, 1 H) 8.73 (d, J = 1.76 Hz, 1 H) 8.35 (d, J = 2.18 Hz, 1 H) 8.20 (d, J = 9.54 Hz, 1 H) 7.84 (dd, J = 8.97, 2.23 Hz, 1 H) 7.48 (s, 1 H) 6.71-6.86 (m, 3 H) 6.44 (d, J = 1.76 Hz, 1 H) 3.67 (s, 3 H) 2.25 (tt, J = 8.44, 5.25 Hz, 1 H) 1.07-1.15 (m, 2H) 0.84-1.00 (m, 2H). |
| 1145 | (P)-1-(4-cyclopropyl-5-fluoro-2-methoxyphenyl)-N-3-isoxazolyl-2-oxo-1,2-dihydro-6-quinolinesulfonamide | 456.1 | 179 | 0.471 | | $^1$H NMR (400 MHz, DMSO-d$_6$) δ ppm 11.65 (s, 1 H) 8.73 (d, J = 1.98 Hz, 1 H) 8.35 (d, J = 2.18 Hz, 1 H) 8.20 (d, J = 9.54 Hz, 1 H) 7.84 (d, J = 9.01 Hz, 1 H) 7.27 (d, J = 10.05 Hz, 1 H) 6.75-6.83 (m, 3 H) 6.45 (d, J = 2.03 Hz, 1 H) 3.63 (s, 3 H) 2.11-2.19 (m, 1 H) 1.03-1.11 (m, 2 H) 0.84-1.01 (m, 2 H). |
| 1210 | (P)-1-(4-cyclopropyl-2-methoxyphenyl)-N-3-isoxazolyl-2-oxo-1,2-dihydro-6-quinolinesulfonamide | 438.1 | 179 | 2.372 | | $^1$H NMR (400 MHz, DMSO-d$_6$) δ ppm 11.65 (s, 1 H) 8.73 (d, J = 1.98 Hz, 1 H) 8.35 (d, J = 2.18 Hz, 1 H) 8.20 (d, J = 9.54 Hz, 1 H) 7.84 (d, J = 9.01 Hz, 1 H) 7.27 (d, J = 10.05 Hz, 1 H) 6.75-6.83 (m, 3 H) 6.45 (d, J = 2.03 Hz, 1 H) 3.63 (s, 3 H) 2.11-2.19 (m, 1 H) 1.03-1.11 (m, 2 H) 0.84-1.02 (m, 2 H). |
| 1211 | 1-(5-chloro-6-(2,2-difluoro-2-(tetrahydro-2H-pyran-4-yl)ethoxy)-2-methoxy-3-pyridinyl)-N-3-isoxazolyl-2-oxo-1,2-dihydro-6-quinolinesulfonamide | 597.2 | 185 | 0.793 | | $^1$H NMR (500 MHz, DMSO-d$_6$) δ ppm 8.25 (s, 1 H) 8.11-8.17 (m, 2 H) 8.09 (s, 1 H) 7.74 (dd, J = 8.82, 1.82 Hz, 1 H) 6.77 (d, J = 8.82 Hz, 1 H) 6.69 (d, J = 9.60 Hz, 1 H) 6.14 (d, J = 1.23 Hz, 1 H) 4.55-5.02 (m, 2 H) 3.94 (d, J = 10.96 Hz, 2 H) 3.81 (s, 3 H) 2.40 (t, J = 12.52 Hz, 1 H) 1.75 (d, J = 12.26 Hz, 2 H) 1.46-1.64 (m, 2H). |
| 1212 | 1-(5-chloro-2-methoxy-6-(((1R)-2,2,3,3-tetrafluoro-1-methylpropyl)oxy)-3-pyridinyl)-N-3-isoxazolyl-2-oxo-1,2-dihydro-6-quinolinesulfonamide, 1-(5-chloro-2-methoxy-6-(((1S)-2,2,3,3-tetrafluoro-1-methylpropyl)oxy)-3-pyridinyl)-N-3-isoxazolyl-2-oxo-1,2-dihydro-6-quinolinesulfonamide | 575.0 | 185 | 0.136 | | $^1$H NMR (500 MHz, DMSO-d$_6$) δ ppm 8.17 (s, 1 H) 8.08-8.15 (m, 3 H) 7.68-7.77 (m, 1 H) 6.63-6.83 (m, 3 H) 6.09 (s, 1 H) 5.73-5.88 (m, 1 H) 3.80 (d, J = 2.34 Hz, 3 H) 1.56 (t, J = 6.84 Hz, 3H). |
| 1213 | 1-(5-chloro-6-((2,4-difluorobenzyl)oxy)-2-methoxy-3-pyridinyl)-N-3-isoxazolyl-2-oxo-1,2-dihydro-6-quinolinesulfonamide | 575.2 | 185 | 0.172 | | $^1$H NMR (500 MHz, DMSO-d$_6$) δ = 8.18-8.06 (m, 3H), 8.04 (s, 1H), 7.76-7.66 (m, 2H), 7.37-7.29 (m, 1H), 7.17 (t, J = 8.5 Hz, 1H), 6.72 (d, J = 8.8 Hz, 1H), 6.65 (d, J = 9.6 Hz, 1H), 6.07 (d, J = 1.4 Hz, 1H), 5.59 (d, J = 12.1 Hz, 1H), 5.53 (d, J = 12.4 Hz, 1H), 3.82 (s, 3H). |
| 1214 | 1-(5-chloro-6-((4-fluorobenzyl)oxy)-2-methoxy-3-pyridinyl)-N- | 557.2 | 185 | 0.111 | | $^1$H NMR (500 MHz, DMSO-d$_6$) δ = 8.21-8.15 (m, 1H), 8.14-8.08 (m, 2H), 8.03 (s, J = 7.1 Hz, 1H), 7.73 |

TABLE 4-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | 3-isoxazolyl-2-oxo-1,2-dihydro-6-quinolinesulfonamide | | | | | (dd, J = 1.8, 8.8 Hz, 1H), 7.65-7.54 (m, J = 5.7, 8.3 Hz, 2H), 7.31-7.20 (m, J = 8.2, 8.2 Hz, 2H), 6.73 (d, J = 8.8 Hz, 1H), 6.67 (d, J = 9.6 Hz, 1H), 6.10 (d, J = 1.6 Hz, 1H), 5.59-5.53 (m, 1H), 5.50 (d, J = 12.3 Hz, 1H), 3.81 (s, 3H). |
| 1215 | 1-(5-chloro-6-((4-fluoro-3-(trifluoromethyl)benzyl)oxy)-2-methoxy-3-pyridinyl)-N-3-isoxazolyl-2-oxo-1,2-dihydro-6-quinolinesulfonamide | 625.2 | 185 | 0.024 | | $^1$H NMR (500 MHz, DMSO-d$_6$) δ = 8.14-8.04 (m, 3H), 7.99 (d, J = 6.6 Hz, 1H), 7.96-7.91 (m, 1H), 7.71 (dd, J = 1.8, 8.8 Hz, 1H), 7.59 (t, J = 9.0 Hz, 1H), 6.71 (d, J = 8.8 Hz, 1H), 6.66 (d, J = 9.6 Hz, 1H), 6.07 (d, J = 1.5 Hz, 1H), 5.67-5.61 (m, 1H), 5.61-5.55 (m, 1H), 3.80 (s, 3H), 2.50 (br. s., 6H). |
| 1216 | 1-(5-chloro-2-methoxy-6-((2,3,4-trifluorobenzyl)oxy)-3-pyridinyl)-N-3-isoxazolyl-2-oxo-1,2-dihydro-6-quinolinesulfonamide | 593.2 | 185 | 0.119 | | $^1$H NMR (500 MHz, DMSO-d$_6$) δ = 8.14-8.03 (m, 4H), 7.71 (d, J = 8.6 Hz, 1H), 7.57-7.48 (m, 1H), 7.40 (q, J = 8.0 Hz, 1H), 6.72 (d, J = 8.8 Hz, 1H), 6.66 (d, J = 9.6 Hz, 1H), 6.07 (d, J = 1.6 Hz, 1H), 5.65 (d, J = 12.6 Hz, 1H), 5.58 (d, J = 12.6 Hz, 1H), 3.81 (s, 3H). |
| 1217 | 1-(5-chloro-6-((3,4-difluorobenzyl)oxy)-2-methoxy-3-pyridinyl)-N-3-isoxazolyl-2-oxo-1,2-dihydro-6-quinolinesulfonamide | 575.2 | 185 | 0.096 | | $^1$H NMR (500 MHz, DMSO-d$_6$) δ = 8.16 (s, 1H), 8.13-8.08 (m, 2H), 8.05 (s, 1H), 7.72 (dd, J = 1.8, 8.8 Hz, 1H), 7.61 (t, J = 8.8 Hz, 1H), 7.54-7.44 (m, 1H), 7.41 (br. s., 1H), 6.72 (d, J = 8.8 Hz, 1H), 6.66 (d, J = 9.6 Hz, 1H), 6.12-6.05 (m, 1H), 5.54 (d, J = 12.7 Hz, 1H), 5.50 (d, J = 12.5 Hz, 1H), 3.80 (s, 3H). |
| 1218 | 1-(5-chloro-2-methoxy-6-((3,4,5-trifluorobenzyl)oxy)-3-pyridinyl)-N-3-isoxazolyl-2-oxo-1,2-dihydro-6-quinolinesulfonamide | 593.2 | 185 | 0.039 | | $^1$H NMR (500 MHz, DMSO-d$_6$) δ = 8.16-8.04 (m, 4H), 7.72 (dd, J = 1.7, 8.8 Hz, 1H), 7.55-7.46 (m, J = 7.6, 7.6 Hz, 2H), 6.72 (d, J = 8.8 Hz, 1H), 6.66 (d, J = 9.6 Hz, 1H), 6.07 (s, 1H), 5.55 (d, J = 12.9 Hz, 1H), 5.50 (d, J = 13.0 Hz, 1H), 3.79 (s, 3H). |
| 1219 | 1-(5-chloro-6-(cyclohexylmethoxy)-2-methoxy-3-pyridinyl)-N-3-isoxazolyl-2-oxo-1,2-dihydro-6-quinolinesulfonamide | 543.0 | 185 | 0.052 | | $^1$H NMR (500 MHz, DMSO-d$_6$) δ ppm 8.19 (s, 1 H) 8.07-8.14 (m, 2 H) 7.98 (s, 1 H) 7.72 (dd, J = 8.82, 1.82 Hz, 1 H) 6.75 (d, J = 8.82 Hz, 1 H) 6.67 (d, J = 9.67 Hz, 1 H) 6.10 (d, J = 1.43 Hz, 1 H) 4.27-4.34 (m, 1 H) 4.20-4.26 (m, 1 H) 3.77 (s, 3 H) 1.79-1.90 (m, 3 H) 1.61-1.78 (m, 3H) 1.04-1.37 (m, 6 H). |
| 1220 | 1-(5-chloro-6-(4-fluorophenoxy)-2-methoxy-3-pyridinyl)-N-3-isoxazolyl-2-oxo-1,2-dihydro-6-quinolinesulfonamide | 543.0 | 185 | 3.1 | | $^1$H NMR (500 MHz, DMSO-d$_6$) δ ppm 8.23 (s, J = 8.66 Hz, 1 H) 8.07-8.16 (m, 3 H) 7.72 (dd, J = 8.79, 1.78 Hz, 1 H) 7.59 (td, J = 8.97, 5.74 Hz, 1 H) 7.48-7.55 (m, 1 H) 7.20 (t, J = 8.32 Hz, 1 H) 6.74 (d, J = 8.76 Hz, 1 H) 6.66 (d, J = 9.60 Hz, 1 H) 6.07 (s, 1 H) 3.43 (s, 3 H). |
| 1221 | 1-(5-chloro-6-(2,4-difluorophenoxy)-2-methoxy-3-pyridinyl)-N-3-isoxazolyl-2-oxo-1,2-dihydro-6-quinolinesulfonamide | 561.2 | 185 | 2.589 | | $^1$H NMR (500 MHz, DMSO-d$_6$) δ ppm 8.23 (s, J = 8.66 Hz, 1 H) 8.07-8.16 (m, 3 H) 7.72 (dd, J = 8.79, 1.78 Hz, 1 H) 7.48-7.63 (m, 2 H) 7.20 (t, J = 8.32 Hz, 1 H) 6.74 (d, J = 8.76 Hz, 1 H) 6.66 (d, J = 9.60 Hz, 1 H) 6.07 (s, 1 H) 3.43 (s, 3 H). |
| 1222 | 1-(5-chloro-6-(3,4-difluorophenoxy)-2-methoxy-3-pyridinyl)-N-3-isoxazolyl-2-oxo-1,2-dihydro-6-quinolinesulfonamide | 561.2 | 185 | 0.903 | | $^1$H NMR (500 MHz, DMSO-d$_6$) δ ppm 8.21 (s, 1 H) 8.07-8.16 (m, 3 H) 7.72 (dd, J = 8.79, 1.85 Hz, 1 H) 7.59-7.67 (m, 1 H) 7.49-7.58 (m, 1 H) 7.21-7.27 (m, 1 H) 6.79 (d, J = 8.76 Hz, 1 H) 6.66 (d, J = 9.54 Hz, 1 H) 6.07 (d, J = 1.62 Hz, 1 H) 3.49 (s, 3 H). |
| 1223 | 1-(6-((1R,2S,4S)-bicyclo[2.2.1]hept-2-yloxy)-5-chloro-2-methoxy-3-pyridinyl)-N- | 543.2 | 185 | 0.416 | | $^1$H NMR (500 MHz, DMSO-d$_6$) δ ppm 8.18 (s, 1 H) 8.07-8.13 (m, 2 H) 7.97 (d, J = 5.93 Hz, 1 H) 7.68-7.75 (m, 1 H) 6.73 (d, J = 8.69 Hz, 1 |

TABLE 4-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | 3-isoxazolyl-2-oxo-1,2-dihydro-6-quinolinesulfonamide | | | | | H) 6.66 (d, J = 9.54 Hz, 1 H) 6.10 (d, J = 1.30 Hz, 1 H) 5.25 (dd, J = 9.21, 3.96 Hz, 1 H) 3.76 (s, 3 H) 2.67 (d, J = 13.95 Hz, 1 H) 2.27 (br. s., 1 H) 2.13-2.23 (m, 1 H) 1.85-2.04 (m, 1 H) 1.62 (br. s., 1 H) 1.32-1.55 (m, 4H) 1.04-1.22 (m, 1 H). |
| 1224 | 1-(5-chloro-2-methoxy-6-(((1S,2R)-2-methylcyclohexyl)oxy)-3-pyridinyl)-N-3-isoxazolyl-2-oxo-1,2-dihydro-6-quinolinesulfonamide | 545.2 | 185 | 0.088 | | $^1$H NMR (500 MHz, DMSO-d$_6$) δ ppm 8.05-8.15 (m, 3 H) 7.97 (d, J = 5.36 Hz, 1 H) 7.72 (d, J = 8.76 Hz, 1 H) 6.73 (t, J = 9.02 Hz, 1 H) 6.65 (d, J = 9.60 Hz, 1 H) 6.07 (d, J = 1.49 Hz, 1 H) 5.24 (d, J = 16.35 Hz, 1 H) 3.75 (s, 3 H) 2.09 (br. s., 1 H) 1.90 (br. s., 1 H) 1.31-1.75 (m, 6 H) 0.99 (dd, J = 17.06, 6.81 Hz, 2 H). |
| 1225 | 1-(5-chloro-6-(2,5-difluorophenoxy)-2-methoxy-3-pyridinyl)-N-3-isoxazolyl-2-oxo-1,2-dihydro-6-quinolinesulfonamide | 561.2 | 185 | 0.846 | | $^1$H NMR (500 MHz, DMSO-d$_6$) δ ppm 8.26 (s, 1 H) 8.06-8.15 (m, 3 H) 7.73 (dd, J = 8.79, 1.78 Hz, 1 H) 7.44-7.59 (m, 2 H) 7.17-7.27 (m, 1 H) 6.74 (d, J = 8.76 Hz, 1 H) 6.67 (d, J = 9.60 Hz, 1 H) 6.07 (d, J = 1.62 Hz, 1 H) 3.45 (s, 3 H). |
| 1226 | 1-(5-chloro-6-(3-chloro-2-methylphenoxy)-2-methoxy-3-pyridinyl)-N-3-isoxazolyl-2-oxo-1,2-dihydro-6-quinolinesulfonamide | 573.0 | 185 | 0.316 | | $^1$H NMR (500 MHz, DMSO-d$_6$) δ ppm 8.29 (br. s., 1 H) 8.23 (s, 1 H) 8.11-8.19 (m, 2 H) 7.75 (d, J = 8.32 Hz, 1 H) 7.29-7.41 (m, 3 H) 6.85 (d, J = 8.76 Hz, 1 H) 6.70 (d, J = 9.60 Hz, 1 H) 6.18 (br. s., 1 H) 3.42 (s, 3 H) 2.28 (s, 3 H). |
| 1227 | 1-((1S,2S)-2-methoxycyclohexyl)-2-oxo-N-1,2,4-thiadiazol-5-yl-1,2-dihydro-6-quinolinesulfonamide | 421.2 | 218 | | | $^1$H NMR (500 MHz, DMSO-d$_6$) δ ppm 8.44 (s, 1 H) 8.20 (s, 1 H) 8.04 (d, J = 9.54 Hz, 1 H) 7.90-7.96 (m, 1 H) 7.84-7.90 (m, 1 H) 6.61 (d, J = 9.47 Hz, 1 H) 4.41 (br. s., 2 H) 3.03 (s, 3 H) 2.90 (br. s., 1 H) 2.22 (d, J = 11.48 Hz, 1 H) 1.61-1.85 (m, 3 H) 1.38-1.57 (m, 1 H) 1.07-1.37 (m, 2 H). |
| 1228 | 1-((1S,2S)-2-methoxycyclopentyl)-2-oxo-N-1,2,4-thiadiazol-5-yl-1,2-dihydro-6-quinolinesulfonamide | 407.2 | 218 | | | $^1$H NMR (500 MHz, DMSO-d$_6$) δ ppm 8.43 (s, 1 H) 8.24 (d, J = 1.88 Hz, 1 H) 8.09 (d, J = 9.47 Hz, 1 H) 7.93 (dd, J = 9.08, 2.14 Hz, 1 H) 7.86 (br. s., 1 H) 6.67 (d, J = 9.54 Hz, 1 H) 5.10 (br. s., 1 H) 4.38 (d, J = 3.89 Hz, 1 H) 3.05 (s, 3 H) 2.18-2.31 (m, 1 H) 1.89-2.14 (m, 3 H) 1.66-1.83 (m, 2H). |
| 1229 | (M)-1-(5-chloro-6-cyclopropyl-2-methoxy-3-pyridinyl)-N-3-isoxazolyl-2-oxo-1,2-dihydro-6-quinolinesulfonamide | 473.0 | 179 | 17.25 | | $^1$H NMR (400 MHz, CHLOROFORM-d) δ ppm 8.23 (d, J = 1.76 Hz, 1 H) 8.13 (d, J = 1.97 Hz, 1 H) 7.74-7.80 (m, 2 H) 7.46 (s, 1 H) 6.82 (d, J = 9.64 Hz, 1 H) 6.75 (d, J = 9.02 Hz, 1 H) 6.56 (d, J = 1.66 Hz, 1 H) 3.76 (s, 3 H) 2.41-2.61 (m, 1 H) 1.14-1.23 (m, 2 H) 1.09 (dd, J = 8.09, 3.21 Hz, 2H). |
| 1230 | (P)-1-(5-chloro-6-cyclopropyl-2-methoxy-3-pyridinyl)-N-3-isoxazolyl-2-oxo-1,2-dihydro-6-quinolinesulfonamide | 473.0 | 179 | 0.472 | | $^1$H NMR (400 MHz, CHLOROFORM-d) δ ppm 8.23 (d, J = 1.76 Hz, 1 H) 8.13 (d, J = 1.97 Hz, 1 H) 7.74-7.80 (m, 2 H) 7.46 (s, 1 H) 6.82 (d, J = 9.64 Hz, 1 H) 6.75 (d, J = 9.02 Hz, 1 H) 6.56 (d, J = 1.66 Hz, 1 H) 3.76 (s, 3 H) 2.41-2.61 (m, 1 H) 1.14-1.23 (m, 2 H) 1.09 (dd, J = 8.09, 3.21 Hz, 2H). |
| 1231 | 1-(5-chloro-6-(cyclopentyl(methyl)amino)-2-methoxy-3-pyridinyl)-N-3-isoxazolyl-2-oxo-1,2-dihydro-6-quinolinesulfonamide | 530.0 | 195 | 0.115 | | 1H NMR (400 MHz, CHLOROFORM-d) δ ppm 8.35 (br. s, 1 H) 8.18 (d, J = 1.66 Hz, 1 H) 8.04 (d, J = 2.07 Hz, 1 H) 7.64-7.72 (m, 2 H) 7.19 (s, 1 H) 6.81 (d, J = 8.97 Hz, 1 H) 6.74 (d, J = 9.64 Hz, 1 H) 6.53 (d, J = 1.71 Hz, 1 H) 4.47 (m, 1 H) 3.73 (s, 3 H) 2.92 (s, 3 H) 1.81-1.98 (m, 2 H) 1.48-1.71 (m, 6H) |

TABLE 4-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| 1232 | 1-(5-chloro-6-((((2R)-5,5-dimethyltetrahydro-2-furanyl)methyl)amino)-2-methoxy-3-pyridinyl)-N-3-isoxazolyl-2-oxo-1,2-dihydro-6-quinolinesulfonamide, 1-(5-chloro-6-((((2S)-5,5-dimethyltetrahydro-2-furanyl)methyl)amino)-2-methoxy-3-pyridinyl)-N-3-isoxazolyl-2-oxo-1,2-dihydro-6-quinolinesulfonamide | 560.4 | 195 | 2.938 | | |
| 1152 | (P)-1-(5-fluoro-2-methoxy-4-((3-methyl-3-oxetanyl)ethynyl)phenyl)-N-3-isoxazolyl-2-oxo-1,2-dihydro-6-quinolinesulfonamide | 510.0 | 225 | 1.551 | | |
| 1233 | (P)-1-(5-fluoro-4-((1-hydroxycyclopentyl)ethynyl)-2-methoxyphenyl)-N-3-isoxazolyl-2-oxo-1,2-dihydro-6-quinolinesulfonamide | 524.0 | 190 | 0.631 | | |
| 1153 | (P)-1-(5-fluoro-4-((1-fluorocyclopentyl)ethynyl)-2-methoxyphenyl)-N-3-isoxazolyl-2-oxo-1,2-dihydro-6-quinolinesulfonamide | 526.0 | 226 | 0.035 | | 1H NMR (400 MHz, DMSO-d6) δ ppm 11.60 (br. s, 1 H) 8.66 (d, J = 1.76 Hz, 1 H) 8.30 (d, J = 2.13 Hz, 1 H) 8.16 (d, J = 9.64 Hz, 1 H) 7.74-7.79 (m, 1 H) 7.49 (d, J = 9.17 Hz, 1 H) 7.40 (d, J = 8.46 Hz, 1 H) 6.77 (d, J = 8.61 Hz, 1 H) 6.73 (d, J = 9.64 Hz, 1 H) 6.38 (d, J = 1.81 Hz, 1 H) 3.62 (s, 3 H) 2.23-2.35 (m, 2 H) 1.96-2.15 (m, 2 H) 1.70-1.78 (m, 4 H). |
| 1234 | (P)-1-(5-fluoro-2-methoxy-4-((3S)-tetrahydro-3-furanylmethyl)phenyl)-N-3-isoxazolyl-2-oxo-1,2-dihydro-6-quinolinesulfonamide | 500.0 | 209 | 1.144 | | |
| 1235 | (P)-1-(5-fluoro-2-methoxy-4-((3R)-tetrahydro-3-furanylmethyl)phenyl)-N-3-isoxazolyl-2-oxo-1,2-dihydro-6-quinolinesulfonamide | 500.0 | 209 | 2.129 | | |
| 1236 | 1-(5-chloro-2-methoxy-6-(((1-methylcyclopentyl)methyl)amino)-3-pyridinyl)-N-3-isoxazolyl-2-oxo-1,2-dihydro-6-quinolinesulfonamide | 544.0 | 195 | 0.507 | | |
| 1237 | 1-(5-chloro-2-methoxy-6-((((2R)-2-methyltetrahydro-2-furanyl)methyl)amino)-3-pyridinyl)-N-3-isoxazolyl-2-oxo-1,2-dihydro-6-quinolinesulfonamide, 1-(5-chloro-2-methoxy-6-((((2S)-2-methyltetrahydro-2-furanyl)methyl)amino)-3-pyridinyl)-N-3-isoxazolyl-2-oxo-1,2-dihydro-6-quinolinesulfonamide | 546.0 | 195 | | | |
| 1238 | (P)-1-(5-fluoro-4-((1-fluorocyclopentyl)ethynyl)-2-methoxyphenyl)-2- | 537.0 | 226 | 0.094 | | 1H NMR (400 MHz, DMSO-d6) δ ppm 14.44 (br. s, 1 H) 8.34 (s, J = 4.91 Hz, 1 H) 8.25-8.31 (m, 1 |

TABLE 4-continued

| Example No. | Compound name | LCMS | Method Use to Make | Nav 1.7 PX IC$_{50}$ (µM) | Nav 1.5 PX IC$_{50}$ (µM) | NMR |
|---|---|---|---|---|---|---|
| | oxo-N-3-pyridazinyl-1,2-dihydro-6-quinolinesulfonamide | | | | | H) 8.19 (d, J = 9.95 Hz, 1 H) 7.89-7.98 (m, 1 H) 7.78-7.85 (m, 1 H) 7.66-7.73 (m, 1 H) 7.53 (d, J = 9.02 Hz, 1 H) 7.46 (d, J = 6.03 Hz, 1 H) 6.72-6.79 (m, 2 H) 3.68 (s, 3 H) 2.23-2.34 (m, 2 H) 2.06-2.21 (m, 2 H) 1.78-1.85 (m, 4H) |
| 1239 | (P)-1-(4-(cyclopentylethynyl)-2-methoxyphenyl)-2-oxo-N-3-pyridazinyl-1,2-dihydro-6-quinolinesulfonamide | 501.0 | 192 | 0.113 | | 1H NMR (400 MHz, DMSO-d6) δ ppm 14.48 (br. s, 1 H) 8.33 (d, J = 2.07 Hz, 2 H) 8.18 (d, J = 9.43 Hz, 1 H) 7.79-7.92 (m, 2 H) 7.68 (dd, J = 9.54, 4.15 Hz, 1 H) 7.22-7.35 (m, 2 H) 7.15 (dd, J = 8.03, 1.61 Hz, 1 H) 6.76 (d, J = 9.64 Hz, 1 H) 6.65 (d, J = 8.91 Hz, 1 H) 3.68 (s, 3 H) 2.88-2.94 (m, 1 H) 1.97-2.06 (m, 2H) 1.56-1.79 (m, 6H) |
| 1240 | (P)-1-(5-chloro-6-(cyclopentylethynyl)-2-methoxy-3-pyridinyl)-2-oxo-N-3-pyridazinyl-1,2-dihydro-6-quinolinesulfonamide | 536.0 | 193 | 0.124 | | 1H NMR (400 MHz, DMSO-d6) δ ppm 14.44 (br. s, 1 H) 8.29-8.38 (m, 2 H) 8.19-8.22 (m, 2 H) 7.81 (m, 2 H) 7.60-7.69 (m, 1 H) 6.88 (d, J = 8.91 Hz, 1 H) 6.77 (d, J = 9.64 Hz, 1 H) 3.75 (s, 3 H) 2.92-3.03 (m, 1 H) 1.99-2.09 (m, 2 H) 1.56-1.80 (m, 6 H) |
| 1241 | (M)-1-(5-chloro-6-(cyclopentylethynyl)-2-methoxy-3-pyridinyl)-2-oxo-N-3-pyridazinyl-1,2-dihydro-6-quinolinesulfonamide | 536.0 | 193 | | | |
| 1242 | (P)-N-(6-fluoro-2-pyridinyl)-1-(3-methoxy-3'-(trifluoromethyl)-4-biphenylyl)-2-oxo-1,2-dihydro-6-quinolinesulfonamide | 570.2 | 73 | 0.079 | | 1H NMR (500 MHz, DMSO-d6) δ ppm 11.43 (br. s, 1 H) 8.44 (d, J = 2.01 Hz, 1 H) 8.23 (d, J = 9.73 Hz, 1 H) 8.08-8.17 (m, 2 H) 7.92 (dd, J = 8.99, 2.11 Hz, 1 H) 7.74-7.88 (m, 3 H) 7.56-7.65 (m, 1 H) 7.51 (d, J = 7.90 Hz, 1 H) 7.42 (d, J = 7.75 Hz, 1 H) 6.92-7.02 (m, 1 H) 6.78-6.88 (m, 2 H) 6.73 (dd, J = 7.91, 2.08 Hz, 1 H) 3.79 (s, 3H) |
| 1140 | 8-(2-chloro-3'-fluoro-5-methoxy-[1,1'-biphenyl]-4-yl)-N-(isoxazol-3-yl)-7-oxo-7,8-dihydro-1,8-naphthyridine-3-sulfonamide | 525.0 | 213 | | | $^1$H NMR (400 MHz, DMSO-d$_6$) δ ppm 3.70 (s, 3 H) 6.47-6.52 (m, 1 H) 6.88-6.95 (m, 1 H) 7.25-7.28 (m, 1 H) 7.28-7.34 (m, 1 H) 7.41-7.47 (m, 2 H) 7.54-7.61 (m, 1 H) 7.63 (s, 1H) 8.23-8.31 (m, 1 H) 8.78 (d, J = 1.87 Hz, 2 H) 8.84-8.88 (m, 1H) 11.88 (br s, 1 H). |
| 1148 | (P)-1-(4-(5-chloro-6-methoxy-3-pyridinyl)-5-fluoro-2-methoxyphenyl)-2-oxo-N-2-pyrimidinyl-1,2-dihydro-6-quinolinesulfonamide | 568.2 | 221 | 0.136 | | $^1$H NMR (500 MHz, DMSO-d$_6$) δ ppm 3.68 (s, 3 H) 3.93 (s, 3 H) 6.80 (dd, J = 9.28, 2.40 Hz, 2 H) 7.05 (t, J = 4.74 Hz, 1 H) 7.40 (d, J = 8.10 Hz, 1 H) 7.47 (d, J = 8.86 Hz, 1 H) 7.96-8.07 (m, 2 H) 8.27 (d, J = 9.67 Hz, 1 H) 8.35 (d, J = 2.53 Hz, 1 H) 8.42-8.58 (m, 3 H) 11.58-12.24 (m, 1 H). |
| 1156 | (P)-1-(4-(5-chloro-6-methoxy-3-pyridinyl)-5-fluoro-2-methoxyphenyl)-N-(5-fluoro-2-pyrimidinyl)-2-oxo-1,2-dihydro-6-quinolinesulfonamide | 586.2 | 221 | 0.042 | | $^1$H NMR (500 MHz, DMSO-d$_6$) δ ppm 3.69 (s, 3 H) 3.93 (s, 3 H) 6.81 (dd, J = 9.31, 4.18 Hz, 2 H) 7.41 (d, J = 6.78 Hz, 1 H) 7.48 (d, J = 9.54 Hz, 1 H) 8.01 (d, J = 8.00 Hz, 2 H) 8.26 (d, J = 9.67 Hz, 1 H) 8.36 (d, J = 2.53 Hz, 1 H) 8.48 (d, J = 1.95 Hz, 1 H) 8.62 (s, 2 H) 11.88-12.02 (m, 1 H). |
| 1157 | (P)-1-(4-(5-chloro-6-methoxy-3-pyridinyl)-5-fluoro-2-methoxyphenyl)-2-oxo-N-3-pyridazinyl-1,2- | 568.2 | 221 | 0.063 | | $^1$H NMR (500 MHz, DMSO-d$_6$) δ ppm 3.69 (s, 3 H) 3.90-3.97 (m, 3 H) 6.79 (d, J = 9.67 Hz, 2 H) 7.40 (d, J = 8.11 Hz, 1 H) 7.46 (d, J = 9.54 Hz, 1 H) 7.69 (dd, J = 9.34, 3.96 Hz, 1 H) |

TABLE 4-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | dihydro-6-quinolinesulfonamide | | | | | 8.02 (d, J = 2.53 Hz, 3 H) 8.17-8.47 (m, 4 H) 14.35-14.65 (m, 1 H). |
| 1158 | (P)-1-(4-(5-chloro-6-methoxy-3-pyridinyl)-5-fluoro-2-methoxyphenyl)-N-1,3-oxazol-2-yl-2-oxo-1,2-dihydro-6-quinolinesulfonamide | 557.2 | 221 | 0.089 | | $^1$H NMR (500 MHz, DMSO-d$_6$) δ ppm 3.70 (s, 3 H) 3.93 (s, 3 H) 6.78 (dd, J = 18.00, 9.25 Hz, 2 H) 7.28 (d, J = 1.36 Hz, 1 H) 7.40 (d, J = 6.78 Hz, 1 H) 7.47 (d, J = 9.60 Hz, 1 H) 7.61 (d, J = 1.49 Hz, 1 H) 7.89 (dd, J = 8.89, 1.95 Hz, 1 H) 8.02 (d, J = 2.47 Hz, 1 H) 8.20 (d, J = 9.60 Hz, 1 H) 8.35 (dd, J = 7.85, 2.14 Hz, 2 H) 12.05-12.30 (m, 1 H). |
| 1159 | (P)-1-(4-(5-chloro-6-methoxy-3-pyridinyl)-5-fluoro-2-methoxyphenyl)-N-(6-methyl-4-pyrimidinyl)-2-oxo-1,2-dihydro-6-quinolinesulfonamide | 582.2 | 221 | 0.051 | | $^1$H NMR (500 MHz, DMSO-d$_6$) δ ppm 2.32 (s, 3 H) 3.69 (s, 3 H) 3.93 (s, 3 H) 6.78 (d, J = 9.02 Hz, 1 H) 6.80 (d, J = 19.24 Hz, 1 H) 6.92 (br. s., 1 H) 7.40 (d, J = 7.83 Hz, 1 H) 7.47 (d, J = 9.54 Hz, 1 H) 7.94 (dd, J = 7.90 Hz, 1 H) 8.01 (d, J = 8.23 Hz, 1 H) 8.24 (d, J = 7.97 Hz, 1 H) 8.35 (d, J = 7.13 Hz, 1 H) 8.43 (s, 1 H) 8.51 (s, 1 H) 11.21-11.56 (m, 1 H). |
| 1160 | (P)-1-(4-(5-chloro-6-methoxy-3-pyridinyl)-5-fluoro-2-methoxyphenyl)-N-(2-methyl-4-pyrimidinyl)-2-oxo-1,2-dihydro-6-quinolinesulfonamide | 582.2 | 221 | 0.042 | | $^1$H NMR (500 MHz, DMSO-d$_6$) δ ppm 2.39 (s, 3 H) 3.69 (s, 3 H) 3.93 (s, 3 H) 6.77 (d, J = 8.95 Hz, 1 H) 6.79 (d, J = 9.67 Hz, 1 H) 6.90 (br. s., 1 H) 7.40 (d, J = 6.42 Hz, 1 H) 7.46 (d, J = 9.03 Hz, 1H) 7.91 (dd, J = 8.86, 1.85 Hz, 1 H) 8.02 (d, J = 7.62 Hz, 1 H) 8.13 (d, J = 6.62 Hz, 1 H) 8.24 (d, J = 9.67 Hz, 1 H) 8.35 (d, J = 7.85 Hz, 1 H) 8.38-8.43 (m, 1 H) 11.17-11.61 (m, 1H). |
| 1161 | (P)-1-(4-(5-chloro-6-methoxy-3-pyridinyl)-5-fluoro-2-methoxyphenyl)-N-(5-fluoro-2-pyridinyl)-2-oxo-1,2-dihydro-6-quinolinesulfonamide | 585.2 | 221 | 0.02 | | $^1$H NMR (500 MHz, DMSO-d$_6$) δ ppm 3.68 (s, 3 H) 3.93 (s, 3 H) 6.80 (t, J = 8.59 Hz, 2 H) 7.12 (dd, J = 9.05, 3.67 Hz, 1 H) 7.40 (d, J = 6.36 Hz, 1 H) 7.47 (d, J = 9.54 Hz, 1 H) 7.66 (td, J = 8.68, 3.02 Hz, 1 H) 7.92 (dd, J = 8.92, 2.04 Hz, 1 H) 8.01 (d, J = 23.95 Hz, 1 H) 8.17 (d, J = 2.92 Hz, 1 H) 8.23 (d, J = 9.67 Hz, 1 H) 8.35 (d, J = 2.47 Hz, 1 H) 8.41 (d, J = 1.88 Hz, 1H) 11.04-11.36 (m, 1 H). |
| 1162 | (P)-1-(4-(5-chloro-6-methoxy-3-pyridinyl)-5-fluoro-2-methoxyphenyl)-N-(6-fluoro-2-pyridinyl)-2-oxo-1,2-dihydro-6-quinolinesulfonamide | 585.2 | 221 | 0.012 | | $^1$H NMR (500 MHz, DMSO-d$_6$) δ ppm 3.68 (s, 3 H) 3.93 (s, 3 H) 6.72 (dd, J = 7.98, 2.01 Hz, 1 H) 6.81 (d, J = 9.80 Hz, 2 H) 6.93-7.00 (m, 1 H) 7.39 (d, J = 6.42 Hz, 1 H) 7.48 (d, J = 9.54 Hz, 1 H) 7.84 (q, J = 8.17 Hz, 1 H) 7.95 (dd, J = 8.99, 2.04 Hz, 1 H) 8.01 (d, J = 16.70 Hz, 1 H) 8.24 (d, J = 9.67 Hz, 1 H) 8.35 (d, J = 2.47 Hz, 1 H) 8.45 (d, J = 1.95 Hz, 1 H) 11.39-11.54 (m, 1H). |
| 1163 | (P)-1-(4'-chloro-2-fluoro-5-methoxy-4-biphenylyl)-N-(5-fluoro-2-pyridinyl)-2-oxo-1,2-dihydro-6-quinolinesulfonamide | 554.2 | 150 | 0.159 | | $^1$H NMR (500 MHz, DMSO-d$_6$) δ ppm 3.73 (s, 3 H) 6.80 (d, J = 9.67 Hz, 1 H) 6.85 (d, J = 8.95 Hz, 1 H) 7.12 (dd, J = 8.99, 3.67 Hz, 1 H) 7.40 (d, J = 6.94 Hz, 1 H) 7.51 (d, J = 10.38 Hz, 1 H) 7.61 (d, J = 8.50 Hz, 2 H) 7.66 (td, J = 8.64, 3.08 Hz, 1 H) 7.73 (d, J = 7.33 Hz, 2H) 7.90 (dd, J = 8.95, 2.01 Hz, 1 H) 8.17 (d, J = 2.92 Hz, 1 H) 8.23 (d, J = 9.67 Hz, 1 H) 8.40 (d, J = 1.88 Hz, 1 H) 11.17 (br. s., 1 H). |
| 1149 | (P)-1-(2-chloro-4'-fluoro-5-methoxy-4-biphenylyl)-N-3-isoxazolyl-2-oxo-1,2-dihydro-6-quinolinesulfonamide | 526.2 | 222 | 0.016 | | $^1$H NMR (500 MHz, DMSO-d$_6$) δ ppm 3.72 (s, 3 H) 6.46 (d, J = 1.69 Hz, 1 H) 6.82 (d, J = 9.18 Hz, 1 H) 6.89 (d, J = 8.95 Hz, 1 H) 7.32 (s, 1 H) 7.37 (t, J = 8.82 Hz, 2 H) 7.63 (dd, J = 8.56, 5.51 Hz, 2 H) 7.67 (s, 1 H) 7.88 (dd, J = 8.95, 2.08 Hz, 1 H) 8.23 (d, J = 9.67 Hz, 1 H) 8.38 (d, |

TABLE 4-continued

| Example No. | Compound name | LCMS | Method Use to Make | Nav 1.7 PX IC$_{50}$ (μM) | Nav 1.5 PX IC$_{50}$ (μM) | NMR |
|---|---|---|---|---|---|---|
| | | | | | | J = 1.95 Hz, 1 H) 8.73 (d, J = 1.69 Hz, 1 H) 11.49-11.83 (m, 1 H). |
| 1150 | (P)-1-(3'-(difluoromethoxy)-2,4'-difluoro-5-methoxy-4-biphenylyl)-N-3-isoxazolyl-2-oxo-1,2-dihydro-6-quinolinesulfonamide | 576.2 | 223 | 0.022 | | $^1$H NMR (500 MHz, DMSO-d$_6$) δ ppm 3.74 (s, 3 H) 6.45 (d, J = 1.69 Hz, 1 H) 6.81 (d, J = 9.67 Hz, 1 H) 6.88 (d, J = 8.95 Hz, 1 H) 7.16-7.50 (m, 2 H) 7.53 (d, J = 10.32 Hz, 1 H) 7.56-7.67 (m, 2 H) 7.70 (d, J = 7.27 Hz, 1 H) 7.86 (dd, J = 8.99, 2.04 Hz, 1 H) 8.23 (d, J = 9.73 Hz, 1 H) 8.38 (d, J = 1.95 Hz, 1 H) 8.73 (d, J = 1.69 Hz, 1H) 11.64 (br. s., 1 H). |
| 1164 | (P)-N-3-isoxazolyl-2-oxo-1-(2,3',4',5'-tetrafluoro-5-methoxy-4-biphenylyl)-1,2-dihydro-6-quinolinesulfonamide | 546.2 | 145 | 0.019 | | $^1$H NMR (500 MHz, DMSO-d$_6$) δ ppm 3.75 (s, 3 H) 6.45 (d, J = 1.69 Hz, 1 H) 6.81 (d, J = 10.02 Hz, 1 H) 6.85 (d, J = 9.02 Hz, 1 H) 7.45 (d, J = 6.94 Hz, 1 H) 7.56 (d, J = 9.58 Hz, 1 H) 7.67-7.79 (m, 2 H) 7.86 (dd, J = 8.99,2.11 Hz, 1 H) 8.23 (d, J = 9.67 Hz, 1 H) 8.38 (d, J = 1.95 Hz, 1 H) 8.73 (d, J = 1.62 Hz, 1 H) 11.64 (br. s., 1 H). |
| 1165 | (P)-1-(2-chloro-4'-fluoro-5-methoxy-4-biphenylyl)-2-oxo-N-2-pyrimidinyl-1,2-dihydro-6-quinolinesulfonamide | 537.0 | 222 | | | $^1$H NMR (500 MHz, DMSO-d$_6$) δ ppm 3.71 (s, 3 H) 6.80 (d, J = 9.60 Hz, 1 H) 6.85 (d, J = 9.02 Hz, 1 H) 7.05 (t, J = 4.77 Hz, 1 H) 7.28-7.43 (m, 3 H) 7.55-7.73 (m, 3 H) 8.01 (dd, J = 8.92, 1.98 Hz, 1 H) 8.26 (d, J = 9.67 Hz, 1 H) 8.43-8.56 (m, 3 H) 11.68-12.12 (m, 1 H). |
| 1166 | (P)-1-(2-chloro-4'-fluoro-5-methoxy-4-biphenylyl)-N-(5-fluoro-2-pyrimidinyl)-2-oxo-1,2-dihydro-6-quinolinesulfonamide | 555.2 | 222 | | | $^1$H NMR (500 MHz, DMSO-d$_6$) δ ppm 3.72 (s, 3 H) 6.81 (d, J = 9.67 Hz, 1 H) 6.86 (d, J = 8.95 Hz, 1 H) 7.32 (s, 1 H) 7.37 (t, J = 8.86 Hz, 2 H) 7.59-7.70 (m, 3 H) 7.99 (dd, J = 8.99, 2.04 Hz, 1 H) 8.25 (d, J = 9.67 Hz, 1 H) 8.48 (d, J = 1.88 Hz, 1 H) 8.62 (s, 2 H) 11.96 (br. s., 1 H). |
| 1167 | (P)-1-(2-chloro-4'-fluoro-5-methoxy-4-biphenylyl)-2-oxo-N-3-pyridazinyl-1,2-dihydro-6-quinolinesulfonamide | 537.2 | 222 | | | $^1$H NMR (500 MHz, DMSO-d$_6$) δ ppm 3.72 (s, 3 H) 6.77-6.83 (m, 2 H) 7.30-7.42 (m, 3 H) 7.60-7.71 (m, 4 H) 7.88 (d, J = 8.37 Hz, 1 H) 7.94 (d, J = 8.82 Hz, 1 H) 8.18-8.44 (m, 3 H) 14.34-14.73 (m, 1 H). |
| 1168 | (P)-1-(2-chloro-4'-fluoro-5-methoxy-4-biphenylyl)-N-1,3-oxazol-2-yl-2-oxo-1,2-dihydro-6-quinolinesulfonamide | 526.1 | 222 | | | $^1$H NMR (500 MHz, DMSO-d$_6$) δ ppm 3.73 (s, 3 H) 6.79 (t, J = 8.63 Hz, 2 H) 7.25-7.30 (m, 1 H) 7.30-7.41 (m, 3 H) 7.57-7.70 (m, 4 H) 7.88 (dd, J = 8.92, 1.91 Hz, 1 H) 8.19 (d, J = 9.67 Hz, 1 H) 8.33 (d, J = 1.82 Hz, 1H) 11.98-12.40 (m, 1 H). |

Biological Assays

The following assays were used in testing the exemplary compounds of the invention. Data for those examples tested in accordance with the procedures described below are presented in Table 1 herein.

Nav 1.7 or Nav 1.5 IWQ In Vitro Assay

HEK 293 Cells stably transfected with either Nav 1.7 or Nav 1.5 were recorded in population patch-clamp mode with the IonWorks® Quattro automated electrophysiology system in accordance with the manufacturer's specifications (Molecular Devices, LLC, Sunnyvale, Calif.). Sodium channel currents were measured in response to a train of depolarizations that induced successively greater inactivation.

Cells were held at −110 mV for three seconds (Nav 1.7) or half a second (Nav 1.5) from a holding voltage of −15 mV, then put through a series of 26 pulses of 150 msec duration to −20 mV at a frequency of 5 Hz. Cells were then left unclamped for a period of 3 to 8 minutes while a single concentration of test compound was added. Cells were then reclamped and put through the same voltage protocol. Current at the end of the 26$^{th}$ pulse to −20 mV was subtracted from the peak current evoked by the 26$^{th}$ pulse to −20 mV to correct for leak current. Percent block was calculated for each concentration in duplicate, and IC$_{50}$ curves were fitted to percent block as a function of concentration.

Nav 1.7 In Vitro PX Assay

HEK 293 cells stably transfected with human Nav 1.7 were recorded in whole cell voltage clamp mode with the PatchXpress automated electrophysiology system (Molecular Devices, LLC, Sunnyvale, Calif.). Compound effects were measured on a partially inactivated state of the sodium channel. Cells were clamped to a holding potential yielding 20 to 50% inactivation. To elicit sodium current, channels were activated by pulsing to −10 mV for 20 msec. This voltage protocol was repeated at a rate of 0.1 Hz throughout the experiment. A single concentration of test compound was applied to cells for a duration of 3 minutes. Peak sodium current was measured at the end of the compound addition period to determine percent inhibition. Three to five cells were tested per concentration, and $IC_{50}$ curves were fitted to percent inhibition as a function of concentration. Data for compounds representative of the invention are presented in the Tables herein.

Nav 1.5 In Vitro PX Assay 293 cells stably transfected with Nav 1.5 were recorded in whole cell voltage clamp mode with the PatchXpress automated electrophysiology system according the manufacturer's specifications (Molecular Devices, LLC, Sunnyvale, Calif.). Cells were held at a holding potential of −50 mV to inactivate sodium channels. To elicit sodium currents the voltage was changed to −120 mV to recover a portion of the channels, followed by delivery of test pulses of 20 msec duration to 0 mV, at 0.1 Hz. A single concentration of test compound was applied to cells for a duration of 5 minutes. Peak sodium current was measured at the end of the compound addition period to determine percent inhibition. A minimum of two cells were tested per concentration. $IC_{50}$ curves were fitted to percent inhibition as a function of concentration. Data for compounds representative of the invention are presented in the Tables herein.

The compounds of the present invention may also be tested in the following in vivo assays.

Rat Formalin Model of Persistent Pain

On the test day, animals (Naïve, male Sprague Dawley rats) weighing between 260-300 g at the start of testing can be obtained from Harlan (Indianapolis, Ind.). All animals may be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. Animals are pretreated with the appropriate test compound either by oral gavage or intraperitoneal injection at the desired pretreatment time (typically two hours before test onset) and then returned to their home cages. After dosing and at least 30 minutes prior to test onset, animals can be acclimated to the individual testing chambers. At test time, each animal can be gently wrapped in a towel with the left hindpaw exposed. A dilute solution of formalin (2.5%) in phosphate buffered saline can be injected subcutaneously into the dorsal surface of the left hindpaw in a volume to 50 µL with a 30 g needle. Immediately following injection, a small metal band can be affixed to the plantar side of the left hindpaw with a drop of LOCTITE (adhesive). Animals may be then placed into the testing chambers and the number of flinches can be recorded between 10 to 40 minutes after formalin injection. A flinch is defined as a quick and spontaneous movement of the injected hindpaw not associated with ambulation. Flinches can be quantified with the aid of the Automated Nociception Analyzer built by the University of California, San Diego Department of Anesthesiology. Individual data can be expressed as a % maximal potential effect (% MPE) calculated with the following formula:

(−(Individual score−Vehicle average score)/Vehicle average score))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Rat Open Field Assay

On the test day, animals (Naïve, male Sprague Dawley rats) weighing between 260-300 g at the start of testing may be obtained from Harlan (Indianapolis, Ind.). All animals can be housed under a 12/12 h light/dark cycle with lights on at 0600. Rodents can be housed two to a cage on solid bottom cages with corn cob bedding and can have access to food and water ad libitum. Animals should be allowed to habituate to the vivarium for at least five days before testing is begun and should be brought into the testing room at least 30 minutes prior to dosing. In a room separate from the testing room, animals can be pretreated with the appropriate test compound either by oral gavage or intraperitoneal injection at the desired pretreatment time (typically two hours before test onset) and then can be returned to their home cages until the pretreatment has elapsed. At test time, animal can be transferred to the open field testing room in their home cages. Each animal may be placed in a separate testing chamber and the motion tracking system is started. The house lights in the testing room should be turned off and the animals can be allowed to explore the novel open field for 30 minutes. An automated motion tracker, made by San Diego Instruments, San Diego, Calif., can be used to capture animal exploration with the aid of infrared photo beams to detect animal movement. These behaviors include basic movement and vertical rearing, which can be used as the primary endpoints for this assay. At the end of the test, house lights can be turned on and the animals should be removed from the testing apparatus. Data can be expressed as a percent change from the vehicle control using the following equation.

(1−(Test mean/Vehicle mean))*100=% Change.

Statistical analysis can be performed by analysis of variance (ANOVA), with post-hoc analysis using Dunnett to follow up significant main effects.

Mouse Formalin Model of Persistent Pain

Mice (Naïve, male C57Bl/6) weighing between 22-30 g at the start of testing were obtained from Harlan (Indianapolis, Ind.). All animals were housed under a 12/12 h light/dark cycle with lights on at 0630. Rodents were singly housed on solid bottom cages with corn cob bedding and had access to food and water ad libitum. Animals were allowed to habituate to the vivarium for at least five days before testing was begun and were brought into the testing room at least 30 minutes prior to dosing. Animals were pretreated with the appropriate test compound either by oral gavage or intraperitoneal injection at the desired pretreatment time (typically two hours before test onset) and then returned to their home cages. After dosing and at least 5 minutes prior to test onset, animals were acclimated to the individual testing chambers. At test time, each animal was gently wrapped in a cloth glove with the left hind paw exposed. A dilute solution of formalin (2%) in phosphate buffered saline was injected subcutaneously into the dorsal surface of the left hind paw in a volume to 20 µL with a 30 g needle. Animals were then placed into the observation chambers and the behaviors were recorded for 60 minutes following the formalin injection. A pain-like behavior was defined as licking and/or non-weight bearing of the injected hind paw not associated with ambulation.

Statistical analysis was performed by analysis of variance (ANOVA), with post-hoc analysis using the Dunnett post-hoc test compared to the vehicle group for any significant main effect. Data were represented as mean+/−standard error for each group.

Mouse Open Field Assay

Mice (Naïve, male C57Bl/6) weighing between 22-30 g at the start of testing were obtained from Harlan (Indianapolis, Ind.). All animals were housed under a 12/12 h light/dark cycle with lights on at 0630. Rodents were singly housed on solid bottom cages with corn cob bedding and had access to food and water ad libitum. Animals were allowed to habituate to the vivarium for at least five days before testing was begun and were brought into the testing room at least 30 minutes prior to dosing. In a room separate from the testing room, animals were pretreated with the appropriate test compound either by oral gavage or intraperitoneal injection at the desired pretreatment time (typically two hours before test onset) and then returned to their home cages until the pretreatment has elapsed. At test time, animal were transferred to the open field testing room in their home cages. Each animal was placed in a separate testing chamber and the motion tracking system was started. The house lights in the testing room were turned off and the animals were allowed to explore the novel open field for 30 minutes. An automated motion tracker, made by Kinder Scientific, Poway, Calif., was used to capture animal exploration with the aid of infrared photo beams to detect animal movement. These behaviors include basic movement and vertical rearing, which were used as the primary endpoints for this assay. At the end of the test, house lights were turned on and the animals were removed from the testing apparatus.

Statistical analysis was performed by analysis of variance (ANOVA), with post-hoc analysis using the Dunnett post-hoc test compared to the vehicle group for any significant main effect. Data were represented as mean+/−standard error for each group. Data was also expressed as a percent change from the vehicle control using the following equation:

(1−(Test mean/Vehicle mean))*100=% Change.

CFA-Thermal Assay

Animals (Naïve, male Sprague Dawley rats) weighing between 260-300 g at the start of testing) can be obtained from Harlan (Indianapolis, Ind.). All animals can be housed under a 12/12 h light/dark cycle with lights on at 0600. Rodents may be housed two to a cage on solid bottom cages with corn cob bedding with access to food and water ad libitum. Animals can be allowed to habituate to the vivarium for at least five days before testing was begun and may be brought into the testing room at least 30 minutes prior to dosing. The Complete Freund's Adjuvant (CFA)-thermal assay may use a three continuous day testing schedule consisting of a habituation day, a baseline day, and a test day. On day 1, animals can be brought into the testing room, labeled, and placed in their individual testing boxes on the testing apparatus. Animals may be allowed to explore this environment for at least an hour without actually being tested. After habituating, animals can be placed back in their home cages and returned to the vivarium. On day 2, animals can be brought back into the testing room and placed on the testing apparatus and allowed to calm down (typically 30-45 minutes). A basal thermal threshold should be then taken with the following procedure: once calm, a Ugo Basile plantar device is placed under the animals left hindpaw; the start button is depressed turning on a steadily increasing thermal source and a timer; when the animal reaches its thermal threshold it will flinch its hindpaw, stopping the timer and the thermal stimulus. This latency to flinch can be recorded three times for each animal, with at least 5 minutes between trials, and the mean score can be used as the animal's baseline threshold. After testing, animals can be injected intraplantarly with a 25 µg/50 µl of complete Freund's adjuvant into the left hindpaw. Animals are then returned to their home cages and returned to the vivarium. On test day, animals can be again placed on the thermal testing apparatus and their post-CFA baselines obtained with the procedure outlined above. Animals can be pretreated with the appropriate test compound either by oral gavage or intraperitoneal injection at the desired pretreatment time (typically two hours before test onset) and then can be returned to their home cages. Thirty minutes prior to testing, animals can be placed on the apparatus again. Once the pretreatment time has elapsed, animals can be again tested with the procedure above. Data may be expressed as a percent maximal potential effect with the following formula:

((Post-Drug Mean−Pre-Drug Mean)/(Baseline Mean−Pre-Drug Mean))*100=% MPE

Statistical analysis can be performed by analysis of variance (ANOVA), with post-hoc analysis using Bonferroni compared to the vehicle group for a significant main effect. Data can be represented as mean % MPE+/−standard error for each group.

Spinal Nerve Ligation (Chung)

Animals (Naïve, male Sprague Dawley rats) weighing between 150-200 g at the start of first time testing can be obtained from Harlan (Indianapolis, Ind.). All animals may be housed under a 12/12 h light/dark cycle with lights on at 0600. Rodents can be housed two to a cage on solid bottom cages with corn cob bedding with access to food and water ad libitum. Animals may be allowed to habituate to the vivarium for at least five days before testing is begun. Surgery may be then performed based on the method described by Kim and Chung (1992). Briefly, animals can be placed under isoflurane anesthesia and placed in a sterile surgical field. The area of the lumbar spine is excised and the spinal nerves at L4-L5 are exposed. The L5 spinal nerve is identified and tightly ligated with 5-0 silk suture. The muscle may be closed with absorbable suture and the skin with wound clip. Animals may be returned to the vivarium for 7-14 days and monitored daily. On test day, animals can be brought into the testing room and placed on a wire mesh floor in individual testing chambers. They may be allowed to acclimate to the chambers until they are calm. A series of Semmes-Weinstein monofilaments (von Frey hairs) with calibrated bending forces are then applied to determine a hyperalgesic baseline following the method set forth by Chaplan et al. (1994). Briefly, filaments are applied with an increasing force (if there was not reaction to the previous stimulus) or decreasing force (if there was a reaction to the previous stimulus) until a baseline value is reached. Animals are then pretreated with the appropriate test compound either by oral gavage or intraperitoneal injection at the desired pretreatment time (typically two hours before test onset) and then returned to their home cages. Thirty minutes prior to testing, animals are placed on the apparatus again. After the pretreatment time had elapsed, the procedure above is repeated to determine drug efficacy. Data can be expressed as the mean gram force to elicit a nociceptive behavior. Statistical analysis can be performed by analysis of variance (ANOVA), with post-hoc analysis using Bonferroni compared to the vehicle group for a significant main effect.

What is claimed is:

1. A compound of Formula I, or a pharmaceutically acceptable salt thereof,

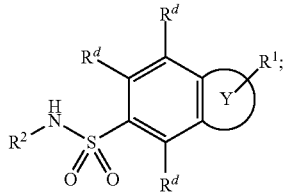

I wherein:

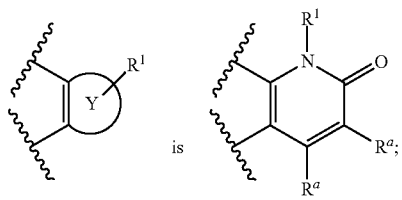

is wherein each $R^a$ is independently H, halo, —OH, —NR$^b$R$^b$, —C$_{1-6}$alkyl, —OC$_{1-6}$alkyl, —C$_{1-6}$haloalkyl, —OC$_{1-6}$haloalkyl or —CN, and $R^1$ is a 5 to 10 membered aryl or heteroaryl, wherein the heteroaryl group can have from 1 to 3 heteroatoms independently selected from O, N or S, and the aryl or heteroaryl group can be unsubstituted or substituted with from 1 to 4 substituents independently selected from halo, —NR$^b$R$^b$, —C$_{1-6}$alkyl, —OC$_{1-6}$alkyl, —OC$_{1-6}$alkylCF$_3$, —OC$_{1-6}$alkylCN, —C$_{1-6}$alkylOC$_{1-6}$alkyl, —(SO$_2$)C$_{1-6}$alkyl, —(SO$_2$)NR$^b$R$^b$, hydroxyC$_{1-6}$alkyl, —CF$_3$, —CHF$_2$, —CH$_2$F, —OCF$_3$, —OCHF$_2$, —OCH$_2$F, —(CR$^e$R$^e$)$_m$CN, —C(=O)NR$^b$R$^b$, —C(=O)OR$^b$, —N(CR$^e$R$^e$)$_m$A, —N(R$^e$)(CR$^e$R$^e$)$_m$A, —(C=N)OC$_{1-6}$alkyl, —(C=O)N(R$^e$)(CR$^e$R$^e$)$_m$A, (C=O)N(R$^e$)(CR$^e$R$^e$)$_m$CF$_3$, —O(CR$^e$R$^e$)$_m$A, —O(CR$^e$R$^e$)$_m$OA or —C(=O)A;

A is a 4 to 9 membered aryl, heteroaryl or heterocycloalkyl group, where the heteroaryl or heterocycloalkyl group can have from 1 to 3 heteroatoms independently selected from O, N or S, or a 3 to 6 membered cycloalkyl group, and the aryl, heteroaryl, heterocycloalkyl or cycloalkyl group can be unsubstituted or substituted with from 1 to 4 substituents independently selected from halo, —NR$^b$R$^b$, —C$_{1-6}$alkyl, —OC$_{1-6}$alkyl, —(CR$^e$R$^e$)$_m$OH, hydroxyC$_{1-6}$alkyl, —CF$_3$, —CHF$_2$, —CH$_2$F, —OCF$_3$, —OCHF$_2$, —OCH$_2$F, —CN, —C(=O)NR$^b$R$^b$, —O(CR$^e$R$^e$)$_m$B or —(CR$^e$R$^e$)$_m$B;

B is a 5 to 6 membered aryl, heteroaryl or heterocycloalkyl group, where the heteroaryl or heterocycloalkyl group can have from 1 to 3 heteroatoms independently selected from O, N or S, or a 3 to 5 membered cycloalkyl group, and the aryl, heteroaryl, cycloalkyl or heterocycloalkyl group can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, —CN or —C(=O)NR$^b$R$^b$;

$R^2$ is a 5 to 10 membered aryl or heteroaryl, where the heteroaryl group can have from 1 to 3 heteroatoms independently selected from O, N or S, and the aryl or heteroaryl group can be unsubstituted or substituted with from 1 to 4 substituents independently selected from halo, —NR$^b$R$^b$, —C$_{1-6}$alkyl, —OC$_{1-6}$alkyl, hydroxyC$_{1-6}$alkyl, —(CR$^c$R$^c$)$_n$NR$^b$R$^b$, —CF$_3$, —CHF$_2$, —CH$_2$F, —OCF$_3$, —OCHF$_2$, —OCH$_2$F, —CN or —C(=O)NR$^b$R$^b$;

each $R^b$ is independently H or —C$_{1-6}$alkyl;

each $R^c$ is independently H or —C$_{1-6}$alkyl; and each $R^d$ is independently H, halo, —CN, —NR$^c$R$^c$, —OH, —C$_{1-6}$alkyl, —C$_{1-6}$haloalkyl, —OC$_{1-6}$haloalkyl or —OC$_{1-6}$alkyl;

each $R^e$ is independently H, halo, —CN, —NR$^c$R$^c$, —OH, —C$_{1-6}$alkyl, —OC$_{1-6}$alkyl or a 5 to 6 membered heterocycloalkyl group having from 1 to 3 heteroatoms independently selected from O, N or S;

each n is independently 0, 1, 2, 3 or 4;

each m is independently 0, 1, 2, 3 or 4.

2. The compound in accordance with claim 1, or a pharmaceutically acceptable salt thereof, wherein each $R^d$ is independently H, F or Cl.

3. The compound in accordance with claim 1, or a pharmaceutically acceptable salt thereof, wherein $R^1$ is a 6 membered aryl or heteroaryl group, where the heteroaryl group can have from 1 to 3 heteroatoms independently selected from O, N or S, and the aryl or heteroaryl group can be unsubstituted or substituted with from 1 to 4 substituents independently selected from halo, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, CN, —C(=O)NR$^b$R$^b$, —C(=O)OR$^b$, —OA or A; and A is a 5 to 6 membered aryl or heteroaryl group, wherein the heteroaryl group can have from 1 to 3 heteroatoms independently selected from O, N or S, and the aryl or heteroaryl group can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN, or —C(=O)NR$^b$R$^b$.

4. The compound in accordance with claim 1, or a pharmaceutically acceptable salt thereof, wherein $R^1$ is a phenyl ring or pyridyl ring, wherein the ring can be unsubstituted or substituted with from 1 to 4 substituents independently selected from halo, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, CN, —C(=O)NR$^b$R$^b$, —C(=O)OR$^b$, —OA or A.

5. The compound in accordance with claim 1, or a pharmaceutically acceptable salt thereof, wherein A is a ring selected from cyclopropyl, cyclopentyl, cyclohexyl, piperidinyl, piperazinyl, pyrrolidinyl, azetidinyl, pyridyl, pyrimidinyl, pyrazinyl, pyridazinyl, wherein the ring can be unsubstituted or substituted with from 1 to 4 substituents independently selected from halo, —C$_{1-6}$alkyl, —OC$_{1-6}$alkyl, hydroxyC$_{1-6}$alkyl —CF$_3$, —CHF$_2$, —CH$_2$F, —OCF$_3$, —OCHF$_2$, —OCH$_2$F, —CN, or —C(=O)NR$^b$R$^b$.

6. The compound in accordance with claim 1, or a pharmaceutically acceptable salt thereof, wherein $R^1$ is a phenyl ring or pyridyl ring, wherein the ring can be unsubstituted or substituted with from 1 to 4 substituents independently selected from halo, —C$_{1-6}$alkyl, —OC$_{1-6}$alkyl, hydroxyC$_{1-6}$alkyl, —CF$_3$, —CHF$_2$, —CH$_2$F, —OCF$_3$, —OCHF$_2$, —OCH$_2$F, CN, —C(=O)NR$^b$R$^b$ —C(=O)OR$^b$, —OA or A; and A is a ring selected from cyclopropyl, cyclopentyl, cyclohexyl, piperidinyl, piperazinyl, pyrrolidinyl, azetidinyl, pyridyl, pyrimidinyl, pyrazolyl, pyridazolyl, wherein the ring can be unsubstituted or substituted with from 1 to 4 substituents independently selected from halo, —$C_{1-6}$alkyl, —$OC_{1-6}$alkyl, hydroxy$C_{1-6}$alkyl —$CF_3$, —$CHF_2$, —$CH_2F$, —$OCF_3$, —$OCHF_2$, —$OCH_2F$, —CN, or —C(=O)$NR^bR^b$.

7. The compound in accordance with claim 1, or a pharmaceutically acceptable salt thereof, wherein A is a ring selected from cyclopropyl or cyclohexyl, wherein the ring can be unsubstituted or substituted with from 1 to 4 substituents independently selected from halo, —$C_{1-6}$alkyl, —$OC_{1-6}$alkyl, hydroxy$C_{1-6}$alkyl —$CF_3$, —$CHF_2$, —$CH_2F$, —$OCF_3$, —$OCHF_2$, —$OCH_2F$, —CN, or —C(=O)$NR^bR^b$.

8. The compound in accordance with claim 1, or a pharmaceutically acceptable salt thereof, wherein $R^1$ is a phenyl ring that can be unsubstituted or substituted with from 1 to 4 substituents independently selected from halo, —$C_{1-6}$alkyl, —$OC_{1-6}$alkyl, hydroxy$C_{1-6}$alkyl, —$CF_3$, —$CHF_2$, —$CH_2F$, —$OCF_3$, —$OCHF_2$, —$OCH_2F$, CN, —C(=O)$NR^bR^b$, —C(=O)$OR^b$, —OA or A; and A is a ring selected from cyclopropyl, cyclohexyl, piperidinyl, pyrrolidinyl, azetidinyl, pyridyl, pyrimidinyl, wherein the ring can be unsubstituted or substituted with from 1 to 4 substituents independently selected from halo, —$C_{1-6}$alkyl, —$OC_{1-6}$alkyl, hydroxy$C_{1-6}$alkyl —$CF_3$, —$CHF_2$, —$CH_2F$, —$OCF_3$, —$OCHF_2$, —$OCH_2F$, —CN or —C(=O)$NR^bR^b$.

9. The compound in accordance with claim 1, or a pharmaceutically acceptable salt thereof, wherein $R^2$ is a 5 to 6 membered aryl or heteroaryl, where the heteroaryl can have from 1 to 3 heteroatoms independently selected from O, N or S, and the aryl or heteroaryl can be unsubstituted or substituted with from 1 to 4 substituents independently selected from halo, —$NR^bR^b$, —$C_{1-6}$alkyl, —$OC_{1-6}$alkyl, hydroxy$C_{1-6}$alkyl, —$(CR^cR^c)_nNR^bR^b$, —$CF_3$, —$CHF_2$, —$CH_2F$, —$OCF_3$, —$OCHF_2$, —$OCH_2F$, —CN or —C(=O)$NR^bR^b$.

10. The compound in accordance with claim 1, or a pharmaceutically acceptable salt thereof, wherein $R^2$ is thiadiazolyl, substituted thiadiazolyl, thiazolyl, substituted thiazolyl, oxazolyl, substituted oxazolyl, oxadiazolyl, substituted oxadiazolyl, pyrimidinyl, substituted pyrimidinyl, isoxazolyl, substituted isoxazolyl, pyrazolyl, substituted pyrazolyl, pyridyl, substituted pyridyl, pyridazinyl, substituted pyridazinyl, pyrazinyl or substituted pyrazinyl.

11. The compound in accordance with claim 1, or a pharmaceutically acceptable salt thereof, wherein $R^2$ is thiadiazolyl.

12. The compound in accordance with claim 1, or a pharmaceutically acceptable salt thereof, wherein $R^2$ is pyrimidinyl.

13. The compound in accordance with claim 1, or a pharmaceutically acceptable salt thereof, wherein $R^2$ is thiazolyl.

14. The compound in accordance with claim 1, or a pharmaceutically acceptable salt thereof, wherein $R^2$ is substituted oxazolyl.

15. The compound in accordance with claim 1, or a pharmaceutically acceptable salt thereof, wherein $R^2$ is isoxazolyl.

16. The compound in accordance with claim 1, or a pharmaceutically acceptable salt thereof, wherein each $R^d$ is independently H.

17. The compound in accordance with claim 1, or a pharmaceutically acceptable salt thereof, selected from:

| COMPOUND NAME | COMPOUND STRUCTURE |
|---|---|
| 1-(5-FLUORO-2-METHOXY-4-NEOPENTYLPHENYL)-N-(ISOXAZOL-3-YL)-2-OXO-1,2-DIHYDROQUINOLINE-6-SULFONAMIDE | 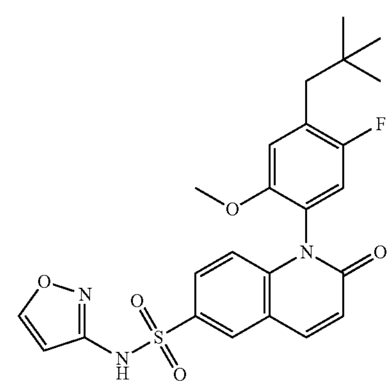 [SMILES: COc1cc(CC(C)(C)C)c(F)cc1-n1c(=O)ccc2cc(S(=O)(=O)Nc3ccon3)ccc21] |
| (P)-1-(4-BROMO-2-METHOXY-5-METHYLPHENYL)-N-3-ISOXAZOLYL-2-OXO-1,2-DIHYDRO-6-QUINOLINESULFONAMIDE (415) AND (M)-1-(4-BROMO-2-METHOXY-5-METHYLPHENYL)-N-3-ISOXAZOLYL-2-OXO-1,2-DIHYDRO-6-QUINOLINESULFONAMIDE (416) | 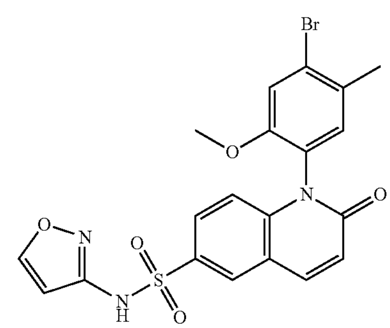 [SMILES: COc1cc(Br)c(C)cc1-n1c(=O)ccc2cc(S(=O)(=O)Nc3ccon3)ccc21] |

-continued

| COMPOUND NAME | COMPOUND STRUCTURE |
|---|---|
| (P)-1-(2-METHOXY-4-(TRIFLUOROMETHYL)PHENYL)-2-OXO-N-(THIAZOL-2-YL)-1,2-DIHYDROQUINOLINE-6-SULFONAMIDE (463) | 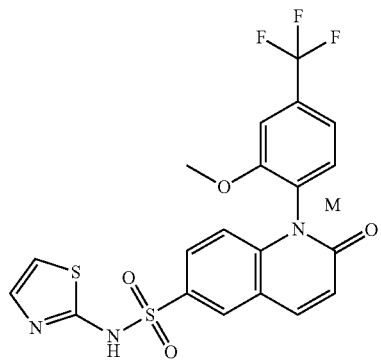 |
| (M)-1-(2-METHOXY-4-(TRIFLUOROMETHYL)PHENYL)-2-OXO-N-(THIAZOL-2-YL)-1,2-DIHYDROQUINOLINE-6-SULFONAMIDE (464) | 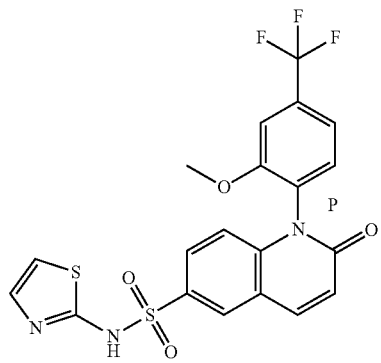 |
| (P)-1-(4-BROMO-5-CHLORO-2-METHOXYPHENYL)-N-(ISOXAZOL-3-YL)-2-OXO-1,2-DIHYDROQUINOLINE-6-SULFONAMIDE (473); and (M)-1-(4-BROMO-5-CHLORO-2-METHOXYPHENYL)-N-(ISOXAZOL-3-YL)-2-OXO-1,2-DIHYDROQUINOLINE-6-SULFONAMIDE (474) | 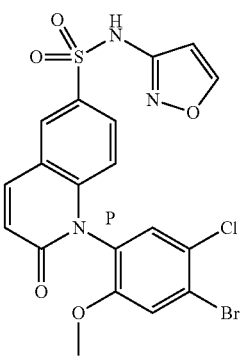<br>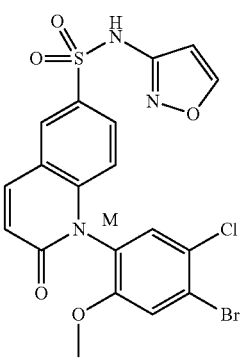 |

-continued

| COMPOUND NAME | COMPOUND STRUCTURE |
|---|---|
| 1-(4-BROMO-2-(CYANOMETHOXY)-5-FLUOROPHENYL)-N-(ISOXAZOL-3-YL)-2-OXO-1,2-DIHYDROQUINOLINE-6-SULFONAMIDE | 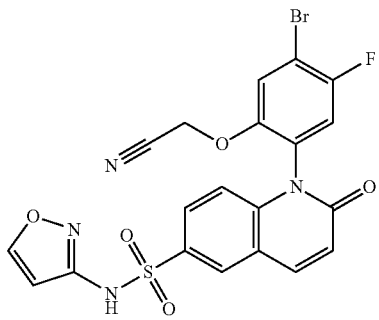 [SMILES: N#CCOc1cc(Br)c(F)cc1-n1c(=O)ccc2cc(S(=O)(=O)Nc3ccon3)ccc21] |
| 1-(5-CHLORO-6-(CYCLOPROPYLMETHOXY)-2-METHOXY-3-PYRIDINYL)-N-3-ISOXAZOLYL-2-OXO-1,2-DIHYDRO-6-QUINOLINESULFONAMIDE | 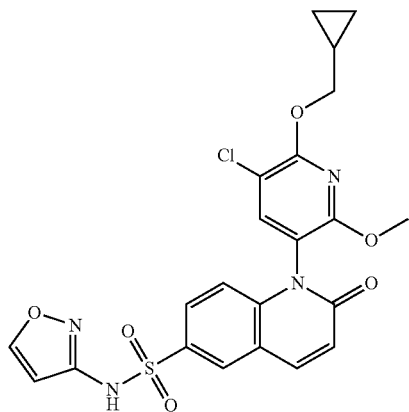 [SMILES: COc1nc(OCC2CC2)c(Cl)cc1-n1c(=O)ccc2cc(S(=O)(=O)Nc3ccon3)ccc21] |
| 1-(4-BROMO-5-FLUORO-2-METHOXYPHENYL)-N-(4,5-DIMETHYL-3-ISOXAZOLYL)-2-OXO-1,2-DIHYDRO-6-QUINOLINESULFONAMIDE | 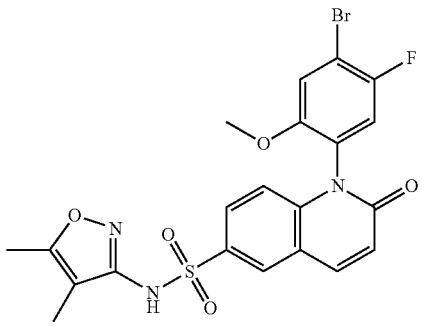 [SMILES: COc1cc(Br)c(F)cc1-n1c(=O)ccc2cc(S(=O)(=O)Nc3noc(C)c3C)ccc21] |
| (P)-1-(4-(CYCLOHEXYLMETHYL)-5-FLUORO-2-METHOXYPHENYL)-2-OXO-N-2-PYRIMIDINYL-1,2-DIHYDRO-6-QUINOLINESULFONAMIDE | 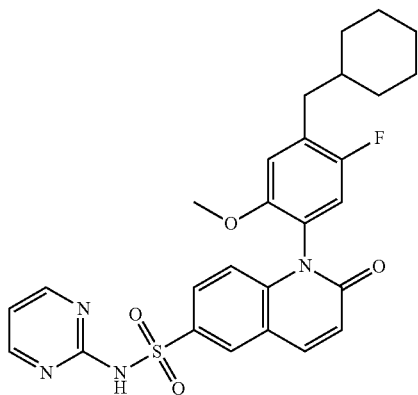 [SMILES: COc1cc(CC2CCCCC2)c(F)cc1-n1c(=O)ccc2cc(S(=O)(=O)Nc3ncccn3)ccc21] |

| COMPOUND NAME | COMPOUND STRUCTURE |
|---|---|
| (P)-1-(4-(CYCLOHEXYLMETHYL)-5-FLUORO-2-METHOXYPHENYL)-N-1,2,4-OXADIAZOL-3-YL-2-OXO-1,2-DIHYDRO-6-QUINOLINESULFONAMIDE | 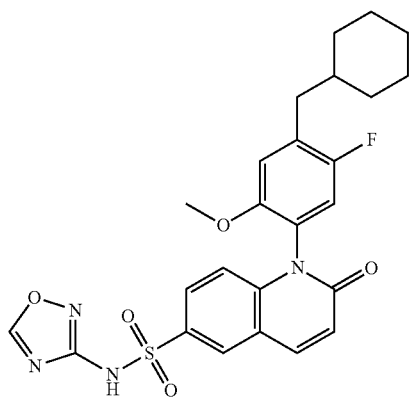 [SMILES: COc1cc(CC2CCCCC2)c(F)cc1-n1c(=O)ccc2cc(S(=O)(=O)Nc3ncon3)ccc21] |
| 1-(5-CHLORO-6-(CYCLOPENTYLAMINO)-2-METHOXY-3-PYRIDINYL)-N-3-ISOXAZOLYL-2-OXO-1,2-DIHYDRO-6-QUINOLINESULFONAMIDE | 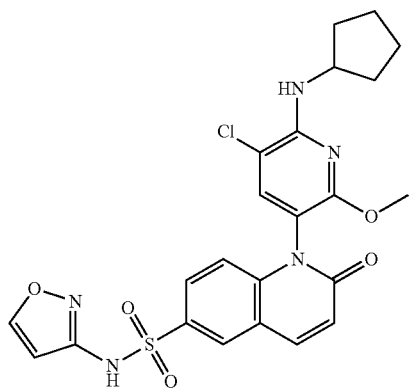 [SMILES: COc1nc(NC2CCCC2)c(Cl)cc1-n1c(=O)ccc2cc(S(=O)(=O)Nc3ccon3)ccc21] |
| 1-(4-BROMO-5-FLUORO-2-METHOXYPHENYL)-N-(2-METHYLPYRIMIDIN-4-YL)-2-OXO-1,2-DIHYDROQUINOLINE-6-SULFONAMIDE | 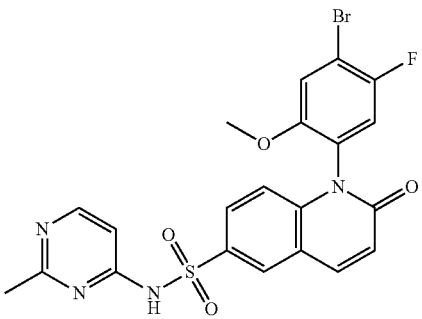 [SMILES: COc1cc(Br)c(F)cc1-n1c(=O)ccc2cc(S(=O)(=O)Nc3ccnc(C)n3)ccc21] |
| (P)-1-(5-CHLORO-2-METHOXY-4-(TRIFLUOROMETHYL)PHENYL)-2-OXO-N-(PYRIMIDIN-4-YL)-1,2-DIHYDROQUINOLINE-6-SULFONAMIDE (656) AND (M)-1-(5-CHLORO-2-METHOXY-4-(TRIFLUOROMETHYL)PHENYL)-2-OXO-N-(PYRIMIDIN-4-YL)-1,2-DIHYDROQUINOLINE-6-SULFONAMIDE (657) | 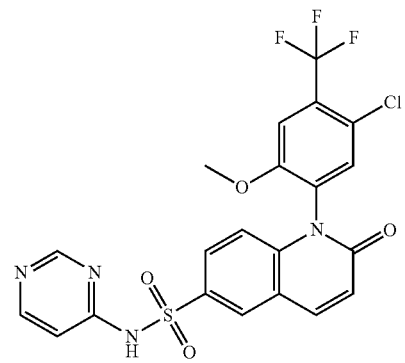 [SMILES: COc1cc(C(F)(F)F)c(Cl)cc1-n1c(=O)ccc2cc(S(=O)(=O)Nc3ccncn3)ccc21] |

| COMPOUND NAME | COMPOUND STRUCTURE |
|---|---|
| 1-(4-BROMO-2-(1-CYANOETHOXY)-5-FLUOROPHENYL)-N-(ISOXAZOL-3-YL)-2-OXO-1,2-DIHYDROQUINOLINE-6-SULFONAMIDE | 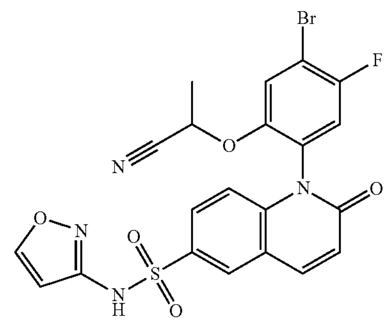 [SMILES: CC(C#N)Oc1cc(Br)c(F)cc1-n1c(=O)ccc2cc(S(=O)(=O)Nc3ccon3)ccc21] |
| 1-(5-BROMO-2-METHOXYPHENYL)-N-3-ISOXAZOLYL-2-OXO-1,2-DIHYDRO-6-QUINOLINESULFONAMIDE | 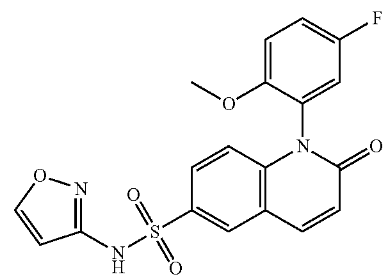 [SMILES: COc1ccc(F)cc1-n1c(=O)ccc2cc(S(=O)(=O)Nc3ccon3)ccc21] |
| 1-(5-CHLORO-2-METHOXY-4-(TRIFLUOROMETHYL)PHENYL)-2-OXO-N-4-PYRIMIDINYL-1,2-DIHYDRO-6-QUINOLINESULFONAMIDE | 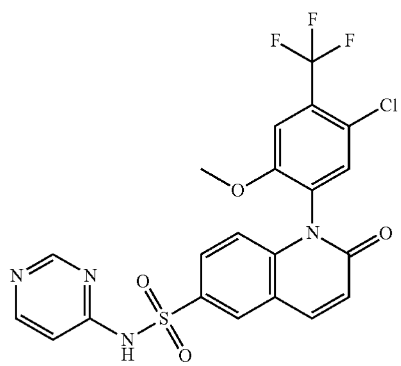 [SMILES: COc1cc(C(F)(F)F)c(Cl)cc1-n1c(=O)ccc2cc(S(=O)(=O)Nc3ccncn3)ccc21] |
| 1-(5-(CYANOMETHYL)-2-METHOXYPHENYL)-N-3-ISOXAZOLYL-2-OXO-1,2-DIHYDRO-6-QUINOLINESULFONAMIDE | 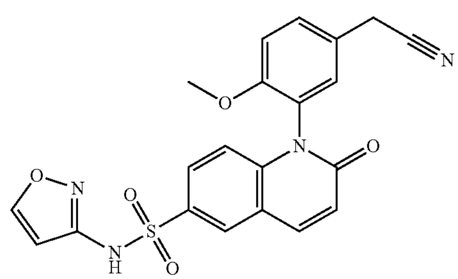 [SMILES: COc1ccc(CC#N)cc1-n1c(=O)ccc2cc(S(=O)(=O)Nc3ccon3)ccc21] |
| N-(ISOXAZOL-3-YL)-1-(2-METHOXYPHENYL)-2-OXO-1,2-DIHYDROQUINOLINE-6-SULFONAMIDE | 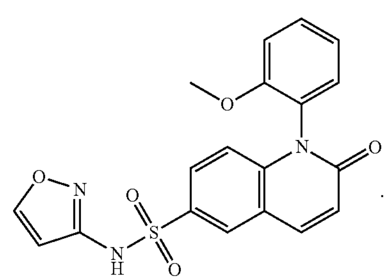 [SMILES: COc1ccccc1-n1c(=O)ccc2cc(S(=O)(=O)Nc3ccon3)ccc21] |

18. The compound in accordance with claim 1, or a pharmaceutically acceptable salt thereof, selected from:

| COMPOUND NAME |
| --- |
| 1-(5-CHLORO-6-(3,3-DIFLUOROAZETIDIN-1-YL)-2-METHOXYPYRIDIN-3-YL)-N-(ISOXAZOL-3-YL)-2-OXO-1,2-DIHYDROQUINOLINE-6-SULFONAMIDE |
| N-3-ISOXAZOLYL-1-(2-METHOXY-5-(4-PYRIDINYL)PHENYL)-2-OXO-1,2-DIHYDRO-6-QUINOLINESULFONAMIDE |
| N-3-ISOXAZOLYL-1-(2-METHOXY-5-(2-PYRIDINYL)PHENYL)-2-OXO-1,2-DIHYDRO-6-QUINOLINESULFONAMIDE |
| N-3-ISOXAZOLYL-1-(2-METHOXY-5-(1-METHYL-1H-PYRAZOL-5-YL)PHENYL)-2-OXO-1,2-DIHYDRO-6-QUINOLINESULFONAMIDE |
| 1-(5-FLUORO-2-METHOXY-4-(3-PYRIDINYL)PHENYL)-N-3-ISOXAZOLYL-2-OXO-1,2-DIHYDRO-6-QUINOLINESULFONAMIDE |
| 1-(5-FLUORO-2-METHOXY-4-(1-METHYL-1H-PYRAZOL-4-YL)PHENYL)-N-3-ISOXAZOLYL-2-OXO-1,2-DIHYDRO-6-QUINOLINESULFONAMIDE |
| 1-(4-(3,3-DIFLUORO-1-AZETIDINYL)-5-FLUORO-2-METHOXYPHENYL)-N-3-ISOXAZOLYL-2-OXO-1,2-DIHYDRO-6-QUINOLINESULFONAMIDE |
| 1-(4-(5-CHLORO-3-PYRIDINYL)-5-FLUORO-2-METHOXYPHENYL)-N-3-ISOXAZOLYL-2-OXO-1,2-DIHYDRO-6-QUINOLINESULFONAMIDE (407), (P)-1-(4-(5-CHLORO-3-PYRIDINYL)-5-FLUORO-2-METHOXYPHENYL)-N-3-ISOXAZOLYL-2-OXO-1,2-DIHYDRO-6-QUINOLINESULFONAMIDE (408) and (M)-1-(4-(5-CHLORO-3-PYRIDINYL)-5-FLUORO-2-METHOXYPHENYL)-N-3-ISOXAZOLYL-2-OXO-1,2-DIHYDRO-6-QUINOLINESULFONAMIDE (409) |
| 1-(5-FLUORO-2-METHOXY-4-(1-METHYL-1H-IMIDAZOL-4-YL)PHENYL)-N-3-ISOXAZOLYL-2-OXO-1,2-DIHYDRO-6-QUINOLINESULFONAMIDE |
| (M)-1-(4-(5-FLUORO-2-METHOXY-3-PYRIDINYL)-2-METHOXY-5-METHYLPHENYL)-N-3-ISOXAZOLYL-2-OXO-1,2-DIHYDRO-6-QUINOLINESULFONAMIDE (425) and (P)-1-(4-(5-FLUORO-2-METHOXY-3-PYRIDINYL)-2-METHOXY-5-METHYLPHENYL)-N-3-ISOXAZOLYL-2-OXO-1,2-DIHYDRO-6-QUINOLINESULFONAMIDE (426) |
| 1-(4-CYCLOPENTYL-5-FLUORO-2-METHOXYPHENYL)-N-(ISOXAZOL-3-YL)-2-OXO-1,2-DIHYDROQUINOLINE-6-SULFONAMIDE |
| 1-(5-(5-FLUORO-3-PYRIDINYL)-2-METHOXYPHENYL)-N-3-ISOXAZOLYL-2-OXO-1,2-DIHYDRO-6-QUINOLINESULFONAMIDE |
| N-3-ISOXAZOLYL-1-(2-METHOXY-5-(1-METHYL-1H-PYRAZOL-4-YL)PHENYL)-2-OXO-1,2-DIHYDRO-6-QUINOLINESULFONAMIDE |
| 1-(5-(6-FLUORO-3-PYRIDINYL)-2-METHOXYPHENYL)-N-3-ISOXAZOLYL-2-OXO-1,2-DIHYDRO-6-QUINOLINESULFONAMIDE |
| 1-(5-(5-FLUORO-2-METHOXY-3-PYRIDINYL)-2-METHOXYPHENYL)-N-3-ISOXAZOLYL-2-OXO-1,2-DIHYDRO-6-QUINOLINESULFONAMIDE |
| N-3-ISOXAZOLYL-1-(2-METHOXY-5-(5-PYRIMIDINYL)PHENYL)-2-OXO-1,2-DIHYDRO-6-QUINOLINESULFONAMIDE |
| N-3-ISOXAZOLYL-1-(2-METHOXY-5-(3-PYRIDINYL)PHENYL)-2-OXO-1,2-DIHYDRO-6-QUINOLINESULFONAMIDE |
| 1-(5-(5-CYANO-3-PYRIDINYL)-2-METHOXYPHENYL)-N-3-ISOXAZOLYL-2-OXO-1,2-DIHYDRO-6-QUINOLINESULFONAMIDE |
| N-3-ISOXAZOLYL-1-(2-METHOXY-5-(5-(TRIFLUOROMETHYL)-3-PYRIDINYL)PHENYL)-2-OXO-1,2-DIHYDRO-6-QUINOLINESULFONAMIDE |
| 1-(5-(5-CHLORO-3-PYRIDINYL)-2-METHOXYPHENYL)-N-3-ISOXAZOLYL-2-OXO-1,2-DIHYDRO-6-QUINOLINESULFONAMIDE |
| 1-(5-(2-FLUORO-3-PYRIDINYL)-2-METHOXYPHENYL)-N-3-ISOXAZOLYL-2-OXO-1,2-DIHYDRO-6-QUINOLINESULFONAMIDE |
| 1-(5-(2-FLUORO-4-PYRIDINYL)-2-METHOXYPHENYL)-N-3-ISOXAZOLYL-2-OXO-1,2-DIHYDRO-6-QUINOLINESULFONAMIDE |
| 1-(4-FLUORO-5-(6-FLUORO-3-PYRIDINYL)-2-METHOXYPHENYL)-N-3-ISOXAZOLYL-6-ISOQUINOLINESULFONAMIDE |
| 1-(5-FLUORO-2-METHOXY-4-(6-METHYL-3-PYRIDINYL)PHENYL)-N-3-ISOXAZOLYL-2-OXO-1,2-DIHYDRO-6-QUINOLINESULFONAMIDE |
| 1-(5-FLUORO-2-METHOXY-4-(4-PYRIDINYL)PHENYL)-N-3-ISOXAZOLYL-2-OXO-1,2-DIHYDRO-6-QUINOLINESULFONAMIDE |
| 1-(5-FLUORO-2-METHOXY-4-(3-(TRIFLUOROMETHYL)-1-AZETIDINYL)PHENYL)-N-3-ISOXAZOLYL-2-OXO-1,2-DIHYDRO-6-QUINOLINESULFONAMIDE |
| 1-(5-FLUORO-4-(5-FLUORO-2-METHOXY-3-PYRIDINYL)-2-METHOXYPHENYL)-N-3-ISOXAZOLYL-2-OXO-1,2-DIHYDRO-6-QUINOLINESULFONAMIDE |
| 1-(4-(5-CHLORO-6-METHYL-3-PYRIDINYL)-5-FLUORO-2-METHOXYPHENYL)-N-3-ISOXAZOLYL-2-OXO-1,2-DIHYDRO-6-QUINOLINESULFONAMIDE |
| 1-(5-FLUORO-2-METHOXY-4-(2-PYRIDINYL)PHENYL)-N-3-ISOXAZOLYL-2-OXO-1,2-DIHYDRO-6-QUINOLINESULFONAMIDE |
| 1-(6-(3-FLUOROPHENYL)-4-METHOXY-3-PYRIDINYL)-N-3-ISOXAZOLYL-2-OXO-1,2-DIHYDRO-6-QUINOLINESULFONAMIDE, (P)-1-(6-(3-FLUOROPHENYL)-4-METHOXY-3-PYRIDINYL)-N-3-ISOXAZOLYL-2-OXO-1,2-DIHYDRO-6-QUINOLINESULFONAMIDE (602), and (M)-1-(6-(3-FLUOROPHENYL)-4-METHOXY-3-PYRIDINYL)-N-3-ISOXAZOLYL-2-OXO-1,2-DIHYDRO-6-QUINOLINESULFONAMIDE (603) |
| (P)-1-(4-(5-CHLORO-2-METHOXY-3-PYRIDINYL)-5-FLUORO-2-METHOXYPHENYL)-2-OXO-N-2-PYRIMIDINYL-1,2-DIHYDRO-6-QUINOLINESULFONAMIDE |
| 1-(2-(3-CHLORO-5-FLUOROPHENYL)-5-METHOXY-4-PYRIDINYL)-N-3-ISOXAZOLYL-2-OXO-1,2-DIHYDRO-6-QUINOLINESULFONAMIDE (618) |

| COMPOUND NAME |
| --- |
| N-3-ISOXAZOLYL-1-(2-METHOXY-5-(TETRAHYDRO-2H-PYRAN-4-YL)PHENYL)-2-OXO-1,2-DIHYDRO-6-QUINOLINESULFONAMIDE |
| 1-(4-BROMO-5-FLUORO-2-(PYRROLIDIN-3-YLOXY)PHENYL)-N-(ISOXAZOL-3-YL)-2-OXO-1,2-DIHYDROQUINOLINE-6-SULFONAMIDE |
| (P)-1-(5-FLUORO-2-METHOXY-4-(2-PYRIDINYL)PHENYL)-N-3-ISOXAZOLYL-2-OXO-1,2-DIHYDRO-6-QUINOLINESULFONAMIDE |
| (P)-1-(5-FLUORO-2-METHOXY-4-(5-(TRIFLUOROMETHYL)-2-PYRIDINYL)PHENYL)-N-3-ISOXAZOLYL-2-OXO-1,2-DIHYDRO-6-QUINOLINESULFONAMIDE |
| 1-(5-CHLORO-6-CYCLOPROPYL-2-METHOXY-3-PYRIDINYL)-N-3-ISOXAZOLYL-2-OXO-1,2-DIHYDRO-6-QUINOLINESULFONAMIDE |
| (P)-1-(4-CYCLOPENTYL-5-FLUORO-2-METHOXYPHENYL)-N-3-ISOXAZOLYL-2-OXO-1,2-DIHYDRO-6-QUINOLINESULFONAMIDE |
| (P)-1-(5-CHLORO-6-(1,5-DIFLUOROPHENYL)-2-METHOXY-3-PYRIDINYL)-N-3-ISOXAZOLYL-2-OXO-1,2-DIHYDRO-6-QUINOLINESULFONAMIDE (665) & (M)-1-(5-CHLORO-6-(3,5-DIFLUOROPHENYL)-2-METHOXY-3-PYRIDINYL)-N-3-ISOXAZOLYL-2-OXO-1,2-DIHYDRO-6-QUINOLINESULFONAMIDE (666) |
| (P)-1-(5-FLUORO-2-METHOXY-4-(TETRAHYDRO-2H-PYRAN-4-YL)PHENYL)-N-3-ISOXAZOLYL-2-OXO-1,2-DIHYDRO-6-QUINOLINESULFONAMIDE |
| (P)-1-(4-(5-CHLORO-2-METHOXY-3-PYRIDINYL)-5-FLUORO-2-METHOXYPHENYL)-N-3-ISOXAZOLYL-2-OXO-1,2-DIHYDRO-6-QUINOLINESULFONAMIDE |
| (P)-1-(5-FLUORO-2-METHOXY-4-(2-METHOXY-5-METHYL-3-PYRIDINYL)PHENYL)-N-3-ISOXAZOLYL-2-OXO-1,2-DIHYDRO-6-QUINOLINESULFONAMIDE |
| (P)-1-(5-FLUORO-2-METHOXY-4-(5-(TRIFLUOROMETHYL)-3 PYRIDINYL)PHENYL)-N-3-ISOXAZOLYL-2-OXO-1,2-DIHYDRO-6-QUINOLINESULFONAMIDE |
| (P)-1-(5-FLUORO-4-(6-FLUORO-5-METHYL-3-PYRIDINYL)-2-METHOXYPHENYL)-N-3-ISOXAZOLYL-2-OXO-1,2-DIHYDRO-6-QUINOLINESULFONAMIDE |
| (P)-1-(3''-CHLORO-2-FLUORO-5,5',5''-TRIMETHOXY-1,1':3',1''-TERPHENYL-4-YL)-N 3-ISOXAZOLYL-2-OXO-1,2-DIHYDRO-6-QUINOLINESULFONAMIDE |
| (P)-1-(5-FLUORO-2-METHOXY-4-(6-METHOXY-3-PYRIDINYL)PHENYL)-N-3-ISOXAZOLYL-2-OXO-1,2-DIHYDRO-6-QUINOLINESULFONAMIDE |
| (P)-1-(5-FLUORO-4-(5-FLUORO-3-PYRIDINYL)-2-METHOXYPHENYL)-N-3-ISOXAZOLYL-2-OXO-1,2-DIHYDRO-6-QUINOLINESULFONAMIDE |
| (P)-1-(5-FLUORO-2-METHOXY-4-(2-METHYL-4-PYRIDINYL)PHENYL)-N-3 ISOXAZOLYL-2-OXO-1,2-DIHYDRO-6-QUINOLINESULFONAMIDE |
| (P)-1-(5-FLUORO-2-METHOXY-4-(2-METHYL-3-PYRIDINYL)PHENYL)-N-3-ISOXAZOLYL-2-OXO-1,2-DIHYDRO-6-QUINOLINESULFONAMIDE |
| (P)-1-(5-FLUORO-2-METHOXY-4-(5-METHOXY-3-PYRIDINYL)PHENYL)-N-3 ISOXAZOLYL-2-OXO-1,2-DIHYDRO-6-QUINOLINESULFONAMIDE |
| (P)-1-(5-FLUORO-2-METHOXY-4-(2-METHOXY-4-PYRIDINYL)PHENYL)-N-3-ISOXAZOLYL-2-OXO-1,2-DIHYDRO-6-QUINOLINESULFONAMIDE |
| (P)-1-(4-(5-CHLORO-6-METHOXY-3-PYRIDINYL)-5-FLUORO-2-METHOXYPHENYL)-N-3-ISOXAZOLYL-2-OXO-1,2-DIHYDRO-6-QUINOLINESULFONAMIDE |
| (P)-1-(4-(3-CHLORO-2-METHOXY-4-PYRIDINYL)-5-FLUORO-2-METHOXYPHENYL)-N-3-ISOXAZOLYL-2-OXO-1,2-DIHYDRO-6-QUINOLINESULFONAMIDE |
| (P)-1-(4-(3-CHLORO-4-PYRIDINYL)-5-FLUORO-2-METHOXYPHENYL)-N-3-ISOXAZOLYL-2-OXO-1,2-DIHYDRO-6-QUINOLINESULFONAMIDE |
| (P)-1-(4-(5-CHLORO-2-METHOXY-4-PYRIDINYL)-5-FLUORO-2-METHOXYPHENYL)-N-3-ISOXAZOLYL-2-OXO-1,2-DIHYDRO-6-QUINOLINESULFONAMIDE |
| (P)-1-(5-FLUORO-2-METHOXY-4-(6-(TRIFLUOROMETHYL)-3-PYRIDINYL)PHENYL)-N-3-ISOXAZOLYL-2-OXO-1,2-DIHYDRO-6-QUINOLINESULFONAMIDE |
| (P)-1-(5-FLUORO-2-METHOXY-4-(2-(TRIFLUOROMETHYL)-4-PYRIDINYL)PHENYL)-N-3-ISOXAZOLYL-2-OXO-1,2-DIHYDRO-6-QUINOLINESULFONAMIDE |
| (P)-1-(4-(5-CHLORO-2-METHOXY-3-PYRIDINYL)-5-FLUORO-2-METHOXYPHENYL)-N-(5-FLUORO-2-PYRIMIDINYL)-2-OXO-1,2-DIHYDRO-6-QUINOLINESULFONAMIDE |
| (P)-1-(4-(5-CHLORO-2-METHOXY-3-PYRIDINYL)-5-FLUORO-2-METHOXYPHENYL)-2-OXO-N-3-PYRIDAZINYL-1,2-DIHYDRO-6-QUINOLINESULFONAMIDE |
| (P)-1-(4-(5-CHLORO-2-METHOXY-3-PYRIDINYL)-5-FLUORO-2-METHOXYPHENYL)-N-1,3-OXAZOL-2-YL-2-OXO-1,2-DIHYDRO-6-QUINOLINESULFONAMIDE |
| (P)-1-(4-(5-CHLORO-2-METHOXY-3-PYRIDINYL)-5-FLUORO-2-METHOXYPHENYL)-N-(6-METHYL-4-PYRIMIDINYL)-2-OXO-1,2-DIHYDRO-6-QUINOLINESULFONAMIDE |
| (P)-1-(4-(5-CHLORO-2-METHOXY-3-PYRIDINYL)-5-FLUORO-2-METHOXYPHENYL)-N-(2-METHYL-4-PYRIMIDINYL)-2-OXO-1,2-DIHYDRO-6-QUINOLINESULFONAMIDE |
| (P)-1-(4-(2,3-DIHYDRO-1-BENZOFURAN-7-YL)-2-METHOXYPHENYL)-N-3 |

| COMPOUND NAME |
|---|
| ISOXAZOLYL-2-OXO-1,2-DIHYDRO-6-QUINOLINESULFONAMIDE |
| (P)-1-(5-FLUORO-2-METHOXY-4-(6-(TRIFLUOROMETHYL)-2-PYRIDINYL)PHENYL)-N-3-ISOXAZOLYL-2-OXO-1,2-DIHYDRO-6-QUINOLINESULFONAMIDE |
| (P)-1-(4-(5-CHLORO-2-PYRIDINYL)-5-FLUORO-2-METHOXYPHENYL)-N-3-ISOXAZOLYL-2-OXO-1,2-DIHYDRO-6-QUINOLINESULFONAMIDE |
| (P)-1-(4-(4-CHLORO-2-PYRIDINYL)-5-FLUORO-2-METHOXYPHENYL)-N-3-ISOXAZOLYL-2-OXO-1,2-DIHYDRO-6-QUINOLINESULFONAMIDE |
| (P)-1-(5-FLUORO-2-METHOXY-4-(6-METHOXY-2-PYRIDINYL)PHENYL)-N-3-ISOXAZOLYL-2-OXO-1,2-DIHYDRO-6-QUINOLINESULFONAMIDE |
| (P)-1-(4-(5-CHLORO-6-METHYL-2-PYRIDINYL)-5-FLUORO-2-METHOXYPHENYL)-N-3-ISOXAZOLYL-2-OXO-1,2-DIHYDRO-6-QUINOLINESULFONAMIDE |
| (P)-1-(5-FLUORO-2-METHOXY-4-(4-METHOXY-2-PYRIMIDINYL)PHENYL)-N-3-ISOXAZOLYL-2-OXO-1,2-DIHYDRO-6-QUINOLINESULFONAMIDE |
| (P)-1-(4-(2,3-DIHYDRO-1-BENZOFURAN-6-YL)-2-METHOXYPHENYL)-N-3-ISOXAZOLYL-2-OXO-1,2-DIHYDRO-6-QUINOLINESULFONAMIDE |
| (P)-1-(4-(5-CHLORO-2-METHOXY-3-PYRIDINYL)-2-METHOXYPHENYL)-N-3-ISOXAZOLYL-2-OXO-1,2-DIHYDRO-6-QUINOLINESULFONAMIDE |
| (P)-1-(4-(5-CHLORO-6-METHOXY-3-PYRIDINYL)-2-METHOXYPHENYL)-N-3-ISOXAZOLYL-2-OXO-1,2-DIHYDRO-6-QUINOLINESULFONAMIDE |
| 1-(5-CHLORO-6-(CYCLOPROPYLMETHOXY)-2-METHOXY-3-PYRIDINYL)-N-3 ISOXAZOLYL-2-OXO-1,2-DIHYDRO-6-QUINOLINESULFONAMIDE |
| 1-(5-CHLORO-6-(CYCLOBUTYLOXY)-2-METHOXY-3-PYRIDINYL)-N-3 ISOXAZOLYL-2-OXO-1,2-DIHYDRO-6-QUINOLINESULFONAMIDE |
| 1-(5-CHLORO-2-METHOXY-6-((1-METHYLCYCLOPROPYL)METHOXY)-3 PYRIDINYL)-N-3-ISOXAZOLYL-2-OXO-1,2-DIHYDRO-6-QUINOLINESULFONAMIDE |
| 1-(5-CHLORO-6-(CYCLOPENTYLMETHOXY)-2-METHOXY-3-PYRIDINYL)-N-3-ISOXAZOLYL-2-OXO-1,2-DIHYDRO-6-QUINOLINESULFONAMIDE |
| 1-(5-CHLORO-6-(CYCLOPENTYLOXY)-2-METHOXY-3-PYRIDINYL)-N-3-ISOXAZOLYL-2-OXO-1,2-DIHYDRO-6-QUINOLINESULFONAMIDE |
| (P)-1-(4-BROMO-5-FLUORO-2-METHOXYPHENYL)-N-(4,5-DIMETHYL-3-ISOXAZOLYL)-2-OXO-1,2-DIHYDRO-6-QUINOLINESULFONAMIDE |
| 1-(5-CHLORO-6-CYCLOPROPYL-2-METHOXY-3-PYRIDINYL)-N-3-ISOXAZOLYL-2-OXO-1,2-DIHYDRO-6-QUINOLINESULFONAMIDE |
| 1-(5-CHLORO-2-METHOXY-6-(2,2,3,3,3-PENTAFLUOROPROPOXY)-3-PYRIDINYL)-N-3-ISOXAZOLYL-2-OXO-1,2-DIHYDRO-6-QUINOLINESULFONAMIDE |
| 1-(5-CHLORO-2-METHOXY-6-(2,2,2-TRIFLUOROETHOXY)-3-PYRIDINYL)-N-3-ISOXAZOLYL-2-OXO-1,2-DIHYDRO-6-QUINOLINESULFONAMIDE |
| 1-(2-CHLORO-5-METHOXY-4-PYRIDINYL)-N-3-ISOXAZOLYL-2-OXO-1,2-DIHYDRO-6-QUINOLINESULFONAMIDE |
| 1-(2-(3-CHLORO-5-FLUOROPHENYL)-5-METHOXY-4-PYRIDINYL)-N-3-ISOXAZOLYL-2-OXO-1,2-DIHYDRO-6-QUINOLINESULFONAMIDE |
| N-3-ISOXAZOLYL-1-(2-METHOXY-5-(TETRAHYDRO-2H-PYRAN-4-YL)PHENYL)-2-OXO-1,2-DIHYDRO-6-QUINOLINESULFONAMIDE |
| 1-(5-CHLORO-2-METHOXY-4-(TRIFLUOROMETHYL)PHENYL)-2-OXO-N-4-PYRIMIDINYL-1,2-DIHYDRO-6-QUINOLINESULFONAMIDE |
| 1-(5-CHLORO-2-METHOXY-4-(TRIFLUOROMETHYL)PHENYL)-2-OXO-N-4-PYRIMIDINYL-1,2-DIHYDRO-6-QUINOLINESULFONAMIDE |
| 1-(4-CHLORO-2-(1-METHYL-1,2,3,6-TETRAHYDRO-4-PYRIDINYL)PHENYL)-N-3-ISOXAZOLYL-2-OXO-1,2-DIHYDRO-6-QUINOLINESULFONAMIDE |
| 1-(4-BROMO-5-FLUORO-2-METHOXYPHENYL)-N-(2-METHYL-4-PYRIMIDINYL)-2-OXO-1,2-DIHYDRO-6-QUINOLINESULFONAMIDE |
| 1-(4-BROMO-5-FLUORO-2-METHOXYPHENYL)-N-(6-METHYL-4-PYRIMIDINYL)-2-OXO-1,2-DIHYDRO-6-QUINOLINESULFONAMIDE |
| 1-(4-BROMO-5-FLUORO-2-METHOXYPHENYL)-N-(2-METHOXY-4-PYRIMIDINYL)-2-OXO-1,2-DIHYDRO-6-QUINOLINESULFONAMIDE |
| 1-(4-BROMO-5-FLUORO-2-METHOXYPHENYL)-N-(6-(METHOXYMETHYL)-4-PYRIMIDINYL)-2-OXO-1,2-DIHYDRO-6-QUINOLINESULFONAMIDE |
| 1-(4-BROMO-5-FLUORO-2-METHOXYPHENYL)-N-(6-METHOXY-4-PYRIMIDINYL)-2-OXO-1,2-DIHYDRO-6-QUINOLINESULFONAMIDE |
| 1-(4-BROMO-5-FLUORO-2-METHOXYPHENYL)-N-(1-METHYL-2-OXO-1,2-DIHYDRO-4-PYRIDINYL)-2-OXO-1,2-DIHYDRO-6-QUINOLINESULFONAMIDE |
| 1-(4-BROMO-5-FLUORO-2-METHOXYPHENYL)-N-(2-ETHYL-4-PYRIMIDINYL)-2-OXO-1,2-DIHYDRO-6-QUINOLINESULFONAMIDE |
| 1-(4-BROMO-5-FLUORO-2-METHOXYPHENYL)-N-(6-METHYL-2-PYRIDINYL)-2-OXO-1,2-DIHYDRO-6-QUINOLINESULFONAMIDE |
| 1-(4-BROMO-5-FLUORO-2-METHOXYPHENYL)-N-(4-METHYL-2-PYRIMIDINYL)-2-OXO-1,2-DIHYDRO-6-QUINOLINESULFONAMIDE |
| 1-(4-BROMO-5-FLUORO-2-METHOXYPHENYL)-N-(2,6-DIMETHYL-4-PYRIMIDINYL)-2-OXO-1,2-DIHYDRO-6-QUINOLINESULFONAMIDE |
| 1-(4-BROMO-5-FLUORO-2-METHOXYPHENYL)-N-(6-METHOXY-2-PYRIDINYL)-2-OXO-1,2-DIHYDRO-6-QUINOLINESULFONAMIDE |
| 1-(4-BROMO-5-FLUORO-2-METHOXYPHENYL)-N-(2-CYANO-4-PYRIDINYL)-2-OXO-1,2-DIHYDRO-6-QUINOLINESULFONAMIDE |
| 1-(4-BROMO-5-FLUORO-2-METHOXYPHENY)-N-(4,6-DIMETHYL-2-PYRIDINYL)-2-OXO-1,2-DIHYDRO-6-QUINOLINESULFONAMIDE |

| COMPOUND NAME |
|---|
| 1-(4-BROMO-5-FLUORO-2-METHOXYPHENYL)-N-(2-(METHOXY-METHYL)-4-PYRIMIDINYL)-2-OXO-1,2-DIHYDRO-6-QUINOLINESULFONAMIDE |
| 1-(5-CHLORO-6-(3-FLUOROPHENYL)-2-OXO-1,2-DIHYDRO-3-PYRIDINYL)-N-3-ISOXAZOLYL-2-OXO-1,2-DIHYDRO-6-QUINOLINESULFONAMIDE |
| N-3-ISOXAZOLYL-1-(2-METHOXY-4-(2-METHOXY-5-METHYL-3-PYRIDINYL)PHENYL)-2-OXO-1,2-DIHYDRO-6-QUINOLINESULFONAMIDE |
| 1-(4-BROMO-2-METHOXYPHENYL)-2-OXO-N-3-PYRIDAZINYL-1,2 DIHYDRO-6-QUINOLINESULFONAMIDE |
| 1-(4-BROMO-2-((1R)-1-CYANOETHOXY)-5-FLUOROPHENYL)-N-3-ISOXAZOLYL-2-OXO-1,2-DIHYDRO-6-QUINOLINESULFONAMIDE, 1-(4-BROMO-2-((1S)-1-CYANOETHOXY)-5-FLUOROPHENYL)-N-3-ISOXAZOLYL-2-OXO-1,2-DIHYDRO-6-QUINOLINESULFONAMIDE |
| 1-(4-BROMO-2-(CYANOMETTIOXY)-5-FLUOROPHENYL)-N-3-ISOXAZOLYL-2-OXO-1,2-DIHYDRO-6-QUINOLINESULFONAMIDE |
| 1-(4-BROMO-5-FLUORO-2-((3R)-3-PYRROLIDINYLOXY)PHENYL)-N-3-ISOXAZOLYL-2-OXO-1,2-DIHYDRO-6-QUINOLINESULFONAMIDE, 1-(4-BROMO-5-FLUORO-2-((3S)-3-PYRROLIDINYLOXY)PHENYL)-N-3-ISOXAZOLYL-2-OXO-1,2-DIHYDRO-6-QUINOLINESULFONAMIDE |
| 1-(5-CHLORO-6-(3,5-DIFLUOROPHENYL)-2-METHOXY-3-PYRIDINYL)-N-3-ISOXAZOLYL-2-OXO-1,2-DIHYDRO-6-QUINOLINESULFONAMIDE |
| 1-(5-CHLORO-6-(3-CHLORO-5-FLUOROPHENYL)-2-METHOXY-3-PYRIDINYL)-N-3-ISOXAZOLYL-2-OXO-1,2-DIHYDRO-6-QUINOLINESULFONAMIDE |
| 1-(4-CYCLOPENTYL-5-FLUORO-2-METHOXYPHENYL)-N-3-ISOXAZOLYL-2-OXO-1,2-DIHYDRO-6-QUINOLINESULFONAMIDE |
| 1-(4-(2,2-DIMETHYLPROPYL)-5-FLUORO-2-METHOXYPHENYL)-N-3-ISOXAZOLYL-2-OXO-1,2-DIHYDRO-6-QUINOLINESULFONAMIDE |
| 1-(4-CYCLOHEXYL-5-FLUORO-2-METHOXYPHENYL)-N-3-ISOXAZOLYL-2-OXO-1,2-DIHYDRO-6-QUINOLINESULFONAMIDE |
| 1-(4-(CYCLOBUTYMETHYL)-5-FLUORO-2-METHOXYPHENYL)-N-3-ISOXAZOLYL-2-OXO-1,2-DIHYDRO-6-QUINOLINESULFONAMIDE |
| 1-(4-(CYCLOHEXYLMETHYL)-5-FLUORO-2-METHOXYPHENYL)-N-3 ISOXAZOLYL-2-OXO-1,2-DIHYDRO-6-QUINOLINESULFONAMIDE |
| 1-(5-CHLORO-6-(3,5-DIFLUOROPHENYL)-2-METHOXY-3-PYRIDINYL)-2-OXO-N-2-PYRIMIDINYL-1,2-DIHYDRO-6-QUINOLINESULFONAMIDE |
| 1-(5-CHLORO-6-(3,5-DIFLUOROPHENYL)-2-METHOXY-3-PYRIDINYL)-2-OXO-N-2-PYRIMIDINYL-1,2-DIHYDRO-6-QUINOLINESULFONAMIDE |
| 1-(4-(CYCLOPENTYLMETHYL)-5-FLUORO-2-METHOXYPHENYL)-N-3-ISOXAZOLYL-2-OXO-1,2-DIHYDRO-6-QUINOLINESULFONAMIDE |
| 1-(4-((1R,2R,4R)-BICYCLO[2.2.1]HEPT-2-YLMETHYL)-5-FLUORO-2-METHOXYPHENYL)-N-3-ISOXAZOLYL-2-OXO-1,2-DIHYDRO-6-QUINOLINESULFONAMIDE, 1-(4-((1R,2R,4S)-BICYCLO[2.2.1]HEPT-2-YLMETHYL)-5-FLUORO-2-METHOXYPHENYL)-N-3-ISOXAZOLYL-2-OXO-1,2-DIHYDRO-6-QUINOLINESULFONAMIDE, 1-(4-((1R,2S,4R)-BICYCLO[2.2.1]HEPT-2-YLMETHYL)-5-FLUORO-2-METHOXYPHENYL)-N-3-ISOXAZOLYL-2-OXO-1,2-DIHYDRO-6-QUINOLINESULFONAMIDE, 1-(4-((1R,2S,4S)-BICYCLO[2.2.1]HEPT-2-YLMETHYL)-5-FLUORO-2-METHOXYPHENYL)-N-3-ISOXAZOLYL-2-OXO-1,2-DIHYDRO-6-QUINOLINESULFONAMIDE, 1-(4-((1S,2R,4R)-BICYCLO[2.2.1]HEPT-2-YLMETHYL)-5-FLUORO-2-METHOXYPHENYL)-N-3-ISOXAZOLYL-2-OXO-1,2-DIHYDRO-6-QUINOLINESULFONAMIDE, 1-(4-((1S,2R,4S)-BICYCLO[2.2.1]HEPT-2-YLMETHYL)-5-FLUORO-2-METHOXYPHENYL)-N-3-ISOXAZOLYL-2-OXO-1,2-DIHYDRO-6-QUINOLINESULFONAMIDE, 1-(4-((1S,2S,4R)-BICYCLO[2.2.1]HEPT-2-YLMETHYL)-5-FLUORO-2-METHOXYPHENYL)-N-3-ISOXAZOLYL-2-OXO-1,2-DIHYDRO-6-QUINOLINESULFONAMIDE, 1-(4-((1S,2S,4S)-BICYCLO[2.2.1]-HEPT-2-YLMETHYL)-5-FLUORO-2-METHOXYPHENYL)-N-3-ISOXAZOLYL-2-OXO-1,2-DIHYDRO-6-QUINOLINESULFONAMIDE |
| 1-(5-FLUORO-2-METHOXY-4-(CIS-4-METHYLCYCLOHEXYL)PHENYL)-N-3-ISOXAZOLYL-2-OXO-1,2-DIHYDRO-6-QUINOLINESULFONAMIDE, 1-(5-FLUORO-2-METHOXY-4-(TRANS-4-METHYLCYCLOHEXYL)PHENYL)-N-3-ISOXAZOLYL-2-OXO-1,2-DIHYDRO-6-QUINOLINESULFONAMIDE |
| 1-(5-CHLORO-6-(4-CHLORO-3-METHYLPHENYL)-2-METHOXY-3-PYRIDINYL)-N-3-ISOXAZOLYL-2-OXO-1,2-DIHYDRO-6-QUINOLINESULFONAMIDE |
| 1-(5-CHLORO-6-(4-CHLORO-3-METHYLPHENYL)-2-METHOXY-3-PYRIDINYL)-N-3-ISOXAZOLYL-2-OXO-1,2-DIHYDRO-6-QUINOLINESULFONAMIDE |
| 1-(5-FLUORO-2-METHOXY-4-(TETRAHYDRO-2H-PYRAN-4-YL)PHENYL)-N-3-ISOXAZOLYL-2-OXO-1,2-DIHYDRO-6-QUINOLINESULFONAMIDE |
| 1-(5-FLUORO-2-METHOXY-4-(CIS-4-METHOXYCYCLOHEXYL)PHENYL)-N-3-ISOXAZOLYL-2-OXO-1,2-DIHYDRO-6-QUINOLINESULFONAMIDE, 1-(5-FLUORO-2-METHOXY-4-(TRANS-4-METHOXYCYCLOHEXYL)PHENYL)-N-3-ISOXAZOLYL-2-OXO-1,2-DIHYDRO-6-QUINOLINESULFONAMIDE |
| 1-(5-FLUORO-2-METHOXY-4-((1R,2R,4S)-7-OXABICYCLO[2.2.1]HEPT-2-YLMETHYL)PHENYL)-N-3-ISOXAZOLYL-2-OXO-1,2-DIHYDRO-6-QUINOLINESULFONAMIDE, 1-(5-FLUORO-2-METHOXY-4-((1S,2S,4R)-7-OXABICYCLO[2.2.1]HEPT-2-YLMETHYL)PHENYL)-N-3-ISOXAZOLYL-2-OXO-1,2-DIHYDRO-6-QUINOLINESULFONAMIDE |
| 1-(5-CHLORO-2-METHOXY-6-(3-METHYLPHENYL)-3-PYRIDINYL)-N-3-ISOXAZOLYL-2-OXO-1,2-DIHYDRO-6-QUINOLINESULFONAMIDE |
| 1-(5-CHLORO-2-METHOXY-6-(3-METHYLPHENYL)-3-PYRIDINYL)-N-3- |

| COMPOUND NAME |
| --- |
| ISOXAZOLYL-2-OXO-1,2-DIHYDRO-6-QUINOLINESULFONAMIDE |
| 1-(5-CHLORO-6-(3-CYANOPHENYL)-2-METHOXY-3-PYRIDINYL)-N-3-ISOXAZOLYL-2-OXO-1,2-DIHYDRO-6-QUINOLINESULFONAMIDE |
| 1-(5-CHLORO-6-(3-CYANOPHENYL)-2-METHOXY-3-PYRIDINYL)-N-3-ISOXAZOLYL-2-OXO-1,2-DIHYDRO-6-QUINOLINESULFONAMIDE |
| 1-(5-CHLORO-2-METHOXY-6-(3-METHOXYPHENYL)-3-PYRIDINYL)-N-3-ISOXAZOLYL-2-OXO-1,2-DIHYDRO-6-QUINOLINESULFONAMIDE |
| 1-(5-CHLORO-2-METHOXY-6-(3-METHOXYPHENYL)-3-PYRIDINYL)-N-3-ISOXAZOLYL-2-OXO-1,2-DIHYDO-6-QUINOLINESULFONAMIDE |
| 1-(4-(4,4-DIFLUOROCYCLOHEXYL)-5-FLUORO-2-METHOXYPHENYL)-N-3-ISOXAZOLYL-2-OXO-1,2-DIHYDRO-6-QUINOLINESULFONAMIDE |
| 1-(4-(2,3-DIHYDRO-1-BENZOFURAN-7-YL)-2-METHOXYPHENYL)-N-3-ISOXAZOLYL-2-OXO-1,2-DIHYDRO-6-QUINOLINESULFONAMIDE |
| 1-(5-FLUORO-2-METHOXY-4-(6-(TRIFLUOROMETHYL)-2-PYRIDINYL)PHENYL)-N-3-ISOXAZOLYL-2-OXO-1,2-DIHYDRO-6-QUINOLINESULFONAMIDE |
| 1-(4''-CHLORO-2-FLUORO-5-METHOXY-1,1':4',1''-TERPHENYL-4-YL)-N-3-ISOXAZOLYL-2-OXO-1,2-DIHYDRO-6-QUINOLINESULFONAMIDE |
| 1-(5-FLUORO-2-METHOXY-4-(2-PYRIDINYL)PHENYL)-N-3-ISOXAZOLYL-2-OXO-1,2-DIHYDRO-6-QUINOLINESULFONAMIDE |
| 1-(4-(5-CHLORO-2-PYRIDINYL)-5-FLUORO-2-METHOXYPHENYL)-N-3-ISOXAZOLYL-2-OXO-1,2-DIHYDRO-6-QUINOLINESULFONAMIDE |
| 1-(4-(4-CHLORO-2-PYRIDINYL)-5-FLUORO-2-METHOXYPHENYL)-N-3-ISOXAZOLYL-2-OXO-1,2-DIHYDRO-6-QUINOLINESULFONAMIDE |
| 1-(5-FLUORO-2-METHOXY-4-(6-METHOXY-2-PYRIDINYL)PHENYL)-N-3-ISOXAZOLYL-2-OXO-1,2-DIHYDRO-6-QUINOLINESULFONAMIDE |
| 1-(5-FLUORO-2-METHOXY-4-(5-(TRIFLUOROMETHYL)-2-PYRIDINYL)PHENYL)-N-3-ISOXAZOLYL-2-OXO-1,2-DIHYDRO-6-QUINOLINESULFONAMIDE |
| 1-(4-(5-CHLORO-6-METHYL-2-PYRIDINYL)-5-FLUORO-2-METHOXYPHENYL)-N-3-ISOXAZOLYL-2-OXO-1,2-DIHYDRO-6-QUINOLINESULFONAMIDE |
| 1-(5-FLUORO-2-METHOXY-4-(4-METHOXY-2-PYRIMIDINYL)PHENYL)-N-3-ISOXAZOLYL-2-OXO-1,2-DIHYDO-6-QUINOLINESULFONAMIDE |
| 1-(4-(2,3-DIHYDRO-1-BENZOFURAN-6-YL)-2-METHOXYPHENYL)-N-3-ISOXAZOLYL-2-OXO-1,2-DIHYDRO-6-QUINOLINESULFONAMIDE |
| 1-(4-(5-CHLORO-2-METHOXY-3-PYRIDINYL)-2-METHOXYPHENYL)-N-3-ISOXAZOLYL-2-OXO-1,2-DIHYDRO-6-QUINOLINESULFONAMIDE |
| 1-(4-(5-CHLORO-6-METHOXY-3-PYRIDINYL)-2-METHOXYPHENYL)-N-3-ISOXAZOLYL-2-OXO-1,2-DIHYDRO-6-QUINOLINESULFONAMIDE |
| 1-(5-CHLORO-6-(CYCLOPROPYLMETHOXY)-2-METHOXY-3-PYRIDINYL)-N-3-ISOXAZOLYL-2-OXO-1,2-DIHYDRO-6-QUINOLINESULFONAMIDE |
| 1-(5-CHLORO-6-(CYCLOBUTYLOXY)-2-METHOXY-3-PYRIDINYL)-N-3-ISOXAZOLYL-2-OXO-1,2-DIHYDRO-6-QUINOLINESULFONAMIDE |
| 1-(5-CHLORO-2-METHOXY-6-((1-METHYLCYCLOPROPYL)METHOXY)-3-PYRIDINYL)-N-3-ISOXAZOLYL-2-OXO-1,2-DIHYDRO-6-QUINOLINESULFONAMIDE |
| 1-(5-CHLORO-6-(CYCLOPENTYLMETHOXY)-2-METHOXY-3-PYRIDINYL)-N-3-ISOXAZOLYL-2-OXO-1,2-DIHYDRO-6-QUINOLINESULFONAMIDE |
| 1-(5-CHLORO-6-(CYCLOPENTYLOXY)-2-METHOXY-3-PYRIDINYL)-N-3-ISOXAZOLYL-2-OXO-1,2-DIHYDRO-6-QUINOLINESULFONAMIDE |
| 1-(4-BROMO-5-FLUORO-2-METHOXYPHENYL)-N-(4,5-DIMETHYL-3-ISOXAZOLYL-2-OXO-1,2-DIHYDRO-6-QUINOLINESULFONAMIDE |
| 1-(5-CHLORO-6-CYCLOPROPYL-2-METHOXY-3-PYRIDINYL)-N-3-ISOXAZOLYL-2-OXO-1,2-DIHYDRO-6-QUINOLINESULFONAMIDE |
| 1-(5-CHLORO-2-MEITHOXY-6-(3-METHOXYPROPOXY)-3-PYRIDINYL)-N-3-ISOXAZOLYL-2-OXO-1,2-DIHYDRO-6-QUINOLINESULFONAMIDE |
| 1-(5-CHLORO-2-METHOXY-6-(2,2,3,3,3-PENTAFLUOROPROPOXY)-3-PYRIDINYL)-N-3-ISOXAZOLYL-2-OXO-1,2-DIHYDRO-6-QUINOLINESULFONAMIDE |
| 1-(5-CHLORO-2-METHOXY-6-(2,2,2-TRIFLUOROETHOXY)-3-PYRIDINYL)-N-3-ISOXAZOLYL-2-OXO-1,2-DIHYDRO-6-QUINOLINESULFONAMIDE |
| 1-(4-(CYCLOHEXYLMETHYL)-5-FLUORO-2-METHOXYPHENYL)-2-OXO-N-2-PYRIMIDINYL-1,2-DIHYDRO-6-QUINOLINESULFONAMIDE |
| 1-(4-(CYCLOHEXYLMETHYL)-5-FLUORO-2-METHOXYPHENYL)-N-1,3-OXAZOL-2-YL-2-OXO-1,2-DIHYDRO-6-QUINOLINESULFONAMIDE |
| 1-(4-(CYCLOHEXYLMETHYL)-5-FLUORO-2-METHOXYPHENYL)-N-(5-FLUORO-2-PYRIMIDINYL)-2-OXO-1,2-DIHYDRO-6-QUINOLINESULFONAMIDE |
| 1-(4-(CYCLOHEXYLMETHYL)-5-FLUORO-2-METHOXYPHENYL)-2-OXO-N-3-PYRIDAZINYL-1,2-DIHYDRO-6-QUINOLINESULFONAMIDE |
| 1-(4-(CYCLOHEXYLMETHYL)-5-FLUORO-2-METHOXYPHENYL)-N-1,2,4-OXADIAZOL-3-YL-2-OXO-1,2-DIHYDRO-6-QUINOLINESULFONAMIDE |
| 1-(4-(CYCLOHEXYLMETHYL)-5-FLUORO-2-METHOXYPHENYL)-2-OXO-N-4-PYRIMIDINYL-1,2-DIHYDRO-6-QUINOLINESULFONAMIDE |
| 1-(4-(CYCLOHEXYLMETHYL)-5-FLUORO-2-METHOXYPHENYL)-2-OXO-N-2-PYRAZINYL-1,2-DIHYDRO-6-QUINOLINESULFONAMIDE |
| 1-(5-FLUORO-2-METHOXY-4-((3R)-TETRAHYDRO-2H-PYRAN-3-YLMETHYL)PHENYL)-N-3-ISOXAZOLYL-2-OXO-1,2-DIHYDRO-6-QUINOLINESULFONAMIDE, 1-(5-FLUORO-2-METHOXY-4-((3S)-TETRAHYDRO-2H-PYRAN-3-YLMETHYL)PHENYL)-N-3-ISOXAZOLYL-2-OXO-1,2-DIHYDRO-6-QUINOLINESULFONAMIDE |

| COMPOUND NAME |
|---|
| 1-(5-FLUORO-2-METHOXY-4-(TETRAHYDRO-2H-PYRAN-4-YLMETHYL)PHENYL)-N-3-ISOXAZOLYL-2-OXO-1,2-DIHYDRO-6-QUINOLINESULFONAMIDE |
| 1-(4-(3,3-DIMETHYL-1-BUTYN-1-YL)-5-FLUORO-2-METHOXYPHENYL)-N-3-ISOXAZOLYL-2-OXO-1,2-DIHYDRO-6-QUINOLINESULFONAMIDE |
| 1-(5-FLUORO-2-METHOXY-4-((3R)-TETRAHYDRO-3-FURANYLMETHYL)PHENYL)-N-3-ISOXAZOLYL-2-OXO-1,2-DIHYDRO-6-QUINOLINESULFONAMIDE, 1-(5-FLUORO-2-METHOXY-4-((3S)-TETRAHYDRO-3-FURANYLMETHYL)PHENYL)-N-3-ISOXAZOLYL-2-OXO-1,2-DIHYDRO-6-QUINOLINESULFONAMIDE |
| 1-(5-FLUORO-2-METHOXY-4-(3,3,3-TRIFLUORO-1-PROPYN-1-YL)PHENYL)-N-3-ISOXAZOLYL-2-OXO-1,2-DIHYDRO-6-QUINOLINESULFONAMIDE |
| 1-(5-FLUORO-2-METHOXY-4-((2R)-TETRAHYDRO-2H-PYRAN-2-YLMETHYL)PHENYL)-N-3-ISOXAZOLYL-2-OXO-1,2-DIHYDRO-6-QUINOLINESULFONAMIDE, 1-(5-FLUORO-2-METHOXY-4-((2S)-TETRAHYDRO-2H-PYRAN-2-YLMETHYL)PHENYL)-N-3-ISOXAZOLYL-2-OXO-1,2-DIHYDRO-6-QUINOLINESULFONAMIDE |
| 1-(5-CHLORO-6-(CYCLOPENTYLAMINO)-2-METHOXY-3-PYRIDINYL)-N-3-ISOXAZOLYL-2-OXO-1,2-DIHYDRO-6-QUINOLINESULFONAMIDE |
| 1-(5-FLUORO-2-METHOXY-4-(2-PYRIDINYL)PHENYL)-N-3-ISOXAZOLYL-2-OXO-1,2-DIHYDRO-6-QUINOLINESULFONAMIDE |
| 1-(5-FLUORO-2-METHOXY-4-(2-METHOXY-5-METHYL-3-PYRIDINYL)PHENYL)-N-3-ISOXAZOLYL-2-OXO-1,2-DIHYDRO-6-QUINOLINESULFONAMIDE |
| 1-(5-FLUORO-2-METHOXY-4-(5-(TRIFLUOROMETHYL)-3-PYRIDINYL)PHENYL)-N-3-ISOXAZOLYL-2-OXO-1,2-DIHYDRO-6-QUINOLINESULFONAMIDE |
| 1-(5-FLUORO-4-(6-FLUORO-5-METHYL-3-PYRIDINYL)-2-METHOXYPHENYL)-N-3-ISOXAZOLYL-2-OXO-1,2-DIHYDRO-6-QUINOLINESULFONAMIDE |
| 1-(3''-CHLORO-2-FLUORO-5,5',5''-TRIMETHOXY-1,1':3',1''-TERPHENYL-4-YL)-N-3-ISOXAZOLYL-2-OXO-1,2-DIHYDRO-6-QUINOLINESULFONAMIDE |
| 1-(5-FLUORO-2-METHOXY-4-(6-METHOXY-3-PYRIDINYL)PHENYL)-N-3-ISOXAZOLYL-2-OXO-1,2-DIHYDRO-6-QUINOLINESULFONAMIDE |
| 1-(5-FLUORO-4-(5-FLUORO-3-PYRIDINYL)-2-METHOXYPHENYL)-N-3-ISOXAZOLYL-2-OXO-1,2-DIHYDRO-6-QUINOLINESULFONAMIDE |
| 1-(4-(5-CHLORO-2-METHOXY-3-PYRIDINYL)-5-FLUORO-2-METHOXYPHENYL)-N-3-ISOXAZOLYL-2-OXO-1,2-DIHYDRO-6-QUINOLINESULFONAMIDE |
| 1-(5-FLUORO-2-METHOXY-4-(2-METHYL-4-PYRIDINYL)PHENYL)-N-3-ISOXAZOLYL-2-OXO-1,2-DIHYDRO-6-QUINOLINESULFONAMIDE |
| 1-(5-FLUORO-2-METHOXY-4-(2-METHYL-3-PYRIDINYL)PHENYL)-N-3-ISOXAZOLYL-2-OXO-1,2-DIHYDRO-6-QUINOLINESULFONAMIDE |
| 1-(5-FLUORO-2-METHOXY-4-(5-METHOXY-3-PYRIDINYL)PHENYL)-N-3-ISOXAZOLYL-2-OXO-1,2-DIHYDRO-6-QUINOLINESULFONAMIDE |
| 1-(5-FLUORO-2-METHOXY-4-(2-METHOXY-4-PYRIDINYL)PHENYL)-N-3-ISOXAZOLYL-2-OXO-1,2-DIHYDRO-6-QUINOLINESULFONAMIDE |
| 1-(4-(5-CHLORO-6-METHOXY-3-PYRIDINYL)-5-FLUORO-2-METHOXYPHENYL)-N-3-ISOXAZOLYL-2-OXO-1,2-DIHYDRO-6-QUINOLINESULFONAMIDE |
| 1-(4-(3-CHLORO-2-METHOXY-4-PYRIDINYL)-5-FLUORO-2-METHOXYPHENYL)-N-3-ISOXAZOLYL-2-OXO-1,2-DIHYDRO-6-QUINOLINESULFONAMIDE |
| 1-(5-FLUORO-2-METHOXY-4-(4-METHYL-2-OXO-1(2H)-PYRIDINYL)PHENYL)-N-3-ISOXAZOLYL-2-OXO-1,2-DIHYDRO-6-QUINOLINESULFONAMIDE |
| 1-(4-(3-CHLORO-4-PYRIDINYL)-5-FLUORO-2-METHOXYPHENYL)-N-3-ISOXAZOLYL-2-OXO-1,2-DIHYDRO-6-QUINOLINESULFONAMIDE |
| 1-(4-(5-CHLORO-2-METHOXY-4-PYRIDINYL)-5-FLUORO-2-METHOXYPHENYL)-N-3-ISOXAZOLYL-2-OXO-1,2-DIHYDRO-6-QUINOLINESULFONAMIDE |
| 1-(5-FLUORO-2-METHOXY-4-(6-(TRIFLUOROMETHYL)-3-PYRIDINYL)PHENYL)-N-3-ISOXAZOLYL-2-OXO-1,2-DIHYDRO-6-QUINOLINESULFONAMIDE |
| 1-(5-FLUORO-2-METHOXY-4-(2-(TRIFLUOROMETHYL)-4-PYRIDINYL)PHENYL)-N-3-ISOXAZOLYL-2-OXO-1,2-DIHYDRO-6-QUINOLINESULFONAMIDE |
| 1-(6-(3-FLUOROPHENYL)-4-METHOXY-3-PYRIDINYL)-N-3-ISOXAZOLYL-2-OXO-1,2-DIHYDRO-6-QUINOLINESULFONAMIDE |
| 1-(6-(3-FLUOROPHENYL)-4-METHOXY-3-PYRIDINYL)-N-3-ISOXAZOLYL-2-OXO-1,2-DIHYDRO-6-QUINOLINESULFONAMIDE |
| 1-(6-(3-FLUOROPHENYL)-4-METHOXY-3-PYRIDINYL)-N-3-ISOXAZOLYL-2-OXO-1,2-DIHYDRO-6-QUINOLINESULFONAMIDE |
| 1-(4-(5-CHLORO-2-METHOXY-3-PYRIDINYL)-5-FLUORO-2-METHOXYPHENYL)-2-OXO-N-2-PYRIMIDINYL-1,2-DIHYDRO-6-QUINOLINESULFONAMIDE |
| 1-(4-(5-CHLORO-2-METHOXY-3-PYRIDINYL)-5-FLUORO-2-METHOXYPHENYL)-N-(5-FLUORO-2-PYRIMIDINYL)-2-OXO-1,2-DIHYDRO-6-QUINOLINESULFONAMIDE |
| 1-(4-(5-CHLORO-2-METHOXY-3-PYRIDINYL)-5-FLUORO-2-METHOXYPHENYL)-2-OXO-N-3-PYRIDAZINYL-1,2-DIHYDRO-6-QUINOLINESULFONAMIDE |
| 1-(4-(5-CHLORO-2-METHOXY-3-PYRIDINYL)-5-FLUORO-2-METHOXYPHENYL)-N-1,3-OXAZOL-2-YL-2-OXO-1,2-DIHYDRO-6-QUINOLINESULFONAMIDE |
| 1-(4-(5-CHLORO-2-METHOXY-3-PYRIDINYL)-5-FLUORO-2-METHOXYPHENYL)-N-(6-METHYL-4-PYRIMIDINYL)-2-OXO-1,2-DIHYDRO-6-QUINOLINESULFONAMIDE |
| 1-(4-(5-CHLORO-2-METHOXY-3-PYRIDINYL)-5-FLUORO-2-METHOXYPHENYL)-N-(2-METHYL-4-PYRIMIDINYL)-2-OXO-1,2-DIHYDRO-6-QUINOLINESULFONAMIDE |
| 1-((1R,3R)-3-(3-FLUOROPHENYL)CYCLOPENTYL)-N-3-ISOXAZOLYL-2-OXO-1,2-DIHYDRO-6-QUINOLINESULFONAMIDE, 1-((1R,3S)-3-(3-FLUOROPHENYL)CYCLOPENTYL)-N-3-ISOXAZOLYL-2-OXO-1,2-DIHYDRO-6-QUINOLINESULFONAMIDE, 1-((1S,3R)-3-(3-FLUOROPHENYL)CYCLOPENTYL)-N- |

| COMPOUND NAME |
|---|
| 3-ISOXAZOLYL-2-OXO-1,2-DIHYDRO-6-QUINOLINESULFONAMIDE, 1-((1S,3S)-3-(3-FLUOROPHENYL)CYCLOPENTYL)-N-3-ISOXAZOLYL-2-OXO-1,2-DIHYDRO-6-QUINOLINESULFONAMIDE |
| (P)-1-(5-CHLORO-4-CYCLOPROPYL-2-METHOXYPHENYL)-N-3-ISOXAZOLYL-2-OXO-1,2-DIHYDRO-6-QUINOLINESULFONAMIDE |
| (±)-1-((1S,2S)-2-METHOXYCYCLOHEXYL)-2-OXO-N-1,2,4-THIADIAZOL-5-YL-1,2-DIHYDRO-6-QUINOLINESULFONAMIDE |
| (P)-1-(4-(5-CHLORO-6-METHOXY-3-PYRIDINYL)-5-FLUORO-2-METHOXYPHENYL)-2-OXO-N-2-PYRIMIDINYL-1,2-DIHYDRO-6-QUINOLINESULFONAMIDE |
| (P)-1-(4-(5-CHLORO-6-METHOXY-3-PYRIDINYL)-5-FLUORO-2-METHOXYPHENYL)-N-(5-FLUORO-2-PYRIMIDINYL)-2-OXO-1,2-DIHYDRO-6-QUINOLINESULFONAMIDE |
| (P)-1-(4-(5-CHLORO-6-METHOXY-3-PYRIDINYL)-5-FLUORO-2-METHOXYPHENYL)-2-OXO-N-3-PYRIDAZINYL-1,2-DIHYDRO-6-QUINOLINESULFONAMIDE |
| (P)-1-(4-(5-CHLORO-6-METHOXY-3-PYRIDINYL)-5-FLUORO-2-METHOXYPHENYL)-N-1,3-OXAZOL-2-YL-2-OXO-1,2-DIHYDRO-6-QUINOLINESULFONAMIDE |
| (P)-1-(4-(5-CHLORO-6-METHOXY-3-PYRIDINYL)-5-FLUORO-2-METHOXYPHENYL)-N-(6-METHYL-4-PYRIMIDINYL)-2-OXO-1,2-DIHYDRO-6-QUINOLINESULFONAMIDE |
| (P)-1-(4-(5-CHLORO-6-METHOXY-3-PYRIDINYL)-5-FLUORO-2-METHOXYPHENYL)-N-(2-METHYL-4-PYRIMIDINYL)-2-OXO-1,2-DIHYDRO-6-QUINOLINESULFONAMIDE |
| (P)-1-(4-(5-CHLORO-6-METHOXY-3-PYRIDINYL)-5-FLUORO-2-METHOXYPHENYL)-N-(5-FLUORO-2-PYRIDINYL)-2-OXO-1,2-DIHYDRO-6-QUINOLINESULFONAMIDE |
| (P)-1-(4-(5-CHLORO-6-METHOXY-3-PYRIDINYL)-5-FLUORO-2-METHOXYPHENYL)-N-(6-FLUORO-2-PYRIDINYL)-2-OXO-1,2-DIHYDRO-6-QUINOLINESULFONAMIDE |
| 1-(2-(5-CHLORO-2-FLUOROPHENYL)-5-METHOXY-4-PYRIDINYL)-N-3-ISOXAZOLYL-2-OXO-1,2-DIHYDRO-6-QUINOLINESULFONAMIDE |
| 1-(2-(4-CHLORO-2-FLUOROPHENYL)-5-METHOXY-4-PYRIDINYL)-N-3-ISOXAZOLYL-2-OXO-1,2-DIHYDRO-6-QUINOLINESULFONAMIDE |
| N-3-ISOXAZOLYL-1-(2-METHOXYPHENYL)-2-OXO-1,2-DIHYDRO-6-QUINOLINESULFONAMIDE |
| 1-(2,6-DIFLUOROPHENYL)-N-3-ISOXAZOLYL-2-OXO-1,2-DIHYDRO-6-QUINOLINESULFONAMIDE |
| 1-(2-FLUOROPHENYL)-N-3-ISOXAZOLYL-2-OXO-1,2-DIHYDRO-6-QUINOLINESULFONAMIDE |
| 1-(2-ETHYLPHENYL)-N-3-ISOXAZOLYL-2-OXO-1,2-DIHYDRO-6-QUINOLINESULFONAMIDE |
| (P)-1-(4-BROMO-5-FLUORO-2-METHOXYPHENYL)-N-(6-(CYCLOPROPYLMETHOXY)-4-PYRIMIDINYL)-2-OXO-1,2-DIHYDRO-6-QUINOLINESULFONAMIDE |
| (P)-1-(4-BROMO-5-FLUORO-2-METHOXYPHENYL)-N-(6-(CYCLOBUTYLMETHOXY)-4-PYRIMIDINYL)-2-OXO-1,2-DIHYDRO-6-QUINOLINESULFONAMIDE |
| (P)-1-(4-BROMO-5-FLUORO-2-METHOXYPHENYL)-N-(6-(CYCLOPENTYLMETHOXY)-4-PYRIMIDINYL)-2-OXO-1,2-DIHYDRO-6-QUINOLINESULFONAMIDE |
| (P)-1-(4-BROMO-5-FLUORO-2-METHOXYPHENYL)-2-OXO-N-(6-PROPOXY-4-PYRIMIDINYL)-1,2-DIHYDRO-6-QUINOLINESULFONAMIDE |
| (P)-1-(4-BROMO-5-FLUORO-2-METHOXYPHENYL)-N-(6-(2-METHYLPROPOXY)-4-PYRIMIDINYL)-2-OXO-1,2-DIHYDRO-6-QUINOLINESULFONAMIDE |
| (P)-1-(4-BROMO-5-FLUORO-2-METHOXYPHENYL)-N-(6-(CYCLOBUTYLOXY)-4-PYRIMIDINYL)-2-OXO-1,2-DIHYDRO-6-QUINOLINESULFONAMIDE |
| (P)-1-(4-BROMO-5-FLUORO-2-METHOXYPHENYL)-N-(6-((1-METHYLCYCLOPROPYL)METHOXY)-4-PYRIMIDINYL)-2-OXO-1,2-DIHYDRO-6-QUINOLINESULFONAMIDE |
| (P)-1-(4-BROMO-5-FLUORO-2-METHOXYPHENYL)-N-(6-(CYCLOPENTYLOXY)-4-PYRIMIDINYL)-2-OXO-1,2-DIHYDRO-6-QUINOLINESULFONAMIDE |
| (P)-1-(4-BROMO-5-FLUORO-2-METHOXYPHENYL)-N-(1-METHYL-1H-PYRAZOL-3-YL)-2-OXO-1,2-DIHYDRO-6-QUINOLINESULFONAMIDE |
| (P)-1-(4-BROMO-5-FLUORO-2-METHOXYPHENYL)-N-(1-ETHYL-1H-PYRAZOL-3-YL)-2-OXO-1,2-DIHYDRO-6-QUINOLINESULFONAMIDE |
| (P)-1-(4-(4-FLUOROPHENOXY)-2-METHOXYPHENYL)-N-3-ISOXAZOLYL-2-OXO-1,2-DIHYDRO-6-QUINOLINESULFONAMIDE |
| (M)-1-(4-(4-FLUOROPHENOXY)-2-METHOXYPHENYL)-N-3-ISOXAZOLYL-2-OXO-1,2-DIHYDRO-6-QUINOLINESULFONAMIDE |
| (P)-1-(5-CHLORO-6-(4-FLUOROPHENYL)-2-METHOXY-3-PYRIDINYL)-N-3-ISOXAZOLYL-2-OXO-1,2-DIHYDRO-6-QUINOLINESULFONAMIDE |
| (M)-1-(5-CHLORO-6-(4-FLUOROPHENYL)-2-METHOXY-3-PYRIDINYL)-N-3-ISOXAZOLYL-2-OXO-1,2-DIHYDRO-6-QUINOLINESULFONAMIDE |
| 1-((1R,3R)-3-(3-FLUOROPHENYL)CYCLOPENTYL)-N-3-ISOXAZOLYL-2-OXO-1,2-DIHYDRO-6-QUINOLINESULFONAMIDE, 1-((1R,3S)-3-(3- |

| COMPOUND NAME |
|---|
| FLUOROPHENYL)CYCLOPENTYL)-N-3-ISOXAZOLYL-2-OXO-1,2-DIHYDRO-6-QUINOLINESULFONAMIDE 1-((1S,3R)-3-(3-FLUOROPHENYL)CYCLOPENTYL)-N-3-ISOXAZOLYL-2-OXO-1,2-DIHYDRO-6-QUINOLINESULFONAMIDE, 1-(1S,3S)-3-(3-FLUOROPHENYL)CYCLOPENTYL)-N-3-ISOXAZOLYL-2-OXO-1,2-DIHYDRO-6-QUINOLINESULFONAMIDE |
| (P)-1-(5-CHLORO-4-CYCLOPROPYL-2-METHOXYPHENYL)-N-3-ISOXAZOLYL-2-OXO-1,2-DIHYDRO-6-QUINOLINESULFONAMIDE |
| (P)-1-(4-CYCLOPROPYL-5-FLUORO-2-METHOXYPHENYL)-N-3-ISOXAZOLYL-2-OXO-1,2-DIHYDRO-6-QUINOLINESULFONAMIDE |
| (P)-1-(4-CYCLOPROPYL-2-METHOXYPHENYL)-N-3-ISOXAZOLYL-2-OXO-1,2-DIHYDRO-6-QUINOLINESULFONAMIDE |
| 1-(5-CHLORO-6-(2,2-DIFLUORO-2-(TETRAHYDRO-2H-PYRAN-4-YL)ETHOXY)-2-METHOXY-3-PYRIDINYL)-N-3-ISOXAZOLYL-2-OXO-1,2-DIHYDRO-6-QUINOLINESULFONAMIDE |
| 1-(5-CHLORO-2-METHOXY-6-((((1R)-2,2,3,3-TETRAFLUORO-1-METHYLPROPYL)OXY)-3-PYRIDINYL)-N-3-ISOXAZOLYL-2-OXO-1,2-DIHYDRO-6-QUINOLINESULFONAMIDE, 1-(5-CHLORO-2-METHOXY-6-(((1S)-2,2,3,3-TETRAFLUORO-1-METHYLPROPYL)OXY)-3-PYRIDINYL)-N-3-ISOXAZOLYL-2-OXO-1,2-DIHYDRO-6-QUINOLINESULFONAMIDE |
| 1-(5-CHLORO-6-((2,4-DIFLUOROBENZYL)OXY)-2-METHOXY-3-PYRIDINYL)-N-3-ISOXAZOLYL-2-OXO-1,2-DIHYDRO-6-QUINOLINESULFONAMIDE |
| 1-(5-CHLORO-6-((4-FLUOROBENZYL)OXY)-2-METHOXY-3-PYRIDINYL)-N-3-ISOXAZOLYL-2-OXO-1,2-DIHYDRO-6-QUINOLINESULFONAMIDE |
| 1-(5-CHLORO-6-((4-FLUORO-3-(TRIFLUOROMETHYL)BENZYL)OXY)-2-METHOXY-3-PYRIDINYL)-N-3-ISOXAZOLYL-2-OXO-1,2-DIHYDRO-6-QUINOLINESULFONAMIDE |
| 1-(5-CHLORO-2-METHOXY-6-((2,3,4-TRIFLUOROBENZYL)OXY-3-PYRIDINYL)-N-3-ISOXAZOLYL-2-OXO-1,2-DIHYDRO-6-QUINOLINESULFONAMIDE |
| 1-(5-CHLORO-6-((3,4-DIFLUOROBENZYL)OXY)-2-METHOXY-3-PYRIDINYL)-N-3-ISOXAZOLYL-2-OXO-1,2-DIHYDRO-6-QUINOLINESULFONAMIDE |
| 1-(5-CHLORO-2-METHOXY-6-((3,4,5-TRIFLUOROBENZYL)OXY)-3-PYRIDINYL)-N-3-ISOXAZOLYL-2-OXO-1,2-DIHYDRO-6-QUINOLINESULFONAMIDE |
| 1-(5-CHLORO-6-(CYCYLOHEXYLMETHOXY)-2-METHOXY-3-PYRIDINYL)-N-3-ISOXAZOLYL-2-OXO-1,2-DIHYDRO-6-QUINOLINESULFONAMIDE |
| 1-(5-CHLORO-6-(4-FLUOROPHENOXY)-2-METHOXY-3-PYRIDINYL)-N-3-ISOXAZOLYL-2-OXO-1,2-DIHYDRO-6-QUINOLINESULFONAMIDE |
| 1-(5-CHLORO-6-(4-FLUOROPHENOXY)-2-METHOXY-3-PYRIDINYL)-N-3-ISOXAZOLYL-2-OXO-1,2-DIHYDRO-6-QUINOLINESULFONAMIDE |
| 1-(5-CHLORO-6-(4-FLUOROPHENOXY)-2-METHOXY-3-PYRIDINYL)-N-3-ISOXAZOLYL-2-OXO-1,2-DIHYDRO-6-QUINOLINESULFONAMIDE |
| 1-(6-((1R,2S,4S)-BICYCLO[2.2.1]HEPT-2-YLOXY)-5-CHLORO-2-METHOXY-3-PYRIDINYL)-N-3-ISOXAZOLYL-2-OXO-1,2-DIHYDRO-6-QUINOLINESULFONAMIDE |
| 1-(5-CHLORO-2-METHOXY-6-(((1S,2R)-2-METHYLCYCLOHEXYL)OXY)-3-PYRIDINYL)-N-3-ISOXAZOLYL-2-OXO-1,2-DIHYDRO-6-QUINOLINESULFONAMIDE |
| 1-(5-CHLORO-6-(2,5-DIFLUOROPHENOXY)-2-METHOXY-3-PYRIDINYL)-N-3-ISOXAZOLYL-2-OXO-1,2-DIHYDRO-6-QUINOLINESULFONAMIDE |
| 1-(5-CHLORO-6-(3-CHLORO-2-METHYLPHENOXY)-2-METHOXY-3-PYRIDINYL)-N-3-ISOXAZOLYL-2-OXO-1,2-DIHYDRO-6-QUINOLINESULFONAMIDE |
| 1-((1S,2S)-2-METHOXYCYCLOHEXYL)-2-OXO-N-1,2,4-THIADIAZOL-5-YL-1,2-DIHYDRO-6-QUINOLINESULFONAMIDE |
| 1-((1S,2S)-2-METHOXYCYCLOPENTYL)-2-OXO-N-1,2,4-THIADIAZOL-5-YL-1,2-DIHYDRO-6-QUINOLINESULFONAMIDE |
| (M)-1-(5-CHLORO-6-CYCLOPROPYL-2-METHOXY-3-PYRIDINYL)-N-3-ISOXAZOLYL-2-OXO-1,2-DIHYDRO-6-QUINOLINESULFONAMIDE |
| (P)-1-(5-CHLORO-6-CYCLOPROPYL-2-METHOXY-3-PYRIDINYL)-N-3-ISOXAZOLYL-2-OXO-1,2-DIHYDRO-6-QUINOLINESULFONAMIDE |
| 1-(5-CHLORO-6-(CYCLOPENTYL(METHYL)AMINO)-2-METHOXY-3-PYRIDINYL)-N-3-ISOXAZOLYL-2-OXO-1,2-DIHYDRO-6-QUINOLINESULFONAMIDE |
| 1-(5-CHLORO-6-((((2R)-5,5-DIMETHYLTETRAHYDRO-2-FURANYL)METHYL)AMINO)-2-METHOXY-3-PYRIDINYL)-N-3-ISOXAZOLYL-2-OXO-1,2-DIHYDRO-6-QUINOLINESULFONAMIDE, 1-(5-CHLORO-6-((((2S)-5,5-DIMETHYLTETRAHYDRO-2-FURANYL)METHYL)AMINO)-2-METHOXY-3-PYRIDINYL)-N-3-ISOXAZOLYL-2-OXO-1,2-DIHYDRO-6-QUINOLINESULFONAMIDE |
| (P)-1-(5-FLUORO-2-METHOXY-4-((3S)-TETRAHYDRO-3-FURANYLMETHYL)PHENYL)-N-3-ISOXAZOLYL-2-OXO-1,2-DIHYDRO-6-QUINOLINESULFONAMIDE |
| (P)-1-(5-FLUORO-2-METHOXY-4-((3R)-TETRAHYDRO-3-FURANYLMETHYL)PHENYL)-N-3-ISOXAZOLYL-2-OXO-1,2-DIHYDRO-6-QUINOLINESULFONAMIDE |
| 1-(5-CHLORO-2-METHOXY-6-(((METHYLCYCLOPENTYL)METHYL)AMINO)-3-PYRIDINYL)-N-3-ISOXAZOLYL-2-OXO-1,2-DIHYDRO-6-QUINOLINESULFONAMIDE |
| 1-(5-CHLORO-2-METHOXY-6-((((2R)-2-METHYLTETRAHYDRO-2-FURANYL)METHYL)AMINO)-3-PYRIDINYL-N-3-ISOXAZOLYL-2-OXO-1,2- |

| COMPOUND NAME |
|---|
| DIHYDRO-6-QUINOLINESULFONAMIDE, 1-(5-CHLORO-2-METHOXY-6-((2S)-2-METHYLTETRAHYDRO-2-FURANYL)METHYL)AMINO)-3-PYRIDINYL)-N-3-ISOXAZOLYL-2-OXO-1,2-DIHYDRO-6-QUINOLINESULFONAMIDE. |

\* \* \* \* \*